US007888376B2

(12) United States Patent
Salvati et al.

(10) Patent No.: US 7,888,376 B2
(45) Date of Patent: Feb. 15, 2011

(54) HETEROCYCLIC CETP INHIBITORS

(75) Inventors: Mark E. Salvati, Lawrenceville, NJ (US); Heather Finlay, Skillman, NJ (US); Lalgudi S. Harikrishnan, Princeton, NJ (US); Ji Jiang, West Windsor, NJ (US); James A. Johnson, Pennington, NJ (US); Muthoni G. Kamau, Lawrenceville, NJ (US); R. Michael Lawrence, Yardley, PA (US); Michael M. Miller, Pennington, NJ (US); Jennifer X. Qiao, Princeton, NJ (US); Tammy C. Wang, Lawrenceville, NJ (US); Yufeng Wang, North Brunswick, NJ (US); Wu Yang, Princeton Junction, NJ (US)

(73) Assignee: Bristol-Myers Squibb Company, Princeton, NJ (US)

( * ) Notice: Subject to any disclaimer, the term of this patent is extended or adjusted under 35 U.S.C. 154(b) by 1005 days.

(21) Appl. No.: 11/559,930

(22) Filed: Nov. 15, 2006

(65) Prior Publication Data

US 2007/0161685 A1 Jul. 12, 2007

Related U.S. Application Data

(60) Provisional application No. 60/739,322, filed on Nov. 23, 2005.

(51) Int. Cl.
*C07D 213/56* (2006.01)
*A61K 31/44* (2006.01)

(52) U.S. Cl. ....................................... 514/357; 546/336

(58) Field of Classification Search ....................... None
See application file for complete search history.

(56) References Cited

U.S. PATENT DOCUMENTS

| | | | |
|---|---|---|---|
| 5,041,458 | A | 8/1991 | Basarab |
| 2002/0177708 | A1 | 11/2002 | Sikorski et al. |
| 2004/0127574 | A1 | 7/2004 | Kori et al. |

FOREIGN PATENT DOCUMENTS

| | | |
|---|---|---|
| WO | WO 02/20015 A1 * | 3/2002 |
| WO | WO 03/064376 | 8/2003 |
| WO | WO 2005/030185 | 4/2005 |
| WO | WO 2005/037796 | 4/2005 |
| WO | WO 2005/092845 | 10/2005 |
| WO | WO 2005/095395 | 10/2005 |
| WO | WO 2005/095409 | 10/2005 |
| WO | WO 2005/097805 | 10/2005 |
| WO | WO 2005/097806 | 10/2005 |
| WO | WO 2005/100298 | 10/2005 |
| WO | WO 2007/062308 | 5/2007 |
| WO | WO 2007/062342 | 5/2007 |

OTHER PUBLICATIONS

Wu et al, Toxicology, 236, pp. 1-6, 2007.*
Alcaide, B. et al., "The reaction of alpha-diketones with primary heteroaromatic amines. Synthesis and reactions of imidazo[1,2-a]pyridine-3(2H0-ones and N-heteroaryl alpha-iminoketones", Tetrahedron, vol. 45, No. 21, pp. 6841-6856 (1989).
Lau, C. K. et al., "Structure based design of a series of potent and selective non peptidic PTP-1B inhibitors", Bioorganic & Medicinal Chemistry Letters, vol. 14, pp. 1043-1048 (2004).
Scapin, G. et al., "The structural basis for the selectivity of benzotriazole inhibitors of PTP1B", Biochemistry, vol. 42, pp. 11451-11459 (2003).
Maeda et al., "*S*-(2-(Acylamino)phenyl) 2,2-dimethylpropanethioates as CETP inhibitors", Bioorganic & Medicinal Chemistry Letters, vol. 14, No. 10, pp. 2589-2591 (2004).

* cited by examiner

*Primary Examiner*—Zinna N Davis
(74) *Attorney, Agent, or Firm*—Terence J. Bogie

(57) ABSTRACT

Compounds of formula Ia and Ib

Ia

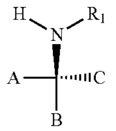

and

Ib

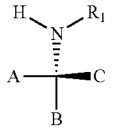

wherein A, B, C and $R_1$ are described herein.

17 Claims, No Drawings

HETEROCYCLIC CETP INHIBITORS

RELATED APPLICATION

This application claims the benefit of U.S. Provisional Application No. 60/739,322, filed on Nov. 23, 2005, incorporated herein by reference in its entirety.

FIELD OF THE INVENTION

This present invention provides for cholesteryl ester transfer protein (CETP) inhibitors, pharmaceutical compositions containing such inhibitors and the use of such inhibitors to elevate certain plasma lipid levels, including high density lipoprotein (HDL)-cholesterol and to lower certain other plasma lipid levels, such as low density lipoprotein (LDL)-cholesterol and triglycerides and accordingly to treat diseases which are affected by low levels of HDL cholesterol and/or high levels of LDL-cholesterol and triglycerides, such as atherosclerosis and cardiovascular diseases in certain mammals (i.e., those which have CETP in their plasma), including humans.

BACKGROUND OF THE INVENTION

Atherosclerosis and its associated coronary artery disease (CAD) is the leading cause of mortality in the industrialized world. Despite attempts to modify secondary risk factors (smoking, obesity, lack of exercise) and treatment of dyslipidemia with dietary modification and drug therapy, coronary heart disease (CHD) remains the most common cause of death in the U.S., where cardiovascular disease accounts for 44% of all deaths, with 53% of these associated with atherosclerotic coronary heart disease.

Risk for development of atherosclerosis has been shown to be strongly correlated with certain plasma lipid levels. While elevated LDL-C may be the most recognized form of dyslipidemia, it is by no means the only significant lipid associated contributor to CHD. Low HDL-C is also a known risk factor for CHD (Gordon, D. J. et al., "High-density Lipoprotein Cholesterol and Cardiovascular Disease", Circulation, 79:8-15 (1989)).

High LDL-cholesterol and triglyceride levels are positively correlated, while high levels of HDL-cholesterol are negatively correlated with the risk for developing cardiovascular diseases. Thus, dyslipidemia is not a unitary risk profile for CHD but may be comprised of one or more lipid aberrations.

Among the many factors controlling plasma levels of these disease dependent principles, cholesteryl ester transfer protein (CETP) activity affects all three. The role of this 70,000 dalton plasma glycoprotein found in a number of animal species, including humans, is to transfer cholesteryl ester and triglyceride between lipoprotein particles, including high density lipoproteins (HDL), low density lipoproteins (LDL), very low density lipoproteins (VLDL), and chylomicrons. The net result of CETP activity is a lowering of HDL cholesterol and an increase in LDL cholesterol. This effect on lipoprotein profile is believed to be pro-atherogenic, especially in subjects whose lipid profile constitutes an increased risk for CHD.

No wholly satisfactory HDL-elevating therapies exist. Niacin can significantly increase HDL, but has serious toleration issues which reduce compliance. Fibrates and the HMG CoA reductase inhibitors raise HDL-C only modestly (about.10-12%). As a result, there is a significant unmet medical need for a well-tolerated agent which can significantly elevate plasma HDL levels, thereby reversing or slowing the progression of atherosclerosis.

Thus, although there are a variety of anti-atherosclerosis therapies, there is a continuing need and a continuing search in this field of art for alternative therapies.

SUMMARY OF THE INVENTION

In accordance with the present invention, heterocyclic compounds and related compounds are provided that have the general structures:

Ia

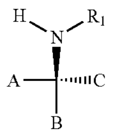

and

Ib

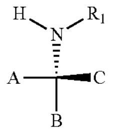

wherein A, B, C and $R_1$ are defined below.

By use of a respective effective amount of at least one compound described herein, provided are methods of treating, preventing or slowing the progression of a disease requiring cholesteryl ester transfer protein inhibition, or inhibiting the cholesteryl ester transfer protein.

Also provided are pharmaceutical compositions comprising a therapeutically effective amount of at least one compound described herein and a pharmaceutically acceptable vehicle or carrier thereof. Such compositions can further comprise one or more additional therapeutic agents.

DEFINITIONS

The terms "alk" or "alkyl" refer to straight or branched chain hydrocarbon groups having 1 to 12 carbon atoms, or 1 to 8 carbon atoms, such as methyl, ethyl, n-propyl, i-propyl, n-butyl, i-butyl, t-butyl, pentyl, hexyl, heptyl, octyl, or any subset of the foregoing. The term "substituted alkyl" refers to alkyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkenyl" refers to straight or branched chain hydrocarbon groups having 2 to 12 carbon atoms, or 2 to 4 carbon atoms, and at least one double carbon to carbon bond (either cis or trans), such as ethenyl. The term "substituted alkenyl" refers to alkenyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "alkynyl" refers to straight or branched chain hydrocarbon groups having 2 to 12 carbon atoms, or 2 to 4 carbon atoms, and at least one triple carbon to carbon bond, such as ethynyl. The term "substituted alkynyl" refers to alkynyl groups substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The term "aryl" refers to aromatic homocyclic (i.e., hydrocarbon) mono-, bi- or tricyclic ring-containing groups such as having 6 to 12 members such as phenyl, naphthyl and biphenyl. Phenyl is an example of an aryl group. The term "substituted aryl" refers to aryl groups substituted with one or more groups (such as by groups described above in the definition of $R^{10}$), such as selected from alkyl, substituted alkyl, alkenyl (optionally substituted), aryl (optionally substituted), heterocyclo (optionally substituted), halo, hydroxy, alkoxy (optionally substituted), aryloxy (optionally substituted), alkanoyl (optionally substituted), aroyl, (optionally substituted), alkylester (optionally substituted), arylester (optionally substituted), cyano, nitro, amino, substituted amino, amido, lactam, urea, urethane and sulfonyl, or any subset of the foregoing, where optionally one or more pair of substituents together with the atoms to which they are bonded form a 3 to 7 member ring.

The term "cycloalkyl" refers to mono-, bi- or tri homocyclic ring groups of 3 to 15 carbon atoms which are, respectively, fully saturated and partially unsaturated. The rings of multi-ring cycloalkyl groups may be either fused, bridged and/or joined through one or more spiro unions. The term "substituted cycloalkyl" refers to a cycloalkyl group substituted with one or more groups (such as by groups described above in the definition of $R^{10}$), such as selected from aryl, substituted aryl, heterocyclo, substituted heterocyclo, carbocyclo, substituted carbocyclo, halo, hydroxy, alkoxy (optionally substituted), aryloxy (optionally substituted), alkylester (optionally substituted), arylester (optionally substituted), alkanoyl (optionally substituted), aryol (optionally substituted), cyano, nitro, amino, substituted amino, amido, lactam, urea, urethane and sulfonyl, or any subset of the foregoing.

The terms "halogen" and "halo" refer to fluorine, chlorine, bromine and iodine.

The terms "heterocycle", "heterocyclic", "heterocyclic group" or "heterocyclyl" refer to fully saturated or partially or completely unsaturated, including aromatic ("heteroaryl") or nonaromatic cyclic groups (for example, 3 to 13 ring member monocyclic, 7 to 17 ring member bicyclic, or 10 to 20 ring member tricyclic ring systems, such as, in certain embodiments, a monocyclic or bicyclic ring containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen atoms, oxygen atoms and/or sulfur atoms, where the nitrogen and sulfur heteroatoms may optionally be oxidized and the nitrogen heteroatoms may optionally be quaternized. The heterocyclic group may be attached at any heteroatom or carbon atom of the ring or ring system. The rings of multi-ring heterocycles may be either fused, bridged and/or joined through one or more spiro unions.

Exemplary monocyclic heterocyclic groups include azetidinyl, pyrrolidinyl, pyrrolyl, pyrazolyl, oxetanyl, pyrazolinyl, imidazolyl, imidazolinyl, imidazolidinyl, oxazolyl, oxazolidinyl, isoxazolinyl, isoxazolyl, thiazolyl, thiadiazolyl, thiazolidinyl, isothiazolyl, isothiazolidinyl, furyl, tetrahydrofuryl, thienyl, oxadiazolyl, piperidinyl, piperazinyl, 2-oxopiperazinyl, 2-oxopiperidinyl, 2-oxopyrrolodinyl, 2-oxoazepinyl, azepinyl, 4-piperidonyl, pyridyl, pyrazinyl, pyrimidinyl, pyridazinyl, triazinyl, tetrahydropyranyl, tetrazoyl, triazolyl, morpholinyl, thiamorpholinyl, thiamorpholinyl sulfoxide, thiamorpholinyl sulfone, 1,3-dioxolane and tetrahydro-1,1 -dioxothienyl,

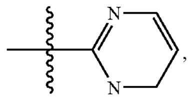,
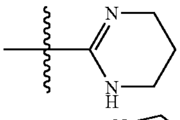,
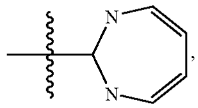,
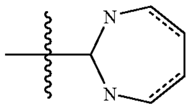

and the like.

Exemplary bicyclic heterocyclic groups include indolyl, benzothiazolyl, benzoxazolyl, benzothienyl, quinuclidinyl, quinolinyl, tetra-hydroisoquinolinyl, isoquinolinyl, benzimidazolyl, benzopyranyl, indolizinyl, benzofuryl, benzofuranyl, dihydrobenzofuranyl, chromonyl, coumarinyl, benzodioxolyl, dihydrobenzodioxolyl, benzodioxinyl, cinnolinyl, quinoxalinyl, indazolyl, pyrrolopyridyl, furopyridinyl (such as furo[2,3-c]pyridinyl, furo[3,2-b]pyridinyl] or furo[2,3-b] pyridinyl), dihydroisoindolyl, dihydroquinazolinyl (such as 3,4-dihydro-4-oxo-quinazolinyl), tetrahydroquinolinyl, azabicycloalkyls (such as 6-azabicyclo [3.2.1]octane), azaspiroalkyls (such as 1,4 dioxa-8-azaspiro[4.5]decane), imidazopyridinyl (such as imidazo[1,5-a]pyridin-3-yl), triazolopyridinyl (such as 1,2,4-triazolo[4,3-a]pyridin-3-yl), and hexahydroimidazopyridinyl (such as 1,5,6,7,8,8a-hexahydroimidazo[1,5-a]pyridin-3-yl),

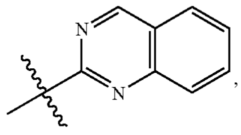,
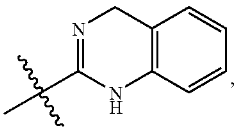,
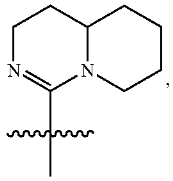,
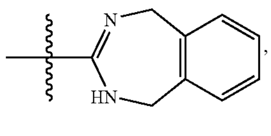,
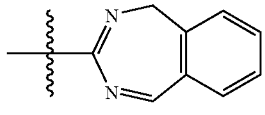

and the like.

Exemplary tricyclic heterocyclic groups include carbazolyl, benzidolyl, phenanthrolinyl, acridinyl, phenanthridinyl, xanthenyl and the like.

The terms "substituted heterocycle", "substituted heterocyclic", "substituted heterocyclic group" and "substituted heterocyclyl" refer to heterocycle, heterocyclic and heterocyclo groups substituted with one or more groups (such as by groups described above in the definition of $R^{10}$), such as selected from alkyl, substituted alkyl, alkenyl, oxo, aryl, substituted aryl, heterocyclo, substituted heterocyclo, carbocyclo (optionally substituted), halo, hydroxy, alkoxy (optionally substituted), aryloxy (optionally substituted), alkanoyl (optionally substituted), aroyl (optionally substituted), alkylester (optionally substituted), arylester (optionally substituted), cyano, nitro, amido, amino, substituted amino, lactam, urea, urethane, sulfonyl, or any subset of the foregoing, where optionally one or more pair of substituents together with the atoms to which they are bonded form a 3 to 7 member ring.

Throughout the specification, groups and substituents thereof may be chosen to provide stable moieties and compounds.

The compounds of formulas Ia and Ib form salts or solvates which are also within the scope of this invention. Reference to a compound of the formula Ia or Ib herein is understood to include reference to salts thereof, unless otherwise indicated. The term "salt(s)", as employed herein, denotes acidic and/or basic salts formed with inorganic and/or organic acids and bases. In addition, when a compound of formula Ia or Ib contains both a basic moiety and an acidic moiety, zwitterions ("inner salts") may be formed and are included within the term "salt(s)" as used herein. Pharmaceutically acceptable (i.e., non-toxic, physiologically acceptable) salts are preferred, although other salts are also useful, e.g., in isolation or purification steps which may be employed during preparation. Salts of the compounds of the formula Ia and Ib may be formed, for example, by reacting a compound of formula Ia or Ib with an amount of acid or base, such as an equivalent amount, in a medium such as one in which the salt precipitates or in an aqueous medium followed by lyophilization.

The compounds of formula Ia and Ib which contain a basic moiety may form salts with a variety of organic and inorganic acids. Exemplary acid addition salts include acetates (such as those formed with acetic acid or trihaloacetic acid, for example, trifluoroacetic acid), adipates, alginates, ascorbates, aspartates, benzoates, benzenesulfonates, bisulfates, borates, butyrates, citrates, camphorates, camphorsulfonates, cyclopentanepropionates, digluconates, dodecylsulfates, ethanesulfonates, fumarates, glucoheptanoates, glycerophosphates, hemisulfates, heptanoates, hexanoates, hydrochlorides (formed with hydrochloric acid), hydrobromides (formed with hydrogen bromide), hydroiodides, 2-hydroxyethanesulfonates, lactates, maleates (formed with maleic acid), methanesulfonates (formed with methanesulfonic acid), 2-naphthalenesulfonates, nicotinates, nitrates, oxalates, pectinates, persulfates, 3-phenylpropionates, phosphates, picrates, pivalates, propionates, salicylates, succinates, sulfates (such as those formed with sulfuric acid), sulfonates (such as those mentioned herein), tartrates, thiocyanates, toluenesulfonates such as tosylates, undecanoates, and the like.

The compounds of formula Ia and Ib which contain an acidic moiety may form salts with a variety of organic and inorganic bases. Exemplary basic salts include ammonium salts, alkali metal salts such as sodium, lithium, and potassium salts, alkaline earth metal salts such as calcium and magnesium salts, salts with organic bases (for example, organic amines) such as benzathines, dicyclohexylamines, hydrabamines (formed with N,N-bis(dehydroabietyl)ethylenediamine), N-methyl-D-glucamines, N-methyl-D-glucamides, t-butyl amines, and salts with amino acids such as arginine, lysine and the like.

Basic nitrogen-containing groups may be quatemized with agents such as lower alkyl halides (e.g. methyl, ethyl, propyl, and butyl chlorides, bromides and iodides), dialkyl sulfates (e.g. dimethyl, diethyl, dibutyl, and diamyl sulfates), long chain halides (e.g. decyl, lauryl, myristyl and stearyl chlorides, bromides and iodides), aralkyl halides (e.g. benzyl and phenethyl bromides), and others.

Any compound that can be converted in vivo to provide the bioactive agent (i.e., a compound of formula Ia or Ib) is a prodrug within the scope and spirit of the invention.

The term "prodrugs" as employed herein includes esters and carbonates formed by reacting one or more hydroxyls of compounds of formula Ia and Ib with alkyl, alkoxy, or aryl substituted acylating agents employing procedures known to those skilled in the art to generate acetates, pivalates, methylcarbonates, benzoates, and the like.

Various forms of prodrugs are well known in the art and are described in:

a) *The Practice of Medicinal Chemistry*, Camille G. Wermuth et al., Ch. 31 (Academic Press, 1996);

b) *Design of Prodrugs*, edited by H. Bundgaard (Elsevier, 1985);

c) *A Textbook of Drug Design* and *Development*, P. Krogsgaard-Larson and H. Bundgaard, eds. Ch. 5, pp. 113-191 (Harwood Academic Publishers, 1991); and d) *Hydrolysis in Drug and Prodrug Metabolism*, Bernard Testa and Joachim M. Mayer (Wiley-VCH, 2003).

Said references are incorporated herein by reference.

In addition, compounds of the present invention are, subsequent to their preparation, preferably isolated and purified to obtain a composition containing an amount by weight equal to or greater than 99% formula Ia or Ib compound ("substantially pure" compound Ia or Ib), which may be used or formulated as described herein. Such "substantially pure" compounds of formula Ia and Ib are also contemplated herein as part of the present invention.

To the extent that compounds of the formula Ia and Ib, and salts thereof, may exist in their tautomeric form, all such tautomeric forms are contemplated herein as part of the present invention.

All stereoisomers of the present compounds, such as those which may exist due to asymmetric carbons on the various substituents, including enantiomeric forms (which may exist even in the absence of asymmetric carbons) and diastereomeric forms, are contemplated within the scope of this invention. Individual stereoisomers of the compounds of the invention may, for example, be substantially free of other isomers, or may be admixed, for example, as racemates or with all other, or other selected, stereoisomers.

The terms "including", "such as", "for example" and the like are intended to refer to exemplary embodiments and not to limit the scope of the present invention.

DETAILED DESCRIPTION OF THE INVENTION

It will be understood that any given exemplary embodiment can be combined with one or more additional exemplary embodiments.

In accordance with the present invention, compounds of formula Ia and Ib are provided Ia

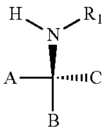

or

Ib

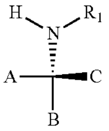

or stereoisomers or prodrugs or pharmaceutically acceptable salt forms thereof, wherein:

A is heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) ═O, 17) —$S(O)_pR_6$, 18) —$SO_2NHR_6$, 19) —$COOR_6$, 20) —$NHC(CN)NHR_6$, 21) —$CONR_6R_6$; and 27) cycloalkyl, which may be optionally substituted with one or more $R_{20}$'s;

B is:

(a) phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —$NHC(CN)NHR_6$, 20) —$CONR_6R_6$; and 21) cycloalkyl, which may be optionally substituted with one or more $R_{20}$'s; or (b) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, 19) —$NHC(CN)NHR_6$, 20) —$CONR_6R_6$; and 21) cycloalkyl, which may be optionally substituted with one or more $R_{20}$'s;

C is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —$NHC(CN)NHR_6$; and 18) cycloalkyl, which may be optionally substituted with one or more $R_{20}$'s;

(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl; and 15) cycloalkyl, which may be optionally substituted with one or more $R_{20}$'s;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —$NHC(CN)NHR_6$; and 18) cycloalkyl, which may be optionally substituted with one or more $R_{20}$'s; or (d) heterocyclo, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, 17) —$NHC(CN)NHR_6$; and 18) cycloalkyl, which may be optionally substituted with one or more $R_{20}$'s;

$R_1$ is —$C(O)R_3$, —$C(O)NR_2R_3$, —$C(O)OR_4$, —$SO_2R_5$, —$CSNHR_7$, —$CR_8R_8R_8$, —$C(S)R_3$, or —$C(=NR_3)$Oalkyl;

$R_2$ is:

(a) H;

(b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$COR_6$, 13) —$CONR_6R_6$, 14) ($C_2$-$C_6$)-alkenyl, 15) ($C_2$-$C_6$)-alkynyl, 16) —$S(O)_pR_6$, 17) —$SO_2NHR_6$, 18) —$COOR_6$, 19) —$NHC(CN)NHR_6$; and 20) cycloalkyl, which may be optionally substituted with one or more $R_{20}$'s;

(c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15)-$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, 22) —$NHC(CN)NHR_6$; and 23) cycloalkyl, which may be optionally substituted with one or more $R_{20}$'s; or (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —$CO_2$($C_1$-$C_6$)-alkyl, 18) —$CONR_6R_6$, 19) ($C_2$-$C_6$)-alkenyl, 20) ($C_2$-$C_6$)-alkynyl; and 21) cycloalkyl, which may be optionally substituted with one or more $R_{20}$'s;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$, 13) ($C_2$-$C_6$)-alkenyl, 14) ($C_2$-$C_6$)-alkynyl, 15) —$COR_6$, 16) —$S(O)_pR_6$, 17) —$SO_2NHR_6$, 18) —$COOR_6$, 19) —$NHC(CN)NHR_6$; and 20) cycloalkyl, which may be optionally substituted with one or more $R_{20}$'s;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —$NHC(CN)NHR_6$; and 24) cycloalkyl, which may be optionally substituted with one or more $R_{20}$'s;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) —$NHC(CN)NHR_6$; and 24) cycloalkyl, which may be optionally substituted with one or more $R_{20}$'s;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, 23) -$NHC(CN)NHR_6$; and 24) cycloalkyl, which may be optionally substituted with one or more $R_{20}$'s;

(e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo $(C_1-C_6)$alkyl, 15) —$CONR_6R_6$, 16) $(C_2-C_6)$-alkenyl, 17) =O, 18) $(C_2-C_6)$-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s; or (f) alkenyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15)-$CONR_6R_6$, 16) $(C_2-C_6)$-alkenyl, 17) $(C_2-C_6)$-alkynyl, 18) —$COR_6$, 19) —$S(O)_pR_6$, 20) —$SO_2NHR_6$, 21) —$COOR_6$, 22) —NHC(CN)$NHR_6$; and 23) cycloalkyl, which may be optionally substituted with one or more $R_{20}$'s;

or $R_2$ and $R_3$ are taken together to form a 3- to 9-membered ring, which optionally may contain 1-4 heteroatoms selected from N, O, and S and be optionally substituted with one or more $R_{20}$'s;

$R_4$ is:

(a) alkyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6$, 16) $(C_2-C_6)$-alkenyl, 17) =O, 18) $(C_2-C_6)$-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

(b) aryl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6$, 16) $(C_2-C_6)$-alkenyl, 17) =O, 18) $(C_2-C_6)$-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

(c) cycloalkyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) =O, 18) $(C_2-C_6)$-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

(d) $(C_2-C_6)$-alkenyl; or (e) $(C_2-C_6)$-alkynyl;

$R_5$ is arylalkyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) =O, 18) $(C_2-C_6)$-alkynyl, 19) —$COR_6$, 20) —$S(O)_pR_6$, 21) —$SO_2NHR_6$, 22) —$COOR_6$, 23) —NHC(CN)$NHR_6$; and 24) cycloalkyl, which may be optionally substituted with one or more $R_{20}$'s;

$R_6$, at each occurrence, is independently:

(a) alkyl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo$(C_1-C_6)$alkyl, 13) $(C_2-C_6)$-alkenyl, 14) —COOH, 15) —$CONR_{36}R_{36}$, 16) =O, 17) $(C_2-C_6)$-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$; and 23) cycloalkyl, which may be optionally substituted with one or more $R_{20}$'s;

(b) aryl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo $(C_1-C_6)$alkyl, 16) —COOH, 17) —$CONR_{36}R_{36}$, 18) ═O, 19) $(C_2-C_6)$-alkynyl, 20) —$COR_{36}$, 21) —$S(O)_pR_{36}$, 22) —$SO_2NHR_{36}$, 23) —$COOR_{36}$, 24) —$NHC(CN)NHR_{36}$; and 25) cycloalkyl, which may be optionally substituted with one or more $R_{20}$'s;

(c) cycloalkyl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo $(C_1-C_6)$alkyl, 16) $(C_2-C_6)$-alkenyl, 17) —COOH, 18) —$CONR_{36}R_{36}$, 19) ═O, 20) $(C_2-C_6)$-alkynyl, 21) —$COR_{36}$, 22) —$S(O)_pR_{36}$, 23) —$SO_2NHR_{36}$, 24) —$COOR_{36}$, 25) —$NHC(CN)NHR_{36}$; and 26) cycloalkyl, which may be optionally substituted with one or more $R_{20}$'s;

(d) heteroaryl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo $(C_1-C_6)$alkyl, 16) $(C_2-C_6)$-alkenyl, 17) —COOH, 18) —$CONR_{36}R_{36}$, 19) ═O, 20) $(C_2-C_6)$-alkynyl, 21) —$COR_{36}$, 22) —$S(O)_pR_{36}$, 23) —$SO_2NHR_{36}$, 24) —$COOR_{36}$, 25) —$NHC(CN)NHR_{36}$; and 26) cycloalkyl, which may be optionally substituted with one or more $R_{20}$'s;

(e) heterocyclyl, other than heteroaryl, which may be optionally substituted with one or more substituents selected from the group consisting of: 1) halo, 2) —OH, 3) $(C_1-C_6)$-alkyl, which may be optionally substituted with one or more $R_{20}$'s, 4) —$OR_{36}$, 5) $(C_1-C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo$(C_1-C_6)$alkyl, 16) $(C_2-C_6)$-alkenyl, 17) —COOH, 18) —$CONR_{36}R_{36}$, 19) ═O, 20) $(C_2-C_6)$-alkynyl, 21) —$COR_{36}$, 22) —$S(O)_pR_{36}$, 23) —$SO_2NHR_{36}$, 24) —$COOR_{36}$, 25) —$NHC(CN)NHR_{36}$; and 26) cycloalkyl, which may be optionally substituted with one or more $R_{20}$'s; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_7$ is aryl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $(C_2-C_6)$-alkenyl, 16) —$CONR_{26}R_{26}$, 17) ═O, 18) $(C_2-C_6)$-alkynyl, 19) —$COR_6$, 20) —$S(O)_pR_{26}$, 21) —$SO_2NHR_{26}$, 22) —$COOR_{26}$, 23) —$NHC(CN)NHR_{26}$; and 24) cycloalkyl, which may be optionally substituted with one or more $R_{20}$'s;

$R_8$ can independently be:

(a) H;

(b) alkyl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo $(C_1-C_6)$alkyl, 12) $(C_2-C_6)$-alkenyl, 13) aryl$(C_2-C_6)$-alkynyl, 14) —$CONR_{26}R_{26}$, 15) ═O, 16) $(C_2-C_6)$-alkynyl, 17) —$COR_{26}$, 18) —$S(O)_pR_{26}$, 19) —$SO_2NHR_{26}$, 20) —$COOR_{26}$, 21) —$NHC(CN)NHR_{26}$; and 22) cycloalkyl, which may be optionally substituted with one or more $R_{20}$'s;

(c) aryl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $(C_2-C_6)$-alkenyl, 16) —$CONR_{26}R_{26}$, 17) ═O, 18) $(C_2-C_6)$-alkynyl, 19) —$COR_{26}$, 20) —$S(O)_pR_{26}$, 21) —$SO_2NHR_{26}$, 22) —$COOR_{26}$, 23) —$NHC(CN)NHR_{26}$; and 24) cycloalkyl, which may be optionally substituted with one or more $R_{20}$'s;

(d) cycloalkyl, which may be optionally substituted with one or more substituents selected from the group consisting of: 1) halo, 2) $(C_1-C_6)$-alkyl, which may be optionally substituted with one or more $R_{20}$'s, 3)

—$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s;

(e) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s; or (f) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_{910}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, 23) —NHC(CN)$NHR_{26}$; and 24) cycloalkyl, which may be optionally substituted with one or more $R_{20}$'s;

or two $R_8$'s are taken together to form a 3- to 9-membered ring, which may optionally contain 1-4 heteroatoms selected from N, O, and S and be optionally substituted with one or more $R_{20}$'s;

$R_9$ and $R_{10}$ are independently: (a) hydrogen; (b) —[(C═O)$O_r$]$_s$aryl, wherein the aryl may be optionally substituted with one or more $R_{20}$'s; (c) —[(C═O)$O_r$]$_s$($C_2$-$C_8$)-alkenyl, wherein the alkenyl may be optionally substituted with one or more $R_{20}$'s; (d) —[(C═O)$O_r$]$_s$($C_1$-$C_8$)alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; j) —$SO_2NHR_{26}$; (k) —$COOR_{26}$; (l) —NHC(CN)$NHR_{26}$; or m) —[(C═O)$O_r$]$_s$cycloalkyl, wherein the cycloalkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (j) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) ═O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)$NHR_{26}$; (w) cycloalkyl, which may be optionally substituted with one or more $R_2$'s; (x) cycloalkylalkyl, which may be optionally substituted with one or more $R_2$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ═O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —NHC(CN)$NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$; and 23) cycloalkyl, which may be optionally substituted with one or more $R_{40}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24)

—NHC(CN)NHR$_{36}$; and 25) cycloalkyl, which may be optionally substituted with one or more R$_{40}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —$NHC(CN)NHR_{36}$; and 26) cycloalkyl, which may be optionally substituted with one or more $R_{40}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —$NHC(CN)NHR_{36}$; and 26) cycloalkyl, which may be optionally substituted with one or more $R_{40}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —$NHC(CN)NHR_{36}$; and 26) cycloalkyl, which may be optionally substituted with one or more $R_{40}$'s; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl, —$CONR_{46}R_{46}$, alkynyl, —$COR_{36}$, —$S(O)_pR_{36}$, —$SO_2NHR_{36}$, —$COOR_{36}$, —$C(CN)NHR_{36}$, or cycloalkyl, wherein the aryl, alkyl, alkenyl, cycloalkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —$NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In one embodiment, compounds of the present invention are provided wherein the compounds are compounds of formula Ia Ia

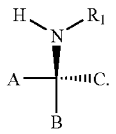

In another embodiment, compounds of the present invention are provided wherein:

A is heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, and 20) —$NHC(CN)NHR_6$;

B is:

(a) phenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, and 19) —$NHC(CN)NHR_6$; or (b) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, and 19) —$NHC(CN)NHR_6$;

C is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —$NHC(CN)NHR_6$;

(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl; or (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$ and 17) —$NHC(CN)NHR_6$;

$R_1$ is —$C(O)R_3$, —$C(O)NR_2R_3$, —$C(O)OR_4$, —$SO_2R_5$, —$CSNHR_7$, —$CR_8R_8R_8$, —$C(S)R_3$, or —$C(=NR_3)$Oalkyl;

$R_2$ is:

(a) H;

(b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) ($C_2$-$C_6$)-alkenyl, 15) ($C_2$-$C_6$)-alkynyl, 16) —$S(O)_pR_6$, 17) —$SO_2NHR_6$, 18) —$COOR_6$, and 19) —$NHC(CN)NHR_6$;

(c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15)-$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —$NHC(CN)NHR_6$; or (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CO(C_1$-$C_6)$-alkyl, 16) —COOH, 17) —$CO_2(C_1$-$C_6)$-alkyl, 18) —$CONR_6R_6$, 19) ($C_2$-$C_6$)-alkenyl, and 20) ($C_2$-$C_6$)-alkynyl;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$CONR_6R_6$, 13) ($C_2$-$C_6$)-alkenyl, 14) ($C_2$-$C_6$)-alkynyl, 15) —$COR_6$, 16) —$S(O)_pR_6$, 17) —$SO_2NHR_6$, 18) —$COOR_6$, and 19) —$NHC(CN)NHR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15)-$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —$NHC(CN)NHR_6$;

or $R_2$ and $R_3$ are taken together to form a 3- to 9-membered ring, which optionally may contain 1-4 heteroatoms selected from N, O, and S and be optionally substituted with one or more $R_{20}$'s;

$R_4$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —$NHC(CN)NHR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-

$C_6$)-alkynyl, 19) —$COR_6$, 20) —$S(O)_pR_6$, 21) —$SO_2NHR_6$, 22) —$COOR_6$, and 23) —NHC(CN)$NHR_6$;

(d) ($C_2$-$C_6$)-alkenyl; or (e) ($C_2$-$C_6$)-alkynyl;

$R_5$ is arylalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, 20) —$S(O)_pR_6$, 21) —$SO_2NHR_6$, 22) —$COOR_6$, and 23) —NHC(CN)$NHR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_7$ is aryl, which may be optionally substituted with one or more substituents selected from the group consisting of: 1) halo, 2) ($C_1$-$C_6$)-alkyl, which may be optionally substituted with one or more R20's, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_6$, 20) —$S(O)_pR_{26}$, 21) —$SO_2NHR_{26}$, 22) —$COOR_{26}$, and 23) —NHC(CN)$NHR_{26}$;

$R_8$ can independently be:

(a) H;

(b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) ($C_2$-$C_6$)-alkenyl, 13) aryl($C_2$-$C_6$)-alkynyl, 14) —$CONR_{26}R_{26}$, 15) ═O, 16) ($C_2$-$C_6$)-alkynyl, 17) —$COR_{26}$, 18) —$S(O)_pR_{26}$, 19) —$SO_2NHR_{26}$, 20) —$COOR_{26}$, and 21) —$NHC(CN)NHR_{26}$;

(c) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$;

(d) cycloalkyl, which may be optionally substituted with one or more substituents selected from the group consisting of: 1) halo, 2) ($C_1$-$C_6$)-alkyl, alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$;

(e) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$; or (f) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$;

or two $R_8$'s are taken together to form a 3- to 9-membered ring, which may optionally contain 1-4 heteroatoms selected from N, O, and S and be optionally substituted with one or more $R_{20}$'s;

$R_9$ and $R_{10}$ are independently: (a) hydrogen; (b) —$[(C{=}O)O_r]_s$aryl, wherein the aryl may be optionally substituted with one or more $R_{20}$'s; (c) —$[(C{=}O)O_r]_s$($C_2$-$C_8$)-alkenyl, wherein the alkenyl may be optionally substituted with one or more $R_{20}$'s; (d) —$[(C{=}O)O_r]_s$($C_1$-$C_8$)alkyl, wherein the alkyl may be optionally substituted with one or more $R_{20}$'s, (e) heterocyclyl optionally substituted with one or more $R_{20}$'s; (f) —$CONR_{26}R_{26}$; (g) -($C_2$-$C_6$)-alkynyl; (h) —$COR_{26}$; (i) —$S(O)_pR_{26}$; (j) —$SO_2NHR_{26}$; (k) —$COOR_{26}$; or (1) —$NHC(CN)NHR_{26}$;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) ═O; (q) -($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ═O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —$NHC(CN)NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) $SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) $SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —S(O)p$R_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl, —$CONR_{46}R_{46}$, alkynyl, —$COR_{36}$, —$S(O)_pR_{36}$, —$SO_2NHR_{36}$, —$COOR_{36}$, or —C(CN)$NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, ═O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In yet another embodiment, compounds of the present invention are provided wherein:

A is heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) =O, 17) —$S(O)_pR_6$, 18) —$SO_2NHR_6$, 19) —$COOR_6$, and 20) —NHC(CN)$NHR_6$;

B is:

(a) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, and 19) —NHC(CN)$NHR_6$; or (b) heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) —$S(O)_pR_6$, 17) —$SO_2NHR_6$, 18) —$COOR_6$, and 19) —NHC(CN)$NHR_6$;

C is:

(a) alkyl, which may be optionally substituted with one or more substituents selected from the group consisting of: 1) halo, 2) (Cl-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —NHC(CN)$NHR_6$;

(b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl; or (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) —$COR_6$, 13) —$CONR_6R_6$, 14) —$S(O)_pR_6$, 15) —$SO_2NHR_6$, 16) —$COOR_6$, and 17) —NHC(CN)$NHR_6$;

$R_1$ is —C(O)$R_3$, —C(O)$NR_2R_3$, —C(O)$OR_4$, —$SO_2R_5$, —$CSNHR_7$, —$CR_8R_8R_8$, —C(S)$R_3$, or —C(=$NR_3$)Oalkyl;

$R_2$ is:

(a) H;

(b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$COR_6$, 13) —$CONR_6R_6$, 14) ($C_2$-$C_6$)-alkenyl, 15) ($C_2$-$C_6$)-alkynyl, 16) —$S(O)_pR_6$, 17) —$SO_2NHR_6$, 18) —$COOR_6$, and 19) —NHC(CN)$NHR_6$;

(c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_{9R10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —NHC(CN)$NHR_6$; or (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —$CO_2$($C_1$-$C_6$)-alkyl, 18) —$CONR_6R_6$, 19) ($C_2$-$C_6$)-alkenyl, and 20) ($C_2$-$C_6$)-alkynyl;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo $(C_1-C_6)$alkyl, 12) —$CONR_6R_6$, 13) $(C_2-C_6)$-alkenyl, 14) $(C_2-C_6)$-alkynyl, 15) —$COR_6$, 16) —$S(O)_pR_6$, 17) —$SO_2NHR_6$, 18) —$COOR_6$, and 19) —NHC(CN)$NHR_6$;

(b) aryl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) ═O, 18) $(C_2-C_6)$-alkynyl, 19) —$COR_6$, 20) —$S(O)_pR_6$, 21) —$SO_2NHR_6$, 22) —$COOR_6$, and 23) —NHC(CN)$NHR_6$;

(c) cycloalkyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) ═O, 18) $(C_2-C_6)$-alkynyl, 19) —$COR_6$, 20) —$S(O)_pR_6$, 21) —$SO_2NHR_6$, 22) —$COOR_6$, and 23) —NHC(CN)$NHR_6$;

(d) heteroaryl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) ═O, 18) $(C_2-C_6)$-alkynyl, 19) —$COR_6$, 20) —$S(O)_pR_6$, 21) —$SO_2NHR_6$, 22) —$COOR_6$, and 23) —NHC(CN)$NHR_6$;

(e) heterocyclyl, other than heteroaryl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo $(C_1-C_6)$alkyl, 15) —$CONR_6R_6$, 16) $(C_2-C_6)$-alkenyl, 17) ═O, 18) $(C_2-C_6)$-alkynyl, 19) —$COR_6$, 20) —$S(O)_pR_6$, 21) —$SO_2NHR_6$, 22) —$COOR_6$, and 23) —NHC(CN)$NHR_6$; or (f) alkenyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) $(C_2-C_6)$-alkynyl, 18) —$COR_6$, 19) —$S(O)_pR_6$, 20) —$SO_2NHR_6$, 21) —$COOR_6$, and 22) —NHC(CN)$NHR_6$;

or $R_2$ and $R_3$ are taken together to form a 3- to 9-membered ring, which optionally may contain 1-4 heteroatoms selected from N, O, and S and be optionally substituted with one or more $R_{20}$'s;

$R_4$ is:

(a) alkyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) ═O, 18) $(C_2-C_6)$-alkynyl, 19) —$COR_6$, 20) —$S(O)_pR_6$, 21) —$SO_2NHR_6$, 22) —$COOR_6$, and 23) —NHC(CN)$NHR_6$;

(b) aryl, which may be optionally substituted with one or more substituents selected from the group consisting of: 1) halo, 2) (cl-$C_6$)-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$CONR_6R_6$, 16) $(C_2-C_6)$-alkenyl, 17) ═O, 18) $(C_2-C_6)$-alkynyl, 19) —$COR_6$, 20) —$S(O)_pR_6$, 21) —$SO_2NHR_6$, 22) —$COOR_6$, and 23) —NHC(CN)$NHR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —NHC(CN)$NHR_6$;

(d) ($C_2$-$C_6$)-alkenyl; or (e) ($C_2$-$C_6$)-alkynyl;

$R_5$ is arylalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, 20) —$S(O)_pR_6$, 21) —$SO_2NHR_6$, 22) —$COOR_6$, and 23) —NHC(CN)$NHR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_{1-C6}$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) -$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_7$ is aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17)═O, 18) ($C_2$-$C_6$)-alkynyl, 19) —$COR_6$, 20) —$S(O)_pR_{26}$, 21) —$SO_2NHR_{26}$, 22) —$COOR_{26}$, and 23) —$NHC(CN)NHR_{26}$;

$R_8$ can independently be:

(a) H;

(b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) ($C_2$-$C_6$)-alkenyl, 13) aryl($C_2$-$C_6$)-alkynyl, 14) —$CONR_{26}R_{26}$, 15) ═O, 16) ($C_2$-$C_6$)-alkynyl, 17) —$COR_{26}$, 18) —$S(O)_pR_{26}$, 19) —$SO_2NHR_{26}$, 20) —$COOR_{26}$, and 21) —$NHC(CN)NHR_{26}$;

(c) aryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$;

(d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$;

(e) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) —$SO_2NHR_{26}$, 22) —$COOR_{26}$, and 23) —$NHC(CN)NHR_{26}$; or (f) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, 20) —$S(O)_pR_{26}$, 21) -$SO_2NHR_{26}$, 22) —$COOR_{26}$, and 23) —$NHC(CN)NHR_{26}$;

or two $R_8$'s are taken together to form a 3- to 9-membered ring, which may optionally contain 1-4 heteroatoms selected from N, O, and S and be optionally substituted with one or more $R_{20}$'s;

$R_9$ and $R_{10}$ are independently: (a) hydrogen; (b) —$[(C{=}O)O_r]_s$aryl, wherein the aryl may be optionally substituted with one or more $R_{20}$'s; (c) —$[(C{=}O)O_r]_s$($C_2$-$C_8$)-alkenyl, wherein the alkenyl may be optionally substituted with one or more $R_{20}$'s; (d) —$[(C{=}O)O_r]_s$($C_1$-$C_8$)alkyl, wherein the alkyl may be optionally substituted with one or more $R_{20}$'s; (e) heterocyclyl optionally substituted with one or more $R_{20}$'s; (f) —$CONR_{26}R_{26}$; (g) -($C_2$-$C_6$)-alkynyl; (h) —$COR_{26}$; (i) —$S(O)_pR_{26}$; i) —$SO_2NHR_{26}$; (k) —$COOR_{26}$; or (l) —$NHC(CN)NHR_{26}$;

or $R_9$ and $R_{10}$ are taken together with the nitrogen to which both are attached to form a 3- to 8-membered ring, which may optionally contain 1-4 heteroatoms selected from N, O, and S and may be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl, (p) ═O; (q) -($C_2$-$C_6$)-alkynyl; (r) —$COR_{26}$; (s) —$S(O)_pR_{26}$; (t) —$SO_2NHR_{26}$; (u) —$COOR_{26}$; (v) —$NHC(CN)NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; 0) heteroaryl; (k) heteroarylalkyl; (l) heterocyclyl;

(m) heterocyclylalkyl; (n) halo($C_1$-$C_6$)alkyl; (o) —$CONR_{26}R_{26}$; (p) ($C_2$-$C_6$)-alkenyl; (q) ═O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) -NHC(CN)$NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more R40's;

$R_{29}$ and $R_{30}$ are independently hydrogen, —[(C═O)$O_r$]$_s$aryl, —[(C═O)$O_r$]$_s$alkenyl, —[(C═O)$O_r$]$_s$alkyl, heterocyclyl, —$CONR_{46}R_{46}$, alkynyl, —$COR_{36}$, —$S(O)_pR_{36}$, —$SO_2NHR_{36}$, —$COOR_{36}$, or —C(CN)$NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, ═O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

In still yet another embodiment, compounds of the present invention are provided wherein:

A is a nitrogen or oxygen containing heteroaryl, which is substituted with one or more substituents selected from the group consisting of: 1) halo, 2) ($C_1$-$C_6$)-alkyl, which may be optionally substituted with one or more $R_{20}$'s, 3) -$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O;

B is:

(a) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl; or (b) a nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) halo, 2) —$OR_6$, 3) —$NR_9R_{10}$, 4) aryl, which may be optionally substituted with one or more $R_{20}$'s, 5) heteroaryl, which may be optionally substituted with one or more $R_{20}$'s, 6) heterocyclyl, which may be optionally substituted with one or more $R_{20}$'s, 7) —$CONR_6R_6$, and 8) —$COOR_6$;

$R_1$ is —$C(O)R_3$, —$C(O)NR_2R_3$, —$C(O)OR_4$, or —$CH_2R_8$;

$R_2$ is:

(a) H;

(b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) -$COR_6$, 13) —$CONR_6R_6$, 14) ($C_2$-$C_6$)-alkenyl, 15) ($C_2$-$C_6$)-alkynyl, and 16) —$COOR_6$;

(c) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, and 19) —$COOR_6$; or (d) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —$CO_2$($C_1$-$C_6$)-alkyl, 18) —$CONR_6R_6$, 19) ($C_2$-$C_6$)-alkenyl, and 20) ($C_2$-$C_6$)-alkynyl;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15)

—$CONR_6R_6$, 16) ($C_2$-$C_6$)-alkenyl, 17) ═O, 18) ($C_2$-$C_6$)-alkynyl, 19) —$COR_6$, and 20) —$COOR_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

(e) heterocyclyl, other than heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, and 19) —$COOR_6$;

or $R_2$ and $R_3$ are taken together to form a 3- to 9-membered ring, which optionally may contain 1-4 heteroatoms selected from N, O, and S and may be optionally substituted with one or more $R_{20}$'s;

$R_4$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$; or (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) —COOH, 17) —$CONR_{36}R_{36}$, 18)

=O, 19) $(C_2\text{-}C_6)$-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) $(C_1\text{-}C_6)$-alkyl, which may be optionally substituted with one or more $R_{20}$'s, 4) —$OR_{36}$, 5) $(C_1\text{-}C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo$(C_1\text{-}C_6)$alkyl, 16) $(C_2\text{-}C_6)$-alkenyl, 17) —COOH, 18) —$CONR_{36}R_{36}$, 19) =O, 20) $(C_2\text{-}C_6)$-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) $(C_1\text{-}C_6)$-alkyl, which may be optionally substituted with one or more $R_{20}$'s, 4) —$OR_{36}$, 5) $(C_1\text{-}C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo$(C_1\text{-}C_6)$alkyl, 16) $(C_2\text{-}C_6)$-alkenyl, 17) —COOH, 18) —$CONR_{36}R_{36}$, 19) =O, 20) $(C_2\text{-}C_6)$-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) $(C_1\text{-}C_6)$-alkyl, which may be optionally substituted with one or more $R_{20}$'s, 4) —$OR_{36}$, 5) $(C_1\text{-}C_6)$-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo$(C_1\text{-}C_6)$alkyl, 16) $(C_2\text{-}C_6)$-alkenyl, 17) —COOH, 18) —$CONR_{36}R_{36}$, 19) =O, 20) $(C_2\text{-}C_6)$-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_8$ can independently be:

(a) alkyl, which may be optionally substituted with one or more substituents selected from the group consisting of: 1) halo, 2) $(C_1\text{-}C_6)$-alkyl, which may be optionally substituted with one or more $R_{20}$'s, 3) —$OR_{26}$, 4) $(C_1\text{-}C_6)$-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo$(C_1\text{-}C_6)$alkyl, 12) $(C_2\text{-}C_6)$-alkenyl, 13) aryl$(C_2\text{-}C_6)$-alkynyl, 14) —$CONR_{26}R_{26}$, 15) =O, 16) $(C_2\text{-}C_6)$-alkynyl, 17) —$COR_{26}$, and 18) —$COOR_{26}$;

(b) aryl, which may be optionally substituted with one or more substituents selected from the group consisting of: 1) halo, 2) $(C_1\text{-}C_6)$-alkyl, which may be optionally substituted with one or more $R_{20}$'s, 3) —$OR_{26}$, 4) $(C_1\text{-}C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1\text{-}C_6)$alkyl, 15) $(C_2\text{-}C_6)$-alkenyl, 16) —$CONR_{26}R_{26}$, 17) =O, 18) $(C_2\text{-}C_6)$-alkynyl, 19) —$COR_{26}$, and 20) —$COOR_{26}$;

(c) cycloalkyl, which may be optionally substituted with one or more substituents selected from the group consisting of: 1) halo, 2) $(C_1\text{-}C_6)$-alkyl, which may be optionally substituted with one or more $R_{20}$'s, 3) —$OR_{26}$, 4) $(C_1\text{-}C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1\text{-}C_6)$alkyl, 15) $(C_2\text{-}C_6)$-alkenyl, 16) —$CONR_{26}R_{26}$, 17) =O, 18) $(C_2\text{-}C_6)$-alkynyl, 19) —$COR_{26}$, and 20) —$COOR_{26}$;

(d) heteroaryl, which may be optionally substituted with one or more substituents selected from the group consisting of: 1) halo, 2) $(C_1\text{-}C_6)$-alkyl, which may be optionally substituted with one or more $R_{20}$'s, 3) —$OR_{26}$, 4) $(C_1\text{-}C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1\text{-}C_6)$alkyl, 15) $(C_2\text{-}C_6)$-alkenyl, 16) —$CONR_{26}R_{26}$, 17) =O, 18) $(C_2\text{-}C_6)$-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) $(C_1\text{-}C_6)$-alkyl, which may be optionally substituted with one or more $R_{20}$'s, 3) —$OR_{26}$, 4) $(C_1\text{-}C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

or two $R_8$'s are taken together to form a 3- to 9-membered ring, which may optionally contain 1-4 heteroatoms selected from N, O, and S and may be optionally substituted with one or more $R_{20}$'s;

$R_9$ and $R_{10}$ are independently: (a) hydrogen; (b) —[(C=O)$O_r$]$_s$aryl, wherein the aryl may be optionally substituted with one or more $R_{20}$'s; (c) —[(C=O)$O_r$]$_s$($C_1$-$C_8$)alkyl, wherein the alkyl may be optionally substituted with one or more $R_{20}$'s; or (d) heterocyclyl optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (1) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) $OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) -$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_4$o's, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —S(O)p$R_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-

$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C═O)$O_r$]$_s$aryl, —[(C═O)$O_r$]$_s$alkyl, or heterocyclyl, wherein the aryl, alkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, ═O, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl, heteroaryl or heterocyclyl, other than heteroaryl;

r is 0 to 3;

s is 0 to 2; and p is 1 or 2.

In one embodiment, compounds of the present invention are provided wherein:

A is a 5- to 10-membered nitrogen or oxygen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9$ $R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) ═O;

B is:

(a) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl; or (b) a 6- to 10-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) halo, 2) —$OR_6$, 3) —$NR_9R_{10}$, 4) aryl, which may be optionally substituted with one or more $R_{20}$'s, 5) a nitrogen containing heteroaryl, which may be optionally substituted with one or more $R_{20}$'s, 6) —$CONR_6R_6$, and 7) —$COOR_6$;

$R_1$ is —$C(O)R_3$, —$C(O)NR_2R_3$, or —$CH_2R_8$;

$R_2$ is:

(a) H;

(b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$COR_6$, 13) —$CONR_6R_6$, 14) ($C_2$-$C_6$)-alkenyl, 15) ($C_2$-$C_6$)-alkynyl, and 16) —$COOR_6$; or (c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —CO($C_1$-$C_6$)-alkyl, 16) —COOH, 17) —$CO_2$($C_1$-$C_6$)-alkyl, 18) —$CONR_6R_6$, 19) ($C_2$-$C_6$)-alkenyl, and 20) ($C_2$-$C_6$)-alkynyl;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or (f) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, and 19) —$COOR_6$;

or $R_2$ and $R_3$ are taken together to form a 3- to 9-membered ring, which optionally may contain 1-4 heteroatoms selected from N, O, and S and may be optionally substituted with one or more $R_{20}$'s;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4)

—$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_8$ can independently be:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) aryl($C_2$-$C_6$)-alkynyl, 14) —$CONR_{26}R_{26}$, 15) ═O, 16) ($C_2$-$C_6$)-alkynyl, 17) —$COR_{26}$ and 18) —$COOR_{26}$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, and 20) —$COOR_{26}$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, and 20) —$COOR_{26}$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, and 20) —$COOR_{26}$;

or two $R_8$'s are taken together to form a 3- to 9-membered ring, which may optionally contain 1-4 heteroatoms selected from N, O, and S and may be optionally substituted with one or more $R_{20}$'s;

$R_9$ and $R_{10}$ are independently: (a) hydrogen; (b) —$[(C{=}O)O_r]_s$aryl, wherein the aryl may be optionally substituted with one or more $R_{20}$'s; or (c) —$[(C{=}O)O_r]_s$($C_1$-$C_8$)alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; 0) heteroaryl, which may be optionally substituted with one or more $R_{21}$'s; (k) heteroarylalkyl, which may be optionally substituted with one or more $R_{21}$'s; (1) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) -($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN) $NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) $OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN) $NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23—$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O) $O_r$]$_s$aryl, or —[(C=O)$O_r$]$_s$alkyl, wherein the aryl or alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl or heteroaryl;

r is 0 to 2;

s is0to 1;and p is 1 or 2.

In another embodiment, compounds of the present invention are provided wherein:

A is a 6-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) -$NRR_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) ═O;

B is:

(a) phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl; or (b) a 6-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) halo, 2) phenyl, which may be optionally substituted with one or more $R_{20}$'s, or 3) a 5- or 6-membered nitrogen containing heteroaryl, which may be optionally substituted with one or more $R_{20}$'s;

$R_1$ is —C(O)$R_3$, —C(O)$NR_2R_3$, or —$CH_2R_8$;

$R_2$ is:

(a) H; or (b) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$COR_6$, 13) —$CONR_6R_6$, 14) ($C_2$-$C_6$)-alkenyl, 15) ($C_2$-$C_6$)-alkynyl, and 16) —$COOR_6$;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) -—$R_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$; or (e) heterocyclyl, other than heteroaryl, which may be optionally substituted with one or more substituents selected from the group consisting of: 1) halo, 2) ($C_1$-

$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

$R_8$ can independently be:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) ($C_2$-$C_6$)-alkenyl, 13) aryl($C_2$-$C_6$)-alkynyl, 14) —$CONR_{26}R_{26}$, 15) =O, 16) ($C_2$-$C_6$)-alkynyl, 17) —$COR_{26}$, and 18) —$COOR_{26}$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

(c) cycloalkyl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo $(C_1-C_6)$alkyl, 15) $(C_2-C_6)$-alkenyl, 16) —$CONR_{26}R_{26}$, 17) =O, 18) $(C_2-C_6)$-alkynyl, 19) —$COR_{26}$, and 20) —$COOR_{26}$;

(d) heteroaryl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo $(C_1-C_6)$alkyl, 15) $(C_2-C_6)$-alkenyl, 16) —$CONR_{26}R_{26}$, 17) =O, 18) $(C_2-C_6)$-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) $(C_1-C_6)$-alkyl, which may be optionally substituted with one or more $R_{20}$'s, 3) —$OR_{26,\ 4}$) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $(C_2-C_6)$-alkenyl, 16) —$CONR_{26}R_{26}$, 17) =O, 18) $(C_2-C_6)$-alkynyl, 19) —$COR_{26}$, and 20) —$COOR_{26}$;

or two $R_8$'s are taken together to form a 3- to 9-membered ring, which may optionally contain 1-4 heteroatoms selected from N, O, and S and may be optionally substituted with one or more $R_{20}$'s;

$R_9$ and $R_{10}$ are independently: (a) hydrogen; or (b) —$[(C{=}O)O_r]_s(C_1-C_8)$alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) $(C_1-C_6)$-alkyl, which may be optionally substituted with one or more $R_{21}$'s; (c) —$OR_{26}$; (d) $(C_1-C_6)$-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo$(C_1-C_6)$alkyl; (o) $(C_2-C_6)$-alkenyl; (p) -$(C_2-C_6)$-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) $(C_1-C_6)$-alkyl; (c) —$OR_{26}$; (d) $(C_1-C_6)$-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo$(C_1-C_6)$alkyl; (o) —$CONR_{26}R_{26}$; (p) $(C_2-C_6)$-alkenyl; (q) $(C_2-C_6)$-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) $(C_1-C_6)$-alkyl, which may be optionally substituted with one or more $R_{40}$'s, 4) —$OR_{36}$, 5) $(C_1-C_6)$-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo$(C_1-C_6)$alkyl, 13) $(C_2-C_6)$-alkenyl, 14) -COOH, 15) —$CONR_{36}R_{36}$, 16) =O, 17) $(C_2-C_6)$-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) $(C_1-C_6)$-alkyl, which may be optionally substituted with one or more $R_{40}$'s, 4) —$OR_{36}$, 5) $(C_1-C_6)$-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo $(C_1-C_6)$alkyl, 16) —COOH, 17) —$CONR_{36}R_{36}$, 18) =O, 19) $(C_2-C_6)$-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) $(C_1-C_6)$-alkyl, which may be optionally substituted with one or more $R_{40}$'s, 4) —$OR_{36}$, 5) $(C_1-C_6)$-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo $(C_1-C_6)$alkyl, 16) $(C_2-C_6)$-alkenyl, 17) —COOH, 18) —$CONR_{36}R_{36}$, 19) =O, 20) $(C_2-C_6)$-alkynyl, 21)

—$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$; or (f) hydrogen;

$R_{29}$ and $R_{30}$ are independently hydrogen or —$[(C{=}O)O_r]_s$ alkyl, wherein the alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl or heteroaryl;

r is 0 to 2;

s is 0 to 1; and p is 1 or 2.

In yet another embodiment, compounds of the present invention are provided wherein:

A is pyridyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O;

B is phenyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is alkyl, which may be optionally substituted with one or more substituents selected from the group consisting of: 1) phenyl, which may be optionally substituted with one or more $R_{20}$'s, or 2) a 5- or 6-membered nitrogen containing heteroaryl, which may be optionally substituted with one or more $R_{20}$'s;

$R_1$ is —$C(O)R_3$, —$C(O)NHR_3$, or —$CH_2R_8$;

$R_3$ is:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$, 13) ($C_2$-$C_6$)-alkenyl, 14) ($C_2$-$C_6$)-alkynyl, 15) —$COR_6$, and 16) —$COOR_6$;

(b) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(c) cycloalkyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(d) heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or (e) heterocyclyl, other than heteroaryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

$R_8$ can independently be:

(a) alkyl, which may be optionally substituted with one or more substituents selected from the group consisting of: 1) halo, 2) ($C_1$-$C_6$)-alkyl, which may be optionally substituted with one or more $R_{20}$'s, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo $(C_1-C_6)$alkyl, 12) $(C_2-C_6)$-alkenyl, 13) aryl$(C_2-C_6)$-alkynyl, 14) —$CONR_{26}R_{26}$, 15) =O, 16) $(C_2-C_6)$-alkynyl, 17) —$COR_{26}$, and 18) —$COOR_{26}$;

(b) aryl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $(C_2-C_6)$-alkenyl, 16) —$CONR_{26}R_{26}$, 17) =O, 18) $(C_2-C_6)$-alkynyl, 19) —$COR_{26}$, and 20) —$COOR_{26}$;

(c) cycloalkyl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo $(C_1-C_6)$alkyl, 15) $(C_2-C_6)$-alkenyl, 16) —$CONR_{26}R_{26}$, 17) =O, 18) $(C_2-C_6)$-alkynyl, 19) —$COR_{26}$, and 20) —$COOR_{26}$;

(d) heteroaryl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo $(C_1-C_6)$alkyl, 15) $(C_2-C_6)$-alkenyl, 16) —$CONR_{26}R_{26}$, 17) =O, 18) $(C_2-C_6)$-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) $(C_1-C_6)$-alkyl, which may be optionally substituted with one or more $R_{20}$'s, 3) —$OR_{26}$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) $(C_2-C_6)$-alkenyl, 16) —$CONR_{26}R_{26}$, 17) =O, 18) $(C_2-C_6)$-alkynyl, 19) —$COR_{26}$, and 20) —$COOR_{26}$;

$R_9$ and $R_{10}$ are independently: (a) hydrogen; or (b) —$[(C{=}O)O_r]_s(C_1-C_8)$alkyl, wherein the alkyl may be optionally substituted with one or more $R_{20}$'s;

$R_{20}$ is: (a) halo; (b) $(C_1-C_6)$-alkyl, which may be optionally substituted with one or more $R_{21}$'s; (c) —$OR_{26}$; (d) $(C_1-C_6)$-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo$(C_1-C_6)$alkyl; (o) $(C_2-C_6)$-alkenyl; (p) -$(C_2-C_6)$-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) $(C_1-C_6)$-alkyl; (c) —$OR_{26}$; (d) $(C_1-C_6)$-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo$(C_1-C_6)$alkyl; (o) —$CONR_{26}R_{26}$; (p) $(C_2-C_6)$-alkenyl; (q) $(C_2-C_6)$-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) $(C_1-C_6)$-alkyl, which may be optionally substituted with one or more $R_{40}$'s, 4) —$OR_{36}$, 5) $(C_1-C_6)$-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo$(C_1-C_6)$alkyl, 13) $(C_2-C_6)$-alkenyl, 14) —COOH, 15) —$CONR_{36}R_{36}$, 16)=O, 17) $(C_2-C_6)$ -alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) $(C_1-C_6)$-alkyl, which may be optionally substituted with one or more $R_{40}$'s, 4) —$OR_{36}$, 5) $(C_1-C_6)$-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo $(C_1-C_6)$alkyl, 16) —COOH, 17) —$CONR_{36}R_{36}$, 18) =O, 19) $(C_2-C_6)$-alkynyl, 20) —$COR_{36}$, 21) —$S(O)_pR_{36}$, 22) —$SO_2NHR_{36}$, 23) —$COOR_{36}$, and 24)—NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_4$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$; or (f) hydrogen;

$R_{29}$ and $R_{30}$ are independently hydrogen or —$[(C{=}O)O_r]_s$alkyl, wherein the alkyl may be optionally substituted with one or more $R_{40}$'s;

$R_{36}$, at each occurrence, is independently alkyl, aryl, heteroaryl or heterocyclyl, other than heteroaryl, wherein the alkyl, aryl, heteroaryl or heterocyclyl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2;

s is 0 to 1; and p is 1 or 2.

In still yet another embodiment, compounds of the present invention are provided wherein:

A is pyridyl, which is substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O;

B is phenyl, which is substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, and 14) halo($C_1$-$C_6$)alkyl;

C is methylphenyl, which may be optionally substituted with one or more $R_{20}$'s;

$R_1$ is —$C(O)R_3$, —$C(O)NHR_3$, or —$CH_2R_8$;

$R_3$ is:

(a) alkyl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) —$CONR_6R_6$) ($C_2$-$C_6$)-alkenyl, 14) ($C_2$-$C_6$)-alkynyl, 15) —$COR_6$, and 16) —$COOR_6$;

(b) aryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

(c) cycloalkyl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'S, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

(d) heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$; or (e) heterocyclyl, other than heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NRR_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$SO_2NHR_{36}$, 20) —$COOR_{36}$, and 21) —NHC(CN)$NHR_{36}$;

(b) aryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$SO_2NHR_{36}$, 22) —$COOR_{36}$, and 23) —NHC(CN)$NHR_{36}$;

(c) heteroaryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo ($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$SO_2NHR_{36}$, 23) —$COOR_{36}$, and 24) —NHC(CN)$NHR_{36}$; or (d) hydrogen;

$R_8$ can independently be:

(a) alkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo ($C_1$-$C_6$)alkyl, 12) ($C_2$-$C_6$)-alkenyl, 13) aryl($C_2$-$C_6$)-alkynyl, 14) —$CONR_{26}R_{26}$, 15) ═O, 16) ($C_2$-$C_6$)-alkynyl, 17) —$COR_{26}$, and 18) —$COOR_{26}$;

(b) aryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, and 20) —$COOR_{26}$;

(c) cycloalkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) ═O, 18) ($C_2$-$C_6$)-alkynyl, 19) —$COR_{26}$, and 20) —$COOR_{26}$;

(d) heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$; or (e) heterocyclyl, other than heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) ($C_2$-$C_6$)-alkenyl, 16) —$CONR_{26}R_{26}$, 17) =O, 18) ($C_2$-$C_6$)-alkynyl, 19) —$COR_{26}$, and 20) —$COOR_{26}$;

$R_9$ and $R_{10}$ are independently: (a) hydrogen; or (b) —$[(C{=}O)O_r]_s(C_1$-$C_8)$alkyl, wherein the alkyl may be optionally substituted with one or more $R_{20}$'s;

$R_{20}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$, s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$, or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$SO_2NHR_{36}$, 20) —$COOR_{36}$, and 2 1) —$NHC(CN)NHR_{36}$;

(b) aryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$SO_2NHR_{36}$, 22) —$COOR_{36}$, and 23) —$NHC(CN)NHR_{36}$;

(c) heteroaryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo ($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$SO_2NHR_{36}$, 23) —$COOR_{36}$, and 24) —$NHC(CN)NHR_{36}$; or (d) hydrogen;

$R_{29}$ and $R_{30}$ are independently hydrogen or —$[(C{=}O)O_r]_s$ alkyl, wherein the alkyl may be optionally substituted with one or more $R_{40}$'s;

$R_{36}$, at each occurrence, is independently alkyl, aryl or heteroaryl, wherein the alkyl, aryl or heteroaryl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2; and s is 0 to 1.

In one embodiment, compounds of the present invention are provided wherein:

A is pyridyl, which is substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, and 14) —$COR_6$;

B is phenyl, which is substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, and 13) halo ($C_1$-$C_6$)alkyl;

C is methylphenyl, which may be optionally substituted with one or more $R_{20}$'s;

$R_1$ is —C(O)$R_3$, —C(O)NH$R_3$, or —$CH_2R_8$;

$R_3$ is:

(a) alkyl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) heteroaryl, which may be optionally substituted with one or more $R_{20}$'s, 9) heterocyclyl, which may be optionally substituted with one or more $R_{20}$'s, 10) halo($C_1$-$C_6$)alkyl, 11) ($C_2$-$C_6$)-alkenyl, 12) ($C_2$-$C_6$)-alkynyl, 13) —$COR_6$, and 14) —$COOR_6$;

(b) aryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'S, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo ($C_1$-$C_6$)alkyl, 14) ($C_2$-$C_6$)-alkenyl, 15) ($C_2$-$C_6$)-alkynyl, 16) —$COR_6$, and 17) —$COOR_6$;

(c) cycloalkyl, which may be optionally substituted with one or more substituents selected from the group consisting of: 1) halo, 2) ($C_1$-$C_6$)-alkyl, 3) alkyl, —$OR_{6, 4)}$ ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_6$, and 17) —$COOR_6$;

(d) heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_6$, and 17) —$COOR_6$; or (e) heterocyclyl, other than heteroaryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$', 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_6$, and 17) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$) alkyl, 12) ($C_2$-$C_6$)-alkenyl, 13) —COOH, 14) ($C_2$-$C_6$)-alkynyl, 15) —$COR_{36}$ and 16) —$COOR_{36}$; or (b) hydrogen;

$R_8$ can independently be:

(a) alkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) heteroaryl, which may be optionally substituted with one or more $R_{20}$'s, 9) heterocyclyl, which may be optionally substituted with one or more $R_{20}$'s, 10) halo($C_1$-$C_6$)alkyl, 11) ($C_2$-$C_6$)-alkenyl, 12) ($C_2$-$C_6$)-alkynyl, 13) —$COR_{26}$, and 14) —$COOR_{26}$;

(b) aryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo ($C_1$-$C_6$)alkyl, 14) ($C_2$-$C_6$)-alkenyl, 15) ($C_2$-$C_6$)-alkynyl, 16) —$COR_{26}$, and 17) —$COOR_{26}$;

(c) cycloalkyl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_{26}$, and 17) —$COOR_{26}$;

(d) heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo(CI-$C_6$)alkyl, 14) ($C_2$-$C_6$)-alkenyl, 15) ($C_2$-$C_6$)-alkynyl, 16) —$COR_{26}$, and 17) —$COOR_{26}$; or (e) heterocyclyl, other than heteroaryl, which may be optionally substituted with one or more substituents selected from the group consisting of: 1) halo, 2) ($C_1$-$C_6$)-alkyl, 3) —$OR_{26}$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_2$o's, 13) halo($C_1$-C6)alkyl, 14) ($C_2$-$C_6$)-alkenyl, 15) ($C_2$-$C_6$)-alkynyl, 16) —$COR_{26}$, and 17) —$COOR_{26}$;

$R_{20}$ is: (a) halo; (b) ($C_1$-$C_6$)-alkyl; (c) —$OR_{26}$; (d) ($C_1$-$C_6$)-alkylthio; (e) cyano; (f) nitro; (g) aryl, which may be optionally substituted with one or more $R_{21}$'s; (h) arylalkyl, which may be optionally substituted with one or more $R_{21}$'s; (i) heteroaryl, which may be optionally substituted with one or more $R_{21}$'s; (j) heteroarylalkyl, which may be optionally substituted with one or more $R_{21}$'s; (k) heterocyclyl, which may be optionally substituted with one or more $R_{21}$'s; (l) heterocyclylalkyl, which may be optionally substituted with one or more $R_{21}$'s; (m) halo($C_1$-$C_6$)alkyl; (n) ($C_2$-$C_6$)-alkenyl; (o) —($C_2$-$C_6$)-alkynyl; (p) —$COR_{26}$; (q) —$COOR_{26}$; (r) cycloalkyl, which may be optionally substituted with one or more $R_{21}$'s; or (s) cycloalkylalkyl, which may be optionally substituted with one or more $R_{21}$'s;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) aryl; (h) arylalkyl; (i) heteroaryl; (j) heteroarylalkyl; (k) heterocyclyl; (l) heterocyclylalkyl; (m) halo($C_1$-$C_6$)alkyl; (n) ($C_2$-$C_6$)-alkenyl; (o) ($C_2$-$C_6$)-alkynyl; (p) cycloalkyl; (q) cycloalkylalkyl; (r) —$COR_{26}$; or (s) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$) alkyl, 12) ($C_2$-$C_6$)-alkenyl, 13) —COOH, 14) ($C_2$-$C_6$)-alkynyl, 15) —$COR_{36}$, or 16) —$COOR_{36}$; or (b) hydrogen;

$R_{36}$, at each occurrence, is independently alkyl, aryl or heteroaryl, wherein the alkyl, aryl or heteroaryl may be optionally substituted with one or more $R_{40}$'s; and $R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl or cycloalkylalkyl.

Also in accordance with the present invention, compounds of the present invention are those wherein:

A is:

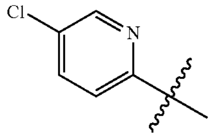
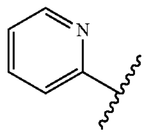
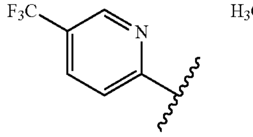
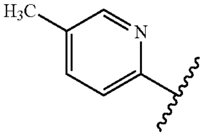
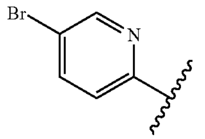
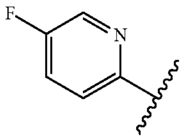
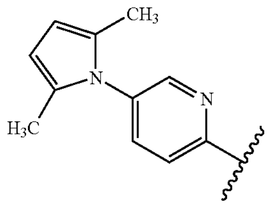
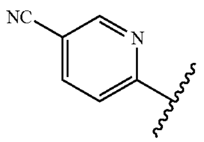
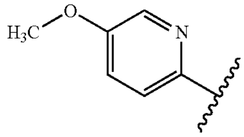
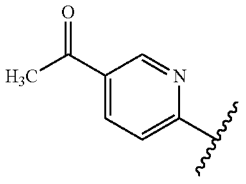
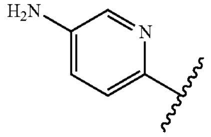
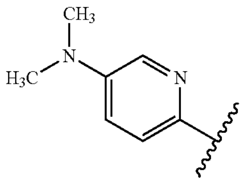
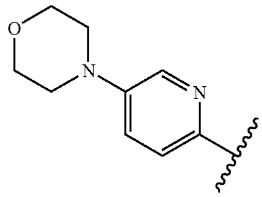
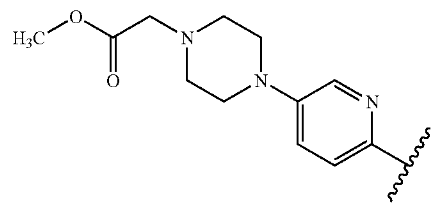
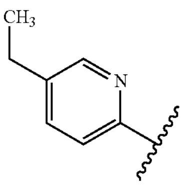
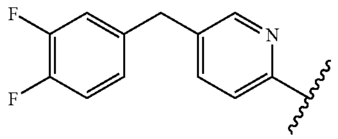

-continued
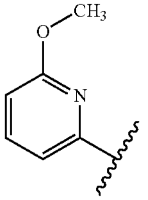
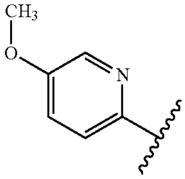
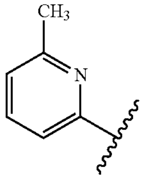
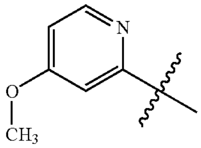
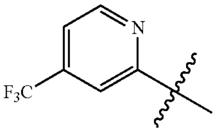
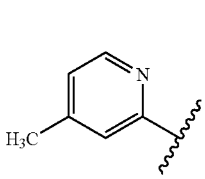
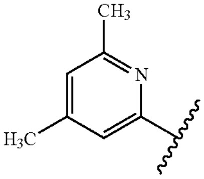
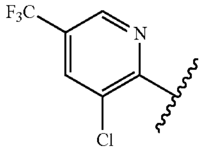
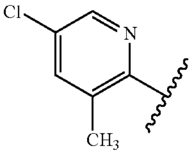
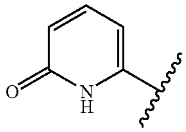
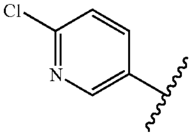
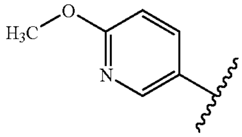
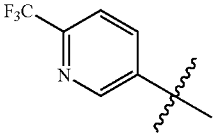
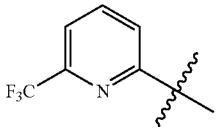
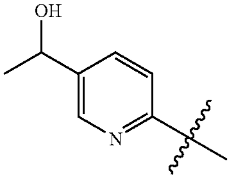
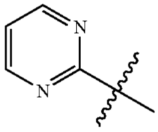
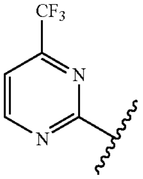
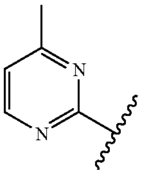
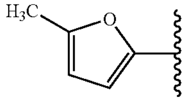
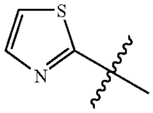
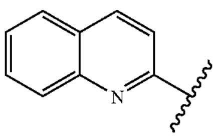 or
-continued
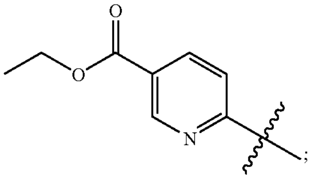;
B is:
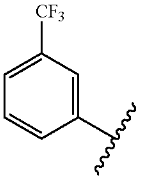
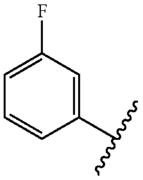
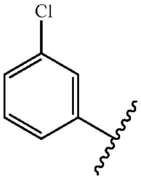
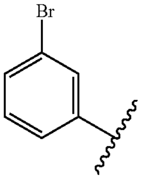
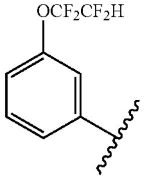
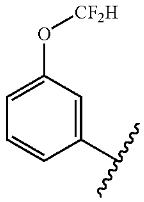
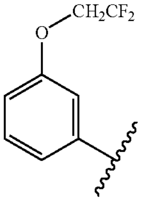
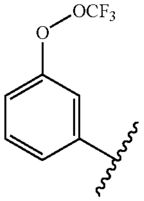
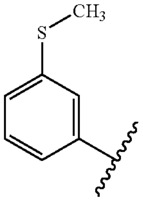
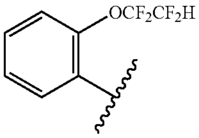
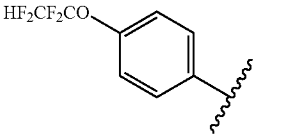
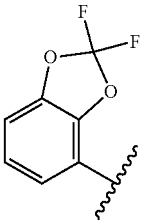
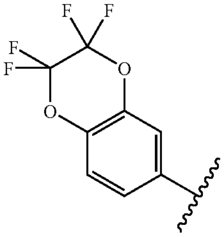
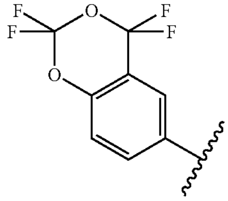
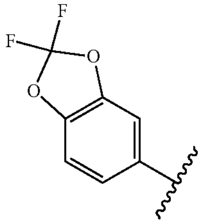
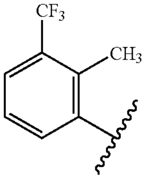
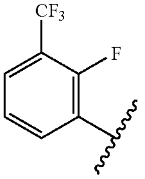
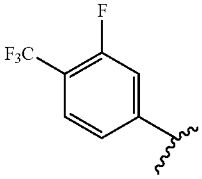

-continued
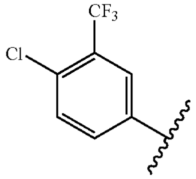
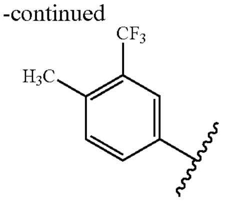
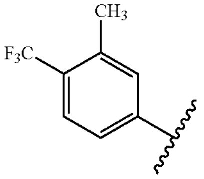
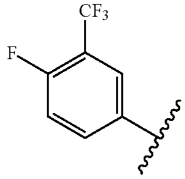
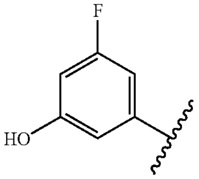
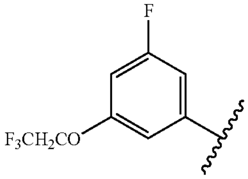
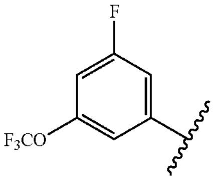
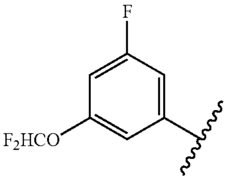
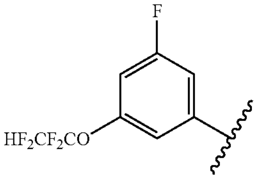
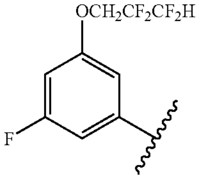
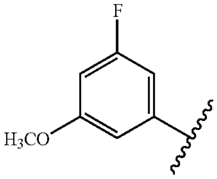
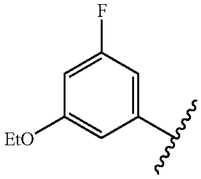
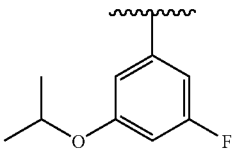
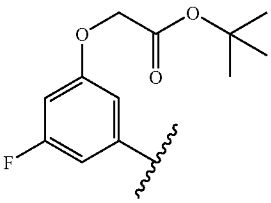
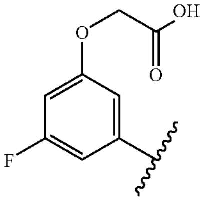
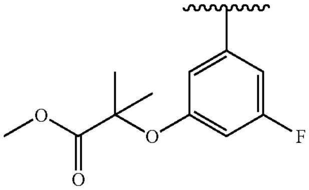
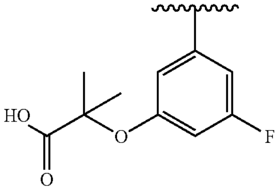
-continued
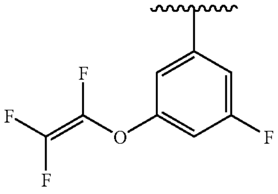
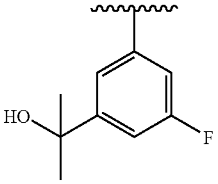
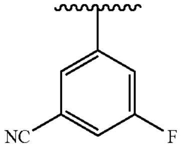
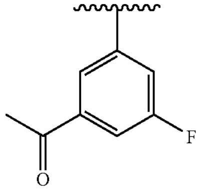
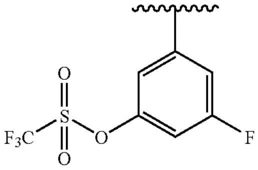
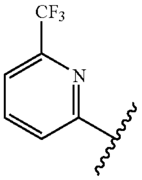
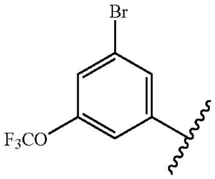
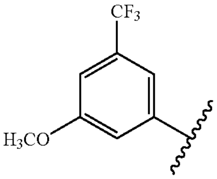
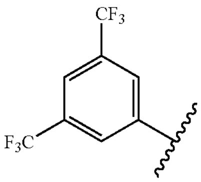
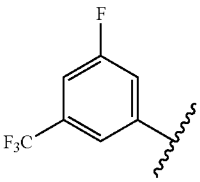
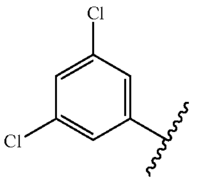
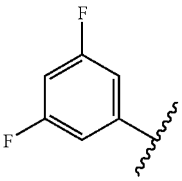
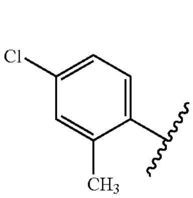
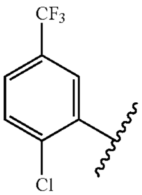
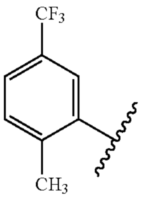
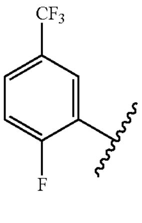
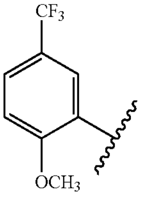
or
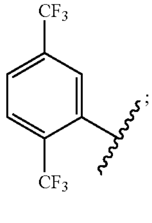
;

C is:
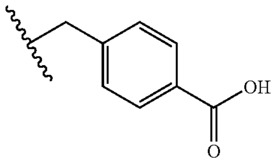
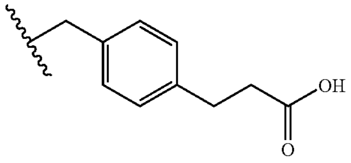
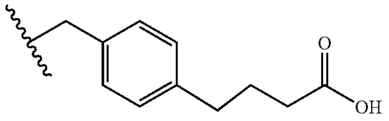
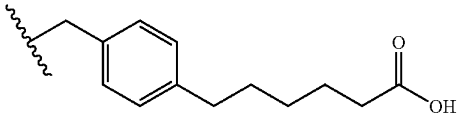
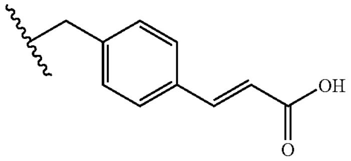
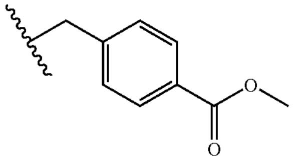
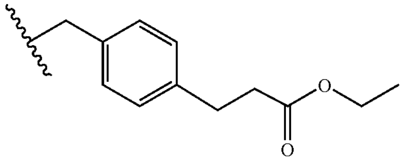
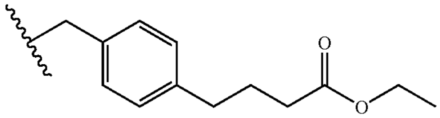
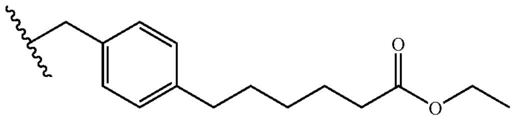
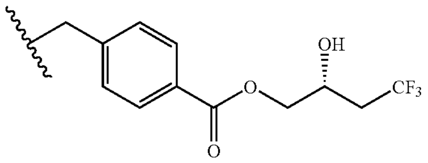
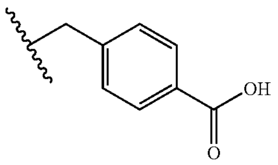
-continued
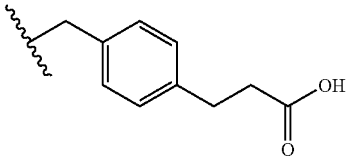
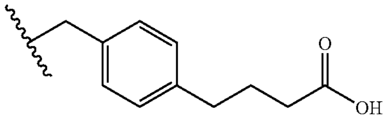
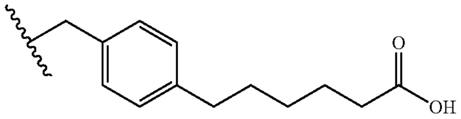
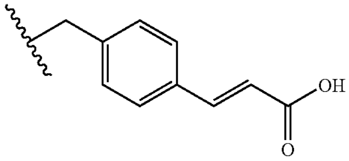
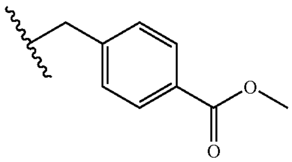
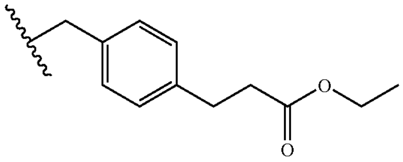
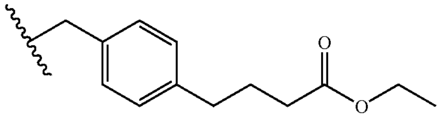
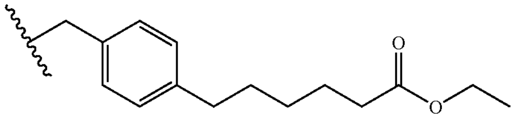
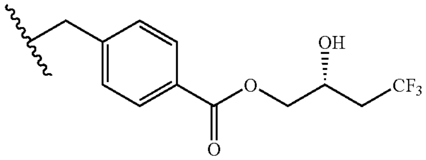
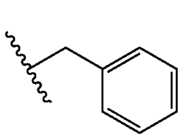
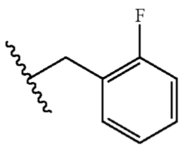
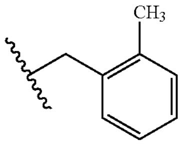
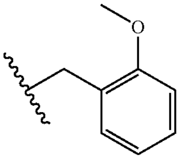

-continued
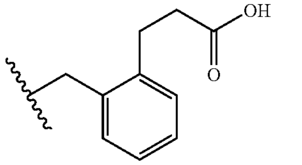
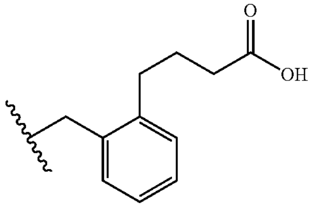
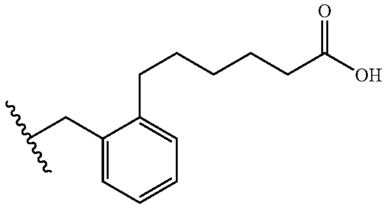
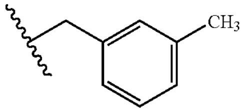
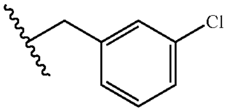
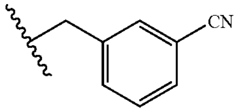
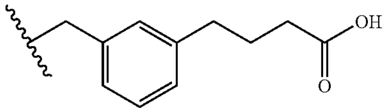
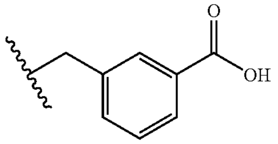
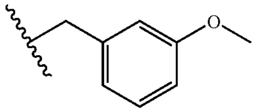
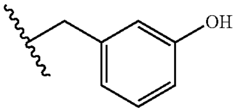
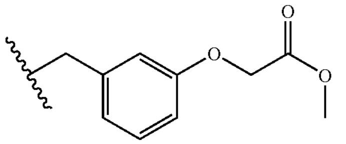
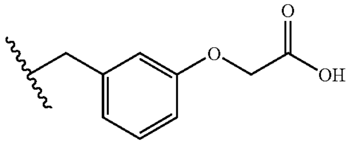
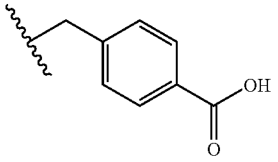
-continued
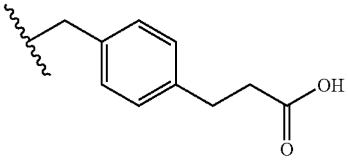
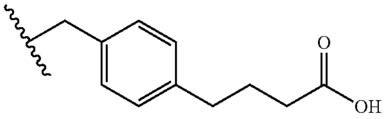
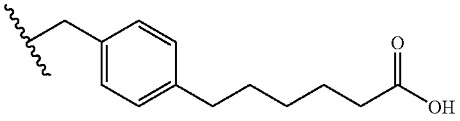
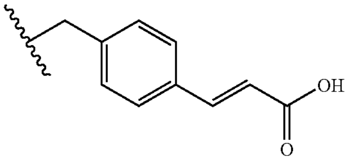
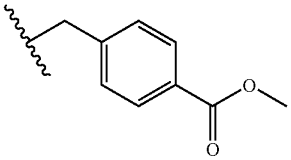
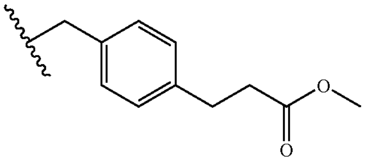
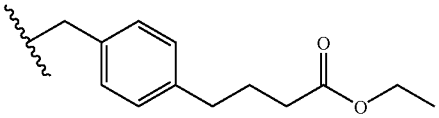
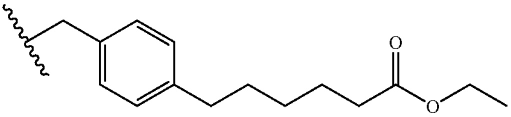
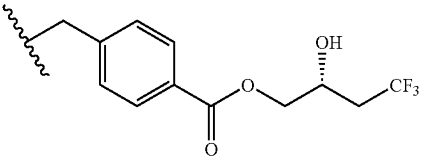
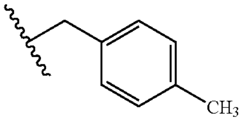
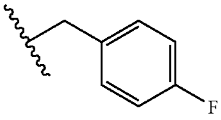
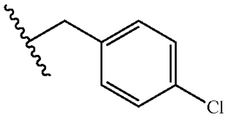
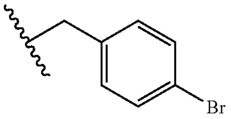
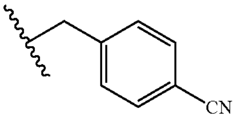
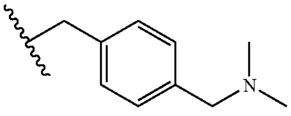

-continued
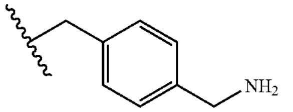
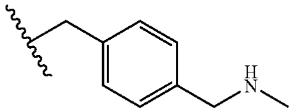
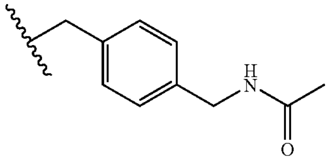
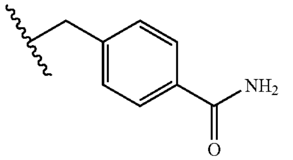
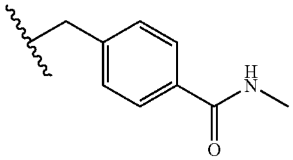
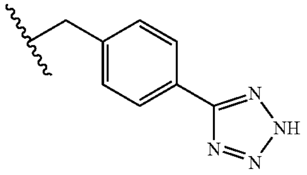
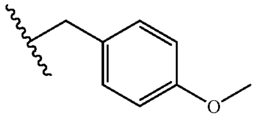
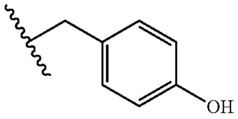
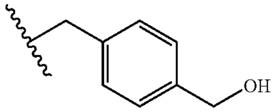
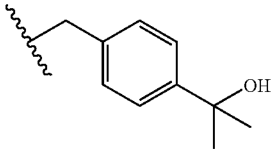
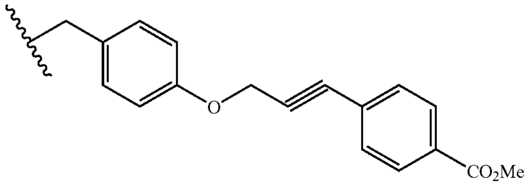
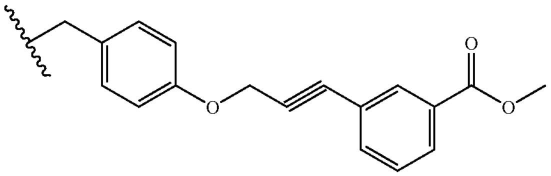
-continued
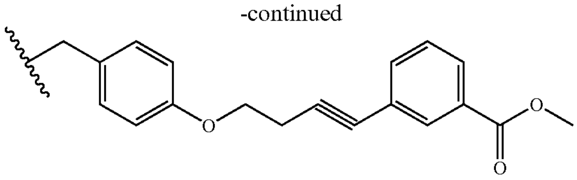
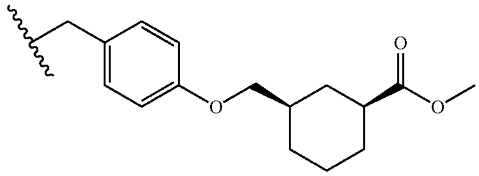
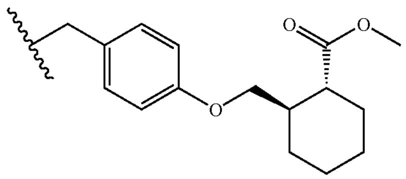
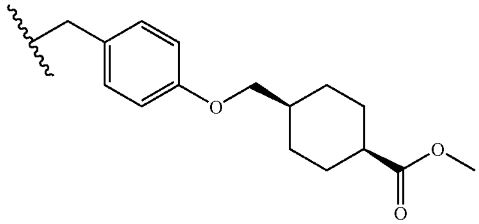
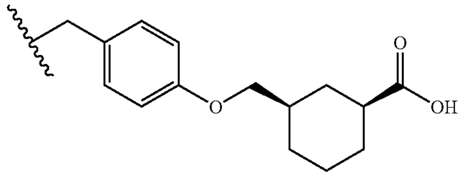
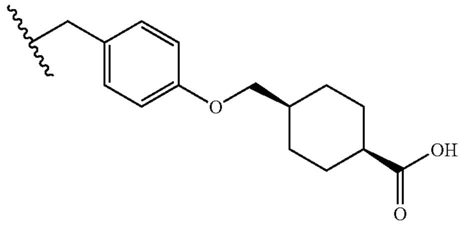
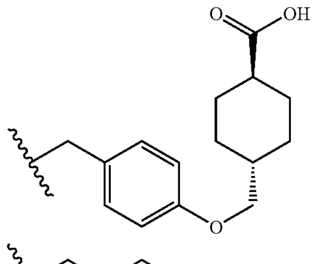
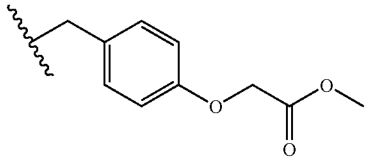
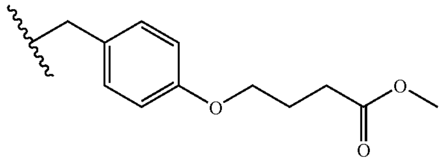

-continued
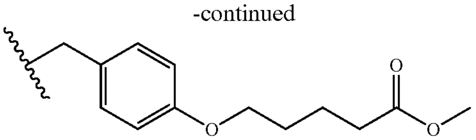
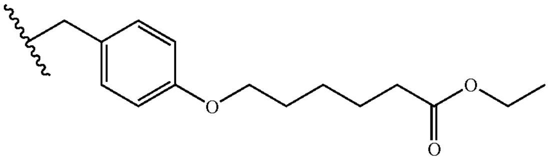
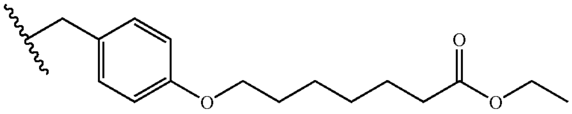
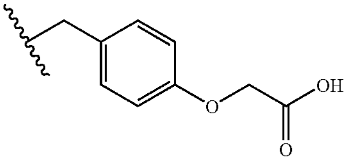
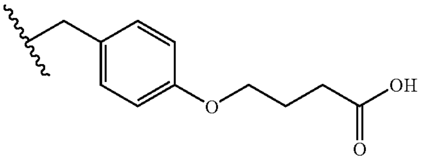
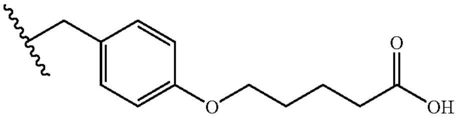
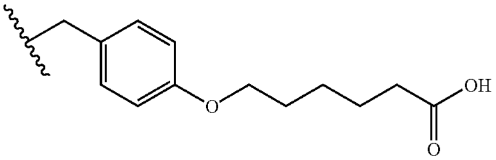
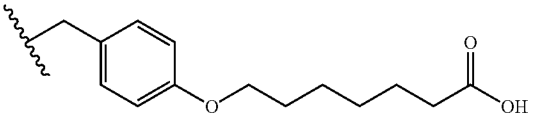
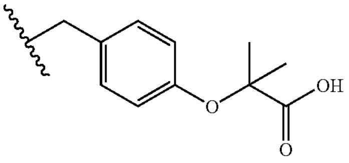
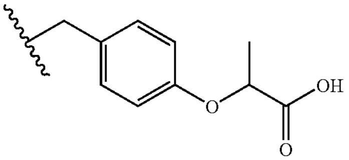
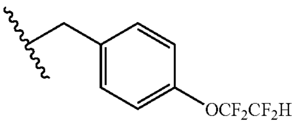
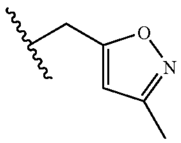
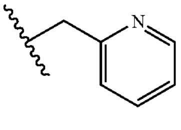
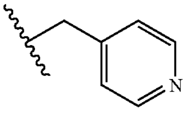
-continued
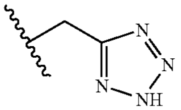
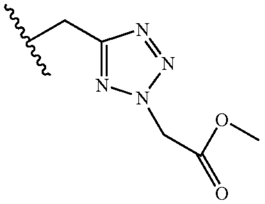
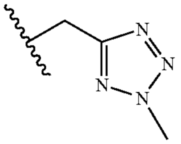
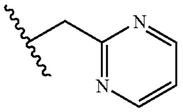
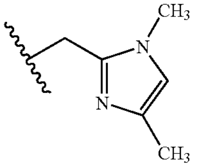
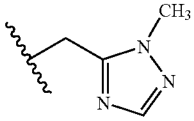
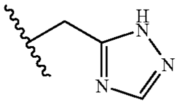
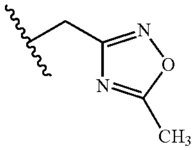
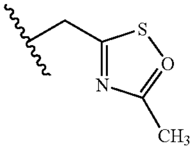
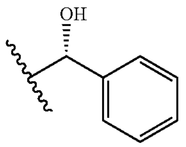
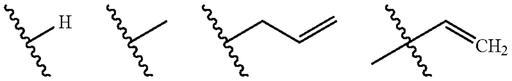
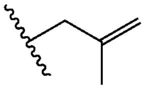
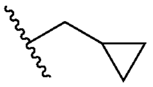
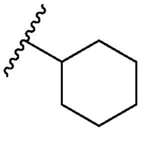
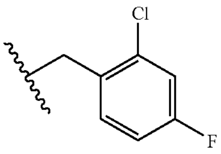
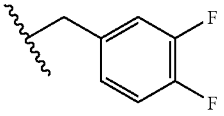
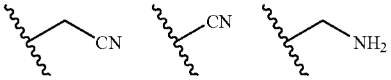
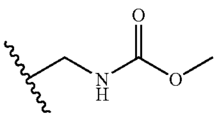
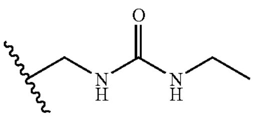
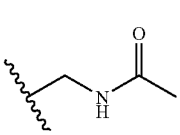
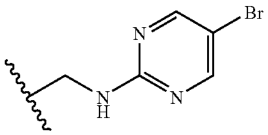
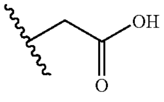
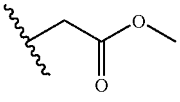

-continued
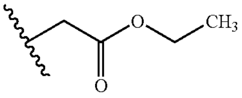 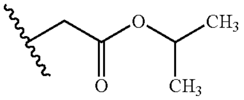
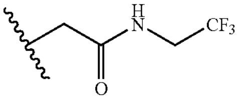 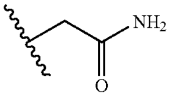
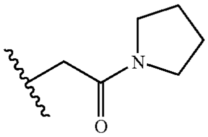 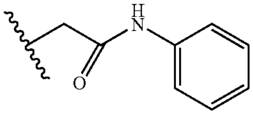
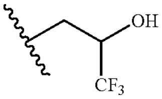 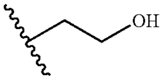
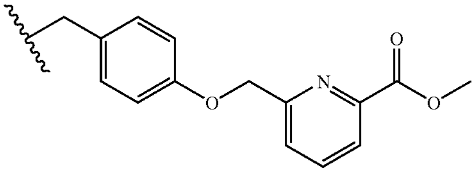 or
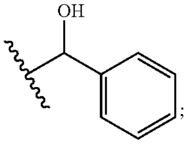 ;
$R_1$ is:
(a) —$C(O)R_3$, wherein $R_3$:
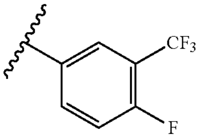 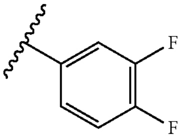
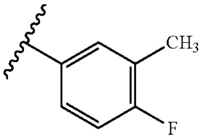 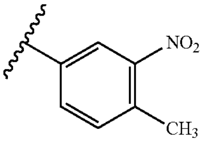
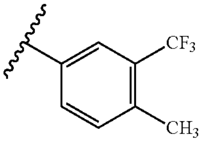 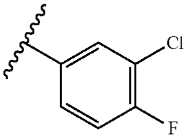
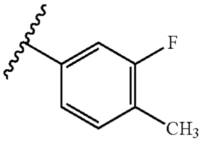 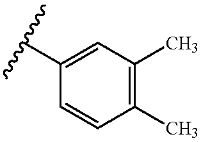
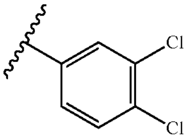 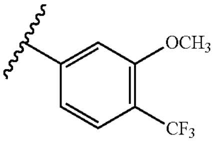
-continued
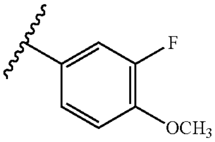 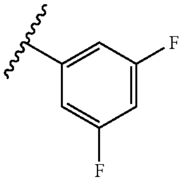
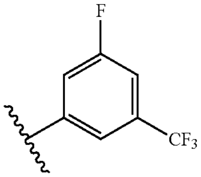 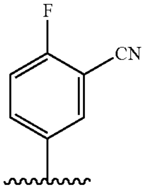
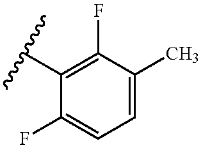 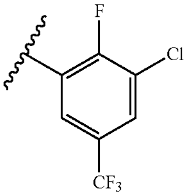
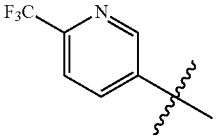 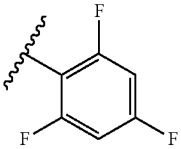
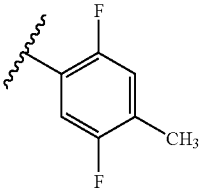 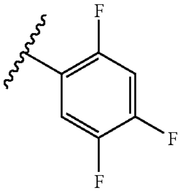
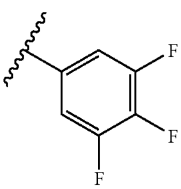 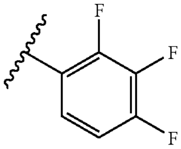
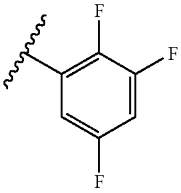 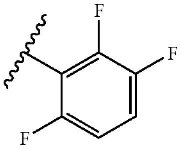
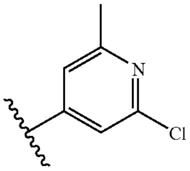 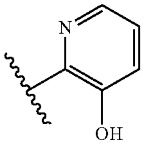
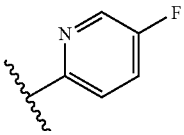 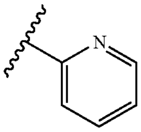

-continued
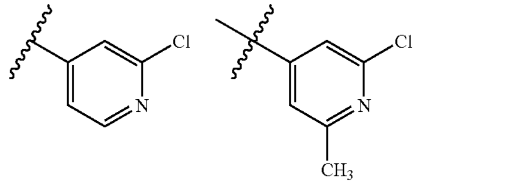
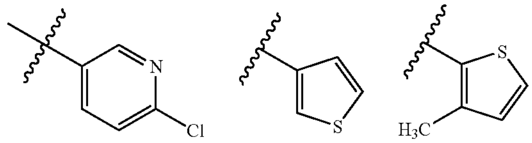
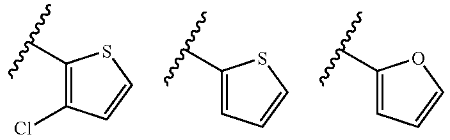
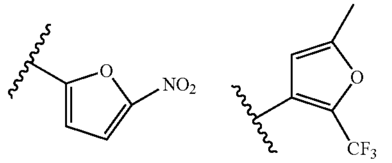
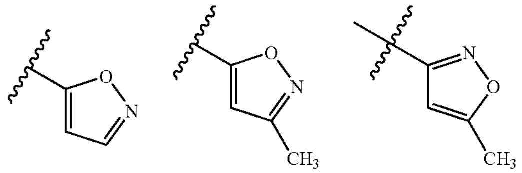
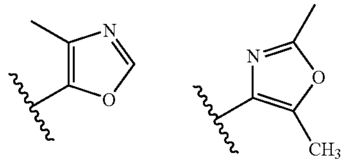
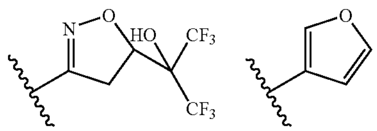
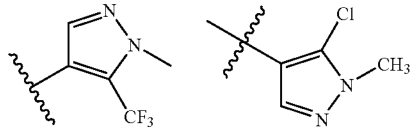
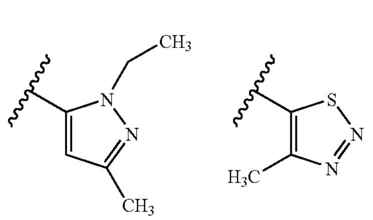
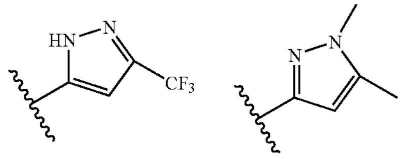
-continued
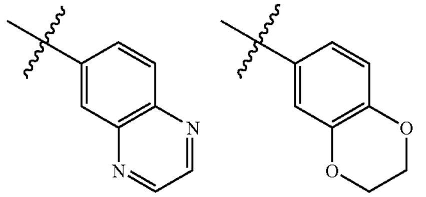
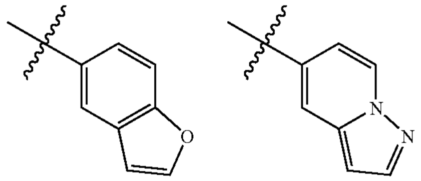
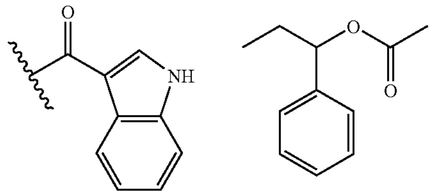
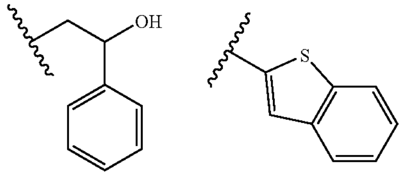
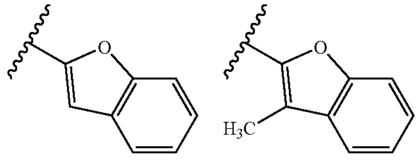
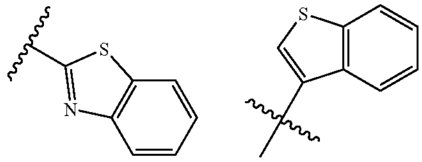
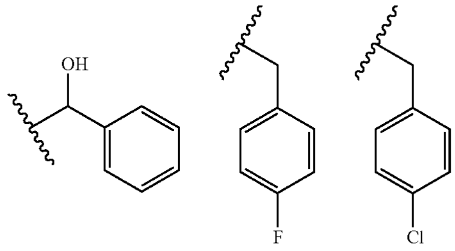
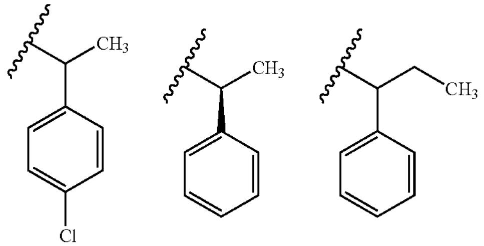

-continued
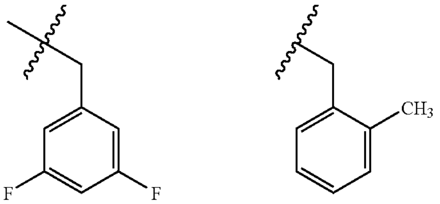
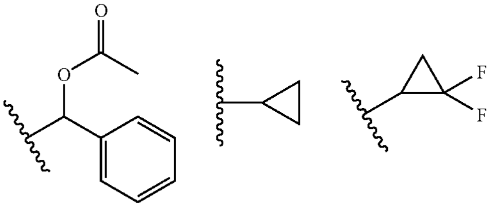
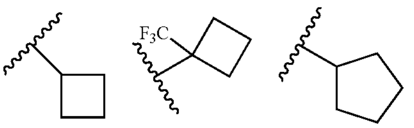
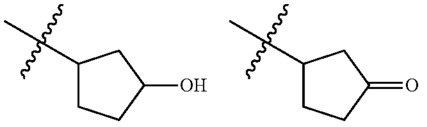
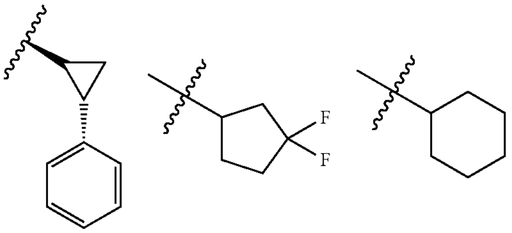
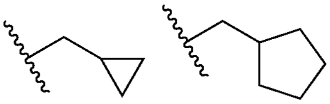
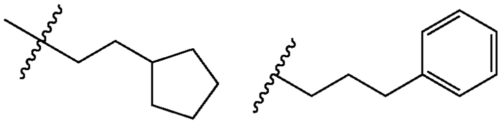
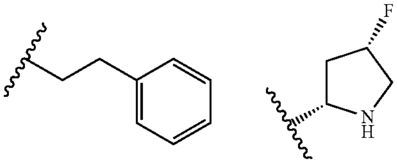
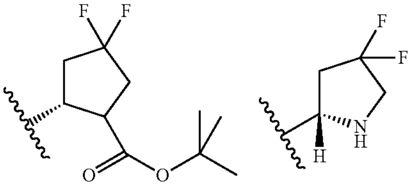
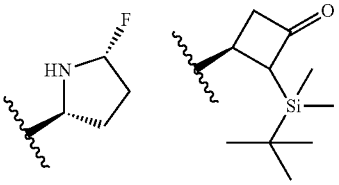
-continued
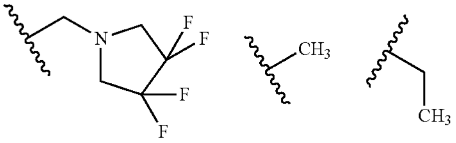
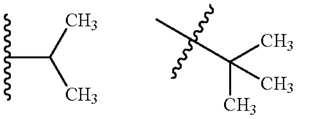
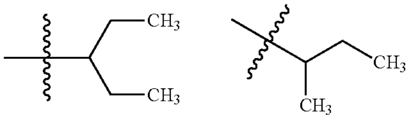
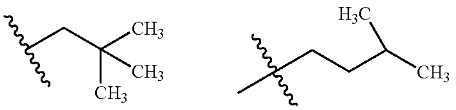
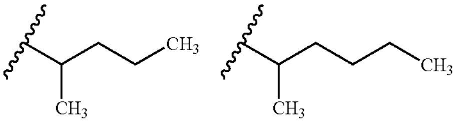
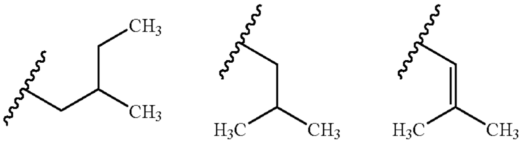
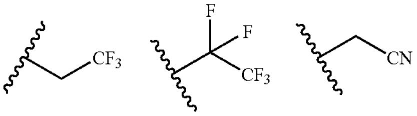
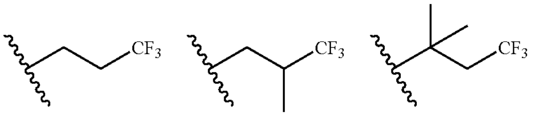
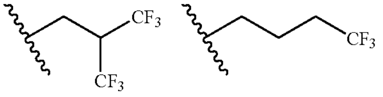
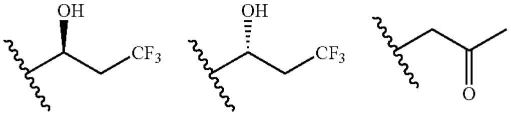
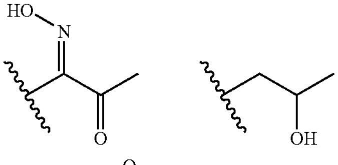
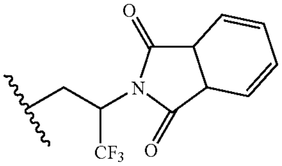
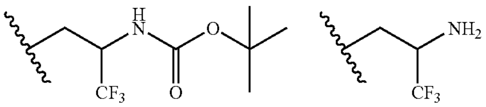

-continued
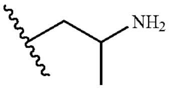
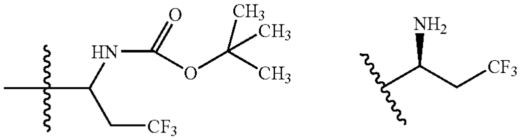
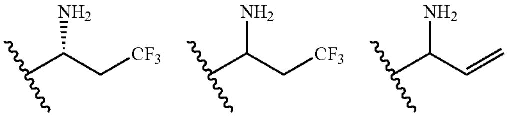
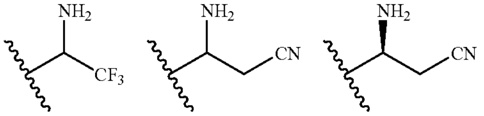
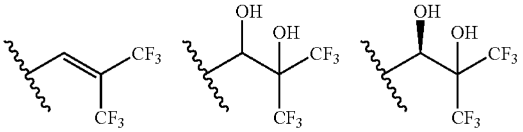
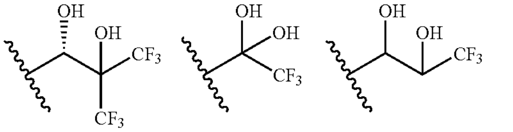
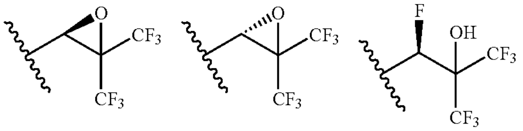
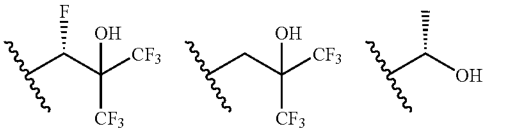
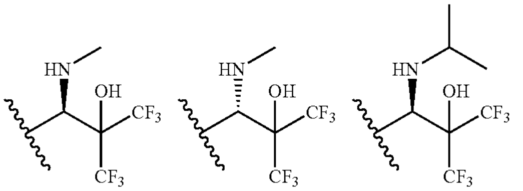
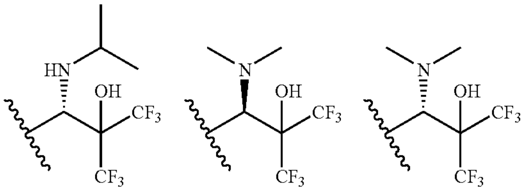
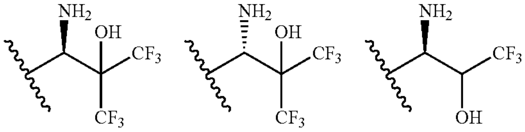
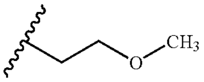
-continued
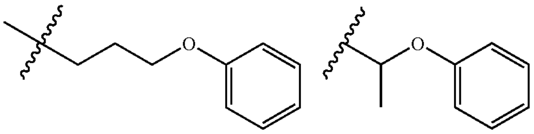
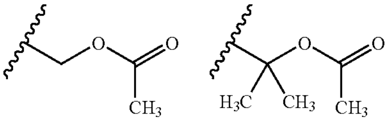
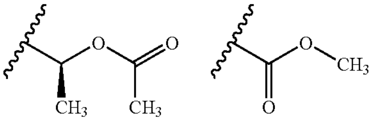
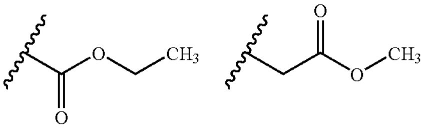
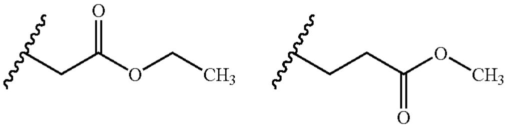
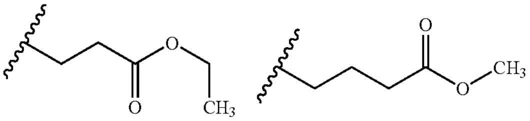
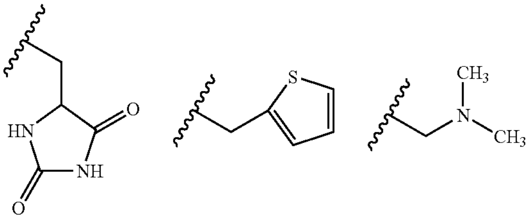
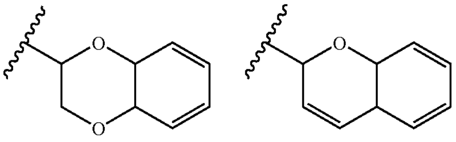
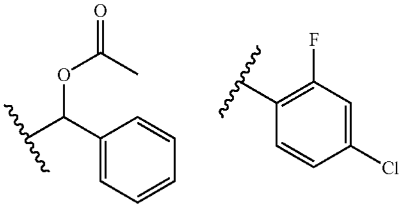
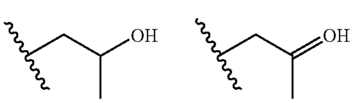
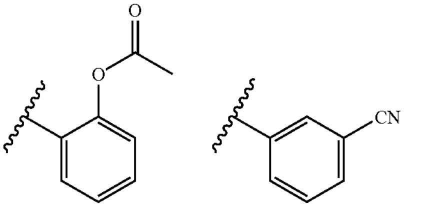

-continued
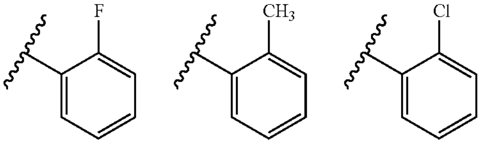
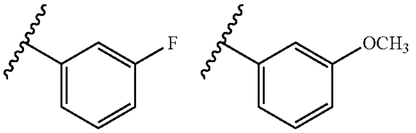
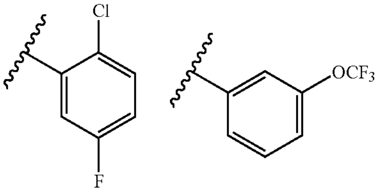
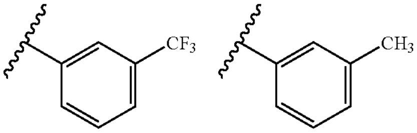
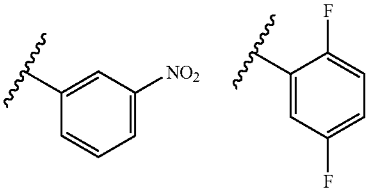
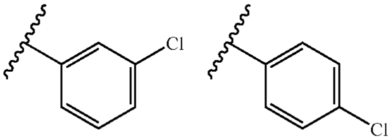
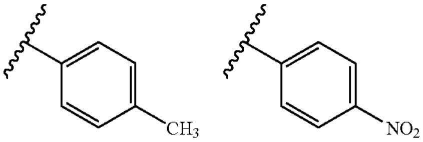
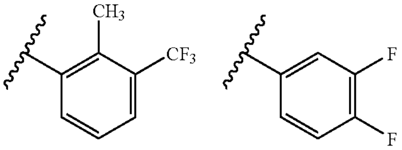
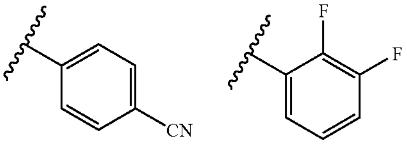
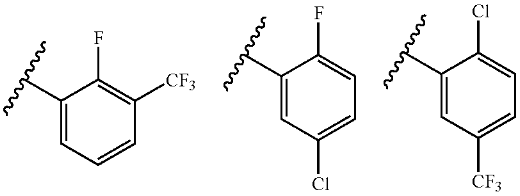
-continued
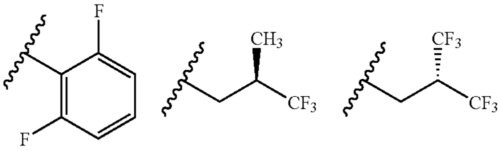
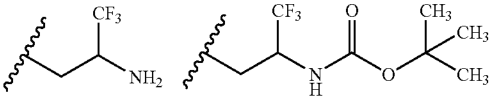
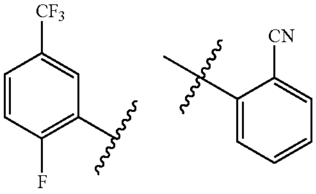
or
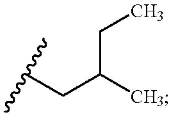
(b) —C(O)NHR$_3$, wherein the R$_3$ is:
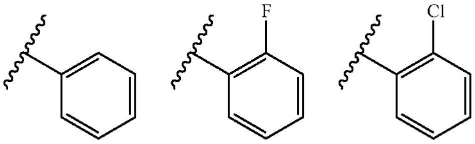
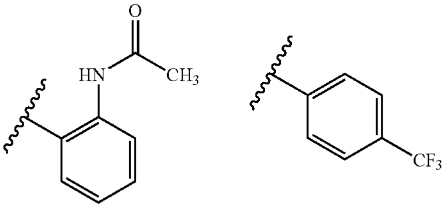
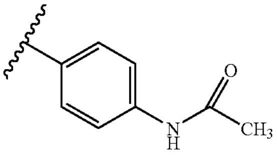
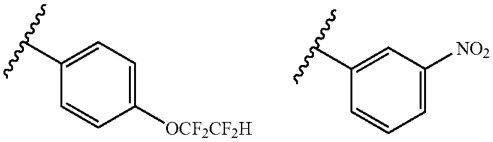
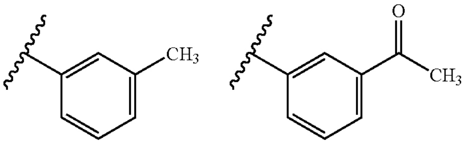
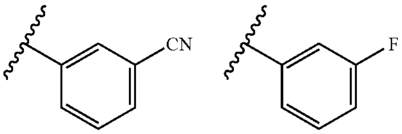

-continued
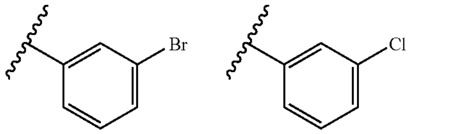
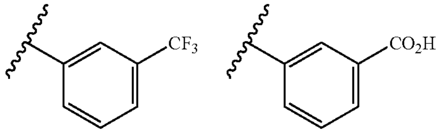
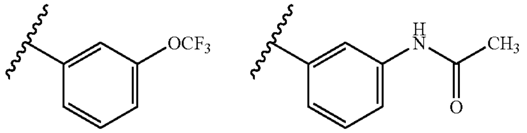
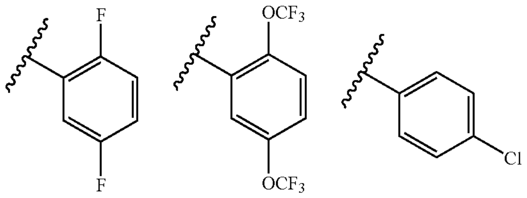
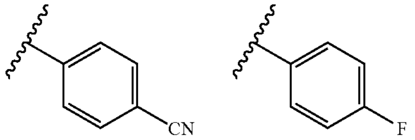
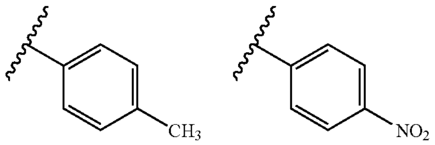
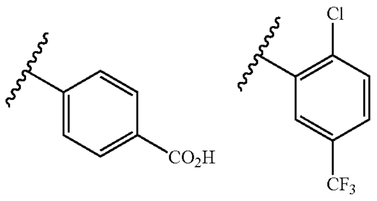
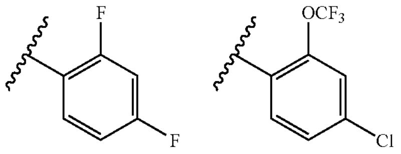
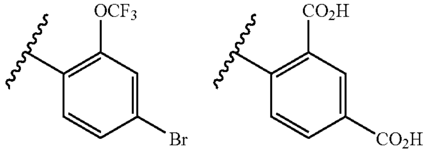
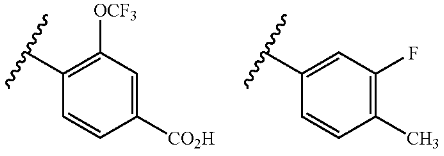
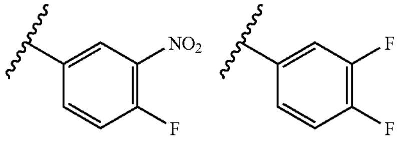
-continued
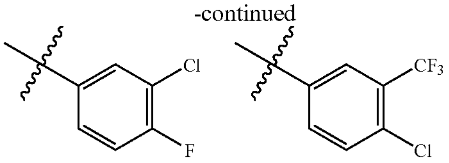
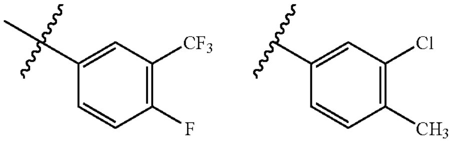
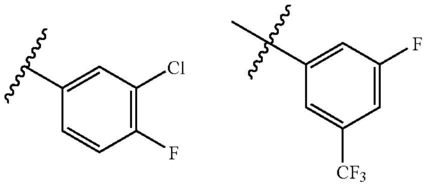
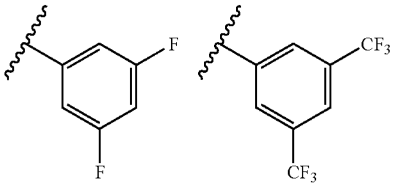
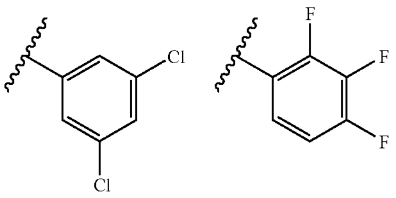
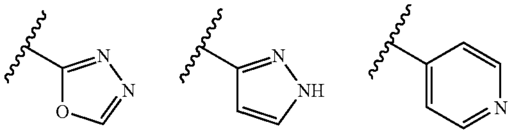
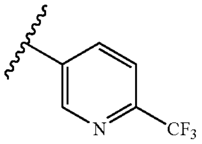
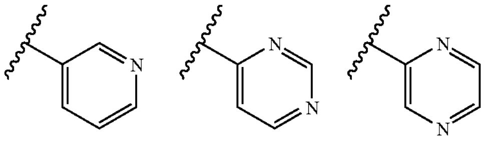
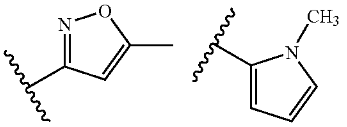
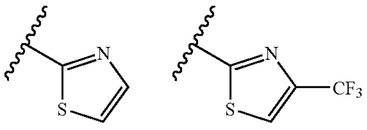
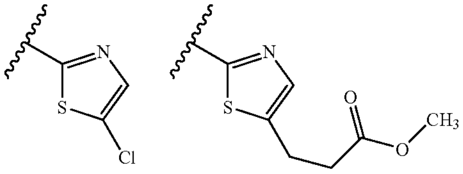

-continued
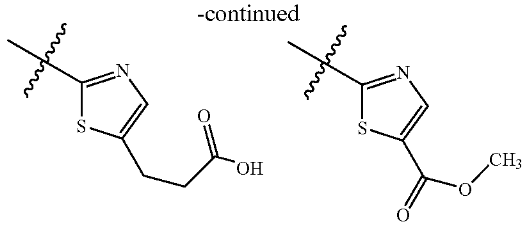
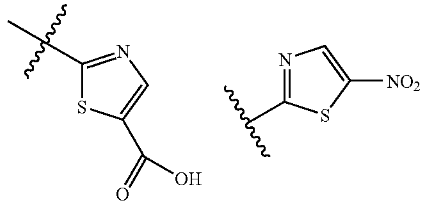
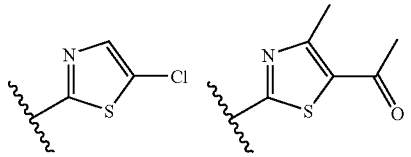
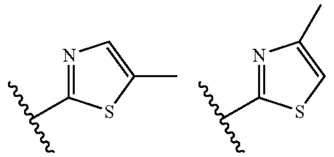
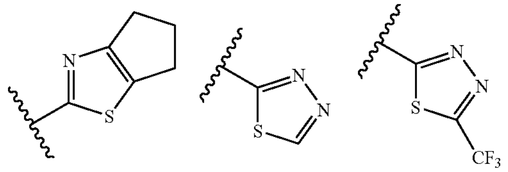
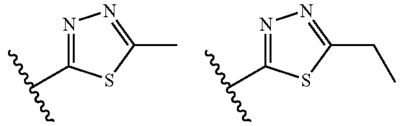
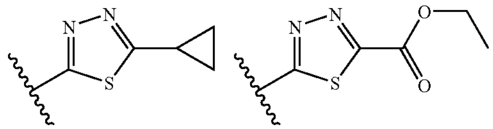
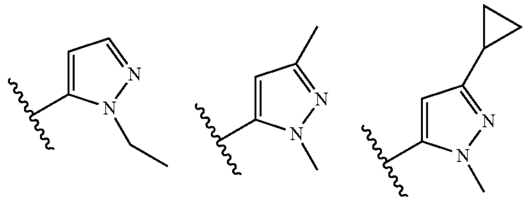
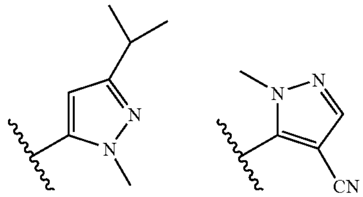
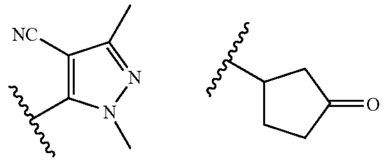
-continued
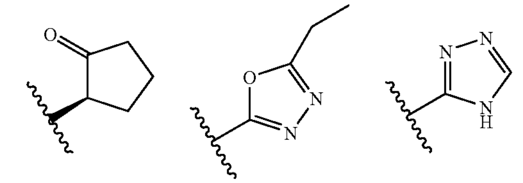
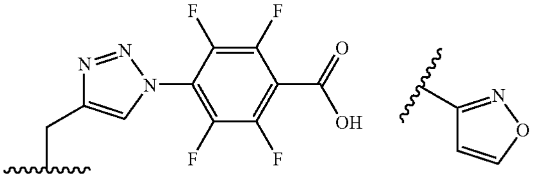
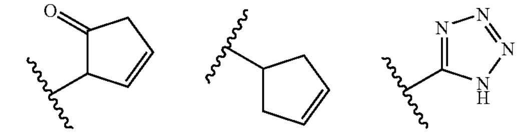
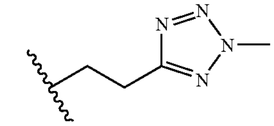
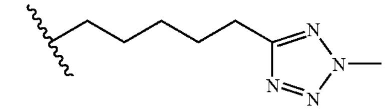
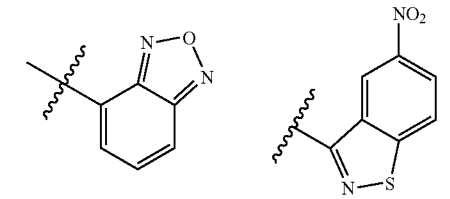
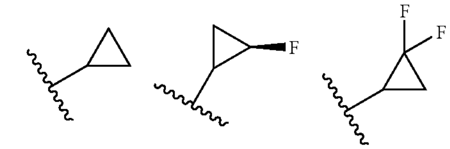
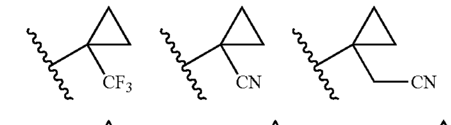
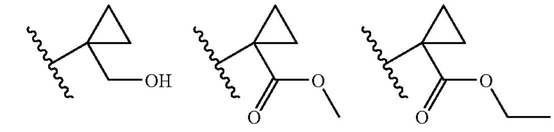
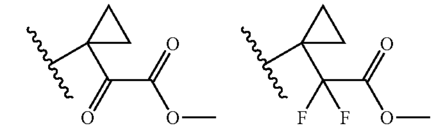
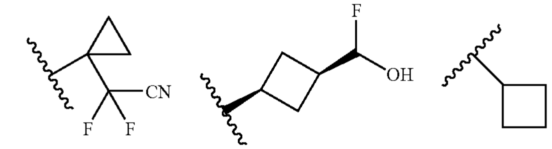

-continued
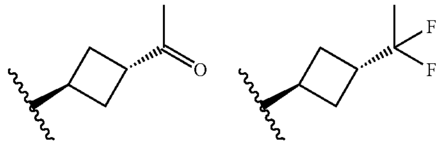
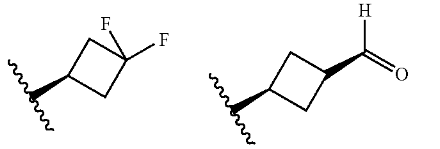
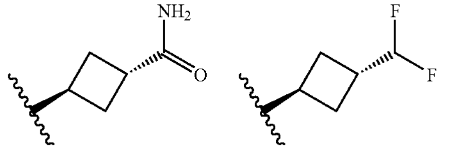
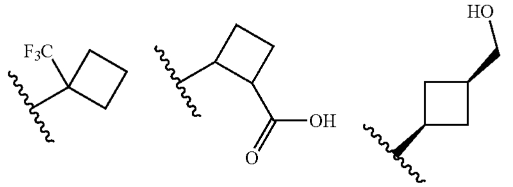
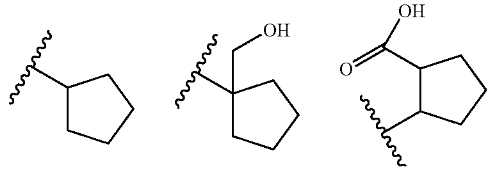
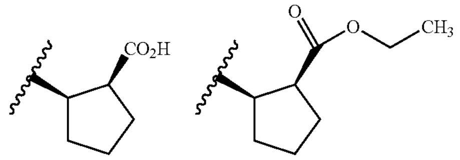
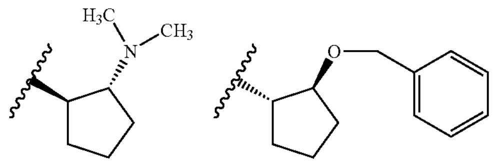
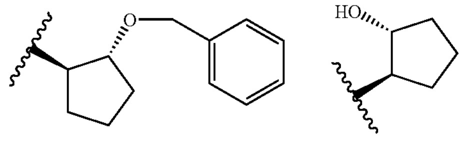
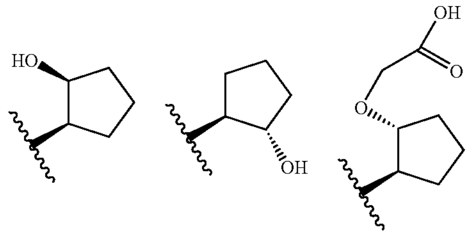
-continued
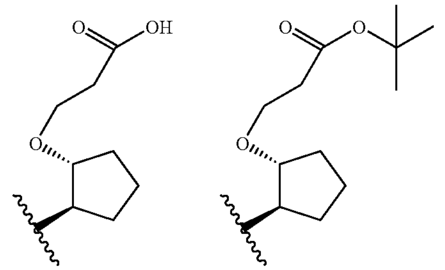
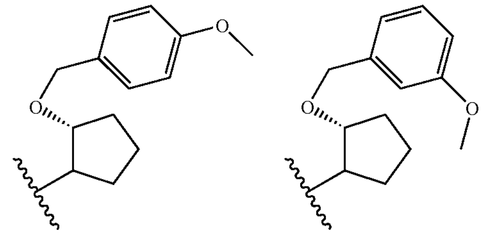
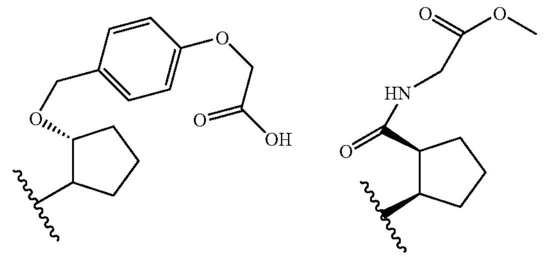
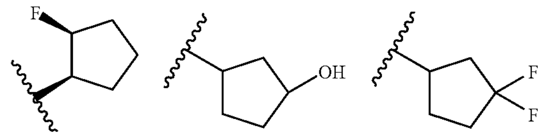
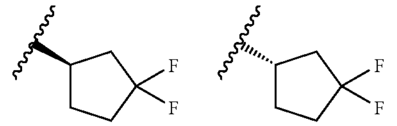
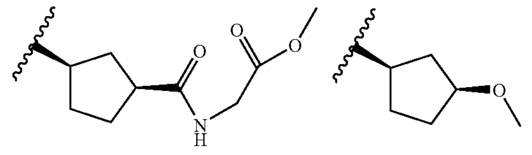
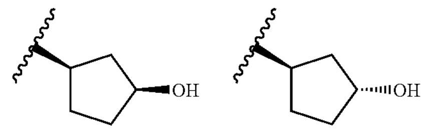
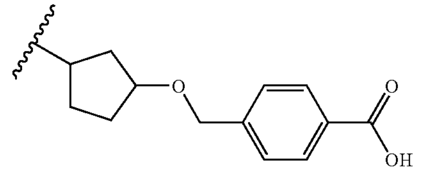
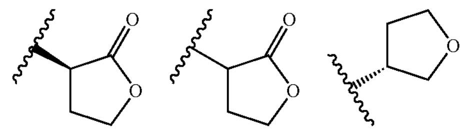

-continued
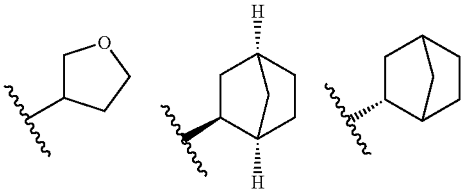
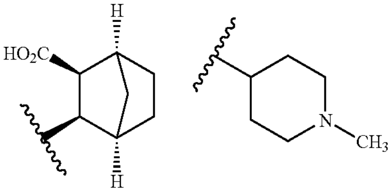
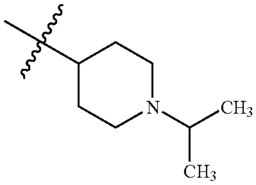
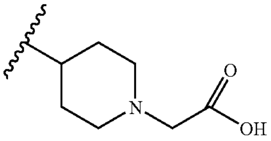
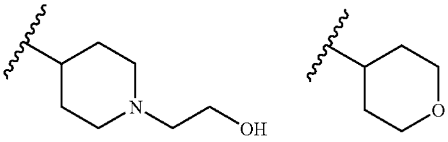
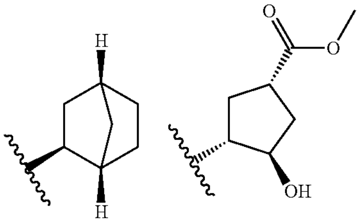
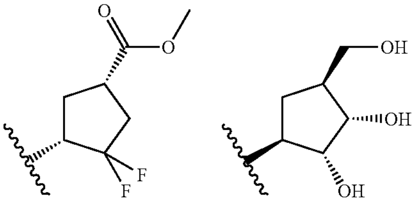
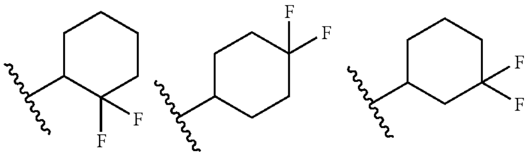
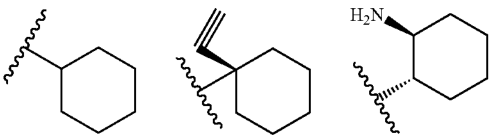
-continued
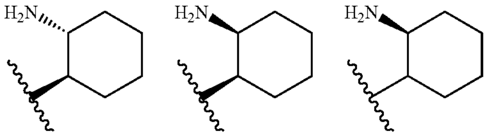
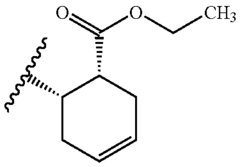
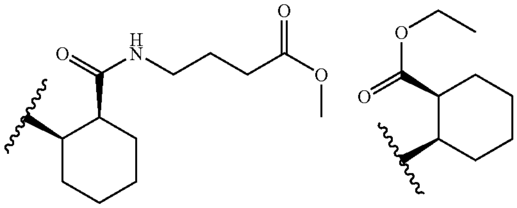
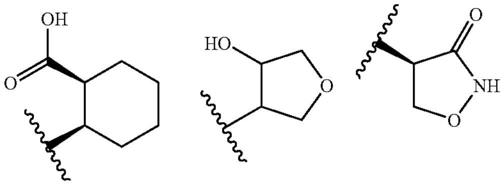
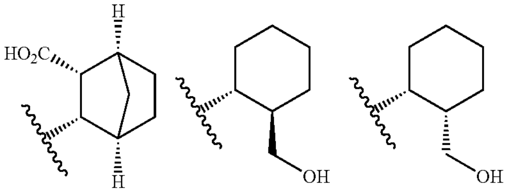
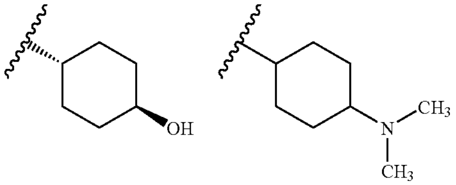
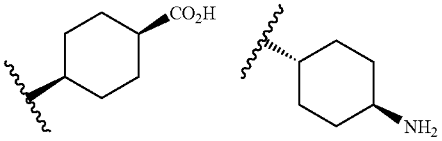
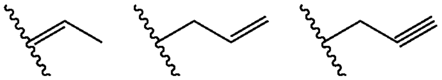
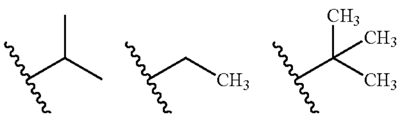
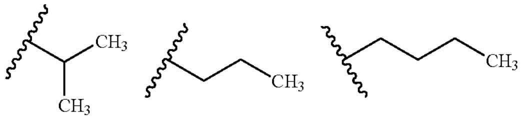
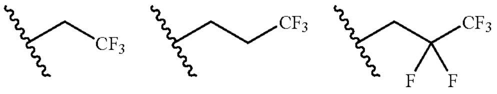

-continued
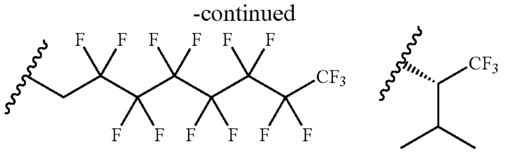
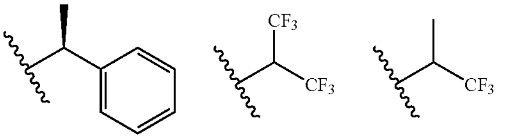
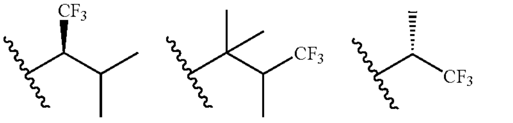
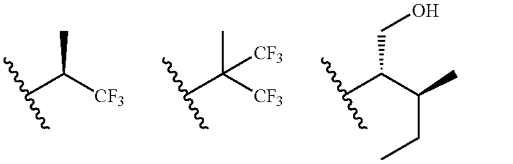
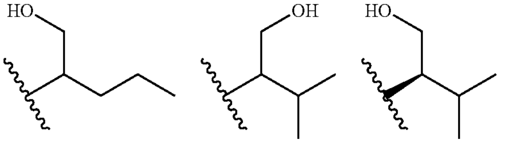
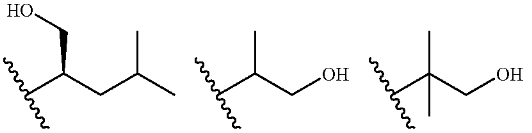
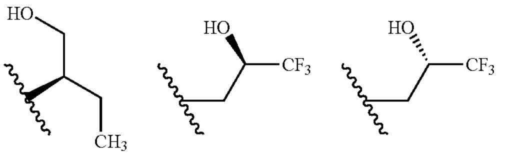
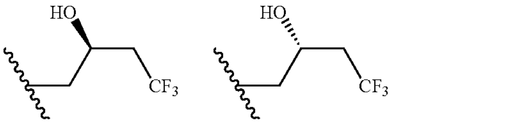
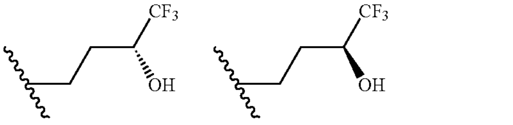
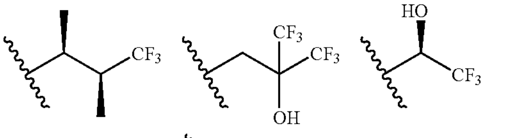
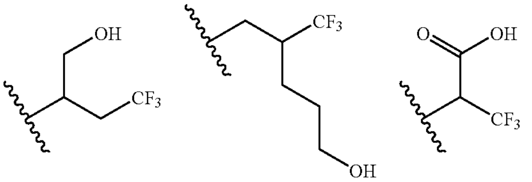
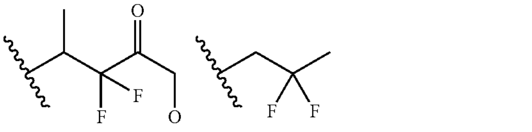
-continued
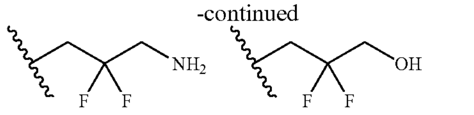
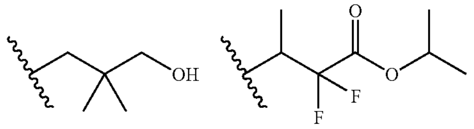
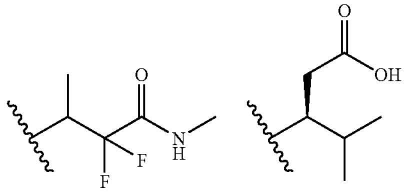
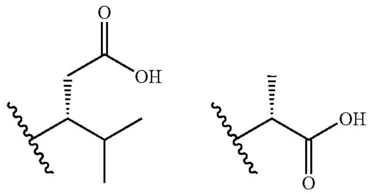
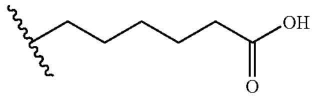
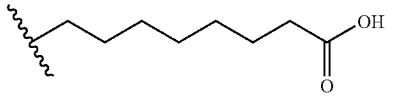
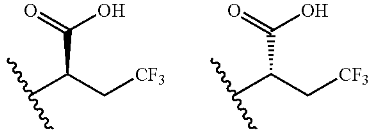
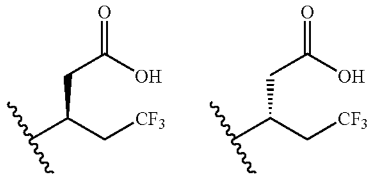
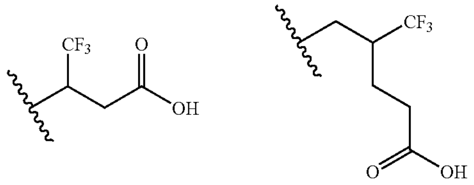
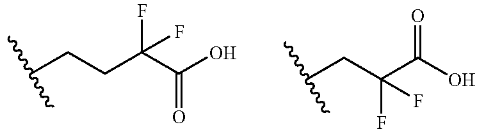
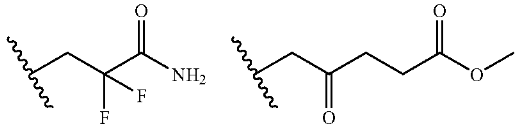
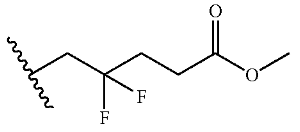

-continued
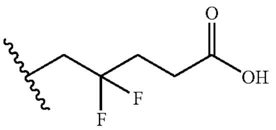
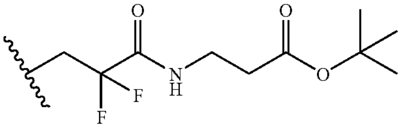
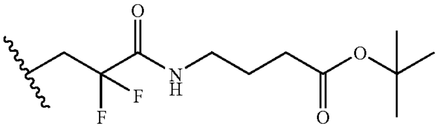
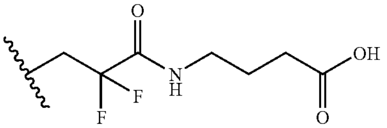
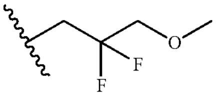
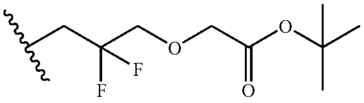
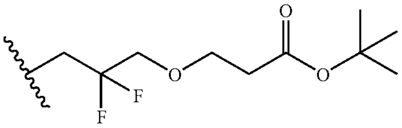
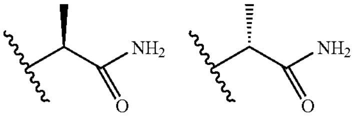
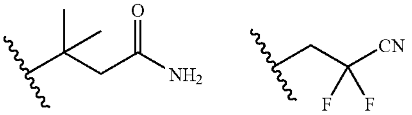
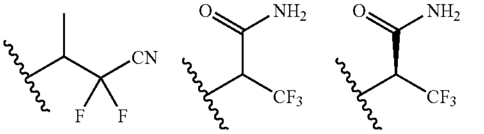
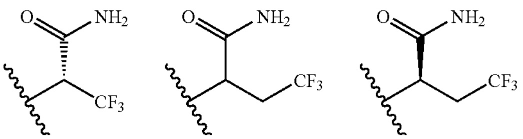
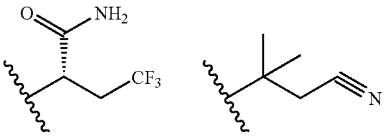
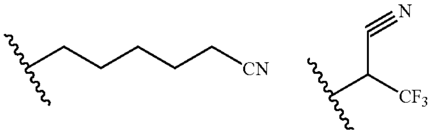
-continued
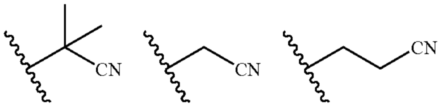
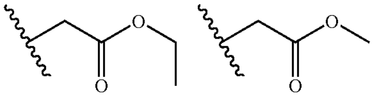
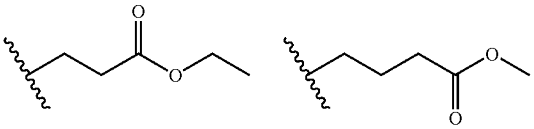
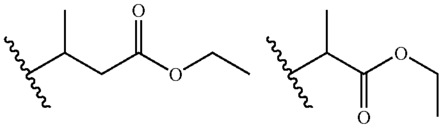
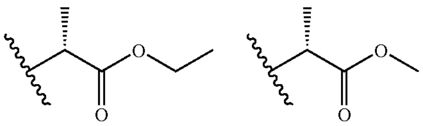
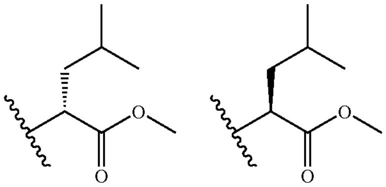
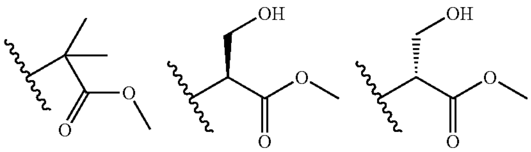
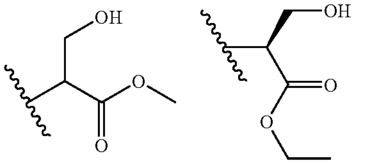
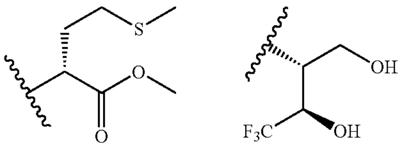
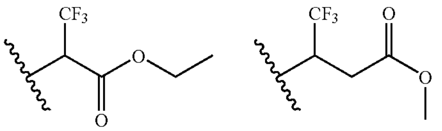
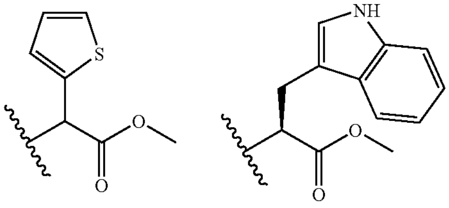

-continued
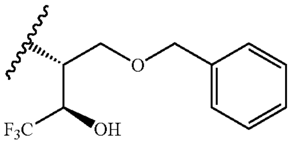
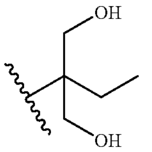
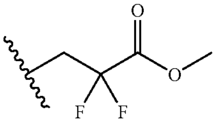
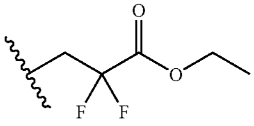
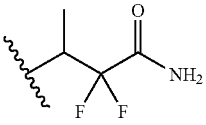
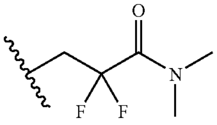
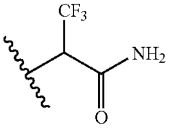
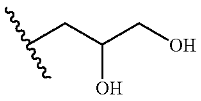
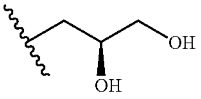
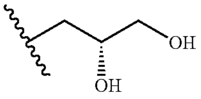
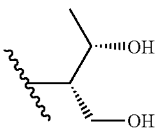
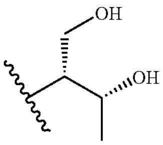
or
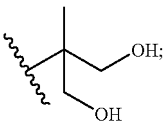
(c) —C(O)$NR_2R_3$, wherein the $NR_2R_3$ is:
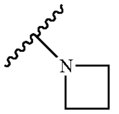
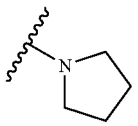
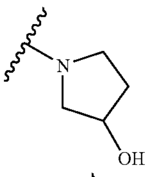
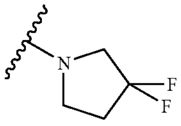
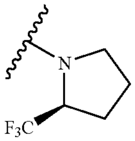
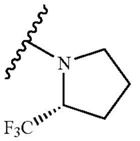
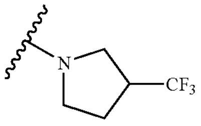
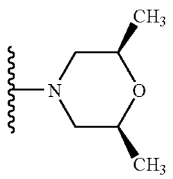
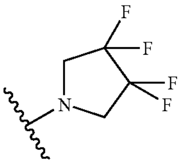
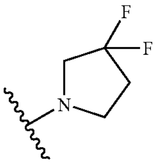
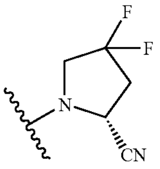
-continued
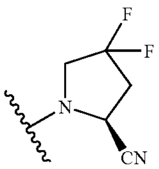
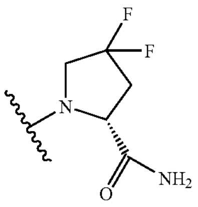
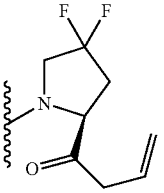
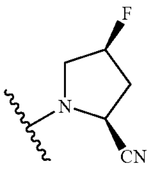
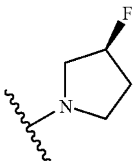
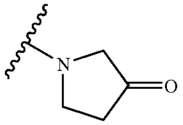
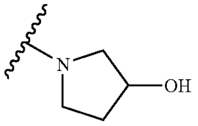
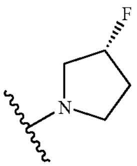
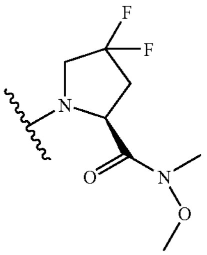
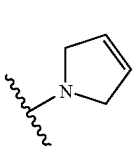
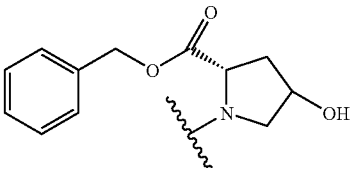
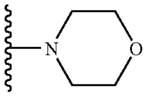
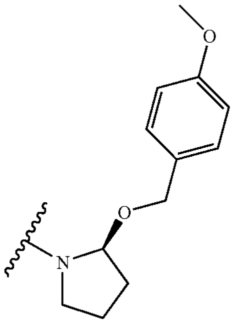
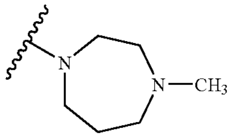
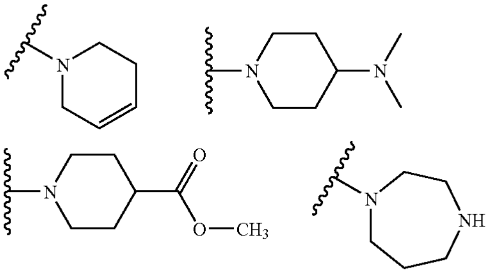
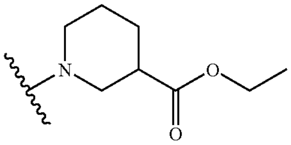

-continued
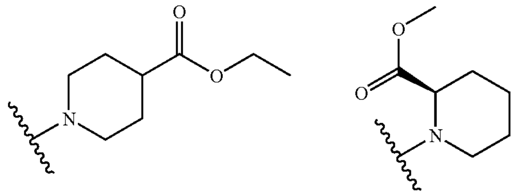
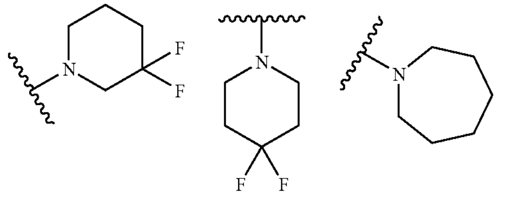
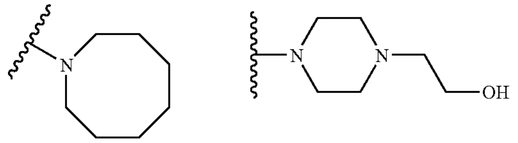
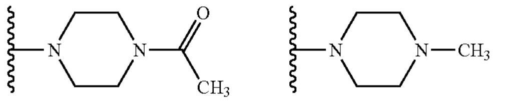
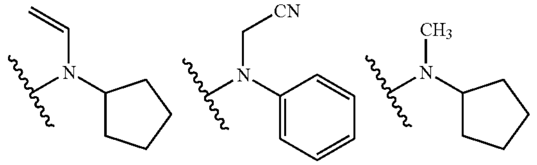
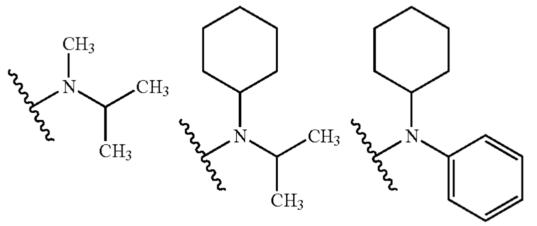
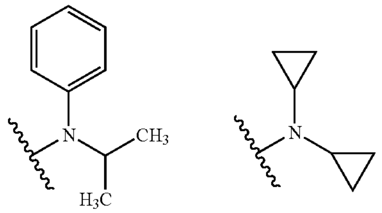
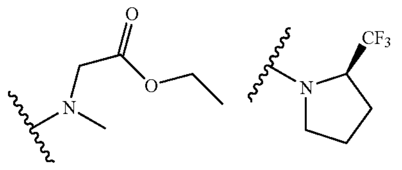
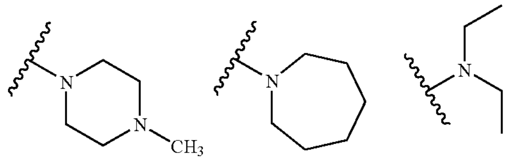
-continued
or 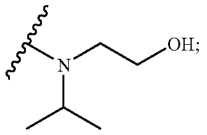
(d) —C(O)OR$_4$ wherein the R$_4$ is:
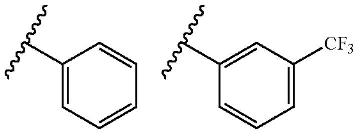
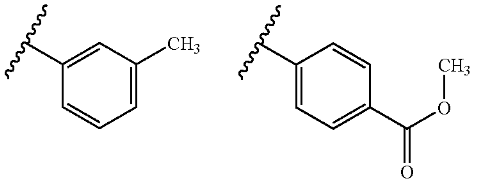
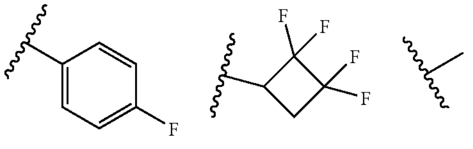
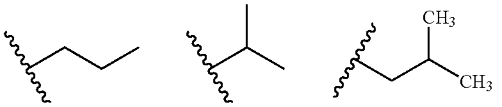
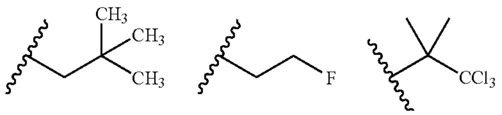
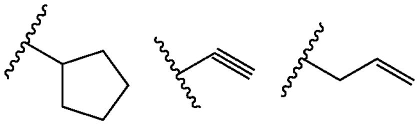
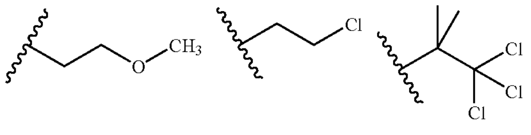
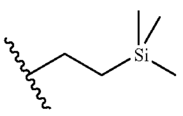 or 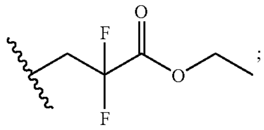 ;
(e) —SO$_2$R$_5$ wherein the R$_5$ is:
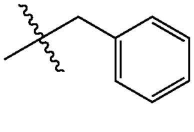 or 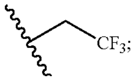

(f) —$CSNHR_7$ wherein the $R_7$ is:
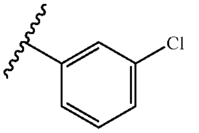
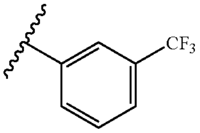
or
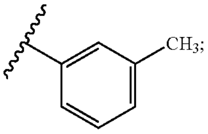
(g) —$CH_2R_8$ wherein $R_8$ is:
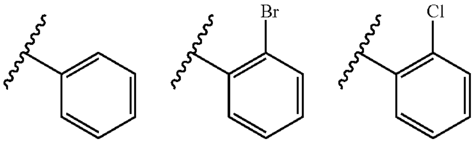
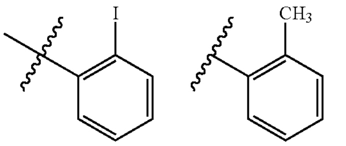
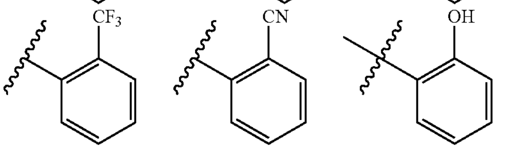
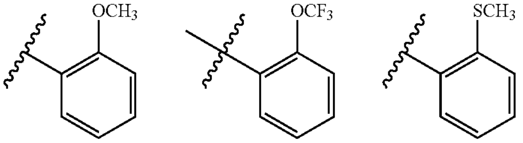
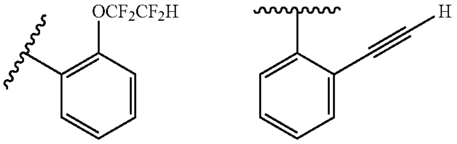
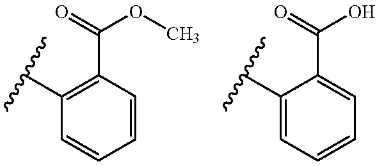
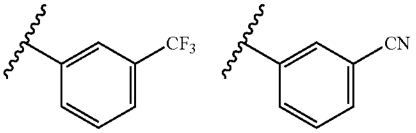
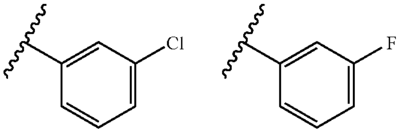
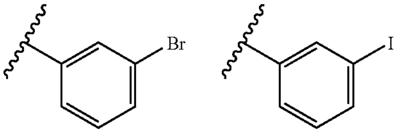
-continued
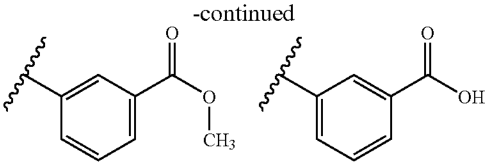
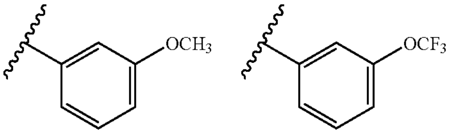
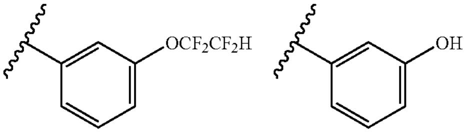
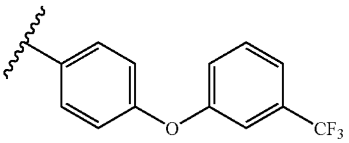
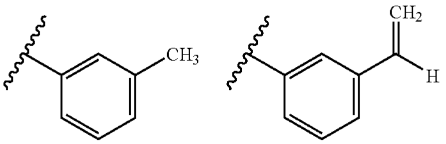
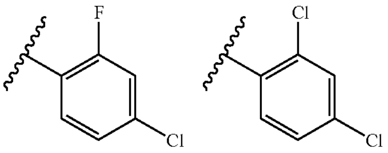
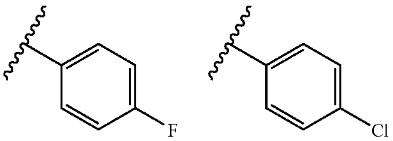
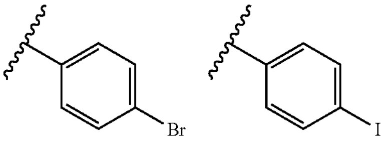
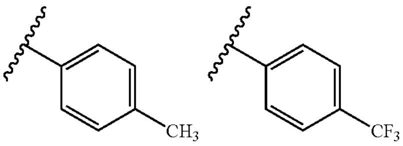
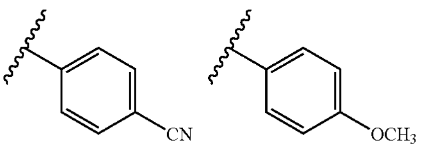
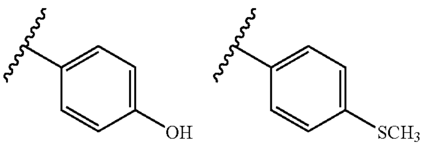

-continued
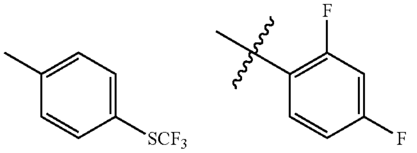
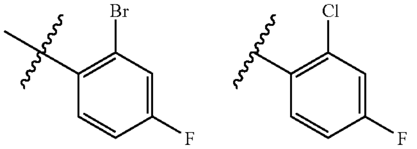
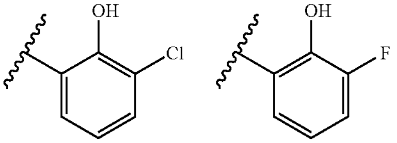
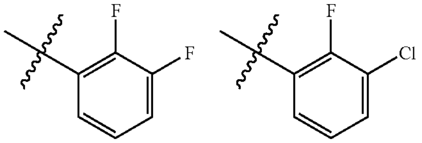
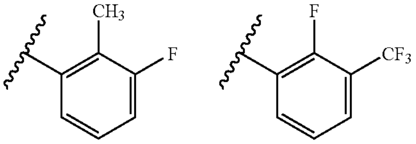
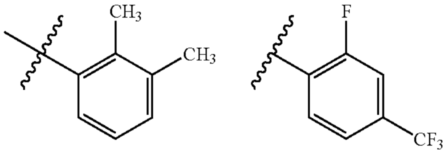
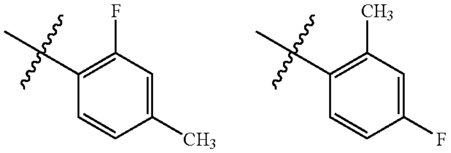
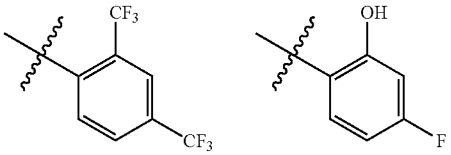
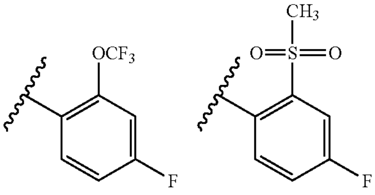
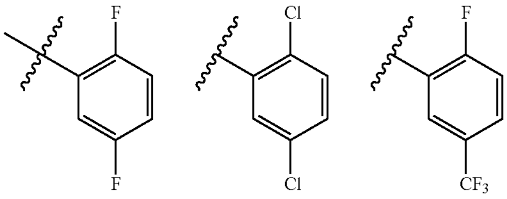
-continued
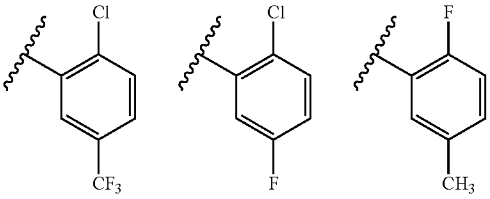
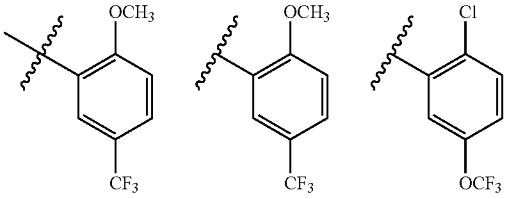
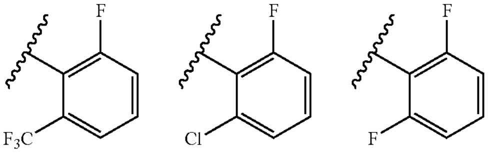
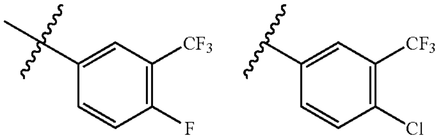
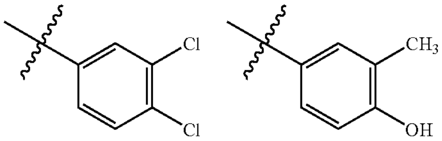
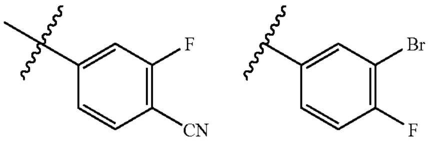
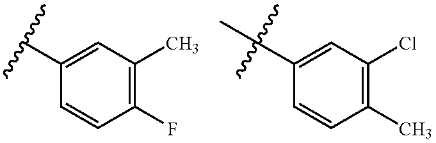
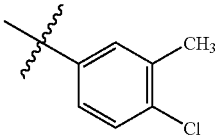
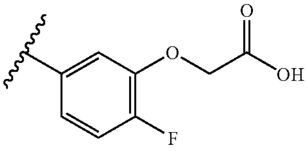
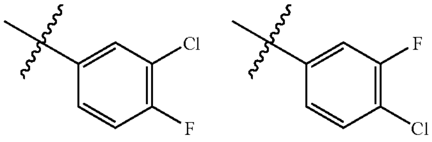
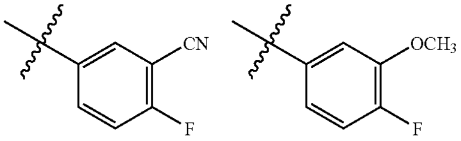

-continued
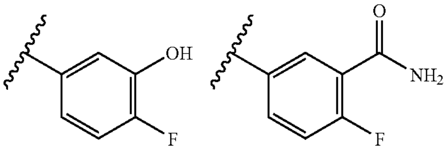
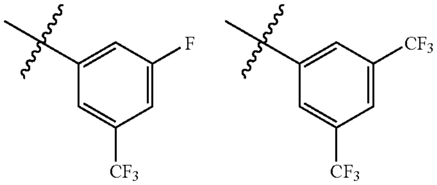
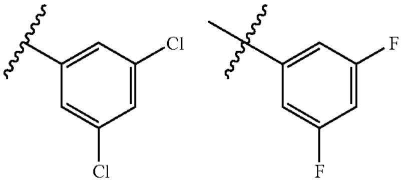
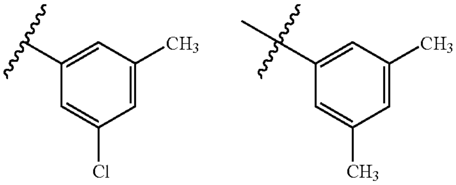
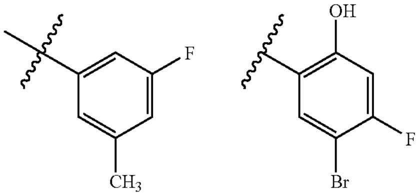
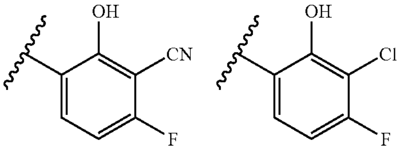
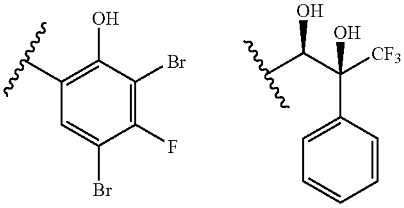
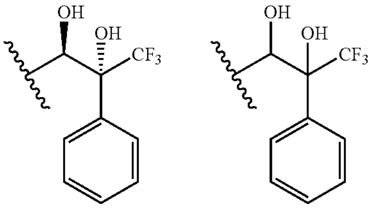
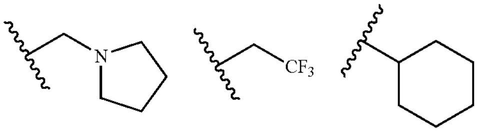
-continued
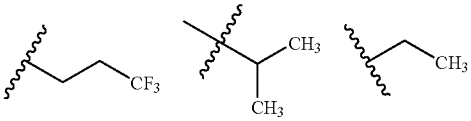
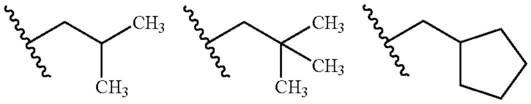
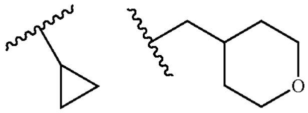
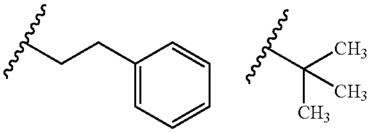
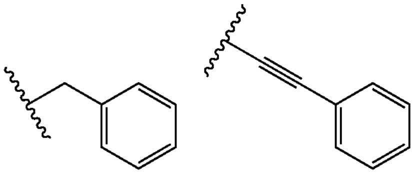
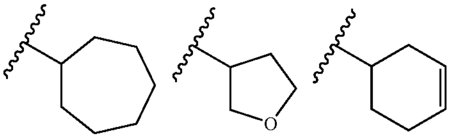
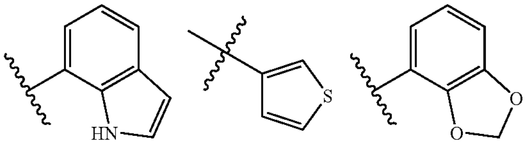
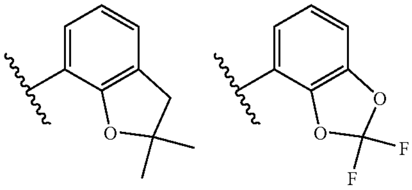
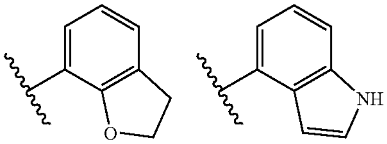
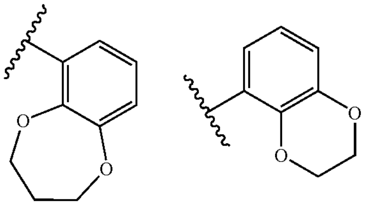
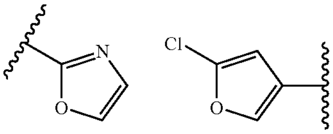

-continued
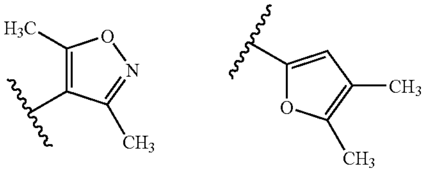
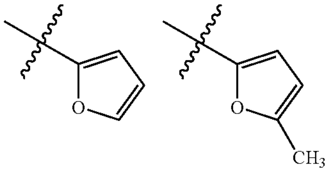
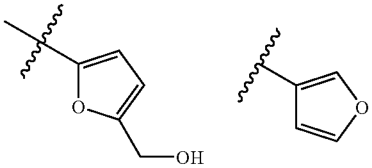
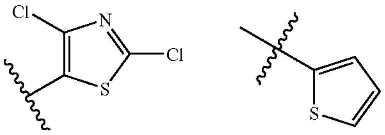
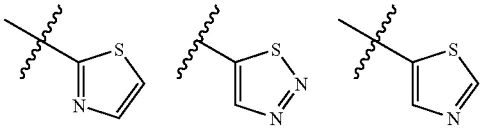
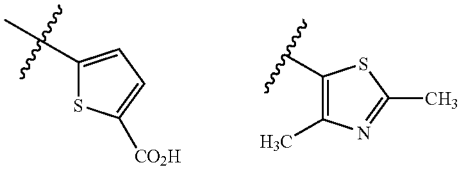
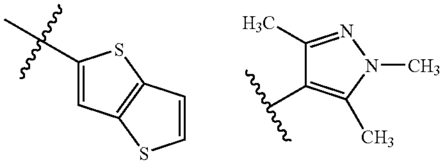
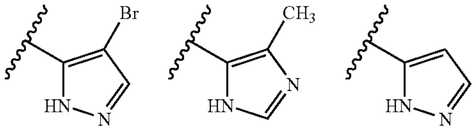
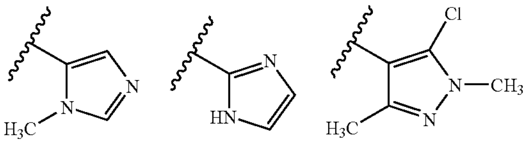
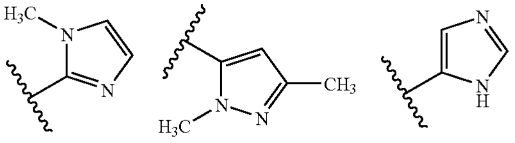
-continued
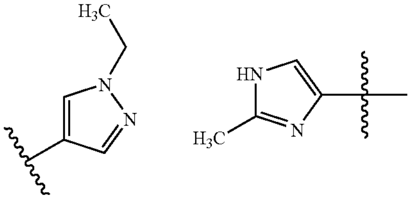
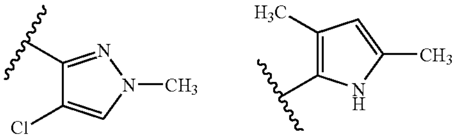
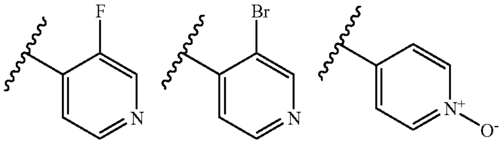
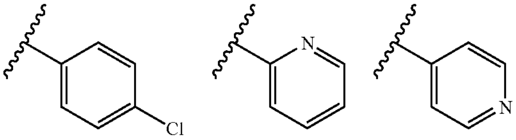
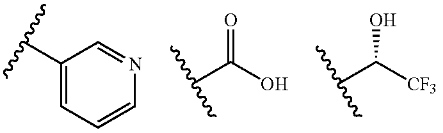
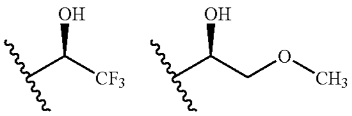
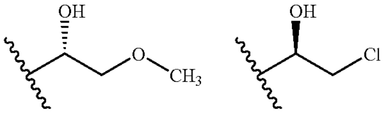
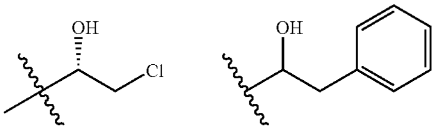
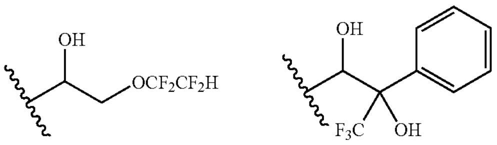
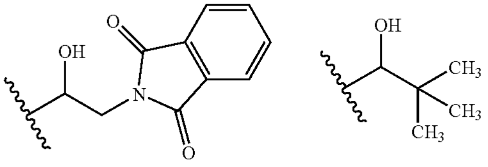
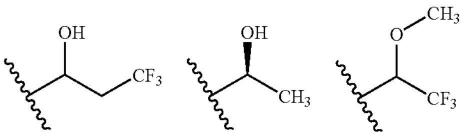

-continued
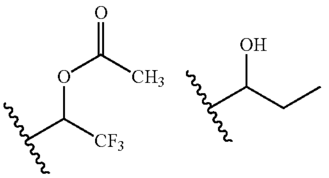
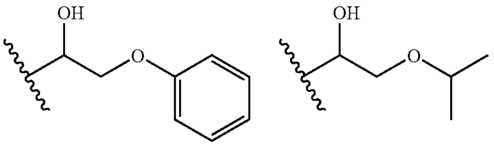
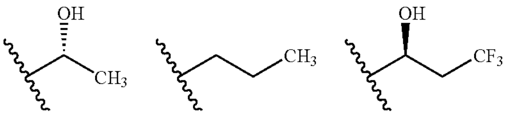
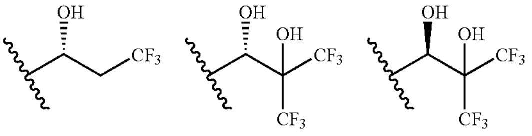
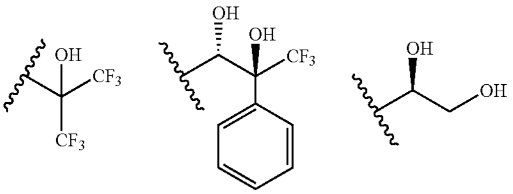
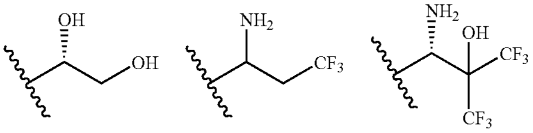
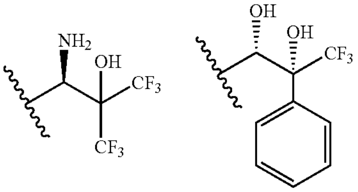
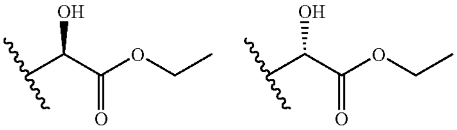
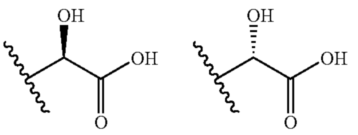
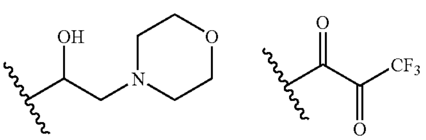
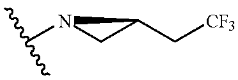 or 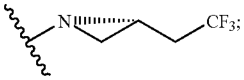
(h) —C(S)$R_3$ wherein the $R_3$ is:
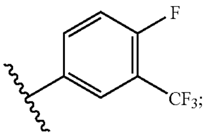
(i) —C(=N$R_3$)Oalkyl wherein the $R_3$ is:
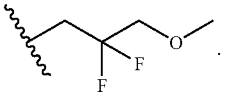
Also in accordance with the present invention, compounds of Formula Ia are provided wherein:
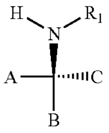
Ia
or stereoisomers or prodrugs or pharmaceutically acceptable salt forms thereof, wherein:
A is:
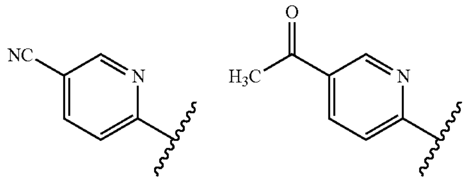
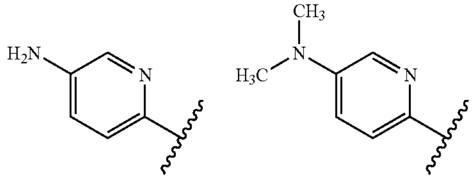
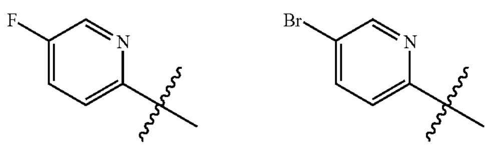
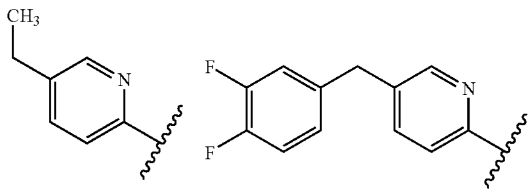

-continued
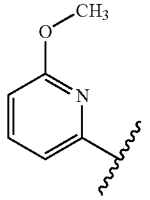 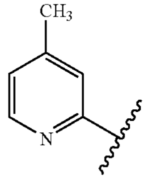 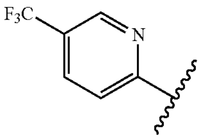
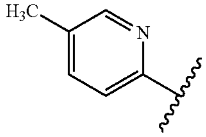 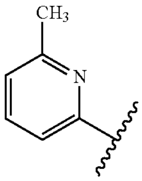 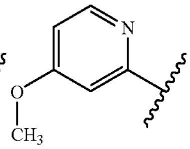
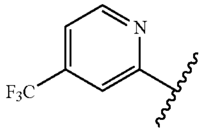 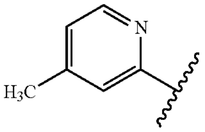
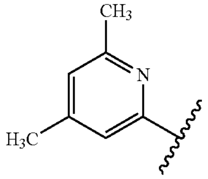 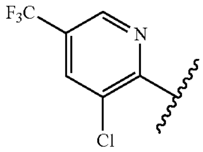
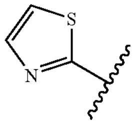 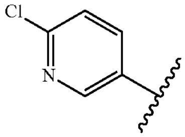
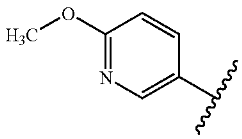 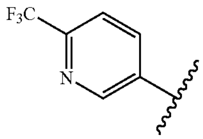
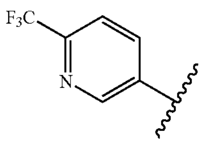 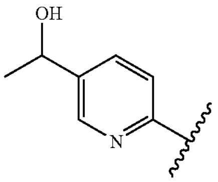
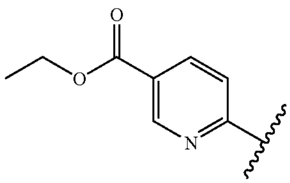 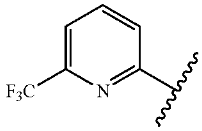
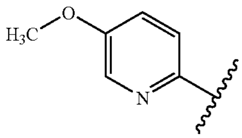 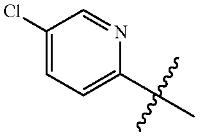
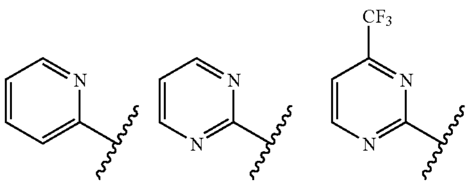
-continued
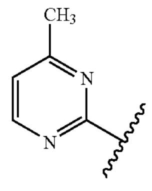 or 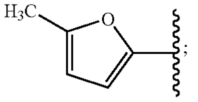
B is:
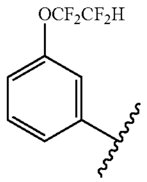 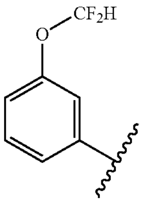 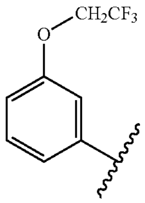
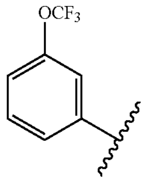 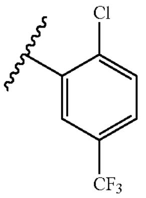
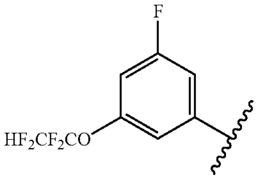 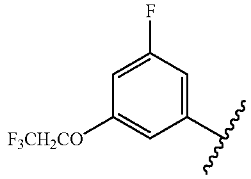
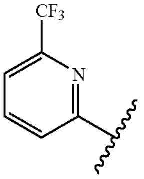 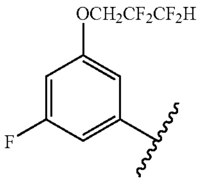 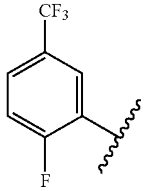
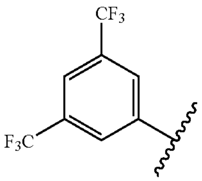 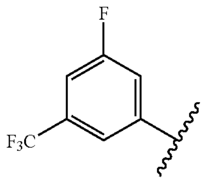
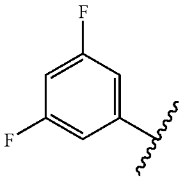 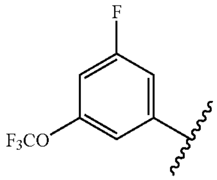
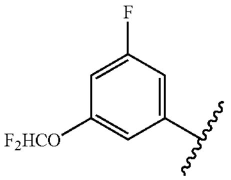 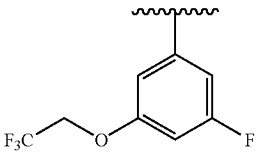

-continued
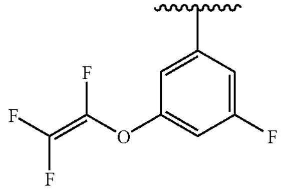
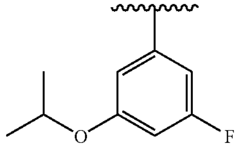
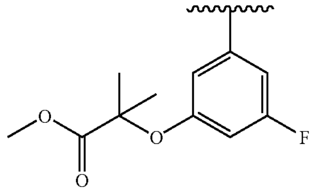
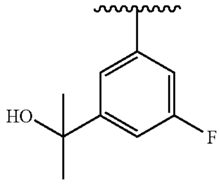
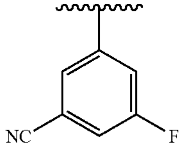
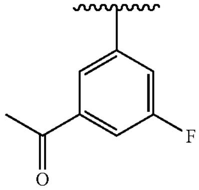
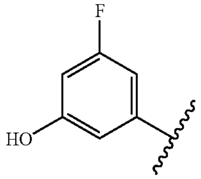
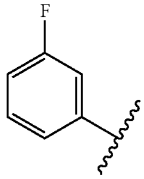
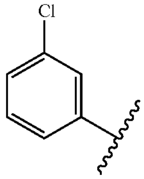
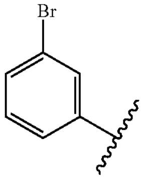
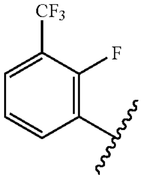
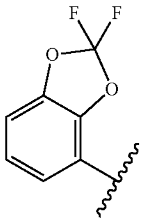
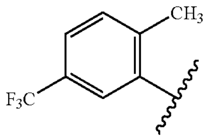
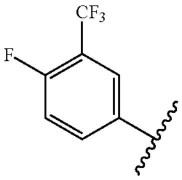
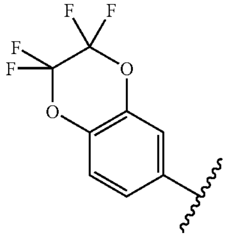
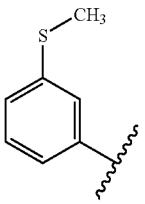
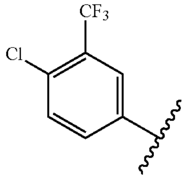
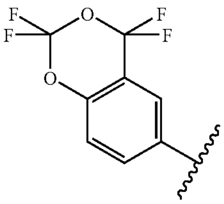
-continued
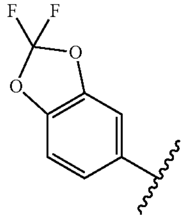
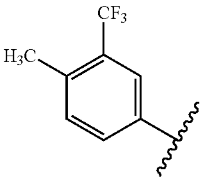
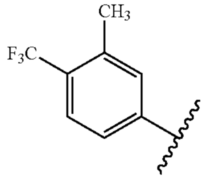
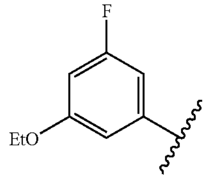
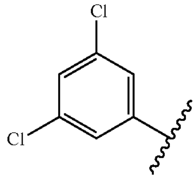
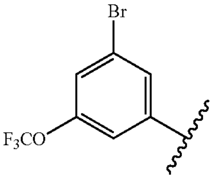
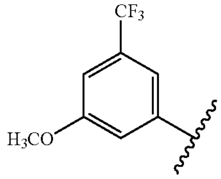
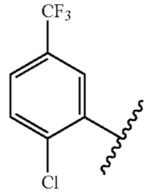
or
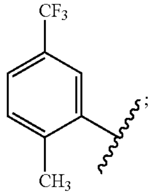
C is:
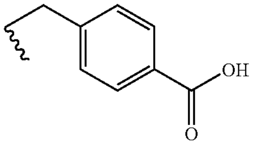
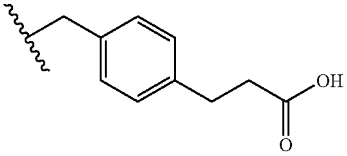
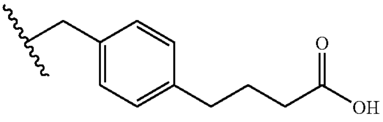
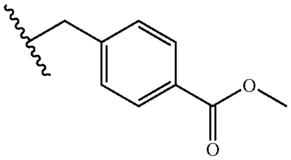

-continued
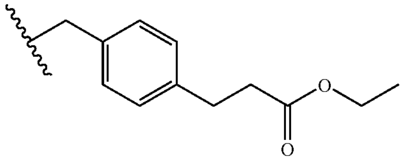
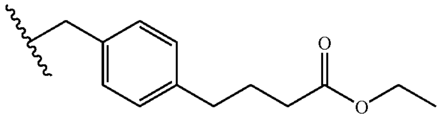
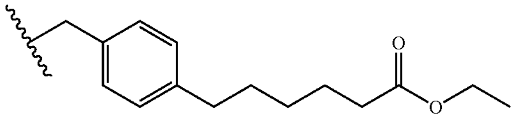
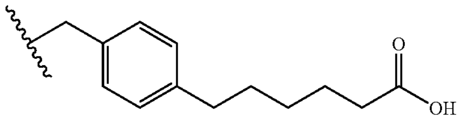
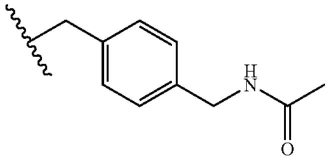
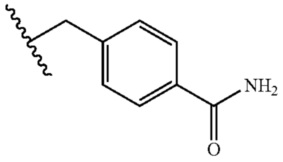
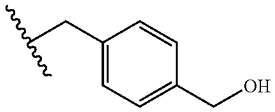
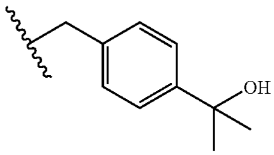
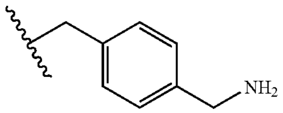
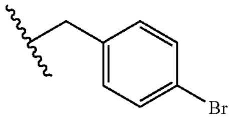
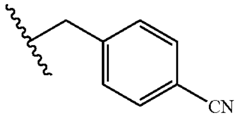
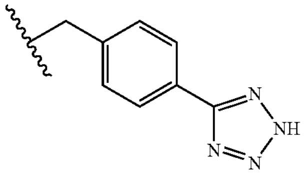
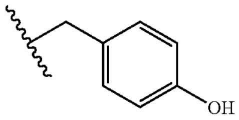
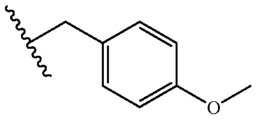
-continued
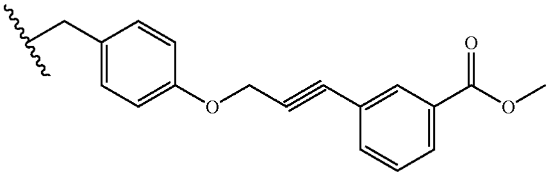
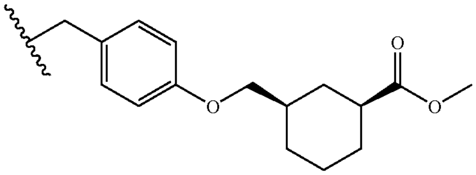
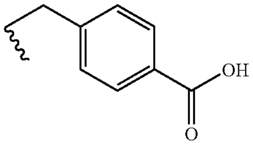
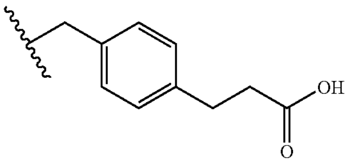
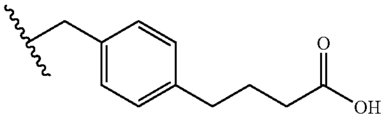
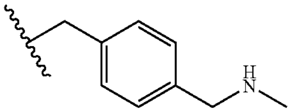
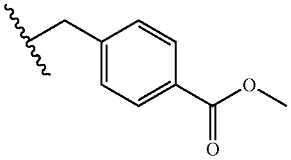
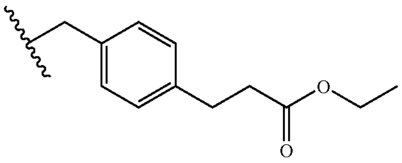
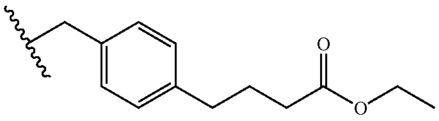
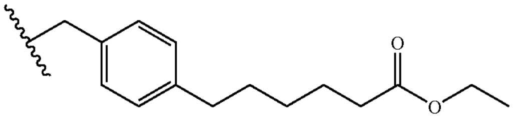
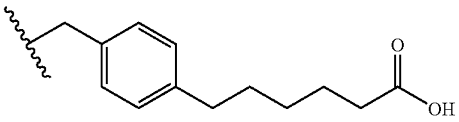

-continued
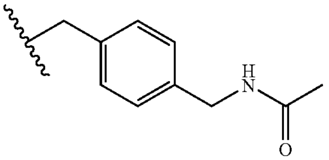
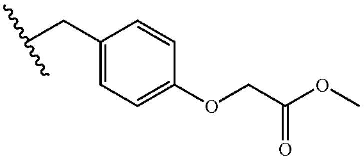
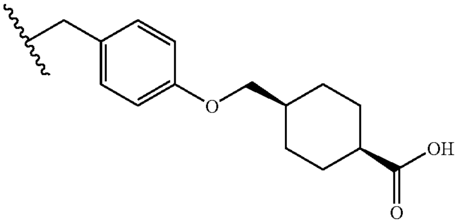
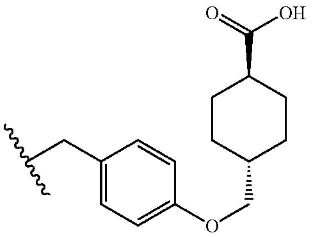
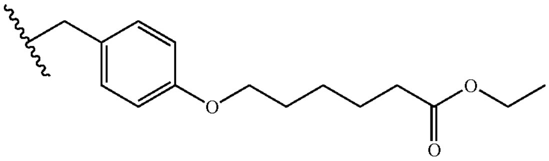
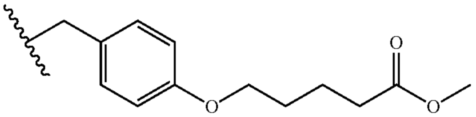
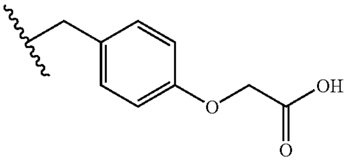
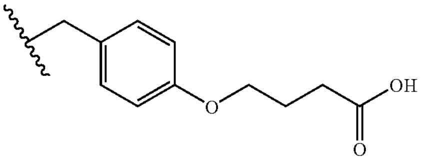
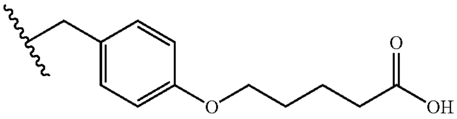
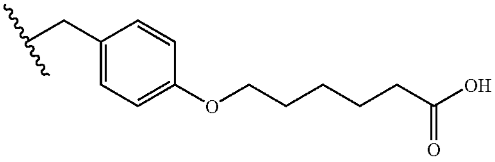
-continued
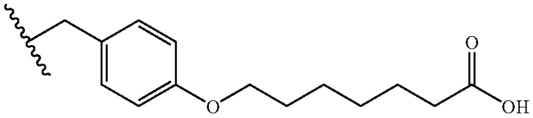
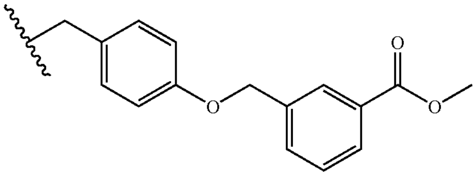
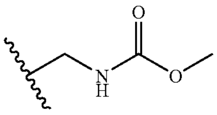 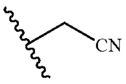 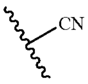
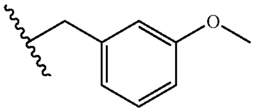 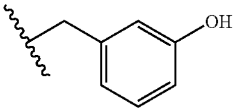
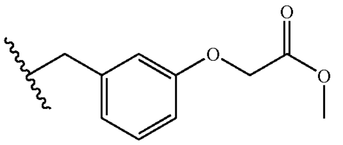
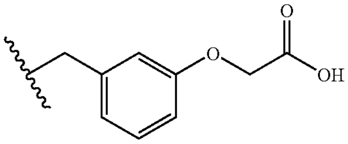
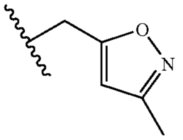 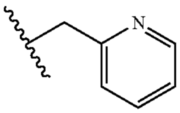
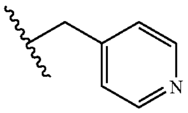 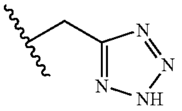
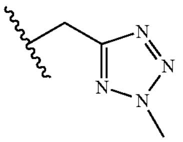 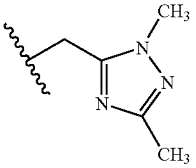
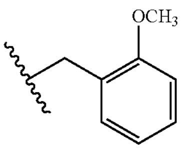 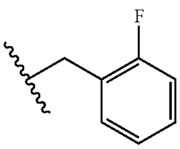
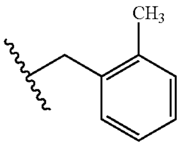 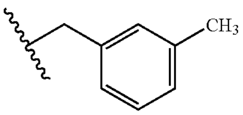
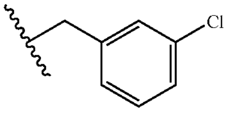 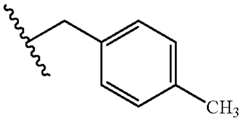

-continued
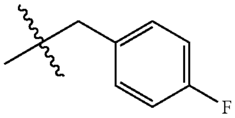
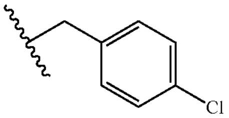
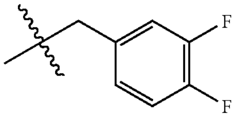
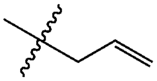
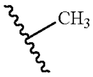
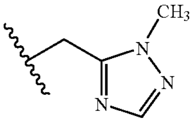
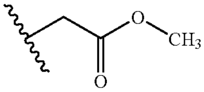
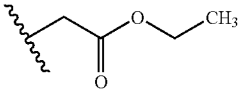
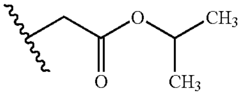
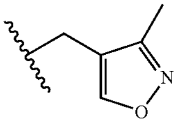
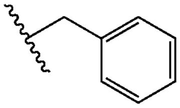
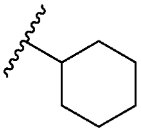
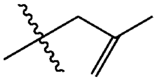
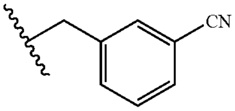
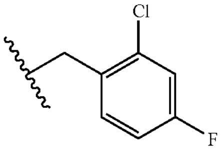
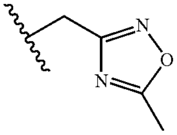
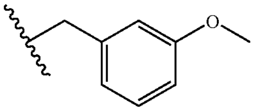
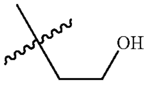
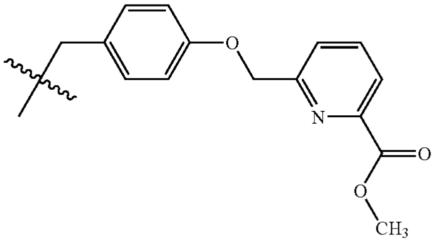
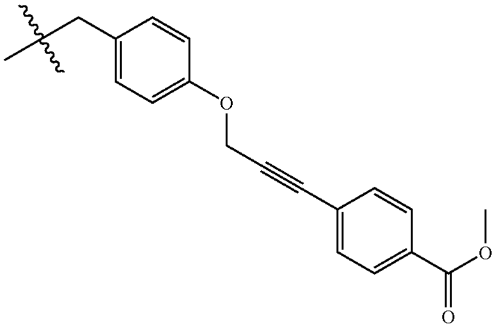
-continued
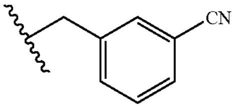
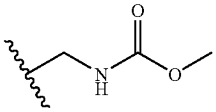
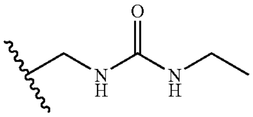
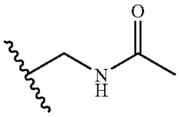
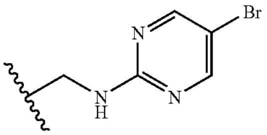
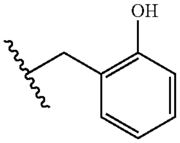
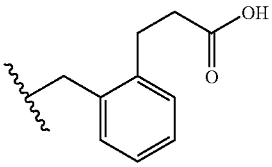
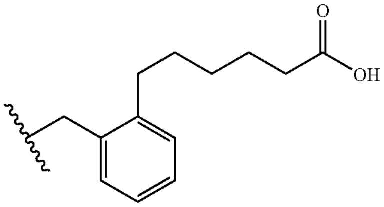
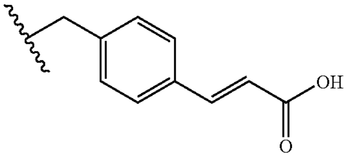
or
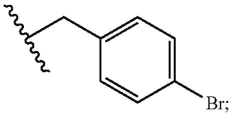
$R_1$ is H or:
(a) —C(O)$R_3$, wherein $R_3$:
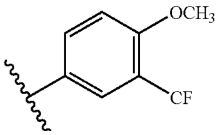
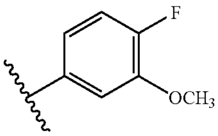
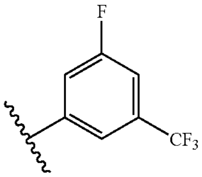
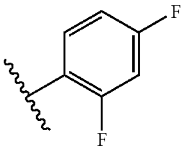
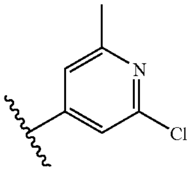
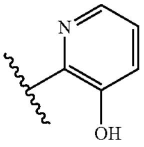

-continued
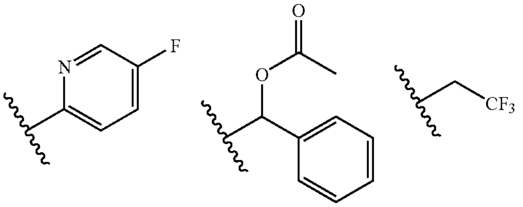
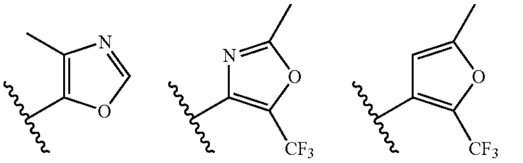
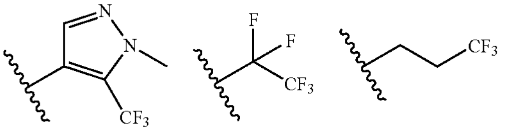
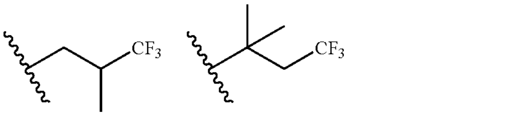
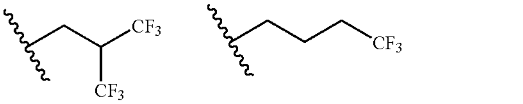
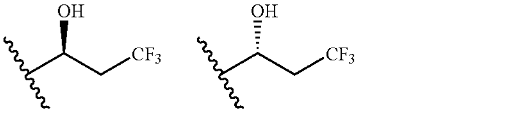
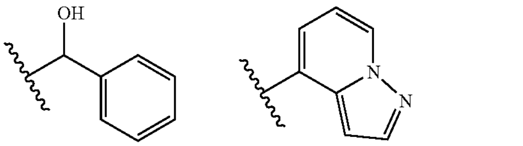
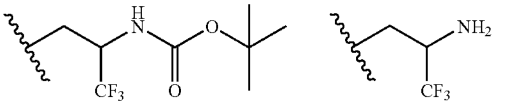
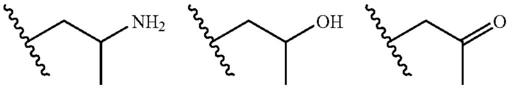
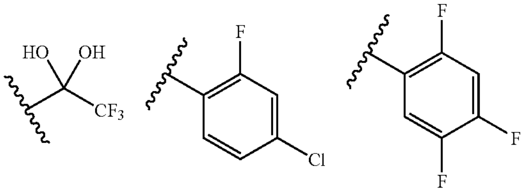
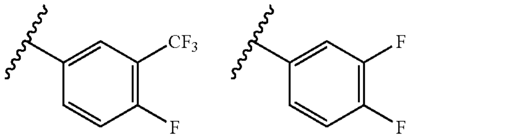
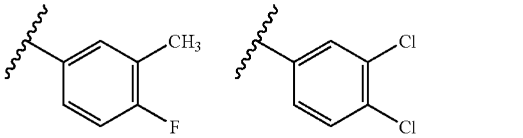
-continued
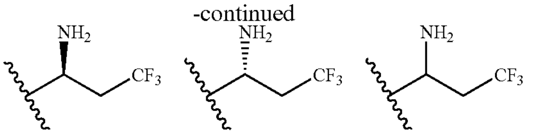
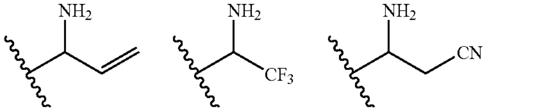
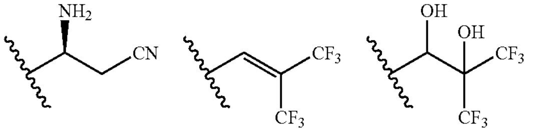
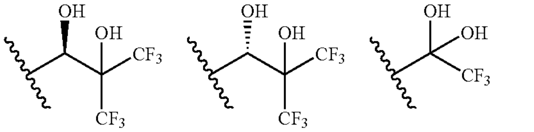
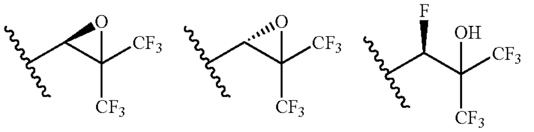
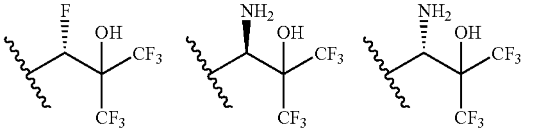
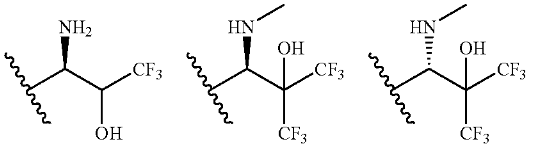
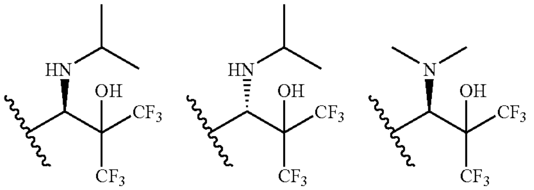
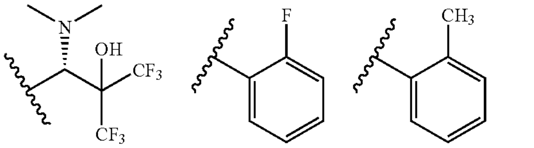
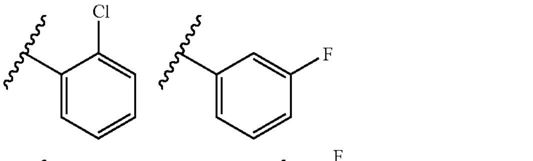
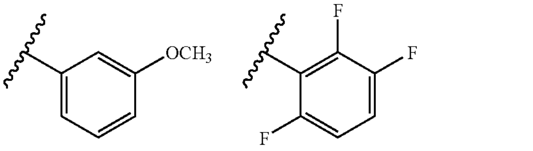
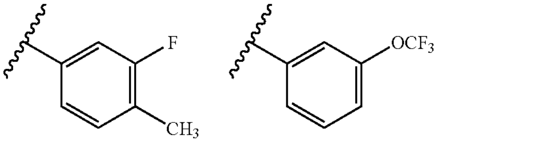

-continued
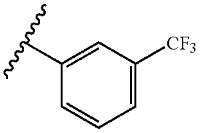
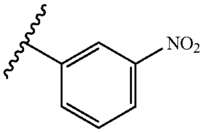
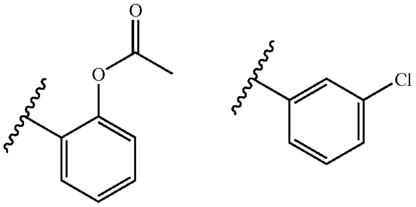
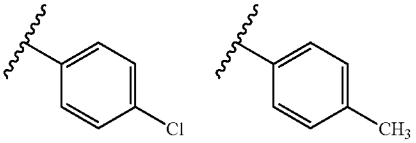
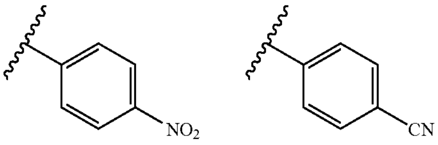
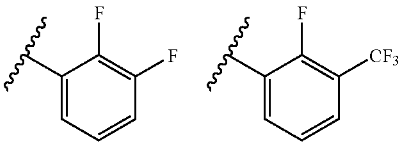
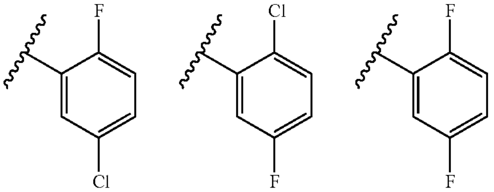
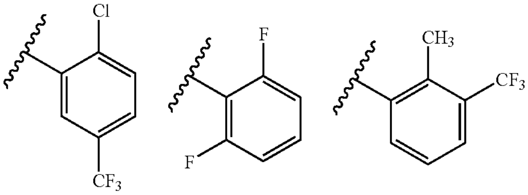
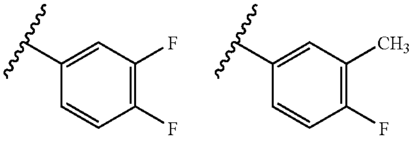
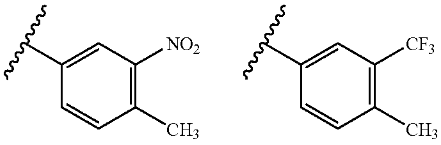
-continued
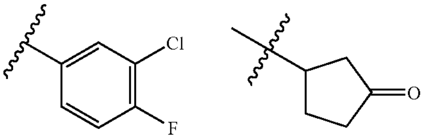
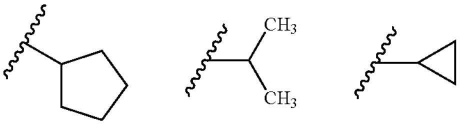
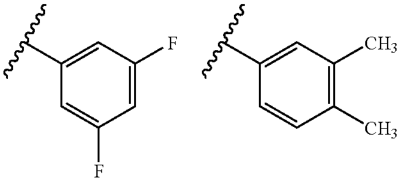
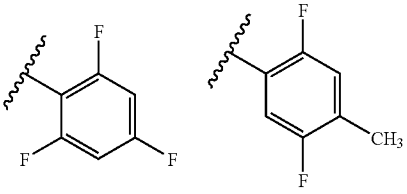
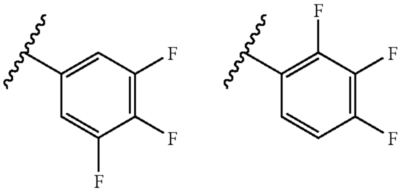
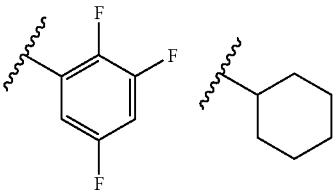
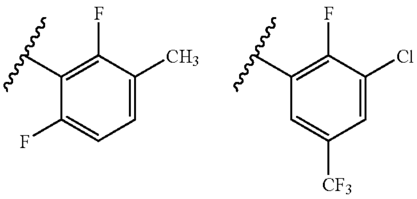
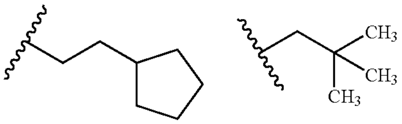
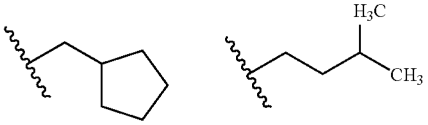
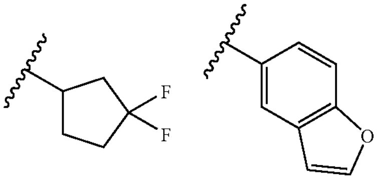

-continued
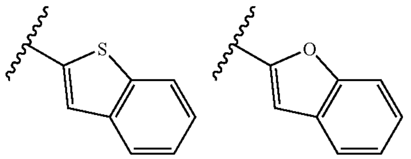
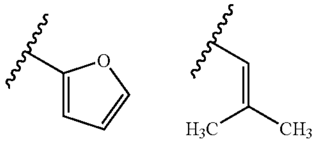
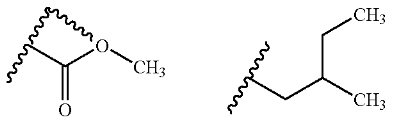
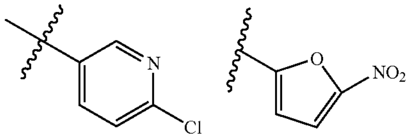
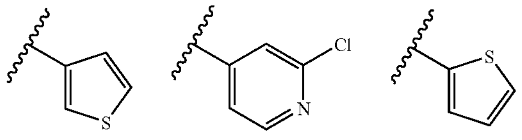
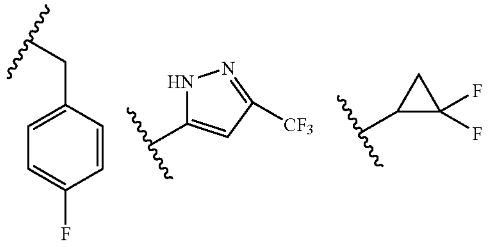
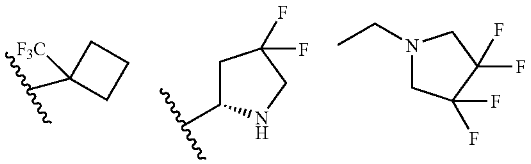
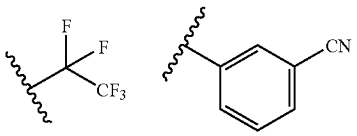
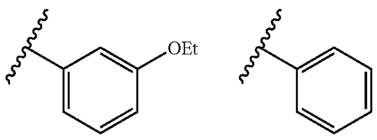
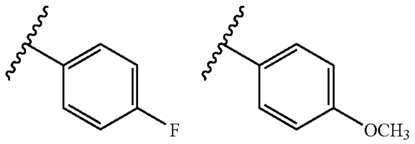
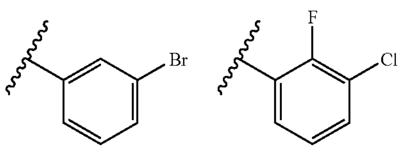
-continued
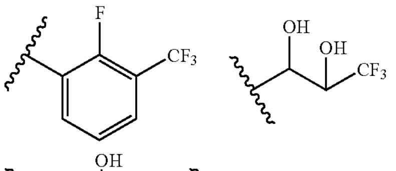
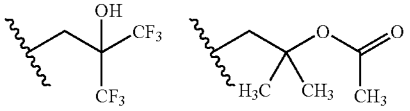
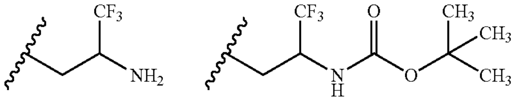
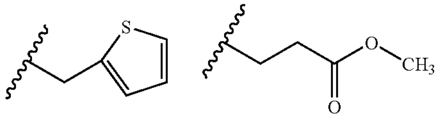
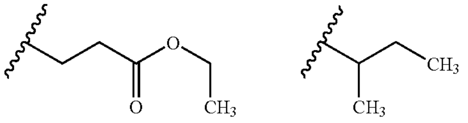
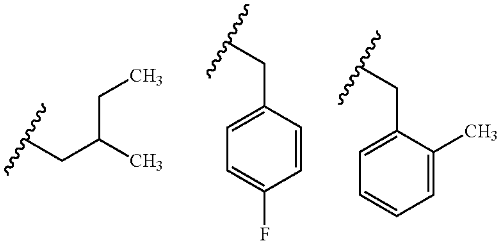
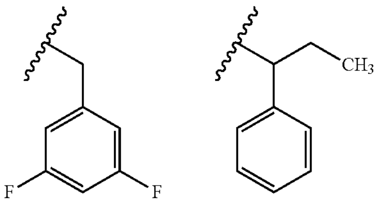
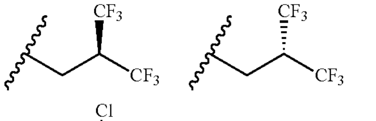
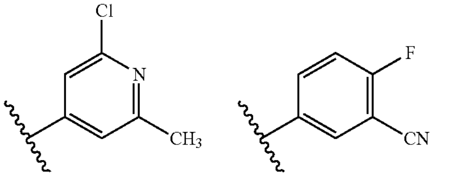
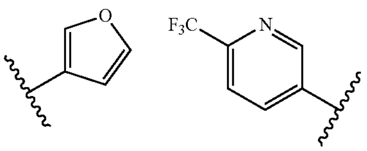
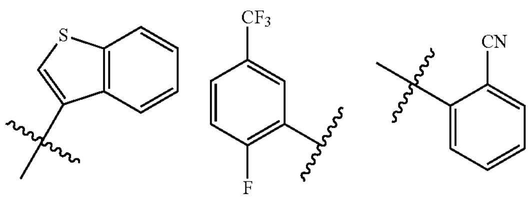

-continued
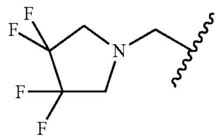
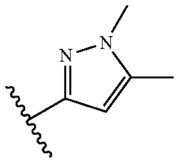
or
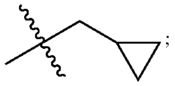
(b) —C(O)NHR$_3$, wherein the R$_3$ is:
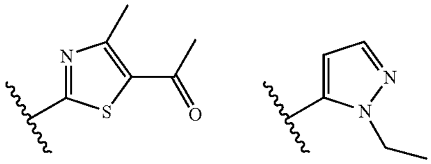
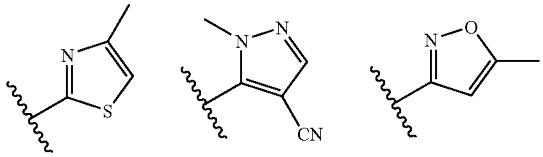
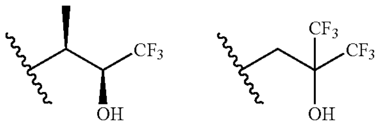
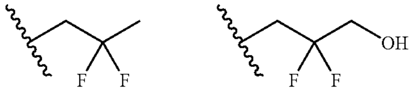
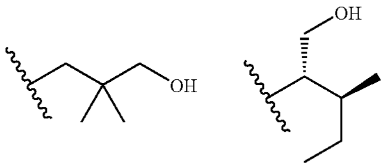
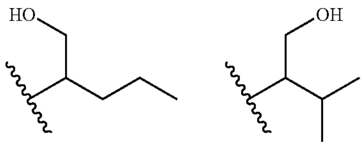
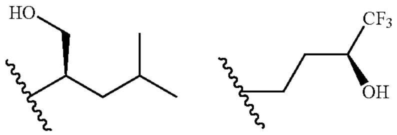
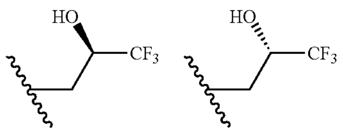
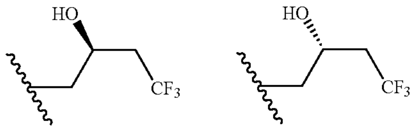
-continued
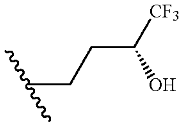
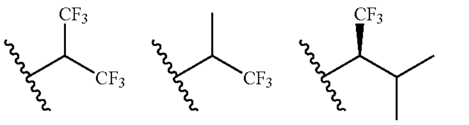
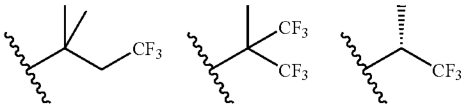
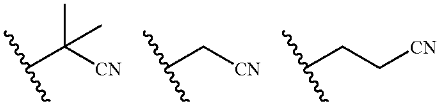
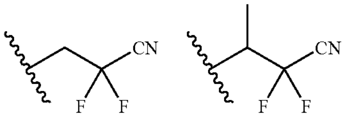
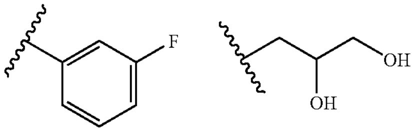
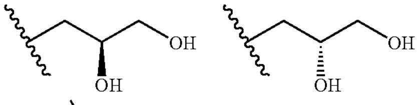
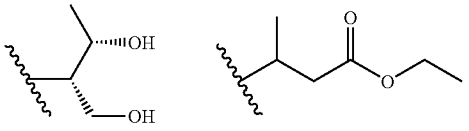
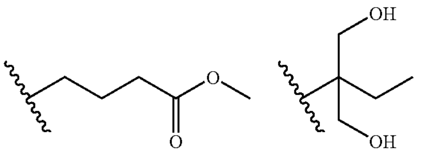
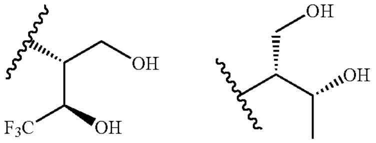
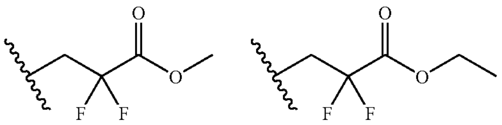
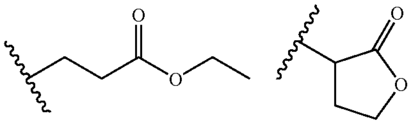
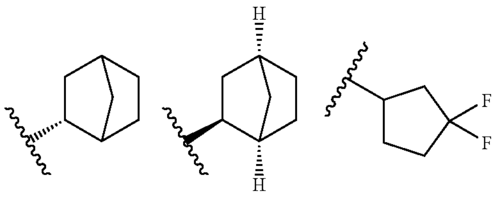

-continued
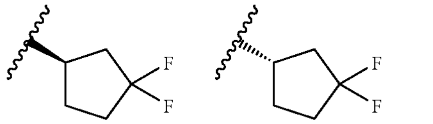
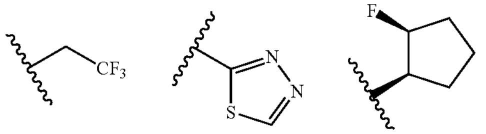
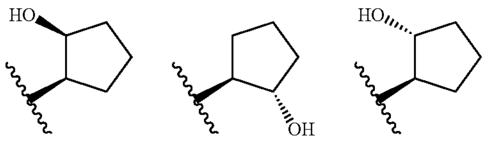
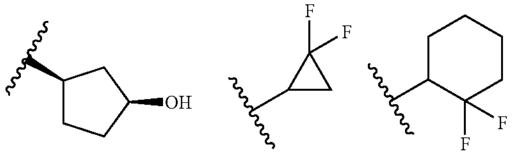
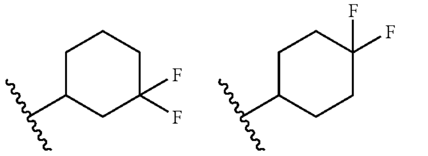
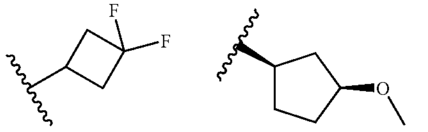
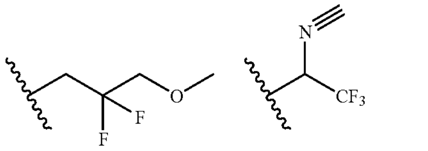
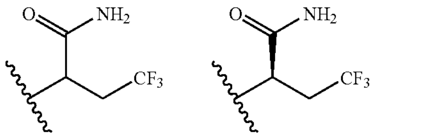
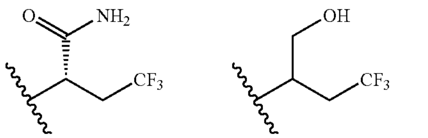
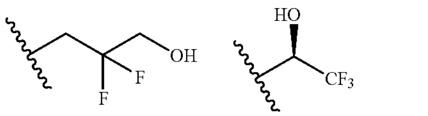
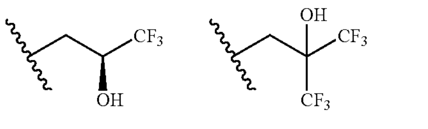
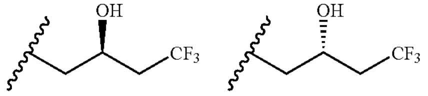
-continued
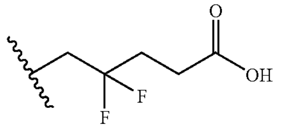
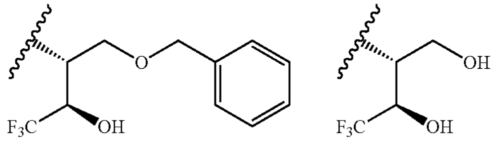
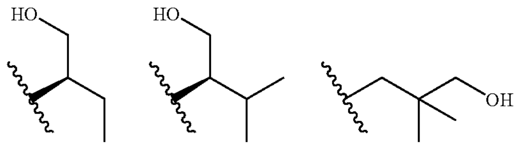
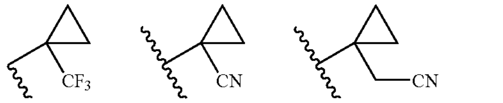
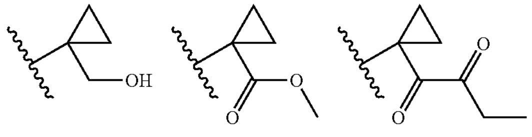
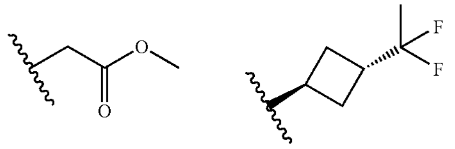
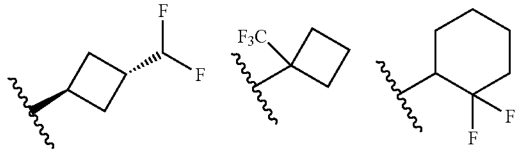
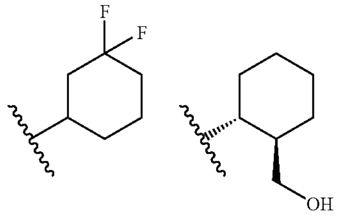
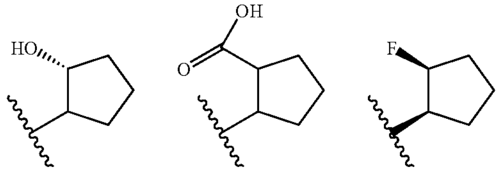
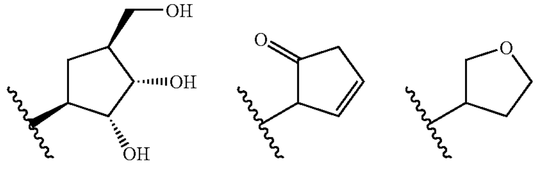
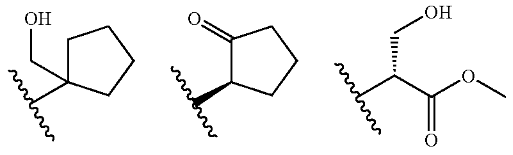

-continued
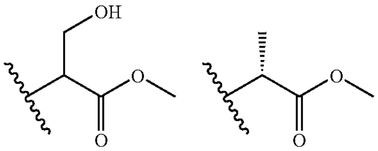
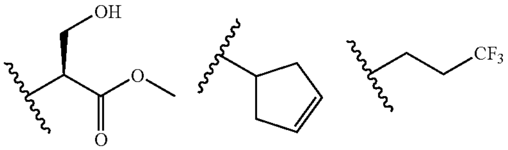
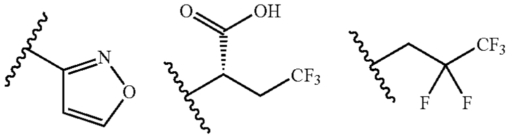
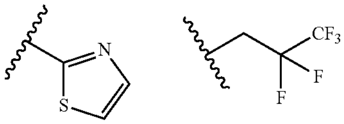
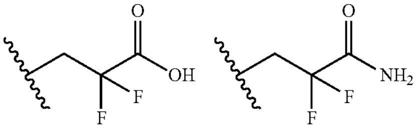
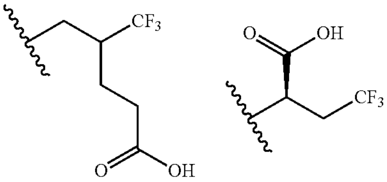
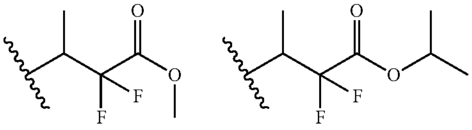
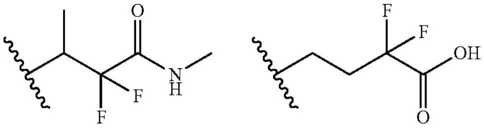
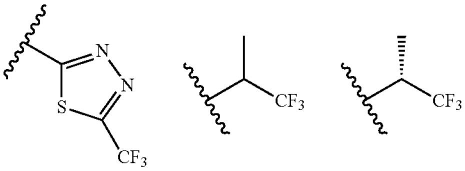
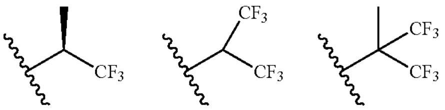
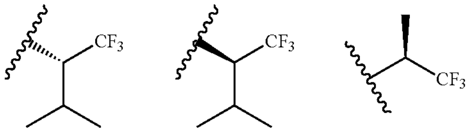
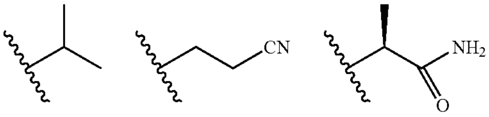
-continued
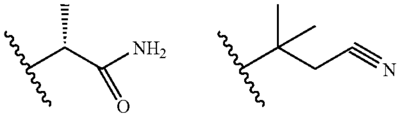
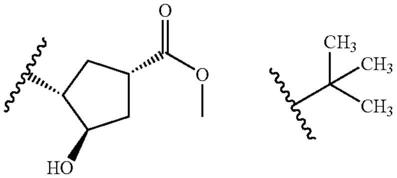
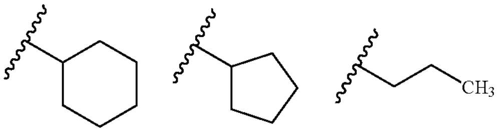
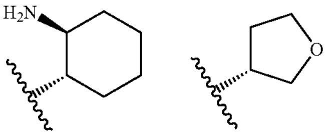
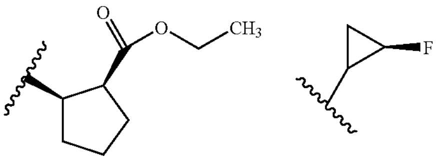
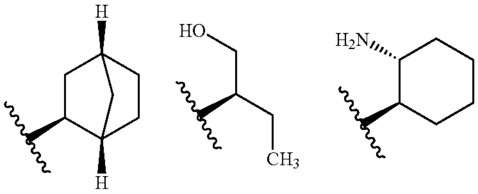
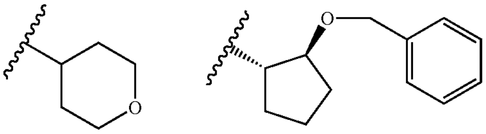
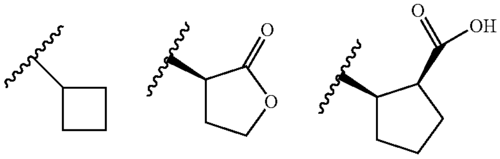
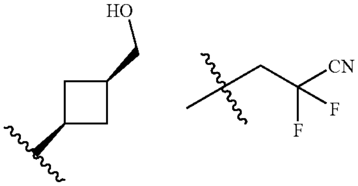
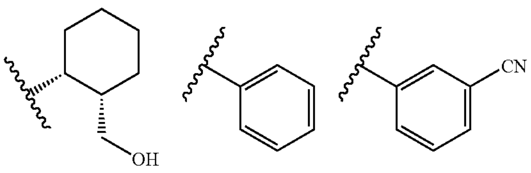

-continued
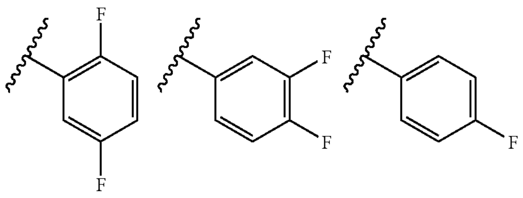
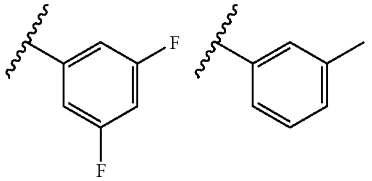
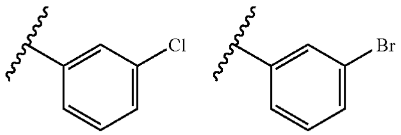
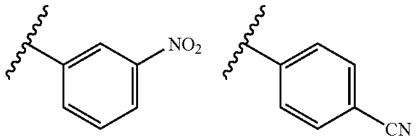
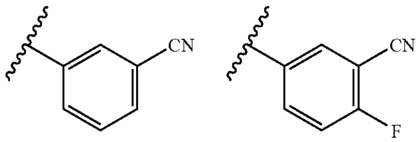
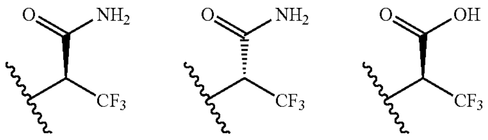
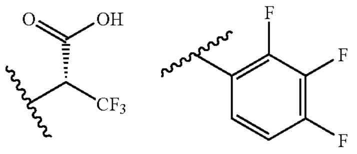
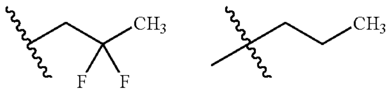
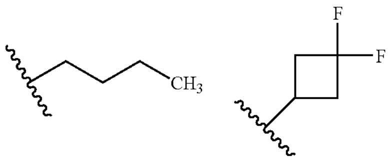
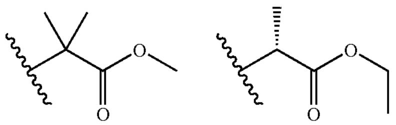
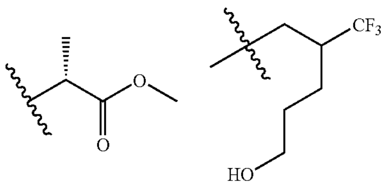
-continued
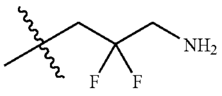
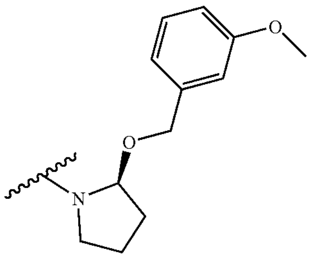
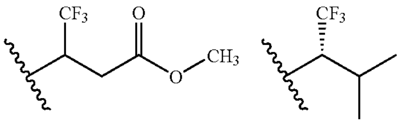
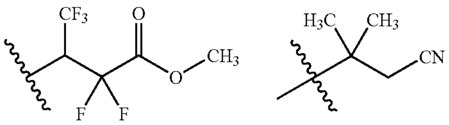
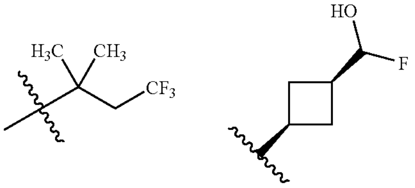
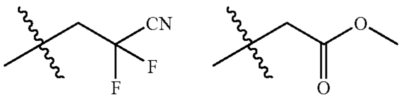
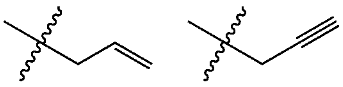
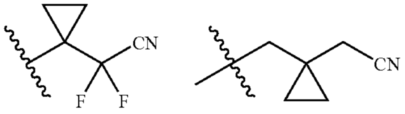
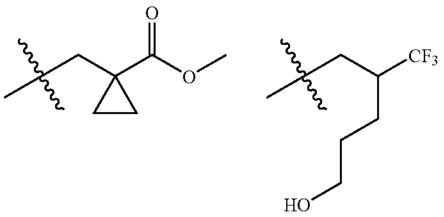
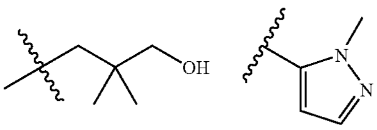

-continued
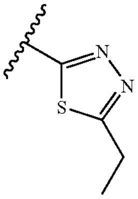
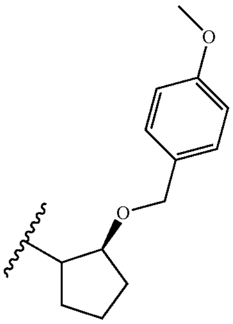
or
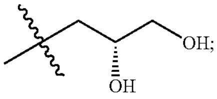
(c) —C(O)$NR_2R_3$, wherein the $NR_2R_3$ is:
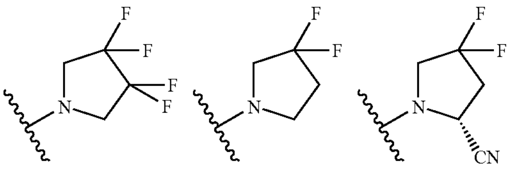
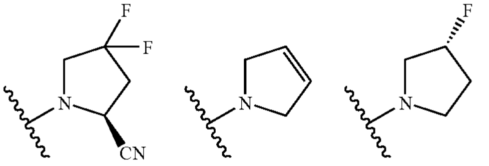
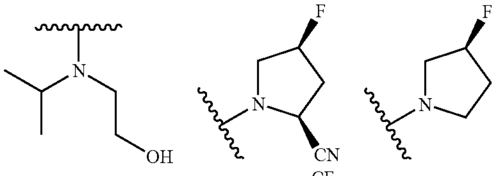
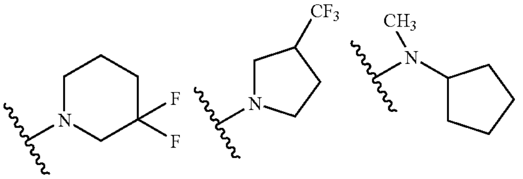
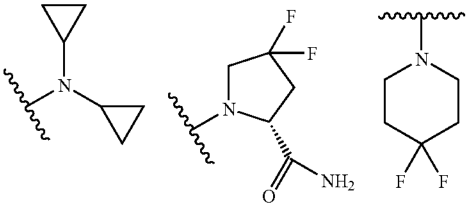
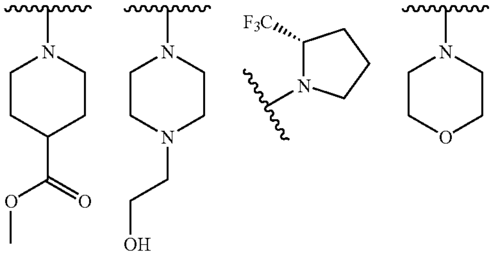
-continued
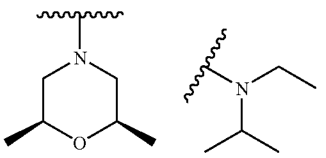
or
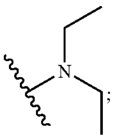
(d) —C(O)$OR_4$ wherein the $R_4$ is:
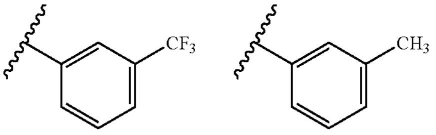
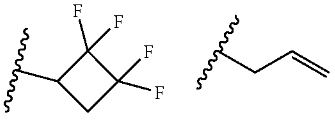
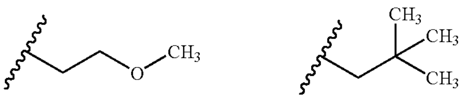
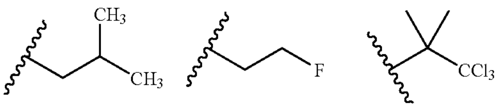
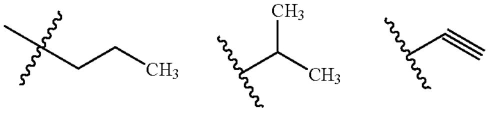
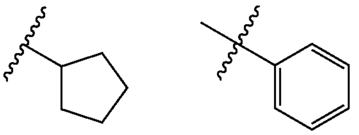
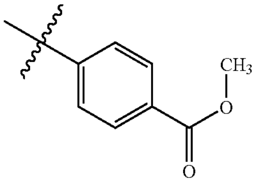
or
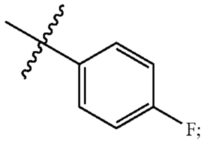
(e) —$SO_2R_5$ wherein the $R_5$ is:
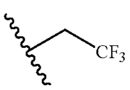
or
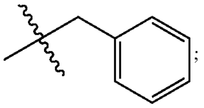
(f) —CSNHR$_7$ wherein the $R_7$ is:
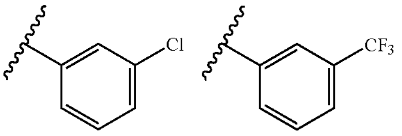
or -continued
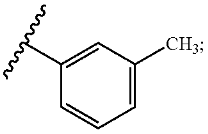
(g) $—CH_2R_8$ wherein the $R_8$ is:
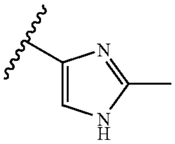 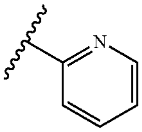 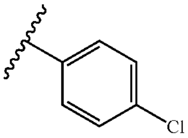
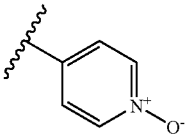 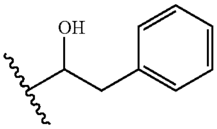
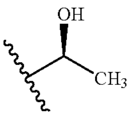 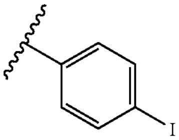
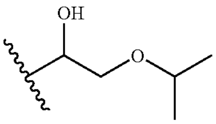 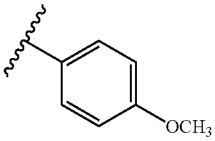
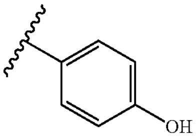 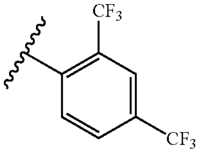
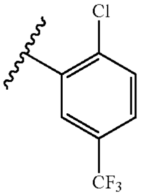 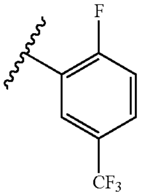 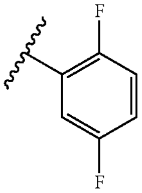
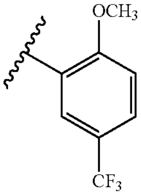 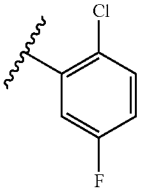 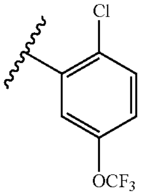
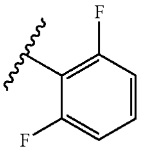 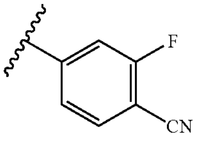
-continued
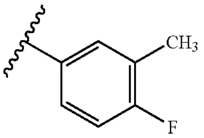 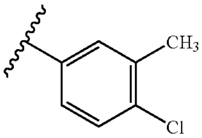
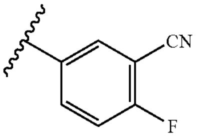 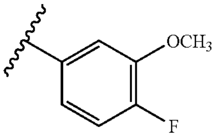
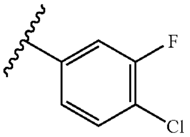 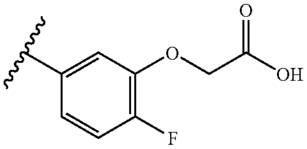
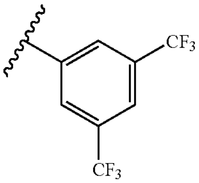 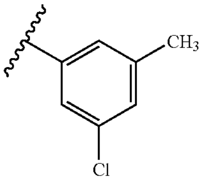
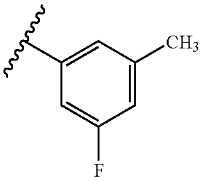 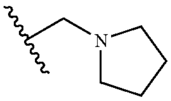 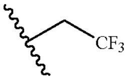
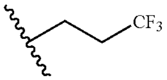 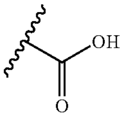 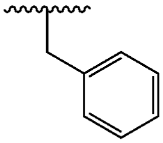
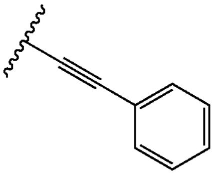 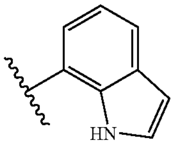
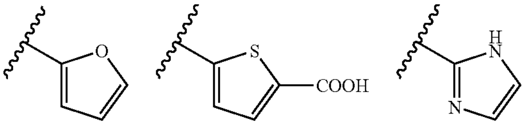
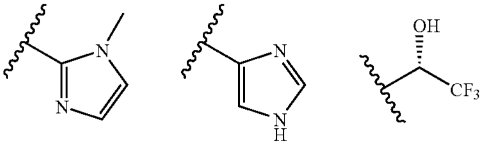
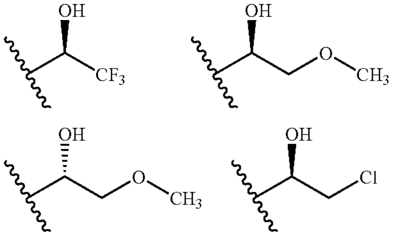

-continued
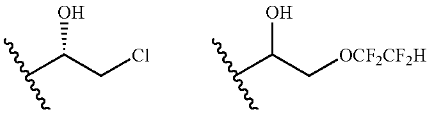
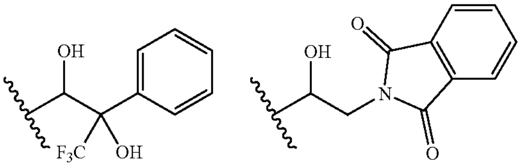
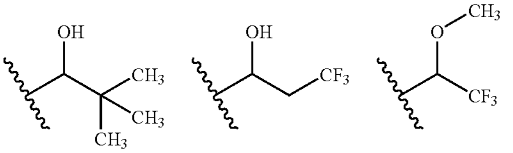
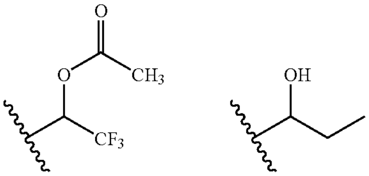
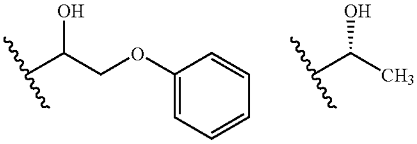
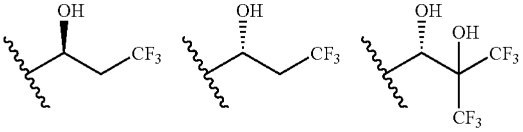
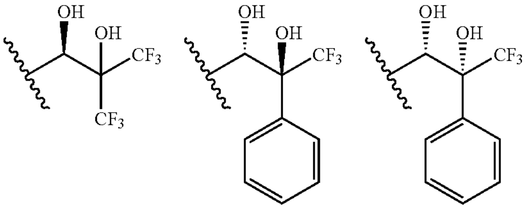
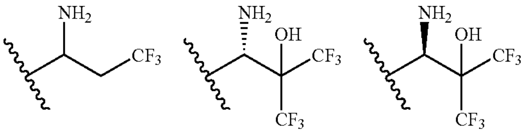
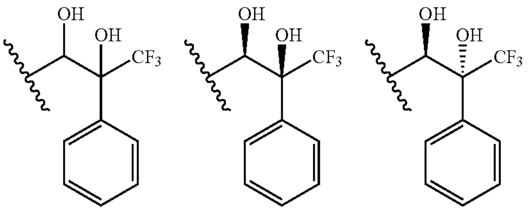
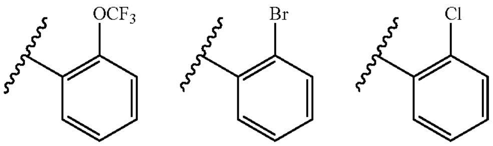
-continued
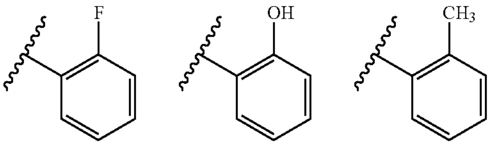
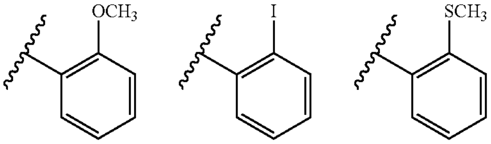
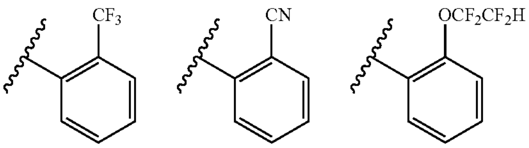
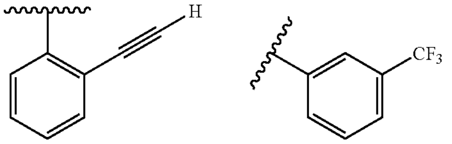
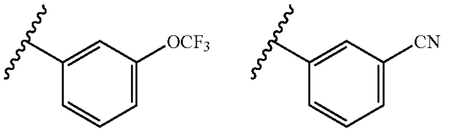
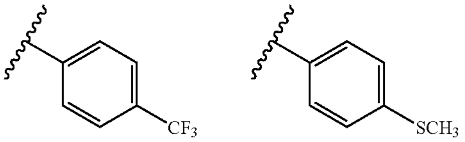
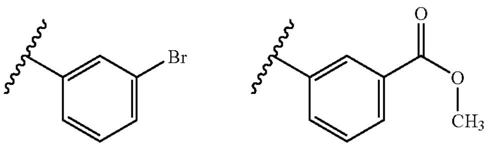
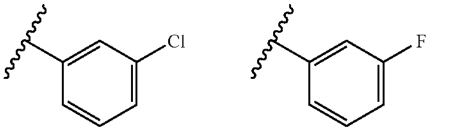
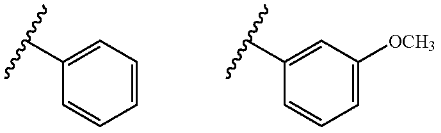
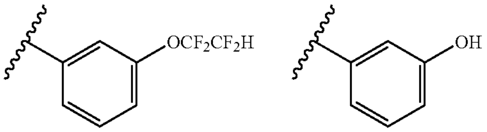
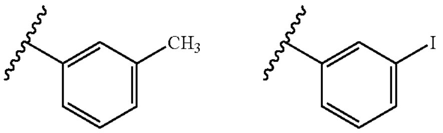

-continued
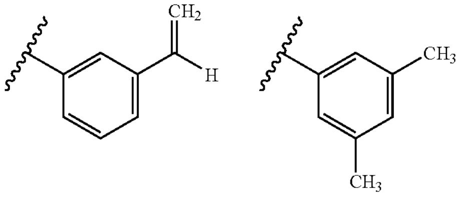
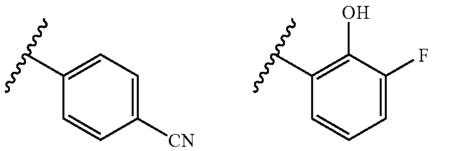
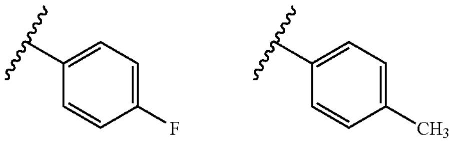
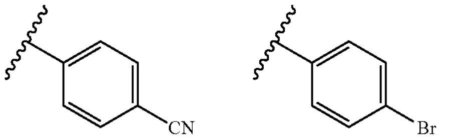
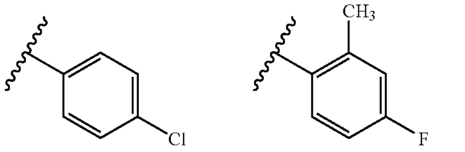
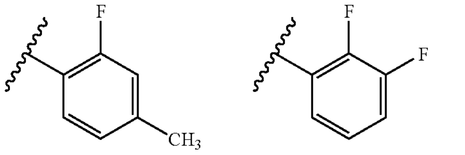
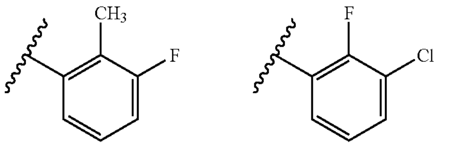
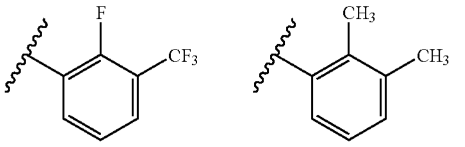
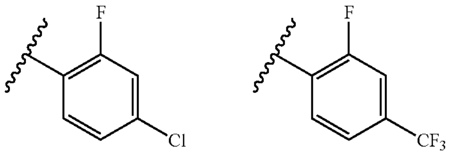
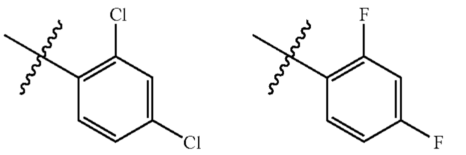
-continued
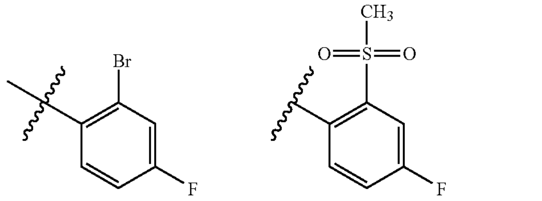
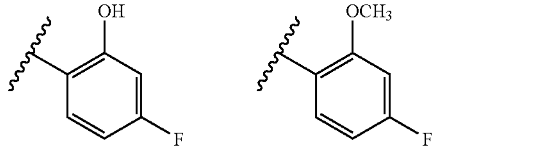
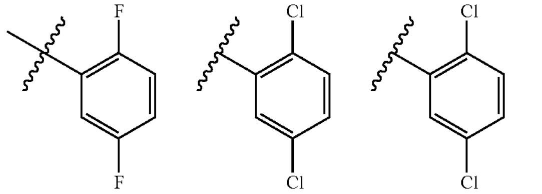
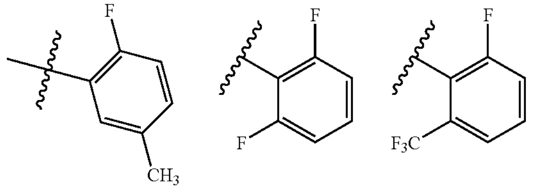
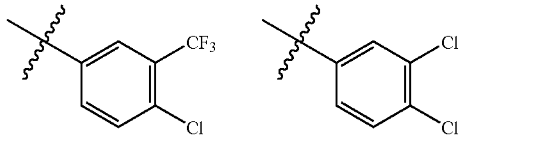
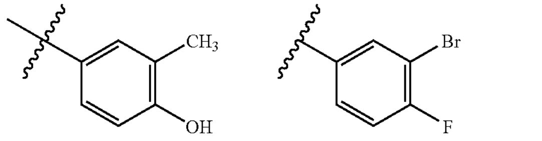
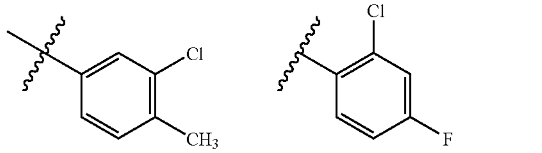
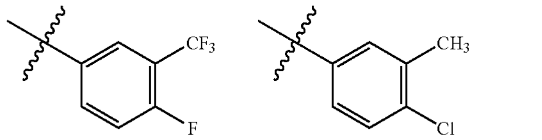
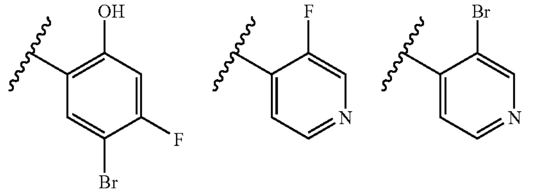
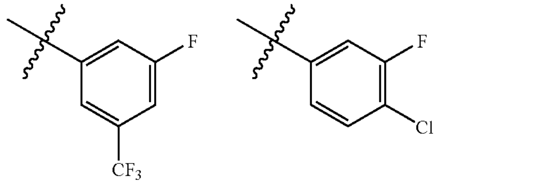

-continued
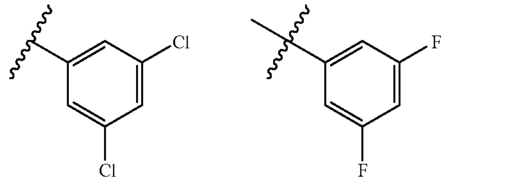
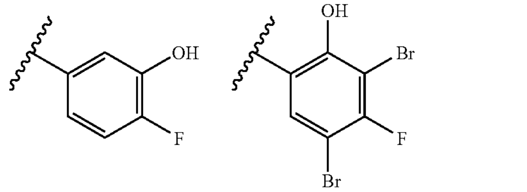
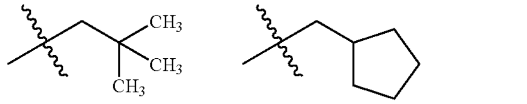
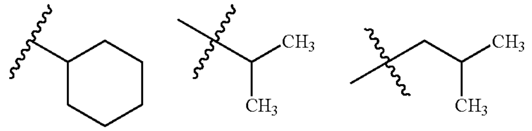
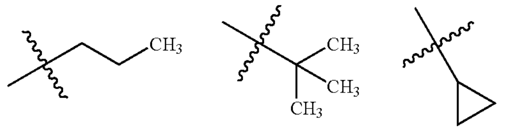
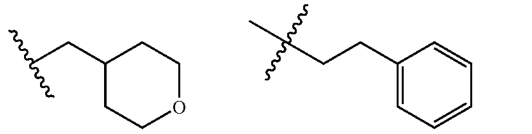
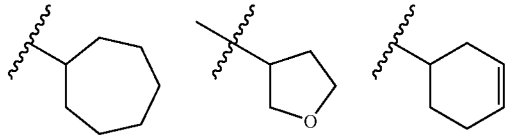
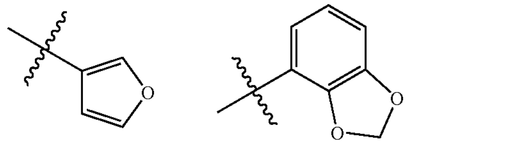
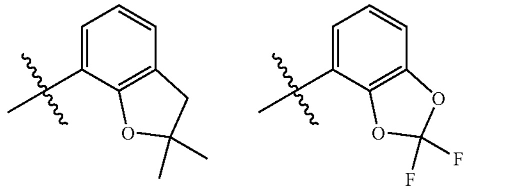
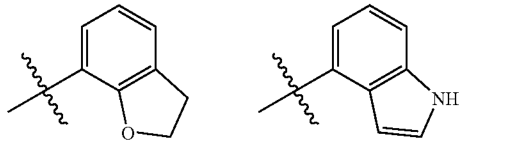
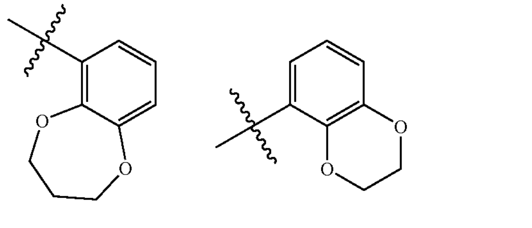
-continued
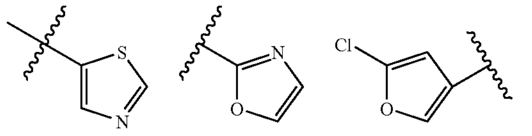
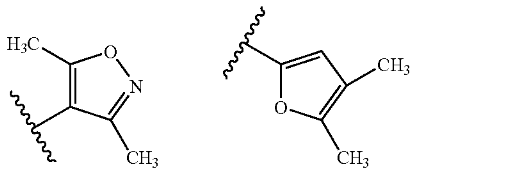
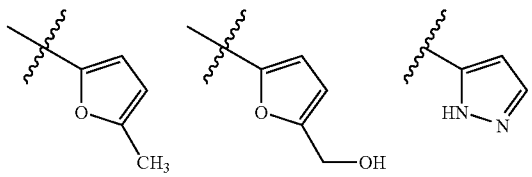
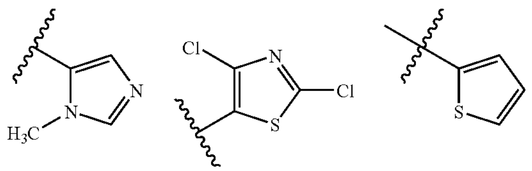
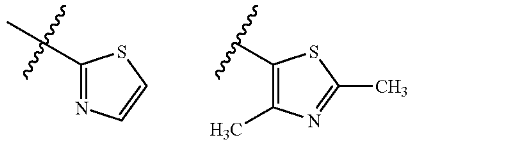
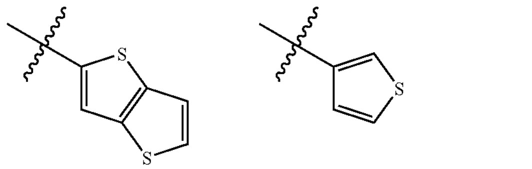
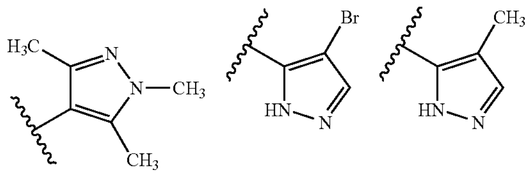
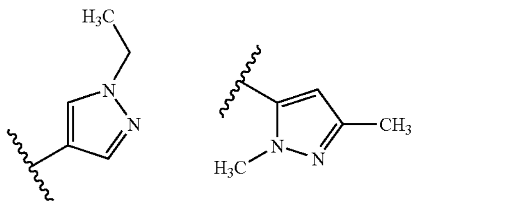
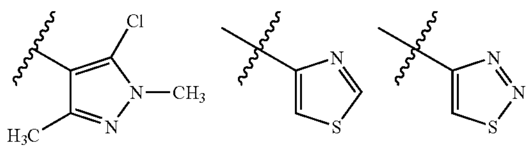
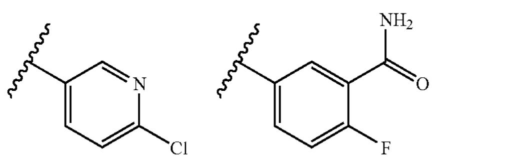

-continued
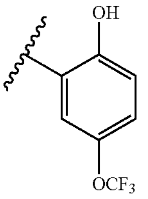
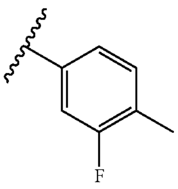
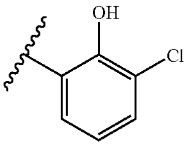
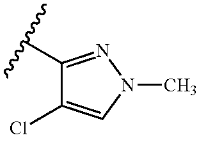
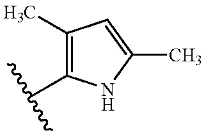
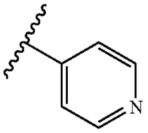
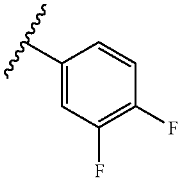
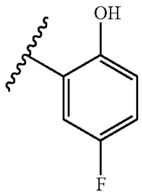
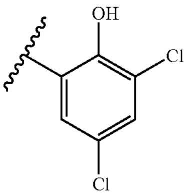
or
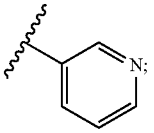
(h) —$C(S)R_3$, wherein $R_3$:
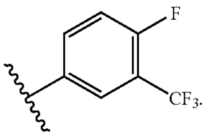
In another embodiment, compounds of formula Ib are provided wherein:
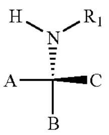
Ib
or stereoisomers or prodrugs or pharmaceutically acceptable salt forms thereof, wherein:
A is:
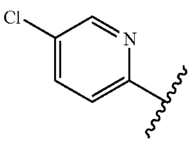
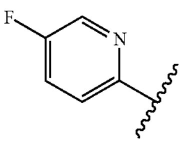
or
-continued
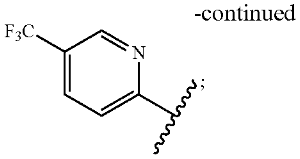
B is:
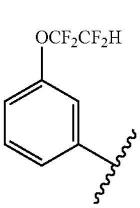
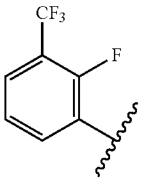
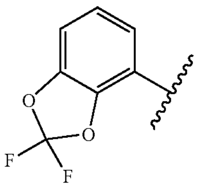
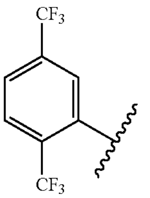
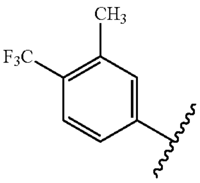
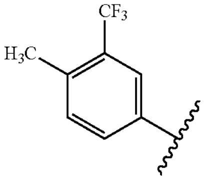
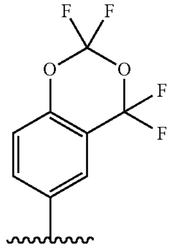
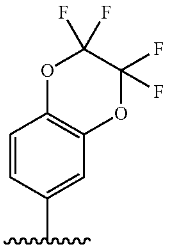
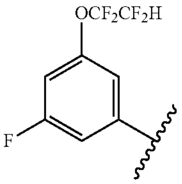
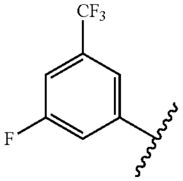
or
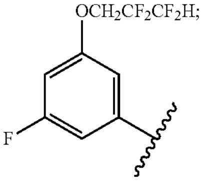
C is:
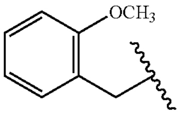
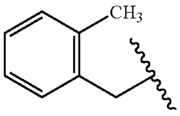
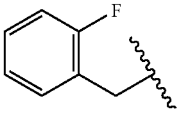
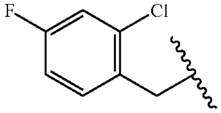

-continued
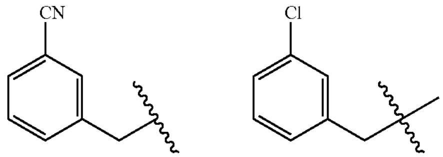
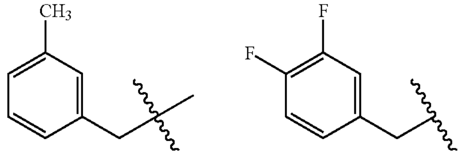
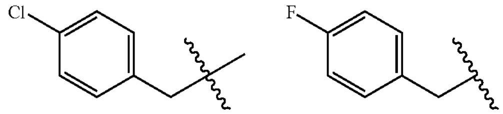
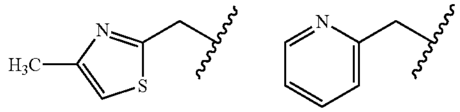
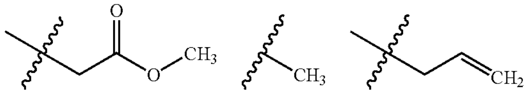
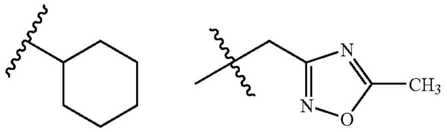
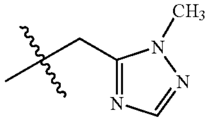
or
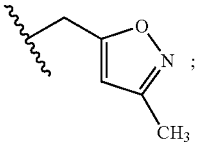
;
$R_1$ is:
(a) —$C(O)R_3$, wherein $R_3$:
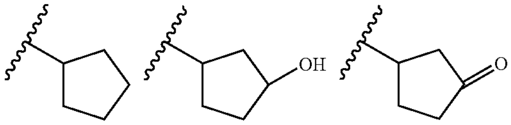
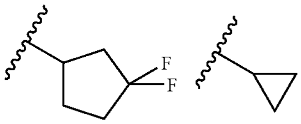
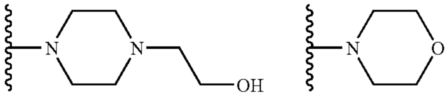
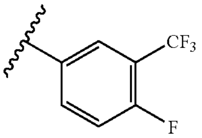
or
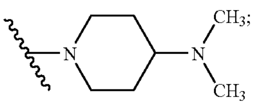
(b) —$C(O)NHR_3$, wherein the $R_3$ is:
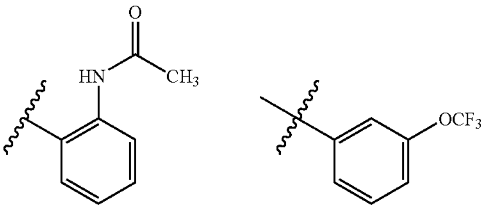
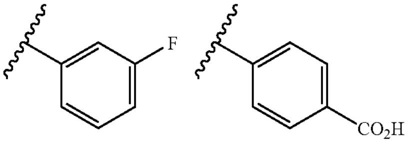
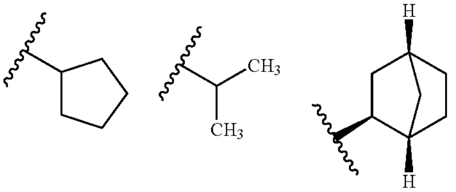
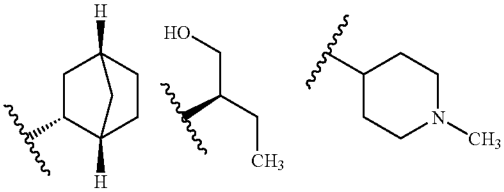
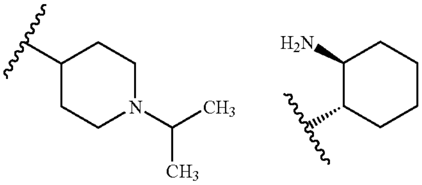
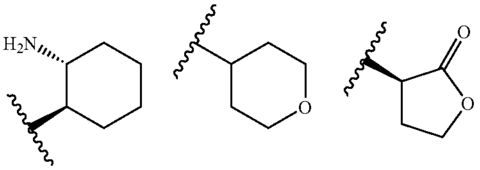
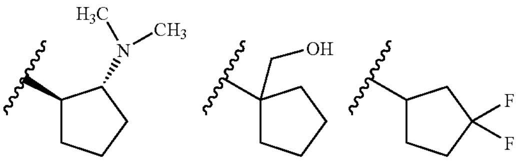
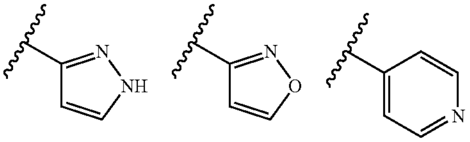
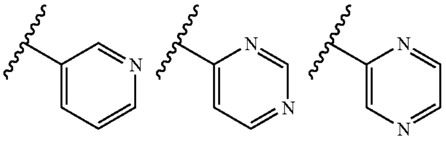
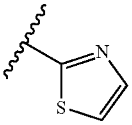
or
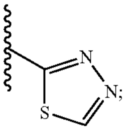

(c) —$C(O)NR_2R_3$, wherein the —$NR_2R_3$ moiety is:

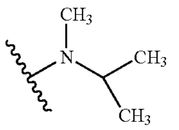

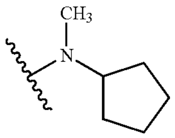

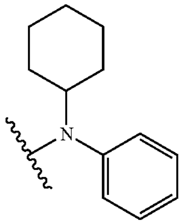

or

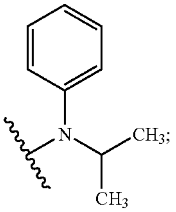

(d) —$C(O)OR_4$, wherein $R_4$ is:

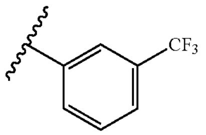

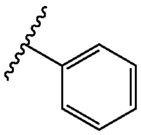

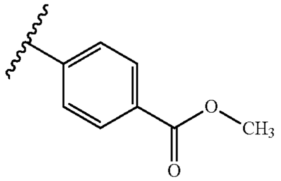

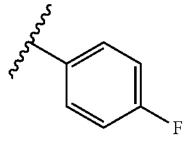

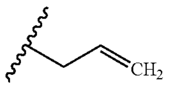

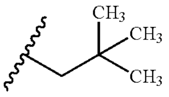

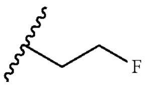

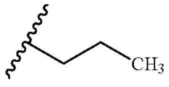

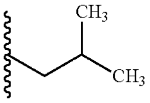

or

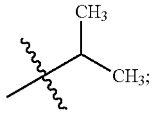

or (e)

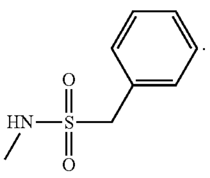

In another embodiment, compounds of the present invention are selected from the compounds exemplified in the examples.

In yet another embodiment, pharmaceutical compositions comprised of compounds of the present invention alone or in combination with a pharmaceutically acceptable carrier and/or at least one additional therapeutic agent.

In still yet another embodiment, methods of inhibiting the cholesteryl ester transfer protein comprising administering to a mammal in need of treatment a compound and/or pharmaceutical composition of the present invention are provided.

In one embodiment, methods for treating, preventing or slowing the progression of Alzheimer's, atherosclerosis, venous thrombosis, coronary artery disease, coronary heart disease, coronary vascular disease, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia in a mammal (including a human being either male or female) by administering to a mammal in need of such treatment an atherosclerosis, peripheral vascular disease, dyslipidemia, hyperbetalipoproteinemia, hypoalphalipoproteinemia, hypercholesterolemia, hypertriglyceridemia, familial-hypercholesterolemia, cardiovascular disorders, angina, ischemia, cardiac ischemia, stroke, myocardial infarction, reperfusion injury, angioplastic restenosis, hypertension, vascular complications of diabetes, obesity or endotoxemia treating, preventing or slowing amount of a compound and/or pharmaceutical composition of the present invention are provided.

In another embodiment, methods for treating, preventing or slowing the progression of atherosclerosis in a mammal by administering to a mammal in need of such treatment an atherosclerotic treating, preventing or slowing amount of a compound and/or pharmaceutical composition of the present invention are provided.

In another embodiment, methods for treating, preventing or slowing the progression of peripheral vascular disease in a mammal by administering to a mammal in need of such treatment a peripheral vascular disease treating, preventing or slowing amount of a compound and/or pharmaceutical composition of the present invention are provided.

In yet another embodiment, methods for treating, preventing or slowing the progression of dyslipidemia in a mammal by administering to a mammal in need of such treatment a dyslipidemia treating, preventing or slowing amount of a compound and/or pharmaceutical composition of the present invention are provided.

In still yet another embodiment, methods for treating, preventing or slowing the progression of hyperbetalipoproteinemia in a mammal by administering to a mammal in need of such treatment a hyperbetalipoproteinemia treating, preventing or slowing amount of a compound and/or pharmaceutical composition of the present invention are provided.

In one embodiment, methods for treating, preventing or slowing the progression of hypoalphalipoproteinemia in a mammal by administering to a mammal in need of such treatment a hypoalphalipoproteinemia treating, preventing or slowing amount of a compound and/or pharmaceutical composition of the present invention are provided.

In another embodiment, methods for treating, preventing or slowing the progression of hypercholesterolemia in a mammal by administering to a mammal in need of such treatment a hypercholesterolemia treating, preventing or slowing amount of a compound and/or pharmaceutical composition of the present invention are provided.

In yet another embodiment, methods for treating, preventing or slowing the progression of hypertriglyceridemia in a mammal by administering to a mammal in need of such treatment a hypertriglyceridemia treating, preventing or slowing amount of a compound and/or pharmaceutical composition of the present invention are provided.

In still yet another embodiment, methods for treating, preventing or slowing the progression of familial-hypercholesterolemia in a mammal by administering to a mammal in need of such treatment a familial-hypercholesterolemia treating, preventing or slowing amount of a compound and/or pharmaceutical composition of the present invention are provided.

In one embodiment, methods for treating, preventing or slowing the progression of cardiovascular disorders in a mammal by administering to a mammal in need of such treatment a cardiovascular disorder treating, preventing or slowing amount of a compound and/or pharmaceutical composition of the present invention are provided.

In another embodiment, methods for treating, preventing or slowing the progression of angina in a mammal by administering to a mammal in need of such treatment an angina treating, preventing or slowing amount of a compound and/or pharmaceutical composition of the present invention are provided.

In yet another embodiment, methods for treating, preventing or slowing the progression of ischemia in a mammal by administering to a mammal in need of such treatment an ischemic disease treating, preventing or slowing amount of a compound and/or pharmaceutical composition of the present invention are provided.

In still yet another embodiment, methods for treating, preventing or slowing the progression of cardiac ischemia in a mammal by administering to a mammal in need of such treatment a cardiac ischemic treating, preventing or slowing amount of a compound and/or pharmaceutical composition of the present invention are provided.

In one embodiment, methods for treating, preventing or slowing the progression of stroke in a mammal by administering to a mammal in need of such treatment a stroke treating, preventing or slowing amount of a compound and/or pharmaceutical composition of the present invention are provided.

In one embodiment, methods for treating, preventing or slowing the progression of a myocardial infarction in a mammal by administering to a mammal in need of such treatment a myocardial infarction treating, preventing or slowing amount of a compound and/or pharmaceutical composition of the present invention are provided.

In another embodiment, methods for treating, preventing or slowing the progression of reperfusion injury in a mammal by administering to a mammal in need of such treatment a reperfusion injury treating, preventing or slowing amount of a compound and/or pharmaceutical composition of the present invention are provided.

In another embodiment, methods for treating, preventing or slowing the progression of angioplastic restenosis in a mammal by administering to a mammal in need of such treatment an angioplastic restenosis treating, preventing or slowing amount of a compound and/or pharmaceutical composition of the present invention are provided.

In yet another embodiment, methods for treating, preventing or slowing the progression of hypertension in a mammal by administering to a mammal in need of such treatment a hypertension treating, preventing or slowing amount of a compound and/or pharmaceutical composition of the present invention are provided.

In yet another embodiment, methods for treating, preventing or slowing the progression of the ascular complications of diabetes in a mammal by administering to a mammal in need of such treatment a vascular complications of diabetes treating, preventing or slowing amount of a compound and/or pharmaceutical composition of the present invention are provided.

In still yet another embodiment, methods for treating, preventing or slowing the progression of obesity in a mammal by administering to a mammal in need of such treatment an obesity treating, preventing or slowing amount of a compound and/or pharmaceutical composition of the present invention are provided.

In one embodiment, methods for treating, preventing or slowing the progression of endotoxemia in a mammal by administering to a mammal in need of such treatment an endotoxemia treating, preventing or slowing amount of a compound and/or pharmaceutical composition of the present invention are provided.

In another embodiment, methods for treating, preventing or slowing the progression of a disease requiring cholesteryl ester transfer protein inhibitor therapy comprising administering, concurrently or sequentially, to a mammal in need of treatment, prevention or slowing a therapeutically effective amount of a compound of the present invention and at least one additional therapeutic agent.

In yet another embodiment, methods of inhibiting remnant lipoprotein production comprising administering to a mammal a compound and/or pharmaceutical composition of the present invention are provided.

In still yet another embodiment, methods of raising HDL cholesterol in a mammal comprising administering to a mammal in need of treatment a compound and/or pharmaceutical composition of the present invention are provided.

SYNTHESIS

Generally, compounds of the present invention may be prepared by methods such as those illustrated in the following Schemes A to N. Exemplary compounds of the present invention were prepared by the methods illustrated in the examples set forth below. Solvents, temperatures, pressures, and other reaction conditions may readily be selected by one of ordinary skill in the art. Starting materials are commercially available or readily prepared by one of ordinary skill in the art. Combinatorial techniques may be employed in the preparation of compounds, for example, where the intermediates possess groups suitable for these techniques.

Scheme A

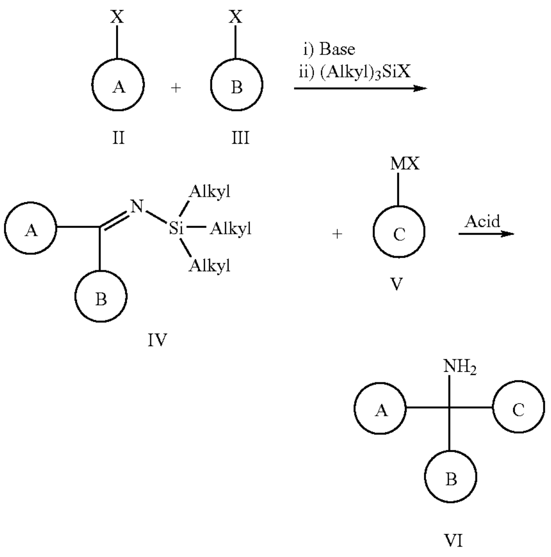

As illustrated in Scheme A, a reagent of Formula II, wherein the composition of A is as described under Formula Ia & Ib, with the requirement that at least one of the substituents (X) attached to the reagent of Formula II is a nitrile group, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi. Alternatively, a substituted phenyl reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi. Alternatively, a substituted phenyl reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with an oxidizing agent such as, $MnO_4$ or Jones'Reagent. The resulting mixture can then be treated with a tri-alkyl silyl halide reagent, such as trimethylsilyl chloride, to yield a trimethylsilyl imide intermediate of Formula IV. It should be evident to one skilled in the art, that a reagent of Formula II, wherein the composition of A is as described under Formula Ia & Ib, with the requirement that at least one of the substituents attached to the reagent of Formula II is a halide group, such as bromine, can be combined with a reagent of Formula III, wherein the composition of B is as described under Formula Ia & Ib, with the requirement that at least one of the substituents (X) attached to the reagent of Formula III is a nitrile group, followed by treatment with a base, such as nBuLi. The resulting mixture can then be treated with a tri-alkyl silyl halide reagent, such as trimethylsilyl chloride, to yield a trimethylsilyl imide intermediate of Formula IV. To the imide intermediate of Formula IV can be added an organometallic reagent, such as an alkyl lithium complex, a magnesium bromide complex or a magnesium chloride complex, or a zinc bromide or zinc chloride complex, of Formula V, where the metal halide complex is made from a reagent wherein the composition of C is as described under Formula Ia & Ib, followed by treatment with acid, such as HCl, to remove the silyl group, to yield the racemic intermediate of Formula VI. As will be described in the proceeding schemes, the racemic intermediate of Formula VI will allow for the generation of compounds of Formula Ia or Ib via the routes to be described.

Scheme B

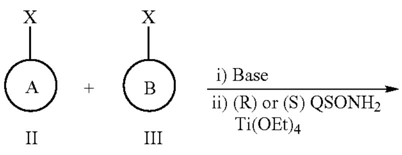

II III

-continued

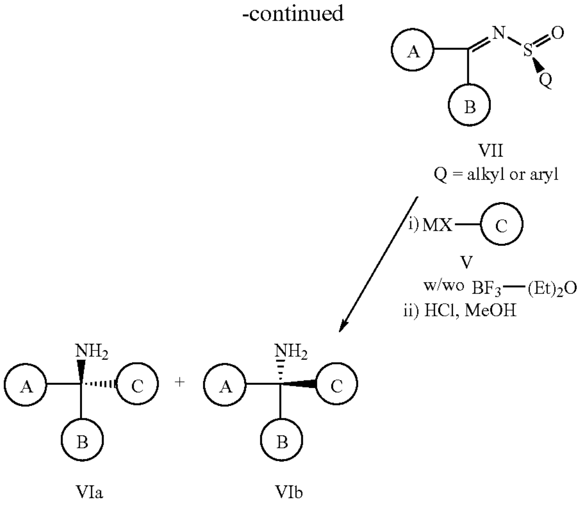

VII

V

VIa VIb

As illustrated in Scheme B, a reagent of Formula II, wherein the composition of A is as described under Formula Ia & Ib, with the requirement that at least one of the substituents (X) attached to the reagent of Formula II is a nitrile group, can be combined with a reagent of Formula III, wherein the composition of B is as described under Formula Ia & Ib, with the requirement that at least one of the substituents (X) attached to the reagent of Formula III is a halide group, such as bromine, followed by treatment with a base, such as nBuLi. Alternatively, a substituted phenyl reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with an oxidizing agent such as, $MnO_4$ or Jones'Reagent. The resulting mixture can then be treated with a substituted sulfinamide reagent, such as 4-methylbenzenesulfinamide or (S)-2-methylpropane-2-sulfinamide or (R)-2-methylpropane-2-sulfinamide, along with $Ti(OEt)_4$, to yield the sulfonylimide intermediate of Formula VII. It should be evident to one skilled in the art, that a reagent of Formula II, wherein the composition of A is as described under Formula Ia & Ib, with the requirement that at least one of the substituents (X) attached to the reagent of Formula II is a halide group, such as bromine, can be combined with a reagent of Formula III, wherein the composition of B is as described under Formula Ia & Ib, with the requirement that at least one of the substituents (X) attached to the reagent of Formula III is a nitrile group, followed by treatment with a base, such as nBuLi. The resulting mixture can then be treated with (S)-2-methylpropane-2-sulfinamide or (R)-2-methylpropane-2-sulfinamide, along with $Ti(OEt)_4$, to yield a the sulfinyl imide intermediate of Formula VII. To the sulfinyl imide intermediate of Formula VII can be added a metal halide reagent, such as an alkyl lithium complex, a magnesium bromide or a magnesium chloride complex, or a zinc bromide or zinc chloride complex, of Formula V, where the metal halide complex is made from a reagent wherein the composition of C is as described under Formula Ia & Ib, with or without a Lewis acid, such as $BF_3.(Et)_2O$, followed by treatment with acid, such as HCl, to hydrolyze the sulfinamide, to yield the intermediates of Formula VIa and VIb. By application of either (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the penultimate intermediate of Formula VIa and VIb will allow for the generation of compounds of Formula Ia or Ib via the routes to be described.

Scheme C

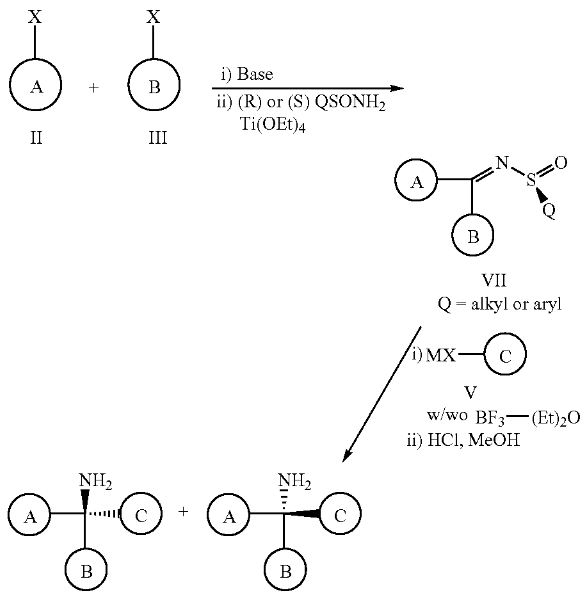

II III VII Q = alkyl or aryl VIa VIb

As illustrated in Scheme C, a reagent of Formula II, wherein the composition of A is as described under Formula Ia & Ib, with the requirement that at least one of the substituents (X) attached to the reagent of Formula III is a halogen, such as bromide, can be combined with a reagent of Formula III, wherein the composition of B is as described under Formula Ia & Ib, with the requirement that at least one of the substituents (X) attached to the reagent of Formula III is an alkyl ester group, such as a methyl or ethyl ester, followed by treatment with a base, such as nBuLi. The resulting mixture can then be treated with a substituted sulfinamide reagent, such as 4-methylbenzenesulfinamide or (S)-2-methylpropane-2-sulfinamide or (R)-2-methylpropane-2-sulfinamide, along with $Ti(OEt)_4$, to yield a the sulfinyl imide intermediate of Formula VII. It should be evident to one skilled in the art, that a reagent of Formula II, wherein the composition of A is as described under Formula Ia & Ib, with the requirement that at least one of the substituents (X) attached to the reagent of Formula II is a alkyl ester, such as a methyl or ethyl ester, can be combined with a reagent of Formula III, wherein the composition of B is as described under Formula Ia & Ib, with the requirement that at least one of the substituents (X) attached to the reagent of Formula VIII is a halide, such as bromide, followed by treatment with a base, such as nBuLi. The resulting mixture can then be treated with (S)-2-methylpropane-2- sulfinamide or (R)-2-methylpropane-2-sulfinamide, along with $Ti(OEt)_4$, to yield a the sulfinyl imide intermediate of Formula VII. To the sulfinyl imide intermediate of Formula VII can be added a metal halide reagent, such as an alkyl lithium complex, a magnesium bromide or a magnesium chloride complex, or a zinc bromide or zinc chloride complex, of Formula V, where the metal halide complex is made from a reagent wherein the composition of C is as described under Formula Ia & Ib, with or without a Lewis acid, such as $BF_3.(Et)_2O$, followed by treatment with acid, such as HCl, to hydrolyze the sulfinamide, to yield the penultimate intermediates of Formula VIa and VIb. By application of either (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the penultimate intermediate of Formula VIa and VIb will allow for the generation of compounds of Formula Ia or Ib via the routes to be described.

Scheme D

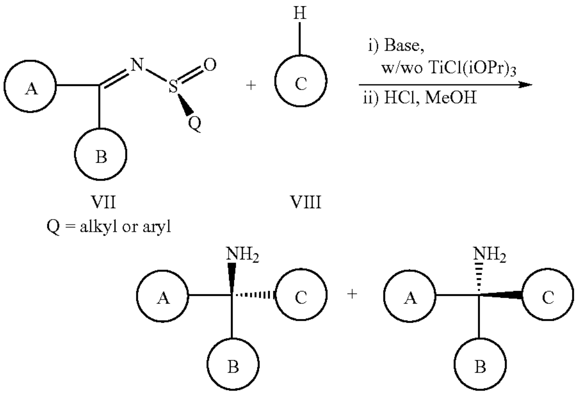

VII VIII Q = alkyl or aryl VIa VIb

As illustrated in Scheme D, to the sulfinyl imide intermediate of Formula VII can be added a base, such as LDA or nBuLi, with or with out the addition of $TiCl(iOPr)_3$, and a reagent of Formula VIII, wherein the composition of C is as described under Formula Ia & Ib, with the requirement that at least one of the substituents attached to the reagent of Formula VIII is a hydrogen that can be deprotonated to yield a reactive anion species, followed by treatment with acid, such as HCl, to hydrolyze the sulfinamide, to yield the intermediates of Formula VIa and VIb. By application of either (S)-2-methylpropane-2-sulfinamide or (R)-2-methylpropane-2-sulfinamide one skilled in the art can enrich the formation of the (R) antipode (Formula VIa) versus the (S) antipode (Formula VIb) or the (S) antipode (Formula VIb) versus the (R) antipode (Formula VIa), respectively. As will be described in the proceeding schemes, the penultimate intermediate of Formula VIa and VIb will allow for the generation of compounds of Formula Ia or Ib via the routes to be described.

Scheme E

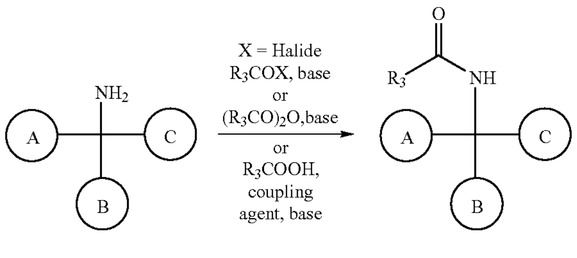

VI IX

As illustrated in Scheme E, an advanced intermediate of Formula VI can be treated with an acylating agent, such as an acid halide of Formula $R_3COX$, where X is a halide, or an anhydride of Formula $(R_3CO)_2O$, with or without the presence of a base, such as triethylamine, pyridine or N-ethyl-N-isopropylpropan-2-amine, to generate an amide derivative of Formula IX, where $R_3$ is derived from the afore mentioned reactive acylating agents and is as described for Formula Ia and Ib.

Alternatively, one can utilize a carboxylate intermediate of Formula $R_3COOH$, along with a coupling agent, such as EDCI, DCC or other agents known to one skilled in the art for facilitating amide bond formation, along with a base, such as triethylamine, pyridine or N-ethyl-N-isopropylpropan-2-amine, to generate an amide derivative of Formula IX, which is a compound of Formula Ia and Ib, where $R_3$ is as described for Formula Ia and Ib.

Scheme F

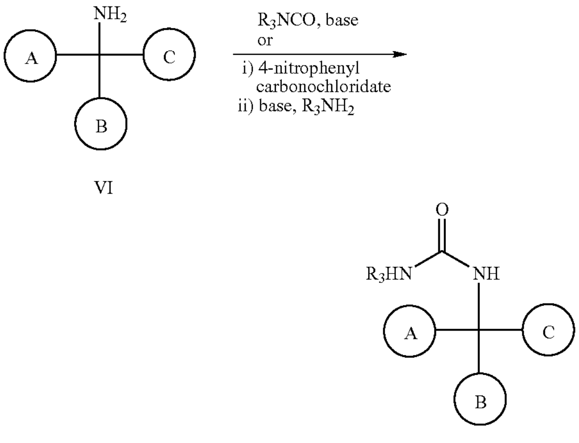

VI

X

As illustrated in Scheme F, an advanced intermediate of Formula VI can be treated with an isocyanate of Formula $R_3NCO$, with or without the presence of a base, such as triethylamine, pyridine or N-ethyl-N-isopropylpropan-2-amine, to generate an urea derivative of Formula X, where $R_3$ is derived from the afore mentioned isocyanate reagents and is as described for Formula Ia and Ib. Alternatively, one can react an advanced intermediate of Formula VI with an agent such as 4-nitrophenyl carbonochloridate, to create a reactive carbamate intermediate which can then be reacted with a amine or amine salt intermediate of Formula $R_3NH_2$, with or without the presence of a base, such as triethylamine, pyridine or N-ethyl-N-isopropylpropan-2-amine, to generate an urea derivative of Formula X, which is a compound of Formula Ia and Ib, where $R_3$ is as described for Formula Ia and Ib.

Scheme G

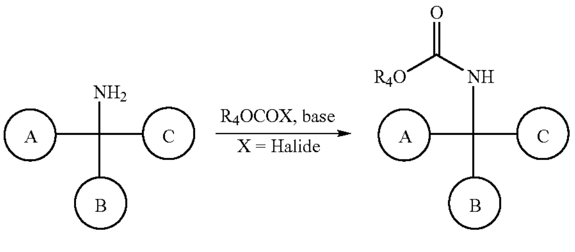

VI XI

As illustrated in Scheme G, an advanced intermediate of Formula VI can be treated with a carbonochloridate of Formula $R_4OCOCl$, in the presence of a base, such as potassium carbonate, to generate a carbamate derivative of Formula XI, which is a compound of Formula Ia and Ib, where $R_4$ is derived from the afore mentioned carbonochloridate reagents and is as described for Formula Ia and Ib.

Scheme H

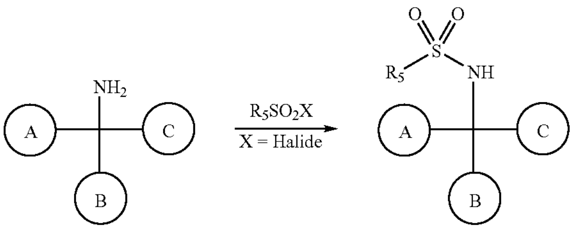

VI XII

As illustrated in Scheme H. an advanced intermediate of Formula VI can be treated with a sulfonyl chloride of Formula $R_5SO_2Cl$, in the presence of a base, such as triethylamine, pyridine or N-ethyl-N-isopropylpropan-2-amine, to generate a sulfonamide derivative of Formula XII, which is a compound of Formula Ia and Ib, where $R_5$ is derived from the afore mentioned sulfonyl chloride reagents and is as described for Formula Ia and Ib.

Scheme I

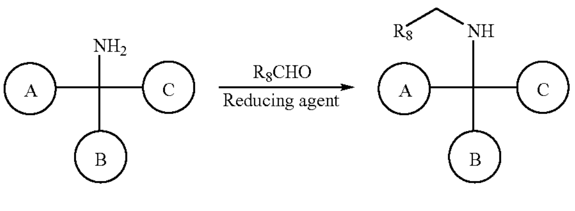

VI XIII

As illustrated in Scheme I, an advanced intermediate of Formula VI can be treated with an aldehyde of Formula $R_8CHO$, with or without a catalytic amount of an acid, such as acetic acid, followed by treatment with a reducing agent, such as $NaBH(OAc)_3$, to generate an alkyl amine derivative of Formula XIII, which is a compound of Formula Ia and Ib, where $R_8$ is derived from the afore mentioned aldehyde reagents and is as described for Formula Ia and Ib.

Scheme J

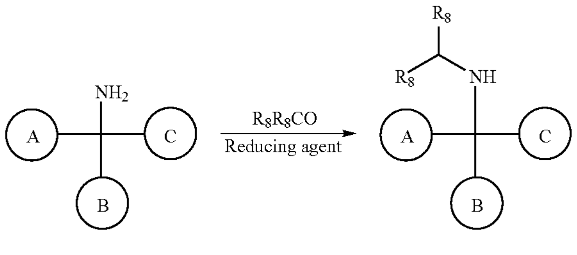

VI XIV

As illustrated in Scheme J, an advanced intermediate of Formula VI can be treated with ketone of Formula $R_8R_8CO$, with or without a catalytic amount of an acid, such as acetic acid, followed by treatment with a reducing agent, such as $NaBH(OAc)_3$, to generate an alkyl amine derivative of Formula XIV, which is a compound of Formula Ia and Ib, where $R_8$ is derived from the afore mentioned ketone reagents and is as described for Formula Ia and Ib.

Scheme K

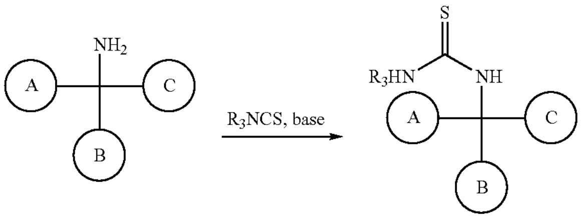

VI XV

As illustrated in Scheme K, an advanced intermediate of Formula VI can be treated with an isothiocyanate of Formula $R_3NCS$, with or without a base, such as triethylamine, pyridine or N-ethyl-N-isopropylpropan-2-amine, to generate a thiourea derivative of Formula XV, which is a compound of Formula Ia and Ib, where $R_3$ is derived from the afore mentioned isothiocyanate reagents and is as described for Formula Ia and Ib.

Scheme L

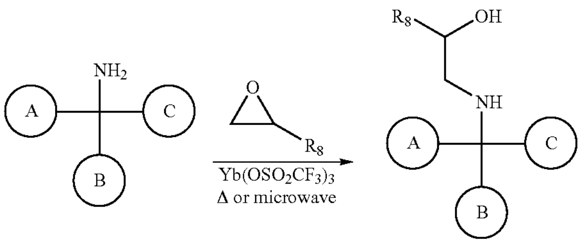

VI XVI

As illustrated in Scheme L, an advanced intermediate of Formula VI can be treated with an oxirane reagent, of Formula $CH_2OCHR_8$, in the presence of a catalyst, such as $Yb(OSO_2CF_3)_3$, with standard heating or via irradiation in a microwave, to generate an alkyl hydoxy amine derivative of Formula XVI, which is a compound of Formula Ia and Ib, where $R_8$ is derived from the afore mentioned oxirane reagents and is as described for Formula Ia and Ib.

Scheme M

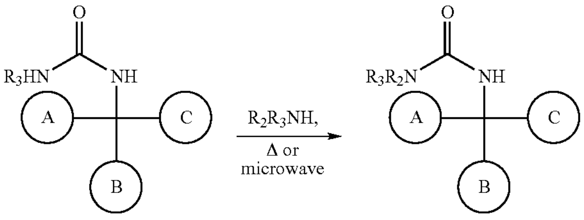

X XVII

As illustrated in Scheme M, a reagent of Formula X, which is a compound of Formula Ia and Ib, can be treated with a disubstituted amine reagent of Formula $R_2R_3NH$, with heating or via irradiation in a microwave, to obtained a disubstituted urea derivative of Formula XVII, which is a compound of Formula Ia and Ib, where $R_2$ and $R_3$ is derived from the afore mentioned disubstituted amine reagent and is as described for Formula Ia and Ib.

Scheme N

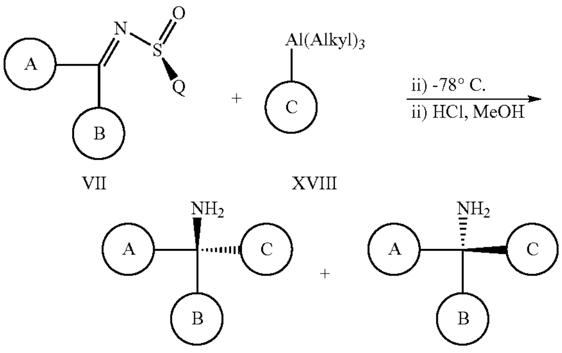

VII XVIII

VIa VIb

Q = alkyl or aryl

As illustrated in Scheme N, a reagent of Formula VII, can be reacted with an alkyl aluminum complex of Formula XVIII, where C is defined as described for Formula Ia and Ib, followed by treatment with acid, such as HCl, to hydrolyze the sulfinamide, to yield an intermediate of Formula VIa and VIb, which is key intermediate for the synthesis of compounds of Formula Ia and Ib.

Scheme O

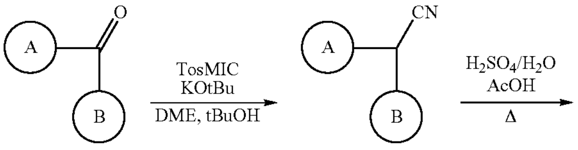

XIX XX

-continued

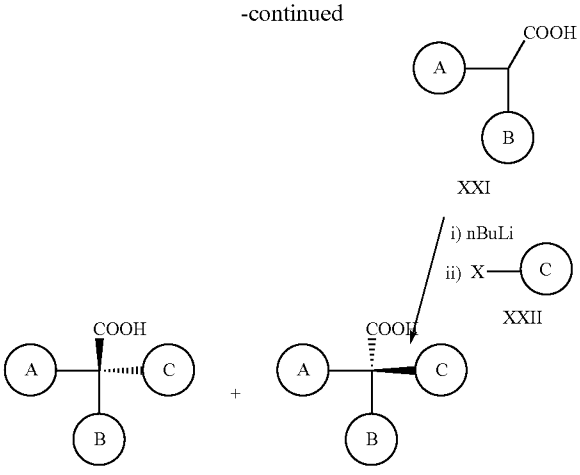

XXI

XXII

XXIIIa + XXIIIb

As illustrated in Scheme A and Scheme O, a reagent of Formula II, wherein the composition of A is as described under Formula Ia & Ib, with the requirement that at least one of the substituents (X) attached to the reagent of Formula II is a nitrile group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or a nitrile group, followed by treatment with a base, such as nBuLi, followed by treatment with aqueous acid, such as 1N HCl, to form a benzophenone intermediate of Formula XIX. Alternatively, a substituted phenyl reagent of Formula II, wherein the composition of A is as described under Formula Ia & Ib, with the requirement that at least one of the substituents (X) attached to the reagent of Formula II is an aldehyde group or a halogen group, such as bromine, can be combined with a reagent of Formula III, wherein the composition of B is as described under Formula Ia & Ib, with the requirement that at least one of the substituents (X) attached to the reagent of Formula III is a halide group, such as bromine, or an aldehyde group, followed by treatment with a base, such as nBuLi, followed by treatment with aqueous acid, such as IN HCl, to form a benzophenone intermediate of Formula XIX. Alternately, as illustrated in Scheme C and Scheme O, a reagent of Formula II, wherein the composition of A is as described under Formula Ia & Ib, with the requirement that at least one of the substituents attached to the reagent of Formula II is an alkyl ester group, such as a methyl or an ethyl ester, can be combined with a reagent of Formula III, wherein the composition of B is as described under Formula Ia & Ib, with the requirement that at least one of the substituents attached to the reagent of Formula III is a halide group, such as bromine, followed by treatment with a base, such as nBuLi, followed by treatment with aqueous acid, to yield a benzophenone intermediate of Formula XIX. In addition, as illustrated in Scheme C and Scheme O, a reagent of Formula II, wherein the composition of A is as described under Formula Ia & Ib, with the requirement that at least one of the substituents (X) attached to the reagent of Formula II is a halide group, such as bromine, can be combined with a reagent of Formula III, wherein the composition of B is as described under Formula Ia & Ib, with the requirement that at least one of the substituents (X) attached to the reagent of Formula III is an alkyl ester group, such as a methyl or an ethyl ester, followed by treatment with a base, such as nBuLi, followed by treatment with aqueous acid, to yield a benzophenone intermediate of Formula XIX. Numerous alternate approaches well known to one skilled in the art can also be employed to generate a benzophenone intermediate of Formula XIX. As illustrated in Scheme O, an intermediate benzophenone of Formula XIX can be treated with an agent such as 1-(isocyanomethylsulfonyl)-4-methylbenzene (TosMIC) and a base, such as potassium tert-butoxide, to yield an intermediate of Formula XX. Hydrolysis of an intermediate of Formula XX can be accomplished by treatment with an acid, such as aqueous $H_2SO_4$ and acetic acid, to yield an intermediate of Formula XXI. An intermediate of Formula XXI can be treated with a base, such as n-butyl lithium, followed by an alkyl halide reagent of Formula XXII, where X is a halide, such as chlorine, bromine or iodine and the composition of C is as described under Formula Ia and Ib, to yield an intermediate of Formula XXIIIa and XXIIIb, which are key intermediates for the synthesis of compounds of Formula Ia and Ib.

Scheme P

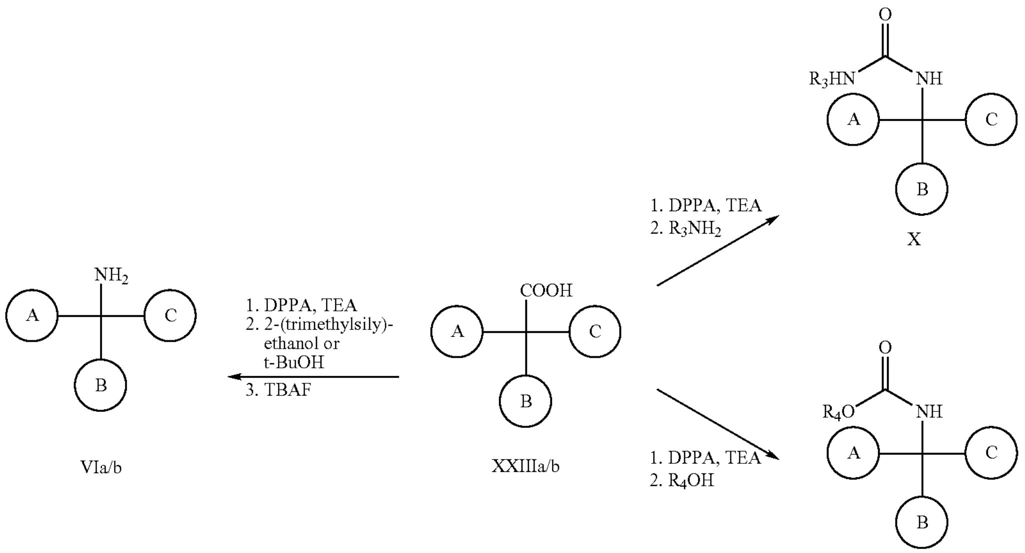

VIa/b

XXIIIa/b

X

XI

As illustrated in Scheme P, an intermediate of Formula XXIIIVa/b can be treated with an agent such as diphenylphosphoryl azide (DPPA) in the presence of a base, such as triethyl amine (TEA), followed by treatment with an agent, such as 2-(trimethylsilyl)ethanol or tert-butyl alcohol and eventual cleavage of the resulting intermediate carbamate by treatment with agents such as tetrabutylammonium fluoride (TBAF) or trifluoroacetic acid, to yield the advanced intermediate of Formula VIa/b, which is a key intermediate for the synthesis of compounds of Formula Ia and Ib. An intermediate of Formula XXIIIa/b can be treated with an agent such as diphenylphosphoryl azide (DPPA) in the presence of a base, such as triethyl amine (TEA), followed by treatment with an agent of formula $R_3NH_2$, were $R_3$ is defined as described under Formula Ia and Ib, to give compounds of Formula X, which are compounds of Formula Ia and Ib. In addition, an intermediate of Formula XXIIIa/b can be treated with an agent such as diphenylphosphoryl azide (DPPA) in the presence of a base, such as triethyl amine (TEA), followed by treatment with an agent of formula $R_4OH$, were $R_4$ is defined as described under Formula Ia and Ib, to give compounds of Formula XI, which are compounds of Formula Ia and Ib.

HCl, followed by treatment with a base such as pyridine, to yield an intermediate of Formula XXV. An intermediate of Formula XXIV can be treated with a reducing metal, such as zinc, followed by $NH_4OAc$ and $NH_4OH$, to yield an intermediate of Formula XXV. An intermediate of Formula XXV can be treated with a formylating agent, such as acetic formic anhydride, followed by dehydration through treatment with an agent such as $POCl_3$, to yield the isonitrile intermediate of Formula XXVI. The isonitrile intermediate of Formula XXVI can be treated with a base, such as aqueous KOH, along with tetrabutylammonium bromide, followed by an alkyl halide reagent of Formula XXII, where the composition of C is as described under Formula Ia and Ib, and the X can be a halide, such as chlorine, bromine or iodine, to yield intermediates of Formula XXVIIa and XXVIIb, which are key intermediates for the synthesis of compounds of Formula Ia and Ib. The formation of an intermediate of Formula XXVIIa or XXVIIb from an intermediate of Formula XXVI, as described above, can also be performed in the presence of a chiral catalyst such as, but not limited to, N-benzylcinchoninium chloride or N-benzylcinchonidinium chloride, to enrich the formation of the intermediate of Formula XXVIIa over the intermediate of Scheme Q

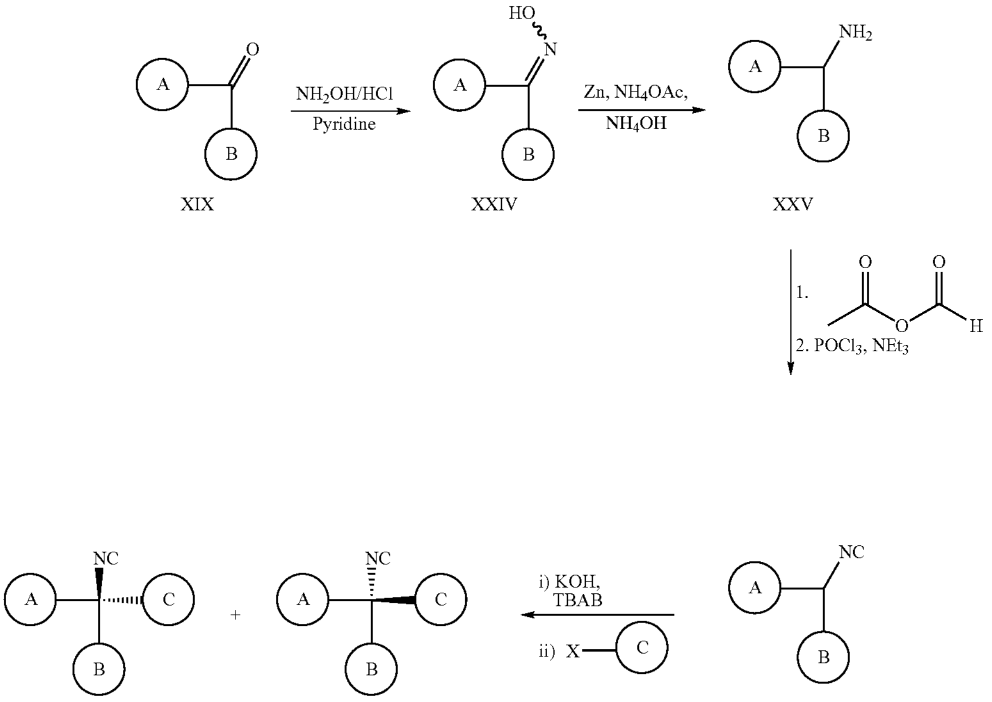

XIX XXIV XXV

XXVIIa + XXVIIb XXII XXVI

As illustrated in Scheme Q, an intermediate of Formula XIX, made as described in Scheme O, can be treated with a reagent such as $NH_2OH$, in the presence of an acid such as Formula XXVIIb or to enrich the formation of the intermediate of Formula XXVIIIb over the intermediate of Formula XXVIIIa as needed to make compounds of Formula Ia and Ib.

Scheme R

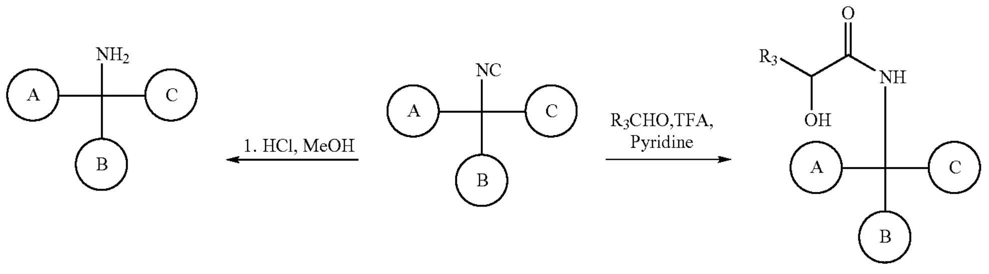

VIa/b XXVIIa/b XXVIIIa/b

As illustrated in Scheme R, an intermediate of Formula XXVIIa/b can be converted to an intermediate of Formula VIa/b by treatment with an acid such as HCl in methanol. As described in earlier schemes, and intermediate of Formula VIa/b is a key intermediate for the synthesis of compounds of Formula Ia and Ib. In addition, an intermediate of Formula XXVIIa/b can be treated directly with an aldehyde of Formula $R_3CHO$, where the definition of $R_3$ is as described under Formula Ia and Ib, and an acid, such as trifluoroacetic acid, in the presence of a base, such as pyridine, to yield compounds of Formula XXVIIIa/b, which are a compounds of Formula Ia and Ib.

MnCl (salen)), to obtain an oxirane intermediate of Formula XXXI. Treatment of the oxirane intermediate of Formula XXXI with an agent such as $NaN_3$, in the presence of a Lewis acid such as ethylaluminum dichloride, yields the azide intermediate of Formula XXXII. Reduction of the azide intermediate of Formula XXXII can be achieved over palladium on charcoal in the presence of $H_2$ gas to generate the advanced intermediate of Formula XXXIII. An intermediate of Formula XXXIII is embodied by the intermediate of Formula VIa/b which is a key intermediate on route to the synthesis of compounds of Formula Ia and Ib.

Scheme S

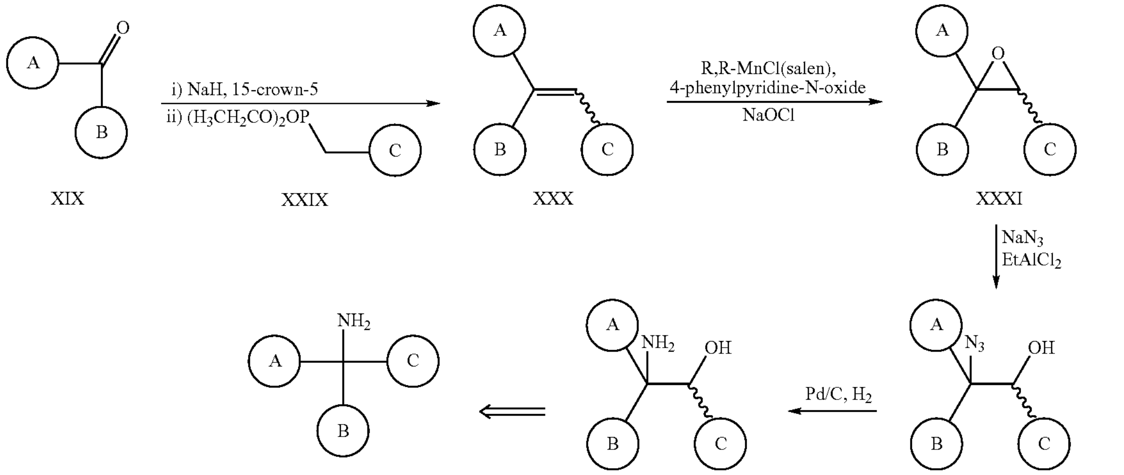

XIX XXIX XXX XXXI

VIa/b XXXIII XXXII

As illustrated in Scheme S, an intermediate of Formula XIX, made as described in Scheme O, can be reacted with a reagent of Formula XXIX, where the composition of C is as described under Formula Ia and Ib, to yield a styrene intermediate of Formula XXX. A reagent of Formula XXX can be derived from a variety of commercially available intermediates or can readily be made by one skilled in the art. A styrene intermediate of Formula XXX can be treated with an expoxidizing agent, such as sodium chlorite in the presence of 4-phenylpyridine-N-oxide, with or without a chiral catalyst such as, (1R, 2R)-(−)-[1,2-cyclo-hexanediamino-N,N'-bis(3, 5-di-t-butyl-salicylidene)] manganese (III) chloride, (R,R—

Scheme T

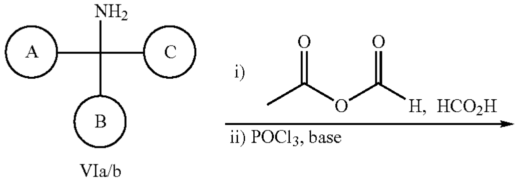

VIa/b

-continued

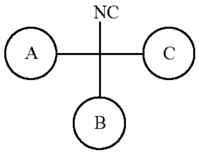

XXVIIIa/b

As illustrated in Scheme T, an intermediate of Formula XXIIIa/b, can be converted to an intermediate of compound XXVIIIa/b by treatment with a fornylating reagent, such as acetic formic anhydride, followed by a dehydrating agent, such as phosphorous oxychloride, along with a base, such as triethylamine. As described in Scheme R, an intermediate of Formula XXVIIa/b can be utilized to make compounds of Formula Ia and Ib.

Scheme U

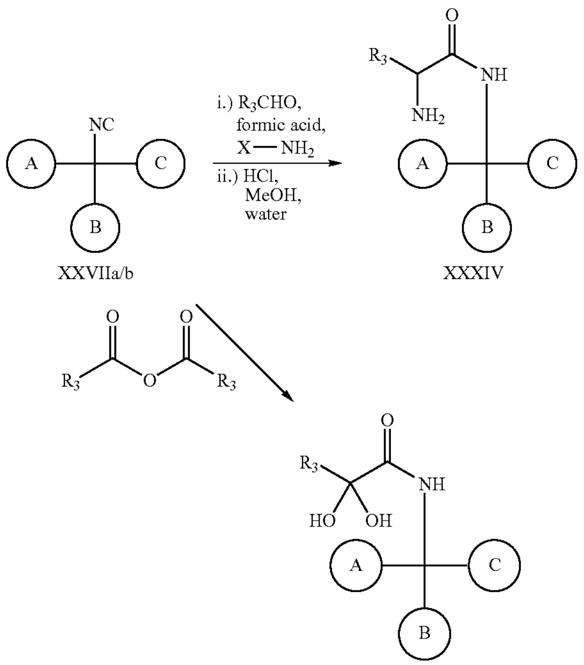

XXVIIa/b

As illustrated in Scheme U, an intermediate of Formula XXVIIa/b, can be treated with an aldehyde reagent of Formula $R_3CHO$, where $R_3$ is as described for Formula Ia and Ib, along with an acid, such as formic acid, and an amine reagent, of general formula $X—NH_2$, where X represents a cleavable protection group selected readily by one skilled in the art, followed by treatment with and acid, such as HCl, in the presence of an alcohol and water, to yield a compound of Formula XXXIV, which is a compound of Formula Ia and Ib. Alternately a reagent of Formula XXVIIa/b can be treated with an anhydride reagent of Formula $(R_3CO)_2O$, where $R_3$ is as described for Formula Ia and Ib, to yield a compound of Formula XXXV, which is a compound of Formula Ia and Ib.

The above schemes give an overview of several general processes for the synthesis of compounds of Formula Ia and Ib. Additional compounds of Formula Ia and Ib can readily be made by one of ordinary skill in the art by further modification of functional groups at positions A, B, C or $R_1$ of compounds of Formula Ia and Ib made by the processes illustrated in the included schemes. The Examples that follow described numerous applications of the routes described in Schemes A-N as well as additional routes to compounds of Formula Ia and Ib achieved through modification of functional groups at positions A, B, C or $R_1$ of compounds of Formula Ia and Ib.

UTILITY

Compounds of the present invention have been shown to inhibit cholesterol ester transfer protein (CETP) by greater than 30% at two different concentrations of less than 100 uM, preferably with a potency less than 5 uM, more preferably with a potency less than 500 nM. Compounds of the invention were also found to inhibit cholesterol ester transfer activity using in vitro assays that contained up to 96% plasma, and to inhibit plasma cholesterol ester transfer activity in animals. Accordingly, compounds within the scope of the present invention inhibit the CETP protein, and as such are expected to be useful in the treatment, prevention, and/or slowing of the progression of various disorders.

For example, the compounds of the present invention, their prodrugs and the salts of such compounds and prodrugs can be adapted to therapeutic use as agents that inhibit cholesterol ester transfer protein activity in mammals, particularly humans. Thus, the compounds of the present invention are expected to be useful in elevating plasma HDL cholesterol, its associated components, and the functions performed by them in mammals, particularly humans. By virtue of their expected activity, these agents are also expected to reduce VLDL cholesterol, LDL cholesterol and their associated components in mammals, particularly humans. Hence, these compounds are expected to be useful for the treatment and correction of the various dyslipidemias observed to be associated with the development and incidence of atherosclerosis and cardiovascular disease, including hypoalphalipoproteinemia, hyperbetalipoproteinemia, hypertriglyceridemia, and familial-hypercholesterolemia (see U.S. Pat. 6,489,478, incorporated herein by reference).

Further, introduction of a functional CETP gene into an animal lacking CETP (mouse) results in reduced HDL levels (Agellon, L. B. et al., J. Biol. Chem., 266:10796-10801 (1991)) and, increased susceptibility to atherosclerosis. (Marotti, K. R. et al., Nature, 364:73-75 (1993)). Also, inhibition of CETP activity with an inhibitory antibody raises HDL-cholesterol in hamster (Evans, G. F. et al., J. Lipid Res., 35:1634-1645 (1994)) and rabbit (Whitlock, M. E. et al., J. Clin. Invest., 84:129-137 (1989)). Suppression of increased plasma CETP by intravenous injection with antisense oligodeoxynucleotides against CETP mRNA reduced atherosclerosis in cholesterol-fed rabbits (Sugano, M. et al., J. Biol. Chem., 273:5033-5036 (1998)). Importantly, human subjects deficient in plasma CETP, due to a genetic mutation possess markedly elevated plasma HDL-cholesterol levels and apolipoprotein A-I, the major apoprotein component of HDL. In addition, most demonstrate markedly decreased plasma LDL cholesterol and apolipoprotein B (the major apolipoprotein component of LDL. (Inazu, A. et al., N. Engl. J. Med., 323: 1234-1238 (1990))

Given the negative correlation between the levels of HDL cholesterol and HDL associated lipoproteins, and the positive correlation between triglycerides, LDL cholesterol, and their associated apolipoproteins in blood with the development of cardiovascular, cerebral vascular and peripheral vascular diseases, the compounds of the present invention, their prodrugs and the salts of such compounds and prodrugs, by virtue of their pharmacologic action, are expected to be useful for the treatment, prevention, the arrestment and/or regression of atherosclerosis and its associated disease states. These include cardiovascular disorders (e.g., angina, cardiac ischemia and myocardial infarction), complications due to cardiovascular disease therapies (e.g., reperfusion injury and angioplastic restenosis), hypertension, stroke, and atherosclerosis associated with organ transplantation.

Because of the beneficial effects widely associated with elevated HDL levels, an agent which inhibits CETP activity in humans, by virtue of its HDL increasing ability, also provides valuable avenues for therapy in a number of other disease areas as well.

Accordingly, given the ability of the compounds of the present invention, their prodrugs and the salts of such compounds and prodrugs to alter lipoprotein composition via inhibition of cholesterol ester transfer, they are expected to be useful in the treatment, prevention and/or slowing of the progression of vascular complications associated with diabetes. Hyperlipidemia is present in most subjects with diabetes mellitus (Howard, B. V., J. Lipid Res., 28:613 (1987)). Even in the presence of normal lipid levels, diabetic subjects experience a greater risk of cardiovascular disease (Kannel, W. B. et al., Diabetes Care, 2:120 (1979)). CETP-mediated cholesteryl ester transfer is known to be abnormally increased in both insulin-dependent (Bagdade, J. D. et al., Eur. J. Clin. Invest., 21:161 (1991)) and non-insulin dependent diabetes (Bagdade, J. D. et al., Atherosclerosis, 104, 69 (1993)). It has been suggested that the abnormal increase in cholesterol transfer results in changes in lipoprotein composition, particularly for VLDL and LDL, that are more atherogenic (Bagdade, J. D. et al., J. Lipid Res., 36:759 (1995)). These changes would not necessarily be observed during routine lipid screening. Thus, it is expected that the present invention will be useful in reducing the risk of vascular complications as a result of the diabetic condition.

In addition, the compounds of the present invention are expected to be useful in the treatment of obesity. In both humans (Radeau, T. et al., J. Lipid Res., 36(12):2552-2561 (1995)) and nonhuman primates (Quinet, E. et al., J. Clin. Inv., 87(5):1559-1566 (1991)) mRNA for CETP is expressed at high levels in adipose tissue. The adipose message increases with fat feeding (Martin, L. J. et al., J. Lipid Res., 34(3):437-446 (1993)), and is translated into functional transfer protein and through secretion contributes significantly to plasma CETP levels. In human adipocytes the bulk of cholesterol is provided by plasma LDL and HDL (Fong, B. S. et al., Biochimica et Biophysica Acta., 1004(1):53-60 (1989)). The uptake of HDL cholesteryl ester is dependent in large part on CETP (Benoist, F. et al., J. Biol. Chem., 272(38):23572-23577 (1997)). This ability of CETP to stimulate HDL cholesteryl uptake, coupled with the enhanced binding of HDL to adipocytes in obese subjects (Jimenez, J. G. et al., Int. J. Obesity, 13(5):699-709 (1989)), suggests a role for CETP, not only in generating the low HDL phenotype for these subjects, but in the development of obesity itself by promoting cholesterol accumulation. Inhibitors of CETP activity that block this process therefore serve as useful adjuvants to dietary therapy in causing weight reduction.

CETP inhibitors are useful in the treatment of inflammation due to Gram-negative sepsis and septic shock. For example, the systemic toxicity of Gram-negative sepsis is in large part due to endotoxin, a lipopolysaccharide (LPS) released from the outer surface of the bacteria, which causes an extensive inflammatory response. Lipopolysaccharide can form complexes with lipoproteins (Ulevitch, R. J. et al., J. Clin. Invest., 67:827-837 (1981)). In vitro studies have demonstrated that binding of LPS to HDL substantially reduces the production and release of mediators of inflammation (Ulevitch, R. J. et al., J. Clin. Invest., 62:1313-1324 (1978)). In vivo studies show that transgenic mice expressing human apo-A1 and elevated HDL levels are protected from septic shock (Levine, D. M. et al., Proc. Natl. Acad. Sci., 90:12040-12044 (1993)). Importantly, administration of reconstituted HDL to humans challenged with endotoxin resulted in a decreased inflammatory response (Pajkrt, D. et al., J. Exp. Med., 184:1601-1608 (1996)). The CETP inhibitors, by virtue of the fact that they raise HDL levels, attenuate the development of inflammation and septic shock.

Thus, the present invention provides methods for the prevention or treatment of one or more of the aforementioned disorders, comprising the step of administering to a subject in need thereof an effective amount of at least one compound of the present invention, its prodrug and the salt of such compound and prodrugs. Other therapeutic agents such as those described below may be employed with the inventive compounds in the present methods. In the methods of the present invention, such other therapeutic agent(s) may be administered prior to, simultaneously with or following the administration of the compound(s) of the present invention.

In addition, the compounds of the present invention are expected to be useful in the inhibition of remnant lipoprotein production (Okamoto et al., WO 2005/030185).

CETP Assay

CETP inhibition can be determined at a specific concentration of test compound in any of the assays described herein. Potencies are more generally calculated by determining $IC_{50}$ values using these assays.

CETP Scintillation Proximity Assay

Compounds of the present invention inhibit CETP-dependent cholesterol ester transfer from HDL to LDL as described here. Dilutions of compounds in DMSO (1 μl) are added to BD plates (#353232). To this is added 20 μl of a mixture containing $^3$H-CE/HDL (0.15 μl), biotinylated LDL (~5 μg protein/ml final concentration) and unlabeled HDL (16 μg/ml final concentration) in a buffer containing 50 mM HEPES, pH 7.4, 150 mM NaCl and 0.05% sodium azide. Reactions are initiated by the addition of 10 μl of buffer containing purified human recombinant CETP, and incubated at 37° C. At the end of the reaction, 60 μl of LEADseeker beads (#RPNQ0261, 2 mg/ml in buffer containing 1 mg/ml BSA and 0.05 mg protein/ml HDL) are added, the plates are covered and subsequently read. Background activity is determined in a set of wells that receive buffer but no CETP. The level of inhibition is determined by comparing the readings in wells that contain compound to the readings in control wells containing DMSO.

Plasma Cholesterol Ester Transfer Assay

Compounds of the present invention were also tested for the ability to inhibit cholesterol ester transfer activity in plasma as described here. Dilutions of compounds in DMSO (1 μl) are added to 384-well polypropylene plates. To each well is added 29 ul of human plasma containing 0.15 ul $^3$H-CE/HDL. The reaction is incubated at 37° C. and terminated by the addition of 6 ul of precipitation reagent (2:1:1 of water: 1M $MgCl_2$:2% Dextralip 50), to precipitate LDL and VLDL. After 10 minutes at room temperature, 15 μl of the reaction is transferred to filter plates (Millipore, #MHVBN45) pre-wetted with 100 ul phosphate buffered saline. The plates are centrifuged (1800 rpm) at room temperature for 10 minutes, and 50 ul Microscint-20 is added. The plates are then sealed and read. Background activity is determined with plasma samples incubated at 4° C. The level of inhibition is determined by comparing the readings in wells that contain compound to the readings in control wells containing DMSO.

In Vivo Cholesterol Ester Transfer Activity

Compounds of the present invention have further been shown to inhibit plasma cholesterol ester transfer activity in mice that are dually transgenic for human CETP and apoB-100 (hCETP/apoB-100) as described here.

Mice (commercially available from Taconic) are fasted for two hours and plasma obtained before dosing. The animals are then dosed with vehicle or compound (p.o.). The vehicle may vary as needed to dissolve the compound, while at the same time having no, or minimal, activity on plasma cholesterol ester transfer activity. Plasma samples are collected again at various times after dosing and assayed for cholesterol ester transfer activity.

To measure CETP activity in plasma samples obtained from animals treated with compounds, the following methodology is employed. To a sample of plasma (typically between 9 and 30 ul), 1 μl of diluted $^3$H-CE/HDL is added (0.15 μl $^3$H-CE/HDL and 0.85 ul assay buffer) to label endogenous HDL. Assay buffer contains 50 mM HEPES, pH 7.4, and 150 mM NaCl. The reaction is incubated at 37° C., and LDL/VLDL precipitated with 3 μl of precipitation reagent (4:1:1 of water:0.5M $MgCl_2$:1% Dextralip 50). The tubes are centrifuged for 15-30 minutes at 10,000xg (10° C.), the supernatants discarded, and the pellets dissolved in 140 μl of 2% SDS. Half of the SDS solution (70 μl) is transferred to scintillation tubes, scintillation fluid is added, and radioactivity measured in a scintillation counter. Background activity is determined for each sample with an aliquot incubated at 4° C. Plasma cholesterol ester transfer inhibition is calculated by comparing the transfer activity in a plasma sample obtained after dosing to the transfer activity in the plasma sample obtained from the same animal before dosing. All data are background subtracted.

The in vivo assay described above (with appropriate modifications within the skill in the art) may be used to determine the activity of other lipid or triglyceride controlling agents as well as the compounds of this invention. The assays set forth above also provide a means whereby the activities of the compounds of the present invention, their prodrugs and the salts of such compounds and prodrugs (or the other agents described herein) can be compared to each other and with the activities of other known compounds. The results of these comparisons are useful for determining dosage levels in mammals, including humans, for the treatment of the above described disease/conditions.

HDL Cholesterol Protocol

The ability of CETP inhibitors to increase HDL cholesterol (HDL-C) can be shown in mammalian subjects via methods known to one of ordinary skill in the art (see Evans, G. F. et al., J. Lipid Res., 35:1634-1645 (1994)). For example, compounds of the present invention have been shown to be efficacious in the elevation of HDL-C in golden syrian hamsters. The hamsters are fed a moderate fat diet containing variable amounts of coconut oil and cholesterol to alter their HDL-C and LDL-C levels. The moderately fat-fed hamsters are fasted and bled to determine baseline HDL-C levels, then dosed orally with compound for three days in an appropriate vehicle. The animals are fasted and bled again on the third day of dosing, and the results are compared to the baseline HDL-C levels. The compounds increase HDL-C in this model in a dose-dependent manner, demonstrating their usefulness to alter plasma lipids.

Antiobesity Protocol

The ability of CETP inhibitors to cause weight loss can be assessed in obese human subjects with body mass index (BMI)≧30 kg/m$^2$. Doses of inhibitor are administered sufficient to result in an increase of ≧25% in HDL cholesterol levels. BMI and body fat distribution, defined as waist (W) to hip (H) ratio (WHR), are monitored during the course of the 3-6 month studies, and the results for treatment groups compared to those receiving placebo.

The above assays can of course be varied by those skilled in the art.

The present invention also provides pharmaceutical compositions comprising at least one of the compounds of the present invention, their prodrugs and the salts of such compounds and prodrugs capable of preventing, treating, and/or slowing the progression of one or more of the aforementioned disorders in an amount effective therefor, and a pharmaceutically acceptable vehicle or diluent. The compositions of the present invention may contain other therapeutic agents as described below, and may be formulated, for example, by employing conventional solid or liquid vehicles or diluents, as well as pharmaceutical additives of a type appropriate to the mode of desired administration (for example, excipients, binders, preservatives, stabilizers, flavors, etc.) according to techniques such as those well known in the art of pharmaceutical formulation.

The compounds of the present invention may be administered by any suitable means, for example, orally, such as in the form of tablets, capsules, granules or powders; sublingually; bucally; parenterally, such as by subcutaneous, intravenous, intramuscular, or intrasternal injection or infusion techniques (e.g., as sterile injectable aqueous or non aqueous solutions or suspensions); nasally such as by inhalation spray; topically, such as in the form of a cream or ointment; or rectally such as in the form of suppositories; in dosage unit formulations containing non toxic, pharmaceutically acceptable vehicles or diluents. The present compounds may, for example, be administered in a form suitable for immediate release or extended release. Immediate release or extended release may be achieved by the use of suitable pharmaceutical compositions comprising the present compounds, or, particularly in the case of extended release, by the use of devices such as subcutaneous implants or osmotic pumps.

Exemplary compositions for oral administration include suspensions which may contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which may contain, for example, microcrystalline cellulose, dicalcium phosphate, starch, magnesium stearate and/or lactose and/or other excipients, binders, extenders, disintegrants, diluents and lubricants such as those known in the art. The compounds of present invention may also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations may also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g., Carbopol 934).

Lubricants, glidants, flavors, coloring agents and stabilizers may also be added for ease of fabrication and use.

Exemplary compositions for nasal aerosol or inhalation administration include solutions in saline which may contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which may contain, for example, suitable non toxic, parenterally acceptable diluents or solvents, such as mannitol, 1,3 butanediol, water, Ringer's solution, an isotonic sodium chloride solution, or other suitable dispersing or wetting and suspending agents, including synthetic mono- or diglycerides, and fatty acids, including oleic acid.

Exemplary compositions for rectal administration include suppositories which may contain, for example, a suitable non irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention may be determined by one of ordinary skill in the art, and includes exemplary dosage amounts for an adult human of from about 0.001 to 100 mg/kg of body weight of active compound per day, which may be administered in a single dose or in the form of individual divided doses, such as from 1 to 4 times per day. It will be understood that the specific dose level and frequency of dosage for any particular subject may be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to the aforementioned disorders.

The compounds of the present invention may be employed alone or in combination with each other and/or other suitable therapeutic agents useful in the treatment of the aforementioned disorders or other disorders.

For example, they may be used in combination with a HMG-CoA reductase inhibitor, a cholesterol synthesis inhibitor, a cholesterol absorption inhibitor, another CETP inhibitor, a MTP/Apo B secretion inhibitor, a PPAR modulator and other cholesterol lowering agents such as a fibrate, niacin, an ion-exchange resin, an antioxidant, an ACAT inhibitor, and a bile acid sequestrant. Other pharmaceutical agents would also include the following: a bile acid reuptake inhibitor, an ileal bile acid transporter inhibitor, an ACC inhibitor, an antihypertensive (such as NORVASC®), a selective estrogen receptor modulator, a selective androgen receptor modulator, an antibiotic, an antidiabetic (such as metformin, a PPARγ activator, a sulfonylurea, insulin, an aldose reductase inhibitor (ARI) and a sorbitol dehydrogenase inhibitor (SDI)), aspirin (acetylsalicylic acid) and niacin and combinations thereof.

Any HMG-CoA reductase inhibitor may be used in the combination aspect of this invention. The term HMG-CoA reductase inhibitor refers to compounds which inhibit the bioconversion of hydroxymethylglutaryl-coenzyme A to mevalonic acid catalyzed by the enzyme HMG-CoA reductase. Such inhibition is readily determined by those skilled in the art according to standard assays (e.g., Meth. Enzymol., 71:455-509 (1981) and references cited therein). A variety of these compounds are described and referenced below however other HMG-CoA reductase inhibitors will be known to those skilled in the art. U.S. Pat. No. 4,231,938 (the disclosure of which is hereby incorporated by reference) discloses certain compounds isolated after cultivation of a microorganism belonging to the genus *Aspergillus*, such as Iovastatin. Also, U.S. Pat. No. 4,444,784 (the disclosure of which is hereby incorporated by reference) discloses synthetic derivatives of the aforementioned compounds, such as simvastatin. Also, U.S. Pat. No. 4,739,073 (the disclosure of which is incorporated by reference) discloses certain substituted indoles, such as fluvastatin. Also, U.S. Pat. No. 4,346,227 (the disclosure of which is incorporated by reference) discloses ML-236B derivatives, such as pravastatin. Also, EP-491226A (the disclosure of which is incorporated by reference) discloses certain pyridyldihydroxyheptenoic acids, such as cerivastatin. In addition, U.S. Pat. No. 5,273,995 (the disclosure of which is incorporated by reference) discloses certain 6-[2-(substituted-pyrrol-1-yl)alkyl]pyran-2-ones such as atorvastatin and any pharmaceutically acceptable form thereof (i.e. LIPITOR®). Additional HMG-CoA reductase inhibitors include rosuvastatin and pitavastatin. Statins also include such compounds as rosuvastatin disclosed in U.S. Pat. No. RE37,314 E, pitavastatin disclosed in EP 304063 B1 and U.S. Pat. No. 5,011,930; mevastatin, disclosed in U.S. Pat. No. 3,983,140; velostatin, disclosed in U.S. Pat. Nos. 4,448,784 and 4,450,171; compactin, disclosed in U.S. Pat. No. 4,804,770; dalvastatin, disclosed in European Patent Application Publication No. 738510 A2; fluindostatin, disclosed in European Patent Application Publication No. 363934 A1; and dihydrocompactin, disclosed in U.S. Pat. No. 4,450,171.

Any PPAR modulator may be used In the combination aspect of this invention. The term PPAR modulator refers to compounds which modulate peroxisome proliferator activator receptor (PPAR) activity in mammals, particularly humans. Such modulation is readily determined by those skilled in the art according to standard assays known in the literature. It is believed that such compounds, by modulating the PPAR receptor, regulate transcription of key genes involved in lipid and glucose metabolism such as those in fatty acid oxidation and also those involved in high density lipoprotein (HDL) assembly (for example, apolipoprotein AI gene transcription), accordingly reducing whole body fat and increasing HDL cholesterol. By virtue of their activity, these compounds also reduce plasma levels of triglycerides, VLDL cholesterol, LDL cholesterol and their associated components such as apolipoprotein B in mammals, particularly humans, as welt as increasing HDL cholesterol and apolipoprotein AI. Hence, these compounds are useful for the treatment and correction of the various dyslipidemias observed to be associated with the development and incidence of atherosclerosis and cardiovascular disease, including hypoalphalipoproteinemia and hypertriglyceridemia. A variety of these compounds are described and referenced below, however, others will be known to those skilled in the art. International Publication Nos. WO 02/064549 and WO 02/064130, U.S. patent application Ser. Nos. 10/720,942, and 60/552,114 disclose certain compounds which are PPARα activators.

Any other PPAR modulator may be used in the combination aspect of this invention. In particular, modulators of PPARβ and/or PPARγ may be useful in combination with compounds of the present invention. An example PPAR inhibitor is described in US 2003/0225158 as {5-Methoxy-2-methyl-4-[4-(4-trifluoromethyt-benzy]oxy)-benzylsulfany]-phenoxy}-acetic acid.

Any MTP/Apo B (microsomal triglyceride transfer protein and or apolipoprotein B) secretion inhibitor may be used in the combination aspect of this invention. The term MTP/Apo B secretion inhibitor refers to compounds which inhibit the secretion of triglycerides, cholesteryl ester, and phospholipids. Such inhibition is readily determined by those skilled in the art according to standard assays (e.g., Wetterau, J. R., Science, 258:999 (1992)). A variety of these compounds are described and referenced below however other MTP/Apo B secretion inhibitors will be known to those skilled in the art, including implitapride (Bayer) and additional compounds such as those disclosed in WO 96/40640 and WO 98/23593, (two exemplary publications). For example, the following MTP/Apo B secretion inhibitors are particularly useful: 4'-trifluoromethyl-biphenyl-2-carboxylic acid [2-(1H-[1,2,4,]triazol-3 -ylmethyl)-1,2,3,4-tetrahydro-isoquinolin-6-yl]-amide; 4'-trifluoromethyl-biphenyl-2-carboxylic acid [2-(2-acetylamino-ethyl)-1,2,3,4-tetrahydro-isoquinolin-6-yl]-amide; (2-{6-[(4'-trifluoromethyl-biphenyl-2-carbonyl)-amino]-3,4-dihydro-1H-isoquinolin-2-yl}-ethyl)-carbamic acid methyl ester; 4'-trifluoromethyl-biphenyl-2-carboxylic acid [2-(1H-imidazol-2-ylmethyl)-1,2,3,4-tetrahydro-isoquinolin-6-yl]-amide; 4'-trifluoromethyl-biphenyl-2-carboxylic acid [2-(2,2-diphenyl-ethyl)-1,2,3,4-tetrahydro-isoquinolin-6-yl]-amide; 4'-trifluoromethyl-biphenyl-2-carboxylic acid [2-(2-ethoxy-ethyl)-1,2,3,4-tetrahydro-isoquinolin-6-yl]-amide; (S)-N-{2-[benzyl(methyl)amino]-2-oxo-1-phenylethyl}-1-methyl-5-[4'-(trifluoromethyl)[1,1'-biphenyl]-2-carboxamido]-1H-indole-2-carboxamide; (S)-2-[(4'-trifluoromethyl-biphenyl-2-carbonyl)-amino]-quinoline-6-carboxy;ic acid (pentylcarbamoyl-phenyl-methyl)-amide; 1H-indole-2-carboxamide, 1-methyl-N-[(1S)-2-[methyl(phenylmethyl)amino]-2-oxo-1-phenylethyl]-5-[[[4'-(trifluoromethyl)[1,1'-biphenyl]-2-yl] carbonyl]amino]; and N-[(1S)-2-(benzylmethylamino)-2-oxo-1-phenylethyl]-1-methyl-5-[[[4'-(trifluoromethyl)[1,1'-biphenyl]-2-yl]carbonyl]amino]-1H-indole-2-carboxamide.

Any HMG-CoA synthase inhibitor may be used in the combination aspect of this invention. The term HMG-CoA synthase inhibitor refers to compounds which inhibit the biosynthesis of hydroxymethylglutaryl-coenzyme A from acetyl-coenzyme A and acetoacetyl-coenzyme A, catalyzed by the enzyme HMG-CoA synthase. Such inhibition is readily determined by those skilled in the art according to standard assays (Meth. Enzymol., 35:155-160 (1975), Meth. Enzymol., 110:19-26 (1985) and references cited therein). A variety of these compounds are described and referenced below, however other HMG-CoA synthase inhibitors will be known to those skilled in the art. U.S. Pat. No. 5,120,729 discloses certain beta-lactam derivatives. U.S. Pat. No. 5,064,856 discloses certain spiro-lactone derivatives prepared by culturing a microorganism (MF5253). U.S. Pat. No. 4,847,271 discloses certain oxetane compounds such as 11-(3-hydroxymethyl-4-oxo-2-oxetayl)-3,5,7-trimethyl-2,4-undecadienoic acid derivatives.

Any compound that decreases HMG-CoA reductase gene expression may be used in the combination aspect of this invention. These agents may be HMG-CoA reductase transcription inhibitors that block the transcription of DNA or translation inhibitors that prevent or decrease translation of mRNA coding for HMG-CoA reductase into protein. Such compounds may either affect transcription or translation directly, or may be biotransformed to compounds that have the aforementioned activities by one or more enzymes in the cholesterol biosynthetic cascade or may lead to the accumulation of an isoprene metabolite that has the aforementioned activities. Such compounds may cause this effect by decreasing levels of SREBP (sterol receptor binding protein) by inhibiting the activity of site-1 protease (SIP) or agonizing the oxysterol receptor or SCAP. Such regulation is readily determined by those skilled in the art according to standard assays (Meth. Enzymol., 110:9-19 (1985)). Several compounds are described and referenced below, however other inhibitors of HMG-CoA reductase gene expression will be known to those skilled in the art. U.S. Pat. No. 5,041,432 discloses certain 15-substituted lanosterol derivatives. Other oxygenated sterols that suppress synthesis of HMG-CoA reductase are discussed by E. I. Mercer (Prog. Lip. Res., 32:357-416 (1993)).

Any compound having activity as a CETP inhibitor can serve as the second compound in the combination therapy aspect of the present invention. The term CETP inhibitor refers to compounds that inhibit the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). A variety of CETP inhibitors will be known to those skilled in the art, for example, those disclosed in U.S. Pat. Nos. 6,140,343 and 6,197,786. CETP inhibitors disclosed in these patents include compounds, such as [2R,4S] 4-[(3,5-bis-trifluoromethylbenzyl)methoxycarbonylamino]-2-ethyl-6-trifluoromethyl-3,4-dihydro-2H-quinoline-1-carboxylic acid ethyl ester (torcetrapib). CETP inhibitors are also described in U.S. Pat. No. 6,723,752, which includes a number of CETP inhibitors including (2R)-3-{[3-(4-chloro-3-ethyl-phenoxy)-phenyl]-[[3-(1,1,2,2-tetrafluoroethoxy) phenyl]methyl]amino}-1,1,1-trifluoro-2-propanol. Moreover, CETP inhibitors included herein are also described in U.S. patent application Ser. No. 10/807,838 and PCT Publication No. WO 2006/090250. U.S. Pat. No. 5,512,548 discloses certain polypeptide derivatives having activity as CETP inhibitors, while certain CETP-inhibitory rosenonolactone derivatives and phosphate-containing analogs of cholesteryl ester are disclosed in J. Antibiot., 49(8):815-816 (1996), and Bioorg. Med. Chem. Lett., 6:1951-1954 (1996), respectively.

Any squalene synthetase inhibitor may be used in the combination aspect of this invention. The term squalene synthetase inhibitor refers to compounds which inhibit the condensation of 2 molecules of farnesylpyrophosphate to form squalene, catalyzed by the enzyme squalene synthetase. Such inhibition is readily determined by those skilled in the art according to standard assays (Meth. Enzymol., 15:393-454 (1969) and Meth. Enzymol., 110:359-373 (1985) and references contained therein). A variety of these compounds are described in and referenced below however other squalene synthetase inhibitors will be known to those skilled in the art. U.S. Pat. No. 5,026,554 discloses fermentation products of the microorganism MF5465 (ATCC 74011) including zaragozic acid. A summary of other patented squalene synthetase inhibitors has been compiled (Curr. Op. Ther. Patents, 861-864 (1993)).

Any squalene epoxidase inhibitor may be used in the combination aspect of this invention. The term squalene epoxidase inhibitor refers to compounds which inhibit the bioconversion of squalene and molecular oxygen into squalene-2,3-epoxide, catalyzed by the enzyme squalene epoxidase. Such inhibition is readily determined by those skilled in the art according to standard assays (Biochim. Biophys. Acta, 794:466-471 (1984)). A variety of these compounds are described and referenced below, however other squalene epoxidase inhibitors will be known to those skilled in the art. U.S. Pat. Nos. 5,011,859 and 5,064,864 disclose certain fluoro analogs of squalene. EP publication 395,768 A discloses certain substituted allylamine derivatives. PCT publication WO 93/12069 A discloses certain amino alcohol derivatives. U.S. Pat. No. 5,051,534 discloses certain cyclopropyloxy-squalene derivatives.

Any squalene cyclase inhibitor may be used as the second component in the combination aspect of this invention. The term squalene cyclase inhibiter refers to compounds which inhibit the bioconversion of squalene-2,3-epoxide to lanosterol, catalyzed by the enzyme squalene cyclase. Such inhibition is readily determined by those skilled in the art according to standard assays (FEBS Lett., 244:347-350 (1989)). In addition, the compounds described and referenced below are squalene cyclase inhibitors, however other squalene cyclase inhibitors will also be known to those skilled in the art. PCT publication WO 94/10150 discloses certain 1,2,3,5,6,7,8,8a-octahydro-5,5,8(beta)-trimethyl-6-isoquinolineamine derivatives, such as N-trifluoroacetyl-1,2,3,5,6,7,8,8a-octahydro-2-allyl-5,5,8(beta)-trimethyl-6(beta)-isoquinolineamine. French patent publication 2697250 discloses certain beta, beta-dimethyl-4-piperidine ethanol derivatives such as 1-(1,5,9-trimethyldecyl)-beta,beta-dimethyl-4-piperidineethanol.

Any combined squalene epoxidase/squalene cyclase inhibitor may be used as the second component in the combination aspect of this invention. The term combined squalene epoxidase/squalene cyclase inhibitor refers to compounds that inhibit the bioconversion of squalene to lanosterol via a squalene-2,3-epoxide intermediate. In some assays it is not possible to distinguish between squalene epoxidase inhibitors and squalene cyclase inhibitors, however, these assays are recognized by those skilled in the art. Thus, inhibition by combined squalene epoxidase/squalene cyclase inhibitors is readily determined by those skilled in art according to the aforementioned standard assays for squalene cyclase or squalene epoxidase inhibitors. A variety of these compounds are described and referenced below, however other squalene epoxidase/squalene cyclase inhibitors will be known to those skilled in the art. U.S. Pat. Nos. 5,084,461 and 5,278,171 disclose certain azadecalin derivatives. EP publication 468,434 discloses certain piperidyl ether and thioether derivatives such as 2-(1-piperidyl)pentyl isopentyl sulfoxide and 2-(1-piperidyl)ethyl ethyl sulfide. PCT publication WO 9401404 discloses certain acyl-piperidines such as 1-(1-oxopentyl-5-phenylthio)-4-(2-hydroxy-1-methyl)-ethyl)piperidine. U.S. Pat. No. 5,102,915 discloses certain cyclopropyloxy-squalene derivatives.

The compounds of the present invention may also be administered in combination with naturally occurring compounds that act to lower plasma LDL cholesterol levels or raise plasma HDL levels via a pathway distinct from CETP inhibitors. These naturally occurring compounds are commonly called nutraceuticals and include, for example, garlic extract and niacin. Niacin is a particularly attractive secondary agent for combination with a CETP inhibitor as it also raises HDL cholesterol levels. Furthermore, niacin lowers LDL cholesterol and triglycerides. Therefore, a combination of niacin and a CETP inhibitor would not only provide the potential for enhanced HDL-raising efficacy, it would yield a very favorable shift in the overall cardiovascular risk profile by decreasing LDL cholesterol and triglycerides. Niacin is commercially available in various dosage forms. Immediate release niacin may be purchase over-the-counter in pharmacies or health-food stores. A slow-release form of niacin is available and is known as Niaspan. Niacin may also be combined with other therapeutic agents such as iovastatin, an HMG-CoA reductase inhibitor. This combination therapy with iovastatin is known as ADVICOR™ (Kos Pharmaceuticals Inc.). In long term clinical trials, niacin either as monotherapy or in combination with HMG-CoA reductase inhibitors has been shown to reduce cardiovascular events, cardiovascular deaths and all cause mortality.

Any cholesterol absorption inhibitor can be used as an additional component in the combination aspect of the present invention. The term cholesterol absorption inhibition refers to the ability of a compound to prevent cholesterol contained within the lumen of the intestine from entering into the intestinal cells and/or passing from within the intestinal cells into the lymph system and/or into the blood stream. Such cholesterol absorption inhibition activity is readily determined by those skilled in the art according to standard assays (e.g., J. Lipid Res., 34:377-395 (1993)). Cholesterol absorption inhibitors are known to those skilled in the art and are described, for example, in PCT WO 94/00480. An example of a recently approved cholesterol absorption inhibitor is ZETIA™ (ezetimibe) (Schering-Plough/Merck).

Any ACAT inhibitor may be used in the combination therapy aspect of the present invention. The term ACAT inhibitor refers to compounds that inhibit the intracellular esterification of dietary cholesterol by the enzyme acyl CoA: cholesterol acyltransferase. Such inhibition may be determined readily by one of skill in the art according to standard assays, such as the method of Heider et al. described in J. Lipid Res., 24:1127 (1983). A variety of these compounds are known to those skilled in the art, for example, U.S. Pat. No. 5,510,379 discloses certain carboxysulfonates, while WO 96/26948 and WO 96/10559 both disclose urea derivatives having ACAT inhibitory activity. Examples of ACAT inhibitors include compounds such as Avasimibe (Pfizer), CS-505 (Sankyo) and Eflucimibe (Ell Lilly and Pierre Fabre).

A lipase inhibitor may be used in the combination therapy aspect of the present invention. A lipase inhibitor is a compound that inhibits the metabolic cleavage of dietary triglycerides or plasma phospholipids into free fatty acids and the corresponding glycerides (e.g. EL, HL, etc.). Under normal physiological conditions, lipolysis occurs via a two-step process that involves acylation of an activated serine moiety of the lipase enzyme. This leads to the production of a fatty acid-lipase hemiacetal intermediate, which is then cleaved to release a diglyceride. Following further deacylation, the lipase-fatty acid intermediate is cleaved, resulting in free lipase, a glyceride and fatty acid. In the intestine, the resultant free fatty acids and monoglycerides are incorporated into bile acid-phospholipid micelles, which are subsequently absorbed at the level of the brush border of the small intestine. The micelles eventually enter the peripheral circulation as chylomicrons. Such lipase inhibition activity is readily determined by those skilled in the art according to standard assays (e.g., Meth. Enzymol., 286:190-23 1). Pancreatic lipase mediates the metabolic cleavage of fatty acids from triglycerides at the 1- and 3-carbon positions. The primary site of the metabolism of ingested fats is in the duodenum and proximal jejunum by pancreatic tipase, which is usually secreted in vast excess of the amounts necessary for the breakdown of fats in the upper small intestine. Because pancreatic lipase is the primary enzyme required for the absorption of dietary triglycerides, inhibitors have utility in the treatment of obesity and the other related conditions. Such pancreatic lipase inhibition activity is readily determined by those skilled in the art according to standard assays (e.g., Meth. Enzymol., 286:190-231).

Gastric lipase is an immunologically distinct lipase that is responsible for approximately 10 to 40% of the digestion of dietary fats. Gastric lipase is secreted in response to mechanical stimulation, ingestion of food, the presence of a fatty meal or by sympathetic agents. Gastric lipolysis of ingested fats is of physiological importance in the provision of fatty acids needed to trigger pancreatic lipase activity in the intestine and is also of importance for fat absorption in a variety of physiological and pathological conditions associated with pancreatic insufficiency. See, for example, C. K. Abrams et al., Gastroenterology, 92:125 (1987). Such gastric lipase inhibition activity is readily determined by those skilled in the art according to standard assays (e.g., Meth. Enzymol., 286:190-231).

A variety of gastric and/or pancreatic lipase inhibitors are known to one of ordinary skill in the art. Preferred lipase inhibitors are those inhibitors that are selected from the group consisting of lipstatin, tetrahydrolipstatin (orlistat), valilactone, esterastin, ebelactone A, and ebelactone B. The compound tetrahydrolipstatin is especially preferred. The lipase inhibitor, N-3-trifluoromethylphenyl-N'-3-chloro-4'-trifluoromethylphenylurea, and the various urea derivatives related thereto, are disclosed in U.S. Pat. No. 4,405,644. The lipase inhibitor, esteracin, is disclosed in U.S. Pat. Nos. 4,189,438 and 4,242,453. The lipase inhibitor, cyclo-O,O'-[(1,6-hexanediyl)-bis-(iminocarbonyl)]dioxime, and the various bis (iminocarbonyl)dioximes related thereto may be prepared as described in Petersen et al., Liebig's Annalen, 562:205-229 (1949).

A variety of pancreatic lipase inhibitors are described herein below. The pancreatic lipase inhibitors lipstatin, (2S, 3S, 5S, 7Z, 10Z)-5-[(S)-2-formamido-4-methyl-valeryloxy]-2-hexyl-3-hydroxy-7,10-hexadecanoic acid lactone, and tetrahydrolipstatin (orlistat), (2S, 3S, 5S)-5-[(S)-2-formamido-4-methyl-valeryloxy]-2-hexyl-3-hydroxy-hexadecanoic 1,3 acid lactone, and the variously substituted N-formylleucine derivatives and stereoisomers thereof, are disclosed In U.S. Pat. No. 4,598,089. For example, tetrahydrolipstatin is prepared as described in, e.g., U.S. Pat. Nos. 5,274,143; 5,420,305; 5,540,917; and 5,643,874. The pancreatic lipase inhibitor, FL-386, 1-[4-(2-methylpropyl)cyclohexyl]-2-[(phenylsulfonyl)oxy]ethanone, and the variously substituted sulfonate derivatives related thereto, are disclosed in U.S. Pat. No. 4,452,813. The pancreatic lipase inhibitor, WAY-121898, 4-phenoxyphenyl-4-methylpiperidin-1-yl-carboxylate, and the various carbamate esters and pharmaceutically acceptable salts related thereto, are disclosed in U.S. Pat. Nos. 5,512,565; 5,391,571; and 5,602,151. The pancreatic lipase inhibitor, valilactone, and a process for the preparation thereof by the microbial cultivation of *Actinomycetes* strain MG147-CF2, are disclosed in Kitahara, et al., J. Antibiotics, 40(11): 1647-1650 (1987). The pancreatic lipase inhibitors, ebelactone A and ebelactone B, and a process for the preparation thereof by the microbial cultivation of *Actinomycetes* strain MG7-G1, are disclosed in Umezawa et al., J. Antibiotics, 33:1594-1596 (1980). The use of ebelactones A and B in the suppression of monoglyceride formation is disclosed in Japanese Kokai 08-143457, published Jun. 4, 1996.

Other compounds that are marketed for hyperlipidemia, including hypercholesterolemia and which are intended to help prevent or treat atherosclerosis include bile acid sequestrants, such as Welchol®, Colestid®, LoCholest® and Questran®; and fibric acid derivatives, such as Atromid®, Lopid® and Tricot®.

Diabetes can be treated by administering to a patient having diabetes (especially Type II), insulin resistance, impaired glucose tolerance, metabolic syndrome, or the like, or any of the diabetic complications such as neuropathy, nephropathy, retinopathy or cataracts, a therapeutically effective amount of a compound of the present invention in combination with other agents (e.g., insulin) that can be used to treat diabetes. This includes the classes of anti-diabetic agents (and specific agents) described herein.

Any glycogen phosphorylase inhibitor can be used as the second agent in combination with a compound of the present invention. The term glycogen phosphorylase inhibitor refers to compounds that inhibit the bioconversion of glycogen to glucose-1-phosphate which is catalyzed by the enzyme glycogen phosphorylase. Such glycogen phosphorylase inhibition activity is readily determined by those skilled in the art according to standard assays (e.g., J. Med. Chem., 41:2934-2938 (1998)). A variety of glycogen phosphorylase inhibitors are known to those skilled in the art including those described in WO 96/39384 and WO 96/39385.

Any aldose reductase inhibitor can be used in combination with a compound of the present invention. The term aldose reductase inhibitor refers to compounds that inhibit the bioconversion of glucose to sorbitol, which is catalyzed by the enzyme aldose reductase. Aldose reductase inhibition is readily determined by those skilled in the art according to standard assays (e.g., Malone, J., "Red Celt Sorbitol, an Indicator of Diabetic Control", Diabetes, 29:861-864 (1980)). A variety of aldose reductase inhibitors are known to those skilled in the art, such as those described in U.S. Pat. No. 6,579,879, which includes 6-(5-chloro-3-methylbenzofuran-2-sulfonyl)-2H-pyridazin-3-one.

Any sorbitol dehydrogenase inhibitor can be used in combination with a compound of the present invention. The term sorbitol dehydrogenase inhibitor refers to compounds that inhibit the bioconversion of sorbitol to fructose which is catalyzed by the enzyme sorbitol dehydrogenase. Such sorbitol dehydrogenase inhibitor activity is readily determined by those skilled in the art according to standard assays (e.g., Analyt. Biochem., 280:329-331 (2000)). A variety of sorbitol dehydrogenase inhibitors are known, for example, U.S. Pat. Nos. 5,728,704 and 5,866,578 disclose compounds and a method for treating or preventing diabetic complications by inhibiting the enzyme sorbitol dehydrogenase.

Any glucosidase inhibitor can be used in combination with a compound of the present invention. A glucosidase inhibitor inhibits the enzymatic hydrolysis of complex carbohydrates by glycoside hydrolases, for example amylase or maltase, into bioavailable simple sugars, for example, glucose. The rapid metabolic action of glucosidases, particularly following the intake of high levels of carbohydrates, results in a state of alimentary hyperglycemia which, in adipose or diabetic subjects, leads to enhanced secretion of insulin, increased fat synthesis and a reduction in fat degradation. Following such hyperglycemias, hypoglycemia frequently occurs, due to the augmented levels of insulin present. Additionally, it is known chyme remaining in the stomach promotes the production of gastric juice, which initiates or favors the development of gastritis or duodenal ulcers. Accordingly, glucosidase inhibitors are known to have utility in accelerating the passage of carbohydrates through the stomach and inhibiting the absorption of glucose from the intestine. Furthermore, the conversion of carbohydrates into lipids of the fatty tissue and the subsequent incorporation of alimentary fat into fatty tissue deposits is accordingly reduced or delayed, with the concomitant benefit of reducing or preventing the deleterious abnormalities resulting therefrom. Such glucosidase inhibition activity is readily determined by those skilled in the art according to standard assays (e.g., Biochemistry, 8:4214 (1969)). A generally preferred glucosidase inhibitor includes an amylase inhibitor. An amylase inhibitor is a glucosidase inhibitor that inhibits the enzymatic degradation of starch or glycogen into maltose. Such amylase inhibition activity is readily determined by those skilled in the art according to standard assays (e.g., Meth. Enzymol., 1:149 (1955)). The inhibition of such enzymatic degradation is beneficial in reducing amounts of bioavailable sugars, including glucose and maltose, and the concomitant deleterious conditions resulting therefrom.

A variety of glucosidase inhibitors are known to one of ordinary skill in the art and examples are provided below. Preferred glucosidase inhibitors are those inhibitors that are selected from the group consisting of acarbose, adiposine, voglibose, miglitol, emiglitate, camiglibose, tendamistate, trestatin, pradimicin-Q and salbostatin. The glucosidase inhibitor, acarbose, and the various amino sugar derivatives related thereto are disclosed in U.S. Pat. Nos. 4,062,950 and 4,174,439 respectively. The glucosidase inhibitor, adiposine, is disclosed in U.S. Pat. No. 4,254,256. The glucosidase inhibitor, voglibose, 3,4-dideoxy-4-[[2-hydroxy-1-(hydroxymethyl)ethyl]amino]-2-C-(hydroxymethyl)-D-epi-inositol and the various N-substituted pseudo-aminosugars related thereto, are disclosed in U.S. Pat. No. 4,701,559. The glucosidase inhibitor, miglitol, (2R,3R,4R,5S)-1-(2-hydroxyethyl)-2-(hydroxymethyl)-3,4,5-piperidinetriol, and the various 3,4,5-trihydroxypiperidines related thereto, are disclosed in U.S. Pat. No. 4,639,436. The glucosidase inhibitor, emiglitate, ethyl p-[2-[(2R,3R,4R,5S)-3,4,5-trihydroxy-2-(hydroxymethyl)piperidino]ethoxy]-benzoate, the various derivatives related thereto and pharmaceutically acceptable acid addition salts thereof, are disclosed in U.S. Pat. No. 5,192,772. The glucosidase inhibitor, MDL-25637, 2,6-dideoxy-7-O-β-D-glucopyrano-syl-2,6-imino-D-glycero-L-gluco-heptitol, the various homodisaccharides related thereto and the pharmaceutically acceptable acid addition salts thereof, are disclosed in U.S. Pat. No. 4,634,765. The glucosidase inhibitor, camiglibose, methyl 6-deoxy-6-[(2R,3R,4R,5 S)-3,4,5-trihydroxy-2-(hydroxymethyl)piperidino]-(α-D-glucopyranoside sesquihydrate, the deoxy-nojirimycin derivatives related thereto, the various pharmaceutically acceptable salts thereof and synthetic methods for the preparation thereof, are disclosed in U.S. Pat. Nos. 5,157,116 and 5,504,078. The glycosidase inhibitor, salbostatin and the various pseudosaccharides related thereto, are disclosed In U.S. Pat. No. 5,091,524.

A variety of amylase inhibitors are known to one of ordinary skill in the art. The amylase inhibitor, tendamistat and the various cyclic peptides related thereto, are disclosed in U.S. Pat. No. 4,451,455. The amylase inhibitor AI-3688 and the various cyclic polypeptides related thereto are disclosed in U.S. Pat. No. 4,623,714. The amylase inhibitor, trestatin, consisting of a mixture of trestatin A, trestatin B and trestatin C and the various trehalose-containing aminosugars related thereto are disclosed in U.S. Pat. No. 4,273,765.

Additional anti-diabetic compounds, which can be used as the second agent in combination with a compound of the present invention, include, for example, the following: biguanides (e.g., metformin), insulin secretagogues (e.g., sulfonylureas and glinides), glitazones, non-glitazone PPARγ agonists, PPARβ agonists, inhibitors of DPP-IV, inhibitors of PDE5, inhibitors of GSK-3, glucagon antagonists, inhibitors of f-1,6-BPase(Metabasis/Sankyo), GLP-1/analogs (AC 2993, also known as exendin-4), insulin and insulin mimetics (Merck natural products). Other examples would include PKC-β inhibitors and AGE breakers.

The compounds of the present invention can be used in combination with anti-obesity agents. Any anti-obesity agent can be used as the second agent in such combinations and examples are provided herein. Such anti-obesity activity is readily determined by those skilled in the art according to standard assays known in the art.

Suitable anti-obesity agents include phenylpropanolamine, ephedrine, pseudoephedrine, phentermine, $\beta_3$ adrenergic receptor agonists, apolipoprotein-B secretion/microsomal triglyceride transfer protein (apo-B/MTP) inhibitors, MCR-4-agonists, cholecystokinin-A (CCK-A) agonists, monoamine reuptake inhibitors (e.g., sibutramine), sympathomimetic agents, serotoninergic agents, cannabinoid receptor (CB-1) antagonists (e.g., rimonabant described in U.S. Pat. No. 5,624,941 (SR-141,716A), purine compounds, such as those described in US Patent Publication No. 2004/0092520; pyrazolo[1,5-a][1,3,5]triazine compounds, such as those described in U.S. Non-Provisional patent application Ser. No. 10/763,105; and bicyclic pyrazolyl and imidazolyl compounds, such as those described in U.S. Provisional Application No. 60/518,280, dopamine agonists (e.g., bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (e.g., tetrahydrolipstatin, i.e. orlistat), bombesin agonists, anorectic agents (e.g., a bombesin agonist), Neuropeptide-Y antagonists, thyroxine, thyromimetic agents, dehydroepiandrosterones or analogs thereof, glucocorticoid receptor agonists or antagonists, orexin receptor antagonists, urocortin binding protein antagonists, glucagon-like peptide-1 receptor agonists, ciliary neurotrophic factors (e.g., Axokine™), human agouti-related proteins (AGRP), ghrelin receptor antagonists, histamine 3 receptor antagonists or inverse agonists, neuromedin U receptor agonists, and the like. Rimonabant (SR-141,716A also known under the trade name Acomplia™ available from Sanofi-Aventis) can be prepared as described in U.S. Pat. No. 5,624,941. Other suitable CB-1 antagonists include those described in U.S. Pat. Nos. 5,747,524, 6,432,984 and 6,518,264; U.S. Patent Publication Nos. US2004/0092520, US2004/0157839, US2004/0214855, and US2004/0214838; U.S. patent application Ser. No. 10/971,599; and PCT Patent Publication Nos. WO 02/076949, WO 031075660, WO 04/048317, WO 04/013120, and WO 04/012671.

Preferred apolipoprotein-B secretion/microsomal triglyceride transfer protein (apo-B/MTP) inhibitors for use as anti-obesity agents are gut-selective MTP inhibitors, such as dirlotapide described in U.S. Pat. No. 6,720,351; 4-(4-(4-(4-((2-((4-methyl-4H-1,2,4-triazol-3 -ylthio)methyl)-2-(4-chlorophenyl)-1,3-dioxolan-4-yl)methoxy)phenyl)piperazin-1-yl)phenyl)-2-sec-butyl-2H-1,2,4-triazol-3(4H)-one (R103757) described in U.S. Pat. Nos. 5,521,186 and 5,929,075; and implitapide (BAY 13-9952) described in U.S. Pat. No. 6,265,43 1. As used herein, the term "gut-selective" means that the MTP Inhibitor has a higher exposure to the gastro-intestinal tissues versus systemic exposure.

Any thyromimetic can be used as the second agent in combination with a compound of the present Invention. Such thyromimetic activity is readily determined by those skilled in the art according to standard assays (e.g., Atherosclerosis, 126: 53-63 (1996)). A variety of thyromimetic agents are known to those skilled in the art, for example those disclosed in U.S. Pat. Nos. 4,766,121; 4,826,876; 4,910,305; 5,061,798; 5,284,971; 5,401,772; 5,654,468; and 5,569,674. Other antiobesity agents include sibutramine which can be prepared as described in U.S. Pat. No. 4,929,629 and bromocriptine which can be prepared as described in U.S. Pat. Nos. 3,752,814 and 3,752,888.

The compounds of the present invention can also be used in combination with other antihypertensive agents. Any antihypertensive agent can be used as the second agent in such combinations and examples are provided herein. Such antihypertensive activity is readily determined by those skilled in the art according to standard assays (e.g., blood pressure measurements).

Examples of presently marketed products containing antihypertensive agents include calcium channel blockers, such as Cardizem®, Adalat®, Calan®, Cardene®, Covera®, Dilacor®, DynaCirc®, Procardia XL®, Sular®, Tiazac®, Vascor®, Verelan®, Isoptin®, Nimotop®, Norvasc®, and Plendile; angiotensin converting enzyme (ACE) inhibitors, such as Accupril®, Altace®, Captopril®, Lotensin®, Mavik®, Monopril®, Prinivil®, Univasc®, Vasotec® and Zestril®.

Amlodipine and related dihydropyridine compounds are disclosed in U.S. Pat. No. 4,572,909, as potent anti-ischemic and antihypertensive agents. U.S. Pat. No.4,879,303 discloses amlodipine benzenesulfonate salt (also termed amlodipine besylate). Amlodipine and amlodipine besylate are potent and long lasting calcium channel blockers. As such, amlodipine, amlodipine besylate, amlodipine maleate and other pharmaceutically acceptable acid addition salts of amlodipine have utility as antihypertensive agents and as antiischemic agents. Amlodipine besylate is currently sold as Norvasc®.

Calcium channel blockers which are within the scope of this invention include, but are not limited to: bepridil, which may be prepared as disclosed in U.S. Pat. No. 3,962,238 or U.S. Reissue No. 30,577; clentiazem, which may be prepared as disclosed in U.S. Pat. No. 4,567,175; diltiazem, fendiline, which may be prepared as disclosed in U.S. Pat. No. 3,262,977; gallopamil, which may be prepared as disclosed in U.S. Pat. No. 3,261,859; mibefradil, which may be prepared as disclosed in U.S. Pat. No. 4,808,605; prenylamine, which may be prepared as disclosed in U.S. Pat. No. 3,152,173; semotiadil, which may be prepared as disclosed in U.S. Pat. No. 4,786,635; terodiline, which may be prepared as disclosed in U.S. Pat. No. 3,371,014; verapamil, which may be prepared as disclosed in U.S. Pat. No. 3,261,859; aranipine, which may be prepared as disclosed in U.S. Pat. No. 4,572,909; barnidipine, which may be prepared as disclosed in U.S. Pat. No. 4,220,649; benidipine, which may be prepared as disclosed in European Patent Application Publication No. 106,275; cilnidipine, which may be prepared as disclosed in U.S. Pat. No. 4,672,068; efonidipine, which may be prepared as disclosed in U.S. Pat. No. 4,885,284; elgodipine, which may be prepared as disclosed in U.S. Pat. No. 4,952,592; felodipine, which may be prepared as disclosed in U.S. Pat. No. 4,264,611; isradipine, which may be prepared as disclosed in U.S. Pat. No. 4,466,972; lacidipine, which may be prepared as disclosed in U.S. Pat. No. 4,801,599; lercanidipine, which may be prepared as disclosed in U.S. Pat. No. 4,705,797; manidipine, which may be prepared as disclosed in U.S. Pat. No. 4,892,875; nicardipine, which may be prepared as disclosed in U.S. Pat. No. 3,985,758; nifedipine, which may be prepared as disclosed in U.S. Pat. No. 3,485,847; nilvadipine, which may be prepared as disclosed in U.S. Pat. No. 4,338,322; nimodipine, which may be prepared as disclosed in U.S. Pat. No. 3,799,934; nisoldipine, which may be prepared as disclosed in U.S. Pat. No. 4,154,839; nitrendipine, which may be prepared as disclosed in U.S. Pat. No. 3,799,934; cinnarizine, which may be prepared as disclosed in U.S. Pat. No. 2,882,271; flunarizine, which may be prepared as disclosed in U.S. Pat. No. 3,773,939; lidoflazine, which may be prepared as disclosed in U.S. Pat. No. 3,267,104; Iomerizine, which may be prepared as disclosed in U.S. Pat. No. 4,663,325; bencyclane, which may be prepared as disclosed in Hungarian Patent No. 151,865; etafenone, which may be prepared as disclosed in German Patent No. 1,265,758; and perhexiline, which may be prepared as disclosed in British Patent No. 1,025,578.

Angiotensin Converting Enzyme Inhibitors (ACE-Inhibitors) which are within the scope of this invention include, but are not limited to: alacepril, which may be prepared as disclosed in U.S. Pat. No. 4,248,883; benazepril, which may be prepared as disclosed in U.S. Pat. No, 4,410,520; captopril, which may be prepared as disclosed in U.S. Pat. Nos. 4,046,889 and 4,105,776; ceronapril, which may be prepared as disclosed in U.S. Pat. No. 4,462,790; delapril, which may be prepared as disclosed in U.S. Pat. No. 4,385,051; enalapril, which may be prepared as disclosed in U.S. Pat. No. 4,374,829; fosinopril, which may be prepared as disclosed in U.S. Pat. No. 4,337,201; imadapril, which may be prepared as disclosed in U.S. Pat. No. 4,508,727; lisinopril, which may be prepared as disclosed in U.S. Pat. No. 4,555,502; moveltopril, which may be prepared as disclosed in Belgian Patent No. 893,553; perindopril, which may be prepared as disclosed in U.S. Pat. No. 4,508,729; quinapril, which may be prepared as disclosed in U.S. Pat. No. 4,344,949; ramipril, which may be prepared as disclosed in U.S. Pat. No. 4,587,258; spirapril, which may be prepared as disclosed in U.S. Pat. No. 4,470,972; temocapril, which may be prepared as disclosed in U.S. Pat. No. 4,699,905; and trandolapril, which may be prepared as disclosed in U.S. Pat. No. 4,933,361.

Angiotensin-JJ receptor antagonists (A-II antagonists) which are within the scope of this invention include, but are not limited to: candesartan, which may be prepared as disclosed in U.S. Pat. No. 5,196,444; eprosartan, which may be prepared as disclosed in U.S. Pat. No. 5,185,351; irbesartan, which may be prepared as disclosed in U.S. Pat. No. 5,270,317; losartan, which may be prepared as disclosed in U.S, Pat. No. 5,138,069; and valsartan, which may be prepared as disclosed in U.S. Pat. No. 5,399,578.

Beta-adrenergic receptor blockers (beta-or β-blockers) which are within the scope of this invention include, but are not limited to: acebutolol, which may be prepared as disclosed in U.S. Pat. No. 3,857,952; alprenolol, which may be prepared as disclosed in Netherlands Patent Application No. 6,605,692; amosulalol, which may be prepared as disclosed in U.S. Pat. No. 4,217,305; arotinolol, which may be prepared as disclosed in U.S. Pat. No. 3,932,400; atenolol, which may be prepared as disclosed in U.S. Pat. No. 3,663,607 or 3,836,671; befunolol, which may be prepared as disclosed in U.S. Pat. No. 3,853,923; betaxolol, which may be prepared as disclosed in U.S. Pat. No. 4,252,984; bevantolol, which may be prepared as disclosed in U.S. Pat. No. 3,857,981; bisoprolol, which may be prepared as disclosed in U.S. Pat. No. 4,171,370; bopindolol, which may be prepared as disclosed in U.S. Pat. No. 4,340,541; bucumolol, which may be prepared as disclosed in U.S. Pat. No. 3,663,570; bufetolol, which may be prepared as disclosed in U.S. Pat. No. 3,723,476; bufuralol, which may be prepared as disclosed in U.S. Pat. No. 3,929,836; bunitrolol, which may be prepared as disclosed in U.S. Pat. Nos. 3,940,489 and 3,961,071; buprandolol, which may be prepared as disclosed in U.S. Pat. No. 3,309,406; butiridine hydrochloride, which may be prepared as disclosed in French Patent No. 1,390,056; butofilolol, which may be prepared as disclosed in U.S. Pat. No. 4,252,825; carazolol, which may be prepared as disclosed in German Patent No. 2,240,599; carteolol, which may be prepared as disclosed in U.S. Pat. No. 3,910,924; carvedilol, which may be prepared as disclosed in U.S. Pat. No. 4,503,067;

celiprolol, which may be prepared as disclosed in U.S. Pat. No. 4,034,009; cetamolol, which may be prepared as disclosed in U.S. Pat. No. 4,059,622; cloranolol, which may be prepared as disclosed in German Patent No. 2,213,044; dilevalol, which may be prepared as disclosed in Clifton et al., J. Med. Chem., 25:670 (1982); epanolol, which may be prepared as disclosed in European Patent Publication Application No. 41,491; indenolol, which may be prepared as disclosed in U.S. Pat. No. 4,045,482; labetalol, which may be prepared as disclosed in U.S. Pat. No. 4,012,444; levobunolol, which may be prepared as disclosed in U.S. Pat. No. 4,463,176; mepindolol, which may be prepared as disclosed in Seeman et al., Heir. Chim. Acta, 54:241 (1971); metipranolol, which may be prepared as disclosed in Czechoslovakian Patent Application No. 128,471; metoprolol, which may be prepared as disclosed in U.S. Pat. No. 3,873,600; moprolol, which may be prepared as disclosed in U.S. Patent No. 3,501,769; nadolol, which may be prepared as disclosed in U.S. Pat. No. 3,935,267; nadoxolol, which may be prepared as disclosed in U.S. Pat. No. 3,819,702; nebivalol, which may be prepared as disclosed in U.S. Pat. No. 4,654,362; nipradilol, which may be prepared as disclosed in U.S. Pat. No. 4,394,382; oxprenolol, which may be prepared as disclosed in British Patent No. 1,077,603; perbutolol, which may be prepared as disclosed in U.S. Pat. No. 3,551,493; pindolol, which may be prepared as disclosed in Swiss Patent Nos. 469,002 and 472,404; practolol, which may be prepared as disclosed in U.S. Pat. No. 3,408,387; pronethalol, which may be prepared as disclosed in British Patent No. 909,357; propranolol, which may be prepared as disclosed in U.S. Pat. Nos. 3,337,628 and 3,520,919; sotalol, which may be prepared as disclosed in Uloth et al., J. Med. Chem., 9:88 (1966); sufinalol, which may be prepared as disclosed in German Patent No. 2,728,641; talindol, which may be prepared as disclosed in U.S. Pat. Nos. 3,935,259 and 4,038,313; tertatolol, which may be prepared as disclosed in U.S. Pat. No. 3,960,891; tilisolol, which may be prepared as disclosed in U.S. Pat. No. 4,129,565; timolol, which may be prepared as disclosed in U.S. Pat. No. 3,655,663; toliprolol, which may be prepared as disclosed in U.S. Pat. No. 3,432,545; and xibenolol, which may be prepared as disclosed in U.S. Pat. No. 4,018,824.

Alpha-adrenergic receptor blockers (alpha- or α-blockers) which are within the scope of this invention include, but are not limited to: amosulalol, which may be prepared as disclosed in U.S. Pat. No. 4,217,307; arotinolol, which may be prepared as disclosed in U.S. Pat. No. 3,932,400; dapiprazole, which may be prepared as disclosed in U.S. Pat. No. 4,252,721; doxazosin, which may be prepared as disclosed in U.S. Pat. No. 4,188,390; fenspiride, which may be prepared as disclosed in U.S. Pat. No. 3,399,192; indoramin, which may be prepared as disclosed in U.S. Pat. No. 3,527,761; labetolol; naftopidil, which may be prepared as disclosed in U.S. Pat. No. 3,997,666; nicergoline, which may be prepared as disclosed in U.S. Pat. No. 3,228,943; prazosin, which may be prepared as disclosed in U.S. Pat. No, 3,511,836; tamsulosin, which may be prepared as disclosed in U.S. Pat. No. 4,703,063; tolazoline, which may be prepared as disclosed in U.S. Pat. No. 2,161,938; trimazosin, which may be prepared as disclosed in U.S. Pat. No. 3,669,968; and yohimbine, which may be isolated from natural sources according to methods well known to those skilled in the art.

The term "vasodilator," where used herein, is meant to include cerebral vasodilators, coronary vasodilators and peripheral vasodilators. Cerebral vasodilators within the scope of this invention include, but are not limited to: bencyclane; cinnarizine; citicoline, which may be isolated from natural sources as disclosed in Kennedy et al., J. Am. Chem. Soc., 77:250 (1955) or synthesized as disclosed in Kennedy, J. Biol. Chem., 1956, 222, 185; cyclandelate, which may be prepared as disclosed in U.S. Pat. No. 3,663,597; ciclonicate, which may be prepared as disclosed in German Patent No, 1,910,481; diisopropylamine dichloroacetate, which may be prepared as disclosed in British Patent No. 862,248; eburnamonine, which may be prepared as disclosed in Hermann et al., J. Am. Chem. Soc., 101:1540 (1979); fasudil, which may be prepared as disclosed in U.S. Pat. No. 4,678,783; fenoxedil, which may be prepared as disclosed in U.S. Pat. No. 3,818,021; flunarizine, which may be prepared as disclosed in U.S. Pat. No, 3,773,939; ibudilast, which may be prepared as disclosed in U.S. Pat. No. 3,850,941; ifenprodil, which may be prepared as disclosed in U.S. Pat. No. 3,509,164; lomerizine, which may be prepared as disclosed in U.S. Pat. No. 4,663,325; nafronyl, which may be prepared as disclosed in U.S. Pat. No. 3,334,096; nicametate, which may be prepared as disclosed in Blicke et al., J. Am. Chem. Soc., 64:1722 (1942); nicergoline, which may be prepared as disclosed above; nimodipine, which may be prepared as disclosed in U.S. Pat. No. 3,799,934; papaverine, which may be prepared as reviewed in Goldberg, Chem. Prod. Chem. News, 17:371 (1954); pentifylline, which may be prepared as disclosed in German Patent No. 860,217; tinofedrine, which may be prepared as disclosed in U.S. Pat. No. 3,563,997; vincamine, which may be prepared as disclosed in U.S. Pat. No. 3,770,724; vinpocetine, which may be prepared as disclosed in U.S. Pat. No. 4,035,750; and viquidil, which may be prepared as disclosed in U.S. Pat. No. 2,500,444.

Coronary vasodilators within the scope of this invention include, but are not limited to: amotriphene, which may be prepared as disclosed in U.S. Pat. No. 3,010,965; bendazol, which may be prepared as disclosed in J. Chem. Soc. 1958, 2426; benfurodil hemisuccinate, which may be prepared as disclosed in U.S. Pat. No. 3,355,463; benziodarone, which may be prepared as disclosed in U.S. Pat. No. 3,012,042; chloracizine, which may be prepared as disclosed in British Patent No. 740,932; chromonar, which may be prepared as disclosed in U.S. Pat. No, 3,282,938; clobenfural, which may be prepared as disclosed in British Patent No. 1,160,925; clonitrate, which may be prepared from propanediol according to methods well known to those skilled in the art, e.g., see Annalen, 1870, 155, 165; cloricromen, which may be prepared as disclosed in U.S. Pat. No. 4,452,811; dilazep, which may be prepared as disclosed in U.S. Pat. No. 3,532,685; dipyridamole, which may be prepared as disclosed in British Patent No. 807,826; droprenilamine, which may be prepared as disclosed in German Patent No. 2,521,113; efloxate, which may be prepared as disclosed in British Patent Nos. 803,372 and 824,547; erythrityl tetranitrate, which may be prepared by nitration of erythritol according to methods well-known to those skilled in the art; etafenone, which may be prepared as disclosed in German Patent No. 1,265,758; fendiline, which may be prepared as disclosed in U.S. Pat. No. 3,262,977; floredil, which may be prepared as disclosed in German Patent No. 2,020,464; ganglefene, which may be prepared as disclosed in U.S.S.R. Patent No. 115,905; hexestrol, which may be prepared as disclosed in U.S. Pat. No. 2,357,985; hexobendine, which may be prepared as disclosed in U.S. Pat. No. 3,267,103; itramin tosylate, which may be prepared as disclosed in Swedish Patent No. 168,308; khellin, which may be prepared as disclosed in Baxter et al., Journal of the Chemical Society, 1949, S 30; lidoflazine, which may be prepared as disclosed in U.S. Pat. No. 3,267,104; mannitol hexanitrate, which may be prepared by the nitration of mannitol according to methods well-known to those skilled in the art; medibazine, which may be prepared as disclosed in U.S. Pat. No. 3,119,826; nitroglycerin; pentaerythritol tetranitrate, which may be prepared by the nitration of pentaerythritol according to methods well-known to those skilled in the art; pentrinitrol, which may be prepared as disclosed in German Patent No. 638,422-3; perhexilline, which may be prepared as disclosed above; pimefylline, which may be prepared as disclosed in U.S. Pat. No. 3,350,400; prenylamine, which may be prepared as disclosed in U.S. Pat. No. 3,152,173; propatyl nitrate, which may be prepared as disclosed in French Patent No. 1, 103,113; trapidil, which may be prepared as disclosed in East German Patent No. 55,956; tricromyl, which may be prepared as disclosed in U.S. Pat. No. 2,769,015; trimetazidine, which may be prepared as disclosed in U.S. Pat. No. 3,262,852; trolnitrate phosphate, which may be prepared by nitration of triethanolamine followed by precipitation with phosphoric acid according to methods well-known to those skilled in the art; visnadine, which may be prepared as disclosed in U.S. Pat. Nos. 2,816,118 and 2,980,699.

Peripheral vasodilators within the scope of this invention include, but are not limited to: aluminum nicotinate, which may be prepared as disclosed in U.S. Pat. No. 2,970,082; bamethan, which may be prepared as disclosed in Corrigan et al., J. Am. Chem. Soc., 67:1894 (1945); bencyclane, which may be prepared as disclosed above; betahistine, which may be prepared as disclosed in Walter et al., J. Am. Chem. Soc., 63:2771 (1941); bradykinin, which may be prepared as disclosed in Hamburg et al., Arch. Biochem. Biophys., 76:252 (1958); brovincamine, which may be prepared as disclosed in U.S. Pat. No. 4,146,643; bufeniode, which may be prepared as disclosed in U.S. Pat. No. 3,542,870; buflomedil, which may be prepared as disclosed in U.S. Pat. No. 3,895,030; butalamine, which may be prepared as disclosed in U.S. Pat. No. 3,338,899; cetiedil, which may be prepared as disclosed in French Patent No. 1,460,571; ciclonicate, which may be prepared as disclosed in German Patent No, 1,910,481; cinepazide, which may be prepared as disclosed in Belgian Patent No. 730,345; cinnarizine, which may be prepared as disclosed above; cyclandelate, which may be prepared as disclosed above; diisopropylamine dichloroacetate, which may be prepared as disclosed above; eledoisin, which may be prepared as disclosed in British Patent No. 984,810; fenoxedil, which may be prepared as disclosed above; flunarizine, which may be prepared as disclosed above; hepronicate, which may be prepared as disclosed in U.S, Pat. No. 3,384,642; ifenprodil, which may be prepared as disclosed above; iloprost, which may be prepared as disclosed in U.S. Pat. No. 4,692,464; inositol niacinate, which may be prepared as disclosed in Badgett et al., J. Am. Chem. Soc., 69:2907 (1947); isoxsuprine, which may be prepared as disclosed in U.S. Pat. No. 3,056,836; kallidin, which may be prepared as disclosed in Biochem. Biophys. Res. Commun., 6:210 (1961); kallikrein, which may be prepared as disclosed in German Patent No. 1,102,973; moxisylyte, which may be prepared as disclosed in German Patent No. 905,738; nafronyl, which may be prepared as disclosed above; nicametate, which may be prepared as disclosed above; nicergoline, which may be prepared as disclosed above; nicofuranose, which may be prepared as disclosed in Swiss Patent No. 366,523; nylidrin, which may be prepared as disclosed in U.S. Pat. Nos. 2,661,372 and 2,661,373; pentifylline, which may be prepared as disclosed above; pentoxifylline, which may be prepared as disclosed in U.S. Pat. No, 3,422,107; piribedil, which may be prepared as disclosed in U.S. Pat. No. 3,299, 067; prostaglandin $E_1$, which may be prepared by any of the methods referenced in the Merck Index, Twelfth Edition, Budaveri, Ed., New Jersey, p. 1353 (1996); suloctidil, which may be prepared as disclosed in German Patent No. 2,334, 404; tolazoline, which may be prepared as disclosed in U.S. Pat. No. 2,161,938; and xanthinol niacinate, which may be prepared as disclosed in German Patent No. 1,102,750.

The term "diuretic," within the scope of this invention, is meant to include diuretic benzothiadiazine derivatives, diuretic organomercurials, diuretic purines, diuretic steroids, diuretic sulfonamide derivatives, diuretic uracils and other diuretics such as amanozine, which may be prepared as disclosed in Austrian Patent No. 168,063; amiloride, which may be prepared as disclosed in Belgian Patent No. 639,386; arbutin, which may be prepared as disclosed in Tschitschibabin, Annalen, 1930, 479, 303; chlorazanil, which may be prepared as disclosed in Austrian Patent No. 168,063; ethacrynic acid, which may be prepared as disclosed in U.S. Pat. No. 3,255, 241; etozolin, which may be prepared as disclosed in U.S. Pat. No. 3,072,653; hydracarbazine, which may be prepared as disclosed in British Patent No. 856,409; isosorbide, which may be prepared as disclosed in U.S. Pat. No. 3,160,641; mannitol; metochalcone, which may be prepared as disclosed in Freudenberg et al., Ber., 90:957 (1957); muzolimine, which may be prepared as disclosed in U.S. Pat. No. 4,018, 890; perhexiline, which may be prepared as disclosed above; ticrynafen, which may be prepared as disclosed in U.S. Pat. No. 3,758,506; triamterene which may be prepared as disclosed in U.S. Pat. No. 3,051,230; and urea.

Diuretic benzothiadiazine derivatives within the scope of this invention include, but are not limited to: althiazide, which may be prepared as disclosed in British Patent No. 902,658; bendroflumethiazide, which may be prepared as disclosed in U.S. Pat. No. 3,265,573; benzthiazide, McManus et al., 136th Am. Soc. Meeting (Atlantic City, September 1959), Abstract of papers, pp 13-O; benzylhydrochlorothiazide, which may be prepared as disclosed in U.S. Pat. No. 3,108,097; buthiazide, which may be prepared as disclosed in British Patent Nos. 861,367 and 885,078; chlorothiazide, which may be prepared as disclosed in U.S. Pat. Nos. 2,809,194 and 2,937,169; chlorthalidone, which may be prepared as disclosed in U.S. Pat. No. 3,055,904; cyclopenthiazide, which maybe prepared as disclosed in Belgian Patent No. 587,225; cyclothiazide, which may be prepared as disclosed in Whitehead et al., J. Org. Chem., 26:2814 (1961); epithiazide, which may be prepared as disclosed in U.S. Pat. No. 3,009,911; ethiazide, which may be prepared as disclosed in British Patent No. 861,367; fenquizone, which may be prepared as disclosed in U.S. Pat. No. 3,870,720; indapamide, which may be prepared as disclosed in U.S. Pat. No. 3,565,911; hydrochlorothiazide, which may be prepared as disclosed in U.S. Pat. No. 3,164, 588; hydroflumethiazide, which may be prepared as disclosed in U.S. Pat. No. 3,254,076; methyclothiazide, which may be prepared as disclosed in Close et al., J. Am. Chem. Soc., 82:1132 (1960); meticrane, which may be prepared as disclosed in French Patent Nos. M2790 and 1,365,504; metolazone, which may be prepared as disclosed in U.S. Pat. No. 3,360,518; paraflutizide, which may be prepared as disclosed in Belgian Patent No. 620,829; polythiazide, which may be prepared as disclosed in U.S. Pat. No. 3,009,911; quinethazone, which may be prepared as disclosed in U.S. Pat. No. 2,976,289; teclothiazide, which may be prepared as disclosed in Close et al., J. Am. Chem. Soc., 82:1132 (1960); and trichlormethiazide, which may be prepared as disclosed in deStevens et al., Experientia, 16:113 (1960).

Diuretic sulfonamide derivatives within the scope of this invention include, but are not limited to: acetazolamide, which may be prepared as disclosed in U.S. Pat. No. 2,980, 679; ambuside, which may be prepared as disclosed in U.S. Pat. No. 3,188,329; azosemide, which may be prepared as disclosed in U.S. Pat. No. 3,665,002; bumetanide, which may be prepared as disclosed in U.S. Pat. No. 3,634,583; butazolamide, which may be prepared as disclosed in British Patent No. 769,757; chloraminophenamide, which may be prepared as disclosed in U.S. Pat. Nos. 2,809,194, 2,965,655 and 2,965,656; clofenamide, which may be prepared as disclosed in Olivier, Rec. Trav. Chim., 37:307 (1918); clopamide, which may be prepared as disclosed in U.S. Pat. No. 3,459,756; clorexolone, which may be prepared as disclosed in U.S. Pat. No. 3,183,243; disulfamide, which may be prepared as disclosed in British Patent No. 851,287; ethoxolamide, which may be prepared as disclosed in British Patent No. 795,174; furosemide, which may be prepared as disclosed in U.S. Pat. No. 3,058,882; mefruside, which may be prepared as disclosed in U.S. Pat. No. 3,356,692; methazolamide, which may be prepared as disclosed in U.S. Pat. No. 2,783,241; piretanide, which may be prepared as disclosed in U.S. Pat. No. 4,010,273; torasemide, which may be prepared as disclosed in U.S. Pat. No. 4,018,929; tripamide, which may be prepared as disclosed in Japanese Patent No. 73 05,585; and xipamide, which may be prepared as disclosed in U.S. Pat. No. 3,567,777.

Osteoporosis is a systemic skeletal disease, characterized by low bone mass and deterioration of bone tissue, with a consequent increase in bone fragility and susceptibility to fracture, in the U.S., the condition affects more than 25 million people and causes more than 1.3 million fractures each year, including 500,000 spine, 250,000 hip and 240,000 wrist fractures annually. Hip fractures are the most serious consequence of osteoporosis, with 5-20% of patients dying within one year, and over 50% of survivors being incapacitated. The elderly are at greatest risk of osteoporosis, and the problem is therefore predicted to increase significantly within the aging of the population. Worldwide fracture incidence is forecasted to increase three-fold over the next 60 years, and one study has estimated that there will be 4.5 million hip fractures worldwide in 2050. Women are at greater risk of osteoporosis than men. Women experience a sharp acceleration of bone loss during the five years following menopause. Other factors that increase the risk include smoking, alcohol abuse, a sedentary lifestyle and low calcium intake.

Those skilled in the art will recognize that anti-resorptive agents (for example progestins, polyphosphonates, bisphosphonate(s), estrogen agonists/antagonists, estrogen, estrogen/progestin combinations, Premarin™, estrone, estriol or 17α- or 170β-ethynyl estradiol) may be used in conjunction with the compounds of the present invention.

Exemplary progestins are available from commercial sources and include: algestone acetophenide, altrenogest, amadinone acetate, anagestone acetate, chlormadinone acetate, cingestol, clogestone acetate, clomegestone acetate, delmadinone acetate, desogestrel, dimethisterone, dydrogesterone, ethynerone, ethynodiol diacetate, etonogestrel, flurogestone acetate, gestaclone, gestodene, gestonorone caproate, gestrinone, haloprogesterone, hydroxyprogesterone caproate, levonorgestrel, lynestrenol, medrogestone, medroxyprogesterone acetate, melengestrol acetate, methynodiol diacetate, norethindrone, norethindrone acetate, norethynodrel, norgestimate, norgestomet, norgestrel, oxogestone phenproprionate, progesterone, quingestanol acetate, quingestrone, and tigestol. Preferred progestins are medroxyprogestrone, norethindrone and norethynedrel.

Exemplary bone resorption inhibiting polyphosphonates include polyphosphenates of the type disclosed in U.S. Pat. No. 3,683,080. Preferred polyphosphonates are geminal diphosphonates (also referred to as bis-phosphonates). Tiludronate disodium is an especially preferred polyphosphonate. Jbandronic acid is an especially preferred polyphosphonate. Alendronate and resindronate are especially preferred polyphosphonates. Zoledronic acid is an especially preferred polyphosphonate. Other preferred polyphosphonates are 6-amino-1-hydroxy-hexylidene-bisphosphonic acid and 1-hydroxy-3(methylpentylamino)-propylidene-bisphosphonic acid. The polyphosphonates may be administered in the form of the acid, or of a soluble alkali metal salt or alkaline earth metal salt. Hydrolyzable esters of the polyphosphonates are likewise included. Specific examples include ethane-1-hydroxy 1,1 -diphosphonic acid, methane diphosphonic acid, pentane-1-hydroxy-1,1-diphosphonic acid, methane dichloro diphosphonic acid, methane hydroxy diphosphonic acid, ethane-1-amino-1,1-diphosphonic acid, ethane-2-amino-1,1-diphosphonic acid, propane-3-amino-1-hydroxy-1,1-diphosphonic acid, propane-N,N-dimethyl-3-amino-1-hydroxy-1,1-diphosphonic acid, propane-3,3-dimethyl-3-amino-1-hydroxy-1,1-diphosphonic acid, phenyl amino methane diphosphonic acid, N,N-dimethylamino methane diphosphonic acid, N-(2-hydroxyethyl) amino methane diphosphonic acid, butane-4-amino-1-hydroxy-1,1-diphosphonic acid, pentane-5-amino-1-hydroxy-1,1-diphosphonic acid, hexane-6-amino-1-hydroxy-1,1-diphosphonic acid and pharmaceutically acceptable esters and salts thereof.

In particular, the compounds of this invention may be combined with a mammalian estrogen agonist/antagonist. Any estrogen agonist/antagonist may be used in the combination aspect of this invention. The term estrogen agonist/antagonist refers to compounds which bind with the estrogen receptor, inhibit bone turnover and/or prevent bone loss. In particular, estrogen agonists are herein defined as chemical compounds capable of binding to the estrogen receptor sites in mammalian tissue, and mimicking the actions of estrogen in one or more tissue. Estrogen antagonists are herein defined as chemical compounds capable of binding to the estrogen receptor sites in mammalian tissue, and blocking the actions of estrogen in one or more tissues. Such activities are readily determined by those skilled in the art of standard assays including estrogen receptor binding assays, standard bone histomorphometric and densitometer methods (Eriksen, E. F. et al., Bone Histomorphometry, Raven Press, New York, pp. 1-74 (1994); Grier, S.J. et al., “The Use of Dual-Energy X-Ray Absorptiometry In Animals”, Inv. Radiol., 31(1):50-62 (1996); Wahner, H. W. et al., The Evaluation of Osteoporosis: Dual Energy X-Ray Absorptiometry in Clinical Practice, Martin Dunitz Ltd., London, pp. 1-296 (1994)). A variety of these compounds are described and referenced below. Another preferred estrogen agonist/antagonist is 3-(4-{1,2-diphenyl-but-1-enyl)-phenyl)-acrylic acid, which is disclosed in Willson et al., Endocrinology, 138:3901-3911 (1997). Another preferred estrogen agonist/antagonist is tamoxifen: (ethanamine,2-(-4-(1,2-diphenyl-1-butenyl)phenoxy)-N,N-dimethyl, (Z)-2-, 2-hydroxy-1,2,3-propanetricarboxylate(1:1)) and related compounds which are disclosed in U.S. Pat. No. 4,536,516. Another related compound is 4-hydroxy tamoxifen, which is disclosed in U.S. Pat. No. 4,623,660. A preferred estrogen agonist/antagonist is raloxifene: (methanone, (6-hydroxy-2-(4-hydroxyphenyl)benzo[b]thien-3-yl)(4-(2-(1-piperidinyl)ethoxy)phenyl)hydrochloride) which is disclosed in U.S. Pat. No. 4,418,068. Another preferred estrogen agonist/antagonist is toremifene: (ethanamine, 2-(4-(4-chloro-1,2-diphenyl-1-butenyl)phenoxy)-N,N-dimethyl-, (Z)-, 2-hydroxy-1,2,3-propanetricarboxylate (1:1) which is disclosed in U.S. Pat. No. 4,996,225. Another preferred estrogen agonist/antagonist is centchroman: 1-(2-((4-(-methoxy-2,2, dimethyl-3-phenyl-chroman- 4-yl)-phenoxy)-ethyl)-pyrrolidine, which is disclosed in U.S. Pat. No. 3,822,287. Also preferred is levormeloxifene.

Another preferred estrogen agonist/antagonist is idoxifene: (E)-1 -(2-(4-(1-(4-iodo-phenyl)-2-phenyl-but-1-enyl)-phenoxy)-ethyl)-pyrrolidinone, which is disclosed in U.S. Pat. No. 4,839,155. Another preferred estrogen agonist/antagonist is 2-(4-methoxy-phenyl)-3-[4-(2-piperidin-1-yl-ethoxy)-phenoxy]-benzo[b]thiophen-6-ol which is disclosed in U.S. Pat. No. 5,488,058. Another referred estrogen agonist/antagonist is 6-(4-hydroxy-phenyl)-5-(4-(2-piperidin-1-yl-ethoxy)-benzyl)-naphthalen-2-ol, which is disclosed in U.S. Pat. No. 5,484,795. Another preferred estrogen agonist/antagonist is (4-(2-(2-aza-bicyclo[2.2.1]hept-2-yl)-ethoxy)-phenyl)-(6-hydroxy-2-(4-hydroxyphenyl)-benzo [b]thiophen-3-yl)-methanone which is disclosed, along with methods of preparation, in PCT Publication No. WO 95/10513. Other preferred estrogen agonist/antagonists include the compounds, TSE-424 (Wyeth-Ayerst Laboratories) and arazoxifene.

Other preferred estrogen agonist/antagonists include compounds as described in U.S. Pat. No. 5,552,412. Especially preferred compounds described therein are: cis-6-(4-fluoro-phenyl)-5-(4-(2-piperidin-1-yl-ethoxy)-phenyl)-5,6,7,8-tetrahydronaphthalene-2-ol; (−)-cis-6-phenyl-5-(4-(2-pyrrolidin-1-yl-ethoxy)-phenyl)-5,6,7,8-tetrahydronaphthalene-2-ol (also known as lasofoxifene); cis-6-phenyl-5-(4-(2-pyrrolidin-1-yl-ethoxy)-phenyl)-5,6,7,8-tetrahydronaphthalene-2-ol; cis-1-(6'-pyrrolodinoethoxy-3'-pyridyl)-2-phenyl-6-hydroxy-1,2,3,4-tetrahydronaphthalene; 1-(4'-pyrrolidinoethoxyphenyl)-2-(4"-fluorophenyl)-6-hydroxy-1,2,3, 44etrahydroisoquinoline; cis-6-(4-hydroxyphenyl)-5-(4-(2-piperidin-1-yl-ethoxy)-phenyl)-5,6,7,8-tetrahydronaphthalene-2-ol; and 1-(4'-pyrrolidinolethoxyphenyl)-2-phenyl-6-hydroxy-1,2,3,4-tetrahydroisoquinoline.

Other estrogen agonist/antagonists are described in U.S. Pat. No. 4,133,814, which discloses derivatives of2-phenyl-3-aroyl-benzothiophene and 2-phenyl-3-aroylbenzothiophene-1-oxide.

Other anti-osteoporosis agents, which can be used as the second agent in combination with a compound of the present invention, include, for example, the following: parathyroid hormone (PTH) (a bone anabolic agent); parathyroid hormone (PTH) secretagogues (see, e.g., U.S. Pat. No. 6,132, 774), particularly calcium receptor antagonists; calcitonin; vitamin D and vitamin D analogs.

Any selective androgen receptor modulator (SARM) can be used in combination with a compound of the present invention. A selective androgen receptor modulator (SARM) is a compound that possesses androgenic activity and which exerts tissue-selective effects. SARM compounds can function as androgen receptor agonists, partial agonists, partial antagonists or antagonists. Examples of suitable SARMs include compounds such as cyproterone acetate, chlormadinone, flutamide, hydroxyflutamide, bicalutamide, nilutamide, spironolactone,4-(trifluoromethyl)-2(1 H)-pyrrolidino [3,2-g]quinoline derivatives, 1,2-dihydropyridino [5,6-g] quinoline derivatives and piperidino[3,2-g]quinolinone derivatives.

Cypterone, also known as (1b,2b)-6-chloro-1,2-dihydro-17-hydroxy-3'H-cyclopropa[1,2]pregna-1,4,6-triene-3,20-dione is disclosed in U.S. Pat. No. 3,234,093. Chlormadinone, also known as 17-(acetyloxy)-6-chloropregna-4-, 6-diene-3,20-dione, in its acetate form, acts as an anti-androgen and is disclosed in U.S. Pat. No. 3,485,852. Nilutamide, also known as 5,5-dimethyl-3-[4-nito-3-(trifluoromethyl) phenyl]-2,4-imidazolidinedione and by the trade name Nilandron® is disclosed in U.S. Pat. No. 4,097,578. Flutamide, also known as2-methyl-N-[4-nitro-3-(trifluoromethyl)phenyl]propanamide and the trade name Eulexin® is disclosed in U.S. Pat. No. 3,847,988. Bicalutamide, also known as 4'-cyano-a',a',a'-trifluoro-3-(4-fluorophenylsulfonyl)-2-hydroxy-2-methylpropiono-m-toluidide and the trade name Casodex® is disclosed in EP-100172. The enantiomers of biclutamide are discussed by Tucker et al., J. Med. Chem., 31:885-887 (1988). Hydroxyflutamide, a known androgen receptor antagonist in most tissues, has been suggested to function as a SARM for effects on IL-6 production by osteoblasts as disclosed in Hofbauer et al., J. Bone Miner. Res.,14:1330-1337 (1999). Additional SARMs have been disclosed in U.S. Pat. No. 6,017,924; WO 01/16108, WO 01/16133, WO 01/16139, WO 02/00617, WO 02/16310, U.S. Patent Application Publication No. US 2002/0099096, U.S. Patent Application Publication No. US 2003/0022868, WO 03/011302 and WO 03/011824.

Any compound having activity as an LXR modulator can serve as the second compound in the combination therapy aspect of the present invention. The term LXR modulator refers to compounds that modulate the liver X receptor (LXR), which has been identified as a regulator of cellular and whole body cholesterol metabolism. Such LXR modulation activity is readily determined by those skilled in the art according to standard assays (e.g., U.S. Pat. No. 6,140,343). A variety of LXR modulators will be known to those skilled in the art, for example, those disclosed in U.S. Patent Application Publication Nos. 2003/01814206, 2005/0080111, and 2005/0245515.

All of the above referenced patents and patent applications are hereby incorporated by reference herein.

The combinations can be co-formulated or in the form of kits packaged to provide appropriate dosages for co-administration.

The above other therapeutic agents, when employed in combination with the compounds of the present invention, may be used, for example, in those amounts indicated in the Physicians' Desk Reference (PDR) or as otherwise determined by one of ordinary skill in the art.

The following examples further illustrate the present invention, but of course, should not be construed as in any way limiting its scope.

The following abbreviations are used herein:

ee=enantiomeric excess
DMF=dimethylformamide
EtOAc=ethyl acetate
LDA=lithium diisopropylamide
Hünig's Base=DIEA=$iPr_2NEt$=N,N-diisopropylethylamine
Me=methyl
Et=ethyl
n-Bu=n-butyl
Bn=benzyl
iPr=isopropyl
Allyl=1-propenyl
RT=retention time
TFA=trifluoroacetic acid
THF=tetrahydrofuran
TLC=thin layer chromatography
TMS=trimethylsilyl
t-Bu=tert-butyl
MeI=methyl iodide
$(BOC)_2O$=di-tert-butyl dicarbonate
$Ac_2O$=acetic anhydride
TEA=$NEt_3$=$Et_3N$=triethylamine
n-BuLi=n-butyllithium rt=room temperature
LC=liquid chromatography
Ph=phenyl
EtOH=ethanol
BuOH=butan-1-ol
DCE=dichloroethane
DMSO=dimethylsulfoxide
MS=molecular sieves
MS(ES)=Electro-Spray Mass Spectrometry
sat=saturated
AcOH=acetic acid
MeOH=methanol
$Et_2O$=diethyl ether
Ac=acetyl
h=hours
EDCI=water soluble dicarbonyl diimide,1-(3-dimethylaminopropyl)-3-ethylcarbodiimide hydrochloride
HOBt=1-hydroxy-benzotriazole
TBAF=tetrabutylammonium fluoride
TBAF.$3H_2O$=tetrabutylammonium fluoride trihydrate
DMA=dimethylacetamide
DME=1,2-dimethoxyethane
HRMS=high resolution mass spectrometry
TBME=MTBE=methyl tert-butyl ether (i.e., 2-methoxy-2-methyl-propane)
PyBroP=bromo-tris-pyrrolidino-phosphonium hexafluorophosphate
PyBOP=benzotriazol-1-yl-oxytripyrrolidinophosphonium hexafluorophosphate
DEA=diethylamine
IPA=isopropylamine
TMSCl=trimethylsilylchloride
MS=mass spectrum
NMR=nuclear magnetic resonance
TMSI=trimethylsilyliodide
TMS=trimethylsilyl
PPA=polyphosphoric acid
LDA=lithium diisopropylamine
UV=ultraviolet
DCM=dichloromethane
DMAC=N,N-dimethylacetamide
DAST=diethylaminosulfurtrifluoride
HPLC=high performance liquid chromatography
SFC=super critical fluid chromatography
TBAB=tetrabutylammonium bromide
ACN=acetonitrile
IIDQ=polystyrene resin
TosMIC=tosylmethyl isocyanide
BINAP=2,2'-bis(diphenylphosphino)-1,1'-binaphthyl
$Pd_2(dba)_3$=tris-(dibenzylideneacetone) dipalladium(0)
$Pd(PPh_3)_4$=tetrakis(triphenylphosphine) palladium(0)
$[Ir(COD)Cl]_2$=Chloro-1,5-cyclooctadiene iridium (I) dimer
Ar=argon
TBAB=tetrabutylammonium bromide
9-BBN=9-borabicyclo[3.3.1]nonane
DEAD=diethyl azodicarboxylate
DPPA=diphenyl phosphoryl azide
NBS=N-bromosuccinimide
DMAP=4-di(methylamino)pyridine
LAH=lithium aluminum hydride
NMP=1-methyl-2-pyrrolidone
NMM=1-methyl-2-morpholine
Super-hydride=lithium triethylborohydride
DIBAL-H=diisobutylaluminum hydride
Dess-Martin periodinane=1,1,1-tris(acetyloxy)-1,1-dihydro-1,2-benziodoxol-3-(1H)-one
Lawesson's reagent=2,4-bis(4-methoxyphenyl)-1,3,2,4-dithiadiphosphetane2,4-disulfide
Jones[O] reagent=$CrO_3/H_2SO_4/H_2O$/acetone
$PCy_3$=tricyclohexylphosphine
$Tf_2O$=triflic anhydride=trifluoromethanesulfonic anhydride
$Bu_4NBr$=tetrabutylammonium bromide
TBDMSCl=tert-butylchlorodimethylsilane
TFFH=fluoro-N,N,N',N'-tetramethylformamidinium hexafluorophosphate
R, R-MnCl (Salen)=(1R,2R)-(−)-[1,2-cyclohexanediamino-N,N'-bis(3,5-di-t-butylsalicylidene)]manganese (III) chloride
LiOTf=lithium trifluoromethanesulfonate
Tf=trifluoromethanesulfonate
$EtAlCl_2$=ethyl aluminum dichloride
$ZnEt_2$=diethyl zinc
TsOH=4-methylbenzenesulfonic acid
Ts=4-methylbenzenesulfonate
n-$Bu_2SnO_2$=dibutyltin(IV) oxide
Boc=t-Boc=t-butoxycarbonyl
$Pd(OH)_2/C$=palladium (II) hydroxide on carbon
Pd/C=palladium on carbon
Fmoc=3,9-fluorenylmethoxycarbonyl
allylMgBr=1-propenyl magnesium bromide
diglyme=diethylene glycol dimethyl ether=1-methoxy-2-(2-methoxyethoxy)ethane
L-proline=(S)-pyrrolidine-2-carboxylic acid
SCX=clean up extraction column
PCC=Pyridium Chlorochromate
PyBrOP=Bromotripyrrolidinophosphonium hexafluorophosphate
$(DHDQ)_2$PHAL=hydroquinidine1,4-phthalazinediyl diether Specifically exemplified compounds of Formula Ia and Ib are listed along with structure, name, HPLC retention time, molecular mass and the procedure employed to make such examples, in the proceeding text and in the tables set forth below. The absolute configuration of chiral examples was assigned by NMR comparison of the intermediate diastereomeric sulfinyl amides, but has not be confirmed by crystallographic assignment. Enantiomerically pure intermediate amines were obtained by separation of the racemic mixtures using SFC or by the chiral synthesis described in Procedures4, 5 and6.

Unless otherwise indicated, the chromatography techniques used to determine the compound retention times are as follows: LCMS=YMC S5 ODS column,4.6×50 mm eluting with 10-90% MeOH/$H_2O$ over 4 minutes containing 0.1% TFA; 4 mL/min, monitoring at 220 nm. LCMS*=YMC S5 ODS column, 4.6×50 mm eluting with10-90% MeOH/$H_2O$ over 2 minutes containing0.1% TFA; 4 mL/min, monitoring at 220 nm. LC=YMC S5 ODS column 4.6×50 mm eluting with 10-90% MeOH/$H_2O$ over 4 minutes containing 0.2% phosphoric acid, 4 mL/min, monitoring at 220 nm.

The molecular mass of the compounds listed in the tables set forth below were determined by MS (ES) by the formula m/z.

EXAMPLE 1

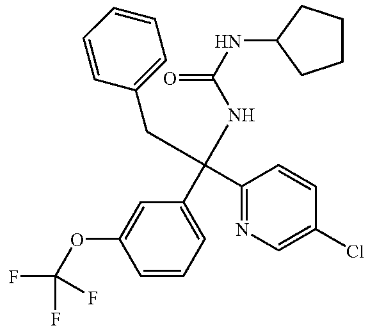

1-(1-(5-chloropyridin-2-yl)-2-phenyl-1-(3-(trifluoromethoxy)phenyl)ethyl)-3-cyclopentylurea Procedure 1

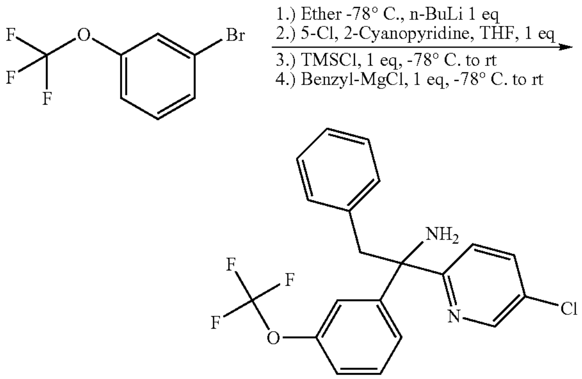

A dry 250 mL pear-shaped flask was equipped with a stir bar and fitted to an adapter connected to the vacuum line. The flask was dried with a heat gun under vacuum, cooled and then purged several times with nitrogen. Under a stream of nitrogen, 3-(trifluoromethoxy)bromobenzene (5.2 g, 21.5 mmoles) was added to the flask and dissolved in anhydrous ether (120 mL). The flask was fitted with a septum which was connected to the nitrogen line via a 16 gauge 1½ Precision-Glide® needle. The stirring solution was cooled to −78° C. for 10 minutes, n-BuLi (1.6M in hexanes, 13.5 mL. 21.5 mmoles) was added drop wise. After 15 minutes, a solution of 2-cyanopyridine (2.99 g, 21.5 mmoles) in anhydrous THF (20 mL) was added from a syringe. The reaction was stirred for 2 hours at −78° C. and trimethylchlorosilane (2.73 mL, 21.5 mmoles) was added. The reaction vessel was removed from the acetone/dry ice bath and the reaction was allowed to warm up to room temperature. After 30 minutes, the reaction vessel was cooled to −78° C., Benzylmagnesium chloride (2.0M in THF, 10.75 mL, 21.5 mmoles) was added and the reaction was allowed to slowly warm to room temperature. The reaction was quenched with $H_2O$ (50 mL). The crude product was poured into 200 mL ethyl acetate in a 1000 mL separatory funnel. The light brown solution was washed with saturated aqueous $NH_4Cl$ (3×100 mL), then with water (2×100 mL). The organic layer was dried over $MgSO_4$, filtered and concentrated in vacuo. The crude residue was purified by column chromatography on a silica gel ISCO with 100-90% hexanes in ethylacetate to yield 1-(5-chloropyridin-2-yl)-2-phenyl-1-(3-(trifluoromethoxy)phenyl)ethanamine 3.63 g (43% yield). LC-MS (methanol) [M+1]=393 $^1H$ NMR ($CDCl_3$) δ1.85 (broad s, 2H), δ 3.49 (d, J=13.20, 1 H), δ 3.87 (d, J=13.20, 1 H), δ6.78-6.80 (d, 2 H), δ 7.08 (d, 1 H) δ 7.12-7.42 (m, 7 H), δ7.58-7.56 (dd, 1 H), δ 8.55 (d, 1 H).

Procedure 2

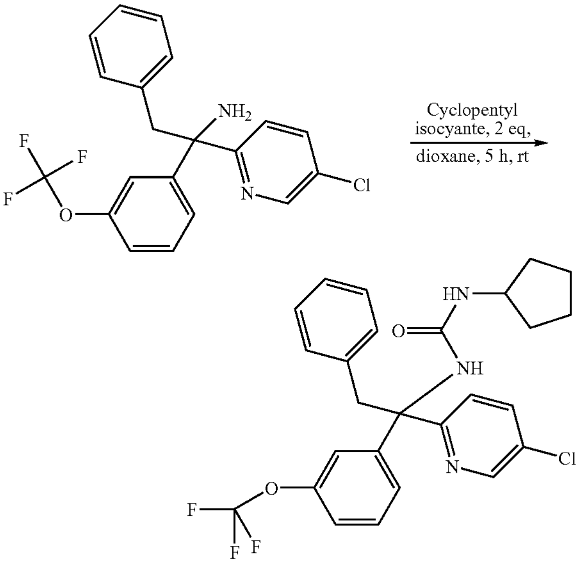

A 20 mL scintillation vial was fitted with a septum cap and a stirring bar and purged with nitrogen. Under a stream of nitrogen, 1-(5-chloropyridin-2-yl)-2-phenyl-1-(3-(trifluoromethoxy)phenyl) ethanamine (300 mg, 0.763 mmoles) was added and dissolved in 3 mL anhydrous dioxane. Cyclopentyl isocyanate (170 mg, 1.53 mmoles, 2 eq.) was added with stirring. After 5 Hours, the crude product was concentrated in vacuo to yield a light yellow fine powder. The product was suspended in 5% ethyl acetate in hexanes, stirred for 20 minutes and filtered with a medium frit funnel to give a colorless solid pure product (218 mg, 57% yield), More product was recovered by pre-HPLC of the filtrate, (32 mg, 6.8% as TFA salt). Total recovery yield of 63.8%: LC-MS ([M+1]=504); $^1H$ NMR ($CDCl_3$) δ 1.26 (ddd J=12.77, J=6.72, J=6.05, 1 H), δ 1.40 (ddd J=12.77, J=6.72, J=6.05, 1 H), δ 1.54 (m, 2 H), δ 1.63 (m, 2 H), δ 1.83 (ddd J=12.77, J=6.72, J=6.05, 1 H) δ 1.99 (ddd J=12.77, J=6.72, J=6.05, 1 H), δ 3.52 (d, J=12.77, 1 H), δ 3.88 (broad t, J=6.05, 1 H ), δ 4.36 (d): for TFA salts this peak is absent or is a smaller broad singlet at δ 4.6), δ 4.44 (d, J=12.77, 1 H), δ 6.59 (s, 1 H), δ 6.61 (2H), δ 7.05-7.13 (m, 6H), δ 7.32-7.36 (t, 1 H), δ 7.40-7.41 (d, 1 H), δ 7.60-7.62 (dd, 1 H), δ 8.23 (d, 1 H); $^{13}C$ NMR ($CDCl_3$) δ 23.6, 33.2, 33.7, 42.7, 52.2, 63.4, 119.2, 119.5, 123.6, 124.8, 126.5, 127.7, 129.7, 130.3, 130.6, 135.9, 136.8, 145.4, 148.4, 149.4, 156.1, 159.5. Racemic 1-(1-(5-chloropyridin-2-yl)-2-phenyl-1-(3-(trifluoromethoxy)phenyl)ethyl)-3-cyclopentylurea (210 mg) was resolved by chiral prep HPLC using Berger SFC (OJ 250×4.6 mm 10 micron, 5% MeOH, 35C) to give pure enantiomer 1 (85 mg, 40%) and enantiomer 2 (86 mg, 41%).

EXAMPLE 2

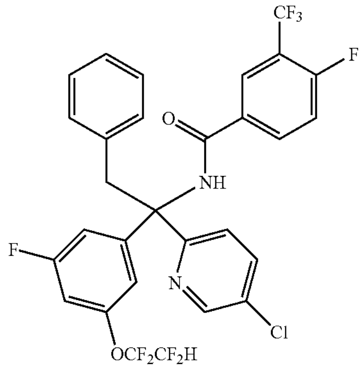

N-(1-(5-chloropyridin-2-yl)-1-(3-fluoro-5-(1,1,2,2-tetrafluoroethoxy)phenyl)-2-phenylethyl)-4-fluoro-3-(trifluoromethyl)benzamide

Procedure 3

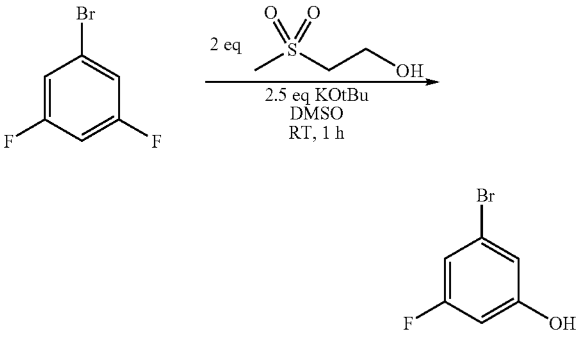

A solution of 1-bromo-3,5-difluorobenzene (20.0 g, 104 mmole) was cooled in a water bath and 2-(methylsulfonyl) ethanol (26.0 g, 207 mmol) in DMSO (100 mL) was added. KOtBu (29.0 g, 260 mmole) was added to this reaction mixture in portions. The reaction mixture turned dark. After the addition was complete, the water bath was removed and the reaction was stirred at room temperature for 1 h. The pH was adjusted to 1 using 1 N HCl, and the reaction was extracted with ether (3×200 mL). The combined organic portions were washed with aqueous 1N NaOH (2×200 mL). The NaOH layer was acidified to pH 1 and extracted with ether (3×200 mL). The combined organic layers were dried over sodium sulfate and filtered. The filtrate solvent volume was concentrated NOT to complete dryness due to volatility of 3-bromo-5-fluorophenol and was used directly in the next step without further purification. NMR: 400 MHz $^1H$ ($CDCl_3$) 6.81 ppm, 1 H, dt, J=8.35 Hz and 1.98 Hz; 6.78 ppm, 1 H, m; 6.50 ppm, 1 H, dt, J=9.67 Hz and 2.20 Hz.

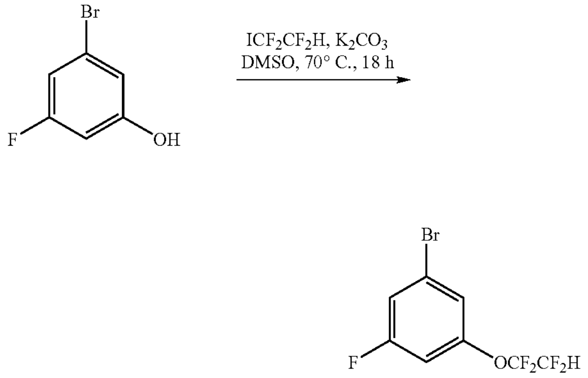

To a solution of 3-bromo-5-fluorophenol (104 mmol crude) and iodo-1,1,2,2,-tetrafluoroethane (28.4 g, 125 mmol) in DMSO (80 mL) was added $K_2CO_3$ (57.0 g, 420 mmol). The reaction mixture was sealed in a thick walled glass pressure round bottom flask and heated at 70° C. for 18 h. The reaction mixture was allowed to cool to room temperature, diluted with water (500 mL) and extracted with ether (3×200 mL). The combined ether layers were washed with 1N NaOH (2×200 mL), water (2×200 mL) and brine (200 mL). The organic layer was dried over sodium sulfate, filtered and concentrated. The residue was dissolved in ether (150 mL) and filtered through a plug of activated basic alumina. The filtrate was concentrated to give 1-bromo-3-fluoro-5-(1,1,2,2-tetrafluoroethoxy)benzene as a pale yellow oil (27.2 g, 88% for two steps) which was used without further purification LCMS: 1.91 min, [M+1] No Ionizable peak (2 min gradient, $MeOH/H_2O$ 0.1% TFA); HPLC: 3.76 min (4 min gradient, $MeOH/H_2O$ 0.2% PPA) Purity 100%; NMR: 400 MHz $^1H$ ($CDCl_3$) 7.19 ppm, 2H, m; 6.92 ppm, 1H, d, J=8.35 Hz; 5.88 ppm, 1H, tt; J=52.95 Hz and J=2.64 Hz.

Procedure 4

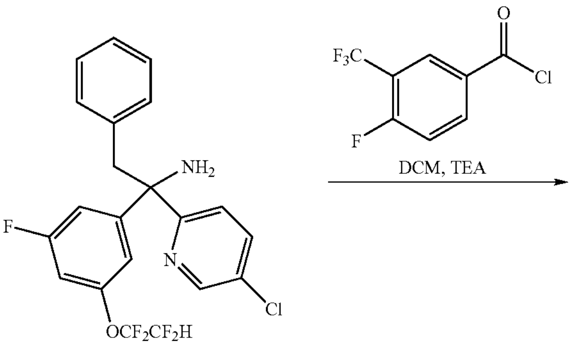

-continued

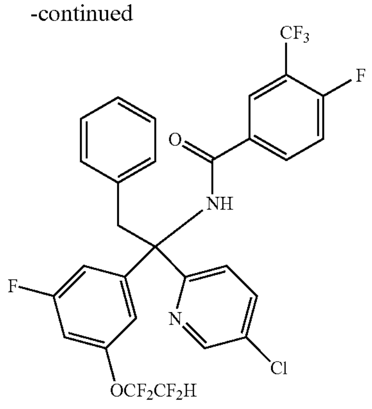

1-(5-chloropyridin-2-yl)-1-(3-fluoro-5-(1,1,2,2-tetrafluoroethoxy) phenyl)-2-phenylethanamine (57 mg, 0.13 mmol) in DCM (1 mL) was added 4-fluoro-3-trifluoromethyl benzoylchloride and TEA (50 μL, 0.36 mmol). The reaction was stirred at room temperature for 1 h and diluted with EtOAc (15 mL). The organic layer was washed with sat. $NaHCO_3$ (1×15 mL), dried over $Na_2SO_4$, filtered and concentrated. The residue was purified by preparative HPLC (YMC ODS S5 28×100 mm Ballistic column 40-100% MeOH (90% in water, 0.1% TFA) using a gradient over 10 min with flow rate 40 mL/min and UV detection at 220 nm. Product eluted at a retention time of 11.6 min and was isolated as a white solid (36 mg, yield 49%) LCMS: 2.21 min [M+1] 633.3 (2 min gradient, MeOH/$H_2O$ 0.1% TFA); HPLC: 4.29 min (4 min gradient, MeOH/H2O 0.2% PPA) Purity 100%; NMR: 400 MHz $^1$H ($CDCl_3$) 9.03 ppm, 1 H, s; 8.27 ppm, 1 H, d, J=2.20 Hz; 7.95 ppm, 1 H, dd, J=6.81 Hz and 1.98 Hz; 7.80 ppm, 1 H, dt, J=8.35 Hz and 2.20 Hz; 7.67 ppm, 1 H, dd, J=8.57 Hz and 2.42 Hz; 7.19 ppm, 1 H, m; 7.14 ppm, 1 H, d, J=8.79 Hz; 7.06 ppm, 3 H, m; 6.96 ppm, 2 H, t, J=7.47 Hz; 6.85 ppm, 1 H, d, J=8.79 Hz; 6.47 ppm, 2 H, d, J=7.47 Hz; 5.81 ppm, 1 H, tt, J=52.95 Hz and 2.64 Hz; 4.48 ppm, 1 H, d, J=12.74 Hz; 3.54 ppm, 1 H, d, J=12.74 Hz.

EXAMPLE 3

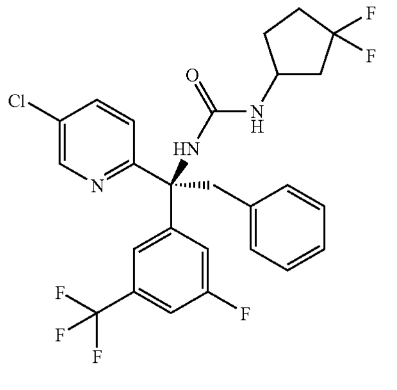

1-((S)-1-(5-chloropyridin-2-yl)-1-(3-fluoro-5-(trifluoromethyl)phenyl)-2-phenylethyl)-3-(3,3-difluorocyclopentyl)urea Procedure 5

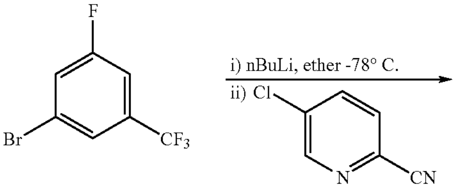

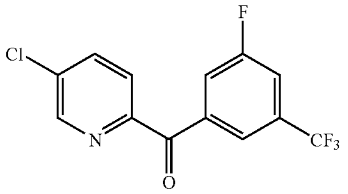

At −78° C. under Ar a dry 250 ml 3 neck flask was charged with 1-bromo-3-fluoro-5-(trifluoromethyl)benzene (4.5 g, 0.018 mol). Dry ether (100 mL) was added and to the stirred solution, nBuLi (9.2 mL, 0.018 mol) was added dropwise via airtight syringe through a rubber septum. The resulting pale orange colored solution was stirred at −78° C. for 30 min. 5-chloropicolinenitrile (2.5 g, 0.018 mol) was then added as a thick slurry in dry ether (approx 10 mL) via wide neck funnel. The resulting solution turned dark red in color and was stirred at −78° C. for 1 hr. LCMS indicated that the reaction was complete and, at −78° C. the reaction mixture was quenched with 1.0M HCl (approx 50 mL). The cooling bath was removed and as the reaction mixture reaction reached ambient temperature, (22° C.), the organic solution turned pale green in color. The solution was transferred to a separation funnel and the organic layer separated. The aqueous phase was washed with EtOAc (20 mL) and the combined organic portions dried over anhydrous $Na_2SO_4$, decanted and concentrated yielding a pale brown oil. This was dissolved in hexane (ca 15 mL) and loaded directly onto a silica gel ISCO cartridge (330 g, previously equilibrated with hexanes) and elution at 100 mL/min gradient 0 to 70% EtOAc in hexanes over 45 min. Elution time of the product was 17 to 20 mins and (5-chloropyridin-2-yl)(3-fluoro-5-(trifluoromethyl)phenyl) methanone (4.1 g, 75% yield) was isolated as a pale yellow oil which crystallized on standing. $R_f$0.74 (Hexane:EtOAc 4:1) LCMS: 2.03 min [M+1] 304.2 (2 min gradient, MeOH/$H_2O$ 0.1% TFA); HPLC: 3.98 min (4 min gradient, MeOH/$H_2O$ 0.2% PPA Purity 98%; NMR: 400 MHz $^1$H ($CDCl_3$) 8.69 ppm, 1H, d, J=2.64 Hz; 8.22 ppm, 1H, s; 8.13 ppm, 1H, d, J=8.36 Hz; 8.07 ppm, 1H, brd, J=8.4 Hz; 7.93 ppm, 1H, dd, J=2.2 and J=8.36 Hz; 7.57 ppm, 1H, brd, J=8.4 Hz.

Procedure 6

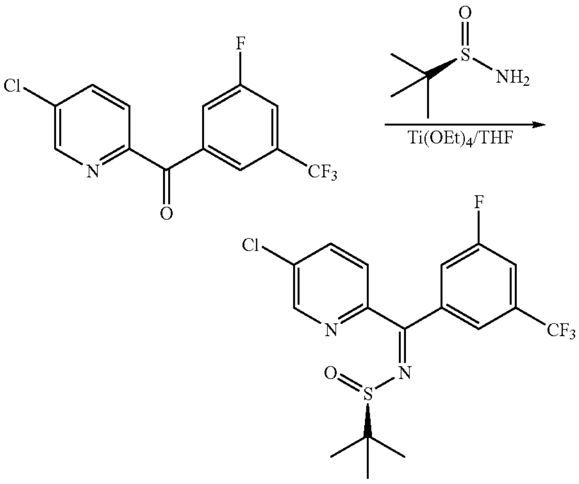

-continued

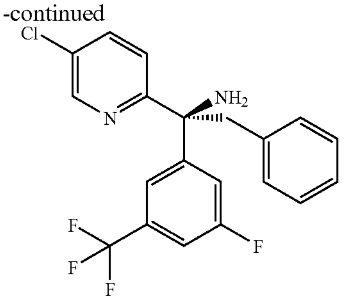

At room temperature, a 50 mL flask fitted with a reflux condenser was charged with (5-chloropyridin-2-yl)(6-(trifluoromethyl)pyridin-2-yl)methanone (0.17 g, 0.60 mmol). Anhydrous THF (10 mL) was added followed by (R+)-2-methylpropane-2-sulfinamide (0.072 g, 0.60 mmol) and $Ti(OEt)_4$ (0.19 mL, 0.90 mol, 1.5 equivalent) in one portion. The pale orange solution was heated to 75° C. for 14 h then allowed to cool to ambient temperature. The solution was concentrated under reduced pressure to half the volume and the resulting orange solution which was loaded directly onto a silica gel ISCO (40 g, previously equilibrated with hexanes) and elution at 80 mL/min gradient 0 to 100% EtOAc in hexanes over 20 min. Elution time of the recovered starting material was 10 mins (0.70 g recovered, 41%) and of the product was 12.5 min. (R)-N-((5-chloropyridin-2-yl)(6-(trifluoromethyl)pyridin-2-yl)methylene)-2-methylpropane-2-sulfinamide (40 mg, 31% yield based on recovered starting material) was isolated as a pale yellow oil. $R_f$0.5 (Hexane:EtOAc 2:1) LCMS: 1.80 min [M+1] 390.1 (2 min gradient, $MeOH/H_2O$ 0.1% TFA); HPLC: 3.50 min (4 min gradient, $MeOH/H_2O$ 0.2% PPA); Purity 83%; NMR: 400 MHz $^1H$ ($CDCl_3$) (2 sets of peaks attributed to E/Z isomerism) 8.62 ppm, d, J=2.2 Hz; 8.46 ppm, bss; 8.18, 1H, d, J=8.0 Hz; 8.13 ppm, d, J=8.0 Hz; 8.02 ppm, d, J=8.0 Hz; 7.91 ppm, brs; 7.82 ppm, d, J=8.0 Hz; 7.74 ppm, d, J=8.0 Hz; 7.68 ppm, d, J=8.0 Hz; 7.5 ppm, brm; 1.37, s; 1.28, s.

To a solution of (R)-N-((5-chloropyridin-2-yl)(3-fluoro-5-(trifluoromethyl)phenyl)methylene)-2-methylpropane-2-sulfinamide (1.09 g, 2.68 mmol) in anhydrous TBME (45 mL) at −78° C. under argon was added $BF_3Et_2O$ (0.57 mL, 5.38 mmol). After 5 min, benzylmagnesium grignard (5.38 mL, 5.38 mmol, 1.0M in ether) was added dropwise with stirring. After 40 min, LCMS indicated that the reaction was complete and the cold solution was quenched with saturated NaCl (ca 20 mL), transferred to a separation funnel and the organic phase extracted with EtOAc (3×20 mL). The combined organic portions were dried, decanted, concentrated and purified by silica gel ISCO chromatography.2×120 g cartridge columns were used 0-60% EtOAc/hexanes over 20 min. A trace amount of minor diastereomer eluted first followed by the major diastereomer (R)-N-((S)-1-(5-chloropyridin-2-yl)-1-(3-fluoro-5-(trifluoromethyl)phenyl)-2-phenylethyl)-2-methylpropane-2-sulfinamide (0.97 g, 72% yield). $R_f$0.4 (Hexane:EtOAc 2:1) LCMS: 2.15 min [M+1] 499.1 (2 min gradient, $MeOH/H_2O$ 0.1% TFA); HPLC: 4.15 min (4 min gradient, $MeOH/H_2O$ 0.2% PPA); Purity 99%; NMR: 400 MHz $^1H$ ($CDCl_3$) 8.65 ppm, d, 1H, J=2.6 Hz; 7.62 ppm, dd, 1H, J=2.6 and J=8.8 Hz; 7.36 ppm, 4H, m; 7.29 ppm, 1H, m; 7.24 ppm, 1H, m; 7.14 ppm, 2H, m; 6.99 ppm, 1H, d, J=10.1 Hz; 6.81 ppm, 1H, d, J=6.6 Hz; 4.09 ppm, 1H, d, J=13.2 Hz; 3.69 ppm, 1H, d, J=13.2 Hz; 1.18 ppm, 9H, s.

(R)-N-((S)-1-(5-chloropyridin-2-yl)-1-(3-fluoro-5-(trifluoromethyl)phenyl)-2-phenylethyl)-2-methylpropane-2-sulfinamide (0.765 g, 1.53 mmol) was dissolved in anhydrous MeOH (4 mL). At RT, 4.0M HCl in dioxane (1.5 mL) was added and the reaction mixture stirred for 20 min. The reaction mixture was diluted with EtOAc (50 mL), transferred to a separation funnel and washed with 1.0M NaOH (ca. 20 mL). The organic portion was dried over anhydrous $Na_2SO_4$, decanted and concentrated yielding (S)-1-(5-chloropyridin-2-yl)-1-(3-fluoro-5-(trifluoromethyl)phenyl)-2-phenylethanamine as a pale yellow oil, (0.745 g, crude quantitative yield). LCMS: 1.51 min [M+1] 395.2 (2 min gradient, $MeOH/H_2O$ 0.1% TFA).

Procedure 7

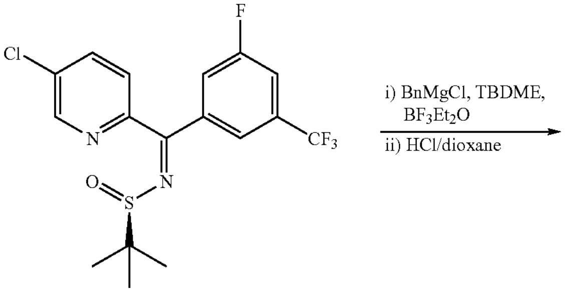

Procedure 8

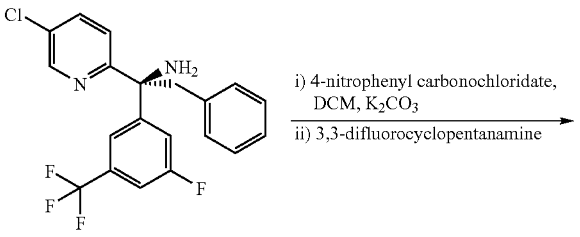

-continued

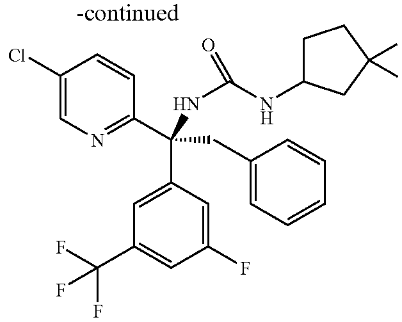

(S)-1-(5-chloropyridin-2-yl)-1-(3-fluoro-5-(trifluoromethyl)phenyl)-2-phenylethanamine (0.15 g, 0.38 mmol) was dissolved in dichloromethane (5 mL) at room temperature. Solid powdered $K_2CO_3$ (0.52 g, 3.8 mmol) was added followed by 4-nitrophenyl carbonochloridate (0.11 g, 0.56 mmol). The resulting slurry was stirred at room temperature for 14 h, diluted with DCM (ca. 50 mL) and washed with sat. $NaHCO_3$ (ca. 4×20 mL). The organic portion was dried over anhydrous $Na_2SO_4$, decanted and concentrated yielding (S)-4-nitrophenyl 1-(5-chloropyridin-2-yl)-1-(3-fluoro-5-(trifluoromethyl)phenyl)-2-phenylethylcarbamate as a pale brown oil, (0.20 g, crude quantitative yield). LCMS: 2.26 min [M+1] 560.2 (2 min gradient, $MeOH/H_2O$ 0.1% TFA)

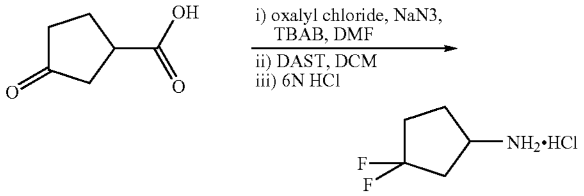

To the solution of 3-oxocyclopentanecarboxylic acid (2.85 g, 22.2 mmol) in dry $CH_2Cl_2$ (4 mL) was added oxalyl chloride (2.0M in dichloromethane, 13 mL) at 0° C. over 15 min followed by DMF (50 mL) After the addition was complete, the reaction mixture was stirred for 2 h (0° C. to rt). Tetrabutylammonium bromide (35 mg) was then added followed by a solution of sodium azide (2.17 g, 26.7 mmol, in the minimum amount of $H_2O$, 9 mL) at 0° C., and the resulting light brown reaction mixture was stirred for 1 h at rt. The reaction was monitored and upon completion, the organic phase was separated. The aqueous phase was extracted with $CH_2Cl_2$ (3×8 mL). The combined organic phases were washed with brine, dried with sodium sulfate, and filtered through a 2 cm plug of silica. The silica gel plug was washed with $CH_2Cl_2$ twice followed with 10% EtOAc in $CH_2Cl_2$. The resulting pale yellow filtrate was partially concentrated. Benzyl alcohol (25 mL) was added and the remainder of $CH_2Cl_2$ was removed under vacuum. The light brown solution was heated at 100° C. for 3 h. After it was cooled to room temperature, the brown solution was vacuum distilled. Benzyl alcohol was collected and the viscous brown oil residue was purified by flash chromatography (120 g $SiO_2$, 0-40% EtOAc/hexane) to provide benzyl 3-oxocyclopentylcarbamate as a pale yellow and colorless oil (2.39 g, 46% yield). $^1H$ NMR ($CDCl_3$, 400 MHz): 7.35 (m, 5H), 5.09 (s, 2H), 4.87 (br, 1H), 4.28 (m, 1H), 2.63 (m, 1H), 2.39-2.15 (m, 4H), 1.86 (m, 1H). $^{13}C$ NMR ($CDCl_3$, 400 MHz): 215.7, 155.8, 136.2, 128.6, 128.3, 128.2, 66.9, 49.3, 45.2, 37.0, 29.9. LC/MS: [M+H]=234.1.

To a solution of benzyl 3-oxocyclopentylcarbamate (2.32 g, 9.96 mmol) in $CH_2Cl_2$ (10 mL) was added DAST (4.3 mL, 28.9 mmol) at rt. The reaction mixture turned brown while shaken at rt overnight. When the transformation was complete by HPLC, brine was added at 0° C. slowly to quench the reaction [Caution: reacted violently]. $CH_2Cl_2$ was added and the solution was extracted with $CH_2Cl_2$ (3×10 mL). The combined organic phases were dried over $Na_2SO_4$, and concentrated. The residue was purified by flash chromatography (40 g $SiO_2$, 0-40% EtOAc/hexane) to furnish benzyl 3,3-difluorocyclopentylcarbamate as an off-white solid (1.5 g, 59%).

$^1H$ NMR ($CDCl_3$, 400 MHz): 7.35 (m, 5H), 5.09 (s, 2H), 4.90 (br, 1H), 4.23 (m, 1H), 2.50 (m, 1H), 2.25-1.98 (m, 4H), 1.70 (m, 1H). $^{13}C$ NMR ($CDCl_3$, 400 MHz): 155.6, 136.2, 128.6, 128.3, 128.2, 66.9, 50.86, 49.3, 42.6 (t), 34.2 (t), 30.6. $^{19}F$ NMR ($CDCl_3$, with $CFCl_3$ as standard, 400 MHz): −88.2 (m, 1F), −91.4 (m, 1F).

Benzyl 3,3-difluorocyclopentylcarbamate (1.5 g, 5.88 mmol) in 6N HCl (6 mL) was heated at 100° C. for 20 h. After the reaction mixture was cooled to rt, the brown solution was extracted with $Et_2O$ (2×2 mL) to remove unreacted starting material and toluene. The aqueous phase was dried in the speed vac with heating to give 3,3-difluorocyclopentanamine hydrochloride as a light brown solid (0.79 g, 85% yield). $^1H$ NMR (MeOD-$d_4$, 400 MHz): 4.79 (m, 1H), 2.62 (m, 1H), 2.32 (m, 2H), 2.18 (m, 2H), 1.87 (m, 1H). $^{13}C$ NMR (MeOD-$d_4$, 400 MHz): 131.4 (t), 41.0 (t), 34.8 (t), 28.9. $^{19}F$ NMR (MeOD-$d_4$, with $CFCl_3$ as standard, 400 MHz): −93.0 (m, 2F). LC/MS: [M+H]=121.9.

To a crude solution of (S)-4-nitrophenyl 1-(5-chloropyridin-2-yl)-1-(3-fluoro-5-(trifluoromethyl)phenyl)-2-phenylethylcarbamate in DCM (1 mL) (29 mg, 0.053 mmol) was added 3,3-difluorocyclopentanamine hydrochloride (17 mg, 0.106 mmol). The reaction mixture was stirred at room temperature for 2 h and the solution turned yellow. The solution was diluted with $CH_2Cl_2$ (1 mL) and washed with 1N NaOH (3×1 mL), dried over $Na_2SO_4$, and concentrated. The yellow residue was purified by flash chromatography (4 g $SiO_2$, 0-40% EtOAc/hexane) to furnish 1-((S)-1-(5-chloropyridin-2-yl)-1-(3-fluoro-5-(trifluoromethyl)phenyl)-2-phenylethyl)-3-(3,3-difluorocyclopentyl)urea as a white solid (13 mg, 45%). LCMS: 4.06 min [M+1] 542.2 (4 min gradient, $MeOH/H_2O$ 0.1% $NH_4OAc$) LC/MS: [M+H]=542.2 $^1H$ NMR ($CDCl_3$, 400 MHz): 8.26 (m, 1H), 7.67 (dd, J=2 Hz, J=4 Hz, 1H), 7.52 (br, 1H), 7.38 (m, 1H), 7.22 (m, 1H), 7.18-7.08 (m, 5H), 6.57 (m, 2H), 4.50 (d, J=8 Hz, 1H), 4.46 (dd, J=4 Hz, J=8 Hz, 1H), 4.25 (m, 1H), 3.55 (d, J=12 Hz, 1H), 2.65-1.54 (m, 6H).

EXAMPLE 4

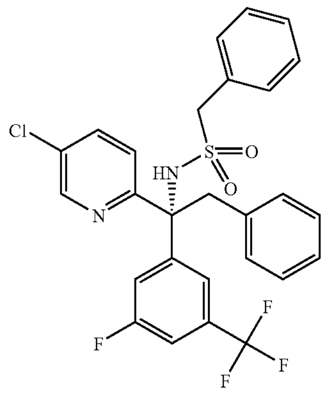

(R)-N-(1-(5-chloropyridin-2-yl)-1-(3-fluoro-5-(trifluoromethyl)phenyl)-2-phenylethyl)(phenyl)methanesulfonamide

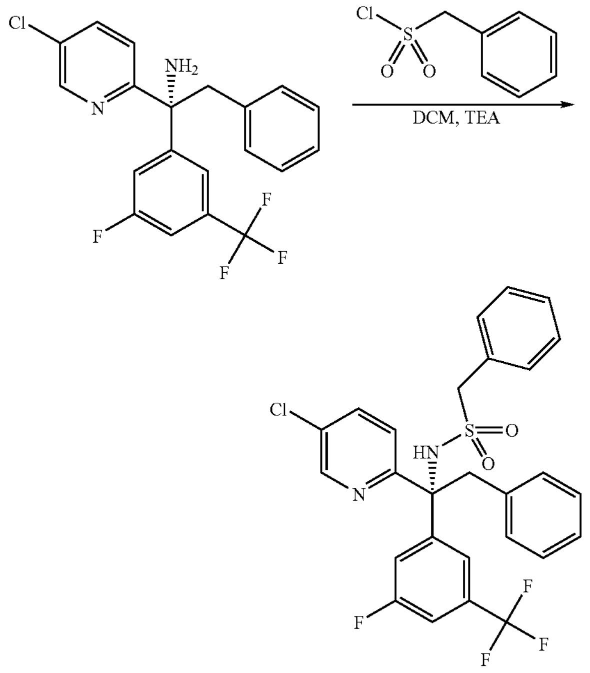

Procedure 9

(R)-1-(5-chloropyridin-2-yl)-1-(3-fluoro-5-(trifluoromethyl)phenyl)-2-phenylethanamine was dissolved in DCE (400 uL, 0.1 M in DCE, 40 umol) and pyridine added (162 uL, 200 umol, 5.0 eq), followed by benzyl sulfonyl chloride (400 uL, 0.25 M in DCE, 100 umol, 2.5 eq). The reaction mixture was shaken at room temperature for 18 h. Evaporated the DCE and redissolved in 1 mL of MeOH and purified by reverse phase preparative HPLC, using MeOH:water:TFA system, to obtain the sulfonamide (1.1 umol, 2.8% yield). LCMS: M+calc=548.09; found=549.29.

EXAMPLE 5

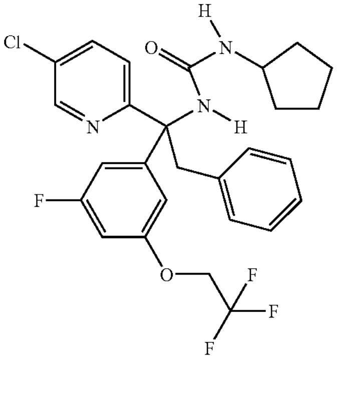

1-(1-(5-chloropyridin-2-yl)-1-(3-fluoro-5-(2,2,2-trifluoroethoxy)phenyl)-2-phenylethyl)-3-cyclopentylurea Procedure 10

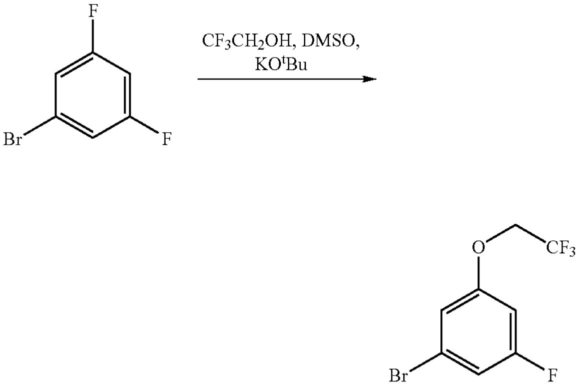

To a 50 mL flask flushed with nitrogen, equipped with a stir bar and cooled in a water bath was added potassium tertbutoxide (1.2 g, 11 mmol, 95%). DMSO was added (4 mL) followed by addition of a solution of 2,2,2-trifluoroethanol (1.1 g, 11 mmol) in DMSO (1 mL). The water bath was removed and 1-bromo-3,5-difluorobenzene (1.1 mL, 9.5 mmol) was added and the reaction mixture stirred at room temperature for 1 h. An additional portion of 2,2,2-trifluoroethanol was added (1.1 g, 11 mmol) and the reaction mixture stirred for 14 h. Additional potassium tertbutoxide (0.24 g, 2.2 mmol, 95%) was added followed by addition of a further aliquot of 2,2,2-trifluoroethanol (0.44 g, 4.4 mmol) and the resulting turbid solution stirred for 2 h. Water was added (200 mL), and the aqueous phase extracted with ether (1×200 mL). The organic portion was then washed successively with water (2×200 mL) and saturated NaCl solution (2×200 mL), dried over $Na_2SO_4$, decanted and concentrated under reduced pressure yielding a crude yellow liquid (2.1 g). A portion of the crude product (1.3 g) was purified by distillation under reduced pressure at 80° C. yielding 1-bromo-3-fluoro-5-(2,2,2-trifluoroethoxy)benzene as a colorless oil (0.70 g, 35% yield). $^1H$ NMR ($CDCl_3$, 400 MHz): 7.05 ppm (d, 1H), 6.90 ppm (s, 1H), 6.55 ppm (d, 1H), 4.32 ppm (q, 2H).

1-Bromo-3-fluoro-5-(2,2,2-trifluoroethoxy)benzene (0.55 g, 2 mmol) was converted to 1-(5-chloropyridin-2-yl)-1-(3-fluoro-5-(2,2,2-trifluoroethoxy)phenyl)-2-phenylethanamine as described in Procedure 1 and then a portion was subsequently converted to 1-(1-(5-chloropyridin-2-yl)-1-(3-fluoro-5-(2,2,2-trifluoroethoxy)phenyl)-2-phenylethyl)-3-cyclopentylurea (0.013 g, 27% yield) as described in Procedure 2. LCMS: 4.02 min [M+1] 536.07 (4 min gradient, MeOH/$H_2O$ 0.1% TFA).

EXAMPLE 6

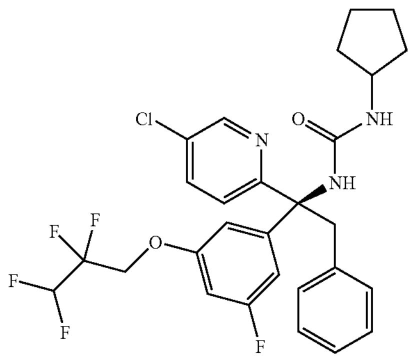

(S)-1-(1-(5-chloropyridin-2-yl)-1-(3-fluoro-5-(2,2,3,3-tetrafluoropropoxy)phenyl)-2-phenylethyl)-3-cyclopentylurea Procedure 11

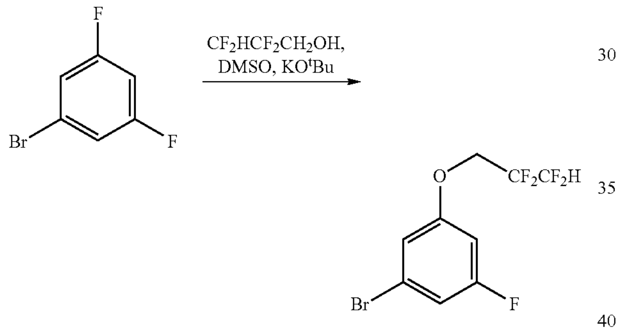

To a 50 mL flask flushed with nitrogen, equipped with a stir bar was added potassium tertbutoxide (1.1 g, 10 mmol, 95%). DMSO was added (10 mL) followed by addition of a solution of 2,2,3,3-tetrafluoropropan-1-ol (0.95 mL, 11 mmol) via syringe. After 5 min, 1-bromo-3,5-difluorobenzene (1.1 mL, 9.5 mmol) was added and the reaction mixture stirred at room temperature for 18 h. Water was added (100 mL), and the aqueous phase extracted with ether (2×100 mL). The organic portion was then washed successively with water (2×100 mL) and saturated NaCl solution (2×100 mL), dried over $Na_2SO_4$, decanted and concentrated under reduced pressure yielding a crude yellow liquid which was purified by distillation under reduced pressure at 140° C. yielding the 1-Bromo-3-fluoro-5-(2,2,3,3-tetrafluoropropoxy)benzene as a colorless oil (1.6 g, 54% yield).

1-Bromo-3-fluoro-5-(2,2,3,3-tetrafluoropropoxy)benzene (1.28 g, 4.2 mmol) was converted to 1-(5-chloropyridin-2-yl)-1-(3-fluoro-5-(2,2,2-trifluoroethoxy)phenyl)-2-phenylethanamine (0.63 g, 33% yield) as described in Procedure 1. LC-MS [M+1]=457 (4 min gradient, MeOH/$H_2O$ 0.1% TFA) NMR (500 MHz, $CDCl_3$) δ 8.54 (1 H, d, J=2.20 Hz), 7.56 (1 H, dd, J=8.52, 2.47 Hz), 7.41 (1 H, d, J=8.25 Hz), 7.09-7.19 (3 H, m), 6.86-6.94 (2 H, m), 6.82 (2 H, dd, J=7.15, 1.65 Hz), 6.45-6.54 (1 H, m), 6.00 (1 H, tt, J=53.06, 4.67 Hz), 4.10-4.35 (2 H, m), 3.83 (1 H, d, J=13.20 Hz), 3.45 (1 H, d, J=13.20 Hz), 1.83 (2 H, broad s).

1-(5-chloropyridin-2-yl)-1-(3-fluoro-5-(2,2,2-trifluoroethoxy)phenyl)-2-phenylethanamine (0.040 mmol) was subsequently converted to (S)-1-(1-(5-chloropyridin-2-yl)-1-(3-fluoro-5-(2,2,3,3-tetrafluoropropoxy)phenyl)-2-phenylethyl)-3-cyclopentylurea as exactly as described in Procedures 2 (96% yield) LCMS: 4.08 min [M+1] 568.2 (4 min gradient, MeOH/$H_2O$ 0.1% TFA).

EXAMPLE 7

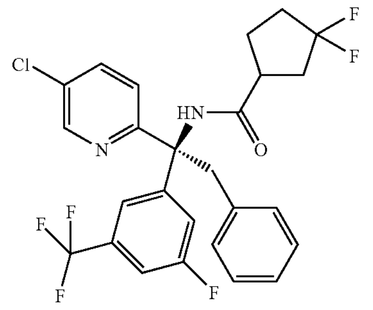

N-((S)-1-(5-chloropyridin-2-yl)-1-(3-fluoro-5-(trifluoromethyl)phenyl)-2-phenylethyl)-3,3-difluorocyclopentanecarboxamide Procedure 12

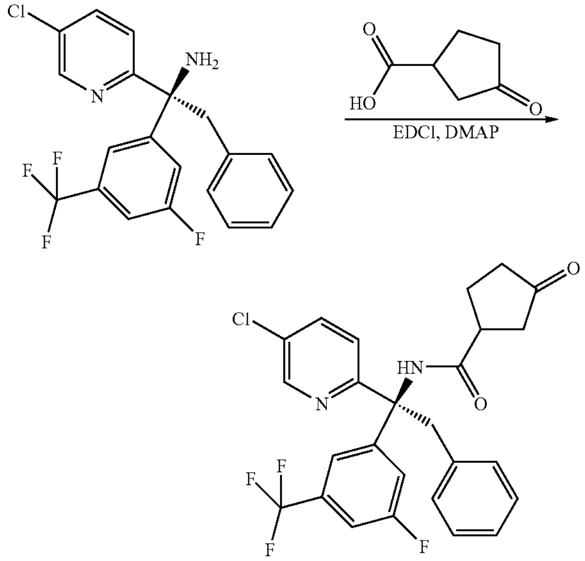

(S)-1-(5-chloropyridin-2-yl)-1-(3-fluoro-5-(trifluoromethyl)phenyl)-2-phenylethanamine (64 mg, 0.16 mmol, prepared as described for procedures 5, 6, 7 and 2) was added to a solution of 3-oxocyclopentanecarboxylic acid (21 mg, 0.16 mmol) in anhydrous $CH_2Cl_2$ (1.7 mL) at rt under Ar. The mixture was cooled to 0° C. and EDCI (41 mg, 0.21 mmol) was added. The resulting mixture was subsequently stirred for 2 min, before the addition of DMAP (26 mg, 0.21 mmol). The reaction mixture was stirred (16 h) while slowly warming to 25° C., at which time the solvent was removed under pressure by absorbing the mixture onto Celite. Flash chromatography ($SiO_2$, 0-100% EtOAc/hexanes) afforded the desired amide (37.5 mg) as a film. $^1H$ NMR (500 MHz, $CDCl_3$, diastereomeric mixture) δ 8.50 (s, 1H), 8.45 (s, 1H), 8.36-8.32 (m, 2H), 7.75-7.71 (m, 2H), 7.47 (b s, 2H), 7.39 (d, J=9.3 Hz, 1H), 7.34 (d, J=9.3 Hz, 1H), 7.26-7.08 (m, 10H), 6.54 (d, J=7.1 Hz, 2H), 6.50 (d, J=7.7 Hz, 2H), 4.47 (app t, J=12.5 Hz, 2H), 3.61 (app t, J=12.5 Hz, 2H), 1.04-2.98 (m, 2H), 2.56-1.98 (m, 12H); LC/MS ($MeOH/H_2O/NH_4OAc$ mobile phase) rt=3.84 min; [M+H]=505.3.

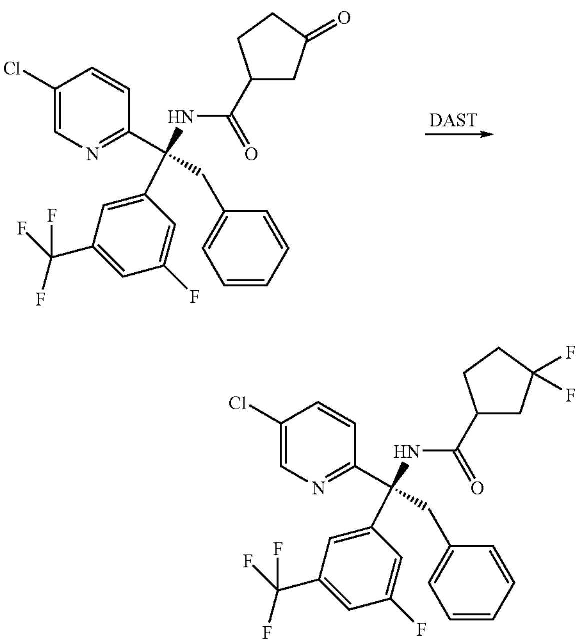

To a solution of N-((S)-1-(5-chloropyridin-2-yl)-1-(3-fluoro-5-(trifluoromethyl)phenyl)-2-phenylethyl)-3-oxocyclopentanecarboxamide (33 mg, 0.065 mmol) in $CH_2Cl_2$ (600 μL), was added DAST (29 μL, 0.21 mmol) dropwise. After stirring at rt for 4 days, LC/MS analysis revealed that the solution was comprised of a 1:1 ratio of starting material : product. Aqueous sat'd NaCl was added and the mixture was extracted 3× with $CH_2Cl_2$. The organics were dried over $Na_2SO_4$, filtered, and absorbed onto Celite under reduced pressure. The residue was purified by flash chromatography ($SiO_2$, 0-100% EtOAc/hexanes) to afford N-((S)-1-(5-chloropyridin-2-yl)-1-(3-fluoro-5-(trifluoromethyl)phenyl)-2-phenylethyl)-3,3-difluorocyclopentanecarboxamide (10 mg) as a yellow oil and recovered starting material (8 mg). $^1H$ NMR (500 MHz, $CDCl_3$, diastereomeric mixture) δ 8.34 (s, 1H), 8.30 (s, 1H), 8.27-8.22 (m, 2H), 7.66-7.61 (m, 2H), 7.38 (s, 2H), 7.31-7.22 (m, 2H), 7.20-6.98 (m, 8H), 6.47-6.39 (m, 4H), 4.38 (d, J=12.6 Hz, 1 H), 4.37 (d, J=12.6 Hz, 1 H), 3.52 (d, J=12.6 Hz, 1 H), 3.51 (d, J=12.6 Hz, 1 H), 2.88-2.77 (m, 2 H), 2.38-0.65 (m, 12 H); LC/MS ($MeOH/H_2O/NH_4OAc$ mobile phase) rt=4.13 min; [M+H]=527.2.

EXAMPLE 8

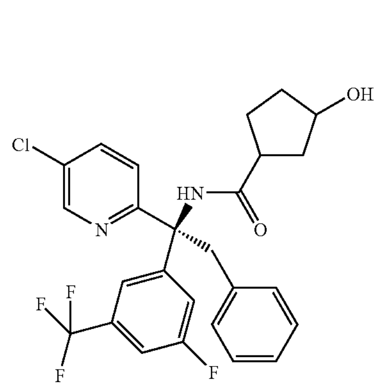

N-((S)-1-(5-chloropyridin-2-yl)-1-(3-fluoro-5-(trifluoromethyl)phenyl)-2-phenylethyl)-3-hydroxycyclopentanecarboxamide Procedure 13

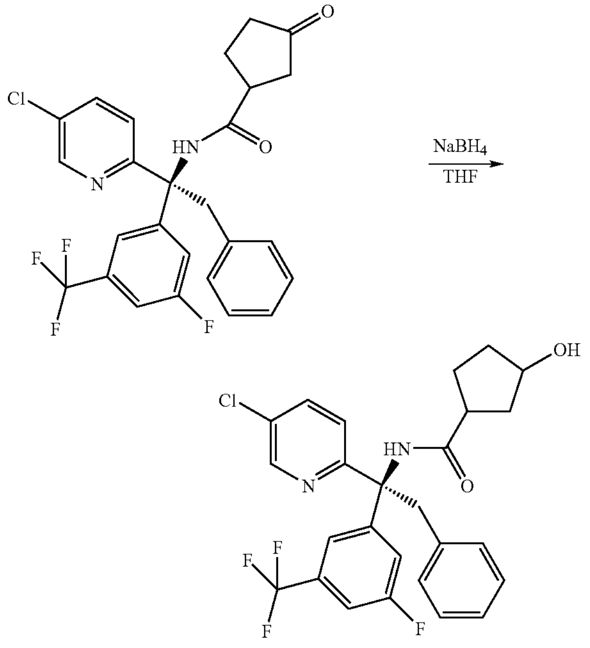

$NaBH_4$ (600 μg, 0.015 mmol) was added to a solution of N-((S)-1-(5-chloropyridin-2-yl)-1-(3-fluoro-5-(trifluoromethyl)phenyl)-2-phenylethyl)-3-oxocyclopentanecarboxamide (prepared as described in Example 7, Procedure 12) (7.7 mg, 0.015 mmol) in THF (1 mL) at room temperature. The reaction was monitored by HPLC and after 16 h, the solution was diluted with $H_2O$ and extracted with EtOAc (3×). The combined EtOAc layers was further washed with 6N HCl and sat'd aqueous NaCl, dried over $Na_2SO_4$, filtered, and concentrated under reduced pressure. Flash chromatography ($SiO_2$, 0-100% EtOAc/hexanes) gave 5.4 mg of N-((S)-1-(5-chloropyridin-2-yl)-1-(3-fluoro-5-(trifluoromethyl)phenyl)-2-phenylethyl)-3-hydroxycyclopentanecarboxamide as a film. $^1H$ NMR (500 MHz, $CDCl_3$, mixture of isomers) δ 8.54 (s, 1H), 8.52 (s, 1H), 8.35-8.29 (m, 2H), 7.72-7.66 (m, 2H), 7.47-7.42 (m, 2H), 7.40-7.32 (m, 2H), 7.25-7.06 (m, 10H), 6.56-6.50 (m, 4H), 4.48-4.38 (m, 2H), 4.30-4.22 (m, 2H), 3.64-3.53 (m, 2H), 2.89-2.80 (m, 2H), 2.10-0.80 (m, 12H); LC/MS (MeOH/$H_2O$/$NH_4OAc$ mobile phase) rt=3.91 min; [M+H]=507.3.

EXAMPLE 9

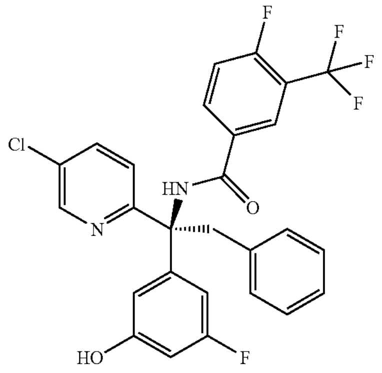

(S)-N-(1-(5-chloropyridin-2-yl)-1-(3-fluoro-5-hydroxyphenyl)-2-phenylethyl)-4-fluoro-3-(trifluoromethyl)benzamide Procedure 14

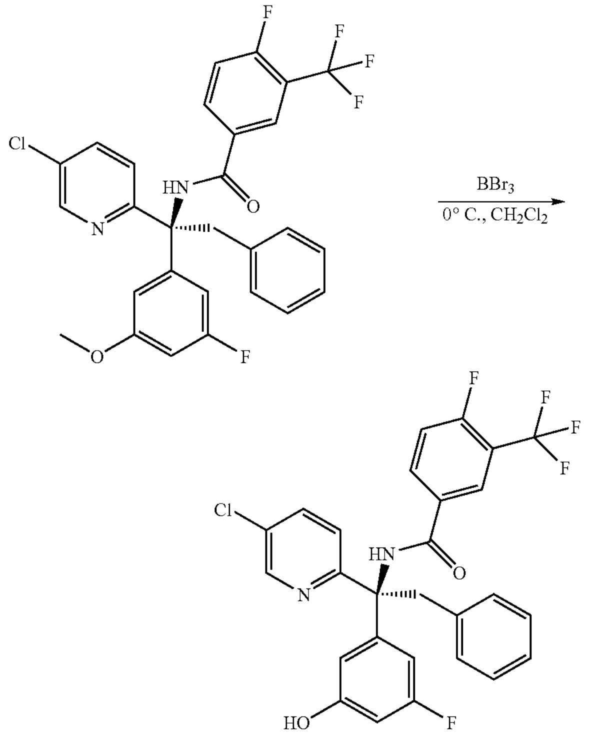

To a solution of (S)-N-(1-(5-chloropyridin-2-yl)-1-(3-fluoro-5-methoxyphenyl)-2-phenylethyl)-4-fluoro-3-(trifluoromethyl)benzamide (696 mg, 1.27 mmol, prepared according to procedures 5, 6, 7 and 2) in $CH_2Cl_2$ at 0° C. was added $BBr_3$ (12.7 mL, 1M, 12.7 mmol). The mixture was stirred at 0° C. for 3 hrs before it was quenched by being carefully poured into cold $Na_2CO_3$ solution. The aqueous was extracted with EtOAc. The combined organic layers were washed with brine, dried over $MgSO_4$, concentrated and the crude mixture was purified by ISCO chromatography (40 g column) using hexanes/EtOAc (0-40% over 25 min) to give (S)-N-(1-(5-chloropyridin-2-yl)-1-(3-fluoro-5-hydroxyphenyl)-2-phenylethyl)-4-fluoro-3-(trifluoromethyl)benzamide as an offwhite solid (606 mg, 90% yield). LCMS: 4.07 min [M+1] 533.30 (4 min gradient, MeOH/$H_2O$ 0.1% TFA); $^1H$ NMR (400 MHz, $CDCl_3$) δ ppm 3.64 (d, J=13.21 Hz, 1 H), 4.48 (d, J=12.96 Hz, 1 H), 6.21 (dt, J=10.03, 2.20 Hz, 1 H), 6.45-6.55 (m, 3 H), 6.95-7.04 (m, 3 H), 7.11 (t, J=7.46 Hz, 1 H), 7.20-7.30 (m, 3 H), 7.53 (s, 1 H), 7.70 (dd, J=8.68, 2.32 Hz, 1 H), 7.90 (ddd, J=8.50, 4.46, 2.45 Hz, 1 H), 8.03 (dd, J=6.72, 2.08 Hz, 1 H), 8.29-8.32 (m, 1 H), 9.33-9.41 (m, 1 H).

EXAMPLE 10

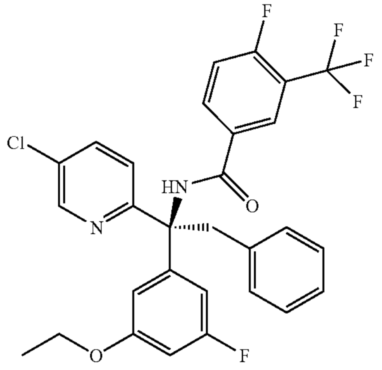

(S)-N-(1-(5-chloropyridin-2-yl)-1-(3-ethoxy-5-fluorophenyl)-2-phenylethyl)-4-fluoro-3-(trifluoromethyl)benzamide Procedure 15

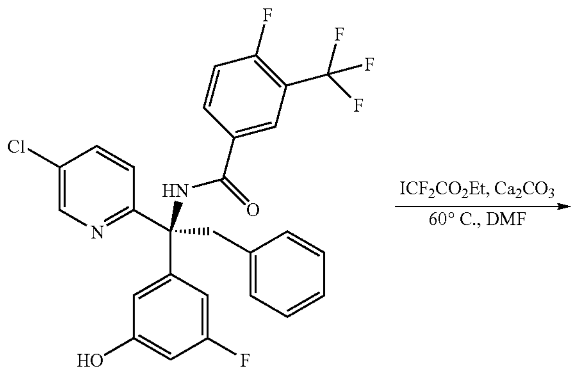

-continued

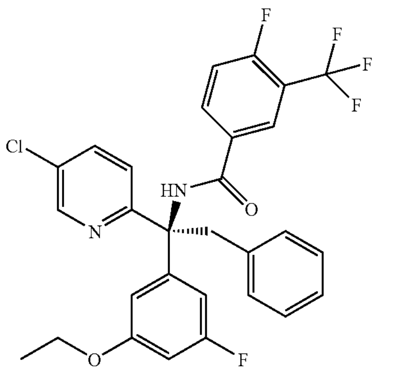

+

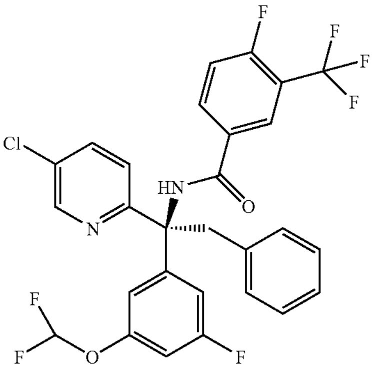

To a solution of (S)-N-(1-(5-chloropyridin-2-yl)-1-(3-fluoro-5-hydroxyphenyl)-2-phenylethyl)-4-fluoro-3-(trifluoromethyl)benzamide (32 mg, 0.06 mmol, prepared as described in Procedure 14) in DMF (0.5 mL) was added $Cs_2CO_3$ (39 mg, 0.12) and $ICF_2CO_2Et$ (28 mg, 0.12 mmol). The mixture was heated at 60° C. for 3 days. $NaHCO_3$ was added. It was extracted with $CH_2Cl_2$. The organic layer was washed with 10% citric acid, brine, dried over $MgSO_4$, concentrated and the crude mixture was purified by preparative HPLC (phenominex C18 column, 21×100 mm, 5 μ) using $MeOH/H_2O$ (0.1% TFA) to give two products, (S)-N-(1-(5-chloropyridin-2-yl)-1-(3-ethoxy-5-fluorophenyl)-2-phenylethyl)-4-fluoro-3-(trifluoromethyl)benzamide (2.5 mg, 7% yield) as a pale yellow solid, LCMS: 4.38 min [M+1] 561.44 (4 min gradient, $MeOH/H_2O$ 0.1% TFA); $^1H$ NMR (400 MHz, $CDCl_3$) δ ppm 1.33-1.40 (m, J=6.88, Hz, 3 H), 3.61 (d, J=12.88 Hz, 1 H), 3.93-4.00 (m, 2 H), 4.54 (d, J=12.88 Hz, 1 H), 6.49-6.56 (m, 3 H), 6.76 (dt, J=9.85, 1.89 Hz, 1 H), 6.84 (s, 1 H), 7.02 (t, J=7.45 Hz, 2 H), 7.11 (t, J=7.33 Hz, 1 H), 7.22-7.31 (m, 3 H), 7.70 (dd, J=8.59, 2.27 Hz, 1 H), 7.85-7.90 (m, 1 H), 8.03 (dd, J=6.82, 2.02 Hz, 1 H), 8.32 (d, J=2.53 Hz, 1 H), 9.11 (s, 1 H), and (S)-N-(1-(5-chloropyridin-2-yl)-1-(3-(difluoromethoxy)-5-fluorophenyl)-2-phenylethyl)-4-fluoro-3-(trifluoromethyl)benzamide (3 mg, 7% yield) as a pale yellow foam, LCMS: 4.28 min [M+1] 583.32 (4 min gradient, $MeOH/H_2O$ 0.1% TFA); 1 H NMR (400 MHz, $CDCl_3$) δ ppm 3.61 (d, J=12.88 Hz, 1 H), 4.54 (d, J=12.88 Hz, 1 H), 6.51 (m, 3 H), 6.76-6.83 (m, 1 H), 7.00-7.08 (m, 4 H), 7.13 (t, J=7.45 Hz, 1 H), 7.20-7.29 (m, 2 H), 7.74 (dd, J=8.59, 2.27 Hz, 1 H), 7.87 (ddd, J=8.46, 4.67, 2.27 Hz, 1 H), 8.02 (dd, J=6.69, 1.89 Hz, 1 H), 8.35 (d, J=2.27 Hz, 1 H), 9.11 (s, 1 H).

EXAMPLE 11

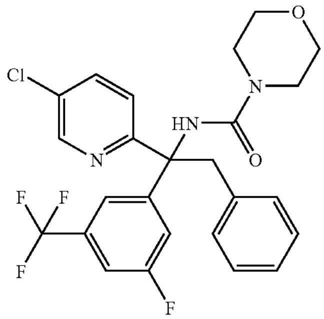

N-(1-(5-chloropyridin-2-yl)-1-(3-fluoro-5-(trifluoromethyl)phenyl)-2-phenylethyl)morpholine-4-carboxamide

Procedure 16

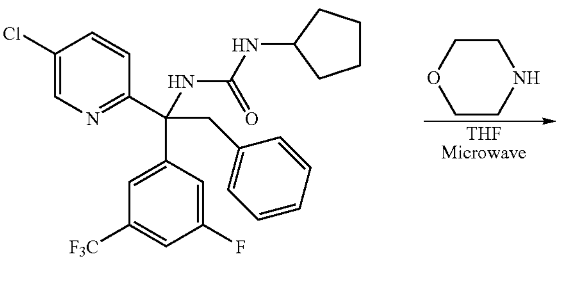

-continued

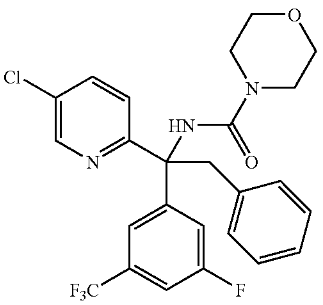

1-(1-(5-chloropyridin-2-yl)-1-(3-fluoro-5-(trifluoromethyl)phenyl)-2-phenylethyl)-3-cyclopentylurea was prepared as described in procedures 1 and 2. To a microwave vial of 1-(1-(5-chloropyridin-2-yl)-1-(3-fluoro-5-(trifluoromethyl)phenyl-2-phenylethyl)-3-cyclopentylurea (20 mg, 0.037 mmol) was added morpholine (0.2 mL). The sealed vial was stirred at 150° C. under microwave irradiation for 1500 sec. The resulting reaction was diluted with MeOH and the desired product was isolated by preparative HPLC using 30-100% acetonitrile in $H_2O$ with 0.1% TFA as mobile phase to afford the title compound (18 mg, 89% yield) as white powder. LC-MS (ESI): 508.27 (M+H), retention time=3.86 min (0-100% MeOH/$H_2O$/0.1-1% TFA, 4 min run); $^1H$ NMR (400 MHz, $CD_3OD$) δ ppm 3.14-3.29 (m, 2H), 3.34-3.45 (m, 2H), 3.56-3.73 (m, 4H), 3.84 (d, J=12.74 Hz, 1H), 4.29 (d, J=12.74 Hz, 1H), 6.61 (d, J=6.59 Hz, 2H), 6.99-7.20 (m, 3H), 7.28-7.42 (m, 2H), 7.50-7.66 (m, 2H), 7.84 (dd, J=8.79, 2.20 Hz, 1H), 8.36 (d, J=2.64 Hz, 1H).

EXAMPLE 12

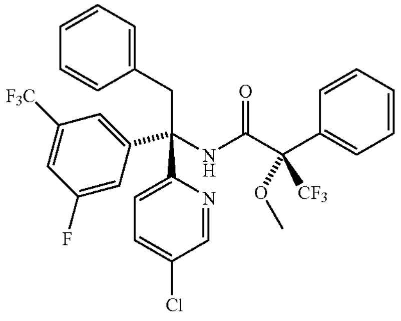

(S)-N-((S)-1-(5-chloropyridin-2-yl)-1-(3-fluoro-5-(trifluoromethyl)phenyl)-2-phenylethyl)-3,3,3-trifluoro-2-methoxy-2-phenylpropanamide Procedure 17

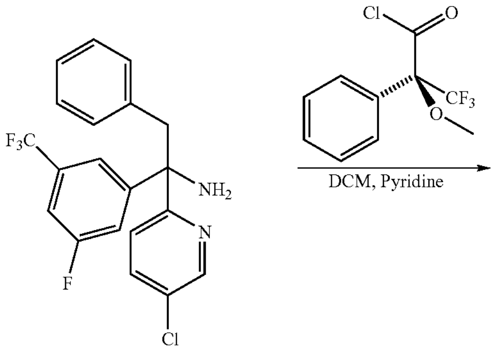

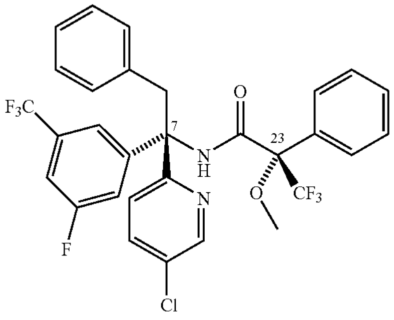

To racemic 1-(5-chloropyridin-2-yl)-1-(3-fluoro-5-(trifluoromethyl)phenyl)-2-phenylethanamine (55 mg, 0.14 mmol) in DCM (1 mL) was added pyridine (56 μL, 55 mmol) and (R)-3,3,3-trifluoro-2-methoxy-2-phenylpropanoyl chloride (52 μL, 0.22 mmol). The reaction was stirred at room temperature for 14 h and the reaction mixture filtered through a silica plug elution with DCM. (S)-N-((S)-1-(5-chloropyridin-2-yl)-1-(3-fluoro-5-(trifluoromethyl)phenyl)-2-phenylethyl)-3,3,3-trifluoro-2-methoxy-2-phenylpropanamide was crystallized from ether heptane:

| Structure | T | a(Å) | b(Å) | c(Å) | α° | β° | γ° | V(Å³) | Z' | Vm | sg | dcalc | mp(° C.) | R | Renan |
|---|---|---|---|---|---|---|---|---|---|---|---|---|---|---|---|
| 738730 N-1 | 25 | 8.9252(5) | 14.5130(7) | 21.853(1) | | | | 2830.7(3) | 1 | 708 | $P2_12_12_1$ | 1.434 | 160-168 | .060 | .067 |

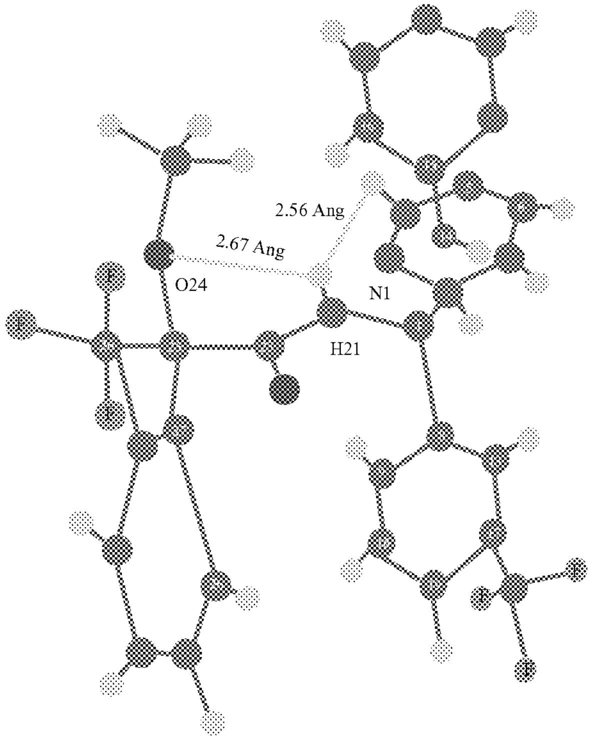

EXAMPLE 13

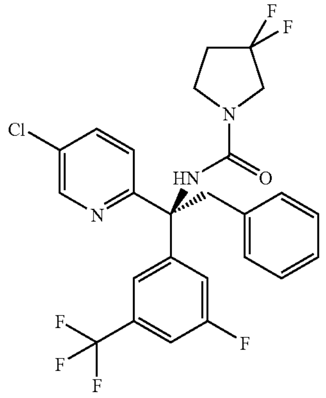

(S)-N-(1-(5-chloropyridin-2-yl)-1-(3-fluoro-5-(trifluoromethyl)phenyl)-2-phenylethyl)-3,3-difluoropyrrolidine-1-carboxamide Procedure 18

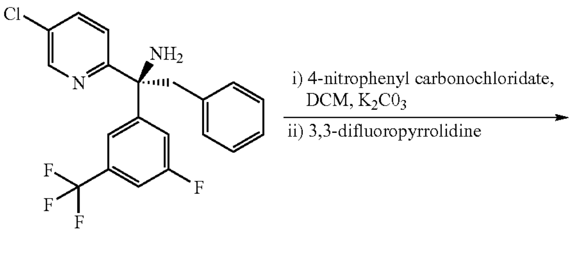

-continued

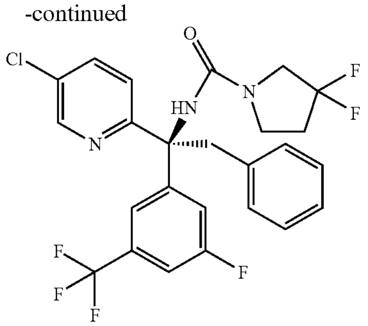

1-(5-chloropyridin-2-yl)-1-(3-fluoro-5-(trifluoromethyl)phenyl)-2-phenylethylcarbamate was prepared as described in Procedure 6 and then converted to (S)-4-nitrophenyl 1-(5-chloropyridin-2-yl)-1-(3-fluoro-5-(trifluoromethyl)phenyl)-2-phenylethylcarbamate as described in Procedure 8.

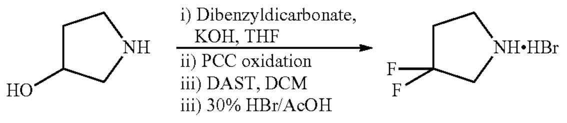

To the solution of pyrrolidin-3-ol (1.0 g, 11 mmol) in THF (5 mL) and 1M NaOH (5 mL) was added dibenzyldicarbonate (3.3, 11 mmol) at room temperature. The reaction mixture was stirred for 3 h then the THF removed under reduced pressure. The residue was dissolved in DCM (50 mL) and washed successively with saturated $NaHCO_3$ (2×20mL) and saturated NaCl (2×20 mL). The solution was dried over $Na_2SO_4$, decanted and concentrated. Benzyl 3-hydroxypyrrolidine-1-carboxylate (1.1 g, 47%) was isolated by prep. HPLC YMC ODSA 30×100 mm, 20-100% $MeOH/H_2O$ (0.1% TFA) gradient over 10 mins at 20 mL/min flow rate at a retention time of 4.93 min. LCMS: 1.21 min [M+1] 222.06 (2 min gradient, $MeOH/H_2O$ 0.1% TFA).

Benzyl 3-hydroxypyrrolidine-1-carboxylate (0.30 g, 1.34 mmol) was dissolved in DCM (20 mL) and pyridinium chlorochromate was added (0.44 g, 2.0 mmol). The resulting slurry was stirred at room temperature for 72 h. Benzyl 3-oxopyrrolidine-1-carboxylate (0.080 g, 27%) was isolated as a colorless oil by prep. HPLC YMC ODSA 30×100 mm, 20-100% $MeOH/H_2O$ (0.1% TFA) gradient over 10 mins at 20 mL/min flow rate at a retention time of 4.25 min. LCMS: 1.20 min [M+1] not observed (2 min gradient, $MeOH/H_2O$ 0.1% TFA).

Benzyl 3-oxopyrrolidine-1-carboxylate (0.080 g, 0.37 mmol) was dissolved at room temperature in DCM. Diethylaminosulfurtrifluoride (0.16 mL, 1.1 mmol) was added and the reaction mixture was stirred for 14 h. The solution was diluted with DCM (ca 20 mL), washed with saturated NaCl (2×20 mL), dried over $Na_2SO_4$, decanted and concentrated. Benzyl 3,3-difluoropyrrolidine-1-carboxylate (0.050 g, 50% yield) was isolated as a yellow oil by prep. HPLC YMC ODSA 30×100 mm, 20-100% $MeOH/H_2O$ (0.1% TFA) gradient over 10 mins at 20 mL/min flow rate at a retention time of 6.38 min. LCMS: 1.58 min [M+Na] 264.50 (2 min gradient, $MeOH/H_2O$ 0.1% TFA). $^1H$ NMR ($CDCl_3$, 400 MHz): 7.29ppm, 5H, m; 5.09 ppm, 2H, s; 3.69 ppm, 2H, m; 3.62 ppm, 2H, m; 2.28 ppm, 2H, m.

To benzyl 3,3-difluoropyrrolidine-1-carboxylate (0.050 g, 0.20 mmol) at room temperature was added HBr in AcOH (30%) neat (0.5 mL). After 30 min, ether was added (50 mL) and the pale brown powder triturated with ether and dried under reduced pressure yielding 3,3-difluoropyrrolidine hydrobromide as a tan powder (0.030 g, 81%) $^1H$ NMR ($CD_3OD$, 400 MHz): 3.71 ppm, 2H, dd; 3.61 ppm, 2H, t; 2.58 ppm, 2H, septet.

To a crude solution of (S)-4-nitrophenyl 1-(5-chloropyridin-2-yl)-1-(3-fluoro-5-(trifluoromethyl)phenyl)-2-phenylethylcarbamate in DCE (1 mL) (67 mg, 0.13 mmol) was added 3,3-difluoropyrrolidine hydrobromide (24 mg, 0. 12 mmol). The reaction mixture was stirred at room temperature for 2 h and the solution turned yellow. The solution was concentrated, dissolved in MeOH (1.5 mL), filtered and purified by reverse phase prep. HPLC YMC ODSA 30×100 mm, 20-100% $MeOH/H_2O$ (0.1% TFA) gradient over 10 mins at 20 mL/min flow rate. (S)-N-(1-(5-chloropyridin-2-yl)-1-(3-fluoro-5-(trifluoromethyl)phenyl)-2-phenylethyl)-3,3-difluoropyrrolidine-1-carboxamide (0.011 g, 17% yield) eluted at a retention time of 11.2 mins and was isolated as colorless oil. LCMS: 2.15 min [M+1] 528.2 (2 min gradient, $MeOH/H_2O$ 0.1% TFA) $^1H$ NMR ($CDCl_3$, 400 MHz): 8.20 (d, J=2.0 Hz, 1H), 7.60 (dd, J=2 Hz, J=8 Hz, 1H), 7.46 (s, 1H), 7.30 (d, J=8 Hz, 1H), 7.15 (m, 2H), 7.05 (m, 1H), 7.03 (m, 3H), 6.44, (d, J=8 Hz, 1H), 4.37, (d, J=12 Hz, 1H), 3.74, (q, J=12 Hz, 1H), 3.54, (m, 1H), 3.44, (m, 2H), 3.32, (q, J=8 Hz, 1H), 2.32, (m, 2H).

TABLE 1

| Ex. No. | Structure | Name | Retention Time Min./ Molecular Mass | Prepared in the manner described in: |
|---|---|---|---|---|
| 14 | 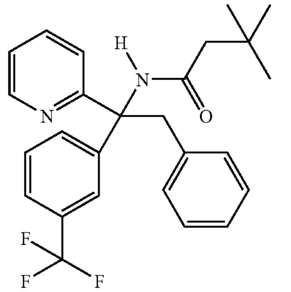 | 3,3-dimethyl-N-(2-phenyl-1-(pyridin-2-yl)-1-(3-(trifluoromethyl)phenyl)ethyl) butanamide | 3.95 LC 441.07 [M + H+] | Procedures 1 and 4 |
| 15 | 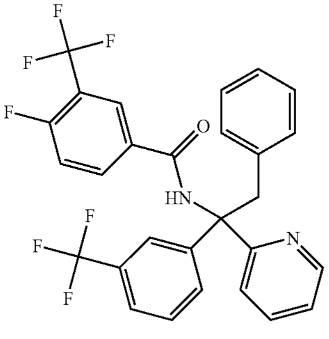 | 4-fluoro-N-(2-phenyl-1-(pyridin-2-yl)-1-(3-(trifluoromethyl) phenyl)ethyl)-3-(trifluoromethyl) benzamide | 4.06 LC 533.03 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 16 | 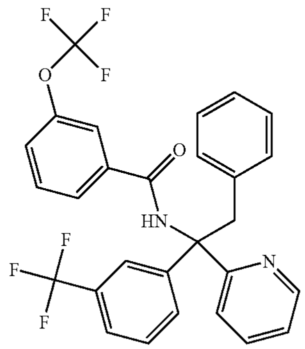 | N-(2-phenyl-1-(pyridin-2-yl)-1-(3-(trifluoromethyl)phenyl)ethyl)-3-(trifluoromethoxy)benzamide | 4.07 LC 531.03 [M + H+] | Procedures 1 and 4 |
| 17 | 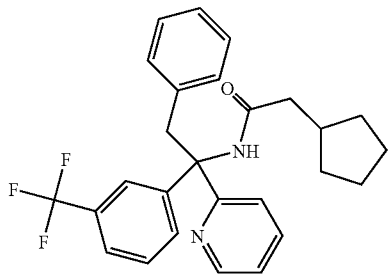 | 2-cyclopentyl-N-(2-phenyl-1-(pyridin-2-yl)-1-(3-(trifluoromethyl)phenyl)ethyl) acetamide | 4.07 LC 531.03 [M + H+] | Procedures 1 and 4 |
| 18 | 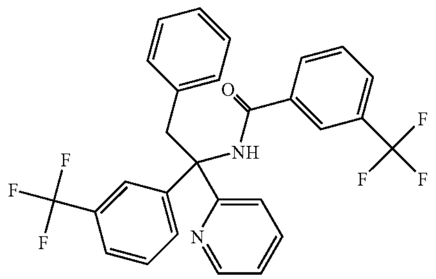 | N-(2-phenyl-1-(pyridin-2-yl)-1-(3-(trifluoromethyl)phenyl)ethyl)-3-(trifluoromethyl)benzamide | 4.01 LC 453.05 [M + H+] | Procedures 1 and 4 |
| 19 | 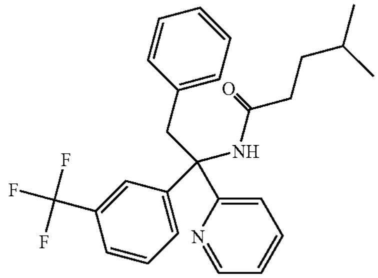 | 4-methyl-N-(2-phenyl-1-(pyridin-2-yl)-1-(3-(trifluoromethyl) phenyl)ethyl)pentanamide | 3.96 LC 440.5 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 20 | 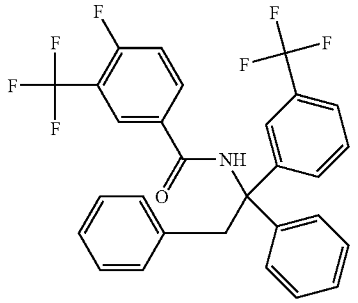 | N-(1-(5-chloropyridin-2-yl)-2-phenyl-1-(3-(trifluoromethyl)phenyl)ethyl)-4-fluoro-3-(trifluoromethyl)benzamide | 3.84 LC 567.25 [M + H+] | Procedures 1 and 4 |
| 21 | 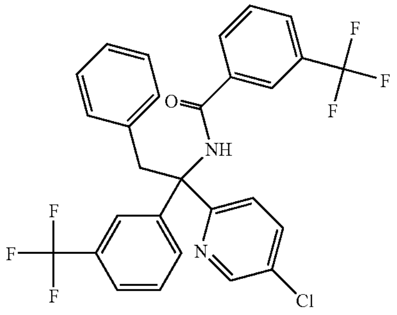 | N-(1-(5-chloropyridin-2-yl)-2-phenyl-1-(3-(trifluoromethyl)phenyl)ethyl)-3-(trifluoromethyl)benzamide | 3.80 LC 549.24 [M + H+] | Procedures 1 and 4 |
| 22 | 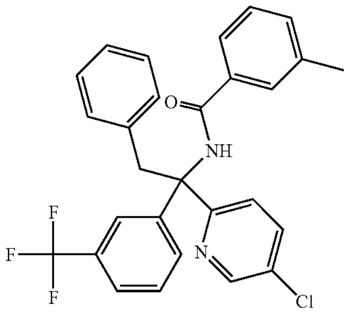 | N-(1-(5-chloropyridin-2-yl)-2-phenyl-1-(3-(trifluoromethyl)phenyl)ethyl)-3-methylbenzamide | 3.76 LC 495.24 [M + H+] | Procedures 1 and 4 |
| 23 | 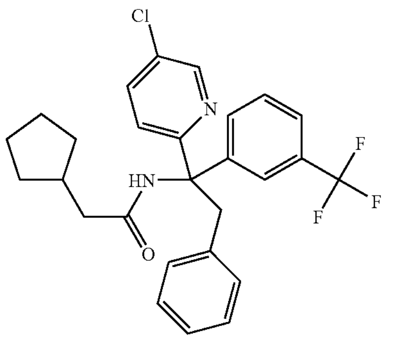 | N-(1-(5-chloropyridin-2-yl)-2-phenyl-1-(3-(trifluoromethyl)phenyl)ethyl)-2-cyclopentylacetamide | 3.85 LC 487.28 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 24 | 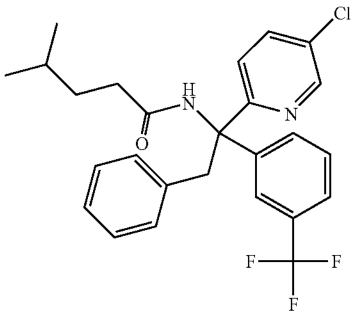 | N-(1-(5-chloropyridin-2-yl)-2-phenyl-1-(3-(trifluoromethyl) phenyl)ethyl)-4-methylpentanamide | 3.79 LC 475.29 [M + H+] | Procedures 1 and 4 |
| 25 | 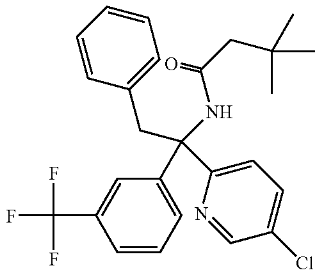 | N-(1-(5-chloropyridin-2-yl)-2-phenyl-1-(3-(trifluoromethyl) phenyl)ethyl)-3,3-dimethylbutanamide | 3.79 LC 441.07 [M + H+] | Procedures 1 and 4 |
| 26 | 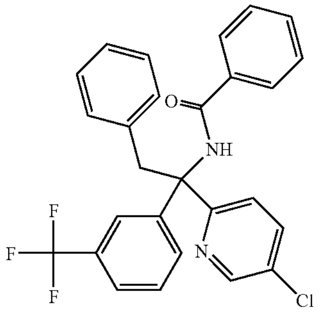 | N-(1-(5-chloropyridin-2-yl)-2-phenyl-1-(3-(trifluoromethyl) phenyl)ethyl)benzamide | 3.65 LC 481.23 [M + H+] | Procedures 1 and 4 |
| 27 | 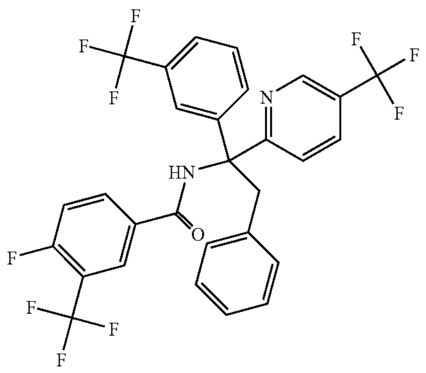 | 4-fluoro-N-(2-phenyl-1-(3-(trifluoromethyl)phenyl)-1-(5-(trifluoromethyl)pyridin-2-yl)ethyl)-3-(trifluoromethyl) benzamide | 3.54 LC 601.2 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 28 | 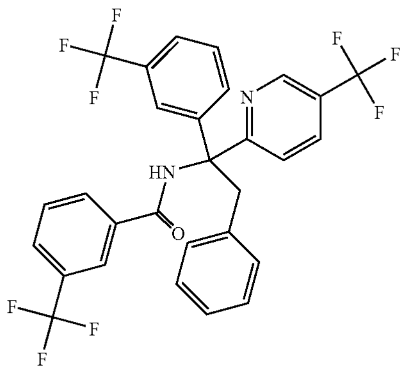 | N-(2-phenyl-1-(3-(trifluoromethyl)phenyl)-1-(5-(trifluoromethyl)pyridin-2-yl)ethyl)-3-(trifluoromethyl) benzamide | 3.49 LC 583.24 [M + H+] | Procedures 1 and 4 |
| 29 | 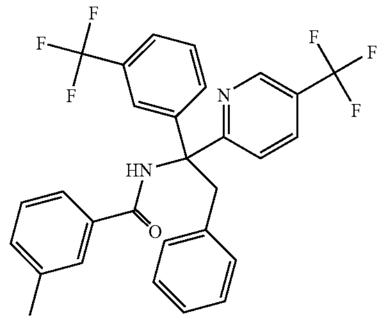 | 3-methyl-N-(2-phenyl-1-(3-(trifluoromethyl)phenyl)-1-(5-(trifluoromethyl)pyridin-2-yl)ethyl)benzamide | 3.44 LC 529.24 [M + H+] | Procedures 1 and 4 |
| 30 | 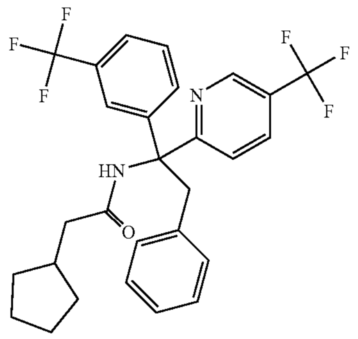 | 2-cyclopentyl-N-(2-phenyl-1-(3-(trifluoromethyl)phenyl)-1-(5-(trifluoromethyl)pyridin-2-yl)ethyl)acetamide | 3.54 LC 541.27 [M + H+] | Procedures 1 and 4 |
| 31 | 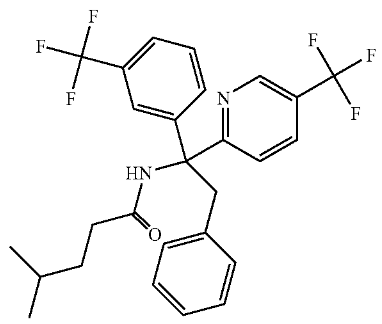 | 4-methyl-N-(2-phenyl-1-(3-(trifluoromethyl)phenyl)-1-(5-(trifluoromethyl)pyridin-2-yl)ethyl)pentanamide | 3.47 LC 509.26 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 32 | 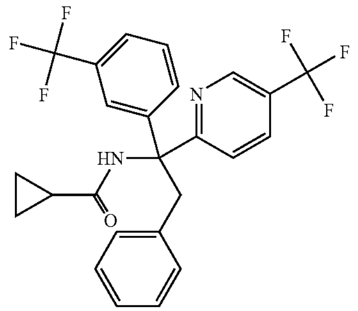 | N-(2-phenyl-1-(3-(trifluoromethyl)phenyl)-1-(5-(trifluoromethyl)pyridin-2-yl)ethyl)cyclopropanecarboxamide | 3.04 LC 479.26 [M + H+] | Procedures 1 and 4 |
| 33 | 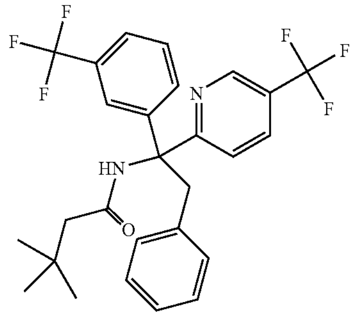 | 3,3-dimethyl-N-(2-phenyl-1-(3-(trifluoromethyl)phenyl)-1-(5-(trifluoromethyl)pyridin-2-yl)ethyl)butanamide | 3.48 LC 509.26 [M + H+] | Procedures 1 and 4 |
| 34 | 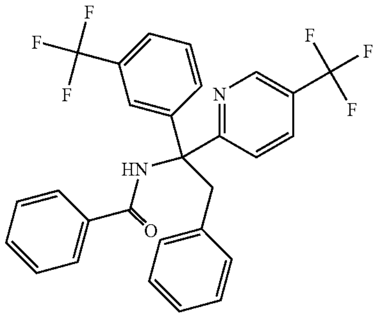 | N-(2-phenyl-1-(3-(trifluoromethyl)phenyl)-1-(5-(trifluoromethyl)pyridin-2-yl)ethyl)benzamide | 3.29 LC 515.2 [M + H+] | Procedures 1 and 4 |
| 35 | 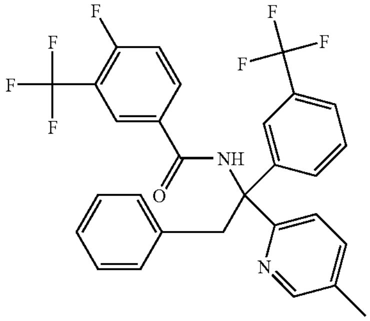 | 4-fluoro-N-(1-(5-methylpyridin-2-yl)-2-phenyl-1-(3-(trifluoromethyl)phenyl)ethyl)-3-(trifluoromethyl)benzamide | 3.38 LC 547.26 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 38 | 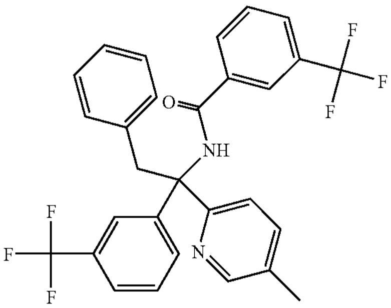 | N-(1-(5-methylpyridin-2-yl)-2-phenyl-1-(3-(trifluoromethyl) phenyl)ethyl)-3-(trifluoromethyl) benzamide | 3.29 LC 529.23 [M + H+] | Procedures 1 and 4 |
| 39 | 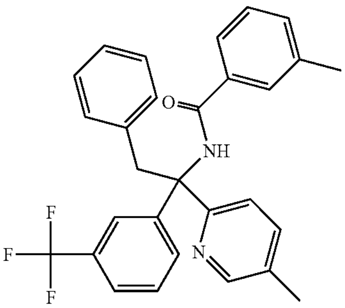 | 3-methyl-N-(1-(5-methylpyridin-2-yl)-2-phenyl-1-(3-(trifluoromethyl)phenyl)ethyl) benzamide | 3.18 LC 475.31 [M + H+] | Procedures 1 and 4 |
| 40 | 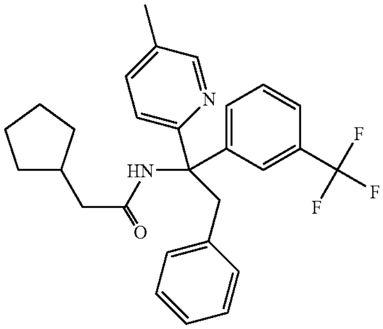 | 2-cyclopentyl-N-(1-(5-methylpyridin-2-yl)-2-phenyl-1-(3-(trifluoromethyl)phenyl)ethyl) acetamide | 3.19 LC 467.34 [M + H+] | Procedures 1 and 4 |
| 41 | 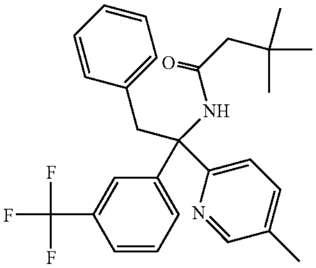 | 3,3-dimethyl-N-(1-(5-methylpyridin-2-yl)-2-phenyl-1-(3-(trifluoromethyl)phenyl)ethyl) butanamide | 3.09 LC 455.31 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 42 | 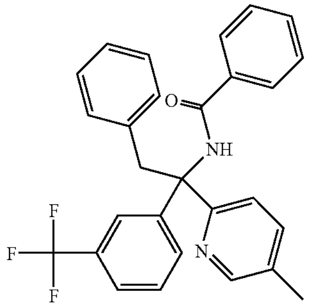 | N-(1-(5-methylpyridin-2-yl)-2-phenyl-1-(3-(trifluoromethyl) phenyl)ethyl)benzamide | 2.99 LC 461.29 [M + H$^+$] | Procedures 1 and 4 |
| 43 | 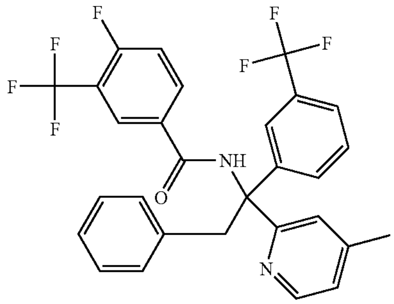 | 4-fluoro-N-(1-(4-methylpyridin-2-yl)-2-phenyl-1-(3-(trifluoromethyl)phenyl)ethyl)-3-(trifluoromethyl)benzamide | 3.26 LC 547.28 [M + H$^+$] | Procedures 1 and 4 |
| 44 | 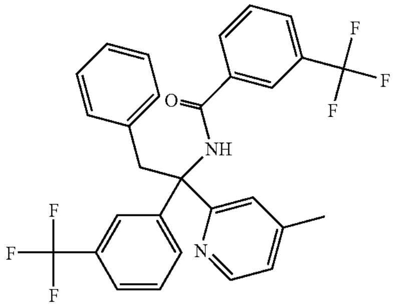 | N-(1-(4-methylpyridin-2-yl)-2-phenyl-1-(3-(trifluoromethyl) phenyl)ethyl)-3-(trifluoromethyl) benzamide | 3.20 LC 529.26 [M + H$^+$] | Procedures 1 and 4 |
| 45 | 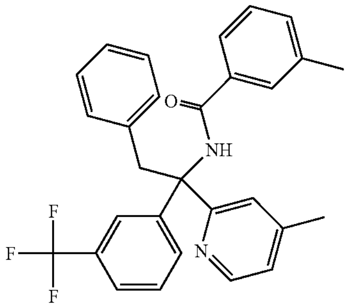 | 3-methyl-N-(1-(4-methylpyridin-2-yl)-2-phenyl-1-(3-(trifluoromethyl)phenyl)ethyl) benzamide | 3.05 LC 475.32 [M + H$^+$] | Procedures 1 and 4 |

TABLE 1-continued

| Ex. No. | Structure | Name | Retention Time Min./ Molecular Mass | Prepared in the manner described in: |
|---|---|---|---|---|
| 46 | 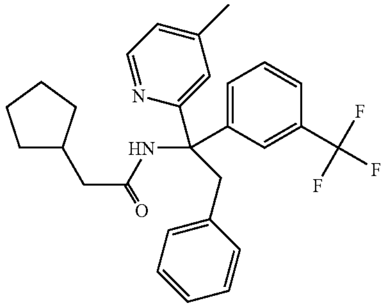 | 2-cyclopentyl-N-(1-(4-methylpyridin-2-yl)-2-phenyl-1-(3-(trifluoromethyl)phenyl)ethyl) acetamide | 2.97 LC 467.35 [M + H+] | Procedures 1 and 4 |
| 47 | 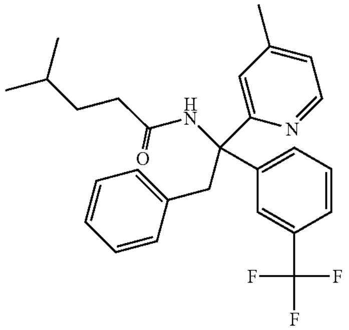 | 4-methyl-N-(1-(4-methylpyridin-2-yl)-2-phenyl-1-(3-(trifluoromethyl)phenyl)ethyl) pentanamide | 2.86 LC 455.33 [M + H+] | Procedures 1 and 4 |
| 48 | 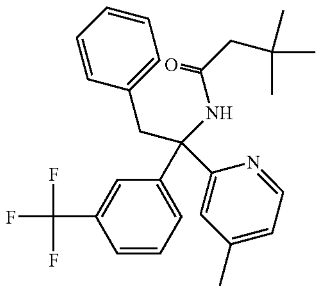 | 3,3-dimethyl-N-(1-(4-methylpyridin-2-yl)-2-phenyl-1-(3-(trifluoromethyl)phenyl)ethyl) butanamide | 2.89 LC 455.33 [M + H+] | Procedures 1 and 4 |
| 49 | 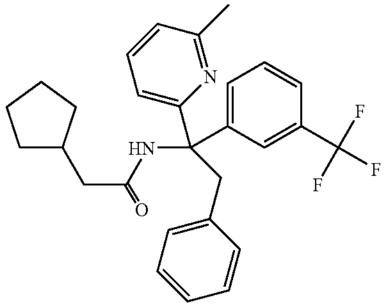 | 2-cyclopentyl-N-(1-(6-methylpyridin-2-yl)-2-phenyl-1-(3-(trifluoromethyl)phenyl)ethyl) acetamide | 3.20 LC 467.34 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 50 | 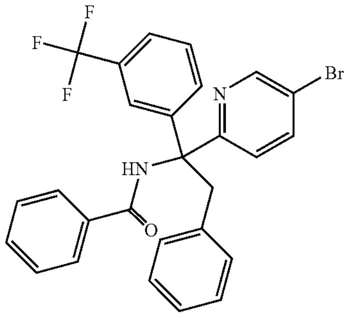 | N-(1-(5-bromopyridin-2-yl)-2-phenyl-1-(3-(trifluoromethyl) phenyl)ethyl)benzamide | 3.65 LC 525.07 [M + H$^+$] | Procedures 1 and 4 |
| 51 | 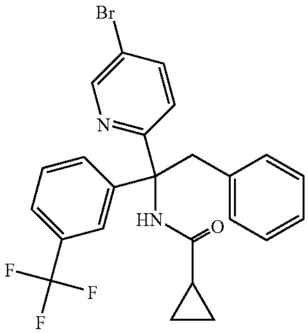 | N-(1-(5-bromopyridin-2-yl)-2-phenyl-1-(3-(trifluoromethyl) phenyl)ethyl) cyclopropanecarboxamide | 3.47 LC 489.1 [M + H$^+$] | Procedures 1 and 4 |
| 52 | 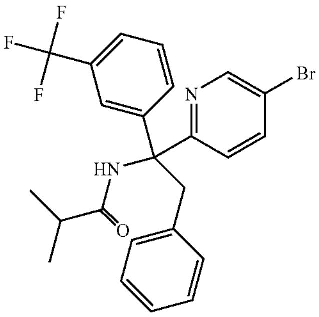 | N-(1-(5-bromopyridin-2-yl)-2-phenyl-1-(3-(trifluoromethyl) phenyl)ethyl)isobutyramide | 3.58 LC 491.1 [M + H$^+$] | Procedures 1 and 4 |
| 53 | 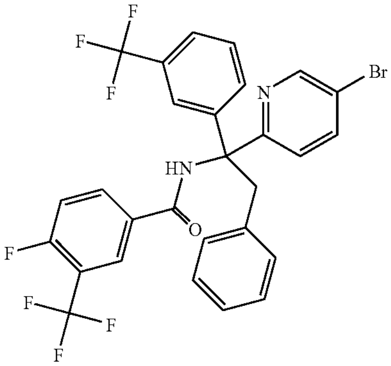 | N-(1-(5-bromopyridin-2-yl)-2-phenyl-1-(3-(trifluoromethyl) phenyl)ethyl)-4-fluoro-3-(trifluoromethyl)benzamide | 3.84 LC 611.02 [M + H$^+$] | Procedures 1 and 4 |

TABLE 1-continued

| Ex. No. | Structure | Name | Retention Time Min./ Molecular Mass | Prepared in the manner described in: |
|---|---|---|---|---|
| 54 | 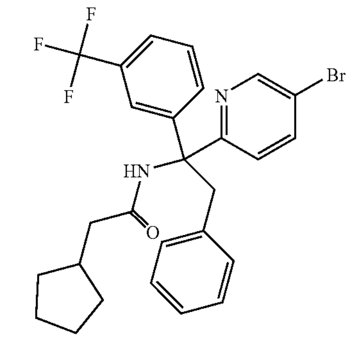 | N-(1-(5-bromopyridin-2-yl)-2-phenyl-1-(3-(trifluoromethyl) phenyl)ethyl)-2-cyclopentylacetamide | 3.84 LC 531.11 [M + H+] | Procedures 1 and 4 |
| 55 | 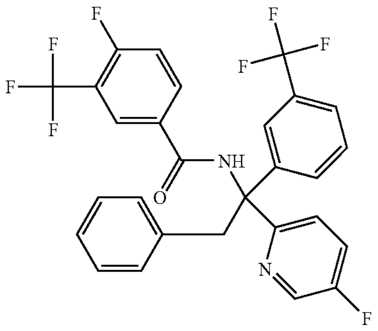 | 4-fluoro-N-(1-(5-fluoropyridin-2-yl)-2-phenyl-1-(3-(trifluoromethyl)phenyl)ethyl)-3-(trifluoromethyl)benzamide | 3.44 LC 551.18 [M + H+] | Procedures 1 and 4 |
| 56 | 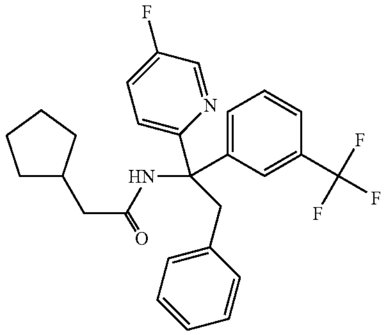 | 2-cyclopentyl-N-(1-(5-fluoropyridin-2-yl)-2-phenyl-1-(3-(trifluoromethyl)phenyl)ethyl) acetamide | 3.65 LC 471.26 [M + H+] | Procedures 1 and 4 |
| 57 | 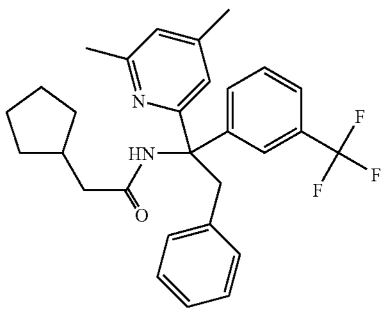 | 2-cyclopentyl-N-(1-(4,6-dimethylpyridin-2-yl)-2-phenyl-(trifluoromethyl)phenyl)ethyl) acetamide | 3.50 LC 481.23 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 58 | 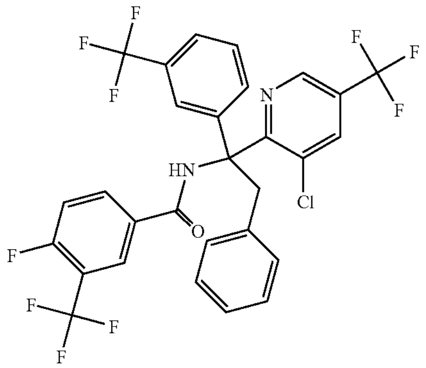 | N-(1-(3-chloro-5-(trifluoromethyl)pyridin-2-yl)-2-phenyl- 1-(3-(trifluoromethyl) phenyl)ethyl)-4-fluoro-3-(trifluoromethyl)benzamide | 3.91 LC 635.09 [M + H+] | Procedures 1 and 4 |
| 59 | 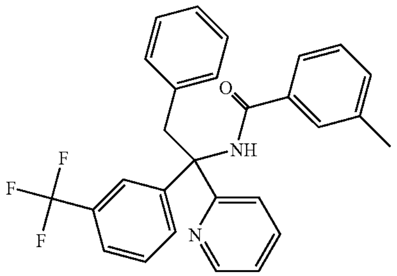 | 3-methyl-N-(2-phenyl-1-(pyridin-2-yl)-1-(3-(trifluoromethyl) phenyl)ethyl)benzamide | 3.94 LC 461.03 [M + H+] | Procedures 1 and 4 |
| 60 | 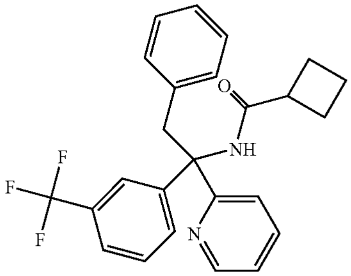 | N-(2-phenyl-1-(pyridin-2-yl)-1-(3-(trifluoromethyl)phenyl)ethyl) cyclobutanecarboxamide | 3.77 LC 425.04 [M + H+] | Procedures 1 and 4 |
| 61 | 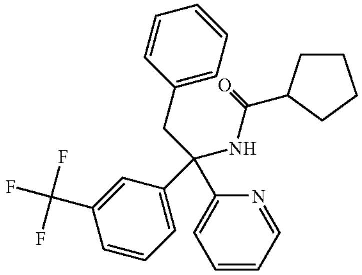 | N-(2-phenyl-1-(pyridin-2-yl)-1-(3-(trifluoromethyl)phenyl)ethyl) cyclopentanecarboxamide | 3.91 LC 439.05 [M + H+] | Procedures 1 and 4 |
| 62 | 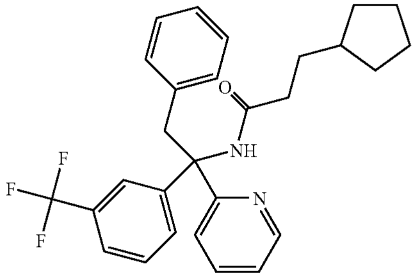 | 3-cyclopentyl-N-(2-phenyl-1-(pyridin-2-yl)-1-(3-(trifluoromethyl)phenyl)ethyl) propanamide | 4.13 LC 467.1 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 63 | 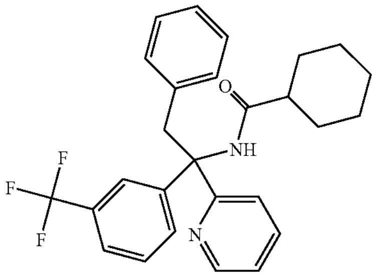 | N-(2-phenyl-1-(pyridin-2-yl)-1-(3-(trifluoromethyl)phenyl)ethyl) cyclohexanecarboxamide | 4.02 LC 453.07 [M + H+] | Procedures 1 and 4 |
| 64 | 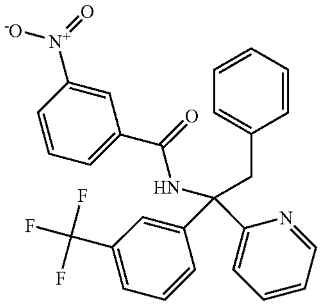 | 3-nitro-N-(2-phenyl-1-(pyridin-2-yl)-1-(3-(trifluoromethyl)phenyl) ethyl)benzamide | 3.83 LC 491.99 [M + H+] | Procedures 1 and 4 |
| 65 | 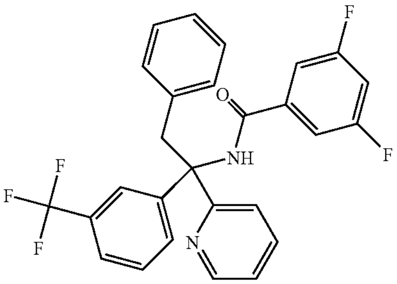 | 3,5-difluoro-N-(2-phenyl-1-(pyridin-2-yl)-1-(3-(trifluoromethyl)phenyl)ethyl) benzamide | 3.99 LC 482.99 [M + H+] | Procedures 1 and 4 |
| 66 | 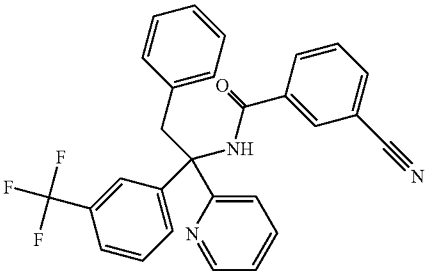 | 3-cyano-N-(2-phenyl-1-(pyridin-2-yl)-1-(3-(trifluoromethyl) phenyl)ethyl)benzamide | 3.67 LC 472.01 [M + H+] | Procedures 1 and 4 |
| 67 | 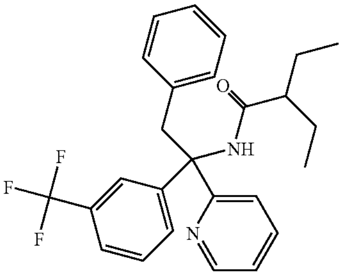 | 2-ethyl-N-(2-phenyl-1-(pyridin-2-yl)-1-(3-(trifluoromethyl)phenyl) ethyl)butanamide | 3.96 LC 441.07 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 68 | 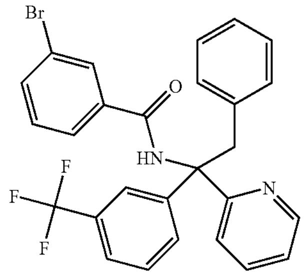 | 3-bromo-N-(2-phenyl-1-(pyridin-2-yl)-1-(3-(trifluoromethyl) phenyl)ethyl)benzamide | 4.05 LC 524.92 [M + H$^+$] | Procedures 1 and 4 |
| 69 | 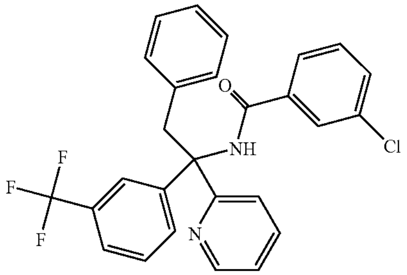 | 3-chloro-N-(2-phenyl-1-(pyridin-2-yl)-1-(3-(trifluoromethyl) phenyl)ethyl)benzamide | 4.01 LC 480.96 [M + H$^+$] | Procedures 1 and 4 |
| 70 | 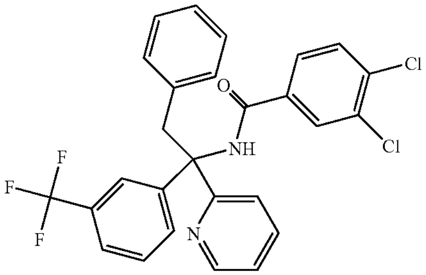 | 3,4-dichloro-N-(2-phenyl-1-(pyridin-2-yl)-1-(3-(trifluoromethyl)phenyl)ethyl) benzamide | 4.21 LC 514.92 [M + H$^+$] | Procedures 1 and 4 |
| 71 | 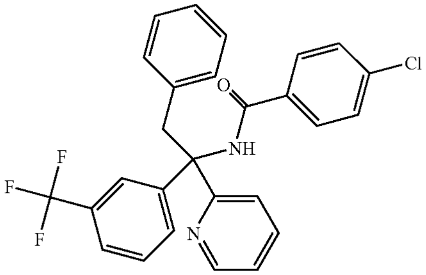 | 4-chloro-N-(2-phenyl-1-(pyridin-2-yl)-1-(3-(trifluoromethyl) phenyl)ethyl)benzamide | 4.03 LC 480.95 [M + H$^+$] | Procedures 1 and 4 |
| 72 | 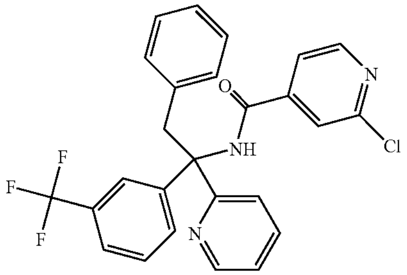 | 2-chloro-N-(2-phenyl-1-(pyridin-2-yl)-1-(3-(trifluoromethyl) phenyl)ethyl)isonicotinamide | 3.77 LC 481.94 [M + H$^+$] | Procedures 1 and 4 |

TABLE 1-continued

| Ex. No. | Structure | Name | Retention Time Min./ Molecular Mass | Prepared in the manner described in: |
|---|---|---|---|---|
| 73 | 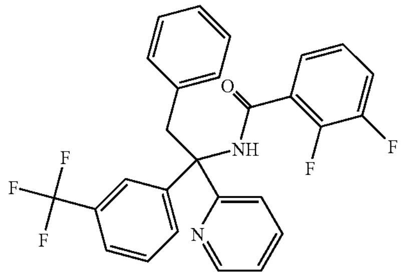 | 2,3-difluoro-N-(2-phenyl-1-(pyridin-2-yl)-1-(3-(trifluoromethyl)phenyl)ethyl) benzamide | 3.90 LC 482.98 [M + H+] | Procedures 1 and 4 |
| 74 | 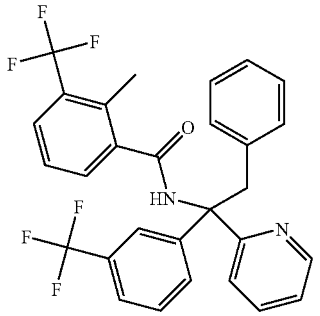 | 2-methyl-N-(2-phenyl-1-(pyridin-2-yl)-1-(3-(trifluoromethyl) phenyl)ethyl)-3-(trifluoromethyl) | 4.10 LC 429.03 [M + H+] | Procedures 1 and 4 |
| 75 | 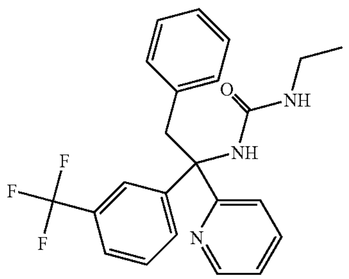 | 1-ethyl-3-(2-phenyl-1-(pyridin-2-yl)-1-(3-(trifluoromethyl)phenyl) ethyl)urea | 1.67 LC 414.02 [M + H+] | Procedures 1 and 4 |
| 76 | 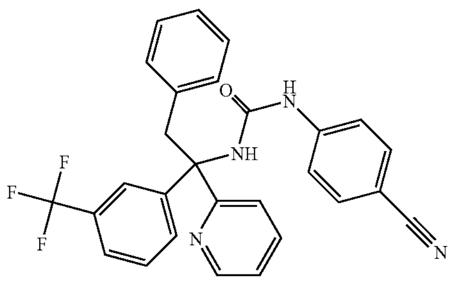 | 1-(4-cyanophenyl)-3-(2-phenyl-1-(pyridin-2-yl)-1-(3-(trifluoromethyl)phenyl)ethyl) urea | 1.92 LC 487.03 [M + H+] | Procedures 1 and 4 |
| 77 | 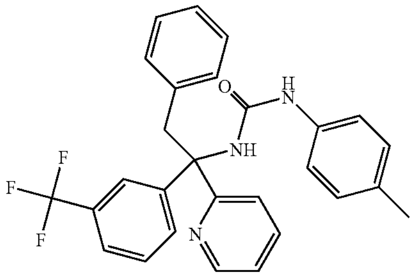 | 1-(2-phenyl-1-(pyridin-2-yl)-1-(3-(trifluoromethyl)phenyl)ethyl)-3-p-tolylurea | 1.93 LC 476.06 [M + H+] | Procedures 1 and 4 |

TABLE 1-continued

| Ex. No. | Structure | Name | Retention Time Min./ Molecular Mass | Prepared in the manner described in: |
|---|---|---|---|---|
| 78 | 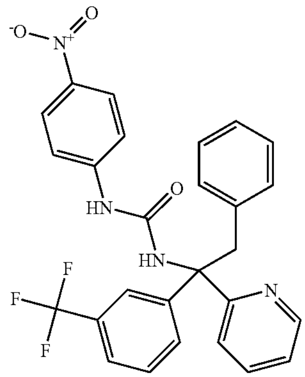 | 1-(4-nitrophenyl)-3-(2-phenyl-1-(pyridin-2-yl)-1-(3-(trifluoromethyl)phenyl)ethyl) urea | 2.00 LC 507.02 $[M + H^+]$ | Procedures 1 and 4 |
| 79 | 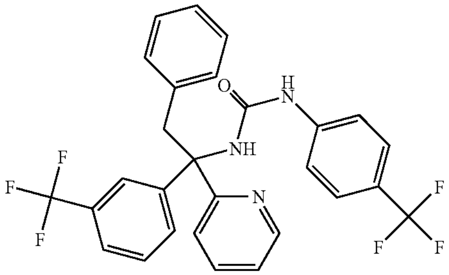 | 1-(2-phenyl-1-(pyridin-2-yl)-1-(3-(trifluoromethyl)phenyl)ethyl)-3-(4-(trifluoromethyl)phenyl)urea | 2.06 LC 503.03 $[M + H^+]$ | Procedures 1 and 4 |

TABLE 2

| Ex. No. | Structure | Name | Retention Time Min./ Molecular Mass | Prepared in the manner described in: |
|---|---|---|---|---|
| 80 | 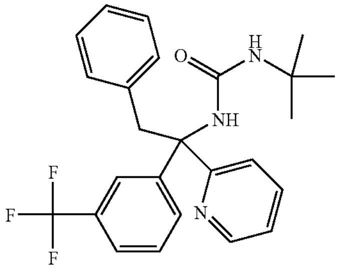 | 1-tert-butyl-3-(2-phenyl-1-(pyridin-2-yl)-1-(3-(trifluoromethyl)phenyl)ethyl)urea | 2.34 LC 525.2 $[M + H^+]$ | Procedures 1 and 2 |
| 81 | 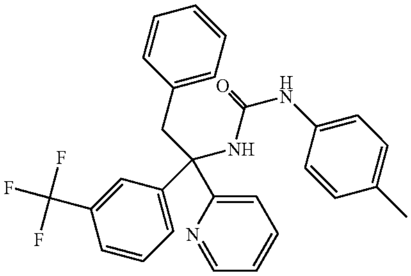 | 1-(2-phenyl-1-(pyridin-2-yl)-1-(3-(trifluoromethyl)phenyl)ethyl)-3-p-tolylurea | 1.93 LC 476.06 $[M + H^+]$ | Procedures 1 and 2 |

TABLE 2-continued

| Ex. No. | Structure | Name | Retention Time Min./ Molecular Mass | Prepared in the manner described in: |
|---|---|---|---|---|
| 82 | 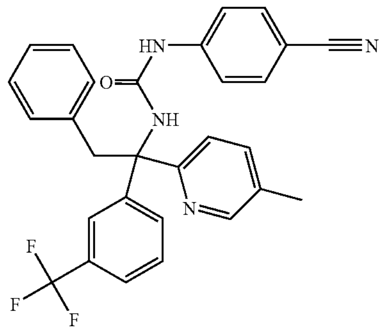 | 1-(4-cyanophenyl)-3-(1-(5-methylpyridin-2-yl)-2-phenyl-1-(3-(trifluoromethyl)phenyl)ethyl) urea | 2.56 LC 501.26 [M + H+] | Procedures 1 and 2 |
| 83 | 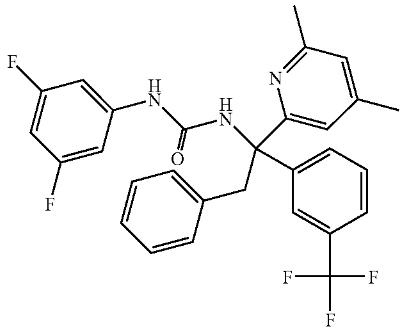 | 1-(3,5-difluorophenyl)-3-(1-(4,6-dimethylpyridin-2-yl)-2-phenyl-1-(3-(trifluoromethyl)phenyl)ethyl) urea | 3.28 LC 526.13 [M + H+] | Procedures 1 and 2 |
| 84 | 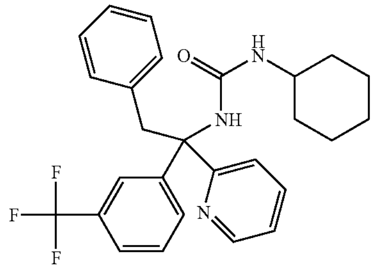 | 1-cyclohexyl-3-(2-phenyl-1-(pyridin-2-yl)-1-(3-(trifluoromethyl)phenyl)ethyl)urea | 1.89 LC 468.1 [M + H+] | Procedures 1 and 2 |
| 85 | 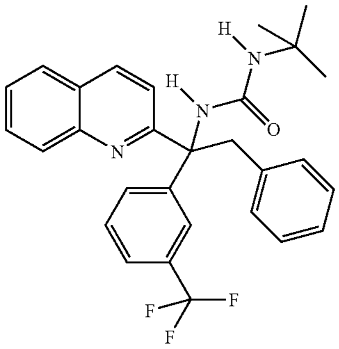 | 1-tert-butyl-3-(2-phenyl-1-(quinolin-2-yl)-1-(3-(trifluoromethyl)phenyl)ethyl)urea | 2.10 LC 492.19 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 86 | 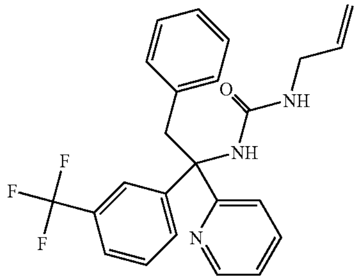 | 1-allyl-3-(2-phenyl-1-(pyridin-2-yl)-1-(3-(trifluoromethyl)phenyl) ethyl)urea | 1.73 LC 426.0 [M + H$^+$] | Procedures 1 and 2 |
| 87 | 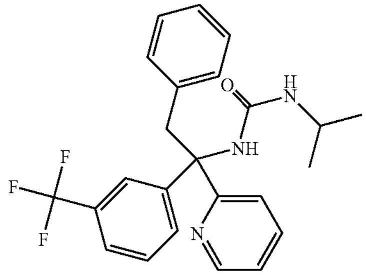 | 1-isopropyl-3-(2-phenyl-1-(pyridin-2-yl)-1-(3-(trifluoromethyl)phenyl)ethyl)urea | 1.73 LC 428.1 [M + H$^+$] | Procedures 1 and 2 |
| 88 | 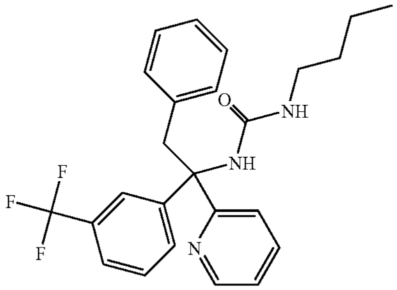 | 1-butyl-3-(2-phenyl- 1-(pyridin-2-yl)-1-(3-(trifluoromethyl)phenyl) ethyl)urea | 1.83 LC 442.1 [M + H$^+$] | Procedures 1 and 2 |
| 89 | 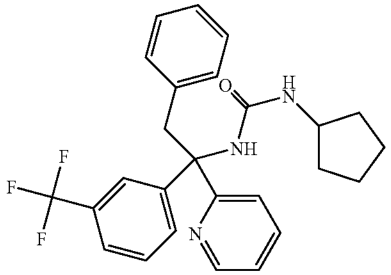 | 1-cyclopentyl-3-(2-phenyl-1-(pyridin-2-yl)-1-(3-(trifluoromethyl)phenyl)ethyl)urea | 1.84 LC 454.0 [M + H$^+$] | Procedures 1 and 2 |
| 90 | 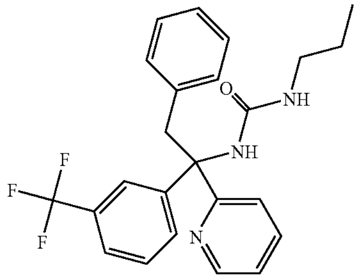 | 1-(2-phenyl-1-(pyridin-2-yl)-1-(3-(trifluoromethyl)phenyl)ethyl)-3-propylurea | 1.75 LC 428.1 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 91 | 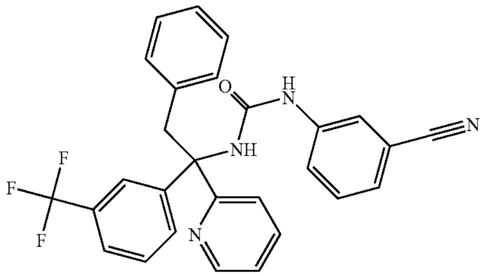 | 1-(3-cyanophenyl)-3-(2-phenyl-1-(pyridin-2-yl)-1-(3-(trifluoromethyl)phenyl)ethyl)urea | 1.93 LC 487.0 [M + H+] | Procedures 1 and 2 |
| 92 | 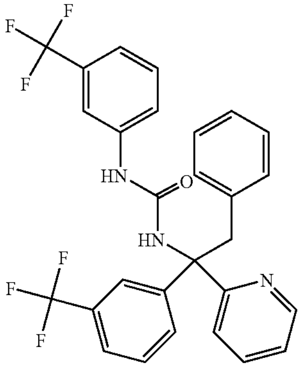 | 1-(2-phenyl-1-(pyridin-2-yl)-1-(3-(trifluoromethyl)phenyl)ethyl)-3-(3-(trifluoromethyl)phenyl)urea | 2.06 LC 530.0 [M + H+] | Procedures 1 and 2 |
| 93 | 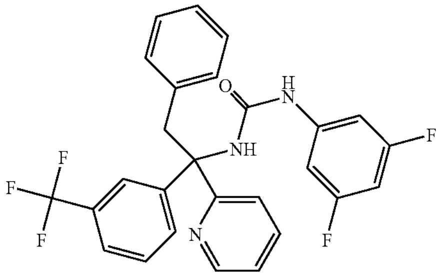 | 1-(3,5-difluorophenyl)-3-(2-phenyl-1-(pyridin-2-yl)-1-(3-(trifluoromethyl)phenyl)ethyl)urea | 2.04 LC 498.0 [M + H+] | Procedures 1 and 2 |
| 94 | 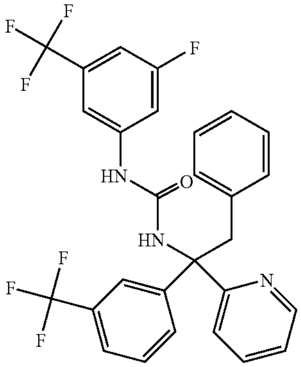 | 1-(3-fluoro-5-(trifluoromethyl)phenyl)-3-(2-phenyl-1-(pyridin-2-yl)-1-(3-(trifluoromethyl)phenyl)ethyl)urea | 2.13 LC 548.0 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 95 | 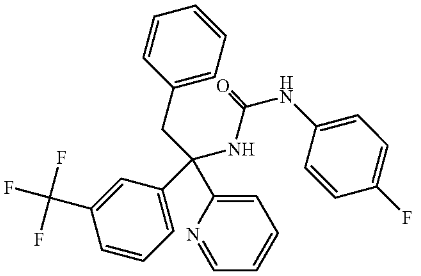 | 1-(4-fluorophenyl)-3-(2-phenyl-1-(pyridin-2-yl)-1-(3-(trifluoromethyl)phenyl)ethyl)urea | 4.01 LC 453.05 [M + H$^+$] | Procedures 1 and 2 |
| 96 | 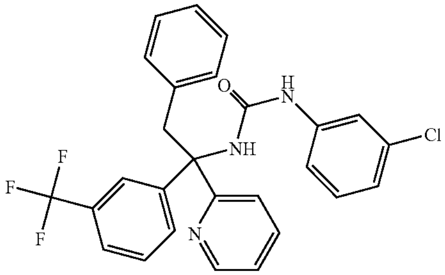 | 1-(3-chlorophenyl)-3-(2-phenyl-1-(pyridin-2-yl)-1-(3-(trifluoromethyl)phenyl)ethyl)urea | 2.02 LC 496.0 [M + H$^+$] | Procedures 1 and 2 |
| 97 | 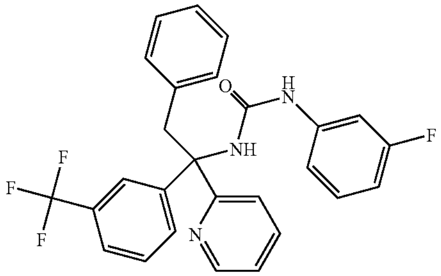 | 1-(3-fluorophenyl)-3-(2-phenyl-1-(pyridin-2-yl)-1-(3-(trifluoromethyl)phenyl)ethyl)urea | 1.95 LC 480.0 [M + H$^+$] | Procedures 1 and 2 |
| 98 | 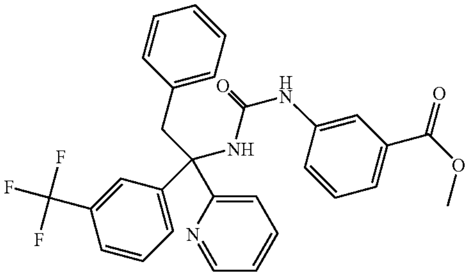 | methyl 3-(3-(2-phenyl-1-(pyridin-2-yl)-1-(3-(trifluoromethyl) phenyl)ethyl)ureido)benzoate | 1.93 LC 520.1 [M + H$^+$] | Procedures 1 and 2 |
| 99 | 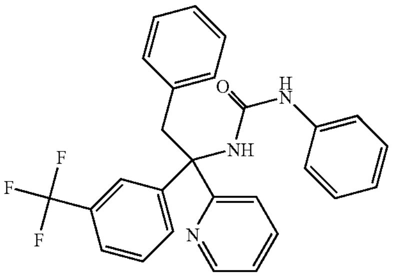 | 1-phenyl-3-(2-phenyl-1-(pyridin-2-yl)-1-(3-(trifluoromethyl) phenyl)ethyl)urea | 1.89 LC 462.0 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 100 | 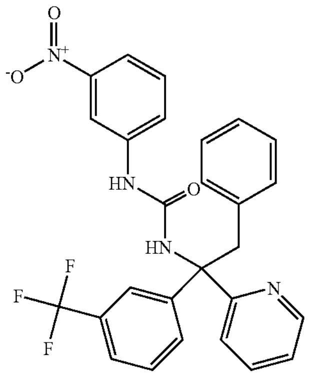 | 1-(3-nitrophenyl)-3-(2-phenyl-1-(pyridin-2-yl)-1-(3-(trifluoromethyl)phenyl)ethyl)urea | 2.00 LC 507.0 [M + H+] | Procedures 1 and 2 |
| 101 | 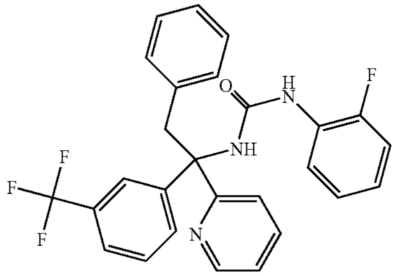 | 1-(2-fluorophenyl)-3-(2-phenyl-1-(pyridin-2-yl)-1-(3-(trifluoromethyl)phenyl)ethyl)urea | 1.89 LC 480.01 [M + H+] | Procedures 1 and 2 |
| 102 | 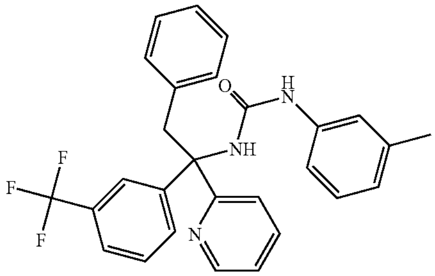 | 1-(2-phenyl-1-(pyridin-2-yl)-1-(3-(trifluoromethyl)phenyl)ethyl)-3-m-tolylurea | 1.95 LC 476.1 [M + H+] | Procedures 1 and 2 |
| 103 | 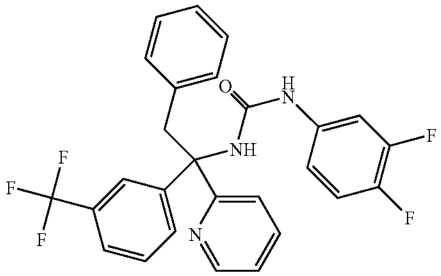 | 1-(3,4-difluorophenyl)-3-(2-phenyl-1-(pyridin-2-yl)-1-(3-(trifluoromethyl)phenyl)ethyl)urea | 2.00 LC 498.0 [M + H+] | Procedures 1 and 2 |
| 104 | 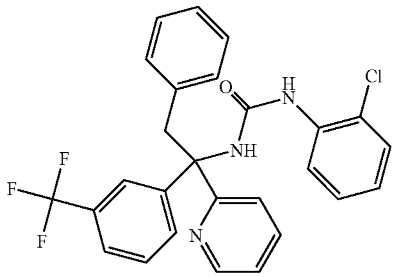 | 1-(2-chlorophenyl)-3-(2-phenyl-1-(pyridin-2-yl)-1-(3-(trifluoromethyl)phenyl)ethyl)urea | 1.94 LC 496.0 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 105 | 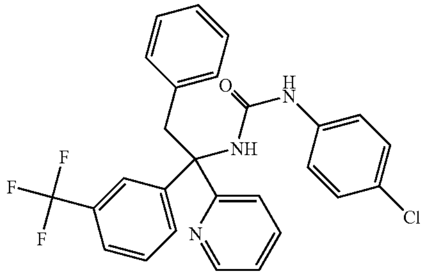 | 1-(4-chlorophenyl)-3-(2-phenyl-1-(pyridin-2-yl)-1-(3-(trifluoromethyl)phenyl)ethyl)urea | 2.01 LC 496.0 [M + H$^+$] | Procedures 1 and 2 |
| 106 | 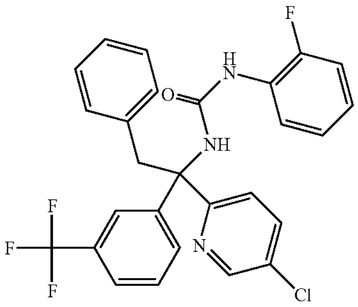 | 1-(1-(5-chloropyridin-2-yl)-2-phenyl-1-(3-(trifluoromethyl) phenyl)ethyl)-3-(2-fluorophenyl) urea | 3.30 LC 514.22 [M + H$^+$] | Procedures 1 and 2 |
| 107 | 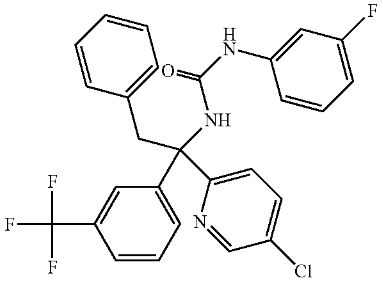 | 1-(1-(5-chloropyridin-2-yl)-2-phenyl-1-(3-(trifluoromethyl) phenyl)ethyl)-3-(3-fluorophenyl) urea | 3.59 LC 514.18 [M + H$^+$] | Procedures 1 and 2 |
| 108 | 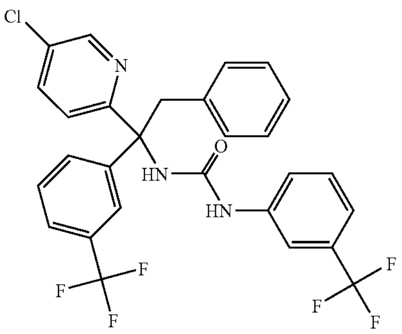 | 1-(1-(5-chloropyridin-2-yl)-2-phenyl-1-(3-(trifluoromethyl) phenyl)ethyl)-3-(3-(trifluoromethyl)phenyl)urea | 3.52 LC 564.29 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 109 | 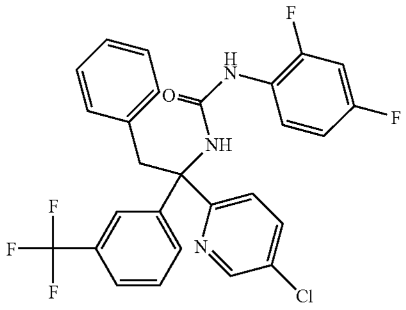 | 1-(1-(5-chloropyridin-2-yl)-2-phenyl-1-(3-(trifluoromethyl) phenyl)ethyl)-3-(2,4-difluorophenyl)urea | 3.35 LC 532.22 [M + H$^+$] | Procedures 1 and 2 |
| 110 | 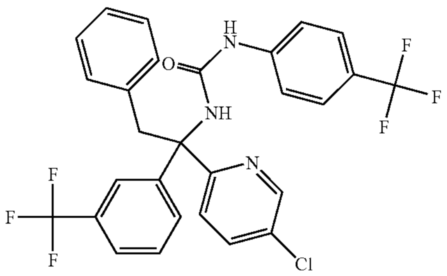 | 1-(1-(5-chloropyridin-2-yl)-2-phenyl-1-(3-(trifluoromethyl) phenyl)ethyl)-3-(4-(trifluoromethyl)phenyl)urea | 3.54 LC 564.28 [M + H$^+$] | Procedures 1 and 2 |
| 111 | 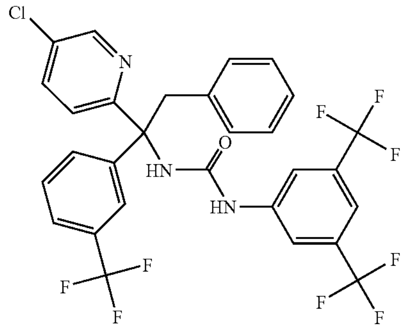 | 1-(3,5-bis(trifluoromethyl) phenyl)-3-(1-(5-chloropyridin-2-yl)-2-phenyl-1-(3-(trifluoromethyl)phenyl)ethyl)urea | 3.75 LC 632.19 [M + H$^+$] | Procedures 1 and 2 |
| 112 | 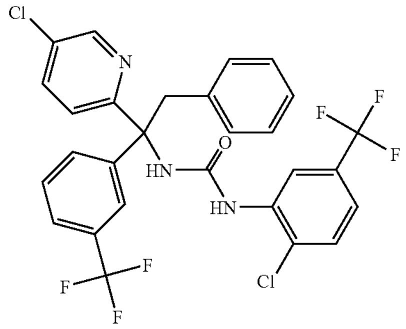 | 1-(2-chloro-5-(trifluoromethyl) phenyl)-3-(1-(5-chloropyridin-2-yl)-2-phenyl-1-(3-(trifluoromethyl)phenyl)ethyl)urea | 3.63 LC 598.15 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 113 | 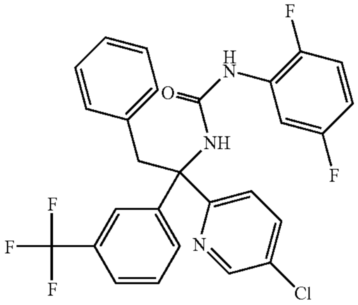 | 1-(1-(5-chloropyridin-2-yl)-2-phenyl-1-(3-(trifluoromethyl) phenyl)ethyl)-3-(2,5-difluorophenyl)urea | 3.40 LC 532.22 [M + H$^+$] | Procedures 1 and 2 |
| 114 | 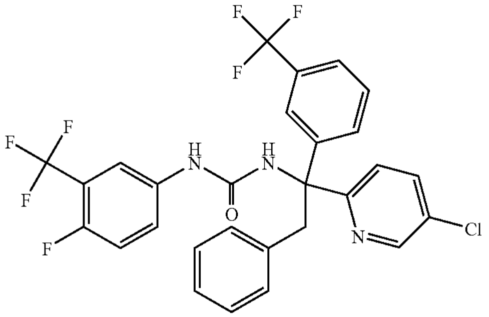 | 1-(1-(5-chloropyridin-2-yl)-2-phenyl-1-(3-(trifluoromethyl) phenyl)ethyl)-3-(4-fluoro-3-(trifluoromethyl)phenyl)urea | 3.54 LC 582.22 [M + H$^+$] | Procedures 1 and 2 |
| 115 | 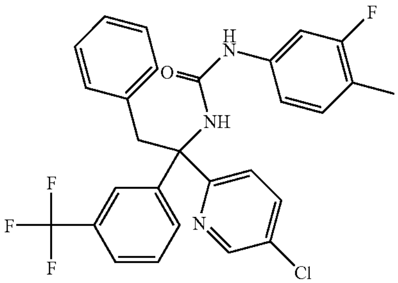 | 1-(1-(5-chloropyridin-2-yl)-2-phenyl-1-(3-(trifluoromethyl) phenyl)ethyl)-3-(3-fluoro-4-methylphenyl)urea | 3.46 LC 528.24 [M + H$^+$] | Procedures 1 and 2 |
| 116 | 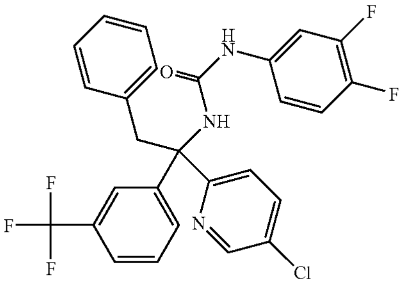 | 1-(1-(5-chloropyridin-2-yl)-2-phenyl-1-(3-(trifluoromethyl) phenyl)ethyl)-3-(3,4-difluorophenyl)urea | 3.40 LC 532.22 [M + H$^+$] | Procedures 1 and 2 |
| 117 | 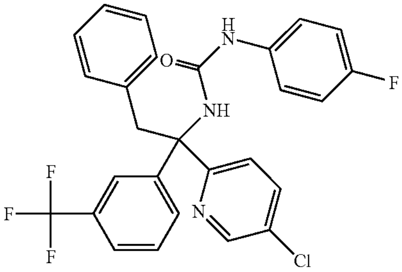 | 1-(1-(5-chloropyridin-2-yl)-2-phenyl-1-(3-(trifluoromethyl) phenyl)ethyl)-3-(4-fluorophenyl) urea | 3.31 LC 514.21 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 118 | 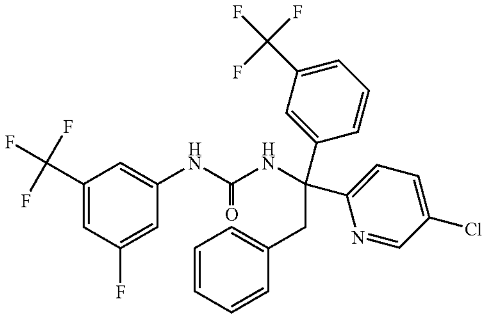 | 1-(1-(5-chloropyridin-2-yl)-2-phenyl-1-(3-(trifluoromethyl) phenyl)ethyl)-3-(3-fluoro-5-(trifluoromethyl)phenyl)urea | 3.64 LC 582.22 [M + H$^+$] | Procedures 1 and 2 |
| 119 | 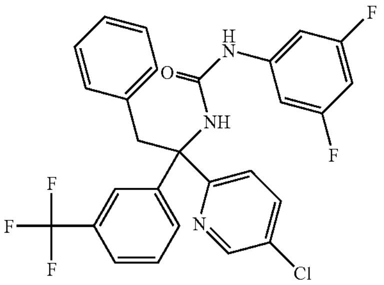 | 1-(1-(5-chloropyridin-2-yl)-2-phenyl-1-(3-(trifluoromethyl) phenyl)ethyl)-3-(3,5-difluorophenyl)urea | 3.42 LC 532.22 [M + H$^+$] | Procedures 1 and 2 |
| 120 | 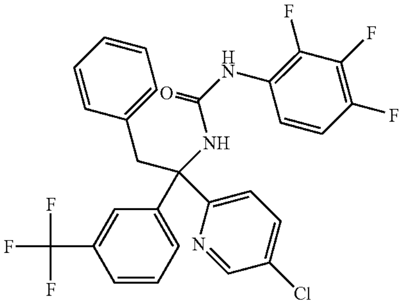 | 1-(1-(5-chloropyridin-2-yl)-2-phenyl-1-(3-(trifluoromethyl) phenyl)ethyl)-3-(2,3,4-trifluorophenyl)urea | 3.43 LC 550.24 [M + H$^+$] | Procedures 1 and 2 |
| 121 | 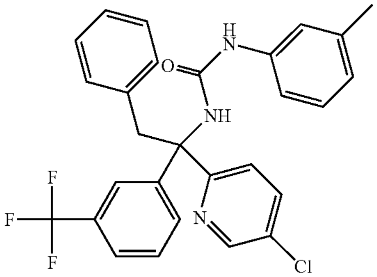 | 1-(1-(5-chloropyridin-2-yl)-2-phenyl-1-(3-(trifluoromethyl) phenyl)ethyl)-3-m-tolylurea | 3.40 LC 510.25 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 122 | 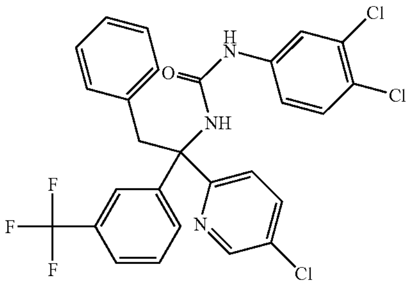 | 1-(1-(5-chloropyridin-2-yl)-2-phenyl-1-(3-(trifluoromethyl) phenyl)ethyl)-3-(3,4-dichlorophenyl)urea | 3.60 LC 564.21 [M + H$^+$] | Procedures 1 and 2 |
| 123 | 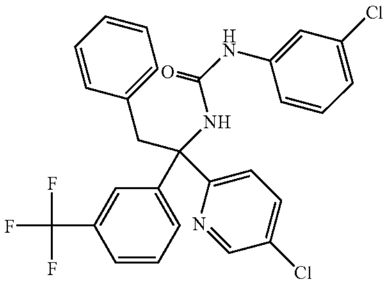 | 1-(3-chlorophenyl)-3-(1-(5-chloropyridin-2-yl)-2-phenyl-1-(3-(trifluoromethyl)phenyl)ethyl) urea | 3.43 LC 530.2 [M + H$^+$] | Procedures 1 and 2 |
| 124 | 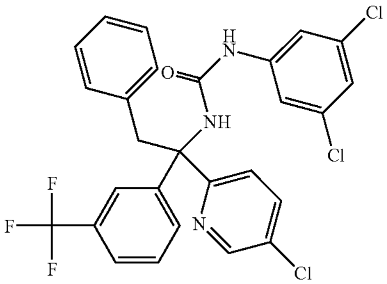 | 1-(1-(5-chloropyridin-2-yl)-2-phenyl-1-(3-(trifluoromethyl) phenyl)ethyl)-3-(3,5-dichlorophenyl)urea | 3.70 LC 564.21 [M + H$^+$] | Procedures 1 and 2 |
| 125 | 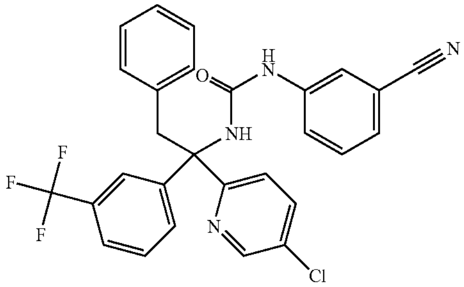 | 1-(1-(5-chloropyridin-2-yl)-2-phenyl-1-(3-(trifluoromethyl) phenyl)ethyl)-3-(3-cyanophenyl) urea | 3.27 LC 521.23 [M + H$^+$] | Procedures 1 and 2 |
| 126 | 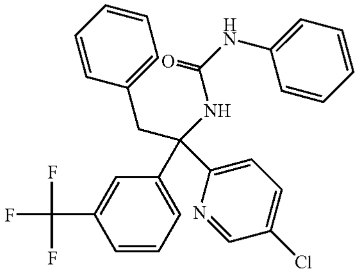 | 1-(1-(5-chloropyridin-2-yl)-2-phenyl-1-(3-(trifluoromethyl) phenyl)ethyl)-3-phenylurea | 3.28 LC 496.26 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 127 | 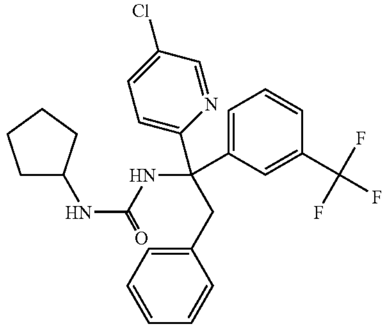 | 1-(1-(5-chloropyridin-2-yl)-2-phenyl-1-(3-(trifluoromethyl) phenyl)ethyl)-3-cyclopentylurea | 3.32 LC 488.3 [M + H+] | Procedures 1 and 2 |
| 128 | 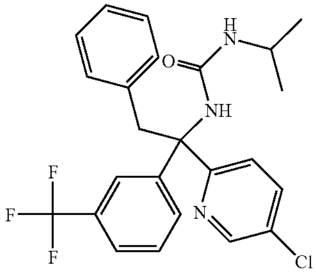 | 1-(1-(5-chloropyridin-2-yl)-2-phenyl-1-(3-(trifluoromethyl) phenyl)ethyl)-3-isopropylurea | 3.17 LC 462.31 [M + H+] | Procedures 1 and 2 |
| 129 | 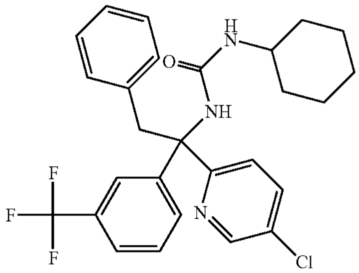 | 1-(1-(5-chloropyridin-2-yl)-2-phenyl-1-(3-(trifluoromethyl) phenyl)ethyl)-3-cyclohexylurea | 3.42 LC 502.3 [M + H+] | Procedures 1 and 2 |
| 130 | 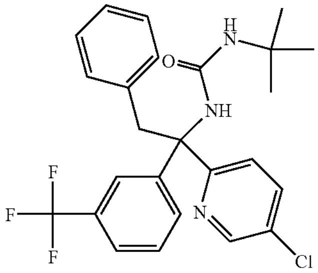 | 1-tert-butyl-3-(1-(5-chloropyridin-2-yl)-2-phenyl-1-(3-(trifluoromethyl)phenyl)ethyl)urea | 3.30 LC 476.32 [M + H+] | Procedures 1 and 2 |
| 131 | 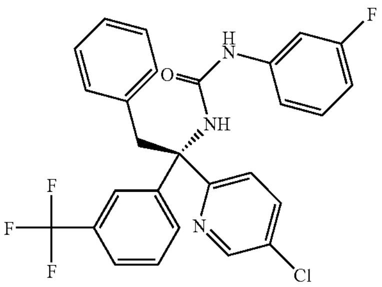 | (S)-1-(1-(5-chloropyridin-2-yl)-2-phenyl-1-(3-(trifluoromethyl) phenyl)ethyl)-3-(3-fluorophenyl) urea | 3.96 LC 514.14 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 132 | 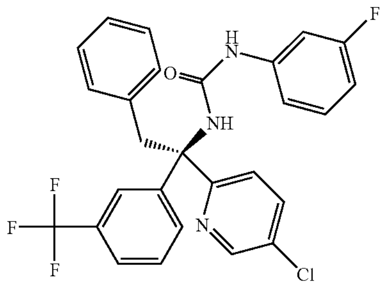 | (R)-1-(1-(5-chloropyridin-2-yl)-2-phenyl-1-(3-(trifluoromethyl) phenyl)ethyl)-3-(3-nuorophenyl) urea | 3.96 LC 514.14 $[M + H^+]$ | Procedures 1 and 2 |
| 133 | 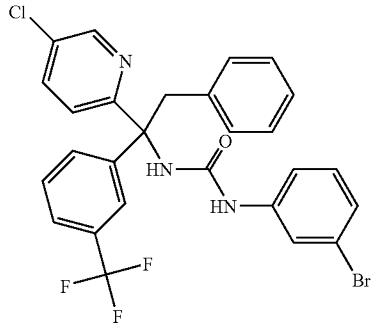 | 1-(3-bromophenyl)-3-(1-(5-chloropyridin-2-yl)-2-phenyl-1-(3-(trifluoromethyl)phenyl)ethyl) urea | 3.74 LC 574.18 $[M + H^+]$ | Procedures 1 and 2 |
| 134 | 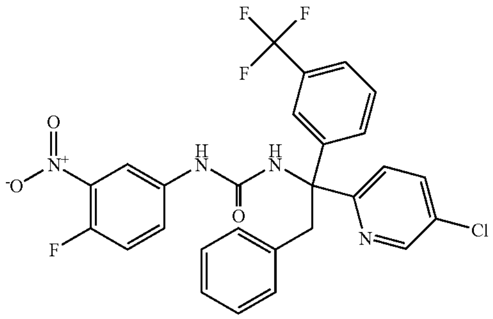 | 1-(1-(5-chloropyridin-2-yl)-2-phenyl-1-(3-(trifluoromethyl) phenyl)ethyl)-3-(4-fluoro-3-nitrophenyl)urea | 3.60 LC 559.24 $[M + H^+]$ | Procedures 1 and 2 |
| 135 | 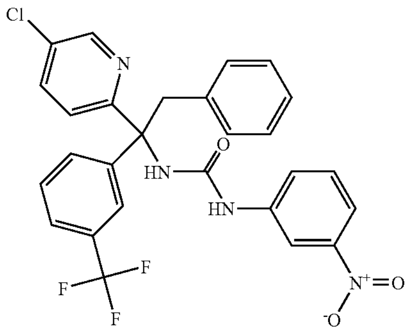 | 1-(1-(5-chloropyridin-2-yl)-2-phenyl-1-(3-(trifluoromethyl) phenyl)ethyl)-3-(3-nitrophenyl) urea | 3.59 LC 541.22 $[M + H^+]$ | Procedures 1 and 2 |

TABLE 2-continued

| Ex. No. | Structure | Name | Retention Time Min./ Molecular Mass | Prepared in the manner described in: |
|---|---|---|---|---|
| 136 | 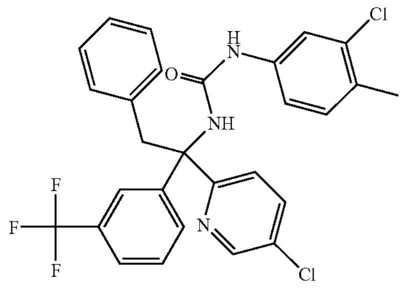 | 1-(3-chloro-4-methylphenyl)-3-(1-(5-chloropyridin-2-yl)-2-phenyl-1-(3-(trifluoromethyl)phenyl) ethyl)urea | 3.79 LC 544.21 [M + H+] | Procedures 1 and 2 |
| 137 | 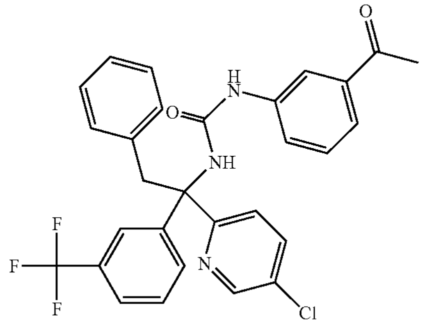 | 1-(3-acetylphenyl)-3-(1-(5-chloropyridin-2-yl)-2-phenyl-1-(3-(trifluoromethyl)phenyl)ethyl) urea | 3.48 LC 538.24 [M + H+] | Procedures 1 and 2 |
| 139 | 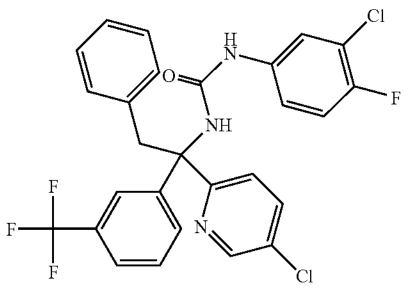 | 1-(3-chloro-4-fluorophenyl)-3-(1-(5-chloropyridin-2-yl)-2-phenyl-1-(3-(trifluoromethyl)phenyl) ethyl)urea | 3.73 LC 548.2 [M + H+] | Procedures 1 and 2 |
| 138 | 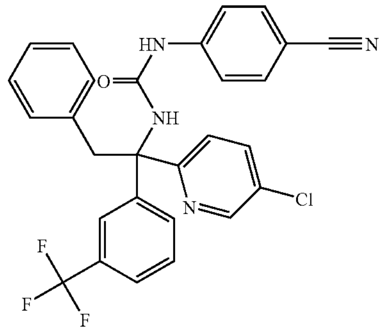 | 1-(1-(5-chloropyridin-2-yl)-2-phenyl-1-(3-(trifluoromethyl) phenyl)ethyl)-3-(4-cyanophenyl) urea | 3.51 LC 521.2 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 139 | 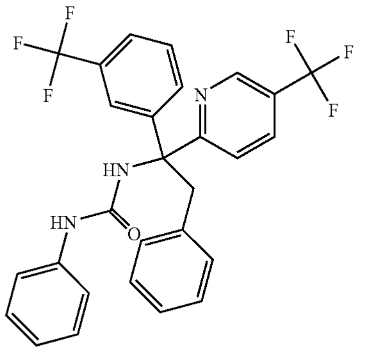 | 1-phenyl-3-(2-phenyl-1-(3-(trifluoromethyl)phenyl)-1-(5-(trifluoromethyl)pyridin-2-yl) ethyl)urea | 3.29 LC 530.23 [M + H+] | Procedures 1 and 2 |
| 140 | 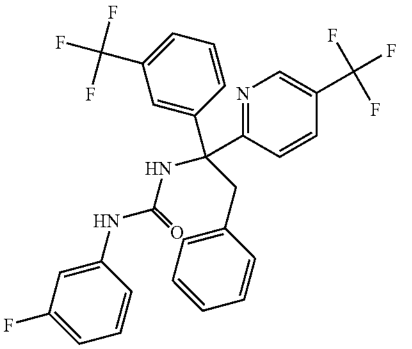 | 1-(3-fluorophenyl)-3-(2-phenyl-1-(3-(trifluoromethyl)phenyl)-1-(5-(trifluoromethyl)pyridin-2-yl) ethyl)urea | 3.19 LC 548.26 [M + H+] | Procedures 1 and 2 |
| 141 | 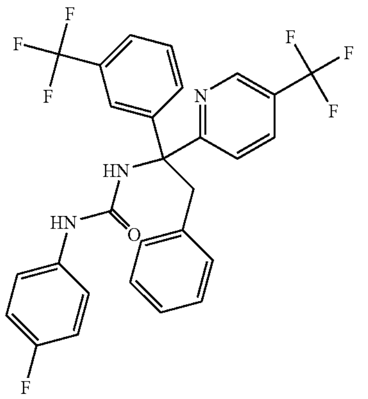 | 1-(4-fluorophenyl)-3-(2-phenyl-1-(3-(trifluoromethyl)phenyl)-1-(5-(trifluoromethyl)pyridin-2-yl) ethyl)urea | 3.16 LC 548.26 [M + H+] | Procedures 1 and 2 |
| 142 | 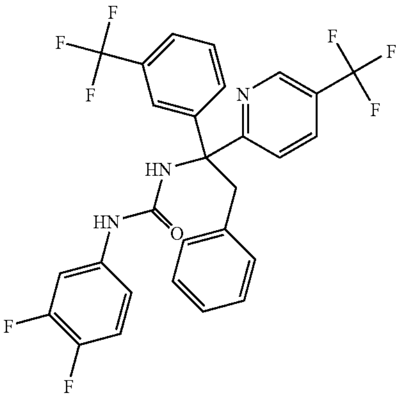 | 1-(3,4-difluorophenyl)-3-(2-phenyl-1-(3-(trifluoromethyl) phenyl)-1-(5-(trifluoromethyl) pyridin-2-yl)ethyl)urea | 3.29 LC 566.26 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 143 | 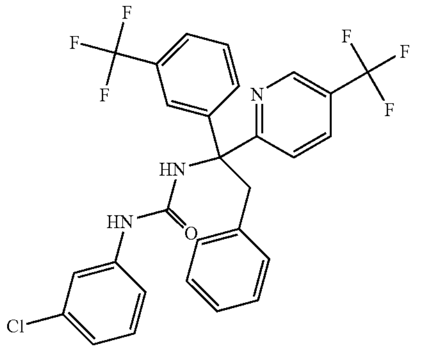 | 1-(3-chlorophenyl)-3-(2-phenyl-1-(3-(trifluoromethyl)phenyl)-1-(5-(trifluoromethyl)pyridin-2-yl)ethyl)urea | 3.36 LC 564.25 [M + H+] | Procedures 1 and 2 |
| 144 | 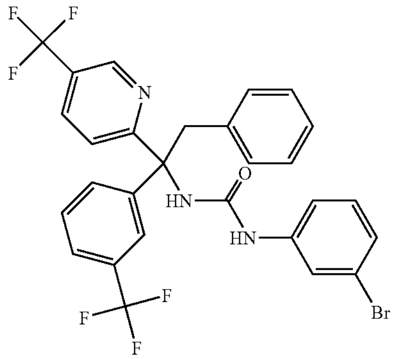 | 1-(3-bromophenyl)-3-(2-phenyl-1-(3-(trifluoromethyl)phenyl)-1-(5-(trifluoromethyl)pyridin-2-yl)ethyl)urea | 3.40 LC 608.12 [M + H+] | Procedures 1 and 2 |
| 145 | 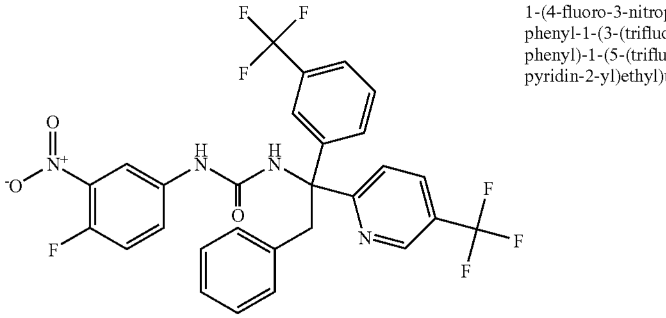 | 1-(4-fluoro-3-nitrophenyl)-3-(2-phenyl-1-(3-(trifluoromethyl)phenyl)-1-(5-(trifluoromethyl)pyridin-2-yl)ethyl)urea | 3.23 LC 593.22 [M + H+] | Procedures 1 and 2 |
| 146 | 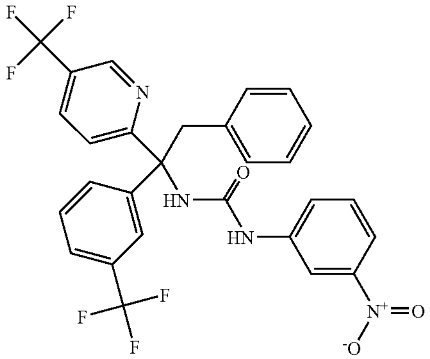 | 1-(3-nitrophenyl)-3-(2-phenyl-1-(3-(trifluoromethyl)phenyl)-1-(5-(trifluoromethyl)pyridin-2-yl)ethyl)urea | 3.20 LC 575.25 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 147 | 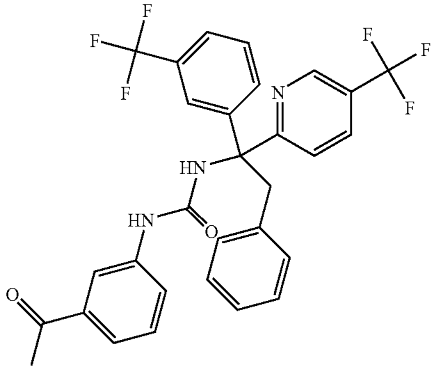 | 1-(3-acetylphenyl)-3-(2-phenyl-1-(3-(trifluoromethyl)phenyl)-1-(5-(trifluoromethyl)pyridin-2-yl) ethyl)urea | 3.05 LC 572.29 [M + H⁺] | Procedures 1 and 2 |
| 148 | 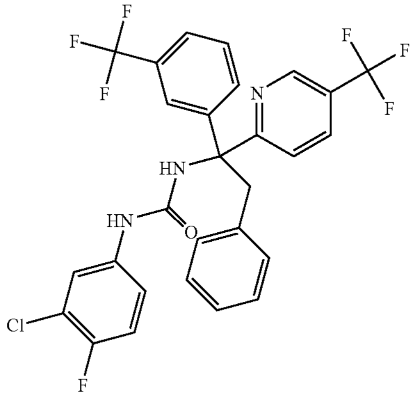 | 1-(3-chloro-4-fluorophenyl)-3-(2-phenyl-1-(3-(trifluoromethyl) phenyl)-1-(5-(trifluoromethyl) pyridin-2-yl)ethyl)urea | 3.40 LC 582.21 [M + H⁺] | Procedures 1 and 2 |
| 149 | 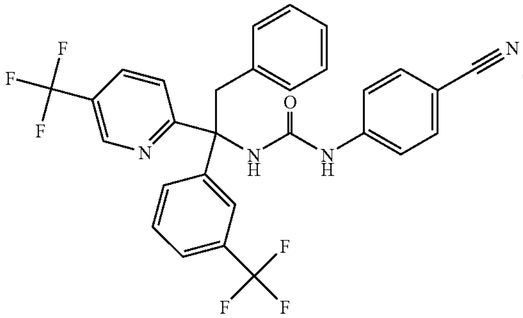 | 1-(4-cyanophenyl)-3-(2-phenyl-1-(3-(trifluoromethyl)phenyl)-1-(5-(trifluoromethyl)pyridin-2-yl) ethyl)urea | 3.08 LC 555.27 [M + H⁺] | Procedures 1 and 2 |
| 150 | 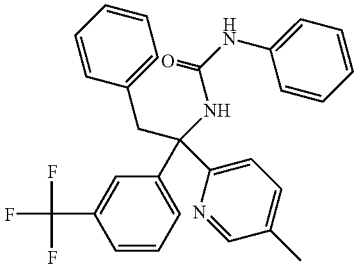 | 1-(1-(5-methylpyridin-2-yl)-2-phenyl-1-(3-(trifluoromethyl) phenyl)ethyl)-3-phenylurea | 2.36 LC 476.29 [M + H⁺] | Procedures 1 and 2 |

TABLE 2-continued

| Ex. No. | Structure | Name | Retention Time Min./ Molecular Mass | Prepared in the manner described in: |
|---|---|---|---|---|
| 151 | 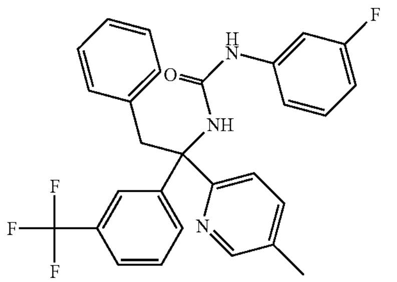 | 1-(3-fluorophenyl)-3-(1-(5-methylpyridin-2-yl)-2-phenyl-1-(3-(trifluoromethyl)phenyl)ethyl) urea | 2.57 LC 494.26 [M + H+] | Procedures 1 and 2 |
| 152 | 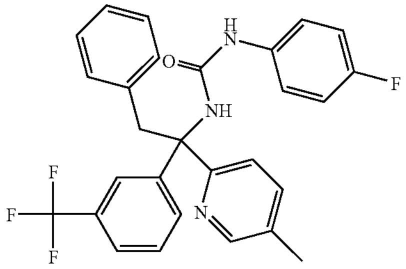 | 1-(4-fluorophenyl)-3-(1-(5-methylpyridin-2-yl)-2-phenyl-1-(3-(trifluoromethyl)phenyl)ethyl) urea | 2.48 LC 494.26 [M + H+] | Procedures 1 and 2 |
| 153 | 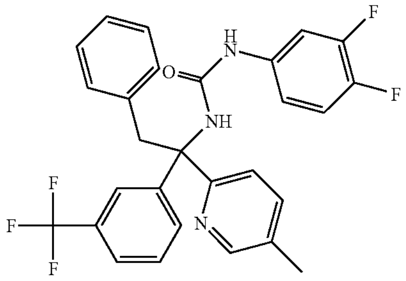 | 1-(3,4-difluorophenyl)-3-(1-(5-methylpyridin-2-yl)-2-phenyl-1-(3-(trifluoromethyl)phenyl)ethyl) urea | 2.72 LC 512.22 [M + H+] | Procedures 1 and 2 |
| 154 | 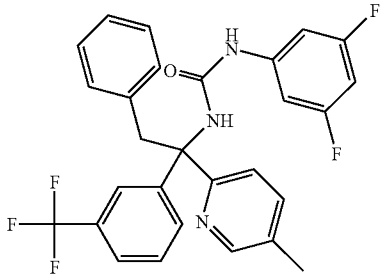 | 1-(3,5-difluorophenyl)-3-(1-(5-methylpyridin-2-yl)-2-phenyl-1-(3-(trifluoromethyl)phenyl)ethyl) urea | 2.86 LC 512.23 [M + H+] | Procedures 1 and 2 |
| 155 | 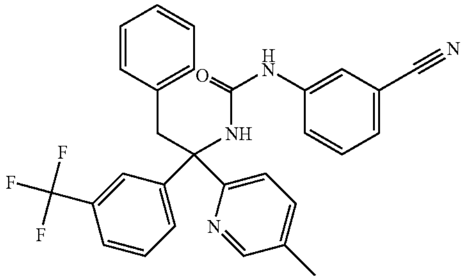 | 1-(3-cyanophenyl)-3-(1-(5-methylpyridin-2-yl)-2-phenyl-1-(3-(trifluoromethyl)phenyl)ethyl) urea | 2.51 LC 501.26 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 156 | 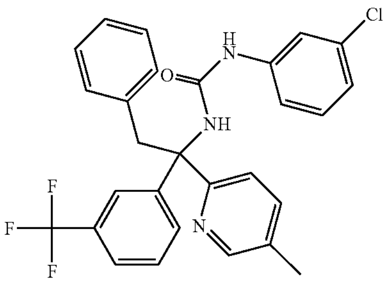 | 1-(3-chlorophenyl)-3-(1-(5-methylpyridin-2-yl)-2-phenyl-1-(3-(trifluoromethyl)phenyl)ethyl) urea | 2.80 LC 510.21 $[M + H^+]$ | Procedures 1 and 2 |
| 157 | 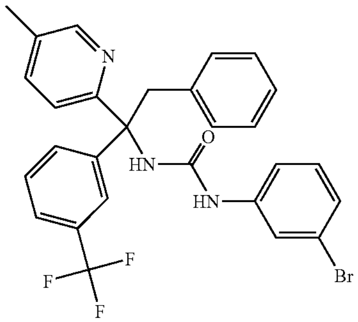 | 1-(3-bromophenyl)-3-(1-(5-methylpyridin-2-yl)-2-phenyl-1-(3-(trifluoromethyl)phenyl)ethyl) urea | 2.86 LC 554.21 $[M + H^+]$ | Procedures 1 and 2 |
| 158 | 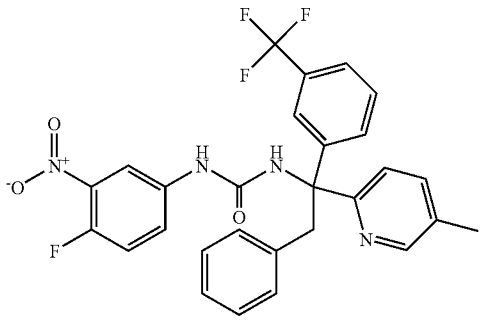 | 1-(4-fluoro-3-nitrophenyl)-3-(1-(5-methylpyridin-2-yl)-2-phenyl-1-(3-(trifluoromethyl)phenyl) ethyl)urea | 2.73 LC 539.25 $[M + H^+]$ | Procedures 1 and 2 |
| 159 | 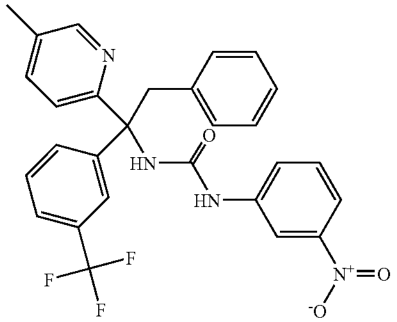 | 1-(1-(5-methylpyridin-2-yl)-2-phenyl-1-(3-(trifluoromethyl) phenyl)ethyl)-3-(3-nitrophenyl) urea | 2.69 LC 521.24 $[M + H^+]$ | Procedures 1 and 2 |

TABLE 2-continued

| Ex. No. | Structure | Name | Retention Time Min./ Molecular Mass | Prepared in the manner described in: |
|---|---|---|---|---|
| 160 | 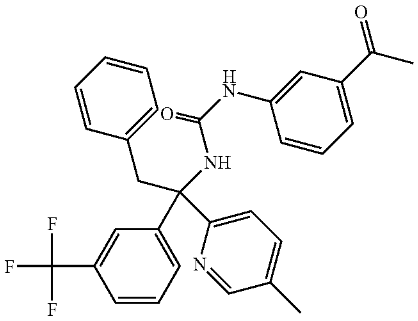 | 1-(3-acetylphenyl)-3-(1-(5-methylpyridin-2-yl)-2-phenyl-1-(3-(trifluoromethyl)phenyl)ethyl) urea | 2.40 LC 518.25 [M + H+] | Procedures 1 and 2 |
| 161 | 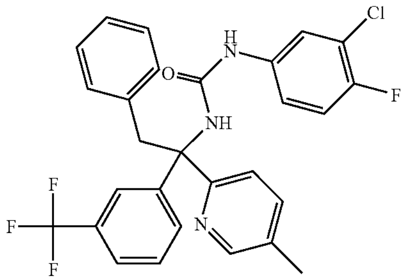 | 1-(3-chloro-4-fluorophenyl)-3-(1-(5-methylpyridin-2-yl)-2-phenyl-1-(3-(trifluoromethyl)phenyl) ethyl)urea | 2.91 LC 528.21 [M + H+] | Procedures 1 and 2 |
| 162 | 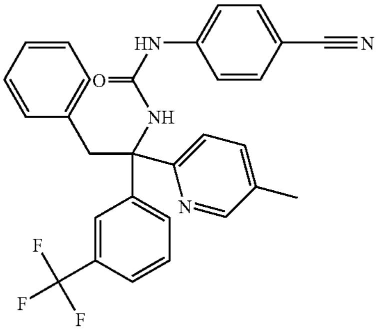 | 1-(4-cyanophenyl)-3-(1-(5-methylpyridin-2-yl)-2-phenyl-1-(3-(trifluoromethyl)phenyl)ethyl) urea | 2.56 LC 501.26 [M + H+] | Procedures 1 and 2 |
| 163 | 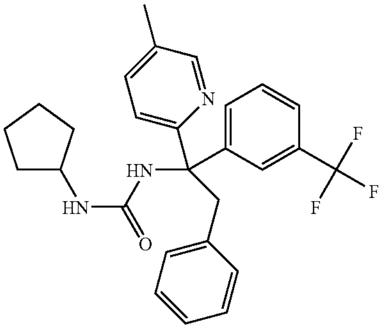 | 1-cyclopentyl-3-(1-(5-methylpyridin-2-yl)-2-phenyl-1-(3-(trifluoromethyl)phenyl)ethyl) urea | 3.18 LC 468.5 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 164 | 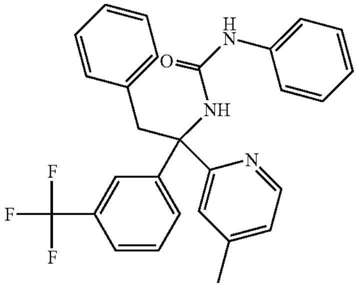 | 1-(1-(4-methylpyridin-2-yl)-2-phenyl-1-(3-(trifluoromethyl) phenyl)ethyl)-3-phenylurea | 2.15 LC 476.3 [M + H$^+$] | Procedures 1 and 2 |
| 165 | 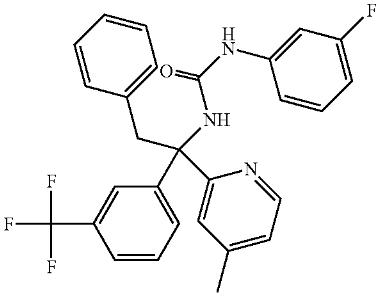 | 1-(3-fluorophenyl)-3-(1-(4-methylpyridin-2-yl)-2-phenyl-1-(3-(trifluoromethyl)phenyl)ethyl) urea | 2.36 LC 494.27 [M + H$^+$] | Procedures 1 and 2 |
| 166 | 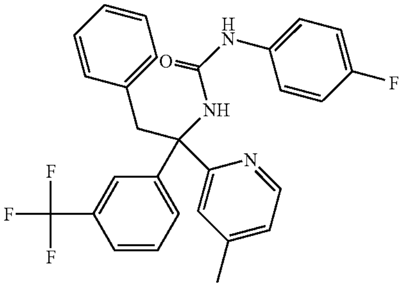 | 1-(4-fluorophenyl)-3-(1-(4-methylpyridin-2-yl)-2-phenyl-1-(3-(trifluoromethyl)phenyl)ethyl) urea | 2.27 LC 494.26 [M + H$^+$] | Procedures 1 and 2 |
| 167 | 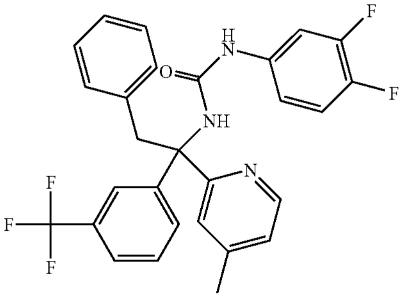 | 1-(3,4-difluorophenyl)-3-(1-(4-methylpyridin-2-yl)-2-phenyl-1-(3-(trifluoromethyl)phenyl)ethyl) urea | 2.50 LC 512.23 [M + H$^+$] | Procedures 1 and 2 |
| 168 | 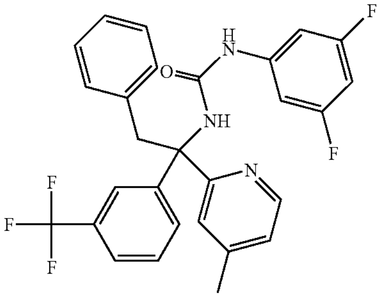 | 1-(3,5-difluorophenyl)-3-(1-(4-methylpyridin-2-yl)-2-phenyl-1-(3-(trifluoromethyl)phenyl)ethyl) urea | 2.65 LC 512.23 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 169 | 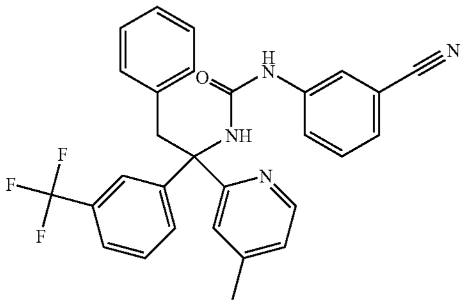 | 1-(3-cyanophenyl)-3-(1-(4-methylpyridin-2-yl)-2-phenyl-1-(3-(trifluoromethyl)phenyl)ethyl) urea | 2.27 LC 501.26 [M + H+] | Procedures 1 and 2 |
| 170 | 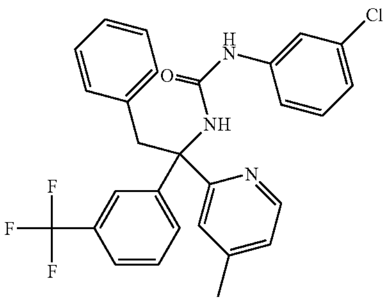 | 1-(3-chlorophenyl)-3-(1-(4-methylpyridin-2-yl)-2-phenyl-1-(3-(trifluoromethyl)phenyl)ethyl) urea | 2.59 LC 510.22 [M + H+] | Procedures 1 and 2 |
| 171 | 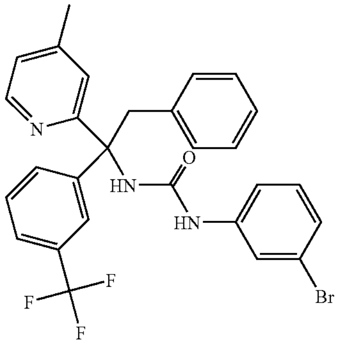 | 1-(3-bromophenyl)-3-(1-(4-methylpyridin-2-yl)-2-phenyl-1-(3-(trifluoromethyl)phenyl) ethyl)urea | 2.67 LC 554.22 [M + H+] | Procedures 1 and 2 |
| 172 | 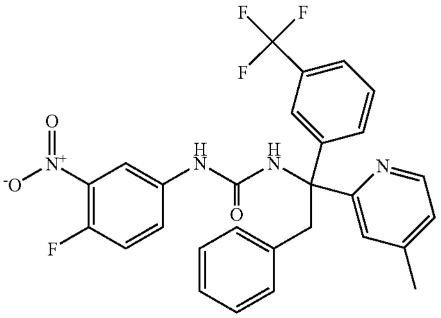 | 1-(4-fluoro-3-nitrophenyl)-3-(1-(4-methylpyridin-2-yl)-2-phenyl-1-(3-(trifluoromethyl)phenyl) ethyl)urea | 2.50 LC 539.25 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 173 | 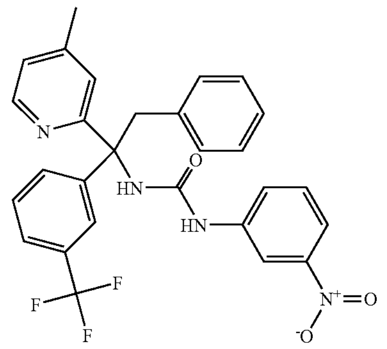 | 1-(1-(4-methylpyridin-2-yl)-2-phenyl-1-(3-(trifluoromethyl) phenyl)ethyl)-3-(3-nitrophenyl) urea | 2.44 LC 521.23 [M + H+] | Procedures 1 and 2 |
| 174 | 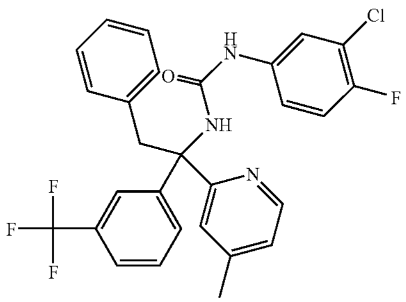 | 1-(3-chloro-4-fluorophenyl)-3-(1-(4-methylpyridin-2-yl)-2-phenyl-1-(3-(trifluoromethyl)phenyl) ethyl)urea | 2.69 LC 528.21 [M + H+] | Procedures 1 and 2 |
| 175 | 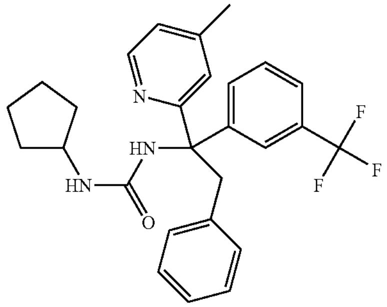 | 1-cyclopentyl-3-(1-(4-methylpyridin-2-yl)-2-phenyl-1-(3-(trifluoromethyl)phenyl) ethyl)urea | 2.09 LC 468.34 [M + H+] | Procedures 1 and 2 |
| 176 | 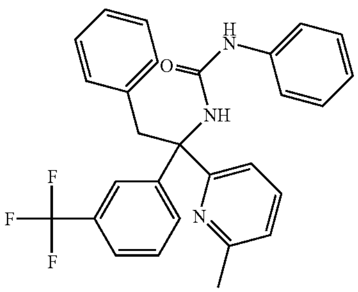 | 1-(1-(6-methylpyridin-2-yl)-2-phenyl-1-(3-(trifluoromethyl) phenyl)ethyl)-3-phenylurea | 2.49 LC 476.3 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 177 | 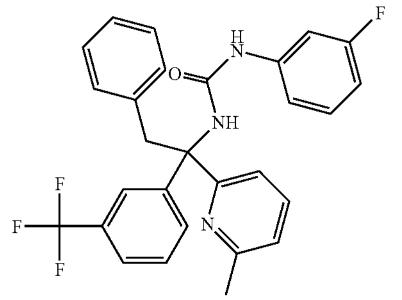 | 1-(3-fluorophenyl)-3-(1-(6-methylpyridin-2-yl)-2-phenyl-1-(3-(trifluoromethyl)phenyl)ethyl) urea | 2.68 LC 494.26 [M + H+] | Procedures 1 and 2 |
| 178 | 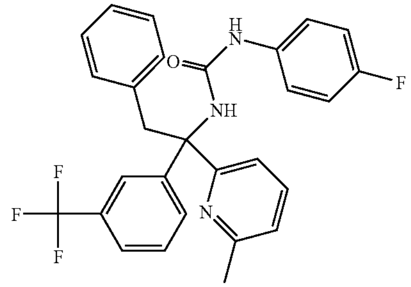 | 1-(4-fluorophenyl)-3-(1-(6-methylpyridin-2-yl)-2-phenyl-1-(3-(trifluoromethyl)phenyl)ethyl) urea | 2.60 LC 494.26 [M + H+] | Procedures 1 and 2 |
| 179 | 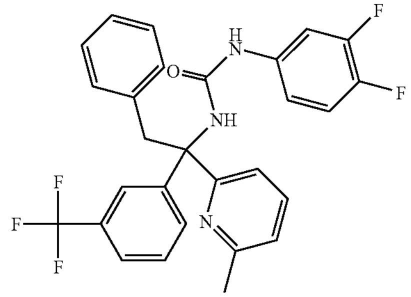 | 1-(3,4-difluorophenyl)-3-(1-(6-methylpyridin-2-yl)-2-phenyl-1-(3-(trifluoromethyl)phenyl)ethyl) urea | 2.82 LC 512.22 [M + H+] | Procedures 1 and 2 |
| 180 | 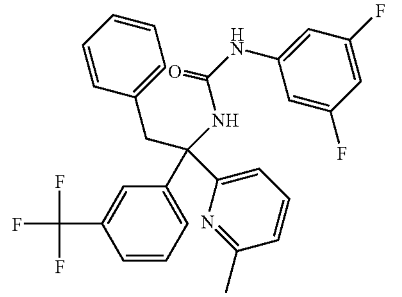 | 1-(3,5-difluorophenyl)-3-(1-(6-methylpyridin-2-yl)-2-phenyl-1-(3-(trifluoromethyl)phenyl)ethyl) urea | 2.94 LC 512.22 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 181 | 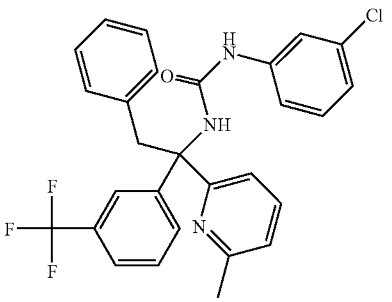 | 1-(3-chlorophenyl)-3-(1-(6-methylpyridin-2-yl)-2-phenyl-1-(3-(trifluoromethyl)phenyl)ethyl) urea | 2.90 LC 510.22 [M + H+] | Procedures 1 and 2 |
| 182 | 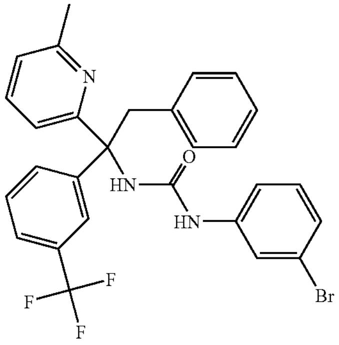 | 1-(3-bromophenyl)-3-(1-(6-methylpyridin-2-yl)-2-phenyl-1-(3-(trifluoromethyl)phenyl)ethyl) urea | 2.96 LC 554.22 [M + H+] | Procedures 1 and 2 |
| 183 | 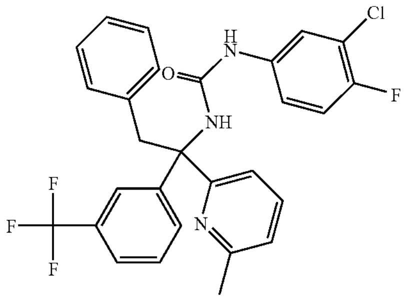 | 1-(3-chloro-4-fluorophenyl)-3-(1-(6-methylpyridin-2-yl)-2-phenyl-1-(3-(trifluoromethyl)phenyl) ethyl)urea | 2.98 LC 528.21 [M + H+] | Procedures 1 and 2 |
| 184 | 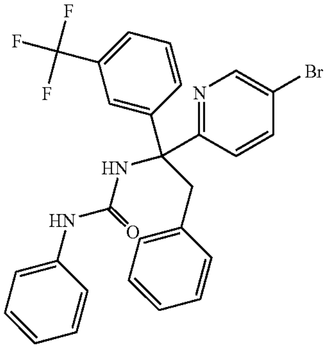 | 1-(1-(5-bromopyridin-2-yl)-2-phenyl-1-(3-(trifluoromethyl) phenyl)ethyl)-3-phenylurea | 3.65 LC 540.09 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 185 | 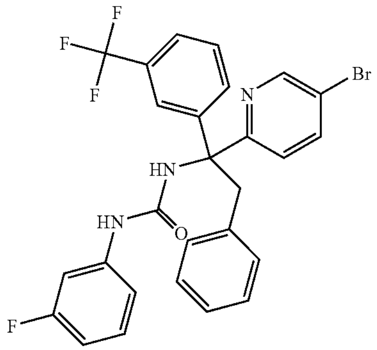 | 1-(1-(5-bromopyridin-2-yl)-2-phenyl-1-(3-(trifluoromethyl) phenyl)ethyl)-3-(3-fluorophenyl) urea | 3.56 LC 540.09 [M + H+] | Procedures 1 and 2 |
| 186 | 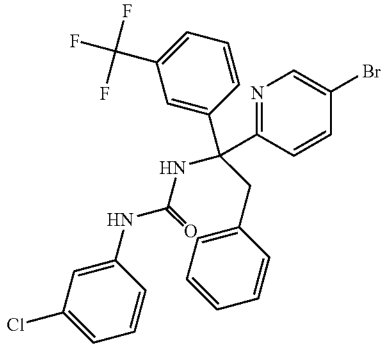 | 1-(1-(5-bromopyridin-2-yl)-2-phenyl-1-(3-(trifluoromethyl) phenyl)ethyl)-3-(3-chiorophenyl) urea | 3.68 LC 574.07 [M + H+] | Procedures 1 and 2 |
| 187 | 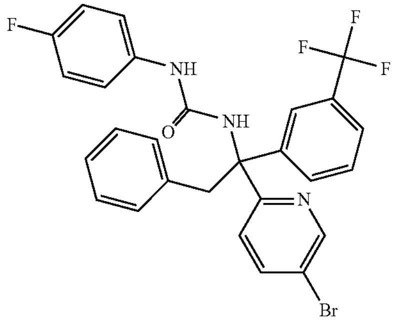 | 1-(1-(5-bromopyridin-2-yl)-2-phenyl-1-(3-(trifluoromethyl) phenyl)ethyl)-3-(4-fluorophenyl) urea | 3.54 LC 558.11 [M + H+] | Procedures 1 and 2 |
| 188 | 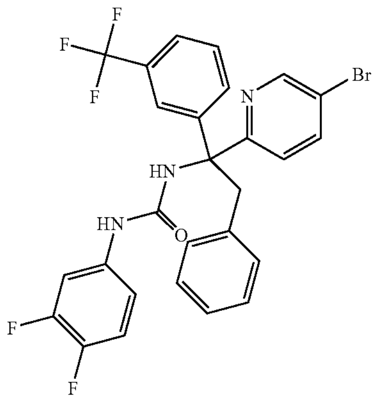 | 1-(1-(5-bromopyridin-2-yl)-2-phenyl-1-(3-(trifluoromethyl) phenyl)ethyl)-3-(3,4-difluorophenyl)urea | 3.62 LC 576.08 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 189 | 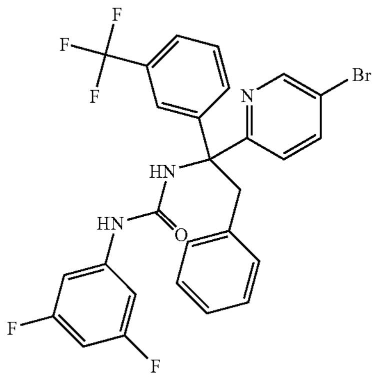 | 1-(1-(5-bromopyridin-2-yl)-2-phenyl-1-(3-(trifluoromethyl) phenyl)ethyl)-3-(3,5-difluorophenyl)urea | 3.62 LC 576.08 [M + H+] | Procedures 1 and 2 |
| 190 | 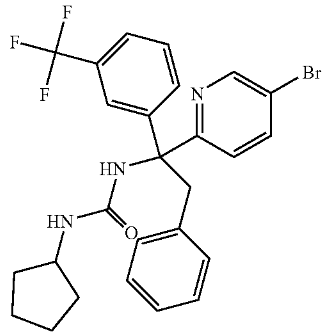 | 1-(1-(5-bromopyridin-2-yl)-2-phenyl-1-(3-(trifluoromethyl) phenyl)ethyl)-3-cyclopentylurea | 3.56 LC 532.11 [M + H+] | Procedures 1 and 2 |
| 191 | 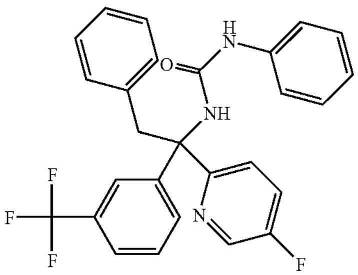 | 1-(1-(5-fluoropyridin-2-yl)-2-phenyl-1-(3-(trifluoromethyl) phenyl)ethyl)-3-phenylurea | 3.32 LC 480.2 [M + H+] | Procedures 1 and 2 |
| 192 | 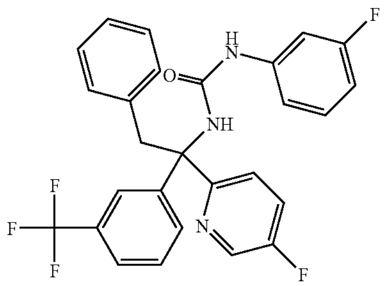 | 1-(3-fluorophenyl)-3-(1-(5-fluoropyridin-2-yl)-2-phenyl-1-(3-(trifluoromethyl)phenyl)ethyl)urea | 3.39 LC 498.17 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 193 | 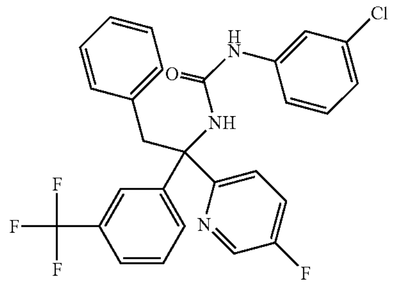 | 1-(3-chlorophenyl)-3-(1-(5-fluoropyridin-2-yl)-2-phenyl-1-(3-(trifluoromethyl)phenyl)ethyl)urea | 3.54 LC 514.11 [M + H$^+$] | Procedures 1 and 2 |
| 194 | 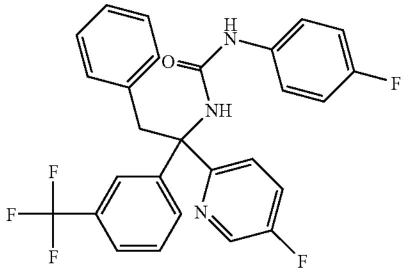 | 1-(4-fluorophenyl)-3-(1-(5-fluoropyridin-2-yl)-2-phenyl-1-(3-(trifluoromethyl)phenyl)ethyl)urea | 3.37 LC 498.17 [M + H$^+$] | Procedures 1 and 2 |
| 195 | 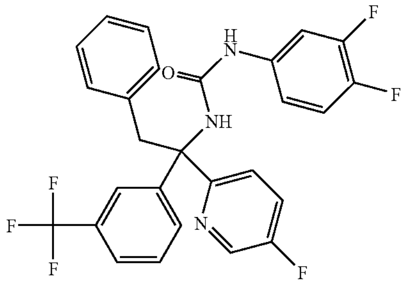 | 1-(3,4-difluorophenyl)-3-(1-(5-fluoropyridin-2-yl)-2-phenyl-1-(3-(trifluoromethyl)phenyl)ethyl)urea | 3.47 LC 516.09 [M + H$^+$] | Procedures 1 and 2 |
| 196 | 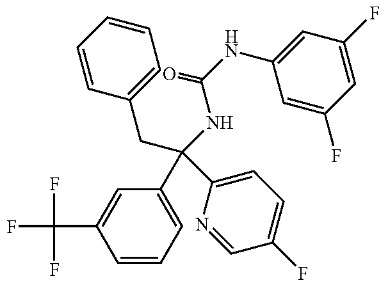 | 1-(3,5-difluorophenyl)-3-(1-(5-fluoropyridin-2-yl)-2-phenyl-1-(3-(trifluoromethyl)phenyl)ethyl)urea | 3.54 LC 516.1 [M + H$^+$] | Procedures 1 and 2 |
| 197 | 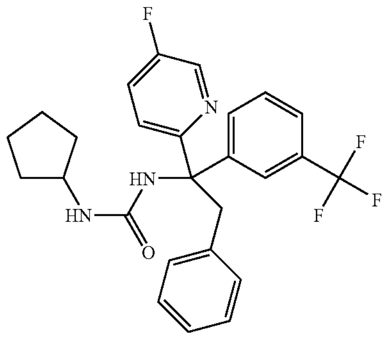 | 1-cyclopentyl-3-(1-(5-fluoropyridin-2-yl)-2-phenyl-1-(3-(trifluoromethyl)phenyl)ethyl)urea | 3.38 LC 472.21 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 198 | 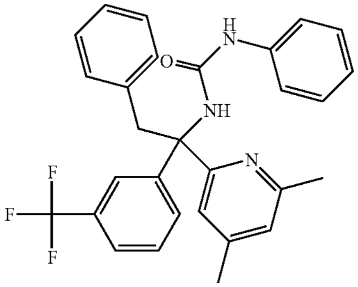 | 1-(1-(4,6-dimethylpyridin-2-yl)-2-phenyl-1-(3-(trifluoromethyl) phenyl)ethyl)-3-phenylurea | 2.99 LC 490.18 [M + H+] | Procedures 1 and 2 |
| 199 | 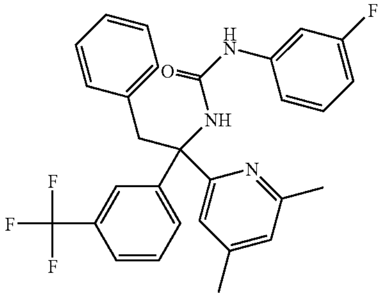 | 1-(1-(4,6-dimethylpyridin-2-yl)-2-phenyl-1-(3-(trifluoromethyl) phenyl)ethyl)-3-(3-fluorophenyl) urea | 3.09 LC 508.14 [M + H+] | Procedures 1 and 2 |
| 200 | 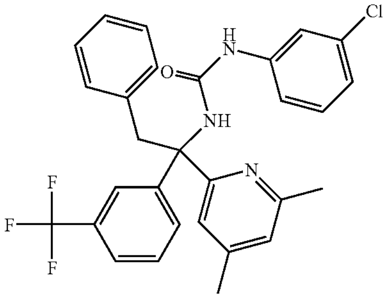 | 1-(3-chlorophenyl)-3-(1-(4,6-dimethylpyridin-2-yl)-2-phenyl-1-(3-(trifluoromethyl)phenyl)ethyl) urea | 3.25 LC 524.11 [M + H+] | Procedures 1 and 2 |
| 201 | 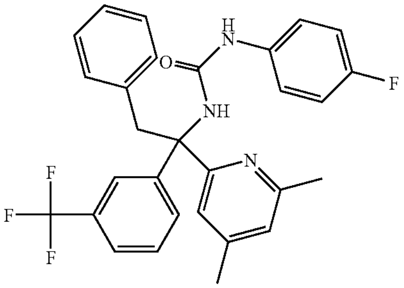 | 1-(1-(4,6-dimethylpyridin-2-yl)-2-phenyl-1-(3-(trifluoromethyl) phenyl)ethyl)-3-(4-fluorophenyl) urea | 3.05 LC 508.14 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 202 | 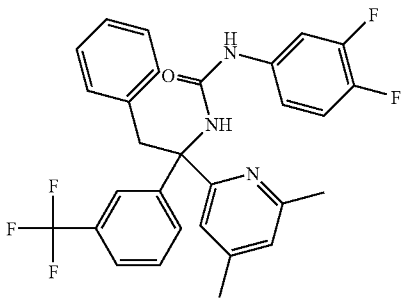 | 1-(3,4-difluorophenyl)-3-(1-(4,6-dimethylpyridin-2-yl)-2-phenyl-1-(3-(trifluoromethyl)phenyl)ethyl) urea | 3.19 LC 526.13 [M + H$^+$] | Procedures 1 and 2 |
| 203 | 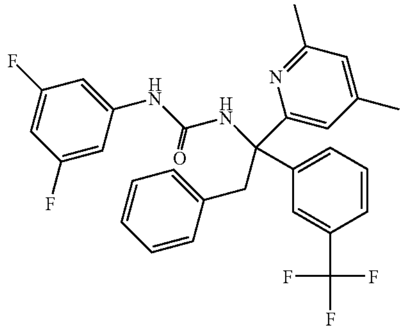 | 1-(3,5-difluorophenyl)-3-(1-(4,6-dimethylpyridin-2-yl)-2-phenyl-1-(3-(trifluoromethyl)phenyl)ethyl) urea | 3.28 LC 526.13 [M + H$^+$] | Procedures 1 and 2 |
| 204 | 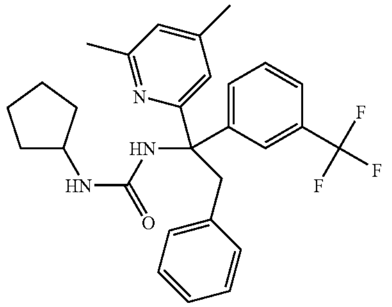 | 1-cyclopentyl-3-(1-(4,6-dimethylpyridin-2-yl)-2-phenyl-1-(3-(trifluoromethyl)phenyl)ethyl) urea | 2.94 LC 482.23 [M + H$^+$] | Procedures 1 and 2 |
| 205 | 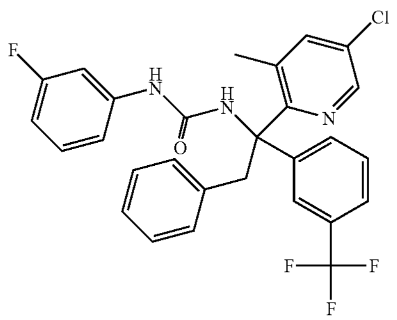 | 1-(1-(5-chloro-3-methylpyridin-2-yl)-2-phenyl-1-(3-(trifluoromethyl)phenyl)ethyl)-3-(3-fluorophenyl)urea | 3.67 LC 528.14 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 206 | 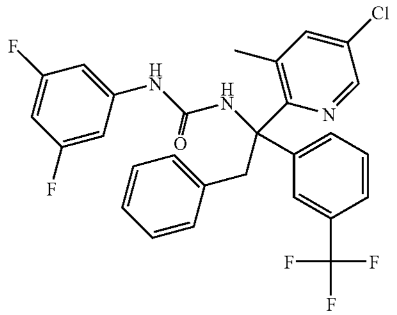 | 1-(1-(5-chloro-3-methylpyridin-2-yl)-2-phenyl-1-(3-(trifluoromethyl)phenyl)ethyl)-3-(3,5-difluorophenyl)urea | 3.77 LC 546.15 [M + H$^+$] | Procedures 1 and 2 |
| 207 | 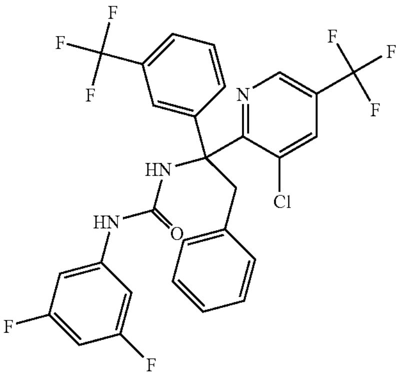 | 1-(1-(3-chloro-5-(trifluoromethyl) pyridin-2-yl)-2-phenyl-1-(3-(trifluoromethyl)phenyl)ethyl)-3-(3,5-difluorophenyl)urea | 3.86 LC 600.08 [M + H$^+$] | Procedures 1 and 2 |
| 208 | 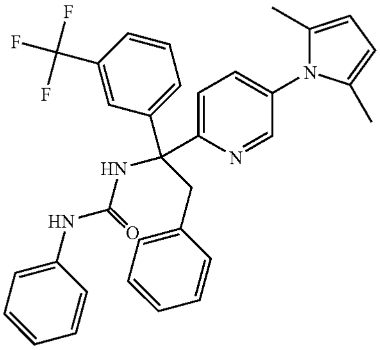 | 1-(1-(5-(2,5-dimethyl-1H-pyrrol-1-yl)pyridin-2-yl)-2-phenyl-1-(3-(trifluoromethyl)phenyl)ethyl)-3-phenylurea | 3.63 LC 555.26 [M + H$^+$] | Procedures 1 and 2 |
| 209 | 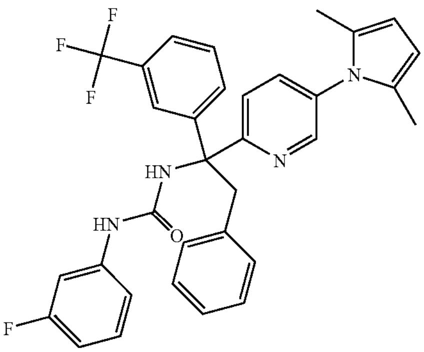 | 1-(1-(5-(2,5-dimethyl-1H-pyrrol-1-yl)pyridin-2-yl)-2-phenyl-1-(3-(trifluoromethyl)phenyl)ethyl)-3-(3-fluorophenyl)urea | 3.69 LC 573.24 [M + H$^+$] | Procedures 1 and 2 |

TABLE 2-continued

| Ex. No. | Structure | Name | Retention Time Min./ Molecular Mass | Prepared in the manner described in: |
|---|---|---|---|---|
| 210 | 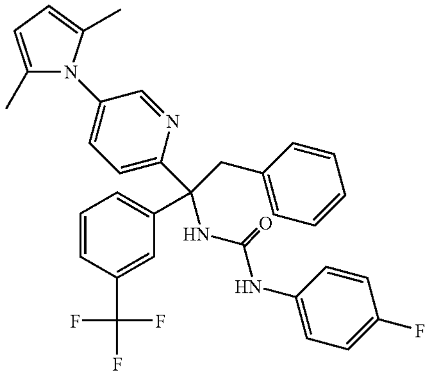 | 1-(1-(5-(2,5-dimethyl-1H-pyrrol-1-yl)pyridin-2-yl)-2-phenyl-1-(3-(trifluoromethyl)phenyl)ethyl)-3-(4-fluorophenyl)urea | 3.67 LC 573.24 [M + H+] | Procedures 1 and 2 |
| 211 | 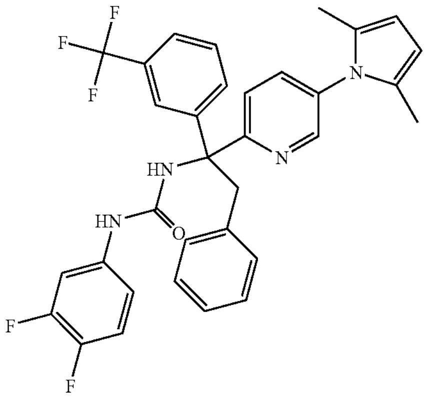 | 1-(3,4-difluorophenyl)-3-(1-(5-(2,5-dimethyl-1H-pyrrol-1-yl) pyridin-2-yl)-2-phenyl-1-(3-(trifluoromethyl)phenyl)ethyl)urea | 3.75 LC 591.2 [M + H+] | Procedures 1 and 2 |
| 212 | 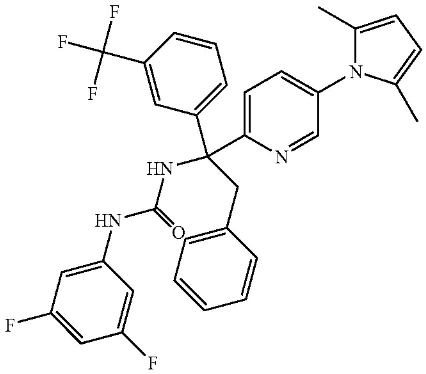 | 1-(3,5-difluorophenyl)-3-(1-(5-(2,5-dimethyl-1H-pyrrol-1-yl) pyridin-2-yl)-2-phenyl-1-(3-(trifluoromethyl)phenyl)ethyl)urea | 3.79 LC 591.2 [M + H+] | Procedures 1 and 2 |
| 213 | 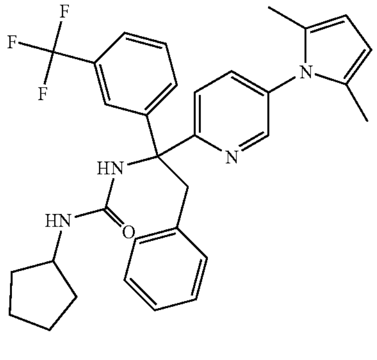 | 1-cyclopentyl-3-(1-(5-(2,5-dimethyl-1H-pyrrol-1-yl)pyridin-2-yl)-2-phenyl-1-(3-(trifluoromethyl)phenyl)ethyl)urea | 3.67 LC 547.28 [M + H+] | Procedures 1 and 2 |

TABLE 2-continued

| Ex. No. | Structure | Name | Retention Time Min./ Molecular Mass | Prepared in the manner described in: |
|---|---|---|---|---|
| 214 | 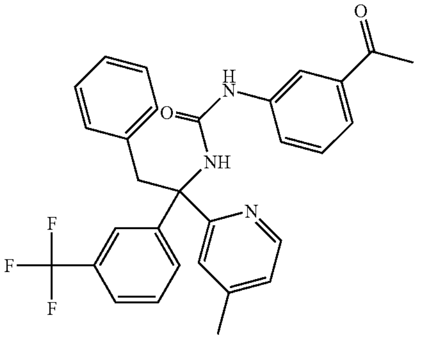 | 1-(3-acetylphenyl)-3-(1-(4-methylpyridin-2-yl)-2-phenyl-1-(3-(trifluoromethyl)phenyl)ethyl) urea | 2.15 LC 518.25 [M + H$^+$] | Procedures 1 and 2 |
| 215 | 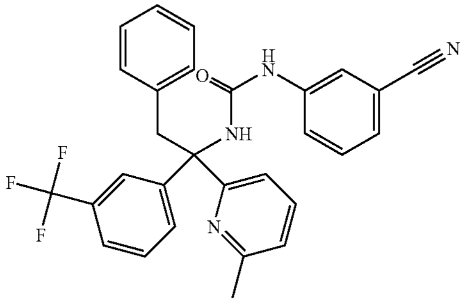 | 1-(3-cyanophenyl)-3-(1-(6-methylpyridin-2-yl)-2-phenyl-1-(3-(trifluoromethyl)phenyl)ethyl) urea | 2.60 LC 501.26 [M + H$^+$] | Procedures 1 and 2 |

TABLE 3

| Ex. No. | Structure | Name | Retention Time Min./ Molecular Mass | Prepared in the manner described in: |
|---|---|---|---|---|
| 216 | 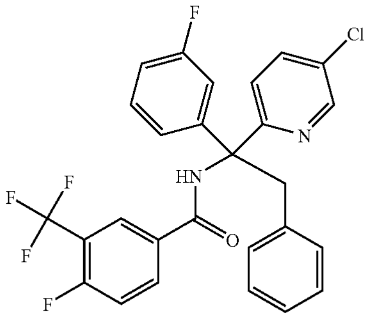 | N-(1-(5-chloropyridin-2-yl)-1-(3-fluorophenyl)-2-phenylethyl)-4-fluoro-3-(trifluoromethyl) benzamide | 3.69 LC 517.16 [M + H]$^+$ | Procedures 1 and 4 |

TABLE 3-continued

| Ex. No. | Structure | Name | Retention Time Min./ Molecular Mass | Prepared in the manner described in: |
|---|---|---|---|---|
| 217 | 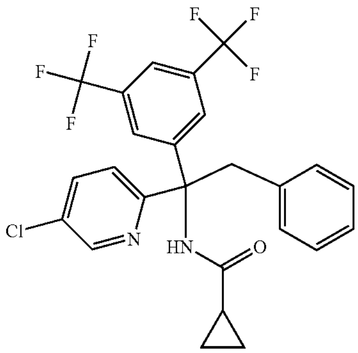 | N-(1-(3,5-bis(trifluoromethyl) phenyl)-1-(5-chloropyridin-2-yl)-2-phenylethyl) cyclopropanecarboxamide | 3.59 LC 513.06 $[M + H]^+$ | Procedures 1 and 4 |
| 218 | 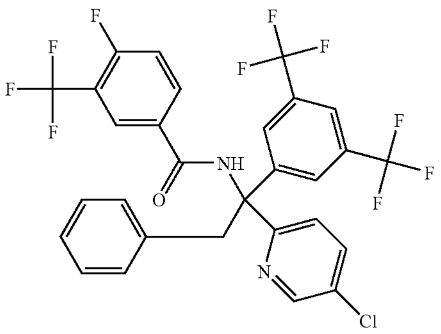 | N-(1-(3,5-bis(trifluoromethyl) phenyl)-1-(5-chloropyridin-2-yl)-2-phenylethyl)-4-fluoro-3-(trifluoromethyl)benzamide | 3.91 LC 635.13 $[M + H]^+$ | Procedures 1 and 4 |
| 219 | 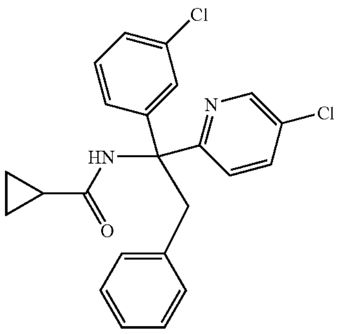 | N-(1-(3-chlorophenyl)-1-(5-chloropyridin-2-yl)-2-phenylethyl) cyclopropanecarboxamide | 3.39 LC 410.96 $[M + H]^+$ | Procedures 1 and 4 |
| 220 | 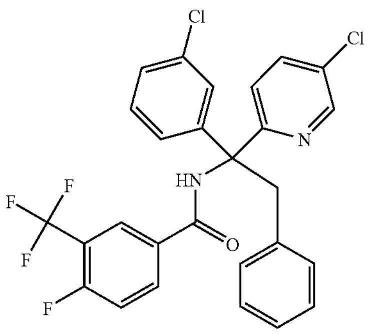 | N-(1-(3-chlorophenyl)-1-(5-chloropyridin-2-yl)-2-phenylethyl)-4-fluoro-3-(trifluoromethyl)benzamide | 3.80 LC 533.03 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 221 | 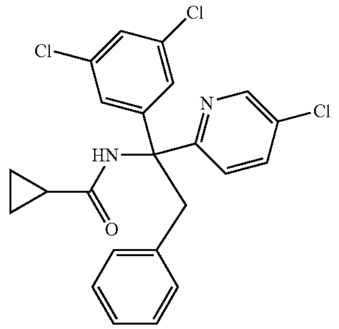 | N-(1-(5-chloropyridin-2-yl)-1-(3,5-dichlorophenyl)-2-phenylethyl) cyclopropanecarboxamide | 3.58 LC 444.95 $[M + H]^+$ | Procedures 1 and 4 |
| 222 | 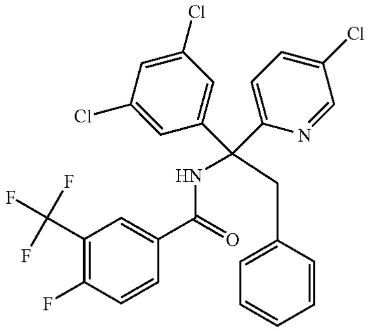 | N-(1-(5-chloropyridin-2-yl)-1-(3,5-dichlorophenyl)-2-phenylethyl)-4-fluoro-3-(trifluoromethyl)benzamide | 3.95 LC 567.05 $[M + H]^+$ | Procedures 1 and 4 |
| 223 | 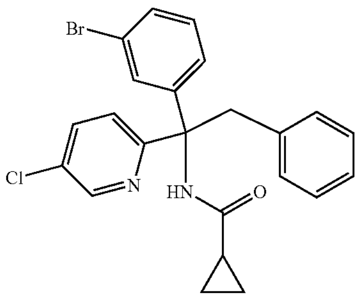 | N-(1-(3-bromophenyl)-1-(5-chloropyridin-2-yl)-2-phenylethyl) cyclopropanecarboxamide | 3.43 LC 454.95 $[M + H]^+$ | Procedures 1 and 4 |
| 224 | 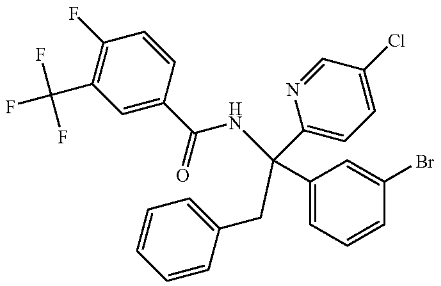 | N-(1-(3-bromophenyl)-1-(5-chloropyridin-2-yl)-2-phenylethyl)-4-fluoro-3-(trifluoromethyl)benzamide | 3.81 LC 577.01 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 225 | 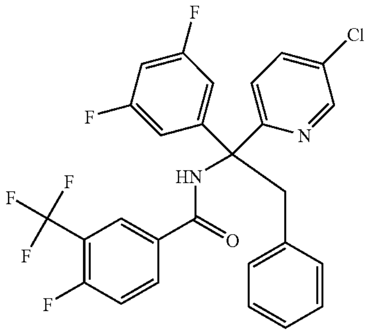 | N-(1-(5-chloropyridin-2-yl)-1-(3,5-difluorophenyl)-2-phenylethyl)-4-fluoro-3-(trifluoromethyl)benzamide | 3.75 LC 535.04 $[M + H]^+$ | Procedures 1 and 4 |
| 226 | 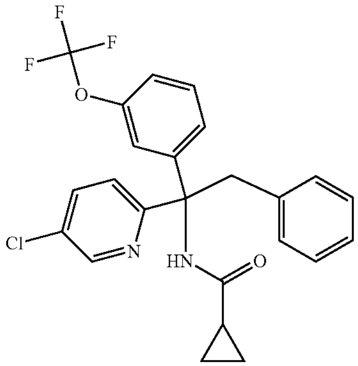 | N-(1-(5-chloropyridin-2-yl)-2-phenyl-1-(3-(trifluoromethoxy) phenyl)ethyl) cyclopropanecarboxamide | 3.51 LC 461.04 $[M + H]^+$ | Procedures 1 and 4 |
| 227 | 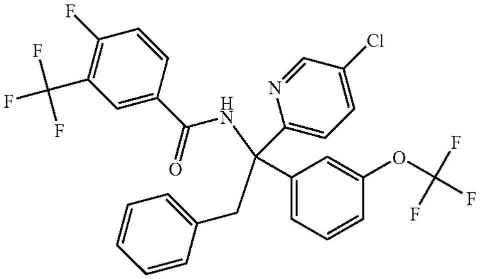 | N-(1-(5-chloropyridin-2-yl)-2-phenyl-1-(3-(trifluoromethoxy) phenyl)ethyl)-4-fluoro-3-(trifluoromethyl)benzamide | 3.86 LC 583.06 $[M + H]^+$ | Procedures 1 and 4 |
| 228 | 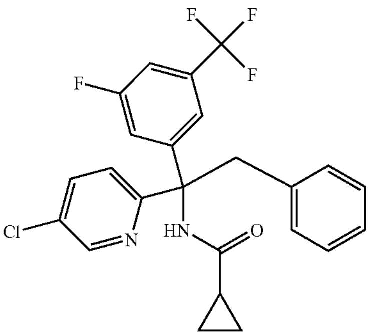 | N-(1-(5-chloropyridin-2-yl)-1-(3-fluoro-5-(trifluoromethyl)phenyl)-2-phenylethyl) cyclopropanecarboxamide | 3.46 LC 463.03 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 229 | 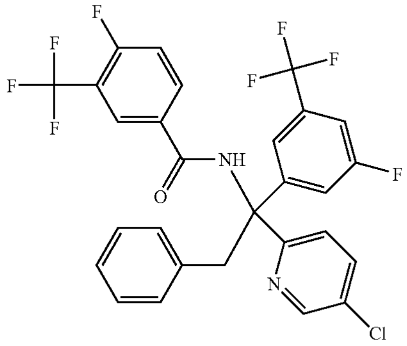 | N-(1-(5-chloropyridin-2-yl)-1-(3-fluoro-5-(trifluoromethyl)phenyl)-2-phenylethyl)-4-fluoro-3-(trifluoromethyl)benzamide | 3.85 LC 585.06 [M + H]$^+$ | Procedures 1 and 4 |
| 230 | 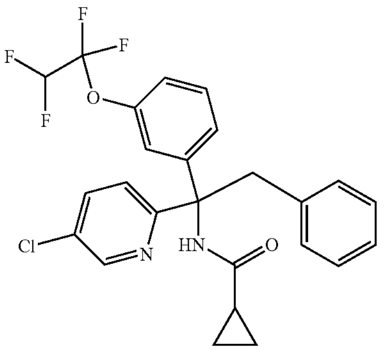 | N-(1-(5-chloropyridin-2-yl)-2-phenyl-1-(3-(1,1,2,2-tetrafluoroethoxy)phenyl)ethyl) cyclopropanecarboxamide | 3.92 LC 493.1 [M + H]$^+$ | Procedures 1 and 4 |
| 231 | 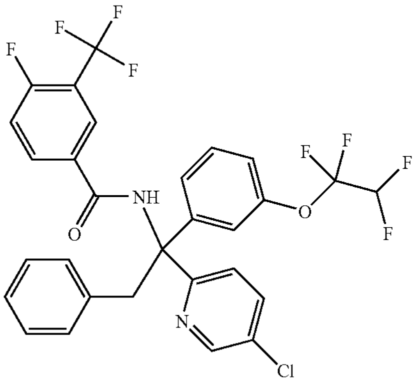 | N-(1-(5-chloropyridin-2-yl)-2-phenyl-1-(3-(1,1,2,2-tetrafluoroethoxy)phenyl)ethyl)-4-fluoro-3-(trifluoromethyl) benzamide | 4.22 LC 614.96 [M + H]$^+$ | Procedures 1 and 4 |
| 232 | 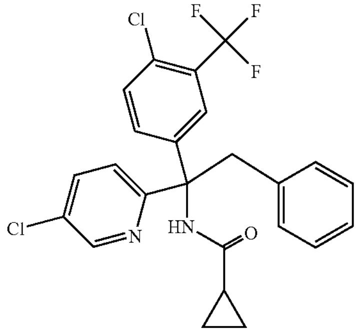 | N-(1-(4-chloro-3-(trifluoromethyl) phenyl)-1-(5-chloropyridin-2-yl)-2-phenylethyl) cyclopropanecarboxamide | 4.12 LC 479.11 [M + H]$^+$ | Procedures 1 and 4 |

TABLE 3-continued

| Ex. No. | Structure | Name | Retention Time Min./ Molecular Mass | Prepared in the manner described in: |
|---|---|---|---|---|
| 233 | 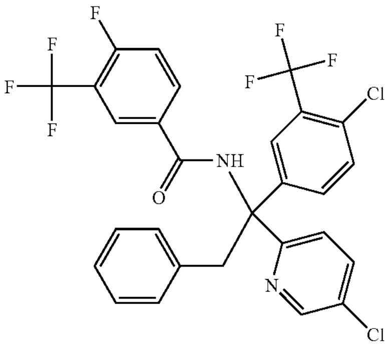 | N-(1-(4-chloro-3-(trifluoromethyl) phenyl)-1-(5-chloropyridin-2-yl)-2-phenylethyl)-4-fluoro-3-(trifluoromethyl)benzamide | 4.41 LC 601.05 [M + H]$^+$ | Procedures 1 and 4 |
| 234 | 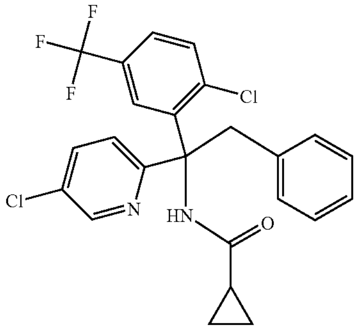 | N-(1-(2-chloro-5-(trifluoromethyl) phenyl)-1-(5-chloropyridin-2-yl)-2-phenylethyl) cyclopropanecarboxamide | 4.09 LC 479.1 [M + H]$^+$ | Procedures 1 and 4 |
| 235 | 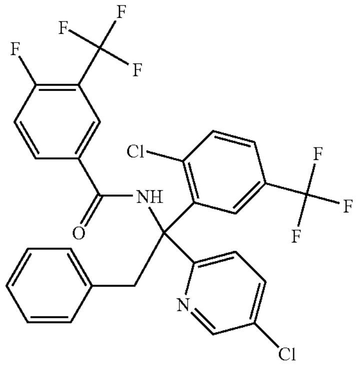 | N-(1-(2-chloro-5-(trifluoromethyl) phenyl)-1-(5-chloropyridin-2-yl)-2-phenylethyl)-4-fluoro-3-(trifluoromethyl)benzamide | 4.38 LC 601.05 [M + H]$^+$ | Procedures 1 and 4 |
| 236 | 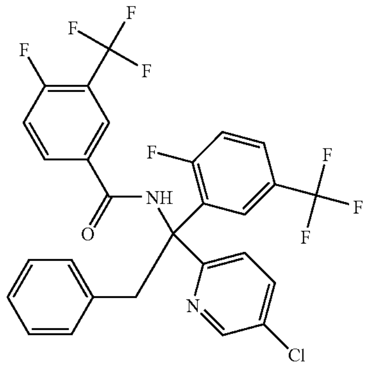 | N-(1-(5-chloropyridin-2-yl)-1-(2-fluoro-5-(trifluoromethyl)phenyl)-2-phenylethyl)-4-fluoro-3-(trifluoromethyl)benzamide | 4.30 LC 585.1 [M + H]$^+$ | Procedures 1 and 4 |

TABLE 3-continued

| Ex. No. | Structure | Name | Retention Time Min./ Molecular Mass | Prepared in the manner described in: |
|---|---|---|---|---|
| 237 | 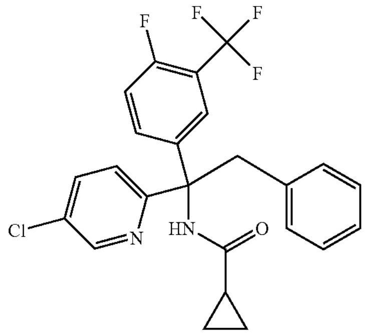 | N-(1-(5-chloropyridin-2-yl)-1-(4-fluoro-3-(trifluoromethyl)phenyl)-2-phenylethyl) cyclopropanecarboxamide | 4.00 LC 463.14 $[M + H]^+$ | Procedures 1 and 4 |
| 238 | 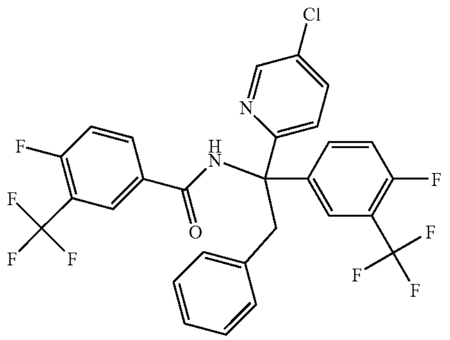 | N-(1-(5-chloropyridin-2-yl)-1-(4-fluoro-3-(trifluoromethyl)phenyl)-2-phenylethyl)-4-fluoro-3-(trifluoromethyl)benzamide | 4.32 LC 585.1 $[M + H]^+$ | Procedures 1 and 4 |
| 239 | 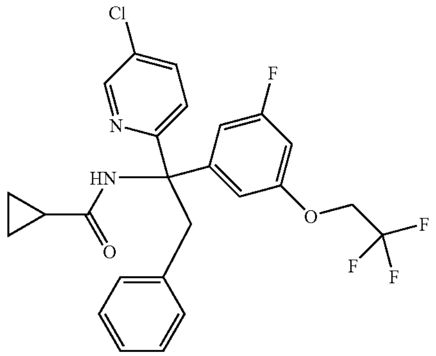 | N-(1-(5-chloropyridin-2-yl)-1-(3-fluoro-5-(2,2,2-trifluoroethoxy) phenyl)-2-phenylethyl) cyclopropanecarboxamide | 4.04 LC 493.11 $[M + H]^+$ | Procedures 3, 1 and 4 |
| 240 | 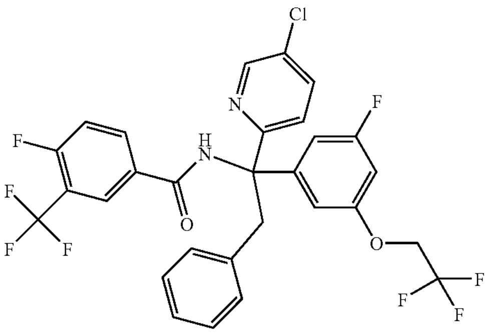 | N-(1-(5-chloropyridin-2-yl)-1-(3-fluoro-5-(2,2,2-trifluoroethoxy) phenyl)-2-phenylethyl)-4-fluoro-3-(trifluoromethyl)benzamide | 4.32 LC 615.08 $[M + H]^+$ | Procedures 3, 1 and 4 |

TABLE 3-continued

| Ex. No. | Structure | Name | Retention Time Min./ Molecular Mass | Prepared in the manner described in: |
|---|---|---|---|---|
| 241 | 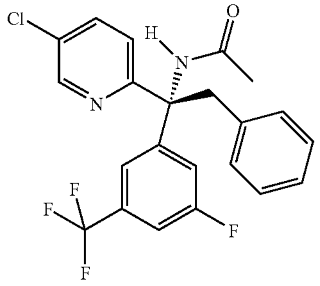 | (R)-N-(1-(5-chloropyridin-2-yl)-1-(3-fluoro-5-(trifluoromethyl) phenyl)-2-phenylethyl)acetamide | 436.83 | Procedures 1 and 4 |
| 242 | 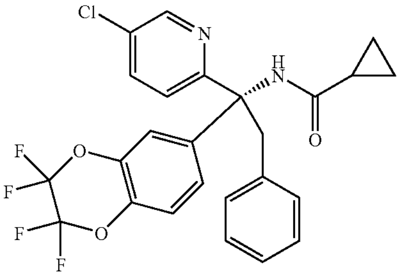 | (R)-N-(1-(5-chloropyridin-2-yl)-2-phenyl-1-(2,2,3,3-tetrafluoro-2,3-dihydrobenzo[b][1,4]dioxin-6-yl)ethyl)cyclopropanecarboxamide | 4.16 LC 507.3 $[M + H]^+$ | Procedures 1 and 4 |
| 243 | 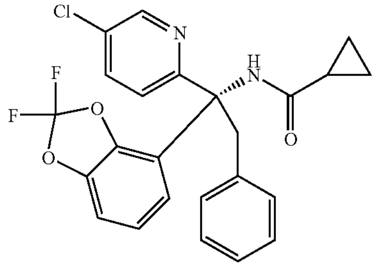 | (R)-N-(1-(5-chloropyridin-2-yl)-1-(2,2-difluorobenzo[d][1,3]dioxol-4-yl)-2-phenylethyl) cyclopropanecarboxamide | 3.98 LC 457.3 $[M + H]^+$ | Procedures 1 and 4 |
| 244 | 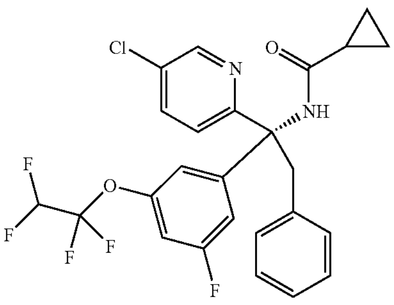 | (R)-N-(1-(5-chloropyridin-2-yl)-1-(3-fluoro-5-(1,1,2,2-tetrafluoroethoxy)phenyl)-2-phenylethyl) cyclopropanecarboxamide | 3.99 LC 511.3 $[M + H]^+$ | Procedures 3, 1 and 4 |

TABLE 3-continued

| Ex. No. | Structure | Name | Retention Time Min./ Molecular Mass | Prepared in the manner described in: |
|---|---|---|---|---|
| 245 | 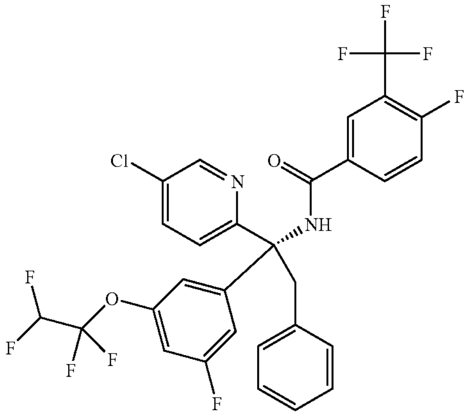 | (R)-N-(1-(5-chloropyridin-2-yl)-1-(3-fluoro-5-(1,1,2,2-tetrafluoroethoxy)phenyl)-2-phenylethyl)-4-fluoro-3-(trifluoromethyl)benzamide | 4.29 LC 633.2 $[M + H]^+$ | Procedures 3, 1 and 4 |
| 246 | 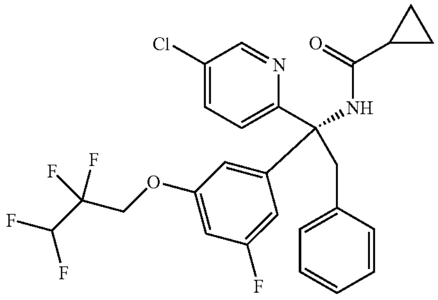 | (R)-N-(1-(5-chloropyridin-2-yl)-1-(3-fluoro-5-(2,2,3,3-tetrafluoropropoxy)phenyl)-2-phenylethyl) cyclopropanecarboxamide | 3.99 LC 525.28 $[M + H]^+$ | Procedures 3, 1 and 4 |
| 247 | 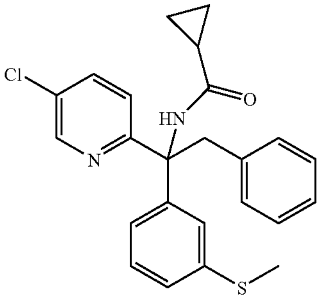 | N-(1-(5-chloropyridin-2-yl)-1-(3-(methylthio)phenyl)-2-phenylethyl) cyclopropanecarboxamide | 3.82 LC 423.14 $[M + H]^+$ | Procedures 1 and 4 |
| 248 | 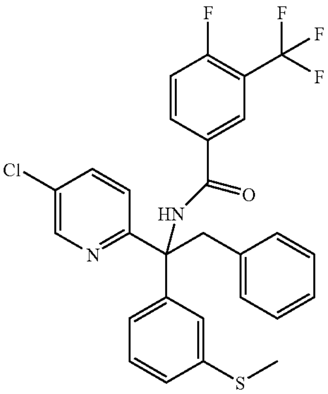 | N-(1-(5-chloropyridin-2-yl)-1-(3-(methylthio)phenyl)-2-phenylethyl)-4-fluoro-3-(trifluoromethyl)benzamide | 4.19 LC 545.16 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 249 | 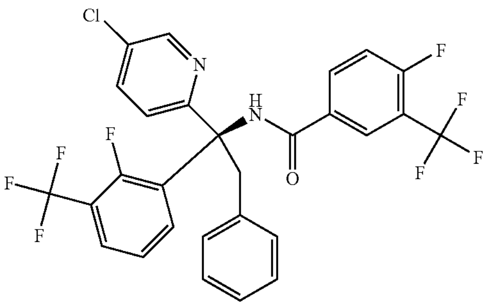 | (S)-N-(1-(5-chloropyridin-2-yl)-1-(2-fluoro-3-(trifluoromethyl) phenyl)-2-phenylethyl)-4-fluoro-3-(trifluoromethyl)benzamide | 4.27 LC 585.3 $[M + H]^+$ | Procedures 1 and 4 |
| 250 | 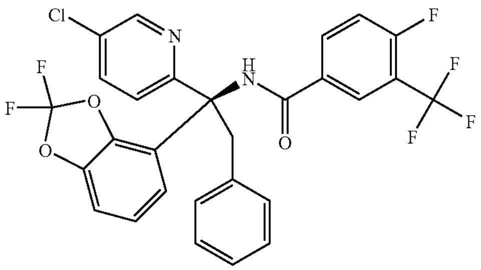 | (S)-N-(1-(5-chloropyridin-2-yl)-1-(2,2-difluorobenzo[d][1,3]dioxol-4-yl)-2-phenylethyl)-4-fluoro-3-(trifluoromethyl)benzamide | 4.24 LC 579.3 $[M + H]^+$ | Procedures 1 and 4 |
| 251 | 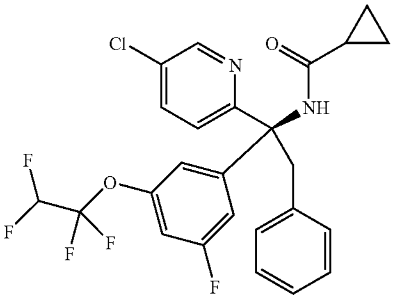 | (S)-N-(1-(5-chloropyridin-2-yl)-1-(3-fluoro-5-(1,1,2,2-tetrafluoroethoxy)phenyl)-2-phenylethyl) cyclopropanecarboxamide | 3.97 LC 511.36 $[M + H]^+$ | Procedures 3, 1 and 4 |
| 253 | 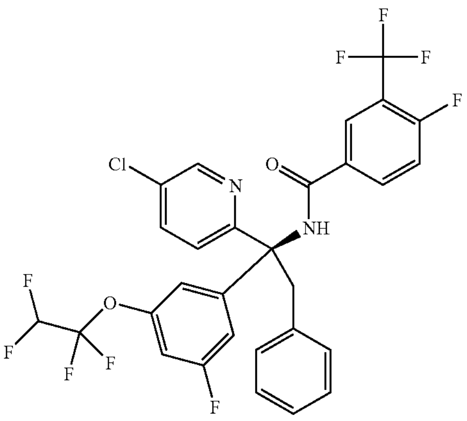 | (S)-N-(1-(5-chloropyridin-2-yl)-1-(3-fluoro-5-(1,1,2,2-tetrafluoroethoxy)phenyl)-2-phenylethyl)-4-fluoro-3-(trifluoromethyl)benzamide | 4.26 LC 633.31 $[M + H]^+$ | Procedures 3, 5, 6, 7 and 4 |

TABLE 3-continued

| Ex. No. | Structure | Name | Retention Time Min./ Molecular Mass | Prepared in the manner described in: |
|---|---|---|---|---|
| 254 | 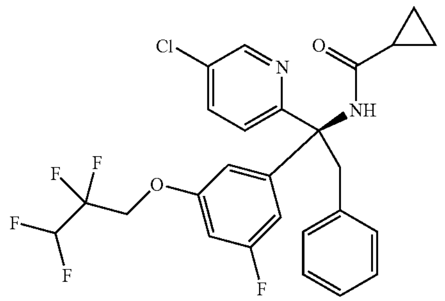 | (S)-N-(1-(5-chloropyridin-2-yl)-1-(3-fluoro-5-(2,2,3,3-tetrafluoropropoxy)phenyl)-2-phenylethyl) cyclopropanecarboxamide | 3.97 LC 525.4 $[M + H]^+$ | Procedures 3, 1 and 4 |
| 255 | 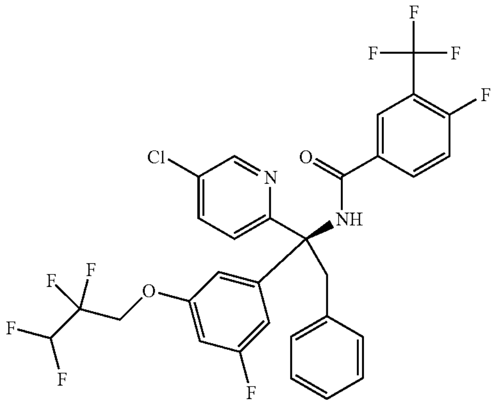 | (S)-N-(1-(5-chloropyridin-2-yl)-1-(3-fluoro-5-(2,2,3,3-tetrafluoropropoxy)phenyl)-2-phenylethyl)-4-fluoro-3-(trifluoromethyl)benzamide | 4.29 LC 647.3 $[M + H]^+$ | Procedures 3, 1 and 4 |
| 256 | 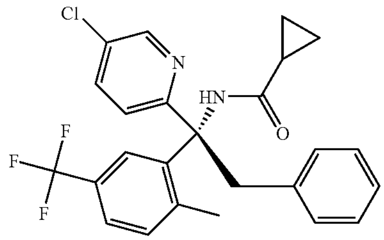 | (R)-N-(1-(5-chloropyridin-2-yl)-1-(2-methyl-5-(trifluoromethyl) phenyl)-2-phenylethyl) cyclopropanecarboxamide | 4.05 LC 459.3 $[M + H]^+$ | Procedures 1 and 4 |
| 257 | 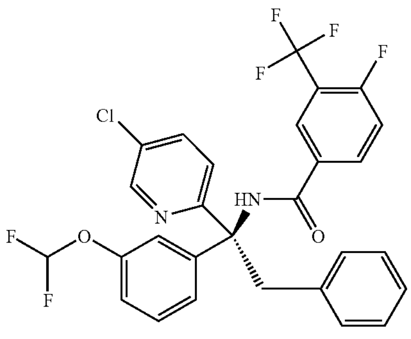 | (S)-N-(1-(5-chloropyridin-2-yl)-1-(3-(difluoromethoxy)phenyl)-2-phenylethyl)-4-fluoro-3-(trifluoromethyl)benzamide | 4.18 LC 565.3 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 258 | 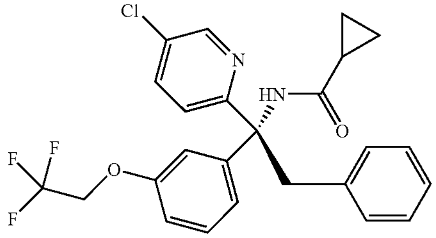 | (R)-N-(1-(5-chloropyridin-2-yl)-2-phenyl-1-(3-(2,2,2-trifluoroethoxy) phenyl)ethyl) cyclopropanecarboxamide | 3.96 LC 475.4 $[M + H]^+$ | Procedures 1 and 4 |
| 259 | 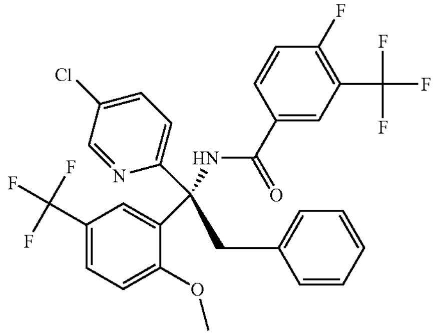 | (R)-N-(1-(5-chloropyridin-2-yl)-1-(2-methoxy-5-(trifluoromethyl) phenyl)-2-phenylethyl)-4-fluoro-3-(trifluoromethyl)benzamide | 4.22 LC 597.3 $[M + H]^+$ | Procedures 1 and 4 |
| 260 | 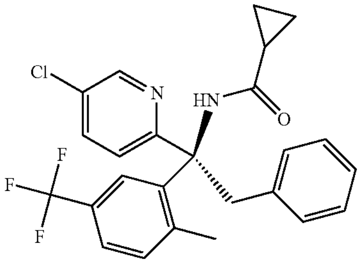 | (S)-N-(1-(5-chloropyridin-2-yl)-1-(2-methyl-5-(trifluoromethyl) phenyl)-2-phenylethyl) cyclopropanecarboxamide | 4.04 LC 459.5 $[M + H]^+$ | Procedures 1 and 4 |
| 261 | 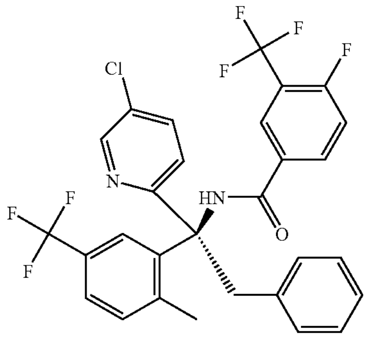 | (S)-N-(1-(5-chloropyridin-2-yl)-1-(2-methyl-5-(trifluoromethyl) phenyl)-2-phenylethyl)-4-fluoro-3-(trifluoromethyl)benzamide | 4.32 LC 581.4 $[M + H]^+$ | Procedures 1 and 4 |
| 262 | 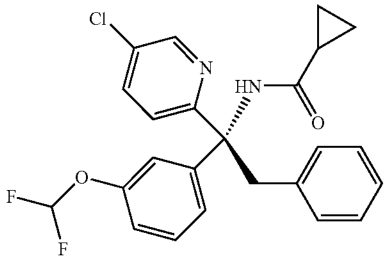 | (R)-N-(1-(5-chloropyridin-2-yl)-1-(3-(difluoromethoxy)phenyl)-2-phenylethyl) cyclopropanecarboxamide | 3.82 LC 443.5 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 263 | 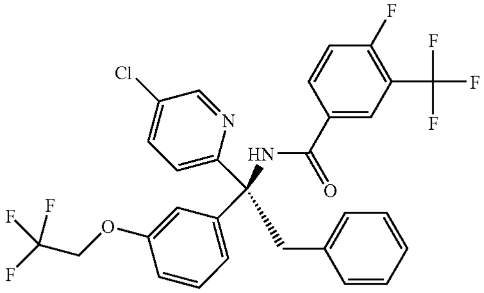 | (S)-N-(1-(5-chloropyridin-2-yl)-2-phenyl-1-(3-(2,2,2-trifluoroethoxy) phenyl)ethyl)-4-fluoro-3-(trifluoromethyl)benzamide | 4.25 LC 597.4 $[M + H]^+$ | Procedures 1 and 4 |
| 264 | 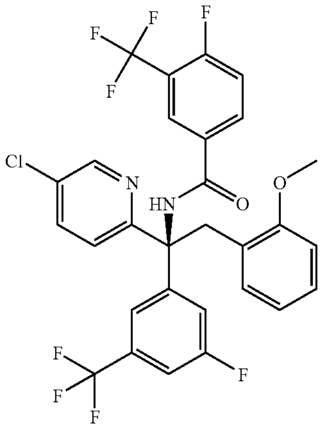 | (S)-N-(1-(5-chloropyridin-2-yl)-1-(3-fluoro-5-(trifluoromethyl) phenyl)-2-(2-methoxyphenyl) ethyl)-4-fluoro-3-(trifluoromethyl) benzamide | 4.38 LC 637.39 $[M + Na]^+$ | Procedures 1 and 4 |
| 265 | 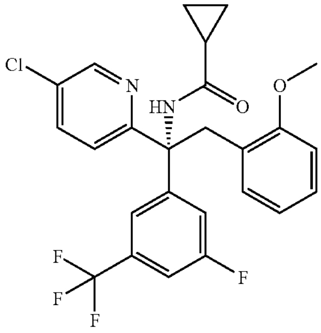 | (R)-N-(1-(5-chloropyridin-2-yl)-1-(3-fluoro-5-(trifluoromethyl) phenyl)-2-(2-methoxyphenyl) ethyl)cyclopropanecarboxamide | 4.05 LC 493.48 $[M + H]^+$ | Procedures 1 and 4 |
| 266 | 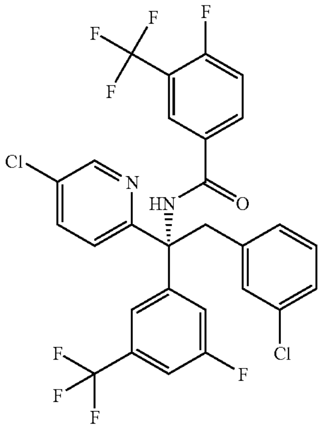 | (R)-N-(2-(3-chlorophenyl)-1-(5-chloropyridin-2-yl)-1-(3-fluoro-5-(trifluoromethyl)phenyl)ethyl)-4-fluoro-3-(trifluoromethyl) benzamide | 4.35 LC 619.40 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 267 | 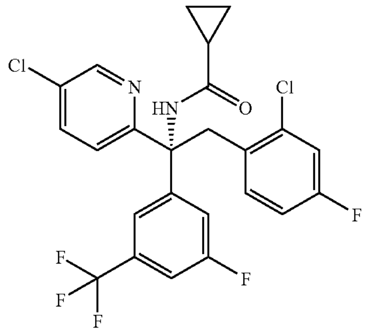 | (R)-N-(2-(2-chloro-4-fluorophenyl)-1-(5-chloropyridin-2-yl)-1-(3-fluoro-5-(trifluoromethyl)phenyl)ethyl) cyclopropanecarboxamide | 4.14 LC 515.42 $[M + H]^+$ | Procedures 1 and 4 |
| 268 | 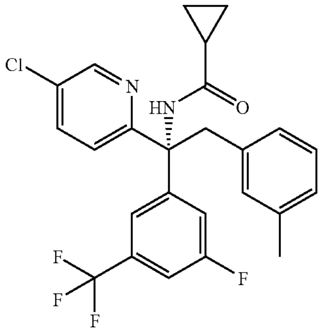 | (R)-N-(1-(5-chloropyridin-2-yl)-1-(3-fluoro-5-(trifluoromethyl) phenyl)-2-m-tolylethyl) cyclopropanecarboxamide | 4.11 LC 477.48 $[M + H]^+$ | Procedures 1 and 4 |
| 269 | 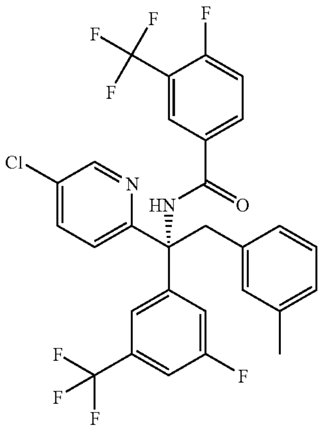 | (R)-N-(1-(5-chloropyridin-2-yl)-1-(3-fluoro-5-(trifluoromethyl) phenyl)-2-m-tolylethyl)-4-fluoro-3-(trifluoromethyl)benzamide | 4.38 LC 599.44 $[M + H]^+$ | Procedures 1 and 4 |
| 270 | 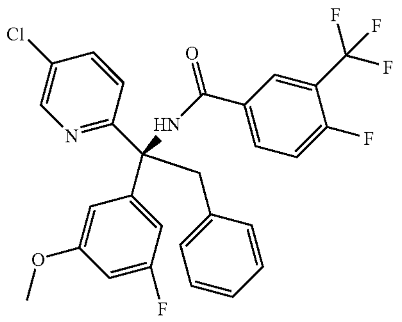 | (S)-N-(1-(5-chloropyridin-2-yl)-1-(3-fluoro-5-methoxyphenyl)-2-phenylethyl)-4-fluoro-3-(trifluoromethyl)benzamide | 4.20 LC 547.33 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 271 | 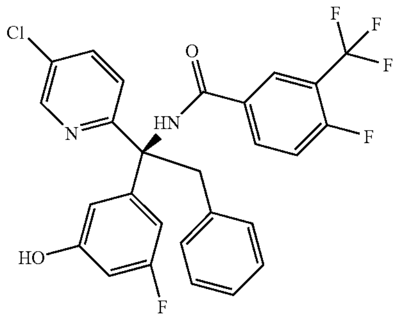 | (S)-N-(1-(5-chloropyridin-2-yl)-1-(3-fluoro-5-hydroxyphenyl)-2-phenylethyl)-4-fluoro-3-(trifluoromethyl)benzamide | 4.07 LC 533.30 $[M + H]^+$ | Procedures 1N and 4 |
| 272 | 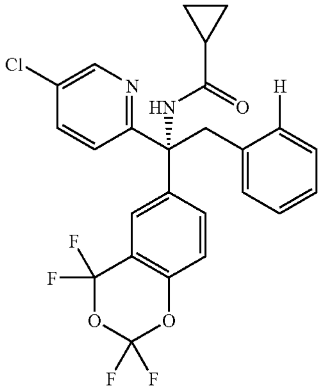 | (R)-N-(1-(5-chloropyridin-2-yl)-2-phenyl-1-(2,2,4,4-tetrafluoro-4H-benzo[d][1,3]dioxin-6-yl)ethyl) cylcopropanecarboxamide | 4.06 LC 507.14 $[M + H]^+$ | Procedures 1 and 4 |
| 273 | 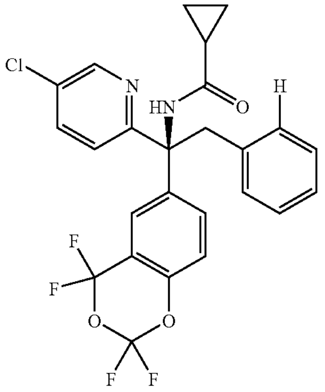 | (S)-N-(1-(5-chloropyridin-2-yl)-2-phenyl-1-(2,2,4,4-tetrafluoro-4H-benzo[d][1,3]dioxin-6-yl)ethyl) cyclopropanecarboxamide | 4.05 LC 507.17 $[M + H]^+$ | Procedures 1 and 4 |

TABLE 3-continued

| Ex. No. | Structure | Name | Retention Time Min./ Molecular Mass | Prepared in the manner described in: |
|---|---|---|---|---|
| 274 | 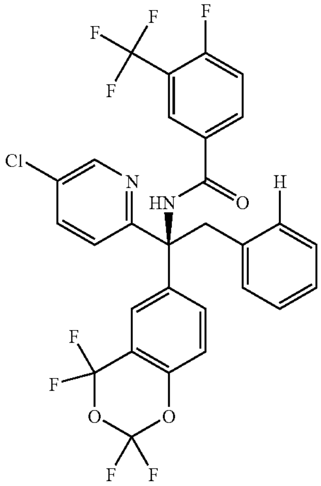 | (S)-N-(1-(5-chloropyridin-2-yl)-2-phenyl-1-(2,2,4,4-tetrafluoro-4H-benzo[d][1,3]dioxin-6-yl)ethyl)-4-fluoro-3-(trifluoromethyl) benzamide | 4.33 LC 629.22 $[M + H]^+$ | Procedures 1 and 4 |
| 275 | 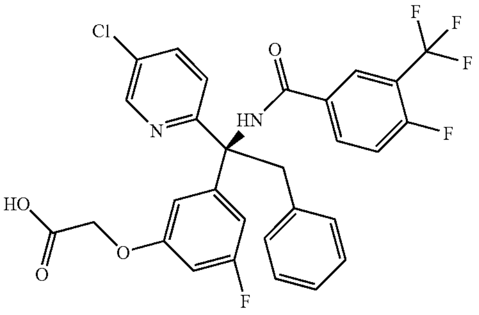 | (S)-2-(3-(1-(5-chloropyridin-2-yl)-1-(4-fluoro-3-(trifluoromethyl) benzamido)-2-phenylethyl)-5-fluorophenoxy)acetic acid | 4.35 LC 591.45 $[M + H]^+$ | Procedures 5, 6, 7, 14 and 15 |
| 276 | 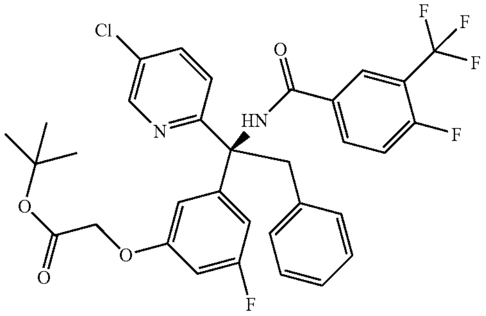 | (S)-tert-butyl 2-(3-(1-(5-chloropyridin-2-yl)-1-(4-fluoro-3-(trifluoromethyl)benzamido)-2-phenylethyl)-5-fluorophenoxy) acetate | 4.31 LC 647.44 $[M + H]^+$ | Procedures 5, 6, 7, 14 and 15 |
| 277 | 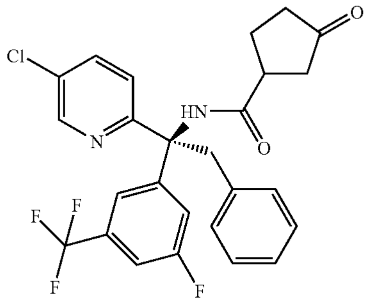 | N-((S)-1-(5-chloropyridin-2-yl)-1-(3-fluoro-5-(trifluoromethyl) phenyl)-2-phenylethyl)-3-oxocyclopentanecarboxamide | 3.84 LC 505.3 $[M + H]^+$ | Procedures 5, 6, 7 and 4 |

TABLE 3-continued

| Ex. No. | Structure | Name | Retention Time Min./ Molecular Mass | Prepared in the manner described in: |
|---|---|---|---|---|
| 278 | 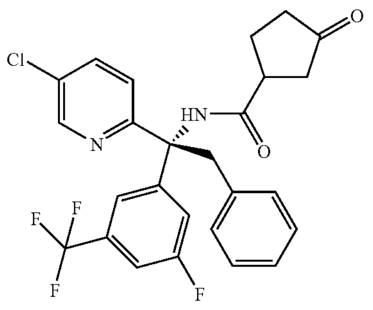 | N-((R)-1-(5-chloropyridin-2-yl)-1-(3-fluoro-5-(trifluoromethyl) phenyl)-2-phenylethyl)-3-oxocyclopentanecarboxamide | 3.84 LC 505.3 [M + H]+ | Procedures 5, 6, 7 and 4 |
| 279 | 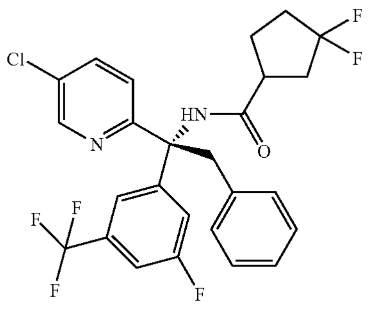 | N-((R)-1-(5-chloropyridin-2-yl)-1-(3-fluoro-5-(trifluoromethyl) phenyl)-2-phenylethyl)-3,3-difluorocyclopentanecarboxamide | 4.13 LC 527.2 [M + H]+ | Procedures 5, 6, 7 and 8 |
| 280 | 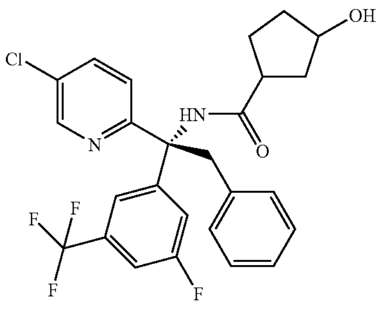 | N-((R)-1-(5-chloropyridin-2-yl)-1-(3-fluoro-5-(trifluoromethyl) phenyl)-2-phenylethyl)-3-hydroxycyclopentanecarboxamide | 3.91 LC 507.3 [M + H]+ | Procedures 5, 6, 7 and 4 |
| 281 | 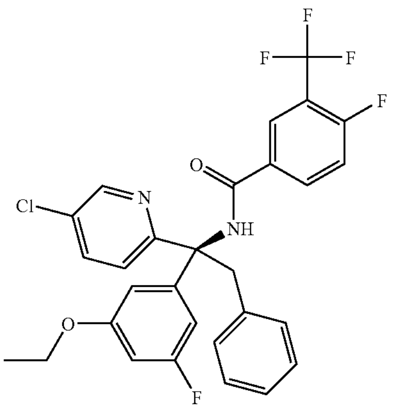 | (S)-N-(1-(5-chloropyridin-2-yl)-1-(3-ethoxy-5-fluorophenyl)-2-phenylethyl)-4-fluoro-3-(trifluoromethyl)benzamide | 4.38 LC 561.44 [M + H]+ | Procedures 5, 6, 7 and 4 |

TABLE 3-continued

| Ex. No. | Structure | Name | Retention Time Min./ Molecular Mass | Prepared in the manner described in: |
| --- | --- | --- | --- | --- |
| 282 | 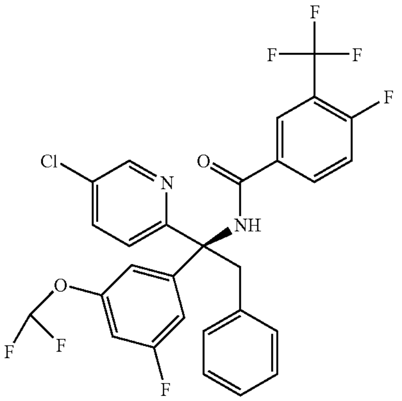 | (S)-N-(1-(5-chloropyridin-2-yl)-1-(3-(difluoromethoxy)-5-fluorophenyl)-2-phenylethyl)-4-fluoro-3-(trifluoromethyl) benzamide | 4.28 LC 583.32 $[M + H]^+$ | Procedures 5, 6, 7 and 4 |
| 283 | 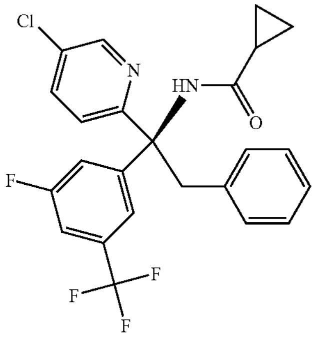 | (S)-N-(1-(5-chloropyridin-2-yl)-1-(3-fluoro-5-(trifluoromethyl) phenyl)-2-phenylethyl) cyclopropanecarboxamide | 4.01 LC 463.23 $[M + H]^+$ | Procedures 5, 6, 7 and 4 |
| 284 | 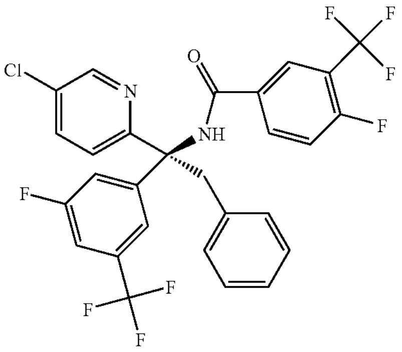 | (S)-N-(1-(5-chloropyridin-2-yl)-1-(3-fluoro-5-(trifluoromethyl) phenyl)-2-phenylethyl)-4-fluoro-3-(trifluoromethyl)benzamide | 4.32 LC 585.15 $[M + H]^+$ | Procedures 5, 6, 7 and 4 |
| 285 | 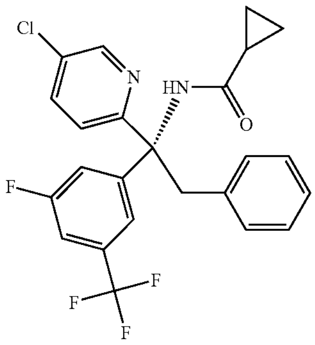 | (R)-N-(1-(5-chloropyridin-2-yl)-1-(3-fluoro-5-(trifluoromethyl) phenyl)-2-phenylethyl) cyclopropanecarboxamide | 4.02 LC 463.25 $[M + H]^+$ | Procedures 5, 6, 7 and 4 |

TABLE 3-continued

| Ex. No. | Structure | Name | Retention Time Min./ Molecular Mass | Prepared in the manner described in: |
|---|---|---|---|---|
| 286 | 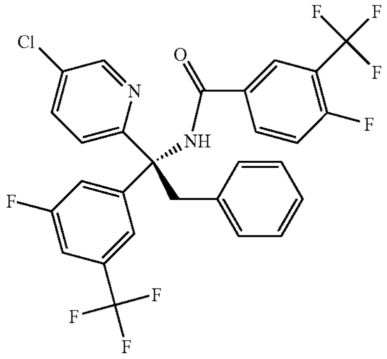 | (R)-N-(1-(5-chloropyridin-2-yl)-1-(3-fluoro-5-(trifluoromethyl) phenyl)-2-phenylethyl)-4-fluoro-3-(trifluoromethyl)benzamide | 4.32 LC 585/15 [M + H]+ | Procedures 5, 6, 7 and 4 |

TABLE 4

| Ex. No. | Structure | Name | Retention Time Min./ Molecular Mass | Prepared in the manner described in: |
|---|---|---|---|---|
| 287 | 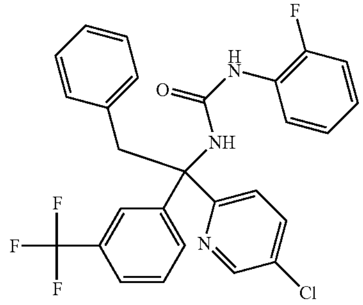 | 1-(1-(5-chloropyridin-2-yl)-2-phenyl-1-(3-(trifluoromethyl) phenyl)ethyl)-3-(2-fluorophenyl)urea | 2.34 LC 513.914 [M + H]+ | Procedures 1 and 2 |
| 288 | 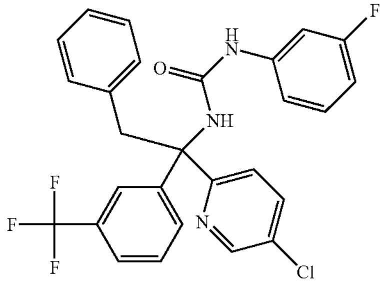 | 1-(1-(5-chloropyridin-2-yl)-2-phenyl-1-(3-(trifluoromethyl) phenyl)ethyl)-3-(3-fluorophenyl)urea | 3.59 LC 514.18 [M + H]+ | Procedures 1 and 2 |
| 289 | 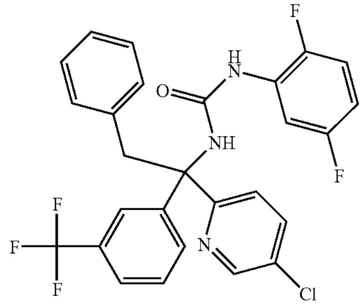 | 1-(1-(5-chloropyridin-2-yl)-2-phenyl-1-(3-(trifluoromethyl) phenyl)ethyl)-3-(2,5-difluorophenyl)urea | 3.40 LC 532.2 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 290 | 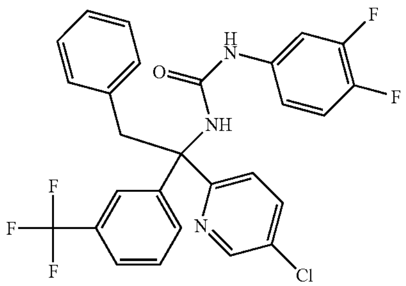 | 1-(1-(5-chloropyridin-2-yl)-2-phenyl-1-(3-(trifluoromethyl) phenyl)ethyl)-3-(3,4-difluorophenyl)urea | 3.64 LC 532.2 [M + H]+ | Procedures 1 and 2 |
| 291 | 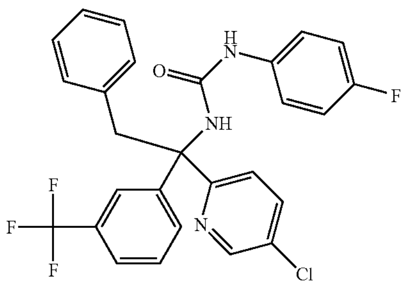 | 1-(1-(5-chloropyridin-2-yl)-2-phenyl-1-(3-(trifluoromethyl) phenyl)ethyl)-3-(4-fluorophenyl)urea | 3.55 LC 514.19 [M + H]+ | Procedures 1 and 2 |
| 292 | 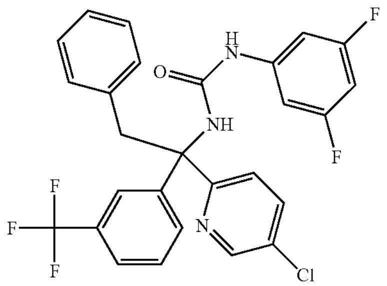 | 1-(1-(5-chloropyridin-2-yl)-2-phenyl-1-(3-(trifluoromethyl) phenyl)ethyl)-3-(3,5-difluorophenyl)urea | 3.69 LC 532.2 [M + H]+ | Procedures 1 and 2 |
| 293 | 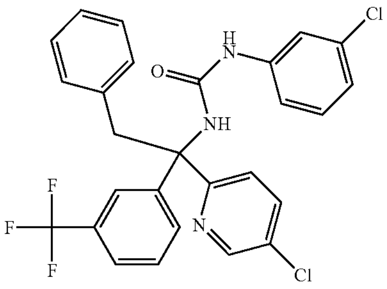 | 1-(3-chlorophenyl)-3-(1-(5-chloropyridin-2-yl)-2-phenyl-1-(3-(trifluoromethyl)phenyl)ethyl) urea | 3.66 LC 530.17 [M + H]+ | Procedures 1 and 2 |
| 294 | 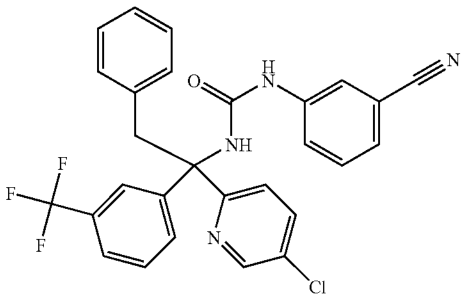 | 1-(1-(5-chloropyridin-2-yl)-2-phenyl-1-(3-(trifluoromethyl) phenyl)ethyl)-3-(3-cyanophenyl)urea | 3.27 LC 521.2 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 295 | 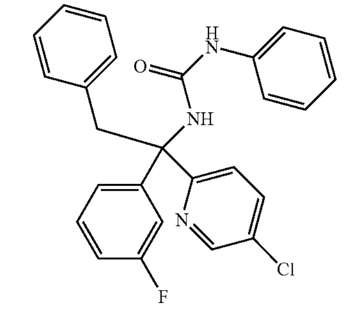 | 1-(1-(5-chloropyridin-2-yl)-1-(3-fluorophenyl)-2-phenylethyl)-3-phenylurea | 3.29 LC 446.07 $[M + H]^+$ | Procedures 1 and 2 |
| 296 | 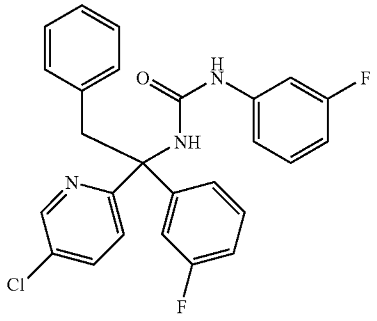 | 1-(1-(5-chloropyridin-2-yl)-1-(3-fluorophenyl)-2-phenylethyl)-3-(3-fluorophenyl)urea | 3.37 LC 464.11 $[M + H]^+$ | Procedures 1 and 2 |
| 297 | 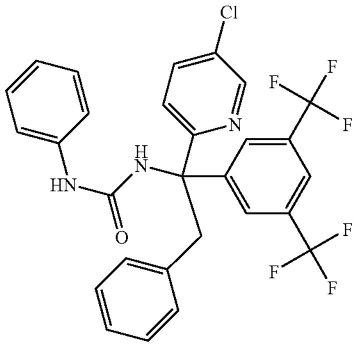 | 1-(1-(3,5-bis(trifluoromethyl) phenyl)-1-(5-chloropyridin-2-yl)-2-phenylethyl)-3-phenylurea | 3.64 LC 564.18 $[M + H]^+$ | Procedures 1 and 2 |
| 298 | 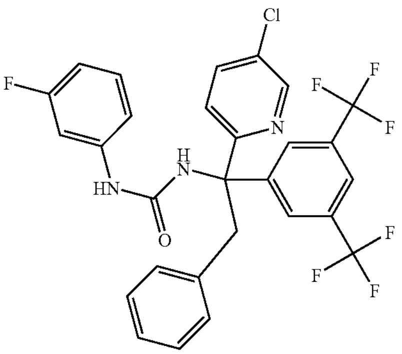 | 1-(1-(3,5-bis(trifluoromethyl) phenyl)-1-(5-chloropyridin-2-yl)-2-phenylethyl)-3-(3-fluorophenyl)urea | 3.69 LC 582.15 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 299 | 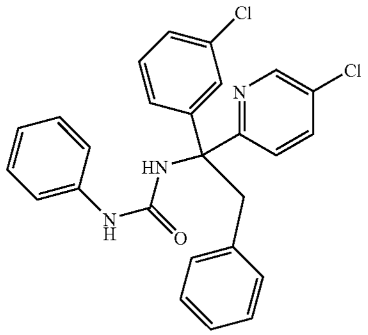 | 1-(1-(3-chlorophenyl)-1-(5-chloropyridin-2-yl)-2-phenylethyl)-3-phenylurea | 3.42 LC 462.05 $[M + H]^+$ | Procedures 1 and 2 |
| 300 | 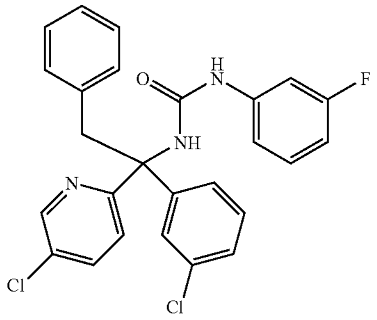 | 1-(1-(3-chlorophenyl)-1-(5-chloropyridin-2-yl)-2-phenylethyl)-3-(3-fluorophenyl) urea | 3.49 LC 480.05 $[M + H]^+$ | Procedures 1 and 2 |
| 301 | 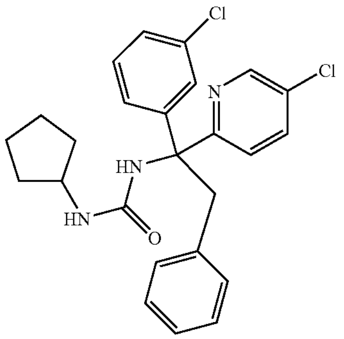 | 1-(1-(3-chlorophenyl)-1-(5-chloropyridin-2-yl)-2-phenylethyl)-3-cyclopentylurea | 3.48 LC 454.06 $[M + H]^+$ | Procedures 1 and 2 |
| 302 | 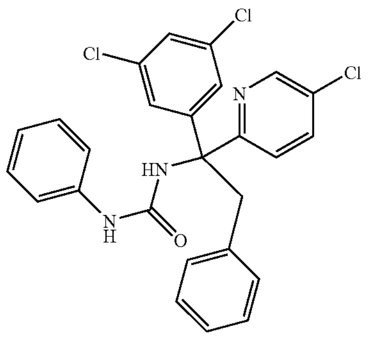 | 1-(1-(5-chloropyridin-2-yl)-1-(3,5-dichlorophenyl)-2-phenylethyl)-3-phenylurea | 3.64 LC 496.0 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 303 | 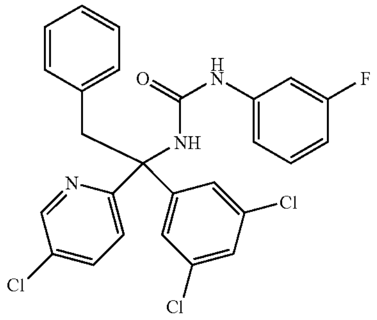 | 1-(1-(5-chloropyridin-2-yl)-1-(3,5-dichlorophenyl)-2-phenylethyl)-3-(3-fluorophenyl) urea | 3.70 LC 513.98 $[M + H]^+$ | Procedures 1 and 2 |
| 304 | 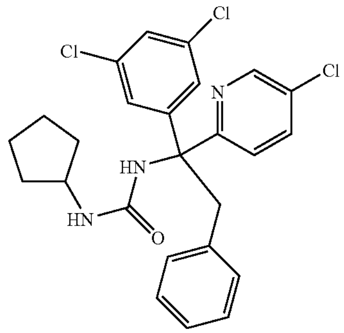 | 1-(1-(5-chloropyridin-2-yl)-1-(3,5-dichlorophenyl)-2-phenylethyl)-3-cyclopentylurea | 3.69 LC 488.04 $[M + H]^+$ | Procedures 1 and 2 |
| 305 | 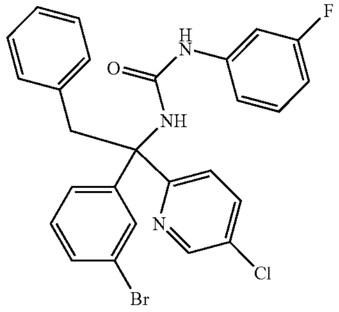 | 1-(1-(3-bromophenyl)-1-(5-chloropyridin-2-yl)-2-phenylethyl)-3-(3-fluorophenyl) urea | 3.54 LC 523.97 $[M + H]^+$ | Procedures 1 and 2 |
| 306 | 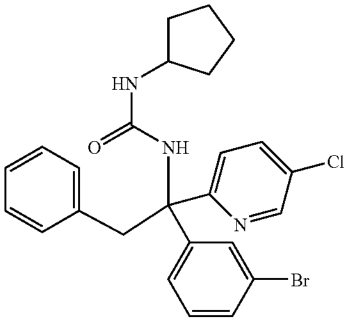 | 1-(1-(3-bromophenyl)-1-(5-chloropyridin-2-yl)-2-phenylethyl)-3-cyclopentylurea | 3.53 LC 498.01 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 307 | 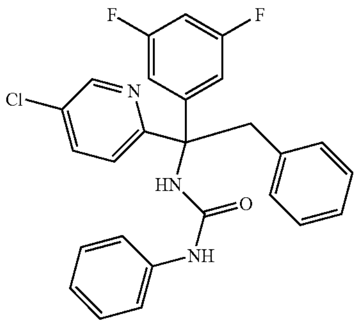 | 1-(1-(5-chloropyridin-2-yl)-1-(3,5-difluorophenyl)-2-phenylethyl)-3-phenylurea | 3.39 LC 464.06 $[M + H]^+$ | Procedures 1 and 2 |
| 308 | 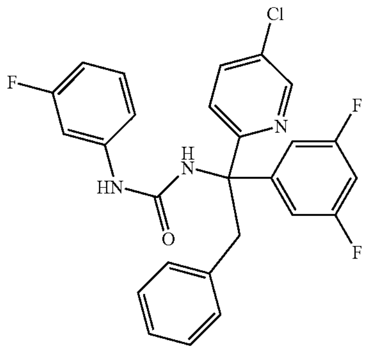 | 1-(1-(5-chloropyridin-2-yl)-1-(3,5-difluorophenyl)-2-phenylethyl)-3-(3-fluorophenyl) urea | 3.45 LC 482.05 $[M + H]^+$ | Procedures 1 and 2 |
| 309 | 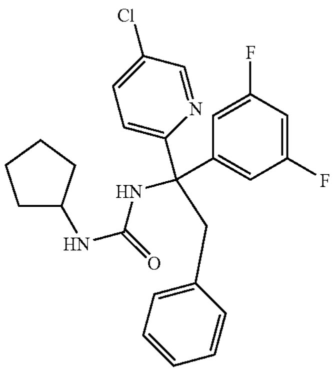 | 1-(1-(5-chloropyridin-2-yl)-1-(3,5-difluorophenyl)-2-phenylethyl)-3-cyclopentylurea | 3.43 LC 456.07 $[M + H]^+$ | Procedures 1 and 2 |
| 310 | 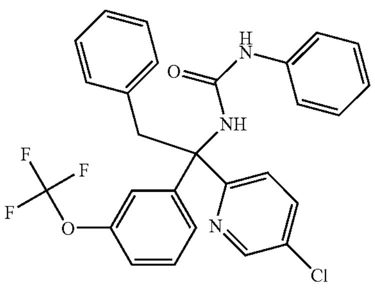 | 1-(1-(5-chloropyridin-2-yl)-2-phenyl-1-(3-(trifluoromethoxy) phenyl)ethyl)-3-phenylurea | 3.51 LC 512.03 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 311 | 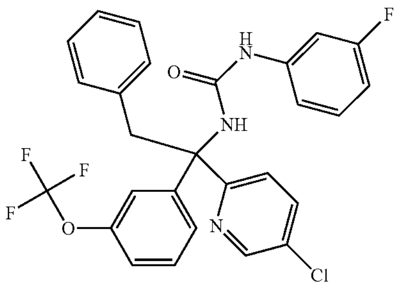 | 1-(1-(5-chloropyridin-2-yl)-2-phenyl-1-(3-(trifluoromethoxy) phenyl)ethyl)-3-(3-fluorophenyl)urea | 3.59 LC 530.04 [M + H]$^+$ | Procedures 1 and 2 |
| 312 | 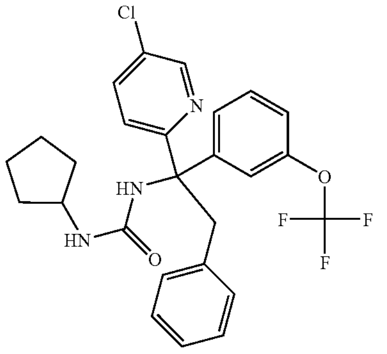 | 1-(1-(5-chloropyridin-2-yl)-2-phenyl-1-(3-(trifluoromethoxy) phenyl)ethyl)-3-cyclopentylurea | 3.59 LC 583.06 [M + H]$^+$ | Procedures 1 and 2 |
| 313 | 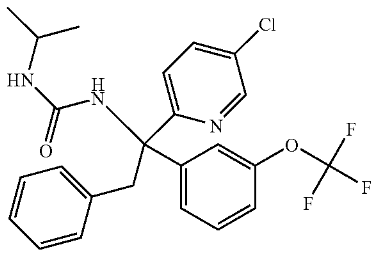 | 1-(1-(5-chloropyridin-2-yl)-2-phenyl-1-(3-(trifluoromethoxy) phenyl)ethyl)-3-isopropylurea | 3.44 LC 478.07 [M + H]$^+$ | Procedures 1 and 2 |
| 314 | 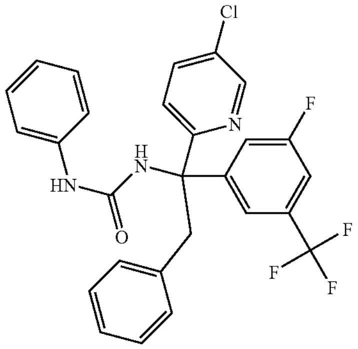 | 1-(1-(5-chloropyridin-2-yl)-1-(3-fluoro-5-(trifluoromethyl) phenyl)-2-phenylethyl)-3-phenylurea | 3.54 LC 514.02 [M + H]$^+$ | Procedures 1 and 2 |

TABLE 4-continued

| Ex. No. | Structure | Name | Retention Time Min./ Molecular Mass | Prepared in the manner described in: |
|---|---|---|---|---|
| 315 | 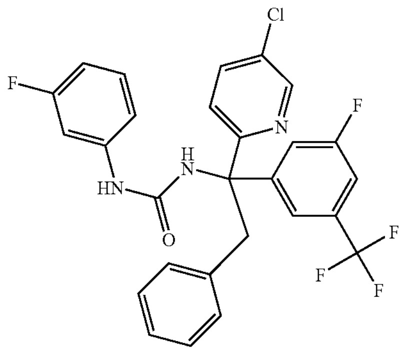 | 1-(1-(5-chloropyridin-2-yl)-1-(3-fluoro-5-(trifluoromethyl) phenyl)-2-phenylethyl)-3-(3-fluorophenyl)urea | 3.60 LC 532.04 $[M + H]^+$ | Procedures 1 and 2 |
| 316 | 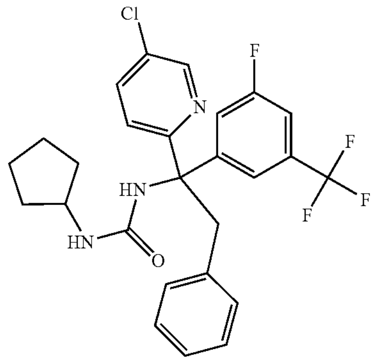 | 1-(1-(5-chloropyridin-2-yl)-1-(3-fluoro-5-(trifluoromethyl) phenyl)-2-phenylethyl)-3-cyclopentylurea | 3.59 LC 506.06 $[M + H]^+$ | Procedures 1 and 2 |
| 317 | 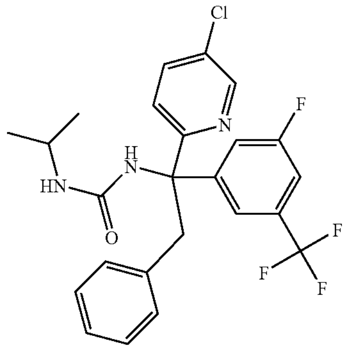 | 1-(1-(5-chloropyridin-2-yl)-1-(3-fluoro-5-(trifluoromethyl) phenyl)-2-phenylethyl)-3-isopropylurea | 3.44 LC 480.06 $[M + H]^+$ | Procedures 1 and 2 |
| 318 | 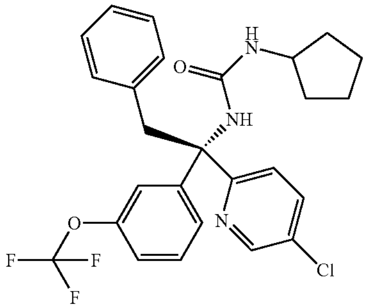 | (S)-1-(1-(5-chloropyridin-2-yl)-2-phenyl-1-(3-(trifluoromethoxy)phenyl)ethyl)-3-cyclopentylurea | 4.15 LC 504.00 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 319 | 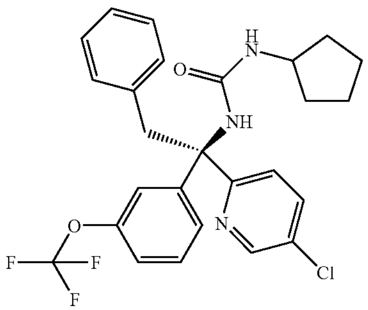 | (R)-1-(1-(5-chloropyridin-2-yl)-2-phenyl-1-(3-(trifluoromethoxy)phenyl)ethyl)-3-cyclopentylurea | 4.15 LC 504.00 [M + H]$^+$ | Procedures 1 and 2 |
| 320 | 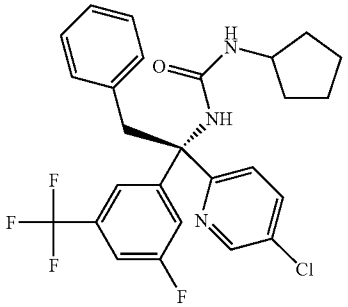 | (S)-1-(1-(5-chloropyridin-2-yl)-1-(3-fluoro-5-(trifluoromethyl) phenyl)-2-phenylethyl)-3-cyclopentylurea | 4.11 LC 506.24 [M + H]$^+$ | Procedures 1 and 2 |
| 321 | 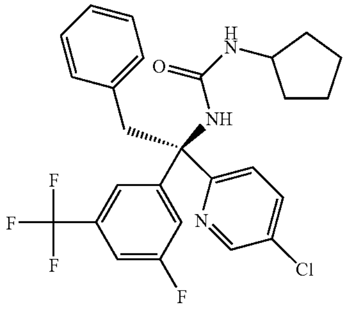 | (R)-1-(1-(5-chloropyridin-2-yl)-1-(3-fluoro-5-(trifluoromethyl) phenyl)-2-phenylethyl)-3-cyclopentylurea | 4.11 LC 506.24 [M + H]$^+$ | Procedures 1 and 2 |
| 322 | 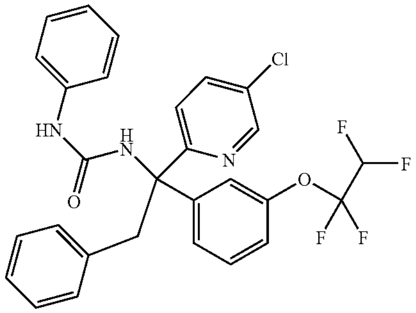 | 1-(1-(5-chloropyridin-2-yl)-2-phenyl-1-(3-(1,1,2,2-tetrafluoroethoxy)phenyl)ethyl)-3-phenylurea | 3.92 LC 544.06 [M + H]$^+$ | Procedures 1 and 2 |

TABLE 4-continued

| Ex. No. | Structure | Name | Retention Time Min./ Molecular Mass | Prepared in the manner described in: |
|---|---|---|---|---|
| 324 | 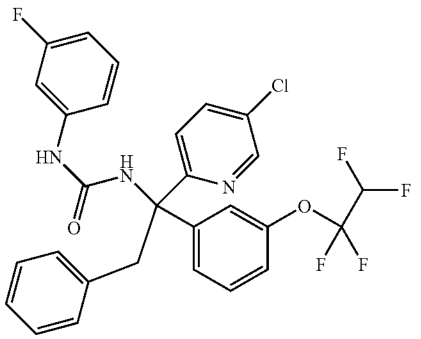 | 1-(1-(5-chloropyridin-2-yl)-2-phenyl-1-(3-(1,1,2,2-tetrafluoroethoxy)phenyl)ethyl)-3-(3-fluorophenyl)urea | 4.00 LC 544.06 $[M + H]^+$ | Procedures 1 and 2 |
| 325 | 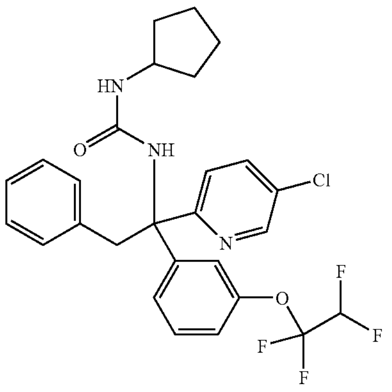 | 1-(1-(5-chloropyridin-2-yl)-2-phenyl-1-(3-(1,1,2,2-tetrafluoroethoxy)phenyl)ethyl)-3-cyclopentylurea | 3.97 LC 536.09 $[M + H]^+$ | Procedures 1 and 2 |
| 326 | 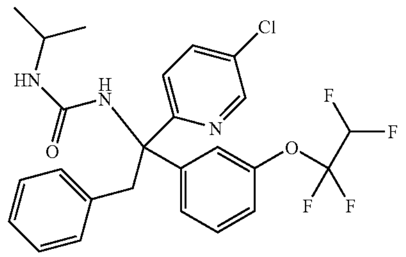 | 1-(1-(5-chloropyridin-2-yl)-2-phenyl-1-(3-(1,1,2,2-tetrafluoroethoxy)phenyl)ethyl)-3-isopropylurea | 3.88 LC 510.08 $[M + H]^+$ | Procedures 1 and 2 |
| 327 | 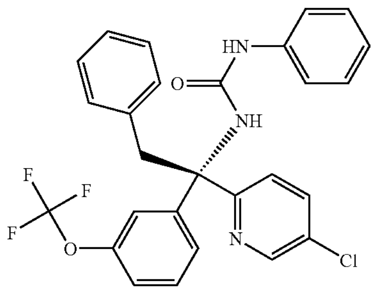 | (S)-1-(1-(5-chloropyridin-2-yl)-2-phenyl-1-(3-(trifluoromethoxy)phenyl)ethyl)-3-phenylurea | 4.11 LC 512.17 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 328 | 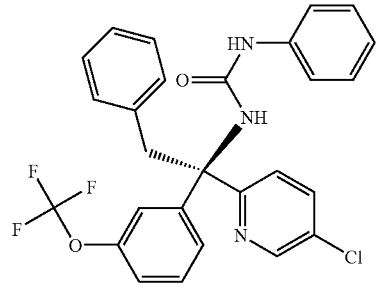 | (R)-1-(1-(5-chloropyridin-2-yl)-2-phenyl-1-(3-(trifluoromethoxy)phenyl)ethyl)-3-phenylurea | 4.11 LC 512.14 [M + H]+ | Procedures 1 and 2 |
| 329 | 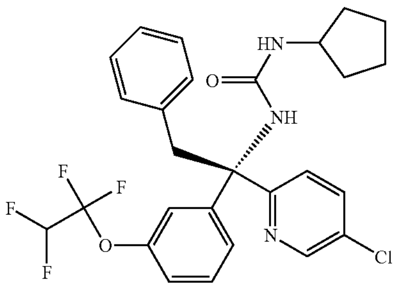 | (S)-1-(1-(5-chloropyridin-2-yl)-2-phenyl-1-(3-(1,1,2,2-tetrafluoroethoxy)phenyl)ethyl)-3-cyclopentylurea | 3.99 LC 536.46 [M + H]+ | Procedures 1 and 2 |
| 330 | 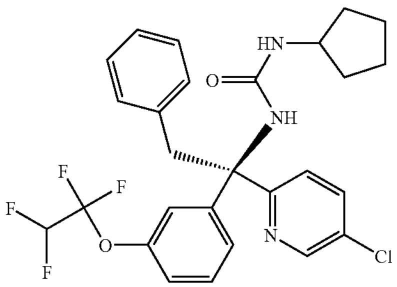 | (R)-1-(1-(5-chloropyridin-2-yl)-2-phenyl-1-(3-(1,1,2,2-tetrafluoroethoxy)phenyl)ethyl)-3-cyclopentylurea | 4.02 LC 536.42 [M + H]+ | Procedures 1 and 2 |
| 331 | 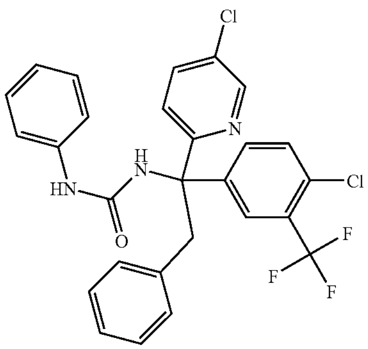 | 1-(1-(4-chloro-3-(trifluoromethyl)phenyl)-1-(5-chloropyridin-2-yl)-2-phenylethyl)-3-phenylurea | 4.13 LC 530.09 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 332 | 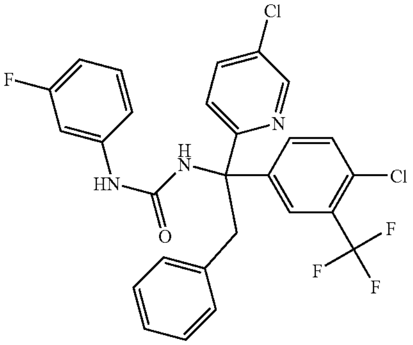 | 1-(1-(4-chloro-3-(trifluoromethyl)phenyl)-1-(5-chloropyridin-2-yl)-2-phenylethyl)-3-(3-fluorophenyl) urea | 4.22 LC 548.11 [M + H]+ | Procedures 1 and 2 |
| 333 | 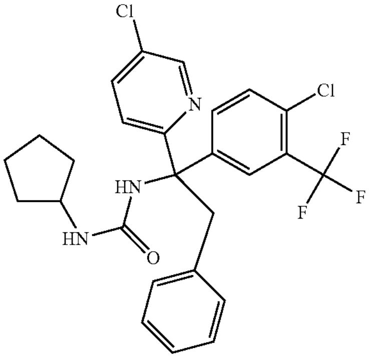 | 1-(1-(4-chloro-3-(trifluoromethyl)phenyl)-1-(5-chloropyridin-2-yl)-2-phenylethyl)-3-cyclopentylurea | 4.17 LC 522.11 [M + H]+ | Procedures 1 and 2 |
| 334 | 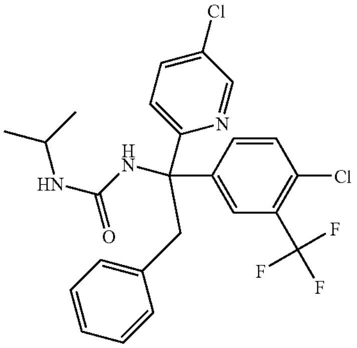 | 1-(1-(4-chloro-3-(trifluoromethyl)phenyl)-1-(5-chloropyridin-2-yl)-2-phenylethyl)-3-isopropylurea | 4.05 LC 496.11 [M + H]+ | Procedures 1 and 2 |
| 335 | 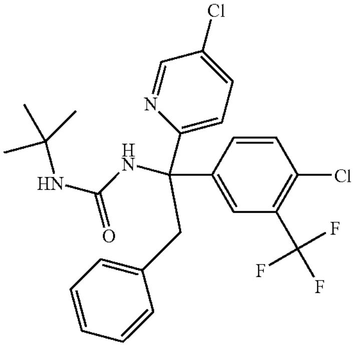 | 1-tert-butyl-3-(1-(4-chloro-3-(trifluoromethyl)phenyl)-1-(5-chloropyridin-2-yl)-2-phenylethyl)urea | 4.16 LC 510.11 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 336 | 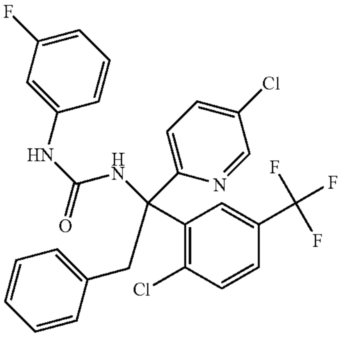 | 1-(1-(2-chloro-5-(trifluoromethyl)phenyl)-1-(5-chloropyridin-2-yl)-2-phenylethyl)-3-(3-fluorophenyl) urea | 4.19 LC 548.1 [M + H]+ | Procedures 1 and 2 |
| 337 | 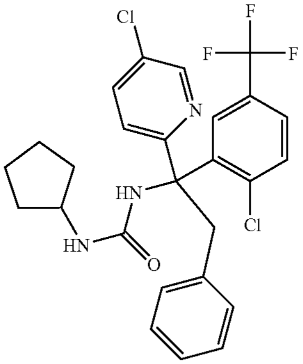 | 1-(1-(2-chloro-5-(trifluoromethyl)phenyl)-1-(5-chloropyridin-2-yl)-2-phenylethyl)-3-cyclopentylurea | 4.16 LC 522.1 [M + H]+ | Procedures 1 and 2 |
| 338 | 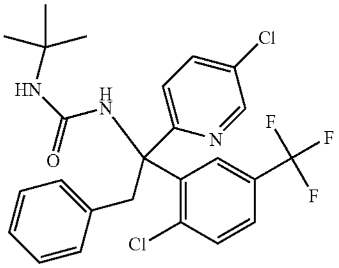 | 1-tert-butyl-3-(1-(2-chloro-5-(trifluoromethyl)phenyl)-1-(5-chloropyridin-2-yl)-2-phenylethyl)urea | 4.15 LC 510.11 [M + H]+ | Procedures 1 and 2 |
| 339 | 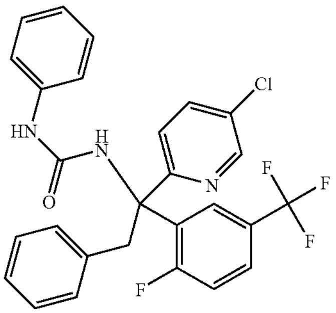 | 1-(1-(5-chloropyridin-2-yl)-1-(2-fluoro-5-(trifluoromethyl) phenyl)-2-phenylethyl)-3-phenylurea | 4.05 LC 514.1 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 340 | 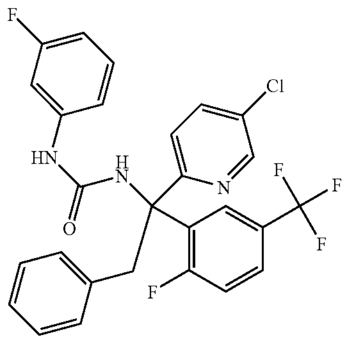 | 1-(1-(5-chloropyridin-2-yl)-1-(2-fluoro-5-(trifluoromethyl) phenyl)-2-phenylethyl)-3-(3-fluorophenyl)urea | 4.12 LC 532.11 $[M + H]^+$ | Procedures 1 and 2 |
| 341 | 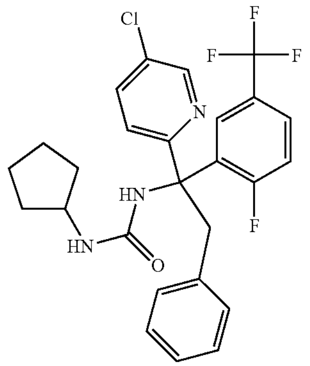 | 1-(1-(5-chloropyridin-2-yl)-1-(2-fluoro-5-(trifluoromethyl) phenyl)-2-phenylethyl)-3-cyclopentylurea | 4.07 LC 506.14 $[M + H]^+$ | Procedures 1 and 2 |
| 342 | 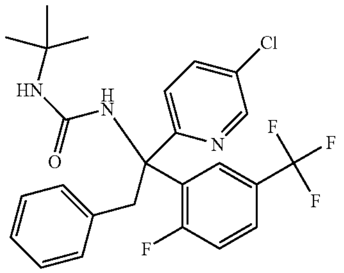 | 1-tert-butyl-3-(1-(5-chloropyridin-2-yl)-1-(2-fluoro-5-(trifluoromethyl)phenyl)-2-phenylethyl)urea | 4.05 LC 494.15 $[M + H]^+$ | Procedures 1 and 2 |
| 343 | 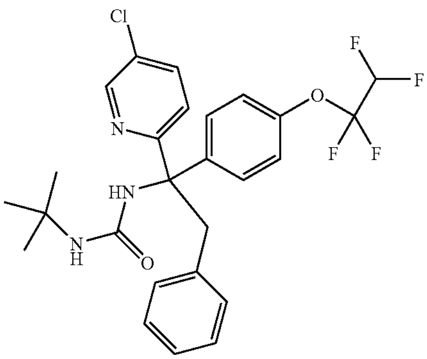 | 1-tert-butyl-3-(1-(5-chloropyridin-2-yl)-2-phenyl-1-(4-(1,1,2,2-tetrafluoroethoxy) phenyl)ethyl)urea | 4.04 LC 524.15 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 344 | 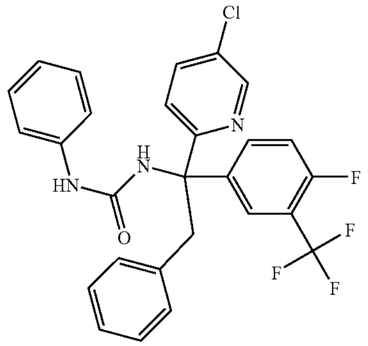 | 1-(1-(5-chloropyridin-2-yl)-1-(4-fluoro-3-(trifluoromethyl) phenyl)-2-phenylethyl)-3-phenylurea | 4.02 LC 514.1 $[M + H]^+$ | Procedures 1 and 2 |
| 345 | 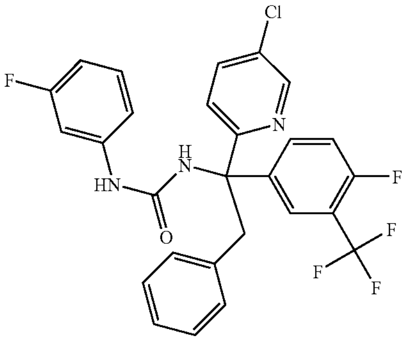 | 1-(1-(5-chloropyridin-2-yl)-1-(4-fluoro-3-(trifluoromethyl) phenyl)-2-phenylethyl)-3-(3-fluorophenyl)urea | 4.11 LC 532.11 $[M + H]^+$ | Procedures 1 and 2 |
| 346 | 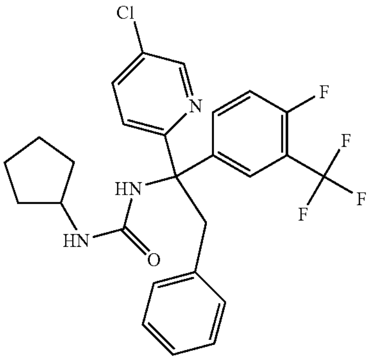 | 1-(1-(5-chloropyridin-2-yl)-1-(4-fluoro-3-(trifluoromethyl) phenyl)-2-phenylethyl)-3-cyclopentylurea | 4.07 LC 506.14 $[M + H]^+$ | Procedures 1 and 2 |
| 347 | 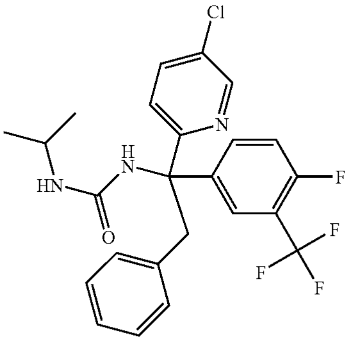 | 1-(1-(5-chloropyridin-2-yl)-1-(4-fluoro-3-(trifluoromethyl) phenyl)-2-phenylethyl)-3-isopropylurea | 3.97 LC 480.15 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 348 | 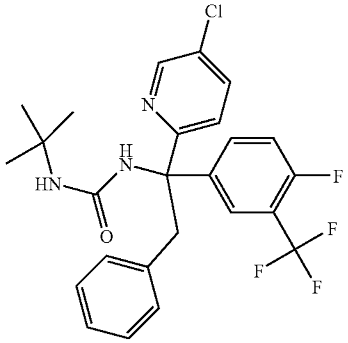 | 1-tert-butyl-3-(1-(5-chloropyridin-2-yl)-1-(4-fluoro-3-(trifluoromethyl)phenyl)-2-phenylethyl)urea | 4.06 LC 494.15 [M + H]+ | Procedures 1 and 2 |
| 349 | 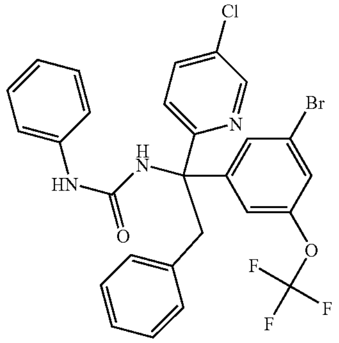 | 1-(1-(3-bromo-5-(trifluoromethoxy)phenyl)-1-(5-chloropyridin-2-yl)-2-phenylethyl)-3-phenylurea | 4.30 LC 590.04 [M + H]+ | Procedures 1 and 2 |
| 350 | 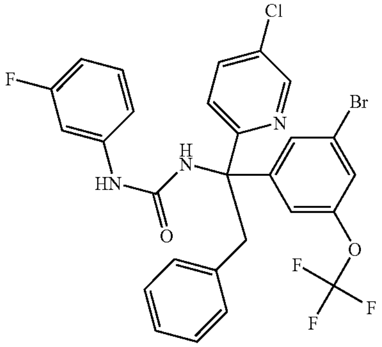 | 1-(1-(3-bromo-5-(trifluoromethoxy)phenyl)-1-(5-chloropyridin-2-yl)-2-phenylethyl)-3-(3-fluorophenyl) urea | 4.34 LC 608.0 [M + H]+ | Procedures 1 and 2 |
| 351 | 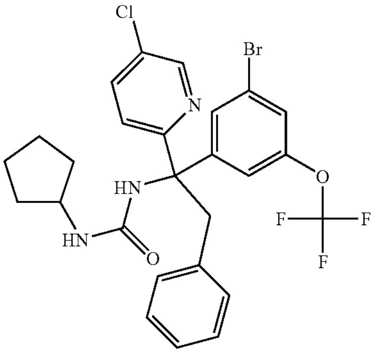 | 1-(1-(3-bromo-5-(trifluoromethoxy)phenyl)-1-(5-chloropyridin-2-yl)-2-phenylethyl)-3-cyclopentylurea | 4.32 LC 582.08 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 352 | 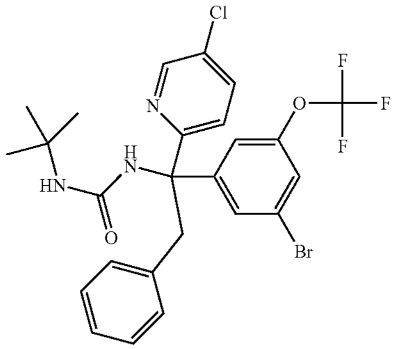 | 1-(1-(3-bromo-5-(trifluoromethoxy)phenyl)-1-(5-chloropyridin-2-yl)-2-phenylethyl)-3-tert-butylurea | 4.29 LC 570.1 $[M + H]^+$ | Procedures 1 and 2 |
| 353 | 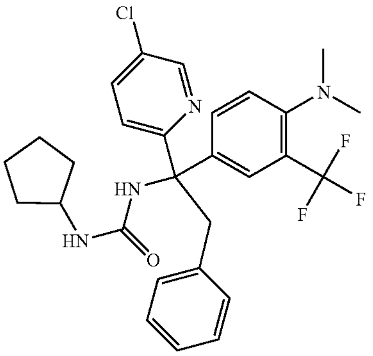 | 1-(1-(5-chloropyridin-2-yl)-1-(4-(dimethylamino)-3-(trifluoromethyl)phenyl)-2-phenylethyl)-3-cyclopentylurea | 4.05 LC 531.21 $[M + H]^+$ | Procedures 1 and 2 |
| 355 | 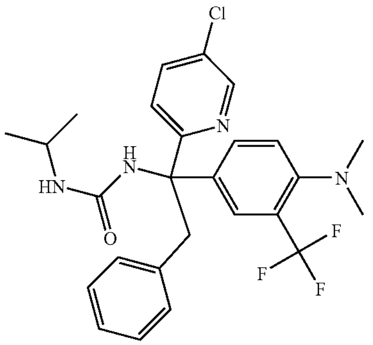 | 1-(1-(5-chloropyridin-2-yl)-1-(4-(dimethylamino)-3-(trifluoromethyl)phenyl)-2-phenylethyl)-3-isopropylurea | 3.89 LC 505.19 $[M + H]^+$ | Procedures 1 and 2 |
| 355 | 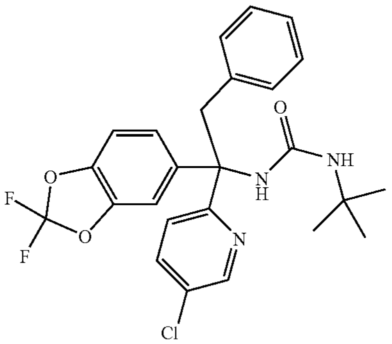 | 1-tert-butyl-3-(1-(5-chloropyridin-2-yl)-1-(2,2-difluorobenzo[d][1,3]dioxol-5-yl)-2-phenylethyl)urea | 4.10 LC 488.16 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 356 | 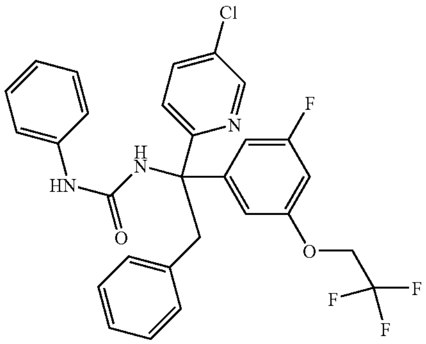 | 1-(1-(5-chloropyridin-2-yl)-1-(3-fluoro-5-(2,2,2-trifluoroethoxy)phenyl)-2-phenylethyl)-3-phenylurea | 4.04 LC 544.15 $[M + H]^+$ | Procedures 3, 1 and 2 |
| 357 | 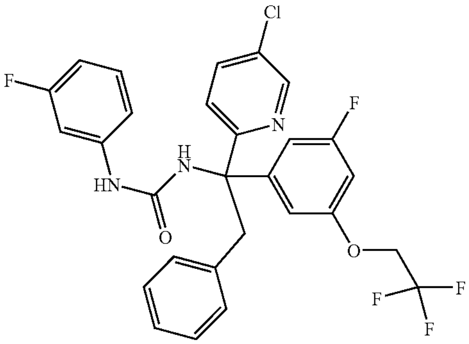 | 1-(1-(5-chloropyridin-2-yl)-1-(3-fluoro-5-(2,2,2-trifluoroethoxy)phenyl)-2-phenylethyl)-3-(3-fluorophenyl)urea | 4.09 LC 562.17 $[M + H]^+$ | Procedures 3, 1 and 2 |
| 358 | 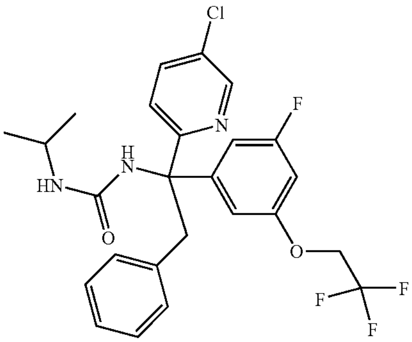 | 1-(1-(5-chloropyridin-2-yl)-1-(3-fluoro-5-(2,2,2-trifluoroethoxy) phenyl)-2-phenylethyl)-3-isopropylurea | 3.99 LC 510.13 $[M + H]^+$ | Procedures 3, 1 and 2 |
| 359 | 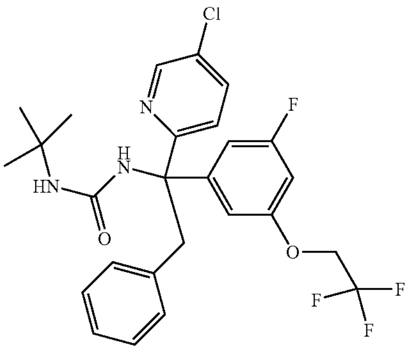 | 1-tert-butyl-3-(1-(5-chloropyridin-2-yl)-1-(3-fluoro-5-(2,2,2-trifluoroethoxy)phenyl)-2-phenylethyl)urea | 4.07 LC 524.14 $[M + H]^+$ | Procedures 3, 1 and 2 |

TABLE 4-continued

| Ex. No. | Structure | Name | Retention Time Min./ Molecular Mass | Prepared in the manner described in: |
|---|---|---|---|---|
| 360 | 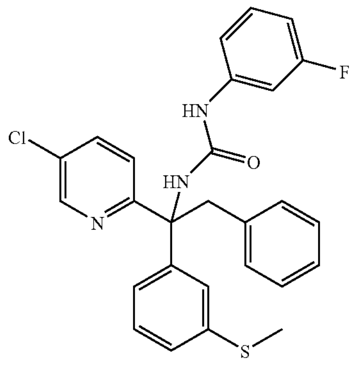 | 1-(1-(5-chloropyridin-2-yl)-1-(3-(methylthio)phenyl)-2-phenylethyl)-3-(3-fluorophenyl) urea | 3.92 LC 492.17 [M + H]+ | Procedures 1 and 2 |
| 361 | 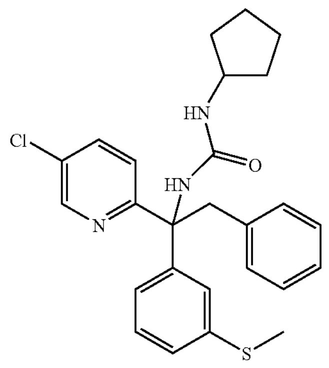 | 1-(1-(5-chloropyridin-2-yl)-1-(3-(methylthio)phenyl)-2-phenylethyl)-3-cyclopentylurea | 3.91 LC 466.24 [M + H]+ | Procedures 1 and 2 |
| 362 | 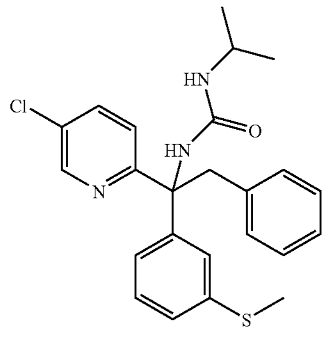 | 1-(1-(5-chloropyridin-2-yl)-1-(3-(methylthio)phenyl)-2-phenylethyl)-3-isopropylurea | 3.76 LC 440.19 [M + H]+ | Procedures 1 and 2 |
| 363 | 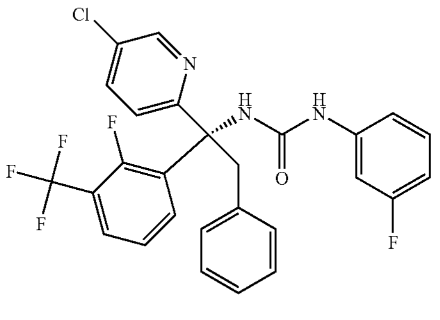 | (R)-1-(1-(5-chloropyridin-2-yl)-1-(2-fluoro-3-(trifluoromethyl) phenyl)-2-phenylethyl)-3-(3-fluorophenyl)urea | 4.02 LC 532.28 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 364 | 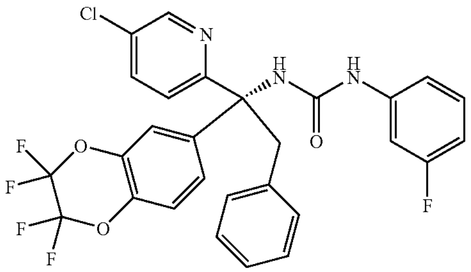 | (R)-1-(1-(5-chloropyridin-2-yl)-2-phenyl-1-(2,2,3,3-tetrafluoro-2,3-dihydrobenzo[b][1,4]dioxin-6-yl)ethyl)-3-(3-fluorophenyl) urea | 4.27 LC 576.23 $[M + H]^+$ | Procedures 1 and 2 |
| 365 | 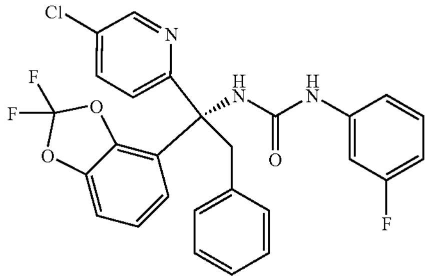 | (R)-1-(1-(5-chloropyridin-2-yl)-1-(2,2-difluorobenzo[d][1,3] dioxol-4-yl)-2-phenylethyl)-3-(3-fluorophenyl)urea | 4.05 LC 526.28 $[M + H]^+$ | Procedures 1 and 2 |
| 366 | 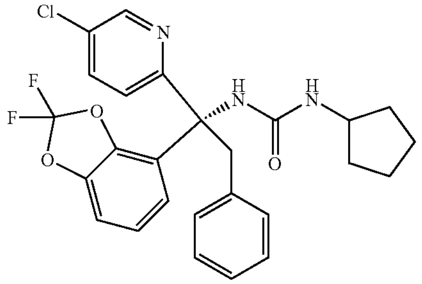 | (R)-1-(1-(5-chloropyridin-2-yl)-1-(2,2-difluorobenzo[d][1,3] dioxol-4-yl)-2-phenylethyl)-3-cyclopentylurea | 4.05 LC 500.28 $[M + H]^+$ | Procedures 1 and 2 |
| 367 | 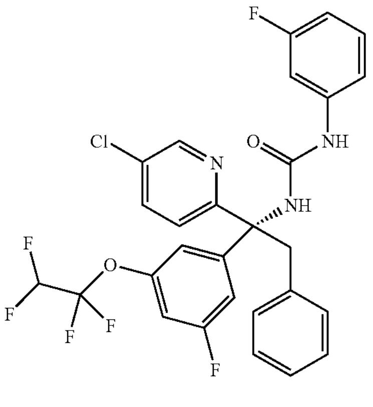 | (R)-1-(1-(5-chloropyridin-2-yl)-1-(3-fluoro-5-(1,1,2,2-tetrafluoroethoxy)phenyl)-2-phenylethyl)-3-(3-fluorophenyl) urea | 4.12 LC 580.23 $[M + H]^+$ | Procedures 3, 1 and 2 |

TABLE 4-continued

| Ex. No. | Structure | Name | Retention Time Min./ Molecular Mass | Prepared in the manner described in: |
|---|---|---|---|---|
| 368 | 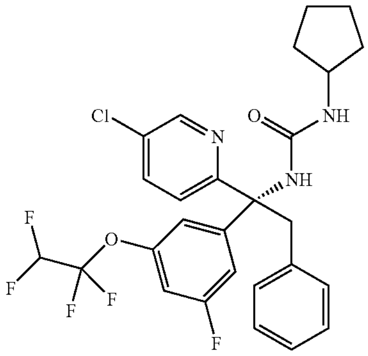 | (R)-1-(1-(5-chloropyridin-2-yl)-1-(3-fluoro-5-(1,1,2,2-tetrafluoroethoxy)phenyl)-2-phenylethyl)-3-cyclopentylurea | 4.09 LC 554.06 $[M + H]^+$ | Procedures 3, 1 and 2 |
| 369 | 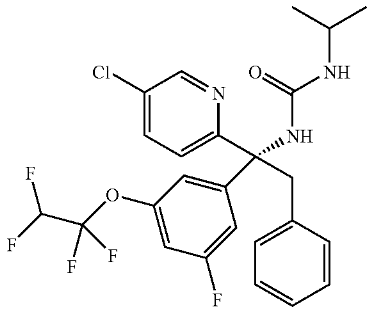 | (R)-1-(1-(5-chloropyridin-2-yl)-1-(3-fluoro-5-(1,1,2,2-tetrafluoroethoxy)phenyl)-2-phenylethyl)-3-isopropylurea | 3.97 LC 528.28 $[M + H]^+$ | Procedures 3, 1 and 2 |
| 370 | 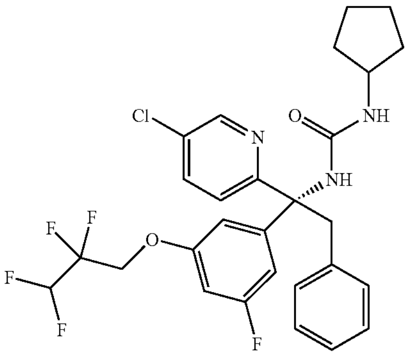 | (R)-1-(1-(5-chloropyridin-2-yl)-1-(3-fluoro-5-(2,2,3,3-tetrafluoropropoxy)phenyl)-2-phenylethyl)-3-cyclopentylurea | 4.09 LC 568.29 $[M + H]^+$ | Procedures 3, 1 and 2 |
| 371 | 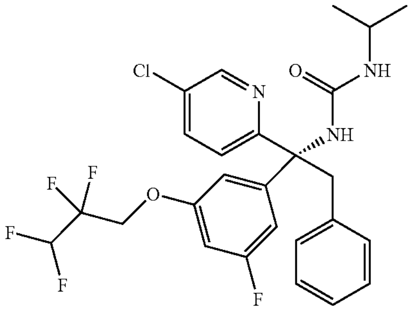 | (R)-1-(1-(5-chloropyridin-2-yl)-1-(3-fluoro-5-(2,2,3,3-tetrafluoropropoxy)phenyl)-2-phenylethyl)-3-isopropylurea | 3.97 LC 542.29 $[M + H]^+$ | Procedures 3, 1 and 2 |

TABLE 4-continued

| Ex. No. | Structure | Name | Retention Time Min./ Molecular Mass | Prepared in the manner described in: |
|---|---|---|---|---|
| 372 | 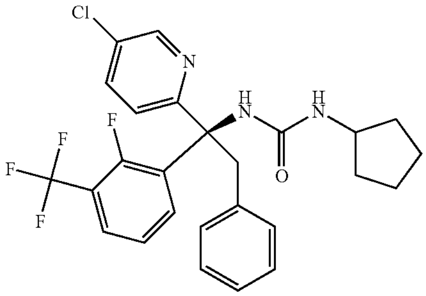 | (S)-1-(1-(5-chloropyridin-2-yl)-1-(2-fluoro-3-(trifluoromethyl) phenyl)-2-phenylethyl)-3-cyclopentylurea | 4.02 LC 506.41 [M + H]+ | Procedures 1 and 2 |
| 373 | 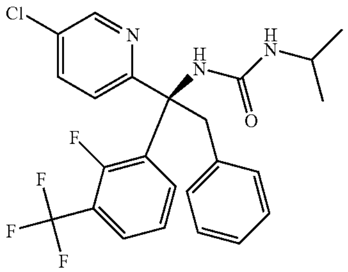 | (S)-1-(1-(5-chloropyridin-2-yl)-1-(2-fluoro-3-(trifluoromethyl) phenyl)-2-phenylethyl)-3-isopropylurea | 3.85 LC 480.41 [M + H]+ | Procedures 1 and 2 |
| 374 | 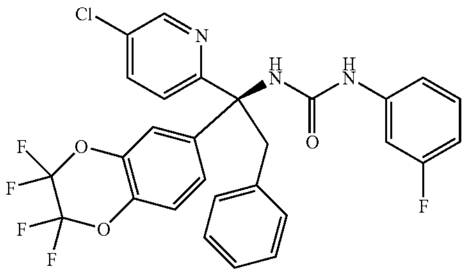 | (S)-1-(1-(5-chloropyridin-2-yl)-2-phenyl-1-(2,2,3,3-tetrafluoro-2,3-dihydrobenzo[b][1,4]dioxin-6-yl)ethyl)-3-(3-fluorophenyl) urea | 4.23 LC 576.3 [M + H]+ | Procedures 1 and 2 |
| 375 | 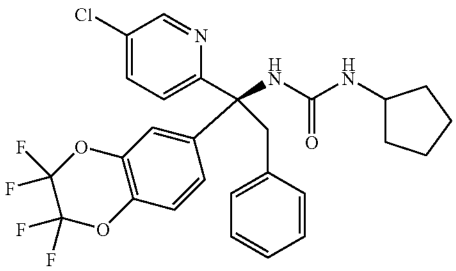 | (S)-1-(1-(5-chloropyridin-2-yl)-2-phenyl-1-(2,2,3,3-tetrafluoro-2,3-dihydrobenzo[b][1,4]dioxin-6-yl)ethyl)-3-cyclopentylurea | 4.24 LC 550.29 [M + H]+ | Procedures 1 and 2 |
| 376 | 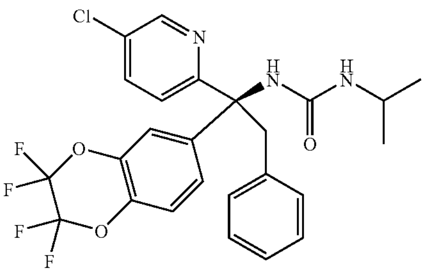 | (S)-1-(1-(5-chloropyridin-2-yl)-2-phenyl-1-(2,2,3,3-tetrafluoro-2,3-dihydrobenzo[b][1,4]dioxin-6-yl)ethyl)-3-isopropylurea | 4.12 LC 524.5 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 377 | 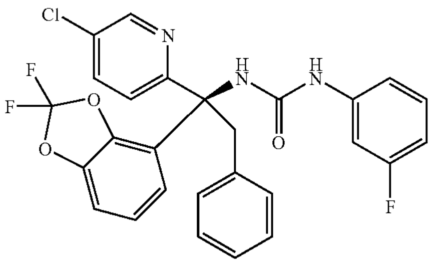 | (S)-1-(1-(5-chloropyridin-2-yl)-1-(2,2-difluorobenzo[d][1,3] dioxol-4-yl)-2-phenylethyl)-3-(3-fluorophenyl)urea | 4.04 LC 526.35 $[M + H]^+$ | Procedures 1 and 2 |
| 378 | 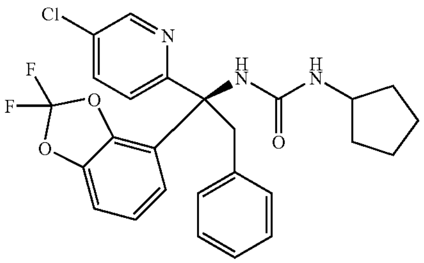 | (S)-1-(1-(5-chloropyridin-2-yl)-1-(2,2-difluorobenzo[d][1,3] dioxol-4-yl)-2-phenylethyl)-3-cyclopentylurea | 4.05 LC 500.35 $[M + H]^+$ | Procedures 1 and 2 |
| 379 | 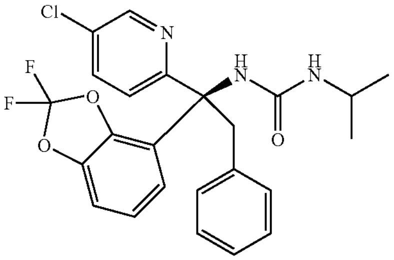 | (S)-1-(1-(5-chloropyridin-2-yl)-1-(2,2-difluorobenzo[d][1,3] dioxol-4-yl)-2-phenylethyl)-3-isopropylurea | 3.90 LC 474.41 $[M + H]^+$ | Procedures 1 and 2 |
| 380 | 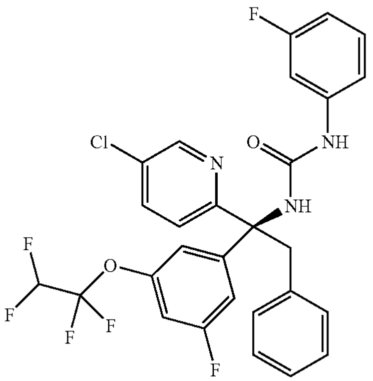 | (S)-1-(1-(5-chloropyridin-2-yl)-1-(3-fluoro-5-(1,1,2,2-tetrafluoroethoxy)phenyl)-2-phenylethyl)-3-(3-fluorophenyl) urea | 4.09 LC 580.36 $[M + H]^+$ | Procedures 3, 1 and 2 |

TABLE 4-continued

| Ex. No. | Structure | Name | Retention Time Min./ Molecular Mass | Prepared in the manner described in: |
|---|---|---|---|---|
| 381 | 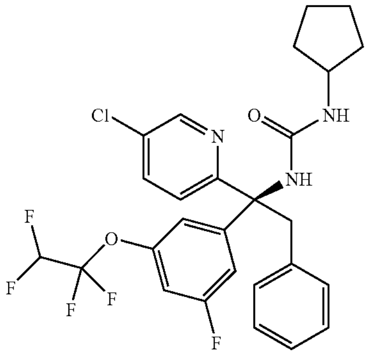 | (S)-1-(1-(5-chloropyridin-2-yl)-1-(3-fluoro-5-(1,1,2,2-tetrafluoroethoxy)phenyl)-2-phenylethyl)-3-cyclopentylurea | 4.08 LC 554.42 $[M + H]^+$ | Procedures 3, 1 and 2 |
| 382 | 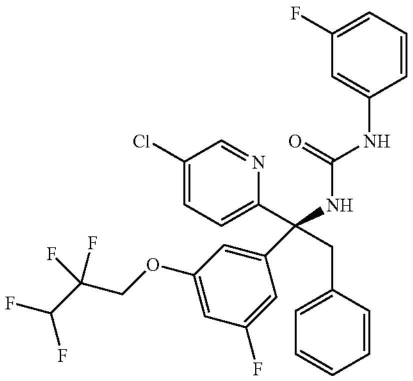 | (S)-1-(1-(5-chloropyridin-2-yl)-1-(3-fluoro-5-(2,2,3,3-tetrafluoropropoxy)phenyl)-2-phenylethyl)-3-(3-fluorophenyl) urea | 4.10 LC 594.35 $[M + H]^+$ | Procedures 3, 1 and 2 |
| 383 | 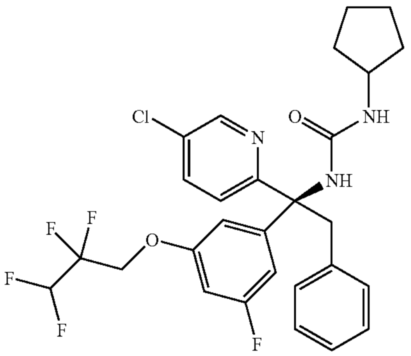 | (S)-1-(1-(5-chloropyridin-2-yl)-1-(3-fluoro-5-(2,2,3,3-tetrafluoropropoxy)phenyl)-2-phenylethyl)-3-cyclopentylurea | 4.08 LC 568.42 $[M + H]^+$ | Procedures 3, 1 and 2 |
| 384 | 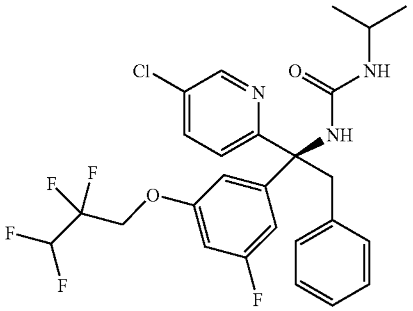 | (S)-1-(1-(5-chloropyridin-2-yl)-1-(3-fluoro-5-(2,2,3,3-tetrafluoropropoxy)phenyl)-2-phenylethyl)-3-isopropylurea | 3.95 LC 542.4 $[M + H]^+$ | Procedures 3, 1 and 2 |

TABLE 4-continued

| Ex. No. | Structure | Name | Retention Time Min./ Molecular Mass | Prepared in the manner described in: |
|---|---|---|---|---|
| 385 | 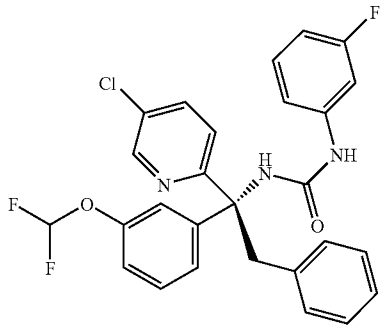 | (R)-1-(1-(5-chloropyridin-2-yl)-1-(3-(difluoromethoxy)phenyl)-2-phenylethyl)-3-(3-fluorophenyl)urea | 3.95 LC 512.44 $[M + H]^+$ | Procedures 1 and 2 |
| 386 | 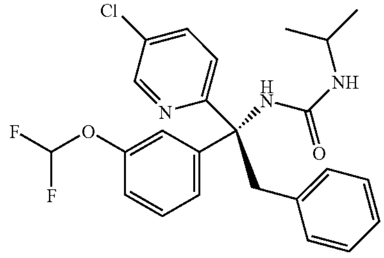 | (R)-1-(1-(5-chloropyridin-2-yl)-1-(3-(difluoromethoxy)phenyl)-2-phenylethyl)-3-isopropylurea | 3.79 LC 460.50 $[M + H]^+$ | Procedures 1 and 2 |
| 387 | 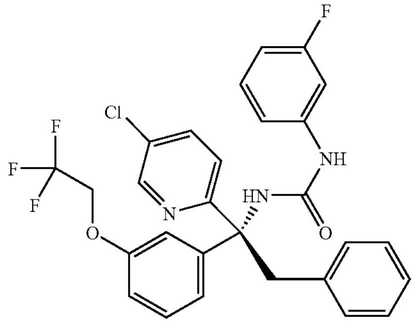 | (R)-1-(1-(5-chloropyridin-2-yl)-2-phenyl-1-(3-(2,2,2-trifluoroethoxy)phenyl)ethyl)-3-(3-fluorophenyl)urea | 4.04 LC 544.30 $[M + H]^+$ | Procedures 1 and 2 |
| 388 | 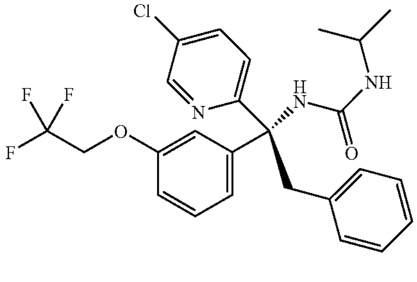 | (R)-1-(1-(5-chloropyridin-2-yl)-2-phenyl-1-(3-(2,2,2-trifluoroethoxy)phenyl)ethyl)-3-isopropylurea | 3.91 LC 492.41 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 389 | 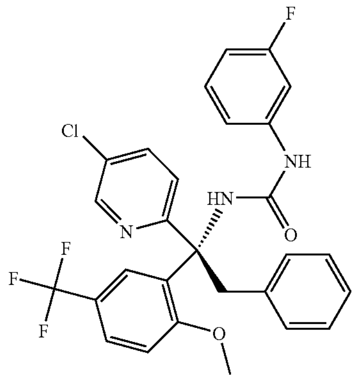 | (R)-1-(1-(5-chloropyridin-2-yl)-1-(2-methoxy-5-(trifluoromethyl)phenyl)-2-phenylethyl)-3-(3-fluorophenyl) urea | 4.07 LC 544.29 $[M + H]^+$ | Procedures 1 and 2 |
| 390 | 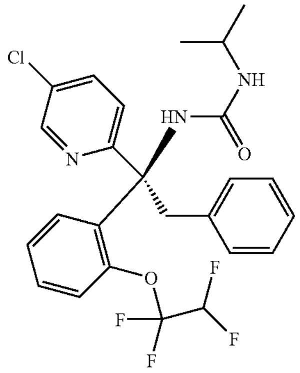 | (S)-1-(1-(5-chloropyridin-2-yl)-2-phenyl-1-(2-(1,1,2,2-tetrafluoroethoxy)phenyl)ethyl)-3-isopropylurea | 3.87 LC 510.48 $[M + H]^+$ | Procedures 1 and 2 |
| 391 | 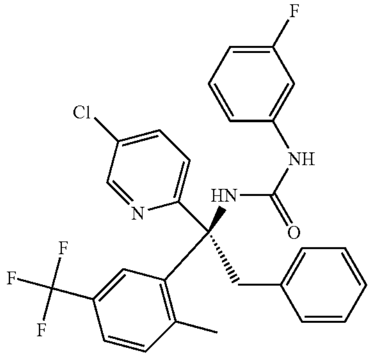 | (S)-1-(1-(5-chloropyridin-2-yl)-1-(2-methyl-5-(trifluoromethyl) phenyl)-2-phenylethyl)-3-(3-fluorophenyl)urea | 4.18 LC 528.42 $[M + H]^+$ | Procedures 1 and 2 |
| 392 | 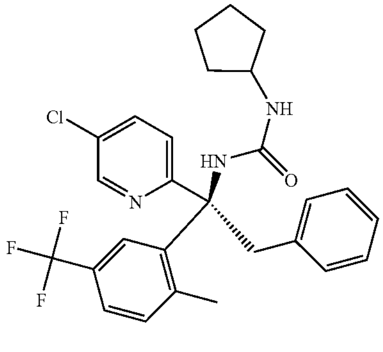 | (S)-1-(1-(5-chloropyridin-2-yl)-1-(2-methyl-5-(trifluoromethyl) phenyl)-2-phenylethyl)-3-cyclopentylurea | 4.17 LC 502.51 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 393 | 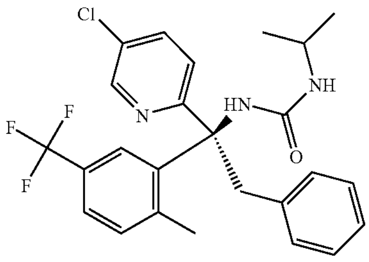 | (S)-1-(1-(5-chloropyridin-2-yl)-1-(2-methyl-5-(trifluoromethyl) phenyl)-2-phenylethyl)-3-isopropylurea | 4.05 LC 476.49 $[M + H]^+$ | Procedures 1 and 2 |
| 394 | 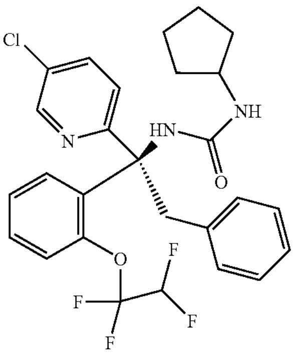 | (S)-1-(1-(5-chloropyridin-2-yl)-2-phenyl-1-(2-(1,1,2,2-tetrafluoroethoxy)phenyl)ethyl)-3-cyclopentylurea | 3.98 LC 536.45 $[M + H]^+$ | Procedures 1 and 2 |
| 395 | 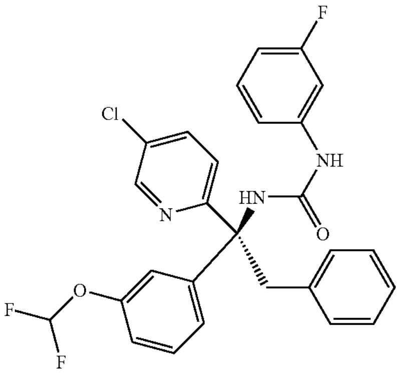 | (S)-1-(1-(5-chloropyridin-2-yl)-1-(3-(difluoromethoxy)phenyl)-2-phenylethyl)-3-(3-fluorophenyl)urea | 3.95 LC 512.33 $[M + H]^+$ | Procedures 1 and 2 |
| 396 | 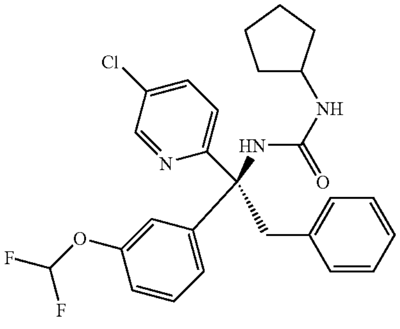 | (S)-1-(1-(5-chloropyridin-2-yl)-1-(3-(difluoromethoxy)phenyl)-2-phenylethyl)-3-cyclopentylurea | 3.55 LC 486.1 $[M + H]^+$ | Procedures 1 and 2 |

TABLE 4-continued

| Ex. No. | Structure | Name | Retention Time Min./ Molecular Mass | Prepared in the manner described in: |
| --- | --- | --- | --- | --- |
| 397 | 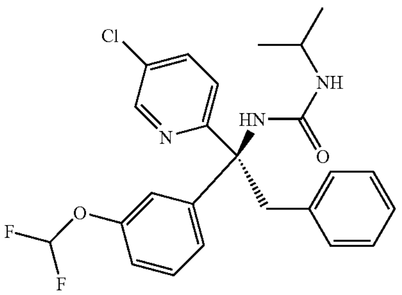 | (S)-1-(1-(5-chloropyridin-2-yl)-1-(3-(difluoromethoxy)phenyl)-2-phenylethyl)-3-isopropylurea | 3.80 LC 460.42 $[M + H]^+$ | Procedures 1 and 2 |
| 398 | 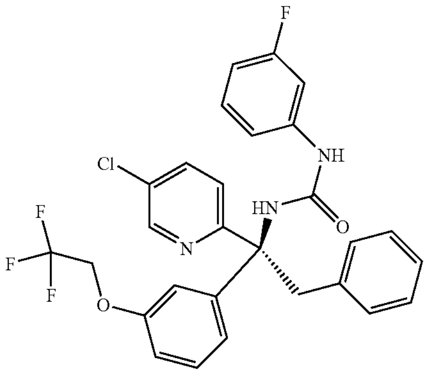 | (S)-1-(1-(5-chloropyridin-2-yl)-2-phenyl-1-(3-(2,2,2-trifluoroethoxy)phenyl)ethyl)-3-(3-fluorophenyl)urea | 4.04 LC 544.44 $[M + H]^+$ | Procedures 1 and 2 |
| 399 | 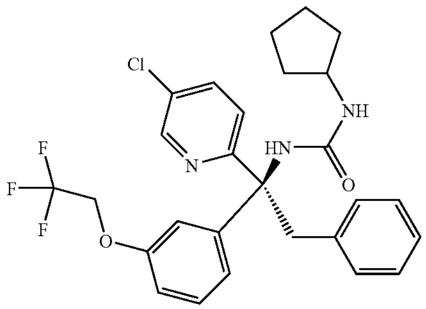 | (S)-1-(1-(5-chloropyridin-2-yl)-2-phenyl-1-(3-(2,2,2-trifluoroethoxy)phenyl)ethyl)-3-cyclopentylurea | 4.04 LC 518.48 $[M + H]^+$ | Procedures 1 and 2 |
| 401 | 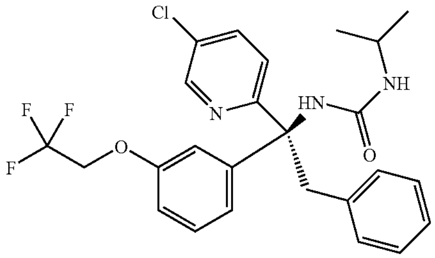 | (S)-1-(1-(5-chloropyridin-2-yl)-2-phenyl-1-(3-(2,2,2-trifluoroethoxy)phenyl)ethyl)-3-isopropylurea | 3.91 LC 492.48 $[M + H]^+$ | Procedures 1 and 2 |

TABLE 4-continued

| Ex. No. | Structure | Name | Retention Time Min./ Molecular Mass | Prepared in the manner described in: |
| --- | --- | --- | --- | --- |
| 402 | 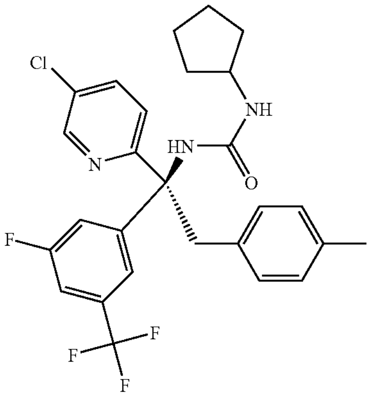 | (S)-1-(1-(5-chloropyridin-2-yl)-1-(3-fluoro-5-(trifluoromethyl) phenyl)-2-p-tolylethyl)-3-cyclopentylurea | 4.21 LC 520.48 [M + H]+ | Procedures 1 and 2 |
| 403 | 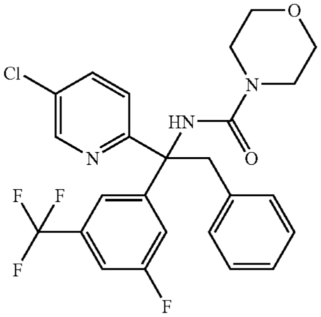 | N-(1-(5-chloropyridin-2-yl)-1-(3-fluoro-5-(trifluoromethyl) phenyl)-2-phenylethyl) morpholine-4-carboxamide | 3.37 LC 508.27 [M + H]+ | Procedures 1 and 43 |
| 404 | 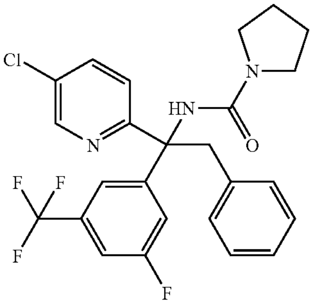 | N-(1-(5-chloropyridin-2-yl)-1-(3-fluoro-5-(trifluoromethyl) phenyl)-2-phenylethyl) pyrrolidine-1-carboxamide | 3.68 LC 492.27 [M + H]+ | Procedures 1 and 43 |
| 405 | 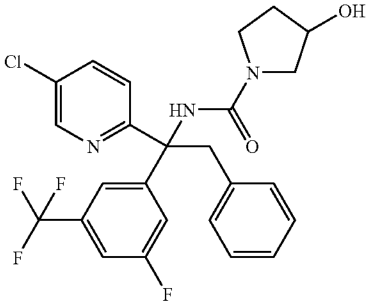 | N-(1-(5-chloropyridin-2-yl)-1-(3-fluoro-5-(trifluoromethyl) phenyl)-2-phenylethyl)-3-hydroxypyrrolidine-1-carboxamide | 3.00 LC 508.30 [M + H]+ | Procedures 1 and 43 |

TABLE 4-continued

| Ex. No. | Structure | Name | Retention Time Min./ Molecular Mass | Prepared in the manner described in: |
|---|---|---|---|---|
| 406 | 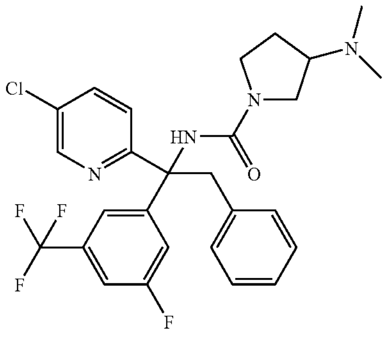 | N-(1-(5-chloropyridin-2-yl)-1-(3-fluoro-5-(trifluoromethyl) phenyl)-2-phenylethyl)-3-(dimethylamino)pyrrolidine-1-carboxamide | 2.49 LC 535.35 $[M + H]^+$ | Procedures 1 and 43 |
| 407 | 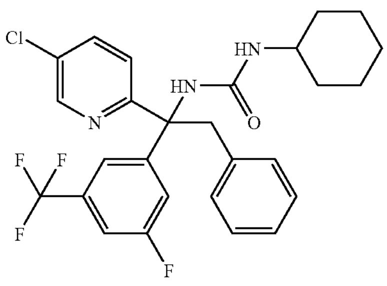 | 1-(1-(5-chloropyridin-2-yl)-1-(3-fluoro-5-(trifluoromethyl) phenyl)-2-phenylethyl)-3-cyclohexylurea | 3.83 LC 520.33 $[M + H]^+$ | Procedures 1 and 43 |
| 408 | 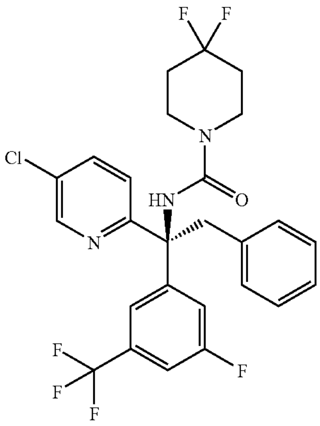 | (S)-N-(1-(5-chloropyridin-2-yl)-1-(3-fluoro-5-(trifluoromethyl) phenyl)-2-phenylethyl)-4,4-difluoropiperidine-1-carboxamide | 4.09 LC 542.44 $[M + H]^+$ | Procedures 1 and 2 |
| 409 | 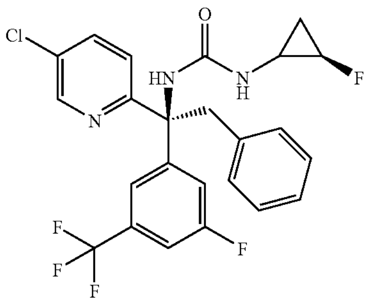 | 1-((S)-1-(5-chloropyridin-2-yl)-1-(3-fluoro-5-(trifluoromethyl) phenyl)-2-phenylethyl)-3-((2R)-2-fluorocyclopropyl)urea | 2.02 LC 496.2 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 410 | 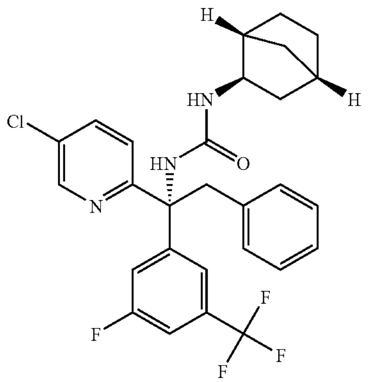 | 1-((1R,2R,4S)-bicyclo[2.2.1] heptan-2-yl)-3-((R)-1-(5-chloropyridin-2-yl)-1-(3-fluoro-5-(trifluoromethyl)phenyl)-2-phenylethyl)urea | 4.26 LC 532.45 $[M + H]^+$ | Procedures 1 and 2 |
| 411 | 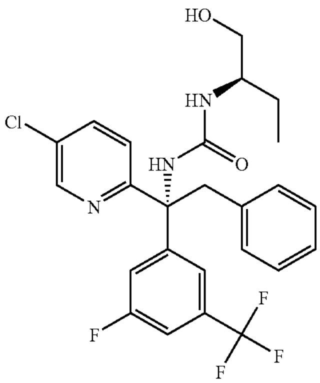 | 1-((R)-1-(5-chloropyridin-2-yl)-1-(3-fluoro-5-(trifluoromethyl) phenyl)-2-phenylethyl)-3-((R)-1-hydroxybutan-2-yl)urea | 3.92 LC 510.42 $[M + H]^+$ | Procedures 1 and 2 |
| 412 | 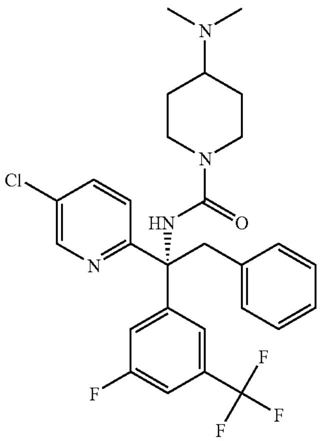 | (R)-N-(1-(5-chloropyridin-2-yl)-1-(3-fluoro-5-(trifluoromethyl) phenyl)-2-phenylethyl)-4-(dimethylamino)piperidine-1-carboxamide | 3.26 LC 549.47 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 413 | 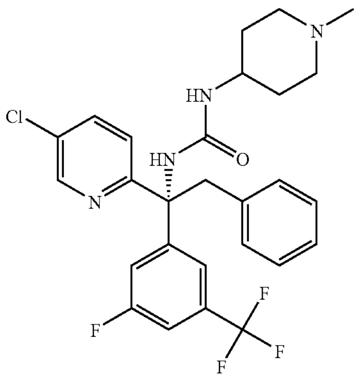 | (R)-1-(1-(5-chloropyridin-2-yl)-1-(3-fluoro-5-(trifluoromethyl) phenyl)-2-phenylethyl)-3-(1-methylpiperidin-4-yl)urea | 3.38 LC 535.48 $[M + H]^+$ | Procedures 1 and 2 |
| 414 | 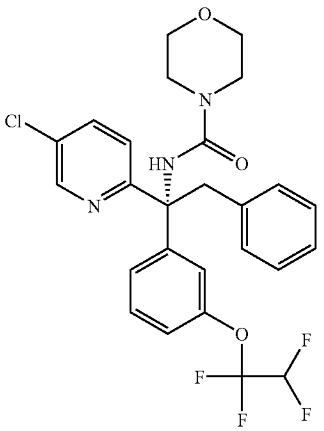 | (R)-N-(1-(5-chloropyridin-2-yl)-2-phenyl-1-(3-(1,1,2,2-tetrafluoroethoxy)phenyl)ethyl) morpholine-4-carboxamide | 3.82 LC 538.4 $[M + H]^+$ | Procedures 1 and 2 |
| 415 | 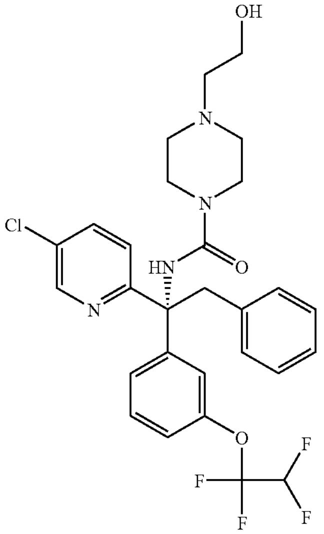 | (R)-N-(1-(5-chloropyridin-2-yl)-2-phenyl-1-(3-(1,1,2,2-tetrafluoroethoxy)phenyl)ethyl)-4-(2-hydroxyethyl)piperazine-1-carboxamide | 3.18 LC 518.43 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 416 | 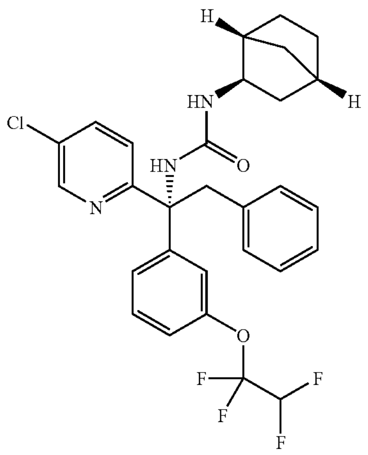 | 1-((1R,2R,4S)-bicyclo[2.2.1] heptan-2-yl)-3-((R)-1-(5-chloropyridin-2-yl)-2-phenyl-1-(3-(1,1,2,2-tetrafluoroethoxy) phenyl)ethyl)urea | 4.14 LC 562.49 [M + H]+ | Procedures 1 and 2 |
| 417 | 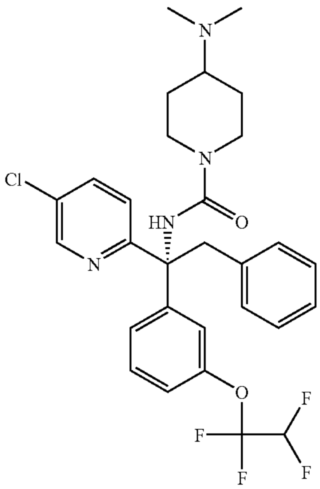 | (R)-N-(1-(5-chloropyridin-2-yl)-2-phenyl-1-(3-(1,1,2,2-tetrafluoroethoxy)phenyl)ethyl)-4-(dimethylamino)piperidine-1-carboxamide | 3.21 LC 579.49 [M + H]+ | Procedures 1 and 2 |
| 418 | 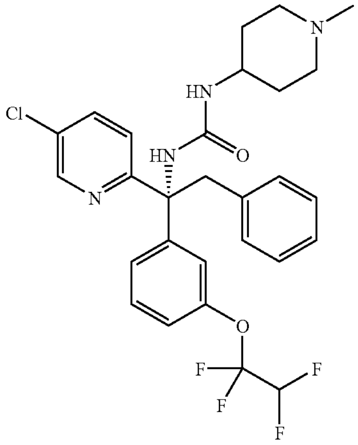 | (R)-1-(1-(5-chloropyridin-2-yl)-2-phenyl-1-(3-(1,1,2,2-tetrafluoroethoxy)phenyl)ethyl)-3-(1-methylpiperidin-4-yl)urea | 3.30 LC 565.48 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 419 | 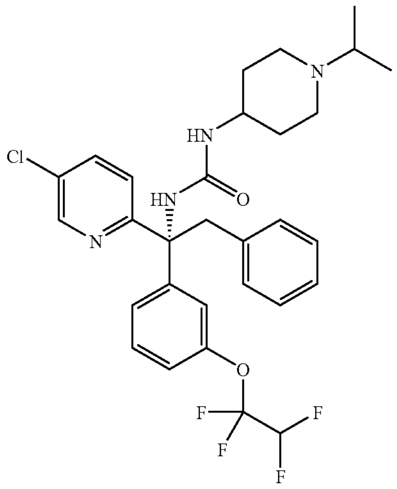 | (R)-1-(1-(5-chloropyridin-2-yl)-2-phenyl-1-(3-(1,1,2,2-tetrafluoroethoxy)phenyl)ethyl)-3-(1-isopropylpiperidin-4-yl) urea | 3.32 LC 593.5 [M + H]+ | Procedures 1 and 2 |
| 420 | 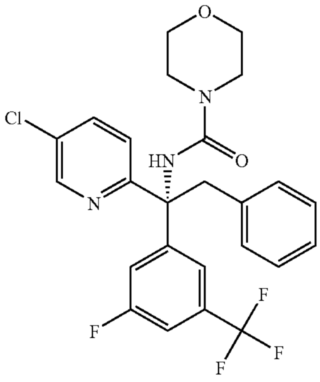 | (R)-N-(1-(5-chloropyridin-2-yl)-1-(3-fluoro-5-(trifluoromethyl) phenyl)-2-phenylethyl) morpholine-4-carboxamide | 3.92 LC 510.42 [M + H]+ | Procedures 1 and 2 |
| 421 | 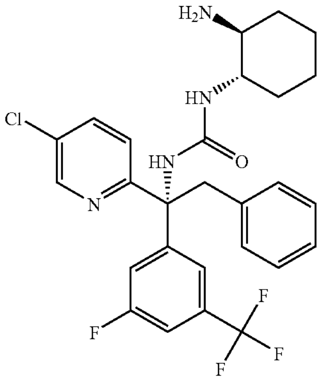 | 1-((1S,2S)-2-aminocyclohexyl)-3-((R)-1-(5-chloropyridin-2-yl)-1-(3-fluoro-5-(trifluoromethyl) phenyl)-2-phenylethyl)urea | 3.50 LC 535.46 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 422 | 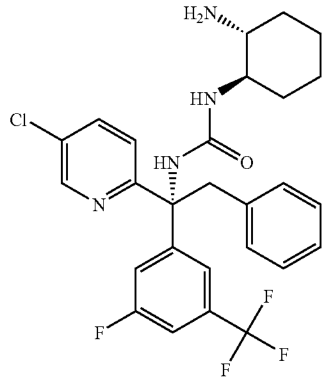 | 1-((1R,2R)-2-aminocyclohexyl)-3-((R)-1-(5-chloropyridin-2-yl)-1-(3-fluoro-5-(trifluoromethyl) phenyl)-2-phenylethyl)urea | 3.49 LC 535.45 $[M + H]^+$ | Procedures 1 and 2 |
| 423 | 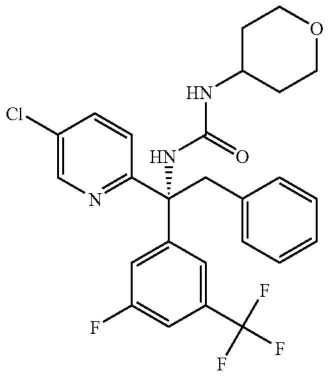 | (R)-1-(1-(5-chloropyridin-2-yl)-1-(3-fluoro-5-(trifluoromethyl) phenyl)-2-phenylethyl)-3-(tetrahydro-2H-pyran-4-yl)urea | 3.90 LC 522.46 $[M + H]^+$ | Procedures 1 and 2 |
| 424 | 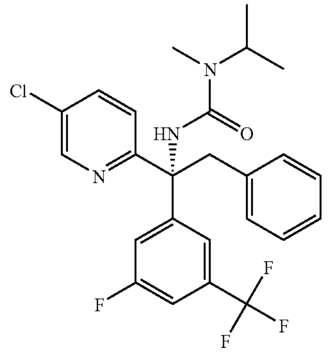 | (R)-3-(1-(5-chloropyridin-2-yl)-1-(3-fluoro-5-(trifluoromethyl) phenyl)-2-phenylethyl)-1-isopropyl-1-methylurea | 4.13 LC 494.49 $[M + H]^+$ | Procedures 1 and 2 |
| 425 | 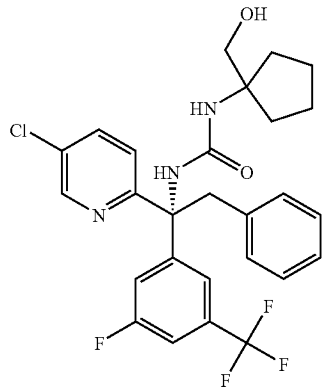 | (R)-1-(1-(5-chloropyridin-2-yl)-1-(3-fluoro-5-(trifluoromethyl) phenyl)-2-phenylethyl)-3-(1-(hydroxymethyl)cyclopentyl) urea | 4.01 LC 536.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 426 | 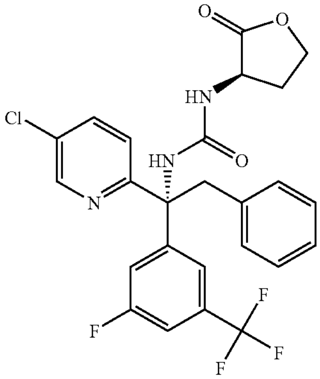 | 1-((R)-1-(5-chloropyridin-2-yl)-1-(3-fluoro-5-(trifluoromethyl)phenyl)-2-phenylethyl)-3-((R)-2-oxo-tetrahydrofuran-3-yl)urea | 3.73 LC 522.4 $[M + H]^+$ | Procedures 1 and 2 |
| 427 | 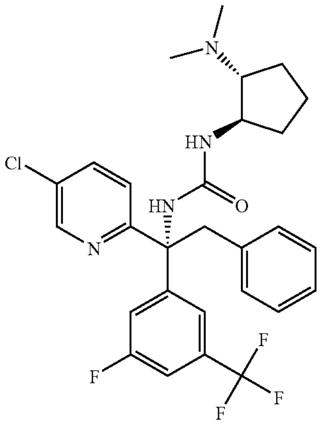 | 1-((R)-1-(5-chloropyridin-2-yl)-1-(3-fluoro-5-(trifluoromethyl)phenyl)-2-phenylethyl)-3-((1R,2R)-2-(dimethylamino)cyclopentyl)urea | 3.43 LC 549.49 $[M + H]^+$ | Procedures 1 and 2 |
| 428 | 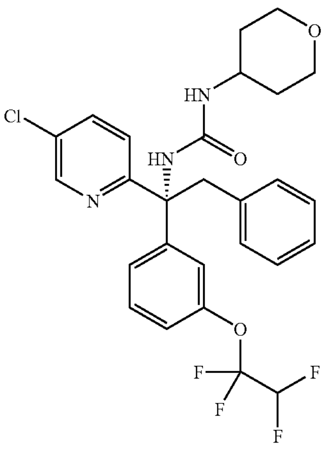 | (R)-1-(1-(5-chloropyridin-2-yl)-2-phenyl-1-(3-(1,1,2,2-tetrafluoroethoxy)phenyl)ethyl)-3-(tetrahydro-2H-pyran-4-yl)urea | 3.77 LC 552.45 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 429 | 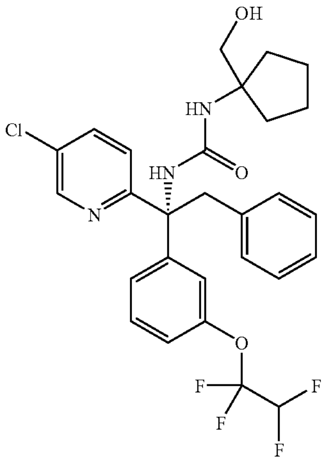 | (R)-1-(1-(5-chloropyridin-2-yl)-2-phenyl-1-(3-(1,1,2,2-tetrafluoroethoxy)phenyl)ethyl)-3-(1-(hydroxymethyl) cyclopentyl)urea | 3.87 LC 566.48 $[M+H]^+$ | Procedures 1 and 2 |
| 430 | 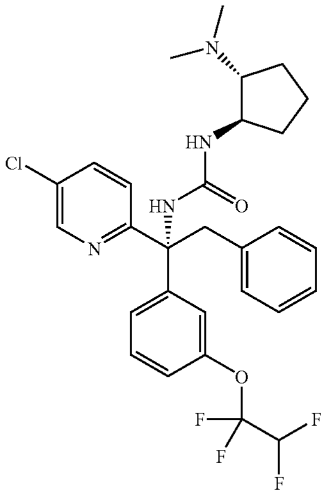 | 1-((R)-1-(5-chloropyridin-2-yl)-2-phenyl-1-(3-(1,1,2,2-tetrafluoroethoxy)phenyl)ethyl)-3-((1R,2R)-2-(dimethylamino) cyclopentyl)urea | 3.34 LC 579.49 $[M+H]^+$ | Procedures 1 and 2 |
| 431 | 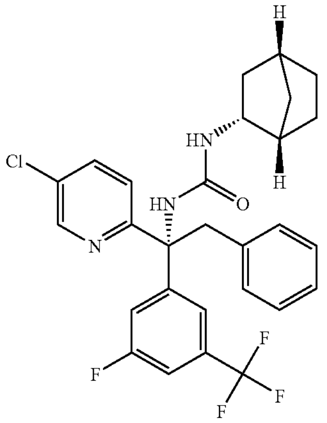 | 1-((1S,2R,4R)-bicyclo[2.2.1] heptan-2-yl)-3-((R)-1-(5-chloropyridin-2-yl)-1-(3-fluoro-5-(trifluoromethyl)phenyl)-2-phenylethyl)urea | 4.21 LC 532.46 $[M+H]^+$ | Procedures 1 and 2 |

TABLE 4-continued

| Ex. No. | Structure | Name | Retention Time Min./ Molecular Mass | Prepared in the manner described in: |
|---|---|---|---|---|
| 432 | 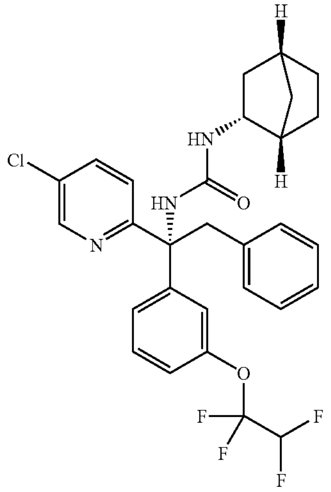 | 1-((1S,2R,4R)-bicyclo[2.2.1] heptan-2-yl)-3-((R)-1-(5-chloropyridin-2-yl)-2-phenyl-1-(3-(1,1,2,2-tetrafluoroethoxy) phenyl)ethyl)urea | 4.09 LC 562.49 $[M + H]^+$ | Procedures 1 and 2 |
| 433 | 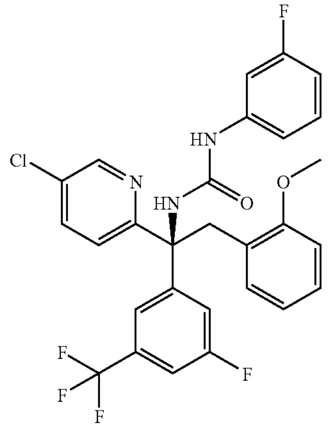 | (S)-1-(1-(5-chloropyridin-2-yl)-1-(3-fluoro-5-(trifluoromethyl) phenyl)-2-(2-methoxyphenyl) ethyl)-3-(3-fluorophenyl)urea | 4.14 LC 562.48 $[M + H]^+$ | Procedures 1 and 2 |
| 434 | 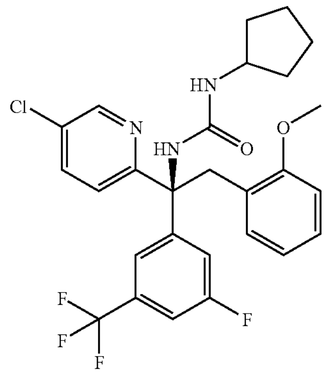 | (S)-1-(1-(5-chloropyridin-2-yl)-1-(3-fluoro-5-(trifluoromethyl) phenyl)-2-(2-methoxyphenyl) ethyl)-3-cyclopentylurea | 4.14 LC 536.54 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 435 | 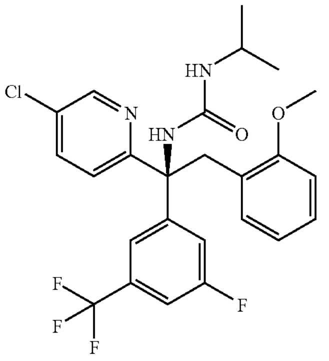 | (S)-1-(1-(5-chloropyridin-2-yl)-1-(3-fluoro-5-(trifluoromethyl) phenyl)-2-(2-methoxyphenyl) ethyl)-3-isopropylurea | 4.02 LC 510.52 [M + H]$^+$ | Procedures 1 and 2 |
| 436 | 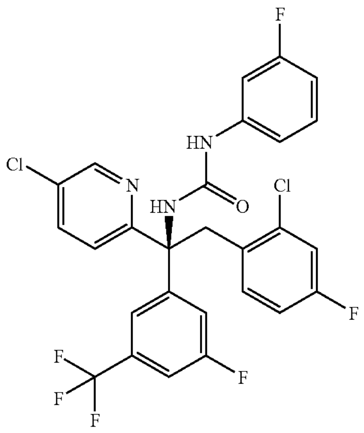 | (S)-1-(2-(2-chloro-4-fluorophenyl)-1-(5-chloropyridin-2-yl)-1-(3-fluoro-5-(trifluoromethyl)phenyl)ethyl)-3-(3-fluorophenyl)urea | 4.25 LC 584.43 [M + H]$^+$ | Procedures 1 and 2 |
| 437 | 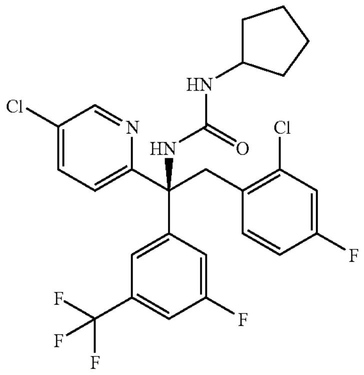 | (S)-1-(2-(2-chloro-4-fluorophenyl)-1-(5-chloropyridin-2-yl)-1-(3-fluoro-5-(trifluoromethyl)phenyl)ethyl)-3-cyclopentylurea | 4.25 LC 558.47 [M + H]$^+$ | Procedures 1 and 2 |

TABLE 4-continued

| Ex. No. | Structure | Name | Retention Time Min./ Molecular Mass | Prepared in the manner described in: |
|---|---|---|---|---|
| 438 | 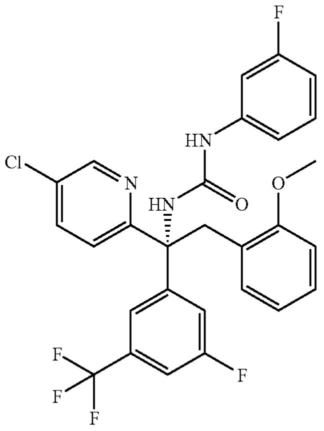 | (R)-1-(1-(5-chloropyridin-2-yl)-1-(3-fluoro-5-(trifluoromethyl) phenyl)-2-(2-methoxyphenyl) ethyl)-3-(3-fluorophenyl)urea | 4.14 LC 562.49 $[M + H]^+$ | Procedures 1 and 2 |
| 439 | 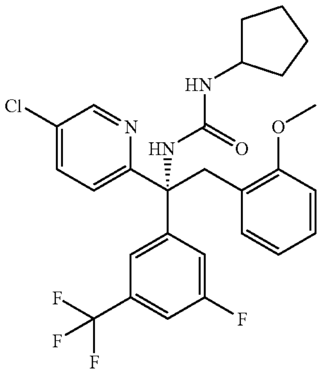 | (R)-1-(1-(5-chloropyridin-2-yl)-1-(3-fluoro-5-(trifluoromethyl) phenyl)-2-(2-methoxyphenyl) ethyl)-3-cyclopentylurea | 4.14 LC 536.52 $[M + H]^+$ | Procedures 1 and 2 |
| 440 | 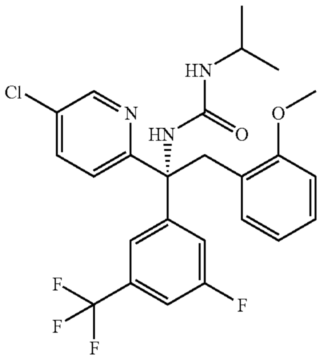 | (R)-1-(1-(5-chloropyridin-2-yl)-1-(3-fluoro-5-(trifluoromethyl) phenyl)-2-(2-methoxyphenyl) ethyl)-3-isopropylurea | 4.02 LC 510.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 441 | 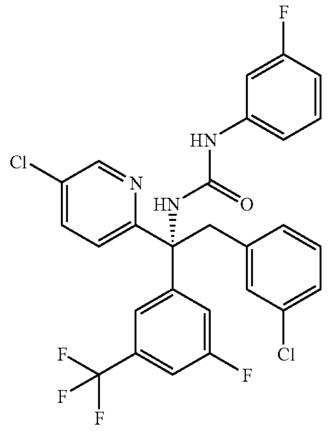 | (R)-1-(2-(3-chlorophenyl)-1-(5-chloropyridin-2-yl)-1-(3-fluoro-5-(trifluoromethyl)phenyl)ethyl)-3-(3-fluorophenyl)urea | 4.17 LC 566.42 $[M + H]^+$ | Procedures 1 and 2 |
| 442 | 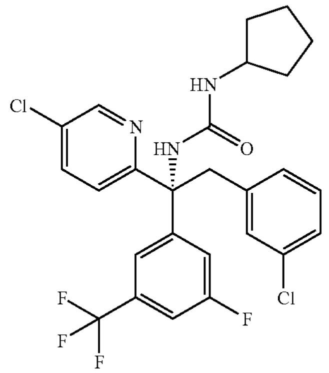 | (R)-1-(2-(3-chlorophenyl)-1-(5-chloropyridin-2-yl)-1-(3-fluoro-5-(trifluoromethyl)phenyl)ethyl)-3-cyclopentylurea | 4.16 LC 540.48 $[M + H]^+$ | Procedures 1 and 2 |
| 443 | 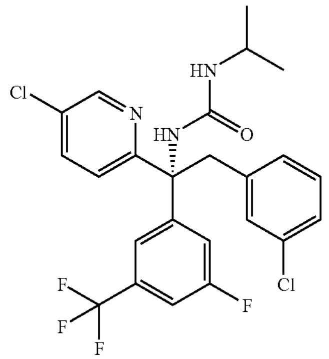 | (R)-1-(2-(3-chlorophenyl)-1-(5-chloropyridin-2-yl)-1-(3-fluoro-5-(trifluoromethyl)phenyl)ethyl)-3-isopropylurea | 4.06 LC 514.47 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 444 | 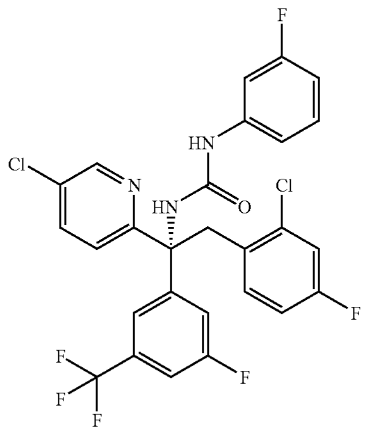 | (R)-1-(2-(2-chloro-4-fluorophenyl)-1-(5-chloropyridin-2-yl)-1-(3-fluoro-5-(trifluoromethyl)phenyl)ethyl) 3-(3-fluorophenyl)urea | 4.35 LC 619.40 [M + H]+ | Procedures 1 and 2 |
| 445 | 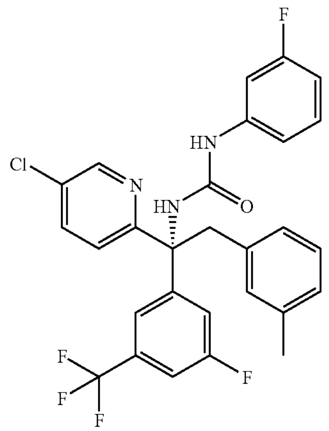 | (R)-1-(1-(5-chloropyridin-2-yl)-1-(3-fluoro-5-(trifluoromethyl) phenyl)-2-m-tolylethyl)-3-(3-fluorophenyl)urea | 4.19 LC 546.49 [M + H]+ | Procedures 1 and 2 |
| 446 | 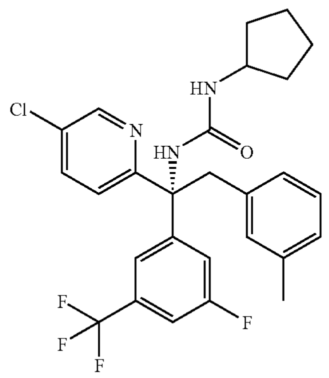 | (R)-1-(1-(5-chloropyridin-2-yl)-1-(3-fluoro-5-(trifluoromethyl) phenyl)-2-m-tolylethyl)-3-cyclopentylurea | 4.18 LC 520.53 [M + H]+ | Procedures 1 and 2 |

TABLE 4-continued

| Ex. No. | Structure | Name | Retention Time Min./ Molecular Mass | Prepared in the manner described in: |
| --- | --- | --- | --- | --- |
| 447 | 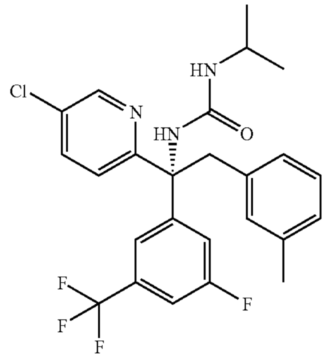 | (R)-1-(1-(5-chloropyridin-2-yl)-1-(3-fluoro-5-(trifluoromethyl) phenyl)-2-m-tolylethyl)-3-isopropylurea | 4.07 LC 494.52 $[M + H]^+$ | Procedures 1 and 2 |
| 448 | 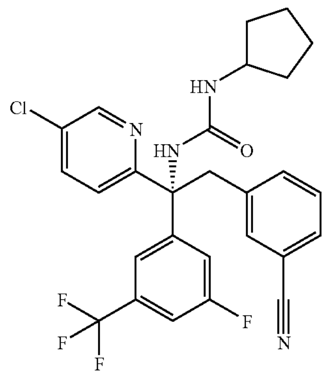 | (R)-1-(1-(5-chloropyridin-2-yl)-2-(3-cyanophenyl)-1-(3-fluoro-5-(trifluoromethyl)phenyl)ethyl)-3-cyclopentylurea | 3.90 LC 531.50 $[M + H]^+$ | Procedures 1 and 2 |
| 449 | 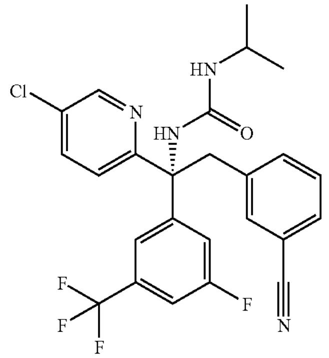 | (R)-1-(1-(5-chloropyridin-2-yl)-2-(3-cyanophenyl)-1-(3-fluoro-5-(trifluoromethyl)phenyl)ethyl)-3-isopropylurea | 3.77 LC 505.48 $[M + H]^+$ | Procedures 1 and 2 |
| 450 | 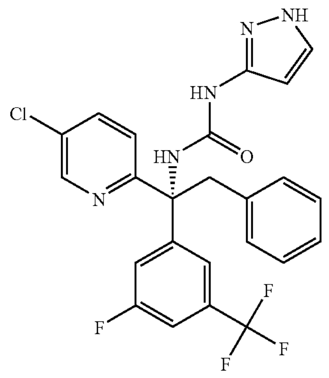 | (R)-1-(1-(5-chloropyridin-2-yl)-1-(3-fluoro-5-(trifluoromethyl) phenyl)-2-phenylethyl)-3-(1H-pyrazol-3-yl)urea | 3.75 LC 504.49 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 451 | 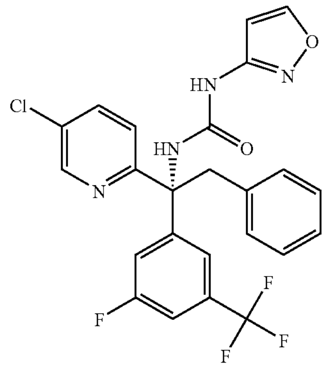 | (R)-1-(1-(5-chloropyridin-2-yl)-1-(3-fluoro-5-(trifluoromethyl) phenyl)-2-phenylethyl)-3-(isoxazol-3-yl)urea | 3.91 LC 505.48 [M + H]+ | Procedures 1 and 2 |
| 452 | 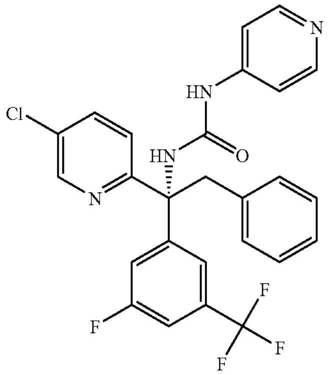 | (R)-1-(1-(5-chloropyridin-2-yl)-1-(3-fluoro-5-(trifluoromethyl) phenyl)-2-phenylethyl)-3-(pyridin-4-yl)urea | 3.35 LC 515.48 [M + H]+ | Procedures 1 and 2 |
| 453 | 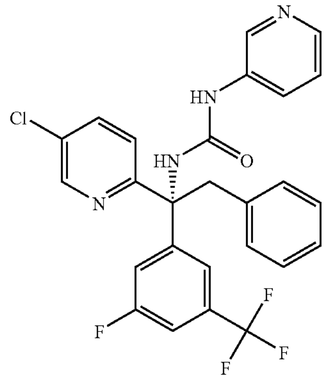 | (R)-1-(1-(5-chloropyridin-2-yl)-1-(3-fluoro-5-(trifluoromethyl) phenyl)-2-phenylethyl)-3-(pyridin-3-yl)urea | 3.37 LC 515.48 [M + H]+ | Procedures 1 and 2 |
| 454 | 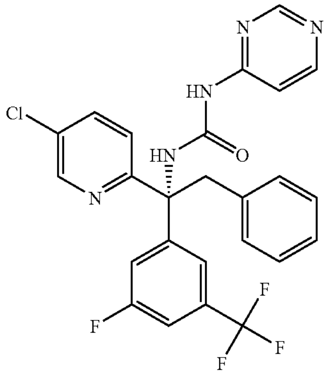 | (R)-1-(1-(5-chloropyridin-2-yl)-1-(3-fluoro-5-(trifluoromethyl) phenyl)-2-phenylethyl)-3-(pyrimidin-4-yl)urea | 3.71 LC 516.45 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 455 | 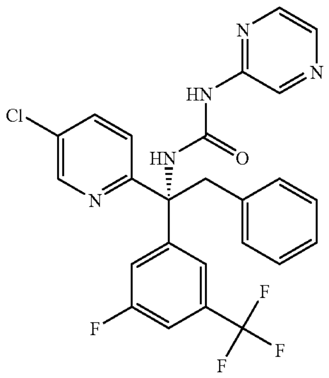 | (R)-1-(1-(5-chloropyridin-2-yl)-1-(3-fluoro-5-(trifluoromethyl) phenyl)-2-phenylethyl)-3-(pyrazin-2-yl)urea | 4.00 LC 516.47 $[M + H]^+$ | Procedures 1 and 2 |
| 456 | 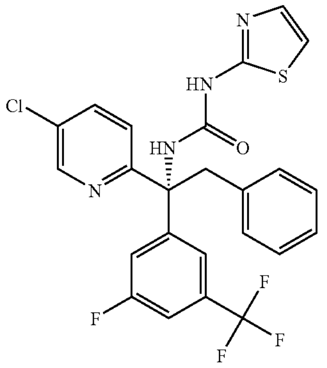 | (R)-1-(1-(5-chloropyridin-2-yl)-1-(3-fluoro-5-(trifluoromethyl) phenyl)-2-phenylethyl)-3-(thiazol-2-yl)urea | 3.91 LC 521.42 $[M + H]^+$ | Procedures 1 and 2 |
| 457 | 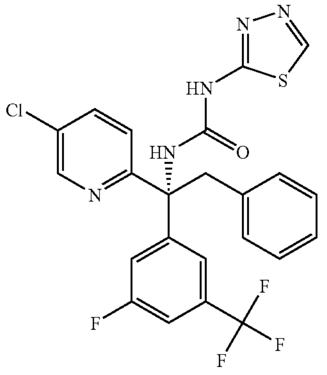 | (R)-(1-(5-chloropyridin-2-yl)-1-(3-fluoro-5-(trifluoromethyl) phenyl)-2-phenylethyl)-3-(1,3,4-thiadiazol-2-yl)urea | 3.85 LC 522.43 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 458 | 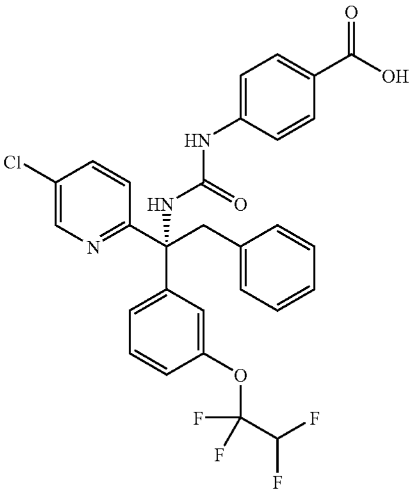 | (R)-4-(3-(1-(5-chloropyridin-2-yl)-2-phenyl-1-(3-(1,1,2,2-tetrafluoroethoxy)phenyl)ethyl) ureido)benzoic acid | 3.84 LC 588.47 $[M + H]^+$ | Procedures 1 and 2 |
| 459 | 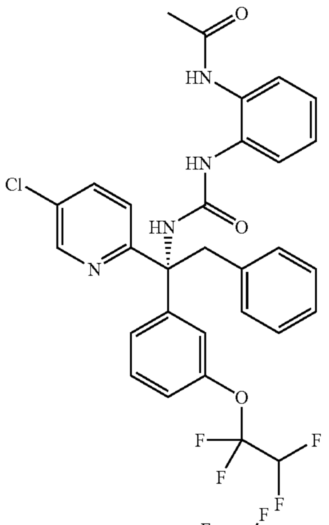 | (R)-1-(2-acetamidophenyl)-3-(1-(5-chloropyridin-2-yl)-2-phenyl-1-(3-(1,1,2,2-tetrafluoroethoxy) phenyl)ethyl)urea | 3.82 LC 601.5 $[M + H]^+$ | Procedures 1 and 2 |
| 460 | 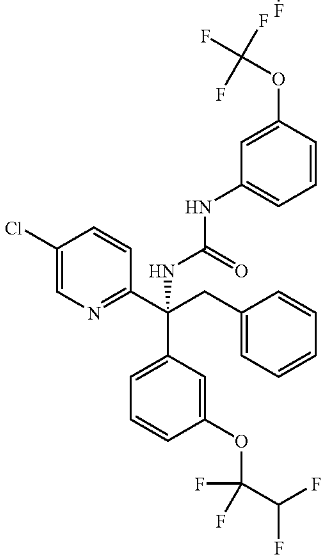 | (R)-1-(1-(5-chloropyridin-2-yl)-2-phenyl-1-(3-(1,1,2,2-tetrafluoroethoxy)phenyl)ethyl)-3-(3-(trifluoromethoxy)phenyl) urea | 4.18 LC 628.49 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 461 | 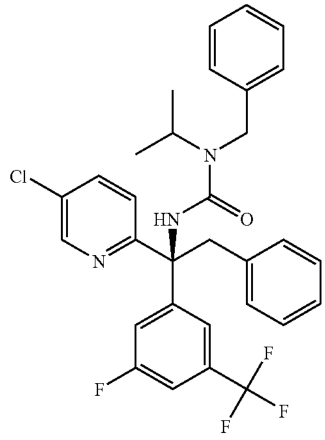 | (S)-1-benzyl-3-(1-(5-chloropyridin-2-yl)-1-(3-fluoro-5-(trifluoromethyl)phenyl)-2-phenylethyl)-1-isopropylurea | 4.39 LC 570.47 [M + H]$^+$ | Procedures 1 and 2 |
| 462 | 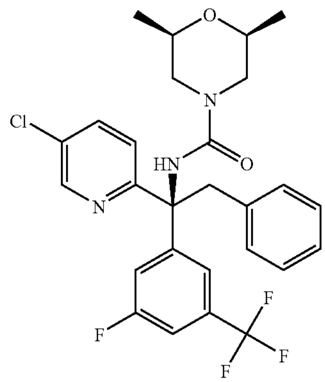 | (2R,6S)-N-((S)-1-(5-chloropyridin-2-yl)-1-(3-fluoro-5-(trifluoromethyl)phenyl)-2-phenylethyl)-2,6-dimethylmorpholine-4-carboxamide | 4.11 LC 536.44 [M + H]$^+$ | Procedures 1 and 2 |
| 463 | 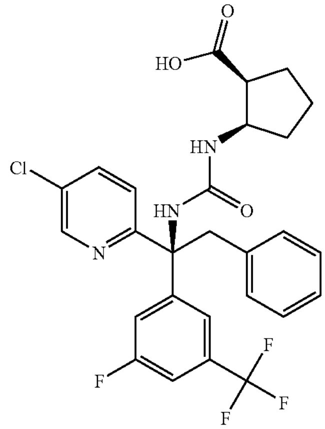 | (1S,2R)-2-(3-((S)-1-(5-chloropyridin-2-yl)-1-(3-fluoro-5-(trifluoromethyl)phenyl)-2-phenylethyl)ureido) cyclopentanecarboxylic acid | 3.96 LC 550.44 [M + H]$^+$ | Procedures 1 and 2 |

TABLE 4-continued

| Ex. No. | Structure | Name | Retention Time Min./ Molecular Mass | Prepared in the manner described in: |
|---|---|---|---|---|
| 464 | 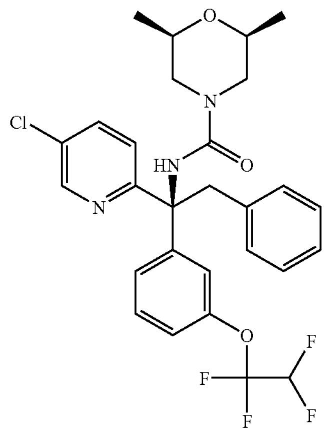 | (2R,6S)-N-((S)-1-(5-chloropyridin-2-yl)-2-phenyl-1-(3-(1,1,2,2-tetrafluoroethoxy) phenyl)ethyl)-2,6-dimethylmorpholine-4-carboxamide | 4.01 LC 566.46 $[M + H]^+$ | Procedures 1 and 2 |
| 465 | 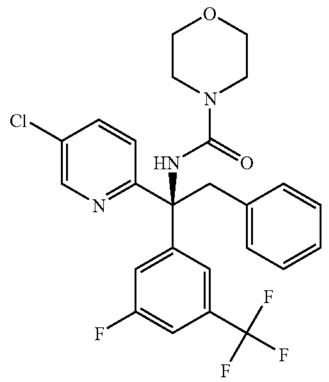 | (S)-N-(1-(5-chloropyridin-2-yl)-1-(3-fluoro-5-(trifluoromethyl) phenyl)-2-phenylethyl) morpholine-4-carboxamide | 3.93 LC 508.41 $[M + H]^+$ | Procedures 1 and 2 |
| 466 | 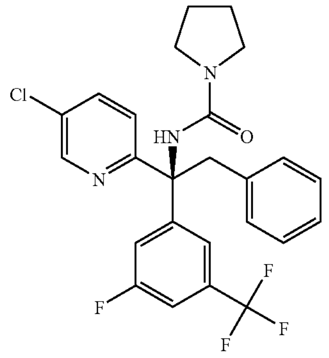 | (S)-N-(1-(5-chloropyridin-2-yl)-1-(3-fluoro-5-(trifluoromethyl) phenyl)-2-phenylethyl) pyrrolidine-1-carboxamide | 4.13 LC 492.42 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 467 | 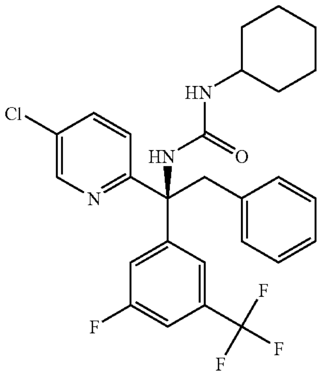 | (S)-1-(1-(5-chloropyridin-2-yl)-1-(3-fluoro-5-(trifluoromethyl) phenyl)-2-phenylethyl)-3-cyclohexylurea | 4.23 LC 520.45 $[M + H]^+$ | Procedures 1 and 2 |
| 468 | 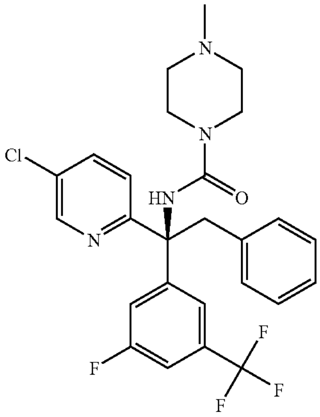 | (S)-N-(1-(5-chloropyridin-2-yl)-1-(3-fluoro-5-(trifluoromethyl) phenyl)-2-phenylethyl)-4-methylpiperazine-1-carboxamide | 3.23 LC 521.45 $[M + H]^+$ | Procedures 1 and 2 |
| 469 | 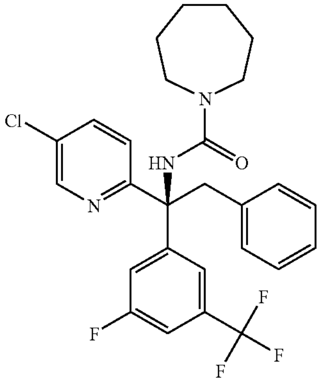 | (S)-N-(1-(5-chloropyridin-2-yl)-1-(3-fluoro-5-(trifluoromethyl) phenyl)-2-phenylethyl)azepane-1-carboxamide | 4.30 LC 520.44 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 470 | 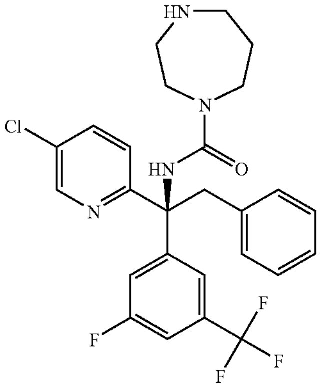 | (S)-N-(1-(5-chloropyridin-2-yl)-1-(3-fluoro-5-(trifluoromethyl) phenyl)-2-phenylethyl)-1,4-diazepane-1-carboxamide | 3.26 LC 521.44 $[M + H]^+$ | Procedures 1 and 2 |
| 471 | 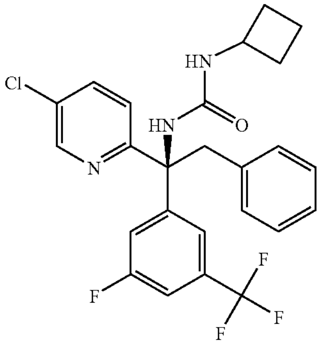 | (S)-1-(1-(5-chloropyridin-2-yl)-1-(3-fluoro-5-(trifluoromethyl) phenyl)-2-phenylethyl)-3-cyclobutylurea | 4.09 LC 492.42 $[M + H]^+$ | Procedures 1 and 2 |
| 472 | 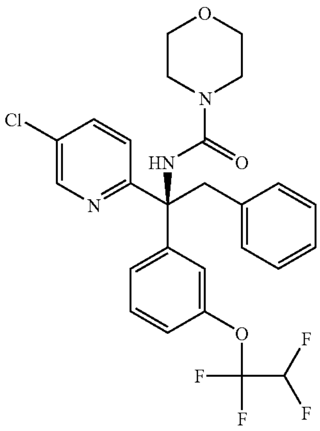 | (S)-N-(1-(5-chloropyridin-2-yl)-2-phenyl-1-(3-(1,1,2,2-tetrafluoroethoxy)phenyl)ethyl) morpholine-4-carboxamide | 3.82 LC 538.41 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 473 | 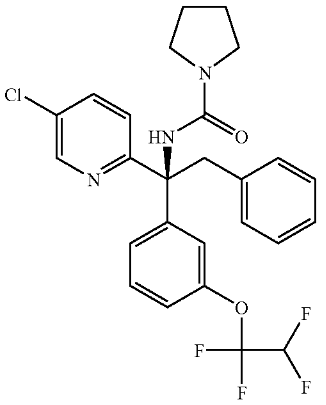 | (S)-N-(1-(5-chloropyridin-2-yl)-2-phenyl-1-(3-(1,1,2,2-tetrafluoroethoxy)phenyl)ethyl) pyrrolidine-1-carboxamide | 4.03 LC 522.42 [M + H]+ | Procedures 1 and 2 |
| 474 | 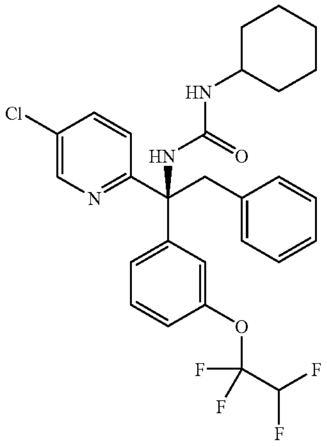 | (S)-1-(1-(5-chloropyridin-2-yl)-2-phenyl-1-(3-(1,1,2,2-tetrafluoroethoxy)phenyl)ethyl)-3-cyclohexylurea | 4.10 LC 550.45 [M + H]+ | Procedures 1 and 2 |
| 475 | 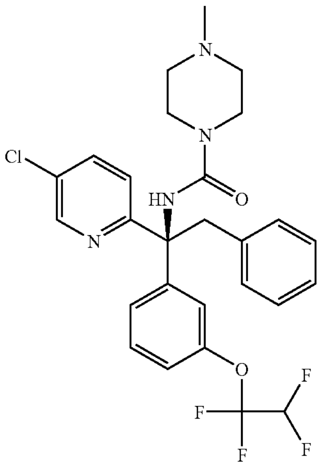 | (S)-N-(1-(5-chloropyridin-2-yl)-2-phenyl-1-(3-(1,1,2,2-tetrafluoroethoxy)phenyl)ethyl)-4-methylpiperazine-1-carboxamide | 3.17 LC 551.46 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 476 | 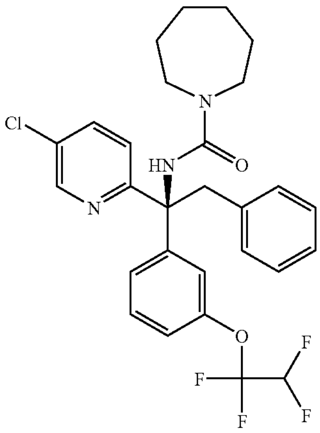 | (S)-N-(1-(5-chloropyridin-2-yl)-2-phenyl-1-(3-(1,1,2,2-tetrafluoroethoxy)phenyl)ethyl) azepane-1-carboxamide | 4.19 LC 550.46 $[M + H]^+$ | Procedures 1 and 2 |
| 477 | 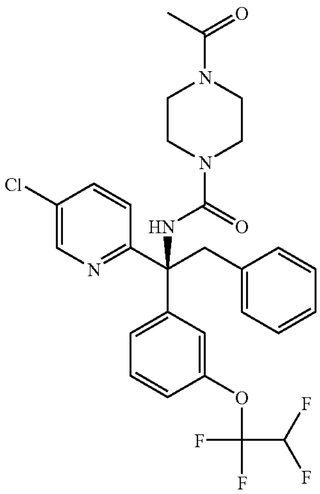 | (S)-4-acetyl-N-(1-(5-chloropyridin-2-yl)-2-phenyl-1-(3-(1,1,2,2-tetrafluoroethoxy) phenyl)ethyl)piperazine-1-carboxamide | 3.68 LC 579.48 $[M + H]^+$ | Procedures 1 and 2 |
| 478 | 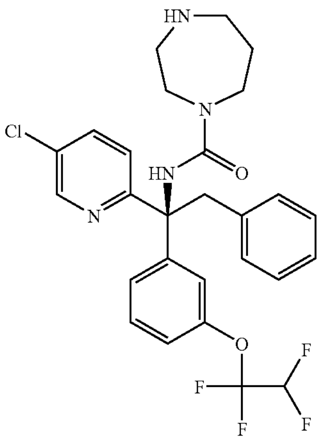 | (S)-N-(1-(5-chloropyridin-2-yl)-2-phenyl-1-(3-(1,1,2,2-tetrafluoroethoxy)phenyl)ethyl)-1,4-diazepane-1-carboxamide | 3.21 LC 551.47 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 479 | 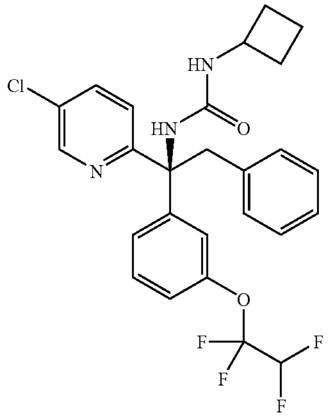 | (S)-1-(1-(5-chloropyridin-2-yl)-2-phenyl-1-(3-(1,1,2,2-tetrafluoroethoxy)phenyl)ethyl)-3-cyclobutylurea | 3.96 LC 522.43 $[M + H]^+$ | Procedures 1 and 2 |
| 480 | 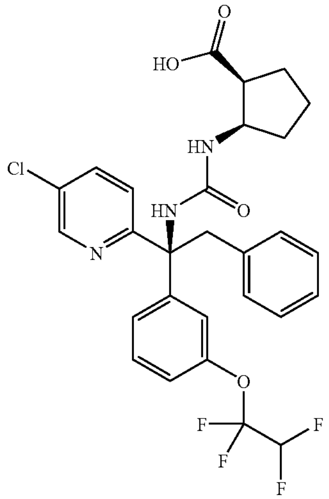 | (1S,2R)-2-(3-((S)-1-(5-chloropyridin-2-yl)-2-phenyl-1-(3-(1,1,2,2-tetrafluoroethoxy) phenyl)ethyl)ureido) cyclopentanecarboxylic acid | 3.82 LC 580.44 $[M + H]^+$ | Procedures 1 and 2 |
| 481 | 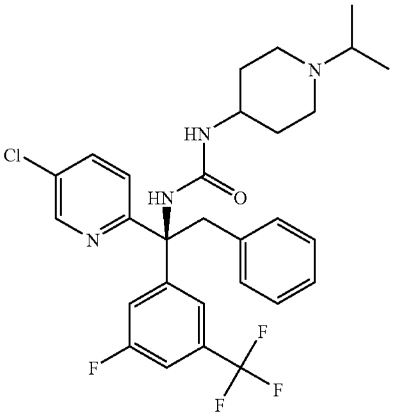 | (S)-1-(1-(5-chloropyridin-2-yl)-1-(3-fluoro-5-(trifluoromethyl) phenyl)-2-phenylethyl)-3-(1-isopropylpiperidin-4-yl)urea | 3.41 LC 563.51 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 482 | 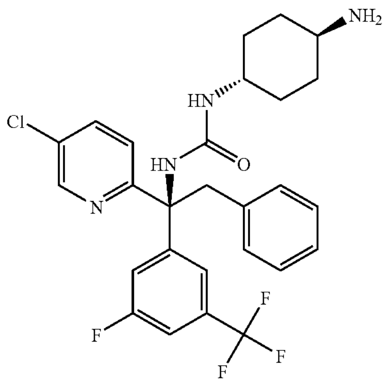 | 1-((1r,4S)-4-aminocyclohexyl)-3-((S)-1-(5-chloropyridin-2-yl)-1-(3-fluoro-5-(trifluoromethyl) phenyl)-2-phenylethyl)urea | 3.47 LC 535.46 $[M + H]^+$ | Procedures 1 and 2 |
| 483 | 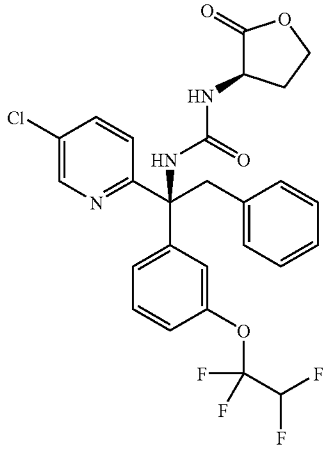 | 1-((S)-1-(5-chloropyridin-2-yl)-2-phenyl-1-(3-(1,1,2,2-tetrafluoroethoxy)phenyl)ethyl)-3-((R)-2-oxo-tetrahydrofuran-3-yl)urea | 3.67 LC 552.41 $[M + H]^+$ | Procedures 1 and 2 |
| 484 | 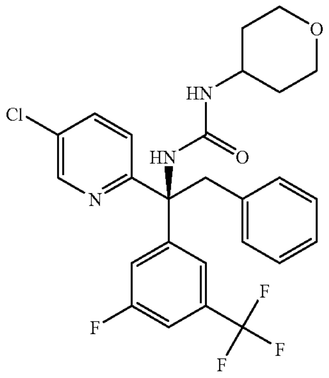 | (S)-1-(1-(5-chloropyridin-2-yl)-1-(3-fluoro-5-(trifluoromethyl) phenyl)-2-phenylethyl)-3-(tetrahydro-2H-pyran-4-yl)urea | 3.95 LC 522.42 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 485 | 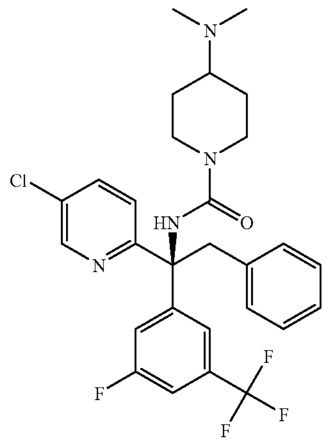 | (S)-N-(1-(5-chloropyridin-2-yl)-1-(3-fluoro-5-(trifluoromethyl) phenyl)-2-phenylethyl)-4-(dimethylamino)piperidine-1-carboxamide | 3.28 LC 549.47 [M + H]+ | Procedures 1 and 2 |
| 486 | 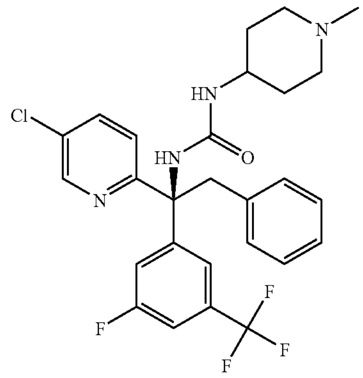 | (S)-1-(1-(5-chloropyridin-2-yl)-1-(3-fluoro-5-(trifluoromethyl) phenyl)-2-phenylethyl)-3-(1-methylpiperidin-4-yl)urea | 3.39 LC 535.47 [M + H]+ | Procedures 1 and 2 |
| 487 | 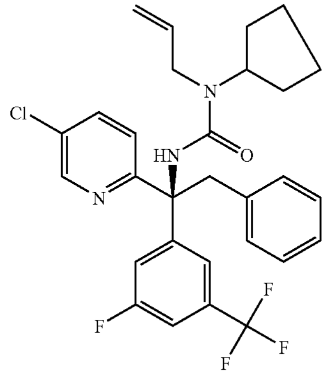 | (S)-1-allyl-3-(1-(5-chloropyridin-2-yl)-1-(3-fluoro-5-(trifluoromethyl)phenyl)-2-phenylethyl)-1-cyclopentylurea | 4.45 LC 546.47 [M + H]+ | Procedures 1 and 2 |

TABLE 4-continued

| Ex. No. | Structure | Name | Retention Time Min./ Molecular Mass | Prepared in the manner described in: |
| --- | --- | --- | --- | --- |
| 488 | 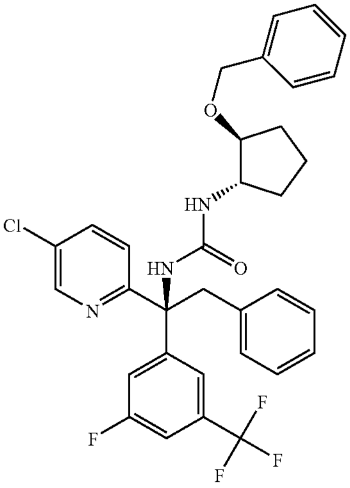 | 1-((1S,2S)-2-(benzyloxy) cyclopentyl)-3-((S)-1-(5-chloropyridin-2-yl)-1-(3-fluoro-5-(trifluoromethyl)phenyl)-2-phenylethyl)urea | 4.34 LC 612.5 $[M + H]^+$ | Procedures 1 and 2 |
| 489 | 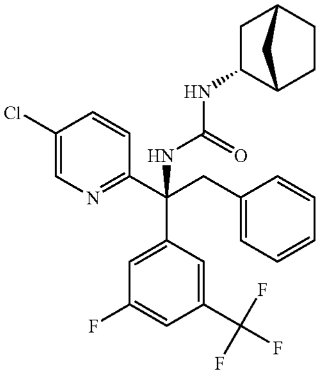 | 1-((1S,2R,4R)-bicyclo[2.2.1] heptan-2-yl)-3-((S)-1-(5-chloropyridin-2-yl)-1-(3-fluoro-5-(trifluoromethyl)phenyl)-2-phenylethyl)urea | 4.27 LC 532.45 $[M + H]^+$ | Procedures 1 and 2 |
| 490 | 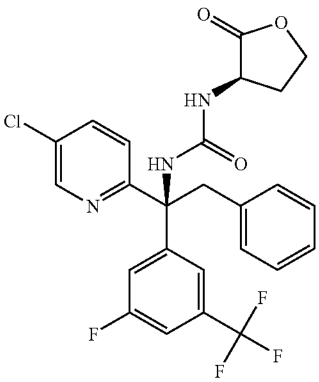 | 1-((S)-1-(5-chloropyridin-2-yl)-1-(3-fluoro-5-(trifluoromethyl) phenyl)-2-phenylethyl)-3-((R)-2-oxo-tetrahydrofuran-3-yl)urea | 3.79 LC 522.39 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 491 | 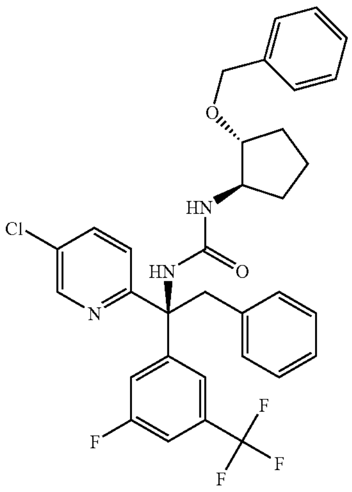 | 1-((1R,2R)-2-(benzyloxy) cyclopentyl)-3-((S)-1-(5-chloropyridin-2-yl)-1-(3-fluoro-5-(trifluoromethyl)phenyl)-2-phenylethyl)urea | 4.32 LC 612.51 $[M + H]^+$ | Procedures 1 and 2 |
| 492 | 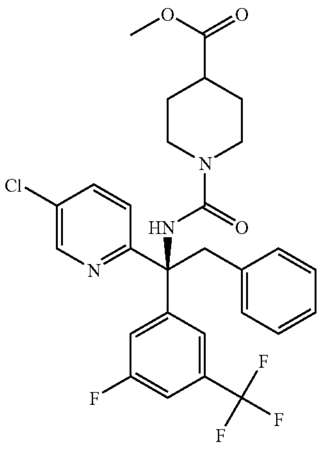 | (S)-methyl 1-((1-(5-chloropyridin-2-yl)-1-(3-fluoro-5-(trifluoromethyl)phenyl)-2-phenylethyl)carbamoyl)piperidine-4-carboxylate | 4.04 LC 564.45 $[M + H]^+$ | Procedures 1 and 2 |
| 493 | 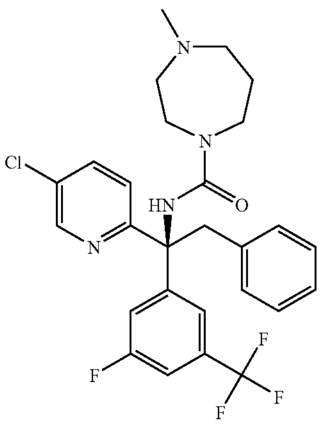 | (S)-N-(1-(5-chloropyridin-2-yl)-1-(3-fluoro-5-(trifluoromethyl) phenyl)-2-phenylethyl)-4-methyl-1,4-diazepane-1-carboxamide | 3.46 LC 535.46 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 494 | 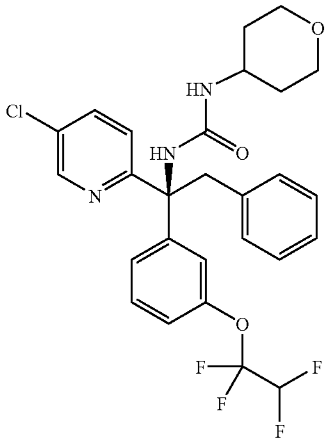 | (S)-1-(1-(5-chloropyridin-2-yl)-2-phenyl-1-(3-(1,1,2,2-tetrafluoroethoxy)phenyl)ethyl)-3-(tetrahydro-2H-pyran-4-yl) urea | 3.81 LC 522.43 $[M + H]^+$ | Procedures 1 and 2 |
| 495 | 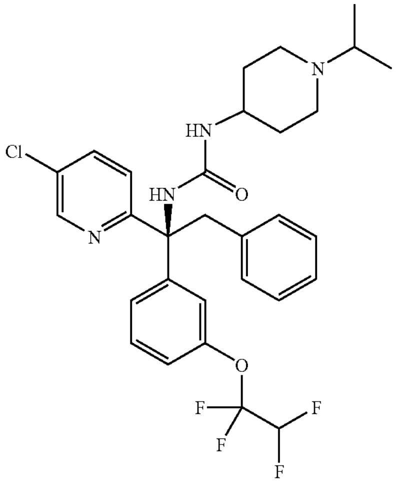 | (S)-1-(1-(5-chloropyridin-2-yl)-2-phenyl-1-(3-(1,1,2,2-tetrafluoroethoxy)phenyl)ethyl)-3-(1-isopropylpiperidin-4-yl) urea | 3.32 LC 593.53 $[M + H]^+$ | Procedures 1 and 2 |
| 496 | 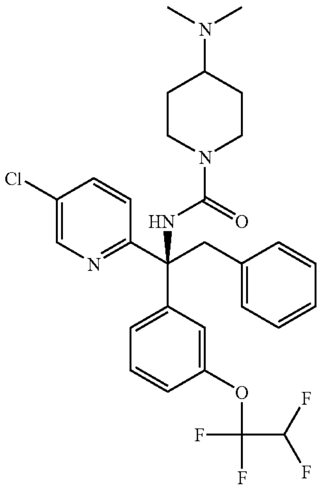 | (S)-N-(1-(5-chloropyridin-2-yl)-2-phenyl-1-(3-(1,1,2,2-tetrafluoroethoxy)phenyl)ethyl)-4-(dimethylamino)piperidine-1-carboxamide | 3.21 LC 579.5 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 497 | 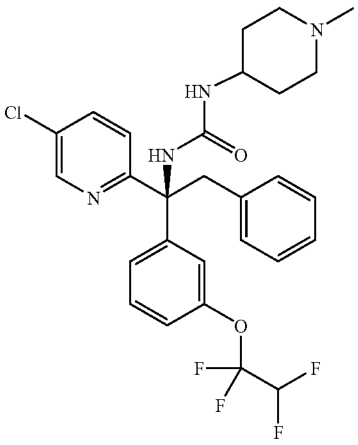 | (S)-1-(1-(5-chloropyridin-2-yl)-2-phenyl-1-(3-(1,1,2,2-tetrafluoroethoxy)phenyl)ethyl)-3-(1-methylpiperidin-4-yl)urea | 3.29 LC 565.48 $[M + H]^+$ | Procedures 1 and 2 |
| 498 | 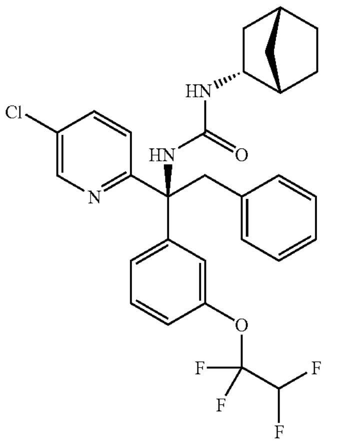 | 1-((1S,2R,4R)-bicyclo[2.2.1]heptan-2-yl)-3-((S)-1-(5-chloropyridin-2-yl)-2-phenyl-1-(3-(1,1,2,2-tetrafluoroethoxy)phenyl)ethyl)urea | 4.15 LC 562.46 $[M + H]^+$ | Procedures 1 and 2 |
| 499 | 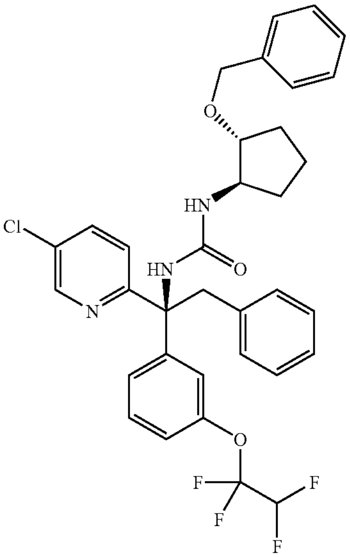 | 1-((1R,2R)-2-(benzyloxy)cyclopentyl)-3-((S)-1-(5-chloropyridin-2-yl)-2-phenyl-1-(3-(1,1,2,2-tetrafluoroethoxy)phenyl)ethyl)urea | 4.21 LC 642.53 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 500 | 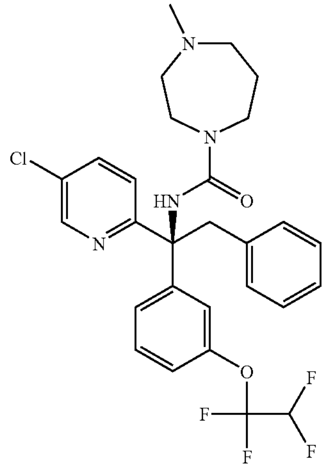 | (S)-N-(1-(5-chloropyridin-2-yl)-2-phenyl-1-(3-(1,1,2,2-tetrafluoroethoxy)phenyl)ethyl)-4-methyl-1,4-diazepane-1-carboxamide | 3.20 LC 642.53 $[M + H]^+$ | Procedures 1 and 2 |
| 501 | 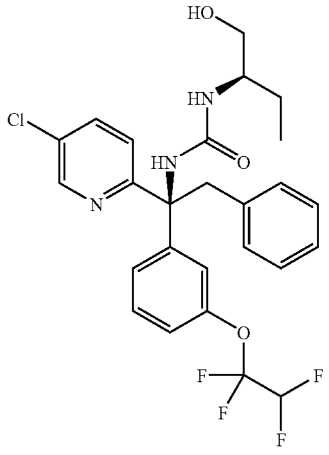 | 1-((S)-1-(5-chloropyridin-2-yl)-2-phenyl-1-(3-(1,1,2,2-tetrafluoroethoxy)phenyl)ethyl)-3-((R)-1-hydroxybutan-2-yl)urea | 3.75 LC 540.48 $[M + H]^+$ | Procedures 1 and 2 |
| 502 | 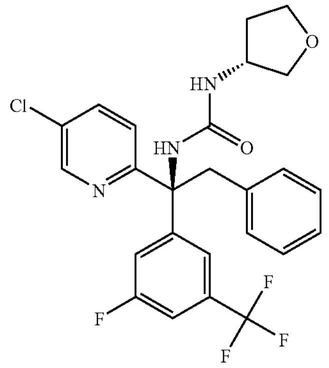 | 1-((S)-1-(5-chloropyridin-2-yl)-1-(3-fluoro-5-(trifluoromethyl) phenyl)-2-phenylethyl)-3-((R)-tetrahydrofuran-3-yl)urea | 3.87 LC 508.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 503 | 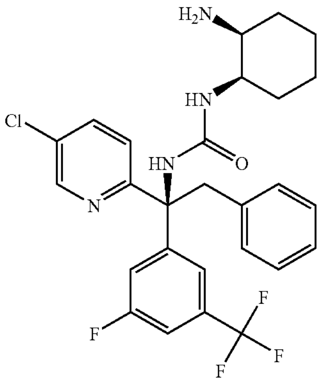 | 1-((1R,2S)-2-aminocyclohexyl)-3-((S)-1-(5-chloropyridin-2-yl)-1-(3-fluoro-5-(trifluoromethyl) phenyl)-2-phenylethyl)urea | 3.54 LC 535.49 $[M + H]^+$ | Procedures 1 and 2 |
| 504 | 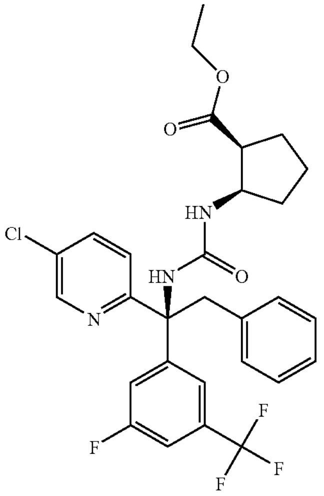 | (1S,2R)-ethyl 2-(3-((S)-1-(5-chloropyridin-2-yl)-1-(3-fluoro-5-(trifluoromethyl)phenyl)-2-phenylethyl)ureido) cyclopentanecarboxylate | 4.12 LC 578.49 $[M + H]^+$ | Procedures 1 and 2 |
| 505 | 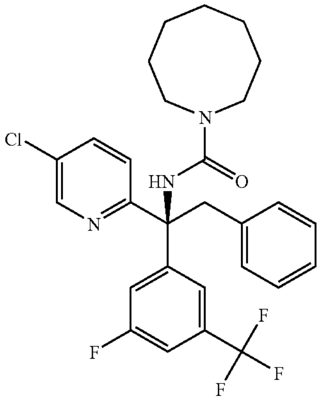 | (S)-N-(1-(5-chloropyridin-2-yl)-1-(3-fluoro-5-(trifluoromethyl) phenyl)-2-phenylethyl)azocane-1-carboxamide | 4.36 LC 534.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 506 | 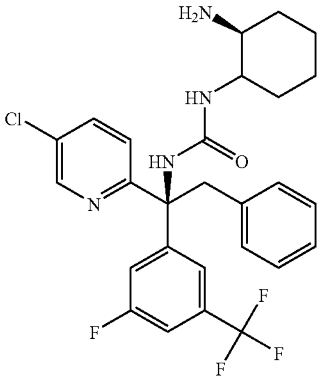 | 1-((2S)-2-aminocyclohexyl)-3-((S)-1-(5-chloropyridin-2-yl)-1-(3-fluoro-5-(trifluoromethyl) phenyl)-2-phenylethyl)urea | 3.53 LC 535.48 $[M + H]^+$ | Procedures 1 and 2 |
| 507 | 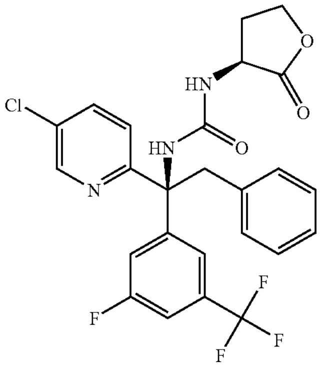 | 1-((S)-1-(5-chloropyridin-2-yl)-1-(3-fluoro-5-(trifluoromethyl) phenyl)-2-phenylethyl)-3-((S)-2-oxo-tetrahydrofuran-3-yl)urea | 3.74 LC 522.42 $[M + H]^+$ | Procedures 1 and 2 |
| 508 | 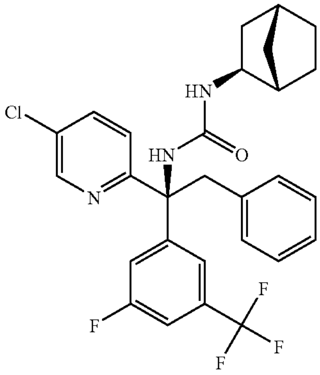 | 1-((1S,2S,4R)-bicyclo[2.2.1] heptan-2-yl)-3-((S)-1-(5-chloropyridin-2-yl)-1-(3-fluoro-5-(trifluoromethyl)phenyl)-2-phenylethyl)urea | 4.22 LC 532.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 509 | 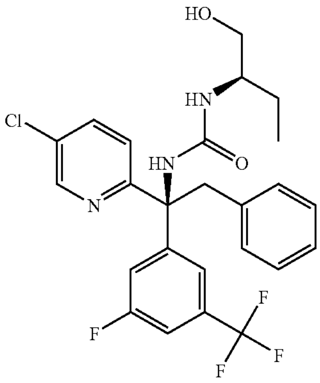 | 1-((S)-1-(5-chloropyridin-2-yl)-1-(3-fluoro-5-(trifluoromethyl) phenyl)-2-phenylethyl)-3-((R)-1-hydroxybutan-2-yl)urea | 3.90 LC 510.47 $[M + H]^+$ | Procedures 1 and 2 |
| 510 | 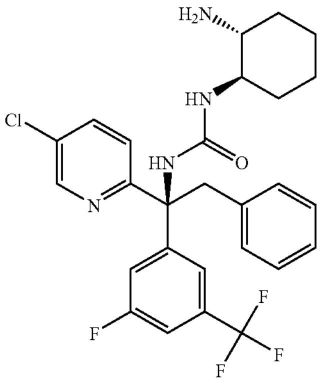 | 1-((1R,2R)-2-aminocyclohexyl)-3-((S)-1-(5-chloropyridin-2-yl)-1-(3-fluoro-5-(trifluoromethyl) phenyl)-2-phenylethyl)urea | 3.55 LC 535.5 $[M + H]^+$ | Procedures 1 and 2 |
| 511 | 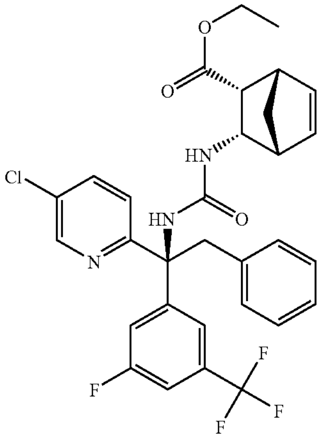 | (1S,2R,3S,4R)-ethyl 3-(3-((S)-1-(5-chloropyridin-2-yl)-1-(3-fluoro-5-(trifluoromethyl) phenyl)-2-phenylethyl)ureido) bicyclo[2.2.1]hept-5-ene-2-carboxylate | 4.21 LC 602.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 512 | 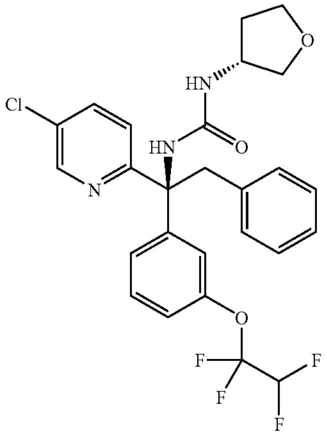 | 1-((S)-1-(5-chloropyridin-2-yl)-2-phenyl-1-(3-(1,1,2,2-tetrafluoroethoxy)phenyl)ethyl)-3-((R)-tetrahydrofuran-3-yl)urea | 3.73 LC 538.48 $[M + H]^+$ | Procedures 1 and 2 |
| 513 | 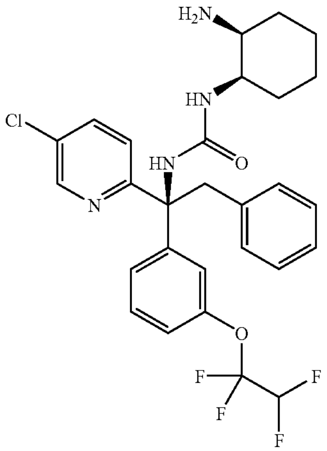 | 1-((1R,2S)-2-aminocyclohexyl)-3-((S)-1-(5-chloropyridin-2-yl)-2-phenyl-1-(3-(1,1,2,2-tetrafluoroethoxy)phenyl)ethyl) urea | 3.47 LC 565.49 $[M + H]^+$ | Procedures 1 and 2 |
| 514 | 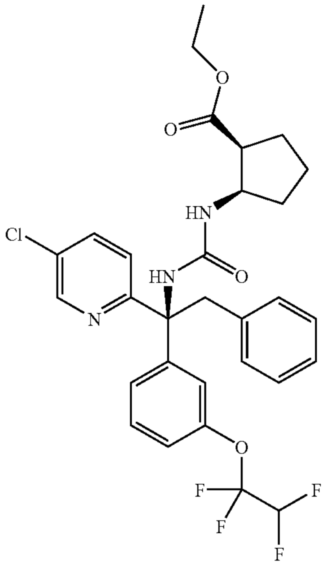 | (1S,2R)-ethyl 2-(3-((S)-1-(5-chloropyridin-2-yl)-2-phenyl-1-(3-(1,1,2,2-tetrafluoroethoxy) phenyl)ethyl)ureido) cyclopentanecarboxylate | 4.00 LC 608.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 515 | 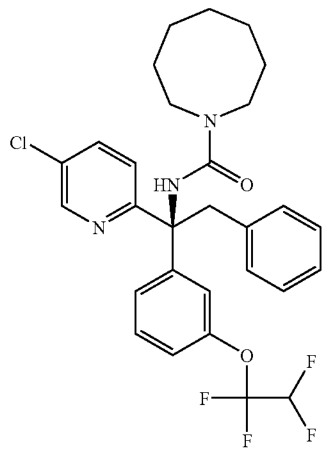 | (S)-N-(1-(5-chloropyridin-2-yl)-2-phenyl-1-(3-(1,1,2,2-tetrafluoroethoxy)phenyl)ethyl) azocane-1-carboxamide | 4.25 LC 564.51 $[M + H]^+$ | Procedures 1 and 2 |
| 516 | 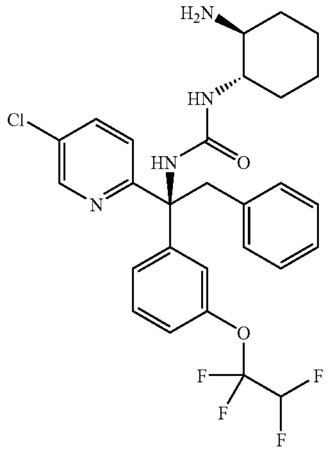 | 1-((1S,2S)-2-aminocyclohexyl)-3-((S)-1-(5-chloropyridin-2-yl)-2-phenyl-1-(3-(1,1,2,2-tetrafluoroethoxy)phenyl)ethyl) urea | 3.75 LC 565.48 $[M + H]^+$ | Procedures 1 and 2 |
| 517 | 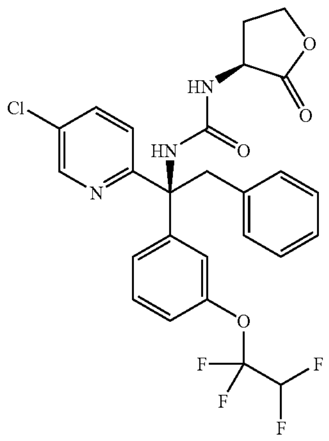 | 1-((S)-1-(5-chloropyridin-2-yl)-2-phenyl-1-(3-(1,1,2,2-tetrafluoroethoxy)phenyl)ethyl)-3-((S)-2-oxo-tetrahydrofuran-3-yl)urea | 3.62 LC 552.42 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 518 | 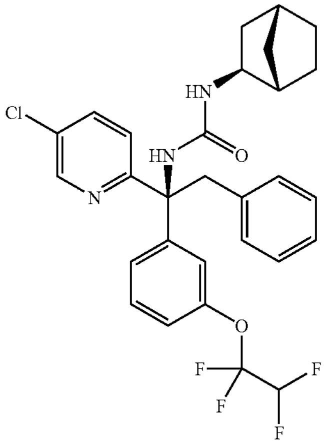 | 1-((1S,2S,4R)-bicyclo[2.2.1]heptan-2-yl)-3-((S)-1-(5-chloropyridin-2-yl)-2-phenyl-1-(3-(1,1,2,2-tetrafluoroethoxy)phenyl)ethyl)urea | 4.11 LC 562.49 $[M + H]^+$ | Procedures 1 and 2 |
| 519 | 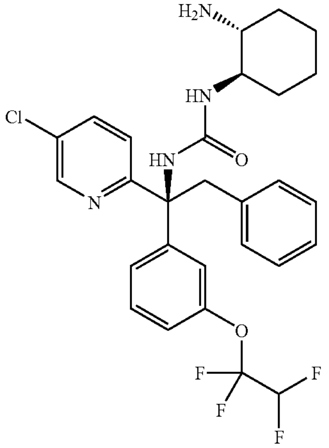 | 1-((1R,2R)-2-aminocyclohexyl)-3-((S)-1-(5-chloropyridin-2-yl)-2-phenyl-1-(3-(1,1,2,2-tetrafluoroethoxy)phenyl)ethyl)urea | 3.43 LC 565.49 $[M + H]^+$ | Procedures 1 and 2 |
| 520 | 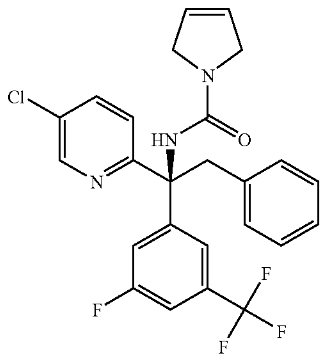 | (S)-N-(1-(5-chloropyridin-2-yl)-1-(3-fluoro-5-(trifluoromethyl)phenyl)-2-phenylethyl)-2H-pyrrole-1(5H)-carboxamide | 4.09 LC 490.46 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 521 | 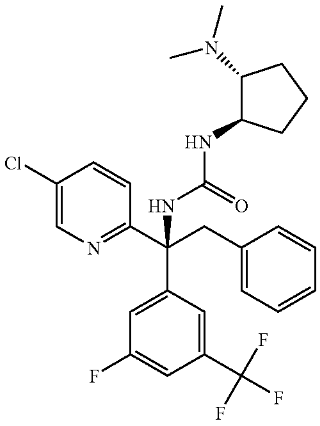 | 1-((S)-1-(5-chloropyridin-2-yl)-1-(3-fluoro-5-(trifluoromethyl) phenyl)-2-phenylethyl)-3-((1R,2R)-2-(dimethylamino) cyclopentyl)urea | 3.40 LC 549.49 [M + H]+ | Procedures 1 and 2 |
| 522 | 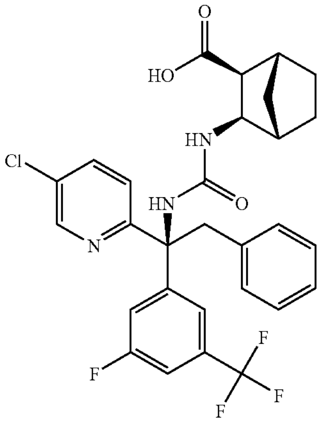 | (1R,2S,3R,4S)-3-(3-((S)-1-(5-chloropyridin-2-yl)-1-(3-fluoro-5-(trifluoromethyl)phenyl)-2-phenylethyl)ureido)bicycle [2.2.1]heptane-2-carboxylic acid | 4.09 LC 576.48 [M + H]+ | Procedures 1 and 2 |
| 523 | 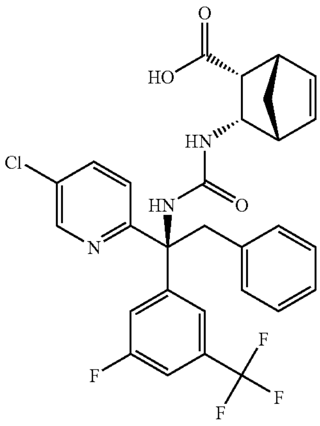 | (1S,2R,3S,4R)-3-(3-((S)-1-(5-chloropyridin-2-yl)-1-(3-fluoro-5-(trifluoromethyl)phenyl)-2-phenylethyl)ureido)bicycle [2.2.1]hept-5-ene-2-carboxylic acid | 4.07 LC 574.43 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 524 | 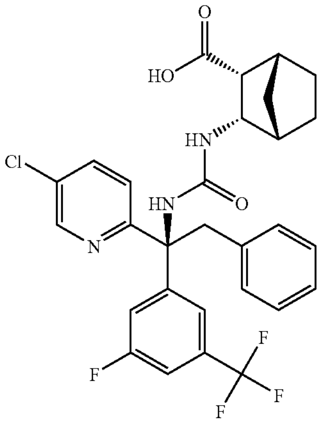 | (1R,2R,3S,4S)-3-(3-((S)-1-(5-chloropyridin-2-yl)-1-(3-fluoro-5-(trifluoromethyl)phenyl)-2-phenylethyl)ureido)bicycle [2.2.1]heptane-2-carboxylic acid | 4.12 LC 576.46 $[M + H]^+$ | Procedures 1 and 2 |
| 525 | 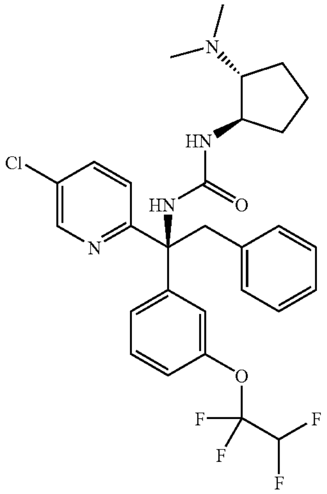 | 1-((S)-1-(5-chloropyridin-2-yl)-2-phenyl-1-(3-(1,1,2,2-tetrafluoroethoxy)phenyl)ethyl)-3-((1R,2R)-2-(dimethylamino) cyclopentyl)urea | 3.29 LC 579.49 $[M + H]^+$ | Procedures 1 and 2 |
| 526 | 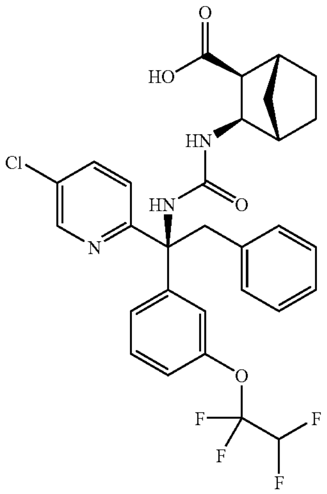 | (1R,2S,3R,4S)-3-(3-((S)-1-(5-chloropyridin-2-yl)-2-phenyl-1-(3-(1,1,2,2-tetrafluoroethoxy) phenyl)ethyl)ureido)bicycle [2.2.1]heptane-2-carboxylic acid | 3.95 LC 606.47 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 527 | 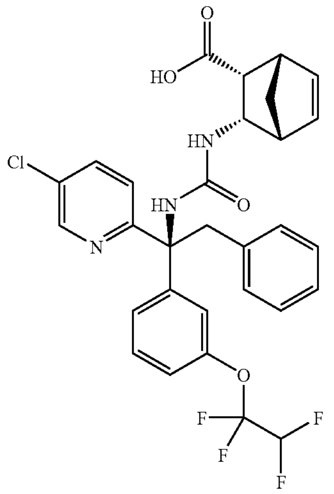 | (1S,2R,3S,4R)-3-(3-((S)-1-(5-chloropyridin-2-yl)-2-phenyl-1-(3-(1,1,2,2-tetrafluoroethoxy) phenyl)ethyl)ureido)bicycle [2.2.1]hept-5-ene-2-carboxylic acid | 3.91 LC 604.46 $[M + H]^+$ | Procedures 1 and 2 |
| 528 | 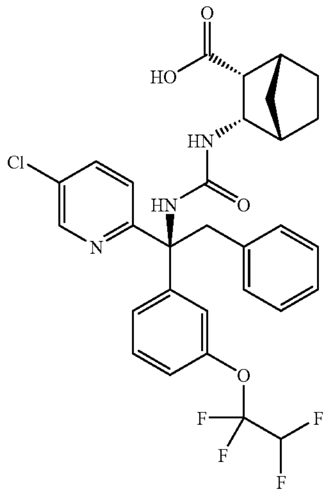 | (1R,2R,3S,4S)-3-(3-((S)-1-(5-chloropyridin-2-yl)-2-phenyl-1-(3-(1,1,2,2-tetrafluoroethoxy) phenyl)ethyl)ureido)bicycle [2.2.1]heptane-2-carboxylic acid | 3.97 LC 606.49 $[M + H]^+$ | Procedures 1 and 2 |
| 529 | 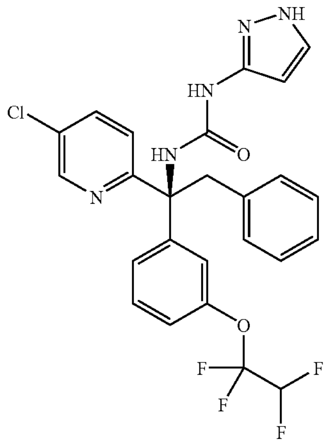 | (S)-1-(1-(5-chloropyridin-2-yl)-2-phenyl-1-(3-(1,1,2,2-tetrafluoroethoxy)phenyl)ethyl)-3-(1H-pyrazol-3-yl)urea | 3.62 LC 534.42 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 530 | 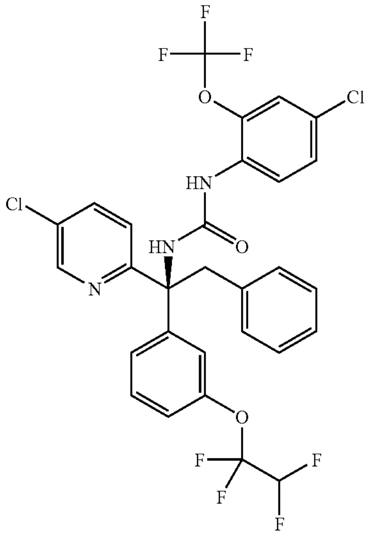 | (S)-1-(4-chloro-2-(trifluoromethoxy)phenyl)-3-(1-(5-chloropyridin-2-yl)-2-phenyl-1-(3-(1,1,2,2-tetrafluoroethoxy) phenyl)ethyl)urea | 4.32 LC 662.38 $[M + H]^+$ | Procedures 1 and 2 |
| 531 | 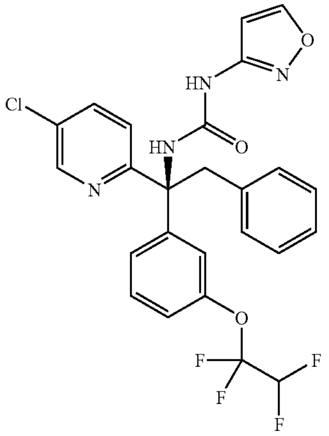 | (S)-1-(1-(5-chloropyridin-2-yl)-2-phenyl-1-(3-(1,1,2,2-tetrafluoroethoxy)phenyl)ethyl)-3-(isoxazol-3-yl)urea | 3.76 LC 535.42 $[M + H]^+$ | Procedures 1 and 2 |
| 532 | 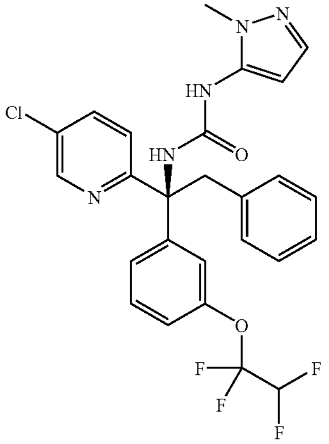 | (S)-1-(1-(5-chloropyridin-2-yl)-2-phenyl-1-(3-(1,1,2,2-tetrafluoroethoxy)phenyl)ethyl)-3-(1-methyl-1H-pyrazol-5-yl) urea | 3.67 LC 548.44 $[M + H]^+$ | Procedures 1 and 2 |

TABLE 4-continued

| Ex. No. | Structure | Name | Retention Time Min./ Molecular Mass | Prepared in the manner described in: |
| --- | --- | --- | --- | --- |
| 533 | 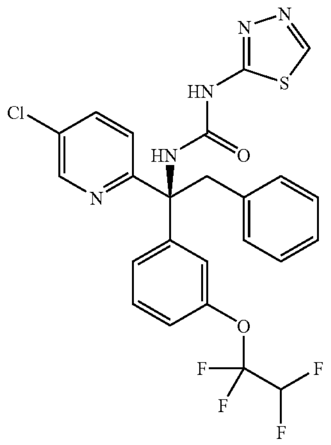 | (S)-1-(1-(5-chloropyridin-2-yl)-2-phenyl-1-(3-(1,1,2,2-tetrafluoroethoxy)phenyl)ethyl)-3-(1,3,4-thiadiazol-2-yl)urea | 3.71<br>LC<br>552.38<br>[M + H]$^+$ | Procedures 1 and 2 |
| 534 | 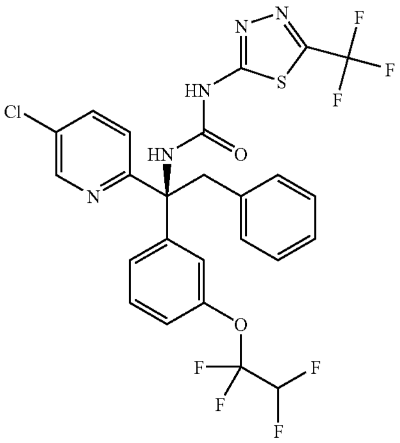 | (S)-1-(1-(5-chloropyridin-2-yl)-2-phenyl-1-(3-(1,1,2,2-tetrafluoroethoxy)phenyl)ethyl)-3-(5-(trifluoromethyl)-1,3,4-thiadiazol-2-yl)urea | 4.15<br>LC<br>620.37<br>[M + H]$^+$ | Procedures 1 and 2 |
| 535 | 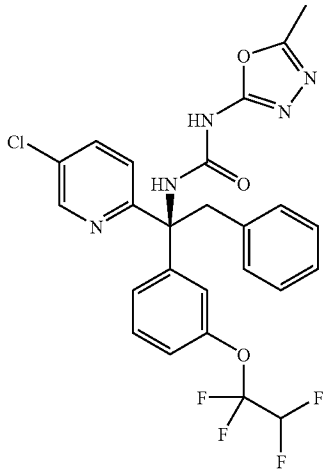 | (S)-1-(1-(5-chloropyridin-2-yl)-2-phenyl-1-(3-(1,1,2,2-tetrafluoroethoxy)phenyl)ethyl)-3-(5-methyl-1,3,4-oxadiazol-2-yl)urea | 3.68<br>LC<br>550.42<br>[M + H]$^+$ | Procedures 1 and 2 |

TABLE 4-continued

| Ex. No. | Structure | Name | Retention Time Min./ Molecular Mass | Prepared in the manner described in: |
|---|---|---|---|---|
| 536 | 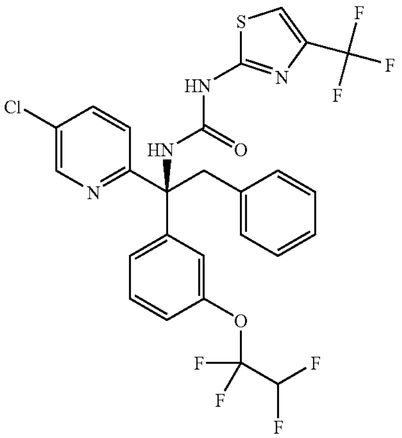 | (S)-1-(1-(5-chloropyridin-2-yl)-2-phenyl-1-(3-(1,1,2,2-tetrafluoroethoxy)phenyl)ethyl)-3-(4-(trifluoromethyl)thiazol-2-yl)urea | 4.06 LC 619.37 $[M + H]^+$ | Procedures 1 and 2 |
| 537 | 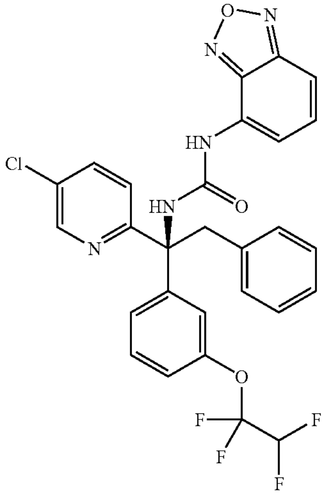 | (S)-1-(benzo[c][1,2,5]oxadiazol-4-yl)-3-(1-(5 -chloropyridin-2-yl)-2-phenyl-1-(3-(1,1,2,2-tetrafluoroethoxy)phenyl)ethyl) urea | 4.10 LC 586.43 $[M + H]^+$ | Procedures 1 and 2 |
| 538 | 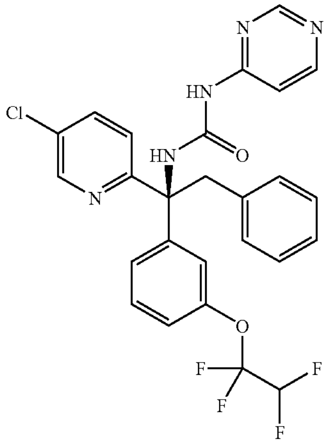 | (S)-1-(1-(5-chloropyridin-2-yl)-2-phenyl-1-(3-(1,1,2,2-tetrafluoroethoxy)phenyl)ethyl)-3-(pyrimidin-4-yl)urea | 3.53 LC 546.42 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 539 | 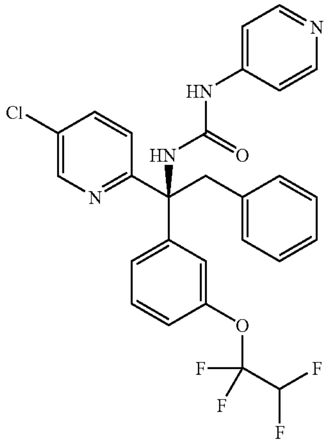 | (S)-1-(1-(5-chloropyridin-2-yl)-2-phenyl-1-(3-(1,1,2,2-tetrafluoroethoxy)phenyl)ethyl)-3-(pyridin-4-yl)urea | 3.26 LC 545.43 [M + H]$^+$ | Procedures 1 and 2 |
| 540 | 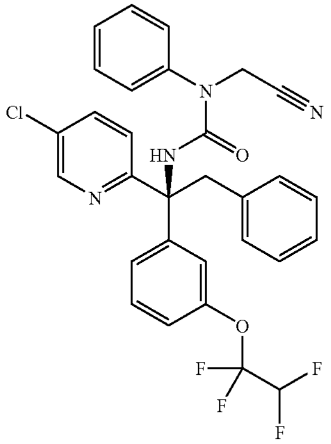 | (S)-3-(1-(5-chloropyridin-2-yl)-2-phenyl-1-(3-(1,1,2,2-tetrafluoroethoxy)phenyl)ethyl)-1-(cyanomethyl)-1-phenylurea | 3.93 LC 583.45 [M + H]$^+$ | Procedures 1 and 2 |
| 541 | 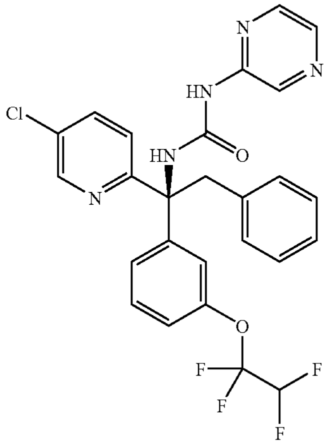 | (S)-1-(1-(5-chloropyridin-2-yl)-2-phenyl-1-(3-(1,1,2,2-tetrafluoroethoxy)phenyl)ethyl)-3-(pyrazin-2-yl)urea | 3.83 LC 546.43 [M + H]$^+$ | Procedures 1 and 2 |

TABLE 4-continued
| Ex. No. | Structure | Name | Retention Time Min./ Molecular Mass | Prepared in the manner described in: |
|---|---|---|---|---|
| 542 | 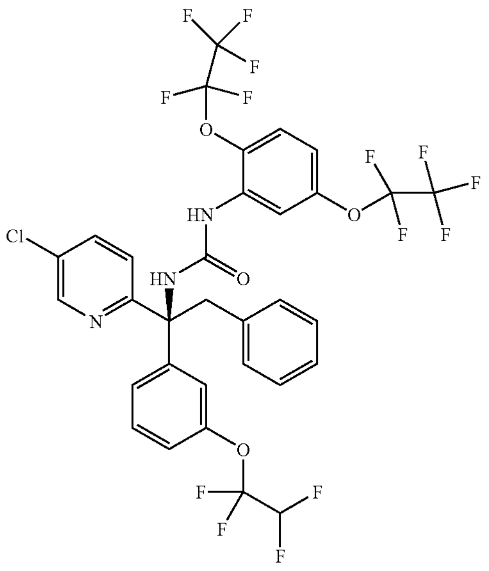 | (S)-1-(2,5-bis(perfluoroethoxy) phenyl)-3-(1-(5-chloropyridin-2-yl)-2-phenyl-1-(3-(1,1,2,2-tetrafluoroethoxy)phenyl)ethyl) urea | 4.42 LC 812.39 $[M + H]^+$ | Procedures 1 and 2 |
| 543 | 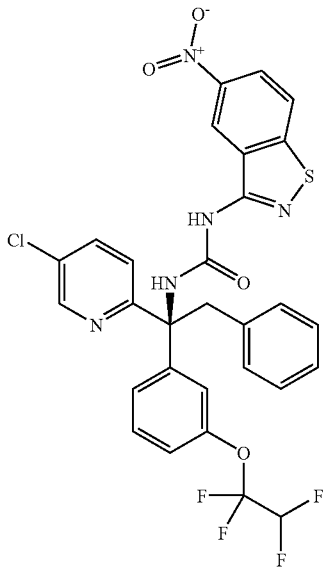 | (S)-1-(1-(5-chloropyridin-2-yl)-2-phenyl-1-(3-(1,1,2,2-tetrafluoroethoxy)phenyl)ethyl)-3-(5-nitrobenzo[d]isothiazol-3-yl)urea | 4.17 LC 646.39 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 544 | 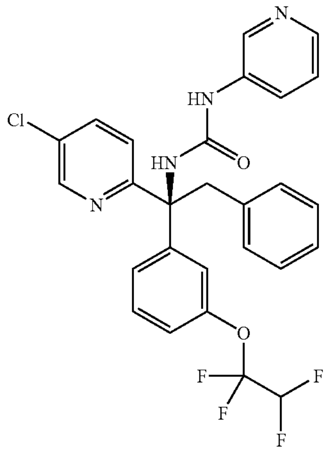 | (S)-1-(1-(5-chloropyridin-2-yl)-2-phenyl-1-(3-(1,1,2,2-tetrafluoroethoxy)phenyl)ethyl)-3-(pyridin-3-yl)urea | 3.27 LC 545.44 [M + H]+ | Procedures 1 and 2 |
| 545 | 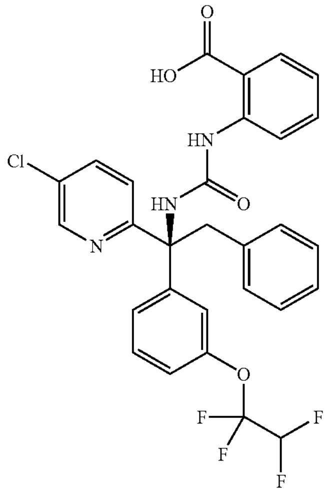 | (S)-2-(3-(1-(5-chloropyridin-2-yl)-2-phenyl-1-(3-(1,1,2,2-tetrafluoroethoxy)phenyl)ethyl) ureido)benzoic acid | 4.03 LC 588.41 [M + H]+ | Procedures 1 and 2 |
| 546 | 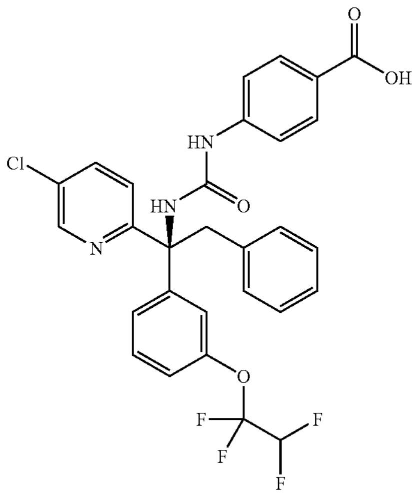 | (S)-4-(3-(1-(5-chloropyridin-2-yl)-2-phenyl-1-(3-(1,1,2,2-tetrafluoroethoxy)phenyl)ethyl) ureido)benzoic acid | 3.84 LC 588.42 [M + H]+ | Procedures 1 and 2 |

TABLE 4-continued
| Ex. No. | Structure | Name | Retention Time Min./ Molecular Mass | Prepared in the manner described in: |
| --- | --- | --- | --- | --- |
| 547 | 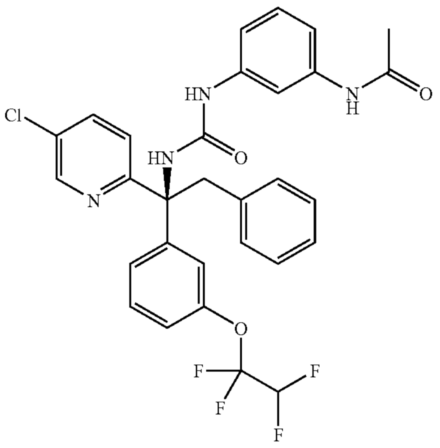 | (S)-1-(3-acetamidophenyl)-3-(1-(5-chloropyridin-2-yl)-2-phenyl-1-(3-(1,1,2,2-tetrafluoroethoxy)phenyl)ethyl)urea | 3.81 LC 601.44 $[M + H]^+$ | Procedures 1 and 2 |
| 548 | 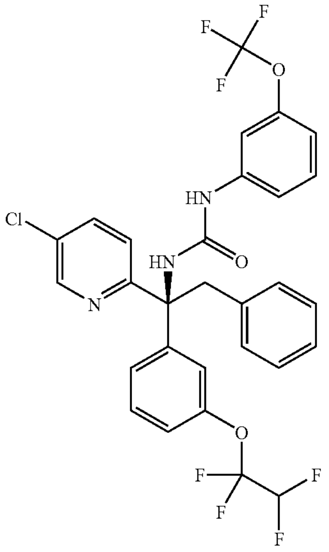 | (S)-1-(1-(5-chloropyridin-2-yl)-2-phenyl-1-(3-(1,1,2,2-tetrafluoroethoxy)phenyl)ethyl)-3-(3-(trifluoromethoxy)phenyl)urea | 4.18 LC 628.41 $[M + H]^+$ | Procedures 1 and 2 |

TABLE 4-continued
| Ex. No. | Structure | Name | Retention Time Min./ Molecular Mass | Prepared in the manner described in: |
| --- | --- | --- | --- | --- |
| 549 | 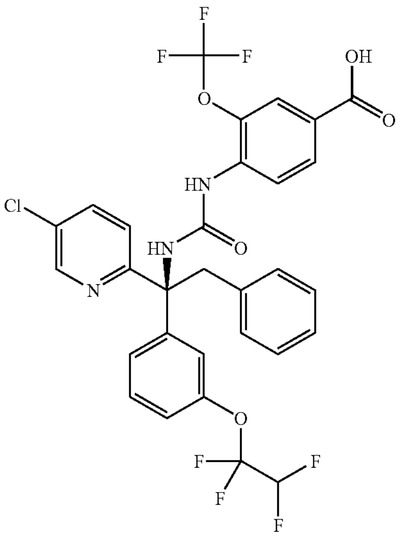 | (S)-4-(3-(1-(5-chloropyridin-2-yl)-2-phenyl-1-(3-(1,1,2,2-tetrafluoroethoxy)phenyl)ethyl) ureido)-3-(trifluoromethoxy) benzoic acid | 4.03 LC 672.4 $[M + H]^+$ | Procedures 1 and 2 |
| 550 | 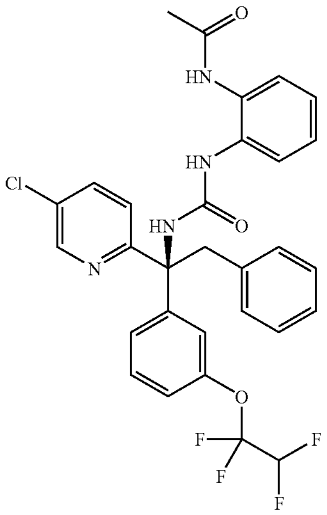 | (S)-1-(2-acetamidophenyl)-3-(1-(5-chloropyridin-2-yl)-2-phenyl-1-(3-(1,1,2,2-tetrafluoroethoxy) phenyl)ethyl)urea | 3.83 LC 601.44 $[M + H]^+$ | Procedures 1 and 2 |

TABLE 4-continued
| Ex. No. | Structure | Name | Retention Time Min./ Molecular Mass | Prepared in the manner described in: |
|---|---|---|---|---|
| 551 | 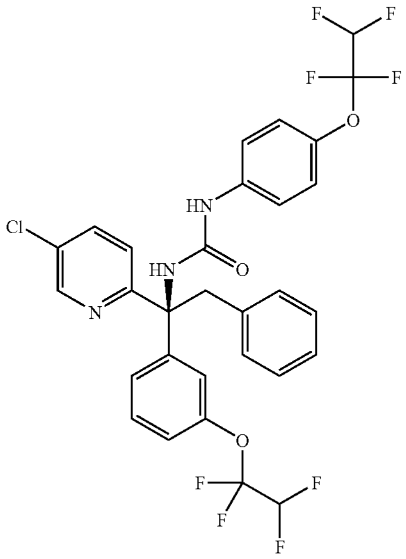 | (S)-1-(1-(5-chloropyridin-2-yl)-2-phenyl-1-(3-(1,1,2,2-tetrafluoroethoxy)phenyl)ethyl)-3-(4-(1,1,2,2-tetrafluoroethoxy) phenyl)urea | 4.07 LC 660.42 $[M + H]^+$ | Procedures 1 and 2 |
| 552 | 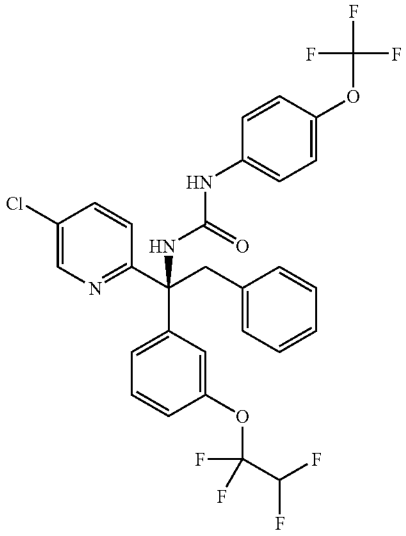 | (S)-1-(1-(5-chloropyridin-2-yl)-2-phenyl-1-(3-(1,1,2,2-tetrafluoroethoxy)phenyl)ethyl)-3-(4-(trifluoromethoxy)phenyl) urea | 4.19 LC 628.41 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 553 | 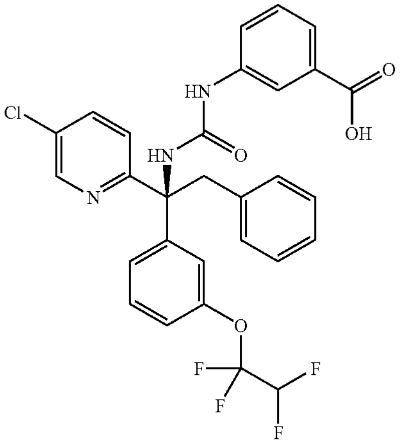 | (S)-3-(3-(1-(5-chloropyridin-2-yl)-2-phenyl-1-(3-(1,1,2,2-tetrafluoroethoxy)phenyl)ethyl) ureido)benzoic acid | 3.85 LC 588.43 [M + H]+ | Procedures 1 and 2 |
| 554 | 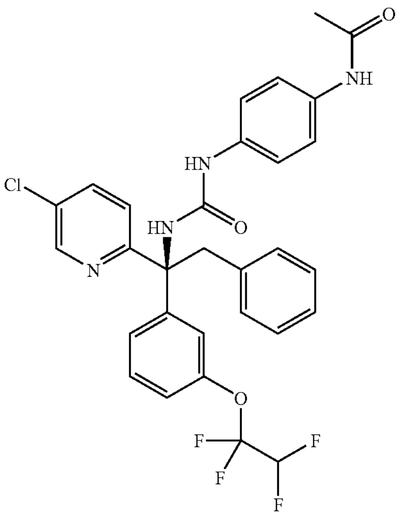 | (S)-1-(4-acetamidophenyl)-3-(1-(5-chloropyridin-2-yl)-2-phenyl-1-(3-(1,1,2,2-tetrafluoroethoxy) phenyl)ethyl)urea | 3.74 LC 601.46 [M + H]+ | Procedures 1 and 2 |
| 555 | 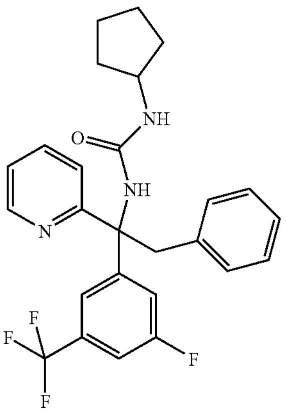 | 1-cyclopentyl-3-(1-(3-fluoro-5-(trifluoromethyl)phenyl)-2-phenyl-1-(pyridin-2-yl)ethyl) urea | 3.85 LC 472.30 [M + H]+ | Procedures 1 and 2 |

TABLE 4-continued

| Ex. No. | Structure | Name | Retention Time Min./ Molecular Mass | Prepared in the manner described in: |
| --- | --- | --- | --- | --- |
| 556 | 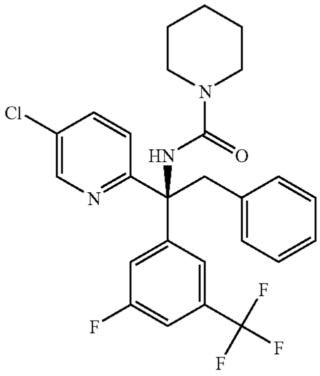 | (S)-N-(1-(5-chloropyridin-2-yl)-1-(3-fluoro-5-(trifluoromethyl) phenyl)-2-phenylethyl) piperidine-1-carboxamide | 4.20 LC 506.47 $[M + H]^+$ | Procedures 1 and 2 |
| 557 | 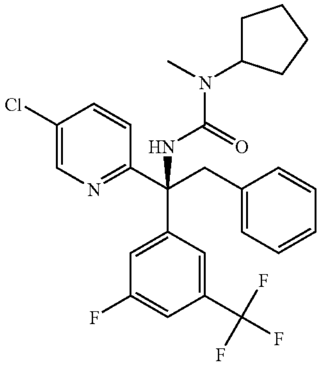 | (S)-3-(1-(5-chloropyridin-2-yl)-1-(3-fluoro-5-(trifluoromethyl) phenyl)-2-phenylethyl)-1-cyclopentyl-1-methylurea | 4.30 LC 520.48 $[M + H]^+$ | Procedures 1 and 2 |
| 558 | 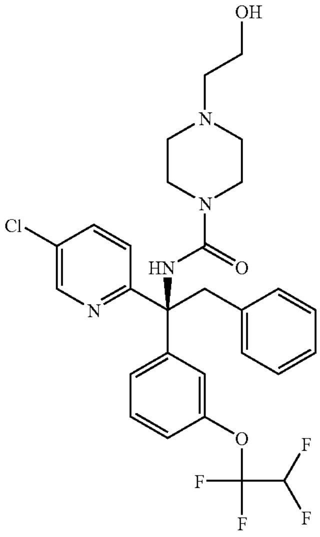 | (S)-N-(1-(5-chloropyridin-2-yl)-2-phenyl-1-(3-(1,1,2,2-tetrafluoroethoxy)phenyl)ethyl)-4-(2-hydroxyethyl)piperazine-1-carboxamide | 3.19 LC 581.48 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 559 | 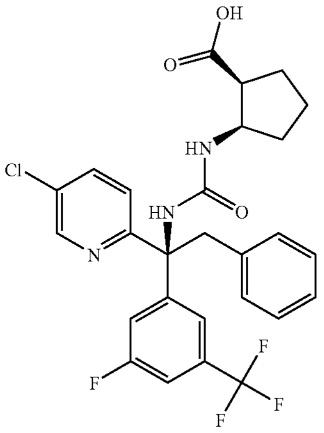 | (1S,2R)-2-(3-((S)-1-(5-chloropyridin-2-yl)-1-(3-fluoro-5-(trifluoromethyl)phenyl)-2-phenylethyl)ureido) cyclopentanecarboxylic acid | 3.97 LC 550.42 $[M + H]^+$ | Procedures 1 and 2 |
| 560 | 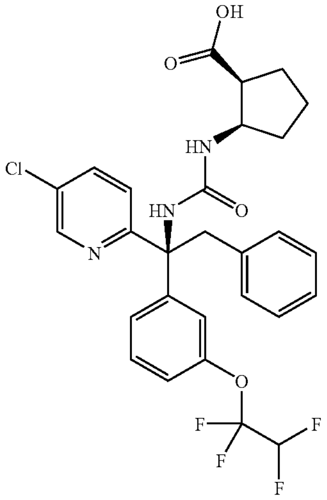 | (1S,2R)-2-(3-((S)-1-(5-chloropyridin-2-yl)-2-phenyl-1-(3-(1,1,2,2-tetrafluoroethoxy) phenyl)ethyl)ureido) cyclopentanecarboxylic acid | 3.83 LC 580.46 $[M + H]^+$ | Procedures 1 and 2 |
| 561 | 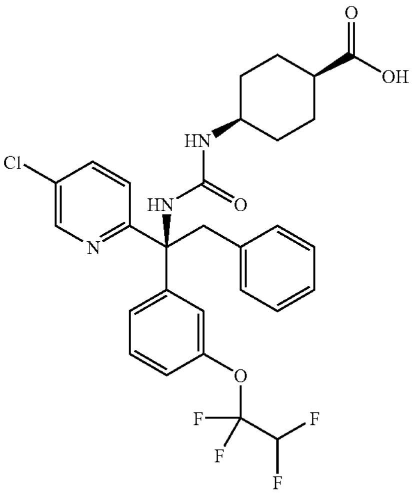 | (1R,4s)-4-(3-((S)-1-(5-chloropyridin-2-yl)-2-phenyl-1-(3-(1,1,2,2-tetrafluoroethoxy) phenyl)ethyl)ureido) cyclohexanecarboxylic acid | 3.86 LC 594.47 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 562 | 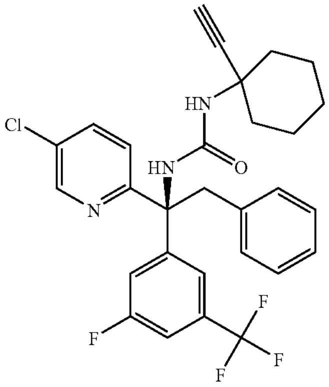 | (S)-1-(1-(5-chloropyridin-2-yl)-1-(3-fluoro-5-(trifluoromethyl) phenyl)-2-phenylethyl)-3-(1-ethynylcyclohexyl)urea | 4.21 LC 544.46 $[M + H]^+$ | Procedures 1 and 2 |
| 563 | 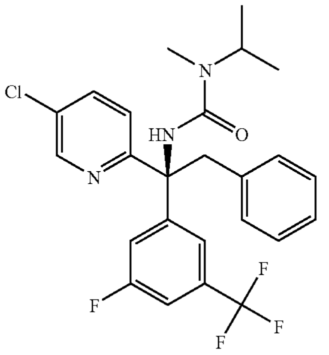 | (S)-3-(1-(5-chloropyridin-2-yl)-1-(3-fluoro-5-(trifluoromethyl) phenyl)-2-phenylethyl)-1-isopropyl-1-methylurea | 4.15 LC 494.44 $[M + H]^+$ | Procedures 1 and 2 |
| 564 | 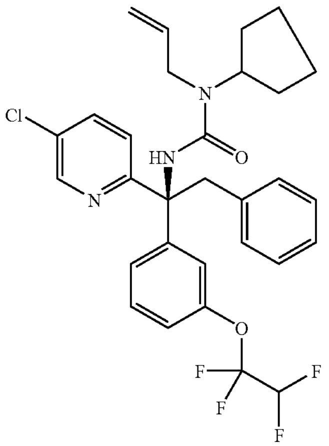 | (S)-1-allyl-3-(1-(5-chloropyridin-2-yl)-2-phenyl-1-(3-(1,1,2,2-tetrafluoroethoxy) phenyl)ethyl)-1-cyclopentylurea | 4.30 LC 576.49 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 565 | 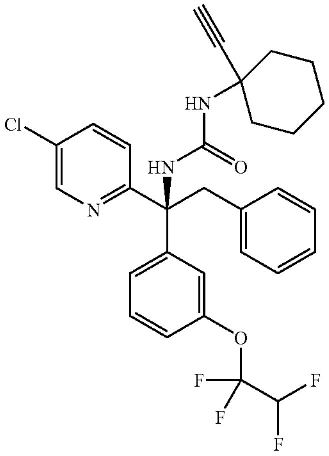 | (S)-1-(1-(5-chloropyridin-2-yl)-2-phenyl-1-(3-(1,1,2,2-tetrafluoroethoxy)phenyl)ethyl)-3-(1-ethynylcyclohexyl)urea | 4.08 LC 575.47 [M + H]+ | Procedures 1 and 2 |
| 566 | 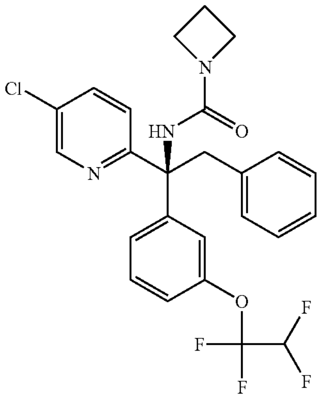 | (S)-N-(1-(5-chloropyridin-2-yl)-2-phenyl-1-(3-(1,1,2,2-tetrafluoroethoxy)phenyl)ethyl) azetidine-1-carboxamide | 3.89 LC 508.42 [M + H]+ | Procedures 1 and 2 |
| 567 | 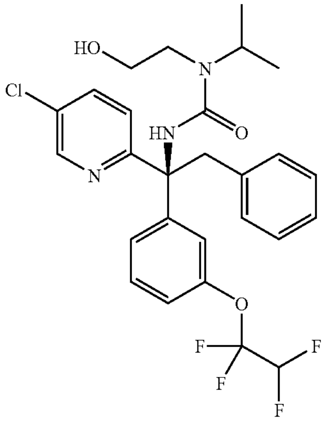 | (S)-3-(1-(5-chloropyridin-2-yl)-2-phenyl-1-(3-(1,1,2,2-tetrafluoroethoxy)phenyl)ethyl)-1-(2-hydroxyethyl)-1-isopropylurea | 3.84 LC 554.47 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 568 | 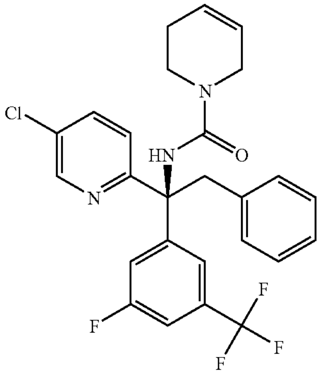 | (S)-N-(1-(5-chloropyridin-2-yl)-1-(3-fluoro-5-(trifluoromethyl) phenyl)-2-phenylethyl)-5,6-dihydropyridine-1(2H)-carboxamide | 4.15 LC 504.44 [M + H]+ | Procedures 1 and 2 |
| 569 | 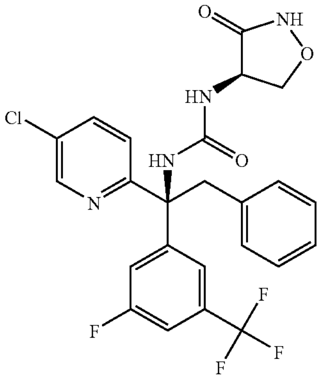 | 1-((S)-1-(5-chloropyridin-2-yl)-1-(3-fluoro-5-(trifluoromethyl) phenyl)-2-phenylethyl)-3-((R)-3-oxoisoxazolidin-4-yl)urea | 3.76 LC 523.42 [M + H]+ | Procedures 1 and 2 |
| 570 | 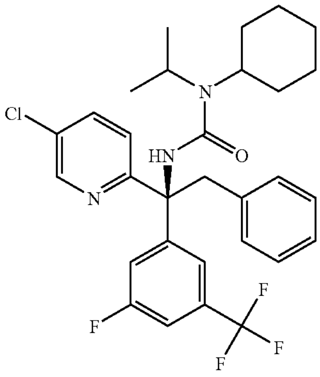 | (S)-3-(1-(5-chloropyridin-2-yl)-1-(3-fluoro-5-(trifluoromethyl) phenyl)-2-phenylethyl)-1-cyclohexyl-1-isopropylurea | 4.62 LC 562.51 [M + H]+ | Procedures 1 and 2 |

TABLE 4-continued

| Ex. No. | Structure | Name | Retention Time Min./Molecular Mass | Prepared in the manner described in: |
|---|---|---|---|---|
| 571 | 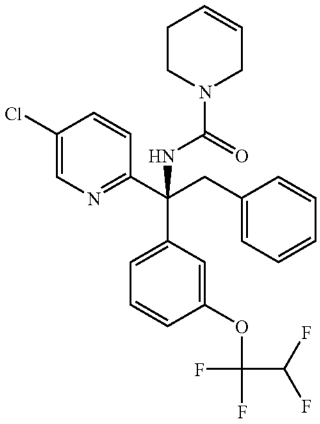 | (S)-N-(1-(5-chloropyridin-2-yl)-2-phenyl-1-(3-(1,1,2,2-tetrafluoroethoxy)phenyl)ethyl)-5,6-dihydropyridine-1(2H)-carboxamide | 4.06 LC 534.45 $[M + H]^+$ | Procedures 1 and 2 |
| 572 | 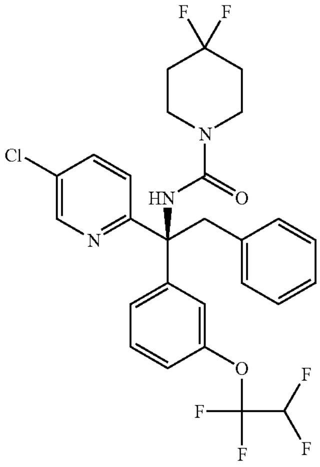 | (S)-N-(1-(5-chloropyridin-2-yl)-2-phenyl-1-(3-(1,1,2,2-tetrafluoroethoxy)phenyl)ethyl)-4,4-difluoropiperidine-1-carboxamide | 4.00 LC 572.43 $[M + H]^+$ | Procedures 1 and 2 |
| 573 | 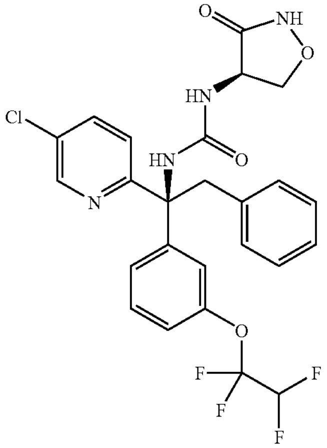 | 1-((S)-1-(5-chloropyridin-2-yl)-2-phenyl-1-(3-(1,1,2,2-tetrafluoroethoxy)phenyl)ethyl)-3-((R)-3-oxoisoxazolidin-4-yl) urea | 3.64 LC 553.42 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 574 | 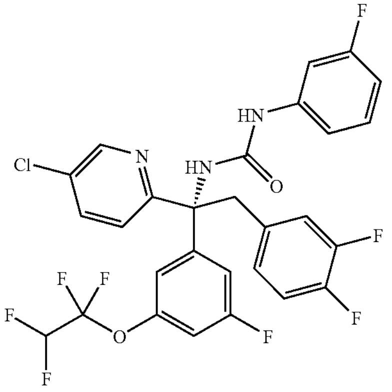 | (R)-1-(1-(5-chloropyridin-2-yl)-2-(3,4-difluorophenyl)-1-(3-fluoro-5-(1,1,2,2-tetrafluoroethoxy)phenyl)ethyl)-3-(3-fluorophenyl)urea | 3.64 LC 616.01 [M + H]+ | Procedures 3, 1 and 2 |
| 575 | 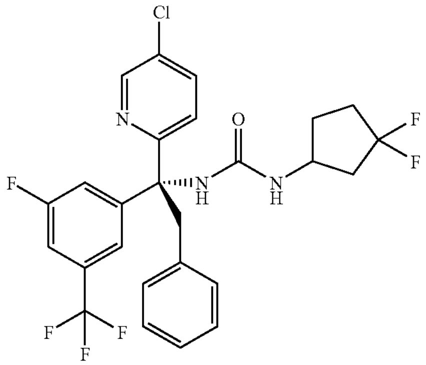 | 1-((R)-1-(5-chloropyridin-2-yl)-1-(3-fluoro-5-(trifluoromethyl) phenyl)-2-phenylethyl)-3-(3,3-difluorocyclopentyl)urea | 4.05 LC 542.20 [M + H]+ | Procedures 5, 6, 7 and 8 |
| 576 | 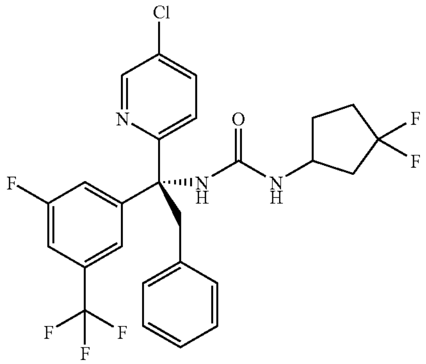 | 1-((S)-1-(5-chloropyridin-2-yl)-1-(3-fluoro-5-(trifluoromethyl) phenyl)-2-phenylethyl)-3-(3,3-difluorocyclopentyl)urea | 4.06 LC 542.20 [M + H]+ | Procedures 5, 6, 7 and 8 |

TABLE 4-continued

| Ex. No. | Structure | Name | Retention Time Min./ Molecular Mass | Prepared in the manner described in: |
|---|---|---|---|---|
| 577 | 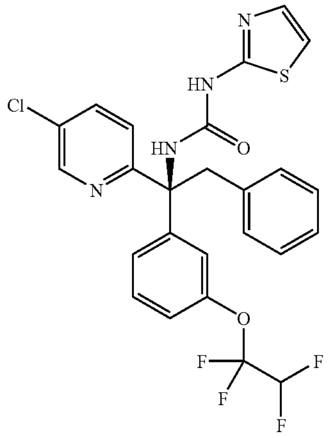 | (S)-1-(1-(5-chloropyridin-2-yl)-2-phenyl-1-(3-(1,1,2,2-tetrafluoroethoxy)phenyl)ethyl)-3-(thiazol-2-yl)urea | 3.73 LC 551.42 [M + H]+ | Procedures 1 and 2 |
| 578 | 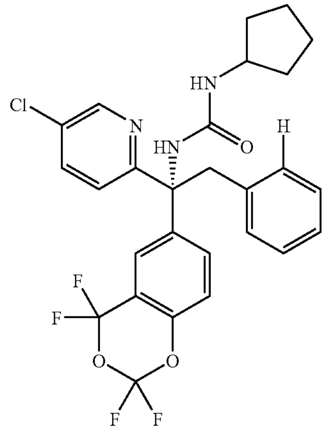 | (R)-1-(1-(5-chloropyridin-2-yl)-2-phenyl-1-(2,2,4,4-tetrafluoro-4H-benzo[d][1,3]dioxin-6-yl)ethyl)-3-cyclopentylurea | 4.15 LC 550.23 [M + H]+ | Procedures 1 and 2 |
| 579 | 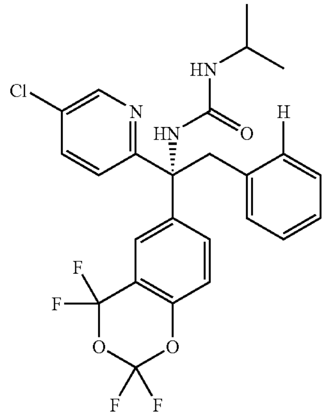 | (R)-1-(1-(5-chloropyridin-2-yl)-2-phenyl-1-(2,2,4,4-tetrafluoro-4H-benzo[d][1,3]dioxin-6-yl)ethyl)-3-isopropylurea | 4.04 LC 524.20 [M + H]+ | Procedures 1 and 2 |

TABLE 4-continued

| Ex. No. | Structure | Name | Retention Time Min./ Molecular Mass | Prepared in the manner described in: |
|---|---|---|---|---|
| 580 | 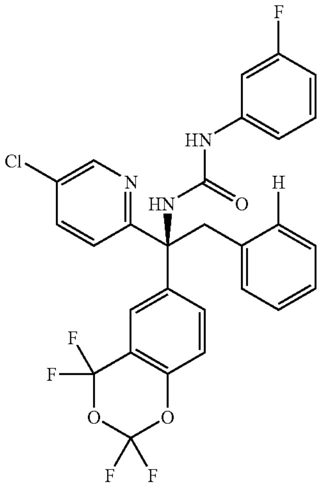 | (S)-1-(1-(5-chloropyridin-2-yl)-2-phenyl-1-(2,2,4,4-tetrafluoro-4H-benzo[d][1,3]dioxin-6-yl)ethyl)-3-(3-fluorophenyl)urea | 4.16 LC 576.18 $[M + H]^+$ | Procedures 1 and 2 |
| 581 | 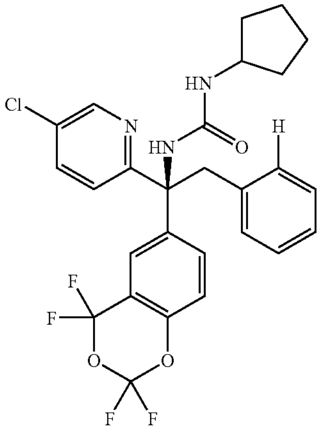 | (S)-1-(1-(5-chloropyridin-2-yl)-2-phenyl-1-(2,2,4,4-tetrafluoro-4H-benzo[d][1,3]dioxin-6-yl)ethyl)-3-cyclopentylurea | 4.14 LC 550.22 $[M + H]^+$ | Procedures 1 and 2 |
| 582 | 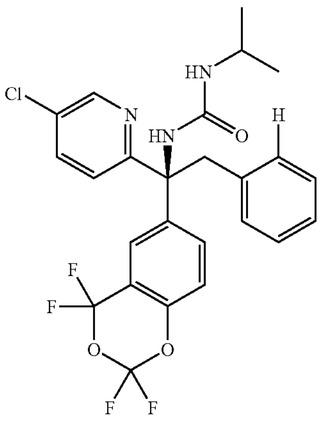 | (S)-1-(1-(5-chloropyridin-2-yl)-2-phenyl-1-(2,2,4,4-tetrafluoro-4H-benzo[d][1,3]dioxin-6-yl)ethyl)-3-isopropylurea | 4.03 LC 524.20 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 583 | 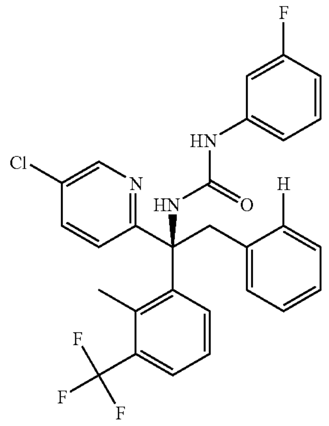 | (S)-1-(1-(5-chloropyridin-2-yl)-1-(2-methyl-3-(trifluoromethyl) phenyl)-2-phenylethyl)-3-(3-fluorophenyl)urea | 4.09 LC 528.22 $[M + H]^+$ | Procedures 1 and 2 |
| 584 | 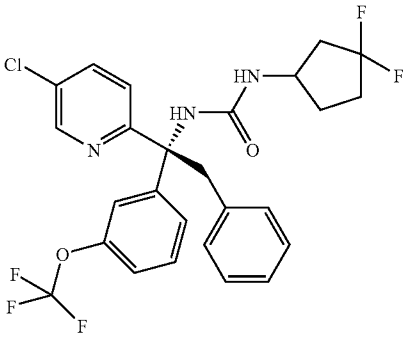 | 1-((R)-1-(5-chloropyridin-2-yl)-2-phenyl-1-(3-(trifluoromethoxy)phenyl)ethyl)-3-(3,3-difluorocyclopentyl)urea | 4.05 LC 540.3 $[M + H]^+$ | Procedures 5, 6, 7 and 2 |
| 585 | 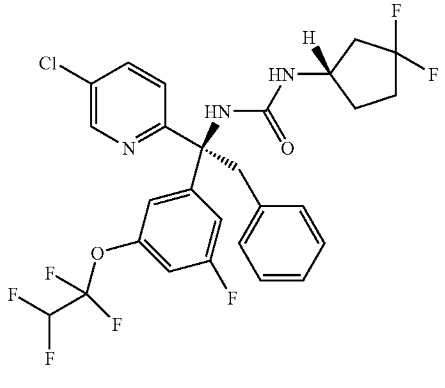 | 1-((S)-1-(5-chloropyridin-2-yl)-1-(3-fluoro-5-(1,1,2,2-tetrafluoroethoxy)phenyl)-2-phenylethyl)-3-((S)-3,3-difluorocyclopentyl)urea | 4.00 LC 590.3 $[M + H]^+$ | Procedures 3, 5, 6, 7 and 8 |

TABLE 4-continued

| Ex. No. | Structure | Name | Retention Time Min./ Molecular Mass | Prepared in the manner described in: |
|---|---|---|---|---|
| 586 | 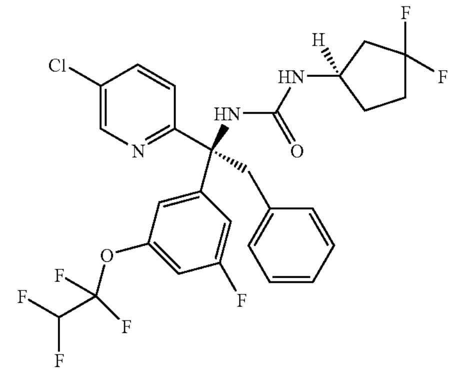 | 1-((S)-1-(5-chloropyridin-2-yl)-1-(3-fluoro-5-(1,1,2,2-tetrafluoroethoxy)phenyl)-2-phenylethyl)-3-((R)-3,3-difluorocyclopentyl)urea | 4.00 LC 590.3 $[M + H]^+$ | Procedures 3, 5, 6, 7 and 8 |
| 587 | 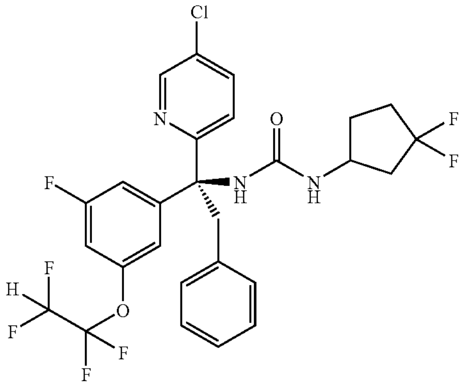 | 1-((S)-1-(5-chloropyridin-2-yl)-1-(3-fluoro-5-(1,1,2,2-tetrafluoroethoxy)phenyl)-2-phenylethyl)-3-(3,3-difluorocyclopentyl)urea | 4.00 LC 590.3 $[M + H]^+$ | Procedures 3, 5, 6, 7 and 8 |
| 588 | 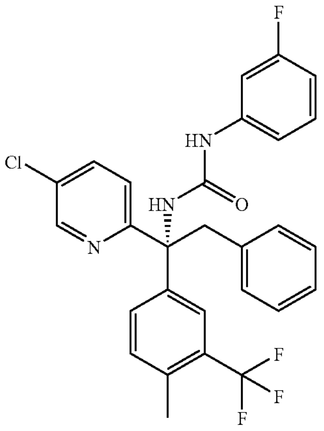 | (R)-1-(1-(5-chloropyridin-2-yl)-1-(4-methyl-3-(trifluoromethyl)phenyl)-2-phenylethyl)-3-(3-fluorophenyl)urea | 4.15 LC 528.13 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 589 | 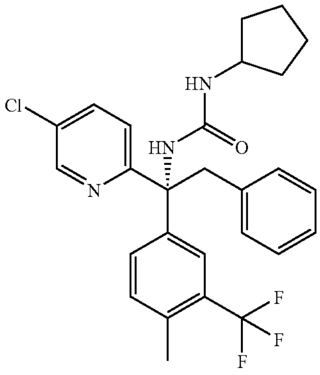 | (R)-1-(1-(5-chloropyridin-2-yl)-1-(4-methyl-3-(trifluoromethyl) phenyl)-2-phenylethyl)-3-cyclopentylurea | 4.15 LC 502.19 $[M + H]^+$ | Procedures 1 and 2 |
| 590 | 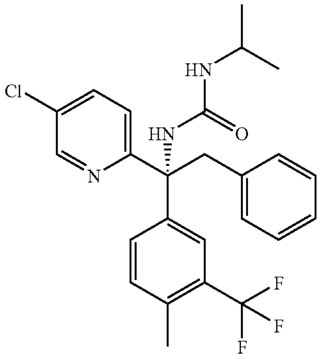 | (R)-1-(1-(5-chloropyridin-2-yl)-1-(4-methyl-3-(trifluoromethyl) phenyl)-2-phenylethyl)-3-isopropylurea | 4.03 LC 476.19 $[M + H]^+$ | Procedures 1 and 2 |
| 591 | 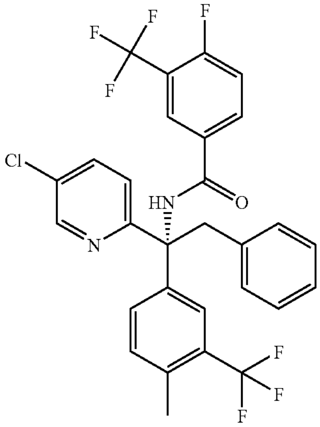 | (R)-N-(1-(5-chloropyridin-2-yl)-1-(4-methyl-3-(trifluoromethyl) phenyl)-2-phenylethyl)-4-fluoro-3-(trifluoromethyl)benzamide | 4.37 LC 581.04 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 592 | 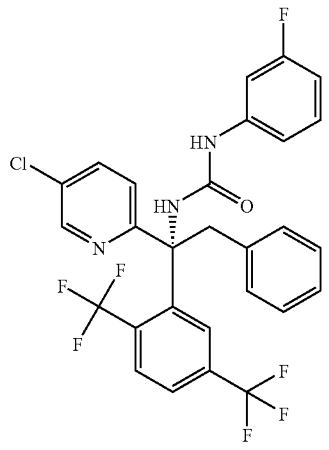 | (R)-1-(1-(2,5-bis(trifluoromethyl)phenyl)-1-(5-chloropyridin-2-yl)-2-phenylethyl)-3-(3-fluorophenyl) urea | 4.14 LC 582.10 $[M + H]^+$ | Procedures 1 and 2 |
| 593 | 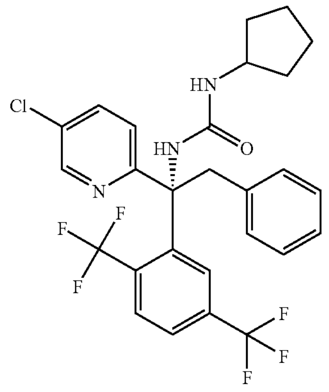 | (R)-1-(1-(2,5-bis(trifluoromethyl)phenyl)-1-(5-chloropyridin-2-yl)-2-phenylethyl)-3-cyclopentylurea | 4.16 LC 556.14 $[M + H]^+$ | Procedures 1 and 2 |
| 594 | 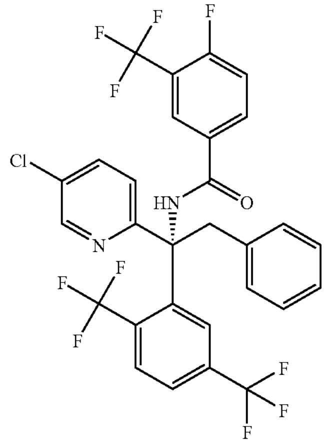 | (R)-N-(1-(2,5-bis(trifluoromethyl)phenyl)-1-(5-chloropyridin-2-yl)-2-phenylethyl)-4-fluoro-3-(trifluoromethyl)benzamide | 4.33 LC 635.05 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 595 | 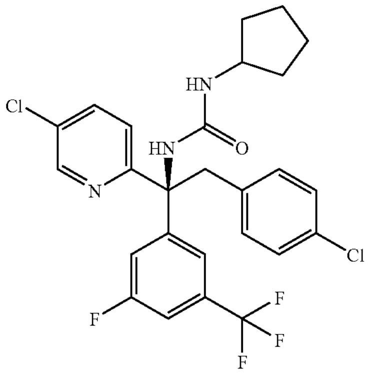 | (S)-1-(2-(4-chlorophenyl)-1-(5-chloropyridin-2-yl)-1-(3-fluoro-5-(trifluoromethyl)phenyl)ethyl)-3-cyclopentylurea | 4.22 LC 540.09 $[M + H]^+$ | Procedures 1 and 2 |
| 596 | 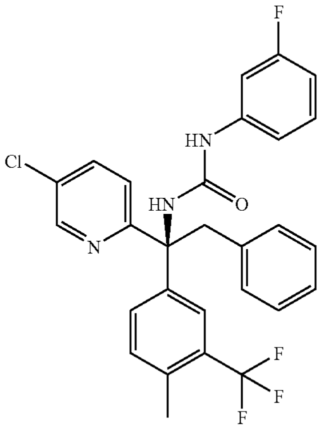 | (S)-1-(1-(5-chloropyridin-2-yl)-1-(4-methyl-3-(trifluoromethyl) phenyl)-2-phenylethyl)-3-(3-fluorophenyl)urea | 4.15 LC 528.13 $[M + H]^+$ | Procedures 1 and 2 |
| 597 | 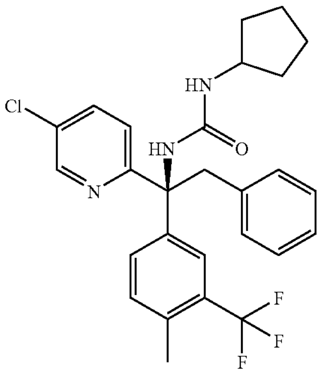 | (S)-1-(1-(5-chloropyridin-2-yl)-1-(4-methyl-3-(trifluoromethyl) phenyl)-2-phenylethyl)-3-cyclopentylurea | 4.13 LC 502.19 $[M + H]^+$ | Procedures 1 and 2 |

TABLE 4-continued

| Ex. No. | Structure | Name | Retention Time Min./ Molecular Mass | Prepared in the manner described in: |
|---|---|---|---|---|
| 598 | 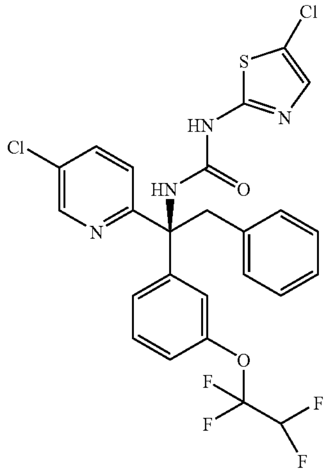 | (S)-1-(1-(5-chloropyridin-2-yl)-2-phenyl-1-(3-(1,1,2,2-tetrafluoroethoxy)phenyl)ethyl)-3-(5-chlorothiazol-2-yl)urea | 585.401 (LH) | Procedures 1 and 2 |
| 599 | 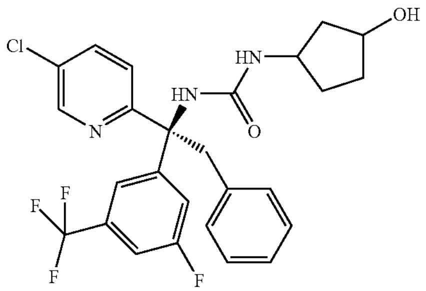 | 1-((S)-1-(5-chloropyridin-2-yl)-1-(3-fluoro-5-(trifluoromethyl) phenyl)-2-phenylethyl)-3-(3-hydroxycyclopentyl)urea | 3.89 LC 522.2 [M + H]$^+$ | Procedures 5, 6, 7 and 2 |
| 600 | 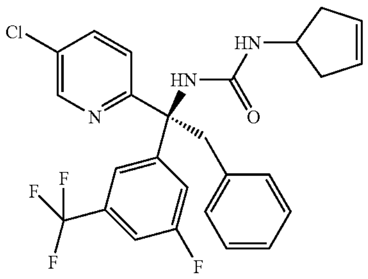 | (S)-1-(1-(5-chloropyridin-2-yl)-1-(3-fluoro-5-(trifluoromethyl) phenyl)-2-phenylethyl)-3-(cyclopent-3-enyl)urea | 4.14 LC 504.3 [M + H]$^+$ | Procedures 5, 6, 7 and 2 |
| 601 | 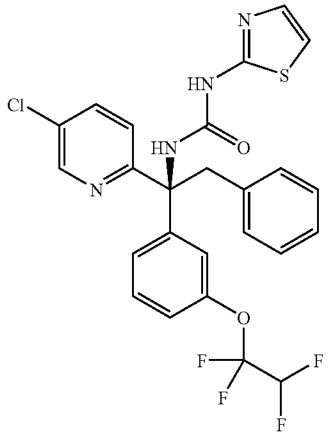 | (S)-1-(1-(5-chloropyridin-2-yl)-2-phenyl-1-(3-(1,1,2,2-tetrafluoroethoxy)phenyl)ethyl)-3-(thiazol-2-yl)urea | 3.73 LC 551.42 [M + H]$^+$ | Procedures 1 and 2 |

TABLE 4-continued

| Ex. No. | Structure | Name | Retention Time Min./ Molecular Mass | Prepared in the manner described in: |
|---|---|---|---|---|
| 602 | 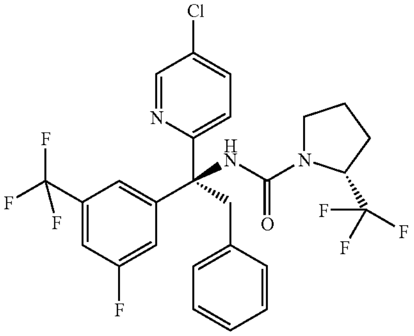 | (R)-N-((S)-1-(5-chloropyridin-2-yl)-1-(3-fluoro-5-(trifluoromethyl)phenyl)-2-phenylethyl)-2-(trifluoromethyl) pyrrolidine-1-carboxamide | 4.30 LC 560.00 $[M + H]^+$ | Procedures 5, 6, 7 and 8 |
| 603 | 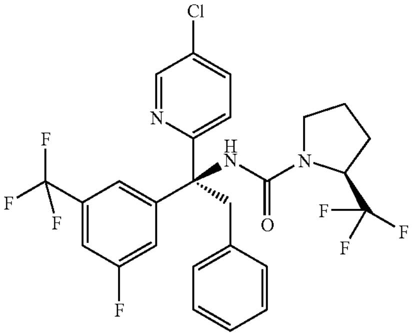 | (S)-N-((S)-1-(5-chloropyridin-2-yl)-1-(3-fluoro-5-(trifluoromethyl)phenyl)-2-phenylethyl)-2-(trifluoromethyl) pyrrolidine-1-carboxamide | 4.33 LC 560.02 $[M + H]^+$ | Procedures 5, 6, 7 and 8 |
| 604 | 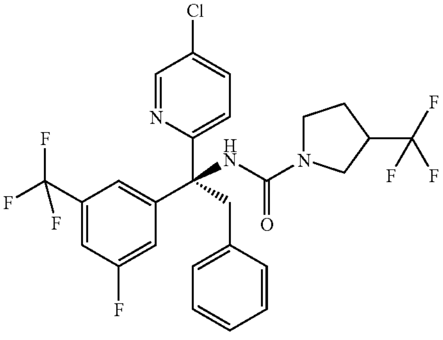 | N-((S)-1-(5-chloropyridin-2-yl)-1-(3-fluoro-5-(trifluoromethyl) phenyl)-2-phenylethyl)-3-(trifluoromethyl)pyrrolidine-1-carboxamide | 4.30 LC 560.02 $[M + H]^+$ | Procedures 5, 6, 7 and 8 |
| 605 | 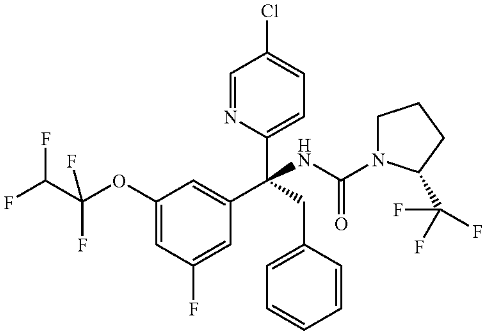 | (R)-N-((S)-1-(5-chloropyridin-2-yl)-1-(3-fluoro-5-(1,1,2,2-tetrafluoroethoxy)phenyl)-2-phenylethyl)-2-(trifluoromethyl) pyrrolidine-1-carboxamide | 4.27 LC 608.01 $[M + H]^+$ | Procedures 3, 5, 6 7 and 8 |

TABLE 4-continued

| Ex. No. | Structure | Name | Retention Time Min./ Molecular Mass | Prepared in the manner described in: |
|---|---|---|---|---|
| 606 | 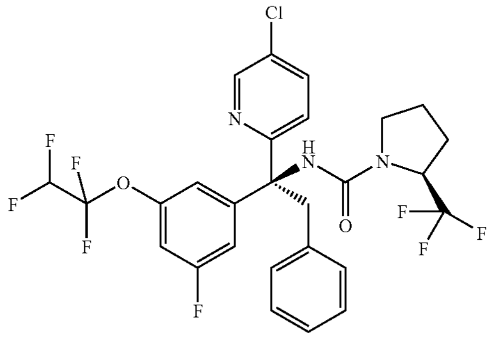 | (S)-N-((S)-1-(5-chloropyridin-2-yl)-1-(3-fluoro-5-(1,1,2,2-tetrafluoroethoxy)phenyl)-2-phenylethyl)-2-(trifluoromethyl) pyrrolidine-1-carboxamide | 4.28 LC 607.98 [M + H]+ | Procedures 3, 5, 6, 7 and 8 |
| 607 | 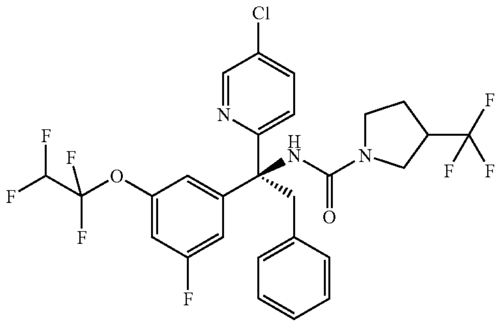 | N-((S)-1-(5-chloropyridin-2-yl)-1-(3-fluoro-5-(1,1,2,2-tetrafluoroethoxy)phenyl)-2-phenylethyl)-3-(trifluoromethyl) pyrrolidine-1-carboxamide | 4.25 LC 608.00 [M + H]+ | Procedures 3, 5, 6, 7 and 8 |
| 608 | 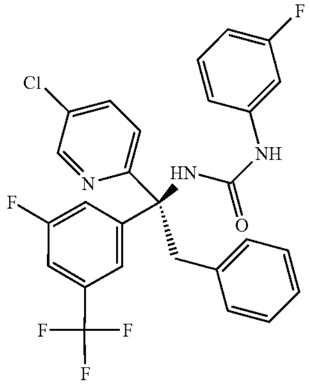 | (S)-1-(1-(5-chloropyridin-2-yl)-1-(3-fluoro-5-(trifluoromethyl) phenyl)-2-phenylethyl)-3-(3-fluorophenyl)urea | 4.12 LC 532.20 [M + H]+ | Procedures 3, 5, 6, 7 and 2 |
| 609 | 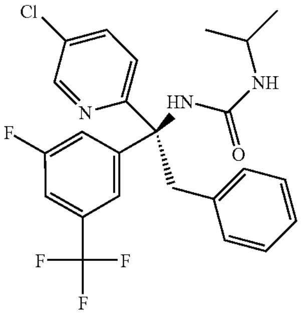 | (S)-1-(1-(5-chloropyridin-2-yl)-1-(3-fluoro-5-(trifluoromethyl) phenyl)-2-phenylethyl)-3-isopropylurea | 3.98 LC 480.24 [M + H]+ | Procedures 3, 5, 6, 7 and 2 |

TABLE 4-continued

| Ex. No. | Structure | Name | Retention Time Min./ Molecular Mass | Prepared in the manner described in: |
|---|---|---|---|---|
| 610 | 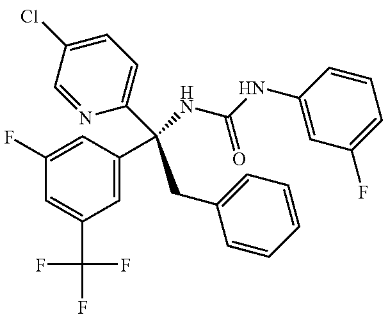 | (R)-1-(1-(5-chloropyridin-2-yl)-1-(3-fluoro-5-(trifluoromethyl) phenyl)-2-phenylethyl)-3-(3-fluorophenyl)urea | 4.12 LC 532.20 [M + H]+ | Procedures 3, 5, 6, 7 and 2 |
| 611 | 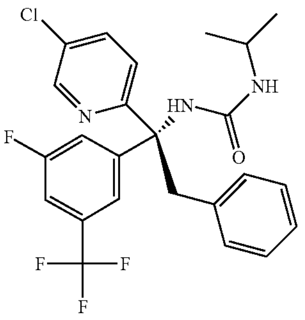 | (R)-1-(1-(5-chloropyridin-2-yl)-1-(3-fluoro-5-(trifluoromethyl) phenyl)-2-phenylethyl)-3-isopropylurea | 3.99 LC 480.25 [M + H]+ | Procedures 3, 5, 6, 7 and 2 |

TABLE 5

| Ex. No. | Structure | Name | Retention Time Min./ Molecular Mass | Prepared in the manner described in: |
|---|---|---|---|---|
| 612 | 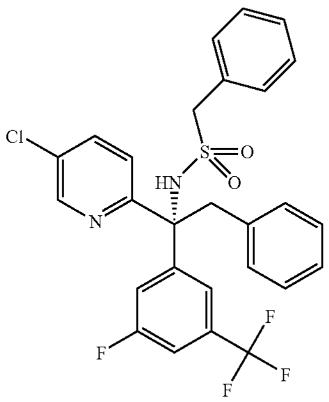 | (R)-N-(1-(5-chloropyridin-2-yl)-1-(3-fluoro-5-(trifluoromethyl)phenyl)-2-phenylethyl)(phenyl) methanesulfonamide | 4.18 LC 549.29 [M + H]+ | Procedure 1 and 9 |

Additional compounds of the present invention were prepared by procedures analogous to those described above and by the additional procedures described below. In the following examples, when the chiral hydroxy center is denoted, the pure diastereomers have been determined based on the chiral starting material epoxide or from chiral separation of the diastereotopic mixture using silica gel chromatography or chiral chromatography.

EXAMPLE 613

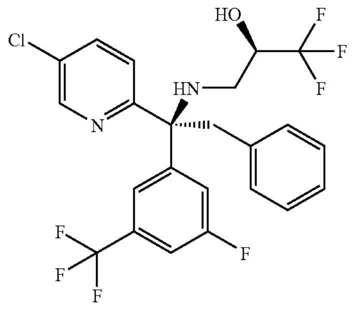

(R)-3-((S)-1-(5-chloropyridin-2-yl)-1-(3-fluoro-5-(trifluoromethyl)phenyl)-2-phenylethylamino)-1,1,1-trifluoropropan-2-ol Procedure 19

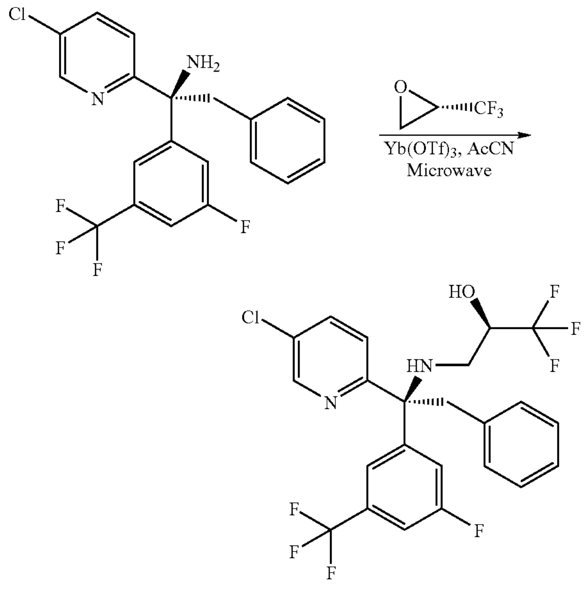

(S)-1-(5-chloropyridin-2-yl)-1-(3-fluoro-5-(trifluoromethyl)phenyl)-2-phenyl ethanamine (0.148 g, 0.376 mmol, prepared as described in Procedures 5, 6 and 7) was dissolved in anhydrous acetonitrile (1 mL). (S)-2-(trifluoromethyl)oxirane (approximate 85:15 ratio of R to S) (0.20 mL, excess) was added to the solution in a microwave vial followed by $Yb(OSO_2CF_3)_3$ (0.020 g, mmol). The sealed vial was heated to 140° C. for 20 mins in the microwave. The reaction mixture was taken from the reaction vial via syringe and injected directly onto a silica gel ISCO cartridge column (40 g). The product eluted at 8 minutes with a gradient of 0-50% EtOAc in hexanes over 18 minutes and flow rate of 40 mL/min, (0.122 mg, 64% yield). The crude NMR of this material showed an 85:15 ratio of R to S at the hydroxy centre. The material was further purified on a Chiral cell AD column with 5% IPA in hexane as the mobile phase yielding 0.068 g of (R)-3-((S)-1-(5-chloropyridin-2-yl)-1-(3fluoro-5-(trifluoromethyl)phenyl)-2-phenylethylamino)-1,1,1-trifluoropropan-2-ol as a colorless oil and a further 0.044 g of mixed fractions. LCMS: 2.06 min [M+1] 507.2 (2 min gradient, $MeOH/H_2O$ 0.1% TFA); HPLC: 7.88 min (8 min gradient, $MeOH/H_2O$ 0.2% PPA Purity 100%; NMR: 400 MHz $^1H$ ($CDCl_3$) 8.42 ppm, 1H, d, J=2.2 Hz; 7.55 ppm, 1H, dd, J=8.36 and J=2.64 Hz; 7.30 ppm, 1H, s; 7.13 ppm, 3H, m; 7.08 ppm, 2H, m; 6.57 ppm, 2H, d, J=7.04 Hz; 3.85 ppm, IH, m; 3.76 ppm, 1H, d, J=12.2 Hz; 3.50 ppm, 1H, d, J=12.2 Hz; 2.78 ppm, 1H, dd, J=6.12 and 12.0 Hz; 2.64 ppm, 1H, dd, J=3.96 and J=12.2 Hz.

EXAMPLE 614

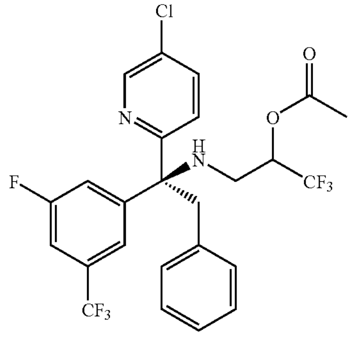

3-((S)-1-(5-chloropyridin-2-yl)-1-(3-fluoro-5-(trifluoromethyl)phenyl)-2-phenylethylamino)-1,1,1-trifluoropropan-2-yl acetate Procedure 20

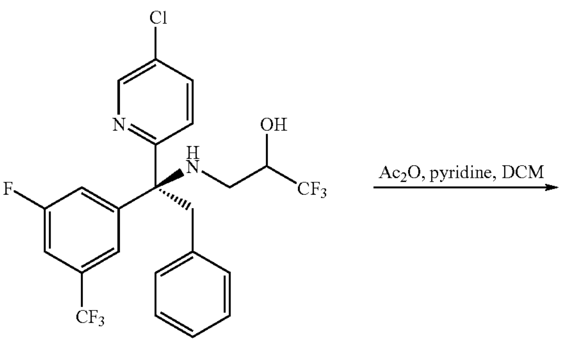

-continued

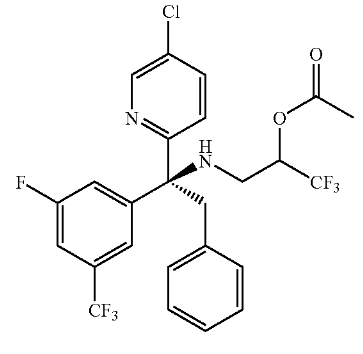

3-((S)-1-(5-chloropyridin-2-yl)-1-(3-fluoro-5-(trifluoromethyl)phenyl)-2-phenylethylamino)-1,1,1-trifluoropropan-2-ol (an approximate 85:15 ratio of SR to SS material) (0.020 g, 0.040 mmol) in dichloromethane (1.0 mL) was added acetic anhydride (0.004 g, 0.040 mmol) and pyridine (0.003 mg, 0.040 mmol) and the reaction mixture was stirred at room temperature for 18 h. The reaction was concentrated and the residue was purified by preparative HPLC YMC ODS S5 28×100 mm Ballistic column 20-100% MeOH (90% in water, 0.1% TFA) gradient over 10 min with flow rate 40 mL/min and UV detection at 220 nm. 3-((S)-1-(5-chloropyridin-2-yl)-1-(3-fluoro-5-(trifluoromethyl)phenyl)-2-phenylethylamino)-1,1,1-trifluoropropan-2-yl acetate eluted at a retention time of 12.25 min and was isolated as a clear oil (17 mg, yield 76%) LCMS: 2.28 min [M+1] 549.2 (2 min gradient, MeOH/$H_2O$ 0.1% TFA); HPLC: 4.40 min (4 min gradient, MeOH/H2O 0.2% PPA); Purity 100%; NMR: 400 MHz $^1H$ ($CDCl_3$) 8.48 ppm, 1 H, d, J=2.20 Hz; 7.54 ppm, 1 H, dd, J=8.35, 2.64 Hz; 7.31 ppm, 1 H, m; 7.15 ppm, 3 H, m; 7.06 ppm, 3 H, m; 6.58 ppm, 2 H, d, J=6.59 Hz; 5.26 ppm, 1 H, m; 3.79 ppm, 1 H, d, J=13.62 Hz; 3.49 ppm, 1 H, d, J=13.62 Hz; 2.69 ppm, 2 H, m; 2.03 ppm, 3 H, s.

EXAMPLE 615

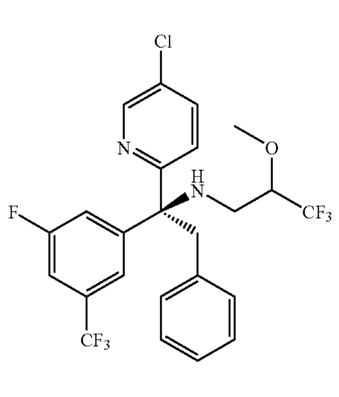

N-((S)-1-(5-chloropyridin-2-yl)-1-(3-fluoro-5-(trifluoromethyl)phenyl)-2-phenylethyl)-3,3,3-trifluoro-2-methoxypropan-1-amine Procedure 21

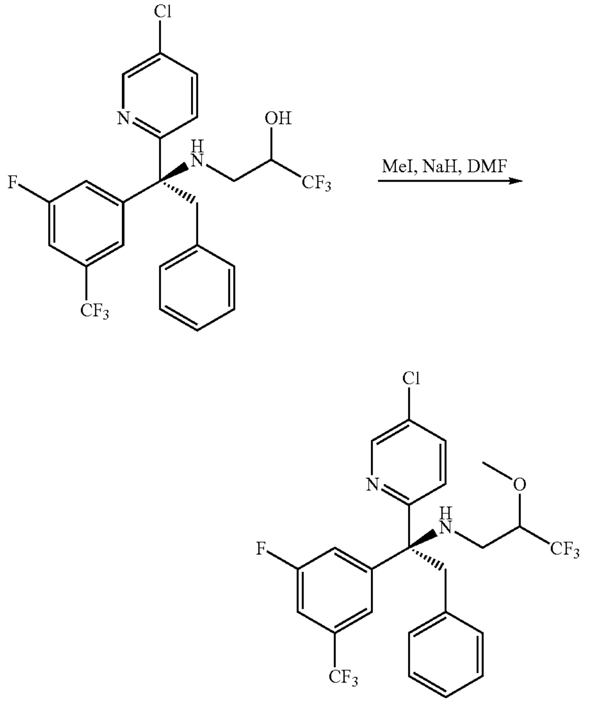

NaH (0.0016 g, 60% dispersed, 0.040 mmol) was added to a solution of 3-((S)-1-(5-chloropyridin-2-yl)-1-(3-fluoro-5-(trifluoromethyl)phenyl)-2-phenylethylamino)-1,1,1-trifluoropropan-2-ol (an approximate 85:15 ratio of SR to SS material) (0.020 g, 0.040 mmol) in DMF (1.0 mL). After 10 min at room temperature, MeI (0.0057 g, 0.040 mmol) was added and stirred for 18 h. The reaction was diluted with EtOAc (20 mL) and was washed with 10% aq. LiCl (2×20 mL). The organic layer was dried over $MgSO_4$ and was filtered. The filtrate was concentrated and was purified by preparative HPLC YMC ODS S5 28×100 mm Ballistic column 20-100% MeOH (90% in water, 0.1% TFA) gradient over 10 min with flow rate 40 mL/min and UV detection at 220 nm. N-((S)-1-(5-chloropyridin-2-yl)-1-(3-fluoro-5-(trifluoromethyl)phenyl)-2-phenylethyl)-3,3,3-trifluoro-2-methoxypropan-1-amine eluted at a retention time of 11.93 min and was isolated as a clear oil (13 mg, yield 62%) LCMS: 2.22 min [M+1] 521.2 (2 min gradient, MeOH/$H_2O$ 0.1% TFA); HPLC: 4.41 min (4 min gradient, MeOH/H2O 0.2% PPA); Purity 100%; NMR: 400 MHz $^1H$ ($CDCl_3$) 8.46 ppm, 1 H, d, J=2.20 Hz; 7.52 ppm, 1 H, dd, J=8.35, 2.20 Hz; 7.30 ppm, 1 H, s; 7.20 ppm, 1 H, m; 7.14 ppm, 2 H, m; 7.05 ppm, 3 H, m; 6.62 ppm, 2 H, d, J=6.59 Hz; 3.77 ppm, 1 H, d, J=13.18 Hz; 3.57 ppm, 1 H, m; 3.49 ppm, 4 H, m; 2.64 ppm, 1 H, m; 2.54 ppm, 1 H, m.

TABLE 6

| Ex. No. | Structure | Name | Retention Time Min./ Molecular Mass | Prepared in the manner described in: |
|---|---|---|---|---|
| 616 | 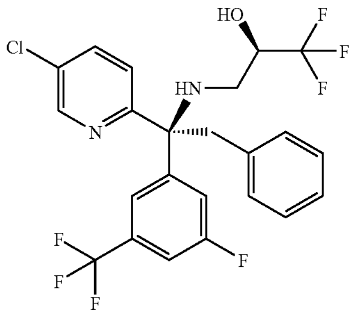 | (R)-3-((S)-1-(5-chloropyridin-2-yl)-1-(3-fluoro-5-(trifluoromethyl)phenyl)-2-phenylethylamino)-1,1,1-trifluoropropan-2-ol | 2.06 LC 507.2 $[M + H]^+$ | Procedure 5, 6, 7 and 19 |
| 617 | 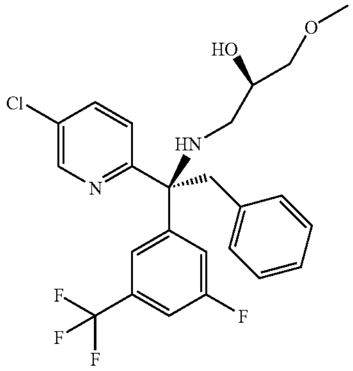 | (R)-1-((S)-1-(5-chloropyridin-2-yl)-1-(3-fluoro-5-(trifluoromethyl)phenyl)-2-phenylethylamino)-3-methoxypropan-2-ol | 1.49 LC 483.3 $[M + H]^+$ | Procedure 5, 6, 7 and 19 |
| 618 | 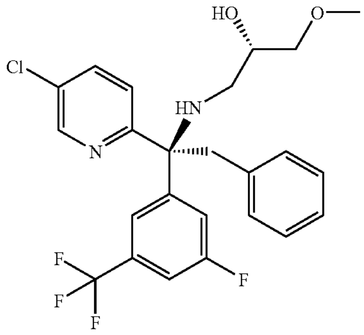 | (S)-1-((S)-1-(5-chloropyridin-2-yl)-1-(3-fluoro-5-(trifluoromethyl)phenyl)-2-phenylethylamino)-3-methoxypropan-2-ol | 1.50 LC 483.3 $[M + H]^+$ | Procedure 5, 6, 7 and 19 |
| 619 | 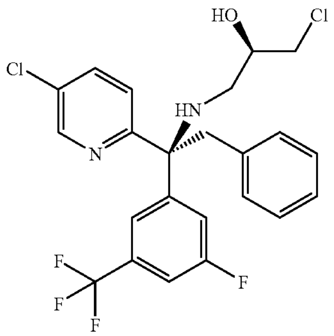 | (R)-1-chloro-3-((S)-1-(5-chloropyridin-2-yl)-1-(3-fluoro-5-(trifluoromethyl)phenyl)-2-phenylethylamino)propan-2-ol | 1.76 LC 487.2 $[M + H]^+$ | Procedure 5, 6, 7 and 19 |

TABLE 6-continued

| Ex. No. | Structure | Name | Retention Time Min./ Molecular Mass | Prepared in the manner described in: |
|---|---|---|---|---|
| 620 | 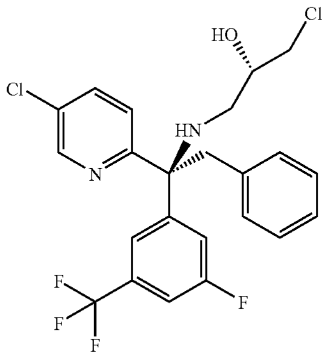 | (S)-1-chloro-3-((S)-1-(5-chloropyridin-2-yl)-1-(3-fluoro-5-(trifluoromethyl)phenyl)-2-phenylethylamino)propan-2-ol | 1.72 LC 487.2 $[M + H]^+$ | Procedure 5, 6, 7 and 19 |
| 621 | 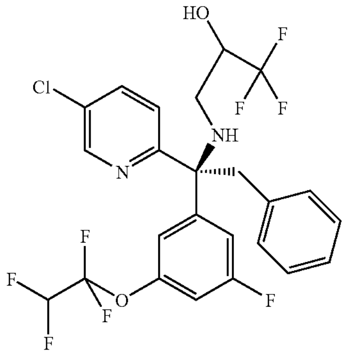 | 3-((S)-1-(5-chloropyridin-2-yl)-1-(3-fluoro-5-(1,1,2,2-tetrafluoroethoxy)phenyl)-2-phenylethylamino)-1,1,1-trifluoropropan-2-ol | 4.03 LC 555.1 $[M + H]^+$ 90:10 ratio of SR:SS | Procedure 3, 5, 6, 7 and 19 |
| 622 | 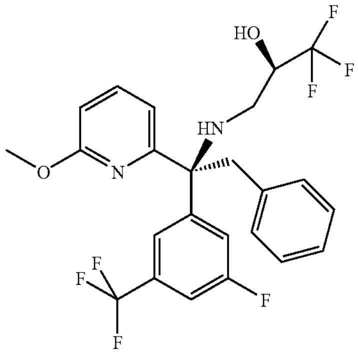 | (R)-1,1,1-trifluoro-3-((S)-1-(3-fluoro-5-(trifluoromethyl)phenyl)-1-(6-methoxypyridin-2-yl)-2-phenylethylamino)propan-2-ol | 3.80 LC 503.26 $[M + H]^+$ 85:15 ratio of SR:SS | Procedure 5, 6, 7 and 19 |
| 623 | 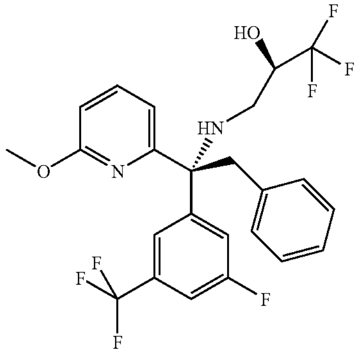 | (R)-1,1,1-trifluoro-3-((R)-1-(3-fluoro-5-(trifluoromethyl)phenyl)-1-(6-methoxypyridin-2-yl)-2-phenylethylamino)propan-2-ol | 3.71 LC 503.26 $[M + H]^+$ 85:15 ratio of SR:SS | Procedure 5, 6, 7 and 19 |

TABLE 6-continued

| Ex. No. | Structure | Name | Retention Time Min./ Molecular Mass | Prepared in the manner described in: |
|---|---|---|---|---|
| 624 | 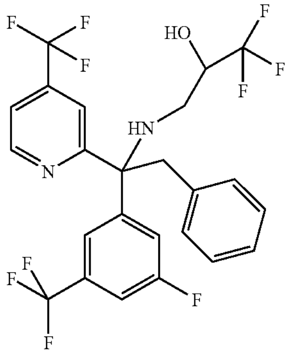 | 1,1,1-trifluoro-3-(1-(3-fluoro-5-(trifluoromethyl)phenyl)-2-phenyl-1-(4-(trifluoromethyl) pyridin-2-yl)ethylamino)propan-2-ol | 4.10 LC 541.29 $[M + H]^+$ 85:15 ratio R:S at hydroxyl center | Procedure 5, 6, 7 and 19 |
| 625 | 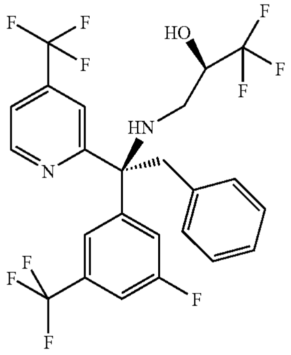 | (R)-1,1,1-trifluoro-3-((S)-1-(3-fluoro-5-(trifluoromethyl) phenyl)-2-phenyl-1-(4-(trifluoromethyl)pyridin-2-yl)ethylamino)propan-2-ol | 4.10 LC 541.29 $[M + H]^+$ 85:15 ratio of SR:SS | Procedure 5, 6, 7 and 19 |
| 626 | 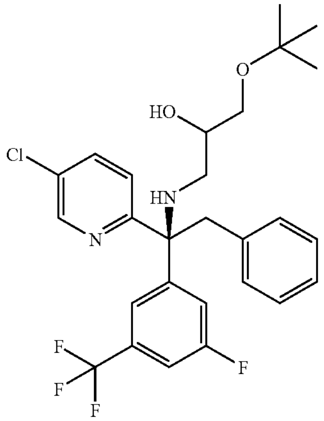 | 1-tert-butoxy-3-((S)-1-(5-chloropyridin-2-yl)-1-(3-fluoro-5-(trifluoromethyl)phenyl)-2-phenylethylamino)propan-2-ol | 3.38 LC 525.2 $[M + H]^+$ 50:50 ratio R:S at hydroxy center | Procedure 5, 6, 7 and 19 |

TABLE 6-continued

| Ex. No. | Structure | Name | Retention Time Min./ Molecular Mass | Prepared in the manner described in: |
|---|---|---|---|---|
| 627 | 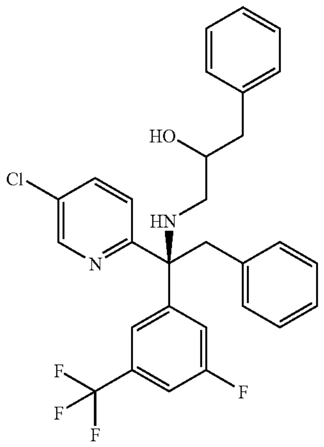 | 1-((S)-1-(5-chloropyridin-2-yl)-1-(3-fluoro-5-(trifluoromethyl) phenyl)-2-phenylethylamino)-3-phenylpropan-2-ol | 3.43 LC 529.19 $[M + H]^+$ 50:50 ratio R:S at hydroxy center | Procedure 5, 6, 7 and 19 |
| 628 | 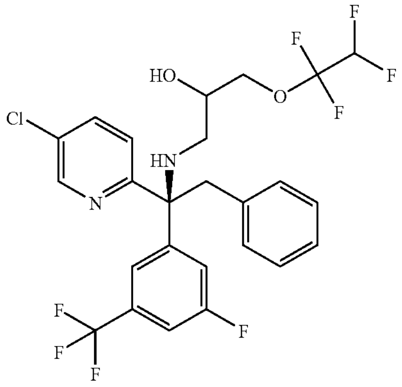 | 1-((S)-1-(5-chloropyridin-2-yl)-1-(3-fluoro-5-(trifluoromethyl) phenyl)-2-phenylethylamino)-3-(1,1,2,2-tetrafluoroethoxy) propan-2-ol | 3.47 LC 569.15 $[M + H]^+$ 50:50 ratio R:S at hydroxy center | Procedure 5, 6, 7 and 19 |
| 629 | 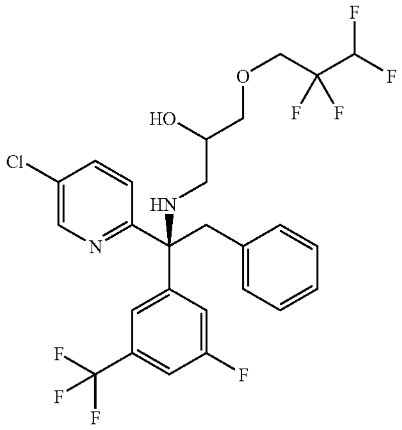 | 1-((S)-1-(5-chloropyridin-2-yl)-1-(3-fluoro-5-(trifluoromethyl) phenyl)-2-phenylethylamino)-3-(2,2,3,3-tetrafluoropropoxy) propan-2-ol | 3.37 LC 583.17 $[M + H]^+$ 50:50 ratio R:S at hydroxy center | Procedure 5, 6, 7 and 19 |

TABLE 6-continued

| Ex. No. | Structure | Name | Retention Time Min./ Molecular Mass | Prepared in the manner described in: |
|---|---|---|---|---|
| 630 | 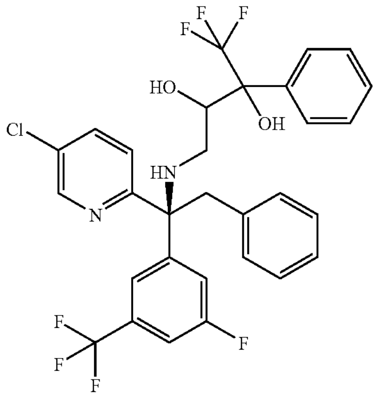 | 4-((S)-1-(5-chloropyridin-2-yl)-1-(3-fluoro-5-(trifluoromethyl) phenyl)-2-phenylethylamino)-1,1,1-trifluoro-2-phenylbutane-2,3-diol | 3.53 LC 613.2 $[M + H]^+$ racemic at both hydroxy centers | Procedure 5, 6, 7 and 19 |
| 631 | 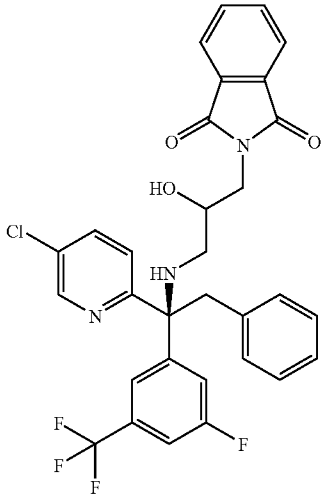 | 2-(3-((S)-1-(5-chloropyridin-2-yl)-1-(3-fluoro-5-(trifluoromethyl)phenyl)-2-phenylethylamino)-2-hydroxypropyl)isoindoline-1,3-dione | 3.38 LC 598.19 $[M + H]^+$ 50:50 ratio R:S at hydroxy center | Procedure 5, 6, 7 and 19 |
| 632 | 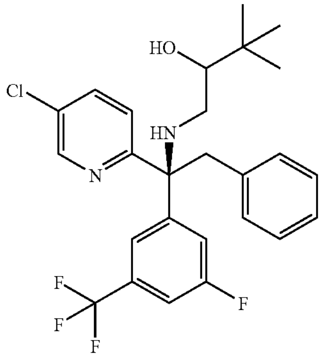 | 1-((S)-1-(5-chloropyridin-2-yl)-1-(3-fluoro-5-(trifluoromethyl) phenyl)-2-phenylethylamino)-3,3-dimethylbutan-2-ol | 3.37 LC 495.18 $[M + H]^+$ 50:50 ratio R:S at hydroxyl center | Procedure 5, 6, 7 and 19 |

TABLE 6-continued

| Ex. No. | Structure | Name | Retention Time Min./ Molecular Mass | Prepared in the manner described in: |
|---|---|---|---|---|
| 633 | 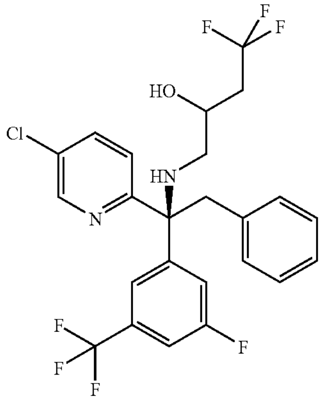 | 1-((S)-1-(5-chloropyridin-2-yl)-1-(3-fluoro-5-(trifluoromethyl) phenyl)-2-phenylethylamino)-4,4,4-trifluorobutan-2-ol | 3.41 LC 521.13 [M + H]+ 50:50 ratio R:S at hydroxyl center | Procedure 5, 6, 7 and 19 |
| 634 | 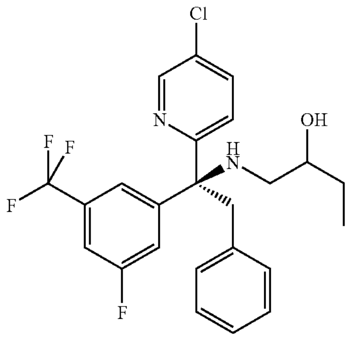 | 1-((S)-1-(5-chloropyridin-2-yl)-1-(3-fluoro-5-(trifluoromethyl) phenyl)-2-phenylethylamino) butan-2-ol | 3.64 LC 467.18 [M + H]+ 50:50 ratio R:S at hydroxyl center | Procedure 5, 6, 7 and 19 |
| 635 | 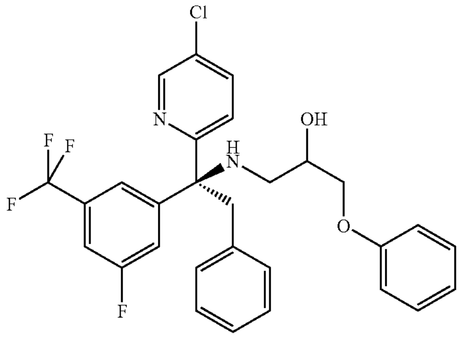 | 1-((S)-1-(5-chloropyridin-2-yl)-1-(3-fluoro-5-(trifluoromethyl) phenyl)-2-phenylethylamino)-3-phenoxypropan-2-ol | 4.04 LC 545.1 [M + H]+ 50:50 ratio R:S at hydroxyl center | Procedure 5, 6, 7 and 19 |
| 636 | 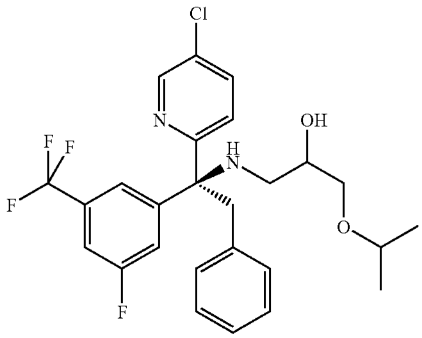 | 1-((S)-1-(5-chloropyridin-2-yl)-1-(3-fluoro-5-(trifluoromethyl) phenyl)-2-phenylethylamino)-3-isopropoxypropan-2-ol | 3.87 LC 511.00 [M + H]+ 50:50 ratio R:S at hydroxyl center | Procedure 5, 6, 7 and 19 |

TABLE 6-continued

| Ex. No. | Structure | Name | Retention Time Min./ Molecular Mass | Prepared in the manner described in: |
|---|---|---|---|---|
| 637 | 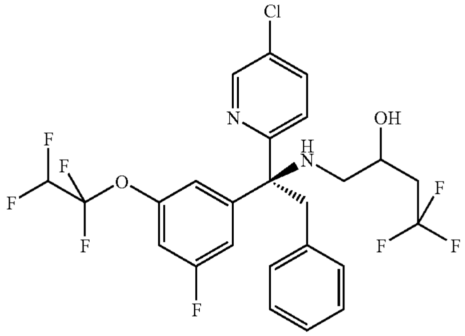 | 1-((S)-1-(5-chloropyridin-2-yl)-1-(3-fluoro-5-(1,1,2,2-tetrafluoroethoxy)phenyl)-2-phenylethylamino)-4,4,4-trifluorobutan-2-ol | 4.00 LC 568.94 $[M + H]^+$ 50:50 ratio R:S at hydroxyl center | Procedure 3, 5, 6, 7 and 19 |
| 638 | 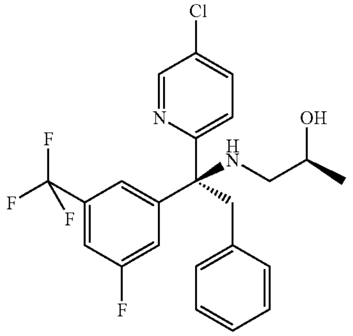 | (S)-1-((S)-1-(5-chloropyridin-2-yl)-1-(3-fluoro-5-(trifluoromethyl)phenyl)-2-phenylethylamino)propan-2-ol | 3.61 LC 453.33 $[M + H]^+$ | Procedure 5, 6, 7 and 19 |
| 639 | 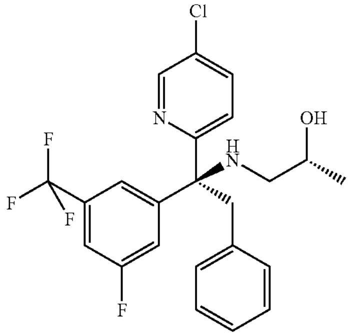 | (R)-1-((S)-1-(5-chloropyridin-2-yl)-1-(3-fluoro-5-(trifluoromethyl)phenyl)-2-phenylethylamino)propan-2-ol | 3.66 LC 453.35 $[M + H]^+$ | Procedure 5, 6, 7 and 19 |

Additional compounds of the present invention were prepared by procedures analogous to those described above and by additional procedures described below. The absolute configuration of chiral examples was initially determined by obtaining an X-ray of crystalline material intermediate sulfinyl amides and subsequently by NMR comparison of the diastereomers.

EXAMPLE 640

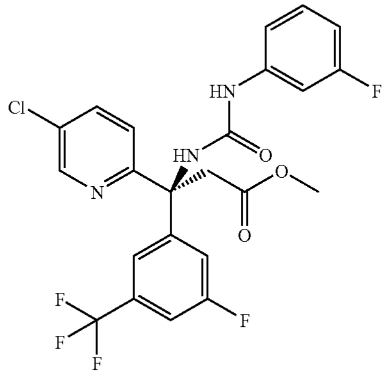

(S)-methyl 3-(5-chloropyridin-2-yl)-3-(3-fluoro-5-(trifluoromethyl)phenyl)-3-(3-(3-fluorophenyl)ureido)propanoate Procedure 22

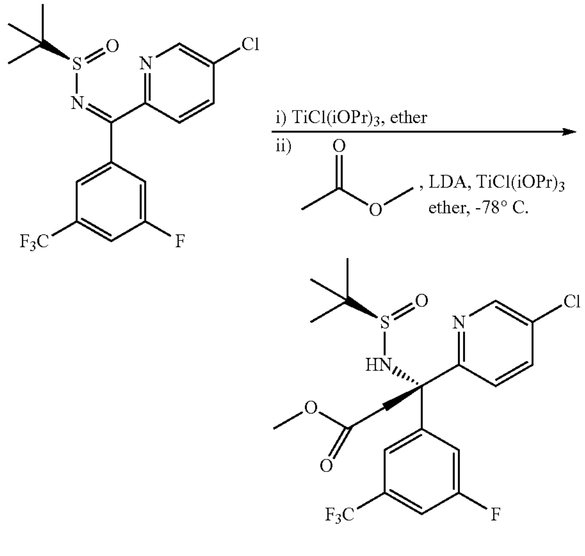

At −78° C. under argon, LDA (3.97 mL, 7.94 mmol, 2.0M solution in cyclohexane) was added to a solution of methylacetoacetate (0.587 g, 7.95 mmol) in anhydrous ether (40 mL). After 30 min at −78° C., $TiCl(iOPr)_3$ (11.9 mL, 11.9 mmol, 1.0M solution in hexanes) was added to the stirred solution. In a separate flask at room temperature, (R)-N-((5-chloropyridin-2-yl)(6-(trifluoromethyl)pyridin-2-yl)methylene)-2-methylpropane-2-sulfinamide (1.61 g, 3.97 mmol, prepared as described in Procedures 9 and 10) was dissolved in anhydrous ether (40 mL) and $TiCl(iOPr)_3$ (3.97 mL, 3.97 mmol, 1.0M solution in hexanes) was added. After 30 mins, the pre-complexed solution was removed via syringe and added to the enolate dropwise at −78° C. under argon. The resulting pale orange solution was stirred at −78° C. for 1 h then quenched by addition of 1.0M HCl solution (ca. 50 mL). On reaching room temperature, the solution was transferred to a separation funnel and extracted with EtOAc (2×50 mL). The combined organic portion was dried over $Na_2SO_4$, decanted, concentrated and purified by silica gel ISCO chromatography (120 g column) using hexanes/EtOAc (0-80% over 25 min). (S)-methyl 3-(5-chloropyridin-2-yl)-3-(3-fluoro-5-(trifluoromethyl)phenyl)-3-((R)-2-methylpropan-2-ylsulfinamido)propanoate was isolated as a crude white foam, (1.47 g, 77% yield). NMR analysis of (S)-methyl 3-(5-chloropyridin-2-yl)-3-(3-fluoro-5-(trifluoromethyl)phenyl)-3-((R)-2-methylpropan-2-ylsulfinamido)propanoate showed a diastereomeric ratio of 93:7 by integration. The (S)-methyl 3-(5-chloropyridin-2-yl)-3-(3-fluoro-5-(trifluoromethyl)phenyl)-3-((R)-2-methylpropan-2-ylsulfinamido)propanoate (1.25 g, 2.60 mmol) was dissolved in MeOH (5 mL) and water was added dropwise until turbidity was observed. The solution was kept at 4° C. for 2.5 h then the remaining solution removed by pipet. The crystalline material was azeotroped with ether and dried under vacuum yielding (S)-methyl 3-(5-chloropyridin-2-yl)-3-(3-fluoro-5-(trifluoromethyl)phenyl)-3-((R)-2-methylpropan-2-ylsulfinamido)propanoate as a white crystalline foam, (1.04 g, 83% yield). $R_f$ 0.3 (Hexane:EtOAc 4:1) LCMS: 2.00 min [M+1] 481.1 (2 min gradient, MeOH/$H_2O$ 0.1% TFA); HPLC: 3.89 min (4 min gradient, MeOH/$H_2O$ 0.2% PPA); Purity 99%; NMR: 400 MHz $^1H$ ($CDCl_3$) 8.54 ppm, d, J=2.2 Hz; 7.62 ppm, dd, J=4.0 and J=8.0 Hz; 7.40, 1H, s; 7.37 ppm, 1H, d, J=12.0 Hz; 7.20 ppm, 2H, m; 3.98 ppm, 1H, d, J=20 Hz; 3.73 ppm, 1H, d, J=16.0 Hz; 3.60 ppm, 3H, s; 1.31 ppm, 9H, s.

Procedure 23

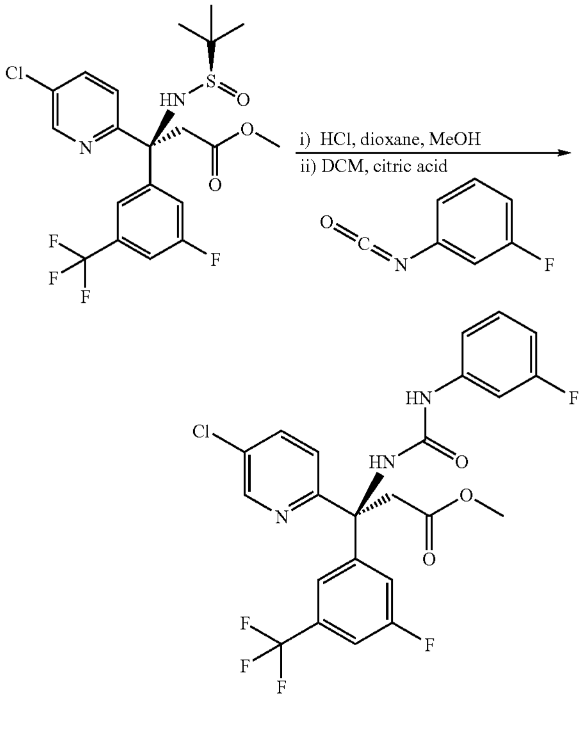

(S)-methyl 3-(5-chloropyridin-2-yl)-3-(3-fluoro-5-(trifluoromethyl)phenyl)-3-((R)-2-methylpropan-2-ylsulfinamido)propanoate (0.075 g, 0.16 mmol) was dissolved in MeOH (2 mL). At RT, 4.0M HCl in dioxane (2 mL) was added and the reaction mixture stirred for 30 min. The reaction mixture was diluted with EtOAc (50 mL), transferred to a separation funnel and washed with 1.0M NaOH (ca.20 mL). The organic portion was dried over anhydrous $Na_2SO_4$, decanted and concentrated yielding (S)-methyl 3-amino-3-(5-chloropyridin-2-yl)-3-(3-fluoro-5-(trifluoromethyl)phenyl)propanoate as a colorless oil, (0.062 g, crude quantitative yield). LCMS: 1.37 min [M+1] 377.1 (2 min gradient, MeOH/$H_2O$ 0.1% TFA).

(S)-methyl 3-(5-chloropyridin-2-yl)-3-(3-fluoro-5-(trifluoromethyl)phenyl)-3-(3-(3-fluorophenyl)ureido)propanoate was prepared from (S)-methyl 3-amino-3-(5-chloropyridin-2-yl)-3-(3-fluoro-5-(trifluoromethyl)phenyl) propanoate as described in Procedure 2, yielding 0.015 g of (S)-methyl 3-(5-chloropyridin-2-yl)-3-(3-fluoro-5-(trifluoromethyl)phenyl)-3-(3-(3-fluorophenyl)ureido)propanoate (55% yield) as a colorless oil after preparative HPLC (YMC ODSA 30×100 mm, 0-100% over 10 min, MeOH/$H_2O$/0.1% TFA). LCMS: 2.03 min [M+1] 514.1 (2 min gradient, MeOH/$H_2O$ 0.1% TFA); HPLC: 3.92 min (4 min gradient, MeOH/$H_2O$ 0.2% PPA); Purity 100%; NMR: 400 MHz $^1H$ ($CDCl_3$) 8.45 ppm, 1H, d, J=2.0 Hz; 8.05 ppm, 1H, s; 7.64 ppm, 1H, dd, J=2.0 and J=8.0 Hz; 7.40 ppm, 1H, s; 7.26 ppm, 1H, m; 7.17 ppm, 2H, m; 7.08 ppm, 1H, d, J=8.0 Hz; 6.95 ppm, 1H, dd, J=4.0 and J=8.0 Hz; 6.79 ppm, 1H, tm; 4.28 ppm, 1H, d, J=16 Hz; 3.56 ppm, 1H, d, J=16 Hz; 3.56 ppm, 3H, s.

EXAMPLE 641

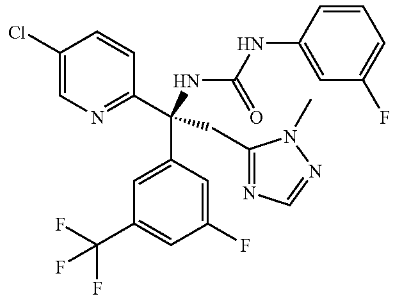

(S)-1-(1-(5-chloropyridin-2-yl)-1-(3-fluoro-5-(trifluoromethyl)phenyl)-2-(2-methyl-2H-1,2,4-triazol-3-yl)ethyl)-3-(3-fluorophenyl)urea Procedure 24

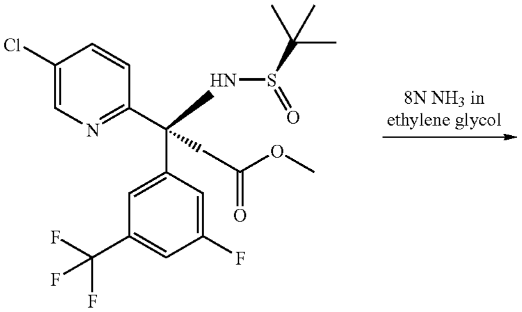

-continued

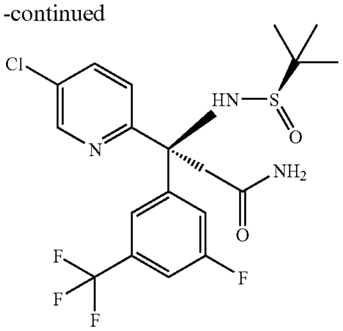

(S)-methyl 3-(5-chloropyridin-2-yl)-3-(3-fluoro-5-(trifluoromethyl)phenyl)-3-((R)-2-methylpropan-2-ylsulfinamido)propanoate (0.10 g, 0.20 mmol) was dissolved in 8N $NH_3$ solution in ethylene glycol (1 mL) in a microwave vial. The reaction mixture was heated to 180° C. for 300 sec, the pressure was cautiously vented and the reaction mixture purified directly by prep HPLC (YMC ODSA30×100 mm, 0-100% over 10 min, MeOH/$H_2O$/0.1% TFA). (S)-3-(5-chloropyridin-2-yl)-3-(3-fluoro-5-(trifluoromethyl)phenyl)-3-((R)-2-methylpropan-2-ylsulfinamido)propanamide was isolated as a white solid (0.041 g, 41% yield) LCMS: 1.85 min [M+1] 466.1 (2 min gradient, MeOH/$H_2O$ 0.1% TFA). Starting material was also recovered (0.055 g, 55% recovered yield).

Procedure 25

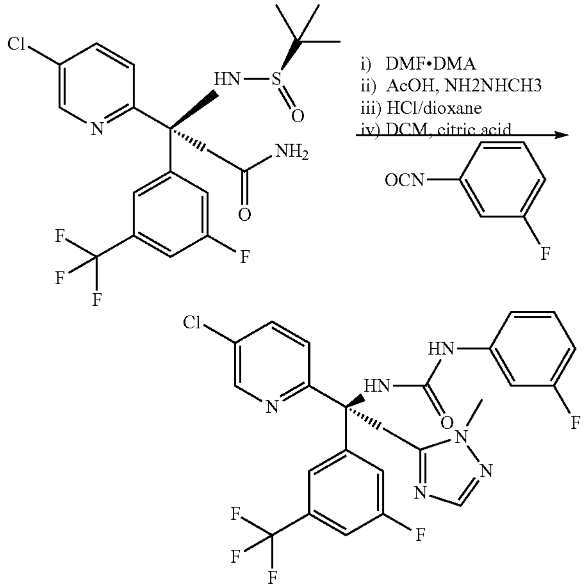

(S)-3-(5-chloropyridin-2-yl)-3-(3-fluoro-5-(trifluoromethyl)phenyl)-3-((R)-2-methylpropan-2-ylsulfinamido)propanamide (0.041 g, 0.088 mmol) was dissolved at room temperature in dimethoxy-N,N-dimethylmethanamine (1 mL). The solution was stirred for 2 h then the solvent removed under reduced pressure. The residual yellow oil was dissolved in AcOH (1 mL) and methylhydrazine (0.3 mL, excess) was added. The reaction mixture was heated to 60° C., the solvents removed under reduced pressure, the residue redissolved in MeOH (1 mL) and the crude material purified by prep HPLC (YMC ODSA 30×100 mm, 0-100% over 10 min, MeOH/$H_2O$/0.1% TFA). (R)-N-((S)-1-(5-chloropyridin-2-yl)-1-(3-fluoro-5-(trifluoromethyl)phenyl)-2-(2-methyl-2H-1,2,4-triazol-3-yl)ethyl)-2-methylpropane-2-sulfinamide was isolated as a colorless oil (0.017 g, 38% yield). LCMS: 1.93 min [M+1] 504.1 (2 min gradient, MeOH/$H_2O$ 0.1% TFA); HPLC: 3.72 min (4 min gradient, MeOH/$H_2O$ 0.2% PPA); Purity 100%. This material was treated with HCl/dioxane and then the amine converted to (S)-1-(1-(5-chloropyridin-2-yl)-1-(3-fluoro-5-(trifluoromethyl)phenyl)-2-(2-methyl-2H-1,2,4-triazol-3-yl)ethyl)-3-(3-fluorophenyl)urea as described Procedure 13. (S)-1-(1-(5-chloropyridin-2-yl)-1-(3-fluoro-5-(trifluoromethyl)phenyl)-2-(2-methyl-2H-1,2,4-triazol-3-yl) ethyl)-3-(3-fluorophenyl)urea was isolated as a colorless glass (0.010 g, 57% yield 2 steps). LCMS: 2.01 min [M+1] 537.1 (2 min gradient, MeOH/$H_2O$ 0.1% TFA); HPLC: 3.82 min (4 min gradient, MeOH/$H_2O$ 0.2% PPA); Purity 100%; NMR: 400 MHz $^1H$ ($CDCl_3$) 9.23 ppm, 1H, brs; 8.44 ppm, 1H, d, J=2.2 Hz; 8.16 ppm, 1H, s; 7.94 ppm, 1H, brs; 7.68 ppm, 1H, dd, J=2.0 and J=8.0 Hz; 7.41 ppm, 1H, s; 7.32 ppm, 1H, dm, J=8.0 Hz; 7.28 ppm, 2H, m; 7.19 ppm, 2H, m; 6.86 ppm, 1H, dd, J=4.0 and J=8.0 Hz 6.72 ppm, 1H, dt, J=4.0 and J=8.0 Hz; 4.78 ppm, 1H, d, J=15.4 Hz; 4.50 ppm, 1H, d, J=15.4 Hz; 4.06 ppm, 3H, d, J=16 Hz; 3H, s.

EXAMPLE 642

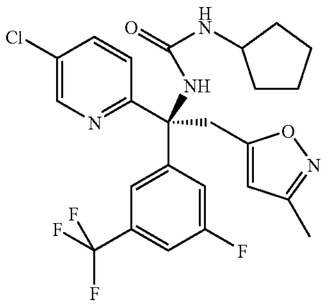

(S)-1-(1-(5-chloropyridin-2-yl)-1-(3-fluoro-5-(trifluoromethyl)phenyl)-2-(3-methylisoxazol-5-yl) ethyl)-3-cyclopentylurea Procedure 26

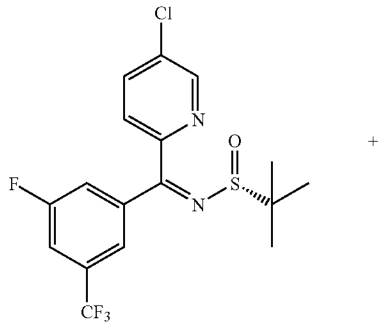

-continued

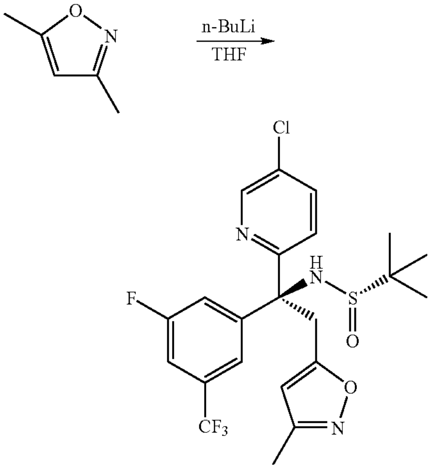

3,5-Dimethyl isoxazole (30 μL, 0.30 mmol) in anhydrous THF (90 μL) was cooled at −78° C. for 10 min, followed by the addition of n-BuLi (150 PL, 0.30 mmol, 2M solution in cyclohexane). The reaction turned yellow and was stirred at −78° C. for 40 min. (R,Z)-N-((5-chloropyridin-2-yl)(3-fluoro-5-(trifluoromethyl)phenyl)methylene)-2-methylpropane-2-sulfinamide (60 mg, 0.15 mmol) in THF (1 mL) was added and the maroon colored reaction mixture was stirred at −78° C. for a further 2 h. The reaction mixture was quenched with $H_2O$ (10 mL) and extracted with EtOAc (2×15 mL). The combined organic layers were dried over $MgSO_4$, filtered and concentrated. The residue was purified by preparative HPLC YMC ODS S5 28×100 mm Ballistic column 50-100% MeOH (90% in water, 0.1% TFA) gradient over 14 min with flow rate 40 mL/min and UV detection at 220 nm. (S)-N-((S)-1-(5-chloropyridin-2-yl)-1-(3-fluoro-5-(trifluoromethyl)phenyl)-2-(3-methylisoxazol-5-yl)ethyl)-2-methylpropane-2-sulfinamide eluted at a retention time of 11.60 min and was isolated as a yellow oil (14 mg, yield 38%) LCMS: 1.93 min [M+1] 504.1 (2 min gradient, MeOH/$H_2O$ 0.1% TFA); HPLC: 3.73 min (4 min gradient, MeOH/$H_2O$ 0.2% PPA); Purity 100%; NMR: 400 MHz $^1H$ ($CDCl_3$) 8.53 ppm, 1 H, d, J=2.64 Hz; 7.58 ppm, 1 H, dd, J=8.79, 2.20 Hz; 7.29 ppm, 1 H, d, J=3.08 Hz; 7.17 ppm, 1 H, d, J=7.91 Hz; 7.05 ppm, 1 H, d, J=9.67 Hz; 5.59 ppm, 1 H, s; 5.01 ppm, 1 H, s; 4.13 ppm, 1H, d, J=12 Hz; 3.96 ppm, 1 H, d, J=16 Hz; 2.09 ppm, 3 H, s; 1.20 ppm, 9 H, s.

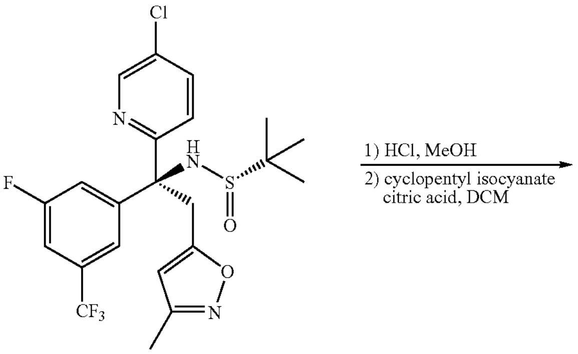

-continued

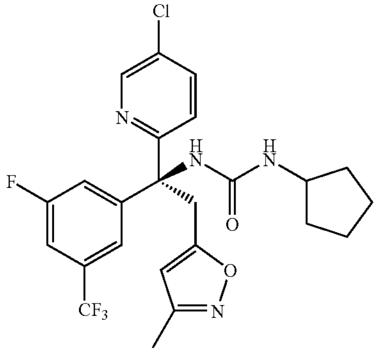

To a solution of (S)-N-((S)-1-(5-chloropyridin-2-yl)-1-(3-fluoro-5-(trifluoromethyl)phenyl)-2-(3-methylisoxazol-5-yl)ethyl)-2-methylpropane-2-sulfinamide (12 mg, 0.024 mmol) in MeOH (0.5 mL) was added HCl (0.5 mL, 2 mmol, 4N solution in dioxane). The reaction was stirred at room temperature for 0.5 h. The solution was concentrated, diluted with EtOAc (20 mL), washed with sat. $NaHCO_3$ (20 mL), dried over $Na_2SO_4$, filtered and concentrated. The residue was dissolved in DCM (1 mL) and cyclopentyl isocyanate (5 mg, 0.048 mmol) was added, followed by two crystals of citric acid. The reaction was stirred overnight, concentrated and purified by Prep TLC (Uniplate, Silica Gel GF, 20×20 cm, 1000 Microns) using Hexane/EtOAc (1/1) to yield product as a white solid (7 mg, 54% yield) LCMS: 1.99 min [M+1] 511.2 (2 min gradient, MeOH/$H_2O$ 0.1% TFA); HPLC: 3.85 min (4 min gradient, MeOH/$H_2O$ 0.2% PPA); Purity 100%; NMR: 400 MHz $^1H$ ($CDCl_3$) 8.31 ppm, 1 H, d, J=2.20 Hz; 7.58 ppm, 1 H, dd, J=8.57 Hz and 2.42 Hz; 7.39 ppm, 1 H, s; 7.26 ppm, 1 H, m; 7.24 ppm, 1 H, d, J=1.76 Hz; 7.13 ppm, 1 H, d, J=8.35 Hz; 7.03 ppm, 1 H, d, J=8.35 Hz; 5.65 ppm, 1 H, s; 4.69 ppm, 1 H, d, J=14.06 Hz; 4.40 ppm, 1 H, m; 3.88 ppm, 1 H, m; 3.69 ppm, 1 H, d, J=14.06 Hz; 2.11 ppm, 3 H, s; 1.96, 1 H, m; 1.87 ppm, 1 H, m; 1.57 ppm, 4 H, m; 1.36 ppm, 1 H, m; 1.28 ppm, 1 H, m.

EXAMPLE 643

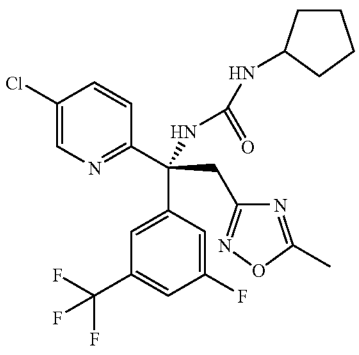

(R)-1-(1-(5-chloropyridin-2-yl)-1-(3-fluoro-5-(trifluoromethyl)phenyl)-2-(5-methyl-1,2,4-oxadiazol-3-yl)ethyl)-3-cyclopentylurea Procedure 27

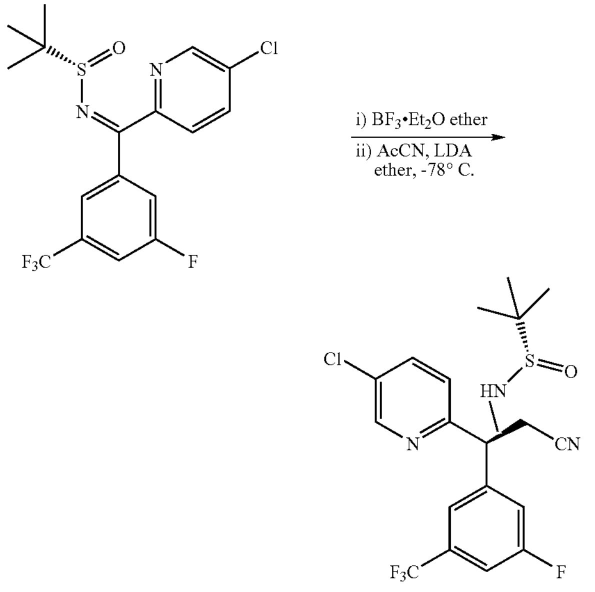

At −78° C. in a 3 neck flask under argon atmosphere, anhydrous acetonitrile (0.150 g, 3.68 mmol) was added to dry ether (2 mL) followed by dropwise addition of LDA (1.84 mL, 3.68 mmol, 2.0M solution in cyclohexanes). The solution was stirred at −78° C. for 20 min. In a separate flask at 0° C. under argon, $BF_3Et_2O$ (0.260 g, 0.19 mmol) was added to a solution of (S)-N-((5-chloropyridin-2-yl)(3-fluoro-5-(trifluoromethyl)phenyl)methylene)-2-methylpropane-2-sulfinamide (0.750 g, 1.84 mmol) in dry ether (10 mL). The pre-complexed sulfinylimine solution was transferred to the anion solution via syringe dropwise at −78° C. After 30 min the orange solution was quenched by the addition of 1.0M HCl (ca. 10 mL) and the reaction mixture transferred to a separation funnel and extracted with EtOAc (3×20 mL). The combined organic portions were dried over $Na_2SO_4$, decanted, concentrated and the diastereomers purified by silica gel ISCO chromatography on 120 g column, 0-90% EtOAc/hexanes. (S)-N-((R)-1-(5-chloropyridin-2-yl)-2-cyano-1-(3-fluoro-5-(trifluoromethyl)phenyl)ethyl)-2-methylpropane-2-sulfinamide eluted next and was isolated as the major product (0.23 mg, 28% yield). $R_f$0.8 (Hexane:EtOAc 1:1) LCMS: 1.84 min [M+1] 448.1 (2 min gradient, MeOH/$H_2O$ 0.1% TFA); HPLC: 3.58 min (4 min gradient, MeOH/$H_2O$ 0.2% PPA); Purity 99%; NMR: 400 MHz $^1H$ ($CDCl_3$) 8.62 ppm, d, J=2.6 Hz; 7.73 ppm, dd, J=2.6 and J=8.8 Hz; 7.38, 1H, s; 7.32 ppm, 1H, d, J=7.9 Hz; 7.20 ppm, 2H, d, J=8.8 Hz; 5.87 ppm, 1H, s; 3.76 ppm, 1H, d, J=16.7 Hz; 3.67 ppm, 1H, d, J=16.7 Hz; 1.36 ppm, 3H, s. (S)-N-((S)-1-(5-chloropyridin-2-yl)-2-cyano-1-(3-fluoro-5-(trifluoromethyl)phenyl)ethyl)-2-methylpropane-2-sulfinamide eluted last and was isolated as the a pale yellow oil (0.088 mg, 11% yield). $R_f$0.7 (Hexane:EtOAc 1:1) LCMS: 1.90 min [M+1] 448.1 (2 min gradient, $MeOH/H_2O$ 0.1% TFA); HPLC: 3.65 min (4 min gradient, $MeOH/H_2O$ 0.2% PPA); Purity 99%.

Procedure 28

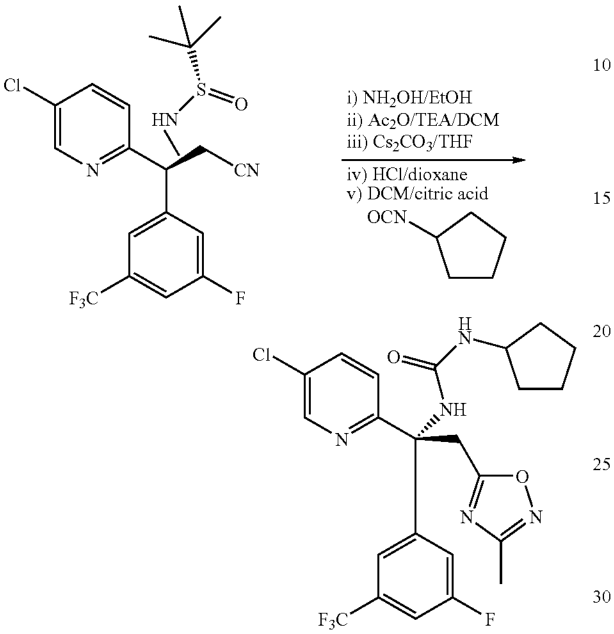

(S)-N-((R)-1-(5-chloropyridin-2-yl)-2-cyano-1-(3-fluoro-5-(trifluoromethyl) phenyl)ethyl)-2-methylpropane-2-sulfinamide (0.030 g, 0.067 mmol) was dissolved in EtOH (1 mL) in a 2 dram vial. $NH_2OH$ (1 mL, 50% solution in water) was added and the sealed screw capped vial was heated to 70° C. for 3 h. The cooled solution was diluted with DCM (10 mL) and transferred to a separation funnel. The organic layer was separated and the aqueous portion was washed further with DCM (5 mL). The combined organic portions were dried, decanted and concentrated yielding (R,Z)-3-(5-chloropyridin-2-yl)-3-(3-fluoro-5-(trifluoromethyl)phenyl)-N'-hydroxy-3-((S)-2-methylpropan-2-ylsulfinamido)propanamidine as a tan oil (0.032 mg, quantitative yield). LCMS: 1.50 min [M+1] 481.1 (2 min gradient, $MeOH/H_2O$ 0.1% TFA). The crude oil was dissolved in dry DCM (1 mL), cooled to 0° C. and TEA (25pL) was added followed by acetic anhydride (11 μL). The reaction mixture was allowed to reach room temperature with stirring over 18 h. The solution was diluted with DCM (10 mL), transferred to a separation funnel, washed with sat. NaCl (10 mL), dried, decanted and concentrated yielding a white solid. LCMS: 1.87 min [M+1] 523.1 (2 min gradient, $MeOH/H_2O$ 0.1% TFA). The intermediate N-((R,Z)-3-(5-chloropyridin-2-yl)-3-(3-fluoro-5-(trifluoromethyl)phenyl)-1-(hydroxyimino)-3-((S)-2-methylpropan-2-ylsulfinamido)propyl)acetamide was redissolved in anhydrous THF (2 mL) and anhydrous $Cs_2CO_3$ was added (0.063 g). The solution was heated to 105° C. for 3 h whereupon the solvent evaporated leaving a pale brown solid which was dissolved in MeOH (1 mL) and purified by prep HPLC (YMC ODSA30×100 mm, 0-100% over 10 min, MeOH/$H_2O$/0.1% TFA) yielding (S)-N-((R)-1-(5-chloropyridin-2-yl)-1-(3-fluoro-5-(trifluoromethyl)phenyl)-2-(3-methyl-1,2,4-oxadiazol-5-yl)ethyl)-2-methylpropane-2-sulfinamide as a colorless oil (0.015 g, 44% yield over 3 steps). LCMS: 1.96 min [M+1] 505.1 (2 min gradient, $MeOH/H_2O$ 0.1% TFA); HPLC: 3.80 min (4 min gradient, $MeOH/H_2O$ 0.2% PPA) Purity 96%.

(S)-N-((R)-1-(5-chloropyridin-2-yl)-1-(3-fluoro-5-(trifluoromethyl)phenyl)-2-(3-methyl-1,2,4-oxadiazol-5-yl)ethyl)-2-methylpropane-2-sulfinamide was cleaved to (R)-1-(5-chloropyridin-2-yl)-1-(3-fluoro-5-(trifluoromethyl)phenyl)-2-(3-methyl-1,2,4-oxadiazol-5-yl)ethanamine as described in Procedure 13 and the amine subsequently converted to (R)-1-(1-(5-chloropyridin-2-yl)-1-(3-fluoro-5-(trifluoromethyl)phenyl)-2-(3-methyl-1,2,4-oxadiazol-5-yl)ethyl)-3-cyclopentylurea using the conditions described in Procedure 2. (R)-1-(1-(5-chloropyridin-2-yl)-1-(3-fluoro-5-(trifluoromethyl)phenyl)-2-(3-methyl-1,2,4-oxadiazol-5-yl)ethyl)-3-cyclopentylurea (0.0063 g, 41% yield over 2 steps) was isolated as a colorless oil. $R_f$0.2 (Hexane:EtOAc 2:1) LCMS: 2.00 min [M+1] 512.2 (2 min gradient, $MeOH/H_2O$ 0.1% TFA); HPLC: 3.82 min (4 min gradient, $MeOH/H_2O$ 0.2% PPA); Purity 100%; NMR: 400 MHz $^1H$ ($CD_3OD$) 8.45 ppm, d, J=0.88 Hz; 7.75 ppm, dd, J=0.88 and J=8.8 Hz; 7.53, 3H, m; 7.38 ppm, 1H, d, J=8.8 Hz; 7.30 ppm, 1H, d, J=8.4 Hz; 4.46 ppm, 1H, d, J=14.1 Hz; 4.07 ppm, 1H, d, J=14.1 Hz; 3.88 ppm, 1H, m; 2.40 ppm, 3H, s; 1.86 ppm, 2H, m; 1.68 ppm, 4H, m; 1.57 ppm, 2H, m.

EXAMPLE 644

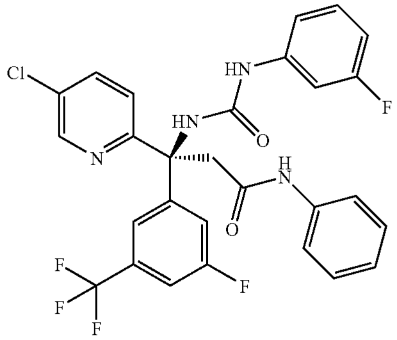

(S)-1-(1-(5-chloropyridin-2-yl)-1-(3-fluoro-5-(trifluoromethyl)phenyl)-3-oxo-3-(phenylamino)propyl)-3-(3-fluorophenyl)urea Procedure 29

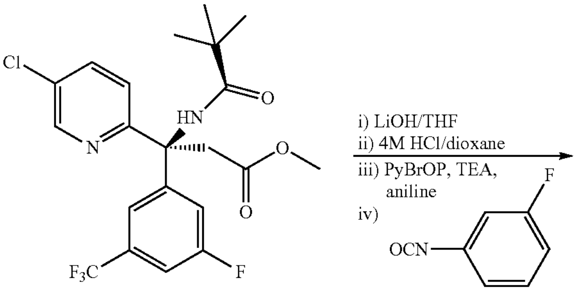

-continued

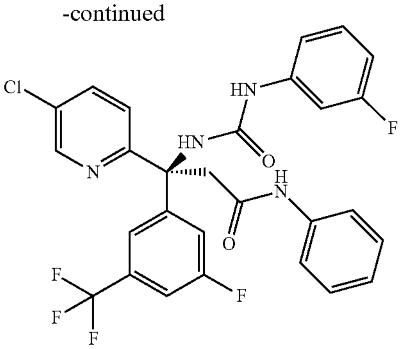

(S)-methyl 3-(5-chloropyridin-2-yl)-3-(3-fluoro-5-(trifluoromethyl)phenyl)-3-pivalamidopropanoate (1.04 g, 2.16 mmol, prepared as described in Procedure 11) was dissolved in THF (30 mL) at room temperature. A4M LiOH solution was added (20 mL) and the reaction mixture stirred at RT for 14 h. The RM was diluted with EtOAc (ca. 100 mL) and the pH adjusted to pH1-2 by addition of 1 M HCl. The organic portion was separated and the aqueous washed with EtOAc (ca.2×20 mL). The combined organic portions were dried over anhydrous $Na_2SO_4$, decanted and concentrated yielding (S)-3-(5-chloropyridin-2-yl)-3-(3-fluoro-5-(trifluoromethyl)phenyl)-3-pivalamidopropanoic acid as a colorless oil (0.856 g, 85% yield) LCMS: 1.90 min [M+1] 467.2 (2 min gradient, $MeOH/H_2O$ 0.1% TFA).

(S)-3-(5-chloropyridin-2-yl)-3-(3-fluoro-5-(trifluoromethyl)phenyl)-3-pivalamidopropanoic acid (0.10 g, 0.21 mmol) was dissolved in MeOH (2 mL) and 4M HCl in dioxanes added (2 mL). The resulting solution was stirred at RT for 30 mins then the solvents were removed under reduced pressure yielding a pale yellow oil (crude quantative) LCMS: 1.31 min [M+1] 363.2 (2 min gradient, $MeOH/H_2O$ 0.1% TFA). The residue was dissolved in acetonitrile (5 mL) and TEA, (0.3 mL, excess), aniline (0.030 g, 0.32 mmol) and PyBrOP (0.11 g, 0.24 mmol) added at RT. The RM was stirred for 14 h, concentrated to 1.5 mL, filtered and purified by prep HPLC: YMC ODSA30×100 mm, 40ml/min, 20-100% MeOH (0.1% TFA) over 10 min. The product (S)-3-amino-3-(5-chloropyridin-2-yl)-3-(3-fluoro-5-(trifluoromethyl)phenyl)-N-phenylpropanamide with a retention time of 7.52 min was isolated as a pale yellow oil, (0.054 g, 58% yield). LCMS: 1.48 min [M+1] 438.2 (2 min gradient, $MeOH/H_2O$ 0.1% TFA).

To a solution of (S)-3-amino-3-(5-chloropyridin-2-yl)-3-(3-fluoro-5-(trifluoromethyl)phenyl)-N-phenylpropanamide (0.018 g, 0.041 mmol) in DCM (2 mL) was added 3-fluorobenzenene isocyanate (0.008 mg, 0.062 mmol) and citric acid (0.002 g, catalytic). The resulting solution was stirred at RT for 14 h, concentrated and the residue dissolved in MeOH (1.5 mL). (S)-1-(1-(5-chloropyridin-2-yl)-1-(3-fluoro-5-(trifluoromethyl)phenyl)-3-oxo-3-(phenylamino)propyl)-3-(3-fluorophenyl)urea was purified by prep HPLC YMC ODSA30×100 mm, 40ml/min, 20-100% MeOH (0.1% TFA) over 10 min. Retention time of product was 11.06 min and (S)-1-(1-(5-chloropyridin-2-yl)-1-(3-fluoro-5-(trifluoromethyl)phenyl)-3-oxo-3-(phenylamino) propyl)-3-(3-fluorophenyl)urea was isolated as a pale yellow oil, (0.0064 g, 27% yield). LCMS: 2.10 min [M+1] 575.1 (2 min gradient, $MeOH/H_2O$ 0.1% TFA). HPLC: 4.04 min, purity 100% (4 min gradient, $MeOH/H_2O$ 0.2% PPA). NMR: 400 MHz $^1H$ ($CDCl_3$) Rotomers observed: major rotomer: 8.33 ppm, 1H, d, J=2.2 Hz; 8.18 ppm, 1H, s; 8.09 ppm, 1H, s; 7.54 ppm, 1H, dd, J=2.2 and J=8.8 Hz; 7.38, 1H, s; 7.32 ppm, 2H, d, J=7.9 Hz; 7.20 ppm, 6H, m; 7.08 ppm, 3H, m; 6.81 ppm, 1H, d, J=8.36 Hz; 6.74 ppm, 1H, dt, J=2.2 and J=8.8 Hz; 4.23 ppm, 1H, d, J=14.0 Hz; 3.71 ppm, 1H, d, J=14.0 Hz; 2.53 ppm, 2H, brs.

EXAMPLE 645

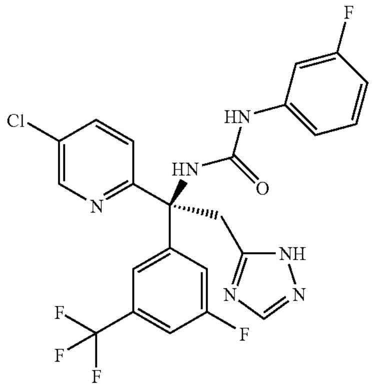

(S)-1-(1-(5-chloropyridin-2-yl)-1-(3-fluoro-5-(trifluoromethyl)phenyl)-2-(2H-1,2,4-triazol-3-yl)ethyl)-3-(3-fluorophenyl)urea Procedure 30

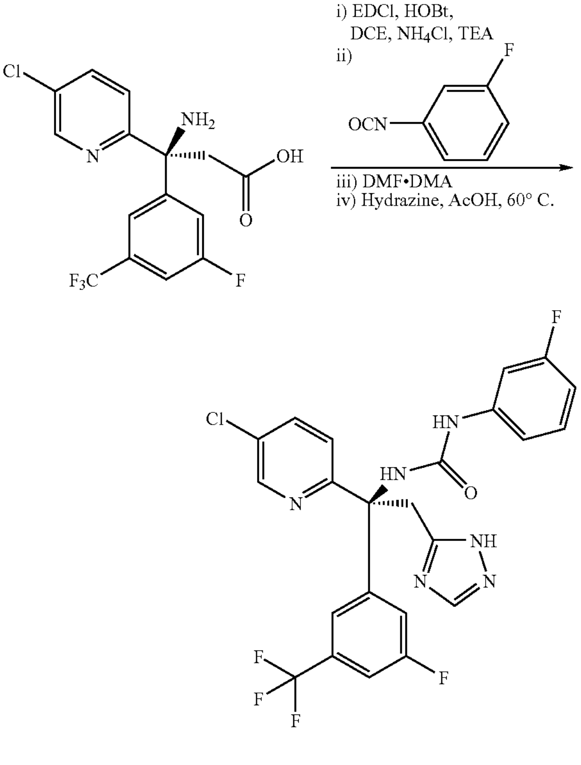

(S)-3-amino-3-(5-chloropyridin-2-yl)-3-(3-fluoro-5-(trifluoromethyl)phenyl)propanoic acid (0.047 g, 0.13 mmol, prepared as described in Procedure 29) was dissolved in DCE (5 mL) at room temperature. To the solution was added EDCI (0.035 g, 0.14 mmol), HOBt (0.025 mg, 0.14 mmol), $NH_4Cl$ (0.075 g, 1.3 mmol) and TEA (ca.0.070 g). The resulting solution was stirred for 18 h then heated to 50° C. for 8 h. On cooling the reaction mixture was diluted with DCM (ca. 10 mL) and washed with saturated NaCl solution (ca.2×10 mL). (S)-3-amino-3-(5-chloropyridin-2-yl)-3-(3-fluoro-5-(trifluoromethyl)phenyl) propanamide was isolated as a colorless oil (0.03 lg, 65% yield) and was used without further purification. LCMS: 1.25 min [M+1] 362.2 (2 min gradient, $MeOH/H_2O$ 0.1% TFA).

(S)-3-amino-3-(5-chloropyridin-2-yl)-3-(3-fluoro-5-(trifluoromethyl)phenyl) propanamide (0.031 g, 0.085 mmol) was converted to the urea as described in Procedure 2. (S)-1-(3-amino-1-(5-chloropyridin-2-yl)-1-(3-fluoro-5-(trifluoromethyl)phenyl)-3-oxopropyl)-3-(3-fluorophenyl)urea (0.023 g, 56% yield) was isolated after purification by reverse phase prep HPLC: YMC ODSA 30×100 mm, 20-100% $MeOH/H_2O$ (0.1% TFA) gradient over 10 min, flow rate 20 mL/min eluting at a retention time of 10.3 min. LCMS: 1.98 min [M+1] 499.1 (2 min gradient, $MeOH/H_2O$ 0.1% TFA).

(S)-1-(3-amino-1-(5-chloropyridin-2-yl)-1-(3-fluoro-5-(trifluoromethyl)phenyl)-3-oxopropyl)-3-(3-fluorophenyl) urea (0.023 g, 0.046 mmol) was converted to the corresponding unsubstituted triazole exactly as described in Procedure 25 using hydrazine hydrate in place of methylhydrazine. (S)-1-(1-(5-chloropyridin-2-yl)-1-(3-fluoro-5-(trifluoromethyl) phenyl)-2-(2H-1,2,4-triazol-3-yl)ethyl)-3-(3-fluorophenyl) urea (0.003 g, 12% yield) was isolated by reverse phase prep HPLC: YMC ODSA 30×100 mm, 20-100% $MeOH/H_2O$ (0.1% TFA) gradient over 10 min, flow rate 20 mL/min eluting at a retention time of 9.96 min. LCMS: 1.92 min [M+1] 523.2 (2 min gradient, $MeOH/H_2O$ 0.1% TFA). HPLC: 3.74 min 100% purity (4 min gradient, $MeOH/H_2O$ 0.2% PPA). NMR: 400 MHz $^1H$ ($CDCl_3$) 8.36 ppm, 1H, s; 8.26 ppm, 1H, s; 8.05 ppm, 1H, s; 7.65 ppm, 2H, m; 7.43, 1H, s; 7.20 ppm, 2H, m; 7.13 ppm, 1H, m; 6.98 ppm, 1H, d, J=12 Hz; 6.77 ppm, 2H, m; 4.56, 1H, d, J=20 Hz; 4.34 ppm, 1H, d, J=20 Hz.

EXAMPLE 646

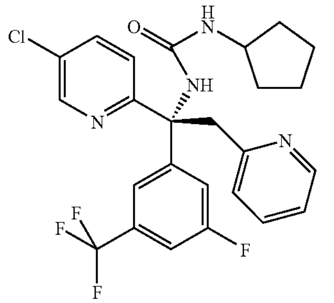

(R)-1-(1-(5-chloropyridin-2-yl)-1-(3-fluoro-5-(trifluoromethyl)phenyl)-2-(pyridin-2-yl)ethyl)-3-cyclopentylurea Procedure 31

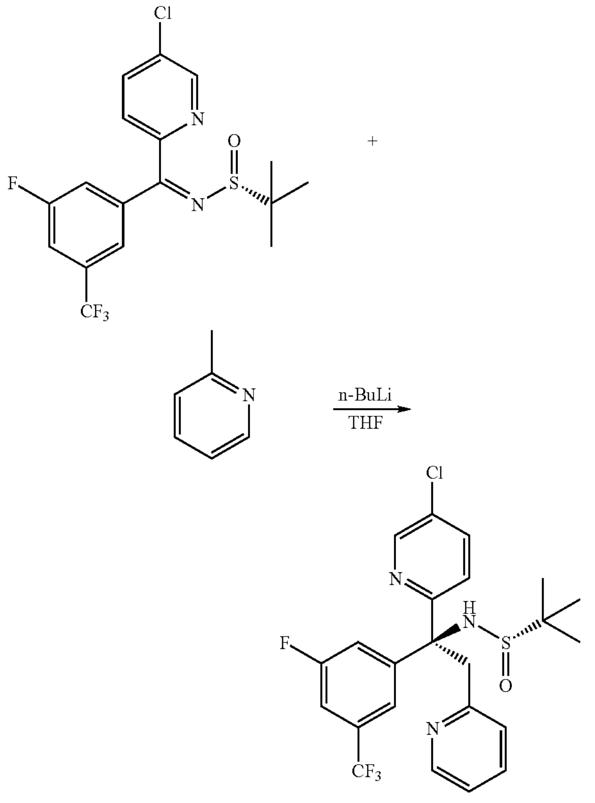

2-Methyl pyridine (48 μL, 0.49 mmol) in THF (90 μL) was cooled at −78° C. for 10 min, followed by the addition of n-BuLi (246 μL, 0.49 mmol, 2M solution in cyclohexane). The reaction turned into maroon and was stirred at −78° C. for 40 min. (R,Z)-N-((5-chloropyridin-2-yl)(3-fluoro-5-(trifluoromethyl)phenyl)methylene)-2-methylpropane-2-sulfinamide (100 mg, 0.25 mmol) in THF (1 mL) was added and the dark green colored reaction mixture was stirred at −78° C. for another 2 h. Quenched with $H_2O$ (10 mL), the reaction mixture was extracted by EtOAc (2×15 mL). The combined organic layers were dried over $MgSO_4$, filtered and concentrated. The residue was purified by preparative HPLC YMC ODS S5 28×100 mm Ballistic column 40-100% MeOH (90% in water, 0.1% TFA) gradient over 12 min with flow rate 40 mL/min and UV detection at 220 nm. (S)-N-((S)-1-(5-chloropyridin-2-yl)-1-(3-fluoro-5-(trifluoromethyl)phenyl)-2-(pyridin-2-yl)ethyl)-2-methylpropane-2-sulfinamide at a retention time of 9.66 min and was isolated as a clear oil (48 mg, yield 38%) LCMS: 1.76 min [M+1] 500.2 (2 min gradient, $MeOH/H_2O$ 0.1% TFA); HPLC: 3.72 min (4 min gradient, $MeOH/H_2O$ 0.2% PPA); Purity 100%; NMR: 400 MHz $^1H$ ($CDCl_3$) 8.45 ppm, 1 H, d, J=2.64 Hz; 8.28 ppm, 1 H, d, J=4.39 Hz; 7.93 ppm, 1 H, s; 7.68 ppm, 1 H, d, J=8.79 Hz; 7.48 ppm, 1 H, dd, J=8.57, 2.42 Hz; 7.35 ppm, 1 H, t, J=6.81 Hz; 7.31 ppm, 1 H, s; 7.10 ppm, 1 H, d, J=7.91 Hz; 6.97 ppm, 2 H, m; 6.79 ppm, 1 H, d, J=7.47 Hz; 4.10 ppm, 1 H, d, J=14.06 Hz; 3.86 ppm, 1 H, d, J=14.50 Hz; 1.25 ppm, 9 H, s.

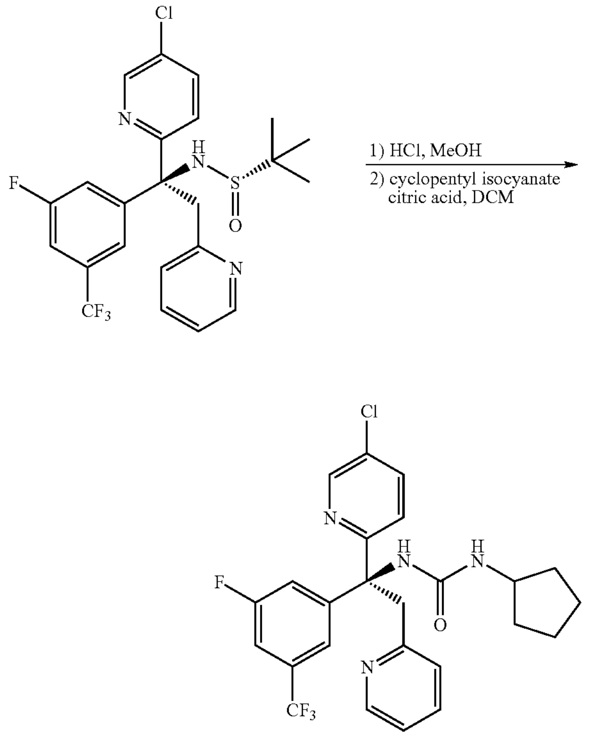

(S)-N-((S)-1-(5-chloropyridin-2-yl)-1-(3-fluoro-5-(trifluoromethyl)phenyl)-2-(pyridin-2-yl)ethyl)-2-methylpropane-2-sulfinamide (11 mg, 0.022 mmol) in MeOH (0.5 mL) was added HCl (0.5 mL, 2 mmol, 4N solution in dioxane) and the reaction was stirred at room temperature for 0.5 h. The mixture was concentrated, diluted with EtOAc (20 mL), washed with sat. $NaHCO_3$ (20 mL), dried over $Na_2SO_4$, filtered and concentrated. The residue was dissolved in DCM (1 mL), cyclopentyl isocyanate (12 μL, 0.11 mmol) was added followed by two crystals of citric acid. The reaction was stirred overnight, concentrated and purified by preparative HPLC YMC ODS S5 28×100 mm Ballistic column 30-100% MeOH (90% in water, 0.1% TFA) gradient over 12 min with flow rate 40 mL/min and UV detection at 220 nm. (S)-1-(1-(5-chloropyridin-2-yl)-1-(3-fluoro-5-(trifluoromethyl)phenyl)-2-(pyridin-2-yl)ethyl)-3-cyclopentylurea eluted at a retention time of 9.33 min and was isolated as a clear oil (8 mg, yield 72%) LCMS: 1.69 min [M+1] 507.1 (2 min gradient, MeOH/H2O 0.1% TFA); HPLC: 3.26 min (4 min gradient, MeOH/H2O 0.2% PPA); Purity 100%; NMR: 400 MHz $^1H$ ($CDCl_3$) 8.29 ppm, 1 H, d, J=2.20 Hz; 8.26 ppm, 1 H, d, J=4.83 Hz; 7.53 ppm, 3 H, dd, J=8.57, 2.42 Hz; 7.40 ppm, 1 H, s; 7.28 ppm, 1 H, d, J=10.11 Hz; 7.12 ppm, 3 H, m; 6.98 ppm, 1 H, d, J=7.47 Hz; 4.54 ppm, 1 H, s; 4.12 ppm, 1 H, d, J=12.74 Hz; 3.93 ppm, 1 H, d, J=12.74 Hz; 3.83 ppm, 1 H, m; 1.88 ppm, 2 H, m; 1.58 ppm, 2 H, m; 1.51 ppm, 2 H, m; 1.32 ppm, 1 H, dd, J=12.30, 6.59 Hz; 1.25 ppm, 1 H, dd, J=12.96, 6.81 Hz.

EXAMPLE 647

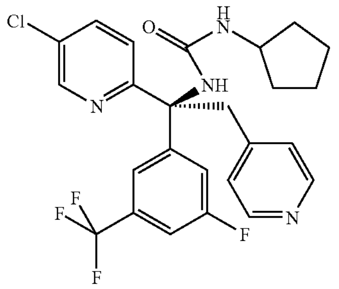

(S)-1-(1-(5-chloropyridin-2-yl)-1-(3-fluoro-5-(trifluoromethyl)phenyl)-2-(pyridin-4-yl)ethyl)-3-cyclopentylurea Procedure 32

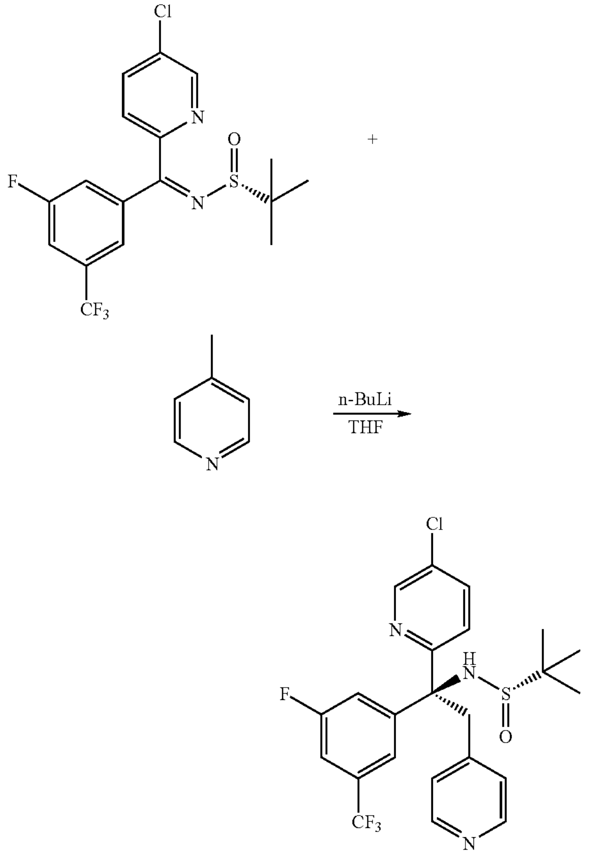

4-Methyl pyridine (48 μL, 0.49 mmol) in THF (90 μL) was cooled at −78° C. for 10 min, followed by the addition of n-BuLi (246 μL, 0.49 mmol, 2M solution in cyclohexane). The reaction turned into maroon and was stirred at −78° C. for 40 min. (R,Z)-N-((5-chloropyridin-2-yl)(3-fluoro-5-(trifluoromethyl)phenyl)methylene)-2-methylpropane-2-sulfinamide (100 mg, 0.25 mmol) in THF (1 mL) was added and the dark green colored reaction mixture was stirred at −78° C. for another 2 h. Quenched with $H_2O$ (10 mL), the reaction mixture was extracted by EtOAc (2×15 mL). The combined organic layers were dried over $MgSO_4$, filtered and concentrated. The residue was purified by preparative HPLC YMC ODS S5 28×100 mm Ballistic column 20-100% MeOH (90% in water, 0.1% TFA) gradient over 14 min with flow rate 40 mL/min and UV detection at 220 nm. Diastereoisomer SR eluted at a retention time of 9.95 min and was isolated as a clear oil (25 mg, yield 20%) LCMS: 1.58 min [M+1] 500.1 (2 min gradient, MeOH/H2O 0.1% TFA); NMR: 400 MHz $^1H$ ($CDCl_3$) 8.59 ppm, 1 H, d, J=2.20 Hz; 8.32 ppm, 2 H, d, J=5.71 Hz; 7.57 ppm, 1 H, dd, J=8.35, 2.64 Hz; 7.18 ppm, 2 H, m; 7.12 ppm, 1 H, d, J=8.79 Hz; 6.95 ppm, 1 H, d, J=9.67 Hz; 6.81 ppm, 2 H, d, J=5.71 Hz; 4.31 ppm, 1 H, s; 4.09 ppm, 1 H, m; 3.76 ppm, 1 H, d, J=13.62 Hz; 1.15 ppm, 9 H, m.

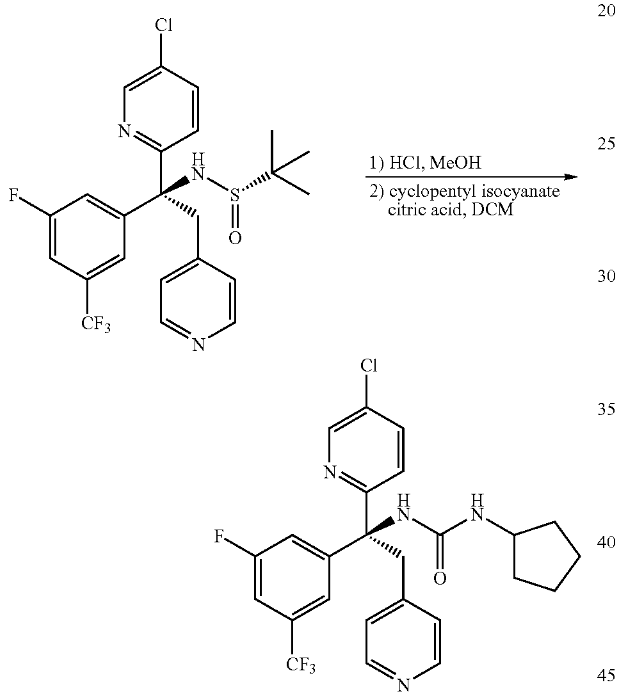

(S)-N-((S)-1-(5-chloropyridin-2-yl)-1-(3-fluoro-5-(trifluoromethyl)phenyl)-2-(pyridin-4-yl)ethyl)-2-methylpropane-2-sulfinamide (10 mg, 0.020 mmol) in MeOH (0.5 mL) was added HCl (0.5 mL, 2 mmol, 4N solution in dioxane) and the reaction was stirred at room temperature for 0.5 h. The mixture was concentrated, diluted with EtOAc (20 mL), washed with sat. $NaHCO_3$ (20 mL), dried over $Na_2SO_4$, filtered and concentrated. The residue was dissolved in DCM (1 mL) and cyclopentyl isocyanate (100 μL, 0.89 mmol) was added followed by two crystals of citric acid. The reaction was stirred overnight, concentrated and purified by silica gel ISCO chromatography (4 g column) using hexanes/EtOAc (0-70% over 10 min). The product was isolated as a clear oil, (5 mg, 49% yield). LCMS: 1.73 min [M+1] 507.2 (2 min gradient, MeOH/$H_2O$ 0.1% TFA); HPLC: 3.17 min (4 min gradient, MeOH/$H_2O$ 0.2% PPA); Purity 100%; NMR: 400 MHz $^1H$ ($CDCl_3$) 8.27 ppm, 2 H, d, J=5.71 Hz; 8.23 ppm, 1 H, d, J=2.64 Hz; 7.63 ppm, 1 H, dd, J=8.57, 2.42 Hz; 7.43 ppm, 1 H, s; 7.27 ppm, 1 H, d, J=9.67 Hz; 7.16 ppm, 1 H, d, J=8.35 Hz; 7.06 ppm, 1 H, d, J=8.35 Hz; 6.64 ppm, 2 H, d, J=5.71 Hz; 4.55 ppm, 1 H, d, J=12.30 Hz; 4.50 ppm, 1 H, d, J=6.59 Hz; 3.86 ppm, 1 H, d, J=6.59 Hz; 3.56 ppm, 1 H, d, J=12.30 Hz; 1.97 ppm, 1 H, m; 1.83 ppm, 1 H, dd, J=12.74, 5.71 Hz; 1.61 ppm, 2 H, m; 1.53 ppm, 2 H, m; 1.35 ppm, 1 H, ddd, J=11.97, 5.82, 5.49 Hz; 1.23 ppm, 2 H, m.

EXAMPLE 648

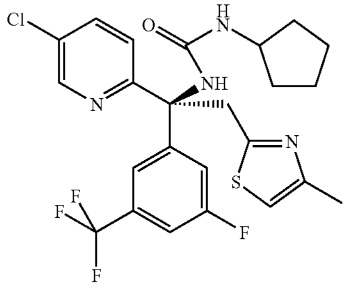

(S)-1-(1-(5-chloropyridin-2-yl)-1-(3-fluoro-5-(trifluoromethyl)phenyl)-2-(4-methylthiazol-2-yl)ethyl)-3-cyclopentylurea Procedure 33

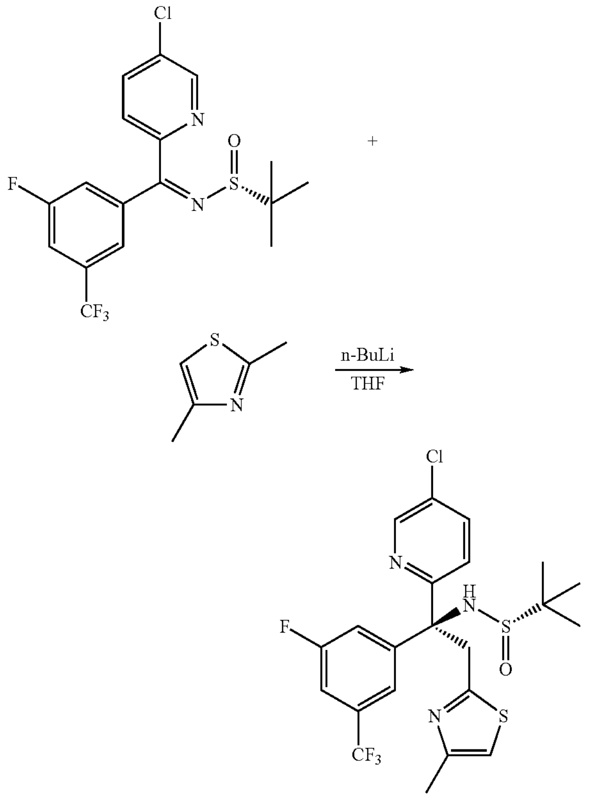

2,4-Dimethyl thiazole (53 μL, 0.49 mmol) in THF (0.20 mL) was cooled at −78° C. for 10 min, followed by the addition of n-BuLi (246 μL, 0.49 mmol, 2M solution in cyclohexane). The reaction turned yellow and was stirred at −78° C. for 30 min. (R,Z)-N-((5-chloropyridin-2-yl)(3-fluoro-5-

(trifluoromethyl)phenyl)methylene)-2-methylpropane-2-sulfinamide (100 mg, 0.25 mmol) in THF (1.0 mL) was added and the reaction mixture was stirred at −78° C. for another 2 h. The reaction mixture was quenched with $H_2O$ (10 mL), and extracted by EtOAc (2×15 mL). The combined organic layers were dried over $MgSO_4$, filtered and concentrated. The residue was purified by preparative HPLC Phenomenex Luna 5μ, C18, 250×21 mm 20-98% ACN (90% in water, 0.1% TFA) gradient over 28 min with flow rate 15 mL/min and UV detection at 220 nm. (S)-N-((S)-1-(5-chloropyridin-2-yl)-1-(3-fluoro-5-(trifluoromethyl)phenyl)-2-(4-methylthiazol-2-yl)ethyl)-2-methylpropane-2-sulfinamide eluted at a retention time of 32 min and was isolated as a clear oil (34 mg, yield 30%) LCMS: 2.06 min [M+1] 520.2 (2 min gradient, MeOH/$H_2O$ 0.1% TFA); NMR: 400 MHz $^1H$ ($CDCl_3$) 8.50 ppm, 1 H, s; 7.54 ppm, 2 H, m; 7.29 ppm, 2 H, s; 7.11 ppm, 1 H, d, J=7.91 Hz; 7.00 ppm, 1 H, d,J=9.67 Hz; 6.53 ppm, 1 H, s; 4.33 ppm, 1 H, d, J=14.94 Hz; 4.03 ppm, 1 H, d, J=14.94 Hz; 2.25 ppm, 3 H, s; 1.27 ppm, 9 H, s.

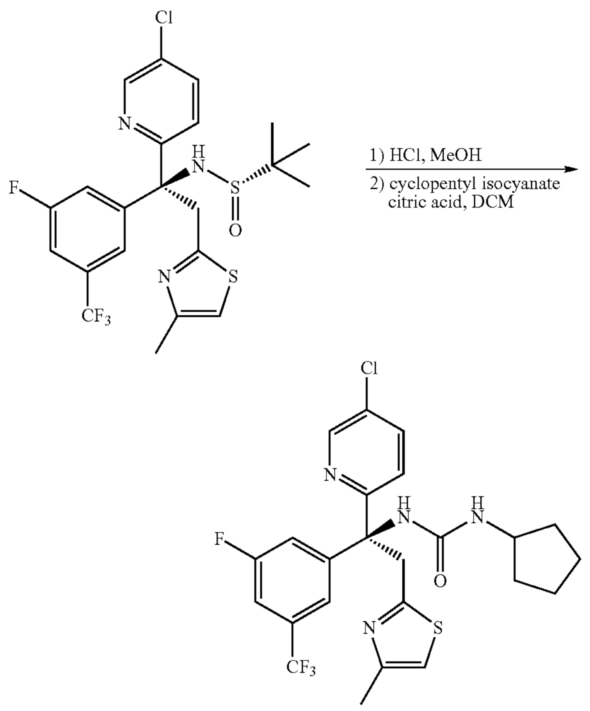

(S)-N-((S)-1-(5-chloropyridin-2-yl)-1-(3-fluoro-5-(trifluoromethyl)phenyl)-2-(4-methylthiazol-2-yl)ethyl)-2-methylpropane-2-sulfinamide (29 mg, 0.058 mmol) in MeOH (1.0 mL) was added HCl (0.5 mL, 2 mmol, 4N solution in dioxane) and the reaction was stirred at room temperature for 0.5 h. The mixture was concentrated, diluted with EtOAc (20 mL), washed with sat. $NaHCO_3$ (20 mL), dried over $Na_2SO_4$, filtered and concentrated. The residue was dissolved in DCM (1 mL) and cyclopentyl isocyanate (9 mg, 0.083 mmol) was added followed by two crystals of citric acid. The reaction was stirred overnight, concentrated and purified by Prep TLC (Uniplate, Silica Gel GF, 20×20 cm, 1000 Microns) using Hexane/EtOAc (1/1) to yield (S)-1-(1-(5-chloropyridin-2-yl)-1-(3-fluoro-5-(trifluoromethyl)phenyl)-2-(4-methylthiazol-2-yl)ethyl)-3-cyclopentylurea as a clear oil (10 mg, 70% yield) LCMS: 1.91 min [M+1] 527.2 (2 min gradient, MeOH/$H_2O$ 0.1% TFA); HPLC: 3.91 min (4 min gradient, MeOH/$H_2O$ 0.2% PPA); Purity 100%; NMR: 400 MHz $^1H$ ($CDCl_3$) 8.29 ppm, 1 H, d, J=2.64 Hz; 7.54 ppm, 1 H, dd, J=8.57, 2.42 Hz; 7.40 ppm, 1 H, s; 7.32 ppm, 1 H, s; 7.26 ppm, 1 H, d, J=9.67 Hz; 7.12 ppm, 2 H, d, J=8.35 Hz; 6.60 ppm, 1 H, s; 4.58 ppm, 1 H, d, J=13.62 Hz; 4.43 ppm, 1 H, d, J=7.03 Hz; 4.08 ppm, 1 H, d, J=13.62 Hz; 3.92 ppm, 1 H, m; 2.20 ppm, 3 H, s; 1.93 ppm, 2 H, m; 1.61 ppm, 2 H, m; 1.53 ppm, 2 H, m; 1.40 ppm, 1 H, m; 1.32 ppm, 1 H, dd, J=13.18, 7.03 Hz.

EXAMPLE 649

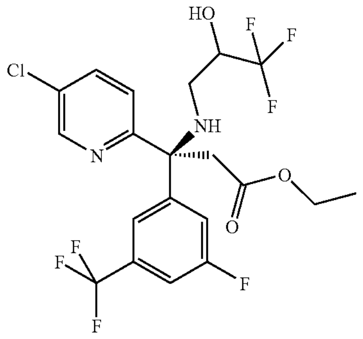

(3S)-ethyl 3-(5-chloropyridin-2-yl)-3-(3-fluoro-5-(trifluoromethyl)phenyl)-3-(3,3,3-trifluoro-2-hydroxypropylamino)propanoate Procedure 34

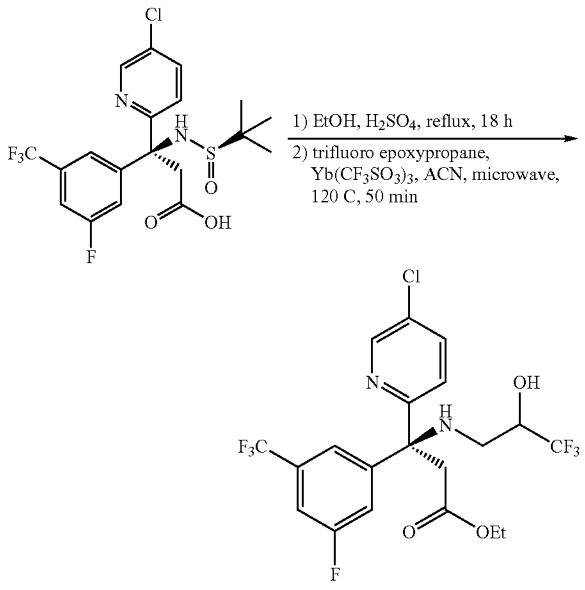

(S)-3-(5-chloropyridin-2-yl)-3-(3-fluoro-5-(trifluoromethyl)phenyl)-3-((R)-2-methylpropan-2-ylsulfinamido)propanoic acid (0.040 g, 0.089 mmol) in EtOH (1.0 mL) was added two drops of concentrated sulfuric acid. The reaction was heated at 80° C. for 18 h and then concentrated under reduced pressure. The residue was dissolved in EtOAc (30 mL), washed with sat. $NaHCO_3$ (20 mL), dried over $MgSO_4$ and filtered. The concentrated filtrate was dissolved in ACN (0.50 mL), followed by the addition of $Yb(CF_3OSO_2)_3$ (0.020 g) and trifluoro epoxypropane (0.20 mL). The reaction was subject to microwave at 120° C. for 50 min. After concentration, the residue was purified by silica gel ISCO chromatography (4 g column) using hexanes/EtOAc (0-30% over 10 min). (3S)-ethyl 3-(5-chloropyridin-2-yl)-3-(3-fluoro-5-(trifluoromethyl)phenyl)-3-(3,3,3-trifluoro-2-hydroxypropylamino)propanoate was isolated as a clear oil, (22 mg, 54% yield). LCMS: 2.00 min [M+1] 503.3 (2 min gradient, $MeOH/H_2O$ 0.1% TFA); HPLC: 4.05 min (4 min gradient, $MeOH/H_2O$ 0.2% PPA); Purity 100%; NMR: 400 MHz $^1H$ ($CDCl_3$) 8.40 ppm, 1 H, d, J=2.20 Hz; 7.57 ppm, 1 H, m; 7.40 ppm, 1 H, s; 7.27 ppm, 2 H, m; 7.15 ppm, 1 H, d, J=7.91 Hz; 3.97 ppm, 4 H, m; 3.57 ppm, 1 H, d, J=15.38 Hz; 3.28 ppm, 1 H, d, J=15.38 Hz; 2.68 ppm, 2 H, m; 1.01 ppm, 3 H, t, J=7.25 Hz.

TABLE 7

| Ex. No. | Compound Structure | Compound Name | Retention Time Min./ Molecular Mass | Prepared in the manner described in: |
|---|---|---|---|---|
| 650 | 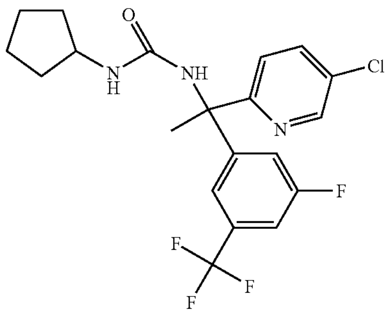 | 1-(1-(5-chloropyridin-2-yl)-1-(3-fluoro-5-(trifluoromethyl)phenyl) ethyl)-3-cyclopentylurea | 3.88 LC 430.1 $[M + H]^+$ | Procedures 1 and 2 |
| 651 | 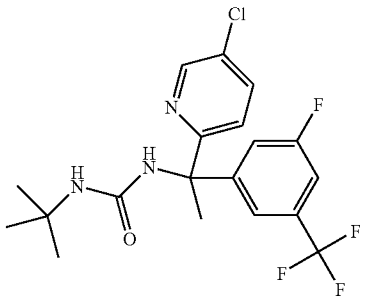 | 1-tert-butyl-3-(1-(5-chloropyridin-2-yl)-1-(3-fluoro-5-(trifluoromethyl)phenyl)ethyl) urea | 3.85 LC 418.09 $[M + H]^+$ | Procedures 1 and 2 |
| 652 | 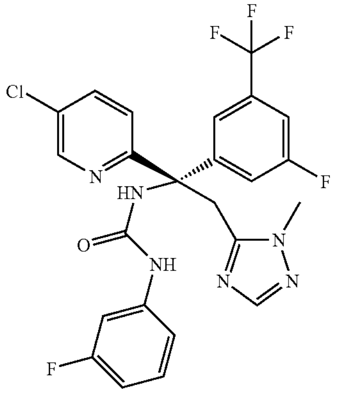 | (S)-1-(1-(5-chloropyridin-2-yl)-1-(3-fluoro-5-(trifluoromethyl) phenyl)-2-(2-methyl-2H-1,2,4-triazol-3-yl)ethyl)-3-(3-fluorophenyl)urea | 1.96 LC 537.1 $[M + H]^+$ | Procedures 22, 23, 24 and 2 |

TABLE 7-continued

| Ex. No. | Compound Structure | Compound Name | Retention Time Min./ Molecular Mass | Prepared in the manner described in: |
|---|---|---|---|---|
| 653 | 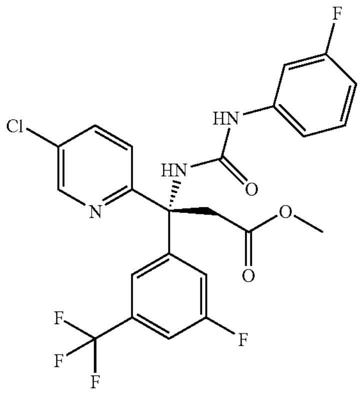 | (R)-methyl 3-(5-chloropyridin-2-yl)-3-(3-fluoro-5-(trifluoromethyl)phenyl)-3-(3-(3-fluorophenyl)ureido)propanoate | 1.99 LC 514.1 $[M + H]^+$ | Procedures 22 and 2 |
| 654 | 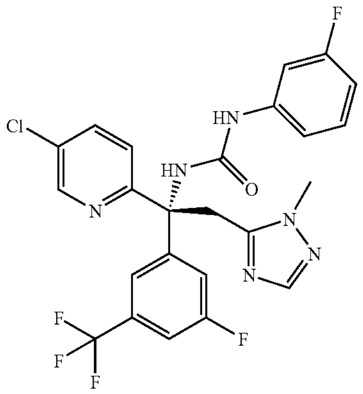 | (R)-1-(1-(5-chloropyridin-2-yl)-1-(3-fluoro-5-(trifluoromethyl) phenyl)-2-(2-methyl-2H-1,2,4-triazol-3-yl)ethyl)-3-(3-fluorophenyl)urea | 2.01 LC 537.1 $[M + H]^+$ | Procedures 22, 23, 24 and 2 |
| 655 | 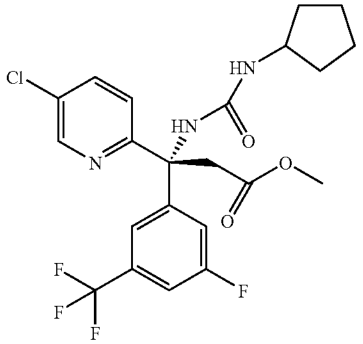 | (R)-methyl 3-(5-chloropyridin-2-yl)-3-(3-cyclopentylureido)-3-(3-fluoro-5-(trifluoromethyl)phenyl) propanoate | 2.25 LC 488.1 $[M + H]^+$ | Procedures 22 and 2 |
| 656 | 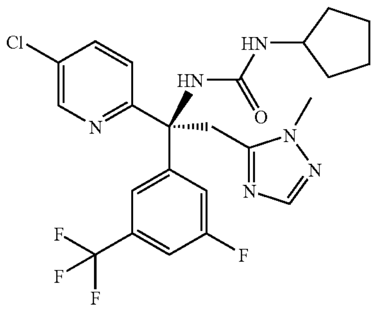 | (S)-1-(1-(5-chloropyridin-2-yl)-1-(3-fluoro-5-(trifluoromethyl) phenyl)-2-(2-methyl-2H-1,2,4-triazol-3-yl)ethyl)-3-cyclopentylurea | 1.95 LC 511.21 $[M + H]^+$ | Procedures 22, 23, 24 and 2 |

TABLE 7-continued

| Ex. No. | Compound Structure | Compound Name | Retention Time Min./ Molecular Mass | Prepared in the manner described in: |
|---|---|---|---|---|
| 658 | 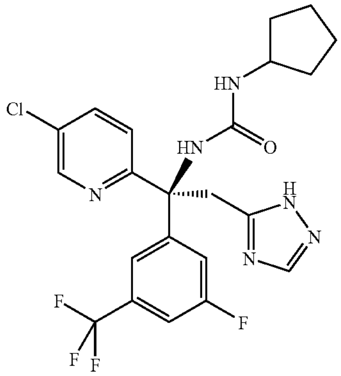 | (S)-1-(1-(5-chloropyridin-2-yl)-1-(3-fluoro-5-(trifluoromethyl) phenyl)-2-(2H-1,2,4-triazol-3-yl)ethyl)-3-cyclopentylurea | 1.88 LC 497.2 $[M + H]^+$ | Procedure 30 |
| 659 | 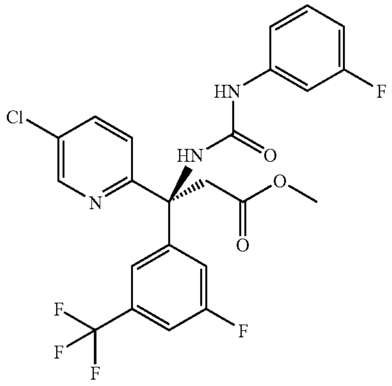 | (S)-methyl 3-(5-chloropyridin-2-yl)-3-(3-fluoro-5-(trifluoromethyl)phenyl)-3-(3-(3-fluorophenyl)ureido)propanoate | 2.03 LC 514.1 $[M + H]^+$ | Procedures 22 and 2 |
| 660 | 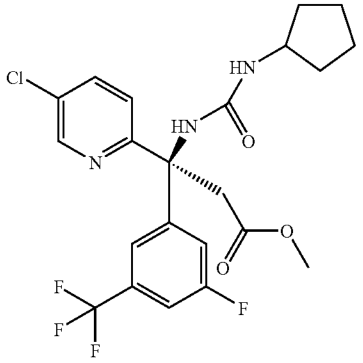 | (S)-methyl 3-(5-chloropyridin-2-yl)-3-(3-cyclopentylureido)-3-(3-fluoro-5-(trifluoromethyl)phenyl) propanoate | 2.00 LC 488.2 $[M + H]^+$ | Procedures 22 and 2 |
| 661 | 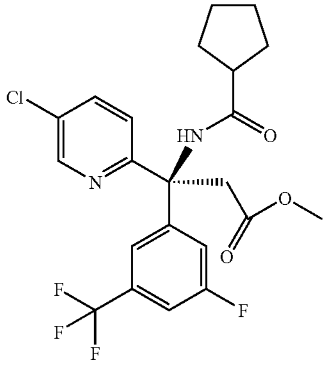 | (S)-methyl 3-(5-chloropyridin-2-yl)-3-(cyclopentanecarboxamido)-3-(3-fluoro-5-(trifluoromethyl)phenyl) propanoate | 2.07 LC 473.2 $[M + H]^+$ | Procedures 22 and 4 |

TABLE 7-continued

| Ex. No. | Compound Structure | Compound Name | Retention Time Min./ Molecular Mass | Prepared in the manner described in: |
|---|---|---|---|---|
| 662 | 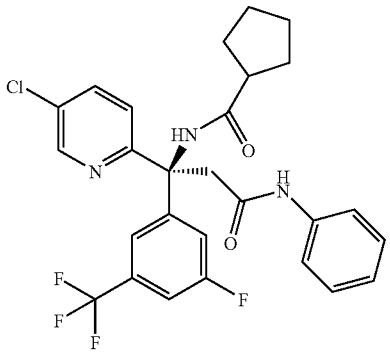 | (S)-N-(1-(5-chloropyridin-2-yl)-1-(3-fluoro-5-(trifluoromethyl) phenyl)-3-oxo-3-(phenylamino) propyl)cyclopentanecarboxamide | 2.13 LC 534.1 [M + H]+ | Procedures 29 and 4 |
| 664 | 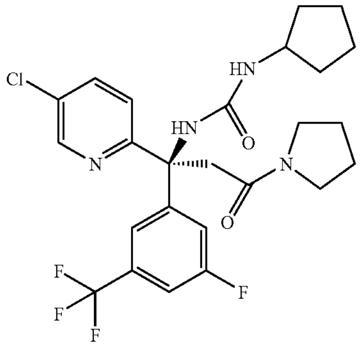 | (S)-1-(1-(5-chloropyridin-2-yl)-1-(3-fluoro-5-(trifluoromethyl) phenyl)-3-oxo-3-(pyrrolidin-1-yl)propyl)-3-cyclopentylurea | 2.03 LC 527.2 [M + H]+ | Procedures 29 and 2 |
| 665 | 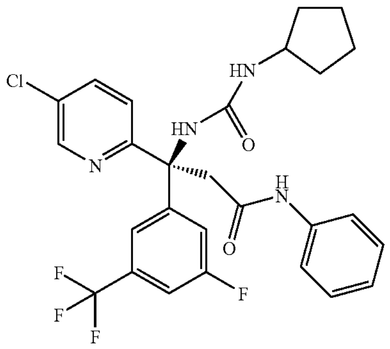 | (S)-1-(1-(5-chloropyridin-2-yl)-1-(3-fluoro-5-(trifluoromethyl) phenyl)-3-oxo-3-(phenylamino) propyl)-3-cyclopentylurea | 2.09 LC 549.2 [M + H]+ | Procedures 29 and 2 |
| 666 | 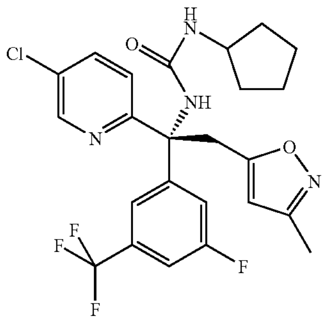 | (R)-1-(1-(5-chloropyridin-2-yl)-1-(3-fluoro-5-(trifluoromethyl) phenyl)-2-(3-methylisoxazol-5-yl)ethyl)-3-cyclopentylurea | 3.85 LC 511.2 [M + H]+ | Procedures 26 and 2 |

TABLE 7-continued

| Ex. No. | Compound Structure | Compound Name | Retention Time Min./ Molecular Mass | Prepared in the manner described in: |
|---|---|---|---|---|
| 667 | 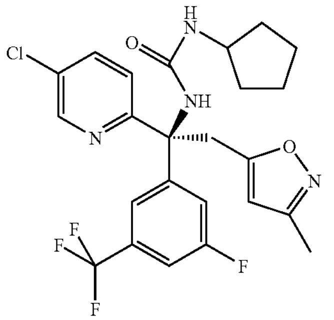 | (S)-1-(1-(5-chloropyridin-2-yl)-1-(3-fluoro-5-(trifluoromethyl) phenyl)-2-(3-methylisoxazol-5-yl)ethyl)-3-cyclopentylurea | 3.85 LC 511.2 $[M + H]^+$ | Procedures 26 and 2 |
| 668 | 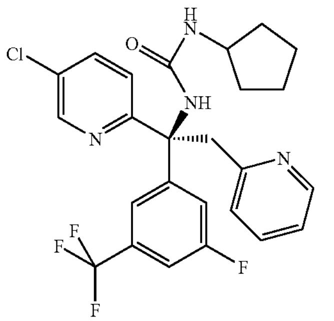 | (S)-1-(1-(5-chloropyridin-2-yl)-1-(3-fluoro-5-(trifluoromethyl) phenyl)-2-(pyridin-2-yl)ethyl)-3-cyclopentylurea | 3.26 LC 507.1 $[M + H]^+$ | Procedures 31 and 2 |
| 669 | 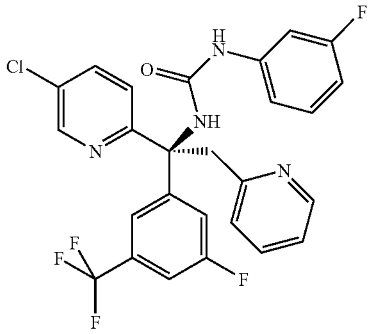 | (S)-1-(1-(5-chloropyridin-2-yl)-1-(3-fluoro-5-(trifluoromethyl) phenyl)-2-(pyridin-2-yl)ethyl)-3-(3-fluorophenyl)urea | 3.47 LC 533.1 $[M + H]^+$ | Procedures 31 and 2 |
| 670 | 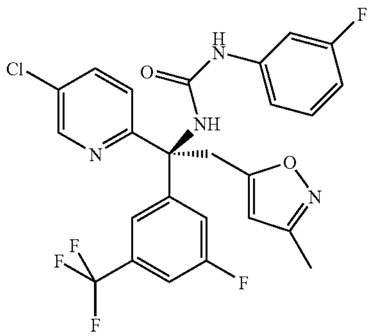 | (S)-1-(1-(5-chloropyridin-2-yl)-1-(3-fluoro-5-(trifluoromethyl) phenyl)-2-(3-methylisoxazol-5-yl)ethyl)-3-(3-fluorophenyl)urea | 3.90 LC 537.1 $[M + H]^+$ | Procedures 26 and 2 |

TABLE 7-continued

| Ex. No. | Compound Structure | Compound Name | Retention Time Min./ Molecular Mass | Prepared in the manner described in: |
|---|---|---|---|---|
| 671 | 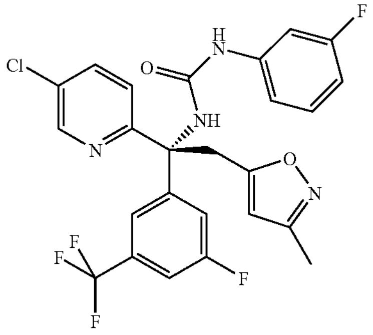 | (R)-1-(1-(5-chloropyridin-2-yl)-1-(3-fluoro-5-(trifluoromethyl) phenyl)-2-(3-methylisoxazol-5-yl)ethyl)-3-(3-fluorophenyl)urea | 3.90 LC 537.1 $[M + H]^+$ | Procedures 26 and 2 |
| 672 | 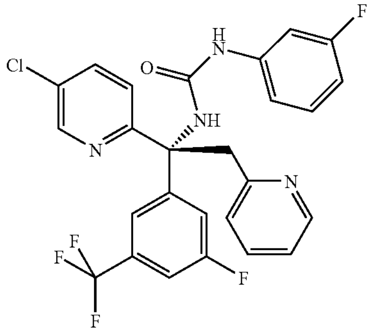 | (R)-1-(1-(5-chloropyridin-2-yl)-1-(3-fluoro-5-(trifluoromethyl) phenyl)-2-(pyridin-2-yl)ethyl)-3-(3-fluorophenyl)urea | 3.47 LC 533.1 $[M + H]^+$ | Procedures 31 and 2 |
| 673 | 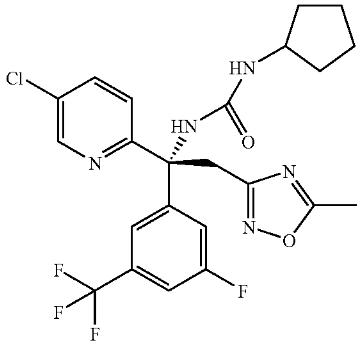 | (R)-1-(1-(5-chloropyridin-2-yl)-1-(3-fluoro-5-(trifluoromethyl) phenyl)-2-(5-methyl-1,2,4-oxadiazol-3-yl)ethyl)-3-cyclopentylurea | 2.00 LC 512.22 $[M + H]^+$ | Procedures 27, 28 and 2 |
| 675 | 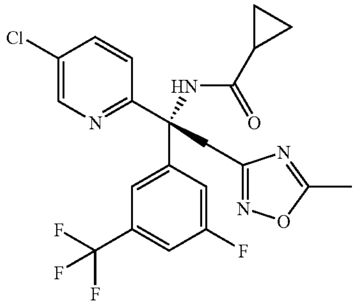 | (R)-N-(1-(5-chloropyridin-2-yl)-1-(3-fluoro-5-(trifluoromethyl) phenyl)-2-(5-methyl-1,2,4-oxadiazol-3-yl)ethyl) cyclopropanecarboxamide | 1.91 LC 469.2 $[M + H]^+$ | Procedures 27, 28 and 4 |

TABLE 7-continued

| Ex. No. | Compound Structure | Compound Name | Retention Time Min./ Molecular Mass | Prepared in the manner described in: |
|---|---|---|---|---|
| 676 | 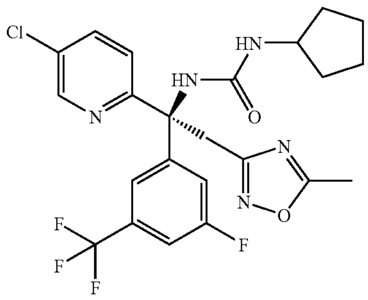 | (S)-1-(1-(5-chloropyridin-2-yl)-1-(3-fluoro-5-(trifluoromethyl) phenyl)-2-(5-methyl-1,2,4-oxadiazol-3-yl)ethyl)-3-cyclopentylurea | 1.99 LC 512.2 $[M + H]^+$ | Procedures 27, 28 and 2 |
| 677 | 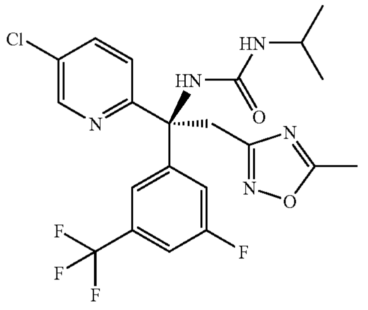 | (S)-1-(1-(5-chloropyridin-2-yl)-1-(3-fluoro-5-(trifluoromethyl) phenyl)-2-(5-methyl-1,2,4-oxadiazol-3-yl)ethyl)-3-isopropylurea | 1.89 LC 486.2 $[M + H]^+$ | Procedures 27, 28 and 2 |
| 678 | 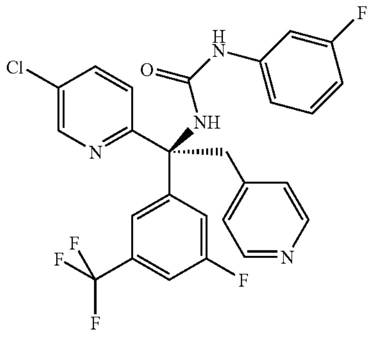 | (S)-1-(1-(5-chloropyridin-2-yl)-1-(3-fluoro-5-(trifluoromethyl) phenyl)-2-(pyridin-4-yl)ethyl)-3-(3-fluorophenyl)urea | 3.32 LC 533.1 $[M + H]^+$ | Procedures 32 and 2 |
| 679 | 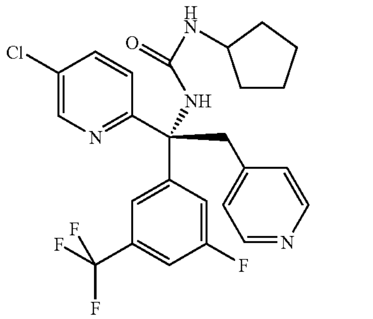 | (R)-1-(1-(5-chloropyridin-2-yl)-1-(3-fluoro-5-(trifluoromethyl) phenyl)-2-(pyridin-4-yl)ethyl)-3-cyclopentylurea | 3.18 LC 507.2 $[M + H]^+$ | Procedures 32 and 2 |

TABLE 7-continued

| Ex. No. | Compound Structure | Compound Name | Retention Time Min./ Molecular Mass | Prepared in the manner described in: |
|---|---|---|---|---|
| 680 | 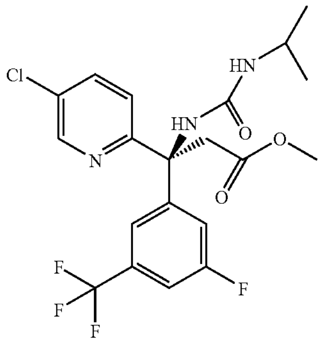 | (S)-methyl 3-(5-chloropyridin-2-yl)-3-(3-fluoro-5-(trifluoromethyl)phenyl)-3-(3-isopropylureido)propanoate | 1.93 LC 462.2 [M + H]+ | Procedures 22 and 2 |
| 681 | 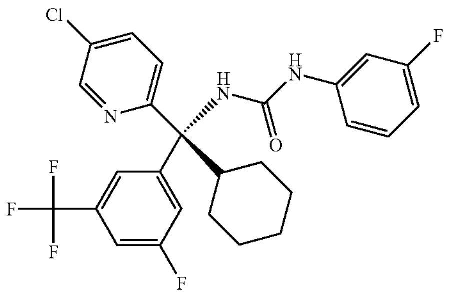 | (R)-1-((5-chloropyridin-2-yl)(cyclohexyl)(3-fluoro-5-(trifluoromethyl)phenyl)methyl)-3-(3-fluorophenyl)urea | 4.35 LC 524.38 [M + H]+ | Procedures 1 and 2 |
| 682 | 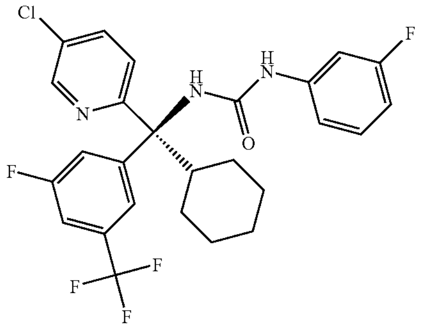 | (S)-1-((5-chloropyridin-2-yl)(cyclohexyl)(3-fluoro-5-(trifluoromethyl)phenyl)methyl)-3-(3-fluorophenyl)urea | 4.34 LC 524.42 [M + H]+ | Procedures 1 and 2 |
| 683 | 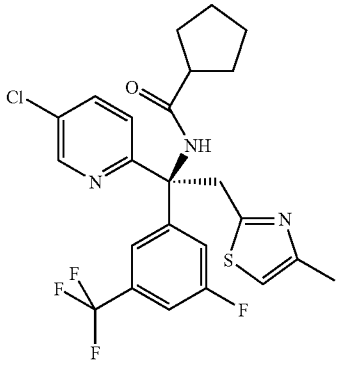 | (S)-N-(1-(5-chloropyridin-2-yl)-1-(3-fluoro-5-(trifluoromethyl)phenyl)-2-(4-methylthiazol-2-yl)ethyl)cyclopentanecarboxamide | 4.12 LC 512.2 [M + H]+ | Procedures 33 and 4 |

TABLE 7-continued

| Ex. No. | Compound Structure | Compound Name | Retention Time Min./ Molecular Mass | Prepared in the manner described in: |
| --- | --- | --- | --- | --- |
| 684 | 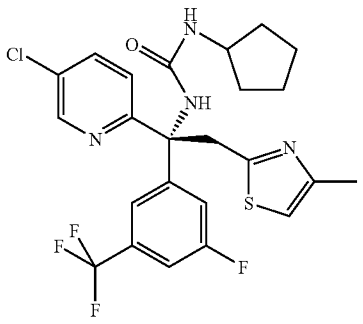 | (R)-1-(1-(5-chloropyridin-2-yl)-1-(3-fluoro-5-(trifluoromethyl) phenyl)-2-(4-methylthiazol-2-yl) ethyl)-3-cyclopentylurea | 3.92 LC 527.2 $[M + H]^+$ | Procedures 33 and 2 |
| 685 | 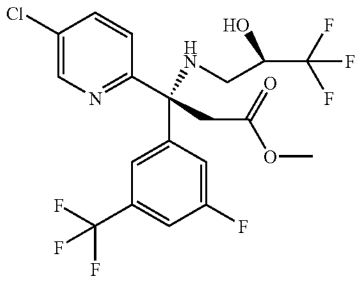 | (R)-methyl 3-(5-chloropyridin-2-yl)-3-(3-fluoro-5-(trifluoromethyl)phenyl)-3-((R)-3,3,3-trifluoro-2-hydroxypropylamino)propanoate | 1.99 LC 489.1 $[M + H]^+$ 85:15 ratio at hydroxyl center | Procedures 22 and 19 |
| 686 | 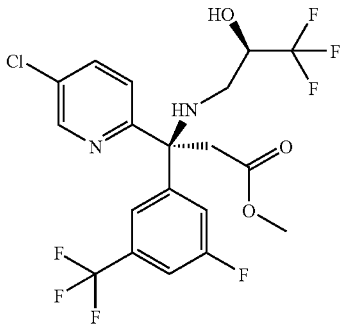 | (S)-methyl 3-(5-chloropyridin-2-yl)-3-(3-fluoro-5-(trifluoromethyl)phenyl)-3-((R)-3,3,3-trifluoro-2-hydroxypropylamino)propanoate | 1.96 LC 489.1 $[M + H]^+$ 85:15 ratio at hydroxyl center | Procedures 22 and 19 |
| 687 | 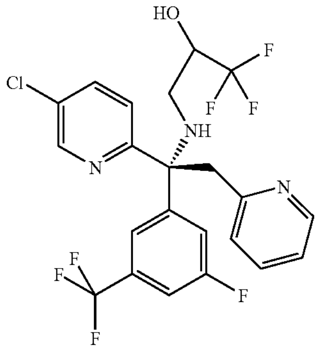 | 3-((R)-1-(5-chloropyridin-2-yl)-1-(3-fluoro-5-(trifluoromethyl) phenyl)-2-(pyridin-2-yl) ethylamino)-1,1,1-trifluoropropan-2-ol | 3.00 LC 508.2 $[M + H]^+$ single isomer at hydroxyl center | Procedures 31 and 19 |

TABLE 7-continued

| Ex. No. | Compound Structure | Compound Name | Retention Time Min./ Molecular Mass | Prepared in the manner described in: |
|---|---|---|---|---|
| 688 | 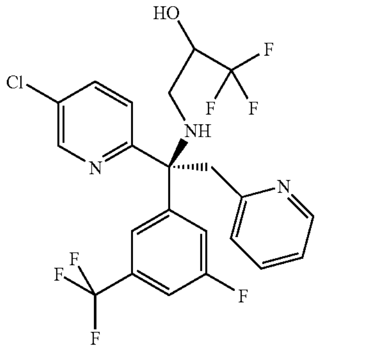 | 3-((S)-1-(5-chloropyridin-2-yl)-1-(3-fluoro-5-(trifluoromethyl) phenyl)-2-(pyridin-2-yl) ethylamino)-1,1,1-trifluoropropan-2-ol | 2.92 LC 508.2 $[M + H]^+$ single isomer at hydroxyl center | Procedures 31 and 19 |
| 689 | 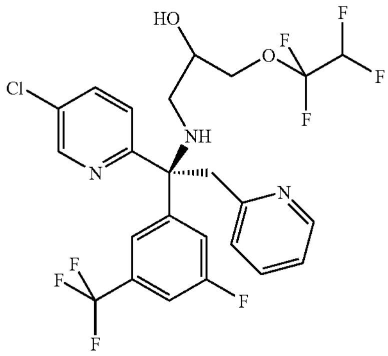 | 1-((S)-1-(5-chloropyridin-2-yl)-1-(3-fluoro-5-(trifluoromethyl) phenyl)-2-(pyridin-2-yl) ethylamino)-3-(1,1,2,2-tetrafluoroethoxy)propan-2-ol | 2.92 LC 570.2 $[M + H]^+$ 50:50 ratio at hydroxyl center | Procedures 31 and 19 |
| 690 | 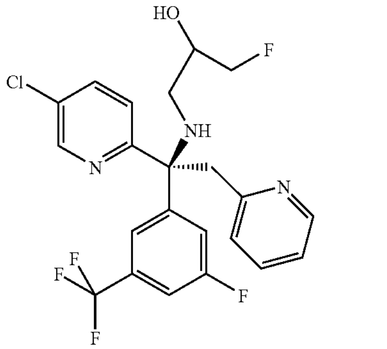 | 1-((S)-1-(5-chloropyridin-2-yl)-1-(3-fluoro-5-(trifluoromethyl) phenyl)-2-(pyridin-2-yl) ethylamino)-3-fluoropropan-2-ol | 2.48 LC 472.2 $[M + H]^+$ 50:50 ratio at hydroxyl center | Procedures 31 and 19 |
| 691 | 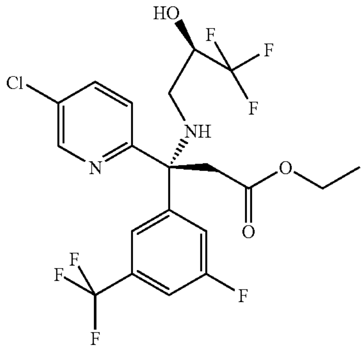 | (R)-ethyl 3-(5-chloropyridin-2-yl)-3-(3-fluoro-5-(trifluoromethyl)phenyl)-3-((R)-3,3,3-trifluoro-2-hydroxypropylamino)propanoate | 4.07 LC 503.3 $[M + H]^+$ 85:15 ratio at hydroxyl center | Procedures 34 and 19 |

TABLE 7-continued

| Ex. No. | Compound Structure | Compound Name | Retention Time Min./ Molecular Mass | Prepared in the manner described in: |
|---|---|---|---|---|
| 692 | 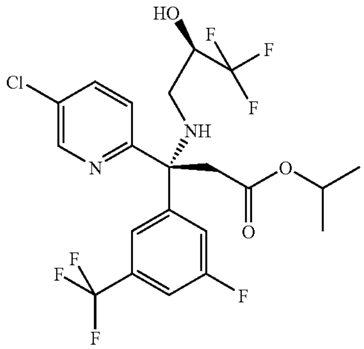 | (R)-isopropyl 3-(5-chloropyridin-2-yl)-3-(3-fluoro-5-(trifluoromethyl)phenyl)-3-((R)-3,3,3-trifluoro-2-hydroxypropylamino)propanoate | 4.16 LC 517.3 [M + H]+ 85:15 ratio at hydroxyl center | Procedures 34 and 19 |
| 693 | 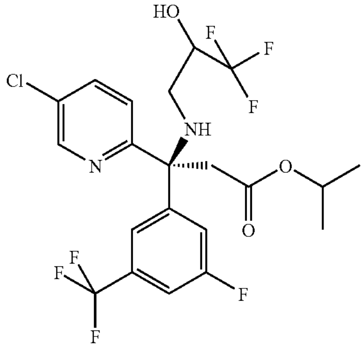 | (3S)-isopropyl 3-(5-chloropyridin-2-yl)-3-(3-fluoro-5-(trifluoromethyl)phenyl)-3-(3,3,3-trifluoro-2-hydroxypropylamino)propanoate | 4.15 LC 517.3 [M + H]+ 85:15 ratio at hydroxyl center | Procedures 34 and 19 |
| 694 | 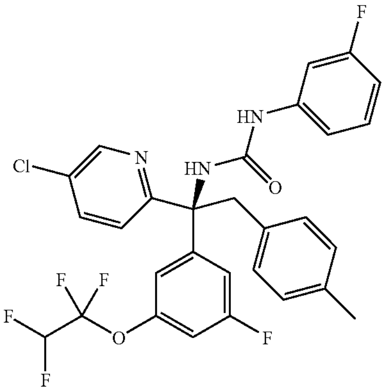 | (S)-1-(1-(5-chloropyridin-2-yl)-1-(3-fluoro-5-(1,1,2,2-tetrafluoroethoxy)phenyl)-2-p-tolylethyl)-3-(3-fluorophenyl) urea | 3.78 LC 594.10 [M + H]+ | Procedures 3, 5, 6, 7 and 2 |
| 695 | 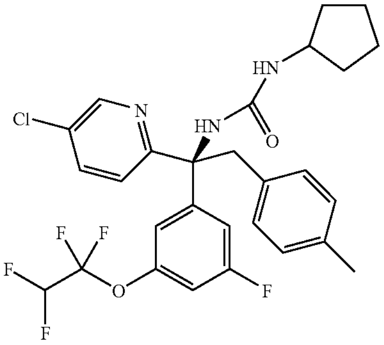 | (S)-1-(1-(5-chloropyridin-2-yl)-1-(3-fluoro-5-(1,1,2,2-tetrafluoroethoxy)phenyl)-2-p-tolylethyl)-3-cyclopentylurea | 3.76 LC 568.13 [M + H]+ | Procedures 3, 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 696 | 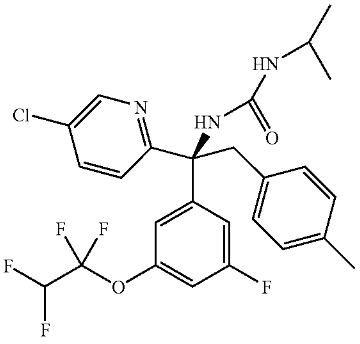 | (S)-1-(1-(5-chloropyridin-2-yl)-1-(3-fluoro-5-(1,1,2,2-tetrafluoroethoxy)phenyl)-2-p-tolylethyl)-3-isopropylurea | 3.57 LC 542.11 $[M + H]^+$ | Procedures 3, 5, 6, 7 and 2 |
| 697 | 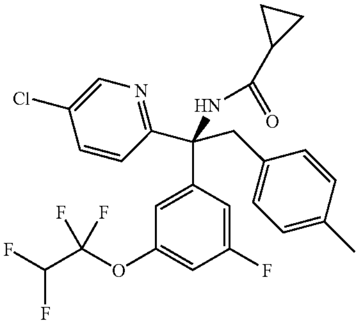 | (S)-N-(1-(5-chloropyridin-2-yl)-1-(3-fluoro-5-(1,1,2,2-tetrafluoroethoxy)phenyl)-2-p-tolylethyl) cyclopropanecarboxamide | 3.66 LC 525.12 $[M + H]^+$ | Procedures 3, 5, 6, 7 and 4 |
| 698 | 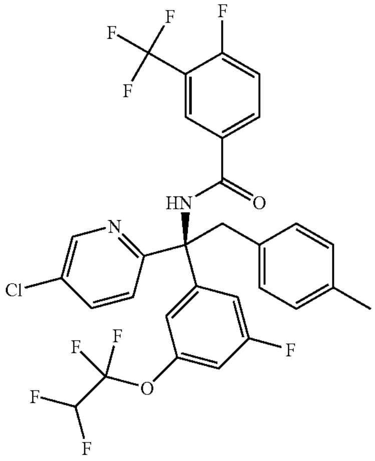 | (S)-N-(1-(5-chloropyridin-2-yl)-1-(3-fluoro-5-(1,1,2,2-tetrafluoroethoxy)phenyl)-2-p-tolylethyl)-4-fluoro-3-(trifluoromethyl)benzamide | 4.00 LC 647.07 $[M + H]^+$ | Procedures 3, 5, 6, 7 and 4 |

TABLE 7-continued

| Ex. No. | Compound Structure | Compound Name | Retention Time Min./ Molecular Mass | Prepared in the manner described in: |
| --- | --- | --- | --- | --- |
| 699 | 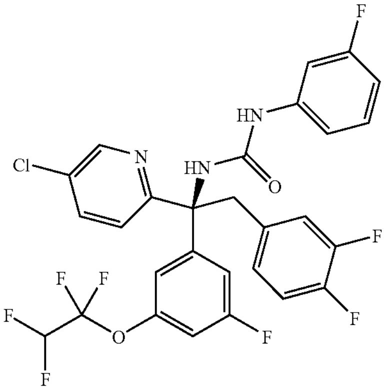 | (S)-1-(1-(5-chloropyridin-2-yl)-2-(3,4-difluorophenyl)-1-(3-fluoro-5-(1,1,2,2-tetrafluoroethoxy)phenyl)ethyl)-3-(3-fluorophenyl)urea | 3.67 LC 616.04 [M + H]+ | Procedures 3, 5, 6, 7 and 2 |
| 700 | 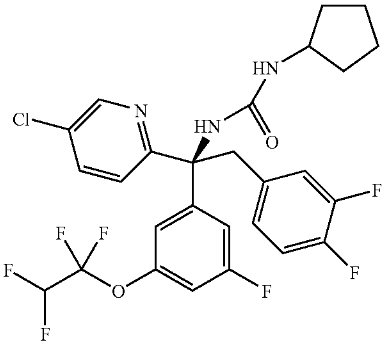 | (S)-1-(1-(5-chloropyridin-2-yl)-2-(3,4-difluorophenyl)-1-(3-fluoro-5-(1,1,2,2-tetrafluoroethoxy)phenyl)ethyl)-3-cyclopentylurea | 3.69 LC 590.07 [M + H]+ | Procedures 3, 5, 6, 7 and 2 |
| 701 | 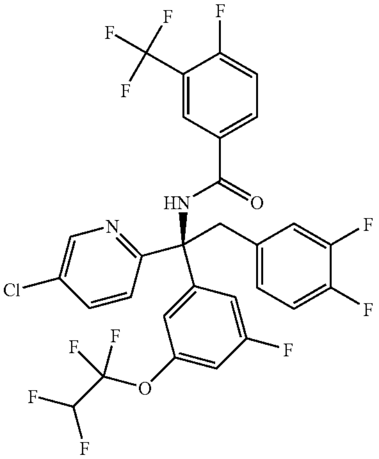 | (S)-N-(1-(5-chloropyridin-2-yl)-2-(3,4-difluorophenyl)-1-(3-fluoro-5-(1,1,2,2-tetrafluoroethoxy)phenyl)ethyl)-4-fluoro-3-(trifluoromethyl) benzamide | 3.95 LC 668.97 [M + H]+ | Procedures 3, 5, 6, 7 and 4 |

TABLE 7-continued

| Ex. No. | Compound Structure | Compound Name | Retention Time Min./ Molecular Mass | Prepared in the manner described in: |
|---|---|---|---|---|
| 702 | 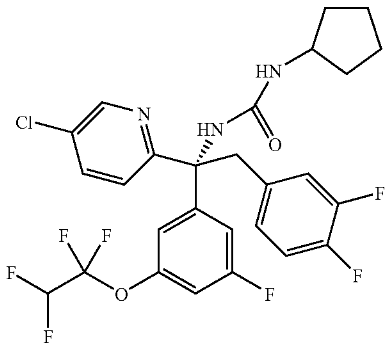 | (R)-1-(1-(5-chloropyridin-2-yl)-2-(3,4-difluorophenyl)-1-(3-fluoro-5-(1,1,2,2-tetrafluoroethoxy)phenyl)ethyl)-3-cyclopentylurea | 3.62 LC 590.07 $[M + H]^+$ | Procedures 3, 5, 6, 7 and 2 |
| 703 | 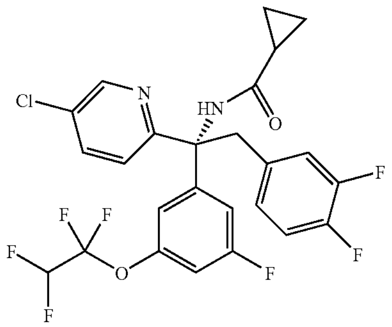 | (R)-N-(1-(5-chloropyridin-2-yl)-2-(3,4-difluorophenyl)-1-(3-fluoro-5-(1,1,2,2-tetrafluoroethoxy)phenyl)ethyl) cyclopropanecarboxamide | 3.61 LC 547.05 $[M + H]^+$ | Procedures 3, 5, 6, 7 and 4 |
| 704 | 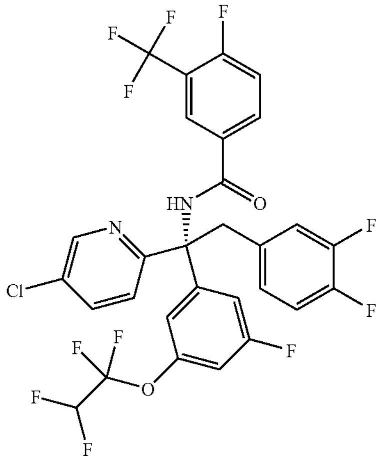 | (R)-N-(1-(5-chloropyridin-2-yl)-2-(3,4-difluorophenyl)-1-(3-fluoro-5-(1,1,2,2-tetrafluoroethoxy)phenyl)ethyl)-4-fluoro-3-(trifluoromethyl) benzamide | 3.95 LC 668.97 $[M + H]^+$ | Procedures 3, 5, 6, 7 and 4 |
| 705 | 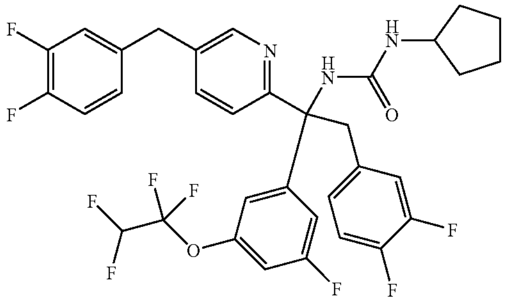 | 1-(1-(5-(3,4-difluorobenzyl) pyridin-2-yl)-2-(3,4-difluorophenyl)-1-(3-fluoro-5-(1,1,2,2-tetrafluoroethoxy) phenyl)ethyl)-3-cyclopentylurea | 3.79 LC 682.13 $[M + H]^+$ | Procedures 41 and 2 |

TABLE 7-continued

| Ex. No. | Compound Structure | Compound Name | Retention Time Min./ Molecular Mass | Prepared in the manner described in: |
|---|---|---|---|---|
| 706 | 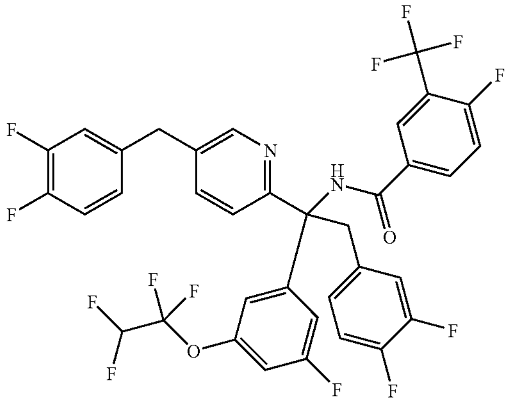 | N-(1-(5-(3,4-difluorobenzyl) pyridin-2-yl)-2-(3,4-difluorophenyl)-1-(3-fluoro-5-(1,1,2,2-tetrafluoroethoxy) phenyl)ethyl)-4-fluoro-3-(trifluoromethyl)benzamide | 4.07 LC 761.04 $[M + H]^+$ | Procedures 41 and 4 |
| 707 | 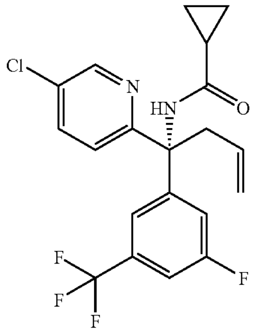 | (R)-N-(1-(5-chloropyridin-2-yl)-1-(3-fluoro-5-(trifluoromethyl) phenyl)but-3-enyl) cyclopropanecarboxamide | 3.88 LC 413.48 $[M + H]^+$ | Procedures 1 and 4 |
| 708 | 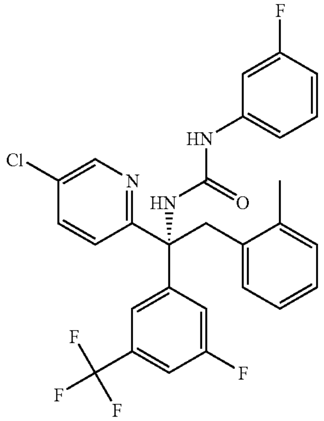 | (R)-1-(1-(5-chloropyridin-2-yl)-1-(3-fluoro-5-(trifluoromethyl) phenyl)-2-o-tolylethyl)-3-(3-fluorophenyl)urea | 4.17 LC 546.21 $[M + H]^+$ | Procedures 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 709 | 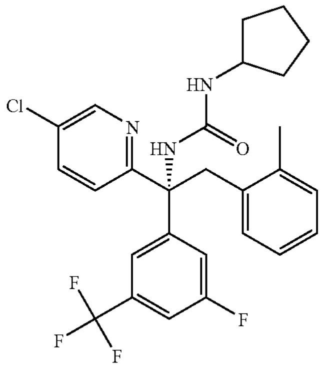 | (R)-1-(1-(5-chloropyridin-2-yl)-1-(3-fluoro-5-(trifluoromethyl) phenyl)-2-o-tolylethyl)-3-cyclopentylurea | 4.17 LC 520.26 [M + H]$^+$ | Procedures 5, 6, 7 and 2 |
| 710 | 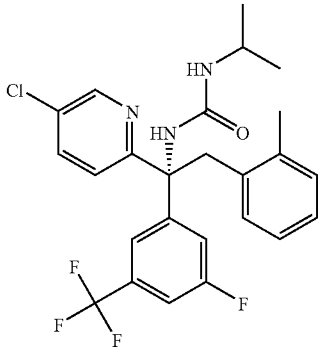 | (R)-1-(1-(5-chloropyridin-2-yl)-1-(3-fluoro-5-(trifluoromethyl) phenyl)-2-o-tolylethyl)-3-isopropylurea | 4.06 LC 494.25 [M + H]$^+$ | Procedures 5, 6, 7 and 2 |
| 711 | 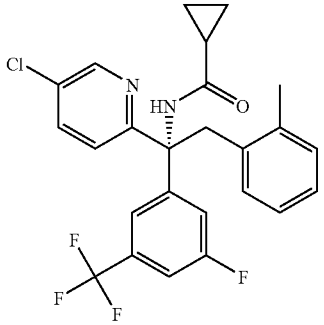 | (R)-N-(1-(5-chloropyridin-2-yl)-1-(3-fluoro-5-(trifluoromethyl) phenyl)-2-o-tolylethyl) cyclopropanecarboxamide | 4.06 LC 477.21 [M + H]$^+$ | Procedures 5, 6, 7 and 4 |
| 712 | 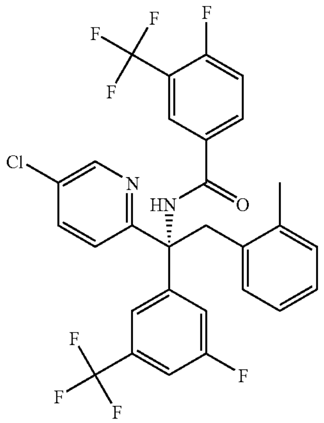 | (R)-N-(1-(5-chloropyridin-2-yl)-1-(3-fluoro-5-(trifluoromethyl) phenyl)-2-o-tolylethyl)-4-fluoro-3-(trifluoromethyl)benzamide | 4.36 LC 599.21 [M + H]$^+$ | Procedures 5, 6, 7 and 4 |

TABLE 7-continued

| Ex. No. | Compound Structure | Compound Name | Retention Time Min./ Molecular Mass | Prepared in the manner described in: |
|---|---|---|---|---|
| 713 | 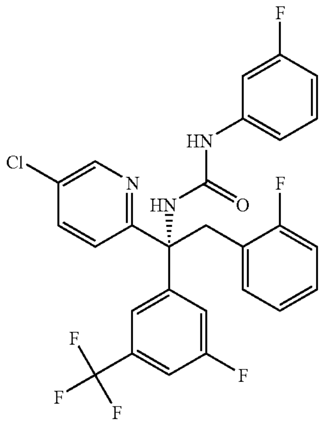 | (R)-1-(1-(5-chloropyridin-2-yl)-1-(3-fluoro-5-(trifluoromethyl) phenyl)-2-(2-fluorophenyl)ethyl)-3-(3-fluorophenyl)urea | 4.10 LC 550.19 [M + H]+ | Procedures 5, 6, 7 and 2 |
| 714 | 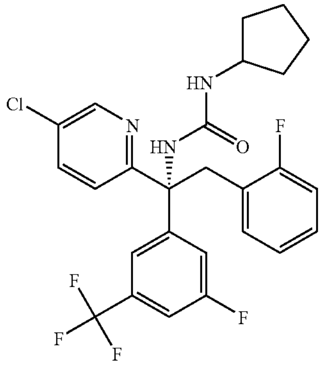 | (R)-1-(1-(5-chloropyridin-2-yl)-1-(3-fluoro-5-(trifluoromethyl) phenyl)-2-(2-fluorophenyl)ethyl)-3-cyclopentylurea | 4.10 LC 524.20 [M + H]+ | Procedures 5, 6, 7 and 2 |
| 715 | 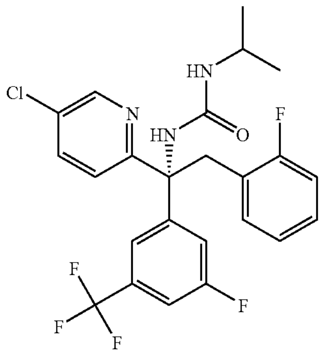 | (R)-1-(1-(5-chloropyridin-2-yl)-1-(3-fluoro-5-(trifluoromethyl) phenyl)-2-(2-fluorophenyl)ethyl)-3-isopropylurea | 3.98 LC 498.20 [M + H]+ | Procedures 5, 6, 7 and 2 |
| 716 | 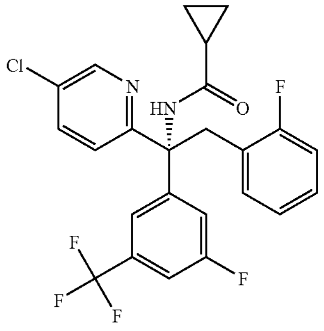 | (R)-N-(1-(5-chloropyridin-2-yl)-1-(3-fluoro-5-(trifluoromethyl) phenyl)-2-(2-fluorophenyl)ethyl) cyclopropanecarboxamide | 3.99 LC 481.17 [M + H]+ | Procedures 5, 6, 7 and 4 |

TABLE 7-continued

| Ex. No. | Compound Structure | Compound Name | Retention Time Min./ Molecular Mass | Prepared in the manner described in: |
|---|---|---|---|---|
| 717 | 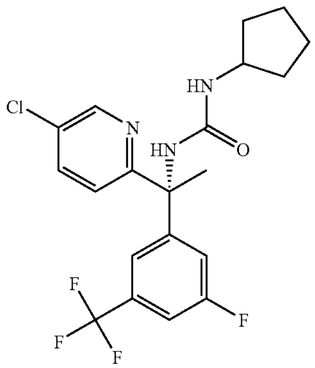 | (R)-1-(1-(5-chloropyridin-2-yl)-1-(3-fluoro-5-(trifluoromethyl) phenyl)ethyl)-3-cyclopentylurea | 3.84 LC 430.21 $[M + H]^+$ | Procedures 1 and 2 |
| 718 | 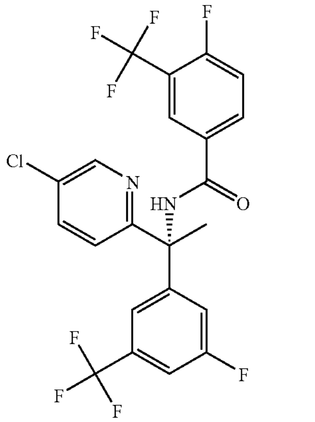 | (R)-N-(1-(5-chloropyridin-2-yl)-1-(3-fluoro-5-(trifluoromethyl) phenyl)ethyl)-4-fluoro-3-(trifluoromethyl)benzamide | 4.07 LC 509.12 $[M + H]^+$ | Procedures 1 and 4 |
| 719 | 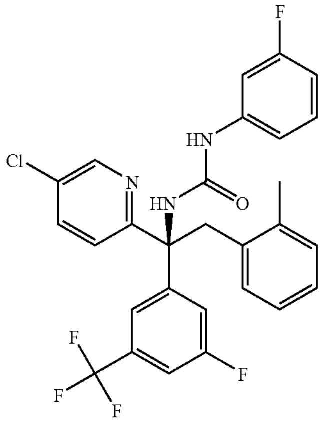 | (S)-1-(1-(5-chloropyridin-2-yl)-1-(3-fluoro-5-(trifluoromethyl) phenyl)-2-o-tolylethyl)-3-(3-fluorophenyl)urea | 4.17 LC 546.19 $[M + H]^+$ | Procedures 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 720 | 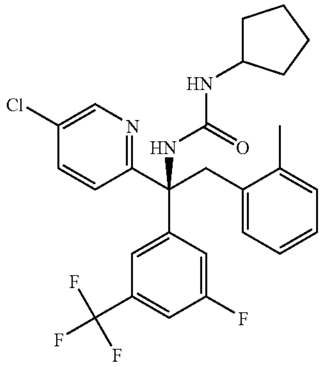 | (S)-1-(1-(5-chloropyridin-2-yl)-1-(3-fluoro-5-(trifluoromethyl) phenyl)-2-o-tolylethyl)-3-cyclopentylurea | 4.17 LC 520.26 $[M + H]^+$ | Procedures 5, 6, 7 and 2 |
| 721 | 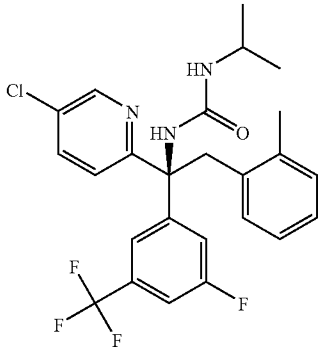 | (S)-1-(1-(5-chloropyridin-2-yl)-1-(3-fluoro-5-(trifluoromethyl) phenyl)-2-o-tolylethyl)-3-isopropylurea | 4.06 LC 494.21 $[M + H]^+$ | Procedures 5, 6, 7 and 2 |
| 722 | 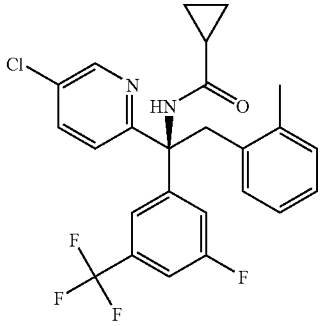 | (S)-N-(1-(5-chloropyridin-2-yl)-1-(3-fluoro-5-(trifluoromethyl) phenyl)-2-o-tolylethyl) cyclopropanecarboxamide | 4.06 LC 477.24 $[M + H]^+$ | Procedures 5, 6, 7 and 4 |
| 723 | 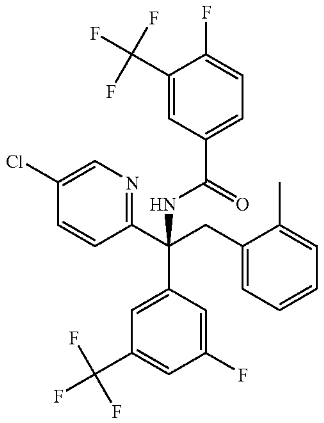 | (S)-N-(1-(5-chloropyridin-2-yl)-1-(3-fluoro-5-(trifluoromethyl) phenyl)-2-o-tolylethyl)-4-fluoro-3-(trifluoromethyl)benzamide | 4.35 LC 599.19 $[M + H]^+$ | Procedures 5, 6, 7 and 4 |

TABLE 7-continued

| Ex. No. | Compound Structure | Compound Name | Retention Time Min./ Molecular Mass | Prepared in the manner described in: |
|---|---|---|---|---|
| 724 | 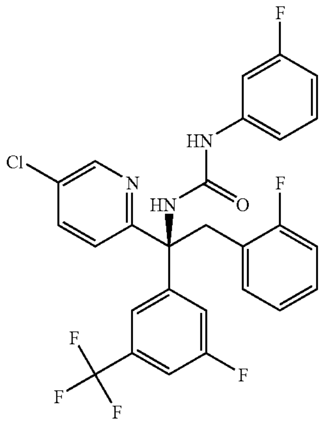 | (S)-1-(1-(5-chloropyridin-2-yl)-1-(3-fluoro-5-(trifluoromethyl) phenyl)-2-(2-fluorophenyl)ethyl)-3-(3-fluorophenyl)urea | 4.11 LC 550.16 $[M + H]^+$ | Procedures 5, 6, 7 and 2 |
| 725 | 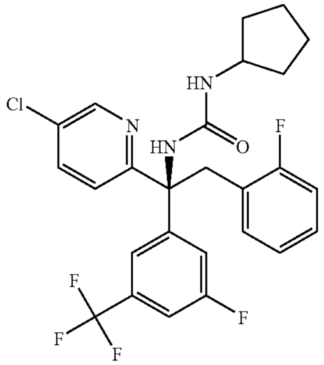 | (S)-1-(1-(5-chloropyridin-2-yl)-1-(3-fluoro-5-(trifluoromethyl) phenyl)-2-(2-fluorophenyl)ethyl)-3-cyclopentylurea | 4.10 LC 524.20 $[M + H]^+$ | Procedures 5, 6, 7 and 2 |
| 726 | 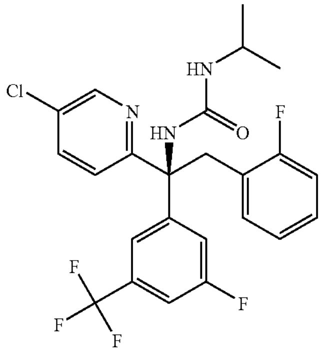 | (S)-1-(1-(5-chloropyridin-2-yl)-1-(3-fluoro-5-(trifluoromethyl) phenyl)-2-(2-fluorophenyl)ethyl)-3-isopropylurea | 3.98 LC 498.21 $[M + H]^+$ | Procedures 5, 6, 7 and 2 |
| 727 | 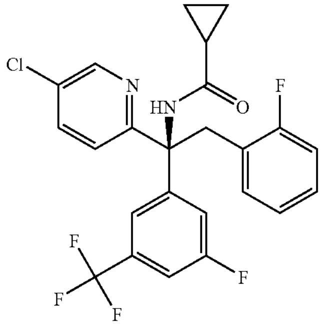 | (S)-N-(1-(5-chloropyridin-2-yl)-1-(3-fluoro-5-(trifluoromethyl) phenyl)-2-(2-fluorophenyl)ethyl) cyclopropanecarboxamide | 3.98 LC 481.17 $[M + H]^+$ | Procedures 5, 6, 7 and 4 |

TABLE 7-continued

| Ex. No. | Compound Structure | Compound Name | Retention Time Min./ Molecular Mass | Prepared in the manner described in: |
|---|---|---|---|---|
| 728 | 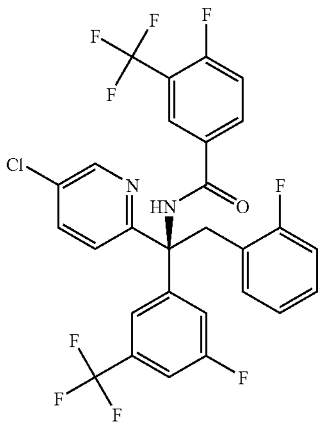 | (S)-N-(1-(5-chloropyridin-2-yl)-1-(3-fluoro-5-(trifluoromethyl) phenyl)-2-(2-fluorophenyl)ethyl)-4-fluoro-3-(trifluoromethyl) benzamide | 4.28 LC 603.16 $[M + H]^+$ | Procedures 5, 6, 7 and 4 |
| 729 | 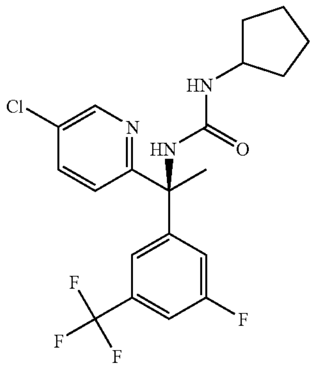 | (S)-1-(1-(5-chloropyridin-2-yl)-1-(3-fluoro-5-(trifluoromethyl) phenyl)ethyl)-3-cyclopentylurea | 3.82 LC 430.23 $[M + H]^+$ | Procedures 1 and 2 |
| 730 | 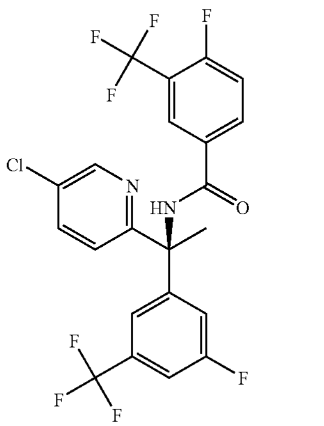 | (S)-N-(1-(5-chloropyridin-2-yl)-1-(3-fluoro-5-(trifluoromethyl) phenyl)ethyl)-4-fluoro-3-(trifluoromethyl)benzamide | 4.06 LC 509.14 $[M + H]^+$ | Procedures 1 and 4 |

TABLE 7-continued

| Ex. No. | Compound Structure | Compound Name | Retention Time Min./ Molecular Mass | Prepared in the manner described in: |
|---|---|---|---|---|
| 731 | 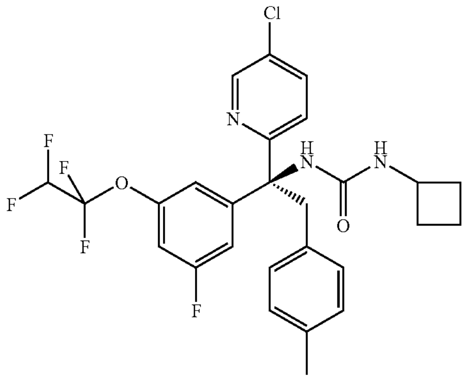 | (S)-1-(1-(5-chloropyridin-2-yl)-1-(3-fluoro-5-(1,1,2,2-tetrafluoroethoxy)phenyl)-2-p-tolylethyl)-3-cyclobutylurea | 4.251 LC 554.2 $[M + H]^+$ | Procedures 3, 5, 6, 7 and 2 |
| 732 | 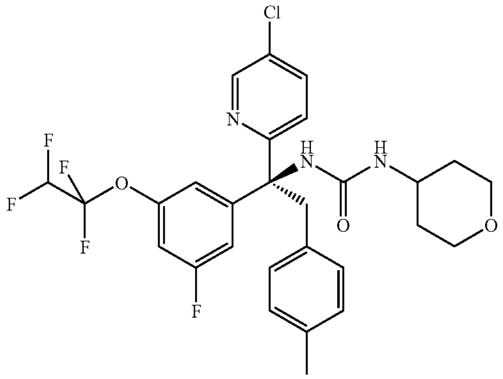 | (S)-1-(1-(5-chloropyridin-2-yl)-1-(3-fluoro-5-(1,1,2,2-tetrafluoroethoxy)phenyl)-2-p-tolylethyl)-3-(tetrahydro-2H-pyran-4-yl)urea | 4.171 LC 584.2 $[M + H]^+$ | Procedures 3, 5, 6, 7 and 2 |
| 733 | 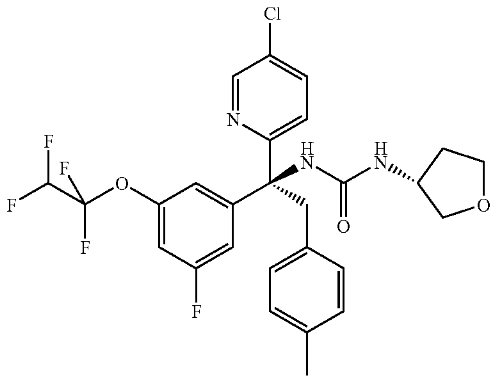 | 1-((S)-1-(5-chloropyridin-2-yl)-1-(3-fluoro-5-(1,1,2,2-tetrafluoroethoxy)phenyl)-2-p-tolylethyl)-3-((R)-tetrahydrofuran-3-yl)urea | 4.13 LC 570.2 $[M + H]^+$ | Procedures 3, 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 734 | 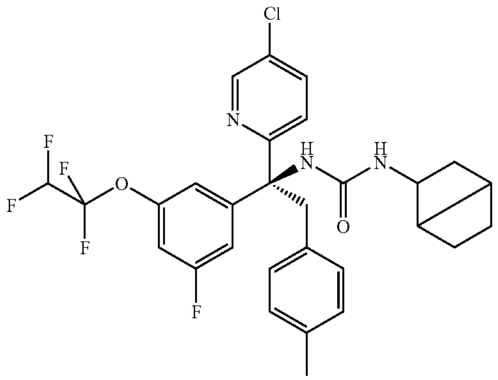 | 1-(bicyclo[2.2.1]heptan-2-yl)-3-((S)-1-(5-chloropyridin-2-yl)-1-(3-fluoro-5-(1,1,2,2-tetrafluoroethoxy)phenyl)-2-p-tolylethyl)urea | 4.395 LC 594.2 [M + H]$^+$ | Procedures 3, 5, 6, 7 and 2 |
| 735 | 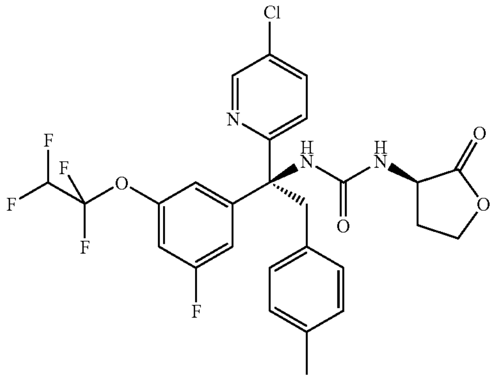 | 1-((S)-1-(5-chloropyridin-2-yl)-1-(3-fluoro-5-(1,1,2,2-tetrafluoroethoxy)phenyl)-2-p-tolylethyl)-3-((R)-2-oxo-tetrahydrofuran-3-yl)urea | 4.076 LC 584.15 [M + H]$^+$ | Procedures 3, 5, 6, 7 and 2 |
| 736 | 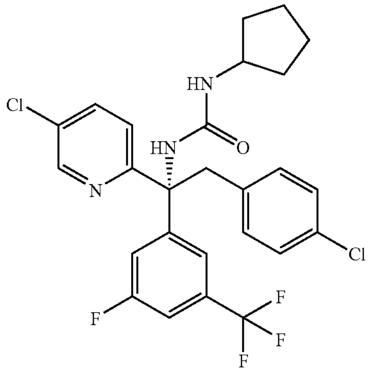 | (R)-1-(2-(4-chlorophenyl)-1-(5-chloropyridin-2-yl)-1-(3-fluoro-5-(trifluoromethyl)phenyl)ethyl)-3-cyclopentylurea | 4.21 LC 540.12 [M + H]$^+$ | Procedures 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 737 | 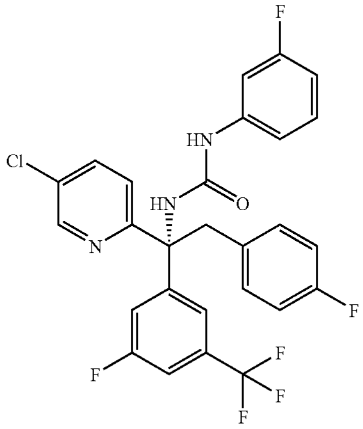 | (R)-1-(1-(5-chloropyridin-2-yl)-1-(3-fluoro-5-(trifluoromethyl) phenyl)-2-(4-fluorophenyl)ethyl)-3-(3-fluorophenyl)urea | 4.13 LC 550.09 $[M + H]^+$ | Procedures 5, 6, 7 and 2 |
| 738 | 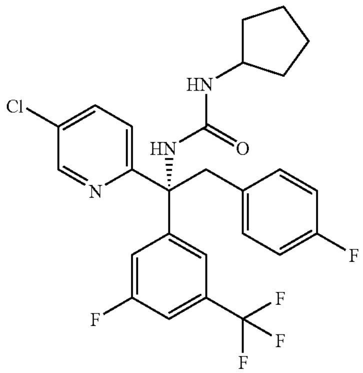 | (R)-1-(1-(5-chloropyridin-2-yl)-1-(3-fluoro-5-(trifluoromethyl) phenyl)-2-(4-fluorophenyl)ethyl)-3-cyclopentylurea | 4.10 LC 524.13 $[M + H]^+$ | Procedures 5, 6, 7 and 2 |
| 739 | 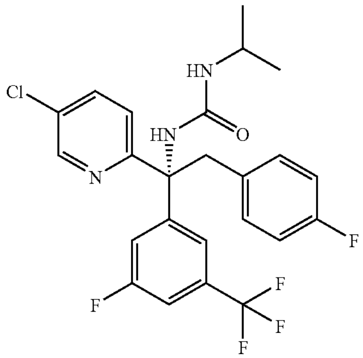 | (R)-1-(1-(5-chloropyridin-2-yl)-1-(3-fluoro-5-(trifluoromethyl) phenyl)-2-(4-fluorophenyl)ethyl)-3-isopropylurea | 3.97 LC 498.13 $[M + H]^+$ | Procedures 5, 6, 7 and 2 |
| 740 | 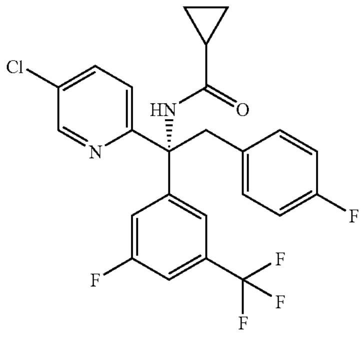 | (R)-N-(1-(5-chloropyridin-2-yl)-1-(3-fluoro-5-(trifluoromethyl) phenyl)-2-(4-fluorophenyl)ethyl) cyclopropanecarboxamide | 4.01 LC 481.12 $[M + H]^+$ | Procedures 5, 6, 7 and 4 |

TABLE 7-continued

| Ex. No. | Compound Structure | Compound Name | Retention Time Min./ Molecular Mass | Prepared in the manner described in: |
|---|---|---|---|---|
| 741 | 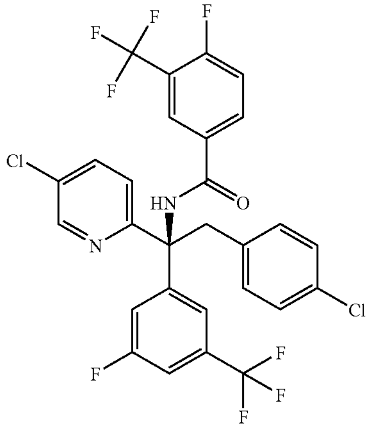 | (S)-N-(2-(4-chlorophenyl)-1-(5-chloropyridin-2-yl)-1-(3-fluoro-5-(trifluoromethyl)phenyl)ethyl)-4-fluoro-3-(trifluoromethyl) benzamide | 4.42 LC 619.04 $[M + H]^+$ | Procedures 5, 6, 7 and 4 |
| 742 | 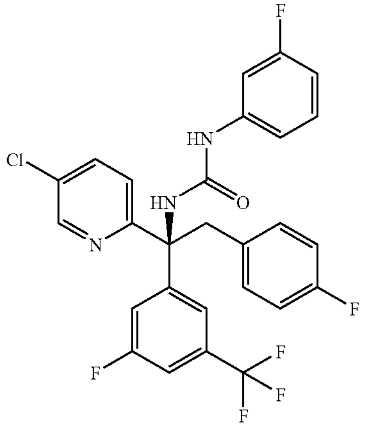 | (S)-1-(1-(5-chloropyridin-2-yl)-1-(3-fluoro-5-(trifluoromethyl) phenyl)-2-(4-fluorophenyl)ethyl)-3-(3-fluorophenyl)urea | 4.14 LC 550.09 $[M + H]^+$ | Procedures 5, 6, 7 and 2 |
| 743 | 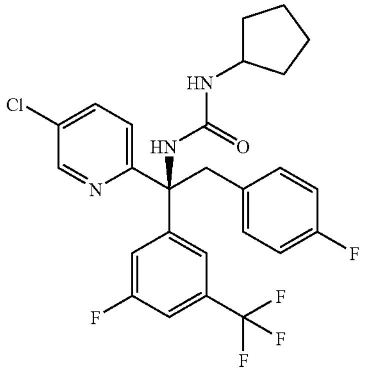 | (S)-1-(1-(5-chloropyridin-2-yl)-1-(3-fluoro-5-(trifluoromethyl) phenyl)-2-(4-fluorophenyl)ethyl)-3-cyclopentylurea | 4.12 LC 524.13 $[M + H]^+$ | Procedures 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 744 | 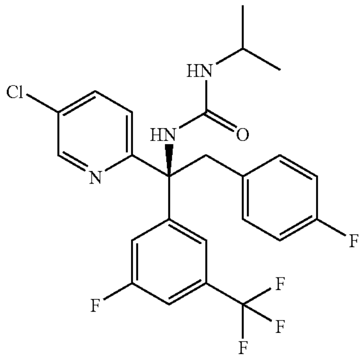 | (S)-1-(1-(5-chloropyridin-2-yl)-1-(3-fluoro-5-(trifluoromethyl) phenyl)-2-(4-fluorophenyl)ethyl)-3-isopropylurea | 4.00 LC 498.12 $[M + H]^+$ | Procedures 5, 6, 7 and 2 |
| 745 | 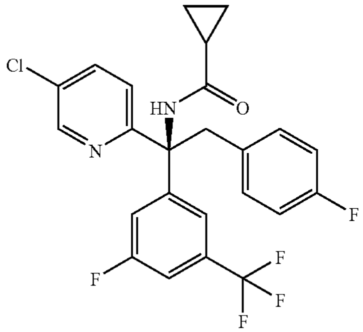 | (S)-N-(1-(5-chloropyridin-2-yl)-1-(3-fluoro-5-(trifluoromethyl) phenyl)-2-(4-fluorophenyl)ethyl) cyclopropanecarboxamide | 4.03 LC 481.12 $[M + H]^+$ | Procedures 5, 6, 7 and 4 |
| 746 | 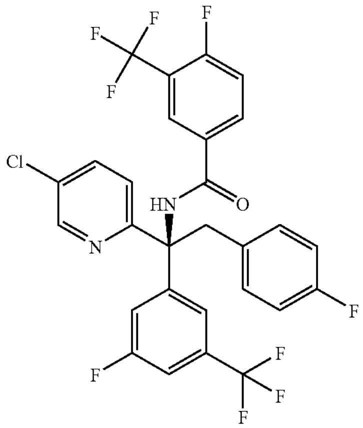 | (S)-N-(1-(5-chloropyridin-2-yl)-1-(3-fluoro-5-(trifluoromethyl) phenyl)-2-(4-fluorophenyl)ethyl)-4-fluoro-3-(trifluoromethyl) benzamide | 4.33 LC 603.05 $[M + H]^+$ | Procedures 5, 6, 7 and 4 |
| 747 | 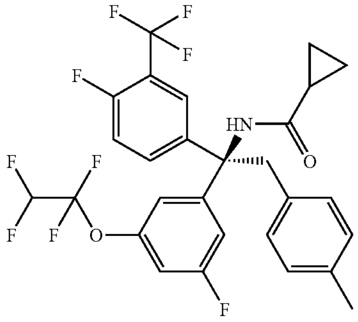 | (R)-N-(1-(4-fluoro-3-(trifluoromethyl)phenyl)-1-(3-fluoro-5-(1,1,2,2-tetrafluoroethoxy)phenyl)-2-p-tolylethyl) cyclopropanecarboxamide | 3.76 LC 576.47 $[M + H]^+$ | Procedures 3, 5, 6, 7 and 4 |

TABLE 7-continued

| Ex. No. | Compound Structure | Compound Name | Retention Time Min./ Molecular Mass | Prepared in the manner described in: |
| --- | --- | --- | --- | --- |
| 748 | 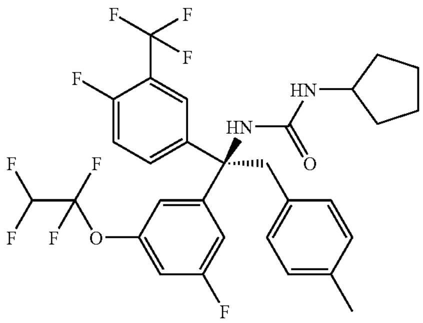 | (R)-1-cyclopentyl-3-(1-(4-fluoro-3-(trifluoromethyl)phenyl)-1-(3-fluoro-5-(1,1,2,2-tetrafluoroethoxy)phenyl)-2-p-tolylethyl)urea | 3.86 LC 619.44 [M + H]+ | Procedures 3, 5, 6, 7 and 2 |
| 749 | 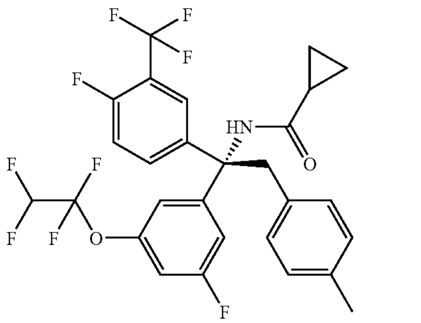 | (S)-N-(1-(4-fluoro-3-(trifluoromethyl)phenyl)-1-(3-fluoro-5-(1,1,2,2-tetrafluoroethoxy)phenyl)-2-p-tolylethyl) cyclopropanecarboxamide | 3.76 LC 576.47 [M + H]+ | Procedures 3, 5, 6, 7 and 4 |
| 780 | 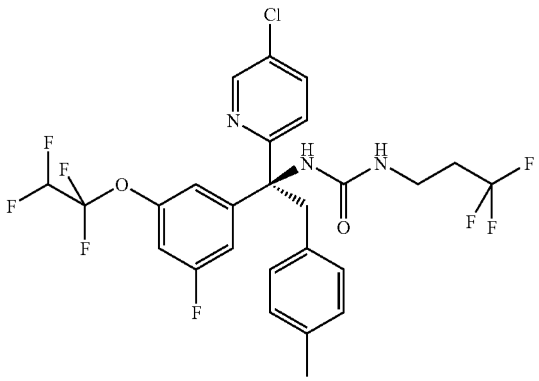 | (S)-1-(1-(5-chloropyridin-2-yl)-1-(3-fluoro-5-(1,1,2,2-tetrafluoroethoxy)phenyl)-2-p-tolylethyl)-3-(3,3,3-trifluoropropyl)urea | 4.228 LC 596.09 [M + H]+ | Procedures 3, 5, 6, 7 and 2 |
| 781 | 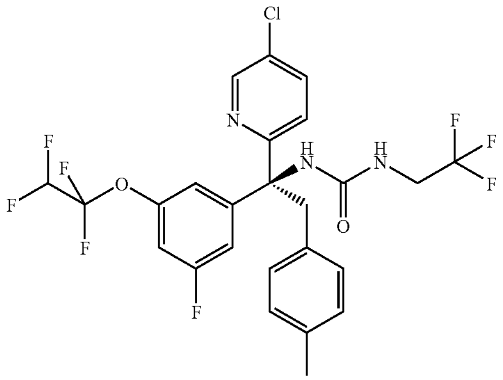 | (S)-1-(1-(5-chloropyridin-2-yl)-1-(3-fluoro-5-(1,1,2,2-tetrafluoroethoxy)phenyl)-2-p-tolylethyl)-3-(2,2,2-trifluoroethyl)urea | 4.186 LC 582.10 [M + H]+ | Procedures 3, 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 782 | 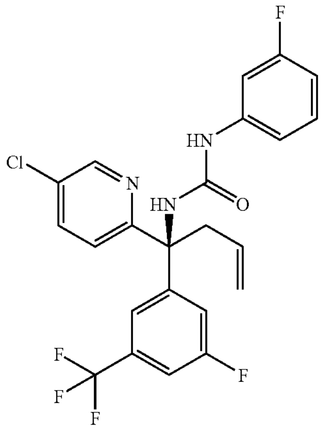 | (S)-1-(1-(5-chloropyridin-2-yl)-1-(3-fluoro-5-(trifluoromethyl) phenyl)but-3-enyl)-3-(3-fluorophenyl)urea | 4.03 LC 482.48 $[M + H]^+$ | Procedure 1 and 2 |
| 783 | 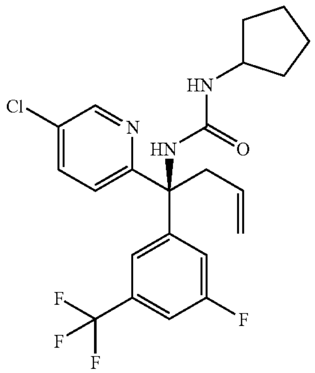 | (S)-1-(1-(5-chloropyridin-2-yl)-1-(3-fluoro-5-(trifluoromethyl) phenyl)but-3-enyl)-3-cyclopentylurea | 4.00 LC 456.55 $[M + H]^+$ | Procedure 1 and 2 |
| 784 | 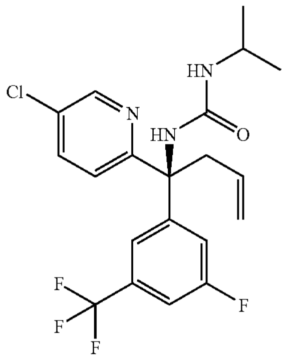 | (S)-1-(1-(5-chloropyridin-2-yl)-1-(3-fluoro-5-(trifluoromethyl) phenyl)but-3-enyl)-3-isopropylurea | 3.87 LC 430.55 $[M + H]^+$ | Procedure 1 and 2 |
| 785 | 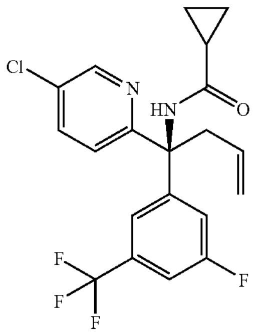 | (S)-N-(1-(5-chloropyridin-2-yl)-1-(3-fluoro-5-(trifluoromethyl) phenyl)but-3-enyl) cyclopropanecarboxamide | 3.89 LC 413.48 $[M + H]^+$ | Procedure 1 and 4 |

TABLE 7-continued

| Ex. No. | Compound Structure | Compound Name | Retention Time Min./ Molecular Mass | Prepared in the manner described in: |
|---|---|---|---|---|
| 786 | 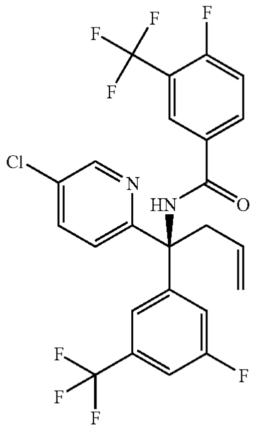 | (S)-N-(1-(5-chloropyridin-2-yl)-1-(3-fluoro-5-(trifluoromethyl) phenyl)but-3-enyl)-4-fluoro-3-(trifluoromethyl)benzamide | 4.25 LC 535.42 $[M + H]^+$ | Procedure 1 and 4 |
| 787 | 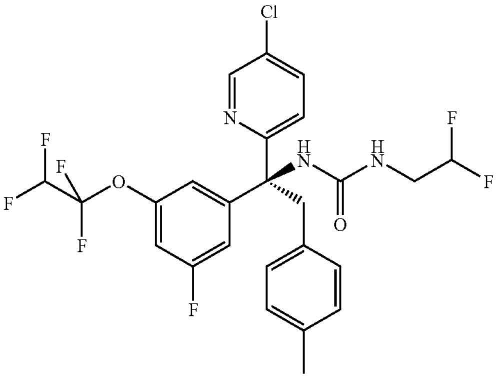 | (S)-1-(1-(5-chloropyridin-2-yl)-1-(3-fluoro-5-(1,1,2,2-tetrafluoroethoxy)phenyl)-2-p-tolylethyl)-3-(2,2-difluoroethyl) urea | 4.16 LC 564.10 $[M + H]^+$ | Procedures 3, 5, 6, 7 and 2 |
| 788 | 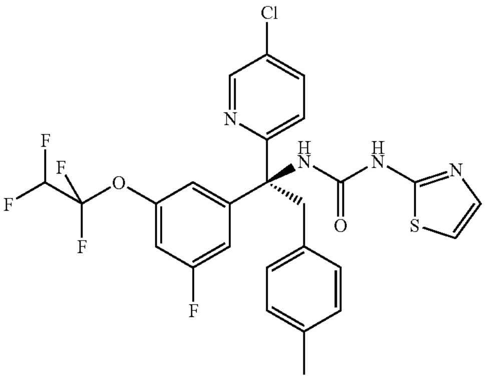 | (S)-1-(1-(5-chloropyridin-2-yl)-1-(3-fluoro-5-(1,1,2,2-tetrafluoroethoxy)phenyl)-2-p-tolylethyl)-3-(thiazol-2-yl)urea | 4.198 LC 583.07 $[M + H]^+$ | Procedures 3, 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 789 | 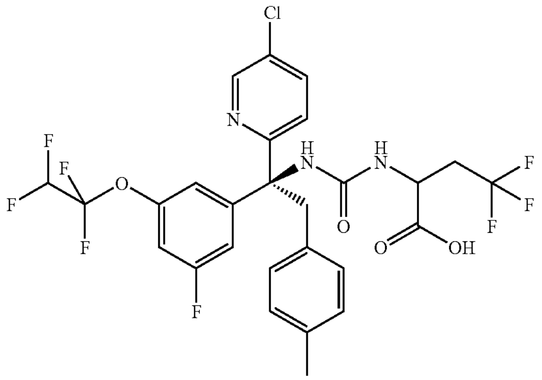 | 2-(3-((S)-1-(5-chloropyridin-2-yl)-1-(3-fluoro-5-(1,1,2,2-tetrafluoroethoxy)phenyl)-2-p-tolylethyl)ureido)-4,4,4-trifluorobutanoic acid | 4.135 LC 640.07 $[M + H]^+$ YMC ODSA 30 × 100 mm 40–100% MeOH/$H_2$0 0.1% TFA 40 mL/min RT 10.76 min | Procedures 3, 5, 6, 7 and 2 |
| 790 | 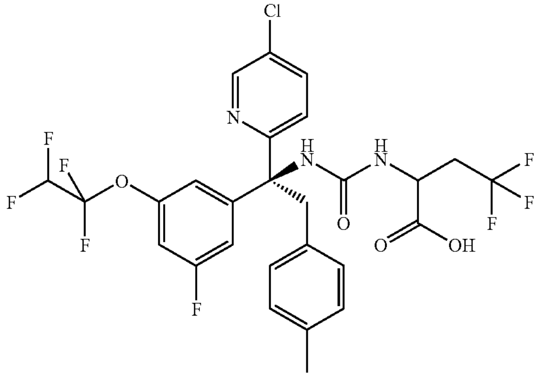 | 2-(3-((S)-1-(5-chloropyridin-2-yl)-1-(3-fluoro-5-(1,1,2,2-tetrafluoroethoxy)phenyl)-2-p-tolylethyl)ureido)-4,4,4-trifluorobutanoic acid | 4.148 LC 640.07 $[M + H]^+$ YMC ODSA 30 × 100 mm 40–100% MeOH/$H_2$0 0.1% TFA 40 mL/min RT 10.89 min | Procedures 3, 5, 6, 7 and 2 |
| 791 | 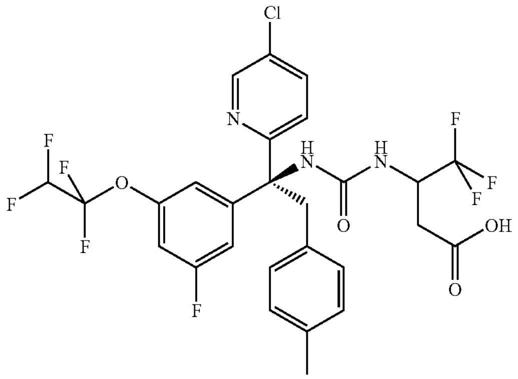 | 3-(3-((S)-1-(5-chloropyridin-2-yl)-1-(3-fluoro-5-(1,1,2,2-tetrafluoroethoxy)phenyl)-2-p-tolylethyl)ureido)-4,4,4-trifluorobutanoic acid | 4.088 LC 640.07 $[M + H]^+$ YMC ODSA 30 × 100 mm 40–100% MeOH/$H_2$0 0.1% TFA 40 mL/min RT 9.87 min | Procedures 3, 5, 6, 7 and 2 |

TABLE 7-continued

| Ex. No. | Compound Structure | Compound Name | Retention Time Min./ Molecular Mass | Prepared in the manner described in: |
|---|---|---|---|---|
| 792 | 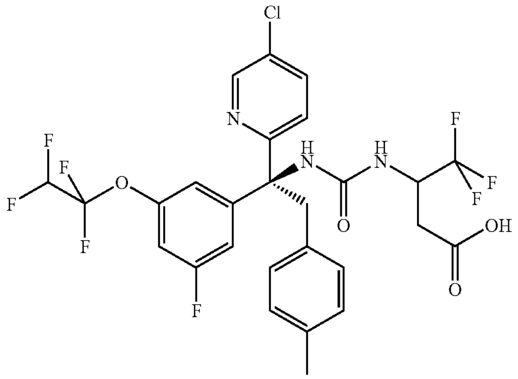 | 3-(3-((S)-1-(5-chloropyridin-2-yl)-1-(3-fluoro-5-(1,1,2,2-tetrafluoroethoxy)phenyl)-2-p-tolylethyl)ureido)-4,4,4-trifluorobutanoic acid | 4.135 LC 640.07 $[M + H]^+$ YMC ODSA 30 x 100 mm 40–100% MeOH/$H_2$0 0.1% TFA 40 mL/min RT 10.20 min | Procedures 3, 5, 6, 7 and 2 |

Additional compounds of the present invention were prepared by procedures analogous to those described above and to the additional procedures described below.

EXAMPLE 793

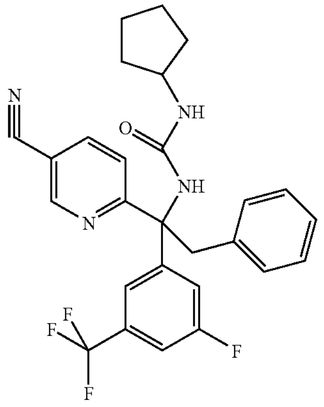

(R)-1-(1-(5-cyanopyridin-2-yl)-1-(3-fluoro-5-(trifluoromethyl)phenyl)-2-phenylethyl)-3-cyclopentylurea and (S)-1-(1-(5-cyanopyridin-2-yl)-1-(3-fluoro-5-(trifluoromethyl)phenyl)-2-phenylethyl)-3-cyclopentylurea Procedure 35

1-(1-(5-Bromopyridin-2-yl)-1-(3-fluoro-5-(trifluoromethyl)phenyl)-2-phenylethyl)-3-cyclopentylurea (100 mg, 0.18 mmol, prepared in a similar manner as described in Example 1), $K_4Fe(CN)_6$ (45 mg, 0.107 mmol), $Pd(OAc)_2$ (catalytic amount, spatula tip), and $Na_2CO_3$ (31 mg, 0.29 mmol) were stirred in DMAC (0.4 mL) at room temperature. Argon was purged several times. The reaction mixture was stirred and heated at 120° C. for 6 h. After cooling, EtOAc was added. The reaction mixture was filtered through Celite and the filtrate was washed with $H_2O$, 5% $NH_4OH$, dried ($MgSO_4$), filtered, and concentrated to dryness. The crude reaction mixture was purified by flash chromatography (silica gel, hexanes/EtOAc, came out 50% EtOAc). The reaction mixture was then further purified by reverse phase HPLC (20%-100% $CH_3CN$ in $H_2O$ with 0.1 TFA in a 18 min run, came out at 13.38 to 13.88 min) to give pure racemic mixture of (R)-1-(1-(5-cyanopyridin-2-yl)-1-(3-fluoro-5-(trifluoromethyl)phenyl)-2-phenylethyl)-3-cyclopentylurea and (S)-1-(1-(5-cyanopyridin-2-yl)-1-(3-fluoro-5-(trifluoromethyl)phenyl)-2-phenylethyl)-3-cyclopentylurea as white solids (16 mg, yield: 18%). LC-MS ESI (10-90% MeOH in $H_2O$ with 10 mM $NH_4Cl$ in a 4-min run), retention time=3.93 min, 494.9 (M−H);

$^1H$ NMR (400 MHz, $CDCl_3$) δ ppm 8.58 (d, J=1.5 Hz, 1 H), 7.92 (dd, J=8.4, 2.1 Hz, 1 H), 7.51 (s, br, 1H), 7.37 (d, J=9.3 Hz, 1 H), 7.20-7.30 (m, 3 H), 7.15 (t, J=7.1 Hz, 1 H), 7.08 (t, J=7.3 Hz, 2 H), 6.99 (s, br, 1 H), 6.57 (d, J=7.3 Hz, 2 H), 4.52 (d, J=12.7 Hz, 1 H), 4.50 (m, 1H), 3.91 (m, 1 H), 3.55 (d, J=12.5 Hz, 1 H), 2.02 (m, 1 H), 1.88 (m, 1 H), 1.69-1.57 (m, 4 H), 1.44 (m, 1 H) 1.30 (m, 1 H). The individual antipodes were separated by chiral prep HPLC using AD column (20% iPA/heptane/DEA, isocratic) to give (R)-1-(1-(5-cyanopyridin-2-yl)-1-(3-fluoro-5-(trifluoromethyl)phenyl)-2-phenylethyl)-3-cyclopentylurea as the fast eluting enantiomer: analytical chiral HPLC AD (25% iPA/heptane/DEA, isocratic), retention time=5.30 min, and (S)-1-(1-(5-cyanopyridin-2-yl)-1-(3-fluoro-5-(trifluoromethyl)phenyl)-2-phenylethyl)-3-cyclopentylurea as the slow eluting enantiomer: analytical chiral HPLC AD (25% iPA/heptane/DEA, isocratic), retention time=9.72 min.

EXAMPLE 794

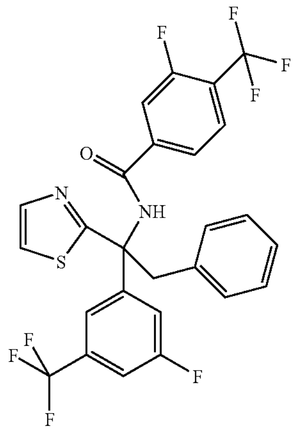

3-fluoro-N-(1-(3-fluoro-5-(trifluoromethyl)phenyl)-2-phenyl-1-(thiazol-2-yl)ethyl)-4-(trifluoromethyl)benzamide Procedure 36

1-(3-fluoro-5-(trifluoromethyl)phenyl)-2-phenyl-1-(thiazol-2-yl)ethanamine

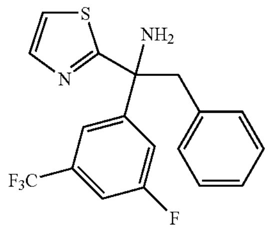

To an oven-dried round bottomed flask cooled at −78° C. under $N_2$, was added anhydrous $Et_2O$ (15 mL) and nBuLi (1.6 M in hexanes, 2.5 mL, 4.0 mmol, 1 eq.) sequentially. An $Et_2O$ solution (3 mL) of 2-bromothiazole (0.66 g, 4.0 mmol) was added to the above solution at −78° C. dropwise. The resulting solution was stirred at −78° C. to −70° C. for 20 min. To the lightly pale yellow solution, was added 3-fluoro-5-trifluoromethyl-benzonitrile in THF (2 mL) dropwise at −78° C. The resulting mixture was stirred at −78 to −70° C. for 2.5 h. Pretreated TMSCl (10:1 v/v TMSCl:$Et_3N$, then centrifuge at r.t. for 15 min, 0.51 mL of the clear solution, 1.01 eq) was added to the stirred mixture dropwise at −78° C. The resulting mixture was stirred at −78 to −60° C. for 15 min, then room temperature for 30 min, during which period the solution changed from dark brown to light tan. The reaction mixture was cooled back to −78° C., benzyl magnesium chloride (2.0 M in THF, 2.0 mL) was added dropwise. The resulting mixture was stirred at −78° C. for 15 min, then gradually warmed up to room temperature for 1.5 h. The reaction mixture was quenched by adding sat'd $NH_4Cl$ and 1 N HCl, and stirred for 20 min. The resulting crude reaction mixture was extracted with EtOAc, washed with 1N NaOH, sat'd $NaHCO_3$, $H_2O$, brine, dried over $MgSO_4$, filtered, and concentrated to dryness in vacuo. The residue was purified by flash chromatography (silica gel, hexanes/EtOAc, came out 20% EtOAc) to give racemic 1-(3-fluoro-5-(trifluoromethyl)phenyl)-2-phenyl-1-(thiazol-2-yl)ethanamine as light brownish viscous oil (0.35 g, yield: 24%). LC-MS ESI (10-90% MeOH in $H_2O$ with 0.1% TFA in a 4-min run), retention time=2.97 min 367.04 (M+H), 350.02 (M−$NH_3$). $^1H$ NMR (400 MHz, CHLOROFORM-D) δ ppm 7.78 (d, J=3.18 Hz, 1 H), 7.66 (s, 1 H), 7.52-7.61 (m, 1 H), 7.08-7.19 (m, 5 H), 6.82 (dd, J=7.6, 2.0 Hz, 2 H), 3.86 (d, J=13.2 Hz, 1 H), 3.35 (d, J=13.2 Hz, 1 H).

Following the same procedure as that for procedure 4 in Example 2, 3-fluoro-N-(1-(3-fluoro-5-(trifluoromethyl)phenyl)-2-phenyl-1-(thiazol-2-yl)ethyl)-4-(trifluoromethyl)benzamide was obtained as white solids (57.3 mg, yield 71.1%) from the above 1-(3-fluoro-5-(trifluoromethyl)phenyl)-2-phenyl-1-(thiazol-2-yl)ethanamine (53 mg) and 3-fluoro-4-trifluoromethylbenzoyl chloride (0.02 mL) in $CH_2Cl_2$ (1 mL) and pyridine (0.04 mL). LC-MS ESI (10-90% MeOH in $H_2O$ with 0.1% TFA in a 4-min run), retention time=2.97 min, 557.17 (M+H), 579.17 (M+Na). $^1H$ NMR (400 MHz, $CDCl_3$) δ ppm 8.57 (s, 1 H), 7.65-7.73 (m, 2 H), 7.54-7.63 (m, 3 H), 7.47-7.51 (m, 2 H), 7.28-7.38 (m, 1 H), 7.19-7.25 (m, 1 H), 7.13 (t, J=7.5 Hz, 2 H), 6.72 (d, J=7.1 Hz, 2 H), 4.58 (d, J=13.0 Hz, 1 H), 3.84 (d, J=13.0 Hz, 1 H).

EXAMPLE 795

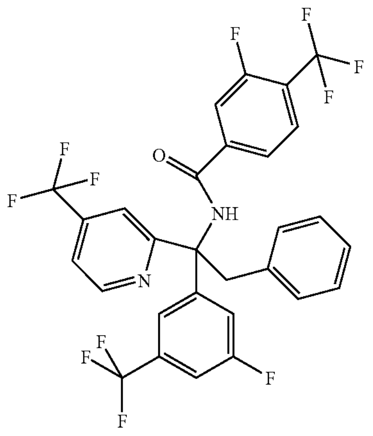

3-fluoro-N-(1-(3-fluoro-5-(trifluoromethyl)phenyl)-2-phenyl-1-(4-(trifluoromethyl)pyridin-2-yl)ethyl)-4-(trifluoromethyl)benzamide Procedure 37

1-(3-fluoro-5-(trifluoromethyl)phenyl)-2-phenyl-1-(4-(trifluoromethyl)pyridin-2-yl)ethanamine

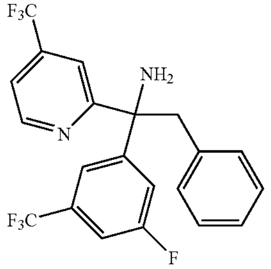

To an oven-dried round bottomed flask was added nBuLi (2.5 M in hexanes, 0.95 ml, 2.38 mmol, 1.17 eq) at −60° C. under $N_2$. An $Et_2O$ solution (5 mL) of 2-bromo-4-trifluoromethylpyridine (448 mg, 2.0 mmol) was added dropwise at −60 to −55° C. The resulting solution was stirred at the above temperate for 30 min. The mixture was cooled to −78° C., an $Et_2O$ solution (2 mL) of 3-fluoro-5-trifluoromethyl-benzonitrile (390 g, 2.06 mmol) was added dropwise. The resulting solution was stirred −78 to −70° C. for 1.5 h. Pretreated TMSCl (0.26 ml) was added dropwise at −78° C. The mixture was stirred at −78° C. for 15 min, and then warmed up to r.t. for 45 min. It was cooled back to −78° C., and benzyl magnesium chloride (1.0 ml, 2.0 mmol) was added dropwise. The resulting mixture was stirred at −78° C. for 1 h, and then at r.t. for 0.5 h. It was quenched by adding sat'd $NH_4Cl$ and 1N HCl, and stirred for 10 min. It was extracted with EtOAc, washed with 1N NaOH, sat'd $NaHCO_3$, $H_2O$, brine, dried ($MgSO_4$), filtered, and concentrated to dryness. The residue was purified by flash chromatography (silica gel, hexanes/EtOAc) to give 1-(3-fluoro-5-(trifluoromethyl)phenyl)-2-phenyl-1-(4-(trifluoromethyl)pyridin-2-yl)ethanamine as light brownish gum (0.57 g, yield: 66.6%). LC-MS ESI (10-90% MeOH in $H_2O$ with 0.1% TFA in a 4-min run), retention time=3.32 min, 429.13 (M+H).

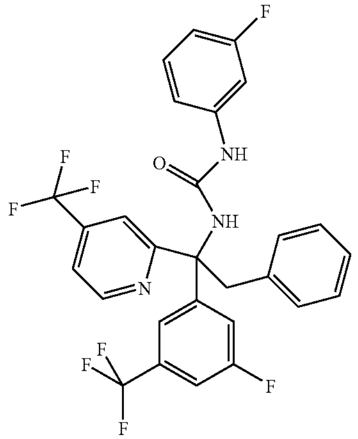

Using similar procedure as Example 1, Procedure 2, 1-(1-(3-fluoro-5-(trifluoromethyl)phenyl)-2-phenyl-1-(4-(trifluoromethyl)pyridin-2-yl)ethyl)-3-(3-fluorophenyl)urea was obtained as a white solid. LC-MS ESI (10-90% MeOH in $H_2O$ with 0.1% TFA in a 4-min run), retention time=4.30 min, 566.18 (M+H); $^1H$ NMR (400 MHz, CHLOROFORM-D) δ ppm 8.50 (d, J=5.1 Hz, 1 H), 7.69 (s, 1 H), 7.57 (s, 1 H), 7.44-7.49 (m, 2 H), 7.37 (s, 1 H), 7.21-7.30 (m, 2 H), 7.07-7.18 (m, 4 H), 6.93 (dd, J=8.2, 1.3 Hz, 1 H), 6.77 (td, J=8.1, 2.1 Hz, 1 H), 6.59 (d, J=7.1 Hz, 2 H), 6.52 (s, 1 H), 4.60 (d, J=12.7 Hz, 1 H), 3.66 (d, J=12.7 Hz, 1 H).

EXAMPLE 796

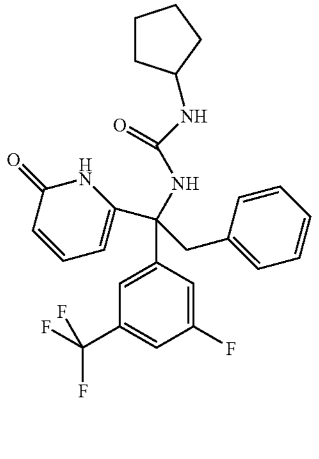

1-cyclopentyl-3-(1-(3-fluoro-5-(trifluoromethyl)phenyl)-1-(6-oxo-1,6-dihydropyridin-2-yl)-2-phenylethyl)urea

Procedure 38

1-(3-fluoro-5-(trifluoromethyl)phenyl)-1-(6-methoxypyridin-2-yl)-2-phenylethanamine

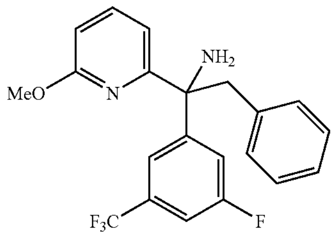

To an oven-dried round bottomed flask was added nBuLi (2.5 M in hexanes, 3.6 mL, 9.0 mmol, 1.1 eq) at −45 to −40° C. under $N_2$. An $Et_2O$ solution (12 mL) of 2-bromo-6-methoxypyridine (1 mL, 8.14 mmol) was added dropwise at the above temperature. The resulting light brownish yellow solution was stirred at −40 to −35° C. for 20 min. The mixture was cooled to −78° C., an $Et_2O$ solution (3 ml) of 3-fluoro-5-trifluoromethyl-benzonitrile (1.50 g, 7.94 mmol) was added dropwise at −78 to −70° C. The resulting solution was stirred at this temperature for 1 h. Pretreated TMSCl (1.08 mL, 8.55 mmol, 1.05 eq) was added dropwise at −78° C. The mixture was allowed to warm to room temperature for 30 min, and then stirred at room temperature for 30 min. The reaction mixture was cooled back to −78° C., and benzyl magnesium chloride (4.1 ml, 8.2 mmol) was added dropwise. The resulting mixture was stirred at −78° C. for 0.8 h, and then warmed up to room temperature for 1 h. The reaction mixture was quenched by adding sat'd $NH_4Cl$ and 1N HCl, and stirred for 10 min. The resulting solution was extracted with EtOAc, washed with 1N NaOH, saturated $NaHCO_3$, $H_2O$, brine, dried over $MgSO_4$, filtered, and concentrated to dryness. The residue was purified by flash chromatography (silica gel, hexanes/EtOAc) to give 1-(3-fluoro-5-(trifluoromethyl)phenyl)-1-(6-methoxypyridin-2-yl)-2-phenylethanamine as light brownish gum (1.42 g, yield: 44.7%). LC-MS ESI (10-90% MeOH in $H_2O$ with 0.1% TFA in a 4-min run), retention time=3.20 min, 391.12 (M+H); $^1H$ NMR (400 MHz, $CDCl_3$) δ ppm 7.73 (s, 1 H), 7.47-7.57 (m, 2 H), 7.11-7.21 (m, 4 H), 6.99 (d, J=7.6 Hz, 1 H), 6.80 (dd, J=7.6, 2.0 Hz, 2 H), 6.61 (d, J=8.1 Hz, 1 H), 3.93 (s, 3H), 3.92 (d, J=13 Hz, 1 H) 3.40 (d, J=13 Hz, 1 H).

1-cyclopentyl-3-(1-(3-fluoro-5-(trifluoromethyl) phenyl)-1-(6-methoxypyridin-2-yl)-2-phenylethyl) urea

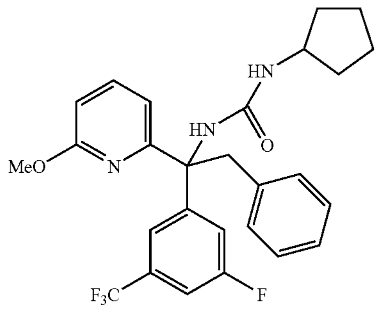

Using similar procedure as Procedure 2 of Example 1, 1-cyclopentyl-3-(1-(3-fluoro-5-(trifluoromethyl)phenyl)-1-(6-methoxypyridin-2-yl)-2-phenylethyl)urea (40.5 mg, yield: 85.1%) was obtained as a white solids from 1-(3-fluoro-5-(trifluoromethyl)phenyl)-1-(6-methoxypyridin-2-yl)-2-phenylethanamine (37 mg, 0.095 mmol) and cyclopentyl isocyanate (0.03 mL). LC-MS ESI (10-90% MeOH in $H_2O$ with 0.1% TFA in a 4-min run), retention time=4.28 min, 502.24 (M+H); $^1H$ NMR (400 MHz, $CDCl_3$) δ ppm 7.59 (s, 1 H), 7.54 (t, J=7.95 Hz, 1 H), 7.42 (d, J=9.8 Hz, 1 H), 7.20 (d, J=8.1 Hz, 1 H), 7.04-7.15 (m, 3 H), 7.00 (s, 1 H), 6.57-6.65 (m, 4 H), 4.41 (d, J=12.2 Hz, 1 H), 4.31 (d, J=6.9 Hz, 1 H), 3.75-3.84 (m, 1 H), 3.58 (s, 3H), 3.49 (d, J=12.5 Hz, 1 H), 1.93-2.04 (m, 1 H), 1.82-1.74 (m, 1 H), 1.61-1.69 (m, 2 H), 1.49-1.60 (m, 2 H), 1.38-1.48 (m, 1 H), 1.23-1.34 (m, 1 H).

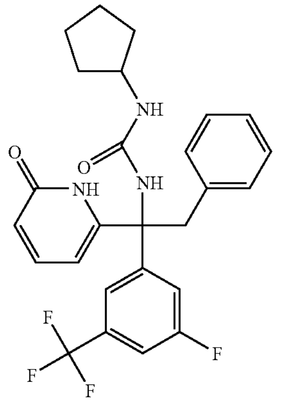

1-Cyclopentyl-3-(1-(3-fluoro-5-(trifluoromethyl)phenyl)-1-(6-methoxypyridin-2-yl)-2-phenylethyl)urea (25 mg, 0.049 mmol) was stirred in $CHCl_3$ (1 mL) in a pyrex tube at room temperature. TMSI (0.04 mL) was added and the reaction mixture was refluxed for 3 h. Additional TMSI (0.04 mL) was added. The mixture was refluxed for an additional two hours. The mixture was cooled to room temperature and MeOH (1 mL) was added. The reaction mixture was concentrated. The residue was purified by flash chromatography (silica gel, hexanes/EtOAc, came out 100% EtOAc) to give 1-cyclopentyl-3-(1-(3-fluoro-5-(trifluoromethyl)phenyl)-1-(6-oxo-1,6-dihydropyridin-2-yl)-2-phenylethyl)urea (13 mg, yield: 54%) as a white solid. LC-MS ESI (10-90% MeOH in $H_2O$ with 0.1% TFA in a 4-min run), retention time=3.75 min, 488.12 (M+H); $^1H$ NMR (400 MHz, $CDCl_3$) δ ppm 12.06 (s, br, 1H), 7.52 (dd, J=8.8, 7.3 Hz, 1 H), 7.19 (t, J=7.0 Hz, 2 H), 7.12 (t, J=7.3 Hz, 2 H), 6.94 (s, br, 1 H), 6.83 (d, J=10 Hz, 1 H), 6.68 (d, J=7.3 Hz, 2 H), 6.61 (d, J=7.1 Hz, 1 H), 6.30 (d, J=8.8 Hz, 1 H), 6.15 (s, br, 1 H), 5.22 (s, br, 1 H), 4.32 (d, J=12.2 Hz, 1 H), 3.88-3.98 (m, 1 H), 3.19 (d, J=12.7 Hz, 1 H), 1.92-1.86 (m, 1 H), 1.83-1.74 (m, 1 H) 1.65-1.48 (m, 4 H), 1.43-1.35 (m, 1 H) 1.25-1.18 (m, 1 H).

EXAMPLE 797

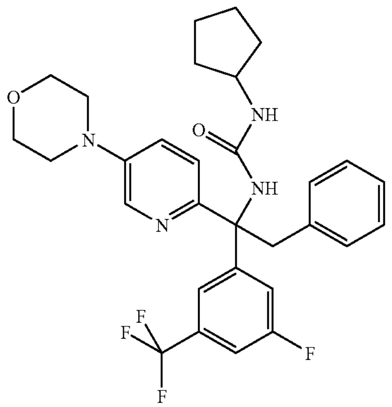

1-cyclopentyl-3-(1-(3-fluoro-5-(trifluoromethyl) phenyl)-1-(5-morpholinopyridin-2-yl)-2-phenyl-ethyl)urea

Procedure 39

1-(1-(5-Bromopyridin-2-yl)-1-(3-fluoro-5-(trifluoromethyl)phenyl)-2-phenylethyl)-3-cyclopentylurea (64 mg, 0.12 mmol), morpholine (1.3 eq), $Pd_2(dba)_3$ (0.2 eq), Xantphos (0.6 eq) and Na—O-t-Bu (3.2 eq) were stirred in toluene (0.5 mL) at room temperature. The reaction mixture was purged with $N_2$ several times and then was heated at 100° C. for 3.5 h. The reaction mixture was cooled to room temperature, and $Et_2O$ was added. The resulting solution was washed with $H_2O$, brine, dried ($MgSO_4$), filtered, and concentrated to dryness. The residue was purified by chromatography (silica gel, hexanes/EtOAc) to give 1-cyclopentyl-3-(1-(3-fluoro-5-(trifluoromethyl)phenyl)-1-(5-morpholinopyridin-2-yl)-2-phenylethyl)urea (39 mg, yield: 60.9%). LC-MS ESI 557.28 (M+H) (10-90% MeOH in $H_2O$ with 0.1% TFA in a 4-min run, retention time=3.63 min); $^1H$ NMR (400 MHz, $CDCl_3$) δ ppm 7.94 (d, J=2.9 Hz, 1 H), 7.57 (s, 1 H), 7.40 (d, J=10.0 Hz, 1 H), 7.28 (s, 1 H), 7.24-7.17 (m, 2 H), 7.14 (d, J=7.3 Hz, 1 H), 7.09 (t, J=7.5 Hz, 2 H), 7.02 (d, J=8.8 Hz, 1 H), 6.66 (d, J=7.6 Hz, 2 H), 4.48 (d, J=12.5 Hz, 1 H), 4.34 (d, J=7.1 Hz, 1 H), 4.00-3.91 (m, 1 H), 3.90-3.87 (m, 4 H), 3.56 (d, J=12.5 Hz, 1

H), 3.18 (m, 4 H), 2.09-2.01 (m, 1 H), 1.92-1.83 (m, 1 H), 1.68-1.57(m, 4 H), 1.49-1.40 (m, 1H), 1.32-1.24 (m, 1 H).

EXAMPLE 798

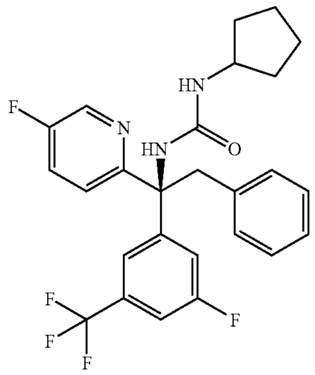

(S)-1-cyclopentyl-3-(1-(3-fluoro-5-(trifluoromethyl) phenyl)-1-(5-fluoropyridin-2-yl)-2-phenylethyl)urea Procedure 40

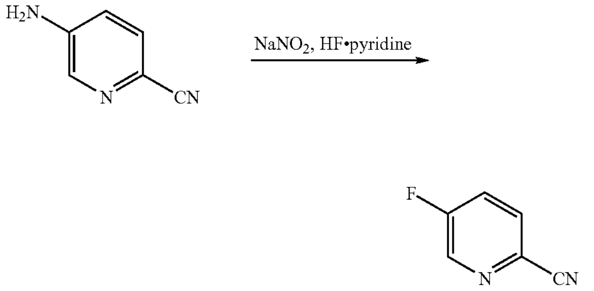

At 0° C. HF.pyridine (5 mL) was added to 5-aminopicolinonitrile (285 mg, 2.44 mmol) under $N_2$ in a 100 mL round bottom flask. A pale brown solution formed. In 4 aliquots, $NaNO_2$ (250 mg, 3.62 mmol) was added with stirring. The solution turned green and a brown gas was liberated. After 20 min at 0° C. the solution was allowed to reach room temperature and stirred for a further 20 min. A reflux condenser was attached and the reaction mixture heated to 65° C. for 20 min then allowed to cool. The orange slurry was quenched by the addition of crushed ice and the aqueous extracted with DCM (3×10 mL). The combined organic portions were dried over $Na_2SO_4$, decanted and concentrated yielding 5-fluoropicolinonitrile (152 mg, 52% yield) as a pale orange powder. LCMS: 0.63 min [M+1] 122.9 (2 min gradient, MeOH/$H_2O$ 0.1% TFA); HPLC: 0.99 min (4 min gradient, MeOH/$H_2O$ 0.2% PPA Purity 96%; NMR: 400 MHz $^1$H ($CDCl_3$) 8.52 ppm, 1H, d, J=2.64 Hz; 7.70 ppm, 1H, dd, J=4.4 and J=8.36 Hz; 7.50 ppm, 1H, m.

EXAMPLE 799

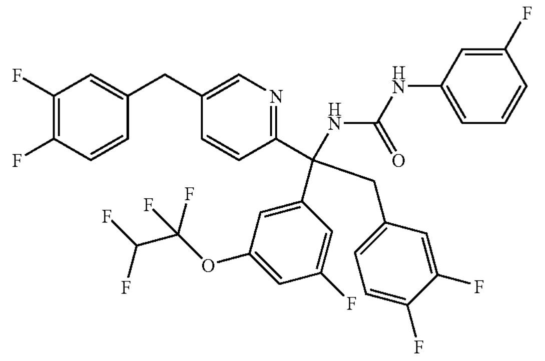

1-(1-(5-(3,4-difluorobenzyl)pyridin-2-yl)-2-(3,4-difluorophenyl)-1-(3-fluoro-5-(1,1,2,2-tetrafluoroethoxy)phenyl)ethyl)-3-(3-fluorophenyl)urea Procedure 41

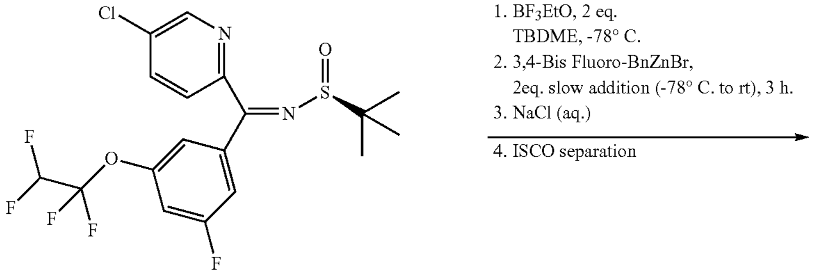

-continued

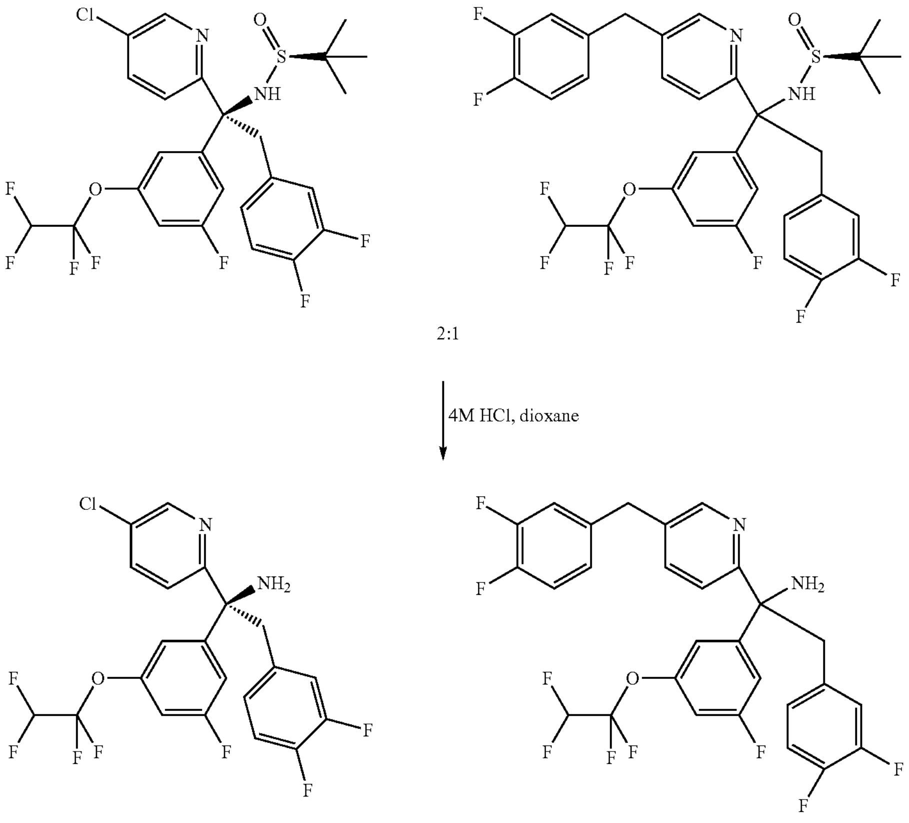

(S,Z)-N-((5-chloropyridin-2-yl)(3-fluoro-5-(1,1,2,2-tetrafluoroethoxy)phenyl)methylene)-2-methylpropane-2-sulfinamide was prepared from 1-bromo-3-fluoro-5-(1,1,2,2-tetrafluoroethoxy)benzene (described in Procedure 3) and 5-chloro-2-cyanopyridine (as described in Procedures 5 and 6). A 100 mL flask equipped with a stir bar was charged with (S,Z)-N-((5-chloropyridin-2-yl)(3-fluoro-5-(1,1,2,2-tetrafluoroethoxy)phenyl)methylene)-2-methylpropane-2-sulfinamide (300 mg, 0.66 mmoles) under nitrogen. 12 mL tert-butyl methyl ether was added followed by cooling the reaction to −78° C. in a dry ice and acetone bath for 5 minutes. $BF_3.Et_2O$ (2 eq. 166μ) was added and the mixture was stirred for 5 minutes followed by drop wise addition of 3,4-difluorobenzyl zinc bromide (0.5M in THF, 2 eq. 2.64 mL). The reaction vessel was removed from the dry ice and acetone bath and allowed to warm up to room temperature over 3 h. LC-MS shows reaction was 90% complete with 10% starting material. The reaction mixture was warmed to 40° C. for 30 min. and then quenched with aq. NaCl. The reaction mixture was transferred to a 250 mL separator funnel, 100 mL ethyl acetate was added and the organic layer was washed 75 mL×3 with saturated NaCl. The organic layer was dried over $Na_2SO_4$ and concentrated. Purification on silica gel ISCO obtained clean (S)—N—((S)-1-(5-chloropyridin-2-yl)-2-(3,4-difluorophenyl)-1-(3-fluoro-5-(1,1,2,2-tetrafluoroethoxy)phenyl)ethyl)-2-methylpropane-2-sulfinamide, (S)—N—((R)-1-(5-chloropyridin-2-yl)-2-(3,4-difluorophenyl)-1-(3-fluoro-5-(1,1,2,2-tetrafluoroethoxy)phenyl)ethyl)-2-methylpropane-2-sulfinamide was contaminated with (15S)—N—(1-(5-(3,4-difluorobenzyl)pyridin-2-yl)-2-(3,4-difluorophenyl)-1-(3-fluoro-5-(1,1,2,2-tetrafluoroethoxy)phenyl)ethyl)-2-methylpropane-2-sulfinamide. The 2:1 mixture of (S)—N—((S)-1-(5-chloropyridin-2-yl)-2-(3,4-difluorophenyl)-1-(3-fluoro-5-(1,1,2,2-tetrafluoroethoxy)phenyl)ethyl)-2-methylpropane-2-sulfinamide and (15S)—N-(1-(5-(3,4-difluorobenzyl)pyridin-2-yl)-2-(3,4-difluorophenyl)-1-(3-fluoro-5-(1,1,2,2-tetrafluoroethoxy)phenyl)ethyl)-2-methylpropane-2-sulfinamide was hydrolyzed with 4N HCl-Dioxane/MeOH (1:1) for 30 min and concentrated to dryness. The crude product was dissolved in ethyl acetate, transferred to a separator funnel and the organic layer was washed successively with aq. $NaHCO_3$ (100 mL×3) and water (100 mL). The organic portion was dried over $Na_2SO_4$, decanted and concentrated under reduced pressure.

1-(5-(3,4-difluorobenzyl)pyridin-2-yl)-2-(3,4-difluorophenyl)-1-(3-fluoro-5-(1,1,2,2-tetrafluoroethoxy)phenyl)ethanamine was converted to 1-(1-(5-(3,4-difluorobenzyl)pyridin-2-yl)-2-(3,4-difluorophenyl)-1-(3-fluoro-5-(1,1,2,2-tetrafluoroethoxy)phenyl)ethyl)-3-(3-fluorophenyl)urea as described in Procedure 2. 1-(1-(5-(3,4-difluorobenzyl)pyridin-2-yl)-2-(3,4-difluorophenyl)-1-(3-fluoro-5-(1,1,2,2-tetrafluoroethoxy)phenyl)ethyl)-3-(3-fluorophenyl)urea in 96% yield LCMS: 3.85 min [M+1] 708.05 (4min gradient, MeOH/$H_2O$ 0.1% TFA).

EXAMPLE 800

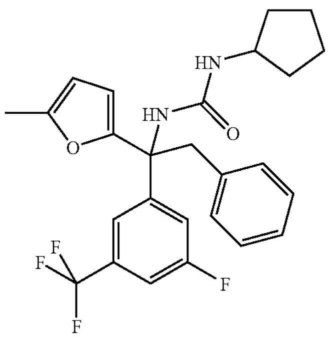

1-cyclopentyl-3-(1-(3-fluoro-5-(trifluoromethyl)phenyl)-1-(5-methylfuran-2-yl)-2-phenylethyl)urea Procedure 42

1-(3-fluoro-5-(trifluoromethyl)phenyl)-1-(5-methylfuran-2-yl)-2-phenylethanamine

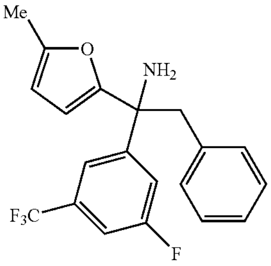

To an oven-dried round bottomed flask was added 2-methylfuran (0.5 mL, 5.58 mmol) in Et2O (4 mL) at −30° C. nBuLi (2.5 M in hexanes, 0.95 ml, 2.38 mmol, 1.17 eq) was added dropwise at −30° C. under $N_2$. The reaction mixture was slowly warmed up to room temperature and stirred at room temperature overnight. To the resulting light tan solution, cooled at −40° C., was added an $Et_2O$ solution (5 mL) of 3-fluoro-5-trifluoromethyl-benzonitrile (1.05 g, 5.58 mmol), added dropwise. The resulting solution was stirred −50 to −10° C. for 3 h. Pretreated TMSCl (0.78 ml, 1.1 eq) was added dropwise at −78° C. The dry ice bath was removed, and the mixture was stirred at r.t. for 1.5 h. It was cooled back to −78° C., and benzylmagnesium chloride (2.7 ml, 5.4 mmol, 0.97 eq) was added dropwise. The resulting mixture was stirred at −78° C. for 30 min, and then at r.t. for 2 h. The reaction mixture was quenched by adding sat'd $NH_4Cl$ and 1N HCl, and stirred for 10 min. The resulting solution was extracted with EtOAc, washed with 1N NaOH, sat'd $NaHCO_3$, $H_2O$, brine, dried ($MgSO_4$), filtered, and concentrated to dryness. The residue was purified by flash chromatography (silica gel, hexanes/EtOAc, 1-(3-fluoro-5-(trifluoromethyl)phenyl)-1-(5-methylfuran-2-yl)-2-phenylethanamine eluted with 15-30% EtOAc in hexanes) to give pure 1-(3-fluoro-5-(trifluoromethyl)phenyl)-1-(5-methylfuran-2-yl)-2-phenylethanamine as light brownish gum (1.1 g, yield: 71.4%). LC-MS ESI (10-90% MeOH in $H_2O$ with 0.1% TFA in a 4-min run), retention time=3.16 min, 347.13 ($M-NH_2+H$); $^1H$ NMR (400 MHz, $CDCl_3$) δ ppm 7.42 (s, br, 1 H), 7.25 (d, J=10.0 Hz, 1 H), 7.14-7.04 (m, 4 H), 6.77-6.70 (m, 2 H), 5.97 (d, J=3.0 Hz, 1 H), 5.86-5.80 (m, 1 H), 3.41 (d, J=13.2 Hz, 1 H), 3.09 (d, J=13.2 Hz, 1 H), 2.21 (s, 3 H). $^1H$ NMR (xx MHz, $CDCl_3$) δ ppm −63.05 ($CF_3$), −111.53 (F).

Using the procedure described for Example 1, Procedure 2, 1-cyclopentyl-3-(1-(3-fluoro-5-(trifluoromethyl)phenyl)-1-(5-methylfuran-2-yl)-2-phenylethyl)urea (65 mg, 75.5%) was obtained as white solids from 1-(3-fluoro-5-(trifluoromethyl)phenyl)-1-(5-methylfuran-2-yl)-2-phenylethanamine (66 mg) and cyclopentyl isocyanate (0.06 mL). LC-MS ESI (10-90% MeOH in $H_2O$ with 0.1% TFA in a 4-min run), retention time=4.21 min, 475.28 (M+H). $^1H$ NMR (400 MHz, $CDCl_3$) δ ppm 7.45 (s, 1 H), 7.33 (d, J=10.0 Hz, 1 H), 7.17-7.29 (m, 4 H), 6.78 (d, J=7.6 Hz, 2 H), 6.01 (d, J=3.2 Hz, 1 H), 5.94 (d, J=2.5 Hz, 1 H), 4.99 (s, 1H), 4.39 (m, 1 H), 3.89 (m, 1 H), 3.71-3.76 (m, 1 H), 3.62-3.68 (m, 1H), 2.32 (s, 3 H), 1.83 (m, 2H), 1.47-1.58 (m, 4 H), 1.20-1.31 (m, 2H). $^{13}C$ NMR (101 MHz, $CDCl_3$) δ ppm 163.56, 161.09, 156.27, 152.82, 152.01, 147.78, 147.71, 135.23, 130.46, 128.10, 127.11, 119.36, 117.74, 117.51, 114.53, 111.64, 109.08, 106.59, 61.63, 52.06, 45.19, 37.62, 23.39, 23.36, 13.59. The racemic 1-cyclopentyl-3-(1-(3-fluoro-5-(trifluoromethyl)phenyl)-1-(5-methylfuran-2-yl)-2-phenylethyl)urea was separated by chiral HPLC using chiral AD column and eluting with 20% IPA/heptane/0.1% DEA to give (R)-1-cyclopentyl-3-(1-(3-fluoro-5-(trifluoromethyl)phenyl)-1-(5-methylfuran-2-yl)-2-phenylethyl)urea (30 mg, white solids) as the faster eluting enantiomer (analytical chiral AD, 10% isopropanol/heptane/0.1% DEA, retention time=5.48 min) and (S)-1-cyclopentyl-3-(1-(3-fluoro-5-(trifluoromethyl)phenyl)-1-(5-methylfuran-2-yl)-2-phenylethyl)urea (28 mg, white solids) as the slower eluting enantiomer (analytical chiral AD, 10% isopropanol/heptane/0.1% DEA, retention time=8.14 min).

EXAMPLE 801

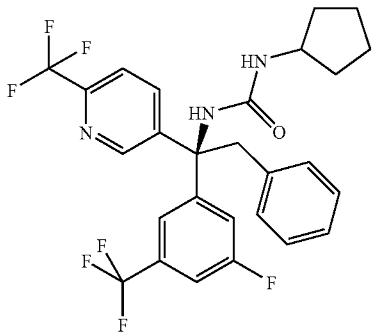

(S)-1-cyclopentyl-3-(1-(3-fluoro-5-(trifluoromethyl)phenyl)-2-phenyl-1-(6-(trifluoromethyl)pyridin-3-yl)ethyl)urea Procedure 43

Using similar procedures as those of procedures 5, 6, 7 and 1, (S)-1-cyclopentyl-3-(1-(3-fluoro-5-(trifluoromethyl)phenyl)-2-phenyl-1-(6-(trifluoromethyl)pyridin-3-yl)ethyl)urea was obtained. LC-MS ESI 540.30 (M+H) (10-90% MeOH in $H_2O$ with 0.1% TFA in a 4-min run, retention time=4.02 min); 1H NMR (400 MHz, CDCl3) δ ppm 1.36 (d, m, 2 H), 1.62-

1.68 (m, 4 H), 1.95 (m, 2 H), 3.81 (d, J=12.96 Hz, 1 H), 3.89 (br, s, 1 H), 4.00 (d, J=13.20 Hz, 1 H), 4.84 (br, s, 1 H), 6.72 (d, J=7.58 Hz, 2 H), 7.12 (d, J=9.78 Hz, 1 H), 7.18-7.30 (m, 5 H), 7.67 (d, J=8.31 Hz, 1 H), 7.80-7.84 (m, 1 H), 8.67 (s, 1 H).

EXAMPLE 802

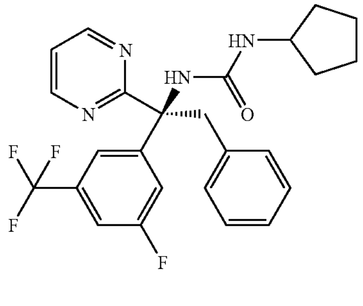

(S)-1-cyclopentyl-3-(1-(3-fluoro-5-(trifluoromethyl)phenyl)-2-phenyl-1-(pyrimidin-2-yl)ethyl)urea Procedure 44

(3-fluoro-5-(trifluoromethyl)phenyl)(pyrimidin-2-yl)methanone

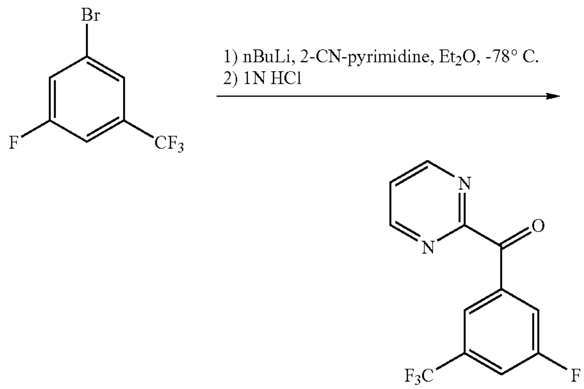

To a solution of 1-bromo-3-fluoro-5-trifluorobenzene (500 mg, 2.05 mmol) in anhydrous ether (15 mL) cooled at −78° C. was added n-BuLi (1 mL, 2.5 mmol, 2.5M in hexane) dropwise. The reaction mixture was stirred at −74° C. for 30 min. An $Et_2O$ solution (5 mL) of 2-cyano-pyrimidine (214 mg, 2.05 mmol) was added dropwise. The resulting solution was stirred at −78° C. for 2 h. The reaction mixture was quenched by adding 1N HCl (10 mL), and dry ice-acetone bath was removed. The resulting slurry was stirred with additional Et O (10 mL) at room temperature for 1 h. The organic layer was separated, and washed with sat'd $NaHCO_3$, $H_2O$, brine, and dried over $MgSO_4$. The solvent was evaporated under reduced pressure to yield the crude product. The desired product was purified by flash chromatography using 0-30% EtOAc in hexanes over 20 minutes as eluting gradient to give (3-fluoro-5-(trifluoromethyl)phenyl)(pyrimidin-2-yl)methanone as yellowish oil (400 mg, 72.3% yield). LC-MS (ESI): 271.26 (M+H), retention time=3.00 minutes (0-100% $MeOH/H_2O$/0.1% TFA, 4 min run); $^1H$ NMR (400 MHz, $CDCl_3$) δ ppm 7.47 (t, J=5.05 Hz, 1H), 7.60 (q, J=4.83 Hz, 1H), 8.07 (d, J=10.11 Hz, 1H), 8.23 (s, 1H), 9.03 (t, J=4.83 Hz, 2H).

(R,E)-N-((3-fluoro-5-(trifluoromethyl)phenyl)(pyrimidin-2-yl)methylene)-2-methylpropane-2-sulfinamide

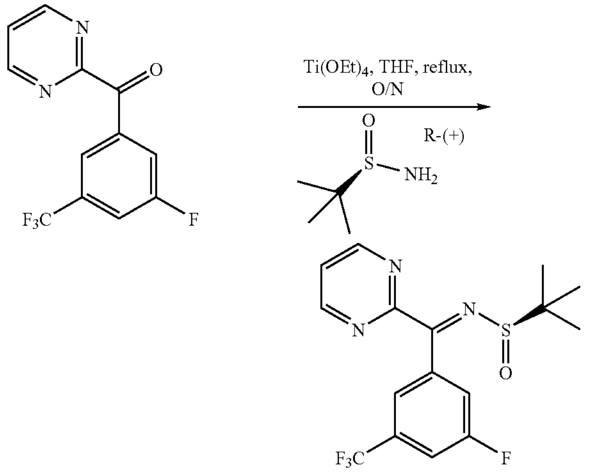

To a stirred solution of (3-Fluoro-5-(1,1,2,2-tetrafluoroethoxy)phenyl)(pyrimidine-2-yl)methanone (400 mg, 1.48 mmol) in anhydrous THF (2 mL) at room temperature under $N_2$ was added R-(+)-t-Butyl sulfinylamine (182 mg, 1.62 mmol), followed by addition of $Ti(OEt)_4$ (506 mg, 2.22 mmol). The resulting solution was heated at reflux for 16 h. The cooled mixture was quenched with brine. The precipitate was removed by filtration and washed with EtOAc (5 mL). The organic layer was separated from the aqueous and evaporated under reduced pressure. The crude product was purified by silica gel flash chromatography using 0-100% EtOAc in hexane over 20 minutes as eluting gradient to afford (R,E)-N-((3-fluoro-5-(1,1,2,2-tetrafluoroethoxy)phenyl) (pyrimidine-2-yl)methylene)-2-methylpropane-2-sulfinamide (200 mg, 36% yield) as a yellowish viscous oil. LC-MS (ESI): 396.23 (M+Na), retention time=3.51 min (0-100% MeOH/$H_2O$/0.1% TFA, 4 min run); $^1H$ NMR (400 MHz, $CDCl_3$) δ ppm 1.35 (s, 9H), 7.42 (t, J=5.05 Hz, 1H), 7.46 (d, J=7.91 Hz, 1H), 7.58 (d, J=9.23 Hz, 1H), 7.66 (s, 1H), 8.88 (d, J=4.83 Hz, 2H).

(R)—N—((S)-1-(3-fluoro-5-(trifluoromethyl)phenyl)-2-phenyl-1-(pyrimidin-2-yl)ethyl)-2-methylpropane-2-sulfinamide

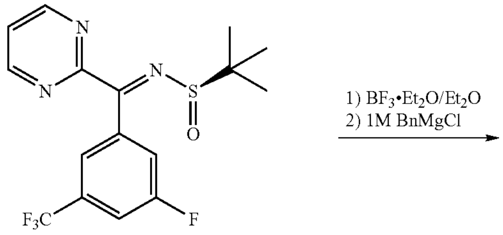

-continued

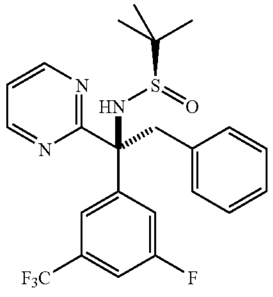

To a solution of (R,E)-N-((3-fluoro-5-(1,1,2,2-tetrafluoroethoxy)phenyl) (pyrimidine-2-yl)methylene)-2-methylpropane-2-sulfinamide (200 mg, 0.536 mmol) in anhydrous ether (3 mL) was added $BF_3Et_2O$ (0.135 mL, 1.07 mmol) dropwise at −78° C. The mixture was stirred at −78° C. for 10 min. Benzyl magnesium chloride (1M in $Et_2O$, 1.5 mL, 3.0 eq) was added slowly at −78° C., and the resulting mixture was stirred at −70° C. for 1.5 h. The reaction mixture was quenched with sat'd $NH_4Cl$ and extracted with $Et_2O$ (2×10 mL). The organic solvent was evaporated under reduced pressure. The crude product was then purified by flash chromatography using 0-100% EtOAc in hexane over 20 minutes as eluting solvent to afford (R)—N—((R)-1-(3-fluoro-5-(1,1,2,2-tetrafluoroethoxy)phenyl)-1-(4-fluorophenyl)-2-phenylethyl)-2-methylpropane-2-sulfinamide (38 mg, 23% yield). LC-MS (ESI) 488.28 (M+Na), retention time=3.82 min (0-100% MeOH/$H_2O$/0.1% TFA, 4 min run); $^1H$ NMR (400 MHz, $CD_3OD$) δ ppm 1.17 (s, 9H), 3.89 (d, J=14.06 Hz, 1H), 4.20 (d, J=14.06 Hz, 1H), 6.75 (d, J=6.59 Hz, 2H), 6.98-7.15 (m, 3H), 7.28-7.40 (m, 2H), 7.40-7.49 (m, 2H), 8.83 (d, J=4.83 Hz, 2H).

(R)-1-(3-fluoro-5-(1,1,2,2-tetrafluoroethoxy)phenyl)-1-(4-fluorophenyl)-2-phenylethanamine

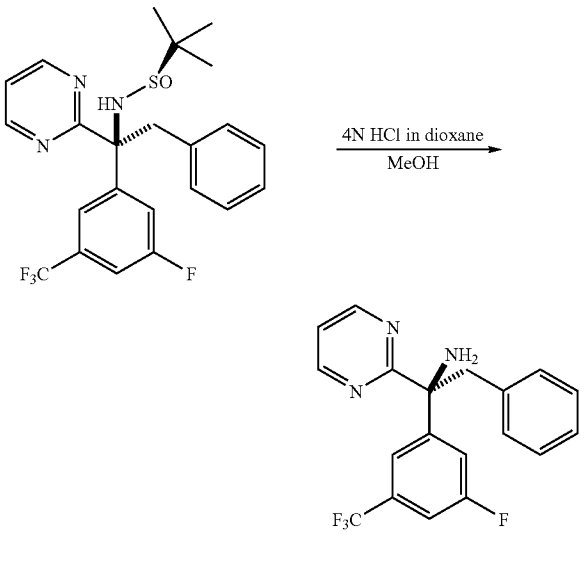

To a solution of (R)—N—((R)-1-(3-fluoro-5-(1,1,2,2-tetrafluoroethoxy)phenyl)-1-(4-fluorophenyl)-2-phenylethyl)-2-methylpropane-2-sulfinamide (38 mg, 0.081 mmol) in methanol (0.2 mL) was added 4N HCl in dioxane (0.2 mL). The resulting reaction was stirred at room temperature for 5 minutes and the solvent was evaporated under reduced pressure. The crude product was diluted in EtOAc and washed with sat'd. $NaHCO_3$ and dried over $Na_2SO_4$. The EtOAc was evaporated under reduced pressure and pumped to dryness to afford (R)-1-(3-fluoro-5-(1,1,2,2-tetrafluoroethoxy)phenyl)-1-(4-fluorophenyl)-2-phenylethanamine (26 mg, 92% yield) as a colorless oil. LC-MS (ESI) 345.17 (M+H−17), 362.19 (M+H), retention time=3.26 minutes (0-100% MeOH/$H_2O$/0.1% TFA, 4 min run).

(S)-1-cyclopentyl-3-(1-(3-fluoro-5-(trifluoromethyl)phenyl)-2-phenyl-1-(pyrimidin-2-yl)ethyl)urea

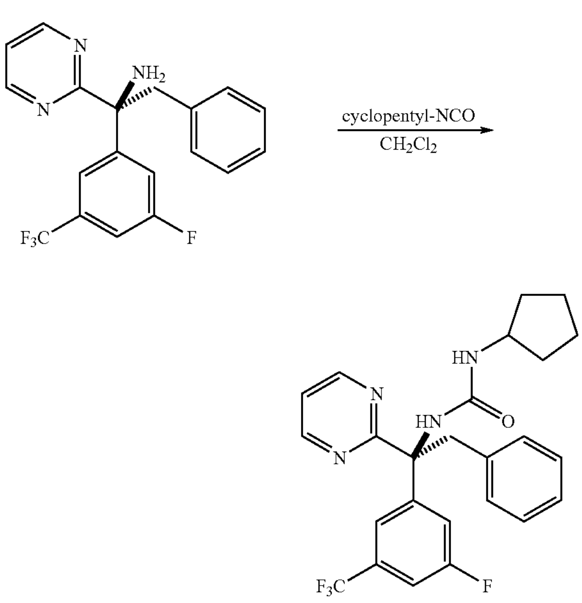

To a solution of (R)-1-(3-fluoro-5-(1,1,2,2-tetrafluoroethoxy)phenyl)-1-(4-fluorophenyl)-2-phenylethanamine (26 mg, 0.072 mmol) in $CH_2Cl_2$ (0.3 mL) was added cyclopentyl isocyanate (0.070 mL, 0.63 mmol). The resulting mixture was stirred at room temperature for 16 h. The crude product was purified by flash chromatography using 0-50% EtOAc in hexane over 20 minutes as eluting gradient. The solvent was removed under reduced pressure and pumped to dryness to afford (S)-1-cyclopentyl-3-(1-(3-fluoro-5-(trifluoromethyl)phenyl)-2-phenyl-1-(pyrimidin-2-yl)ethyl)urea (20 mg, 59% yield) as a white powder. LC-MS (ESI): 473.32 (M+H), retention time=3.76 min (0-100% MeOH/$H_2O$/0.1% TFA, 4 min run); Analytical HPLC: 3.27 min (0-100% ACN/$H_2O$/0.1% TFA, 4 min run); $^1H$ NMR (400 MHz, $CD_3OD$) δ ppm 1.32-1.44 (m, 1H), 1.44-1.78 (m, 5H), 1.79-1.99 (m, 2H), 3.88-3.99 (m, 1H), 4.23 (d, J=7.03 Hz, 2H), 6.69 (d, J=6.59 Hz, 2H), 6.96-7.12 (m, 3H), 7.21-7.36 (m, 2H), 7.45-7.65 (m, 2H), 8.72 (d, J=4.83 Hz, 2H).

EXAMPLE 803

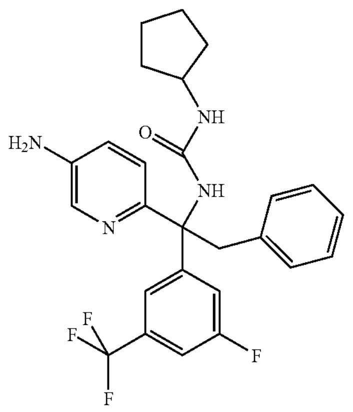

1-(1-(5-aminopyridin-2-yl)-1-(3-fluoro-5-(trifluoromethyl)phenyl)-2-phenylethyl)-3-cyclopentylurea Procedure 45

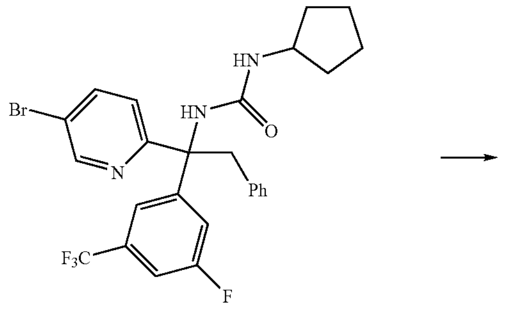

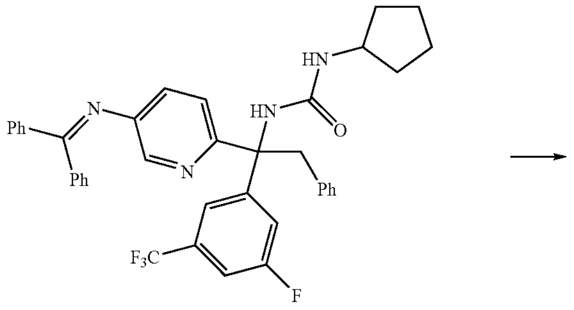

-continued

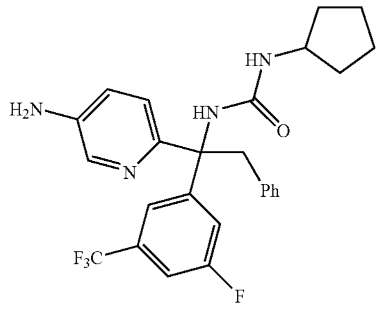

1-(1-(5-Bromopyridin-2-yl)-1-(3-fluoro-5-(trifluoromethyl)phenyl)-2-phenylethyl)-3-cyclopentylurea (122 mg, 0.22 mmol), morpholine (1.3 eq), $Pd_2(dba)_3$ (70 mg), Xantphos (95 mg) and Na—O-t-Bu (84 mg) were stirred in toluene (0.7 mL) at room temperature. The reaction mixture was purged with $N_2$ several times and then was heated at 100° C. for 2 h. The reaction mixture was cooled to room temperature, and $CH_2Cl_2$ was added. The resulting solution was filtered through Celite and concentrated to dryness. The residue was purified by chromatography (silica gel, hexanes/EtOAc) to give 1-cyclopentyl-3-(1-(5-(diphenylmethyleneamino)pyridin-2-yl)-1-(3-fluoro-5-(trifluoromethyl)phenyl)-2-phenylethyl)urea as white solids (101 mg, yield: 70.1%). LC-MS ESI 651.45 (M+H) (10-90% MeOH in $H_2O$ with 0.1% TFA in a 4-min run, retention time=4.47min).

1-Cyclopentyl-3-(1-(5-(diphenylmethyleneamino)pyridin-2-yl)-1-(3-fluoro-5-(trifluoromethyl)phenyl)-2-phenylethyl)urea (77 mg, 0. 12 mmol) was stirred in 2N HCl (1.5 mL) and THF (6 mL) at room temperature for 30 min. LC-MS showed completion of the reaction. EtOAc was added and the solution was washed with saturated $NaHCO_3$, $H_2O$, brine, dried ($Na_2SO_4$), filtered, and concentrated to dryness. The residue was purified by flash chromatography (silica gel, hexanes/EtOAc, came out 45-50% EtOAc in hexanes) to give 1-(1-(5-aminopyridin-2-yl)-1-(3-fluoro-5-(trifluoromethyl)phenyl)-2-phenylethyl)-3-cyclopentylurea as colorless film (52 mg, yield: 90.3%). LC-MS ESI 487.32 (M+H) (10-90% MeOH in $H_2O$ with 0.1% TFA in a 4-min run, retention time=3.29 min). 1H NMR (400 MHz, CDCl3) δ ppm 1.23-1.32 (m, 1 H), 1.39-1.50 (m, 1 H), 1.58-1.69 (m, 4 H), 1.86 (dt, J=12.47, 6.24 Hz, 1 H), 1.99-2.08 (m, 1 H), 3.54 (d, J=12.47 Hz, 1 H), 3.74 (s, br, 1 H), 3.89-4.00 (m, 1 H), 4.33 (d, J=7.09 Hz, 1 H), 4.44 (d, J=12.47 Hz, 1H), 6.65-6.72 (m, 2 H), 6.88-6.93 (m, 1 H), 6.97-7.02 (m, 1 H), 7.07-7.19 (m, 4 H), 7.22-7.31 (m, 1 H), 7.39 (d, J=10.03 Hz, 1 H), 7.55 (s, 1 H), 7.75 (d, J=2.69 Hz, 1H).

TABLE 8

| Ex. No. | Structure | Name | Retention Time Min./ Molecular Mass | Prepared in the manner described in: |
|---|---|---|---|---|
| 804 | 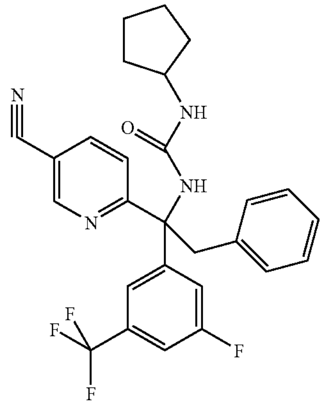 | 1-(1-(5-cyanopyridin-2-yl)-1-(3-fluoro-5-(trifluoromethyl)phenyl)-2-phenylethyl)-3-cyclopentylurea | 3.93 LC 497.3 [M + H]+ | Procedure 35 and 2 |
| 805 | 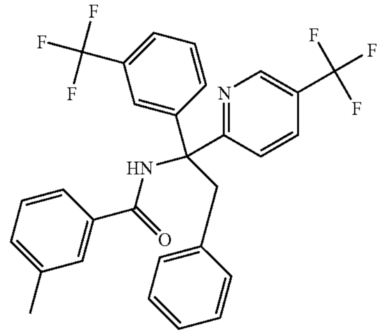 | 3-methyl-N-(2-phenyl-1-(3-(trifluoromethyl)phenyl)-1-(5-(trifluoromethyl)pyridin-2-yl) ethyl)benzamide | 3.44 LC 529.24 [M + H]+ | Procedure 37 and 4 |
| 806 | 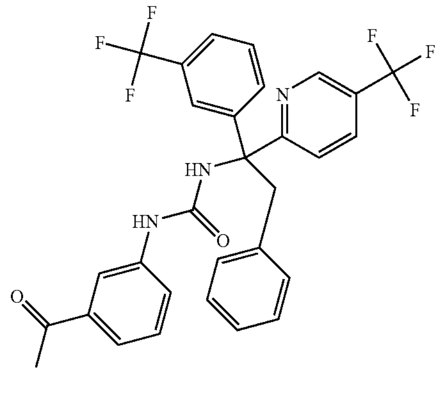 | 1-(3-acetylphenyl)-3-(2-phenyl-1-(3-(trifluoromethyl)phenyl)-1-(5-(trifluoromethyl)pyridin-2-yl) ethyl)urea | 3.05 LC 572.29 [M + H]+ | Procedure 37 and 2 |

TABLE 8-continued

| Ex. No. | Structure | Name | Retention Time Min./ Molecular Mass | Prepared in the manner described in: |
|---|---|---|---|---|
| 807 | 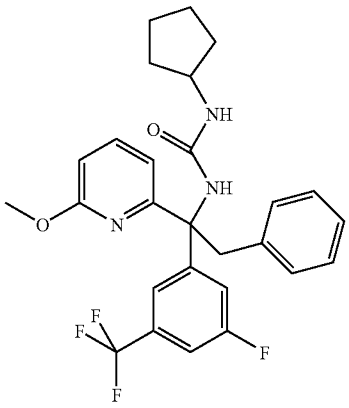 | 1-cyclopentyl-3-(1-(3-fluoro-5-(trifluoromethyl)phenyl)-1-(6-methoxypyridin-2-yl)-2-phenylethyl)urea | 4.28 LC 502.24 $[M + H]^+$ | Procedure 1 and 2 |
| 808 | 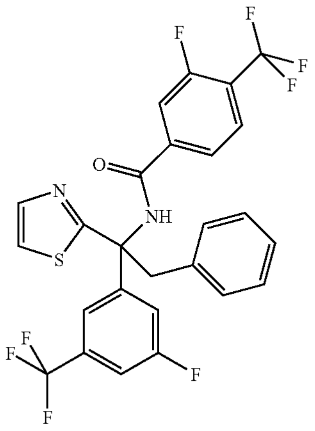 | 3-fluoro-N-(1-(3-fluoro-5-(trifluoromethyl)phenyl)-2-phenyl-1-(thiazol-2-yl)ethyl)-4-(trifluoromethyl)benzamide | 4.32 LC 557.17 $[M + H]^+$ | Procedure 36 and 4 |
| 809 | 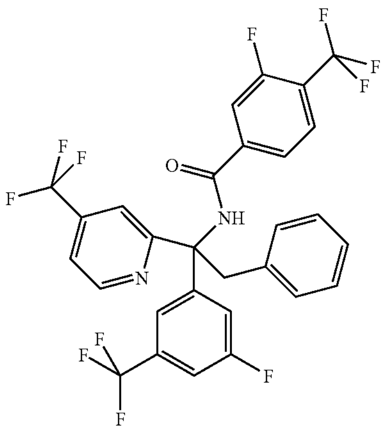 | 3-fluoro-N-(1-(3-fluoro-5-(trifluoromethyl)phenyl)-2-phenyl-1-(4-(trifluoromethyl)pyridin-2-yl)ethyl)-4-(trifluoromethyl) benzamide | 4.49 LC 619.19 $[M + H]^+$ | Procedure 37 and 4 |

TABLE 8-continued

| Ex. No. | Structure | Name | Retention Time Min./ Molecular Mass | Prepared in the manner described in: |
|---|---|---|---|---|
| 810 | 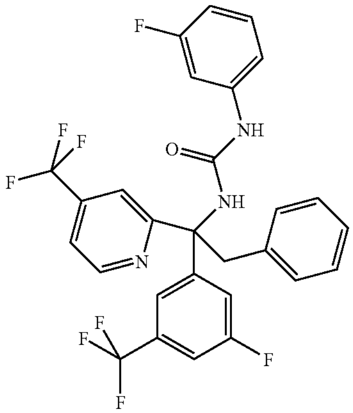 | 1-(1-(3-fluoro-5-(trifluoromethyl) phenyl)-2-phenyl-1-(4-(trifluoromethyl)pyridin-2-yl) ethyl)-3-(3-fluorophenyl)urea | 4.30 LC 566.84 [M + H]$^+$ | Procedure 37 and 2 |
| 811 | 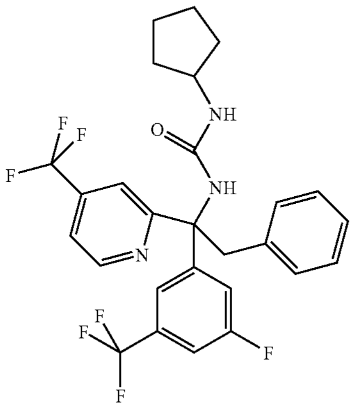 | 1-cyclopentyl-3-(1-(3-fluoro-5-(trifluoromethyl)phenyl)-2-phenyl-1-(4-(trifluoromethyl)pyridin-2-yl) ethyl)urea | 4.27 LC 540.20 [M + H]$^+$ | Procedure 37 and 2 |
| 812 | 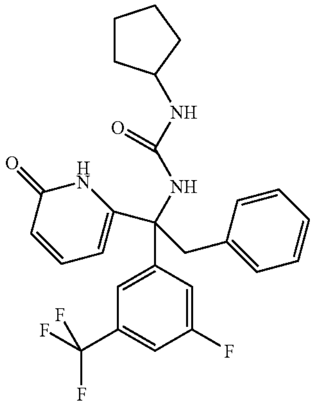 | 1-cyclopentyl-3-(1-(3-fluoro-5-(trifluoromethyl)phenyl)-1-(6-oxo-1,6-dihydropyridin-2-yl)-2-phenylethyl)urea | 3.75 LC 488.12 [M + H]$^+$ | Procedure 38 and 2 |
| 813 | 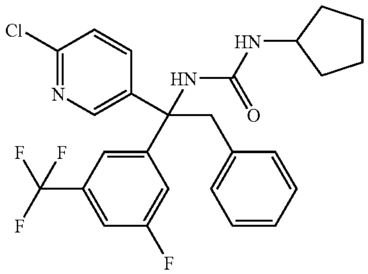 | 1-(1-(6-chloropyridin-3-yl)-1-(3-fluoro-5-(trifluoromethyl)phenyl)-2-phenylethyl)-3-cyclopentylurea | 3.35 LC 506.16 [M + H]$^+$ | Procedures 43 and 2 |

TABLE 8-continued

| Ex. No. | Structure | Name | Retention Time Min./ Molecular Mass | Prepared in the manner described in: |
|---|---|---|---|---|
| 814 | 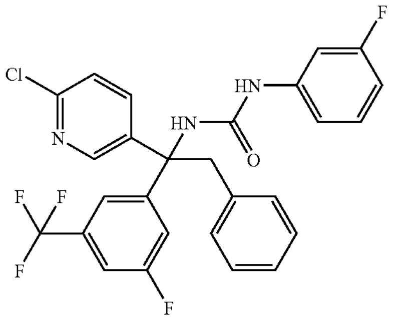 | 1-(1-(6-chloropyridin-3-yl)-1-(3-fluoro-5-(trifluoromethyl)phenyl)-2-phenylethyl)-3-(3-fluorophenyl) urea | 3.78 LC 532.14 [M + H]+ | Procedures 43 and 2 |
| 815 | 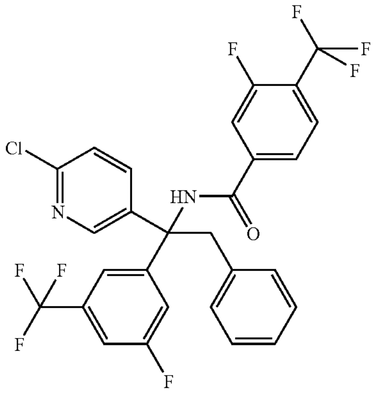 | N-(1-(6-chloropyridin-3-yl)-1-(3-fluoro-5-(trifluoromethyl)phenyl)-2-phenylethyl)-3-fluoro-4-(trifluoromethyl)benzamide | 3.53 LC 585.11 [M + H]+ | Procedures 43 and 4 |
| 816 | 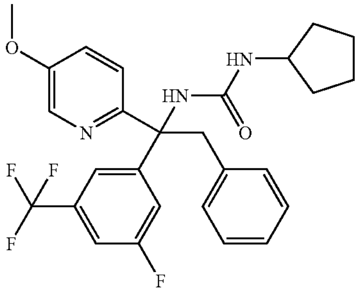 | 1-cyclopentyl-3-(1-(3-fluoro-5-(trifluoromethyl)phenyl)-1-(5-methoxypyridin-2-yl)-2-phenylethyl)urea | 3.33 LC 502.18 [M + H]+ | Procedures 1 and 2 |
| 817 | 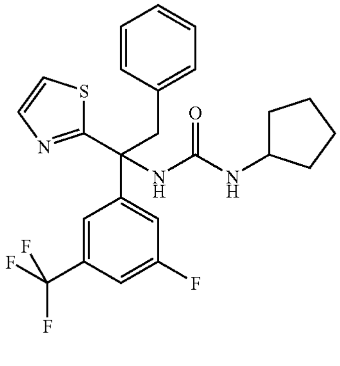 | 1-cyclopentyl-3-(1-(3-fluoro-5-(trifluoromethyl)phenyl)-2-phenyl-1-(thiazol-2-yl)ethyl)urea | 3.98 LC 478.10 [M + H]+ | Procedures 36 and 2 |

TABLE 8-continued

| Ex. No. | Structure | Name | Retention Time Min./ Molecular Mass | Prepared in the manner described in: |
|---|---|---|---|---|
| 818 | 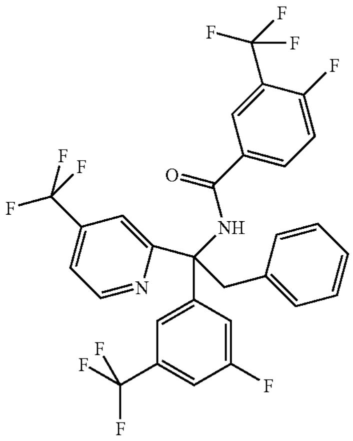 | 4-fluoro-N-(1-(3-fluoro-5-(trifluoromethyl)phenyl)-2-phenyl-1-(4-(trifluoromethyl)pyridin-2-yl)ethyl)-3-(trifluoromethyl) benzamide | 4.41 LC 619.14 [M + H]+ | Procedure 37 and 4 |
| 819 | 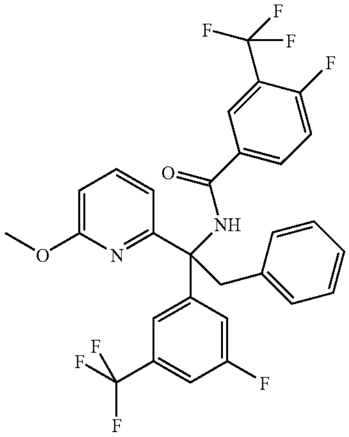 | 4-fluoro-N-(1-(3-fluoro-5-(trifluoromethyl)phenyl)-1-(6-methoxypyridin-2-yl)-2-phenylethyl)-3-(trifluoromethyl) benzamide | 4.46 LC 581.14 [M + H]+ | Procedure 1 and 4 |
| 820 | 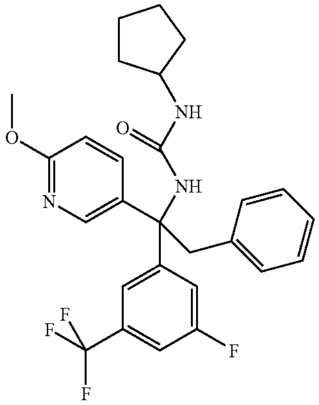 | 1-cyclopentyl-3-(1-(3-fluoro-5-(trifluoromethyl)phenyl)-1-(6-methoxypyridin-3-yl)-2-phenylethyl)urea | 3.99 LC 502.18 [M + H]+ | Procedure 43 and 2 |

TABLE 8-continued

| Ex. No. | Structure | Name | Retention Time Min./ Molecular Mass | Prepared in the manner described in: |
| --- | --- | --- | --- | --- |
| 821 | 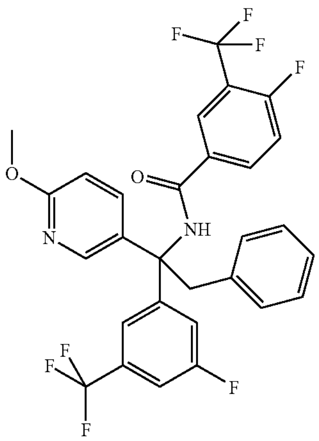 | 4-fluoro-N-(1-(3-fluoro-5-(trifluoromethyl)phenyl)-1-(6-methoxypyridin-3-yl)-2-phenylethyl)-3-(trifluoromethyl) benzamide | 4.29 LC 581.14 $[M + H]^+$ | Procedure 43 and 4 |
| 822 | 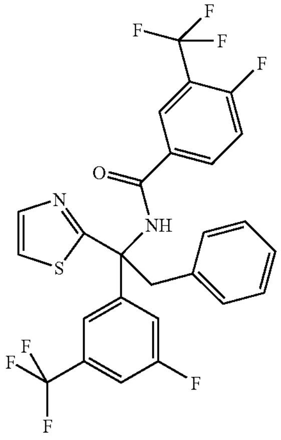 | 4-fluoro-N-(1-(3-fluoro-5-(trifluoromethyl)phenyl)-2-phenyl-1-(thiazol-2-yl)ethyl)-3-(trifluoromethyl)benzamide | 4.27 LC 557.08 $[M + H]^+$ | Procedure 36 and 4 |
| 823 | 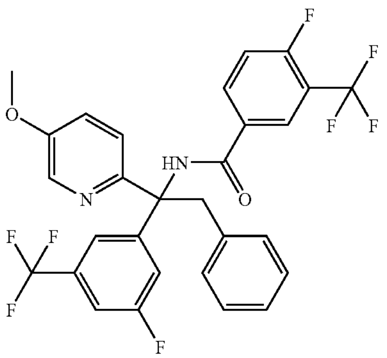 | 4-fluoro-N-(1-(3-fluoro-5-(trifluoromethyl)phenyl)-1-(5-methoxypyridin-2-yl)-2-phenylethyl)-3-(trifluoromethyl) benzamide | 3.96 LC 581.14 $[M + H]^+$ | Procedure 1 and 4 |

TABLE 8-continued

| Ex. No. | Structure | Name | Retention Time Min./ Molecular Mass | Prepared in the manner described in: |
|---|---|---|---|---|
| 824 | 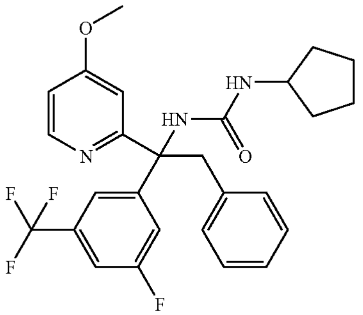 | 1-cyclopentyl-3-(1-(3-fluoro-5-(trifluoromethyl)phenyl)-1-(4-methoxypyridin-2-yl)-2-phenylethyl)urea | 3.30 LC 502.19 [M + H]+ | Procedure 37 and 2 |
| 825 | 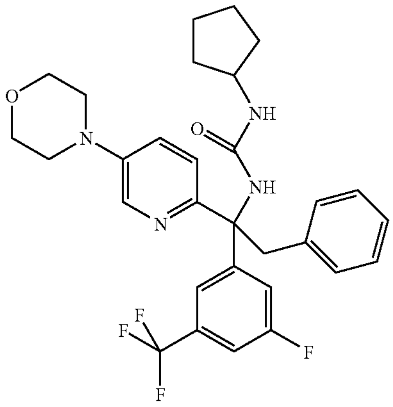 | 1-cyclopentyl-3-(1-(3-fluoro-5-(trifluoromethyl)phenyl)-1-(5-morpholinopyridin-2-yl)-2-phenylethyl)urea | 3.63 LC 557.28 [M + H]+ | Procedures 39 and 2 |
| 826 | 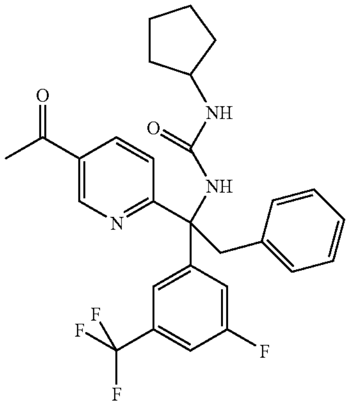 | 1-(1-(5-acetylpyridin-2-yl)-1-(3-fluoro-5-(trifluoromethyl)phenyl)-2-phenylethyl)-3-cyclopentylurea | 3.91 LC 514.16 [M + H]+ | Procedure 1 and 2 |
| 827 | 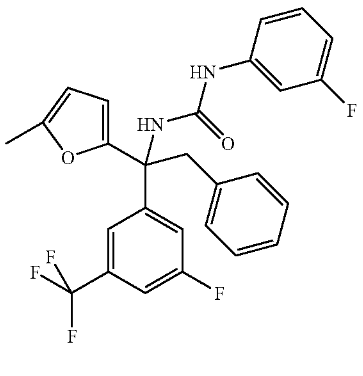 | 1-(1-(3-fluoro-5-(trifluoromethyl) phenyl)-1-(5-methylfuran-2-yl)-2-phenylethyl)-3-(3-fluorophenyl) urea | 4.23 LC 523.22 [M + Na]+ | Procedure 42 and 2 |

TABLE 8-continued

| Ex. No. | Structure | Name | Retention Time Min./ Molecular Mass | Prepared in the manner described in: |
|---|---|---|---|---|
| 828 | 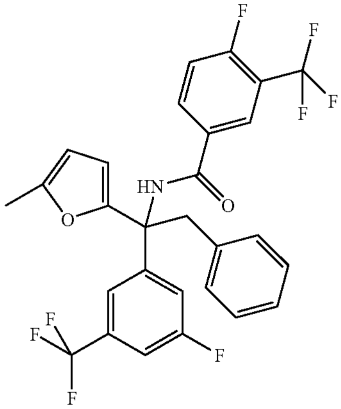 | 4-fluoro-N-(1-(3-fluoro-5-(trifluoromethyl)phenyl)-1-(5-methylfuran-2-yl)-2-phenylethyl)-3-(trifluoromethyl)benzamide | 4.34 LC 554.28 $[M + H]^+$ | Procedure 42 and 4 |
| 829 | 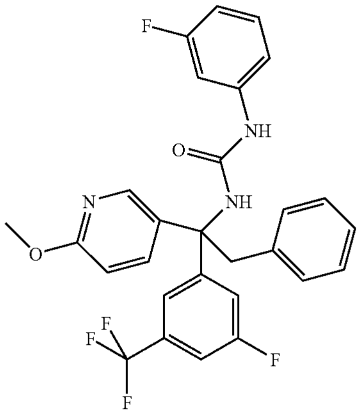 | 1-(1-(3-fluoro-5-(trifluoromethyl) phenyl)-1-(6-methoxypyridin-3-yl)-2-phenylethyl)-3-(3-fluorophenyl)urea | 4.06 LC 528.20 $[M + H]^+$ | Procedure 43 and 2 |
| 830 | 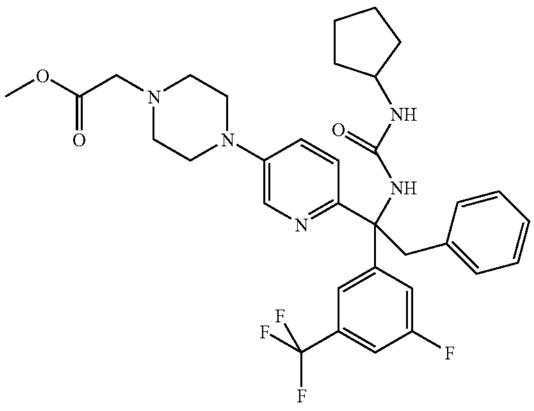 | methyl 2-(4-(6-(1-(3-cyclopentylureido)-1-(3-fluoro-5-(trifluoromethyl)phenyl)-2-phenylethyl)pyridin-3-yl)piperazin-1-yl)acetate | 3.21 LC 628.38 $[M + H]^+$ | Procedures 39 and 2 |

TABLE 8-continued

| Ex. No. | Structure | Name | Retention Time Min./ Molecular Mass | Prepared in the manner described in: |
|---|---|---|---|---|
| 831 | 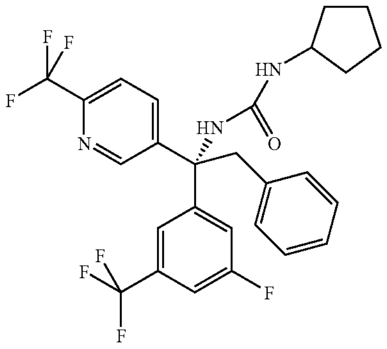 | (R)-1-cyclopentyl-3-(1-(3-fluoro-5-(trifluoromethyl)phenyl)-2-phenyl-1-(6-(trifluoromethyl) pyridin-3-yl)ethyl)urea | 4.02 LC 540.30 $[M + H]^+$ | Procedure 43 and 2 |
| 832 | 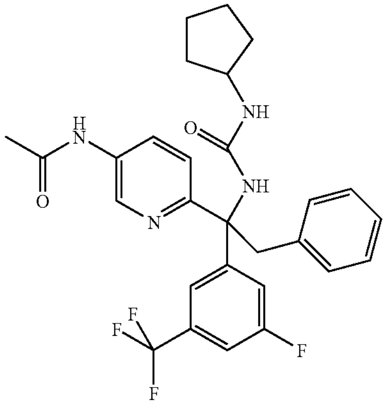 | 1-(1-(5-acetamidopyridin-2-yl)-1-(3-fluoro-5-(trifluoromethyl) phenyl)-2-phenylethyl)-3-cyclopentylurea | 3.75 LC 529.42 $[M + H]^+$ | Procedure 39 and 2 |
| 833 | 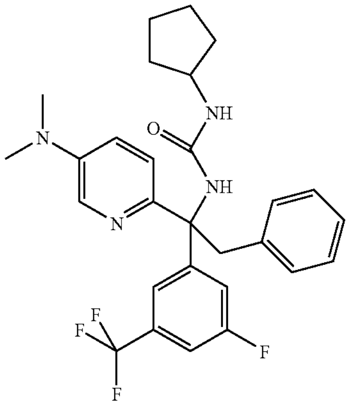 | 1-cyclopentyl-3-(1-(5-(dimethylamino)pyridin-2-yl)-1-(3-fluoro-5-(trifluoromethyl)phenyl)-2-phenylethyl)urea | 3.44 LC 515.38 $[M + H]^+$ | Procedure 39 and 2 |
| 834 | 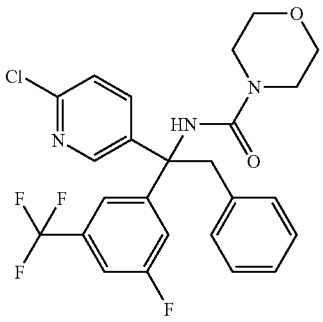 | N-(1-(6-chloropyridin-3-yl)-1-(3-fluoro-5-(trifluoromethyl)phenyl)-2-phenylethyl)morpholine-4-carboxamide | 3.04 LC 530.26 $[M + Na]^+$ | Procedure 43 and 2 |

TABLE 8-continued

| Ex. No. | Structure | Name | Retention Time Min./ Molecular Mass | Prepared in the manner described in: |
|---|---|---|---|---|
| 835 | 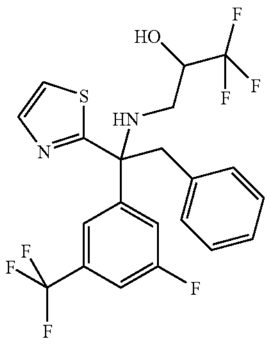 | 1,1,1-trifluoro-3-(1-(3-fluoro-5-(trifluoromethyl)phenyl)-2-phenyl-1-(thiazol-2-yl)ethylamino)propan-2-ol | 3.96 LC 479.31 [M + H]$^+$ | Procedure 36 and 10 |
| 836 | 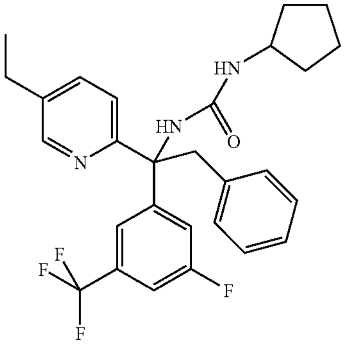 | 1-cyclopentyl-3-(1-(5-ethylpyridin-2-yl)-1-(3-fluoro-5-(trifluoromethyl)phenyl)-2-phenylethyl)urea | 4.24 LC 500.40 [M + H]$^+$ | Procedure 1 and 2 |
| 837 | 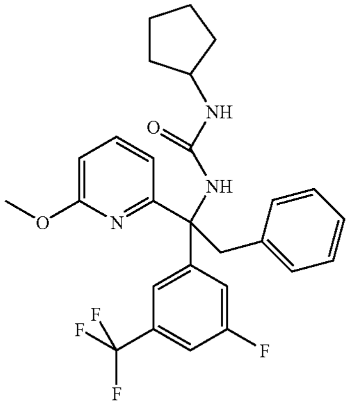 | 1-cyclopentyl-3-(1-(3-fluoro-5-(trifluoromethyl)phenyl)-1-(6-methoxypyridin-2-yl)-2-phenylethyl)urea | 4.29 LC 502.41 [M + H]$^+$ Chiral AD analytical: 20% IPA/heptane 0.1% DEA Retention time: 5.68 min | Procedure 1 and 2 |

TABLE 8-continued

| Ex. No. | Structure | Name | Retention Time Min./ Molecular Mass | Prepared in the manner described in: |
|---|---|---|---|---|
| 838 | 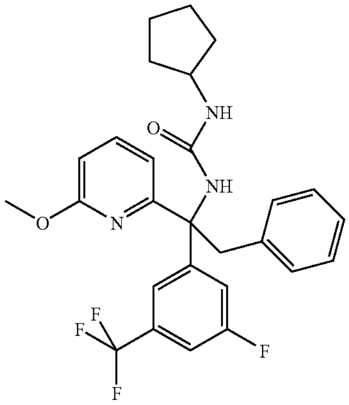 | 1-cyclopentyl-3-(1-(3-fluoro-5-(trifluoromethyl)phenyl)-1-(6-methoxypyridin-2-yl)-2-phenylethyl)urea | 4.29 LC 502.41 [M + H]$^+$ Chiral AD analytical: 20% IPA/heptane 0.1% DEA Retention time: 8.3 min | Procedure 1 and 2 |
| 839 | 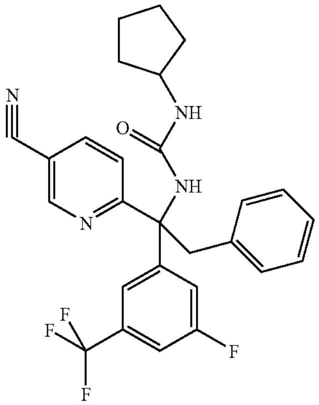 | 1-(1-(5-cyanopyridin-2-yl)-1-(3-fluoro-5-(trifluoromethyl)phenyl)-2-phenylethyl)-3-cyclopentylurea | 3.93 LC 497.3 [M + H]$^+$ Chiral AD analytical: 20% IPA/heptane 0.1% DEA Retention time: 6.65 min | Procedure 35 and 2 |
| 840 | 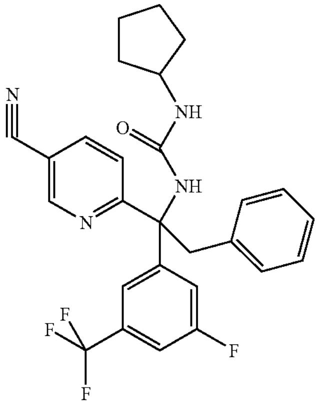 | 1-(1-(5-cyanopyridin-2-yl)-1-(3-fluoro-5-(trifluoromethyl)phenyl)-2-phenylethyl)-3-cyclopentylurea | 3.93 LC 497.3 [M + H]$^+$ Chiral AD analytical: 20% IPA/heptane 0.1% DEA Retention time: 13.8 min | Procedure 35 and 2 |

TABLE 8-continued

| Ex. No. | Structure | Name | Retention Time Min./ Molecular Mass | Prepared in the manner described in: |
|---|---|---|---|---|
| 841 | 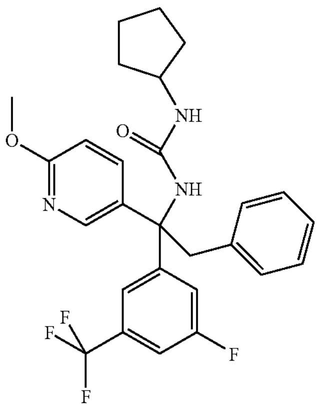 | 1-cyclopentyl-3-(1-(3-fluoro-5-(trifluoromethyl)phenyl)-1-(6-methoxypyridin-3-yl)-2-phenylethyl)urea | 3.99 LC 502.18 [M + H]+ | Procedure 43 and 2 |
| 842 | 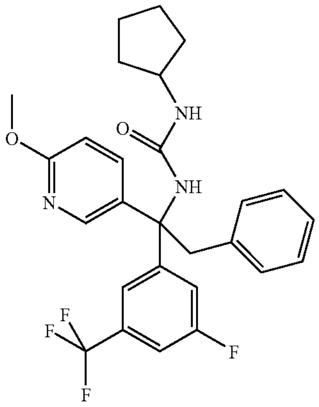 | 1-cyclopentyl-3-(1-(3-fluoro-5-(trifluoromethyl)phenyl)-1-(6-methoxypyridin-3-yl)-2-phenylethyl)urea | 3.99 LC 502.18 [M + H]+ | Procedure 43 and 2 |
| 843 | 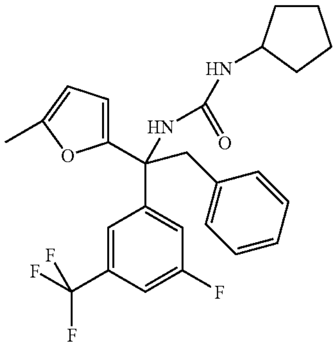 | 1-cyclopentyl-3-(1-(3-fluoro-5-(trifluoromethyl)phenyl)-1-(5-methylfuran-2-yl)-2-phenylethyl) urea | 4.21 LC 475.28 [M + H]+ Chiral AD analytical: 20% IPA/heptane 0.1% DEA Retention time: 8.14 min | Procedure 42, and 2 |

TABLE 8-continued

| Ex. No. | Structure | Name | Retention Time Min./ Molecular Mass | Prepared in the manner described in: |
|---|---|---|---|---|
| 844 | 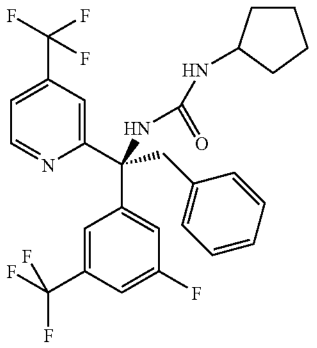 | (S)-1-cyclopentyl-3-(1-(3-fluoro-5-(trifluoromethyl)phenyl)-2-phenyl-1-(4-(trifluoromethyl)pyridin-2-yl)ethyl)urea | 4.20 LC 540.24 $[M + H]^+$ | Procedures 37 and 2 |
| 845 | 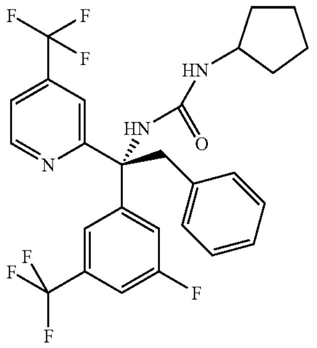 | (R)-1-cyclopentyl-3-(1-(3-fluoro-5-(trifluoromethyl)phenyl)-2-phenyl-1-(4-(trifluoromethyl)pyridin-2-yl)ethyl)urea | 4.20 LC 540.24 $[M + H]^+$ | Procedures 37 and 2 |
| 846 | 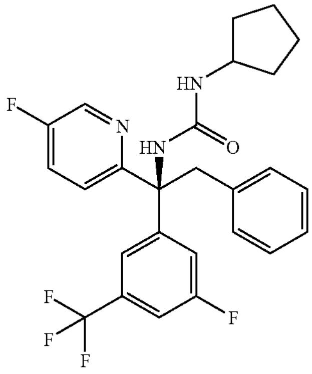 | (S)-1-cyclopentyl-3-(1-(3-fluoro-5-(trifluoromethyl)phenyl)-1-(5-fluoropyridin-2-yl)-2-phenylethyl)urea | 3.96 LC 490.55 $[M + H]^+$ | Procedures 40 and 2 |
| 847 | 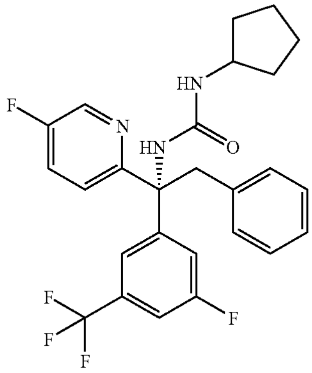 | (R)-1-cyclopentyl-3-(1-(3-fluoro-5-(trifluoromethyl)phenyl)-1-(5-fluoropyridin-2-yl)-2-phenylethyl)urea | 3.97 LC 490.61 $[M + H]^+$ | Procedures 40 and 2 |

TABLE 8-continued

| Ex. No. | Structure | Name | Retention Time Min./ Molecular Mass | Prepared in the manner described in: |
|---|---|---|---|---|
| 848 | 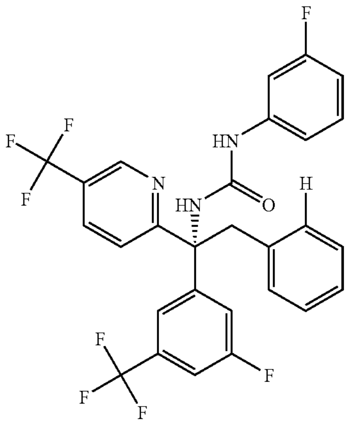 | (R)-1-(1-(3-fluoro-5-(trifluoromethyl)phenyl)-2-phenyl-1-(5-(trifluoromethyl)pyridin-2-yl)ethyl)-3-(3-fluorophenyl)urea | 4.13 LC 566.23 [M + H]+ | Procedure 1 and 2 |
| 849 | 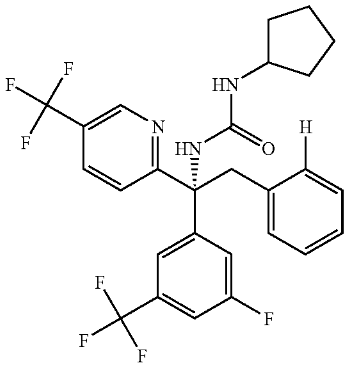 | (R)-1-cyclopentyl-3-(1-(3-fluoro-5-(trifluoromethyl)phenyl)-2-phenyl-1-(5-(trifluoromethyl) pyridin-2-yl)ethyl)urea | 4.12 LC 540.26 [M + H]+ | Procedure 1 and 2 |
| 850 | 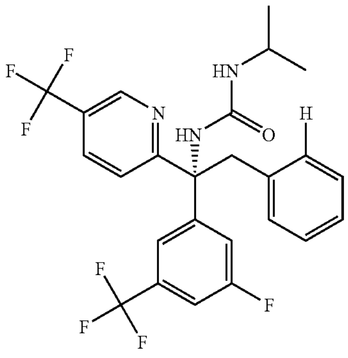 | (R)-1-(1-(3-fluoro-5-(trifluoromethyl)phenyl)-2-phenyl-1-(5-(trifluoromethyl)pyridin-2-yl)ethyl)-3-isopropylurea | 4.00 LC 514.22 [M + H]+ | Procedure 1 and 2 |
| 851 | 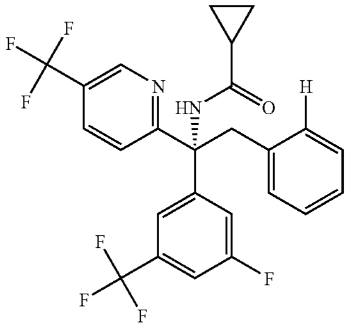 | (R)-N-(1-(3-fluoro-5-(trifluoromethyl)phenyl)-2-phenyl-1-(5-(trifluoromethyl)pyridin-2-yl)ethyl)cyclopropanecarboxamide | 4.02 LC 497.20 [M + H]+ | Procedure 1 and 4 |

TABLE 8-continued

| Ex. No. | Structure | Name | Retention Time Min./ Molecular Mass | Prepared in the manner described in: |
|---|---|---|---|---|
| 852 | 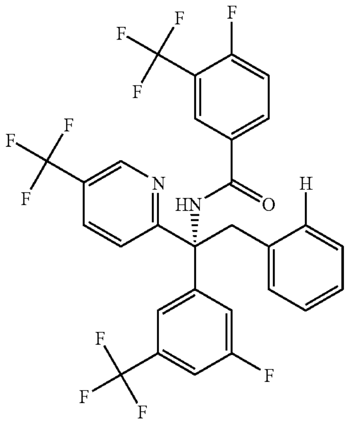 | (R)-4-fluoro-N-(1-(3-fluoro-5-(trifluoromethyl)phenyl)-2-phenyl-1-(5-(trifluoromethyl)pyridin-2-yl)ethyl)-3-(trifluoromethyl) benzamide | 4.30 LC 619.24 [M + H]$^+$ | Procedure 1 and 4 |
| 853 | 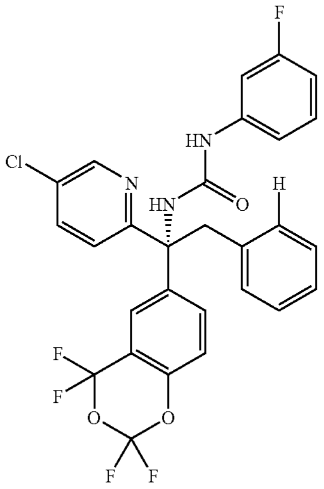 | (R)-1-(1-(5-chloropyridin-2-yl)-2-phenyl-1-(2,2,4,4-tetrafluoro-4H-benzo[d][1,3]dioxin-6-yl)ethyl)-3-(3-fluorophenyl)urea | 4.16 LC 576.17 [M + H]$^+$ | Procedure 1 and 2 |
| 854 | 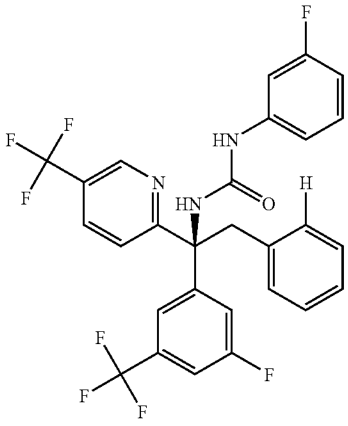 | (S)-1-(1-(3-fluoro-5-(trifluoromethyl)phenyl)-2-phenyl-1-(5-(trifluoromethyl)pyridin-2-yl)ethyl)-3-(3-fluorophenyl)urea | 4.12 LC 566.21 [M + H]$^+$ | Procedure 1 and 2 |

TABLE 8-continued

| Ex. No. | Structure | Name | Retention Time Min./ Molecular Mass | Prepared in the manner described in: |
|---|---|---|---|---|
| 855 | 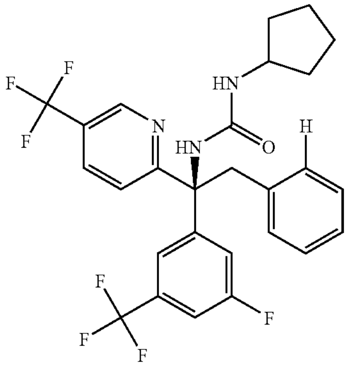 | (S)-1-cyclopentyl-3-(1-(3-fluoro-5-(trifluoromethyl)phenyl)-2-phenyl-1-(5-(trifluoromethyl)pyridin-2-yl) ethyl)urea | 4.11 LC 540.28 [M + H]+ | Procedure 1 and 2 |
| 856 | 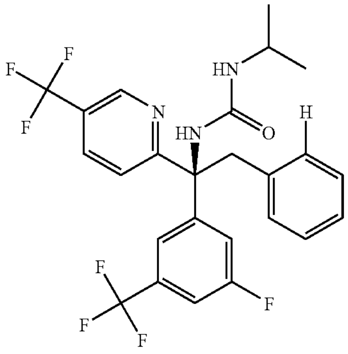 | (S)-1-(1-(3-fluoro-5-(trifluoromethyl)phenyl)-2-phenyl-1-(5-(trifluoromethyl)pyridin-2-yl) ethyl)-3-isopropylurea | 4.00 LC 514.24 [M + H]+ | Procedure 1 and 2 |
| 857 | 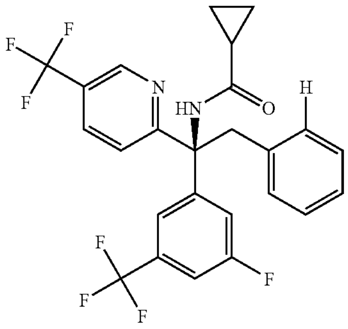 | (S)-N-(1-(3-fluoro-5-(trifluoromethyl)phenyl)-2-phenyl-1-(5-(trifluoromethyl)pyridin-2-yl) ethyl)cyclopropanecarboxamide | 4.00 LC 497.20 [M + H]+ | Procedure 1 and 4 |

Additional compounds of the present invention were prepared by procedures analogous to those described above and to the additional procedures described below. The absolute configuration of chiral examples was initially determined by obtaining an X-ray of crystalline material intermediate sulfinyl amides and subsequently by NMR comparison of the diastereomers.

EXAMPLE 857

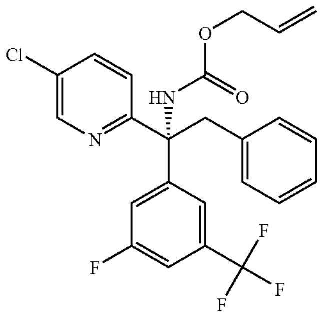

(R)-allyl 1-(5-chloropyridin-2-yl)-1-(3-fluoro-5-(trifluoromethyl)phenyl)-2-phenylethylcarbamate Procedure 46

(R)-1-(5-chloropyridin-2-yl)-1-(3-fluoro-5-(trifluoromethyl)phenyl)-2-phenylethanamine was dissolved in DCE (400 uL, 0.1 M in DCE, 40 umol) and potassium carbonate added (100 mg, 723 umol, 18 eq), followed by allyl carbonochloridate (400 uL, 0.2 M in DCE, 80 umol, 2.0 eq). The reaction mixture was agitated at room temperature for 18 h and then filtered and rinsed with DCE (2×250 uL). The combined filtrate was evaporated and the residue was redissolved in 1 mL of MeOH and purified by reverse phase preparative HPLC using MeOH:water:TFA system. (R)-allyl 1-(5-chloropyridin-2-yl)-1-(3-fluoro-5-(trifluoromethyl)phenyl)-2-phenylethylcarbamate was obtained as a colorless oil (13.2 umol, 33% yield). LCMS: M+calc=478.11; found=479.35.

TABLE 9

| Ex. No. | Structure | Name | Retention Time Min/ Molecular Mass | Prepared in the manner described in: |
|---|---|---|---|---|
| 858 | 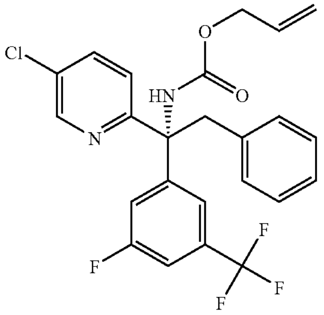 | (R)-allyl 1-(5-chloropyridin-2-yl)-1-(3-fluoro-5-(trifluoromethyl) phenyl)-2-phenylethylcarbamate | 4.23 LC 479.35 $[M + H]^+$ | Procedures 1 and 46 |
| 859 | 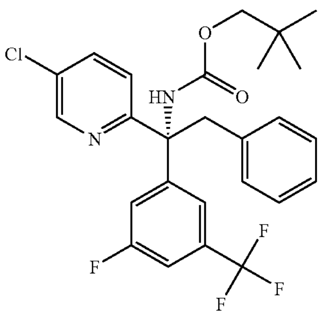 | (R)-neopentyl 1-(5-chloropyridin-2-yl)-1-(3-fluoro-5-(trifluoromethyl)phenyl)-2-phenylethylcarbamate | 4.43 LC 509.35 $[M + H]^+$ | Procedures 1 and 46 |

TABLE 9-continued

| Ex. No. | Structure | Name | Retention Time Min/ Molecular Mass | Prepared in the manner described in: |
|---|---|---|---|---|
| 860 | 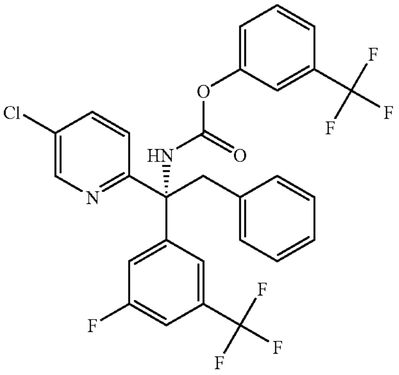 | (R)-3-(trifluoromethyl)phenyl 1-(5-chloropyridin-2-yl)-1-(3-fluoro-5-(trifluoromethyl)phenyl)-2-phenylethylcarbamate | 4.47 LC 583.3 $[M + H]^+$ | Procedures 1 and 46 |
| 861 | 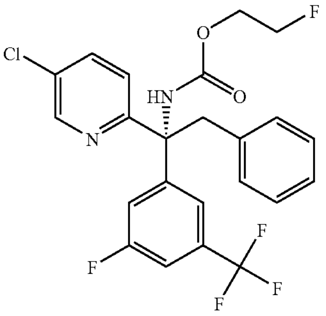 | (R)-2-fluoroethyl 1-(5-chloropyridin-2-yl)-1-(3-fluoro-5-(trifluoromethyl)phenyl)-2-phenylethylcarbamate | 4.05 LC 485.32 $[M + H]^+$ | Procedures 1 and 46 |
| 862 | 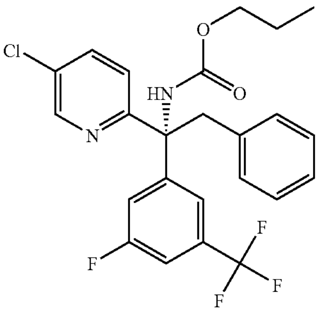 | (R)-propyl 1-(5-chloropyridin-2-yl)-1-(3-fluoro-5-(trifluoromethyl) phenyl)-2-phenylethylcarbamate | 4.28 LC 481.35 $[M + H]^+$ | Procedures 1 and 46 |
| 863 | 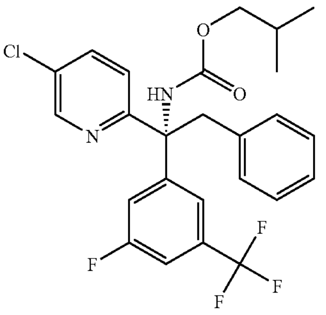 | (R)-isobutyl 1-(5-chloropyridin-2-yl)-1-(3-fluoro-5-(trifluoromethyl) phenyl)-2-phenylethylcarbamate | 4.37 LC 495.35 $[M + H]^+$ | Procedures 1 and 46 |

TABLE 9-continued

| Ex. No. | Structure | Name | Retention Time Min/ Molecular Mass | Prepared in the manner described in: |
|---|---|---|---|---|
| 864 | 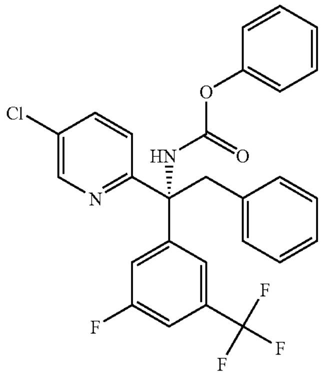 | (R)-phenyl 1-(5-chloropyridin-2-yl)-1-(3-fluoro-5-(trifluoromethyl)phenyl)-2-phenylethylcarbamate | 4.31 LC 515.32 $[M+H]^+$ | Procedures 1 and 46 |
| 865 | 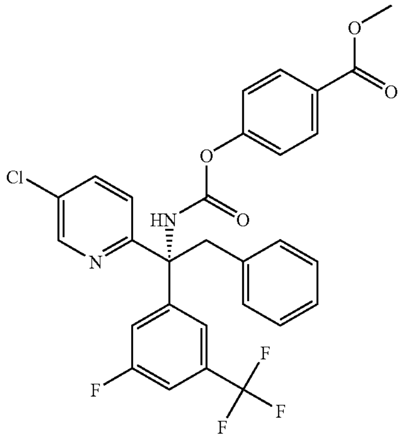 | (R)-methyl 4-(1-(5-chloropyridin-2-yl)-1-(3-fluoro-5-(trifluoromethyl)phenyl)-2-phenylethylcarbamoyloxy) benzoate | 4.33 LC 573.28 $[M+H]^+$ | Procedures 1 and 46 |
| 866 | 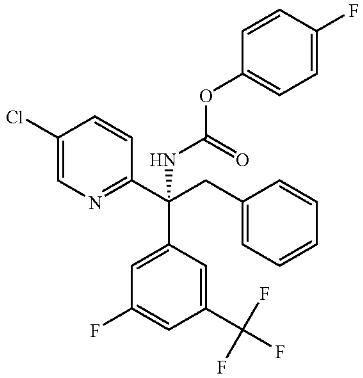 | (R)-4-fluorophenyl 1-(5-chloropyridin-2-yl)-1-(3-fluoro-5-(trifluoromethyl)phenyl)-2-phenylethylcarbamate | 4.32 LC 533.28 $[M+H]^+$ | Procedures 1 and 46 |

TABLE 9-continued

| Ex. No. | Structure | Name | Retention Time Min/ Molecular Mass | Prepared in the manner described in: |
|---|---|---|---|---|
| 867 | 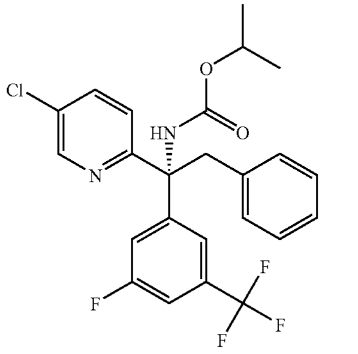 | (R)-isopropyl 1-(5-chloropyridin-2-yl)-1-(3-fluoro-5-(trifluoromethyl)phenyl)-2-phenylethylcarbamate | 4.27 LC 481.35 [M + H]+ | Procedures 1 and 46 |
| 868 | 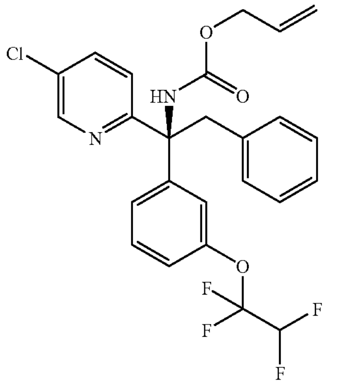 | (S)-allyl 1-(5-chloropyridin-2-yl)-2-phenyl-1-(3-(1,1,2,2-tetrafluoroethoxy)phenyl) ethylcarbamate | 4.09 LC 509.33 [M + H]+ | Procedures 1 and 46 |
| 869 | 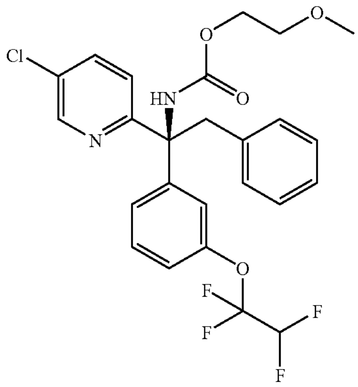 | (S)-2-methoxyethyl 1-(5-chloropyridin-2-yl)-2-phenyl-1-(3-(1,1,2,2-tetrafluoroethoxy)phenyl) ethylcarbamate | 3.91 LC 527.32 [M + H]+ | Procedures 1 and 46 |

TABLE 9-continued

| Ex. No. | Structure | Name | Retention Time Min/ Molecular Mass | Prepared in the manner described in: |
|---|---|---|---|---|
| 870 | 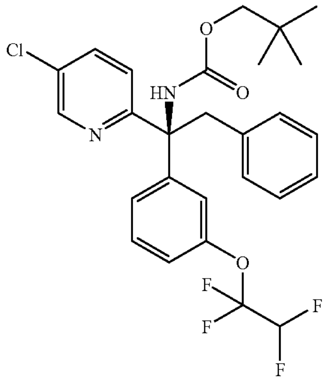 | (S)-neopentyl 1-(5-chloropyridin-2-yl)-2-phenyl-1-(3-(1,1,2,2-tetrafluoroethoxy)phenyl) ethylcarbamate | 4.28 LC 539.35 $[M + H]^+$ | Procedures 1 and 46 |
| 871 | 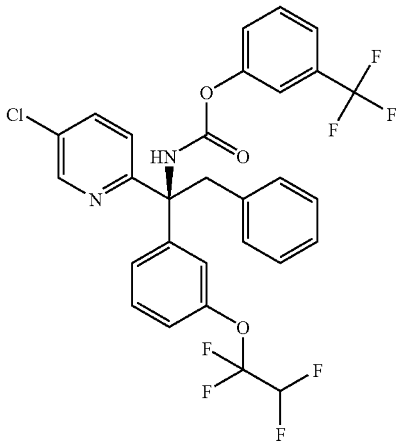 | (S)-3-(trifluoromethyl)phenyl 1-(5-chloropyridin-2-yl)-2-phenyl-1-(3-(1,1,2,2-tetrafluoroethoxy) phenyl)ethylcarbamate | 4.33 LC 613.28 $[M + H]^+$ | Procedures 1 and 46 |
| 872 | 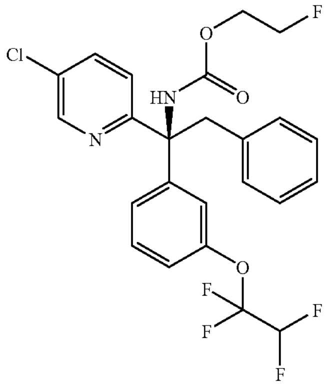 | (S)-2-fluoroethyl 1-(5-chloropyridin-2-yl)-2-phenyl-1-(3-(1,1,2,2-tetrafluoroethoxy)phenyl) ethylcarbamate | 3.93 LC 515.33 $[M + H]^+$ | Procedures 1 and 46 |

TABLE 9-continued

| Ex. No. | Structure | Name | Retention Time Min/ Molecular Mass | Prepared in the manner described in: |
|---|---|---|---|---|
| 873 | 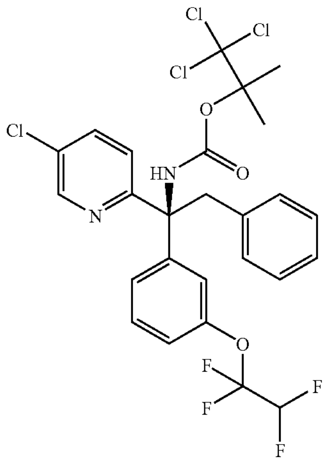 | (S)-1,1,1-trichloro-2-methylpropan-2-yl 1-(5-chloropyridin-2-yl)-2-phenyl-1-(3-(1,1,2,2-tetrafluoroethoxy)phenyl) ethylcarbamate | 4.42 LC 629.17 $[M + H]^+$ | Procedures 1 and 46 |
| 874 | 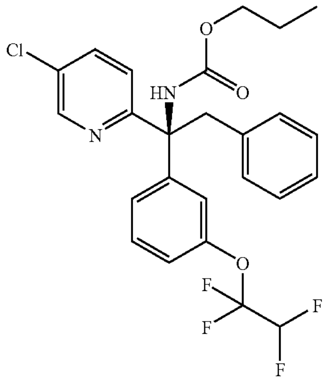 | (S)-propyl 1-(5-chloropyridin-2-yl)-2-phenyl-1-(3-(1,1,2,2-tetrafluoroethoxy)phenyl) ethylcarbamate | 4.15 LC 511.35 $[M + H]^+$ | Procedures 1 and 46 |
| 875 | 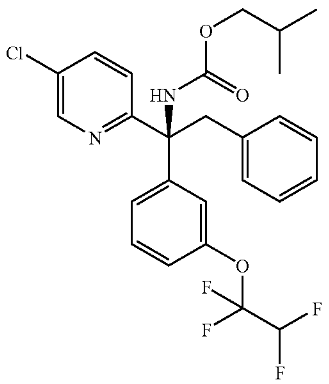 | (S)-isobutyl 1-(5-chloropyridin-2-yl)-2-phenyl-1-(3-(1,1,2,2-tetrafluoroethoxy)phenyl) ethylcarbamate | 4.23 LC 525.35 $[M + H]^+$ | Procedures 1 and 46 |

TABLE 9-continued

| Ex. No. | Structure | Name | Retention Time Min/ Molecular Mass | Prepared in the manner described in: |
|---|---|---|---|---|
| 876 | 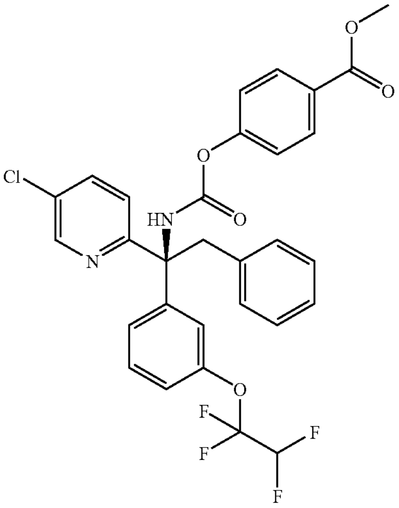 | (S)-methyl 4-(1-(5-chloropyridin-2-yl)-2-phenyl-1-(3-(1,1,2,2-tetrafluoroethoxy)phenyl) ethylcarbamoyloxy)benzoate | 4.22 LC 603.3 [M + H]+ | Procedures 1 and 46 |
| 877 | 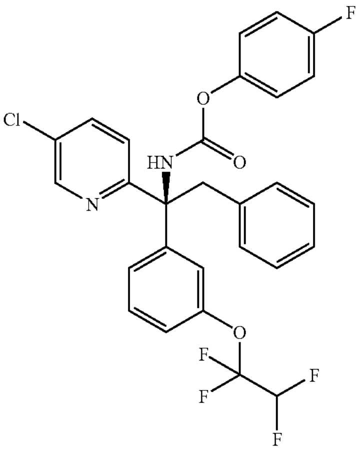 | (S)-4-fluorophenyl 1-(5-chloropyridin-2-yl)-2-phenyl-1-(3-(1,1,2,2-tetrafluoroethoxy)phenyl) ethylcarbamate | 4.20 LC 563.29 [M + H]+ | Procedures 1 and 46 |
| 878 | 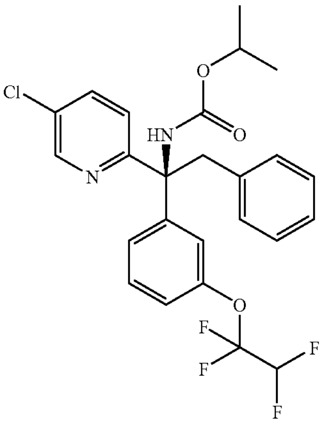 | (S)-isopropyl 1-(5-chloropyridin-2-yl)-2-phenyl-1-(3-(1,1,2,2-tetrafluoroethoxy)phenyl) ethylcarbamate | 4.13 LC 511.35 [M + H]+ | Procedures 1 and 46 |

TABLE 9-continued

| Ex. No. | Structure | Name | Retention Time Min/ Molecular Mass | Prepared in the manner described in: |
|---|---|---|---|---|
| 879 | 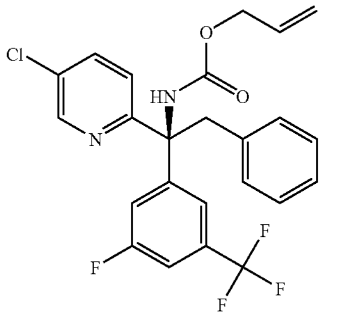 | (S)-allyl 1-(5-chloropyridin-2-yl)-1-(3-fluoro-5-(trifluoromethyl) phenyl)-2-phenylethylcarbamate | 4.23 LC 499.41 $[M + H]^+$ | Procedures 1 and 46 |
| 880 | 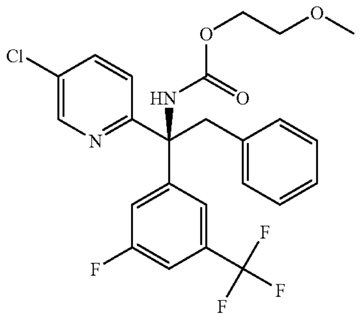 | (S)-2-methoxyethyl 1-(5-chloropyridin-2-yl)-1-(3-fluoro-5-(trifluoromethyl)phenyl)-2-phenylethylcarbamate | 4.05 LC 497.45 $[M + H]^+$ | Procedures 1 and 46 |
| 881 | 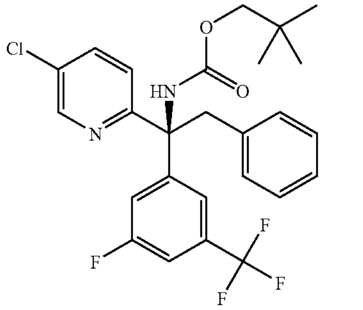 | (S)-neopentyl 1-(5-chloropyridin-2-yl)-1-(3-fluoro-5-(trifluoromethyl)phenyl)-2-phenylethylcarbamate | 4.42 LC 509.48 $[M + H]^+$ | Procedures 1 and 46 |
| 882 | 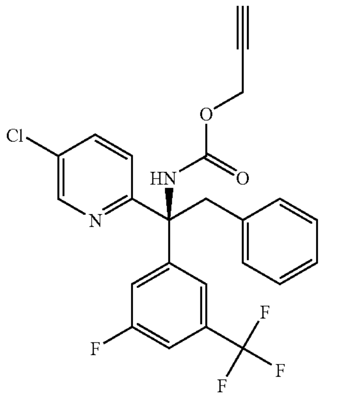 | (S)-prop-2-ynyl 1-(5-chloropyridin-2-yl)-1-(3-fluoro-5-(trifluoromethyl)phenyl)-2-phenylethylcarbamate | 4.08 LC 477.42 $[M + H]^+$ | Procedures 1 and 46 |

TABLE 9-continued

| Ex. No. | Structure | Name | Retention Time Min/ Molecular Mass | Prepared in the manner described in: |
|---|---|---|---|---|
| 883 | 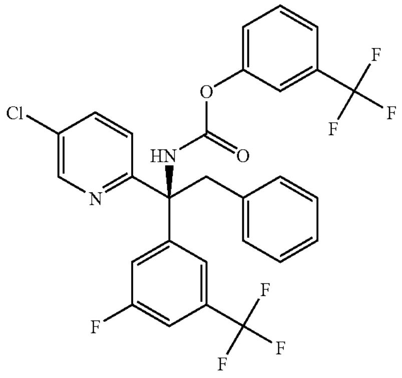 | (S)-3-(trifluoromethyl)phenyl 1-(5-chloropyridin-2-yl)-1-(3-fluoro-5-(trifluoromethyl)phenyl)-2-phenylethylcarbamate | 4.48 LC 583.4 $[M + H]^+$ | Procedures 1 and 46 |
| 884 | 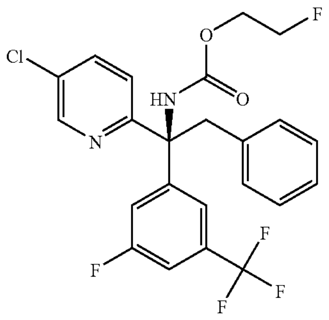 | (S)-2-fluoroethyl 1-(5-chloropyridin-2-yl)-1-(3-fluoro-5-(trifluoromethyl)phenyl)-2-phenylethylcarbamate | 4.05 LC 583.4 $[M + H]^+$ | Procedures 1 and 46 |
| 885 | 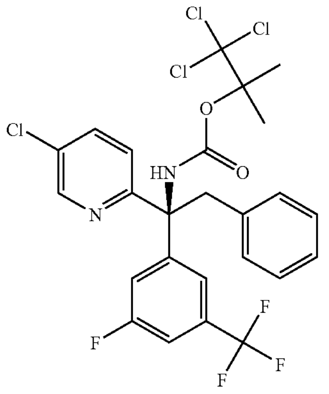 | (S)-1,1,1-trichloro-2-methylpropan-2-yl 1-(5-chloropyridin-2-yl)-1-(3-fluoro-5-(trifluoromethyl)phenyl)-2-phenylethylcarbamate | 4.66 LC 599.31 $[M + H]^+$ | Procedures 1 and 46 |
| 886 | 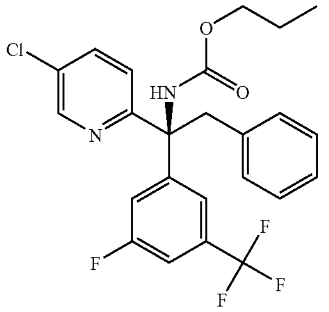 | (S)-propyl 1-(5-chloropyridin-2-yl)-1-(3-fluoro-5-(trifluoromethyl) phenyl)-2-phenylethylcarbamate | 4.28 LC 481.45 $[M + H]^+$ | Procedures 1 and 46 |

TABLE 9-continued

| Ex. No. | Structure | Name | Retention Time Min/ Molecular Mass | Prepared in the manner described in: |
|---|---|---|---|---|
| 887 | 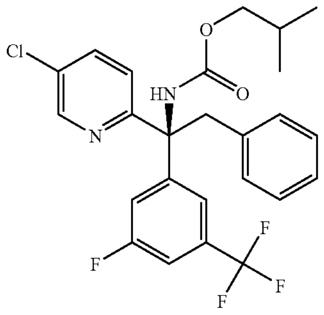 | (S)-isobutyl 1-(5-chloropyridin-2-yl)-1-(3-fluoro-5-(trifluoromethyl) phenyl)-2-phenylethylcarbamate | 4.37 LC 495.47 $[M + H]^+$ | Procedures 1 and 46 |
| 888 | 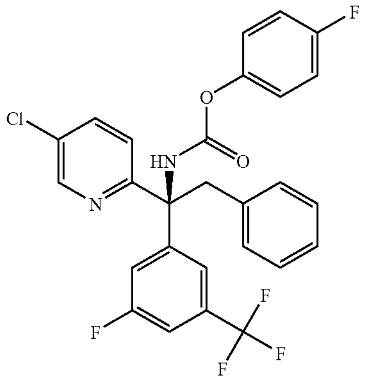 | (S)-4-fluorophenyl 1-(5-chloropyridin-2-yl)-1-(3-fluoro-5-(trifluoromethyl)phenyl)-2-phenylethylcarbamate | 4.32 LC 533.42 $[M + H]^+$ | Procedures 1 and 46 |
| 889 | 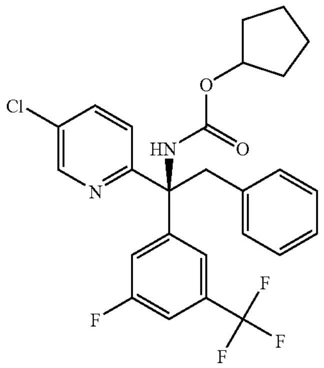 | (S)-cyclopentyl 1-(5-chloropyridin-2-yl)-1-(3-fluoro-5-(trifluoromethyl)phenyl)-2-phenylethylcarbamate | 4.38 LC 507.48 $[M + H]^+$ | Procedures 1 and 46 |

TABLE 9-continued

| Ex. No. | Structure | Name | Retention Time Min/ Molecular Mass | Prepared in the manner described in: |
|---|---|---|---|---|
| 890 | 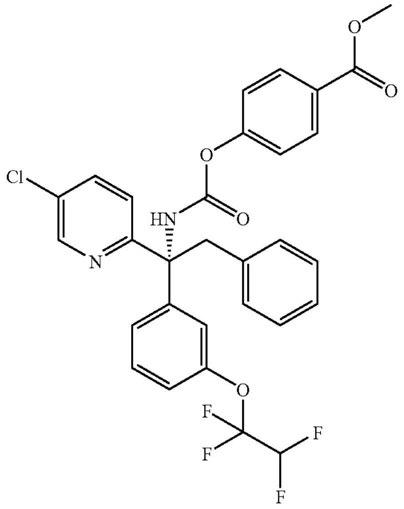 | (R)-methyl 4-((1-(5-chloropyridin-2-yl)-2-phenyl-1-(3-(1,1,2,2-tetrafluoroethoxy)phenyl)ethyl) carbamoyloxy)benzoate | 4.20 LC 603.42 $[M + H]^+$ | Procedures 1 and 46 |
| 891 | 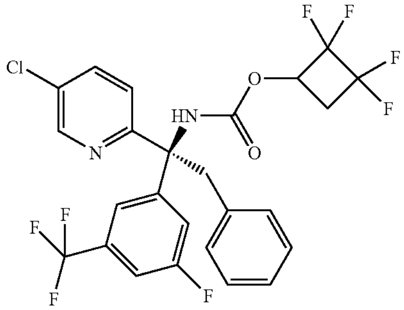 | 2,2,3,3-tetrafluorocyclobutyl (S)-1-(5-chloropyridin-2-yl)-1-(3-fluoro-5-(trifluoromethyl)phenyl)-2-phenylethylcarbamate | 4.23 LC 565.1 $[M + H]^+$ | Procedures 5, 6, 7 and 8 |

Additional compounds of the present invention were prepared by procedures analogous to those described above and to the additional procedures described below. The absolute configuration of chiral examples was initially determined by obtaining an X-ray of crystalline material intermediate sulfinyl amides and subsequently by NMR comparison of the diastereomers.

EXAMPLE 892

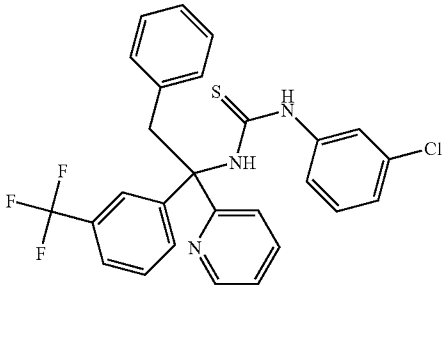

1-(3-chlorophenyl)-3-(2-phenyl-1-(pyridin-2-yl)-1-(3-(trifluoromethyl)phenyl)ethyl)thiourea Procedure 47

1-(Pyridin-2-yl)-1-(3-(trifluoromethyl)phenyl)-2-phenylethanamine was dissolved in dioxane (40 uL, 0.5 M in dioxane, 20 umol) and 3-chlorophenylisothiocyanate was added (200 uL, 0.2 M in dioxane, 40 umol, 2.0 eq). The reaction mixture was agitated at room temperature for 18 h The solvent was evaporated and the residue was redissolved in 1 mL of MeOH and purified by reverse phase preparative HPLC using MeOH:water:TFA system. 1-(3-chlorophenyl)-3-(2-phenyl-1-(pyridin-2-yl)-1-(3-(trifluoromethyl)phenyl) ethyl)thiourea was obtained a colorless oil (13.9 umol, 69% yield). LCMS: M+calc=511.11; found=511.98.

TABLE 10

| Ex. No. | Structure | Name | Retention Time Min./ Molecular Mass | Prepared in the manner described in: |
|---|---|---|---|---|
| 893 | 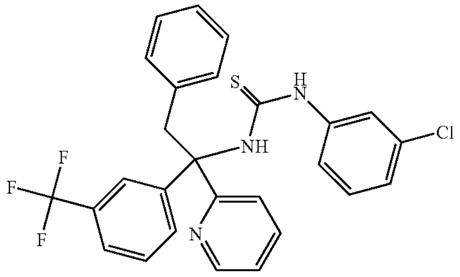 | 1-(3-chlorophenyl)-3-(2-phenyl-1-(pyridin-2-yl)-1-(3-(trifluoromethyl)phenyl)ethyl) thiourea | 2.08 LC 511.98 [M + H]$^+$ | Procedures 1 and 47 |
| 894 | 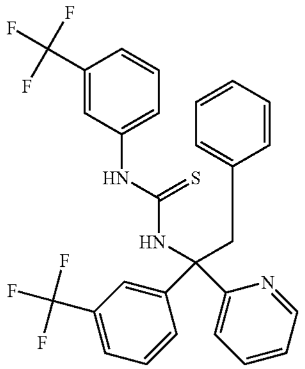 | 1-(2-phenyl-1-(pyridin-2-yl)-1-(3-(trifluoromethyl)phenyl) ethyl)-3-(3-(trifluoromethyl) phenyl)thiourea | 2.09 LC 546.02 [M + H]$^+$ | Procedures 1 and 47 |

Additional compounds of the present invention were prepared by procedures analogous to those described above and to the additional procedures described below.

EXAMPLE 895

1-(5-chloropyridin-2-yl)-1-(3-fluoro-5-(trifluoromethyl)phenyl)-N-((4-methyl-1H-imidazol-5-yl)methyl)-2-phenylethanamine

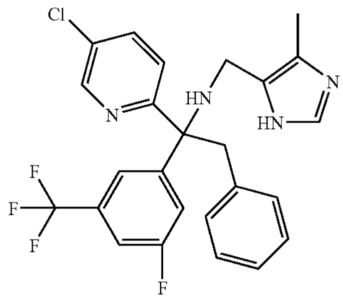

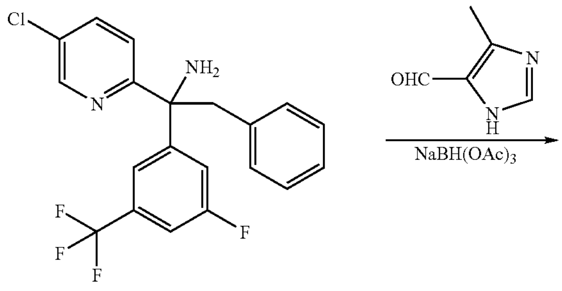

-continued

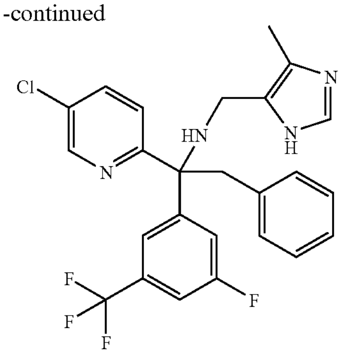

To a solution of 1-(5-chloropyridin-2-yl)-1-(3-fluoro-5-(trifluoromethyl)phenyl)-2-phenylethanamine (0.02 g, 0.051 mmol) in dichloroethane (0.5 mL) in a two dram vial was added 4-methyl-1H-imidazole-5-carbaldehyde (6 mg, 0.051 mmol), followed by a drop of acetic acid. The reaction mixture was shaken for 20 minutes at room temperature and then $NaBH(OAc)_3$ was added (12 mg, 0.056 mmol). The reaction was stirred at room temperature overnight. The solvents were removed and the residue was purified by preparative HPLC (phenominex C18 column, 21×100 mm, 5μ) using MeOH/$H_2O$ (with 0.1% TFA) to give 1-(5-chloropyridin-2-yl)-1-(3-fluoro-5-(trifluoromethyl)phenyl)-N-((4-methyl-1H-imidazol-5-yl)methyl)-2-phenylethanamine as a white solid (23.4 mg, 76% yield). LCMS: 3.6 min [M+1] 489.2 (4 min gradient, MeOH/$H_2O$ 0.1% TFA); 1H NMR (400 MHz, $CDCl_3$) δ ppm 2.27 (s, 3 H), 3.45-3.52 (m, 1 H), 3.88-3.99 (m, 2 H), 4.01-4.07 (m, 1 H), 6.64 (d, J=7.09 Hz, 2 H), 7.02 (d, J=8.56 Hz, 1 H), 7.10 (t, J=7.46 Hz, 2 H), 7.18 (t, J=7.46 Hz, 1 H), 7.49 (d, J=7.58 Hz, 1 H), 7.61 (d, J=9.54 Hz, 1 H), 7.69 (s, 1 H), 7.76 (dd, J=8.56, 2.45 Hz, 1 H), 8.28 (s, 1 H), 8.60 (d, J=1.96 Hz, 1 H).

TABLE 11

| Ex. No. | Structure | Name | Retention Time Min./ Molecular Mass | Prepared in the manner described in: |
|---|---|---|---|---|
| 896 | 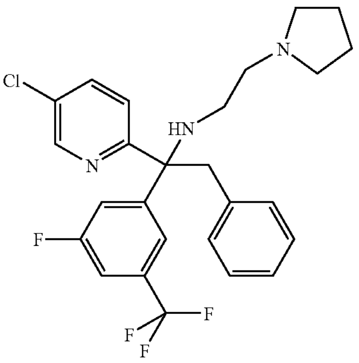 | 1-(5-chloropyridin-2-yl)-1-(3-fluoro-5-(trifluoromethyl) phenyl)-2-phenyl-N-(2-(pyrrolidin-1-yl)ethyl) ethanamine | 3.40 LC 492.27 $[M + H]^+$ | Procedures 1 and 48 |
| 897 | 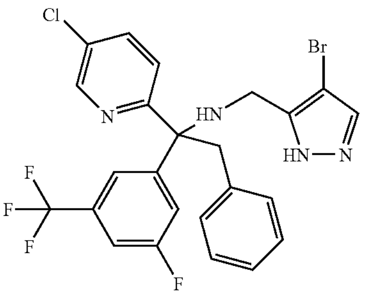 | N-((4-bromo-1H-pyrazol-5-yl) methyl)-1-(5-chloropyridin-2-yl)-1-(3-fluoro-5-(trifluoromethyl)phenyl)-2-phenylethanamine | 3.88 LC 553.23 $[M + H]^+$ | Procedures 1 and 48 |
| 898 | 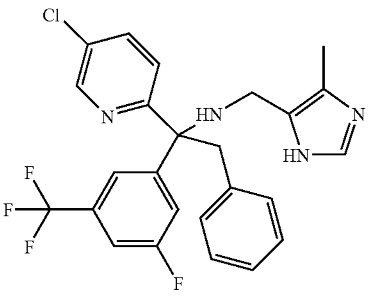 | 1-(5-chloropyridin-2-yl)-1-(3-fluoro-5-(trifluoromethyl) phenyl)-N-((4-methyl-1H-imidazol-5-yl)methyl)-2-phenylethanamine | 3.45 LC 489.29 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 899 | 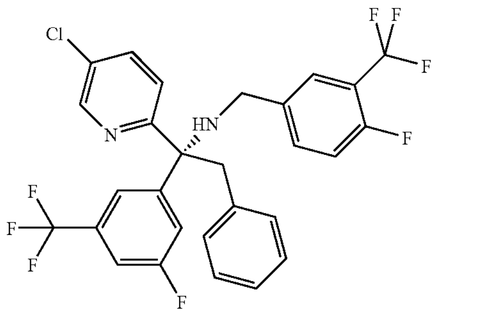 | (R)-N-(4-fluoro-3-(trifluoromethyl)benzyl)-1-(5-chloropyridin-2-yl)-1-(3-fluoro-5-(trifluoromethyl)phenyl)-2-phenylethanamine | 4.14 LC 571.29 $[M + H]^+$ | Procedures 1 and 48 |
| 900 | 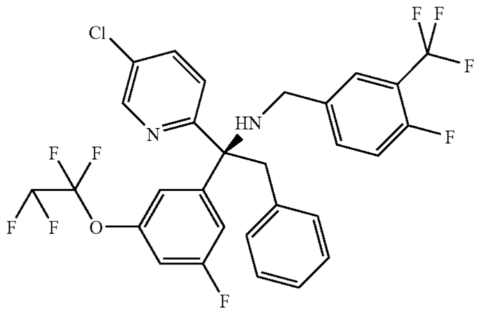 | (S)-N-(4-fluoro-3-(trifluoromethyl)benzyl)-1-(5-chloropyridin-2-yl)-1-(3-fluoro-5-(1,1,2,2-tetrafluoroethoxy) phenyl)-2-phenylethanamine | 3.92 LC 619.39 $[M + H]^+$ | Procedures 3, 5, 6, 7 and 48 |
| 901 | 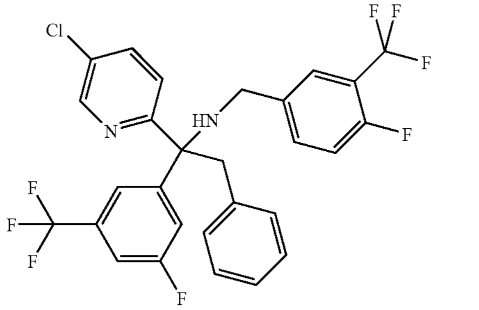 | N-(4-fluoro-3-(trifluoromethyl) benzyl)-1-(5-chloropyridin-2-yl)-1-(3-fluoro-5-(trifluoromethyl)phenyl)-2-phenylethanamine | 4.14 LC 571.14 $[M + H]^+$ | Procedures 1 and 48 |
| 902 | 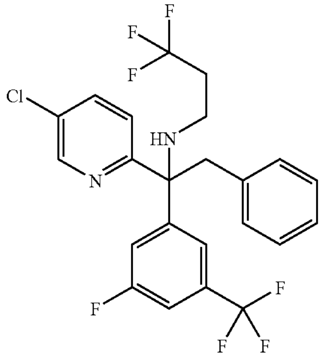 | N-(1-(5-chloropyridin-2-yl)-1-(3-fluoro-5-(trifluoromethyl) phenyl)-2-phenylethyl)-3,3,3-trifluoropropan-1-amine | 3.94 LC 491.18 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 903 | 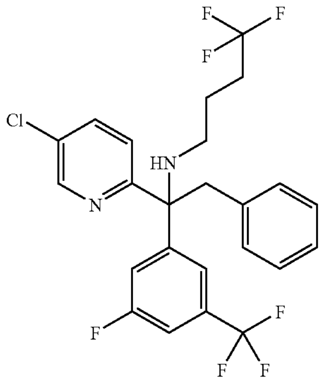 | N-(1-(5-chloropyridin-2-yl)-1-(3-fluoro-5-(trifluoromethyl) phenyl)-2-phenylethyl)-4,4,4-trifluorobutan-1-amine | 3.40 LC 505.19 $[M + H]^+$ | Procedures 1 and 48 |
| 904 | 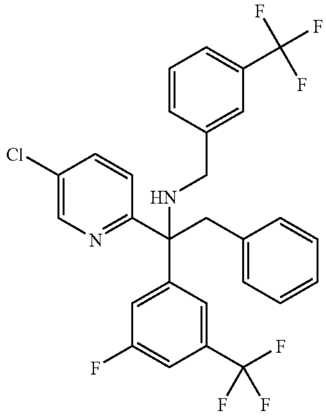 | N-(3-(trifluoromethyl)benzyl)-1-(5-chloropyridin-2-yl)-1-(3-fluoro-5-(trifluoromethyl) phenyl)-2-phenylethanamine | 4.06 LC 553.22 $[M + H]^+$ | Procedures 1 and 48 |
| 905 | 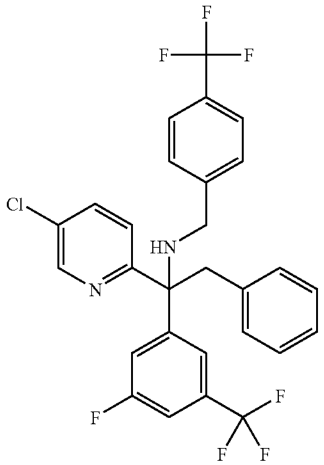 | N-(4-(trifluoromethyl)benzyl)-1-(5-chloropyridin-2-yl)-1-(3-fluoro-5-(trifluoromethyl) phenyl)-2-phenylethanamine | 4.08 LC 553.22 $[M + H]^+$ | Procedures 1 and 48 |

TABLE 11-continued

| Ex. No. | Structure | Name | Retention Time Min./ Molecular Mass | Prepared in the manner described in: |
| --- | --- | --- | --- | --- |
| 906 | 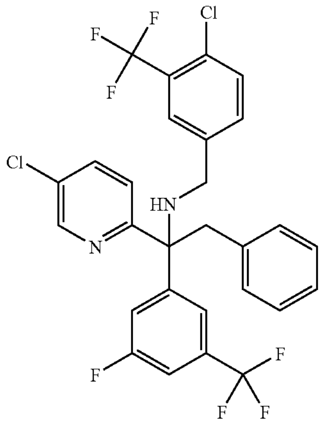 | N-(4-chloro-3-(trifluoromethyl) benzyl)-1-(5-chloropyridin-2-yl)-1-(3-fluoro-5-(trifluoromethyl)phenyl)-2-phenylethanamine | 4.26 LC 587.16 $[M + H]^+$ | Procedures 1 and 48 |
| 907 | 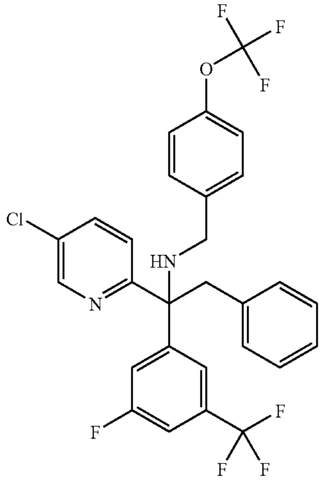 | N-(4-(trifluoromethoxy) benzyl)-1-(5-chloropyridin-2-yl)-1-(3-fluoro-5-(trifluoromethyl)phenyl)-2-phenylethanamine | 4.00 LC 569.18 $[M + H]^+$ | Procedures 1 and 48 |
| 908 | 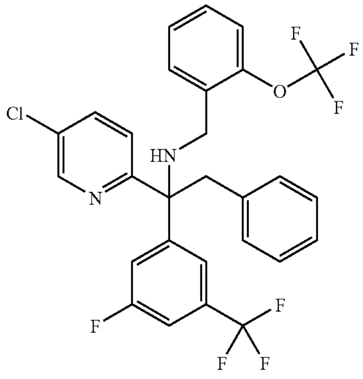 | N-(2-(trifluoromethoxy) benzyl)-1-(5-chloropyridin-2-yl)-1-(3-fluoro-5-(trifluoromethyl)phenyl)-2-phenylethanamine | 4.22 LC 569.19 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 909 | 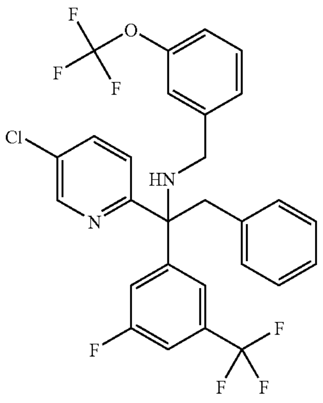 | N-(3-(trifluoromethoxy) benzyl)-1-(5-chloropyridin-2-yl)-1-(3-fluoro-5-(trifluoromethyl)phenyl)-2-phenylethanamine | 4.10 LC 569.16 [M + H]+ | Procedures 1 and 48 |
| 910 | 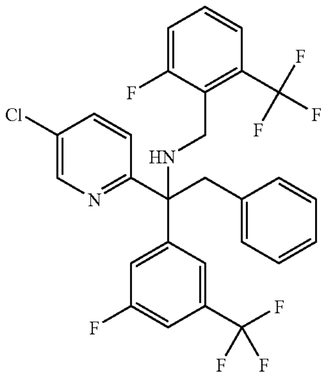 | N-(2-fluoro-6-(trifluoromethyl) benzyl)-1-(5-chloropyridin-2-yl)-1-(3-fluoro-5-(trifluoromethyl)phenyl)-2-phenylethanamine | 4.47 LC 571.17 [M + H]+ | Procedures 1 and 48 |
| 911 | 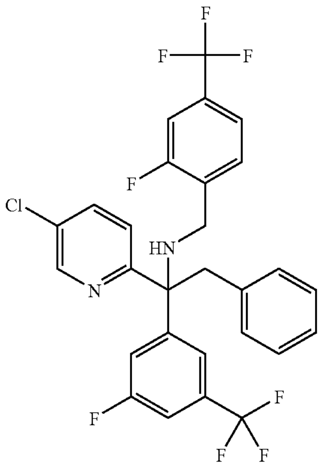 | N-(2-fluoro-4-(trifluoromethyl) benzyl)-1-(5-chloropyridin-2-yl)-1-(3-fluoro-5-(trifluoromethyl)phenyl)-2-phenylethanamine | 4.37 LC 571.18 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 912 | 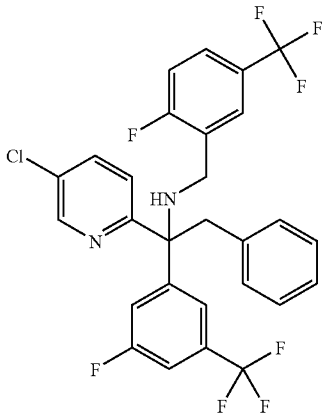 | N-(2-fluoro-5-(trifluoromethyl) benzyl)-1-(5-chloropyridin-2-yl)-1-(3-fluoro-5-(trifluoromethyl)phenyl)-2-phenylethanamine | 4.28 LC 571.17 $[M + H]^+$ | Procedures 1 and 48 |
| 913 | 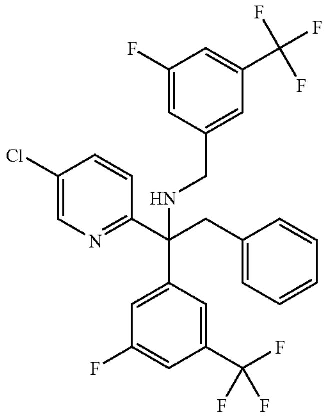 | N-(3-fluoro-5-(trifluoromethyl) benzyl)-1-(5-chloropyridin-2-yl)-1-(3-fluoro-5-(trifluoromethyl)phenyl)-2-phenylethanamine | 4.32 LC 571.19 $[M + H]^+$ | Procedures 1 and 48 |
| 914 | 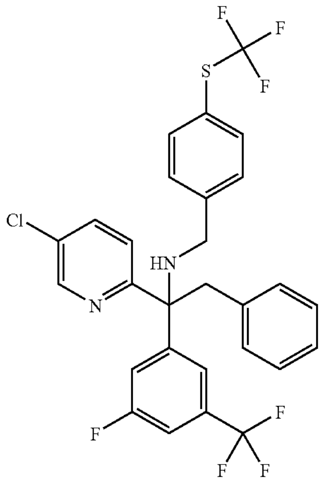 | N-(4-(trifluoromethylthio) benzyl)-1-(5-chloropyridin-2-yl)-1-(3-fluoro-5-(trifluoromethyl)phenyl)-2-phenylethanamine | 4.18 LC 585.18 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 915 | 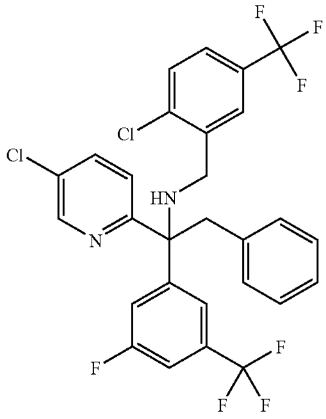 | N-(2-chloro-5-(trifluoromethyl) benzyl)-1-(5-chloropyridin-2-yl)-1-(3-fluoro-5-(trifluoromethyl)phenyl)-2-phenylethanamine | 4.55 LC 587.18 $[M + H]^+$ | Procedures 1 and 48 |
| 916 | 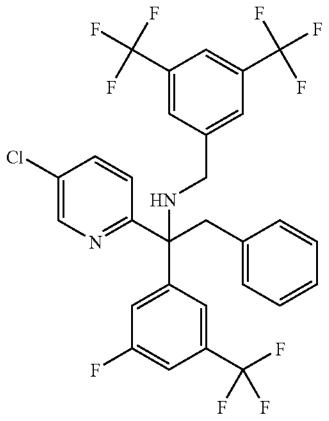 | N-(3,5-bis(trifluoromethyl) benzyl)-1-(5-chloropyridin-2-yl)-1-(3-fluoro-5-(trifluoromethyl)phenyl)-2-phenylethanamine | 4.50 LC 621.2 $[M + H]^+$ | Procedures 1 and 48 |
| 917 | 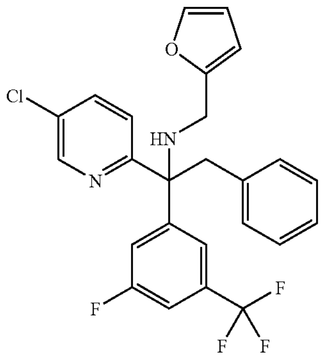 | 1-(5-chloropyridin-2-yl)-1-(3-fluoro-5-(trifluoromethyl) phenyl)-N-(furan-2-ylmethyl)-2-phenylethanamine | 3.53 LC 475.17 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 918 | 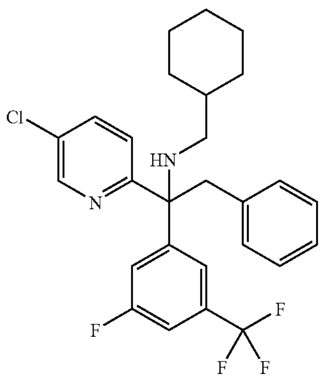 | 1-(5-chloropyridin-2-yl)-N-(cyclohexylmethyl)-1-(3-fluoro-5-(trifluoromethyl)phenyl)-2-phenylethanamine | 3.52 LC 491.23 $[M + H]^+$ | Procedures 1 and 48 |
| 919 | 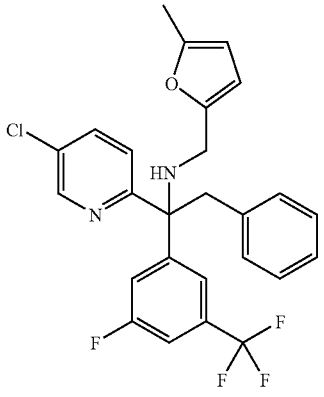 | 1-(5-chloropyridin-2-yl)-1-(3-fluoro-5-(trifluoromethyl) phenyl)-N-((5-methylfuran-2-yl)methyl)-2-phenylethanamine | 3.57 LC 489.19 $[M + H]^+$ | Procedures 1 and 48 |
| 920 | 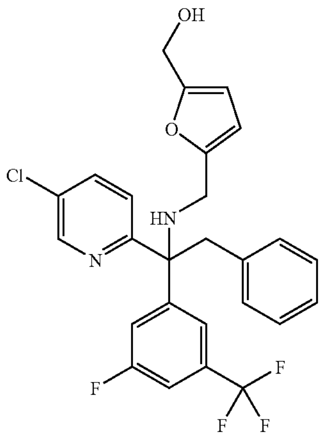 | (5-((1-(5-chloropyridin-2-yl)-1-(3-fluoro-5-(trifluoromethyl) phenyl)-2-phenylethylamino) methyl)furan-2-yl)methanol | 3.26 LC 505.19 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 921 | 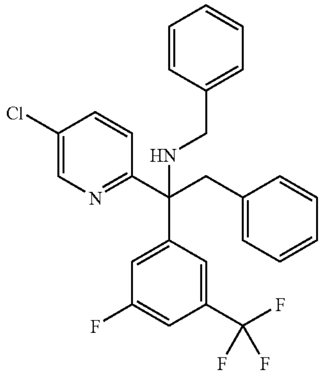 | N-benzyl-1-(5-chloropyridin-2-yl)-1-(3-fluoro-5-(trifluoromethyl)phenyl)-2-phenylethanamine | 3.59 LC 485.2 $[M + H]^+$ | Procedures 1 and 48 |
| 922 | 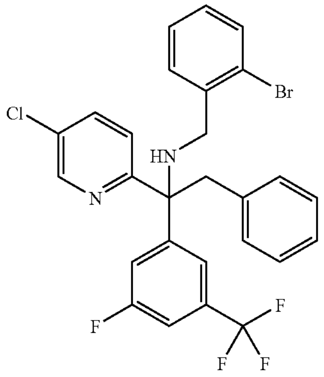 | N-(2-bromobenzyl)-1-(5-chloropyridin-2-yl)-1-(3-fluoro-5-(trifluoromethyl)phenyl)-2-phenylethanamine | 4.22 LC 565.13 $[M + H]^+$ | Procedures 1 and 48 |
| 923 | 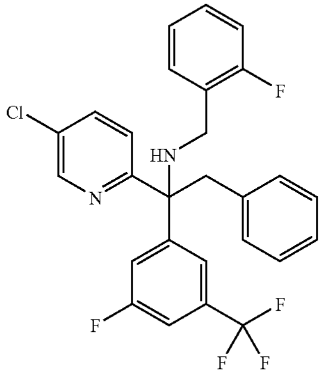 | N-(2-fluorobenzyl)-1-(5-chloropyridin-2-yl)-1-(3-fluoro-5-(trifluoromethyl)phenyl)-2-phenylethanamine | 3.86 LC 503.19 $[M + H]^+$ | Procedures 1 and 48 |
| 924 | 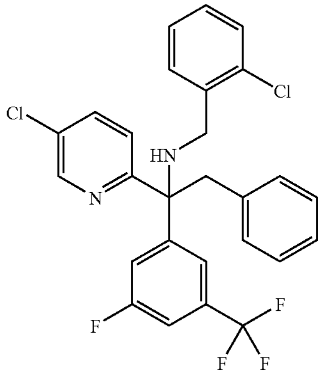 | N-(2-chlorobenzyl)-1-(5-chloropyridin-2-yl)-1-(3-fluoro-5-(trifluoromethyl)phenyl)-2-phenylethanamine | 4.14 LC 519.16 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 925 | 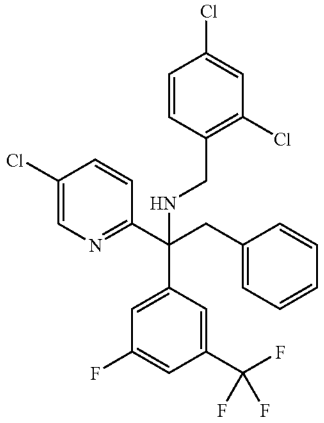 | N-(2,4-dichlorobenzyl)-1-(5-chloropyridin-2-yl)-1-(3-fluoro-5-(trifluoromethyl)phenyl)-2-phenylethanamine | 4.49 LC 553.14 $[M + H]^+$ | Procedures 1 and 48 |
| 926 | 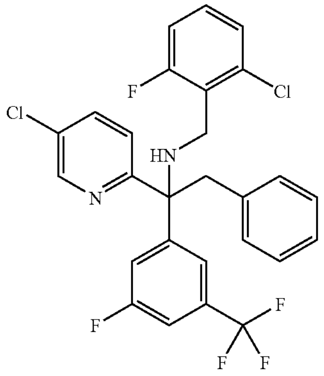 | N-(2-chloro-6-fluorobenzyl)-1-(5-chloropyridin-2-yl)-1-(3-fluoro-5-(trifluoromethyl) phenyl)-2-phenylethanamine | 4.34 LC 537.14 $[M + H]^+$ | Procedures 1 and 48 |
| 927 | 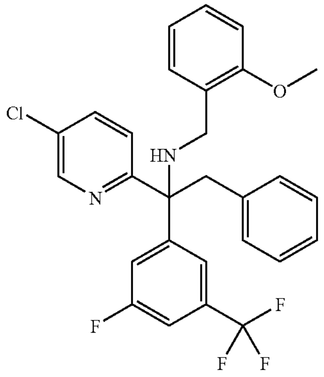 | N-(2-methoxybenzyl)-1-(5-chloropyridin-2-yl)-1-(3-fluoro-5-(trifluoromethyl)phenyl)-2-phenylethanamine | 3.40 LC 515.19 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 928 | 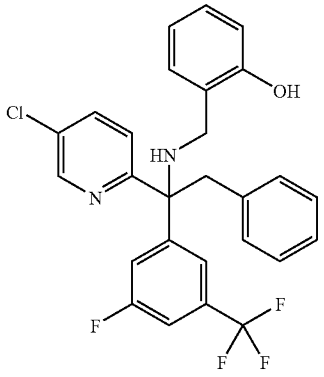 | 2-((1-(5-chloropyridin-2-yl)-1-(3-fluoro-5-(trifluoromethyl)phenyl)-2-phenylethylamino)methyl)phenol | 3.23 LC 501.19 [M + H]+ | Procedures 1 and 48 |
| 929 | 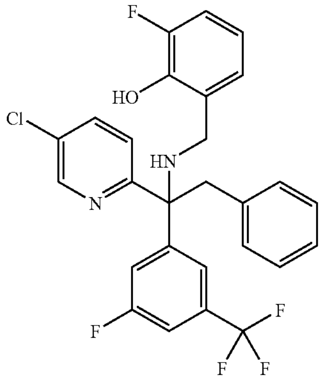 | 2-((1-(5-chloropyridin-2-yl)-1-(3-fluoro-5-(trifluoromethyl)phenyl)-2-phenylethylamino)methyl)-6-fluorophenol | 3.35 LC 519.19 [M + H]+ | Procedures 1 and 48 |
| 930 | 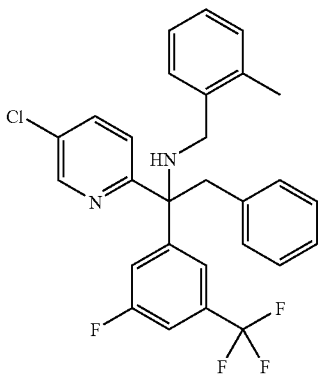 | N-(2-methylbenzyl)-1-(5-chloropyridin-2-yl)-1-(3-fluoro-5-(trifluoromethyl)phenyl)-2-phenylethanamine | 3.81 LC 499.25 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 931 | 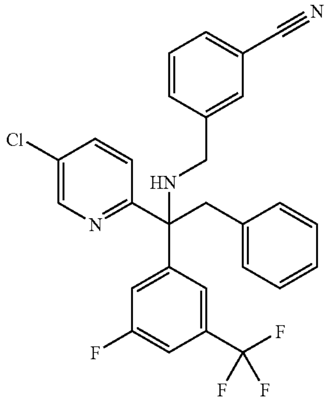 | 3-((1-(5-chloropyridin-2-yl)-1-(3-fluoro-5-(trifluoromethyl) phenyl)-2-phenylethylamino) methyl)benzonitrile | 3.86 LC 510.2 $[M + H]^+$ | Procedures 1 and 48 |
| 932 | 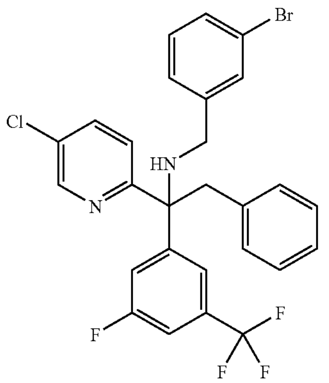 | N-(3-bromobenzyl)-1-(5-chloropyridin-2-yl)-1-(3-fluoro-5-(trifluoromethyl)phenyl)-2-phenylethanamine | 4.04 LC 565.11 $[M + H]^+$ | Procedures 1 and 48 |
| 933 | 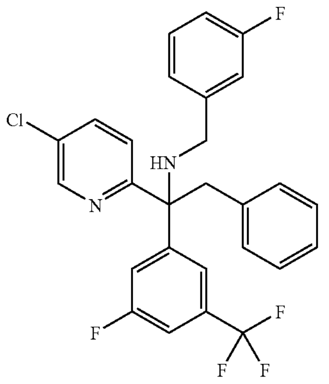 | N-(3-fluorobenzyl)-1-(5-chloropyridin-2-yl)-1-(3-fluoro-5-(trifluoromethyl)phenyl)-2-phenylethanamine | 3.85 LC 503.19 $[M + H]^+$ | Procedures 1 and 48 |

TABLE 11-continued

| Ex. No. | Structure | Name | Retention Time Min./ Molecular Mass | Prepared in the manner described in: |
| --- | --- | --- | --- | --- |
| 934 | 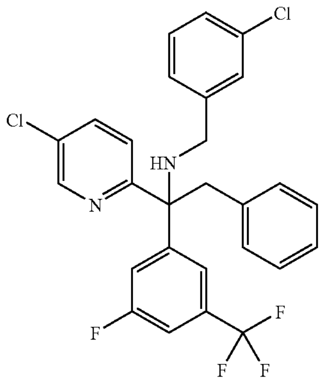 | N-(3-chlorobenzyl)-1-(5-chloropyridin-2-yl)-1-(3-fluoro-5-(trifluoromethyl)phenyl)-2-phenylethanamine | 3.99 LC 519.18 $[M + H]^+$ | Procedures 1 and 48 |
| 935 | 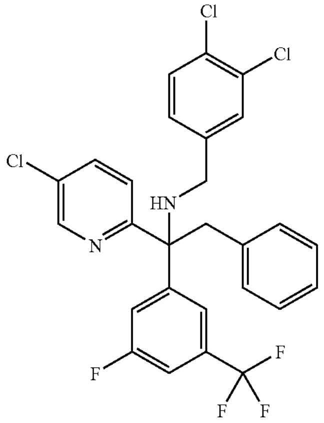 | N-(3,4-dichlorobenzyl)-1-(5-chloropyridin-2-yl)-1-(3-fluoro-5-(trifluoromethyl)phenyl)-2-phenylethanamine | 4.23 LC 553.13 $[M + H]^+$ | Procedures 1 and 48 |
| 936 | 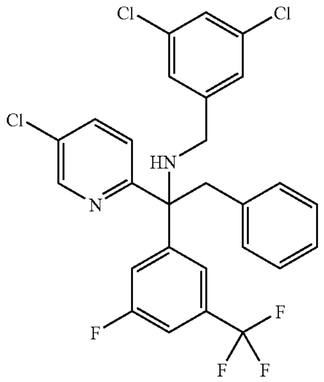 | N-(3,5-dichlorobenzyl)-1-(5-chloropyridin-2-yl)-1-(3-fluoro-5-(trifluoromethyl)phenyl)-2-phenylethanamine | 4.40 LC 553.15 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 937 | 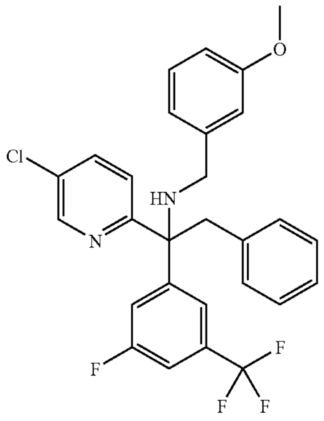 | N-(3-methoxybenzyl)-1-(5-chloropyridin-2-yl)-1-(3-fluoro-5-(trifluoromethyl)phenyl)-2-phenylethanamine | 3.64 LC 515.2 $[M + H]^+$ | Procedures 1 and 48 |
| 938 | 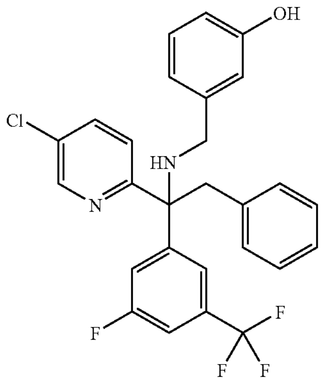 | 3-((1-(5-chloropyridin-2-yl)-1-(3-fluoro-5-(trifluoromethyl) phenyl)-2-phenylethylamino) methyl)phenol | 3.33 LC 501.18 $[M + H]^+$ | Procedures 1 and 48 |
| 939 | 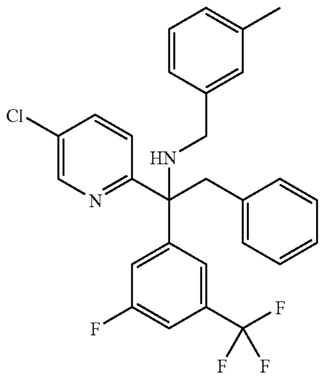 | N-(3-methylbenzyl)-1-(5-chloropyridin-2-yl)-1-(3-fluoro-5-(trifluoromethyl)phenyl)-2-phenylethanamine | 3.68 LC 499.18 $[M + H]^+$ | Procedures 1 and 48 |

TABLE 11-continued

| Ex. No. | Structure | Name | Retention Time Min./Molecular Mass | Prepared in the manner described in: |
|---|---|---|---|---|
| 940 | 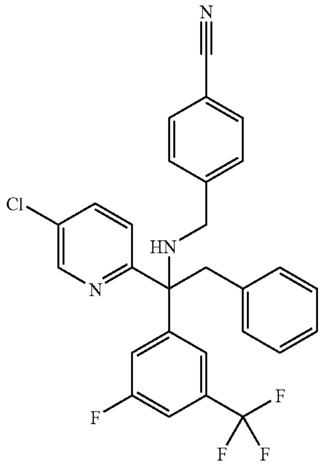 | 4-((1-(5-chloropyridin-2-yl)-1-(3-fluoro-5-(trifluoromethyl) phenyl)-2-phenylethylamino) methyl)benzonitrile | 3.87 LC 510.19 $[M + H]^+$ | Procedures 1 and 48 |
| 941 | 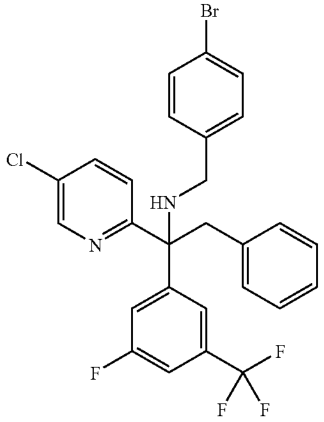 | N-(4-bromobenzyl)-1-(5-chloropyridin-2-yl)-1-(3-fluoro-5-(trifluoromethyl)phenyl)-2-phenylethanamine | 3.93 LC 565.16 $[M + H]^+$ | Procedures 1 and 48 |
| 942 | 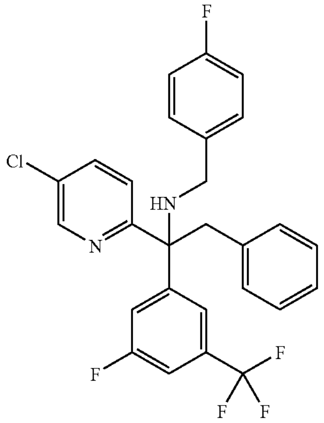 | N-(4-fluorobenzyl)-1-(5-chloropyridin-2-yl)-1-(3-fluoro-5-(trifluoromethyl)phenyl)-2-phenylethanamine | 3.65 LC 503.21 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 943 | 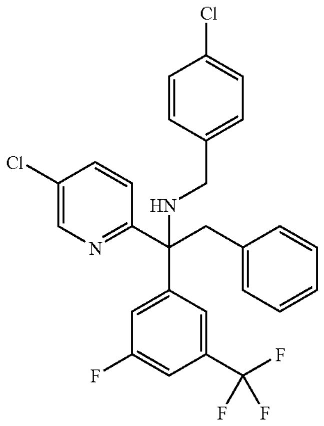 | N-(4-chlorobenzyl)-1-(5-chloropyridin-2-yl)-1-(3-fluoro-5-(trifluoromethyl)phenyl)-2-phenylethanamine | 3.88 LC 519.20 $[M + H]^+$ | Procedures 1 and 48 |
| 944 | 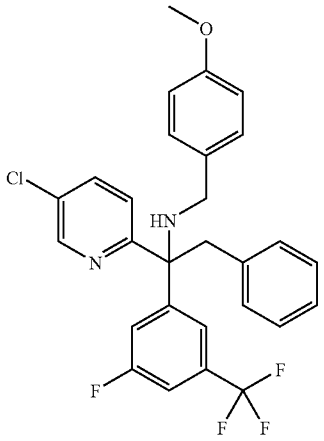 | N-(4-methoxybenzyl)-1-(5-chloropyridin-2-yl)-1-(3-fluoro-5-(trifluoromethyl)phenyl)-2-phenylethanamine | 3.51 LC 515.22 $[M + H]^+$ | Procedures 1 and 48 |
| 945 | 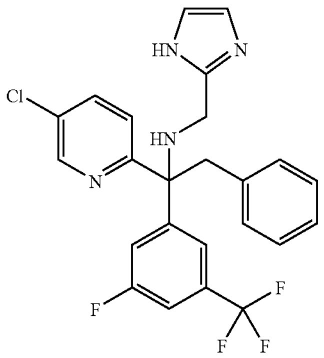 | N-((1H-imidazol-2-yl)methyl)-1-(5-chloropyridin-2-yl)-1-(3-fluoro-5-(trifluoromethyl) phenyl)-2-phenylethanamine | 3.45 LC 475.21 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 946 | 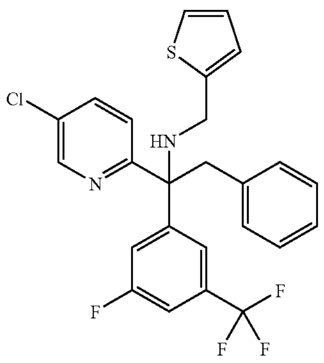 | 1-(5-chloropyridin-2-yl)-1-(3-fluoro-5-(trifluoromethyl) phenyl)-2-phenyl-N-(thiophen-2-ylmethyl)ethanamine | 3.79 LC 491.18 $[M + H]^+$ | Procedures 1 and 48 |
| 947 | 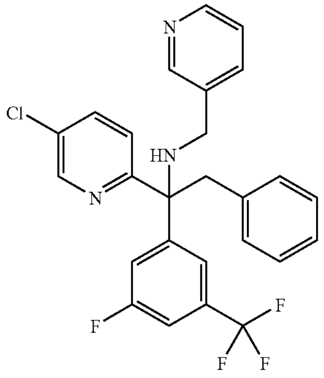 | 1-(5-chloropyridin-2-yl)-1-(3-fluoro-5-(trifluoromethyl) phenyl)-2-phenyl-N-(pyridin-3-ylmethyl)ethanamine | 3.51 LC 486.22 $[M + H]^+$ | Procedures 1 and 48 |
| 948 | 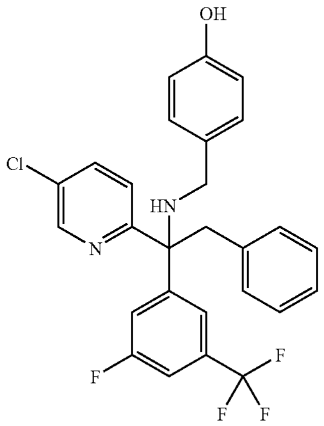 | 4-((1-(5-chloropyridin-2-yl)-1-(3-fluoro-5-(trifluoromethyl) phenyl)-2-phenylethylamino) methyl)phenol | 3.28 LC 501.19 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 949 | 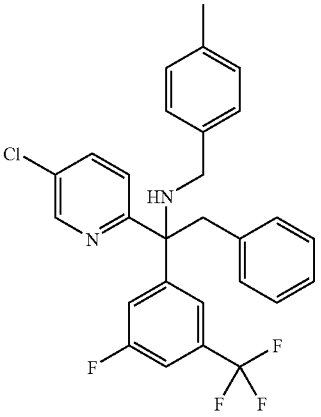 | N-(4-methylbenzyl)-1-(5-chloropyridin-2-yl)-1-(3-fluoro-5-(trifluoromethyl)phenyl)-2-phenylethanamine | 3.65 LC 499.25 $[M + H]^+$ | Procedures 1 and 48 |
| 950 | 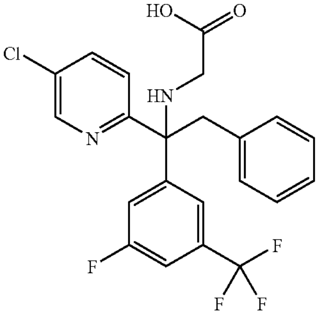 | 2-(1-(5-chloropyridin-2-yl)-1-(3-fluoro-5-(trifluoromethyl) phenyl)-2-phenylethylamino) acetic acid | 3.47 LC 453.19 $[M + H]^+$ | Procedures 1 and 48 |
| 951 | 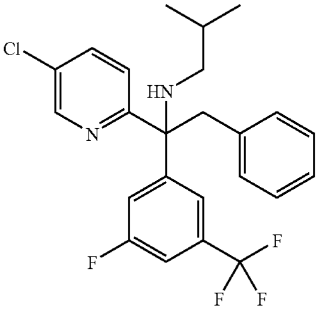 | N-(1-(5-chloropyridin-2-yl)-1-(3-fluoro-5-(trifluoromethyl) phenyl)-2-phenylethyl)-2-methylpropan-1-amine | 3.35 LC 451.22 $[M + H]^+$ | Procedures 1 and 48 |
| 952 | 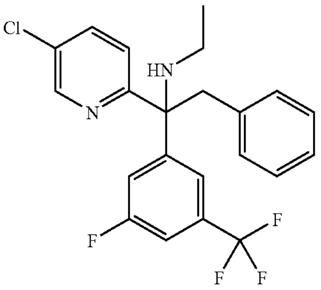 | 1-(5-chloropyridin-2-yl)-N-ethyl-1-(3-fluoro-5-(trifluoromethyl)phenyl)-2-phenylethanamine | 3.08 LC 423.21 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 953 | 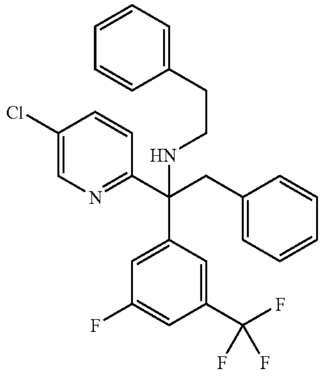 | 1-(5-chloropyridin-2-yl)-1-(3-fluoro-5-(trifluoromethyl) phenyl)-N-phenethyl-2-phenylethanamine | 3.49 LC 499.25 $[M + H]^+$ | Procedures 1 and 48 |
| 954 | 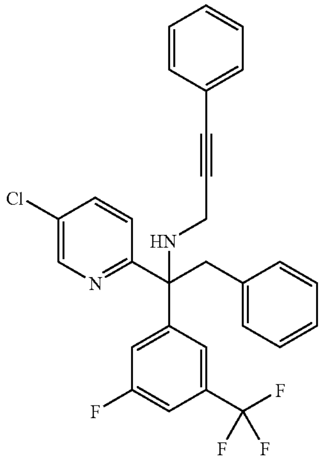 | N-(1-(5-chloropyridin-2-yl)-1-(3-fluoro-5-(trifluoromethyl) phenyl)-2-phenylethyl)-3-phenylprop-2-ynl-1-amine | 3.91 LC 509.23 $[M + H]^+$ | Procedures 1 and 48 |
| 955 | 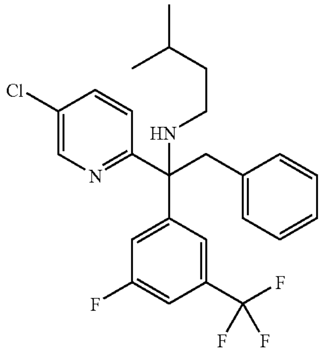 | N-(1-(5-chloropyridin-2-yl)-1-(3-fluoro-5-(trifluoromethyl) phenyl)-2-phenylethyl)-3-methylbutan-1-amine | 3.40 LC 465.24 $[M + H]^+$ | Procedures 1 and 48 |
| 956 | 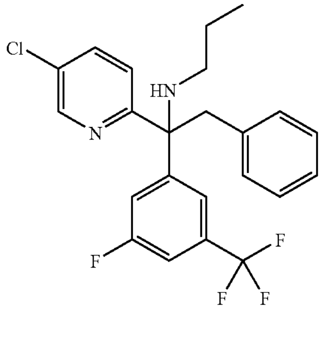 | N-(1-(5-chloropyridin-2-yl)-1-(3-fluoro-5-(trifluoromethyl) phenyl)-2-phenylethyl)propan-1-amine | 3.16 LC 437.22 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 957 | 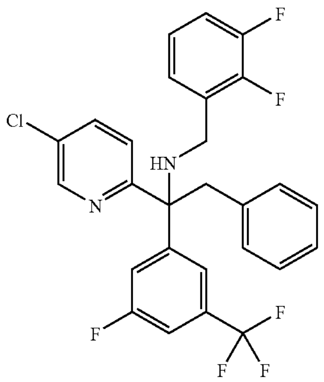 | N-(2,3-difluorobenzyl)-1-(5-chloropyridin-2-yl)-1-(3-fluoro-5-(trifluoromethyl)phenyl)-2-phenylethanamine | 4.06 LC 521.20 $[M + H]^+$ | Procedures 1 and 48 |
| 958 | 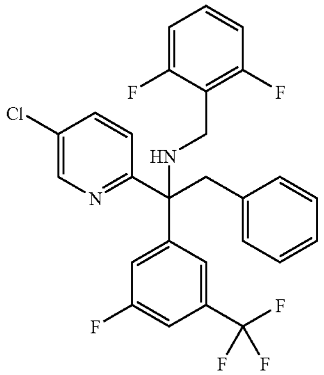 | N-(2,6-difluorobenzyl)-1-(5-chloropyridin-2-yl)-1-(3-fluoro-5-(trifluoromethyl)phenyl)-2-phenylethanamine | 4.10 LC 521.20 $[M + H]^+$ | Procedures 1 and 48 |
| 959 | 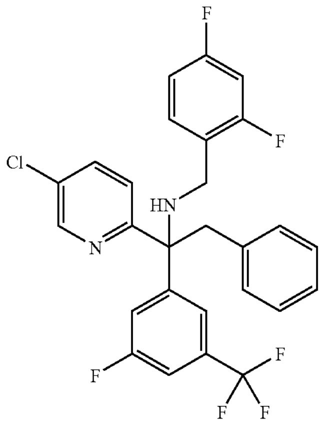 | N-(2,4-difluorobenzyl)-1-(5-chloropyridin-2-yl)-1-(3-fluoro-5-(trifluoromethyl)phenyl)-2-phenylethanamine | 3.92 LC 521.21 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 960 | 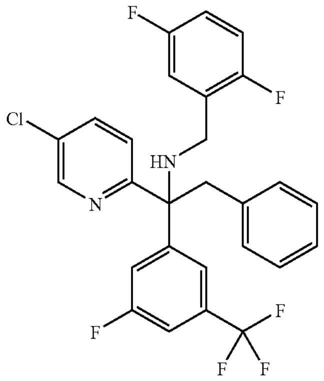 | N-(2,5-difluorobenzyl)-1-(5-chloropyridin-2-yl)-1-(3-fluoro-5-(trifluoromethyl)phenyl)-2-phenylethanamine | 4.06 LC 521.21 $[M + H]^+$ | Procedures 1 and 48 |
| 961 | 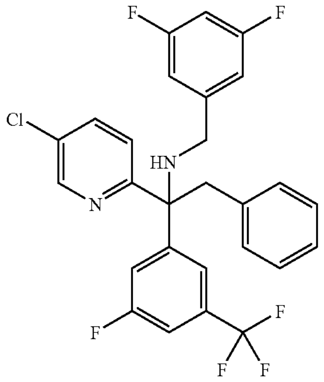 | N-(3,5-difluorobenzyl)-1-(5-chloropyridin-2-yl)-1-(3-fluoro-5-(trifluoromethyl)phenyl)-2-phenylethanamine | 4.09 LC 521.20 $[M + H]^+$ | Procedures 1 and 48 |
| 962 | 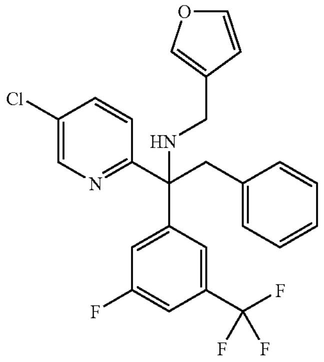 | 1-(5-chloropyridin-2-yl)-1-(3-fluoro-5-(trifluoromethyl) phenyl)-N-(furan-3-ylmethyl)-2-phenylethanamine | 3.33 LC 475.20 $[M + H]^+$ | Procedures 1 and 48 |
| 963 | 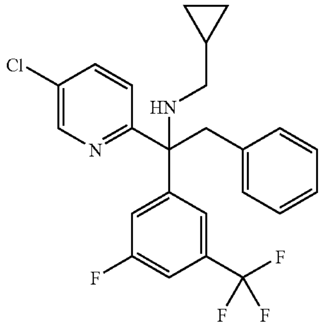 | 1-(5-chloropyridin-2-yl)-N-(cyclopropylmethyl)-1-(3-fluoro-5-(trifluoromethyl) phenyl)-2-phenylethanamine | 3.19 LC 449.22 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 964 | 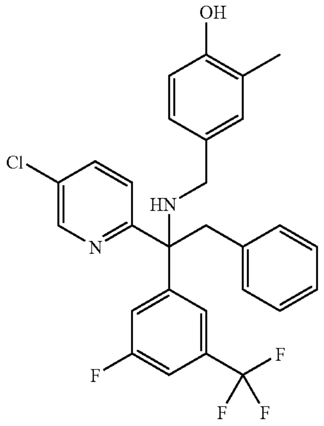 | 4-((1-(5-chloropyridin-2-yl)-1-(3-fluoro-5-(trifluoromethyl) phenyl)-2-phenylethylamino) methyl)-2-methylphenol | 3.38 LC 515.21 $[M + H]^+$ | Procedures 1 and 48 |
| 965 | 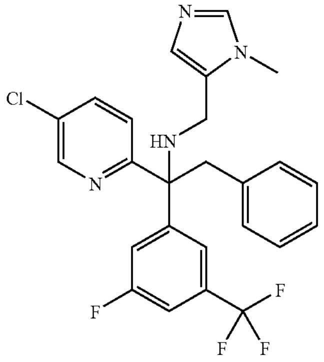 | 1-(5-chloropyridin-2-yl)-1-(3-fluoro-5-(trifluoromethyl) phenyl)-N-((1-methyl-1H-imidazol-5-yl)methyl)-2-phenylethanamine | 3.48 LC 489.24 $[M + H]^+$ | Procedures 1 and 48 |
| 966 | 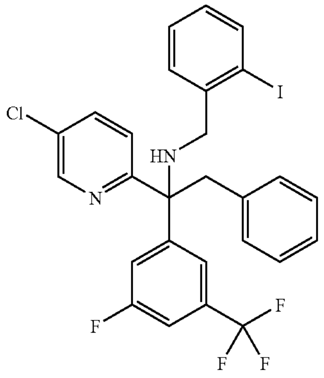 | N-(2-iodobenzyl)-1-(5-chloropyridin-2-yl)-1-(3-fluoro-5-(trifluoromethyl)phenyl)-2-phenylethanamine | 4.26 LC 611.14 $[M + H]^+$ | Procedures 1 and 48 |

TABLE 11-continued

| Ex. No. | Structure | Name | Retention Time Min./Molecular Mass | Prepared in the manner described in: |
|---|---|---|---|---|
| 967 | 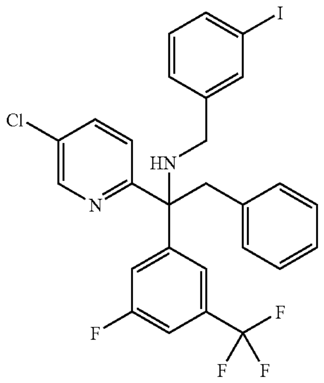 | N-(3-iodobenzyl)-1-(5-chloropyridin-2-yl)-1-(3-fluoro-5-(trifluoromethyl)phenyl)-2-phenylethanamine | 4.01 LC 611.13 $[M + H]^+$ | Procedures 1 and 48 |
| 968 | 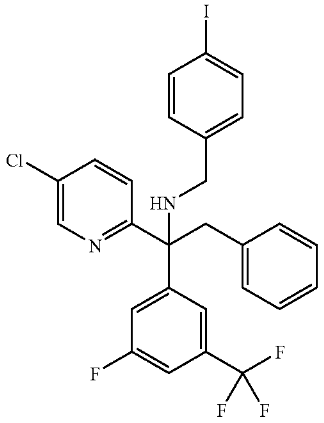 | N-(4-iodobenzyl)-1-(5-chloropyridin-2-yl)-1-(3-fluoro-5-(trifluoromethyl)phenyl)-2-phenylethanamine | 3.97 LC 611.13 $[M + H]^+$ | Procedures 1 and 48 |
| 969 | 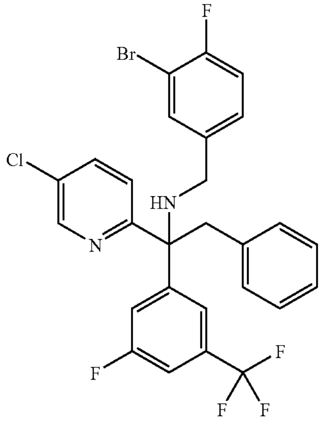 | N-(3-bromo-4-fluorobenzyl)-1-(5-chloropyridin-2-yl)-1-(3-fluoro-5-(trifluoromethyl) phenyl)-2-phenylethanamine | 4.02 LC 583.11 $[M + H]^+$ | Procedures 1 and 48 |

TABLE 11-continued

| Ex. No. | Structure | Name | Retention Time Min./ Molecular Mass | Prepared in the manner described in: |
| --- | --- | --- | --- | --- |
| 970 | 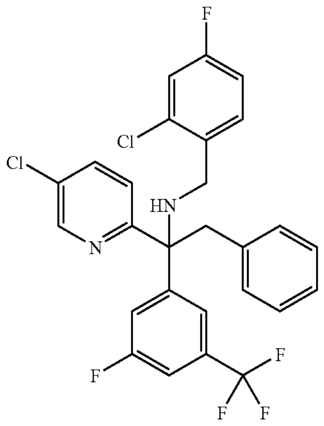 | N-(2-chloro-4-fluorobenzyl)-1-(5-chloropyridin-2-yl)-1-(3-fluoro-5-(trifluoromethyl) phenyl)-2-phenylethanamine | 4.19 LC 537.17 $[M + H]^+$ | Procedures 1 and 48 |
| 972 | 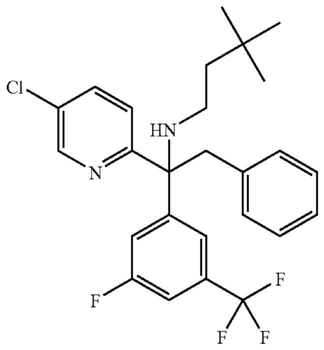 | N-(1-(5-chloropyridin-2-yl)-1-(3-fluoro-5-(trifluoromethyl) phenyl)-2-phenylethyl)-3,3-dimethylbutan-1-amine | 3.49 LC 479.24 $[M + H]^+$ | Procedures 1 and 48 |
| 973 | 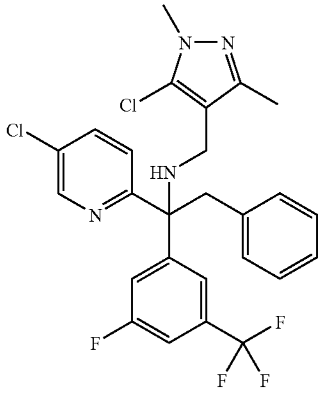 | N-((5-chloro-1,3-dimethyl-1H-pyrazol-4-yl)methyl)-1-(5-chloropyridin-2-yl)-1-(3-fluoro-5-(trifluoromethyl)phenyl)-2-phenylethanamine | 3.76 LC 537.18 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 974 | 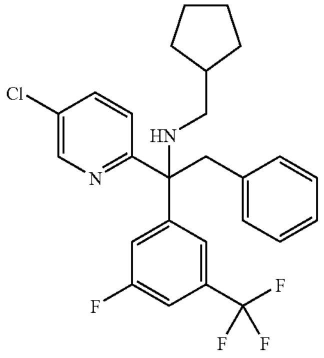 | 1-(5-chloropyridin-2-yl)-N-(cyclopentylmethyl)-1-(3-fluoro-5-(trifluoromethyl) phenyl)-2-phenylethanamine | 3.47 LC 477.23 [M + H]+ | Procedures 1 and 48 |
| 975 | 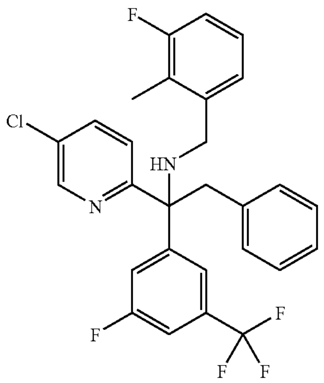 | N-(3-fluoro-2-methylbenzyl)-1-(5-chloropyridin-2-yl)-1-(3-fluoro-5-(trifluoromethyl) phenyl)-2-phenylethanamine | 4.01 LC 517.19 [M + H]+ | Procedures 1 and 48 |
| 976 | 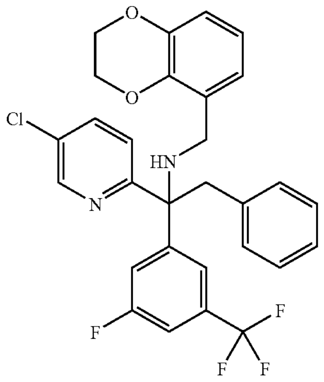 | 1-(5-chloropyridin-2-yl)-N-((2,3-dihydrobenzo[b][1,4] dioxin-5-yl)methyl)-1-(3-fluoro-5-(trifluoromethyl) phenyl)-2-phenylethanamine | 3.47 LC 543.20 [M + H]+ | Procedures 1 and 48 |
| 977 | 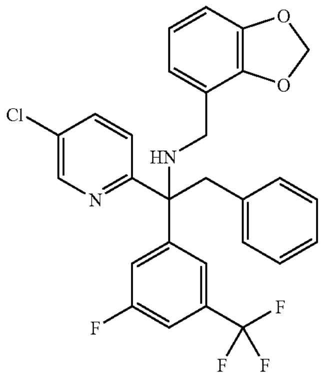 | N-(benzo[d][1,3]dioxol-4-ylmethyl)-1-(5-chloropyridin-2-yl)-1-(3-fluoro-5-(trifluoromethyl)phenyl)-2-phenylethanamine | 3.71 LC 529.19 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 978 | 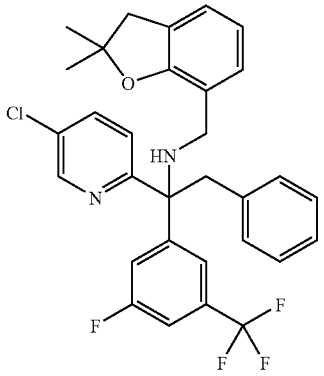 | 1-(5-chloropyridin-2-yl)-N-((2,2-dimethyl-2,3-dihydrobenzofuran-7-yl) methyl)-1-(3-fluoro-5-(trifluoromethyl)phenyl)-2-phenylethanamine | 3.72 LC 555.22 $[M + H]^+$ | Procedures 1 and 48 |
| 979 | 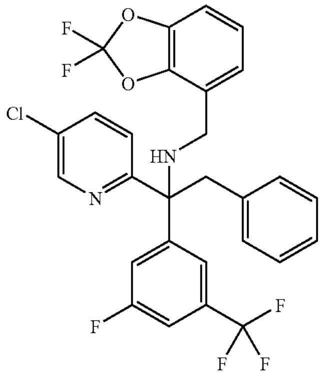 | 1-(5-chloropyridin-2-yl)-N-((2,2-difluorobenzo[d][1,3] dioxol-4-yl)methyl)-1-(3-fluoro-5-(trifluoromethyl) phenyl)-2-phenylethanamine | 4.25 LC 565.16 $[M + H]^+$ | Procedures 1 and 48 |
| 980 | 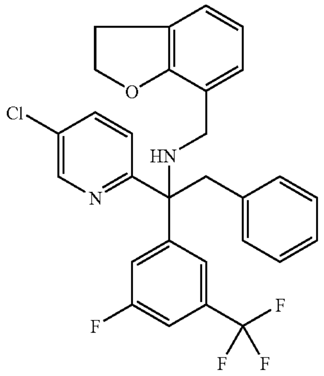 | 1-(5-chloropyridin-2-yl)-N-((2,3-dihydrobenzofuran-7-yl)methyl)-1-(3-fluoro-5-(trifluoromethyl)phenyl)-2-phenylethanamine | 3.54 LC 527.20 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 981 | 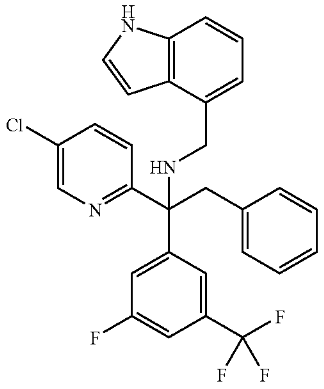 | N-((1H-indol-4-yl)methyl)-1-(5-chloropyridin-2-yl)-1-(3-fluoro-5-(trifluoromethyl) phenyl)-2-phenylethanamine | 3.45 LC 524.20 $[M + H]^+$ | Procedures 1 and 48 |
| 982 | 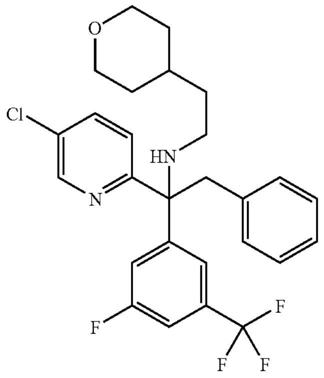 | 1-(5-chloropyridin-2-yl)-1-(3-fluoro-5-(trifluoromethyl) phenyl)-2-phenyl-N-(2-(tetrahydro-2H-pyran-4-yl) ethyl)ethanamine | 3.19 LC 507.19 $[M + H]^+$ | Procedures 1 and 48 |
| 983 | 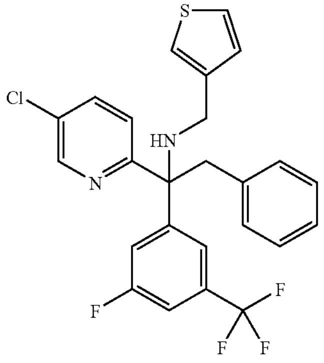 | 1-(5-chloropyridin-2-yl)-1-(3-fluoro-5-(trifluoromethyl) phenyl)-2-phenyl-N-(thiophen-3-ylmethyl)ethanamine | 3.47 LC 491.11 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 984 | 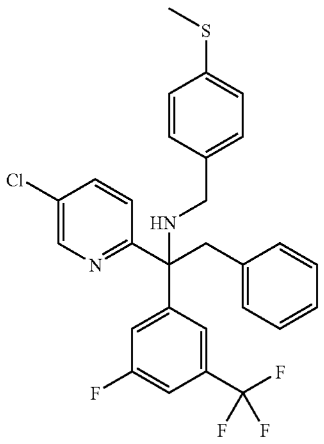 | N-(4-(methylthio)benzyl)-1-(5-chloropyridin-2-yl)-1-(3-fluoro-5-trifluoromethyl)phenyl)-2-phenylethanamine | 3.70 LC 531.14 $[M + H]^+$ | Procedures 1 and 48 |
| 985 | 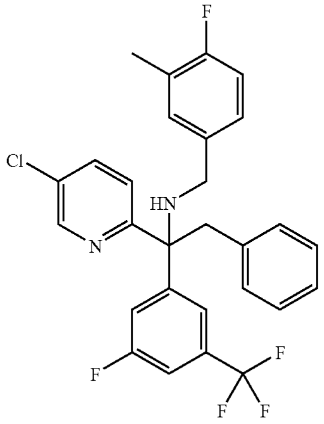 | N-(4-fluoro-3-methylbenzyl)-1-(5-chloropyridin-2-yl)-1-(3-fluoro-5-(trifluoromethyl) phenyl)-2-phenylethanamine | 3.74 LC 517.19 $[M + H]^+$ | Procedures 1 and 48 |
| 986 | 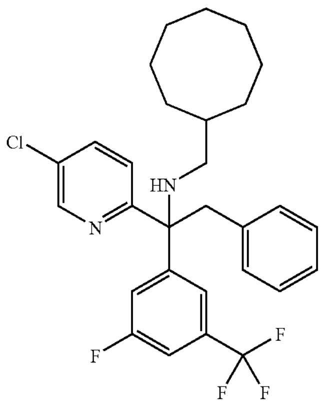 | 1-(5-chloropyridin-2-yl)-N-(cyclooctylmethyl)-1-(3-fluoro-5-(trifluoromethyl)phenyl)-2-phenylethanamine | 3.83 LC 519.26 $[M + H]^+$ | Procedures 1 and 48 |

TABLE 11-continued

| Ex. No. | Structure | Name | Retention Time Min./Molecular Mass | Prepared in the manner described in: |
|---|---|---|---|---|
| 987 | 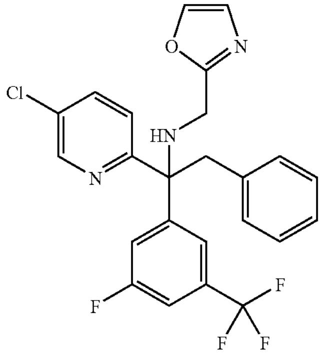 | 1-(5-chloropyridin-2-yl)-1-(3-fluoro-5-(trifluoromethyl) phenyl)-N-(oxazol-2-ylmethyl)-2-phenylethanamine | 3.99 LC 476.10 $[M+H]^+$ | Procedures 1 and 48 |
| 988 | 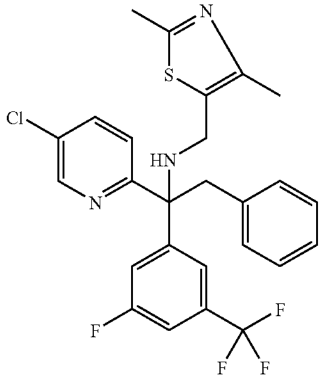 | 1-(5-chloropyridin-2-yl)-N-((2,4-dimethylthiazol-5-yl)methyl)-1-(3-fluoro-5-(trifluoromethyl)phenyl)-2-phenylethanamine | 3.80 LC 520.13 $[M+H]^+$ | Procedures 1 and 48 |
| 989 | 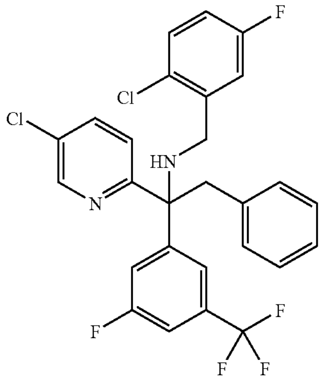 | N-(2-chloro-5-fluorobenzyl)-1-(5-chloropyridin-2-yl)-1-(3-fluoro-5-(trifluoromethyl) phenyl)-2-phenylethanamine | 4.31 LC 537.14 $[M+H]^+$ | Procedures 1 and 48 |

TABLE 11-continued

| Ex. No. | Structure | Name | Retention Time Min./ Molecular Mass | Prepared in the manner described in: |
|---|---|---|---|---|
| 990 | 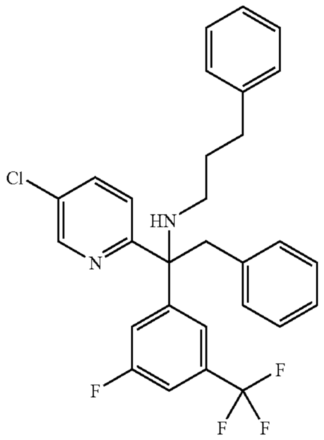 | N-(1-(5-chloropyridin-2-yl)-1-(3-fluoro-5-(trifluoromethyl) phenyl)-2-phenylethyl)-3-phenylpropan-1-amine | 3.52 LC 513.19 $[M + H]^+$ | Procedures 1 and 48 |
| 991 | 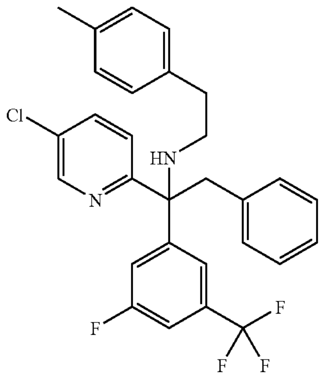 | N-(1-(5-chloropyridin-2-yl)-1-(3-fluoro-5-(trifluoromethyl) phenyl)-(4-methylphenethyl)-2-phenylethanamine | 3.59 LC 513.19 $[M + H]^+$ | Procedures 1 and 48 |
| 992 | 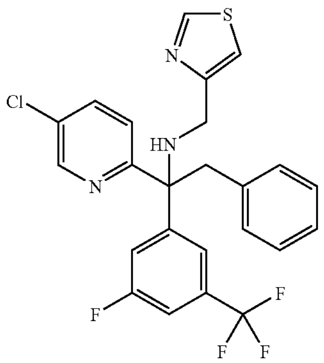 | 1-(5-chloropyridin-2-yl)-1-(3-fluoro-5-(trifluoromethyl) phenyl)-2-phenyl-N-(thiazol-4-ylmethyl)ethanamine | 3.41 LC 492.11 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 993 | 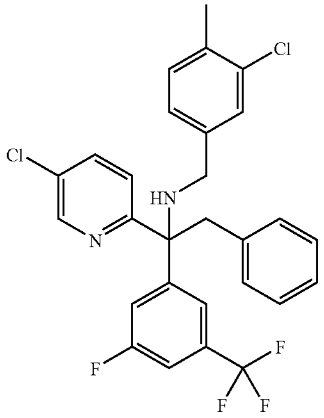 | N-(3-chloro-4-methylbenzyl)-1-(5-chloropyridin-2-yl)-1-(3-fluoro-5-(trifluoromethyl) phenyl)-2-phenylethanamine | 3.98 LC 533.13 $[M + H]^+$ | Procedures 1 and 48 |
| 994 | 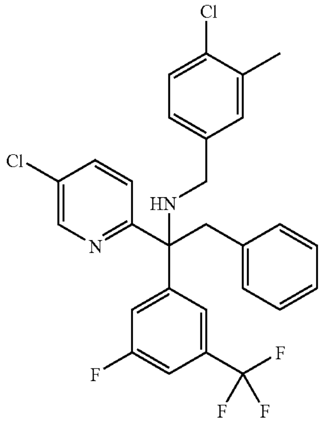 | N-(4-chloro-3-methylbenzyl)-1-(5-chloropyridin-2-yl)-1-(3-fluoro-5-(trifluoromethyl) phenyl)-2-phenylethanamine | 3.94 LC 533.14 $[M + H]^+$ | Procedures 1 and 48 |
| 995 | 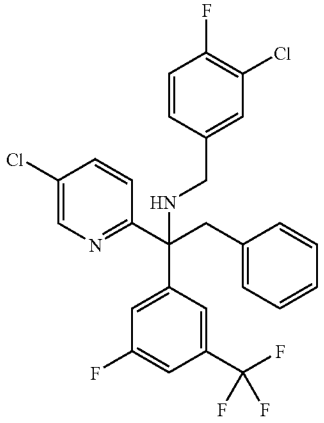 | N-(3-chloro-4-fluorobenzyl)-1-(5-chloropyridin-2-yl)-1-(3-fluoro-5-(trifluoromethyl) phenyl)-2-phenylethanamine | 3.98 LC 537.04 $[M + H]^+$ | Procedures 1 and 48 |

TABLE 11-continued

| Ex. No. | Structure | Name | Retention Time Min./Molecular Mass | Prepared in the manner described in: |
|---|---|---|---|---|
| 996 | 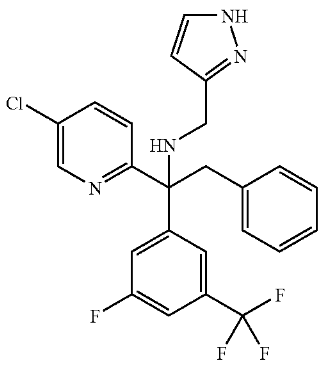 | N-((1H-pyrazol-3-yl)methyl)-1-(5-chloropyridin-2-yl)-1-(3-fluoro-5-(trifluoromethyl)phenyl)-2-phenylethanamine | 3.23 LC 475.16 $[M + H]^+$ | Procedures 1 and 48 |
| 997 | 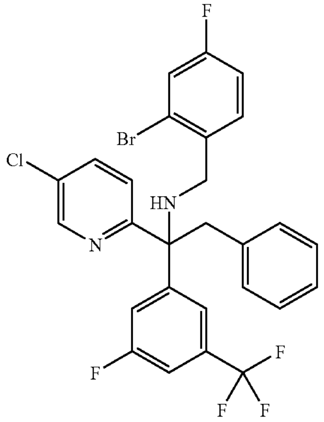 | N-(2-bromo-4-fluorobenzyl)-1-(5-chloropyridin-2-yl)-1-(3-fluoro-5-(trifluoromethyl)phenyl)-2-phenylethanamine | 4.26 LC 583.04 $[M + H]^+$ | Procedures 1 and 48 |
| 998 | 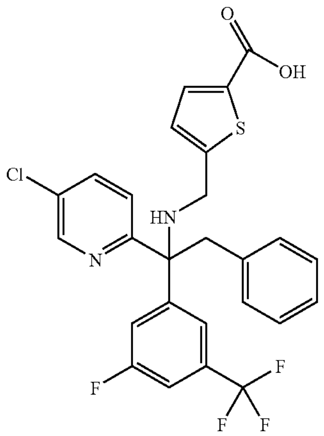 | 5-((1-(5-chloropyridin-2-yl)-1-(3-fluoro-5-(trifluoromethyl)phenyl)-2-phenylethylamino)methyl)thiophene-2-carboxylic acid | 3.93 LC 535.07 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 999 | 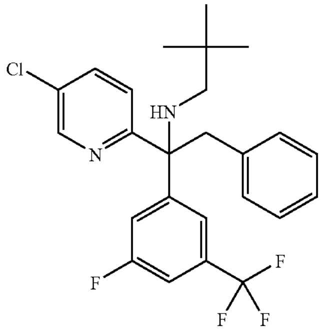 | N-(1-(5-chloropyridin-2-yl)-1-(3-fluoro-5-(trifluoromethyl) phenyl)-2-phenylethyl)-2,2-dimethylpropan-1-amine | 3.70 LC 465.19 $[M + H]^+$ | Procedures 1 and 48 |
| 1000 | 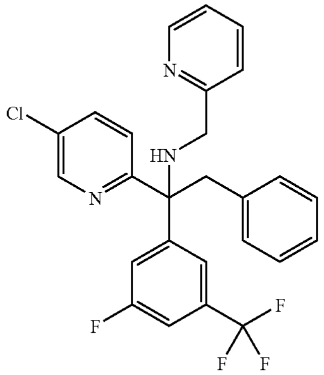 | 1-(5-chloropyridin-2-yl)-1-(3-fluoro-5-(trifluoromethyl) phenyl)-2-phenyl-N-(pyridin-2-ylmethyl)ethanamine | 3.40 LC 486.18 $[M + H]^+$ | Procedures 1 and 48 |
| 1001 | 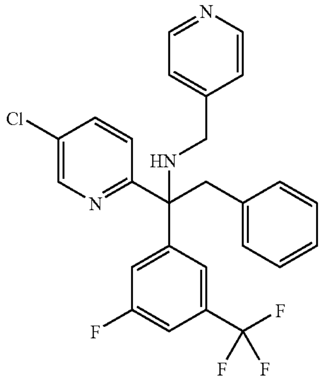 | 1-(5-chloropyridin-2-yl)-1-(3-fluoro-5-(trifluoromethyl) phenyl)-2-phenyl-N-(pyridin-4-ylmethyl)ethanamine | 3.54 LC 486.11 $[M + H]^+$ | Procedures 1 and 48 |
| 1002 | 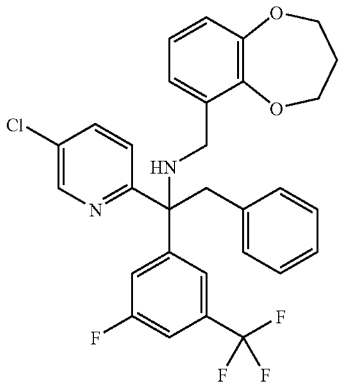 | 1-(5-chloropyridin-2-yl)-N-((3,4-dihydro-2H-benzo[b][1,4] dioxepin-6-yl)methyl)-1-(3-fluoro-5-(trifluoromethyl) phenyl)-2-phenylethanamine | 3.50 LC 557.16 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1003 | 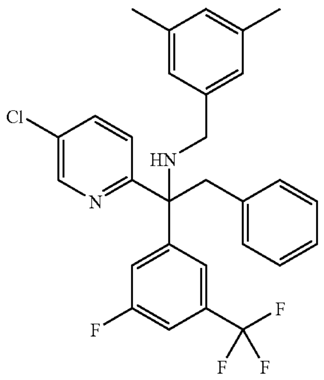 | N-(3,5-dimethylbenzyl)-1-(5-chloropyridin-2-yl)-1-(3-fluoro-5-(trifluoromethyl)phenyl)-2-phenylethanamine | 3.78 LC 513.19 $[M + H]^+$ | Procedures 1 and 48 |
| 1004 | 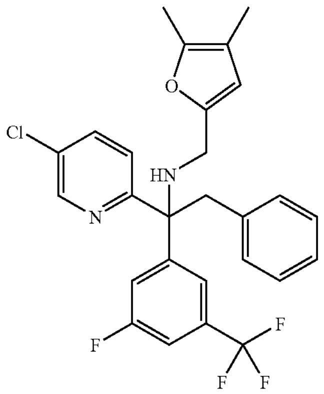 | 1-(5-chloropyridin-2-yl)-N-((4,5-dimethylfuran-2-yl) methyl)-1-(3-fluoro-5-(trifluoromethyl)phenyl)-2-phenylethanamine | 3.64 LC 503.15 $[M + H]^+$ | Procedures 1 and 48 |
| 1005 | 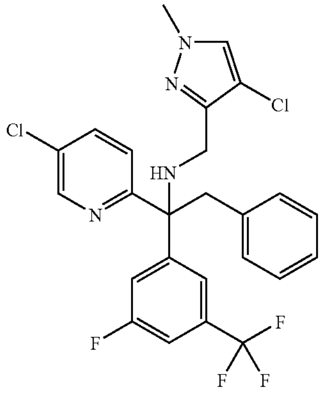 | N-((4-chloro-1-methyl-1H-pyrazol-3-yl)methyl)-1-(5-chloropyridin-2-yl)-1-(3-fluoro-5-(trifluoromethyl)phenyl)-2-phenylethanamine | 3.70 LC 523.13 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1006 | 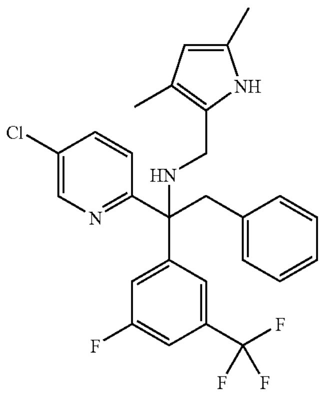 | 1-(5-chloropyridin-2-yl)-N-((3,5-dimethyl-1H-pyrrol-2-yl)methyl)-1-(3-fluoro-5-(trifluoromethyl)phenyl)-2-phenylethanamine | 3.37 LC 502.14 $[M + H]^+$ | Procedures 1 and 48 |
| 1007 | 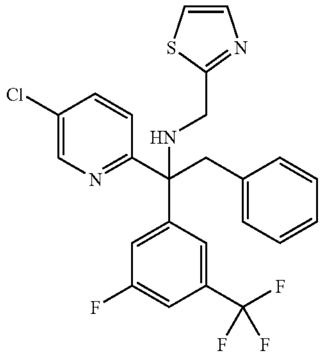 | 1-(5-chloropyridin-2-yl)-1-(3-fluoro-5-(trifluoromethyl) phenyl)-2-phenyl-N-(thiazol-2-ylmethyl)ethanamine | 4.07 LC 492.11 $[M + H]^+$ | Procedures 1 and 48 |
| 1008 | 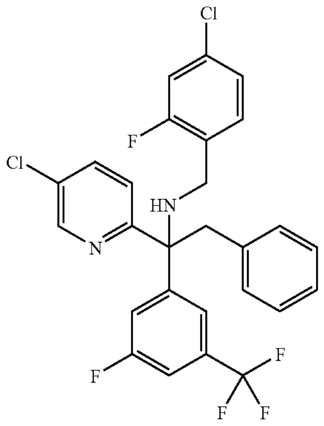 | N-(4-chloro-2-fluorobenzyl)-1-(5-chloropyridin-2-yl)-1-(3-fluoro-5-(trifluoromethyl) phenyl)-2-phenylethanamine | 4.14 LC 537.08 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1009 | 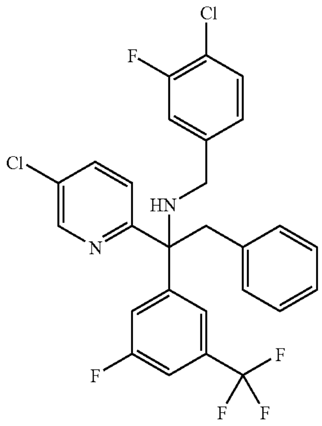 | N-(4-chloro-3-fluorobenzyl)-1-(5-chloropyridin-2-yl)-1-(3-fluoro-5-(trifluoromethyl) phenyl)-2-phenylethanamine | 4.07 LC 537.09 [M + H]$^+$ | Procedures 1 and 48 |
| 1010 | 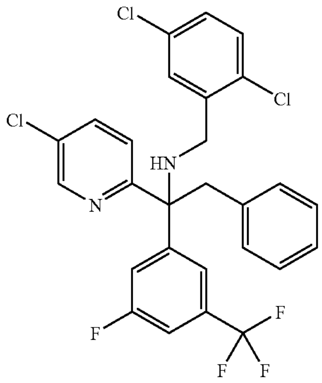 | N-(2,5-dichlorobenzyl)-1-(5-chloropyridin-2-yl)-1-(3-fluoro-5-(trifluoromethyl)phenyl)-2-phenylethanamine | 4.41 LC 553.09 [M + H]$^+$ | Procedures 1 and 48 |
| 1011 | 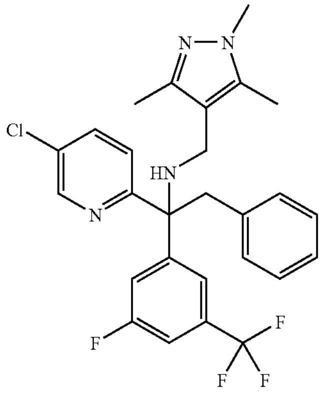 | 1-(5-chloropyridin-2-yl)-1-(3-fluoro-5-(trifluoromethyl) phenyl)-2-phenyl-N-((1,3,5-trimethyl-1H-pyrazol-4-yl) methyl)ethanamine | 3.31 LC 517.19 [M + H]$^+$ | Procedures 1 and 48 |

TABLE 11-continued

| Ex. No. | Structure | Name | Retention Time Min./ Molecular Mass | Prepared in the manner described in: |
|---|---|---|---|---|
| 1012 | 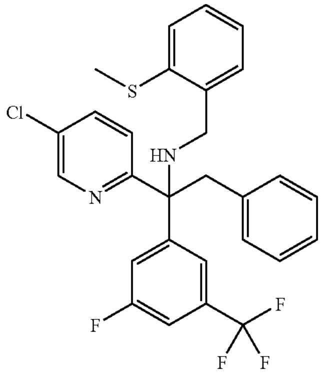 | N-(2-(methylthio)benzyl)-1-(5-chloropyridin-2-yl)-1-(3-fluoro-5-(trifluoromethyl)phenyl)-2-phenylethanamine | 3.90 LC 531.14 [M + H]+ | Procedures 1 and 48 |
| 1013 | 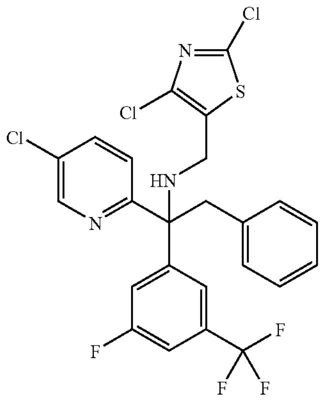 | 1-(5-chloropyridin-2-yl)-N-((2,4-dichlorothiazol-5-yl) methyl)-1-(3-fluoro-5-(trifluoromethyl)phenyl)-2-phenylethanamine | 4.55 LC 462.03 [M + H]+ | Procedures 1 and 48 |
| 1014 | 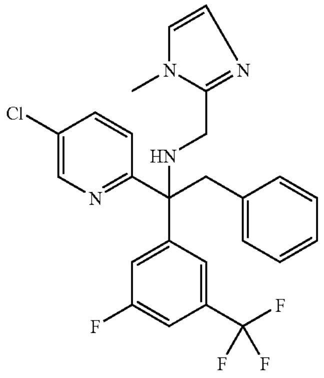 | 1-(5-chloropyridin-2-yl)-1-(3-fluoro-5-(trifluoromethyl) phenyl)-N-((1-methyl-1H-imidazol-2-yl)methyl)-2-phenylethanamine | 3.41 LC 489.12 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 1015 | 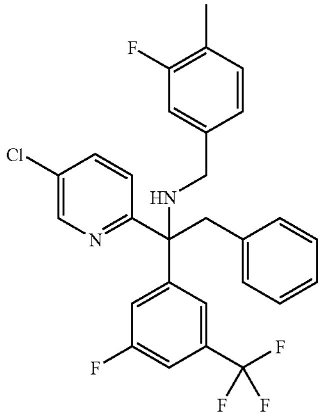 | N-(3-fluoro-4-methylbenzyl)-1-(5-chloropyridin-2-yl)-1-(3-fluoro-5-(trifluoromethyl) phenyl)-2-phenylethanamine | 3.83 LC 517.13 $[M + H]^+$ | Procedures 1 and 48 |
| 1016 | 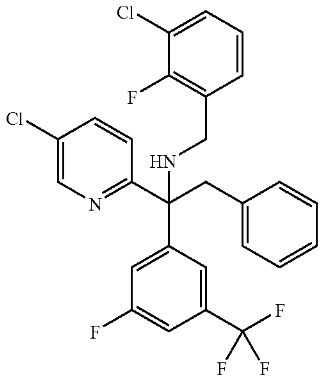 | N-(3-chloro-2-fluorobenzyl)-1-(5-chloropyridin-2-yl)-1-(3-fluoro-5-(trifluoromethyl) phenyl)-2-phenylethanamine | 4.15 LC 537.08 $[M + H]^+$ | Procedures 1 and 48 |
| 1017 | 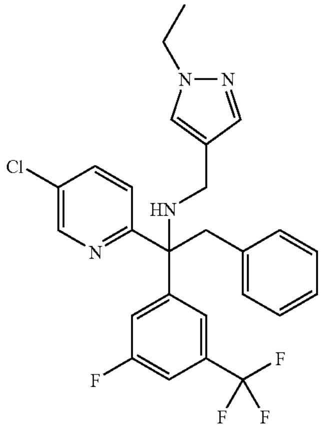 | 1-(5-chloropyridin-2-yl)-N-((1-ethyl-1H-pyrazol-4-yl)methyl)-1-(3-fluoro-5-(trifluoromethyl) phenyl)-2-phenylethanamine | 3.18 LC 503.19 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1018 | 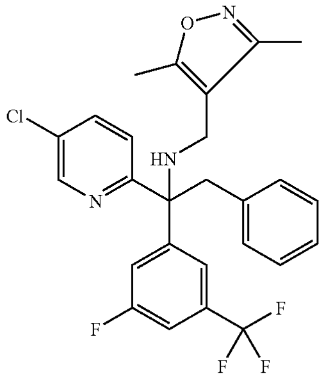 | 1-(5-chloropyridin-2-yl)-N-((3,5-dimethylisoxazol-4-yl) methyl)-1-(3-fluoro-5-(trifluoromethyl)phenyl)-2-phenylethanamine | 3.68 LC 504.15 $[M + H]^+$ | Procedures 1 and 48 |
| 1019 | 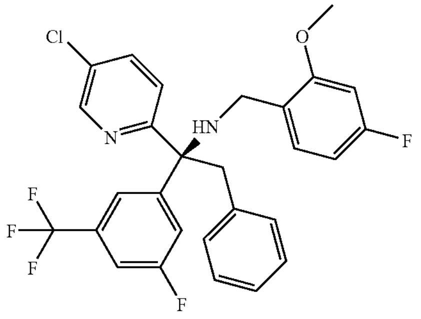 | (S)-N-(4-fluoro-2-methoxybenzyl)-1-(5-chloropyridin-2-yl)-1-(3-fluoro-5-(trifluoromethyl)phenyl)-2-phenylethanamine | 3.50 LC 533.37 $[M + H]^+$ | Procedures 5, 6, 7 and 48 |
| 1020 | 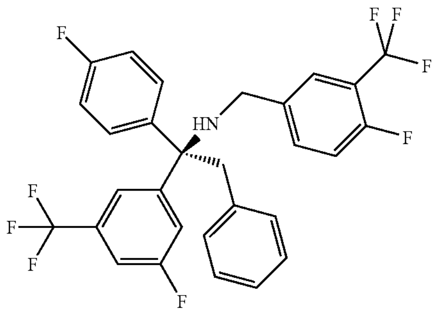 | (R)-N-(4-fluoro-3-(trifluoromethyl)benzyl)-1-(3-fluoro-5-(trifluoromethyl) phenyl)-1-(4-fluorophenyl)-2-phenylethanamine | 4.32 LC 554.42 $[M + H]^+$ | Procedures 5, 6, 7 and 48 |
| 1021 | 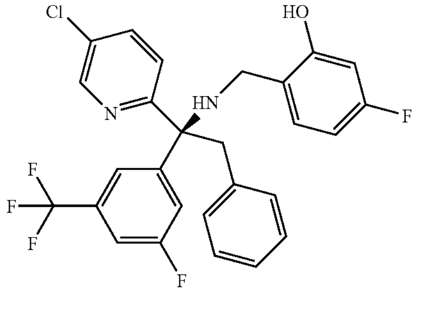 | (S)-2-((1-(5-chloropyridin-2-yl)-1-(3-fluoro-5-(trifluoromethyl)phenyl)-2-phenylethylamino)methyl)-5-fluorophenol | 3.35 LC 519.39 $[M + H]^+$ | Procedures 5, 6, 7 and 48 |

TABLE 11-continued

| Ex. No. | Structure | Name | Retention Time Min./ Molecular Mass | Prepared in the manner described in: |
|---|---|---|---|---|
| 1022 | 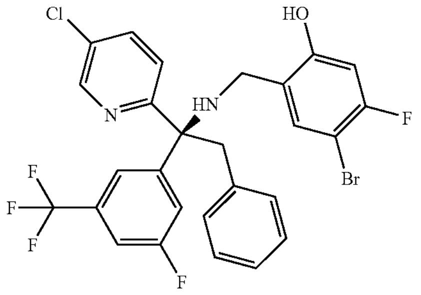 | (S)-4-bromo-2-((1-(5-chloropyridin-2-yl)-1-(3-fluoro-5-(trifluoromethyl)phenyl)-2-phenylethylamino)methyl)-5-fluorophenol | 3.70 LC 599.39 [M + H]$^+$ | Procedures 5, 6, 7 and 48 |
| 1023 | 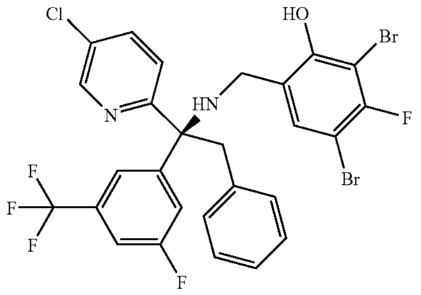 | (S)-2,4-dibromo-6-((1-(5-chloropyridin-2-yl)-1-(3-fluoro-5-(trifluoromethyl)phenyl)-2-phenylethylamino)methyl)-3-fluorophenol | 4.21 LC 677.37 [M + H]$^+$ | Procedures 5, 6, 7 and 48 |
| 1024 | 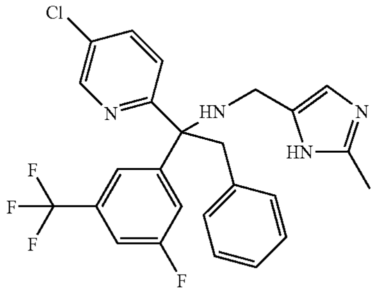 | 1-(5-chloropyridin-2-yl)-1-(3-fluoro-5-(trifluoromethyl) phenyl)-N-((2-methyl-1H-imidazol-5-yl)methyl)-2-phenylethanamine | 3.45 LC 489.28 [M + H]$^+$ | Procedures 1 and 48 |
| 1025 | 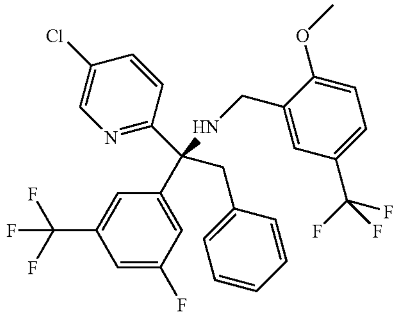 | (S)-N-(2-methoxy-5-(trifluoromethyl)benzyl)-1-(5-chloropyridin-2-yl)-1-(3-fluoro-5-(trifluoromethyl)phenyl)-2-phenylethanamine | 3.86 LC 583.38 [M + H]$^+$ | Procedures 5, 6, 7 and 48 |

TABLE 11-continued

| Ex. No. | Structure | Name | Retention Time Min./ Molecular Mass | Prepared in the manner described in: |
|---|---|---|---|---|
| 1026 | 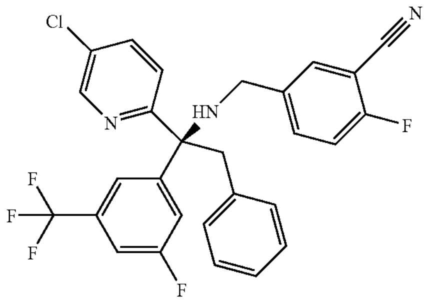 | (S)-5-((1-(5-chloropyridin-2-yl)-1-(3-fluoro-5-(trifluoromethyl)phenyl)-2-phenylethylamino)methyl)-2-fluorobenzonitrile | 3.96 LC 528.36 [M + H]+ | Procedures 5, 6, 7 and 48 |
| 1027 | 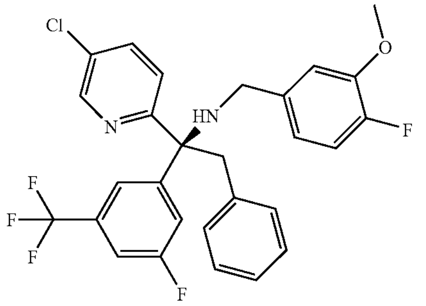 | (S)-N-(4-fluoro-3-methoxybenzyl)-1-(5-chloropyridin-2-yl)-1-(3-fluoro-5-(trifluoromethyl)phenyl)-2-phenylethanamine | 3.71 LC 533.42 [M + H]+ | Procedures 5, 6, 7 and 48 |
| 1028 | 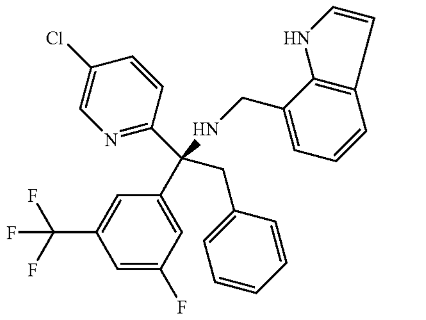 | (S)-N-((1H-indol-7-yl)methyl)-1-(5-chloropyridin-2-yl)-1-(3-fluoro-5-(trifluoromethyl) phenyl)-2-phenylethanamine | 3.71 LC 524.44 [M + H]+ | Procedures 5, 6, 7 and 48 |
| 1029 | 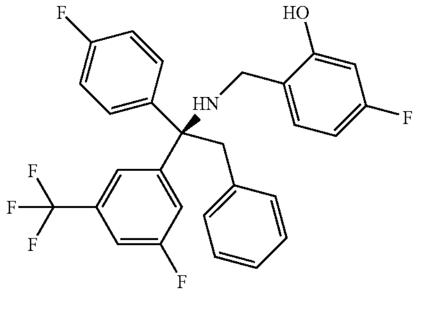 | (R)-5-fluoro-2-((1-(3-fluoro-5-(trifluoromethyl)phenyl)-1-(4-fluorophenyl)-2-phenylethylamino)methyl) phenol | 3.50 LC 501.93 [M + H]+ | Procedures 5, 6, 7 and 48 |

TABLE 11-continued

| Ex. No. | Structure | Name | Retention Time Min./ Molecular Mass | Prepared in the manner described in: |
|---|---|---|---|---|
| 1030 | 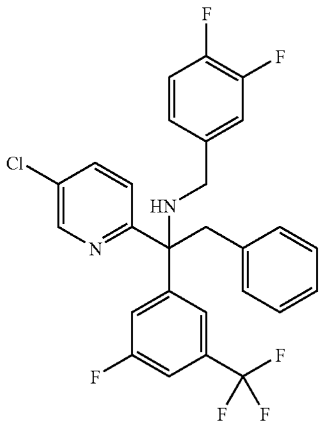 | N-(3,4-difluorobenzyl)-1-(5-chloropyridin-2-yl)-1-(3-fluoro-5-(trifluoromethyl)phenyl)-2-phenylethanamine | 3.90 LC 521.13 $[M+H]^+$ | Procedures 1 and 48 |
| 1031 | 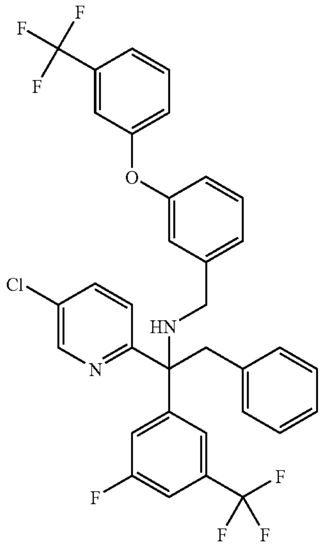 | N-(3-(3-(trifluoromethyl) phenoxy)benzyl)-1-(5-chloropyridin-2-yl)-1-(3-fluoro-5-(trifluoromethyl)phenyl)-2-phenylethanamine | 4.21 LC 645.28 $[M+H]^+$ | Procedures 1 and 48 |
| 1032 | 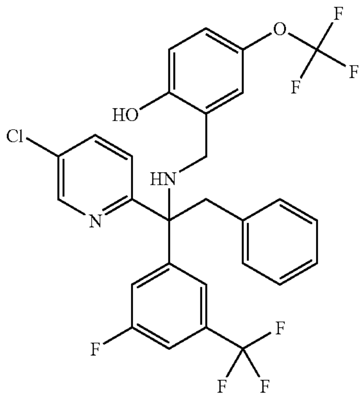 | 2-((1-(5-chloropyridin-2-yl)-1-(3-fluoro-5-(trifluoromethyl) phenyl)-2-phenylethylamino) methyl)-4-(trifluoromethoxy) phenol | 3.75 LC 585.25 $[M+H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1033 | 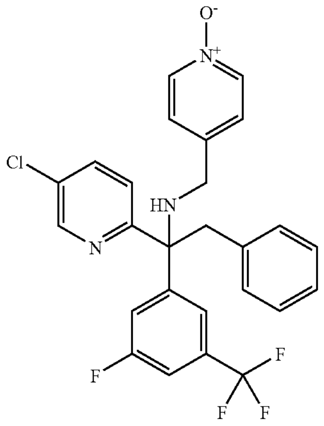 | 4-((1-(5-chloropyridin-2-yl)-1-(3-fluoro-5-(trifluoromethyl) phenyl)-2-phenylethylamino) methyl)pyridine-1-oxide | 3.79 LC 502.26 [M + H]+ | Procedures 1 and 48 |
| 1034 | 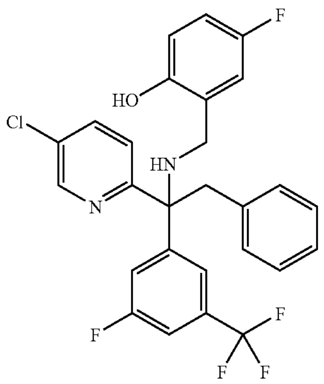 | 2-((1-(5-chloropyridin-2-yl)-1-(3-fluoro-5-(trifluoromethyl) phenyl)-2-phenylethylamino) methyl)-4-fluorophenol | 3.40 LC 519.26 [M + H]+ | Procedures 1 and 48 |
| 1035 | 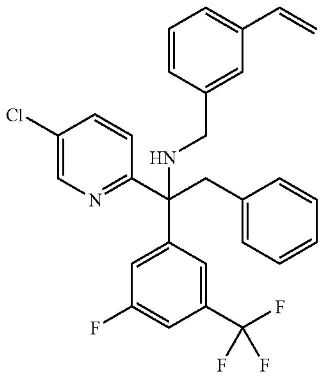 | N-(3-vinylbenzyl)-1-(5-chloropyridin-2-yl)-1-(3-fluoro-5-(trifluoromethyl)phenyl)-2-phenylethanamine | 3.83 LC 511.29 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 1036 | 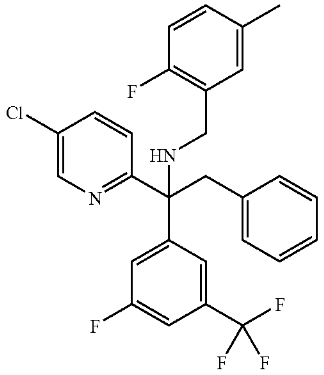 | N-(2-fluoro-5-methylbenzyl)-1-(5-chloropyridin-2-yl)-1-(3-fluoro-5-(trifluoromethyl) phenyl)-2-phenylethanamine | 3.95 LC 517.26 $[M + H]^+$ | Procedures 1 and 48 |
| 1037 | 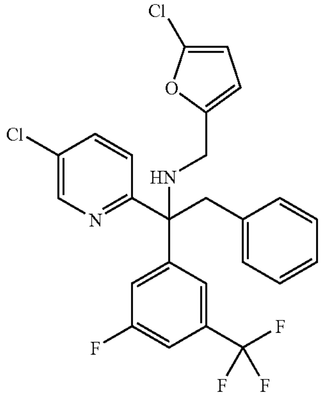 | N-((5-chlorofuran-2-yl)methyl)-1-(5-chloropyridin-2-yl)-1-(3-fluoro-5-(trifluoromethyl)phenyl)-2-phenylethanamine | 3.97 LC 509.19 $[M + H]^+$ | Procedures 1 and 48 |
| 1038 | 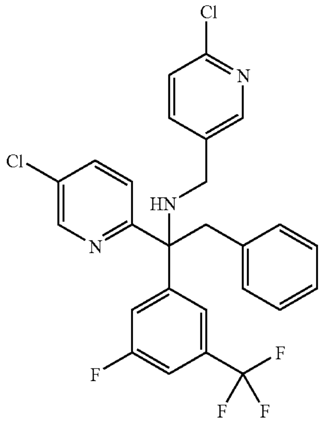 | 1-(5-chloropyridin-2-yl)-N-((6-chloropyridin-3-yl)methyl)-1-(3-fluoro-5-(trifluoromethyl) phenyl)-2-phenylethanamine | 3.95 LC 520.20 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1039 | 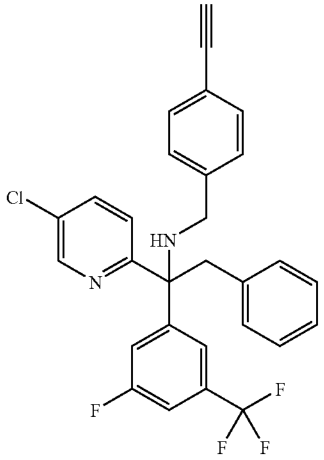 | N-(4-ethynylbenzyl)-1-(5-chloropyridin-2-yl)-1-(3-fluoro-5-(trifluoromethyl)phenyl)-2-phenylethanamine | 3.82 LC 509.26 $[M + H]^+$ | Procedures 1 and 48 |
| 1040 | 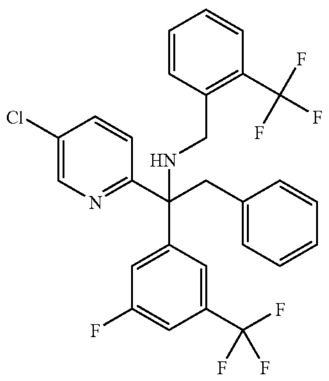 | N-(2-(trifluoromethyl)benzyl)-1-(5-chloropyridin-2-yl)-1-(3-fluoro-5-(trifluoromethyl) phenyl)-2-phenylethanamine | 4.38 LC 553.27 $[M + H]^+$ | Procedures 1 and 48 |
| 1041 | 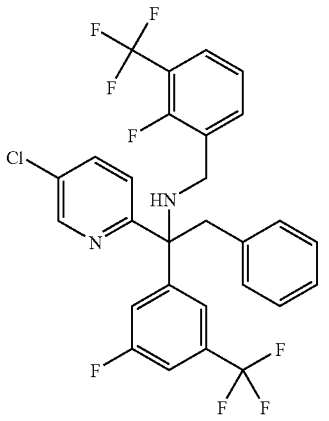 | N-(2-fluoro-3-(trifluoromethyl) benzyl)-1-(5-chloropyridin-2-yl)-1-(3-fluoro-5-(trifluoromethyl)phenyl)-2-phenylethanamine | 4.28 LC 571.22 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1042 | 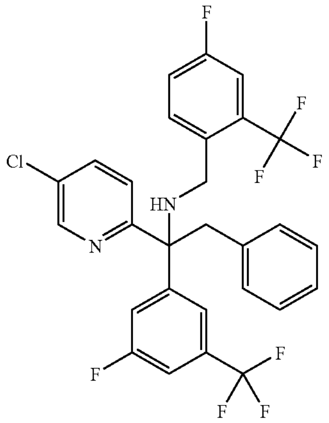 | N-(4-fluoro-2-(trifluoromethyl) benzyl)-1-(5-chloropyridin-2-yl)-1-(3-fluoro-5-(trifluoromethyl)phenyl)-2-phenylethanamine | 4.52 LC 571.22 [M + H]$^+$ | Procedures 1 and 48 |
| 1043 | 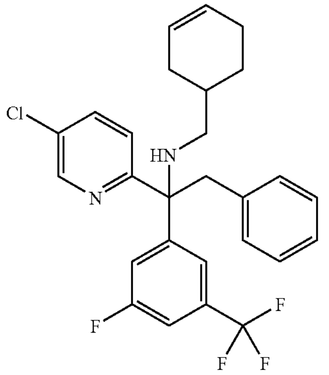 | 1-(5-chloropyridin-2-yl)-N-(cyclohex-3-enylmethyl)-1-(3-fluoro-5-(trifluoromethyl) phenyl)-2-phenylethanamine | 3.56 LC 489.32 [M + H]$^+$ | Procedures 1 and 48 |
| 1044 | 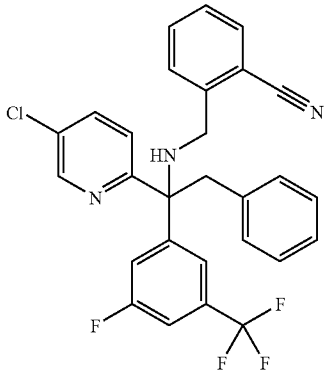 | 2-((1-(5-chloropyridin-2-yl)-1-(3-fluoro-5-(trifluoromethyl) phenyl)-2-phenylethylamino) methyl)benzonitrile | 3.25 LC 510.26 [M + H]$^+$ | Procedures 1 and 48 |

TABLE 11-continued

| Ex. No. | Structure | Name | Retention Time Min./ Molecular Mass | Prepared in the manner described in: |
|---|---|---|---|---|
| 1045 | 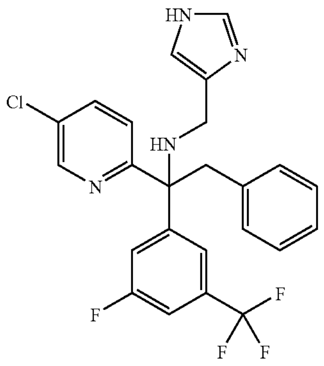 | N-((1H-imidazol-4-yl)methyl)-1-(5-chloropyridin-2-yl)-1-(3-fluoro-5-(trifluoromethyl)phenyl)-2-phenylethanamine | 3.43 LC 475.25 $[M + H]^+$ | Procedures 1 and 48 |
| 1046 | 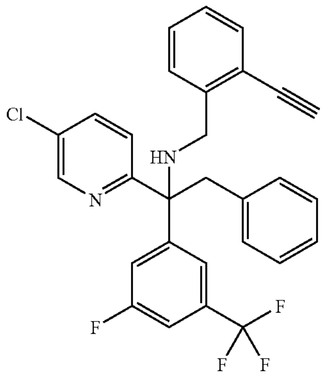 | N-(2-ethynylbenzyl)-1-(5-chloropyridin-2-yl)-1-(3-fluoro-5-(trifluoromethyl)phenyl)-2-phenylethanamine | 3.90 LC 509.26 $[M + H]^+$ | Procedures 1 and 48 |
| 1047 | 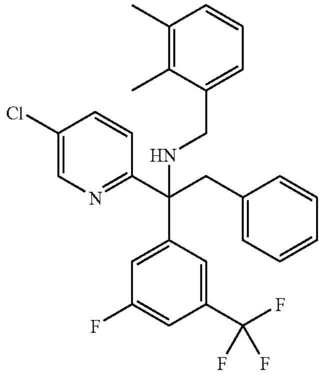 | N-(2,3-dimethylbenzyl)-1-(5-chloropyridin-2-yl)-1-(3-fluoro-5-(trifluoromethyl)phenyl)-2-phenylethanamine | 3.91 LC 513.33 $[M + H]^+$ | Procedures 1 and 48 |

TABLE 11-continued

| Ex. No. | Structure | Name | Retention Time Min./ Molecular Mass | Prepared in the manner described in: |
|---|---|---|---|---|
| 1048 | 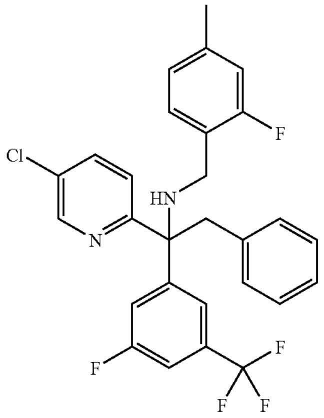 | N-(2-fluoro-4-methylbenzyl)-1-(5-chloropyridin-2-yl)-1-(3-fluoro-5-(trifluoromethyl) phenyl)-2-phenylethanamine | 3.92 LC 517.27 [M + H]+ | Procedures 1 and 48 |
| 1049 | 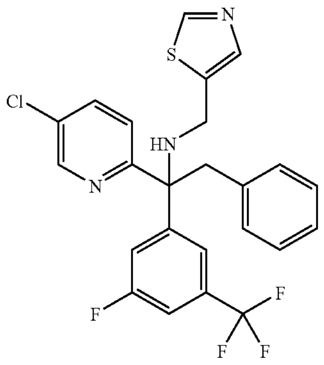 | 1-(5-chloropyridin-2-yl)-1-(3-fluoro-5-(trifluoromethyl) phenyl)-2-phenyl-N-(thiazol-5-ylmethyl)ethanamine | 3.90 LC 492.21 [M + H]+ | Procedures 1 and 48 |
| 1050 | 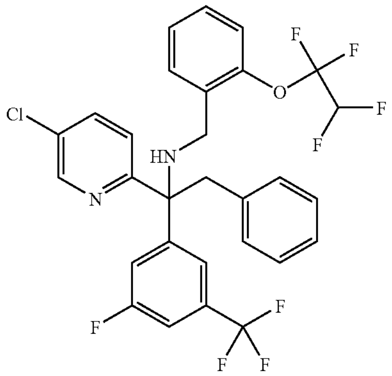 | N-(2-(1,1,2,2-tetrafluoroethoxy)benzyl)-1-(5-chloropyridin-2-yl)-1-(3-fluoro-5-(trifluoromethyl)phenyl)-2-phenylethanamine | 4.08 LC 601.25 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 1051 | 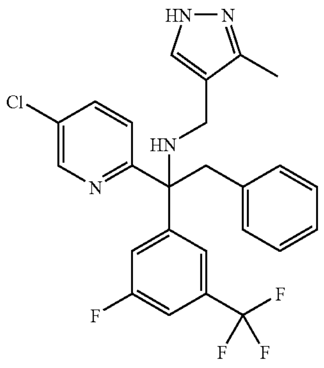 | 1-(5-chloropyridin-2-yl)-1-(3-fluoro-5-(trifluoromethyl) phenyl)-N-((3-methyl-1H-pyrazol-4-yl)methyl)-2-phenylethanamine | 3.13 LC 489.26 [M + H]+ | Procedures 1 and 48 |
| 1052 | 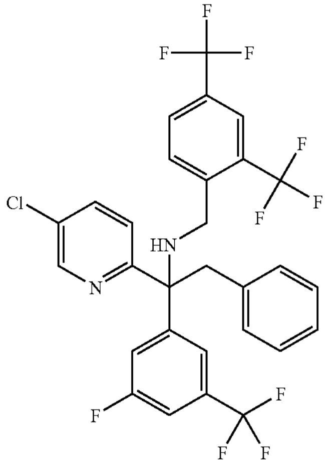 | N-(2,4-bis(trifluoromethyl) benzyl)-1-(5-chloropyridin-2-yl)-1-(3-fluoro-5-(trifluoromethyl)phenyl)-2-phenylethanamine | 4.91 LC 621.24 [M + H]+ | Procedures 1 and 48 |
| 1053 | 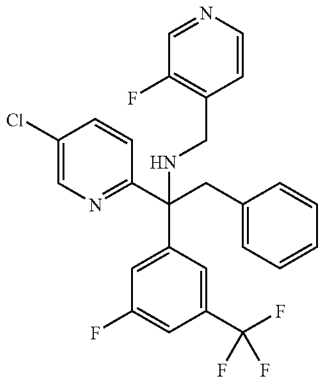 | 1-(5-chloropyridin-2-yl)-1-(3-fluoro-5-(trifluoromethyl) phenyl)-N-((3-fluoropyridin-4-yl)methyl)-2-phenylethanamine | 4.09 LC 504.26 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 1054 | 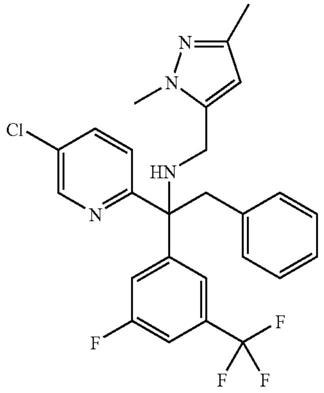 | 1-(5-chloropyridin-2-yl)-N-((1,3-dimethyl-1H-pyrazol-5-yl)methyl)-1-(3-fluoro-5-(trifluoromethyl)phenyl)-2-phenylethanamine | 3.88 LC 503.26 [M + H]+ | Procedures 1 and 48 |
| 1055 | 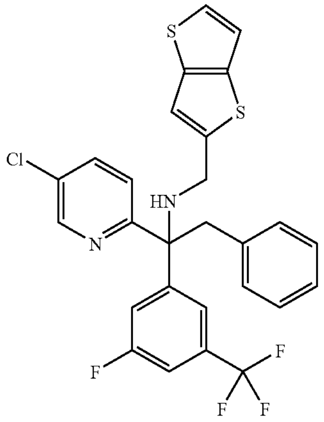 | 1-(5-chloropyridin-2-yl)-1-(3-fluoro-5-(trifluoromethyl) phenyl)-2-phenyl-N-(thieno[3,2-b]thiophen-2-ylmethyl)ethanamine | 4.17 LC 547.20 [M + H]+ | Procedures 1 and 48 |
| 1056 | 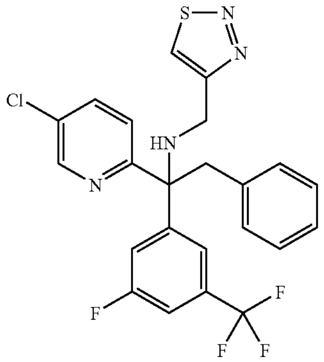 | N-((1,2,3-thiadiazol-4-yl)methyl)-1-(5-chloropyridin-2-yl)-1-(3-fluoro-5-(trifluoromethyl)phenyl)-2-phenylethanamine | 3.81 LC 493.19 [M + H]+ | Procedures 1 and 48 |

TABLE 11-continued

| Ex. No. | Structure | Name | Retention Time Min./ Molecular Mass | Prepared in the manner described in: |
|---|---|---|---|---|
| 1057 | 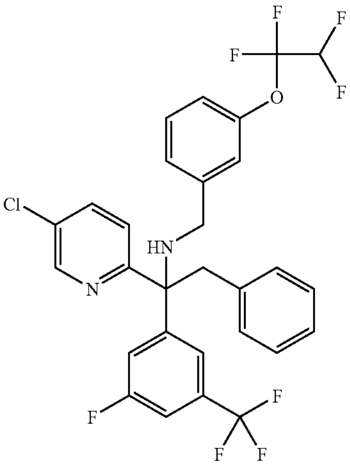 | N-(3-(1,1,2,2-tetrafluoroethoxy)benzyl)-1-(5-chloropyridin-2-yl)-1-(3-fluoro-5-trifluoromethyl)phenyl)-2-phenylethanamine | 3.95 LC 601.23 [M + H]$^+$ | Procedures 1 and 48 |
| 1058 | 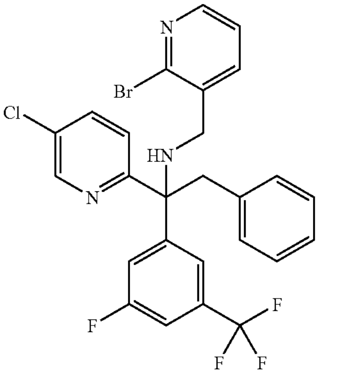 | N-((2-bromopyridin-3-yl)methyl)-1-(5-chloropyridin-2-yl)-1-(3-fluoro-5-(trifluoromethyl)phenyl)-2-phenylethanamine | 4.24 LC 566.16 [M + H]$^+$ | Procedures 1 and 48 |
| 1059 | 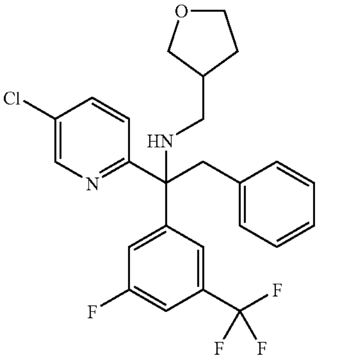 | 1-(5-chloropyridin-2-yl)-1-(3-fluoro-5-(trifluoromethyl) phenyl)-2-phenyl-N-((tetrahydrofuran-3-yl) methyl)ethanamine | 3.20 LC 479.30 [M + H]$^+$ | Procedures 1 and 48 |
| 1060 | 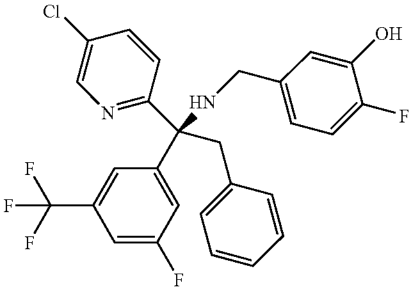 | (S)-5-((1-(5-chloropyridin-2-yl)-1-(3-fluoro-5-(trifluoromethyl)phenyl)-2-phenylethylamino)methyl)-2-fluorophenol | 3.46 LC 518.94 [M + H]$^+$ | Procedures 5, 6, 7 and 48 |

TABLE 11-continued

| Ex. No. | Structure | Name | Retention Time Min./ Molecular Mass | Prepared in the manner described in: |
|---|---|---|---|---|
| 1061 | 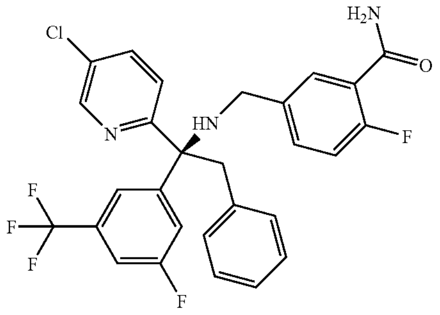 | (S)-5-((1-(5-chloropyridin-2-yl)-1-(3-fluoro-5-(trifluoromethyl)phenyl)-2-phenylethylamino)methyl)-2-fluorobenzamide | 3.40 LC 545.99 $[M + H]^+$ | Procedures 5, 6, 7 and 48 |
| 1062 | 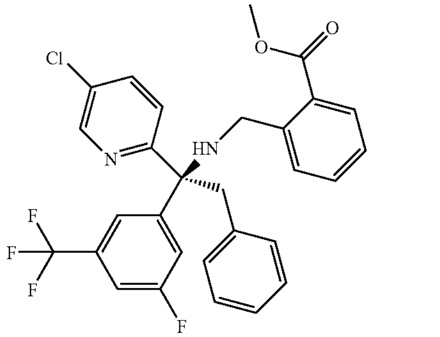 | (S)-methyl 2-((1-(5-chloropyridin-2-yl)-1-(3-fluoro-5-(trifluoromethyl)phenyl)-2-phenylethylamino)methyl) benzoate | 3.53 LC 543.34 $[M + H]^+$ | Procedures 5, 6, 7 and 48 |
| 1063 | 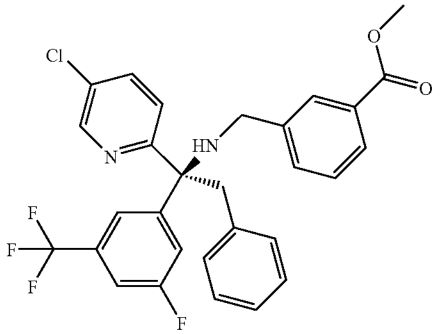 | (S)-methyl 3-((1-(5-chloropyridin-2-yl)-1-(3-fluoro-5-(trifluoromethyl)phenyl)-2-phenylethylamino)methyl) benzoate | 3.76 LC 543.33 $[M + H]^+$ | Procedures 5, 6, 7 and 48 |
| 1064 | 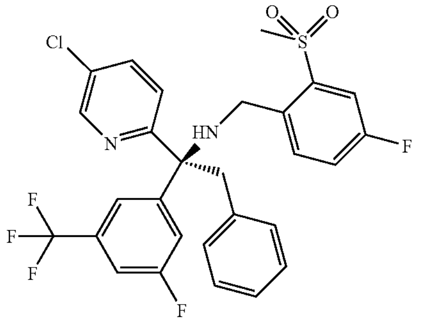 | (S)-N-(4-fluoro-2-(methylsulfonyl)benzyl)-1-(5-chloropyridin-2-yl)-1-(3-fluoro-5-(trifluoromethyl)phenyl)-2-phenylethanamine | 3.93 LC 580.94 $[M + H]^+$ | Procedures 5, 6, 7 and 48 |

In the following examples, the chromatography techniques used to determine the compound retention times are as follows:

LCMS Method 1=Phenomenex Luna C18 column, 4.6×50 mm eluting with 10-90% MeOH/$H_2O$ over 4 minutes containing 0.1% TFA; 4 mL/min, monitoring at 220 nm.

LCMS Method 2=Phenomenex Luna C18 column, 4.6×30 mm eluting with 10-90% MeOH/$H_2O$ over 2 minutes containing 0.1% TFA; 5 mL/min, monitoring at 220 nm.

LCMS Method 3=Phenomenex Luna C18 column, 4.6×50 mm eluting with 10-90% MeOH/$H_2O$ over 4 minutes containing 10mM NH4OAc; 4 mL/min, monitoring at 220 nm.

LCMS Method 4=Phenomenex Luna C18 column, 4.6×50 mm eluting with 10-90% ACN/$H_2O$ over 4 minutes containing 10OmM NH4OAc; 4 mL/min, monitoring at 220 nm.

LCMS Method 5=Waters SunFire C18, 4.6×50 mm×5 μm eluting with 10-90% MeOH/$H_2O$ over 4 minutes containing 0.1% TFA; 4 mL/min, monitoring at 220 nm.

LCMS Method 6=YMC C18 column, 4.6×50 mm eluting with 10-90% MeOH/$H_2O$ over 4 minutes containing 0.1% TFA; 4 mL/min, monitoring at 220 nm. The molecular mass of the compounds listed were determined by MS (ES) by the formula m/z.

HPLC Method 1=Phenomenex Luna C18 column, 4.6×50 mm eluting with 10-90% MeOH/$H_2O$ over 4 minutes containing 0.2% PPA; 4 mL/min, monitoring at 220 nm.

HPLC Method 2=Phenomenex Luna C18 column, 4.6×50 mm eluting with 10-90% ACN/$H_2O$ over 4 minutes containing 0.1% TFA; 4 mL/min, monitoring at 220 nm.

EXAMPLE 1065

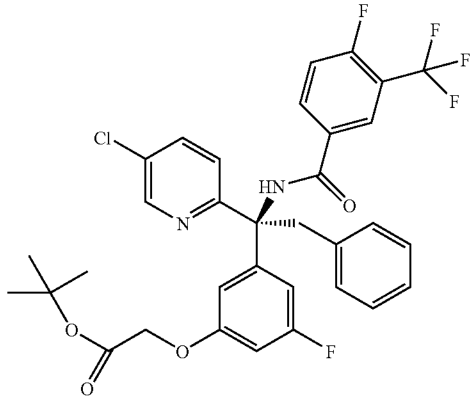

(S)-tert-butyl 2-(3-(1-(5-chloropyridin-2-yl)-1-(4-fluoro-3-(trifluoromethyl)benzamido)-2-phenylethyl)-5-fluorophenoxy)acetate Procedure 49

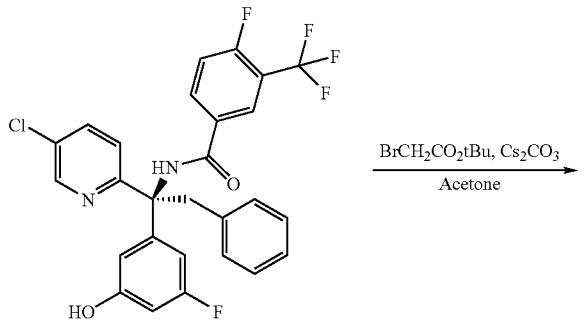

-continued

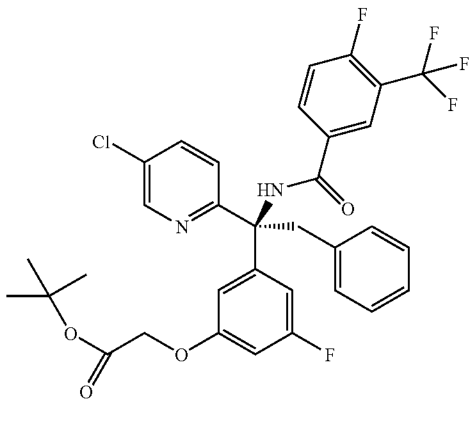

To a solution of (S)—N-(1-(5-chloropyridin-2-yl)-1-(3-fluoro-5-hydroxyphenyl)-2-phenylethyl)-4-fluoro-3-(trifluoromethyl)benzamide (30 mg, 0.06 mmol), prepared as described in Procedures 14, in acetone (1 mL) was added $Cs_2CO_3$ (37 mg, 0.11) and t-butyl-α-bromoacetate (22 mg, 0.11 mmol). The reaction mixture was stirred at room temperature overnight, then purified by ISCO chromatography (4 g column) using hexanes/EtOAc (0-20% over 20 min) to give (S)-tert-butyl-2-(3-(1-(5-chloropyridin-2-yl)-1-(4-fluoro-3-(trifluoromethyl)benzamido)-2-phenylethyl)-5-fluorophenoxy)acetate as a white foam (34 mg, 93% yield).LCMS: RT=4.32 min [M+H] 647.44 (LCMS Method 2); 1H NMR (400 MHz, $CDCl_3$) δ ppm 1.43-1.47 (m, 9H), 3.59 (d, J=12.74 Hz, 1 H) 4.44 (d, J=2.64 Hz, 2 H), 4.54 (d, J=12.74 Hz, 1 H), 6.49 (d, J=10.11 Hz, 1 H), 6.53 (d, J=7.47 Hz, 2 H), 6.85-6.89 (m, 2 H), 7.02 (t, J=7.47 Hz, 2 H), 7.12 (t, J=7.25 Hz, 1 H), 7.22-7.28 (m, 2 H), 7.70 (dd, J=8.57, 2.42 Hz, 1 H), 7.88 (ddd, J=8.57, 2.42, 2.20 Hz, 1 H), 8.05 (d, J=4.83 Hz, 1 H), 8.31 (d, J=2.20 Hz, 1 H), 9.11 (s, 1 H).

EXAMPLE 1066

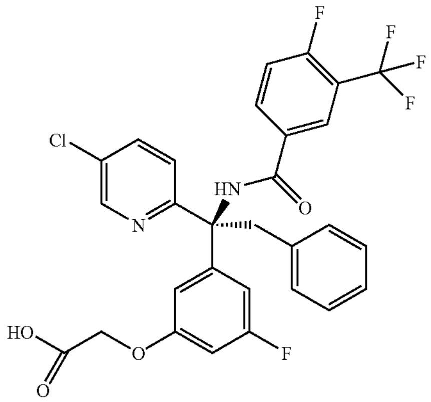

(S)-2-(3-(1-(5-chloropyridin-2-yl)-1-(4-fluoro-3-(trifluoromethyl)benzamido)-2-phenylethyl)-5-fluorophenoxy)acetic acid Procedure 50

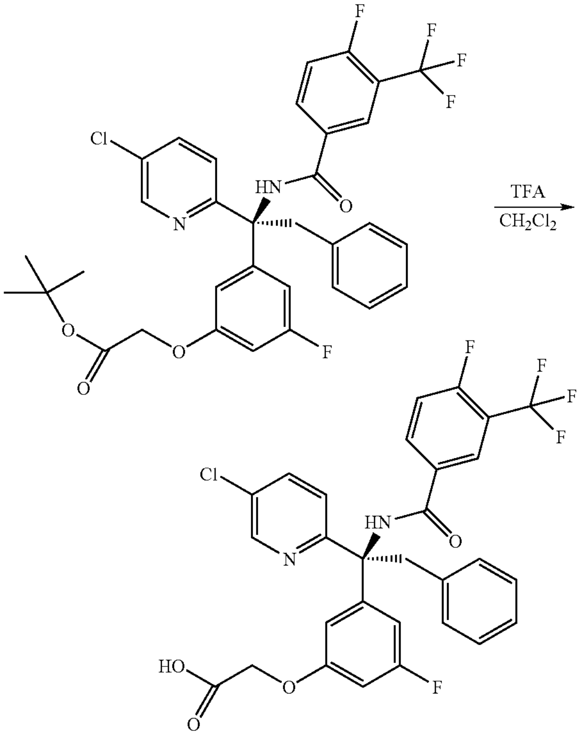

To a solution of (S)-tert-butyl-2-(3-(1-(5-chloropyridin-2-yl)-1-(4-fluoro-3-(trifluoromethyl)benzamido)-2-phenylethyl)-5-fluorophenoxy)acetate (27 mg, 0.04 mmol) in $CH_2Cl_2$ (1 mL) was added TFA (95 mg, 0.836 mmol). The mixture was stirred at room temperature for 2 h, and the solvent was removed to give (S)-2-(3-(1-(5-chloropyridin-2-yl)-1-(4-fluoro-3-(trifluoromethyl)benzamido)-2-phenylethyl)-5-fluorophenoxy)acetic acid as an white foam (25 mg, 100% yield). LCMS: RT=4.08 min [M+H] 591.46 (LCMS Method 1); 1H NMR (400 MHz, $CDCl_3$) δ 3.69 (d, J=12.74 Hz, 1 H), 4.40 (d, J=13.18 Hz, 1 H), 6.53 (d, J=7.47 Hz, 3 H), 6.76 (d, J=9.23 Hz, 1 H), 6.91 (s, 1 H), 7.05 (t, J=7.47 Hz, 2 H), 7.15 (t, J=7.47 Hz, 7.25 -7.34 (m, 2 H), 7.78 (dd, J=8.57, 2.42 Hz, 1 H), 7.86 (ddd, J=8.68, 2.31, 2.20 Hz, 1 H), 7.91-7.98 (m, 1 H), 8.36 (d, J=2.20 Hz, 1 H), 9.30 (s, 1 H).

EXAMPLE 1067

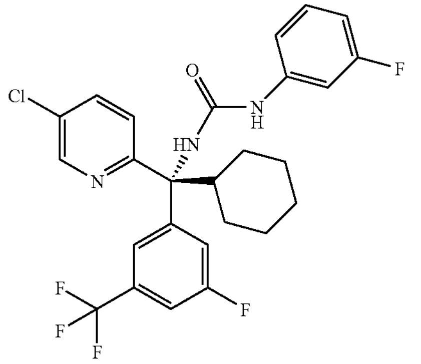

1-((5-chloropyridin-2-yl)(cyclohexyl)(3-fluoro-5-(trifluoromethyl)phenyl)methyl)-3-(3-fluorophenyl) urea [Homochiral. Absolute stereochemistry not determined]

Procedure 51

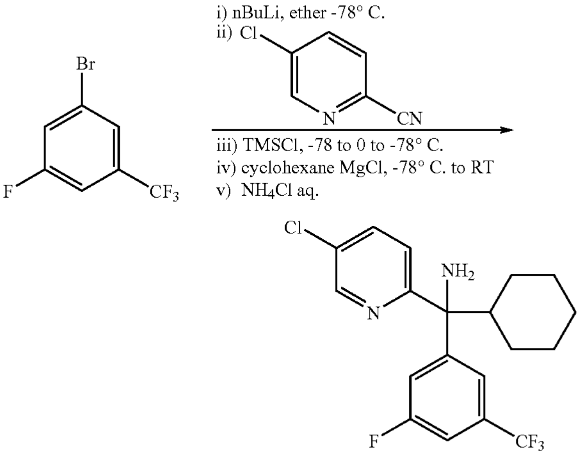

A dry 200 mL flask under nitrogen was charged with 1-bromo-3-fluoro-5-(trifluoromethyl)benzene (1.22 g, 0.005 mol). Dry ether (50mL) was added and the solution was cooled to −78° C. n-BuLi (3.0 mL, 1.6 M in hexanes, 0.0048 mol) was added dropwise and the resulting solution was stirred at −78° C. for 30 min. A solution of 5-chloropicolinonitrile (0.692 g, 0.005 mol) in anhydrous THF (7 mL) was then added. The resulting solution was stirred at −78° C. for 1 hr. Redistilled TMSCl (0.65 mL, 0.00515 mol) was added dropwise. The reaction mixture was allowed to reach 0° C. and then cooled to −78° C. Cyclohexylmagnesium chloride (2.75 mL, 2.0 M, 0.0055 mol) was added dropwise. The solution was allowed to reach room temperature. The reaction was quenched by addition of water followed by aqueous ammonium chloride. The aqueous layer was extracted with ether (2×50 mL). The combined organic portions were filtered through a pad of silica and the silica was washed with 4:1 Hexanes:EtOAc. The solvents were evaporated to get the racemic (5 -chloropyridin-2-yl)(cyclohexyl)(3-fluoro-5-(trifluoromethyl)phenyl)methanamine as an oil (1.39 g, 75% yield). LCMS RT=3.28 min, [M+H] 387.14, Purity 79% (LCMS Method 6).

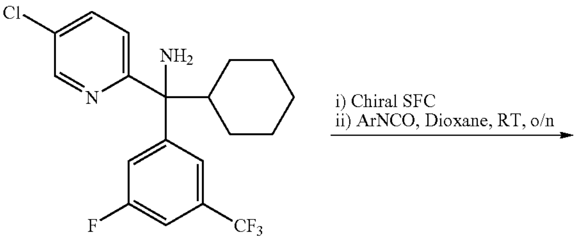

-continued

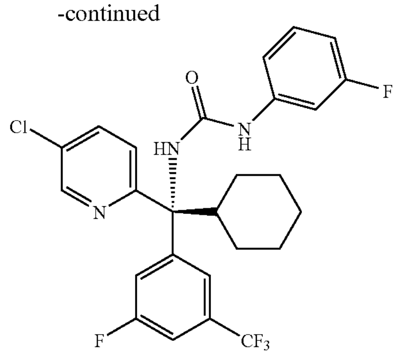

(5-chloropyridin-2-yl)(cyclohexyl)(3-fluoro-5-(trifluoromethyl)phenyl)methanamine was resolved by chiral prep SFC (Chiralpak AD 10µ column, 4.6×250 mm isocratic elution with $CO_2$ (95%) and EtOH (5%) and diethylamine (0.1%); 2 mL/min @ 100 bar, monitoring at 220 nm) to give (S)-(5-chloropyridin-2-yl)(cyclohexyl)(3-fluoro-5-(trifluoromethyl)phenyl)methanamine at retention time of 3.35 min and (R)-(5-chloropyridin-2-yl)(cyclohexyl)(3-fluoro-5-(trifluoromethyl)phenyl)methanamine at retention time of 3.85 min. (R)-1-((5-chloropyridin-2-yl)(cyclohexyl)(3-fluoro-5-(trifluoromethyl)phenyl)methyl)-3-(3-fluorophenyl)urea was prepared by method described in procedure 2, using (R)-(5-chloropyridin-2-yl)(cyclohexyl)(3-fluoro-5-(trifluoromethyl)phenyl)methanamine and 1-fluoro-3-isocyanatobenzene as starting material. LCMS: RT=4.35 min, [M+H] 524.38, 99% purity (LCMS Method 1).

EXAMPLE 1068

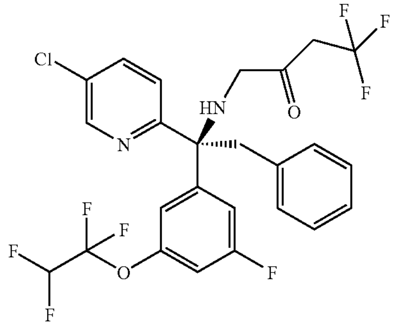

(S)-1-(1-(5-chloropyridin-2-yl)-1-(3-fluoro-5-(1,1,2,2-tetrafluoroethoxy)phenyl)-2-phenylethylamino)-4,4,4-trifluorobutan-2-one Procedure 52

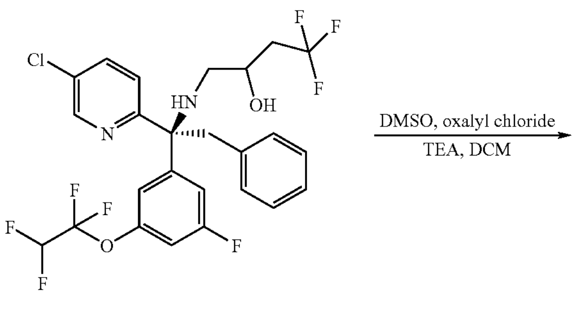

-continued

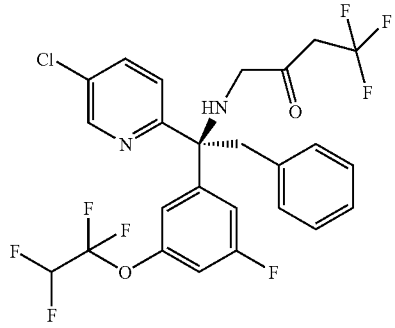

1-((S)-1-(5-chloropyridin-2-yl)-1-(3-fluoro-5-(1,1,2,2-tetrafluoroethoxy)phenyl)-2-phenylethylamino)-4,4,4-trifluorobutan-2-ol was prepared as described in Procedure 19 in 63% yield, using 2-(2,2,2-trifluoroethyl)oxirane as the epoxide starting material. LCMS RT=1.785 min [M+H] 568.94 (LCMS Method 2).

At −78° C. under argon, DMSO (6.6 mg, 0.084 mmol) was added to a solution of oxalyl chloride (27 µL, 2.0 M in dichloromethane, 0.053 mmol) in dichloromethane (1.0 mL). After 10 min, 1-((S)-1-(5-chloropyridin-2-yl)-1-(3-fluoro-5-(11,2,2-tetrafluoroethoxy)phenyl)-2-phenylethylamino)-4,4,4-trifluorobutan-2-ol (20 mg, 0.035 mmol) in dichloromethane (0.5 mL) was added and the reaction mixture stirred at -78° C. for 1 h, followed by the addition of TEA (24 µL, 0.18 mmol). The resulting reaction mixture was stirred at −78° C. for 1 h then quenched by addition of $H_2O$ (10 mL). The aqueous layer was extracted with EtOAc (2×10 mL). The combined organic layers were dried over $MgSO_4$, filtered and concentrated. The residue was purified by preparative HPLC YMC ODS S5 28×100 mm Ballistic column 40-100% MeOH (90% in water, 0.% TFA) gradient over 10 min with flow rate 40 mL/min and UV detection at 220 nm. (S)-1-(1-(5-chloropyridin-2-yl)-1-(3-fluoro-5-(1,1,2,2-tetrafluoroethoxy)phenyl)-2-phenylethylamino)-4,4,4-trifluorobutan-2-one eluted at a retention time of 9.92 min and was isolated as a clear oil (7.1 mg, yield 36%) LCMS: RT=2.03 min [M+H] 566.89 (LCMS Method 2); HPLC: RT=4.17 min, Purity 100% (HPLC Method 1); NMR: 400 MHz $^1H$ ($CDCl_3$) 8.46 ppm, 1 H, d, J=2.20 Hz; 7.53 ppm, 1 H, dd, J=8.79, 2.64 Hz; 7.06 ppm, 4 H, m; 6.90 ppm, 2 H, m; 6.80 ppm, 1 H, d, J=8.79 Hz; 6.55 ppm, 2 H, d, J=6.59 Hz; 3.73 ppm, 1 H, d, J=13.62 Hz; 3.45 ppm, 4 H, m; 3.11 ppm, 2 H, q, J=10.11 Hz.

EXAMPLE 1069

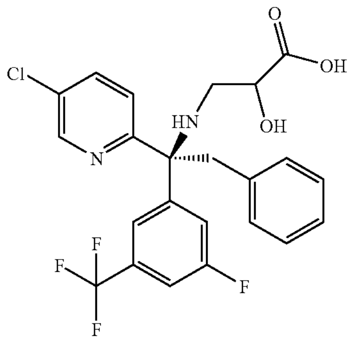

3-((S)-1-(5-chloropyridin-2-yl)-1-(3-fluoro-5-(trifluoromethyl)phenyl)-2-phenylethylamino)-2-hydroxypropanoic acid Procedure 53

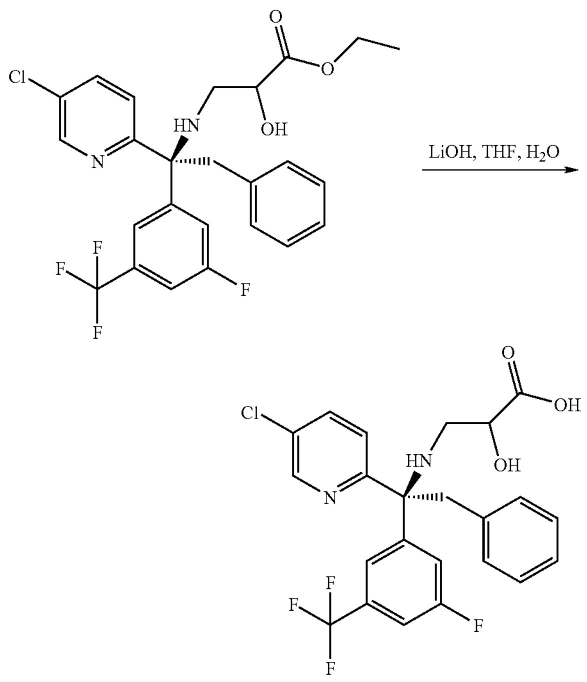

Ethyl 3-((S)-1-(5-chloropyridin-2-yl)-1 -(3-fluoro-5-(trifluoromethyl)phenyl)-2-phenylethylamino)-2-hydroxypropanoate was prepared as described in procedure 19 in the yield of 55% using ethyl oxirane-2-carboxylate as the epoxide starting material. LCMS RT=1.952 min [M+H] 510.88 (LCMS Method 2).

To a solution of ethyl 3-((S)-1-(5-chloropyridin-2-yl)-1-(3-fluoro-5-(trifluoromethyl)phenyl)-2-phenylethylamino)-2-hydroxypropanoate (18 mg, 0.035 mmol) in THF (0.5 mL) and $H_2O$ (0.5 mL) was added LiOH (2 mg, 0.053 mmol). The reaction mixture was stirred at room temperature for 18 h. The reaction mixture was concentrated, made acidic by addition of 1 N HCl (10 mL) and extracted with EtOAc (15 mL). The organic layer was dried over $MgSO_4$, filtered and concentrated. The residue was purified by preparative HPLC YMC ODS S5 28×100 mm Ballistic column 20-100% MeOH (90% in water, 0.1% TFA) gradient over 10 min with flow rate 40 mL/min and UV detection at 220 nm. 3-((S)-1-(5-chloropyridin-2-yl)-1-(3-fluoro-5-(trifluoromethyl)phenyl)-2-phenylethylamino)-2-hydroxypropanoic acid eluted at a retention time of 10.9 min and was isolated as a clear oil (10.7 mg, yield 63%) LCMS: RT=1.76 min [M+H] 482.95 (LCMS Method 2); HPLC: RT=3.91 min, Purity 100% (HPLC Method 1); NMR: 400 MHz $^1H$ ($CDCl_3$) 8.80 ppm, 2 H, s; 8.40 ppm, 1 H, m; 7.67 ppm, 3 H, s; 7.39 ppm, 1 H, d, J=6.59 Hz; 7.12 1 H, t, J=7.03 Hz; 7.04 3 H, t, J=7.03 Hz; 6.85 ppm, 1 H, s; 6.61 ppm, 2 H, d, J=7.03 Hz; 4.76 ppm, 1 H, s; 4.09 ppm, 1 H, m; 3.75 ppm, 1 H, s; 3.08 ppm, 1 H, s; 2.82 ppm 1 H, s.

EXAMPLE 1070

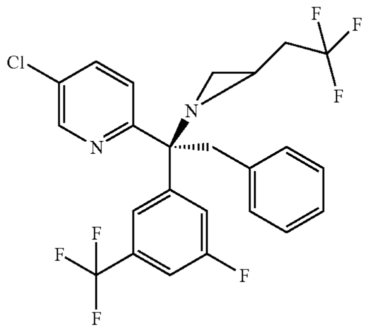

5-chloro-2-((S)-1-(3-fluoro-5-(trifluoromethyl)phenyl)-2-phenyl-1-(2-(2,2,2-trifluoroethyl)aziridin-1-yl)ethyl)pyridine Procedure 54

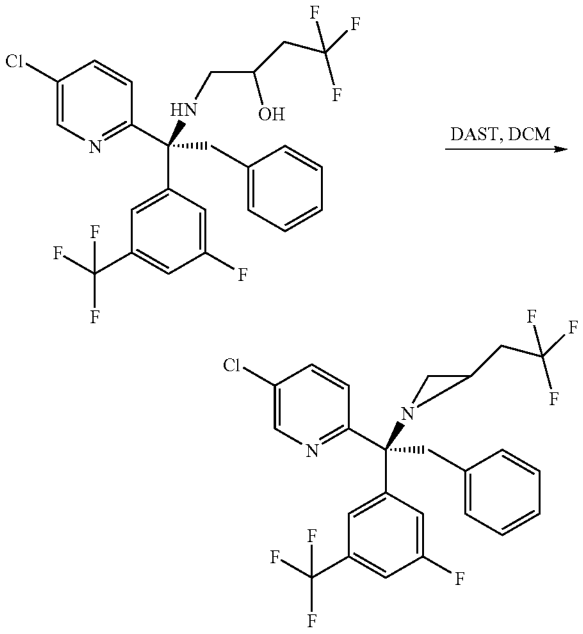

1 -((S)-1-(5-chloropyridin-2-yl)-1-(3-fluoro-5-(1,1,2,2-tetrafluoroethoxy)phenyl)-2-phenylethylamino)-4,4,4-trifluorobutan-2-ol was prepared as described in procedure 19 in the yield of 100% using 2-(2,2,2-trifluoroethyl)oxirane as the epoxide starting material. LCMS RT=1.827 min [M+H] 520.97 (LCMS Method 2).

To a solution of 1-((S)-1-(5-chloropyridin-2-yl)-1-(3-fluoro-5-(trifluoromethyl)phenyl)-2-phenylethylamino)-4,4,4-trifluorobutan-2-ol (60 mg, 0.12 mmol) in dichloromethane (0.5 mL) was added DAST (24 mg, 0.14 mmol) at 0° C. The reaction mixture was allowed to warm up to room temperature and was stirred for 18 h. The reaction mixture was concentrated and purified by silica gel chromatography on ISCO (40 g column) with 0-30% hexanes in ethylacetate gradient over 10 minutes to yield a clear oil as a mixture of two diastereoisomers (40.6 mg, 70% yield). This mixture was separated by semi-preparative chiral HPLC (OD 10u column, 2×25 cm isocratic elution with (5%)EtOH/MeOH(50/50)/(95%)heptane, 15 mL/min). The first isomer of 5-chloro-2-((S)-1-(3-fluoro-5-(trifluoromethyl)phenyl)-2-phenyl-1-(2-(2,2,2-trifluoroethyl)aziridin-1-yl)ethyl)pyridine eluted at a retention time of 9.97 min and was isolated as a clear oil (12.7 mg, yield 22%) LCMS: RT=2.34 min [M+H] 502.89 (LCMS Method 2); HPLC: RT=4.47 min, Purity 100% (HPLC Method 1); NMR: 400 MHz $^1$H ($CDCl_3$) 8.59 ppm, 1 H, d, J=2.64 Hz; 7.56 ppm, 1 H, dd, J=8.35, 2.64 Hz; 7.19 ppm, 1 H, d, J=7.91 Hz; 7.10 ppm, 1 H, s; 7.02 ppm, 5 H, m; 6.72 ppm, 2 H, d, J=7.03 Hz; 3.67 ppm, 1 H, d, J=13.18 Hz; 3.46 ppm, 1 H, d, J=13.18 Hz; 2.59 ppm, 1 H, ddd, J=15.16, 10.33, 4.83 Hz; 2.08 ppm, 1 H, ddd, J=14.83, 10.88, 7.25 Hz; 1.76 ppm, 1 H, d, J=2.64 Hz; 1.55 ppm, 1 H, d, J=6.59 Hz; 1.43 ppm, 1 H, m. The second isomer of 5-chloro-2-((S)-1-(3-fluoro-5-(trifluoromethyl)phenyl)-2-phenyl-1-(2-(2,2,2-trifluoroethyl)aziridin-1-yl)ethyl)pyridine eluted at a retention time of 15.2 min and was isolated as a clear oil (10.2 mg, yield 18%) LCMS: RT=2.34 min [M+H] 502.89 (LCMS Method 2); HPLC: 4.49 min, Purity 100% (HPLC Method 1); NMR: 400 MHz $^1$H ($CDCl_3$) 8.57 ppm, 1 H, d, J=2.20 Hz; 7.48 ppm, 1 H, dd, J=8.35, 2.64 Hz; 7.12 ppm, 1 H, d, J=8.35 Hz; 6.98 ppm, 6 H, m; 6.68 ppm, 2 H, d, J=6.59 Hz; 3.60 ppm, 1 H, m; 3.52 ppm, 1 H, m; 2.59 ppm, 1 H, ddd, J=15.16, 10.33, 5.27 Hz; 2.04 ppm, 1 H, m; 1.68 ppm, 1 H, d, J=3.08 Hz; 1.59 ppm, 1 H, m; 1.25 ppm, 1 H, d, J=6.15 Hz.

EXAMPLE 1071

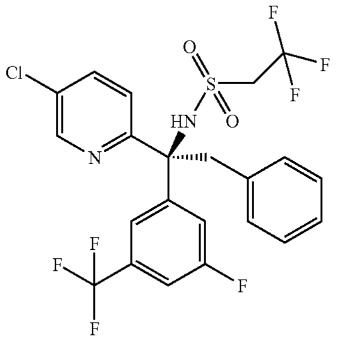

(S)—N-(1-(5-chloropyridin-2-yl)-1-(3-fluoro-5-(trifluoromethyl)phenyl)-2-phenylethyl)-2,2,2-trifluoroethanesulfonamide Procedure 55

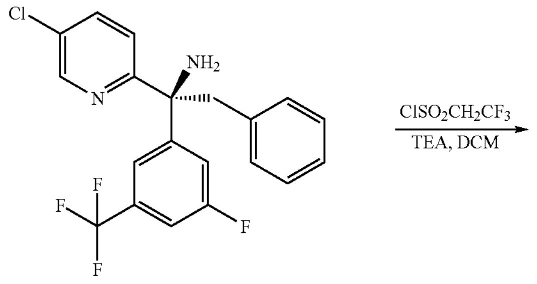

-continued

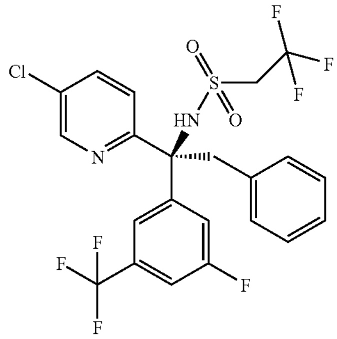

(S)-1-(5-chloropyridin-2-yl)-1-(3-fluoro-5-(trifluoromethyl)phenyl)-2-phenylethanamine was prepared as described in procedures 5, 6 and 7.

To (S)-1-(5-chloropyridin-2-yl)-1-(3-fluoro-5-(trifluoromethyl)phenyl)-2-phenylethanamine (30 mg, 0.076 mmol) in dichloromethane (0.5 mL) was added 2,2,2-trifluoroethanesulfonyl chloride (16 mg, 0.091 mmol) and TEA (32 μL, 0.228 mmol). The reaction mixture was stirred at room temperature for 18 h, then concentrated. The resulting residue was purified by preparative HPLC YMC ODS S5 28×100 mm Ballistic column 40-100% MeOH (90% in water, 0.1% TFA) gradient over 10 min with flow rate 40 mL/min and UV detection at 220 nm. (S)—N-(1-(5-chloropyridin-2-yl)-1-(3-fluoro-5-(trifluoromethyl)phenyl)-2-phenylethyl)-2,2,2-trifluoroethanesulfonamide eluted at a retention time of 11.4 min and was isolated as a clear oil (25 mg, yield 60%) LCMS: RT=2.11 min [M+H] 540.85 (LCMS Method 2); HPLC: RT=4.18 min, Purity 100% (HPLC Method 1); NMR: 400 MHz $^1$H ($CDCl1_3$) 8.20 ppm, 1 H, d, J=2.20 Hz; 7.64 ppm, 1 H, dd, J=8.57, 2.42 Hz; 7.53 ppm, 1 H, s; 7.42 ppm, 1 H, d, J=9.23 Hz; 7.34 ppm, 1 H, d, J=7.91 Hz; 7.3 ppm, 1 H, s; 7.07 ppm, 3 H, m; 6.92 ppm, 1 H, d, J=9.23 Hz; 6.72 ppm, 2 H, d, J=6.59 Hz; 4.36 ppm, 1 H, d, J=13.18 Hz; 3.37 ppm, 1 H, d, J=13.18 Hz; 3.18 ppm, 1 H, m; 2.64 ppm, 1 H, m.

EXAMPLE 1072

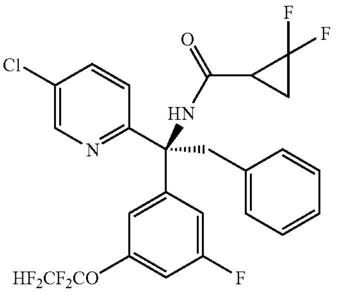

N—((S)-1-(5-chloropyridin-2-yl)-1-(3-fluoro-5-(I,1,2,2-tetrafluoroethoxy)phenyl)-2-phenylethyl)-2,2-difluorocyclopropanecarboxamide Procedure 56

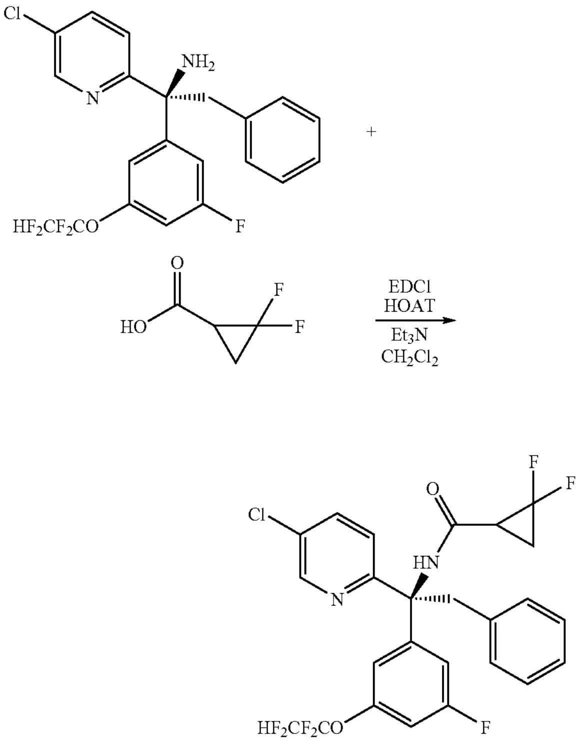

To a solution of (S)-1-(5-chloropyridin-2-yl)-1-(3-fluoro-5-(1,1,2,2-tetrafluoroethoxy)phenyl)-2-phenylethanamine (13 mg, 0.030 mmol), prepared by methods as described in procedures 3, 5, 6 and 7, in $CH_2Cl_2$ (0.5 mL) was added 2,2-difluorocyclopropanecarboxylic acid (5.5 mg, 0.045 mmol), EDCI (5.8 mg, 0.030 mmol) and HOAT (4.0 mg, 0.030 mmol), followed by the addition of TEA (12.5 μL, 0.090 mmol). The reaction was stirred for 16h. Additional 2,2-difluorocyclopropanecarboxylic acid (5.5 mg, 0.045 mmol), EDCI (5.8 mg, 0.030 mmol) and HOAT (4.0 mg, 0.030 mmol) were added and the reaction was stirred for an additional 6 h. The volatiles were removed under a stream of nitrogen and the resulting residue was purified by preparative HPLC Shimadzu-Phenomenex Onyx Monolithic column, 10×100 mm eluting with 10-90% MeOH/$H_2O$ (90% in $H_2O$, 0.% TFA) gradient over 5 min with flow rate 25 mL/min and UV detection at 220 nm. N-((S)-1-(5-chloropyridin-2-yl)-1-(3-fluoro-5-(1,1,2,2-tetrafluoroethoxy)phenyl)-2-phenylethyl)-2,2-difluorocyclopropanecarboxamide eluted at a retention time of 4.93 min and was isolated as a white solid (10.4 mg, yield 63%). LCMS: RT=2.09 min [M+H] 547.1 (LCMS Method 2); NMR: 400 MHz $^1H$ ($CDCl_3$) 8.53 ppm, 1 H, s; 8.28 ppm, 1 H, t, J=2.64 Hz; 7.69 ppm, 1 H, dd, J=8.57, 2.42 Hz; 7.11 ppm, 6 H, m; 6.87 ppm, 1 H, m; 6.53 ppm, 2 H, m; 5.86 ppm, 1 H, m; 4.35 ppm, 1 H, t, J=12.52 Hz; 3.50 ppm, 1 H, m; 2.37 ppm, 1 H, m; 2.04 ppm, 1 H, m; 1.65 ppm, 1 H, m.

EXAMPLE 1073

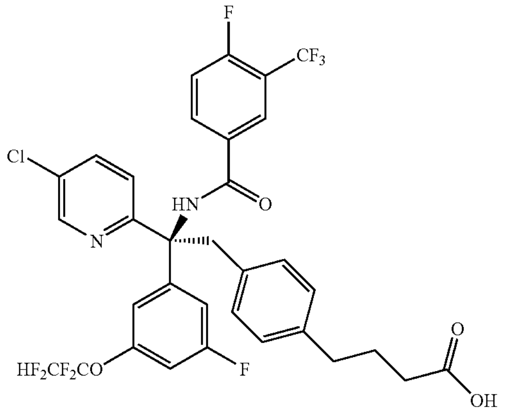

(S)-4-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenyl)butanoic acid Procedure 57

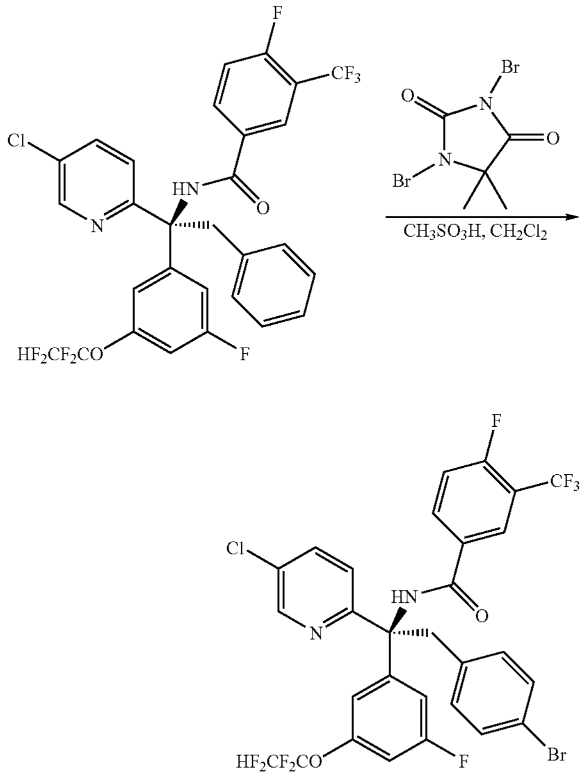

-continued

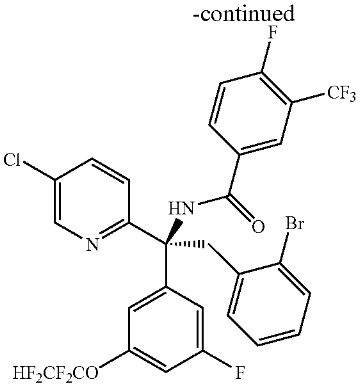

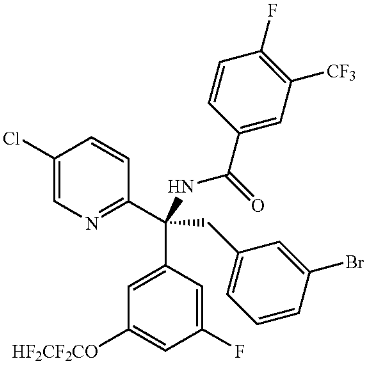

To a solution of (S)-N-(1-(5-chloropyridin-2-yl)-1-(3-fluoro-5-(11,2,2-tetrafluoroethoxy)phenyl)-2-phenylethyl)-4-fluoro-3-(trifluoromethyl)benzamide (351 mg, 0.55 mmol), prepared by methods as described in procedures 3,5, 6, 7 and 4, in $CH_2Cl_2$ (5 mL) at 0° C. was added dropwise methanesulfonic acid (140 μL, 2.2 mmol), followed by 1,3-dibromo-5,5-dimethyl hydantoin (87 mg, 0.30 mmol). The reaction mixture was stirred for 16 h. Additional 1,3-di-bromo-5,5-dimethyl hydantoin (20 mg, 0.070 mmol) was added and the reaction mixture stirred for an additional 3h. The reaction mixture was quenched by the addition of saturated $Na_2SO_3$ (5 mL) and extracted with $CH_2Cl_2$ (2×5 mL). The combined organic fractions were dried over $Na_2SO_4$, filtered and evaporated to dryness. The residue was purified by preparative HPLC Shimadzu-Phenomenex Luna C18 column, 30×250 mm eluting with 10-90% MeOH/$H_2O$ (90% in $H_2O$, 0.1% TFA) gradient over 20 min with flow rate 45 mL/min and UV detection at 220.

(S)-N-(2-(4-bromophenyl)-1-(5-chloropyridin-2-yl)-1-(3-fluoro-5-(1,1,2,2-tetrafluoroethoxy)phenyl)ethyl)-4-fluoro-3-(trifluoromethyl)benzamide eluted at a retention time of 24.5 min and was isolated as a white solid (111 mg, yield 28%) NMR: 400 MHz $^1$H ($CDCl_3$) 9.17 ppm, 1H, s; 8.36 ppm, 1H, d, J=2.20 Hz; 8.02 ppm, 1H, d, J=4.83 Hz; 7.87 ppm, 1H, m; 7.74 ppm, 1H, dd, J=8.57, 2.42 Hz; 7.28 ppm, 1H, 5, J=9.23 Hz; 7.18 ppm, 1H, d, J=8.35 Hz; 7.14 ppm, 2H, d, J=8.35 Hz; 7.11 ppm, 1H, bs; 7.07 ppm, 1H, d, J=9.23 Hz; 6.91 ppm, 1H, d, J=8.79 Hz; 6.39 ppm, 2H, d, J=8.79 Hz; 5.86 ppm, 1H, tt, J=53.17, 2.64 Hz; 4.51 ppm, 1H, d, J=12.74 Hz; 3.54 ppm, 1H, d, J=13.18 Hz. Fraction eluted at retention time of 23.4 min was concentrated and determined to be a mixture of two compounds. Further separation of this mixture was accomplished by ISCO chromatography (40 g column) using hexanes/EtOAc (0-30%) to give (S)-N-(2-(2-bromophenyl)-1-(5-chloropyridin-2-yl)-1-(3-fluoro-5-(1,1,2,2-tetrafluoroethoxy)phenyl)ethyl)-4-fluoro-3-(trifluoromethyl)benzamide as a clear colorless oil (76 mg, 19% yield) and (S)-N-(2-(3 -bromophenyl)-1-(5-chloropyridin-2-yl)-1-(3-fluoro-5-(1,1,2,2-tetrafluoroethoxy)phenyl)ethyl)-4-fluoro-3-(trifluoromethyl)benzamide as a clear colorless oil (35 mg, 9% yield). (S)-N-(2-(2-bromophenyl)-1-(5-chloropyridin-2-yl)-1-(3-fluoro-5-(1,1,2,2-tetrafluoroethoxy)phenyl)ethyl)-4-fluoro-3-(trifluoromethyl)benzamide NMR: 500 MHz $^1$H ($CD_3OD$) 8.45 ppm, 1 H, s; 8.07 ppm, 2 H, d, J=6.60 Hz; 7.81 ppm, 1 H, dd, J=8.52, 2.47 Hz; 7.47 ppm, 1 H, t, J=9.62 Hz; 7.40 ppm, 1 H, m; 7.31 ppm, 2H, m; 7.13 ppm, 1H, s; 7.04 ppm, 3H, m; 6.83 ppm, 1H, m; 6.29 ppm, 1H, t, J=52.23 Hz; 4.46 ppm, 1H, d, J=12 Hz; 4.13 ppm, d, J=15 Hz. (S)-N-(2-(3-bromophenyl)-1-(5-chloropyridin-2-yl)-1-(3-fluoro-5-(1,1,2,2-tetrafluoroethoxy)phenyl)ethyl)-4-fluoro-3-(trifluoromethyl)benzamide NMR: 500 MHz $^1$H ($CD_3OD$) 8.47 ppm, 1 H, s; 8.03 ppm, 2 H, d, J=5.50 Hz; 7.92 ppm, 1 H, dd, J=8.52, 2.47 Hz; 7.48 ppm, 2H, t, J=8.52 Hz; 7.38 ppm, 1H, d, J=9.90 Hz; 7.26 ppm, 2 H, m; 7.02 ppm, 1 H, d, J=8.80 Hz; 6.94 ppm, 1 H, t, J=7.70 Hz; 6.79 ppm, 1 H, s; 6.52 ppm, 1 H, d, J=7.70 Hz; 6.30 ppm, 1 H, t, J=52.51 Hz; 4.39 ppm, 1 H, d, J=12.65 Hz; 3.92 ppm, 1 H, d, J=12.65 Hz.

Procedure 58

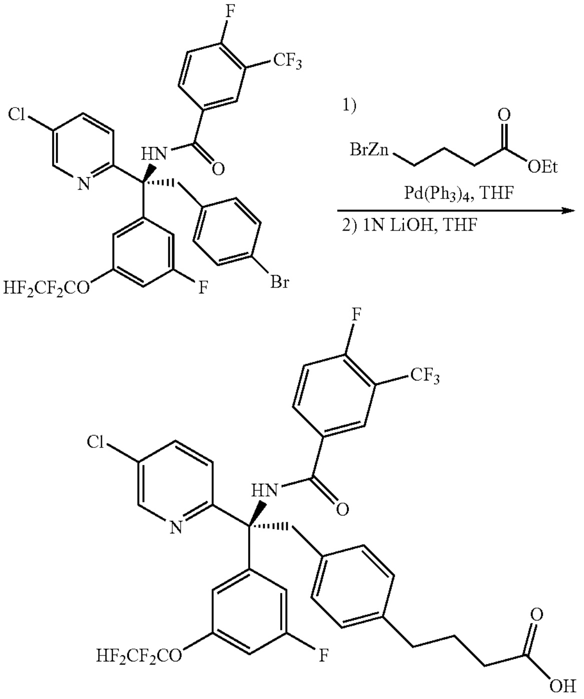

To a solution of (S)-N-(2-(4-bromophenyl)-1-(5-chloropyridin-2-yl)-1-(3-fluoro-5-(,11,2,2-tetrafluoroethoxy)phenyl)ethyl)-4-fluoro-3-(trifluoromethyl)benzamide, prepared as described in procedure 57, (30 mg, 0.042 mmol) in THF (0.6 mL) in a screw cap reaction vial was added tetrakis(triphenylphosphine)palladium(0) (4.9 mg, 0.004 mmol) followed by a 0.5 M solution of 4-ethoxy-4-oxobutylzinc bromide in THF (0.42 mL, 0.21 mmol). The reaction vial was capped under argon and heated at 70° C. for 20 h. The reaction mixture was quenched by the addition of saturated $NH_4Cl$ (5 mL) and the aqueous layer was extracted with EtOAc (2×10 mL). The combined organic portions were dried over $Na_2SO_4$, filtered and the solvent removed in vacuo. The residue was purified by ISCO chromatography using hexanes/EtOAc (0-30%) to give (S)-ethyl 4-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenyl)butanoate as a clear oil (11.2 mg, 36% yield). LCMS: RT=1.87 min [M+H] 747.1 (LCMS Method 2).

(S)-ethyl 4-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenyl)butanoate (11.2 mg, 0.015 mmol) was dissolved in THF (0.2 mL) and a 1N LiOH solution was added. The reaction mixture was stirred at room temperature for 3 days, then diluted with 1N HCl (0.5 mL). The aqueous layer was extracted with $CH_2Cl_2$ (3×0.5 mL). The combined organic portions were dried over $Na_2SO_4$, filtered and the solvent removed in vacuo to yield (S)-4-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenyl)butanoic acid (9.9 mg, 92% yield) as a clear film. LCMS: RT=1.55 min [M+H] 719.0 (LCMS Method 2) NMR: 400 MHz $^1$H ($CDCl_3$) 9.02 ppm, 1H, s; 8.29 ppm, 1H, d, J=2.20 Hz; 7.94 ppm, 1H, m; 7.80 ppm, 1H, m; 7.67 ppm, 1H, dd, J=2.42 and 8.57 ppm, 7.13 ppm, 1H, d, J=8.79 Hz; 7.05 ppm, 2H, m; 6.84 ppm, 1H, d, J=8.79 Hz; 6.77 ppm, 2H, d, J=7.91 Hz; 6.38 ppm, 2H, J=7.91 Hz; 5.81 ppm, 1H, tt, J=2.63 and 52.73 Hz; 4.44 ppm, 1H, d, J=12.74 Hz; 3.51 ppm, 1H, d, J=12.74 Hz; 2.47 ppm, 2H, t, J=7.69 Hz; 2.22 ppm, 2H, t, J=7.25 Hz; 1.80 ppm, 2H, m.

EXAMPLE 1074

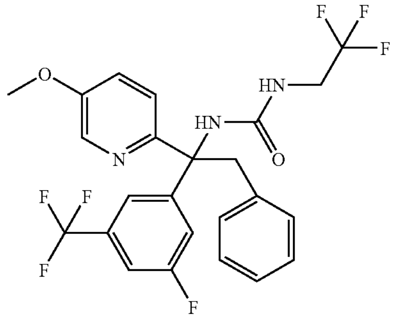

1-(1-(3-fluoro-5-(trifluoromethyl)phenyl)-1-(5-methoxypyridin-2-yl)-2 phenylethyl)-3-(2,2,2-trifluoroethyl)urea Procedure 59

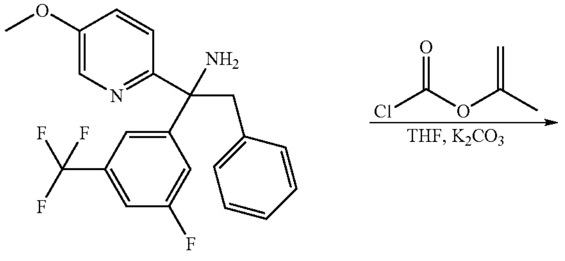

-continued

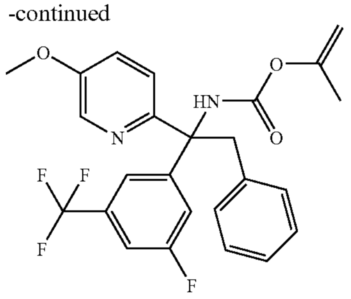

1-(3-fluoro-5-(trifluoromethyl)phenyl)-1-(5-methoxypyridin-2-yl)-2-phenylethanamine was prepared by the method described in Procedure 1 in 25% yield. LCMS: RT=2.56 min [M+H] 391.2 (LCMS Method 1). NMR: 400 MHz $^1$H ($CDCl_3$) 7.91 ppm, 1H, dd, J=4.52, 1.59 Hz; 7.10 ppm, 2H, m; 6.92 ppm, 1H, d, J=10.03 Hz; 6.83 ppm, 3H, m; 6.50 ppm, 2H, m; 4.55 ppm, 2H, s; 3.58 ppm, 1H, d, J=13.21 Hz; 3.32 ppm, 4H, m.

To a solution of 1-(3-fluoro-5-(trifluoromethyl)phenyl)-1-(5-methoxy pyridin-2-yl)-2-phenylethanamine (200 mg, 0.512 mmol) in THF (2 mL) was added 2N $K_2CO_3$ (0.5 mL, 1.0 mmol) and isopropenyl chloroformate (100 μl, 1.02 mmol). The resulting mixture was stirred at room temperature for 30 min. The solvent was evaporated under reduced pressure and the residue was dried in vacuo to yield prop-1-en-2-yl 1-(3-fluoro-5-(trifluoromethyl)phenyl)-1-(5-methoxypyridin-2-yl)-2-phenylethylcarbamate as white powder (120 mg, 50%). LCMS: RT=3.56 min [M+H] 475.2 (LCMS Method 1).

Procedure 60

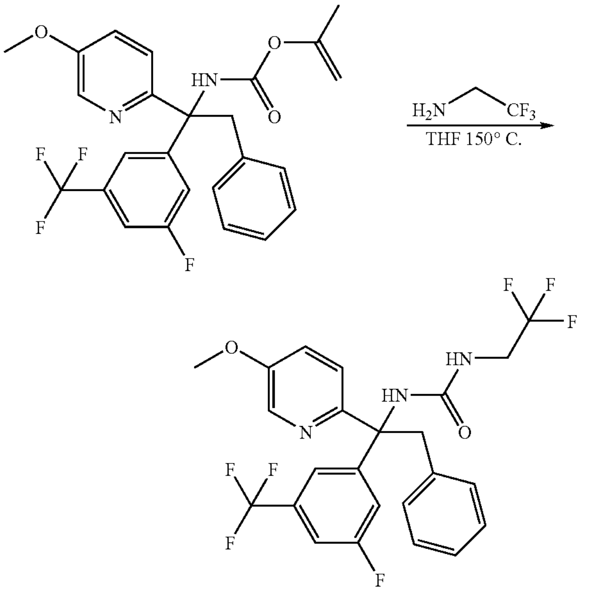

To a solution of prop-1-en-2-yl 1-(3-fluoro-5-(trifluoromethyl)phenyl)-1-(5-methoxypyridin-2-yl)-2-phenylethylcarbamate (100 mg, 0.210 mmol) in THF (200 μl) was added 2,2,2-trifluoroethanamine (200 μl, 2.1 mmol). The resulting mixture was stirred at 100° C. under microwave irradiation for 1200 sec then at 150° C. for 1800 sec. The solvent was evaporated under reduced pressure and the residue was purified by ISCO chromatography (40 g column) using hexanes/EtOAc (0-100% over 12 min) to give (R)-1-(1-(3-fluoro-5-(trifluoromethyl)phenyl)-1-(5-methoxypyridin-2-yl)-2 phenylethyl)-3-(2,2,2-trifluoroethyl)urea as white powder (68 mg, 63% yield) LCMS: RT=2.03 min [M+H] 516.2 (LCMS Method 1); HPLC: RT=3.24 min, Purity 98% (HPLC Method 2); NMR: 400 MHz $^1$H ($CD_3OD$) 8.30 ppm, 1H, s; 7.98 ppm, 1H, dd, J=4.55, 1.26 Hz; 7.46ppm, 1H, s; 7.39 ppm, 2H, m; 7.30 ppm, 1H, m; 7.21 ppm, 1H, m; 7.00 ppm, 3H, m; 6.66 ppm, 2H, m; 4.18 ppm, 2H, m; 3.90 ppm, 1H, m; 3.63 ppm, 4H, m.

EXAMPLE 1075

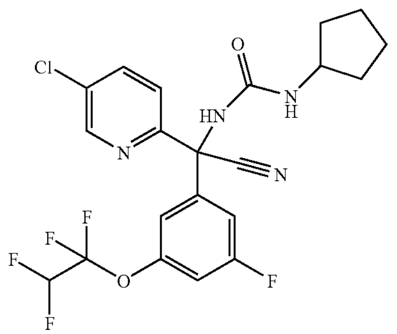

1-((5-chloropyridin-2-yl)(cyano)(3-fluoro-5-(1,1,2,2-tetrafluoroethoxy)phenyl)methyl)-3-cyclopentylurea Procedure 61

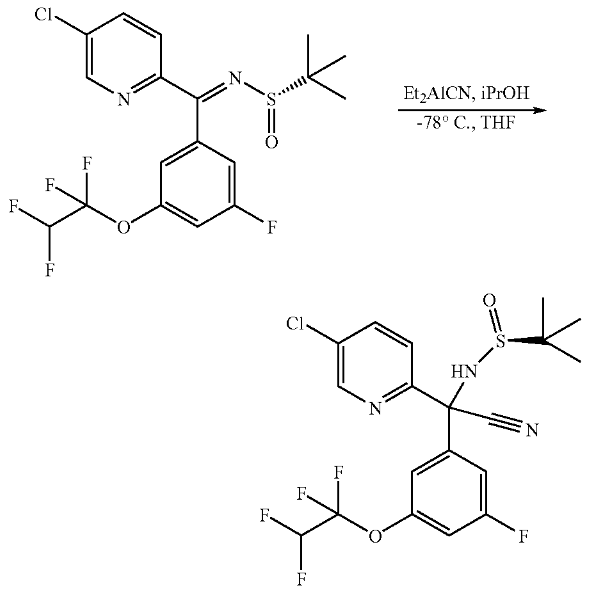

To an oven-dried round bottom flask was added $Et_2AlCN$ (1.02 mL, 1 M in Toluene, 1.02 mmol) and THF (3.4 mL). The reaction mixture was cooled to −78° C. and iPrOH (40.9 μL, 0.681 mmol) was added. The clear colorless mixture was allowed to warm to room temperature and stirred for 30 min, then added via a syringe to a solution of (S)-N-((5-chloropyridin-2-yl)(3-fluoro-5-(1,1,2,2-tetrafluoroethoxy)phenyl)methylene)-2-methylpropane-2-sulfinamide (309 mg, 0.681 mmol), prepared as procedures 3, 5 and 6, in THF (10 mL) at −78° C. Then the reaction mixture was allowed to reach room temperature overnight. The reaction mixture was cooled to −78° C., quenched by addition of saturated $NH_4Cl$, filtered through celite and the aqueous layer extracted with EtOAc. The EtOAc layer was washed with saturated NaCl, dried over $MgSO_4$, filtered and concentrated. The residue oil was purified by ISCO chromatography (40 g column) using hexanes/EtOAc (0-30% over 15 min, 30% for 14 min, flow rate 40 mL/min). The desired isomer of (S)-N-((5-chloropyridin-2-yl)(cyano)(3-fluoro-5-(1,1,2,2-tetrafluoroethoxy)phenyl)methyl)-2-methylpropane-2-sulfinamide eluted at a retention time of 22 min as a white foam (87.1 mg, 27% yield). LCMS: RT=3.56 min [M+H] 481.8 (LCMS Method 1.); NMR: 400 MHz $^1$H ($CDCl_3$) 8.61 ppm, 1H, d, J=1.77 Hz; 7.76 ppm, 1H, dd, J=8.46, 2.40 Hz; 7.24 ppm, 3H, m; 7.05 ppm, 1H, dd, J=8.59, 2.27 Hz; 5.91 ppm, 1H, t, J=53 Hz; 1.26 ppm, 9H, s.

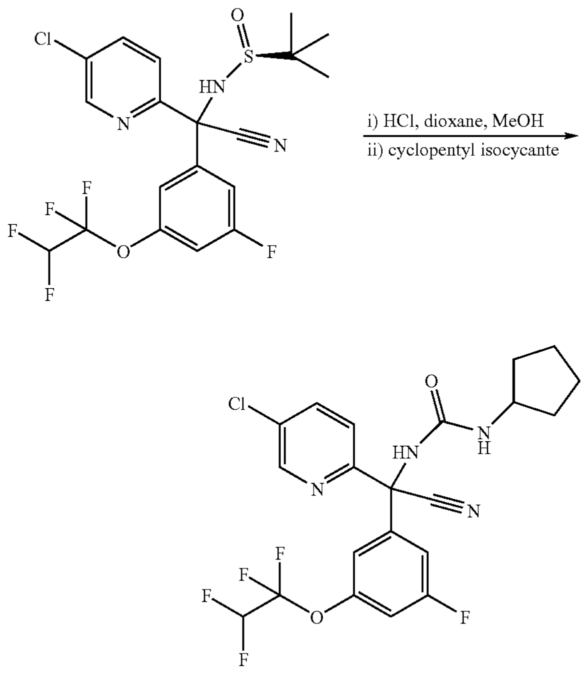

1-((5-chloropyridin-2-yl)(cyano)(3-fluoro-5-(1,1,2,2-tetrafluoroethoxy)phenyl)methyl)-3-cyclopentylurea was prepared by methods described in Procedures 23 in 74% yield. LCMS: RT=3.49 min [M+H] 488.85 (LCMS Method 1); NMR: 400 MHz $^1$H ($CDCl_3$) 8.51 ppm, 1H, d, J=2.20 Hz; 7.73 ppm, 1H, dd, J=8.57, 2.42 Hz; 7.37 ppm, 2H, d, J=8.35 Hz; 7.21 ppm, 2H, m; 6.90 ppm, 1H, d, J=8.79 Hz; 5.89 ppm, 1H, t, J=53 Hz; 5.11 ppm, 1H, d, J=7.03 Hz; 3.99 ppm, 2H, m; 1.94 ppm, 2H, m; 1.62 ppm, 4H, m; 1.38 ppm, 2H, m.

EXAMPLE 1076

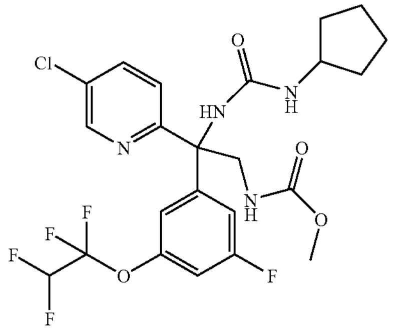

Methyl 2-(5-chloropyridin-2-yl)-2-(3-cyclopentylureido)-2-(3-fluoro-5-(1,1,2,2-tetrafluoroethoxy)phenyl)ethylcarbamate Procedure 62

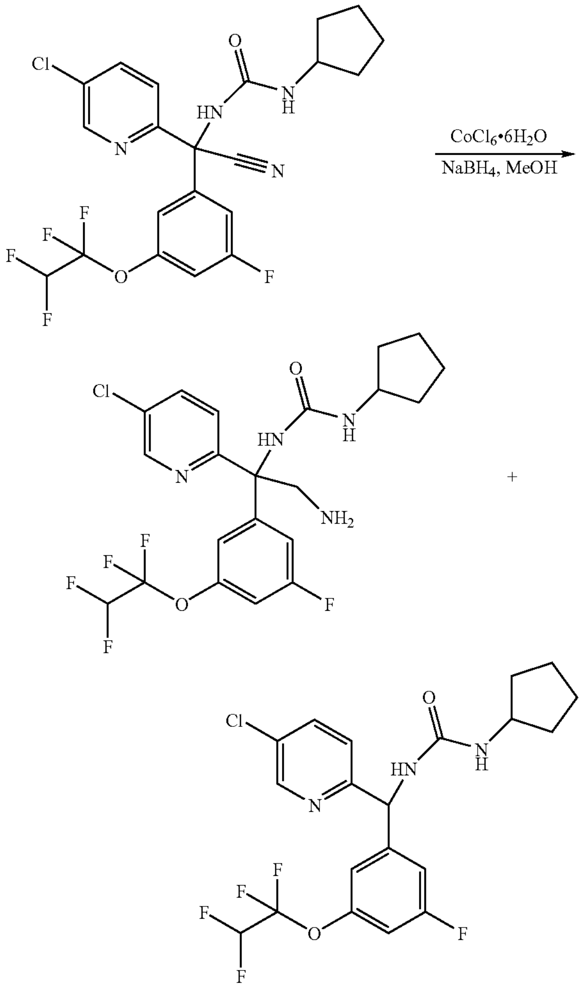

To a solution of 1-((5-chloropyridin-2-yl)(cyano)(3-fluoro-5-(1,1,2,2-tetrafluoroethoxy)phenyl)methyl)-3-cyclopentylurea (example 1075) (28.8 mg, 0.06 mmol) in MeOH (2 mL) was added $COCl_{2.6}$ $H_2O$ (15.3 mg, 0.12 mmol). The reaction mixture was stirred at room temperature for 15 min, cooled to 0° C. and $NaBH_4$ (11.2 mg, 0.295 mmol) was added. The reaction mixture was stirred for 20 min and $NH_4OH$ was added to quench the reaction. The solution was concentrated in vacuo and the crude mixture filtered through SCX column, then purified by preparative HPLC Shimadzu-Phenomenex C18 column, 20×100 mm eluting with 30-100% MeOH (90% in $H_2O$, 0.1% TFA) gradient over 12 min with flow rate 20 mL/min and UV detection at 220 nm. 1-(2-amino-1-(5-chloropyridin-2-yl)-1-(3-fluoro-5-(1,1,2,2-tetrafluoroethoxy)phenyl)ethyl)-3-cyclopentylurea eluted at a retention time of 9.97 min and was isolated as a colorless oil (4 mg, 14% yield). LCMS: RT=3.23 min [M+H] 493.22 (LCMS Method 1); NMR: 400 MHz $^1H$ ($CDCl_3$) 8.51 ppm, 1H, d, J=2.20 Hz; 7.73 ppm, 1H, dd, J=8.57, 2.42 Hz; 7.37 ppm, 2H, d, J=8.35 Hz; 7.22 ppm, 2H, m; 6.90 ppm, 1H, d, J=8.79 Hz; 5.89 ppm, 1H, t, J=53 Hz; 5.11 ppm, 1H, d, J=7.03 Hz; 3.99 ppm, 2H, m; 1.94 ppm, 2H, m; 1.62 ppm, 4H, m; 1.38 ppm, 2H, m.

1-((5-chloropyridin-2-yl)(3-fluoro-5-(1,1,2,2-tetrafluoroethoxy)phenyl)methyl)-3-cyclopentylurea eluted at a retention time of 12.33 min and was isolated as a light brownish oil (1.17 mg, 4% yield). LCMS: Rt=3.75 min [M+H] 464.18 (LCMS Method 1); NMR: 400 Mhz $^1H$ ($CDCl_3$) 8.55 ppm, 1H, s; 7.69 ppm, 1H, dd, J=8.34, 2.27 Hz; 7.22 ppm, 1H, d, J=8.59 Hz; 6.96 ppm, 2H, m; 6.84 ppm, 1H, m; 6.05 ppm, 1H, s; 5.86 ppm, 1H, t, J=53 Hz; 3.90 ppm, 1H, m; 1.97 ppm, 2H, m; 1.69 ppm, 4H, m; 1.49 ppm, 2H, m.

Procedure 63

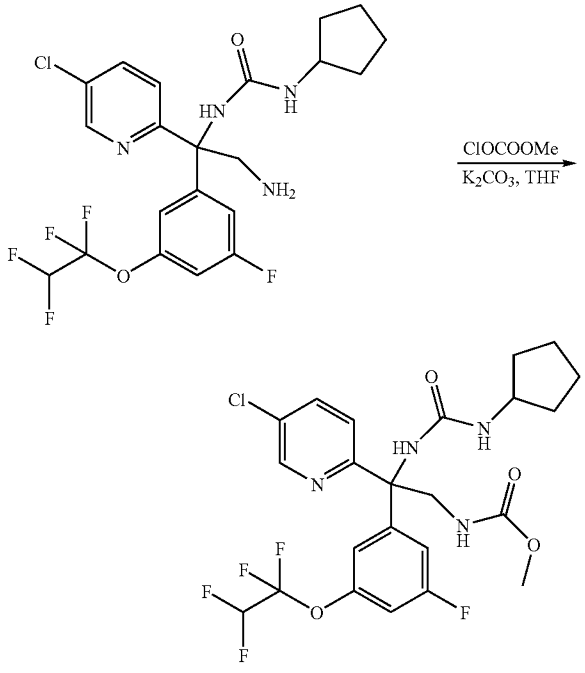

To a solution of 1-(2-amino-1-(5-chloropyridin-2-yl)-1-(3-fluoro-5-(1,1,2,2-tetrafluoroethoxy)phenyl)ethyl)-3-cyclopentylurea (33 mg, 0.067 mmol) in THF (0.5 mL) was added $MeOCO_2Cl$ (30 mg, 0.317 mmol) and $K_2CO_3$ (28 mg, 0.201 mmol). The reaction mixture was stirred at room temperature for 18 h, concentrated and the residue was purified by preparative HPLC Shimadzu-Phenomenex C18 column, 20×100 mm eluting with 30-100% MeOH (90% in $H_2O$, 0.1% TFA) gradient over 10 min with flow rate 20 mL/min and UV detection at 220 nm followed by ISCO chromatography (4 g column) using hexanes/EtOAc (0-50% over 20 min). methyl 2-(5-chloropyridin-2-yl)-2-(3-cyclopentylureido)-2-(3-fluoro-5-(1,1,2,2-tetrafluoroethoxy)phenyl)ethylcarbamate eluted at a retention time of 10.08 min and was isolated as a white foam (3 mg, 8% yield). LCMS: RT=3.69 min [M+H] 551.15 (LCMS Method 1); NMR: 400 Mhz $^1H$ ($CDCl_3$) 8.47 ppm, 1H, d, J=2.53 Hz; 7.63 ppm, 1H, dd, J=8.59, 2.27 Hz; 7.31 ppm, 1H, m; 6.99 ppm, 2H, m; 6.85 ppm, 1H, d, J=8.84 Hz; 5.73 ppm, 1H, s; 5.86 ppm, 1H, t, J=53 Hz; 4.48 ppm, 1H, d, J=7.07 Hz; 4.38 ppm, 1H, d, J=9.35 Hz; 4.15 ppm, 1H, m; 3.96 ppm, 1H, m; 3.60 ppm, 3H, s; 2.01 ppm, 2H, m; 1.66 ppm, 4H, m; 1.40 ppm, 2H, m.

EXAMPLE 1077

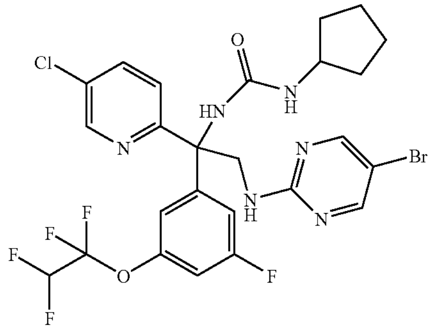

1-(2-(5-bromopyrimidin-2-ylamino)-1-(5-chloropyridin-2-yl)-1-(3-fluoro-5-(1,1,2,2-tetrafluoroethoxy)phenyl)ethyl)-3-cyclopentylurea Procedure 64

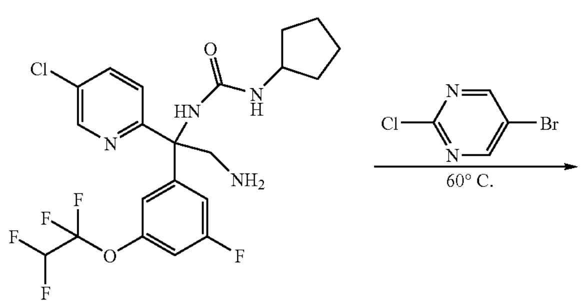

-continued

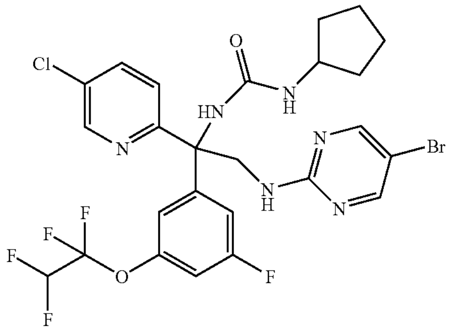

To a solution of 1-(2-amino-1-(5-chloropyridin-2-yl)-1-(3-fluoro-5-(1,1,2,2-tetrafluoroethoxy)phenyl)ethyl)-3-cyclopentylurea (27 mg, 0.055 mmol) in DMF (0.2 mL) was added 4-bromo-2-cloropyrimidine (21 mg, 0.09 mmol). The reaction mixture was stirred at 60° C. for 10 min, then room temperature for 18 h. The reaction mixture was diluted with MeOH and was purified by preparative HPLC Shimadzu-Phenomenex C18 column, 20×100 mm eluting with 40-100% MeOH (90% in $H_2O$, 0.1% TFA) gradient over 10 min with flow rate 20 mL/min and UV detection at 220 nm. 1-(2-(5-bromopyrimidin-2-ylamino)-1-(5-chloropyridin-2-yl)-1-(3-fluoro-5-(1,1,2,2-tetrafluoroethoxy)phenyl)ethyl)-3-cyclopentylurea was isolated as a pale yellow oil (3 mg, 8% yield). LCMS: Rt=4.05 min [M+H] 650.96 (LCMS Method 1); NMR: 400 Mhz $^1H$ ($CDCl_3$) 8.47 ppm, 1H, d, J=2.27 Hz; 7.85 ppm, 1H, brs; 7.63 ppm, 1H, dd, J=8.6, 2.3 Hz; 7.14 ppm, 1H, d, J=8.6 Hz; 6.98 ppm, 2H, m; 6.90 ppm, 1H, d, J=8.8 Hz; 5.88 ppm, 1H, t, J=53 Hz; 4.92 ppm, 1H, d, J=13.6 Hz; 4.60 ppm, 1H, d, J=13.6 Hz; 3.90 ppm, 1H, m; 1.99 ppm, 2H, m; 1.59 ppm, 6 H, m.

EXAMPLE 1078

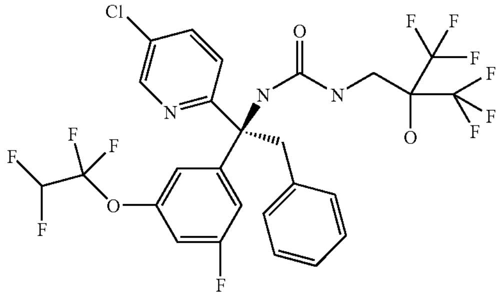

(S)-1-(1-(5-chloropyridin-2-yl)-1-(3-fluoro-5-(1,1,2,2-tetrafluoroethoxy)phenyl)-2-phenylethyl)-3-(3,3,3-trifluoro-2-hydroxy-2-(trifluoromethyl)propyl)urea Procedure 65

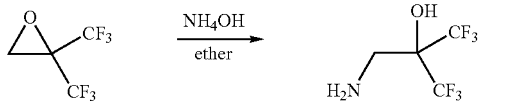

2,2-Bis(trifluoromethyl)oxirane (1 g, 5.5 mmol) was added drop-wise to a 1:1 mixture of ether/30% ammonium hydroxide (1.85 mL/1.85 mL). The reaction mixture was stirred at room temperature for 2 h and then diluted with ether and $H_2O$. The aqueous layer was extracted twice with ether. The combined ether portions was dried over $MgSO_4$, filtered and concentrated to give 2-(aminomethyl)-1,1,1,3,3,3-hexafluoropropan-2-ol as a semi solid (0.87 g, 81%). NMR: 400 Mhz $^1H$ ($CDCl_3$) 3.25 ppm, 1H, s; 3.14 ppm, 2H, s.

1-(1 -(5-chloropyridin-2-yl)-1-(3-fluoro-5-(1,1,2,2-tetrafluoroethoxy)phenyl)-2-phenylethyl)-3-(3,3,3-trifluoro-2-hydroxy-2-(trifluoromethyl)propyl)urea was prepared by method described in Procedure 8 in 69% yield using 2-(aminomethyl)-1,1,1,3,3,3-hexafluoropropan-2-ol. LCMS: RT=4.07 min [M+H] 666.07 (LCMS Method 1). NMR: 400 Mhz $^1H$ ($CDCl_3$) 8.23 ppm, 1 H, d, J=2.02 Hz; 7.69 ppm, 1 H, dd, J=8.59, 2.53 Hz; 7.64 ppm, 1 H, s; 7.31 ppm, 1 H, s; 7.11 ppm, 6 H, m; 6.91 ppm, 1 H, d, J=8.84 Hz; 6.57 ppm, 2 H, d, J=7.07 Hz; 5.87 ppm, 1 H, tt, J=53.05, 2.78 Hz; 5.01 ppm, 1 H, t, J=5.94 Hz; 4.30 ppm, 1 H, d, J=12.88 Hz; 3.81 ppm, 1 H, m; 3.66 ppm, 1 H, m; 3.54 ppm, 1 H, d, J=12.88 Hz.

EXAMPLE 1079

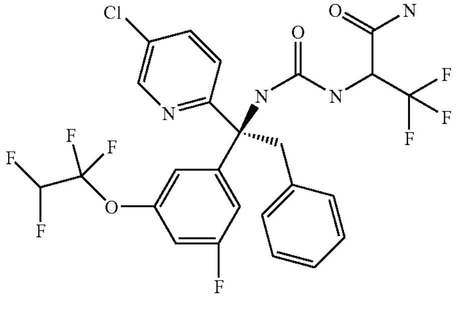

2-(3-((S)-1-(5-chloropyridin-2-yl)-1-(3-fluoro-5-(1,1,2,2-tetrafluoroethoxy)phenyl)-2-phenylethyl)ureido)-3,3,3-trifluoropropanamide diastereomer 1

Procedure 66

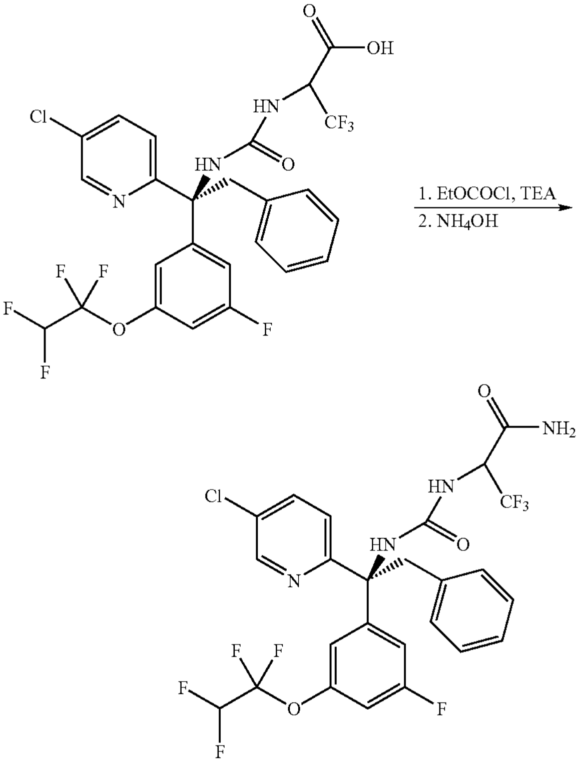

2-(3-((S)-1-(5-chloropyridin-2-yl)-1-(3-fluoro-5-(1,1,2,2-tetrafluoroethoxy)phenyl)-2-phenylethyl)ureido)-3,3,3-trifluoropropanoic acid was prepared by method described in Procedure 8 in 72% yield. LCMS: RT=3.92 min [M+H] 612.63 (LCMS Method 1).

To a solution of 2-(3-((S)-1-(5-chloropyridin-2-yl)-1-(3-fluoro-5-(1,1,2,2-tetrafluoroethoxy)phenyl)-2-phenylethyl)ureido)-3,3,3-trifluoropropanoic acid (31 mg, 0.051 mmol) in DCM (1.0 mL) was added $NEt_3$ (14.2 μL, 0.102 mmol). The reaction mixture was cooled to 0° C. and $EtCO_2Cl$ (7.3 μL, 0.08 mmol) was added. The reaction mixture was stirred at 0° C. for 30 min and $NH_4OH$ was added (0.5 mL). The reaction mixture was stirred at 0° C. for 30 min and then at room temperature for 72 h. The reaction was concentrated and purified by ISCO chromatography (4 g column) using hexanes/EtOAc (0-30% over 18 min) to give two diastereomers.

2-(3-((S)-1-(5-chloropyridin-2-yl)-1-(3-fluoro-5-(1,1,2,2-tetrafluoroethoxy)phenyl)-2-phenylethyl)ureido)-3,3,3-trifluoropropanamide Diastereomer 1 eluted at a retention time of 16-17.5 min and was isolated as a white solid (4.5 mg, 15% yield). LCMS: RT=3.88 min [M+H] 611.05 (LCMS Method 1); NMR: 400 MHz $^1H$ ($CDCl_3$) 8.25 ppm, 1H, s; 7.67 ppm, 1H, d, J=12 Hz; 7.49 ppm, 1H, s; 7.11 ppm, 6 H, m; 6.90 ppm, 1H, d, J=12 Hz; 6.55 ppm, 2H, d, J=12 Hz; 6.22 ppm, 1H, s; 5.87 ppm, 1H, J=53 Hz; 5.66 ppm, 1H, d, J=8 Hz; 5.43 ppm, 1H, s; 5.21 ppm, 1H, m; 4.33 ppm, 1H, d, J=12 Hz; 3.49 ppm, 1H, d, J=12 Hz.

2-(3-((S)-1-(5-chloropyridin-2-yl)-1-(3 -fluoro-5-(1,1,2,2-tetrafluoroethoxy)phenyl)-2-phenylethyl)ureido)-3,3,3-trifluoropropanamide Diastereomer 2 eluted at a retention time of 17.5-18.5 min and was isolated as a white solid (3.2 mg, 10% yield). LCMS: RT=3.88 min [M+H] 611.05 (LCMS Method 1); NMR: 400 Mhz $^1$H ($CDCl_3$) 8.25 ppm, 1H, s; 7.66 ppm, 1H, dd, J=8.6, 2.4 Hz; 7.56 ppm, 1H, s; 7.11 ppm, 6 H, m; 6.90 ppm, 1H, d, J=8 Hz; 6.54 ppm, 2H, d, J=8 Hz; 6.08 ppm, 1H, d, J=12 Hz; 5.83 ppm, 3H, m; 5.13 ppm, 1H, m; 4.22 ppm, 1H, d, J=12 Hz; 3.54 ppm, 1H, d, J=12 Hz.

EXAMPLE 1080

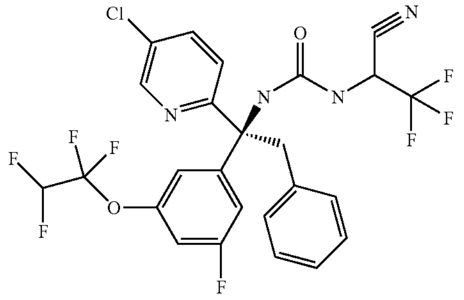

1-((S)-1-(5-chloropyridin-2-yl)-1-(3-fluoro-5-(1,1,2,2-tetrafluoroethoxy)phenyl)-2-phenylethyl)-3-(1-cyano-2,2,2-trifluoroethyl)urea Procedure 67

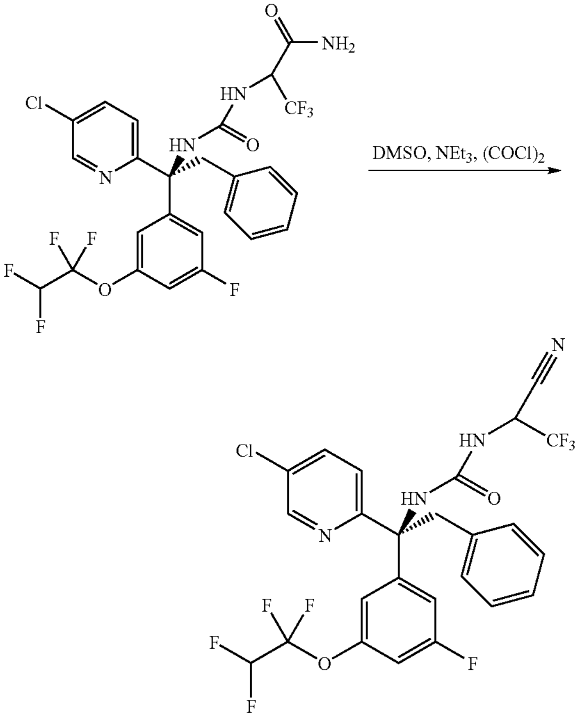

To a solution of 2-(3-((S)-1-(5-chloropyridin-2-yl)-1-(3-fluoro-5-(1,1,2,2-tetrafluoroethoxy)phenyl)-2-phenylethyl)ureido)-3,3,3-trifluoropropanamide (15 mg, 0.024 mmol) in DCM (0.5 mL) was added DMSO (3.74 mg, 0.048 mmol). The reaction mixture was cooled to −78° C. and oxaly chloride (18.4 μL, 2M in DCM, 0.04 mmol) was added. After 15 min at −78° C., $NEt_3$ (10 μL, 0.072 mmol) was added. The reaction mixture was stirred for 1 h and $H_2O$ was added to quench the reaction. The reaction mixture was concentrated and the crude mixture was purified by preparative HPLC Shimadzu-Phenomenex C18 column, 20×100 mm eluting with 30-100% MeOH (90% in $H_2O$, 0.1% TFA) gradient over 12 min with flow rate 20 mL/min and UV detection at 220 nm. 1-((S)-1-(5-chloropyridin-2-yl)-1-(3-fluoro-5-(1,1,2,2-tetrafluoroethoxy)phenyl)-2-phenylethyl)-3-(1-cyano-2,2,2-trifluoroethyl)urea was isolated as a pale yellow solid (7 mg, 50% yield). LCMS: RT=3.96 min [M+H] 593.11 (LCMS Method 1); NMR: 400 MHz $^1$H ($CDCl_3$) 8.27 ppm, 1H, m; 7.72 ppm, 1H, m; 7.63 ppm, 1H, d, J=12.6 Hz; 7.12 ppm, 6H, m; 6.91 ppm, 1H, m; 6.52 ppm, 2H, dd, J=20.2, 6.8 Hz; 5.81 ppm, 2H, m; 5.23 ppm, 1H, dd, J=27.3, 10.1 Hz; 4.33 ppm, 1H, dd, J=12.9, 3.3 Hz; 3.52 ppm, 1H, m.

EXAMPLE 1081

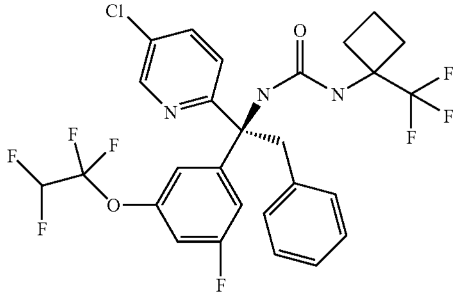

(S)-1-(1-(5-chloropyridin-2-yl)-1-(3-fluoro-5-(1,1,2,2-tetrafluoroethoxy)phenyl)-2-phenylethyl)-3-(1-(trifluoromethyl)cyclobutyl)urea Procedure 68

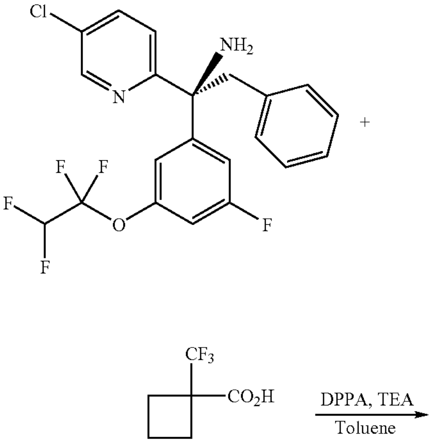

-continued

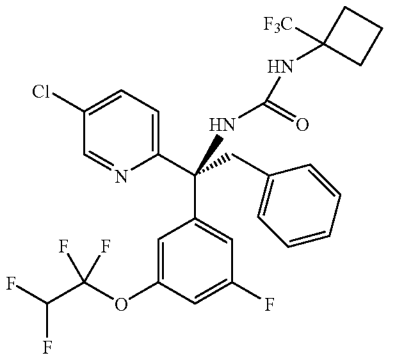

To a solution of 1-(trifluoromethyl)cyclobutanecarboxylic acid (54 mg, 0.354 mmol) in toluene (0.9 mL) was added TEA (35.5 mg, 0.354 mmol), followed by DPPA (76.4 μL, 0.354 mmol). The reaction mixture was heated at 90° C. for 2 h, then allowed to cool to room temperature. (S)-1-(5-chloropyridin-2-yl)-1-(3-fluoro-5-(1,1,2,2-tetrafluoroethoxy)phenyl)-2-phenylethanamine (51 mg, 0.117 mmol) was added and the reaction mixture was stirred for 4.5 hr at room temperature. The reaction mixture was concentrated and purified first by ISCO chromatography (12 g column) using hexanes/EtOAc (0-30% over 18 min) and then by preparative HPLC Shimadzu-AXIA column, 30×100 mm eluting with 40-100% MeOH (90% in $H_2O$, 0.1% TFA) gradient over 10 min with flow rate 40 mL/min and UV detection at 220 nm. 1-(1-(5-chloropyridin-2-yl)-1-(3-fluoro-5-(1,1,2,2-tetrafluoroethoxy)phenyl)-2-phenylethyl)-3-(1-(trifluoromethyl)cyclobutyl)urea was isolated as a white solid (49 mg, 69% yield). LCMS: RT=4.10 min [M+H] 608.15 (LCMS Method 1); NMR: 400 MHz $^1$H ($CDCl_3$) 8.25 ppm, 1H, d, J=2.5 Hz; 7.66 ppm, 1H, dd, J=8.6, 2.5 Hz; 7.14 ppm, 7 H, m; 6.86 ppm, 1H, d, J=8.8 Hz; 6.61 ppm, 2H, d, J=7.1 Hz; 5.86 ppm, 1H, t, J=53 Hz; 4.73 ppm, 1H, s; 4.39 ppm, 1H, d, J=12.9 Hz; 3.52 ppm, 1H, d, J=12.9 Hz; 2.47 ppm, 2H, m; 2.27 ppm, 2H, m; 1.97 ppm, 2H, m.

EXAMPLE 1082

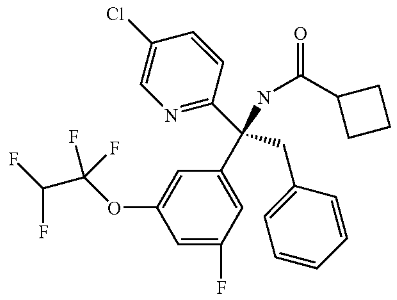

(S)-N-(1-(5-chloropyridin-2-yl)-1-(3-fluoro-5-(1,1,2,2-tetrafluoroethoxy)phenyl)-2-phenylethyl)cyclobutanecarboxamide Procedure 69

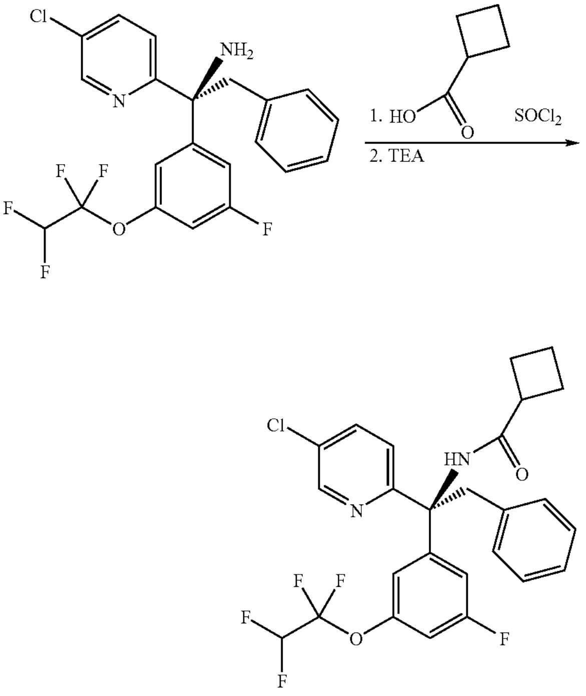

(S)-1-(5-chloropyridin-2-yl)-1-(3-fluoro-5-(1,1,2,2-tetrafluoroethoxy)phenyl)-2-phenylethanamine was prepared as described in Procedures 3, 5, 6 and 7.

To a solution of 1-trifluoromethylcyclobutyl carboxylic acid (22.7 mg, 0.135 mmol) in DCE (1 mL) was added $SOCl_2$ (16 mg, 0.135 mmol) and the resulting mixture was heated at reflux for 2 h. The reaction mixture was allowed to cool down to room temperature and TEA was added (31 μL, 0.23 mmol), followed by the addition of (S)-1-(5-chloropyridin-2-yl)-1-(3-fluoro-5-(1,1,2,2-tetrafluoroethoxy)phenyl)-2-phenylethanamine (20 mg, 0.045 mmol). The reaction was stirred at room temperature for 18 h, concentrated and the residue purified by preparative HPLC Shimadzu-AXIA column, 30×100 mm eluting with 30-100% MeOH (90% in $H_2O$, 0.1% TFA) gradient over 12 min with flow rate 40 mL/min and UV detection at 220 nm to give N-(1-(5-chloropyridin-2-yl)-1-(3-fluoro-5-(1,1,2,2-tetrafluoroethoxy)phenyl)-2-phenylethyl)cyclobutanecarboxamide (5.2 mg, 22% yield). LCMS: RT=2.14 min [M+H] 525.2 (LCMS Method 2.); NMR: 400 MHz $^1$H ($CDCl_3$) 8.29 ppm, 1H, s; 8.13 ppm, 1H, s; 7.68 ppm, 1H, m; 7.11 ppm, 6H, m; 6.87 ppm, 1H, m; 6.57 ppm, 2H, m; 5.87 ppm, 1H, t, J=53 Hz; 4.45 ppm, 1H, dd, J=12.8, 3.6 Hz; 3.51 ppm, 1H, dd, J=12.8, 3.6 Hz; 3.09 ppm, 1H, m; 2.20 ppm, 4H, m; 1.94 ppm, 2H, m.

EXAMPLE 1083

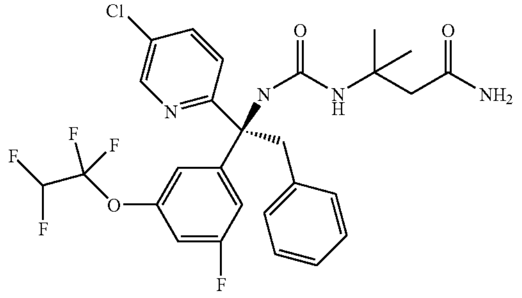

(S)-3-(3-(1-(5-chloropyridin-2-yl)-1-(3-fluoro-5-(1,1,2,2-tetrafluoroethoxy)phenyl)-2-phenylethyl)ureido)-3-methylbutanamide Procedure 70

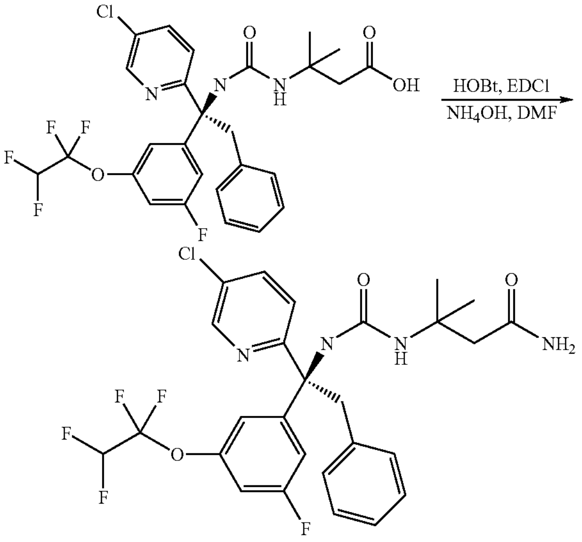

3-(3-(1-(5-chloropyridin-2-yl)-1-(3-fluoro-5-(1,1,2,2-tetrafluoroethoxy)phenyl)-2-phenylethyl)ureido)-3-methylbutanoic acid was prepared by method described in Procedure 8 in the yield of 62%. LCMS: RT=2.00 min [M+H] 586.3 (LCMS Method 2).

To a solution of 3-(3-(1-(5-chloropyridin-2-yl)-1-(3-fluoro-5-(1,1,2,2-tetrafluoroethoxy)phenyl)-2-phenylethyl)ureido)-3-methylbutanoic acid (17.4 mg, 0.03 mmol) in DMF (1 mL) was added HOBt (20 mg, 0.148 mmol) and EDCI (29 mg, 0.151 mmol). The resulting mixture was stirred at room temperature over night, followed by addition of $NH_4OH$ (1 mL). After 5 min, the reaction mixture was concentrated and the residue was purified by preparative HPLC Shimadzu-AXIA column, 30×100 mm eluting with 30-100% MeOH (90% in $H_2O$, 0.1% TFA) gradient over 12 min with flow rate 40 mL/min and UV detection at 220 nm to give 3-(3-(1-(5-chloropyridin-2-yl)-1-(3-fluoro-5-(1,1,2,2-tetrafluoroethoxy)phenyl)-2-phenylethyl)ureido)-3-methylbutanamide as a white foam (15.5 mg, 88% yield). LCMS: RT=1.99 min [M+H] 585.3 (LCMS Method 2); NMR: 400 MHz $^1H$ ($CDCl_3$) 8.30 ppm, 1H, d, J=2.0 Hz; 7.75 ppm, 1H, dd, J=8.7, 2.4 Hz; 7.44 ppm, 1H, br. s; 7.16 ppm, 5H, m; 6.99 ppm, 1H, s; 6.92 ppm, 1H, d, J=8.8 Hz; 6.67 ppm, 1H, br. s; 6.57 ppm, 2H, d, J=7.1 Hz; 5.97 ppm, 1H, t, J=53 Hz; 4.10 ppm, 1H, d, J=12.9 Hz; 3.63 ppm, 1H, d, J=13.1 Hz; 2.97 ppm, 1H, d, d=13.1 Hz; 2.44 ppm, 1H, d, J=13.1 Hz; 1.47 ppm, 3H, s; 1.36 ppm, 3H, s.

EXAMPLE 1084

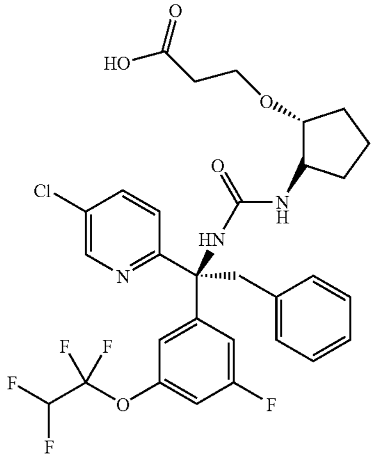

3-((1R,2S)-2-(3-((S)-1-(5-chloropyridin-2-yl)-1-(3-fluoro-5-(1,1,2,2-tetrafluoroethoxy)phenyl)-2-phenylethyl)ureido)cyclopentyloxy)propanoic acid

EXAMPLE 1085

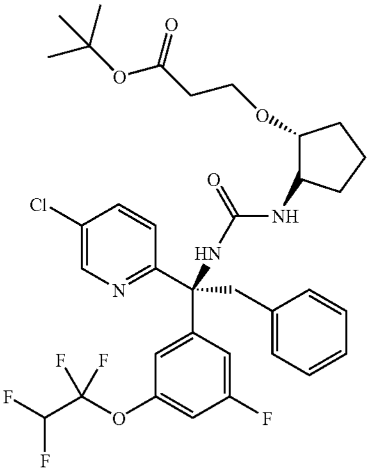

tert-butyl 3-((1R,2S)-2-(3-((S)-1-(5-chloropyridin-2-yl)-1-(3-fluoro-5-(1,1,2,2-tetrafluoroethoxy)phenyl)-2-phenylethyl)ureido)cyclopentyloxy)propanoate

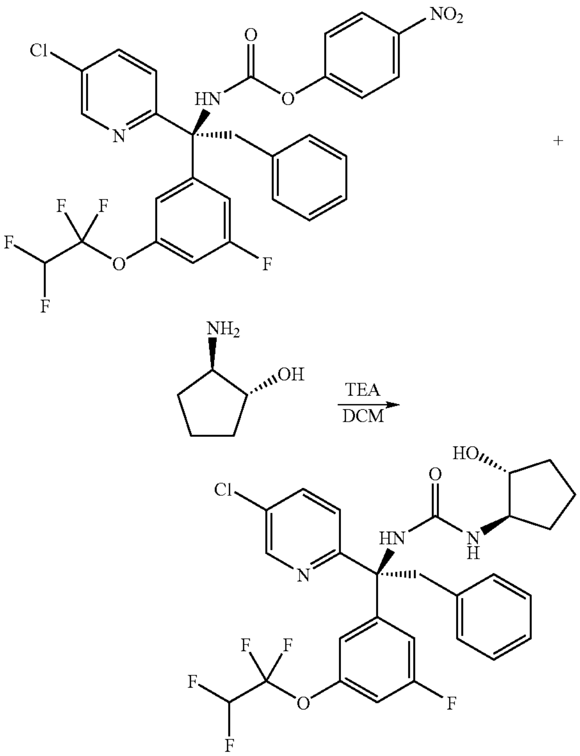

(1R,2R)-2-aminocyclopentanol TFA salt was prepared from (1R,2R)-2-(benzyloxy)cyclopentanamine by method described in Procedure 77 in 100% yield. NMR: 400 MHz $^{1}H$ (DMSO-$d_6$) 7.91 ppm, 2H, m; 3.95 ppm, 1H, m; 3.15 ppm, 1H, m; 2.02 ppm, 1H, m; 1.87 ppm, 1H, m; 1.66 ppm, 2H, m; 1.48 ppm, 2H, m; 1.07 ppm, 1H, m.

1-((S)-1-(5-chloropyridin-2-yl)-1-(3-fluoro-5-(1,1,2,2-tetrafluoroethoxy)phenyl)-2-phenylethyl)-3-((1S,2R)-2-hydroxycyclopentyl)urea was prepared by method described in Procedure 8 in 73% yield. LCMS RT=3.90 min [M+H] 570.24 (LCMS Method 1) NMR: 400 MHz $^{1}H$ ($CDCl_3$) 8.24 ppm, s, 1 H; 7.66 ppm, 1H, d, J=4, 1 Hz; 7.14 ppm, 6H, m; 6.87 ppm, 2H, d, J=8 Hz; 6.62 ppm, 2H, d, J=8 Hz; 5.87 ppm, 1H, t, J=52 Hz; 4.90 ppm, 1H, s; 4.40 ppm, 1H, d, J=12 Hz; 3.98 ppm, 1H, m; 3.66 ppm, 1H, m; 3.56 ppm, 1H, d, J=12 Hz; 1.96 ppm, 1H, m; 1.67 ppm, 3H, m; 1.31 ppm, 2H, m.

Procedure 71

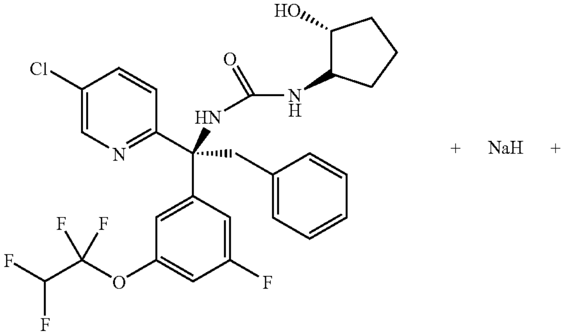

-continued

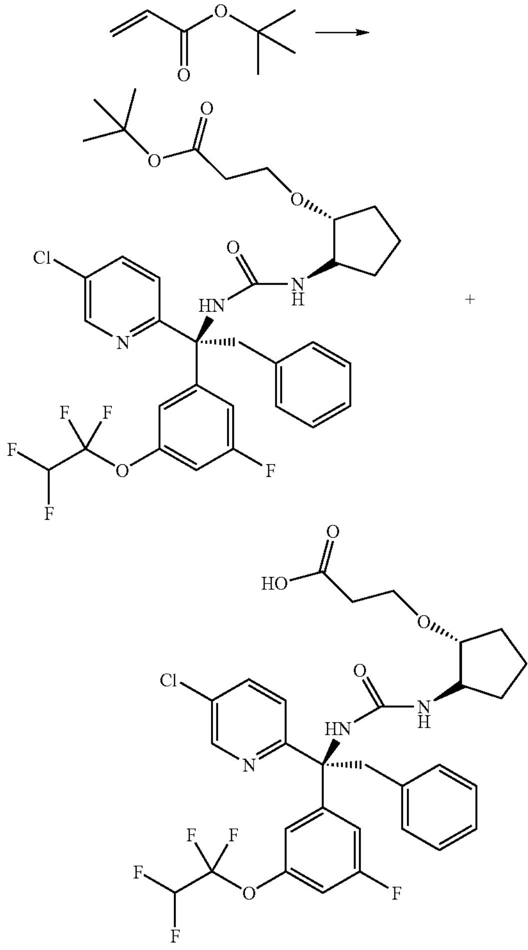

To a solution of 1-((S)-1-(5-chloropyridin-2-yl)-1-(3-fluoro-5-(1,1,2,2-tetrafluoroethoxy)phenyl)-2-phenylethyl)-3-((1S,2R)-2-hydroxycyclopentyl)urea (16 mg, 0.028 mmol) in THF (1 mL) was added NaH (11 mg, 60% in mineral oil, 0.28 mmol). t-Butyl acrylate (18 mg, 0.14 mmol) was added after 1 min and the reaction mixture stirred at ambient temperature for 16 h. The reaction mixture was concentrated in vacuo and purified by preparative HPLC Shimadzu-Phenomenex Luna C18 column, 21.2×100 mm eluting with 10-100% $CH_3CN$ (90% in $H_2O$, 0.1% TFA) gradient over 15 min with flow rate 20 mL/min and UV detection at 220 nm to give 3-((1R,2S)-2-(3-((S)-1-(5-chloropyridin-2-yl)-1-(3-fluoro-5-(1,1,2,2-tetrafluoroethoxy)phenyl)-2-phenylethyl)ureido)cyclopentyloxy)propanoic acid at the retention time of 8.74 min (1.2 mg, 6% yield) and tert-butyl 3-((1R,2S)-2-(3-((S)-1-(5-chloropyridin-2-yl)-1-(3-fluoro-5-(1,1,2,2-tetrafluoroethoxy)phenyl)-2-phenylethyl)ureido)cyclopentyloxy)propanoate at a retention time of 11.32 min (2.5 mg, 14% yield).

3-((1R,2S)-2-(3-((S)-1-(5-chloropyridin-2-yl)-1-(3-fluoro-5-(1,1,2,2-tetrafluoroethoxy)phenyl)-2-phenylethyl)ureido)cyclopentyloxy)propanoic acid LCMS RT=3.88min, [M+H] 642.25 (LCMS Method 1) NMR: 500 MHz $^{1}H$ ($CDCl_3$) 8.28 ppm, 1H, m; 7.67 ppm, 1H, m; 7.14 ppm, 9H, m; 6.88 ppm, 1H, m; 6.70 ppm, 2H, m; 5.90 ppm, 1H, t, 4.35 ppm, 1H, m; 3.81 ppm, 4H, m; 3.57 ppm, 1H, m; 2.59 ppm, 2H, m; 2.04 ppm, 1H, m; 1.91 ppm, 1H, m; 1.67 ppm, 2H, m; 1.34 ppm, 2H, m.

tert-butyl 3-((1R,2S)-2-(3-((S)-1-(5-chloropyridin-2-yl)-1-(3-fluoro-5-(1,1,2,2-tetrafluoroethoxy)phenyl)-2-phenylethyl)ureido)cyclopentyloxy)propanoate LCMS RT=4.23 min, [M+H] 698.30 (LCMS Method 1) NMR: 500 MHz $^1H$ ($CDCl_3$) 8.33 ppm, 1H, m; 7.69 ppm, 1H, d; 7.12 ppm, 7H, m; 6.91 ppm, 1H, m; 6.59 ppm, 2H, m; 5.90 ppm, 1H, t; 4.33 ppm, 1H, m; 3.63 ppm, 5H, m; 2.39 ppm, 2H, m; 1.94 ppm, 2H, m; 1.67 ppm, 3H, m; 1.42 ppm, 9H, m; 1.37 ppm, 1H, m.

EXAMPLE 1086

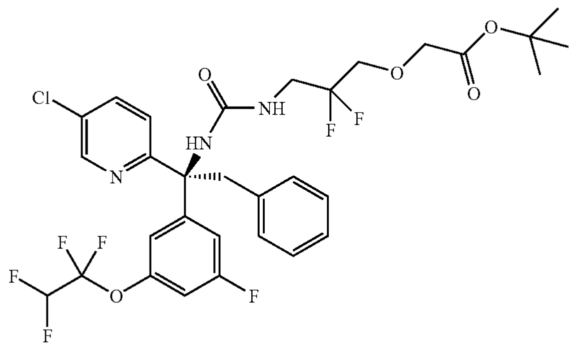

(S)-tert-butyl 2-(3-(3-(1-(5-chloropyridin-2-yl)-1-(3-fluoro-5-(1,1,2,2-tetrafluoroethoxy)phenyl)-2-phenylethyl)ureido)-2,2-difluoropropoxy)acetate Procedure 72

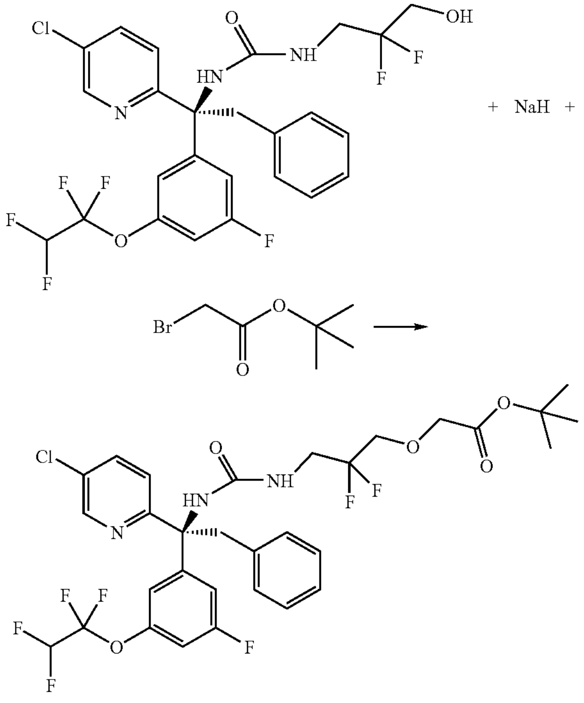

(S)-1-(1-(5-chloropyridin-2-yl)-1-(3-fluoro-5-(1,1,2,2-tetrafluoroethoxy)phenyl)-2-phenylethyl)-3-(2,2-difluoro-3-hydroxypropyl)urea (12 mg, 0.027 mmol), prepared as described in Procedures 3, 5, 6, 7 and 8, in THF (0.5 mL) was added NaH (4 mg, 60% in mineral oil, 0.1 mmol). After 2 min, tert-butyl 2-bromoacetate (6 mg, 0.04 mmol) was added. The reaction mixture was stirred for 15 min, filtered and concentrated in vacuo. The residue was purified by preparative HPLC Shimadzu-Phenomenex Luna C18 column, 21.2×100 mm eluting with 10-90% $CH_3CN$ (90% in $H_2O$, 0.1% TFA) gradient over 15 min with flow rate 20 mL/min and UV detection at 220 nm to give (S)-tert-butyl 2-(3-(3-(1-(5-chloropyridin-2-yl)-1-(3-fluoro-5-(1,1,2,2-tetrafluoroethoxy)phenyl)-2-phenylethyl)ureido)-2,2-difluoropropoxy)acetate as a white solid (8 mg, 43% yield). LCMS RT=4.12 min, [M+H] 694.35 (LCMS Method 1) NMR: 500 MHz $^1H$ ($CDCl_3$) 8.25 ppm, 1H, m; 7.67 ppm, 1H, m; 7.50 ppm, 1H, m; 7.17 ppm, 1H, d; 7.06 ppm, 6H, m; 6.89 ppm, 1H, m; 6.61 ppm, 2H, m; 5.87 ppm, 1H, t; 4.35 ppm, 1H, d; 4.07 ppm, 1H, d; 3.95 ppm, 1H, d; 3.88 ppm, 1H, m; 3.74 ppm, 2H, m; 3.55 ppm, 2H, m; 1.42 ppm, 9H, m.

EXAMPLE 1087

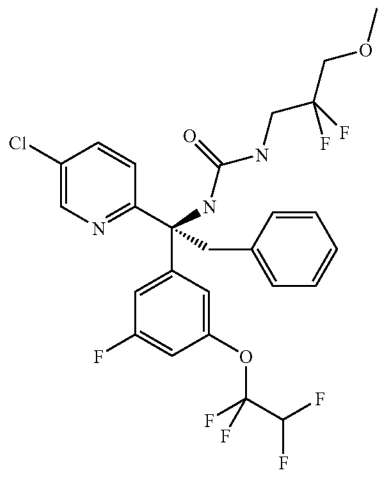

(S)-1-(1-(5-chloropyridin-2-yl)-1-(3-fluoro-5-(1,1,2,2-tetrafluoroethoxy)phenyl)-2-phenylethyl)-3-(2,2-difluoro-3-methoxypropyl)urea

EXAMPLE 1088

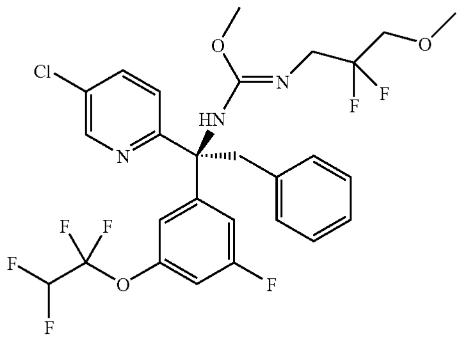

(S,Z)-methyl N-1-(5-chloropyridin-2-yl)-1-(3-fluoro-5-(1,1,2,2-tetrafluoroethoxy)phenyl)-2-phenylethyl-N'-(2,2-difluoro-3-methoxypropyl)carbamimidate Procedure 73

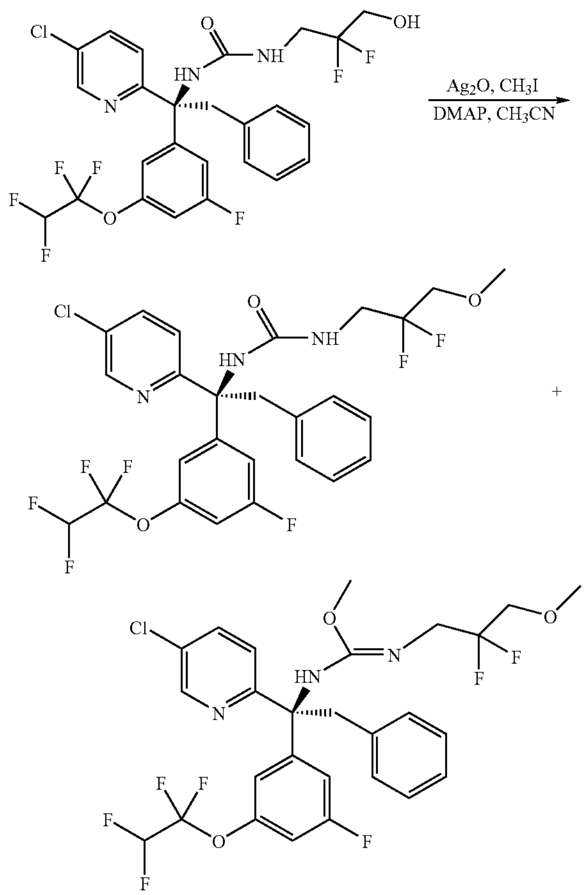

To a solution of (S)-1-(1-(5-chloropyridin-2-yl)-1-(3-fluoro-5-(1,1,2,2-tetrafluoroethoxy)phenyl)-2-phenylethyl)-3-(2,2-difluoro-3-hydroxypropyl)urea (11 mg, 0.019 mmol) in $CH_3CN$ (1 mL) was added $Ag_2O$ (22 mg, 0.095 mmol), followed by the addition of $CH_3I$ (27 mg, 0.19 mmol) and DMAP (5 mg, 0.04 mmol). The reaction mixture was stirred for 1 h, quenched by MeOH. The solid was filtered and the residue was purified by preparative HPLC Shimadzu-Phenomenex Luna C18 column, 21.2×100 mm eluting with 10-90% $CH_3CN$ (90% in $H_2O$, 0.1% TFA) gradient over 15 min with flow rate 20 mL/min and UV detection at 220 nm.

((S)-1-(1-(5-chloropyridin-2-yl)-1-(3-fluoro-5-(1,1,2,2-tetrafluoethoxy)phenyl)-2-phenylethyl)-3-(2,2-difluoro-3-methoxypropyl)urea eluted at a retention time of 8.85 min and was isolated as a colorless gum (3 mg, 27% yield). LCMS RT=3.84 min [M+H] 594.11 (LCMS Method 1) NMR: 500 MHz $^1$H ($CDCl_3$) 8.32 ppm, 1H, m; 7.76 ppm, 1H, d; 7.32 ppm, 1H, d; 7.22 ppm, 2H, m; 7.14 ppm, 2H, m; 7.06 ppm, 2H, m; 6.95 ppm, 1H, d; 6.65 ppm, 2H, d; 6.19 ppm, 1H, t, 5.73 ppm, 1H, m; 4.27 ppm, 1H, d; 3.54 ppm, 4H, m; 3.34 ppm, 3H, m.

(S,Z)-methyl N-1-(5-chloropyridin-2-yl)-1-(3-fluoro-5-(1,1,2,2-tetrafluoroethoxy)phenyl)-2-phenylethyl-N'-(2,2-difluoro-3-methoxypropyl)carbamimidate eluted at a retention time of 10.13 min and was isolated as colorless gum (4 mg, 35%). LCMS RT=4.01 min [M+H] 608.11 (LCMS Method 1) NMR: 500 MHz $^1$H ($CDCl_3$) 8.29 ppm, 1H, m; 7.78 ppm, 1H, d; 7.55 ppm, 1H, d; 7.34 ppm, 1H, m; 7.25 ppm, 1H, m; 7.09 ppm, 3H, m; 6.94 ppm, 2H, m; 6.20 ppm, 1H, t; 4.28 ppm, 1H, d; 3.72 ppm, 3H, m; 3.51 ppm, 2H, m; 3.29 ppm, 3H, m; 2.95 ppm, 3H, m.

EXAMPLE 1089

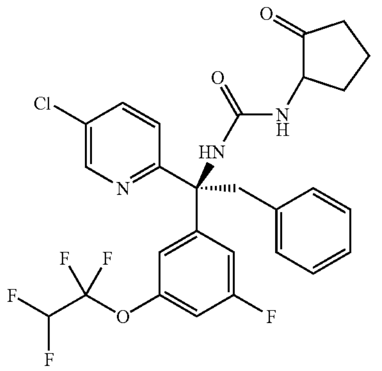

1-((S)-1-(5-chloropyridin-2-yl)-1-(3-fluoro-5-(1,1,2,2-tetrafluoethoxy)phenyl)-2-phenylethyl)-3-(2-oxo-cyclopentyl)urea Procedure 74

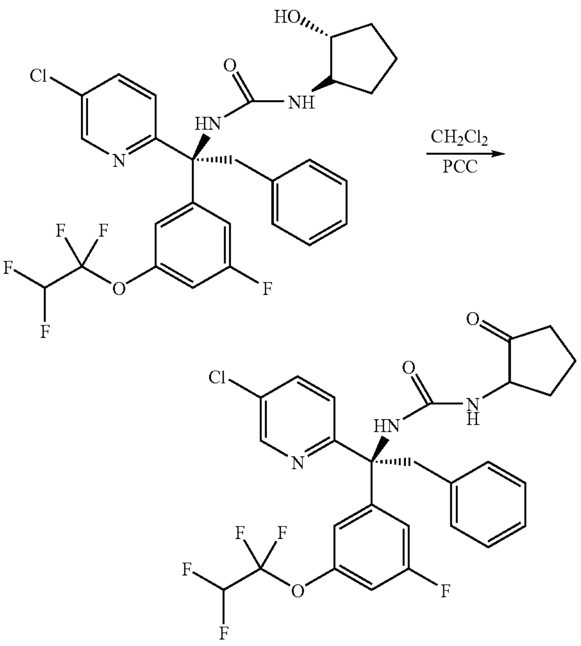

To a solution of 1-((S)-1-(5-chloropyridin-2-yl)-1-(3-fluoro-5-(1,1,2,2-tetrafluoroethoxy)phenyl)-2-phenylethyl)-3-((1S,2R)-2-hydroxycyclopentyl)urea (51 mg, 0.09 mmol), prepared by methods as described in Procedures 3, 5, 6, 7, 77 and 8, in $CH_2Cl_2$ (1 mL) was added PCC (29 mg, 0.13 mmol). The reaction mixture was stirred at ambient temperature for 1 h, and filtered. The solid was rinsed with MeOH. The filtrate was concentrated in vacuo and purified by ISCO chromatography (4 g column) using hexanes/EtOAc (0-60% over 14 min, flow rate 18 mL/min) to give 1-((S)-1-(5-chloropyridin-2-yl)-1-(3-fluoro-5-(1,1,2,2-tetrafluoethoxy)phenyl)-2-phenylethyl)-3-(2-oxocyclopentyl)urea as a white solid (25 mg, 49% yield). LCMS RT=3.82 min [M+H] 568.07 (LCMS Method 1) NMR: 400 MHz $^1$H ($CDCl_3$) 8.21 ppm, 1H, m; 7.68 ppm, 1H, m; 7.12 ppm, 7H, m; 6.87 ppm, 1H, m; 6.66 ppm, 2H, m; 5.86 ppm, 1H, t; 4.69 ppm, 1H, m; 4.38 ppm, 1H, m; 4.05 ppm, 1H, m; 3.59 ppm, 2H, m; 2.47 ppm, 1H, m; 1.68 ppm, 3H, m.

EXAMPLE 1090

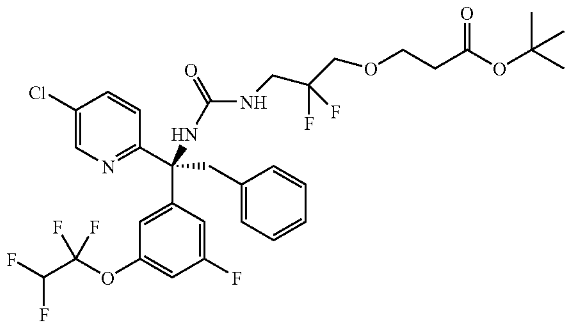

(S)-tert-butyl 3-(3-(3-(1-(5-chloropyridin-2-yl)-1-(3-fluoro-5-(1,1,2,2-tetrafluoroethoxy)phenyl)-2-phenylethyl)ureido)-2,2-difluoropropoxy)propanoate Procedure 75

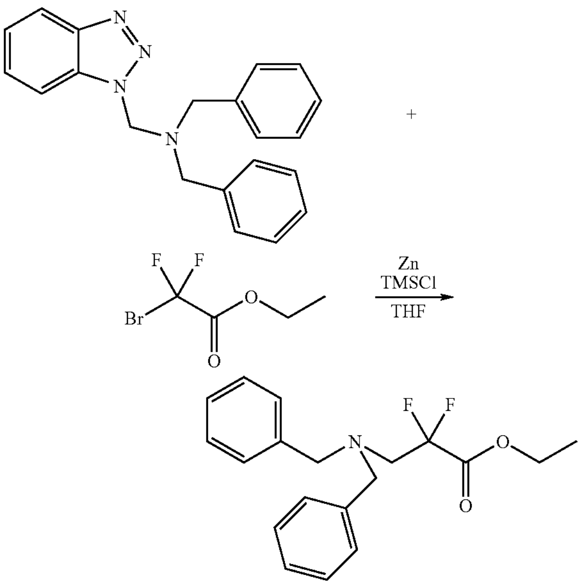

To a suspension of zinc dust (238 mg, 3.66 mmol) in dry THF (3 mL), under Ar, was added TMSCl (234 μL, 1.83 mmol) and the reaction mixture stirred at ambient temperature for 10 min. Ethyl bromodifluoroaetate (260 μL, 2.0 mmol) was added dropwise and the resulting slurry stirred for 10 min. N-((1H-benzo[d] [1,2,3]triazol-1-yl)methyl)-N-benzyl-1-phenylmethanaime (600 mg, 1.83 mmol) in dry THF (3 mL) was then added and the reaction mixture stirred at room temperature for 1 h. To the reaction mixture was added 10 ml 5% $NaHCO_3$ (aq). The resulting mixture was stirred for 10 min, and filtered through a celite pad. The filtrate was extracted with EtOAc and the celite pad was rinsed with EtOAc. The combined EtOAc portions was dried over $MgSO_4$, filtered, concentrated and purified by ISCO flash chromatography, using EtOAc and hexane as eluting solvent, to yield ethyl 3-(dibenzylamino)-2,2-difluoropropanoate as a colorless oil (577 mg, 94% yield). LCMS: RT=4.09 min [M+H] 334.28 (LCMS Method 1).

Procedure 76

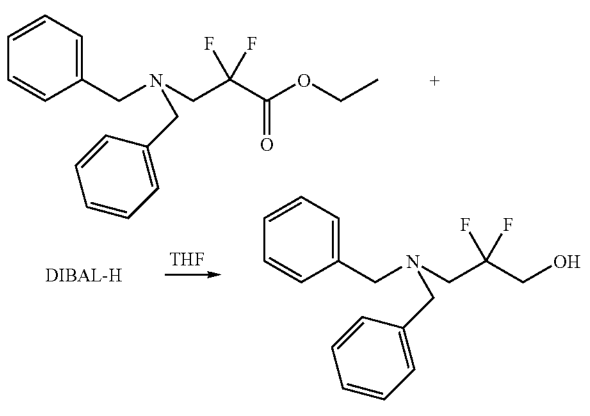

At −78° C. to a solution of ethyl 3-(dibenzylamino)-2,2-difluoropropanoate (1.19 g, 3.5 mmol) in THF (20 mL) was added DIBAL-H (15 mL, 1.0 M in hexane, 15 mmol) dropwise. The temperature was maintained at below −70° C. during the addition. After the addition, the acetone-dry ice bath was removed and the reaction mixture was allowed to warm up to room temperature and stirred for 18 h. Celite was added to the reaction mixture, followed by the slow addition of $H_2O$ (5 mL), 2 N NaOH (5 mL) and $H_2O$ (5 mL). The reaction mixture was filtered, concentrated in vacuo and purified by ISCO chromatography to give 3-(dibenzylamino)-2,2-difluoropropan-1-ol as a colorless oil (810 mg, 80% yield) LCMS: RT=2.48 min [M+H] 292.15 (LCMS Method 1).

Procedure 77

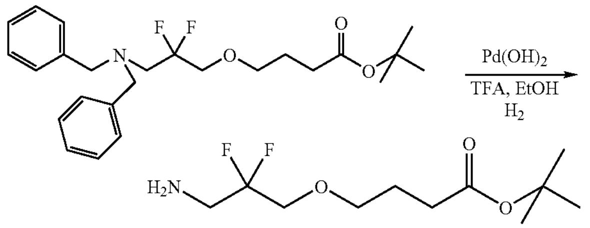

tert-Butyl 4-(3-(dibenzylamino)-2,2-difluoropropoxy)butanoate was prepared by method described in Procedure 71 in 67% yield. LCMS: RT=3.86 min [M+H] 420.3 (LCMS Method 1).

To a solution of tert-butyl 4-(3-(dibenzylamino)-2,2-difluoropropoxy)butanoate (120 mg, 0.29 mmol) in EtOH (1 mL) was added 50 mg $Pd(OH)_2$ (10 mg, 20% on C) followed by the addition of TFA (25 μL). The reaction mixture was stirred at room temperature under $H_2$ for 18 h. The solid was removed by filtration and the filtrate was concentrated under reduced pressure to yield tert-butyl 4-(3-amino-2,2-difluoropropoxy)butanoate (50 mg, 72% yield).

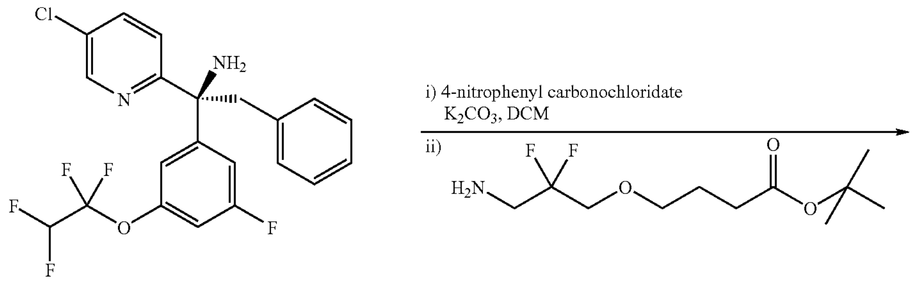

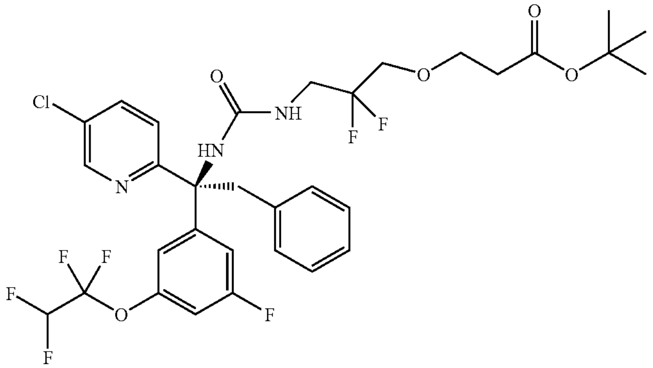

(S)-tert-butyl 3-(3-(3-(1-(5-chloropyridin-2-yl)-1-(3-fluoro-5-(1,1,2,2-tetrafluoroethoxy)phenyl)-2-phenylethyl)ureido)-2,2-difluoropropoxy)propanoate was prepared by method described in Procedure 8 in 13% yield. LCMS RT=4.07 min [M+H] 708.04 (LCMS Method 1) NMR: 500 MHz $^1H$ ($CDCl_3$) 8.32 ppm, 1H, m; 7.75 ppm, 1H, m; 7.34 ppm, 1H, m; 7.22 ppm, 1H, m; 7.09 ppm, 4H, m; 6.96 ppm, 1H; 6.65 ppm, 2H, m; 5.77 ppm, 1H, t, 4.28 ppm, 1H, m; 3.68 ppm, 6H, m; 3.48 ppm, 1H, m; 2.42 ppm, 2H, m; 1.94 ppm, 9H, m.

EXAMPLE 1091

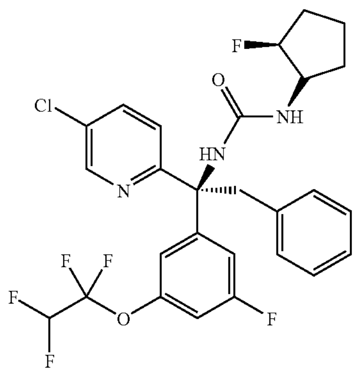

1-((S)-1-(5-chloropyridin-2-yl)-1-(3-fluoro-5-(1,1,2,2-tetrafluoroethoxy)phenyl)-2-phenylethyl)-3-((1S,2S)-2-fluorocyclopentyl)urea Procedure 78

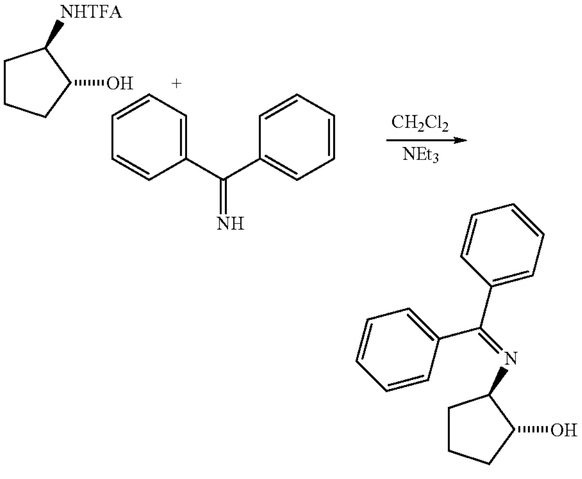

(1R,2R)-2-aminocyclopentanol TFA salt was prepared by method described in Procedure 77 as a yellow oil in 100% yield. NMR: 400 MHz $^1H$ (DMSO-D6) 7.96 ppm, 2H, m; 3.95 ppm, 1H, m; 3.15 ppm, 1H, m; 2.02 ppm, 1H, m; 1.87 ppm, 1H, m; 1.66 ppm, 2H, m; 1.48 ppm, 2H, m; 1.07 ppm, 1H, m.

A solution of (1R,2R)-2-aminocyclopentanol TFA salt (630 mg, 2.93 mmol), diphenylmethanimine (490 uL, 2.93 mmol) and TEA (0.5 mL, 3.58 mmol) in $CH_2Cl_2$ (3 mL) was stirred at ambient temperature for 2 h. The reaction mixture was concentrated in vacuo and the residue purified by ISCO flash chromatography using EtOAc and hexane as eluting solvent to yield (1R,2R)-2-diphenylmethyleneamino)cyclopentanol as a colorless gum. (697 mg, 90% yield). LCMS: RT=1.96 min [M+H] 266.13 (LCMS Method 1); NMR: 400 MHz $^1$H ($CDCl_3$) 7.64 ppm, 2H, m; 7.41 ppm, 6H, m; 7.20 ppm, 2H, m; 4.39 ppm, 1H, m; 3.63 ppm, 1H, m; 2.16 ppm, 1H, m; 1.79 ppm, 3H, m; 1.57 ppm, 2H, m.

Procedure 79

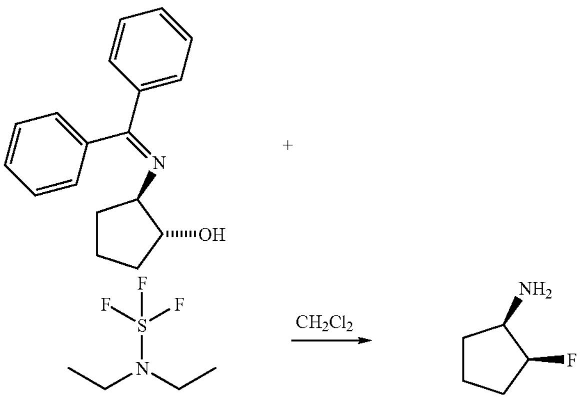

To a solution of (1R,2R)-2-(diphenylmethyleneamino)cyclopentanol (112 mg, 0.42 mmol) in $CH_2Cl_2$ (1 ml) at −20° C. was added DAST (67 uL, 0.5 mmol) dropwise. The reaction mixture was allowed to reach ambient temperature and stirred for 16 h, then concentrated in vacuo to yield (1R,2R)-2-fluorocyclopentanamine (120 mg).

1-((S)-1-(5-chloropyridin-2-yl)-1-(3-fluoro-5-(1,1,2,2-tetrafluoroethoxy)phenyl)-2-phenylethyl)-3-((1S,2S)-2-fluorocyclopentyl)urea was prepared by method described in Procedure 8 in 2% yield. LCMS RT=4.07 min [M+H] 572.75 (LCMS Method 1) NMR: 400 MHz $^1$H ($CDCl_3$) 8.25 ppm, 1H, d; 7.64 ppm, 1H, m; 7.05 ppm, 6H, m; 6.85 ppm, 1H, d; 6.50 ppm, 2H, m; 5.84 ppm, 1H, t, 4.28 ppm, 1H, d, 3.70 ppm, 1H, m; 3.47 ppm, 2H, m; 2.19 ppm, 1H, m; 2.03 ppm, 1H, m; 1.94 ppm, 1H, m; 1.84 ppm, 1H, m; 1.50 ppm, 1H, m; 1.37 ppm, 1H, m.

EXAMPLE 1092

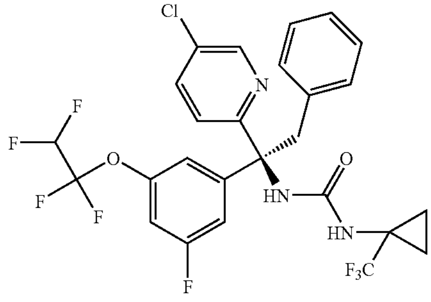

(S)-1-(1-(5-chloropyridin-2-yl)-1-(3-fluoro-5-(1,1,2,2-tetrafluoroethoxy)phenyl)-2-phenylethyl)-3-(1-(trifluoromethyl)cyclopropyl)urea Procedure 80

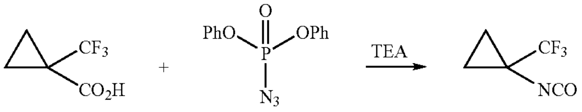

1-(Trifluoromethyl)cyclopropanecarboxylic acid (99 mg, 0.64 mmol) in toluene (1 mL) was added TEA (89 μL, 0.64 mmol) and diphenyl phosphorazidate (139 μL, 0.64 mmol). The reaction mixture was heated at 110° C. for 1 h, then allowed to cool to room temperature. The crude reaction mixture was used to the next step without further purification.

(S)-1-(1-(5-chloropyridin-2-yl)-1-(3-fluoro-5-(1,1,2,2-tetrafluoroethoxy)phenyl)-2-phenylethyl)-3-(1-(trifluoromethyl)cyclopropyl)urea was prepared by method described in Procedure 2 in 12% yield. LCMS RT=2.09 min [M+H]594.1 (LCMS Method 1) NMR: 400 MHz $^1$H ($CDCl_3$) 8.32 ppm, 1H, m; 7.97 ppm, 1H, m; 7.70 ppm, 1H, m; 7.19 ppm, 1H, d; 7.09 ppm, 4H, m; 6.87 ppm, 1H, m; 6.54 ppm, 2H, m; 5.89 ppm, 1H, t, 5.36 ppm, 1H, m; 4.40 ppm, 1H, d; 3.55 ppm, 1H, d; 1.23 ppm, 2H, m; 1.01 ppm, 1H, m; 0.68 ppm, 1H, m.

EXAMPLE 1093

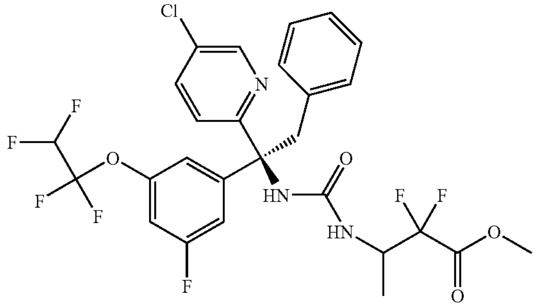

Methyl 3-(3-((S)-1-(5-chloropyridin-2-yl)-1-(3-fluoro-5-(1,1,2,2-tetrafluoroethoxy)phenyl)-2-phenylethyl)ureido)-2,2-difluorobutanoate Procedure 81

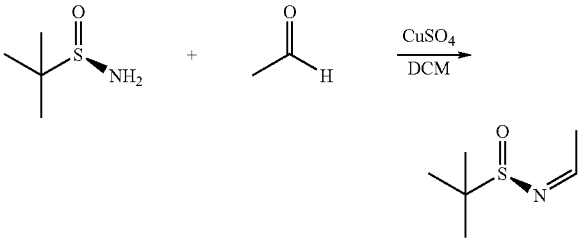

Under argon (R)-2-methylpropane-2-sulfinamide (1 g, 8.2 mmol) was added to a mixture of celite and $CuSO_4$ (6.6 g, 41 mmol) and DCM (10 mL), followed by the addition of acetaldehyde (1 mL, 16.5 mmol). The reaction was stirred at room temperature for 18 h. The celite was filtered and the filtrate was extracted with DCM. The concentrated residue was purified by ISCO chromatography using hexanes/EtOAc (0-30% over 18 min) to give (R,Z)-N-ethylidene-2-methylpropane-2-sulfinamide as a colorless oil (390 mg, 32%). NMR: 400 MHz $^1H$ ($CDCl_3$) 8.10 ppm, 1H, s; 2.23 ppm, 3H, d; 1.20 ppm, 9H, s.

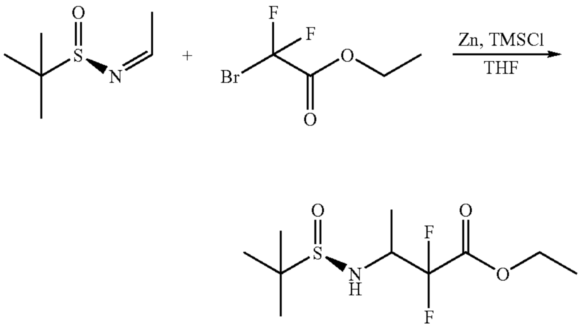

Ethyl 3-((R)-1,1-dimethylethylsulfinamido)-2,2-difluorobutanoate was prepared by method described in Procedure 75 in 36% yield. LCMS RT=1.44 min [M+H ] 272.2 (LCMS Method 2).

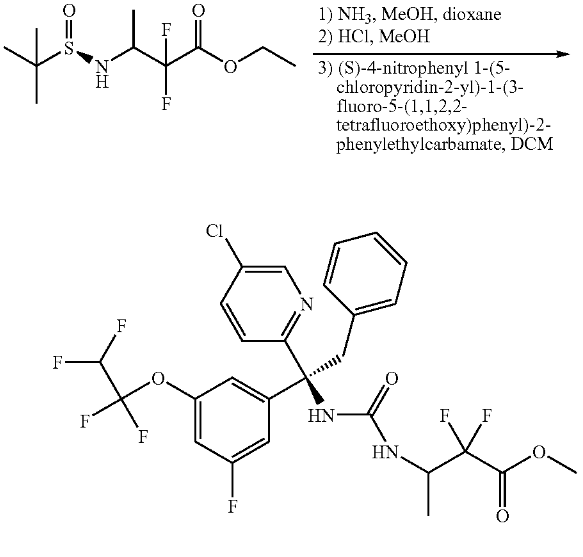

Methyl 3-(3-((S)-1-(5-chloropyridin-2-yl)-1-(3-fluoro-5-(1,1,2,2-tetrafluoroethoxy)phenyl)-2-phenylethyl)ureido)-2,2-difluorobutanoate was prepared by method described in Procedure 24 and 23 (i) and 8. LCMS RT=1.95 min [M+H] 622.2 (LCMS Method 1) NMR: 400 MHz $^1H$ ($CDCl_3$) 8.27 ppm, 1H, m; 7.73 ppm, 1H, m; 7.50 ppm, 1H, m; 7.11 ppm, 6H, m; 6.88 ppm, 1H, m; 6.57 ppm, 2H, m; 5.88 ppm, 1H, t; 4.46 ppm, 1H, m; 4.25 ppm, 1H, m; 3.80 ppm, 3H, m; 3.56 ppm, 1H, d; 1.24 ppm, 3H, m.

EXAMPLE 1094

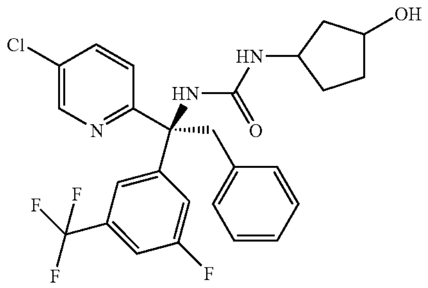

1((S)-1-(5-chloropyridin-2-yl)-1-(fluoro-5-(trifluoromethyl)phenyl-2-phenylethyl)-3-(3-hydroxycyclopentyl)urea Procedure 82

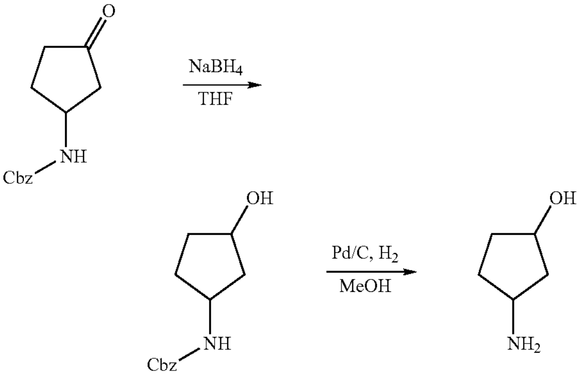

To a stirred solution of benzyl 3-oxocyclopentylcarbamate (1.5 g, 6.4 mmol) in THF (12 mL), was added $NaBH_4$ (243 mg, 6.4 mmol) at room temperature. The reaction mixture was stirred overnight, quenched by addition of $H_2O$ and washed with 6N HCl. EtOAc was added and the biphasic mixture was stirred for 10 min, before being extracted with EtOAc three times. The combined organic portions were dried over $Na_2SO_4$, filtered, and concentrated under reduced pressure. Purification was accomplished by column chromatography (EtOAc/hexane 0-100% , 40 g ISCO column) to provide the reduced product (967 mg, 64%) as a mixture of isomers. The mixture so obtained was used directly in the next step.

To a stirred solution of benzyl 3-hydroxycyclopentylcarbamate (665 mg, 2.8 mmol) in MeOH (8 mL), was added Pd/C (88 mg) and the heterogeneous mixture was carefully placed under an atmosphere of $H_2$ using a gas balloon at room temperature. The mixture was stirred for 2 h, at which point the starting material had been consumed. The mixture was filtered through a pad of celite, washed with MeOH, and concentrated under reduced pressure to provide 3-aminocyclopentanol as an oil (274 mg, 96%). The amino alcohol was used without further purification.

NMR: 500 MHz $^1H$ (MeOH-$d_4$) δ 4.35-4.30 (m, 1H), 4.25-4.20 (m, 1H), 3.57-3.45 (m, 1H), 3.37-3.28 (m, 1H), 2.15-1.25 (m, 12H).

1-((S)-1-(5-chloropyridin-2-yl)-1-(3-fluoro-5-(trifluoromethyl)phenyl)-2-phenylethyl)-3-(3-hydroxycyclopentyl) urea was prepared by method described in Procedure 8. LC/MS RT=3.840 min [M+H] 522.2 (LCMS Method 1); NMR: 500 MHz $^1H$ ($CDCl_3$) 8.30-8.28 (m, 1H), 7.71-7.67 (m, 1H), 7.50-7.48 (m, 1H), 7.36-7.31 (m, 1H), 7.25-7.21 (m, 1H), 7.19-7.13 (m, 1H), 7.12-7.07 (m, 3H), 6.59-6.54 (m 2H), 4.47-4.37 (m, 2H), 4.10-4.00 (m, 1H), 3.55 (d, J=13 Hz, 1H), 2.35-2.00 (m, 3H), 1.95-1.45 (m, 3H), 1.35-1.15 (m, 1H), 1.05-0.90 (m, 1H);

EXAMPLE 1095

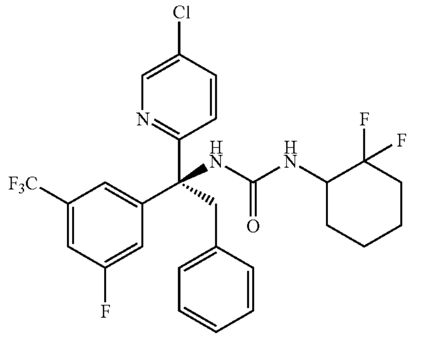

1-((S)-1-(5-chloropyridin-2-yl)-1-(3-fluoro-5-(trifluoromethyl)phenyl)-2-phenylethyl)-3-(2,2-difluorocyclohexyl)urea Procedure 83

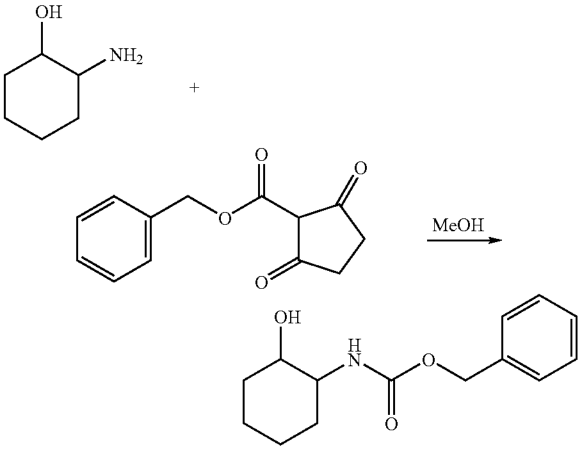

To a solution of benzyl 2,5-dioxocyclopentanecarboxylate (2.58 g, 10.35 mmol) in MeOH (20 mL) at 0° C. was added 2-aminocyclohexanol (1.25 g, 10.87 mmol). The reaction mixture was stirred at room temperature for 18 hr and quenched by addition of 0.25 N HCl (8 mL). MeOH was removed in vacuo and the aqueous layer was extracted with $CH_2Cl_2$ (4×10 mL). The combined organic portions were washed with saturated NaCl (20 mL), dried over $Na_2SO_4$, filtered and concentrated under reduced pressure. The resulted brown oil was purified by ISCO chromatography (40 g column) using hexanes/EtOAc (0-5% over 15 min, 5-10% over 7 min) to give benzyl 2-hydroxycyclohexylcarbamate as a light yellow solid at a retention time of 11-13 min (2.15 g, 83% yield) HPLC: RT=2.83 min, Purity 95% (HPLC Method 1) NMR: 400 MHz $^1H$ ($CDCl_3$) 7.33 ppm, 5 H, m; 5.16 ppm, 1 H, m; 5.09 ppm, 2 H, s; 3.95 ppm, 1 H s; 3.68 ppm, 1 H m; 1.54 ppm, 8 H, m.

Procedure 84

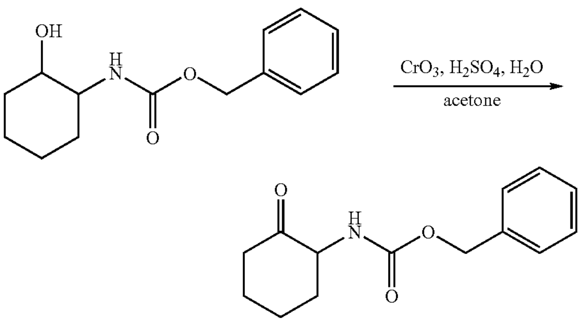

$CrO_3$ (0.70 g) and concentrated $H_2SO_4$ (0.61 mL) was diluted with $H_2O$ to the volume of 6 mL to make Jones Reagent at a concentration of 1.17 M. To a solution of benzyl 2-hydroxycyclohexylcarbamate (1.60 g, 6.43 mmol) in acetone (5.4 mL), cooled in a water bath, was added Jones Reagent (5.51 mL, 1.17 M, 6.43 mmol) dropwise over 5 min. The reaction mixture was stirred at room temperature for 1.5 hr, quenched with 20% aq. $K_2CO_3$ to pH=8. The aqueous layer was extracted with EtOAc (3×15 mL). The combined organic layers were washed with brine (20 mL), dried over $Na_2SO_4$, filtered and concentrated. The residue was purified by ISCO chromatography (40 g column) using hexanes/EtOAc (0-30% over 8 min, 30-45% over 10 min) to give benzyl 2-oxocyclohexylcarbamate as a colorless oil at a retention time of 8.5-11 min (1.26 g, 79% yield) HPLC: RT=2.69 min, Purity 99% (HPLC Method 1) NMR: 400 MHz $^1H$ ($CDCl_3$) 7.33 ppm, 5 H, m; 5.76 ppm, 1 H, s; 5.11 ppm, 2 H, m; 4.27 ppm, 1 H, m; 2.65 ppm, 1 H, dd, J=6.60, 2.75 Hz; 2.52 ppm, 1 H, m; 2.38 ppm, 1 H, m; 2.13 ppm, 1 H, m; 1.89 ppm, 1 H, m; 1.77 ppm, 1 H, m; 1.64 ppm, 1 H, m; 1.42 ppm, 1 H, m.

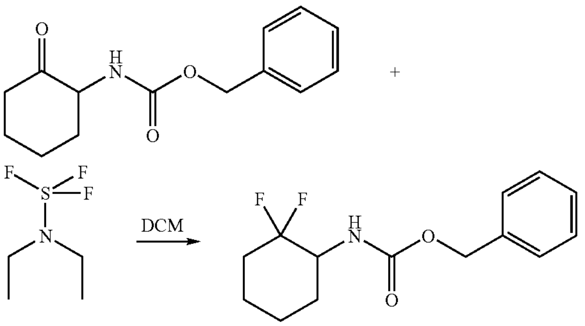

At room temperature to a solution of benzyl 2-oxocyclohexylcarbamate (294 mg, 1.19 mmol) in DCM (5 mL) was added DAST (0.5 mL, 3.92 mmol). The reaction mixture was stirred for 18 hr then cooled to 0° C. The reaction mixture was quenched by addition of saturated NaCl (1 mL). The separated aqueous phase was extracted with DCM (3×8 mL). The combined organic layers were dried over $Na_2SO_4$, filtered and concentrated under reduced pressure. The residue was purified by ISCO chromatography (12 g column) using hexanes/EtOAc (0-30% over 15 min, 30-45% over 10 min) to give benzyl 2,2-difluorocyclohexylcarbamate as a brown oil at a retention time of 7-10 min (272 mg, 85% yield) HPLC: RT=3.03 min, Purity 100% (HPLC Method 1) NMR: 400 MHz $^1H$ ($CDCl_3$) 7.34 ppm, 5 H, m; 5.12 ppm, 2 H, m; 4.99 ppm, 1 H, d, J=8.35 Hz; 3.93 ppm, 1 H, m; 2.18 ppm, 1 H, m; 2.04 ppm, 1 H, m; 1.77 ppm, 2 H, m; 1.46 ppm, 4 H, m.

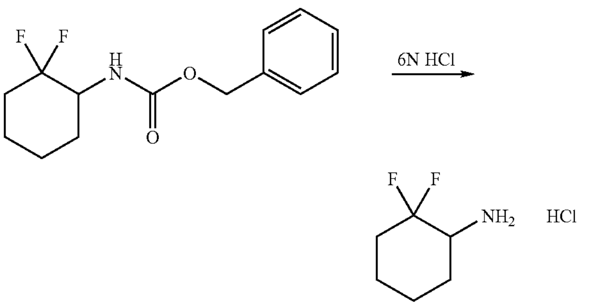

A solution of benzyl 2,2-difluorocyclohexylcarbamate (38 mg, 0.14 mmol) in 6 N HCl (2 mL) was heated at 100° C. for 2 hr. The cooled reaction mixture was washed with ether (3×1 mL) and the aqueous layer was concentrated to give 2,2-difluorocyclohexanamine hydrochloride as a light brown solid (23 mg, 96% crude).

1-((S)-1-(5-chloropyridin-2-yl)-1-(3-fluoro-5-(trifluoromethyl)phenyl)-2-phenylethyl)-3-(2,2-difluorocyclohexyl)urea was prepared by method described in Procedure 8 in 52% yield. NMR: 500 MHz $^1H$ ($CDCl_3$) 8.10-8.26 ppm, 1 H, m; 7.66 ppm, 1 H, dd, J=8.80, 2.20 Hz; 7.56 ppm, 1 H, s; 7.37 ppm, 1 H, d, J=9.90 Hz; 7.18 ppm, 3 H, m; 7.09 ppm, 3 H, m; 6.58-6.74 ppm, 2 H, m; 4.66 ppm, 1 H d, J=9.35 Hz; 4.41 ppm, 1 H, d, J=12.65 Hz; 3.57 ppm, 1 H, d, J=12.65 Hz; 2.11 ppm, 2 H, m; 1.72 ppm, 3 H, m; 1.42 ppm, 3 H, m.

EXAMPLE 1096

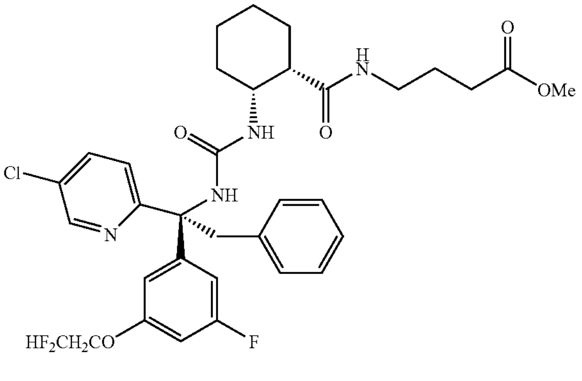

Methyl 4-((1S,2R)-2-(3-((S)-1-(5-chloropyridin-2-yl)-1-(3-fluoro-5-(1,1,2,2-tetrafluoroethoxy)phenyl)-2-phenylethyl)ureido)cyclohexanecarboxamido)butanoate Procedure 85

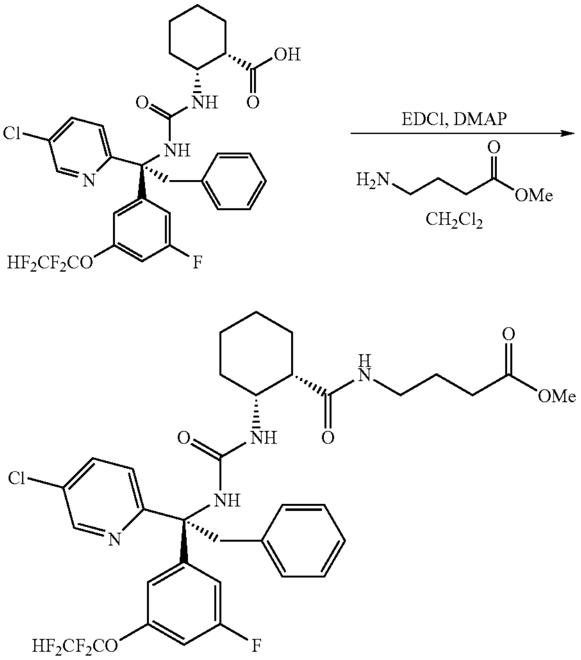

(1S,2R)-2-(3-((S)-1-(5-chloropyridin-2-yl)-1-(3-fluoro-5-(1,1,2,2-tetrafluoroethoxy)phenyl)-2-phenylethyl)ureido)cyclohexanecarboxylic acid was prepared by method described in Procedure 8 in 65% yield. LCMS RT=3.921 min, [M+H] 612.3 (LCMS Method 1).

To a solution of (1S,2R)-2-(3-((S)-1-(5-chloropyridin-2-yl)-1-(3-fluoro-5-(1,1,2,2-tetrafluoroethoxy)phenyl)-2-phenylethyl)ureido)cyclohexanecarboxylic acid (11.6 mg, 0.019 mmol) and methyl 4-aminobutanoate (3.2 mg, 0.027 mmol) in $CH_2Cl_2$ (185 µL), was added EDCI (4.6 mg, 0.024 mmol) followed by DMAP (2.9 mg, 0.024 mmol) at room temperature. The reaction mixture was stirred at room temperature until starting material was consumed as indicated by HPLC analysis. The reaction mixture was concentrated to dryness and the resulting residue was taken up in MeOH and purified by preparative HPLC (Phenoma Luna AXIA 10A, C18; mobile phase: $MeCN/H_2O/TFA$) to provide methyl 4-((1S,2R)-2-(3-((S)-1-(5-chloropyridin-2-yl)-1-(3-fluoro-5-(1,1,2,2-tetrafluoroethoxy)phenyl)-2-phenylethyl)ureido)cyclohexanecarboxamido)butanoate as white solid (7.1 mg, 53% yield). LC/MS RT=3.200 min; [M+H] 711.1 (LCMS Method 4), NMR: 500 MHz $^1H$ ($CDCl_3$) 8.19 ppm, 1 H, d, J=2.20 Hz; 7.57 ppm, 1 H, dd, J=8.25, 2.20 Hz; 7.04 ppm, 6 H, m; 6.99 ppm, 2 H, t, J=7.42 Hz; 6.79 ppm, 1 H, d, J=8.25 Hz; 6.52 ppm, 2 H, d, J=7.15 Hz; 6.18 ppm, 1 H, s; 5.78 ppm, 1 H, m;

4.28 ppm, 1 H, d, J=12.65 Hz; 3.87 ppm, 1 H, s; 3.61 ppm, 3 H, m; 3.47 ppm, 2 H, m; 3.40 ppm, 1 H, m; 2.40 ppm, 5 H, m; 1.58 ppm, 9 H, m.

EXAMPLE 1097

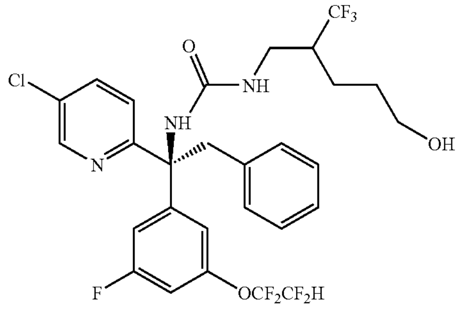

1-((S)-1-(5-chloropyridin-2-yl)-1-(3-fluoro-5-(1,1,2,2-tetrafluoroethoxy)phenyl)-2-phenylethyl)-3-(5-hydroxy-2-(trifluoromethyl)pentyl)urea Procedure 86

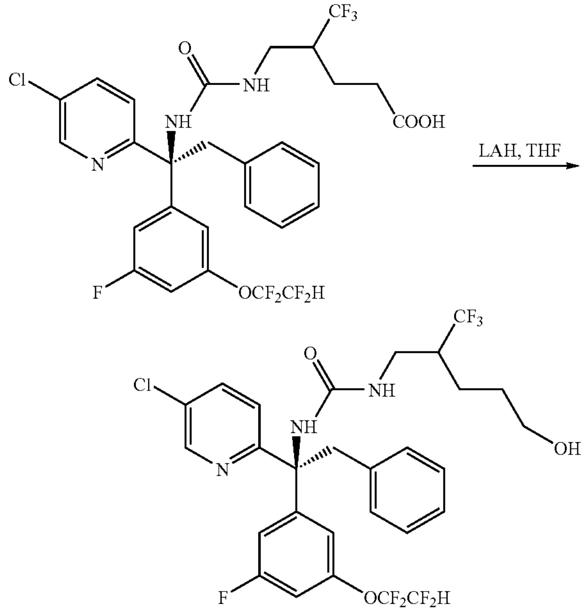

To a solution of 4-((3-((S)-1-(5-chloropyridin-2-yl)-1-(3-fluoro-5-(1,1,2,2-tetrafluoroethoxy)phenyl)-2-phenylethyl)ureido)methyl)-5,5,5-trifluoropentanoic acid (40 mg, 0.061 mmol), prepared by method described in Procedure 3, 5, 6, 7 and 2, in anhydrous THF (1.5 mL) added was dropwise LAH (1.0 M in THF, 0.2 mL). The reaction mixture was stirred at rt for 40 min, then quenched by the addition of 4 N NaOH (1 mL). The aqueous portion was extracted with EtOAc (3×20 mL). The combined organic portions were washed with water and sat. NaCl, dried over $Na_2SO_4$, filtered and concentrated under reduced pressure to yield a yellow oil. The resulting oil was purified by preparative HPLC (YMC ODS S5 30×100 mm column 20-100% MeOH (90% in water, 0.1% TFA) gradient over 10 min with flow rate 40 mL/min and UV detection at 220 nm), then further purified by ISCO chromatography (4 g) with 0-50% EtOAc in hexane over 18 min (RT=14-15.5 min) to yield 1-((S)-1-(5-chloropyridin-2-yl)-1-(3-fluoro-5-(1,1,2,2-tetrafluoroethoxy)phenyl)-2-phenylethyl)-3-(5-hydroxy-2-(trifluoromethyl)pentyl)urea as white solid (30 mg, 77% yield). LCMS: RT=2.003 min [M+H] 639 (LCMS Method 2). HPLC: RT=4.10 min, 100% purity (HPLC Method 1). NMR: 400 MHz $^1$H ($CDCl_3$) 8.17 ppm, 1H, s; 7.59 ppm, 1H, dd, J=8.57, 2.42 Hz; 7.05 ppm, 7H, m; 6.82 ppm, 1H, d, J=8.79 Hz; 6.51 ppm, 2H, t, J=6.81 Hz; 5.82 ppm, 1H, m; 4.60 ppm, 1H, ddd, J=12.08, 6.37, 6.15 Hz; 4.29 ppm, 1H, d, J=12.74 Hz; 3.56 ppm, 2H, dt, J=10.55, 5.27 Hz; 3.43 ppm, 2H, m; 3.34 ppm, 1H, m; 1.64 ppm, 4H, m; 1.54 ppm, 2H, s.

EXAMPLE 1098

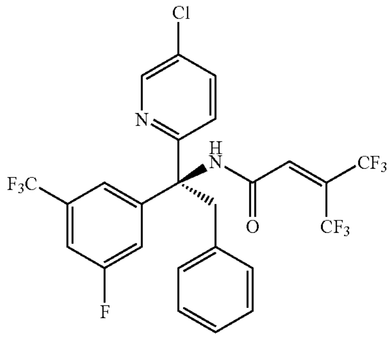

(S)-N-(1-(5-chloropyridin-2-yl)-1-(3-fluoro-5-(trifluoromethyl)phenyl)-2-phenylethyl)-4,4,4-trifluoro-3-(trifluoromethyl)but-2-enamide Procedure 87

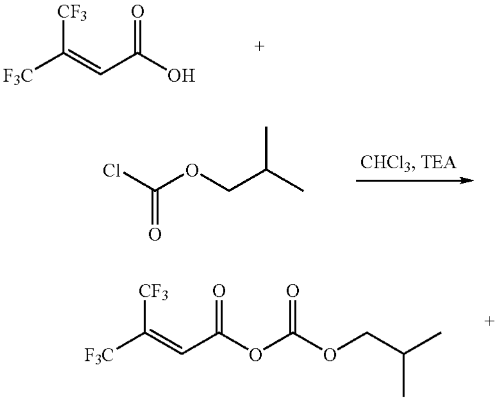

-continued

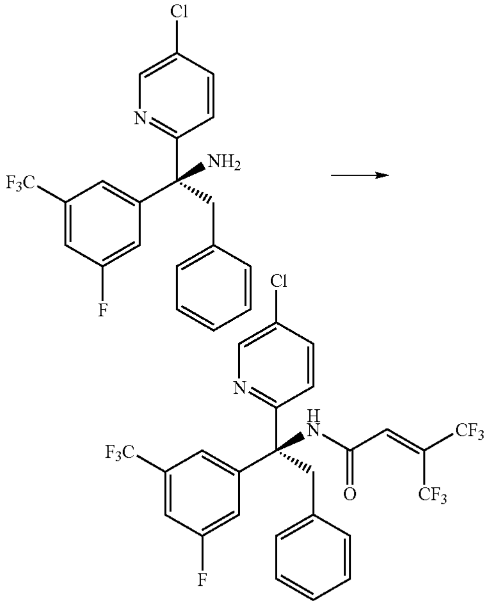

At 0° C. under argon to a solution of 4,4,4-trifluoro-3-(trifluoromethyl)crotonic acid (26 mg, 0.13 mmol) and TEA (19 μL, 0.14 mmol) in $CHCl_3$ (0.5 mL) was added isobutyl chloroformate (18 mg, 0.13 mmol). The reaction mixture was stirred at 0° C. for 10 min. A solution of (S)-1-(5-chloropyridin-2-yl)-1-(3-fluoro-5-(trifluoromethyl)phenyl)-2-phenylethanamine (50 mg, 0.13 mmol), prepared as described in Procedures 5, 6 and 7, in $CHCl_3$ (0.5 mL), was added and the reaction was stirred at room temperature for 18 hr. The reaction mixture was concentrated and purified by preparative HPLC Shimadzu-YMC Sunfire 5μ column, 30×100 mm eluting with 50-100% MeOH (90% in $H_2O$, 0.1% TFA) gradient over 10 min with flow rate 40 mL/min and UV detection at 220 nm. (S)-N-(1-(5-chloropyridin-2-yl)-1-(3-fluoro-5-(trifluoromethyl)phenyl)-2-phenylethyl)-4,4,4-trifluoro-3-(trifluoromethyl)but-2-enamide eluted at a retention time of 11.33 min and was isolated as a clear oil (30 mg, yield 39%) LCMS: RT=2.18 min [M+H] 584.84 (LCMS Method 2); HPLC: RT=4.33 min, Purity 100% (HPLC Method 1) NMR: 400 MHz $^1H$ ($CDCl_3$) 8.61 ppm, 1H, s; 8.25 ppm, 1 H, d, J=2.20 Hz; 7.66 ppm, 1 H, dd, J=8.57, 2.42 Hz; 7.36 ppm, 1 H, s; 7.33 ppm, 1 H, d, J=9.23 Hz; 7.20 ppm, 1 H, m; 7.12 ppm, 1 H, t, J=7.25 Hz; 7.06 ppm, 3 H, m; 6.81 ppm, 1 H, s; 6.46 ppm, 2 H, d, J=7.03 Hz; 4.41 ppm, 1 H, d, J=13.18 Hz; 3.54 ppm, 1 H, d, J=12.74 Hz.

EXAMPLE 1099

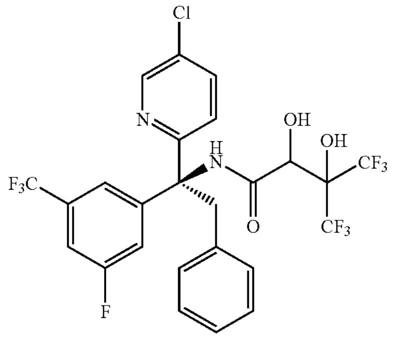

N-((S)-1-(5-chloropyridin-2-yl)-1-(3-fluoro-5-(trifluoromethyl)phenyl)-2-phenylethyl)-4,4,4-trifluoro-2,3-dihydroxy-3-(trifluoromethyl)butanamide Procedure 88

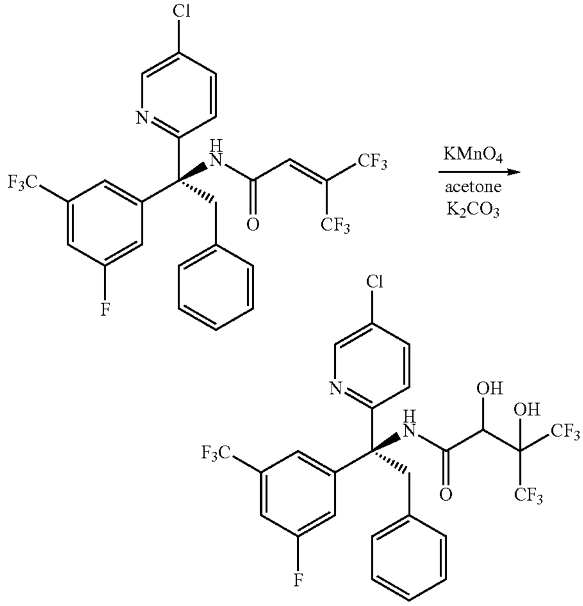

At −78° C. to a mixture of (S)-N-(1-(5-chloropyridin-2-yl)-1-(3-fluoro-5-(trifluoromethyl)phenyl)-2-phenylethyl)-4,4,4-trifluoro-3-(trifluoromethyl)but-2-enamide (8 mg, 0.014 mmol) and $K_2CO_3$ (6.8 mg, 0.049 mmol) in acetone (0.5 mL) $KMnO_4$ (2 mg, 0.013 mmol) was added. The reaction mixture was stirred at −15° C. for 1 hr. EtOAc (15 mL) was added to dilute the reaction mixture and the organic layer was washed with 1N HCl (2×15 mL), dried over $MgSO_4$, filtered and concentrated under reduced pressure. The residue was purified by Prep TLC (Uniplate, Silica Gel GF, 20×20 cm, 1000 Microns) using Hexane/EtOAc (2/1) to yield product as a white solid (2 mg, 23% yield). LCMS: RT=2.08 min [M+H] 618.83 (LCMS Method 2); HPLC: RT=4.27 min, Purity 100% (HPLC Method 1) NMR: 400 MHz $^1H$ ($CDCl_3$) 10.04 ppm, 1 H, s; 8.36 ppm, 1 H, d, J=2.20 Hz; 7.73 ppm, 1 H, dd, J=8.57, 2.42 Hz; 7.55 ppm, 1 H, s; 7.42 ppm, 1 H, s; 7.37 ppm, 1 H, d, J=9.67 Hz; 7.28 ppm, 1 H, d, J=7.91 Hz; 7.20 ppm, 1 H, t, J=7.47 Hz; 7.13 ppm, 3 H, dd, J=8.35, 4.39 Hz; 6.52 ppm, 2 H, d, J=7.03 Hz; 4.51 ppm, 1 H, d, J=6.15 Hz; 4.43 ppm, 1 H, d, J=12.74 Hz; 3.66 ppm, 2 H, m; 2.86 ppm, 1H, m.

EXAMPLE 1100

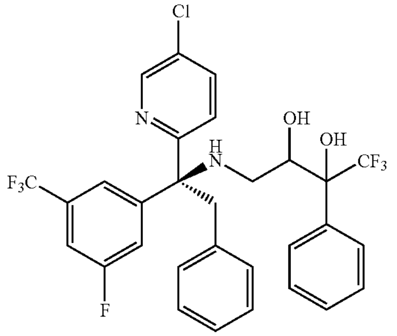

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol (diastereomer 1)

EXAMPLE 1101

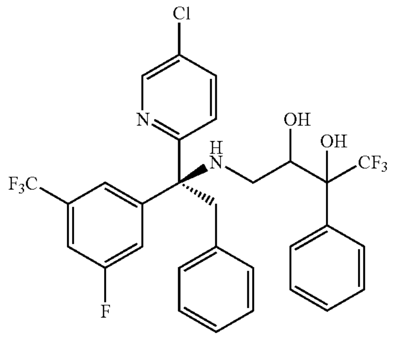

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol (diastereomer 2)

EXAMPLE 1102

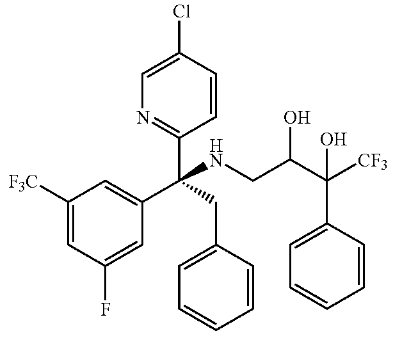

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol (diastereomer 3)

EXAMPLE 1103

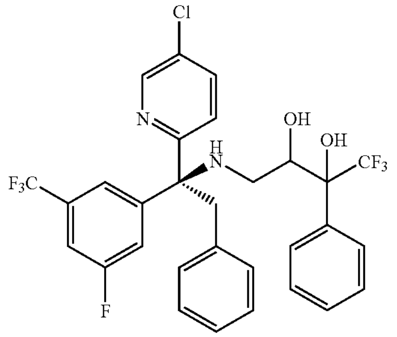

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol (diastereomer 4)

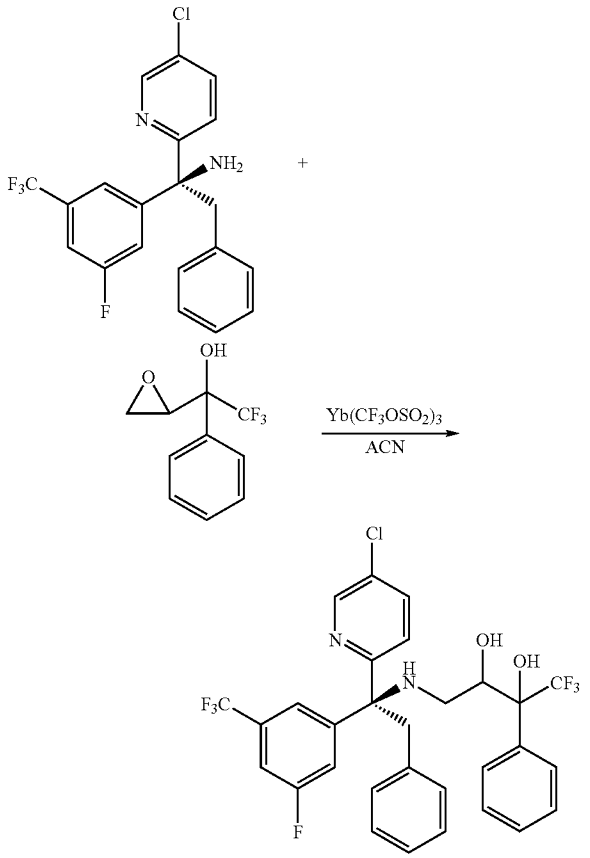

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol was prepared by method described in Procedure 19.

A mixture of (S)-1-(5-chloropyridin-2-yl)-1-(3-fluoro-5-(trifluoromethyl)phenyl)-2-phenylethanamine (250 mg, 0.63 mmol), 2,2,2-trifluoro-1-(oxiran-2-yl)-1-phenylethanol (654 mg, 3.0 mmol), and ytterbium (III) trifluoromethanesulfonate (60 mg) in ACN (3 mL) were heated in microwave reactor at 180° C. for 90 min. The concentrated reaction mixture was purified by preparative HPLC Shimadzu-Phenomenex Luna 10μ column, 50×250 mm eluting with 40-98% ACN (90% in $H_2O$, 0.1% TFA) gradient over 38 min with flow rate 40 mL/min and UV detection at 254 nm. The mixture of four diastereomers of 4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol eluted at a retention time of 30 min and was isolated as a yellow solid (322 mg, 84% yield).

The mixture of four diastereomers (100 mg, 0.16 mmol) were separated by Berger SFC-Chiralpack OD 5μ column, 4.6×250 mm eluting with 95%/5% $C_2$/MeOH with flow rate 70 mL/min and UV detection at 220 nm.

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol diastereomer 1 (example 1100) eluted at a retention time of 18 min and was isolated as a clear oil (33.2 mg, yield 33%) LCMS: RT=1.84 min [M+H] 612.92 (LCMS Method 2); HPLC: RT=4.08 min, Purity 100% (HPLC Method 1) NMR: 400 MHz $^1$H ($CDCl_3$) 8.44 ppm, 1 H, d, J=2.64 Hz; 7.52 ppm, 1 H, dd, J=8.57, 2.42 Hz; 7.34 ppm, 5 H, m; 7.18 ppm, 2 H, m; 7.14 ppm, 1 H d, J=7.03 Hz; 7.08 ppm, 2 H, m; 7.03 ppm, 2 H, m; 6.45 ppm, 2 H, d, J=7.47 Hz; 4.29 ppm, 1 H, s; 4.18 ppm, 1 H, t, J=5.27 Hz; 3.71 ppm, 1 H, s; 3.57 ppm, 1 H, d, J=12 Hz; 3.42 ppm, 1 H, d, J=16 Hz; 2.44 ppm, 1 H, t, J=7.69 H; 2.22 ppm, 2 H, m.

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol diastereomer 1 (example 1101) eluted at a retention time of 19.5 min and was isolated as a clear oil (25.6 mg, yield 26%) LCMS: RT=1.85 min [M+H] 612.91 (LCMS Method 2); HPLC: RT=4.09 min, Purity 100% (HPLC Method 1) NMR: 400 MHz $^1$H ($CDCl_3$) 8.43 ppm, 1 H, d, J=2.64 Hz; 7.54 ppm, 1 H, dd, J=8.35, 2.64 Hz; 7.35 ppm, 6 H, m; 7.24 ppm, 1 H, s; 7.19 ppm, 1 H, d, J=8.35 Hz; 7.14 ppm, 1 H, d, J=7.47 Hz; 7.07 ppm, 3 H, m; 7.00 ppm, 1 H, m; 6.43 ppm, 2 H, d, J=7.47 Hz; 4.23 ppm, 1 H, dd, J=7.03, 3.52 Hz; 3.59 ppm, 1 H, d, J=13.62 Hz; 3.41 ppm, 1 H, d, J=13.62 Hz; 2.37 ppm, 1 H, dd, J=12.30, 3.52 Hz; 2.17 ppm, 1 H, dd, J=12.30, 7.03 Hz.

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol diastereomer 1 (example 1102) eluted at a retention time of 22 min and was isolated as a white solid (6.4 mg, yield 6%) LCMS: RT=1.84 min [M+H] 612.92 (LCMS Method 2); HPLC: RT=4.01 min, Purity 100% (HPLC Method 1) NMR: 400 MHz $^1$H ($CDCl_3$) 8.58 ppm, 1 H, d, J=2.20 Hz; 7.62 ppm, 3 H, d, J=7.91 Hz; 7.40 ppm, 4 H, m; 7.22 ppm, 2 H, m; 7.12 ppm, 6 H, m; 6.64 ppm, 2 H, d, J=7.03 Hz; 4.27 ppm, 1 H, s; 3.83 ppm, 1 H, d, J=14.06 Hz; 3.83 ppm, 1 H, d, J=14.06 Hz; 3.60 ppm, 1 H, d, J=14.06 Hz; 3.18 ppm, 1 H, dd, J=12.52, 3.74 Hz; 2.80 ppm, 1 H, d, J=12 Hz.

4-((S)-1-(5-chloropyridin-2-yl)-1-(3-fluoro-5-(trifluoromethyl)phenyl)-2-phenylethylamino)-1,1,1-trifluoro-2-phenylbutane-2,3-diol diastereomer 1 (example 1103) eluted at a retention time of 26 min and was isolated as a white solid (6.0 mg, yield 6%) LCMS: RT=1.83 min [M+H] 612.90 (LCMS Method 2); HPLC: RT=4.07 min, Purity 100% (HPLC Method 1) NMR: 400 MHz $^1$H ($CDCl_3$) 8.47 ppm, 1 H, d, J=2.20 Hz; 7.63 ppm, 2 H, d, J=7.03 Hz; 7.58 ppm, 1 H, dd, J=8.57, 2.42 Hz; 7.41 ppm, 4 H, m; 7.29 ppm, 2 H, s; 7.23 ppm, 1 H d, J=9.67 Hz; 7.10 ppm, 4 H, m; 6.65 ppm, 2 H, d, J=6.59 Hz; 4.33 ppm, 1 H, s; 3.72 ppm, 2 H, m; 3.32 ppm, 1 H, dd; 2.86 ppm, 1 H, d, J=11.86 Hz.

EXAMPLE 1104

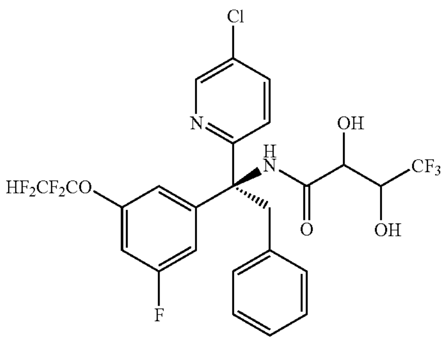

N-((S)-1-(5-chloropyridin-2-yl)-1-(3-fluoro-5-(1,1,2,2-tetrafluoroethoxy)phenyl)-2-phenylethyl)-4,4,4-trifluoro-2,3-dihydroxybutanamide

Procedure 89

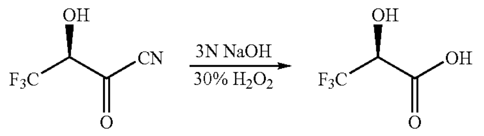

(S)-3,3,3-trifluoro-2-hydroxypropanoyl cyanide was made according to the procedure in J. Org. Chem., 60(1):41-46 (1995).

To a flask charged with (S)-3,3,3-trifluoro-2-hydroxypropanoyl cyanide (139 mg, 1 mmol) was added 3 N NaOH (6 mL) and 30% $H_2O_2$ (2.25 mL). The reaction mixture was heated at 65° C. for 1 h, then at 100° C. for a further 1 h. The reaction mixture was allowed to cooled to room temperature over 1 hr, then cool to 0° C. and the solution acidified with 6 N HCl (3 mL). The aqueous portion was extracted with ether (4×10 mL). The combined organic portions were dried over $MgSO_4$, filtered and concentrated to give (S)-3,3,3-trifluoro-2-hydroxypropanoic acid as a clear oil (129 mg, 90% yield). NMR: 400 MHz $^1$H ($CDCl_3$) 4.45 ppm, 1 H, m; 2.77 ppm, 2 H, m.

Procedure 90

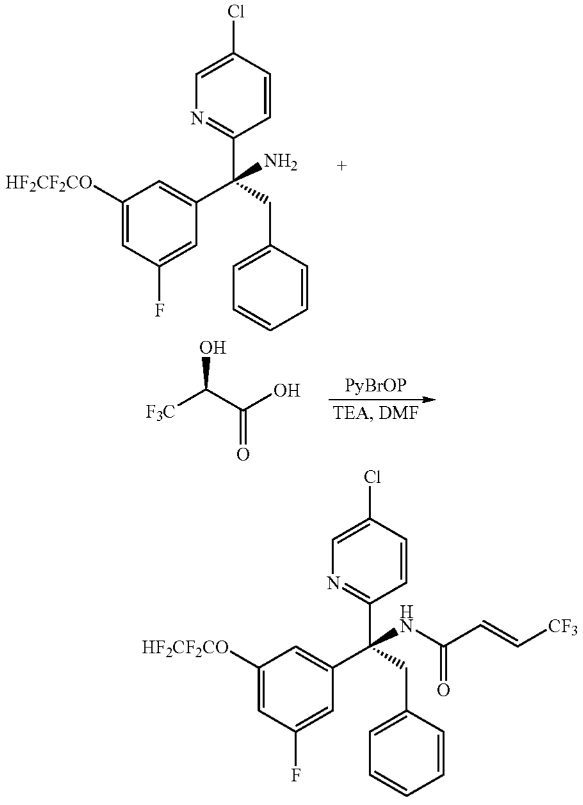

To a solution of (S)-1-(5-chloropyridin-2-yl)-1-(3-fluoro-5-(1,1,2,2-tetrafluoroethoxy)phenyl)-2-phenylethanamine (59 mg, 0.13 mmol), prepared by method described in Procedures 3, 5, 6 and 7, and (S)-3,3,3-trifluoro-2-hydroxypropanoic acid (21 mg, 0.13 mmol) in DMF (0.5 mL) was added TEA (22 μL, 0.16 mmol) followed by the addition of PyBrOP (74 mg, 0.14 mmol). The reaction mixture was stirred at room temperature for 1 h and then heated at 50° C. for 18 h. Additional PyBrOP (74 mg, 0.14 mmol) was added and heating continued for a further 72 h. After cooling to room temperature, the reaction mixture was diluted with EtOAc (25 mL) and the organic portion washed successively with 1 N HCl (20 mL) and saturated $NaHCO_3$ (20 mL). The organic layer was dried over $MgSO_4$, filtered and concentrated under reduced pressure. The residue was purified by preparative HPLC Shimadzu-YMC ODS-A 5μ column, 30×100 mm eluting with 50-100% MeOH (90% in $H_2O$, 0.1% TFA) gradient over 10 min with flow rate 40 mL/min and UV detection at 220 nm. (S,E)-N-(1-(5-chloropyridin-2-yl)-1-(3-fluoro-5-(1,1,2,2-tetrafluoroethoxy)phenyl)-2-phenylethyl)-4,4,4-trifluorobut-2-enamide eluted at a retention time of 10.3 min and was isolated as a clear oil (15 mg, yield 20%) NMR: 400 MHz $^1H$ ($CDCl_3$) 8.63 ppm, 1 H, s; 8.29 ppm, 1 H, d, J=2.20 Hz; 7.72 ppm, 1 H, dd, J=8.57, 2.42 Hz; 7.16 ppm, 2 H, m; 7.08 ppm, 4 H, m; 6.92 ppm, 1 H, d, J=8.79 Hz; 6.71 ppm, 1 H, m; 6.60 ppm, 1 H, m; 6.50 ppm, 2 H, d, J=7.47 Hz; 5.89 ppm, 1 H, tt, J=52.95, 2.64 Hz; 4.46 ppm, 1 H, d, J=12.74 Hz; 3.55 ppm, 1 H, d, J=12.74 Hz.

Procedure 91

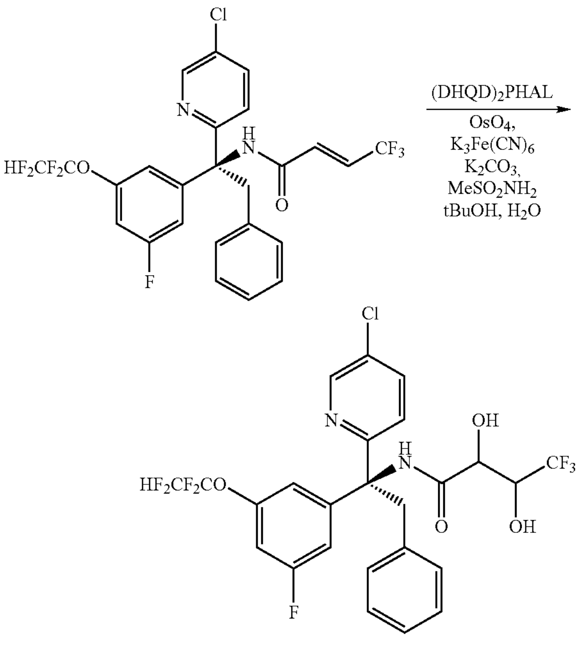

To a solution of (S,E)-N-(1-(5-chloropyridin-2-yl)-1-(3-fluoro-5-(1,1,2,2-tetrafluoroethoxy)phenyl)-2-phenylethyl)-4,4,4-trifluorobut-2-enamide (12 mg, 0.021 mmol) in tBuOH (0.1 mL) and $H_2O$ (0.1 mL) were added $(DHQD)_2PHAL$ (0.3 mg, 0.00042 mmol), $K_3Fe(CN)_6$ (21 mg, 0.063 mmol), $K_2CO_3$ (8.7 mg, 0.063 mmol), $OsO_4$ (2 μL, 2.5% wt in tBuOH, 0.000168 mmol) and $MeSO_2NH_2$ (2 mg, 0.021 mmol). The reaction mixture was stirred at room temperature for 18 h and quenched by addition of saturated $Na_2SO_3$ (10 mL). The aqueous layer was extracted with EtOAc (2×15 mL). The combined organic layers were dried over MgSO4, filtered and concentrated in vacuo. The residue was purified by preparative HPLC Shimadzu-YMC Sunfire 5μ column, 30×100 mm eluting with 40-100% MeOH (90% in $H_2O$, 0.1% TFA) gradient over 10 min with flow rate 40 mL/min and UV detection at 220 nm. N-((S)-1-(5-chloropyridin-2-yl)-1-(3-fluoro-5-(1,1,2,2-tetrafluoroethoxy)phenyl)-2-phenylethyl)-4,4,4-trifluoro-2,3-dihydroxybutanamide eluted at a retention time of 9.66 min and was isolated as a clear oil (2.5 mg, yield 20%) LCMS: RT=1.93 min [M+H] 598.89 (LCMS Method 2); HPLC: RT=4.13 min, Purity 100% (HPLC Method 1) NMR: 400 MHz $^1H$ ($CDCl_3$) 9.40 ppm, 1 H, s; 8.34 ppm, 1 H, d, J=2.20 Hz; 7.71 ppm, 1 H, dd, J=8.57, 2.42 Hz; 7.17 ppm, 2 H, m; 7.09 ppm, 4 H, m; 6.91 ppm, 1 H, d, J=8.79 Hz; 6.58 ppm, 2 H, d, J=7.03 Hz; 5.89 ppm, 1 H, m; 4.57 ppm, 1 H, m; 4.37 ppm, 2 H, m; 3.63 ppm, 1 H, m; 3.04 ppm, 1 H, d, J=7.03 Hz; 2.78 ppm, 1 H, d, J=8.79 Hz.

EXAMPLE 1105

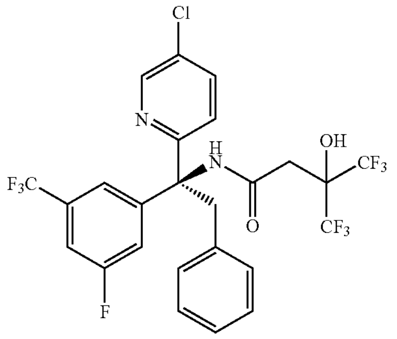

(S)-N-(1-(5-chloropyridin-2-yl)-1-(3-fluoro-5-(trifluoromethyl)phenyl)-2-phenylethyl)-4,4,4-trifluoro-3-hydroxy-3-(trifluoromethyl)butanamide Procedure 92

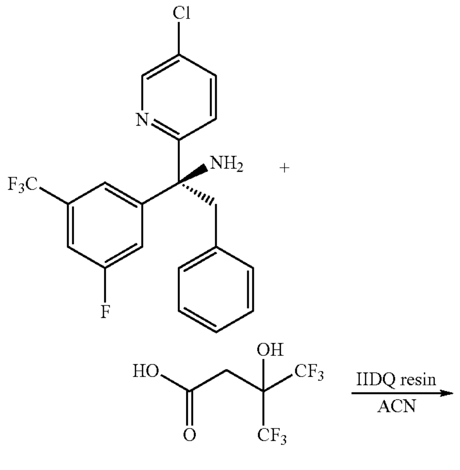

-continued

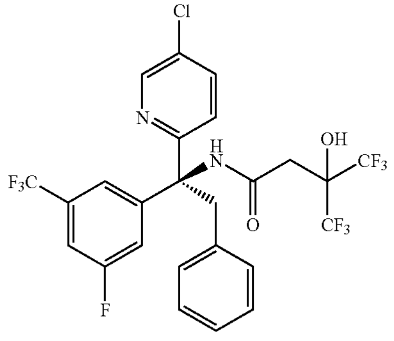

A round bottom flask was charged with IIDQ polystyrene resin (53 mg, 1.9 mmol/g, 0.10 mmol) and acetonitrile (0.5 mL) and was sealed with a rubber septum. The suspension was vacuumed and reflushed with argon for three times. A solution of (S)-1-(5-chloropyridin-2-yl)-1-(3-fluoro-5-(trifluoromethyl)phenyl)-2-phenylethanamine (20 mg, 0.05 mmol), prepared as described in Procedures 5, 6 and 7, and 4,4,4-trifluoro-3-hydroxy-3-(trifluoromethyl)butanoic acid (14 mg, 0.06 mmol) in acetonitrile (0.5 mL) were added to the reaction and the slurry stirred at room temperature for 18 h. The resin was removed by filtration and the residue concentrated and purified by preparative HPLC Shimadzu-YMC Sunfire 5μ column, 30×100 mm eluting with 60-100% MeOH (90% in $H_2O$, 0.1% TFA) gradient over 14 min with flow rate 40 mL/min and UV detection at 220 nm. (S)-N-(1-(5-chloropyridin-2-yl)-1-(3-fluoro-5-(trifluoromethyl)phenyl)-2-phenylethyl)-4,4,4-trifluoro-3-hydroxy-3-(trifluoromethyl)butanamide eluted at a retention time of 13.53 min and was isolated as a clear oil (4.15 mg, yield 14%) LCMS: RT=2.12 min [M+H] 602.89 (LCMS Method 2); HPLC: RT=4.38 min, Purity 100% (HPLC Method 1) NMR: 400 MHz $^1H$ ($CDCl_3$) 8.76 ppm, 1 H, s; 8.32 ppm, 1 H, d, J=2.64 Hz; 7.74 ppm, 1 H, dd, J=8.57, 2.42 Hz; 7.72 ppm, 1 H, m; 7.41 ppm, 1 H, s; 7.34 ppm, 1 H, d, J=9.67 Hz; 7.28 ppm, 1 H, d, J=9.67 Hz; 7.19 ppm, 1 H, d, J=7.03 Hz; 7.13 ppm, 3 H, t, J=8.13 Hz; 6.50 ppm, 2 H, d, J=7.47 Hz; 4.37 ppm, 1 H, d, J=12.74 Hz; 4.37 ppm, 1 H, d, J=12.74 Hz; 3.60 ppm, 1 H, d, J=13.18 Hz; 3.60 ppm, 1 H, d, J=13.18 Hz; 2.73 ppm, 2 H, s.

EXAMPLE 1106

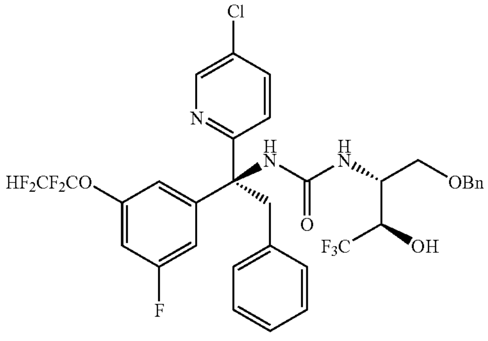

1-((2R,3R)-1-(benzyloxy)-4,4,4-trifluoro-3-hydroxybutan-2-yl)-3-((S)-1-(5-chloropyridin-2-yl)-1-(3-fluoro-5-(1,1,2,2-tetrafluoroethoxy)phenyl)-2-phenylethyl)urea Procedure 93

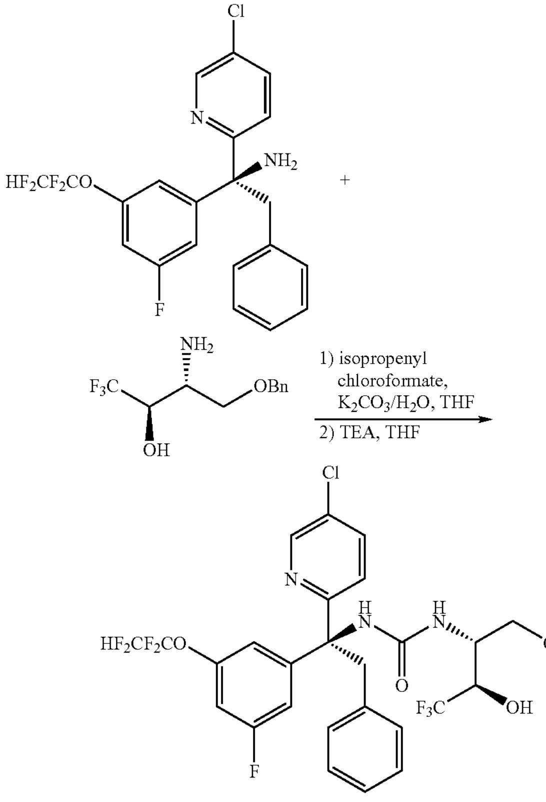

(2R,3R)-3-amino-4-(benzyloxy)-1,1,1-trifluorobutan-2-ol was prepared according to the procedure in J. Org. Chem., 68(19):7545 (2003).

To a solution of (S)-1-(5-chloropyridin-2-yl)-1-(3-fluoro-5-(1,1,2,2-tetrafluoroethoxy)phenyl)-2-phenylethanamine (61.2 mg, 0.14 mmol), prepared as described in Procedures 3, 5, 6 and 7, in THF (1 mL), $K_2CO_3$ in $H_2O$ (28 mg, 2 M in $H_2O$, 0.21 mmol) was added, followed by the addition of isopropenyl chlororoformate (16 μL, 0.15 mmol). The reaction mixture was stirred at room temperature for 2 hr, diluted with EtOAc (25 mL), and the organic portion washed with saturated NaCl (25 mL), dried over $MgSO_4$, filtered and concentrated in vacuo. The residue was combined with (2R,3R)-3-amino-4-(benzyloxy)-1,1,1-trifluorobutan-2-ol (22 mg, 0.09 mmol), TEA (38 uL, 0.27 mmol) in THF (1.0 mL) and the reaction mixture was heated at 50° C. for 18 h. The solvent was removed and the residue purified by ISCO chromatography (12 g column) using hexanes/EtOAc (0-30% over 30 min) to give 1-((2R,3R)-1-(benzyloxy)-4,4,4-trifluoro-3-hydroxybutan-2-yl)-3-((S)-1-(5-chloropyridin-2-yl)-1-(3-fluoro-5-(1,1,2,2-tetrafluoroethoxy)phenyl)-2-phenylethyl) urea as a clear oil at a retention time of 23-25 min (36.8 mg, 57% yield) LCMS: RT=2.13 min [M+H] 718.32 (LCMS Method 2); HPLC: RT=4.33 min, Purity 92% (HPLC Method 1) NMR: 400 MHz $^1H$ ($CDCl_3$) 8.25 ppm, 1 H, d, J=2.20 Hz; 7.66 ppm, 1 H, dd, J=8.57, 2.42 Hz; 7.35 ppm, 6 H, m; 7.13 ppm, 5 H, m; 7.06 ppm, 2 H, t, J=7.47 Hz; 6.88 ppm, 1 H, d, J=8.79 Hz; 6.58 ppm, 2 H, t, J=7.03 Hz; 5.87 ppm, 1 H, tt, J=52.95, 2.64 Hz; 5.23 ppm, 1 H, d, J=8.35 Hz; 4.52 ppm, 3 H, m; 4.36 ppm, 1 H, d, J=12.74 Hz; 4.24 ppm, 1 H, dd, J=8.13, 3.30 Hz; 4.04 ppm, 1 H, m; 3.93 ppm, 1 H, dd, J=9.89, 3.74 Hz; 3.75 ppm, 1 H, dd, J=10.11, 2.20 Hz; 3.53 ppm, 1 H, d, J=12.74 Hz.

EXAMPLE 1107

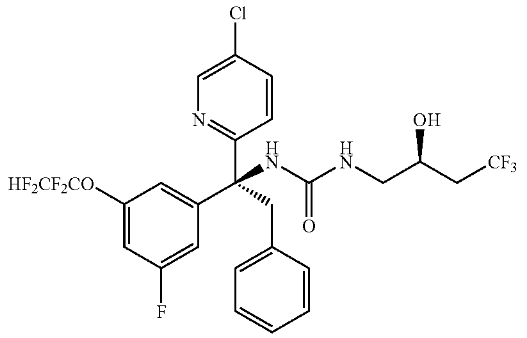

1-((S)-1-(5-chloropyridin-2-yl)-1-(3-fluoro-5-(1,1,2,2-tetrafluoroethoxy)phenyl)-2-phenylethyl)-3-((S)-4,4,4-trifluoro-2-hydroxybutyl)urea Procedure 94

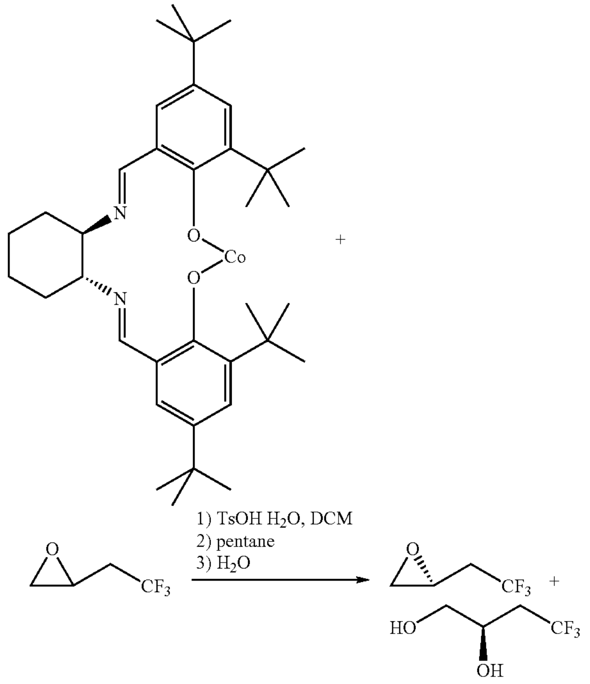

To a solution of (R,R)-(−)-N'N'-bis(3,5-di-tert-butylsalicylidene)-1,2-cyclo-hexanediamine (0.92 g, 1.53 mmol) in DCM (35 mL), was added $TsOH.H_2O$ (308 mg, 1.62 mmol) and the reaction mixture was stirred at room temperature while open to the air for 1 h. The solvent was removed under reduced pressure and pentane was added to suspend the solid. The slurry was filtered and the solid rinsed with pentane, then transferred to the reaction flask using DCM. DCM was then removed by vacuum and 2-(2,2,2-trifluoroethyl)oxirane (37 g, 294 mmol) was added to the residual solid. The reaction mixture was cooled to 0° C. and $H_2O$ (3.7 mL, 206 mmol) was added dropwise. The reaction mixture was stirred at room temperature for 72 h. (S)-2-(2,2,2-trifluoroethyl)oxirane was isolated as a clear oil (10.469 g, 28%) by vacuum distillation from reaction mixture into a cooled (−78° C.) receiving flask. NMR: 400 MHz $^1H$ ($CDCl_3$) 3.16 ppm, 1 H, m; 2.87 ppm, 1 H, t, J=4.39 Hz; 2.59 ppm, 1 H, dd, J=4.61, 2.42 Hz; 2.39 ppm, 1 H, m; 2.29 ppm, 1 H, m, J=10.44, 10.44, 5.05, 4.83 Hz.

The recovered epoxide was determined to be >99% ee according to the procedure used by Jacobsen (J. Am. Chem. Soc., 124 (7):1307-1315 (2004)). (Chiral HPLC analysis of the 2-napthylsulfide derivative (obtained by ring opening with 2-napthalenethiol in MeOH using 1 equiv TEA at 0° C. and direct analysis of the product obtained, Chiralcel® AD, 95:5 hexanes:i-PrOH, 1 mL/min, 254 nm, tR(minor)=16.52 min, tR(major)=19.28 min).

Procedure 95

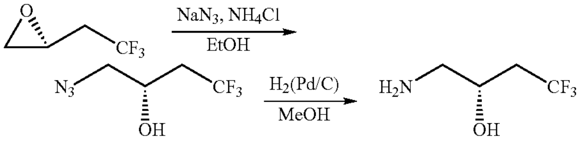

$NaN_3$ (2.06 g, 32 mmol) and $NH_4Cl$ (1.70 g, 32 mmol) were added to a solution of (S)-2-(2,2,2-trifluoroethyl)oxirane (2 g, 16 mmol) in a mixture of EtOH (16 mL) and $H_2O$ (4 mL). The reaction mixture was stirred at room temperature for 18 h, diluted with $H_2O$ (50 mL), and the aqueous portion extracted by $Et_2O$ (2×75 mL). The combined organic layers were dried over $MgSO_4$, filtered and concentrated in vacuo to give (S)-1-azido-4,4,4-trifluorobutan-2-ol as an oil (2.26 g, 83% crude). NMR: 400 MHz $^1H$ ($CDCl_3$) 4.17 ppm, 1 H, ddd, J=6.81, 3.74, 3.52 Hz; 3.48 ppm, 1 H, m; 3.37 ppm, 1 H, m; 2.35 ppm, 2 H, m.

The slurry of (S)-1-azido-4,4,4-trifluorobutan-2-ol (2.26 g, 13 mmol) and Pd/C (200 mg) in MeOH (20 mL) was subjected to balloon hydrogenation for 18 hr. The reaction mixture was filtered through a celite pad and the filtrate was concentrated in vacuo to give (S)-1-amino-4,4,4-trifluorobutan-2-ol as a crude product (1.02 g, 45%). NMR: 400 MHz $^1H$ ($CDCl_3$) 3.88 ppm, 1 H, m, J=7.85, 7.85, 3.84, 3.74 Hz; 2.93 ppm, 1 H, dd, J=12.74, 3.52 Hz; 2.61 ppm, 1H, dd, J=12.52, 8.13 Hz; 2.34 ppm, 1 H, m; 2.21 ppm, 1 H, m; 1.91 ppm, 3 H, s.

1-((S)-1-(5-chloropyridin-2-yl)-1-(3-fluoro-5-(1,1,2,2-tetrafluoroethoxy)phenyl)-2-phenylethyl)-3-((S)-4,4,4-trifluoro-2-hydroxybutyl)urea was prepared by method described in Procedure 93 in 47% yield. LCMS: RT=1.997 min [M+H] 612.24 (LCMS Method 2); HPLC: RT=4.09 min, Purity 92% (HPLC Method 1) NMR: 400 MHz $^1H$ ($CDCl_3$) 8.25 ppm, 1 H, d, J=2.20 Hz; 7.68 ppm, 1 H, dd, J=8.57, 2.42 Hz; 7.33 ppm, 1 H, m; 7.12 ppm, 6 H, m; 6.89 ppm, 1 H, d, J=8.79 Hz; 6.58 ppm, 2 H, d, J=7.03 Hz; 5.88 ppm, 1 H, tt, J=52.95, 2.64 Hz; 4.95 ppm, 1 H, t, J=5.71 Hz; 4.37 ppm, 1 H, d, J=12.74 Hz; 4.02 ppm, 1 H, d; 3.83 ppm, 1 H, s; 3.53 ppm, 1 H, d, J=12.74 Hz; 3.32 ppm, 2 H, m; 2.28 ppm, 2 H, m.

EXAMPLE 1108

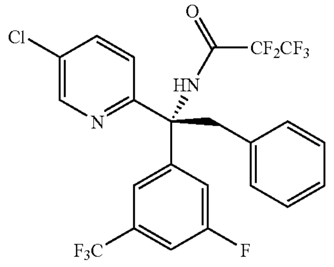

(R)-N-(1-(5-chloropyridin-2-yl)-1-(3-fluoro-5-(trifluoromethyl)phenyl)-2-phenylethyl)-2,2,3,3,3-pentafluoropropanamide Procedure 96

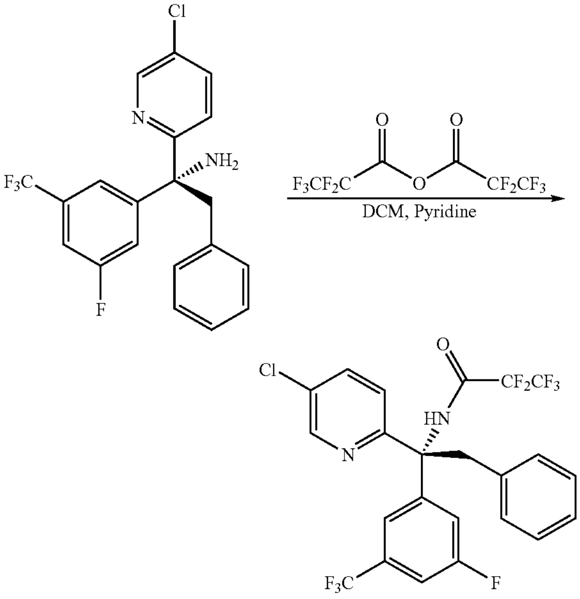

To a solution of (R)-1-(5-chloropyridin-2-yl)-1-(3-fluoro-5-(trifluoromethyl)phenyl)-2-phenylethanamine (15 mg, 0.038 mmol), prepared by method described in Procedures 5, 6 and 7, in anhydrous DCM (0.5 mL), was added pyridine (1 drop) and 2,2,3,3,3-pentafluoropropanoic anhydride (14 mg, 0.040 mmol) at room temperature. The reaction mixture was stirred for 5 mins and the solvents removed under a stream of nitrogen. The resulting residue was diluted with MeOH (0.5 mL) and purified by preparative HPLC (YMC Sunfire 30×100 mm column, eluting with 10-90% MeOH/$H_2O$ over 10 minutes containing 0.1% TFA; 40 mL/min, monitoring at 220 nm); (R)-N-(1-(5-chloropyridin-2-yl)-1-(3-fluoro-5-(trifluoromethyl)phenyl)-2-phenylethyl)-2,2,3,3,3-pentafluoropropanamide (13.4 mg, 65% yield) was isolated as a colorless oil at a retention time of 12.44 min. LCMS: RT=2.12 min [M+H] 541.21 (LCMS Method 2); HPLC: RT=4.28 min, Purity 98% (HPLC Method 1) NMR: 400 MHz $^1$H ($CDCl_3$) 9.60 ppm, 1 H, s; 8.36 ppm, 1 H, s; 7.75 ppm, 1H, d, J=8.0 Hz; 7.44 ppm, 1H, s; 7.34 ppm, 1H, d, J=8.0Hz; 7.30 ppm, 1H, d, J=8.0 Hz; 7.09 ppm, 4 H, m; 6.53 ppm, 2H, d, J=4.0 Hz; 3.38 ppm, 1H, d, J=12.0 Hz; 3.65 ppm, 1H, d, J=12.0 Hz.

EXAMPLE 1109

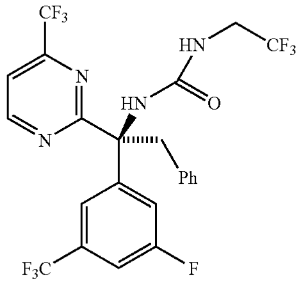

S)-1-(1-(3-fluoro-5-(trifluoromethyl)phenyl)-2-phenyl-1-(4-(trifluoromethyl)pyrimidin-2-yl)ethyl)-3-(2,2,2-trifluoroethyl)urea Procedure 97

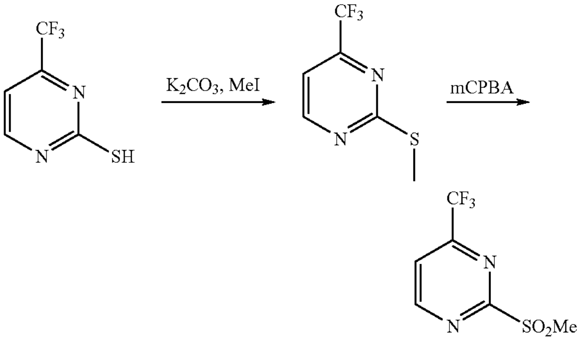

To a solution of 4-(trifluoromethyl)pyrimidine-2-thiol (1.08 g, 6.0 mmol) in THF (40 mL) was added 1N NaOH (10 mL), followed by the addition of MeI (0.8 mL). The reaction mixture was stirred at room temperature overnight, followed by addition of $CH_2Cl_2$. The organic layer was washed with saturated $NaHCO_3$, $H_2O$, and saturated NaCl, dried over $MgSO_4$, filtered and concentrated under reduced pressure. The residue was purified by column chromatography (silica gel, hexanes: EtOAc=1:10) to give 2-(methylthio)-4-(trifluoromethyl)pyrimidine as colorless oil (0.6 g). This colorless oil was dissolved in $CH_2Cl_2$, and to the solution mCPBA (1.8 g) was added. The resulting mixture was stirred at room temperature for 3 h. To the reaction mixture saturated $Na_2SO_4$ (10 mL) was added, followed by the addition of saturated $Na_2CO_3$. The aqueous portion was extracted with $CH_2Cl_2$ twice and the organic portions were dried over $Na_2SO_4$, filtered, and concentrated to give 2-(methylsulfonyl)-4-(trifluoromethyl)pyrimidine as white solids (0.64 g, 46% yield for two steps,). LC-MS RT=1.19 min, [M+Na] 249.06 (LCMS Method 1).

Procedure 98

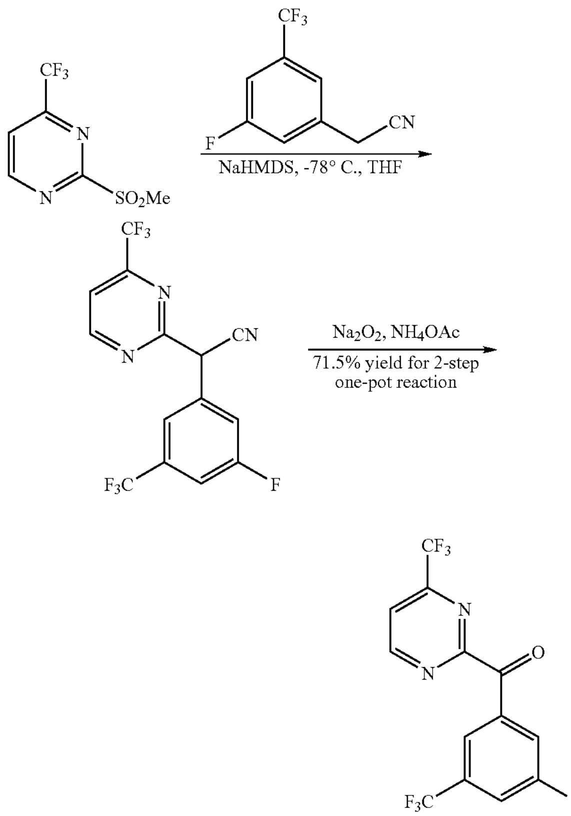

A mixture of 2-(methylsulfonyl)-4-(trifluoromethyl)pyrimidine (1.55 g, 6.63 mmol) and 2-(3-fluoro-5-(trifluoromethyl)phenyl)acetonitrile (1.53 g, 7.23 mmol) in anhydrous THF (45 mL) was stirred at room temperature under Argon. To the reaction mixture NaHMDS (8.8 mL, 1.0 M in THF, 8.8 mmol) was added during a 2-min period. The reaction mixture was stirred at room temperature for 1 h. 12 mL of the above reaction mixture was transferred to another round-bottomed flask. Saturated $NH_4Cl$ (10 mL) and THF (10 mL) were added, followed by the addition of $Na_2O_2$ (1.15 g, 14.7 mmol) at −30° C. The reaction mixture was stirred at room temperature for 5 h, followed by addition of MeOH. The solids were removed by filtration and the filtrate was concentrated. The residue was dissolved in EtOAc and the solution washed with $H_2O$, saturated NaCl, dried over $Na_2SO_4$, filtered, and concentrated to dryness. The residue was purified by flash chromatography (silica gel, hexanes/EtOAc) to give pure (3-fluoro-5-(trifluoromethyl)phenyl)(4-(trifluoromethyl)pyrimidin-2-yl)methanone (0.45 g, 71.5% for two steps). NMR: 400 MHz $^1H$ ($CDCl_3$) 9.18 ppm, d, J=5.1 Hz, 1 H;, 8.08 ppm, s, 1 H;, 7.89 ppm, d, J=8.8 Hz, 1 H;, 7.81 ppm, d, J=5.1 Hz, 1 H;, 7.46 ppm, dt, J=7.8, 1.5 Hz, 1 H.

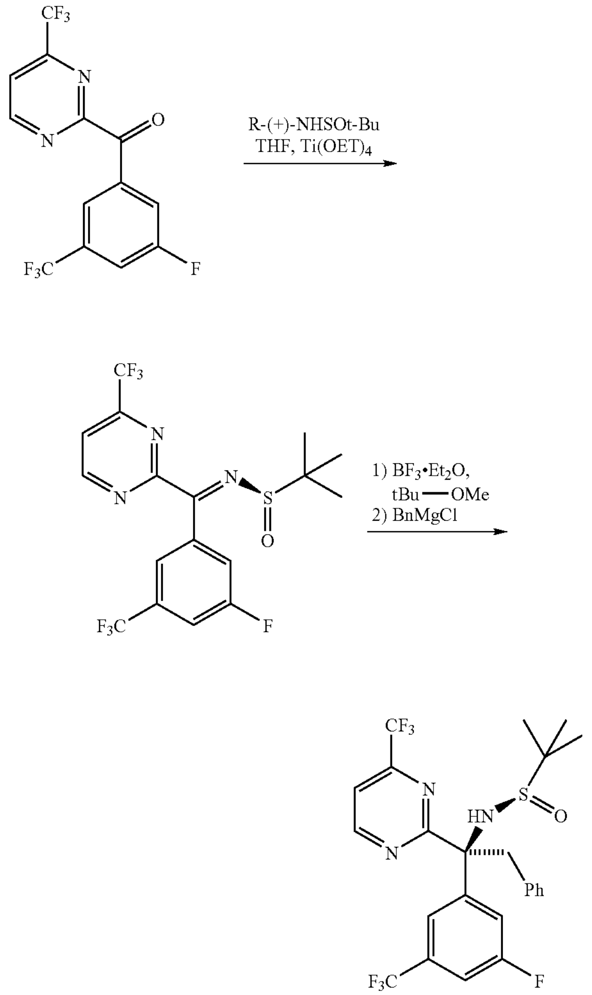

(R)-N-((S)-1-(3-fluoro-5-(trifluoromethyl)phenyl)-2-phenyl-1-(4-(trifluoromethyl)pyrimidin-2-yl)ethyl)-2-methylpropane-2-sulfinamide was prepared by methods described in Procedure 6 and 7 from (R)-N-((3-fluoro-5-(trifluoromethyl)phenyl)(4-(trifluoromethyl)pyrimidin-2-yl)methylene)-2-methylpropane-2-sulfinamide (0.275 g). The residue was purified by flash chromatography (silica gel, hexanes/EtOAc) to give the desired product (0.162 g, 48.6% yield:). LC-MS RT=3.89 min, [M+H] 534.19 (LCMS Method 1).

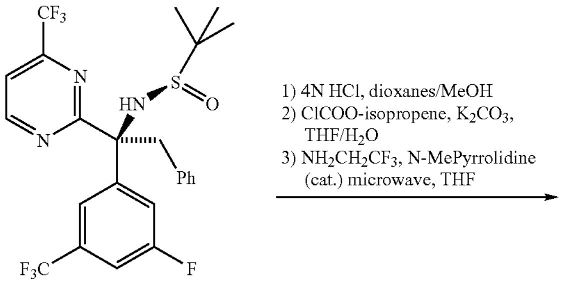

-continued

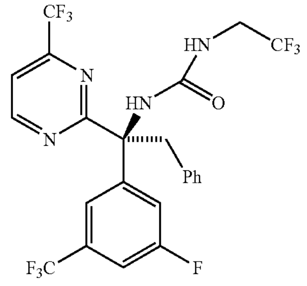

(S)-1-(1-(3-fluoro-5-(trifluoromethyl)phenyl)-2-phenyl-1-(4-(trifluoromethyl)pyrimidin-2-yl)ethyl)-3-(2,2,2-trifluoroethyl)urea was prepared by methods described in Procedures 7 (i), 59 and 60. LC-MS RT=4.02 min, [M+H] 555.19 (LCMS Method 1),; NMR: 400 MHz $^{1}H$ ($CDCl_3$) 8.91 ppm, 1H, J=4.9 Hz; 7.59 ppm, 1H, s; 7.51 ppm, 1H, d, J=4.9 Hz; 7.48 ppm, 1H, d, J=9.9 Hz; 7.19 ppm, 1H, d, J=8.2 Hz; 7.08 ppm, 3H, m; 6.93 ppm, 1H, s; 6.60 ppm, 2H, d, J=7.1 Hz; 4.94 ppm, 1H, t, J=6.3 Hz; 4.34 ppm, 1H, d, J=12.6 Hz; 4.17 ppm, 1H, d, J=12.6 Hz; 4.07 ppm, 1H, m; 3.70 ppm, 1H, m.

EXAMPLE 1110

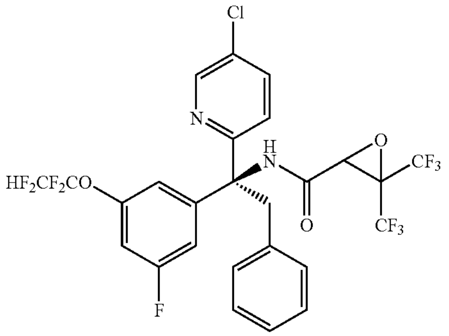

N-((S)-1-(5-chloropyridin-2-yl)-1-(3-fluoro-5-(1,1,2,2-tetrafluoroethoxy)phenyl)-2-phenylethyl)-3,3-bis(trifluoromethyl)oxirane-2-carboxamide (diastereomer 1)

EXAMPLE 1111

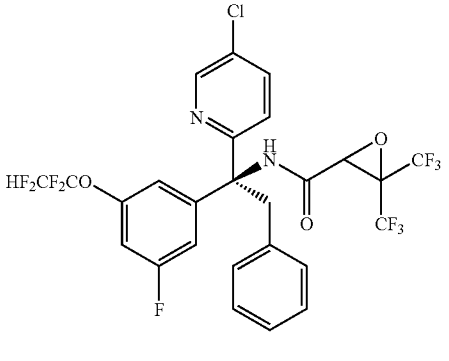

N-((S)-1-(5-chloropyridin-2-yl)-1-(3-fluoro-5-(1,1,2,2-tetrafluoroethoxy)phenyl)-2-phenylethyl)-3,3-bis(trifluoromethyl)oxirane-2-carboxamide (diastereomer 2)

Procedure 99

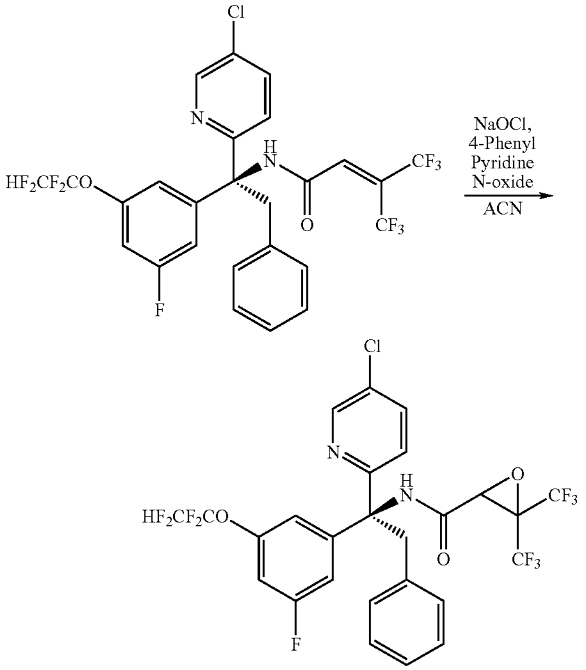

(S)-N-(1-(5-chloropyridin-2-yl)-1-(3-fluoro-5-(1,1,2,2-tetrafluoroethoxy)phenyl)-2-phenylethyl)-4,4,4-trifluoro-3-(trifluoromethyl)but-2-enamide was prepared by method described in Procedure 92 in 62% yield. LCMS: RT=4.133 min [M+H] 633.2 (LCMS Method 3); HPLC: RT=4.161 min, Purity 100% (HPLC Method 1) NMR: 400 MHz $^{1}H$ ($CDCl_3$) 8.64 ppm, 1 H, s; 8.31 ppm, 1 H, d, J=1.76 Hz; 7.74 ppm, 1 H, dd, J=8.57, 2.42 Hz; 7.15 ppm, 6 H, m; 7.05 ppm, 1 H, s; 6.94 ppm, 1 H, d, J=8.79 Hz; 6.88 ppm, 1 H, s; 6.53 ppm, 2 H, d, J=7.47 Hz; 5.89 ppm, 1 H, m; 4.47 ppm, 1 H, d, J=12.74 Hz; 3.56 ppm, 1 H, d, J=12.74 Hz.

At 0° C., to a solution of (S)-N-(1-(5-chloropyridin-2-yl)-1-(3-fluoro-5-(1,1,2,2-tetrafluoroethoxy)phenyl)-2-phenylethyl)-4,4,4-trifluoro-3-(trifluoromethyl)but-2-enamide (260 mg, 0.41 mmol) and 4-phenyl pyridine N-oxide (56 mg, 0.33 mmol) in acetonitrile (16 mL) was added NaOCl solution (363 uL, chlorine wt % 10-3%, 1.23 mmol). The reaction mixture was stirred at 0° C. for 10 min, then at room temperature for 1 h. After removal of the solvents in vacuo the residue was diluted with EtOAc (30 mL) and the solution washed with saturated $Na_2SO_3$ (30 mL), dried over $MgSO_4$, filtered and concentrated. The residue was purified by ISCO chromatography (40 g column, flow rate 20 mL/min) using hexanes/EtOAc (0-10% over 30 min) to give N-((S)-1-(5-chloropyridin-2-yl)-1-(3-fluoro-5-(1,1,2,2-tetrafluoroethoxy)phenyl)-2-phenylethyl)-3,3-bis(trifluoromethyl)oxirane-2-carboxamide as a diastereomer mixture at a retention time of 27-35 min (243.9 mg, 92% yield). The diastereomeric mixture was separated by Chiral preparative HPLC chiralpak AD 20μ column, 5×50 cm, eluting with 10% IPA/Heptane with flow rate 50 mL/min.

N-((S)-1-(5-chloropyridin-2-yl)-1-(3-fluoro-5-(1,1,2,2-tetrafluoroethoxy)phenyl)-2-phenylethyl)-3,3-bis(trifluoromethyl)oxirane-2-carboxamide diastereomer 1 (example 1110) eluted at a retention time of 43-50 min and was isolated as a white solid (64.22 mg, yield 24%) LCMS: RT=4.105 min [M+H] 649.2 (LCMS Method 3); HPLC: RT=4.110 min, Purity 100% (HPLC Method 1) NMR: 400 MHz $^1$H ($CDCl_3$) 8.92 ppm, 1 H, s; 8.41 ppm, 1 H, s; 7.72 ppm, 1 H, d, J=8.79 Hz; 7.10 ppm, 6 H, m; 6.93 ppm, 1 H, d, J=8.35 Hz; 6.55 ppm, 2 H, d, J=7.91 Hz; 5.89 ppm, 1 H, s; 4.37 ppm, 1 H, d, J=13.18 Hz; 3.86 ppm, 1 H, s; 3.70 ppm, 1 H, d, J=13.18 H.

N-((S)-1-(5-chloropyridin-2-yl)-1-(3-fluoro-5-(1,1,2,2-tetrafluoroethoxy)phenyl)-2-phenylethyl)-3,3-bis(trifluoromethyl)oxirane-2-carboxamide diastereomer 2 (example 1111) eluted at a retention time of 60-70 min and was isolated as a white solid (117.87 mg, yield 45%) LCMS: RT=4.225 min [M+H] 649.2 (LCMS Method 3); HPLC: 4.216 min, Purity 100% (HPLC Method 1) NMR: 400 MHz $^1$H ($CDCl_3$) 9.02 ppm, 1 H, s; 7.72 ppm, 1 H, dd, J=8.57, 1.98 Hz; 7.13 ppm, 7 H, m; 6.92 ppm, 2 H, m; 6.55 ppm, 2 H, d, J=7.47 Hz; 5.87 ppm, 1 H, m; 4.48 ppm, 1 H, d, J=13.18 Hz; 4.48 ppm, 1 H, d, J=13.18 Hz; 3.94 ppm, 1 H, s; 3.53 ppm, 1 H, d, J=12.74 Hz; 3.53 ppm, 1 H, d, J=12.74 Hz.

EXAMPLE 1112

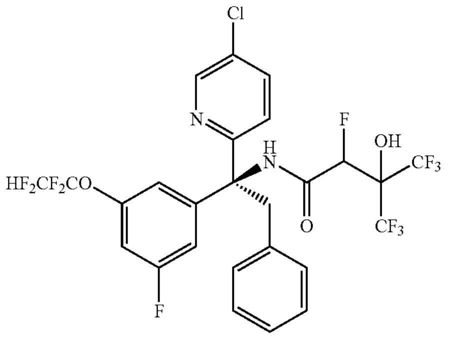

N-((S)-1-(5-chloropyridin-2-yl)-1-(3-fluoro-5-(1,1,2,2-tetrafluoroethoxy)phenyl)-2-phenylethyl)-2,4,4,4-tetrafluoro-3-hydroxy-3-(trifluoromethyl)butanamide Procedure 100

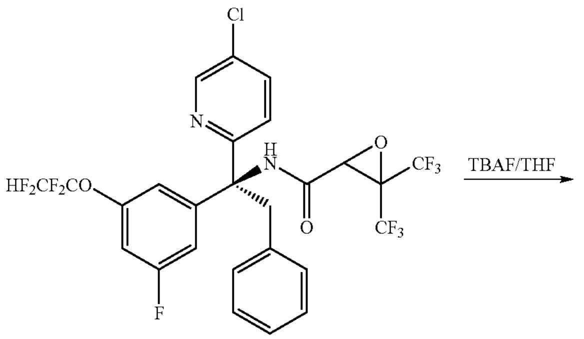

-continued

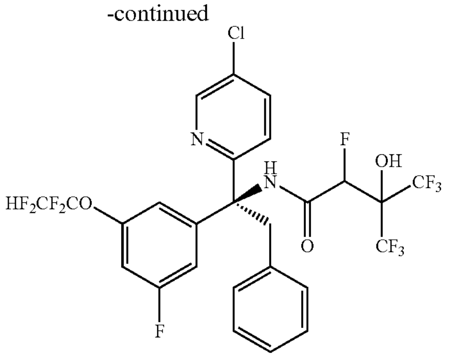

To a solution of N-((S)-1-(5-chloropyridin-2-yl)-1-(3-fluoro-5-(1,1,2,2-tetrafluoroethoxy)phenyl)-2-phenylethyl)-3,3-bis(trifluoromethyl)oxirane-2-carboxamide diastereomer 2 (example 1111) (20 mg, 0.031 mmol) in THF (0.5 mL) was added TBAF (80 uL, 1.0 M solution in THF, 0.08 mmol). The reaction mixture was heated at 60° C. in microwave reactor for 20 min and at 80° C. for 20 min. After removal of the solvents, the residue was purified by preparative HPLC Shimadzu-Phenomenex Luna AXIA 5μ column, 21.2×100 mm eluting with 30-100% ACN(90% in $H_2O$, 0.1% TFA) gradient over 14 min with UV detection at 220 nm. N-((S)-1-(5-chloropyridin-2-yl)-1-(3-fluoro-5-(1,1,2,2-tetrafluoroethoxy)phenyl)-2-phenylethyl)-2,4,4,4-tetrafluoro-3-hydroxy-3-(trifluoromethyl)butanamide eluted at a retention time of 13.377 min and was isolated as a clear oil (8.20 mg, yield 40%) LCMS: RT=3.945 min [M+H] 669.3 (LCMS Method 3); HPLC: RT=3.991 min, Purity 100% (HPLC Method 1) NMR: 400 MHz $^1$H ($CDCl_3$) 9.72 ppm, 1 H, s; 8.35 ppm, 1 H, d, J=2.20 Hz; 8.35 ppm, 1 H, d, J=2.20 Hz; 7.71 ppm, 1 H, dd, J=8.57, 2.42 Hz; 7.71 ppm, 1 H, dd, J=8.57, 2.42 Hz; 7.08 ppm, 8 H, m; 6.59 ppm, 2 H, d, J=7.47 Hz; 5.91 ppm, 1 H, tt, J=52.95, 2.64 Hz; 5.07 ppm, 1 H, d, J=45.70 Hz; 4.24 ppm, 1 H, d, J=13.62 Hz; 3.69 ppm, 1 H, d, J=13.18 Hz.

EXAMPLE 1113

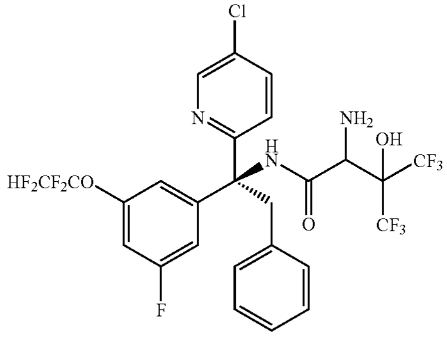

2-amino-N-((S)-1-(5-chloropyridin-2-yl)-1-(3-fluoro-5-(1,1,2,2-tetrafluoroethoxy)phenyl)-2-phenylethyl)-4,4,4-trifluoro-3-hydroxy-3-(trifluoromethyl)butanamide Procedure 101

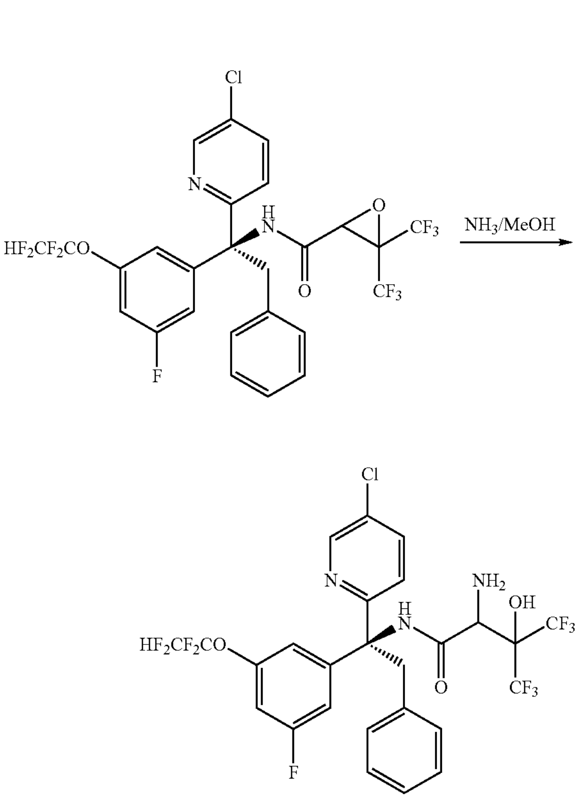

To N-((S)-1-(5-chloropyridin-2-yl)-1-(3-fluoro-5-(1,1,2,2-tetrafluoroethoxy)phenyl)-2-phenylethyl)-3,3-bis(trifluoromethyl)oxirane-2-carboxamide diastereomer 1 (example 1110) (15 mg, 0.023 mmol) was added $NH_3$ in MeOH (0.5 mL, 7 N) and the reaction mixture was stirred at room temperature for 3 h. The solution was concentrated and purified by ISCO chromatography (12 g column) using hexanes/EtOAc (0-15% over 30 min). 2-Amino-N-((S)-1-(5-chloropyridin-2-yl)-1-(3-fluoro-5-(1,1,2,2-tetrafluoroethoxy)phenyl)-2-phenylethyl)-4,4,4-trifluoro-3-hydroxy-3-(trifluoromethyl)butanamide eluted at 25-28 min. Further purification was accomplished by preparative HPLC Shimadzu-YMC ODS-A S-5 μm, 20×100 mm eluting with 40-100% MeOH (90% in $H_2O$, 0.1% TFA) gradient over 14 min with UV detection at 220 nm. 2-amino-N-((S)-1-(5-chloropyridin-2-yl)-1-(3-fluoro-5-(1,1,2,2-tetrafluoroethoxy)phenyl)-2-phenylethyl)-4,4,4-trifluoro-3-hydroxy-3-(trifluoromethyl)butanamide eluted at 12.85 min and was isolated as a clear oil (5.69 mg, yield 38%) LCMS: RT=4.033 min [M+H] 666.3 (LCMS Method 3); HPLC: RT=4.001 min, Purity 100% (HPLC Method 1) NMR: 400 MHz $^1H$ ($CDCl_3$) 10.48 ppm, 1 H, s; 8.35 ppm, 1 H, d, J=1.76 Hz; 8.22 ppm, 1 H, s; 7.71 ppm 1 H, dd, J=8.35, 2.20 Hz; 7.13 ppm, 5 H, m; 7.00 ppm, 1 H, s; 6.93 ppm, 1 H, d, J=8.35 Hz; 6.51 ppm, 2 H, d, J=7.03 Hz; 5.89 ppm, 1 H, t, J=52.95 Hz; 4.38 ppm, 1 H, d, J=13.18 Hz; 3.77 ppm, 1 H, t, J=9.23 Hz; 3.56 ppm, 1 H, d, J=13.18 Hz; 1.77 ppm, 2 H, d, J=9.67 Hz.

EXAMPLE 1114

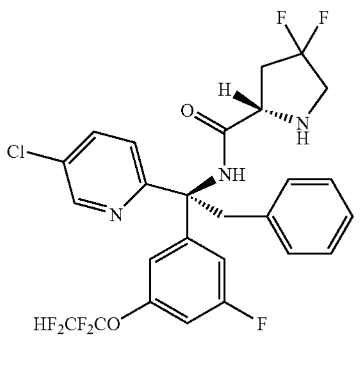

(R)-N-((S)-1-(5-chloropyridin-2-yl)-1-(3-fluoro-5-(1,1,2,2-tetrafluoroethoxy)phenyl)-2-phenylethyl)-4,4-difluoropyrrolidine-2-carboxamide Procedure 102

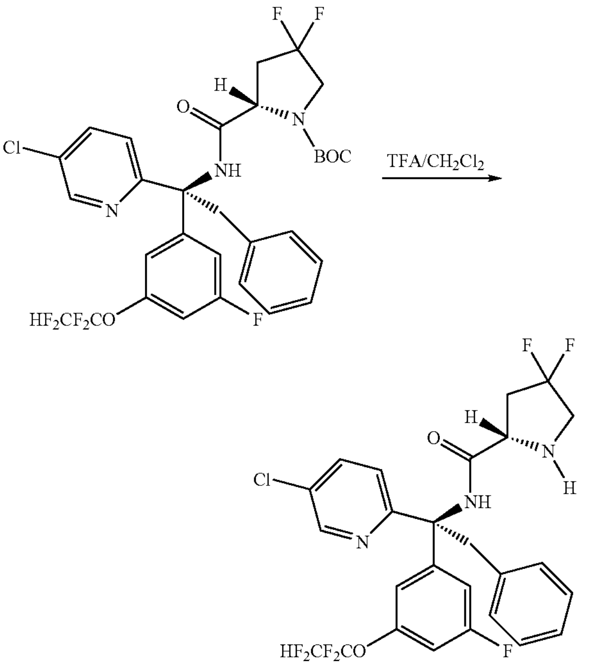

(R)-tert-butyl 2-((S)-1-(5-chloropyridin-2-yl)-1-(3-fluoro-5-(1,1,2,2-tetrafluoroethoxy)phenyl)-2-phenylethylcarbamoyl)-4,4-difluoropyrrolidine-1-carboxylate was prepared by method described in Procedure 85 in 69% yield. LC/MS RT=4.213 min; [M+H]=676.4 (LCMS Method 3) NMR: 500 MHz $^1H$ ($CDCl_3$) 9.03 ppm, 1 H, s; 8.30 ppm, 1 H, s; 7.68 ppm, 1 H, d, J=7.15 Hz; 7.10 ppm, 6 H, m; 6.86 ppm, 1 H, d, J=7.70 Hz; 6.52 ppm, 2 H, d, J=7.15 Hz; 5.83 ppm, 1 H, m; 4.49 ppm, 1 H, dd, J=8.80, 5.50 Hz; 4.25 ppm, 1 H, m; 3.80 ppm, 1 H, d, J=9.90 Hz; 3.66 ppm, 2 H, m; 2.56 ppm, 2 H, m; 1.37 ppm, 9 H, s.

(R)-tert-butyl 2-((S)-1-(5-chloropyridin-2-yl)-1-(3-fluoro-5-(1,1,2,2-tetrafluoroethoxy)phenyl)-2-phenylethylcarbamoyl)-4,4-difluoropyrrolidine-1-carboxylate (33.9 mg, 0.05 mmol) was dissolved in a solution of TFA/$CH_2Cl_2$ (2 mL/2 mL) and the reaction mixture was stirred overnight. The solvent was removed and the residue dissolved in MeOH and purified by preparative HPLC (Phenoma Luna AXIA 100A, C18; mobile phase: MeCN/$H_2O$/TFA) to yield (R)-N-((S)-1-(5-chloropyridin-2-yl)-1-(3-fluoro-5-(1,1,2,2-tetrafluoroethoxy)phenyl)-2-phenylethyl)-4,4-difluoropyrrolidine-2-carboxamide as a white solid (22.4 mg, 78% yield). LC/MS RT=3.876 min; [M+H]=576.2 (LCMS Method 3). NMR: 500 MHz $^1H$ ($CDCl_3$); 8.35 ppm, 1H, d, J=5 Hz;, 7.79 ppm, 1H, m; 7.38 ppm, 1H, d, J=10 Hz; 7.17 ppm, 1H, m; 7.04 ppm, 4H, m; 6.89 ppm, 1H, m; 6.51 ppm, 1H, d, J=5 Hz; 6.21 ppm, 1H; m; 4.56 ppm, 1H' t, J=9 Hz; 4.19 ppm, 1H, d, J=13 Hz; 3.84 ppm, 1H, d, J=13 Hz; 3.60 ppm, 2H' t, J=12 Hz; 2.68 ppm, 1H, m; 2.22 ppm, 1H, m.

EXAMPLE 1115

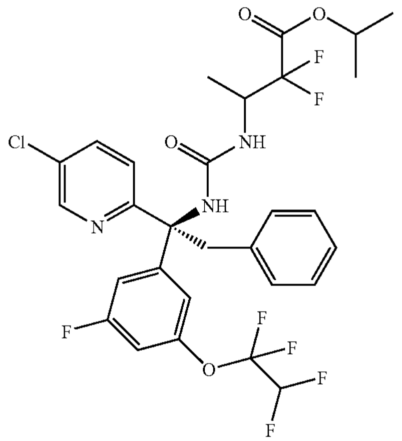

Isopropyl 3-(3-((S)-1-(5-chloropyridin-2-yl)-1-(3-fluoro-5-(1,1,2,2-tetrafluoroethoxy)phenyl)-2-phenylethyl)ureido)-2,2-difluorobutanoate Procedure 103

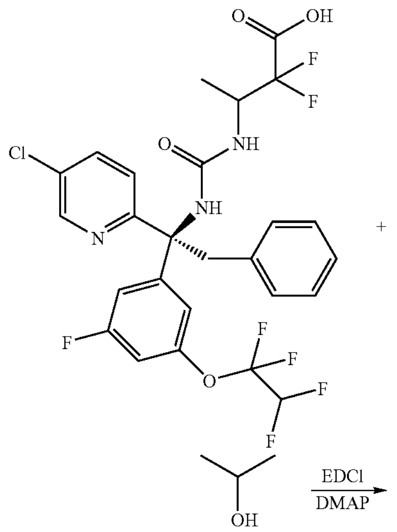

-continued

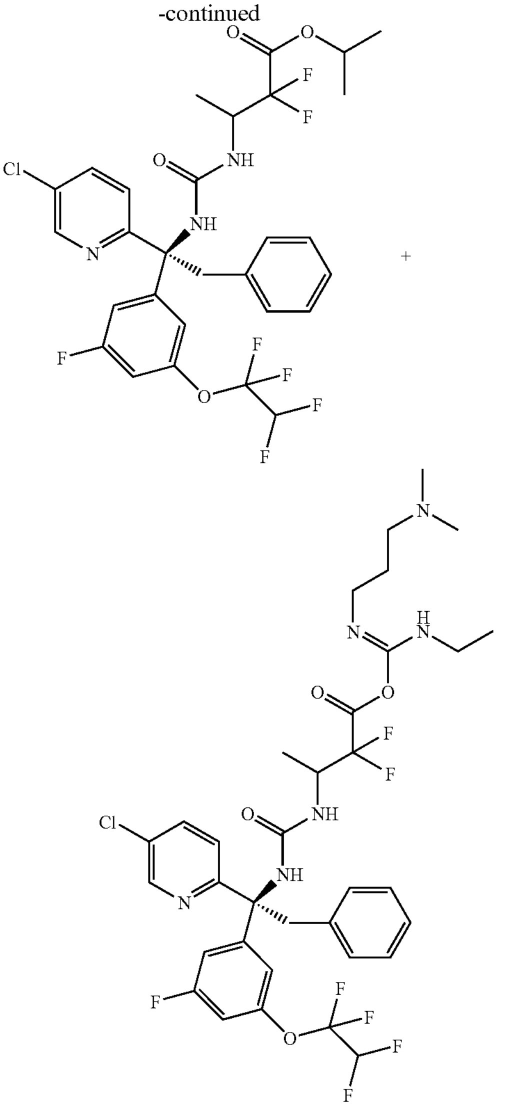

To a solution of 3-(3-((S)-1-(5-chloropyridin-2-yl)-1-(3-fluoro-5-(1,1,2,2-tetrafluoroethoxy)phenyl)-2-phenylethyl)ureido)-2,2-difluorobutanoic acid (16 mg, 0.026 mmol), prepared by methods described in Example 1093 and Procedure 53, in $CH_2Cl_2$ (1 ml) was added DMAP (2 mg, 0.016 mmol), EDCI (14 mg, 0.073 mmol) and isopropanol (30 uL, 0.039 mmol). The reaction mixture was stirred at ambient temperature for 16 h. The solvent was removed and the residue purified by preparative HPLC Shimadzu-Phenomenex Luna AXIA 5 μm, 21.2×100 mm eluting with 30-100% ACN (90% in $H_2O$, 0.1% TFA) gradient over 10 min with UV detection at 220 nm. 3-(3-((S)-1-(5-chloropyridin-2-yl)-1-(3-fluoro-5-(1,1,2,2-tetrafluoroethoxy)phenyl)-2-phenylethyl)ureido)-2,2-difluorobutanoic-(3-(dimethylamino)propyl)-N-ethylcarbamimidic anhydride eluted at retention times of 4.3 min and 6.138 min as a white solid (8 mg, 40% yield). LCMS RT=2.89 min [M+H]=763.2 (LCMS Method 3).

Isopropyl 3-(3-((S)-1-(5-chloropyridin-2-yl)-1-(3-fluoro-5-(1,1,2,2-tetrafluoroethoxy)phenyl)-2-phenylethyl)ureido)-2,2-difluorobutanoate eluted at retention time of 10.81 min as a white solid (5 mg, 30% yield). LCMS RT=3.69 min [M+H]=650.1 (LCMS Method 3). NMR: 500 MHz $^1H$ ($CDCl_3$) 8.25 ppm, 1H, m; 7.68 ppm, 1H, m; 7.10 ppm, 8H, m; 6.88 ppm, 1H, m; 6.58 ppm, 2H, m; 5.87 ppm, 1H, t, J=50 Hz; 5.07 ppm, 1H, m; 4.65 ppm, 2H, m; 4.34 ppm, 1H, m; 3.50 ppm, 1H, m; 1.32 ppm, 9H, m.

EXAMPLE 1116

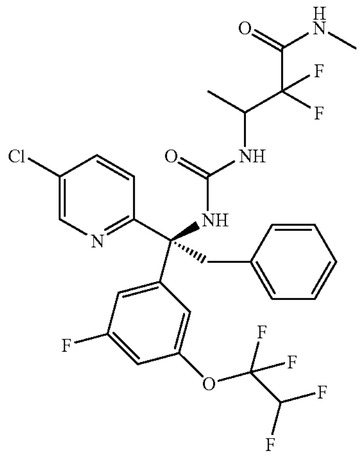

3-(3-((S)-1-(5-chloropyridin-2-yl)-1-(3-fluoro-5-(1,1,2,2-tetrafluoroethoxy)phenyl)-2-phenylethyl)ureido)-2,2-difluoro-N-methylbutanamide Procedure 104

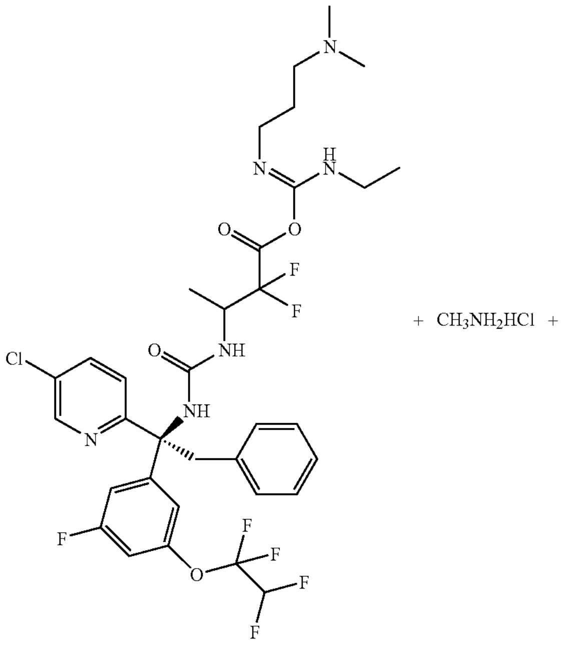

-continued

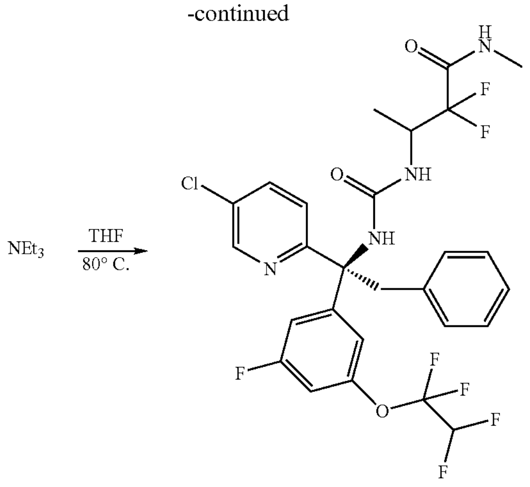

To a solution of 3-(3-((S)-1-(5-chloropyridin-2-yl)-1-(3-fluoro-5-(1,1,2,2-tetrafluoroethoxy)phenyl)-2-phenylethyl)ureido)-2,2-difluorobutanoic-(3-(dimethylamino)propyl)-N-ethylcarbamimidic anhydride (8 mg, 0.01 mmol) in THF (0.5 mL) was added $CH_3NH_2HCl$ (7 mg, 0.10 mmol) and $NEt_3$ (40 uL, 0.29 mmol). The reaction vessel was sealed and heated at 80° C. for 16 h, then allowed to cool to room temperature. The solvents were removed and the residue purified by preparative HPLC Phenomenex Luna AXIA 5u 21.2×100 mm eluting with 30-100% ACN (90% in $H_2O$, 0.1% TFA) gradient over 10 min with UV detection at 220 nm to yield 3-(3-((S)-1-(5-chloropyridin-2-yl)-1-(3-fluoro-5-(1,1,2,2-tetrafluoroethoxy)phenyl)-2-phenylethyl)ureido)-2,2-difluoro-N-methylbutanamide as a white solid (2 mg, 32% yield). LCMS RT=1.97 min [M+H]=621.6 (LCMS Method 2). NMR: 500 MHz $^1H$ ($CDCl_3$) 8.25 ppm, 1H, m; 7.65 ppm, 1H, m; 7.36 ppm, 1H, m; 7.10 ppm, 5H, m; 6.89 ppm, 1H, m; 6.51 ppm, 3H, m; 5.86 ppm, 1H, J=65 Hz; 5.15 ppm, 1H, m; 4.48 ppm, 1H, m; 4.28 ppm, 1H, m; 3.50 ppm, 1H, m; 2.88 ppm, 3H, m; 1.20 ppm, 3H, m.

EXAMPLE 1117

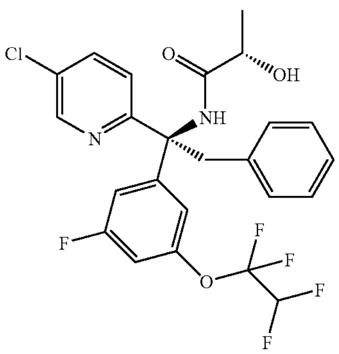

(S)-N-((S)-1-(5-chloropyridin-2-yl)-1-(3-fluoro-5-(1,1,2,2-tetrafluoroethoxy)phenyl)-2-phenylethyl)-2-hydroxypropanamide Procedure 105

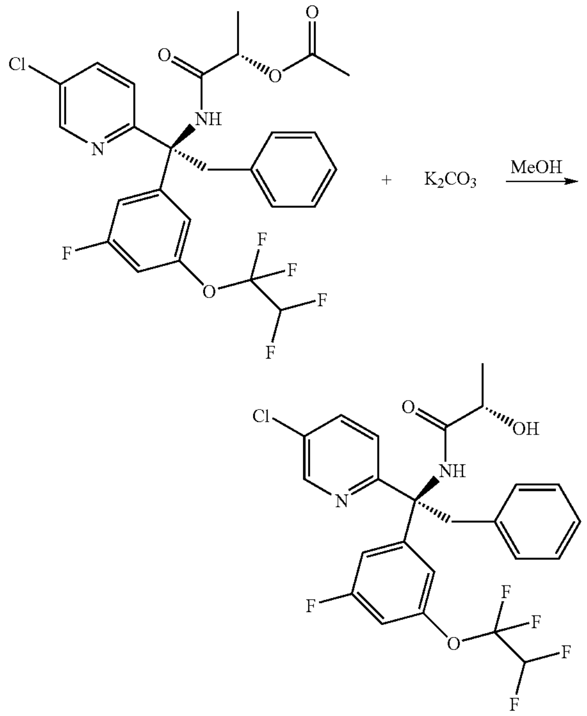

(S)-N-((S)-1-(5-chloropyridin-2-yl)-1-(3-fluoro-5-(1,1,2,2-tetrafluoroethoxy)phenyl)-2-phenylethylamino)1-oxopropan-2-yl acetate was prepared by method described in Procedure 4 in 88% yield. LCMS RT=3.64 min [M+H]=557.2 (LCMS Method 1).

To a solution of (S)-N-((S)-1-(5-chloropyridin-2-yl)-1-(3-fluoro-5-(1,1,2,2-tetrafluoroethoxy)phenyl)-2-phenylethylamino)-1-oxopropan-2-yl acetate (111 mg, 0.2 mmol) in MeOH (3 mL) was added aqueous $K_2CO_3$ solution (0.8 mL, 1N in $H_2O$, 0.8 mmol). The reaction mixture was stirred at ambient temperature for 2 h and then neutralized with 1N HCl. The aqueous portion was extracted with EtOAc. The organic layer was dried over $MgSO_4$, filtered and concentrated in vacuo. The residue was purified by ISCO chromatography (12 g column) using hexanes/EtOAc (0-100% over 14 min) to give (S)-N-((S)-1-(5-chloropyridin-2-yl)-1-(3-fluoro-5-(1,1,2,2-tetrafluoroethoxy)phenyl)-2-phenylethyl)-2-hydroxypropanamide as a colorless oil (101 mg, 98%). LCMS RT=1.98 min [M+H]=515.4 (LCMS Method 2). NMR: 400 MHz $^1H$ ($CDCl_3$) 8.93 ppm, 1 H, s; 8.33 ppm, 1 H, t, J=2.53 Hz; 7.70 ppm, 1 H, dd, J=8.59, 2.53 Hz; 7.12 ppm, 6 H, m; 6.89 ppm, 1 H, d, J=8.84 Hz; 6.55 ppm, 2 H, m; 5.88 ppm, 1 H, tt, J=53.05, 2.78 Hz; 4.41 ppm, 1 H, d, J=12.88 Hz; 4.22 ppm, 1 H, s; 3.74 ppm, 1 H, m; 3.59 ppm, 1 H, d, J=12.88 Hz; 1.33 ppm, 1 H, d, J=6.57 Hz.

EXAMPLE 1118

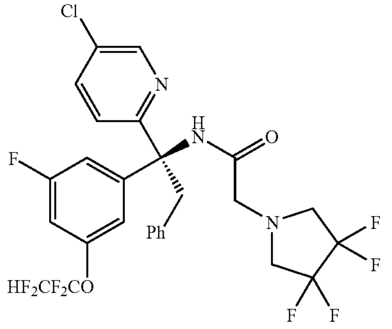

(S)-N-(1-(5-chloropyridin-2-yl)-1-(3-fluoro-5-(1,1,2,2-tetrafluoroethoxy)phenyl)-2-phenylethyl)-2-(3,3,4,4-tetrafluoropyrrolidin-1-yl)acetamide Procedure 106

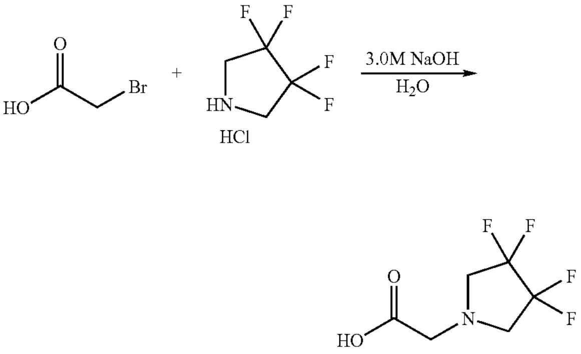

To a solution of bromoactetic acid (0.25 g, 1.8 mmol) in $H_2O$ (2 mL) was added 3 M NaOH dropwise at room temperature until pH of reaction mixture was 14. The reaction mixture was cooled to 0° C. and tetrafluoropyrrolidine HCl (0.26 g, 1.48 mmol) was added portion wise over 5 min. The reaction was stirred at 0° C. for 1 h and then at room temperature for 48 h. The mixture was heated to reflux for 1 h then allowed to cool to room temperature. The resulting white precipitate was filtered to yield 2-(3,3,4,4-tetrafluoropyrrolidin-1-yl)acetic acid (0.09 g, 30%). NMR: 500 MHz $^1H$ (DMSO) 12.68 ppm, 1H, s; 3.42 ppm, 2H, s; 3.36 ppm, 2H, s; 3.33 ppm, 2H, s.

(S)-N-(1-(5-chloropyridin-2-yl)-1-(3-fluoro-5-(1,1,2,2-tetrafluoroethoxy)phenyl)-2-phenylethyl)-2-(3,3,4,4-tetrafluoropyrrolidin-1-yl)acetamide was prepared by method described in Procedure 85 in 80% yield. LCMS RT=4.148 min [M+H]=626 (LCMS Method 1). NMR: 500 MHz $^1H$ ($CDCl_3$) 9.55 ppm, 1H, s; 8.39 ppm, 1H, m; 7.72 ppm, 1H, m; 7.19 ppm, 2H, m; 7.10 ppm, 4H, m; 6.90 ppm, 1H, m; 6.53 ppm, 2H, m; 5.88 ppm, 1H, m; 4.45 ppm, 1H, m; 3.63 ppm, 1H, m; 3.26 ppm, 1H, m; 2.99 ppm, 3H, m; 2.76 ppm, 2H, m.

EXAMPLE 1119

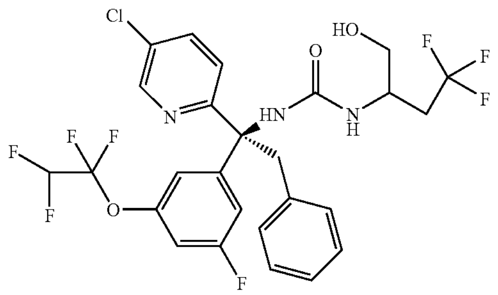

1-((S)-1-(5-chloropyridin-2-yl)-1-(3-fluoro-5-(1,1,2,2-tetrafluoroethoxy)phenyl)-2-phenylethyl)-3-(4,4,4-trifluoro-1-hydroxybutan-2-yl)urea

Procedure 107

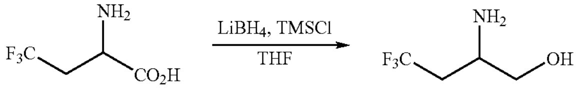

To a suspension of $LiBH_4$ (62.7 mg, 2.88 mmol) in THF (1.5 mL) was added TMSCl (728 μL, 5.76 mmol) and the reaction mixture was stirred at room temperature for 15 min, followed by the addition of 2-amino-4,4,4-trifluorobutanoic acid (226 mg, 1.44 mmol). The reaction mixture was stirred at room temperature for 18 h, and quenched by careful addition of MeOH. The solvents were removed by reduced pressure, and to the residue was added $H_2O$ (2.08 mL). The resulting aqueous portion was made basic by adding 2 N NaOH. The mixture was extracted with $CH_2Cl_2$ three times. The combined organic portions were dried over $MgSO_4$, filtered and concentrated to give 2-amino-4,4,4-trifluorobutan-1-ol as a colorless oil (110 mg, 53% yield). NMR: 400 MHz $^1H$ ($CDCl_3$) 3.61 ppm, 1 H, dd, J=10.61, 4.04 Hz; 3.42 ppm, 1 H, m; 3.28 ppm, 1 H, m; 2.29 ppm, 1 H, m; 2.12 ppm, 1 H, m.

1-((S)-1-(5-chloropyridin-2-yl)-1-(3-fluoro-5-(1,1,2,2-tetrafluoroethoxy)phenyl)-2-phenylethyl)-3-(4,4,4-trifluoro1-hydroxybutan-2-yl)urea was prepared by methods described in Procedure 3, 5, 6, 7 and 8 in 55% yield. NMR: 400 MHz $^1$($CDCl_3$) 8.25 ppm, 1 H, d, J=1.77 Hz; 8.13 ppm, 1 H, m; 7.67 ppm, 1 H, dd, J=8.59, 2.27 Hz; 7.15 ppm, 3 H, m; 7.09 ppm, 3 H, m; 6.84 ppm, 2 H, m; 6.58 ppm, 2 H, m; 5.87 ppm, 1 H, tt, J=52.93, 2.78 Hz; 4.83 ppm, 1 H, d, J=7.83 Hz; 4.34 ppm, 1 H, d, J=12.88 Hz; 4.02 ppm, 1 H, m; 3.73 ppm, 2 H, s; 3.55 ppm, 1 H, d, 15 J=12.63 Hz; 2.42 ppm, 2 H, m.

TABLE 12

| Ex. No. | Structure | Name | Retention Time Min./Molecular Mass | Prepared in the manner described in: |
|---|---|---|---|---|
| 1120 | 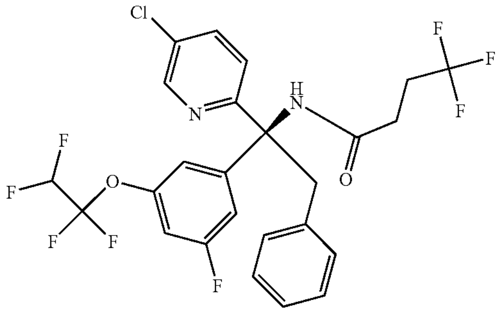 | (S)-N-(1-(5-chloropyridin-2-yl)-1-(3-fluoro-5-(1,1,2,2-tetrafluoroethoxy)phenyl)-2-phenylethyl)-4,4,4-trifluorobutanamide | 4.07 LC (5) 567.120 [M + H]+ | Procedures 3, 5, 6, 7, 30 |
| 1121 | 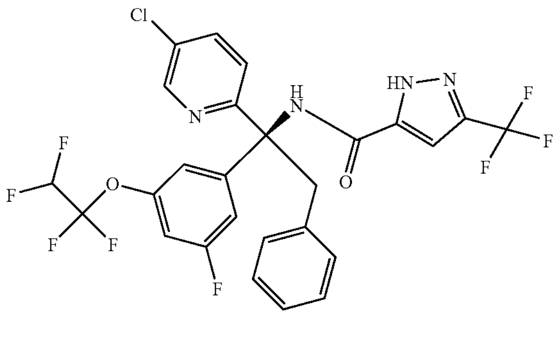 | (S)-N-(1-(5-chloropyridin-2-yl)-1-(3-fluoro-5-(1,1,2,2-tetrafluoroethoxy)phenyl)-2-phenylethyl)-3-(trifluoromethyl)-1H-pyrazole-5-carboxamide | 4.09 LC (5) 567.120 [M + H]+ | Procedures 3, 5, 6, 7, 30 |

TABLE 12-continued

| Ex. No. | Structure | Name | Retention Time Min./ Molecular Mass | Prepared in the manner described in: |
|---|---|---|---|---|
| 1122 | 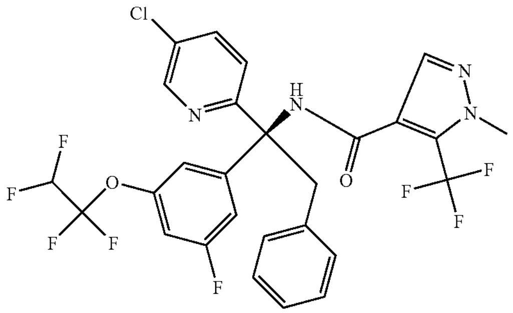 | (S)-N-(1-(5-chloropyridin-2-yl)-1-(3-fluoro-5-(1,1,2,2-tetrafluoroethoxy)phenyl)-2-phenylethyl)-1-methyl-5-(trifluoromethyl)-1H-pyrazole- | 4.01 LC (5) 619.080 [M + H]+ | Procedures 3, 5, 6, 7, 30 |
| 1123 | 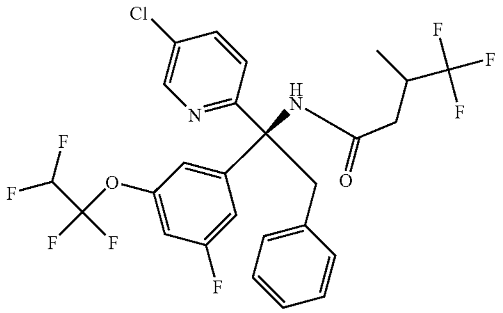 | N-((S)-1-(5-chloropyridin-2-yl)-1-(3-fluoro-5-(1,1,2,2-tetrafluoroethoxy)phenyl)-2-phenylethyl)-4,4,4-trifluoro-3-methylbutanamide | 4.17 LC (5) 581.120 [M + H]+ | Procedures 3, 5, 6, 7, 30 |
| 1124 | 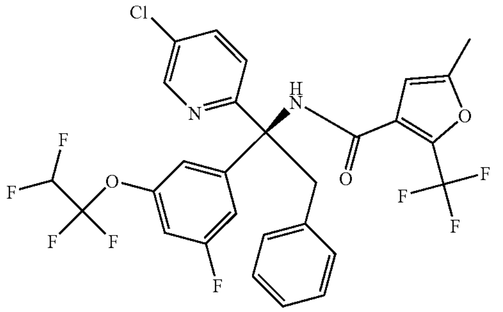 | (S)-N-(1-(5-chloropyridin-2-yl)-1-(3-fluoro-5-(1,1,2,2-tetrafluoroethoxy)phenyl)-2-phenylethyl)-5-methyl-2-(trifluoromethyl)furan-3-carboxamide | 4.20 LC (5) 619.050 [M + H]+ | Procedures 3, 5, 6, 7, 30 |
| 1125 | 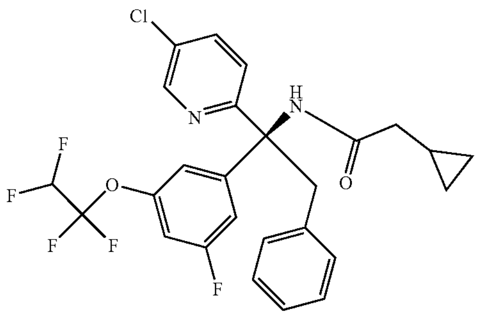 | (S)-N-(1-(5-chloropyridin-2-yl)-1-(3-fluoro-5-(1,1,2,2-tetrafluoroethoxy)phenyl)-2-phenylethyl)-2-cyclopropylacetamide | 4.10 LC (5) 525.200 [M + H]+ | Procedures 3, 5, 6, 7, 30 |

TABLE 12-continued

| Ex. No. | Structure | Name | Retention Time Min./ Molecular Mass | Prepared in the manner described in: |
|---|---|---|---|---|
| 1126 | 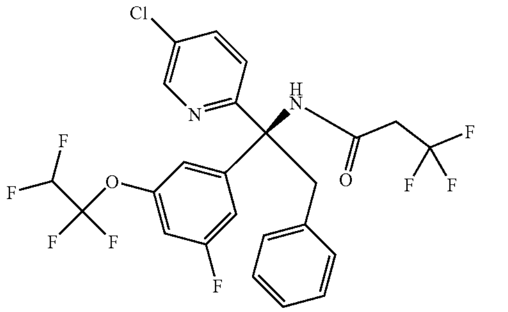 | (S)-N-(1-(5-chloropyridin-2-yl)-1-(3-fluoro-5-(1,1,2,2-tetrafluoroethoxy)phenyl)-2-phenylethyl)-3,3,3-trifluoropropanamide | 3.93 LC (5) 553.110 $[M + H]^+$ | Procedures 3, 5, 6, 7, 30 |
| 1127 | 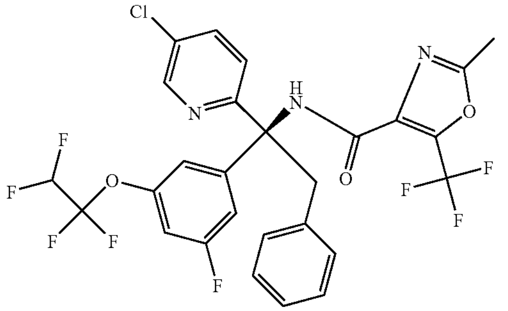 | (S)-N-(1-(5-chloropyridin-2-yl)-1-(3-fluoro-5-(1,1,2,2-tetrafluoroethoxy)phenyl)-2-phenylethyl)-2-methyl-5-(trifluoromethyl)oxazole-4-carboxamide | 4.08 LC (5) 620.080 $[M + H]^+$ | Procedures 3, 5, 6, 7, 30 |
| 1128 | 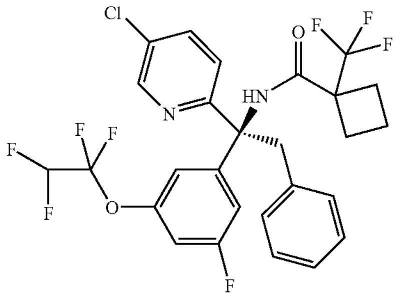 | (S)-N-(1-(5-chloropyridin-2-yl)-1-(3-fluoro-5-(1,1,2,2-tetrafluoroethoxy)phenyl)-2-phenylethyl)-1-(trifluoromethyl) cyclobutanecarboxamide | 2.20 LC (2) 593.2 $[M + H]^+$ | Procedures 3,5,6, 7, 69 |
| 1129 | 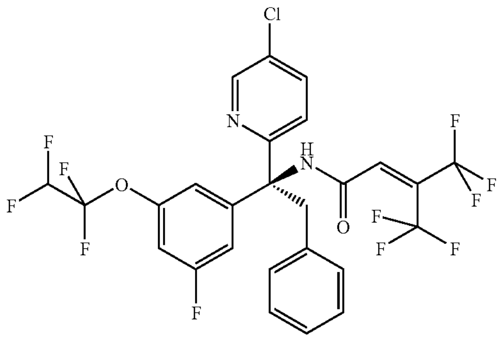 | (S)-N-(1-(5-chloropyridin-2-yl)-1-(3-fluoro-5-(1,1,2,2-tetrafluoroethoxy)phenyl)-2-phenylethyl)-4,4,4-trifluoro-3-(trifluoromethyl)but-2-enamide | 4.133 LC (3) 633.2 $[M + H]^+$ | Procedures 3, 5, 6, 7, 92 |

TABLE 12-continued

| Ex. No. | Structure | Name | Retention Time Min./ Molecular Mass | Prepared in the manner described in: |
|---|---|---|---|---|
| 1130 | 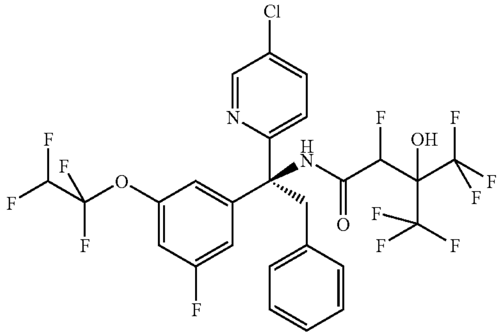 | N-((S)-1-(5-chloropyridin-2-yl)-1-(3-fluoro-5-(1,1,2,2-tetrafluoroethoxy)phenyl)-2-phenylethyl)-2,4,4,4-tetrafluoro-3-hydroxy-3-(trifluoromethyl) butanamide | 3.845 LC (4) 669.0 [M + H]$^+$ | Procedures 3, 5, 6, 7, 92, 99 and 100 |
| 1131 | 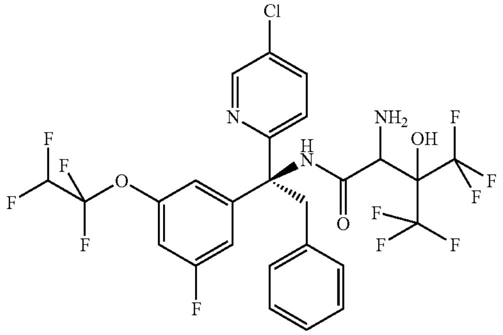 | 2-amino-N-((S)-1-(5-chloropyridin-2-yl)-1-(3-fluoro-5-(1,1,2,2-tetrafluoroethoxy) phenyl)-2-phenylethyl)-4,4,4-trifluoro-3-hydroxy-3-(trifluoromethyl)butanamide | 1.96 LC (2) 666.37 [M + H]$^+$ | Procedures 3,5,6, 7, 92, 99 and 101 |

TABLE 13

| Ex. No. | Structure | Name | Retention Time Min./ Molecular Mass | Prepared in the manner described in: |
|---|---|---|---|---|
| 1132 | 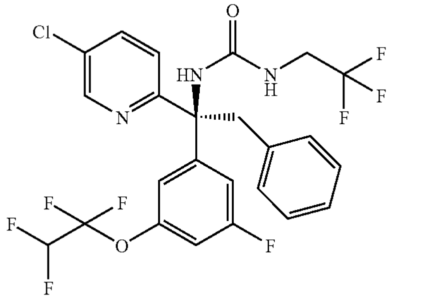 | (S)-1-(1-(5-chloropyridin-2-yl)-1-(3-fluoro-5-(1,1,2,2-tetrafluoroethoxy)phenyl)-2-phenylethyl)-3-(2,2,2-trifluoroethyl)urea | 2.05 LC 567.88 [M + H]$^+$ | Procedures 3, 5, 6, 7 and 8 |
| 1133 | 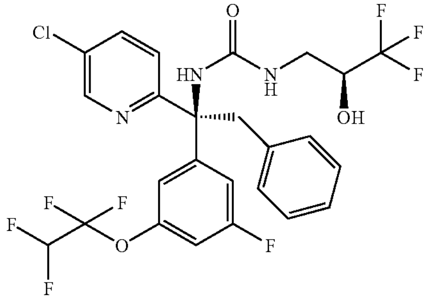 | 1-((S)-1-(5-chloropyridin-2-yl)-1-(3-fluoro-5-(1,1,2,2-tetrafluoroethoxy)phenyl)-2-phenylethyl)-3-((S)-3,3,3-trifluoro-2-hydroxypropyl)urea | 2.04 LC 597.95 [M + H]$^+$ | Procedures 3, 5, 6, 7, 95 and 8 |

TABLE 13-continued

| Ex. No. | Structure | Name | Retention Time Min./ Molecular Mass | Prepared in the manner described in: |
|---|---|---|---|---|
| 1134 | 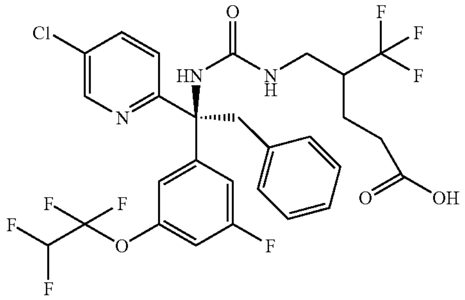 | 4-((3-((S)-1-(5-chloropyridin-2-yl)-1-(3-fluoro-5-(1,1,2,2-tetrafluoroethoxy)phenyl)-2-phenylethyl)ureido)methyl)-5,5,5-trifluoropentanoic acid | 2.04 LC 653.97 $[M + H]^+$ | Procedures 3, 5, 6, 7 and 8 |
| 1135 | 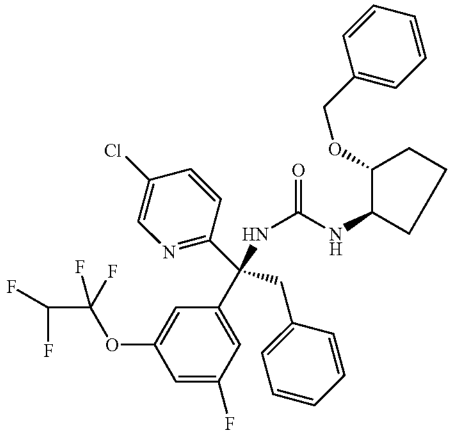 | 1-((1R,2R)-2-(benzyloxy)cyclopentyl)-3-((S)-1-(5-chloropyridin-2-yl)-1-(3-fluoro-5-(1,1,2,2-tetrafluoroethoxy)phenyl)-2-phenylethyl)urea | 4.23 LC 660.24 $[M + H]^+$ | Procedures 3, 5, 6, 7 and 8 |
| 1136 | 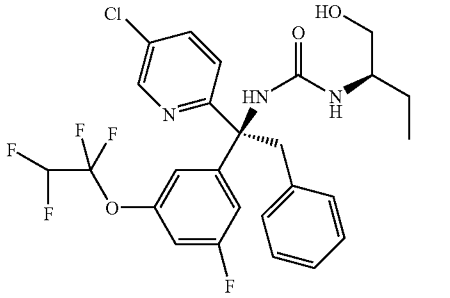 | 1-((S)-1-(5-chloropyridin-2-yl)-1-(3-fluoro-5-(1,1,2,2-tetrafluoroethoxy)phenyl)-2-phenylethyl)-3-((R)-1-hydroxybutan-2-yl)urea | 3.87 LC 558.24 $[M + H]^+$ | Procedures 3, 5, 6, 7 and 8 |
| 1137 | 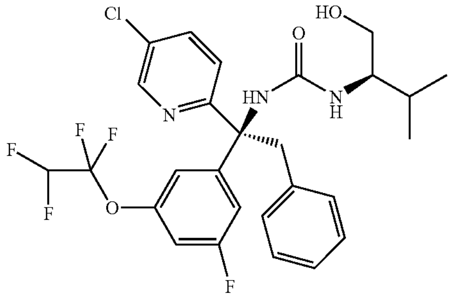 | 1-((S)-1-(5-chloropyridin-2-yl)-1-(3-fluoro-5-(1,1,2,2-tetrafluoroethoxy)phenyl)-2-phenylethyl)-3-((R)-1-hydroxy-3-methylbutan-2-yl)urea | 3.93 LC 572.26 $[M + H]^+$ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1138 | 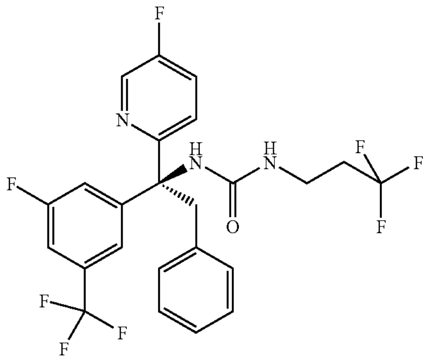 | (S)-1-(1-(3-fluoro-5-(trifluoromethyl)phenyl)-1-(5-fluoropyridin-2-yl)-2-phenylethyl)-3-(3,3,3-trifluoropropyl)urea | 4.128 LC 517.92 $[M + H]^+$ | Procedures 40, 5, 6, 7 and 8 |
| 1139 | 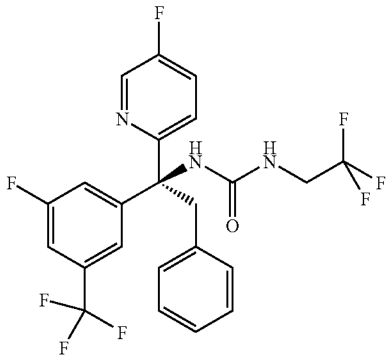 | (S)-1-(1-(3-fluoro-5-(trifluoromethyl)phenyl)-1-(5-fluoropyridin-2-yl)-2-phenylethyl)-3-(2,2,2-trifluoropropyl)urea | 4.098 LC 503.93 $[M + H]^+$ | Procedures 40, 5, 6, 7 and 8 |
| 1140 | 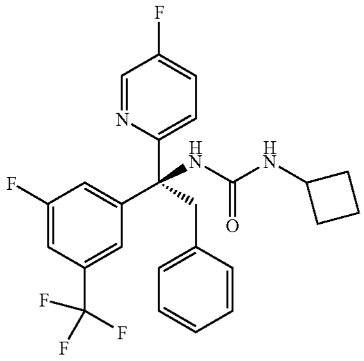 | (S)-1-cyclobutyl-3-(1-(3-fluoro-5-(trifluoromethyl)phenyl)-1-(5-fluoropyridin-2-yl)-2-phenylethyl)urea | 4.161 LC 475.95 $[M + H]^+$ | Procedures 40, 5, 6, 7 and 8 |
| 1141 | 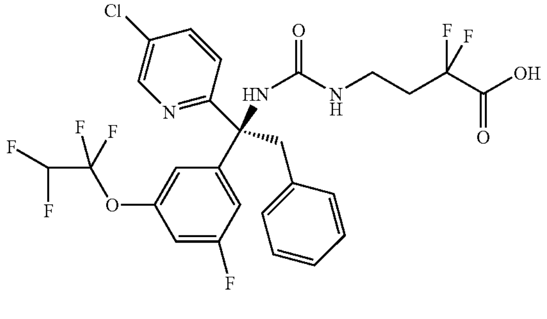 | (S)-4-(3-(1-(5-chloropyridin-2-yl)-1-(3-fluoro-5-(1,1,2,2-tetrafluoroethoxy)phenyl)-2-phenylethyl)ureido)-2,2-difluorobutanoic acid | 3.82 LC 607.7 $[M + H]^+$ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1142 | 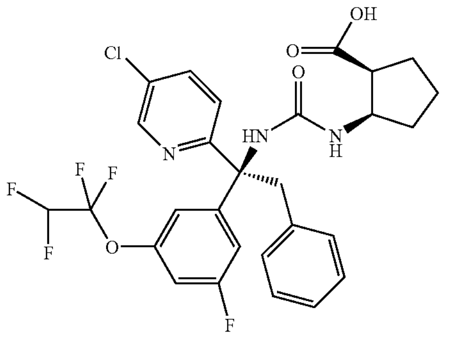 | (1S,2R)-2-(3-((S)-1-(5-chloropyridin-2-yl)-1-(3-fluoro-5-(1,1,2,2-tetrafluoroethoxy)phenyl)-2-phenylethyl)ureido)cyclopentanecarboxylic acid | 3.86 LC 598.15 [M + H]+ | Procedures 3, 5, 6, 7 and 8 |
| 1143 | 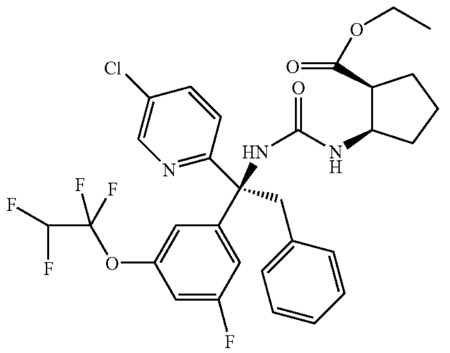 | (1S,2R)-ethyl 2-(3-((S)-1-(5-chloropyridin-2-yl)-1-(3-fluoro-5-(1,1,2,2-tetrafluoroethoxy)phenyl)-2-phenylethyl)ureido)cyclopentanecarboxylate | 4.06 LC 626.18 [M + H]+ | Procedures 3, 5, 6, 7 and 8 |
| 1144 | 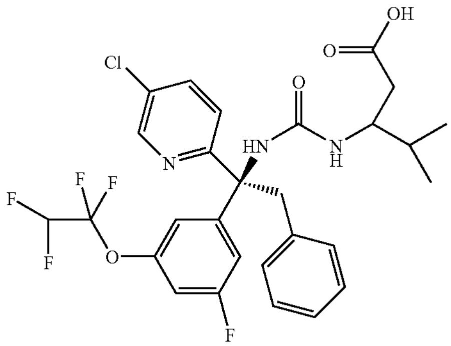 | 3-(3-((S)-1-(5-chloropyridin-2-yl)-1-(3-fluoro-5-(1,1,2,2-tetrafluoroethoxy)phenyl)-2-phenylethyl)ureido)-4-methylpentanoic acid | 3.90 LC 567.88 [M + H]+ | Procedures 3, 5, 6, 7 and 8 |
| 1145 | 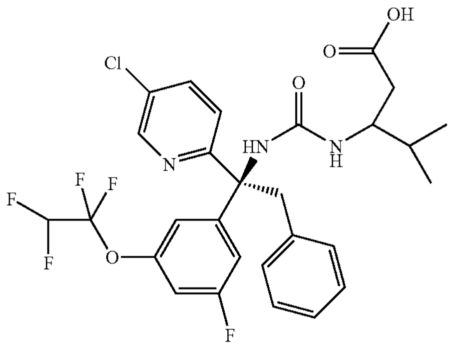 | 3-(3-((S)-1-(5-chloropyridin-2-yl)-1-(3-fluoro-5-(1,1,2,2-tetrafluoroethoxy)phenyl)-2-phenylethyl)ureido)-4-methylpentanoic acid | 3.90 LC 599.87 [M + H]+ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1146 | 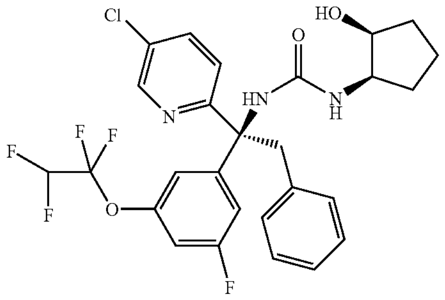 | 1-((S)-1-(5-chloropyridin-2-yl)-1-(3-fluoro-5-(1,1,2,2-tetrafluoroethoxy)phenyl)-2-phenylethyl)-3-((1R,2S)-2-hydroxycyclopentyl)urea | 3.90 LC 570.22 $[M + H]^+$ | Procedures 3, 5, 6, 7 and 8 |
| 1147 | 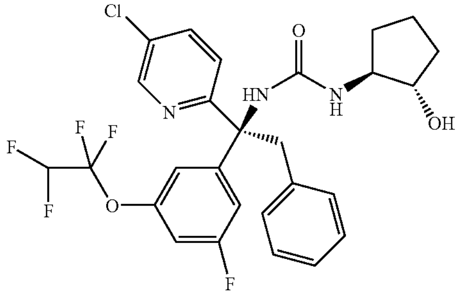 | 1-((S)-1-(5-chloropyridin-2-yl)-1-(3-fluoro-5-(1,1,2,2-tetrafluoroethoxy)phenyl)-2-phenylethyl)-3-((1R,2S)-2-hydroxycyclopentyl)urea | 3.88 LC 570.22 $[M + H]^+$ | Procedures 3, 5, 6, 7 and 8 |
| 1148 | 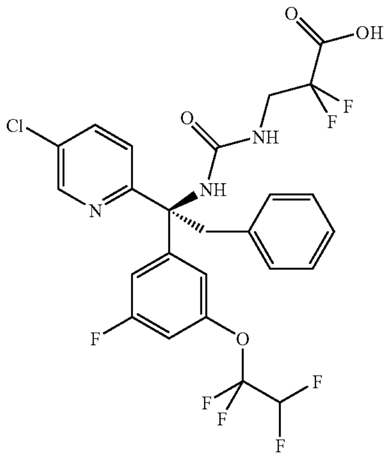 | (S)-3-(3-(1-(5-chloropyridin-2-yl)-1-(3-fluoro-5-(1,1,2,2-tetrafluoroethoxy)phenyl)-2-phenylethyl)ureido)-2,2-difluoropropanoic acid | 3.73 LC 594.25 $[M + H]^+$ | Procedures 3, 5, 6, 7, 75, 77 and 8 |

TABLE 13-continued

| Ex. No. | Structure | Name | Retention Time Min./ Molecular Mass | Prepared in the manner described in: |
|---|---|---|---|---|
| 1149 | 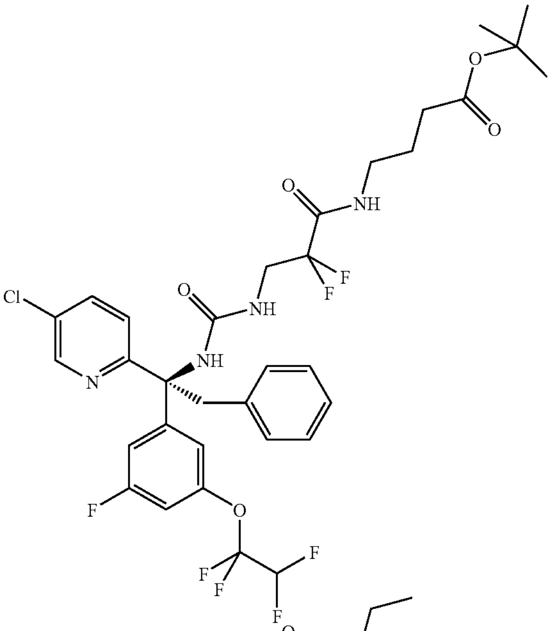 | (S)-tert-butyl 4-(3-(3-(1-(5-chloropyridin-2-yl)-1-(3-fluoro-5-(1,1,2,2-tetrafluoroethoxy) phenyl)-2-phenylethyl)ureido)-2,2-difluoropropanamido) butanoate | 4.08 LC 735.32 $[M + H]^+$ | Procedures 3, 5, 6, 7, 75, 77, 8 and 70 |
| 1150 | 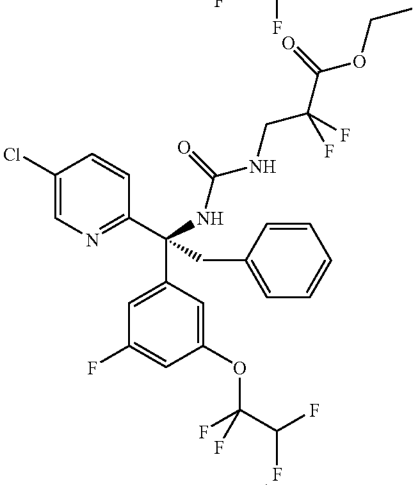 | (S)-ethyl 3-(3-(1-(5-chloropyridin-2-yl)-1-(3-fluoro-5-(1,1,2,2-tetrafluoroethoxy) phenyl)-2-phenylethyl)ureido)-2,2-difluoropropanoate | 3.96 LC 622.32 $[M + H]^+$ | Procedures 3, 5, 6, 7, 75, 77 and 8 |
| 1151 | 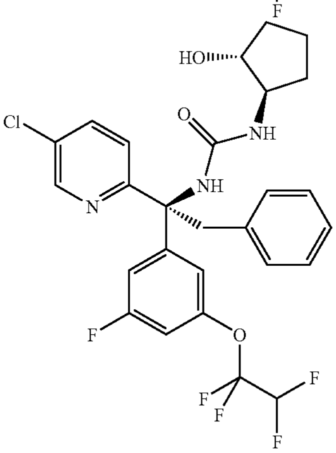 | 1-((S)-1-(5-chloropyridin-2-yl)-1-(3-fluoro-5-(1,1,2,2-tetrafluoroethoxy)phenyl)-2-phenylethyl)-3-((1R,2S)-2-hydroxycyclopentyl)urea | 3.90 LC 570.24 $[M + H]^+$ | Procedures 3, 5, 6, 7, 77 and 8 |

TABLE 13-continued

| Ex. No. | Structure | Name | Retention Time Min./ Molecular Mass | Prepared in the manner described in: |
|---|---|---|---|---|
| 1152 | 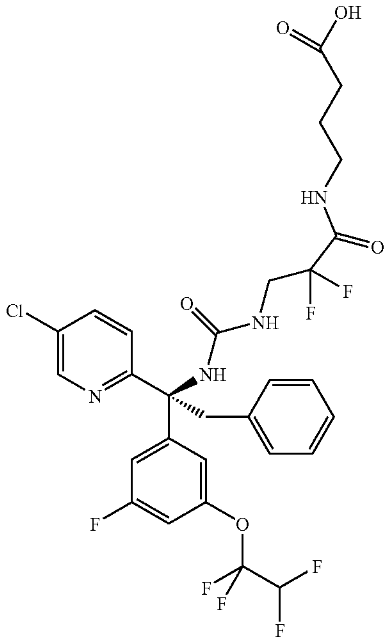 | (S)-4-(3-(3-(1-(5-chloropyridin-2-yl)-1-(3-fluoro-5-(1,1,2,2-tetrafluoroethoxy)phenyl)-2-phenylethyl)ureido)-2,2-difluoropropanamido)butanoic acid | 3.73 LC 679.3 $[M + H]^+$ | Procedures 3, 5, 6, 7, 75, 77, 8, 70 and 50 |
| 1153 | 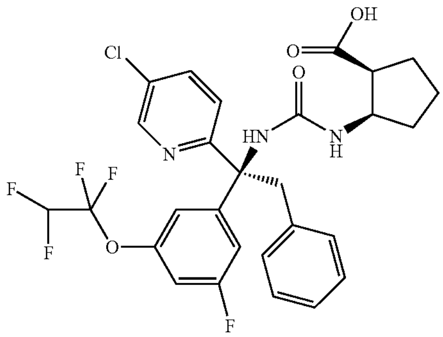 | (1S,2R)-2-(3-((S)-1-(5-chloropyridin-2-yl)-1-(3-fluoro-5-(1,1,2,2-tetrafluoroethoxy) phenyl)-2-phenylethyl)ureido)-cyclopentanecarboxylic acid | 3.91 LC 598.35 $[M + H]^+$ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1154 | 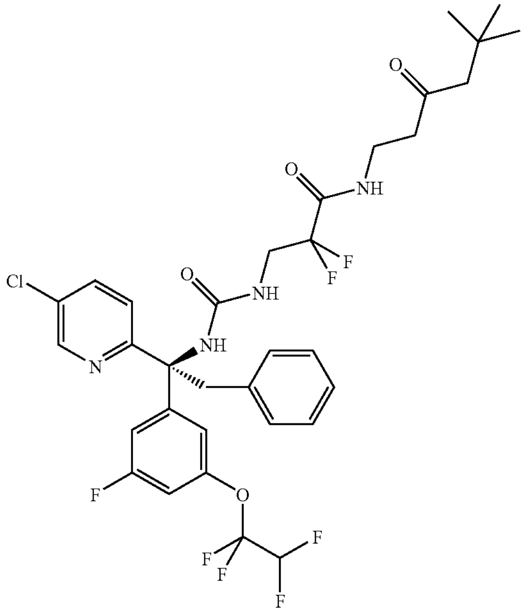 | (S)-tert-butyl 3-(3-(3-(1-(5-chloropyridin-2-yl)-1-(3-fluoro-5-(1,1,2,2-tetrafluoroethoxy) phenyl)-2-phenylethyl)ureido)-2,2-difluoropropanamido) propanoate | 4.06 LC 721.32 [M + H]$^+$ | Procedures 3, 5, 6, 7, 75, 77, 8 and 70 |
| 1155 | 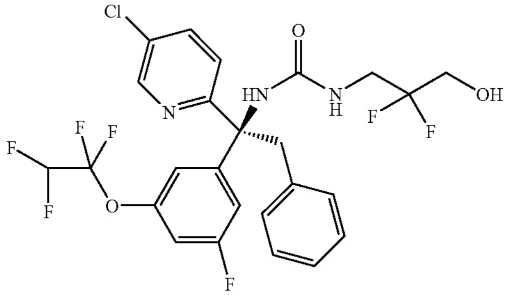 | (S)-1-(1-(5-chloropyridin-2-yl)-1-(3-fluoro-5-(1,1,2,2-tetrafluoroethoxy)phenyl)-2-phenylethyl)-3-(2,2-difluoro-3-hydroxypropyl)urea | 3.81 LC 580.21 [M + H]$^+$ | Procedures 3, 5, 6, 7 and 8 |
| 1156 | 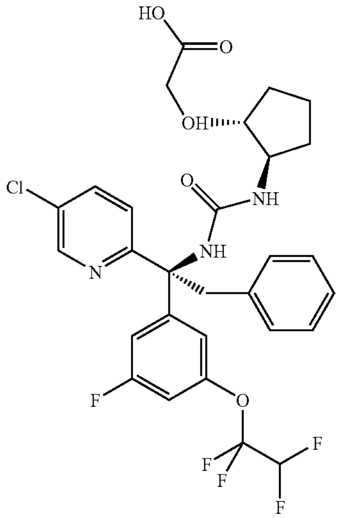 | 2-((1R,2R)-2-(3-((S)-1-(5-chloropyridin-2-yl)-1-(3-fluoro-5-(1,1,2,2-tetrafluoroethoxy) phenyl)-2-phenylethyl)ureido) cyclopentyloxy)acetic acid | 3.85 LC 628.17 [M + H]$^+$ | Procedures 3, 5, 6, 7, 77, 8, 72 and 50 |

TABLE 13-continued

| Ex. No. | Structure | Name | Retention Time Min./ Molecular Mass | Prepared in the manner described in: |
|---|---|---|---|---|
| 1157 | 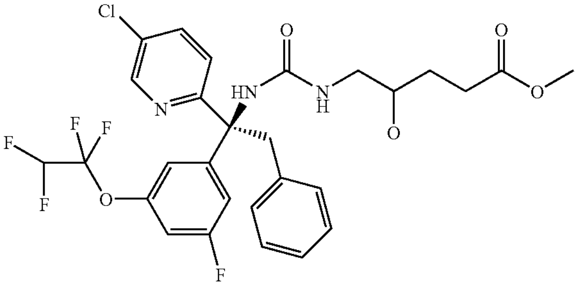 | (S)-methyl 5-(3-(1-(5-chloropyridin-2-yl)-1-(3-fluoro-5-(1,1,2,2-tetrafluoroethoxy) phenyl)-2-phenylethyl)ureido)-4-oxopentanoate | 3.84 LC 614.03 [M + H]+ | Procedures 3, 5, 6, 7 and 8 |
| 1158 | 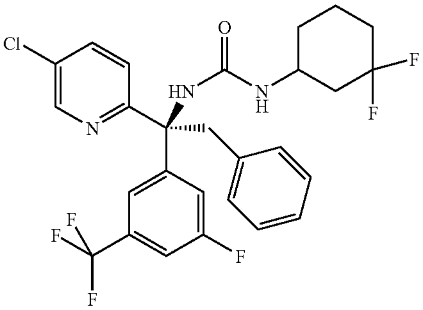 | 1-((S)-1-(5-chloropyridin-2-yl)-1-(3-fluoro-5-(trifluoromethyl) phenyl)-2-phenylethyl)-3-(3,3-difluorocyclohexyl)urea | 4.03 LC (3) 556.2 [M + H]+ | Procedure 5, 6, 7, 83, 84, 8 |
| 1159 | 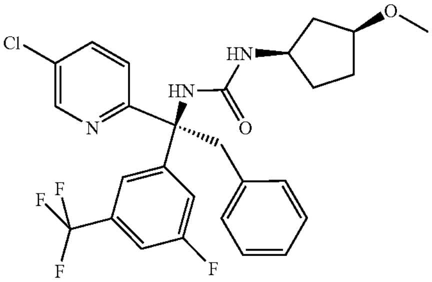 | 1-((S)-1-(5-chloropyridin-2-yl)-1-(3-fluoro-5-(trifluoromethyl) phenyl)-2-phenylethyl)-3-((1R,3S)-3-methoxycyclopentyl)urea | 4.026 LC (1) 536.2 [M + H]+ | Procedure 5, 6, 7, 82 8, and 21 |
| 1160 | 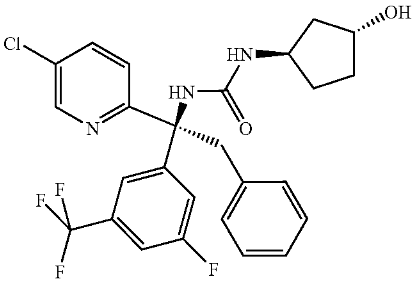 | 1-((S)-1-(5-chloropyridin-2-yl)-1-(3-fluoro-5-(trifluoromethyl) phenyl)-2-phenylethyl)-3-((1R,3R)-3-hydroxycyclopentyl)urea | 3.891 LC (1) 522.2 [M + H]+ | Procedure 5, 6, 7, 82 and 8 |
| 1161 | 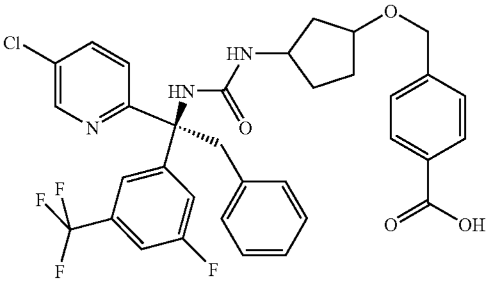 | 4-((3-(3-((S)-1-(5-chloropyridin-2-yl)-1-(3-fluoro-5-(trifluoromethyl)phenyl)-2-phenylethyl)ureido) cyclopentyloxy)methyl)benzoic acid | 4.056 LC (1) 656.4 [M + H]+ | Procedure 5, 6, 7, 82, 8 and 72 |

TABLE 13-continued

| Ex. No. | Structure | Name | Retention Time Min./ Molecular Mass | Prepared in the manner described in: |
|---|---|---|---|---|
| 1162 | 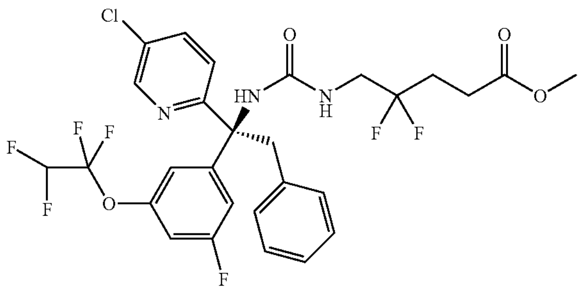 | (S)-methyl 5-(3-(1-(5-chloropyridin-2-yl)-1-(3-fluoro-5-(1,1,2,2-tetrafluoroethoxy) phenyl)-2-phenylethyl)ureido)-4,4-difluoropentanoate | 3.93 LC 636.27 [M + H]$^+$ | Procedures 3, 5, 6, 7, 8 and 12 |
| 1163 | 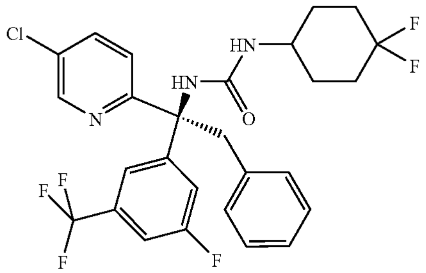 | (S)-1-(1-(5-chloropyridin-2-yl)-1-(3-fluoro-5-(trifluoromethyl) phenyl)-2-phenylethyl)-3-(4,4-difluorocyclohexyl)urea | 4.103 LC (3) 556.1 [M + H]$^+$ | Procedure 5, 6, 7, 83, 84, 8 |
| 1164 | 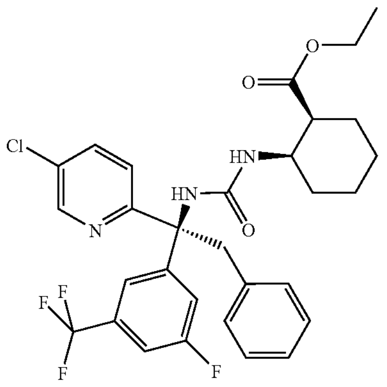 | (1S,2R)-ethyl 2-(3-((S)-1-(5-chloropyridin-2-yl)-1-(3-fluoro-5-(trifluoromethyl)phenyl)-2-phenylethyl)ureido) cyclohexanecarboxylate | 4.168 LC (3) 592.4 [M + H]$^+$ | Procedure 5, 6, 7 and 8 |
| 1165 | 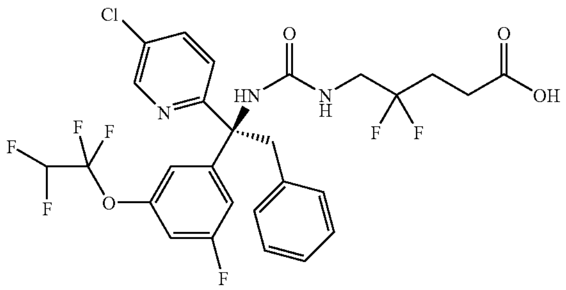 | (S)-5-(3-(1-(5-chloropyridin-2-yl)-1-(3-fluoro-5-(1,1,2,2-tetrafluoroethoxy)phenyl)-2-phenylethyl)ureido)-4,4-difluoropentanoic acid | 3.69 LC 622.14 [M + H]$^+$ | Procedures 3, 5, 6, 7, 8, 12 and 53 |

TABLE 13-continued

| Ex. No. | Structure | Name | Retention Time Min./ Molecular Mass | Prepared in the manner described in: |
|---|---|---|---|---|
| 1166 | 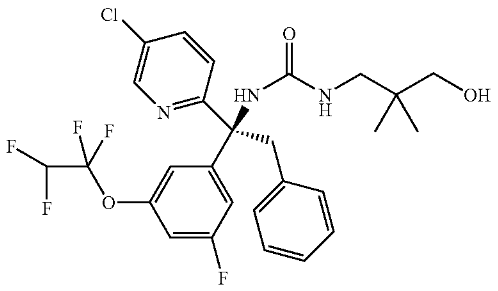 | (S)-5-(3-(1-(5-chloropyridin-2-yl)-1-(3-fluoro-5-(1,1,2,2-tetrafluoroethoxy)phenyl)-2-phenylethyl)-3-(3-hydroxy-2,2-dimethylpropyl)urea | 3.84 LC 572.20 $[M + H]^+$ | Procedures 3, 5, 6, 7 and 8 |
| 1167 | 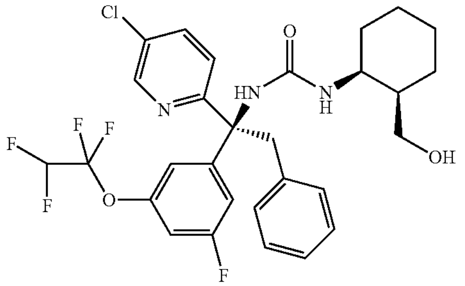 | 1-((S)-1-(5-chloropyridin-2-yl)-1-(3-fluoro-5-(1,1,2,2-tetrafluoroethoxy)phenyl)-2-phenylethyl)-3-((1S,2R)-2-(hydroxymethyl)cyclohexyl)urea | 3.93 LC 598.23 $[M + H]^+$ | Procedures 3, 5, 6, 7 and 8 |
| 1168 | 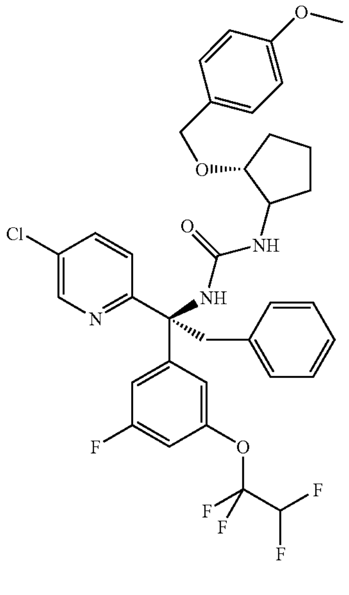 | 1-((S)-1-(5-chloropyridin-2-yl)-1-(3-fluoro-5-(1,1,2,2-tetrafluoroethoxy)phenyl)-2-phenylethyl)-3-((2R)-2-(4-methoxybenzyloxy)cyclopentyl) urea | 4.20 LC (1) 690.04 $[M + H]^+$ | Procedure 3, 5, 6, 7, 8 and 72 |

TABLE 13-continued

| Ex. No. | Structure | Name | Retention Time Min./ Molecular Mass | Prepared in the manner described in: |
|---|---|---|---|---|
| 1169 | 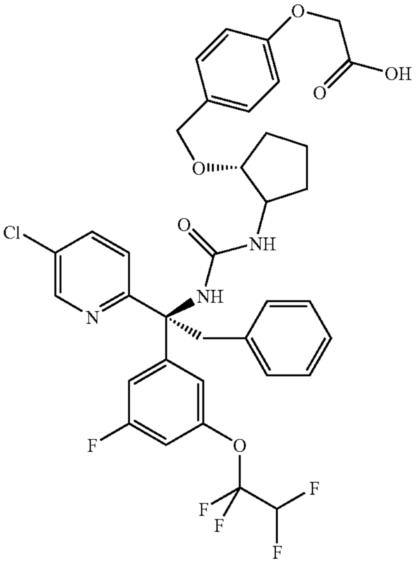 | 2-(4-(((1R)-2-(3-((S)-1-(5-chloropyridin-2-yl)-1-(3-fluoro-5-(1,1,2,2-tetrafluoroethoxy)phenyl)-2-phenylethyl)ureido)cyclopentyloxy)methyl)phenoxy)acetic acid | 3.92 LC (1) 734.28 [M + H]$^+$ | Procedure 3, 5, 6, 7, 8 and 72 |
| 1170 | 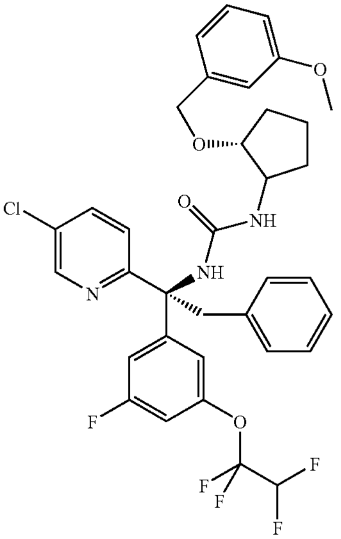 | 1-((S)-1-(5-chloropyridin-2-yl)-1-(3-fluoro-5-(1,1,2,2-tetrafluoroethoxy)phenyl)-2-phenylethyl)-3-((2R)-2-(3-methoxybenzyloxy)cyclopentyl)urea | 4.21 LC (1) 690.10 [M + H]$^+$ | Procedure 3, 5, 6, 7, 8 and 72 |
| 1171 | 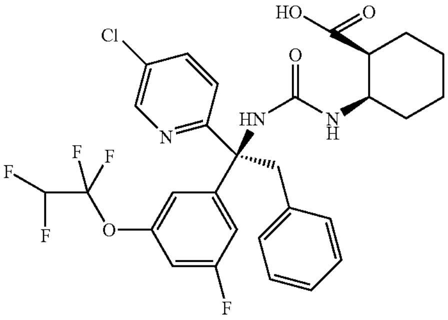 | (1S,2R)-2-(3-((S)-1-(5-chloropyridin-2-yl)-1-(3-fluoro-5-(1,1,2,2-tetrafluoroethoxy)phenyl)-2-phenylethyl)ureido)cyclohexanecarboxylic acid | 3.925 LC (1) 612.3 [M − ] | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1172 | 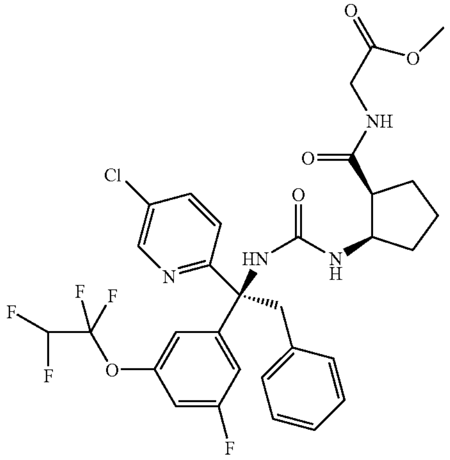 | methyl 2-((1S,2R)-2-(3-((S)-1-(5-chloropyridin-2-yl)-1-(3-fluoro-5-(1,1,2,2-tetrafluoroethoxy)phenyl)-2-phenylethyl)ureido) cyclopentanecarboxamido) acetate | 3.938 LC (3) 669.2 [M − H]+ | Procedure 3, 5, 6, 7, 8 and 85 |
| 1173 | 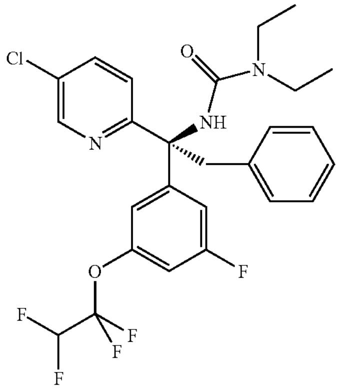 | (S)-3-(1-(5-chloropyridin-2-yl)-1-(3-fluoro-5-(1,1,2,2-tetrafluoroethoxy)phenyl)-2-phenylethyl)-1,1-diethylurea | 4.23 LC (1) 542.75 [M + H]+ | Procedure 3, 5, 6, 7, 8, 78 and 79 |
| 1174 | 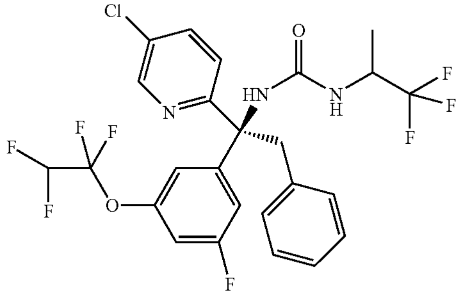 | 1-((S)-1-(5-chloropyridin-2-yl)-1-(3-fluoro-5-(1,1,2,2-tetrafluoroethoxy)phenyl)-2-phenylethyl)-3-(1,1,1-trifluoropropan-2-yl)urea | 3.99 LC 582.06 [M + H]+ | Procedures 3, 5, 6, 7 and 8 |
| 1175 | 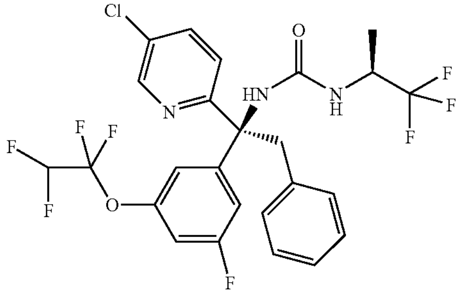 | 1-((S)-1-(5-chloropyridin-2-yl)-1-(3-fluoro-5-(1,1,2,2-tetrafluoroethoxy)phenyl)-2-phenylethyl)-3-((S)-1,1,1-trifluoropropan-2-yl)urea | 4.00 LC (1) 581.97 [M + H]+ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1176 | 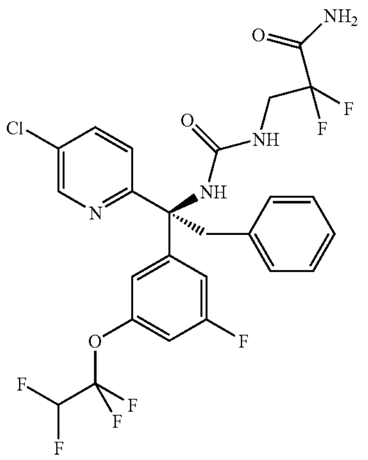 | (S)-3-(3-(1-(5-chloropyridin-2-yl)-1-(3-fluoro-5-(1,1,2,2-tetrafluoroethoxy)phenyl)-2-phenylethyl)ureido)-2,2-difluoropropanamide | 3.74 LC (1) 593.64 $[M + H]^+$ | Procedures 3, 5, 6, 7, 75, 77, 8, 29, and 66 |
| 1177 | 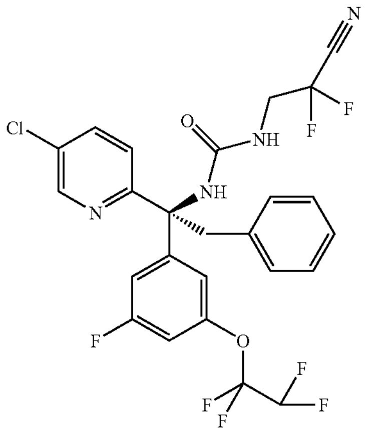 | (S)-1-(1-(5-chloropyridin-2-yl) 1-(3-fluoro-5-(1,1,2,2-tetrafluoroethoxy)phenyl)-2-phenylethyl)-3-(2-cyano-2,2-difluoroethyl)urea | 3.92 LC (1) 575.2 $[M + H]^+$ | Procedures 3, 5, 6, 7, 75, 77, 8, 29, 66 and 67 |
| 1178 | 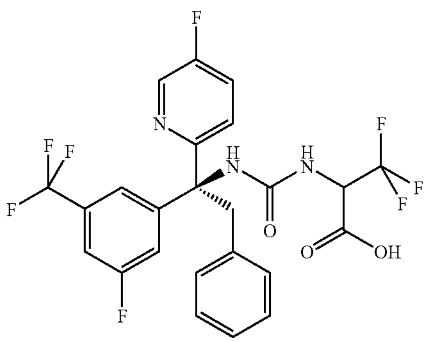 | 3,3,3-trifluoro-2-(3-((S)-1-(3-fluoro-5-(trifluoromethyl) phenyl)-1-(5-fluoropyridin-2-yl)-2-phenylethyl)ureido) propanoic acid | 2.01 LC (2) 548.1 $[M + H]^+$ | Procedures 5, 6, 7 and 8 |

TABLE 13-continued

| Ex. No. | Structure | Name | Retention Time Min./ Molecular Mass | Prepared in the manner described in: |
|---|---|---|---|---|
| 1179 | 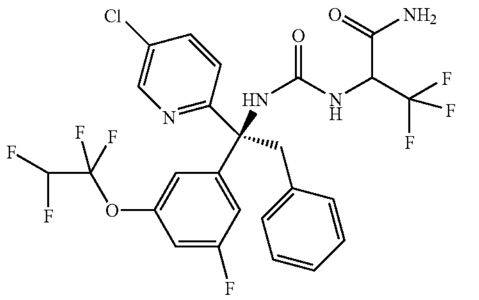 | 2-(3-((S)-1-(5-chloropyridin-2-yl)-1-(3-fluoro-5-(1,1,2,2-tetrafluoroethoxy)phenyl)-2-phenylethyl)ureido)-3,3,3-trifluoropropanamide | 3.75 LC 611.2 $[M + H]^+$ | Procedure 3, 5, 6, 7, 8 and 66 |
| 1180 | 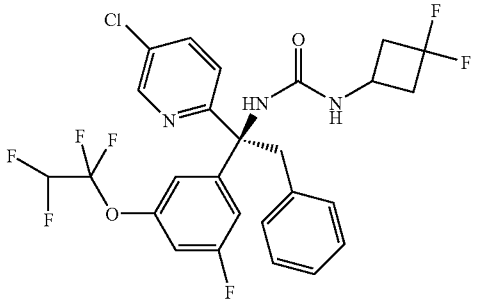 | (S)-1-(1-(5-chloropyridin-2-yl)-1-(3-fluoro-5-(1,1,2,2-tetrafluoroethoxy)phenyl)-2-phenylethyl)-3-(3,3-difluorocyclobutyl)urea | 3.416 LC (4) 576.3 $[M + H]^+$ | Procedure 3, 5, 6, 7 and 8 |
| 1181 | 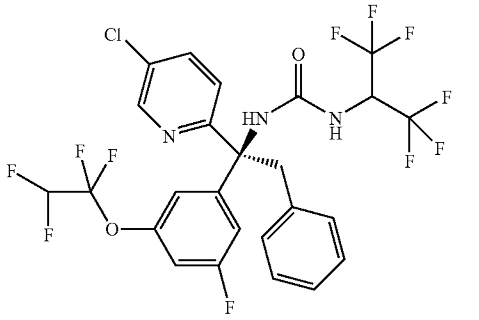 | (S)-1-(1-(5-chloropyridin-2-yl)-1-(3-fluoro-5-(1,1,2,2-tetrafluoroethoxy)phenyl)-2-phenylethyl)-3-(1,1,1,3,3,3-hexafluoropropan-2-yl)urea | 4.12 LC 636.03 $[M + H]^+$ | Procedures 3, 5, 6, 7 and 8 |
| 1182 | 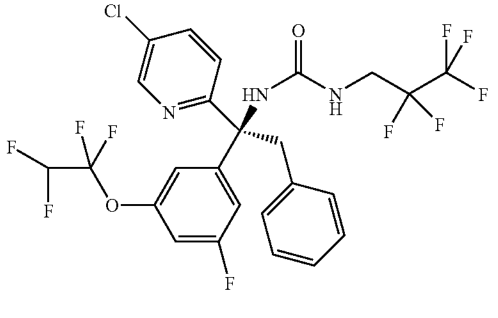 | (S)-1-(1-(5-chloropyridin-2-yl)-1-(3-fluoro-5-(1,1,2,2-tetrafluoroethoxy)phenyl)-2-phenylethyl)-3-(2,2,3,3,3-pentafluoropropyl)urea | 3.560 LC (4) 618.3 [M − ] | Procedure 3, 5, 6, 7 and 8 |

TABLE 13-continued

| Ex. No. | Structure | Name | Retention Time Min./ Molecular Mass | Prepared in the manner described in: |
|---|---|---|---|---|
| 1183 | 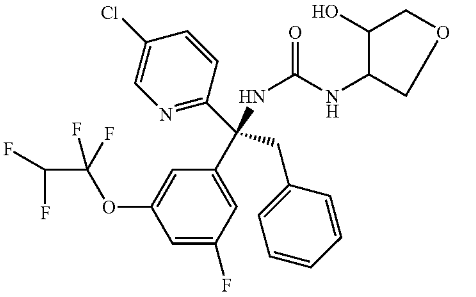 | 1-((S)-1-(5-chloropyridin-2-yl)-1-(3-fluoro-5-(1,1,2,2-tetrafluoroethoxy)phenyl)-2-phenylethyl)-3-(4-hydroxytetrahydrofuran-3-yl) urea | 1.94 LC 572.1 $[M + H]^+$ | Procedures 3, 5, 6, 7 and 8 |
| 1184 | 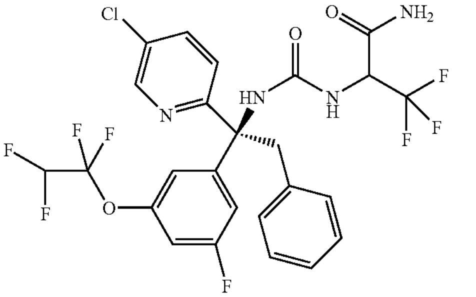 | 2-(3-((S)-1-(5-chloropyridin-2-yl)-1-(3 fluoro-5-(1,1,2,2-tetrafluoroethoxy)phenyl)-2-phenylethyl)ureido)-3,3,3-trifluoropropanamide | 3.75 LC (1) 611.2 $[M + H]^+$ | Procedure 3, 5, 6, 7, 8 and 66 |
| 1185 | 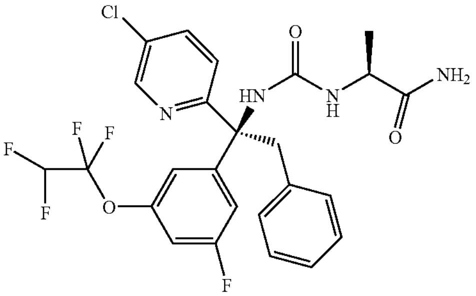 | (S)-2-(3-((S)-1-(5-chloropyridin-2-yl)-1-(3-fluoro-5-(1,1,2,2-tetrafluoroethoxy) phenyl)-2-phenylethyl)ureido) propanamide | 1.96 LC (2) 557.2 $[M + H]^+$ | Procedures 3, 5, 6, 7, and 8 |
| 1186 | 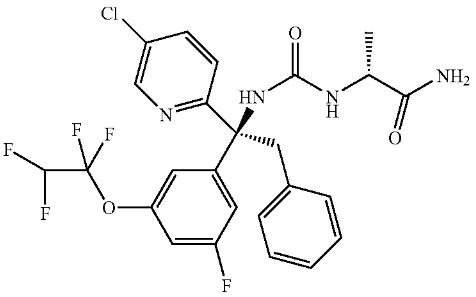 | (R)-2-(3-((S)-1-(5-chloropyridin-2-yl)-1-(3-fluoro-5-(1,1,2,2-tetrafluoroethoxy) phenyl)-2-phenylethyl)ureido) propanamide | 1.95 LC (2) 557.2 $[M + H]^+$ | Procedures 3, 5, 6, 7, and 8 |
| 1187 | 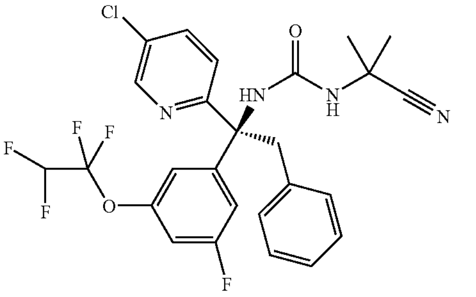 | (S)-1-(1-(5-chloropyridin-2-yl)-1-(3-fluoro-5-(1,1,2,2-tetrafluoroethoxy)phenyl)-2-phenylethyl)-3-(2-cyanopropan-2-yl)urea | 1.93 LC (2) 553.2 $[M + H]^+$ | Procedures 3, 5, 6, 7, and 68 |

TABLE 13-continued

| Ex. No. | Structure | Name | Retention Time Min./ Molecular Mass | Prepared in the manner described in: |
|---|---|---|---|---|
| 1188 | 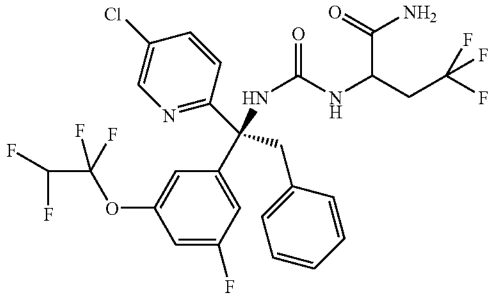 | 2-(3-((S)-1-(5-chloropyridin-2-yl)-1-(3-fluoro-5-(1,1,2,2-tetrafluoroethoxy)phenyl)-2-phenylethyl)ureido)-4,4,4-trifluorobutanamide | 2.996 LC (4) 625.3 [M + H]+ | Procedures 3, 5, 6, 7, 8 and 66 |
| 1189 | 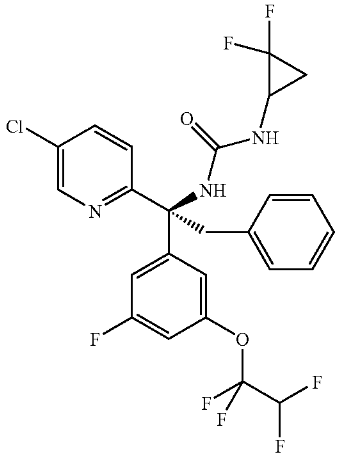 | 1-((S)-1-(5-chloropyridin-2-yl)-1-(3-fluoro-5-(1,1,2,2-tetrafluoroethoxy)phenyl)-2-phenylethyl)-3-(2,2-difluorocyclopropyl)urea | 2.3 LC (2) 562.2 [M + H]+ | Procedure 3, 5, 6, 7, 80 and 2 |
| 1190 | 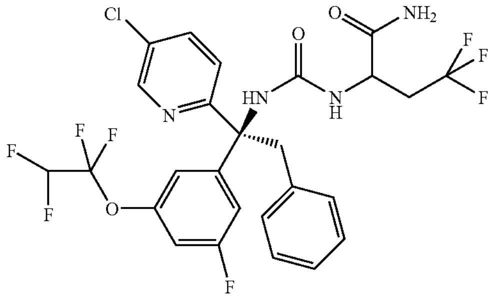 | 2-(3-((S)-1-(5-chloropyridin-2-yl)-1-(3-fluoro-5-(1,1,2,2-tetrafluoroethoxy)phenyl)-2-phenylethyl)ureido)-4,4,4-trifluorobutanamide | 3.02 LC (4) 625.3 [M + H]+ | Procedures 3, 5, 6, 7, 8 and 66 |
| 1191 | 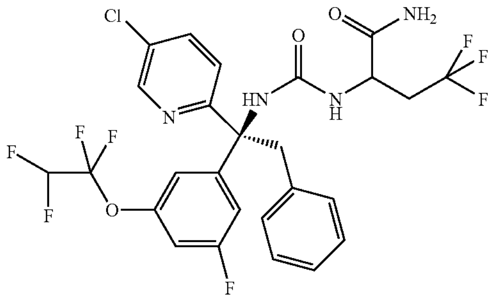 | 2-(3-((S)-1-(5-chloropyridin-2-yl)-1-(3-fluoro-5-(1,1,2,2-tetrafluoroethoxy)phenyl)-2-phenylethyl)ureido)-4,4,4-trifluorobutanamide | 3.02 LC (4) 625.3 [M + H]+ | Procedures 3, 5, 6, 7, 8 and 66 |

TABLE 13-continued

| Ex. No. | Structure | Name | Retention Time Min./ Molecular Mass | Prepared in the manner described in: |
|---|---|---|---|---|
| 1192 | 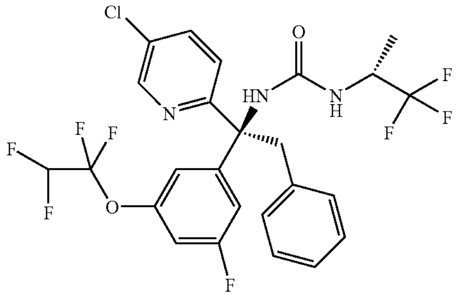 | 1-((S)-(5-chloropyridin-2-yl)-1-(3-fluoro-5-(1,1,2,2-tetrafluoroethoxy)phenyl)-2-phenylethyl)-3-((R)-1,1,1-trifluoropropan-2-yl)urea | 4.09 LC 582.1 [M + H]+ | Procedures 3, 5, 6, 7 and 8 |
| 1193 | 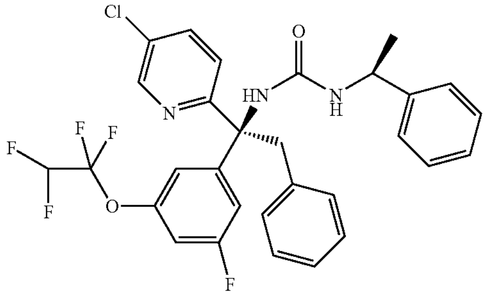 | 1-((S)-(5-chloropyridin-2-yl)-1-(3-fluoro-5-(1,1,2,2-tetrafluoroethoxy)phenyl)-2-phenylethyl)-3-((S)-1-phenylethyl)urea | 4.18 LC 590.1 [M + H]+ | Procedures 3, 5, 6, 7 and 8 |
| 1194 | 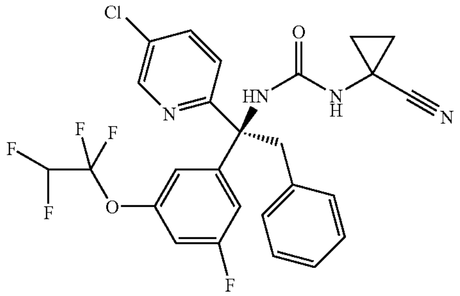 | (S)-1-(1-(5-chloropyridin-2-yl)-1-(3-fluoro-5-(1,1,2,2-tetrafluoroethoxy)phenyl)-2-phenylethyl)-3-(1-cyanocyclopropyl)urea | 3.82 LC 551.1 [M + H]+ | Procedures 3, 5, 6, 7 and 68 |
| 1195 | 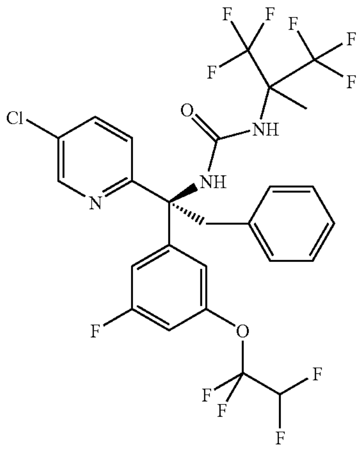 | (S)-1-(1-(5-chloropyridin-2-yl)-1-(3-fluoro-5-(1,1,2,2-tetrafluoroethoxy)phenyl)-2-phenylethyl)-3-(1,1,1,3,3,3-hexafluoro-2-methylpropan-2-yl)urea | 2.16 LC (2) 650.2 [M + H]+ | Procedure 3, 5, 6, 7, 80 and 2 |

TABLE 13-continued

| Ex. No. | Structure | Name | Retention Time Min./ Molecular Mass | Prepared in the manner described in: |
|---|---|---|---|---|
| 1196 | 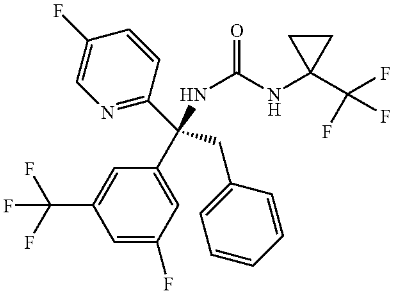 | (S)-1-(1-(3-fluoro-5-(trifluoromethyl)phenyl)-1-(5-fluoropyridin-2-yl)-2-phenylethyl)-3-(1-(trifluoromethyl)cyclopropyl) urea | 2.00 LC (2) 530.2 [M + H]$^+$ | Procedures 3, 5, 6, 7 and 68 |
| 1197 | 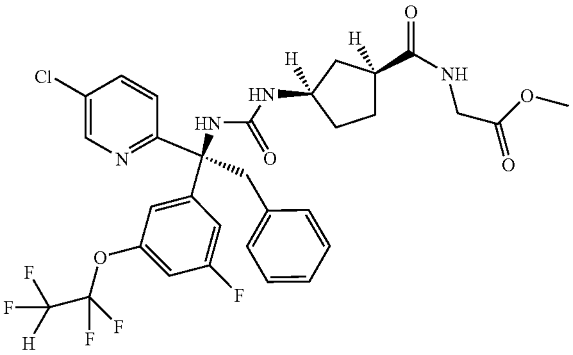 | methyl 2-((1S,3R)-3-(3-((S)-1-(5-chloropyridin-2-yl)-1-(3-fluoro-5-(1,1,2,2-tetrafluoroethoxy)phenyl)-2-phenylethyl)ureido) cyclopentanecarboxamido) acetate | 2.978 LC (4) 669.0 [M + H]$^+$ | Procedure 3, 5, 6, 7, 8 and 85 |
| 1198 | 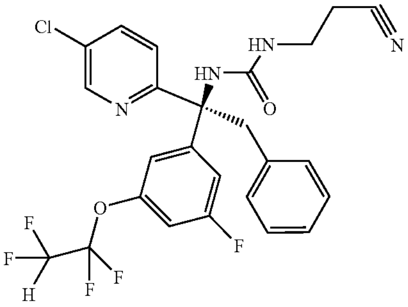 | (S)-1-(1-(5-chloropyridin-2-yl)-1-(3-fluoro-5-(1,1,2,2-tetrafluoroethoxy)phenyl)-2-phenylethyl)-3-(2-cyanoethyl)urea | 3.081 LC (4) 539.1 [M + H]$^+$ | Procedures 3, 5, 6, 7 and 8 |
| 1199 | 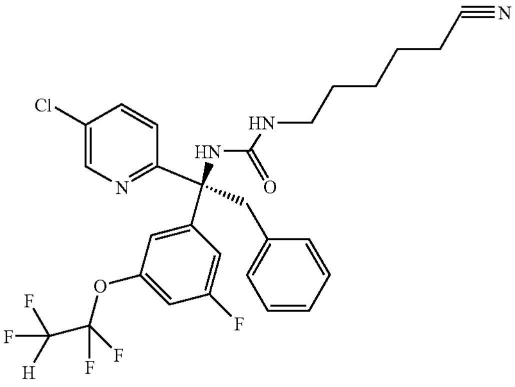 | (S)-1-(1-(5-chloropyridin-2-yl)-1-(3-fluoro-5-(1,1,2,2-tetrafluoroethoxy)phenyl)-2-phenylethyl)-3-(5-cyanopentyl)urea | 3.270 LC (4) 581.1 [M + H]$^+$ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1200 | 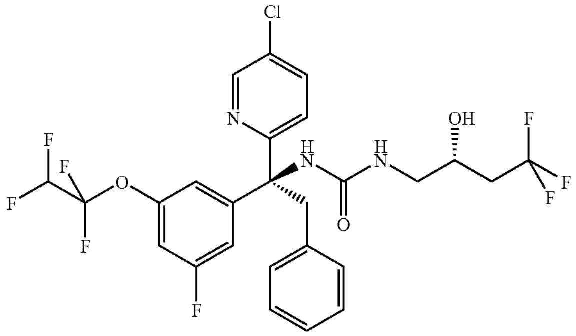 | 1-((S)-1-(5-chloropyridin-2-yl)-1-(3-fluoro-5-(1,1,2,2-tetrafluoroethoxy)phenyl)-2-phenylethyl)-3-((R)-4,4,4-trifluoro-2-hydroxybutyl)urea | 1.995 LC (2) 612.24 $[M + H]^+$ | Procedure 3, 5, 6, 7, 94, 95 and 93 |
| 1201 | 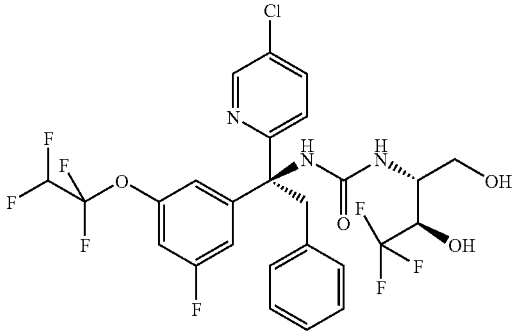 | 1-((S)-1-(5-chloropyridin-2-yl)-1-(3-fluoro-5-(1,1,2,2-tetrafluoroethoxy)phenyl)-2-phenylethyl)-3-((2R,3R)-4,4,4-trifluoro-1,3-dihydroxybutan-2-yl)urea | 1.928 LC (2) 628.29 $[M + H]^+$ | Procedures 3, 5, 6, 7, 8, 70 and 67 |
| 1202 | 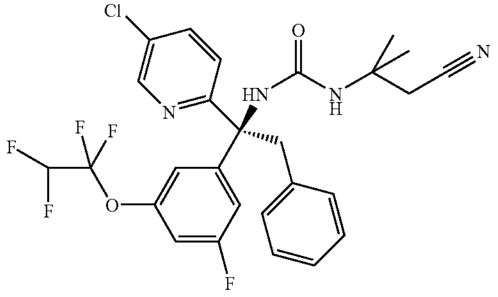 | (S)-1-(1-(5-chloropyridin-2-yl)-1-(3-fluoro-5-(1,1,2,2-tetrafluoroethoxy)phenyl)-2-phenylethyl)-3-(1-cyano-2-methylpropan-2-yl)urea | 3.36 LC (4) 567.2 $[M + H]^+$ | Procedures 3, 5, 6, 7, 8, 70 and 67 |
| 1203 | 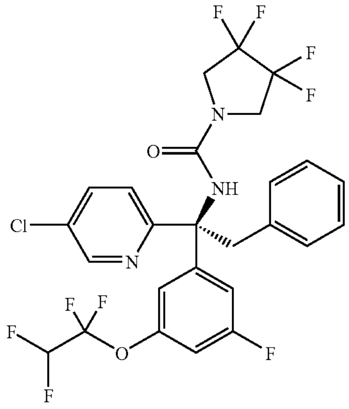 | (S)-N-(1-(5-chloropyridin-2-yl)-1-(3-fluoro-5-(1,1,2,2-tetrafluoroethoxy)phenyl)-2-phenylethyl)-3,3,4,4-tetrafluoropyrrolidine-1-carboxamide | 4.116 LC (4) 612.2 $[M + H]^+$ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1204 | 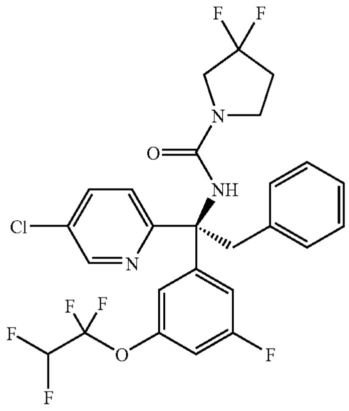 | (S)-N-(1-(5-chloropyridin-2-yl)-1-(3-fluoro-5-(1,1,2,2-tetrafluoroethoxy)phenyl)-2-phenylethyl)-3,3-difluoropyrrolidine-1-carboxamide | 4.030 LC (4) 576.2 [M + H]+ | Procedures 3, 5, 6, 7 and 8 |
| 1205 | 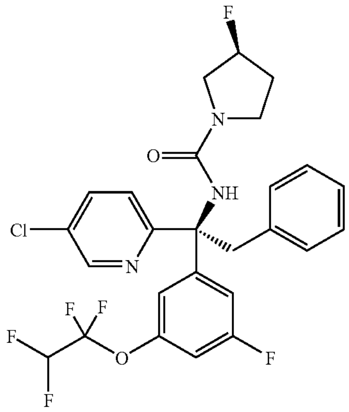 | (S)-N-((S)-1-(5-chloropyridin-2-yl)-1-(3-fluoro-5-(1,1,2,2-tetrafluoroethoxy)phenyl)-2-phenylethyl)-3-fluoropyrrolidine-1-carboxamide | 3.963 LC (4) 558.2 [M + H]+ | Procedures 3, 5, 6, 7 and 8 |
| 1206 | 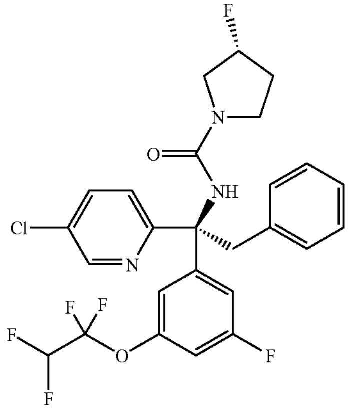 | (R)-N-((S)-1-(5-chloropyridin-2-yl)-1-(3-fluoro-5-(1,1,2,2-tetrafluoroethoxy)phenyl)-2-phenylethyl)-3-fluoropyrrolidine-1-carboxamide | 3.958 LC (4) 558.2 [M + H]+ | Procedures 3, 5, 6, 7 and 8 |

TABLE 13-continued

| Ex. No. | Structure | Name | Retention Time Min./ Molecular Mass | Prepared in the manner described in: |
|---|---|---|---|---|
| 1207 | 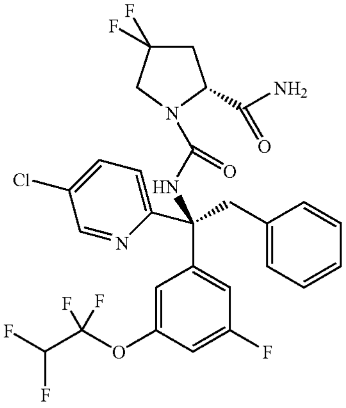 | (R)-N1-((S)-1-(5-chloropyridin-2-yl)-1-(3-fluoro-5-(1,1,2,2-tetrafluoroethoxy)phenyl)-2-phenylethyl)-4,4-difluoropyrrolidine-1,2-dicarboxamide | 3.795 LC (3) 619.3 $[M + H]^+$ | Procedures 3, 5, 6, 7 and 8 |
| 1208 | 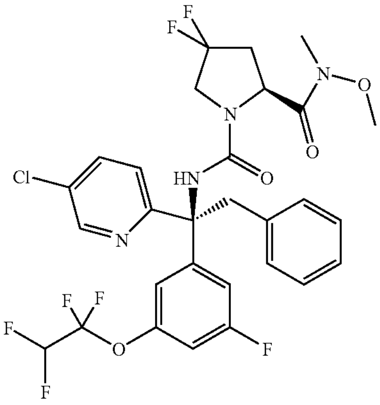 | (S)-N1-((S)-1-(5-chloropyridin-2-yl)-1-(3-fluoro-5-(1,1,2,2-tetrafluoroethoxy)phenyl)-2-phenylethyl)-4,4-difluoro-N2-methoxy-N2-methylpyrrolidine-1,2-dicarboxamide | 3.980 LC (3) 663.3 $[M + H]^+$ | Procedures 3, 5, 6, 7 and 8 |
| 1209 | 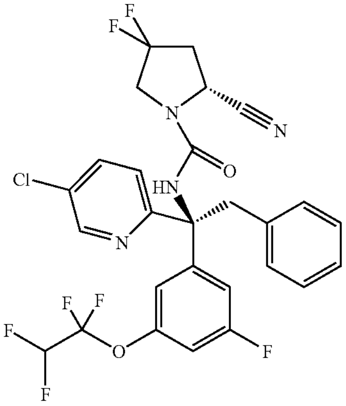 | (R)-N-((S)-1-(5-chloropyridin-2-yl)-1-(3-fluoro-5-(1,1,2,2-tetrafluoroethoxy)phenyl)-2-phenylethyl)-2-cyano-4,4-difluoropyrrolidine-1-carboxamide | 3.863 LC(3) 601.3 $[M + H]^+$ | Procedures 3, 5, 6, 7, 8 and 67 |

TABLE 14

| Ex. No. | Structure | Name | Retention Time Min./ Molecular Mass | Prepared in the manner described in: |
|---|---|---|---|---|
| 1210 | 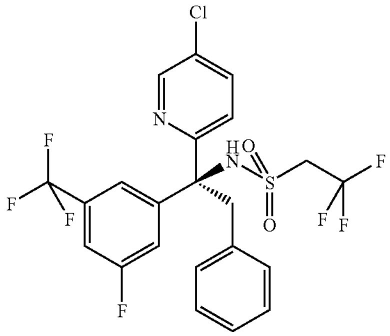 | (S)-N-(1-(5-chloropyridin-2-yl)-1-(3-fluoro-5-(trifluoromethyl)phenyl)-2-phenylethyl)-2,2,2-trifluoroethanesulfonamide | 4.181 LC 540.85 [M + H]+ | Procedures 5, 6, 7 and 9 |
| 1211 | 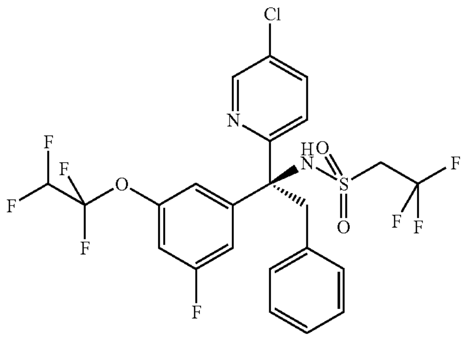 | (S)-N-(1-(5-chloropyridin-2-yl)-1-(3-fluoro-5-(1,1,2,2-tetrafluoroethoxy)phenyl)-2-phenylethyl)-2,2,2-trifluoroethanesulfonamide | 4.151 LC 588.83 [M + H]+ | Procedures 3, 5, 6, 7 and 9 |

TABLE 15

| Ex. No. | Structure | Name | Retention Time Min./ Molecular Mass | Prepared in the manner described in: |
|---|---|---|---|---|
| 1212 | 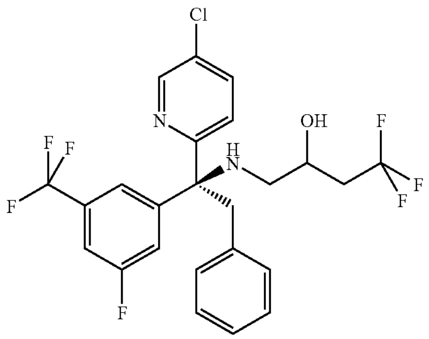 | 1-((S)-1-(5-chloropyridin-2-yl)-1-(3-fluoro-5-(trifluoromethyl)phenyl)-2-phenylethylamino)-4,4,4-trifluorobutan-2-ol | 4.075 LC 520.97 [M + H]+ Diacel Chiralcel OD 10u column, 4.6 x 250 mm isocratic elution with heptane (95%) and IPA (5%); 1 mL/min, monitoring at 254 nm. retention time: 5.80 min | Procedures 5, 6, 7 and 19 |

TABLE 15-continued

| Ex. No. | Structure | Name | Retention Time Min./ Molecular Mass | Prepared in the manner described in: |
|---|---|---|---|---|
| 1213 | 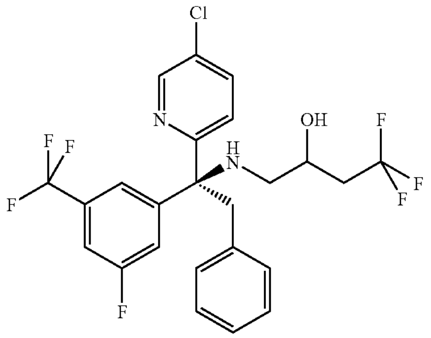 | 1-((S)-1-(5-chloropyridin-2-yl)-1-(3-fluoro-5-(trifluoromethyl)phenyl)-2-phenylethylamino)-4,4,4-trifluorobutan-2-ol | 4.101 LC 520.97 $[M + H]^+$ Diacel Chiralcel OD 10u column, 4.6 × 250 mm isocratic elution with heptane (95%) and IPA (5%); 1 mL/min, monitoring at 254 nm. retention time: 7.46 min | Procedures 5, 6, 7 and 19 |
| 1214 | 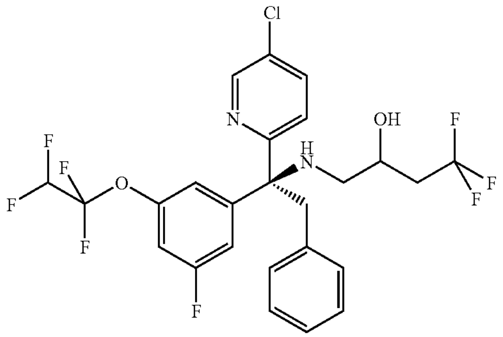 | 1-((S)-1-(5-chloropyridin-2-yl)-1-(3-fluoro-5-(1,1,2,2-tetrafluoroethoxy) phenyl)-2-phenylethylamino)-4,4,4-trifluorobutan-2-ol | 3.961 LC 568.96 $[M + H]^+$ Diacel Chiralcel OD 10u column, 4.6 × 250 mm isocratic elution with heptane (95%) and IPA (5%); 1 mL/min, monitoring at 254 nm. retention time: 7.00 min | Procedures 3, 5, 6, 7 and 19 |
| 1215 | 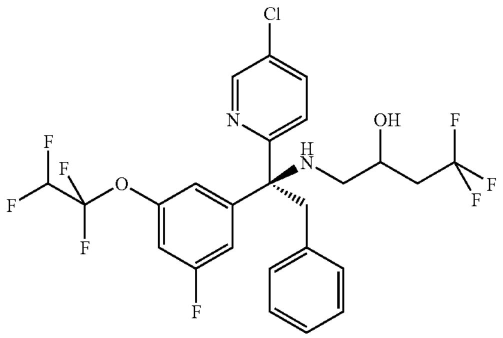 | 1-((S)-1-(5-chloropyridin-2-yl)-1-(3-fluoro-5-(1,1,2,2-tetrafluoroethoxy) phenyl)-2-phenylethylamino)-4,4,4-trifluorobutan-2-ol | 3.976 LC 568.96 $[M + H]^+$ Diacel Chiralcel OD 10u column, 4.6 × 250 mm isocratic elution with heptane (95%) and IPA (5%); 1 mL/min, monitoring at 254 nm. retention time: 8.94 min | Procedures 3, 5, 6, 7 and 19 |
| 1216 | 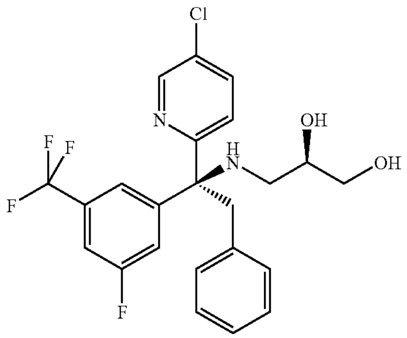 | (R)-3-((S)-1-(5-chloropyridin-2-yl)-1-(3-fluoro-5-(trifluoromethyl) phenyl)-2-phenylethylamino)propane-1,2-diol | 3.508 LC 468.97 $[M + H]^+$ | Procedures 5, 6, 7 and 19 |

TABLE 15-continued

| Ex. No. | Structure | Name | Retention Time Min./ Molecular Mass | Prepared in the manner described in: |
|---|---|---|---|---|
| 1217 | 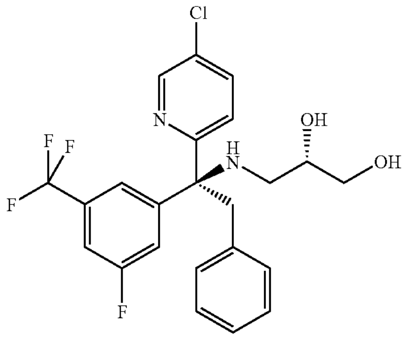 | (S)-3-((S)-1-(5-chloropyridin-2-yl)-1-(3-fluoro-5-(trifluoromethyl) phenyl)-2-phenylethylamino)propane-1,2-diol | 3.508 LC 468.96 $[M + H]^+$ | Procedures 5, 6, 7 and 19 |
| 1218 | 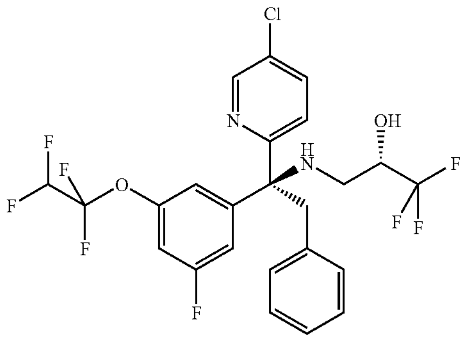 | (S)-3-((S)-1-(5-chloropyridin-2-yl)-1-(3-fluoro-5-(1,1,2,2-tetrafluoroethoxy)phenyl)-2-phenylethylamino)-1,1,1-trifluoropropan-2-ol | 4.191 LC 520.97 $[M + H]^+$ $^5$FC Chiralcel OJ 10u column, 250 × 30 mm isocratic elution with CO2 (95%) and MeOH (5%); 2 mL/min, monitoring at 220 nm. retention time 6.7 min | Procedures 3, 5, 6, 7 and 19 |
| 1219 | 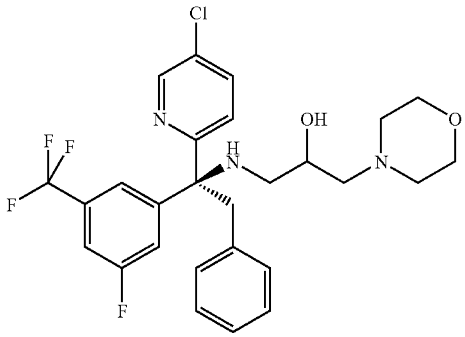 | 1-((S)-1-(5-chloropyridin-2-yl)-1-(3-fluoro-5-(trifluoromethyl)phenyl)-2-phenylethylamino)-3-morpholinopropan-2-ol | 3.486 LC 538.00 $[M + H]^+$ | Procedures 3, 5, 6, 7 and 19 |
| 1220 | 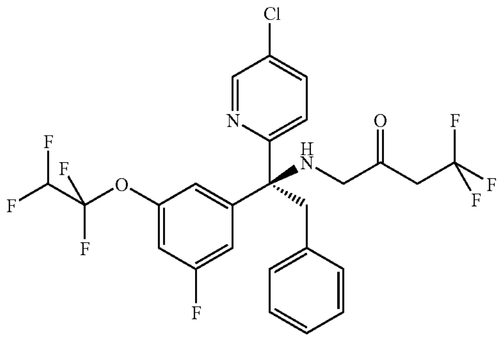 | (S)-1-(1-(5-chloropyridin-2-yl)-1-(3-fluoro-5-(1,1,2,2-tetrafluoroethoxy) phenyl)-2-phenylethylamino)-4,4,4-trifluorobutan-2-one | 4.168 LC 566.89 $[M + H]^+$ | Procedures 3, 5, 6, 7, 19 and 52 |

TABLE 15-continued

| Ex. No. | Structure | Name | Retention Time Min./ Molecular Mass | Prepared in the manner described in: |
|---|---|---|---|---|
| 1221 | 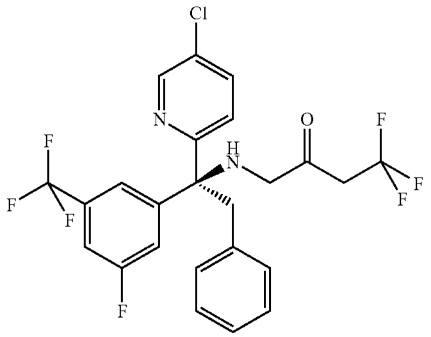 | (S)-1-(1-(5-chloropyridin-2-yl)-1-(3-fluoro-5-(trifluoromethyl)phenyl)-2-phenylethylamino)-4,4,4-trifluorobutan-2-one | 4.271 LC 518.96 $[M + H]^+$ | Procedures 5, 6, 7, 19 and 52 |
| 1222 | 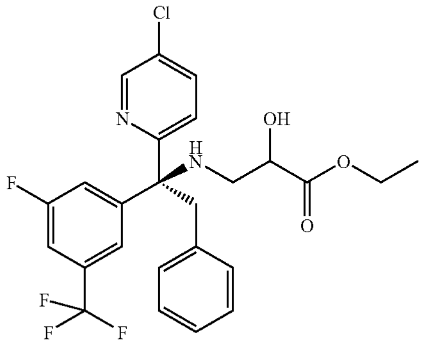 | ethyl 3-((S)-1-(5-chloropyridin-2-yl)-1-(3-fluoro-5-(trifluoromethyl) phenyl)-2-phenylethylamino)-2-hydroxypropanoate | 4.196 LC 510.88 $[M + H]^+$ | Procedures 5, 6, 7 and 19 |
| 1223 | 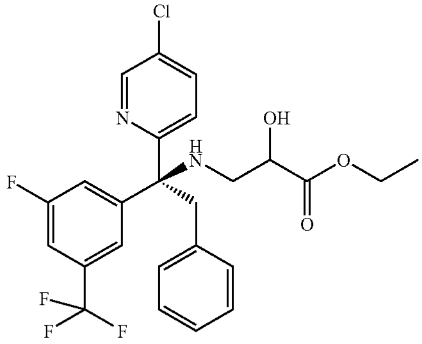 | ethyl 3-((S)-1-(5-chloropyridin-2-yl)-1-(3-fluoro-5-(trifluoromethyl) phenyl)-2-phenylethylamino)-2-hydroxypropanoate | 4.213 LC 510.88 $[M + H]^+$ | Procedures 5, 6, 7 and 19 |
| 1224 | 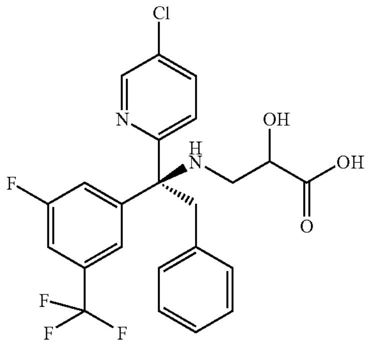 | 3-((S)-1-(5-chloropyridin-2-yl)-1-(3-fluoro-5-(trifluoromethyl)phenyl)-2-phenylethylamino)-2-hydroxypropanoic acid | 3.905 LC 4.82.95 $[M + H]^+$ | Procedures 5, 6, 7, 19 and 53 |

TABLE 15-continued

| Ex. No. | Structure | Name | Retention Time Min./ Molecular Mass | Prepared in the manner described in: |
|---|---|---|---|---|
| 1225 | 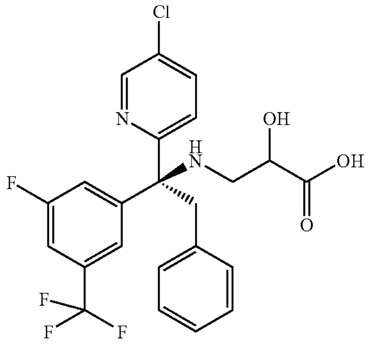 | 3-((S)-1-(5-chloropyridin-2-yl)-1-(3-fluoro-5-(trifluoromethyl)phenyl)-2-phenylethylamino)-2-hydroxypropanoic acid | 3.988 LC 4.82.91 [M + H]+ | Procedures 5, 6, 7, 19 and 53 |
| 1226 | 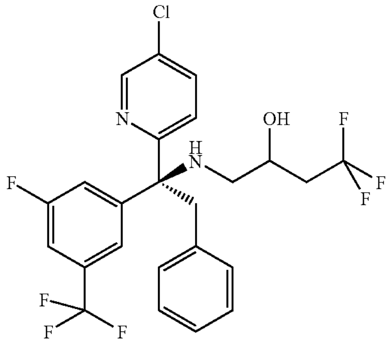 | 4,4,4-trifluoro-1-((S)-1-(3-fluoro-5-(trifluoromethyl) phenyl)-1-(5-fluoropyridin-2-yl)-2-phenylethylamino) butan-2-ol | 3.883 LC 504.97 [M + H]+ Diacel Chiralcel OD 10u column, 4.6 x 250 mm isocratic elution with heptane (95%) and IPA (5%); 1 mL/min, monitoring at 254 nm. retention time: 6.41 min | Procedures 40, 5, 6, 7 and 19 |
| 1227 | 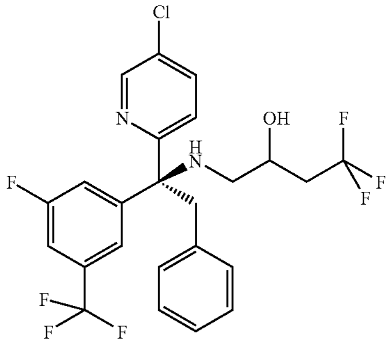 | 4,4,4-trifluoro-1-((S)-1-(3-fluoro-5-(trifluoromethyl) phenyl)-1-(5-fluoropyridin-2-yl)-2-phenylethylamino) butan-2-ol | 3.920 LC 504.97 [M + H]+ Diacel Chiralcel OD 10u column, 4.6 x 250 mm isocratic elution with heptane (95%) and IPA (5%); 1 mL/min, monitoring at 254 nm. retention time: 7.97 min | Procedures 40, 5, 6, 7 and 19 |
| 1228 | 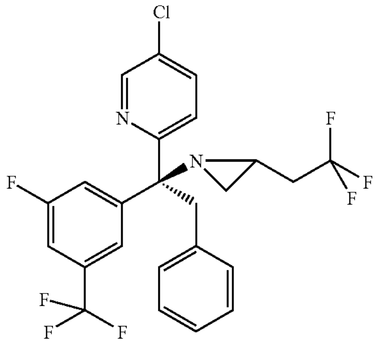 | 5-chloro-2-((S)-1-(3-fluoro-5-(trifluoromethyl)phenyl)-2-phenyl)-1-(2-(2,2,2-trifluoroethyl)aziridin-1yl) ethyl)pyridine | 4.470 LC 502.89 [M + H]+ Diacel Chiralcel OD 10u column, 4.6 x 250 mm isocratic elution with heptane (with 0.1% DEA) (95%) and EtOH/MeOH (50/50) (5%); 1 mL/min, monitoring at 254 nm. retention time: 5.48 min | Procedures 5, 6, 7 and 54 |

TABLE 15-continued

| Ex. No. | Structure | Name | Retention Time Min./ Molecular Mass | Prepared in the manner described in: |
|---|---|---|---|---|
| 1229 | 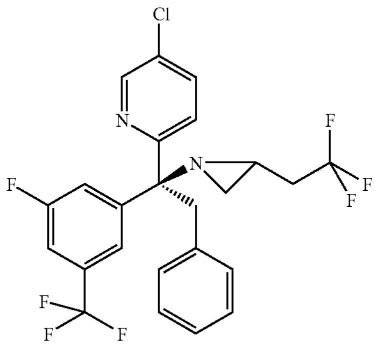 | 5-chloro-2-((S)-1-(3-fluoro-5-(trifluoromethyl)phenyl)-2-phenyl)-1-(2-(2,2,2-trifluoroethyl)aziridin-1-yl)ethyl)pyridine | 4.485 LC 502.89 [M + H]+ Diacel Chiralcel OD 10u column, 4.6 × 250 mm isocratic elution with heptane (with 0.1% DEA) (95%) and EtOH/MeOH (50/50) (5%); 1 mL/min, monitoring at 254 nm. retention time: 8.79 min | Procedures 5, 6, 7 and 54 |
| 1230 | 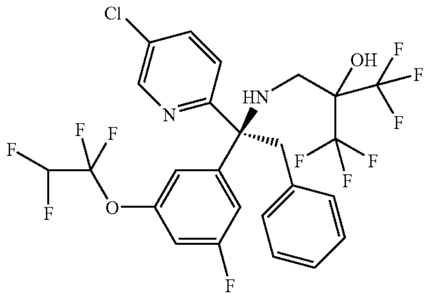 | (S)-2-((1-(5-chloropyridin-2-yl)-1-(3-fluoro-5-(1,1,2,2-tetrafluoroethoxy) phenyl)-2-phenylethylamino)methyl)-1,1,1,3,3,3-hexafluoropropan-2-ol | 4.32 LC 622.98 [M + H]+ | Procedures 3, 5, 6, 7 and 19 |

TABLE 16

| Ex. No. | Structure | Name | Retention Time Min./ Molecular Mass | Prepared in the manner described in: |
|---|---|---|---|---|
| 1231 | 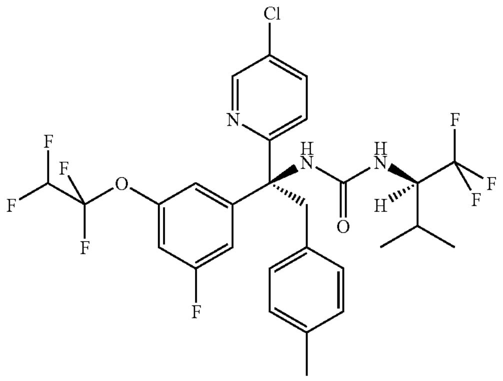 | 1-((S)-1-(5-chloropyridin-2-yl)-1-(3-fluoro-5-(1,1,2,2-tetrafluoroethoxy)phenyl)-2-p-tolylethyl)-3-((R)-1,1,1-trifluoro-3-methylbutan-2-yl) urea | 4.33 LC 624.02 [M + H]+ | Procedures 3, 5, 6, 7 and 8 |

TABLE 16-continued

| Ex. No. | Structure | Name | Retention Time Min./ Molecular Mass | Prepared in the manner described in: |
|---|---|---|---|---|
| 1232 | 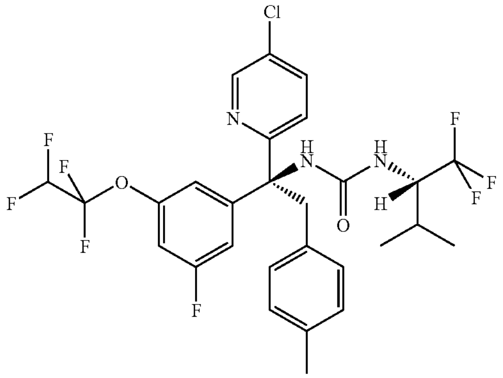 | 1-((S)-1-(5-chloropyridin-2-yl)-1-(3-fluoro-5-(1,1,2,2-tetrafluoroethoxy)phenyl)-2-p-tolylethyl)-3-((S)-1,1,1-trifluoro-3-methylbutan-2-yl) urea | 4.32 LC 624.02 $[M + H]^+$ | Procedures 3, 5, 6, 7 and 8 |
| 1233 | 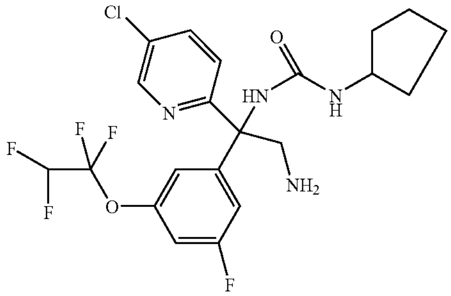 | 1-(2-amino-1-(5-chloropyridin-2-yl)-1-(3-fluoro-5-(1,1,2,2-tetrafluoroethoxy)phenyl)ethyl)-3-cyclopentylurea | 3.26 LC 493.17 $[M + H]^+$ | Procedures 3, 5, 6, 61, 23, and 62 |
| 1234 | 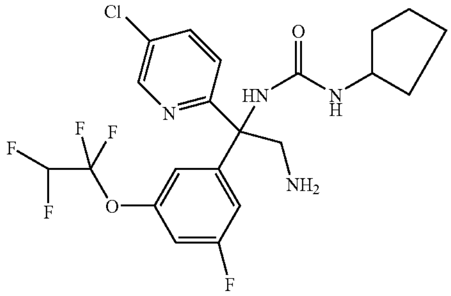 | 1-((5-chloropyridin-2-yl)(3-fluoro-5-(1,1,2,2-tetrafluoroethoxy)phenyl) methyl)-3-cyclopentylurea | 3.75 LC 464.18 $[M + H]^+$ | Procedures 3, 5, 6, 61, 23 and 62 |
| 1235 | 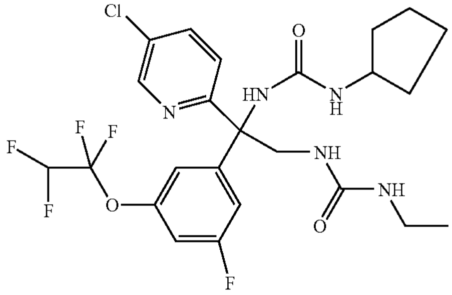 | N-(2-(5-chloropyridin-2-yl)-2-(3-cyclopentylureido)-2-(3-fluoro-5-(1,1,2,2-tetrafluoroethoxy)phenyl)ethyl) ethylurea | 3.71 LC 564.13 $[M + H]^+$ | Procedures 3, 5, 6, 61, 62 and 2 |

TABLE 16-continued

| Ex. No. | Structure | Name | Retention Time Min./ Molecular Mass | Prepared in the manner described in: |
|---|---|---|---|---|
| 1236 | 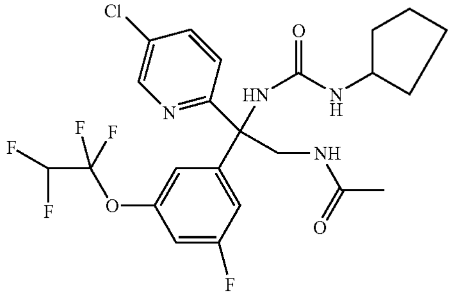 | N-(2-(5-chloropyridin-2-yl)-2-(3-cyclopentylureido)-2-(3-fluoro-5-(1,1,2,2-tetrafluoroethoxy)phenyl)ethyl) acetamide | 3.63 LC 535.11 $[M+H]^+$ | Procedures 3, 5, 6, 61, 62 and 4 |
| 1237 | 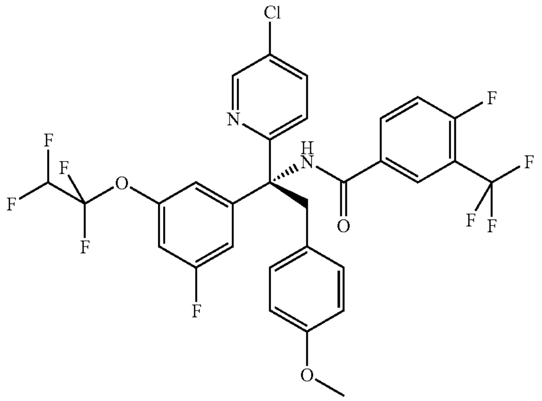 | (R)-N-(1-(5-chloropyridin-2-yl)-1-(3-fluoro-5-(1,1,2,2-tetrafluoroethoxy)phenyl)-2-(4-methoxyphenyl)ethyl)-4-fluoro-3-(trifluoromethyl)benzamide | 4.388 LC (1) 662.85 $[M+H]^+$ | Procedures 3, 5, 6, 7 and 4 |
| 1238 | 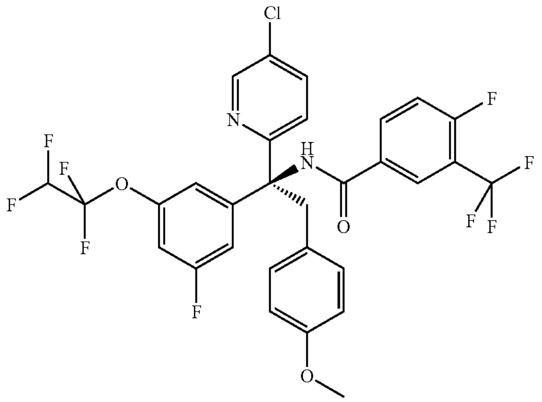 | (S)-N-(1-(5-chloropyridin-2-yl)-1-(3-fluoro-5-(1,1,2,2-tetrafluoroethoxy)phenyl)-2-(4-methoxyphenyl)ethyl)-4-fluoro-3-(trifluoromethyl)benzamide | 4.388 LC (1) 662.85 $[M+H]^+$ | Procedures 3, 5, 6, 7 and 4 |
| 1239 | 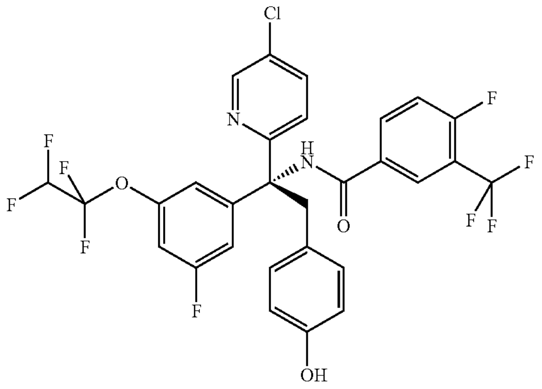 | (R)-N-(1-(5-chloropyridin-2-yl)-1-(3-fluoro-5-(1,1,2,2-tetrafluoroethoxy)phenyl)-2-(4-hydroxyphenyl)ethyl)-4-fluoro-3-(trifluoromethyl)benzamide | 4.23 LC (1) 648.81 $[M+H]^+$ | Procedures 3, 5, 6, 7, 4 and 14 |

TABLE 16-continued

| Ex. No. | Structure | Name | Retention Time Min./ Molecular Mass | Prepared in the manner described in: |
|---|---|---|---|---|
| 1240 | 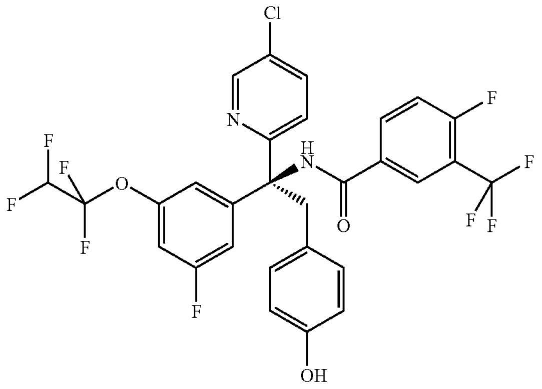 | (S)-N-(1-(5-chloropyridin-2-yl)-1-(3-fluoro-5-(1,1,2,2-tetrafluoroethoxy)phenyl)-2-(4-hydroxyphenyl)ethyl)-4-fluoro-3-(trifluoromethyl)benzamide | 4.226 LC (1) 648.81 $[M + H]^+$ | Procedure 3, 5, 6, 7, 4 and 14 |
| 1241 | 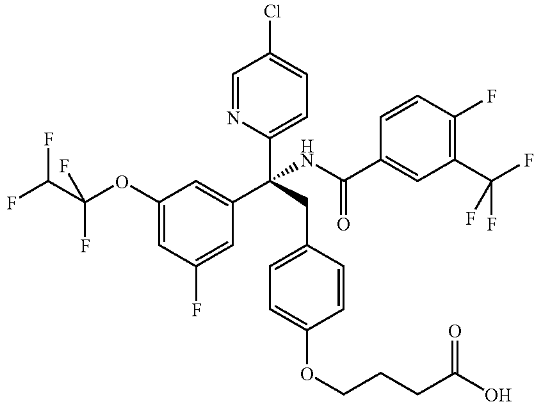 | (R)-4-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenoxy)butanoic acid | 4.290 LC (1) 735.1 $[M + H]^+$ | Procedures 3, 5, 6, 7, 4, 14, 72 and 53 |
| 1242 | 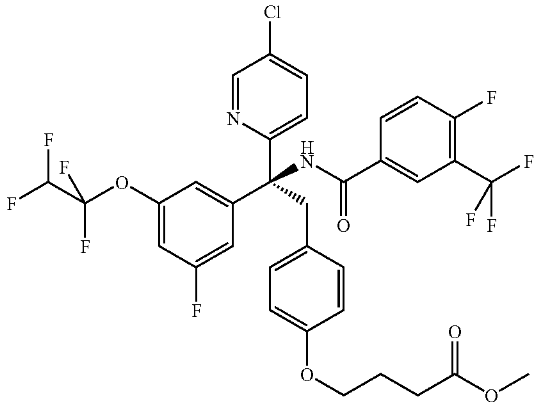 | (S)-methyl 4-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenoxy)butanoate | 4.426 LC (1) 749.1 $[M + H]^+$ | Procedures 3, 5, 6, 7, 4, 14 and 72 |

TABLE 16-continued

| Ex. No. | Structure | Name | Retention Time Min./ Molecular Mass | Prepared in the manner described in: |
|---|---|---|---|---|
| 1243 | 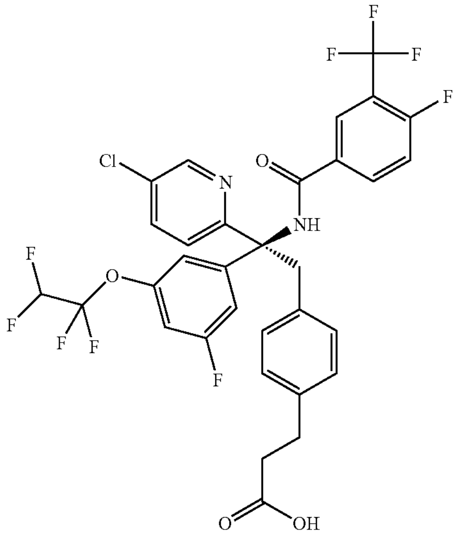 | (S)-3-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenyl)propanoic acid | 1.46 LC (2) (70-100% B) 705.1 [M + H]$^+$ | Procedures 3, 5, 6, 7, 4, 57 and 58 |
| 1244 | 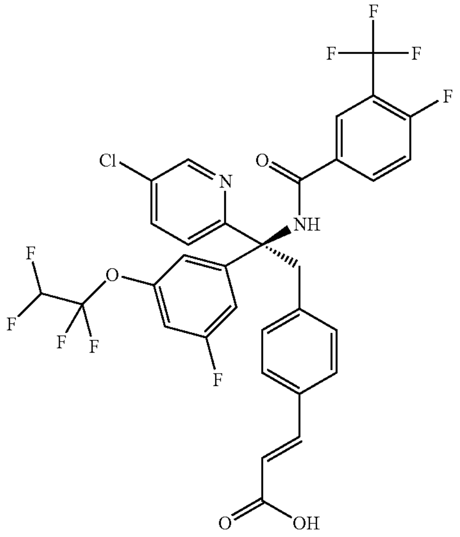 | (S,E)-3-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenyl)acrylic acid | 1.45 LC (2) (70-100% B) 703.1 [M + H]$^+$ | Procedures 3, 5, 6, 7, 4, 57 and 58 |

TABLE 16-continued

| Ex. No. | Structure | Name | Retention Time Min./ Molecular Mass | Prepared in the manner described in: |
|---|---|---|---|---|
| 1245 | 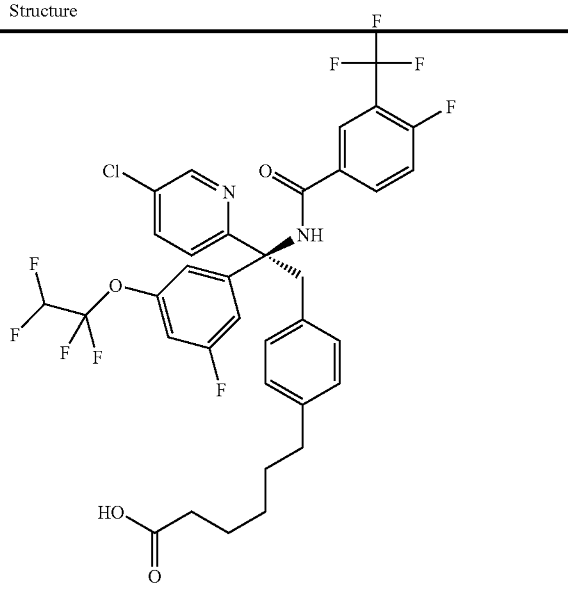 | (S)-6-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenyl)hexanoic acid | 1.75 LC (2) (70-100% B) 747.1 $[M + H]^+$ | Procedures 3, 5, 6, 7, 4, 57 and 58 |
| 1246 | 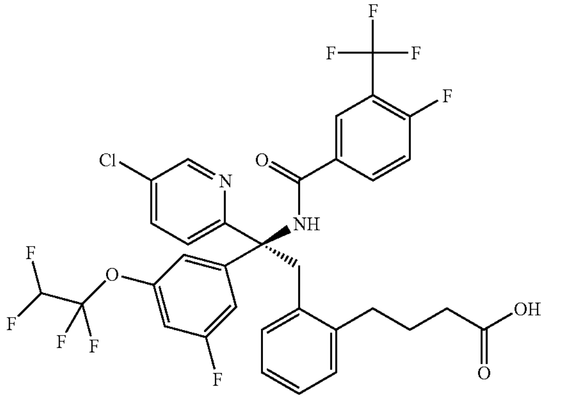 | (S)-4-(2-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenyl)butanoic acid | 1.53 LC (2) (70-100% B) 719.1 $[M + H]^+$ | Procedures 3, 5, 6, 7, 4, 57 and 58 |
| 1247 | 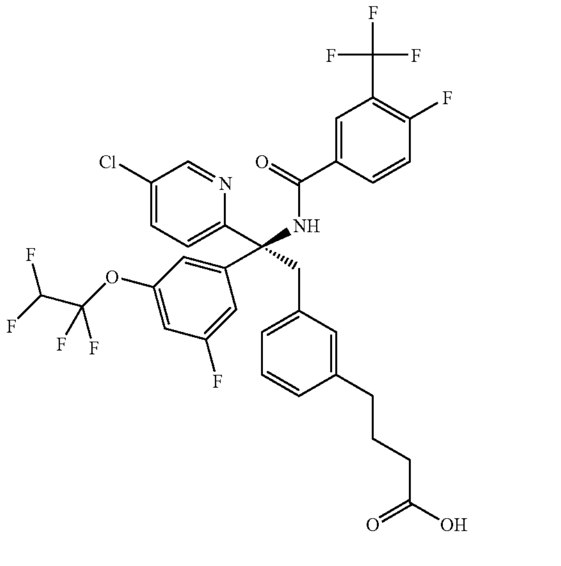 | (S)-4-(3-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenyl)butanoic acid | 1.53 LC (2) (70-100% B) 719.1 $[M + H]^+$ | Procedures 3, 5, 6, 7, 4, 57 and 58 |

TABLE 16-continued

| Ex. No. | Structure | Name | Retention Time Min./ Molecular Mass | Prepared in the manner described in: |
|---|---|---|---|---|
| 1248 | 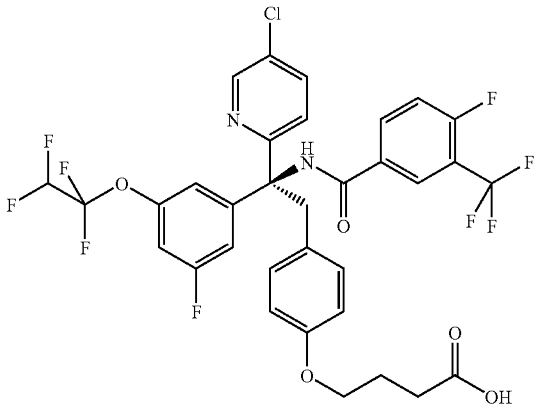 | (S)-4-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenoxy)butanoic acid | 4.305 LC (1) 735.0 [M + H]$^+$ | Procedure 3, 5, 6, 7, 4, 14, 72 and 53 |
| 1249 | 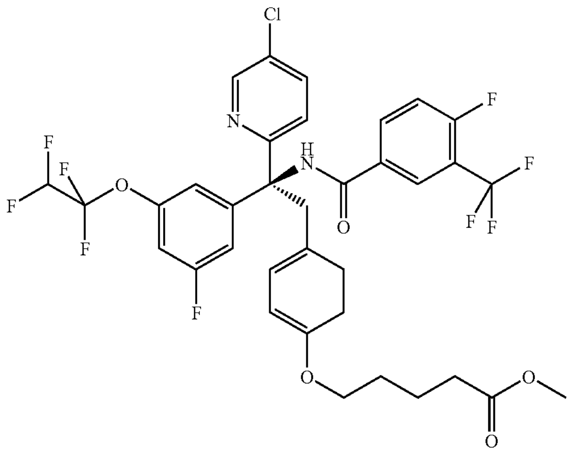 | (S)-methyl 5-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenoxy)pentanoate | 2.253 LC (2) 763.2 [M + H]$^+$ | Procedure 3, 5, 6, 7, 4, 14 and 72 |
| 1250 | 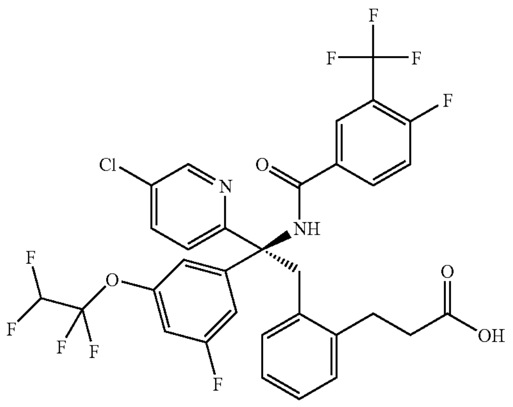 | (S)-3-(2-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenyl)propanoic acid | 2.18 LC (2) 705.2 [M + H]$^+$ | Procedures 3, 5, 6, 7, 4, 57 and 58 |

TABLE 16-continued

| Ex. No. | Structure | Name | Retention Time Min./ Molecular Mass | Prepared in the manner described in: |
|---|---|---|---|---|
| 1251 | 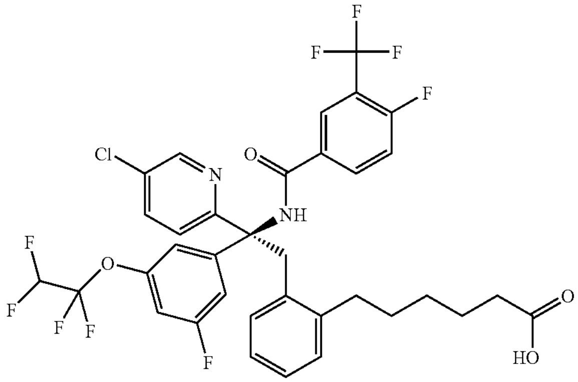 | (S)-6-(2-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenyl)pentanoic acid | 2.23 LC (2) 747.3 $[M + H]^+$ | Procedures 3, 5, 6, 7, 4, 57 and 58 |
| 1252 | 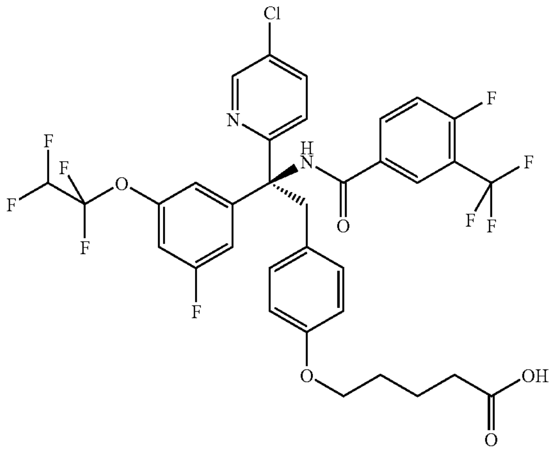 | (S)-5-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl)phenoxy)pentanoic acid | 4.328 LC 749.2 $[M + H]^+$ | Procedure 3, 5, 6, 7, 4, 14, 72 and 53 |
| 1253 | 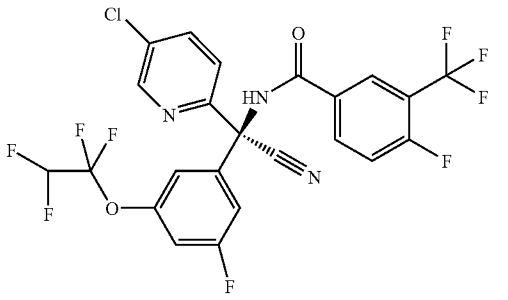 | (S)-N-((5-chloropyridin-2-yl)(cyano)(3-fluoro-5-(1,1,2,2-tetrafluoroethoxy)phenyl)methyl)-4-fluoro-3-(trifluoromethyl)benzamide | 3.95 LC 567.93 $[M + H]^+$ | Procedures 3, 5, 6, 61, 7 and 4 |

TABLE 16-continued

| Ex. No. | Structure | Name | Retention Time Min./ Molecular Mass | Prepared in the manner described in: |
|---|---|---|---|---|
| 1254 | 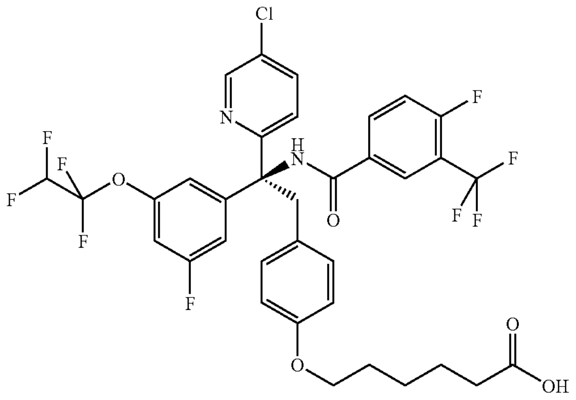 | (S)-6-(4-(2-(5-chloropyridin-2-yl)-2-(4-fluoro-3-(trifluoromethyl)benzamido)-2-(3-fluoro-5-(1,1,2,2-tetrafluoroethoxy)phenyl)ethyl) phenoxy)hexanoic acid | 2.24 LC (2) 763.1 $[M + H]^+$ | Procedures 3, 5, 6, 7, 4, 14, 72 and 53 |

TABLE 17

| Ex. No. | Structure | Name | Retention Time Min./ Molecular Mass | Prepared in the manner described in: |
|---|---|---|---|---|
| 1255 | 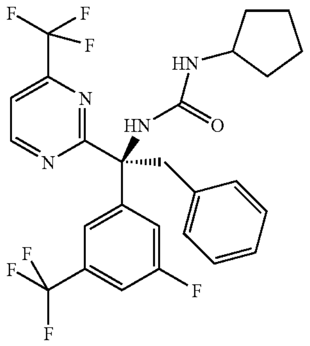 | (S)-1-cyclopentyl-3-(1-(3-fluoro-5-(trifluoromethyl)phenyl)-2-phenyl-1-(4-(trifluoromethyl) pyrimidin-2-yl)ethyl)urea | 4.13 LC 541.23 $[M + H]^+$ | Procedures 97, 98, 6, 7, 59 and 60 |
| 1256 | 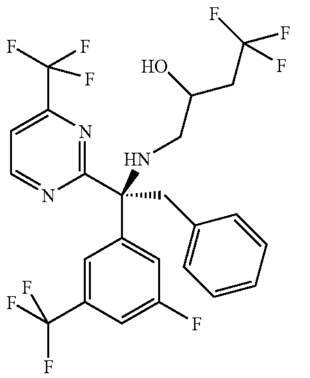 | 4,4,4-trifluoro-1-((S)-1-(3-fluoro-5-(trifluoromethyl) phenyl)-2-phenyl-1-(4-(trifluoromethyl)pyrimidin-2-yl)ethylamino)butan-2-ol | 3.77 LC 556.33 $[M + H]^+$ | Procedures 97, 98, 6, 7, and 19 |

TABLE 17-continued

| Ex. No. | Structure | Name | Retention Time Min./ Molecular Mass | Prepared in the manner described in: |
|---|---|---|---|---|
| 1257 | 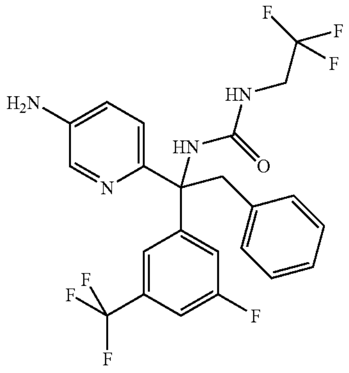 | 1-(1-(5-aminopyridin-2-yl)-1-(3-fluoro-5-(trifluoromethyl) phenyl)-2-phenylethyl)-3-(2,2,2-trifluoroethyl)urea | 3.24 LC 501.24 $[M + H]^+$ | Procedures 1, 2, 45 and 16 |
| 1258 | 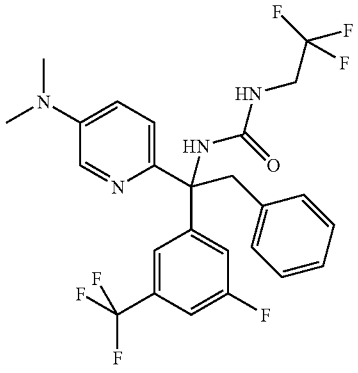 | 1-(1-(5-(dimethylamino)pyridin-2-yl)-1-(3-fluoro-5-(trifluoromethyl)phenyl)-2-phenylethyl)-3-(2,2,2-trifluoroethyl)urea | 3.38 LC 529.2 $[M + H]^+$ | Procedures 1, 2, 39 and 16 |
| 1259 | 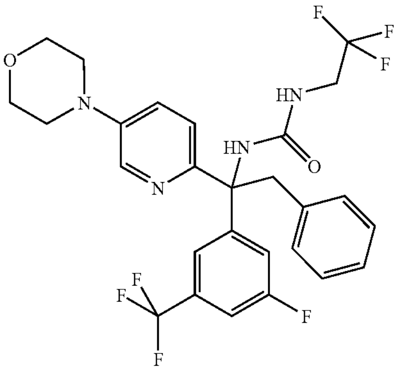 | 1-(1-(3-fluoro-5-(trifluoromethyl)phenyl)-1-(5-morpholinopyridin-2-yl)-2-phenylethyl)-3-(2,2,2-trifluoroethyl)urea | 3.62 LC 571.33 $[M + H]^+$ | Procedures 1, 2, 39 and 16 |
| 1260 | 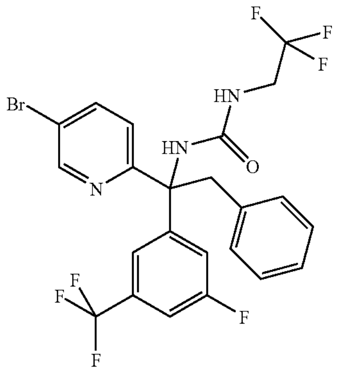 | 1-(1-(5-bromopyridin-2-yl)-1-(3-fluoro-5-(trifluoromethyl) phenyl)-2-phenylethyl)-3-(2,2,2-trifluoroethyl)urea | 4.06 LC 566.12 $[M + H]^+$ | Procedures 1, 2 and 16 |

TABLE 17-continued

| Ex. No. | Structure | Name | Retention Time Min./ Molecular Mass | Prepared in the manner described in: |
|---|---|---|---|---|
| 1261 | 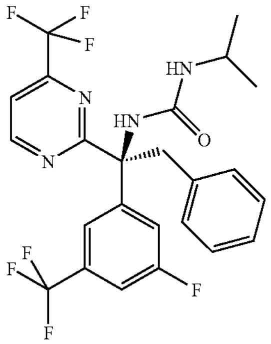 | (S)-1-(1-(3-fluoro-5-(trifluoromethyl)phenyl)-2-phenyl-1-(4-(trifluoromethyl) pyrimidin-2-yl)ethyl)-3-isopropylurea | 4.02 LC 515.21 [M + H]+ | Procedures 97, 98, 6, 7, 59 and 60 |
| 1262 | 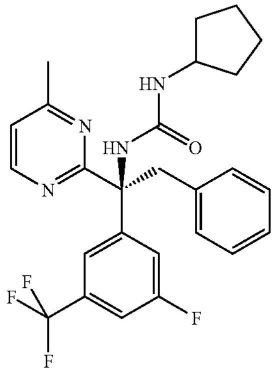 | (S)-1-cyclopentyl-3-(1-(3-fluoro-5-(trifluoromethyl)phenyl)-1-(4-methylpyrimidin-2-yl)-2-phenylethyl)urea | 3.361 LC 487.27 [M + H]+ | Procedure 44 |
| 1263 | 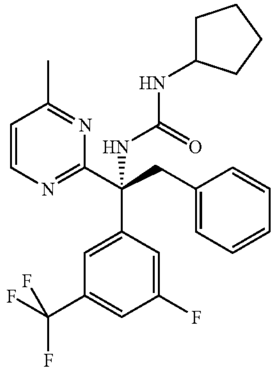 | (R)-1-cyclopentyl-3-(1-(3-fluoro-5-(trifluoromethyl)phenyl)-1-(4-methylpyrimidin-2-yl)-2-phenylethyl)urea | 3.362 LC 487.27 [M + H]+ | Procedure 44 |
| 1264 | 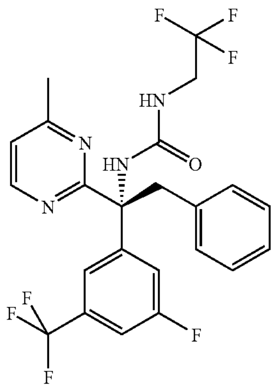 | (R)-1-(1-(3-fluoro-5-(trifluoromethyl)phenyl)-1-(4-methylpyrimidin-2-yl)-2-phenylethyl)-3-(2,2,2-trifluoroethyl)urea | 3.23 LC 501.24 [M + H]+ | Procedures 44 and 16 |

TABLE 17-continued

| Ex. No. | Structure | Name | Retention Time Min./ Molecular Mass | Prepared in the manner described in: |
|---|---|---|---|---|
| 1265 | 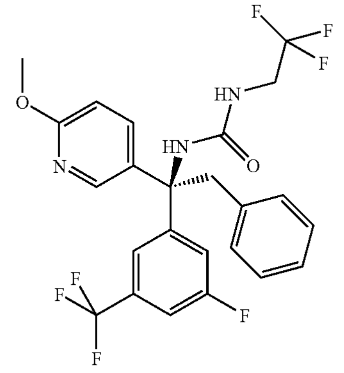 | (S)-1-(1-(3-fluoro-5-(trifluoromethyl)phenyl)-1-(6-methoxypyridin-3-yl)-2-phenylethyl)-3-(2,2,2-trifluoroethyl)urea | 3.90 LC (1) 516.11 [M + H]+ | Procedures 5, 6, 7, 59 and 60 |

TABLE 18

| Ex. No. | Structure | Name | Retention Time Min./ Molecular Mass | Prepared in the manner described in: |
|---|---|---|---|---|
| 1266 | 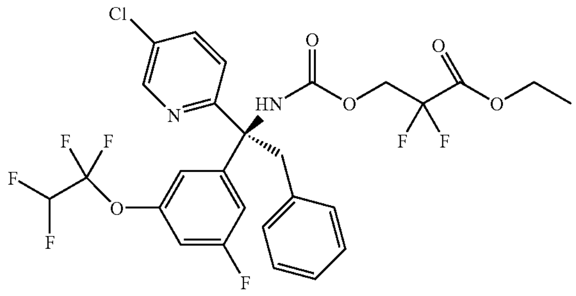 | (S)-ethyl 3-(1-(5-chloropyridin-2-yl)-1-(3-fluoro-5-(1,1,2,2-tetrafluoroethoxy)phenyl)-2-phenylethylcarbamoyloxy)-2,2-difluoropropanoate | 4.14 LC 623.32 [M + H]+ | Procedures 3, 5, 6, 7 and 46 |

TABLE 19

| Ex. No. | Structure | Name | Retention Time Min./ Molecular Mass | Prepared in the manner described in: |
|---|---|---|---|---|
| 1267 | 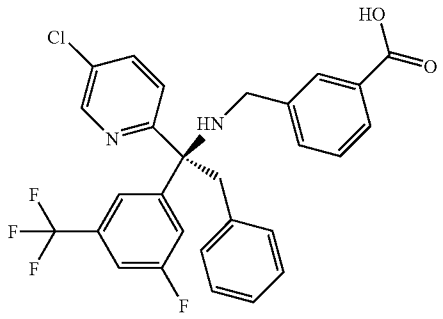 | (S)-3-((1-(5-chloropyridin-2-yl)-1-(3-fluoro-5-(trifluoromethyl) phenyl)-2-phenylethylamino) methyl)benzoic acid | 3.58 LC 529.0 [M + H]+ | Procedures 5, 6, 7 and 48 |

TABLE 19-continued

| Ex. No. | Structure | Name | Retention Time Min./ Molecular Mass | Prepared in the manner described in: |
| --- | --- | --- | --- | --- |
| 1268 | 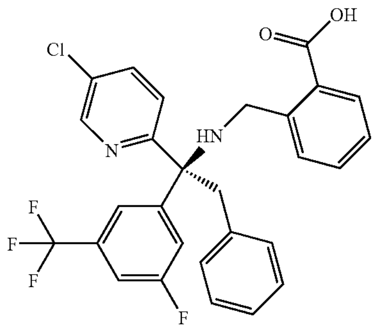 | (S)-2-((1-(5-chloropyridin-2-yl)-1-(3-fluoro-5-(trifluoromethyl) phenyl)-2-phenylethylamino) methyl)benzoic acid | 3.36 LC 529.0 $[M + H]^+$ | Procedures 5, 6, 7 and 48 |
| 1269 | 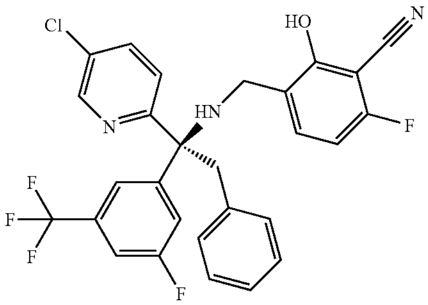 | (S)-3-((1-(5-chloropyridin-2-yl)-1-(3-fluoro-5-(trifluoromethyl) phenyl)-2-phenylethylamino) methyl)-6-fluoro-2-hydroxybenzonitrile | 3.95 LC 544.27 $[M + H]^+$ | Procedures 5, 6, 7 and 48 |
| 1270 | 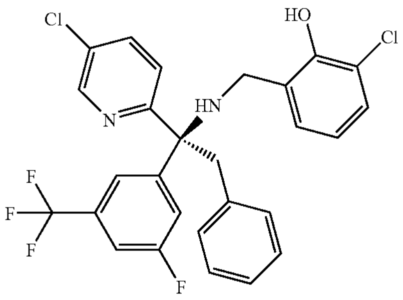 | (S)-2-chloro-6-((1-(5-chloropyridin-2-yl)-1-(3-fluoro-5-(trifluoromethyl)phenyl)-2-phenylethylamino)methyl)phenol | 3.69 LC 535.17 $[M + H]^+$ | Procedures 5, 6, 7 and 48 |
| 1271 | 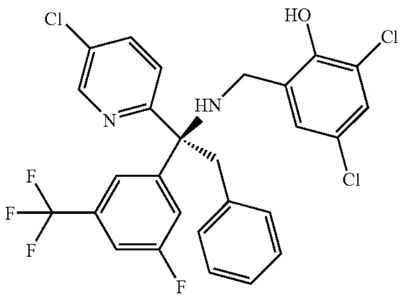 | (S)-2,4-dichloro-6-((1-(5-chloropyridin-2-yl)-1-(3-fluoro-5-(trifluoromethyl)phenyl)-2-phenylethylamino)methyl)phenol | 4.10 LC 569.14 $[M + H]^+$ | Procedures 5, 6, 7 and 48 |

TABLE 19-continued

| Ex. No. | Structure | Name | Retention Time Min./ Molecular Mass | Prepared in the manner described in: |
|---|---|---|---|---|
| 1272 | 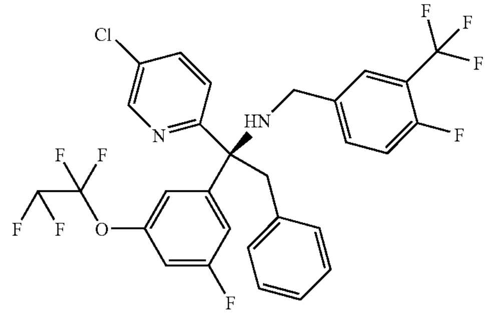 | (S)-1-(5-chloropyridin-2-yl)-N-(4-fluoro-3-(trifluoromethyl) benzyl)-1-(3-fluoro-5-(1,1,2,2-tetrafluoroethoxy)phenyl)-2-phenylethanamine | 2.06 LC (2) 619.3 $[M+H]^+$ | Procedures 3, 5, 6, 7 and 48 |

It is noted that the proceeding examples, while illustrative of the present invention, are not in sequential order and some example numbers may be missing.

What is claimed is:

1. A compound of formula Ia or Ib

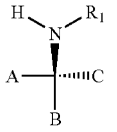

Ia or

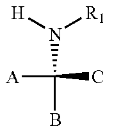

Ib or stereoisomers or pharmaceutically acceptable salt forms thereof, wherein:

A is heteroaryl, which is substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$alkyl, 15) —$COR_6$, 16) =O, 17) —$S(O)_pR_6$, 18) —$SO_2NHR_6$, 19) —$COOR_6$, 20) —$NHC(CN)NHR_6$, 21) —$CONR_6R_6$; and 27) cycloalkyl, which may be optionally substituted with one or more $R_{20}$'S;

B is phenyl, which is substituted with more than one substituent selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo$(C_1-C_6)$alkyl, 14) —$COR_6$, 15) —$S(O)_pR_6$, 16) —$SO_2NHR_6$, 17) —$COOR_6$, 18) —$NHC(CN)NHR_6$, 19) —$CONR_6R_6$; and 20) cycloalkyl, which may be optionally substituted with one or more $R_{20}$'s;

C is alkyl, which is substituted with aryl, which may be optionally substituted with one or more $R_{20}$'s;

$R_1$ is —$C(O)R_3$;

$R_3$ is (a) aryl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo$(C_1-C_6)$ alkyl, 15) —$CONR_6R_6$, 16) $(C_2-C_6)$-alkenyl, 17) =O, 18) $(C_2-C_6)$-alkynyl, 19) —$COR_6$, 20) —$S(O)_pR_6$, 21) —$SO_2NHR_6$, 22) —$COOR_6$, 23) —$NHC(CN)NHR_6$; and 24) cycloalkyl, which may be optionally substituted with one or more $R_{20}$'s; or (b) alkenyl, which may be optionally substituted with one or more substituents selected from the group consisting of: 1) halo, 2) $(C_1-C_6)$-alkyl, which may be optionally substituted with one or more $R_{20}$'s, 3) —$OR_6$, 4) $(C_1-C_6)$-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12)

heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, 22) —$NHC(CN)NHR_6$; and 23) cycloalkyl, which may be optionally substituted with one or more $R_{20}$'S;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$) alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —$NHC(CN)NHR_{36}$; and 23) cycloalkyl, which may be optionally substituted with one or more $R_{20}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —$NHC(CN)NHR_{36}$; and 25) cycloalkyl, which may be optionally substituted with one or more $R_{20}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN) $NHR_{36}$; and 26) cycloalkyl, which may be optionally substituted with one or more $R_{20}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN) $NHR_{36}$; and 26) cycloalkyl, which may be optionally substituted with one or more $R_{20}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —$NHC(CN)NHR_{36}$; and 26) cycloalkyl, which may be optionally substituted with one or more $R_{20}$'s; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —$[(C{=}O)O_r]_s$aryl, wherein the aryl may be optionally substituted with one or more $R_{20}$'s; (c) —$[(C{=}O)O_r]_s$($C_2$-$C_8$)-alkenyl, wherein the alkenyl may be optionally substituted with one or more $R_{20}$'s; (d) —$[(C{=}O)O_r]_s$($C_1$-$C_8$) alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; (l) —$NHC(CN)NHR_{26}$; or m) —$[(C{=}O)O_r]_s$cycloalkyl, wherein the cycloalkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s;

(k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)$NHR_{26}$; (w) cycloalkyl, which may be optionally substituted with one or more $R_{21}$'s; (x) cycloalkylalkyl, which may be optionally substituted with one or more $R_{21}$'s; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —NHC(CN)$NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$) alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, 22) —NHC(CN)$NHR_{36}$; and 23) cycloalkyl, which may be optionally substituted with one or more $R_{40}$'s;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, 24) —NHC(CN)$NHR_{36}$; and 25) cycloalkyl, which may be optionally substituted with one or more $R_{40}$'s;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$; and 26) cycloalkyl, which may be optionally substituted with one or more $R_{40}$'s;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$; and 26) cycloalkyl, which may be optionally substituted with one or more $R_{40}$'s;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, 25) —NHC(CN)$NHR_{36}$; and 26) cycloalkyl, which may be optionally substituted with one or more $R_{40}$'s; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl, —$CONR_{46}R_{46}$, alkynyl, —$COR_{36}$, —$S(O)_pR_{36}$, —$SO_2NHR_{36}$, —$COOR_{36}$, —C(CN)$NHR_{36}$, or cycloalkyl, wherein the aryl, alkyl, alkenyl, cycloalkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, ═O, alkynyl, cycloalkyl, cycloalkylalkyl, —$COR_{49}$, —$S(O)_pR_{49}$, —$SO_2NHR_{49}$, —$COOR_{49}$, or —$NHC(CN)NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2;

excluding compounds having the following formula:

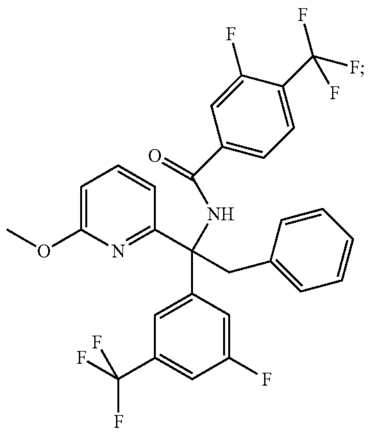

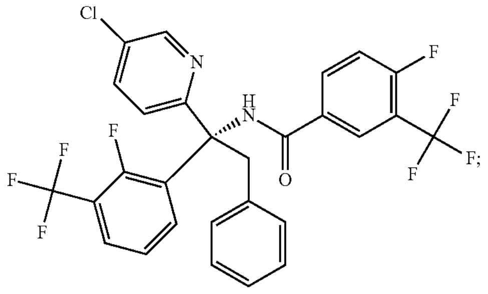

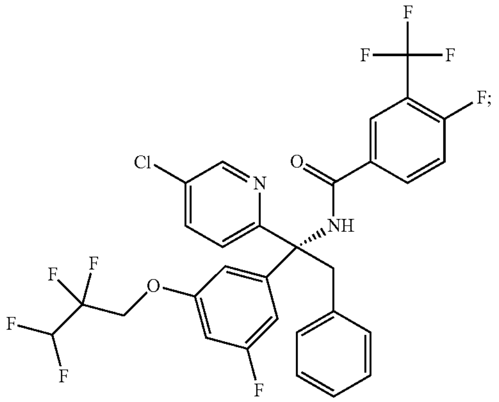

-continued

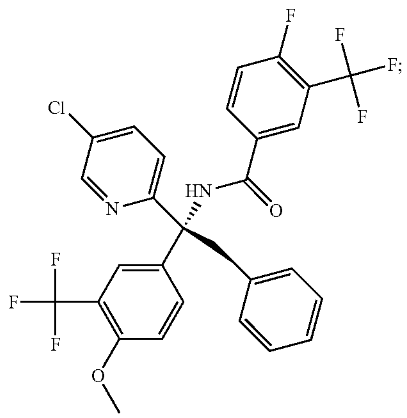

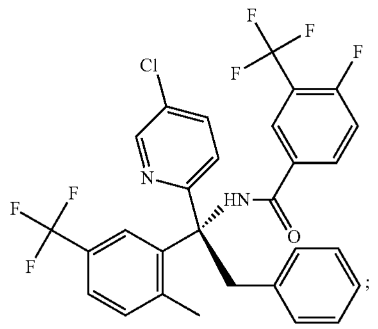

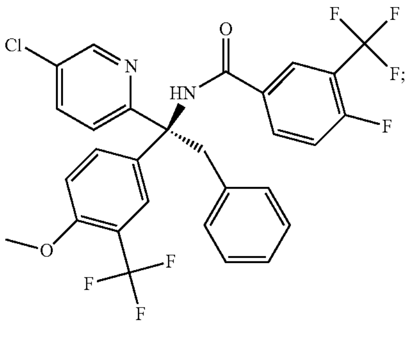

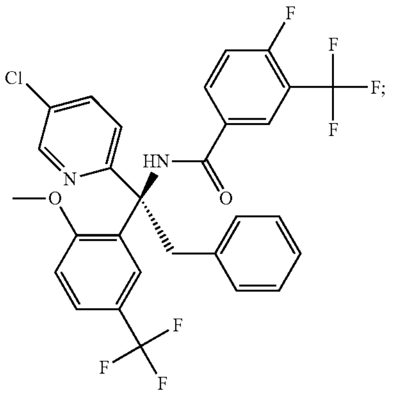

-continued
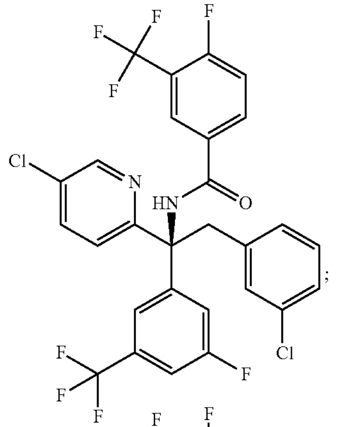
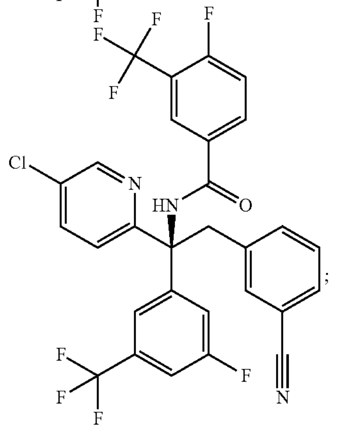
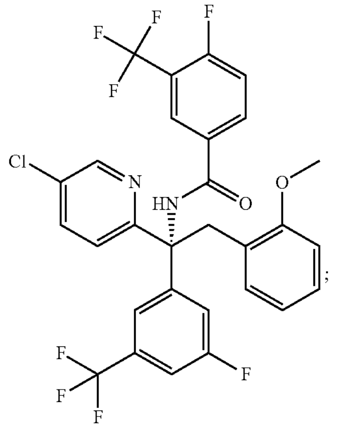
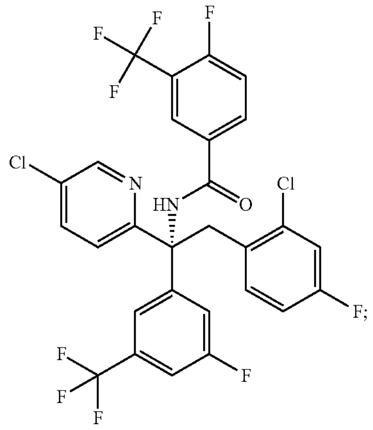
-continued
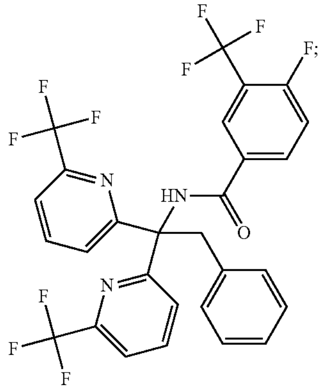
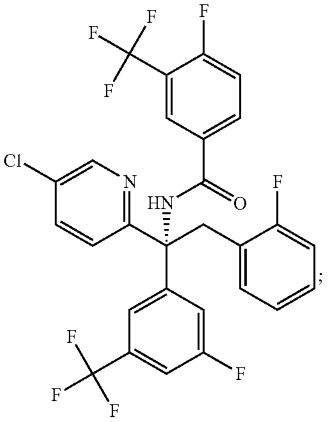
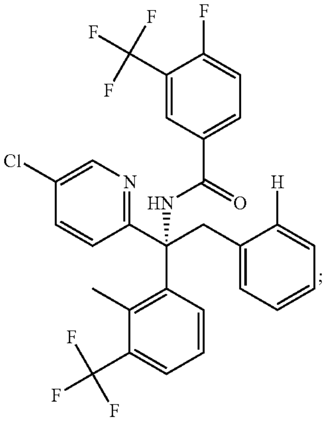
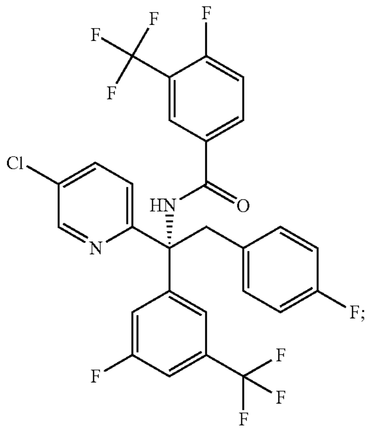

-continued

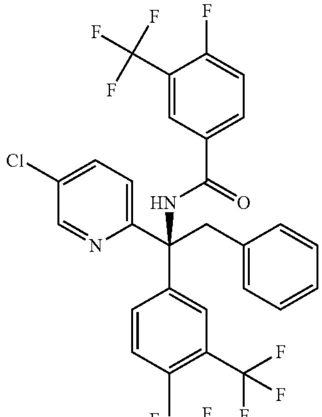

;

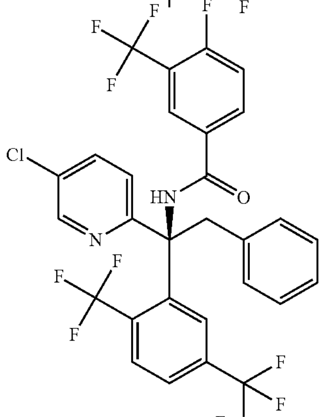

;

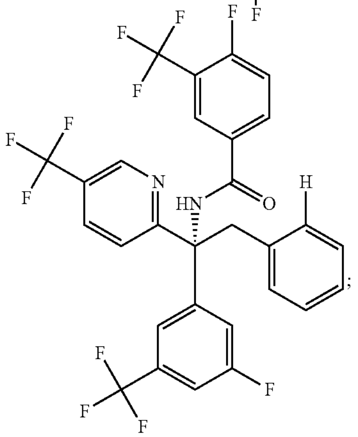

;

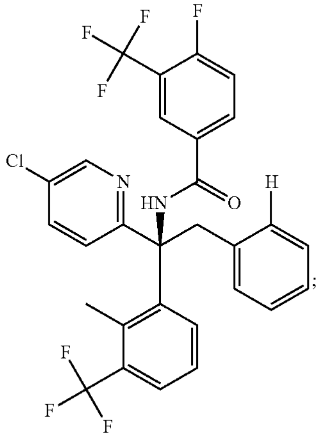

; and

-continued

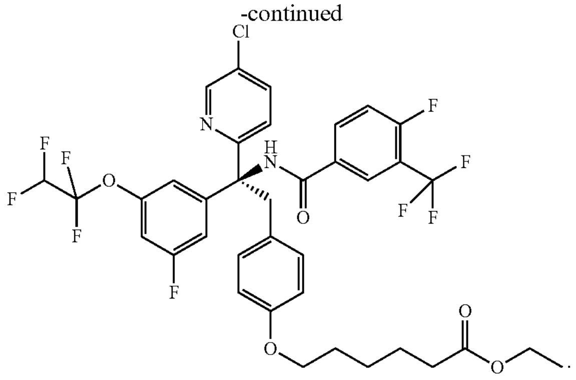

2. A compound of claim 1, wherein the compound is a compound of formula Ia

Ia

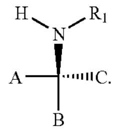

3. A compound of claim 1, wherein:

A is heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$COR_6$, 16) =O, 17) —$S(O)_pR_6$, 18) —$SO_2NHR_6$, 19) —$COOR_6$, and 20) —$NHC(CN)NHR_6$;

B is phenyl, which is substituted with more than one substituent selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) —$COR_6$, 15) —$S(O)_pR_6$, 16) —$SO_2NHR_6$, 17) —$COOR_6$, and 18) —$NHC(CN)NHR_6$;

C is alkyl, which is substituted with aryl, which may be optionally substituted with one or more $R_{20}$'s;

$R_1$ is —C(O)$R_3$;

$R_3$ is:

(a) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$CONR_6R_6$, 16) ($C_2$-$C_6$)-alkenyl, 17) ═O, 18) ($C_2$-$C_6$)-alkynyl, 19) —$COR_6$, 20) —$S(O)_pR_6$, 21) —$SO_2NHR_6$, 22) —$COOR_6$, and 23) —NHC(CN)$NHR_6$; or (b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —NHC(CN)$NHR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$) alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_{1-C6}$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —[(C═O)O$_r$]$_s$aryl, wherein the aryl may be optionally substituted with one or more $R_{20}$'s; (c) —[(C═O)O$_r$]$_s$($C_2$-$C_8$)-alkenyl, wherein the alkenyl may be optionally substituted with one or more $R_{20}$'s; (d) —[(C═O)O$_r$]$_s$($C_1$-$C_8$) alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; or (l) —NHC(CN) $NHR_{26}$;

or $R_9$ and $R_{10}$ are taken together with the nitrogen to which both are attached to form a 3-to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$ 's; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) ═O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)$NHR_{26}$; (w) cycloalkyl, which may be optionally substituted with one or more $R_{21}$'s; (x) cycloalkylalkyl, which may be optionally substituted with one or more $R_{21}$ 's; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ═O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —NHC(CN)$NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$) alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) ═O, 20) ($C_2$-$C_6$)-alkynyl, 21)

—$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C═O)$O_r$]$_s$aryl, —[(C═O)$O_r$]$_s$alkenyl, —[(C═O)$O_r$]$_s$alkyl, heterocyclyl, —$CONR_{46}R_{46}$, alkynyl, —$COR_{36}$, —$S(O)_pR_{36}$, —$SO_2NHR_{36}$, —$COOR_{36}$, or —C(CN)$NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, ═O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

4. A compound of claim 1, wherein:

A is heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, 16) ═O, 17) —$S(O)_pR_6$, 18) —$SO_2NHR_6$, 19) —$COOR_6$, and 20) —NHC(CN)$NHR_6$;

B is phenyl, which is substituted with more than one substituent selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) —$COR_6$, 15) —$S(O)_pR_6$, 16) —$SO_2NHR_6$, 17) —$COOR_6$, and 18) —NHC(CN)$NHR_6$;

C is alkyl, which is substituted with aryl, which may be optionally substituted with one or more $R_{20}$'s;

$R_1$ is —C(O)$R_3$;

$R_3$ is:

(a) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$CONR_6R_6$, 16) ($C_2$-$C_6$)-alkenyl, 17) ═O, 18) ($C_2$-$C_6$)-alkynyl, 19) —$COR_6$, 20) —$S(O)_pR_6$, 21) —$SO_2NHR_6$, 22) —$COOR_6$, and 23) —NHC(CN)$NHR_6$; or (b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, 19) —$S(O)_pR_6$, 20) —$SO_2NHR_6$, 21) —$COOR_6$, and 22) —NHC(CN)$NHR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$) alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and be optionally substituted with one or more $R_{20}$'s;

$R_9$ and $R_{10}$ are independently: (a) hydrogen; (b) —[(C=O)$O_r$]$_s$aryl, wherein the aryl may be optionally substituted with one or more $R_{20}$'s; (c) —[(C=O)$O_r$]$_s$($C_2$-$C_8$)-alkenyl, wherein the alkenyl may be optionally substituted with one or more $R_{20}$'s; (d) —[(C=O)$O_r$]$_s$($C_1$-$C_8$) alkyl, wherein the alkyl may be optionally substituted with one or more $R_{20}$'s; (e) heterocyclyl optionally substituted with one or more $R_{20}$'s; (f) —$CONR_{26}R_{26}$; (g) —($C_2$-$C_6$)-alkynyl; (h) —$COR_{26}$; (i) —$S(O)_pR_{26}$; (j) —$SO_2NHR_{26}$; (k) —$COOR_{26}$; or (l) —NHC(CN)$NHR_{26}$;

or $R_9$ and $R_{10}$ are taken together with the nitrogen to which both are attached to form a 3- to 8-membered ring, which may optionally contain 1-4 heteroatoms selected from N, O, and S and may be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{20}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) =O; (q) —($C_2$-$C_6$)-alkynyl; (r) —$COR_{26}$; (s) —$S(O)_pR_{26}$; (t) —$SO_2NHR_{26}$; (u) —$COOR_{26}$; (v) —NHC(CN)$NHR_{26}$; (w) cycloalkyl, which may be optionally substituted with one or more $R_{21}$'s; (x) cycloalkylalkyl, which may be optionally substituted with one or more $R_{21}$ 's; or (y) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) =O; (r) ($C_2$-$C_6$)-alkynyl; (s) cycloalkyl; (t) cycloalkylalkyl; (u) —$COR_{26}$; (v) —$S(O)_pR_{26}$; (w) —$SO_2NHR_{26}$; (x) —$COOR_{26}$; or (y) —NHC(CN)$NHR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —$[(C{=}O)O_r]_s$aryl, —$[(C{=}O)O_r]_s$alkenyl, —$[(C{=}O)O_r]_s$alkyl, heterocyclyl, —$CONR_{46}R_{46}$, alkynyl, —$COR_{36}$, —$S(O)_pR_{36}$, —$SO_2NHR_{36}$, —$COOR_{36}$, or —C(CN)$NHR_{36}$, wherein the aryl, alkyl, alkenyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and may be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, —$S(O)_pR_{49}$, —$SO_2NHR_{49}$, —$COOR_{49}$, or —NHC(CN)$NHR_{49}$;

$R_{49}$ and $R_{50}$, at each occurrence, are independently hydrogen, alkyl, aryl, cycloalkyl, heteroaryl or heterocyclyl, other than heteroaryl;

r is 0 to 5;

s is 0 to 4; and p is 1 or 2.

5. A compound of claim 1, wherein:

A is a nitrogen or oxygen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo ($C_1$-$C_6$)alkyl, 15) —$COR_6$, and 16) =O;

B is phenyl, which is substituted with more than one substituent selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, and 13) halo($C_1$-$C_6$)alkyl;

C is alkyl, which is substituted with aryl, which may be optionally substituted with one or more $R_{20}$'s;

$R_1$ is —C(O)$R_3$;

$R_3$ is:

(a) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$; or (b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, and 19) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN) $NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen; (b) —[(C═O)$O_r$]$_s$aryl, wherein the aryl may be optionally substituted with one or more $R_{20}$'s; (c) —[(C═O)$O_r$]$_s$($C_1$-$C_8$)alkyl, wherein the alkyl may be optionally substituted with one or more $R_{20}$'s; or (d) heterocyclyl optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$ 's; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —$NHC(CN)NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C═O)$O_r$]$_s$aryl, —[(C═O)$O_r$]$_s$alkyl, or heterocyclyl, wherein the aryl, alkyl or heterocyclyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, ═O, alkynyl, cycloalkyl, cycloalkylalkyl, —$COR_{49}$, or —$COOR_{49}$;

$R_{49}$ and $R_{50}$, at each occurrence, are independently hydrogen, alkyl, aryl, heteroaryl or heterocyclyl, other than heteroaryl;

r is 0 to 3;

s is 0 to 2; and p is 1 or 2.

6. A compound of claim 1, wherein:

A is a 5- to 10-membered nitrogen or oxygen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) ═O;

B is phenyl, which is substituted with more than one substituent selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, and 13) halo($C_1$-$C_6$)alkyl;

C is alkyl, which is substituted with aryl, which may be optionally substituted with one or more $R_{20}$'s:

$R_1$ is —C(O)$R_3$;

$R_3$ is:

(a) aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10b}$ , 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$; or (b) alkenyl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) ($C_2$-$C_6$)-alkynyl, 18) —$COR_6$, and 19) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_6$'s are taken together to form a 3- to 9-membered ring, which optionally may contain 1-4 heteroatoms selected from N, O, and S and may be optionally substituted with one or more $R_{20}$'s;

$R_9$ and $R_{10}$ are independently: (a) hydrogen; (b) —[(C=O)$O_r$]$_s$aryl, wherein the aryl may be optionally substituted with one or more $R_{20}$'s; or (c) —[(C=O)$O_r$]$_s$($C_1$-$C_8$) alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$ s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

or two $R_{26}$'s are taken together to form a 3- to 9-membered ring, which optionally may contain 1-4 heteroatoms selected from N, O, and S and be optionally substituted with one or more $R_{40}$'s;

$R_{29}$ and $R_{30}$ are independently hydrogen, —[(C=O)$O_r$]$_s$aryl, or —[(C=O)$O_r$]$_s$alkyl, wherein the aryl or alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$, or —$COOR_{49}$;

$R_{49}$ and $R_{50}$, at each occurrence, are independently hydrogen, alkyl, aryl or heteroaryl;

r is 0 to 2;

s is 0 to 1; and p is 1 or 2.

7. A compound of claim 1, wherein:

A is a 6-membered nitrogen containing heteroaryl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O;

B is phenyl, which is substituted with more than one substituent selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, and 13) halo($C_1$-$C_6$)alkyl;

C is alkyl, which is substituted with phenyl, which may be optionally substituted with one or more $R_{20}$'s;

$R_1$ is —C(O)$R_3$;

$R_3$ is aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6R_6$, 16) ($C_2$-$C_6$)-alkenyl, 17) =O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

$R_9$ and $R_{10}$ are independently: (a) hydrogen; or (b) —$[(C{=}O)O_r]_s$($C_1$-$C_8$)alkyl, wherein the alkyl may be optionally substituted with one or more $R_{20}$'s;

or $R_9$ and $R_{10}$ are taken together with the nitrogen to which both are attached to form a 3- to 8-membered ring, which may optionally contain 1-4 heteroatoms selected from N, O, and S and be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl, m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —$NHC(CN)NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —$NHC(CN)NHR_{36}$; or (f) hydrogen;

$R_{29}$ and $R_{30}$ are independently hydrogen or —$[(C{=}O)O_r]_s$alkyl, wherein the alkyl may be optionally substituted with one or more $R_{40}$'s;

or $R_{29}$ and $R_{30}$ are taken together with the nitrogen to which both are attached to form a 3- to 8-membered ring, which may optionally contain 1-4 heteroatoms selected from N, O, and S and be optionally substituted with one or more $R_{40}$'s;

$R_{36}$, at each occurrence, is independently alkyl, aryl, cycloalkyl, heteroaryl or heterocyclyl, other than heteroaryl, wherein the alkyl, aryl, cycloalkyl, heteroaryl or heterocyclyl may be optionally substituted with one or more $R_{40}$'s;

$R_{40}$ is halo, —OH, alkyl, alkyloxy, alkylthio, cyano, nitro, —$NR_{49}R_{50}$, aryl, arylalkyl, heteroaryl, heteroarylalkyl, heterocyclyl, heterocyclylalkyl, haloalkyl, haloalkyloxy, —$CONR_{49}R_{50}$, alkenyl, arylalkyloxy, =O, alkynyl, cycloalkyl, cycloalkylalkyl, —$COR_{49}$ or —$COOR_{49}$;

$R_{49}$ and $R_{50}$, at each occurrence, are independently hydrogen, alkyl, aryl, or heteroaryl;

r is 0 to 2;

s is 0 to 1; and p is 1 or 2.

8. A compound of claim 1, wherein:

A is pyridyl, which is substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O;

B is phenyl, which is substituted with more than one substituent selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7)aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, and 13) halo($C_1$-$C_6$)alkyl;

C is alkyl, which is substituted with phenyl, which may be optionally substituted with one or more $R_{20}$'s;

$R_1$ is —C(O)$R_3$;

$R_3$ is aryl, which may be optionally substituted with one or more substituents selected from the group consisting of: 1) halo, 2) ($C_1$-$C_6$)-alkyl, which may be optionally substituted with one or more $R_{20}$'s, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$) alkyl, 15) —$CONR_6R_6$, 16) ($C_2$-$C_6$)-alkenyl, 17) ═O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) ═O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) —COOH, 17) —$CONR_{36}R_{36}$, 18) ═O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{20}$'s, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) ($C_2$-$C_6$)-alkenyl, 17) —COOH, 18) —$CONR_{36}R_{36}$, 19) ═O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

$R_9$ and $R_{10}$ are independently: (a) hydrogen; or (b) —$[(C{=}O)O_r]_s$($C_1$-$C_8$)alkyl, wherein the alkyl may be optionally substituted with one or more $R_{20}$'s;

$R_{20}$ is: (a) halo; (b) ($C_1$-$C_6$)-alkyl, which may be optionally substituted with one or more $R_{21}$'s; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl;

(o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 1 1) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$S(O)_pR_{36}$, 20) —$SO_2NHR_{36}$, 21) —$COOR_{36}$, and 22) —NHC(CN)$NHR_{36}$;

(b) aryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) —COOH, 17) —$CONR_{36}R_{36}$, 18) =O, 19) ($C_2$-$C_6$)-alkynyl, 20) —$COR_{36}$, 21) —$S(O)_pR_{36}$, 22) —$SO_2NHR_{36}$, 23) —$COOR_{36}$, and 24) —NHC(CN)$NHR_{36}$;

(c) cycloalkyl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(d) heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$;

(e) heterocyclyl, other than heteroaryl, which may be optionally substituted with one or more substituents selected from the group consisting of: 1) halo, 2) —OH, 3) ($C_1$-$C_6$)-alkyl, which may be optionally substituted with one or more $R_{40}$'s, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$S(O)_pR_{36}$, 23) —$SO_2NHR_{36}$, 24) —$COOR_{36}$, and 25) —NHC(CN)$NHR_{36}$; or (f) hydrogen;

$R_{29}$ and $R_{30}$ are independently hydrogen or —[(C=O)$O_r$]$_s$alkyl, wherein the alkyl may be optionally substituted with one or more $R_{40}$'s;

$R_{36}$, at each occurrence, is independently alkyl, aryl, heteroaryl or heterocyclyl, other than heteroaryl, wherein the alkyl, aryl, heteroaryl or heterocyclyl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2;

s is 0 to 1; and p is 1 or 2.

9. A compound of claim 1, wherein:

A is pyridyl, which is substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$COR_6$, and 16) =O;

B is phenyl, which is substituted with more than one substituent selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, and 13) halo($C_1$-$C_6$)alkyl;

C is methylphenyl, which may be optionally substituted with one or more $R_{20}$'s;

$R_1$ is —C(O)$R_3$;

$R_3$ is aryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) —$NR_9R_{10}$, 8) aryl, which may be optionally substituted with one or more $R_{20}$'s, 9) arylalkyl, which may be optionally substituted with one or more $R_{20}$'s, 10) heteroaryl, which may be optionally substituted with one or more $R_{20}$'s, 11) heteroarylalkyl, which may be optionally substituted with one or more $R_{20}$'s, 12) heterocyclyl, which may be optionally substituted with one or more $R_{20}$'s, 13) heterocyclylalkyl, which may be optionally substituted with one or more $R_{20}$'s, 14) halo($C_1$-$C_6$)alkyl, 15) —$CONR_6R_6$, 16) ($C_2$-$C_6$)-alkenyl, 17) =O, 18) ($C_2$-$C_6$)-alkynyl, 19) —$COR_6$, and 20) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) heteroaryl, which may be optionally substituted with one or more $R_{20}$'s, 11) heterocyclyl, which may be optionally substituted with one or more $R_{20}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$SO_2NHR_{36}$, 20) —$COOR_{36}$, and 21) —NHC(CN)$NHR_{36}$;

(b) aryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$) alkyl, 16) —COOH, 17) —$CONR_{36}R_{36}$, 18) =O, 19) ($C_2$-$C_6$)-alkynyl, 20) —$COR_{36}$, 21) —$SO_2NHR_{36}$, 22) —$COOR_{36}$, and 23) —NHC(CN)$NHR_{36}$;

(c) heteroaryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_9R_{10}$, 9) aryl, which may be optionally substituted with one or more $R_{20}$'s, 10) arylalkyl, which may be optionally substituted with one or more $R_{20}$'s, 11) heteroaryl, which may be optionally substituted with one or more $R_{20}$'s, 12) heteroarylalkyl, which may be optionally substituted with one or more $R_{20}$'s, 13) heterocyclyl, which may be optionally substituted with one or more $R_{20}$'s, 14) heterocyclylalkyl, which may be optionally substituted with one or more $R_{20}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$SO_2NHR_{36}$, 23) —$COOR_{36}$, and 24) —NHC(CN)$NHR_{36}$; or (d) hydrogen;

$R_9$ and $R_{10}$ are independently: (a) hydrogen; or (b) —[(C=O)$O_r$]$_s$($C_1$-$C_8$)alkyl, wherein the alkyl may be optionally substituted with one or more $R_{20}$'s;

$R_{20}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl, which may be optionally substituted with one or more $R_{21}$'s; (i) arylalkyl, which may be optionally substituted with one or more $R_{21}$'s; (j) heteroaryl, which may be optionally substituted with one or more $R_{21}$'s; (k) heteroarylalkyl, which may be optionally substituted with one or more $R_{21}$'s; (l) heterocyclyl, which may be optionally substituted with one or more $R_{21}$'s; (m) heterocyclylalkyl, which may be optionally substituted with one or more $R_{21}$'s; (n) halo($C_1$-$C_6$)alkyl; (o) ($C_2$-$C_6$)-alkenyl; (p) —($C_2$-$C_6$)-alkynyl; (q) —$COR_{26}$; (r) —$COOR_{26}$; (s) cycloalkyl, which may be optionally substituted with one or more $R_{21}$'s; (t) cycloalkylalkyl, which may be optionally substituted with one or more $R_{21}$'s; or (u) —$CONR_{26}R_{26}$;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) —$NR_{29}R_{30}$; (h) aryl; (i) arylalkyl; (j) heteroaryl; (k) heteroarylalkyl; (l) heterocyclyl; (m) heterocyclylalkyl; (n) halo($C_1$-$C_6$)alkyl; (o) —$CONR_{26}R_{26}$; (p) ($C_2$-$C_6$)-alkenyl; (q) ($C_2$-$C_6$)-alkynyl; (r) cycloalkyl; (s) cycloalkylalkyl; (t) —$COR_{26}$; or (u) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) heteroaryl, which may be optionally substituted with one or more $R_{40}$'s, 11) heterocyclyl, which may be optionally substituted with one or more $R_{40}$'s, 12) halo($C_1$-$C_6$)alkyl, 13) ($C_2$-$C_6$)-alkenyl, 14) —COOH, 15) —$CONR_{36}R_{36}$, 16) =O, 17) ($C_2$-$C_6$)-alkynyl, 18) —$COR_{36}$, 19) —$SO_2NHR_{36}$, 20) —$COOR_{36}$, and 21) —NHC(CN)$NHR_{36}$;

(b) aryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$) alkyl, 16) —COOH, 17) —$CONR_{36}R_{36}$, 18) =O, 19) ($C_2$-$C_6$)-alkynyl, 20) —$COR_{36}$, 21) —$SO_2NHR_{36}$, 22) —$COOR_{36}$, and 23) —NHC(CN)$NHR_{36}$;

(c) heteroaryl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) —$NR_{29}R_{30}$, 9) aryl, which may be optionally substituted with one or more $R_{40}$'s, 10) arylalkyl, which may be optionally substituted with one or more $R_{40}$'s, 11) heteroaryl, which may be optionally substituted with one or more $R_{40}$'s, 12) heteroarylalkyl, which may be optionally substituted with one or more $R_{40}$'s, 13) heterocyclyl, which may be optionally substituted with one or more $R_{40}$'s, 14) heterocyclylalkyl, which may be optionally substituted with one or more $R_{40}$'s, 15) halo($C_1$-$C_6$)alkyl, 16) ($C_2$-$C_6$)-alkenyl, 17) —COOH, 18) —$CONR_{36}R_{36}$, 19) =O, 20) ($C_2$-$C_6$)-alkynyl, 21) —$COR_{36}$, 22) —$SO_2NHR_{36}$, 23) —$COOR_{36}$, and 24) —NHC(CN)$NHR_{36}$; or (d) hydrogen;

$R_{29}$ and $R_{30}$ are independently hydrogen or —[(C=O)$O_r$]$_s$alkyl, wherein the alkyl may be optionally substituted with one or more $R_{40}$'s;

$R_{36}$, at each occurrence, is independently alkyl, aryl or heteroaryl, wherein the alkyl, aryl or heteroaryl may be optionally substituted with one or more $R_{40}$'s;

$R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, =O, alkynyl, cycloalkyl or cycloalkylalkyl;

r is 0 to 2; and s is 0 to 1.

10. A compound of claim 1, wherein:

A is pyridyl, which is substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo ($C_1$-$C_6$)alkyl, and 14) —$COR_6$;

B is phenyl, which is substituted with more than one substituent selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, and 13) halo($C_1$-$C_6$)alkyl;

C is methylphenyl, which may be optionally substituted with one or more $R_{20}$'s;

$R_1$ is —C(O)$R_3$;

$R_3$ is aryl, which may be optionally substituted with one or more substituents selected from the group consisting of: 1) halo, 2) ($C_1$-$C_6$)-alkyl, 3) —$OR_6$, 4) ($C_1$-$C_6$)-alkylthio, 5) cyano, 6) nitro, 7) aryl, which may be optionally substituted with one or more $R_{20}$'s, 8) arylalkyl, which may be optionally substituted with one or more $R_{20}$'s, 9) heteroaryl, which may be optionally substituted with one or more $R_{20}$'s, 10) heteroarylalkyl, which may be optionally substituted with one or more $R_{20}$'s, 11) heterocyclyl, which may be optionally substituted with one or more $R_{20}$'s, 12) heterocyclylalkyl, which may be optionally substituted with one or more $R_{20}$'s, 13) halo($C_1$-$C_6$)alkyl, 14) ($C_2$-$C_6$)-alkenyl, 15) ($C_2$-$C_6$)-alkynyl, 16) —$COR_6$, and 17) —$COOR_6$;

$R_6$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) aryl, which may be optionally substituted with one or more $R_{20}$'s, 9) heteroaryl, which may be optionally substituted with one or more $R_{20}$'s, 10) heterocyclyl, which may be optionally substituted with one or more $R_{20}$'s, 11) halo($C_1$-$C_6$)alkyl, 12) ($C_2$-$C_6$)-alkenyl, 13) —COOH, 14) ($C_2$-$C_6$)-alkynyl, 15) —$COR_{36}$, and 16) —$COOR_{36}$; or (b) hydrogen;

$R_{20}$ is: (a) halo; (b) ($C_1$-$C_6$)-alkyl; (c) —$OR_{26}$; (d) ($C_1$-$C_6$)-alkylthio; (e) cyano; (f) nitro; (g) aryl, which may be optionally substituted with one or more $R_{21}$'s; (h) arylalkyl, which may be optionally substituted with one or more $R_{21}$'s; (i) heteroaryl, which may be optionally substituted with one or more $R_{21}$'s; (j) heteroarylalkyl, which may be optionally substituted with one or more $R_{21}$'s; (k) heterocyclyl, which may be optionally substituted with one or more $R_{21}$'s; (l) heterocyclylalkyl, which may be optionally substituted with one or more $R_{21}$'s; (m) halo($C_1$-$C_6$)alkyl; (n) ($C_2$-$C_6$)-alkenyl; (o) —($C_2$-$C_6$)-alkynyl; (p) —$COR_{26}$; (q) —$COOR_{26}$; (r) cycloalkyl, which may be optionally substituted with one or more $R_{21}$'s; or (s) cycloalkylalkyl, which may be optionally substituted with one or more $R_{21}$'s;

$R_{21}$ is: (a) halo; (b) ($C_1$-$C_6$)-alkyl; (c) —$OR_{26}$; (d) ($C_1$-$C_6$)-alkylthio; (e) cyano; (f) nitro; (g) aryl; (h) arylalkyl; (i) heteroaryl; (j) heteroarylalkyl; (k) heterocyclyl; (l) heterocyclylalkyl; (m) halo($C_1$-$C_6$)alkyl; (n) ($C_2$-$C_6$)-alkenyl; (o) ($C_2$-$C_6$)-alkynyl; (p) cycloalkyl; (q) cycloalkylalkyl; (r) —$COR_{26}$; or (s) —$COOR_{26}$;

$R_{26}$, at each occurrence, is independently:

(a) alkyl, which may be optionally substituted with one or more substituents selected from the group consisting of: 1) halo, 2) —OH, 3) ($C_1$-$C_6$)-alkyl, 4) —$OR_{36}$, 5) ($C_1$-$C_6$)-alkylthio, 6) cyano, 7) nitro, 8) aryl, which may be optionally substituted with one or more $R_{40}$'s, 9) heteroaryl, which may be optionally substituted with one or more $R_{40}$'s, 10) heterocyclyl, which may be optionally substituted with one or more $R_{40}$'s, 11) halo($C_1$-$C_6$)alkyl, 12) ($C_2$-$C_6$)-alkenyl, 13) —COOH, 14) ($C_2$-$C_6$)-alkynyl, 15) —$COR_{36}$, or 16) —$COOR_{36}$; or (b) hydrogen;

$R_{36}$, at each occurrence, is independently alkyl, aryl or heteroaryl, wherein the alkyl, aryl or heteroaryl may be optionally substituted with one or more $R_{40}$'s; and $R_{40}$ is halo, —OH, alkyl, alkyloxy, alkylthio, cyano, nitro, aryl, arylalkyl, heteroaryl, heteroarylalkyl, heterocyclyl, heterocyclylalkyl, haloalkyl, haloalkyloxy, alkenyl, arylalkyloxy, alkynyl, cycloalkyl or cycloalkylalkyl.

11. A compound of formula Ib
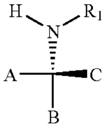
Ib
or stereoisomers or pharmaceutically acceptable salt forms thereof, wherein:
A is:
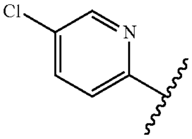
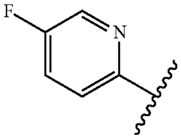
or
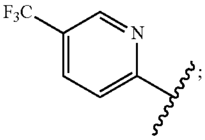
B is:
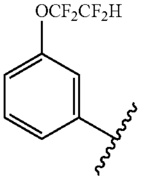
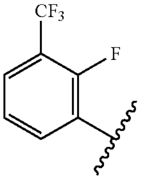
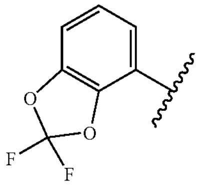
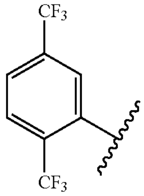
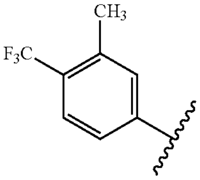
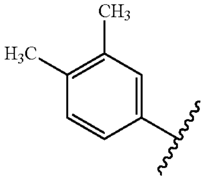
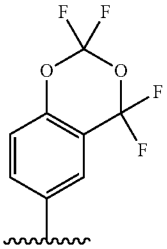
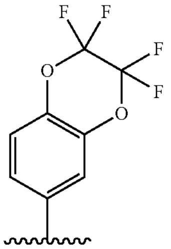
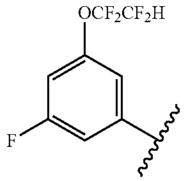
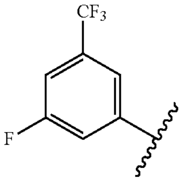
or
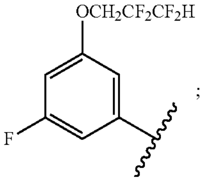
C is:
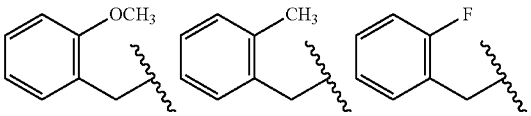
-continued
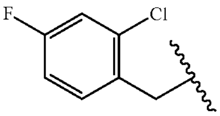
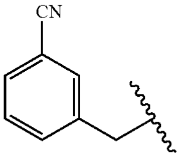
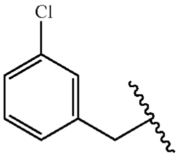
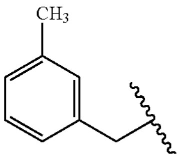
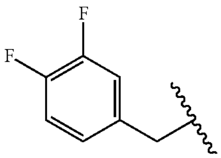
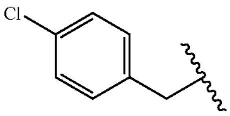
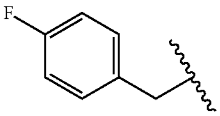
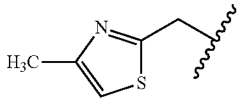
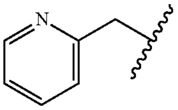
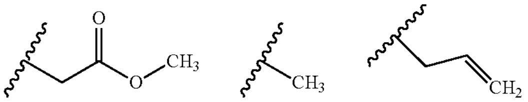
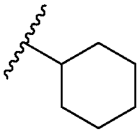
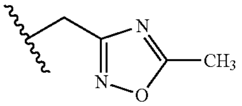
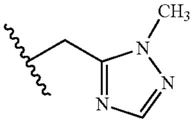
or
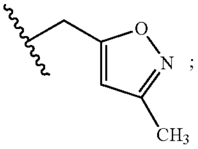
and $R_1$ is
—$C(O)R_3$, wherein $R_3$:
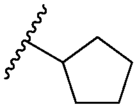
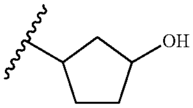
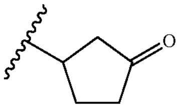
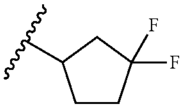
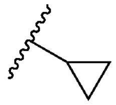
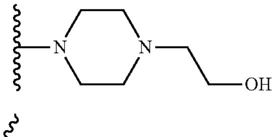
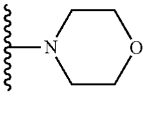
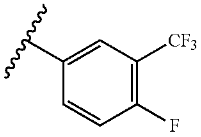
or
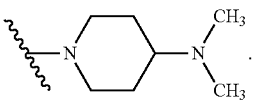

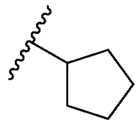
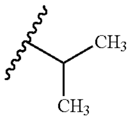
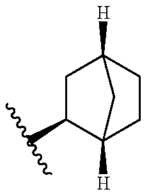
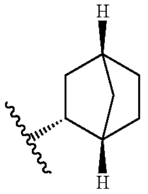
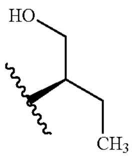
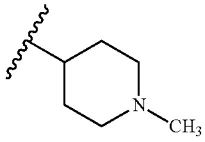
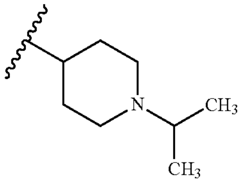
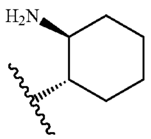
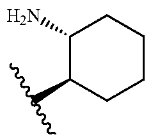
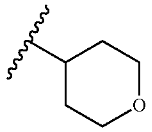
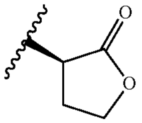
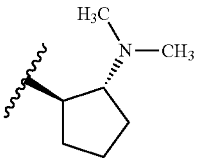
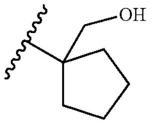
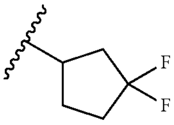
12. A compound of claim 1, wherein the compound is selected from the group consisting of:
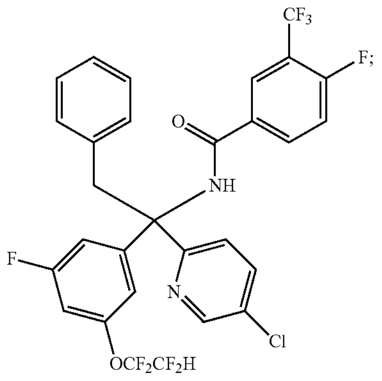
-continued
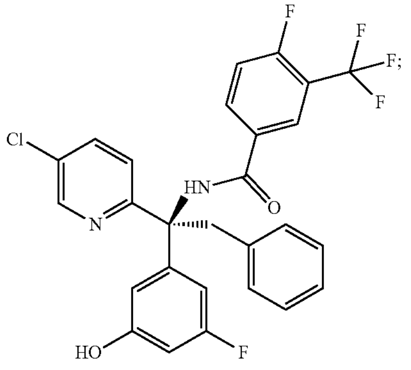
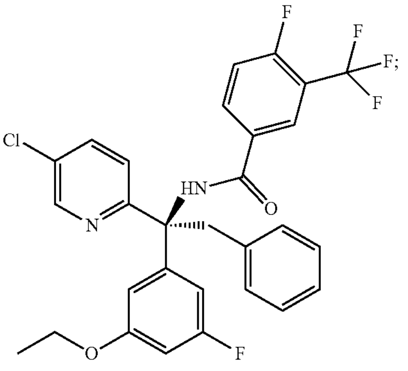
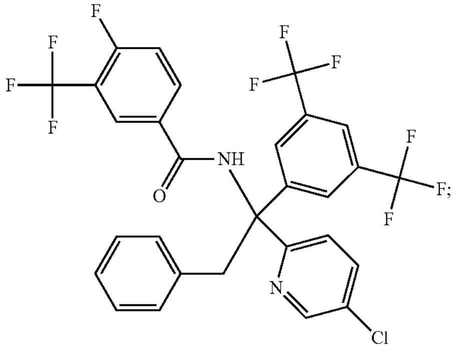
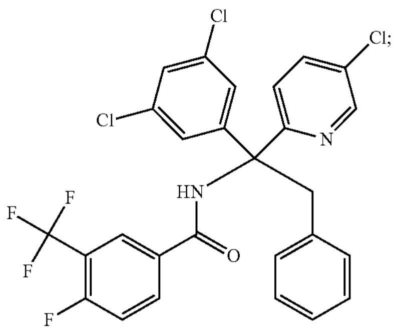

-continued
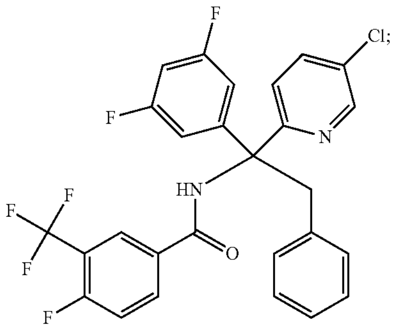
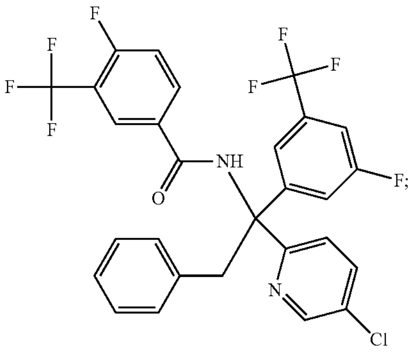
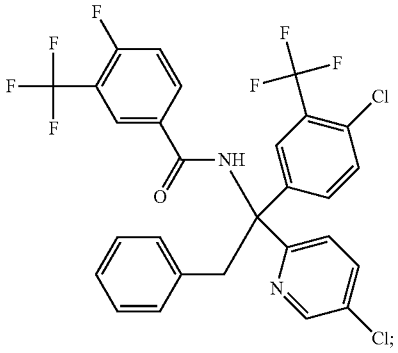
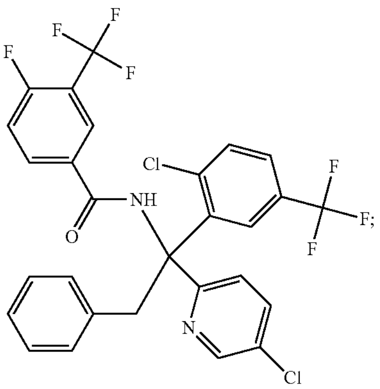
-continued
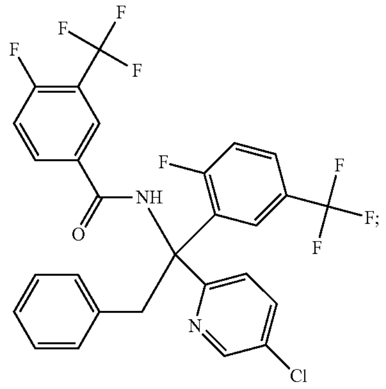
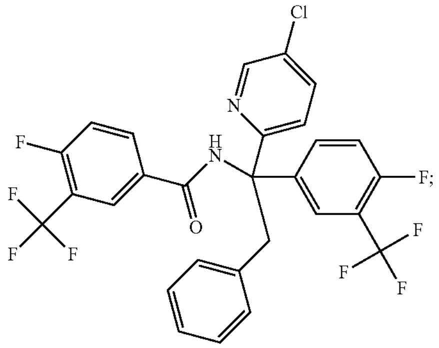
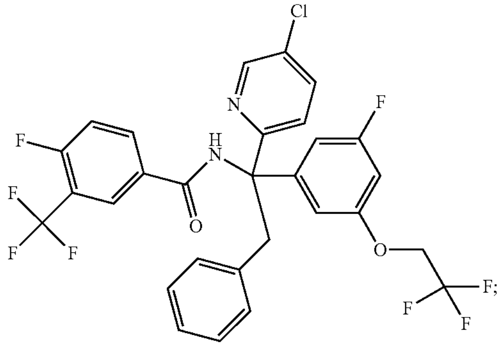
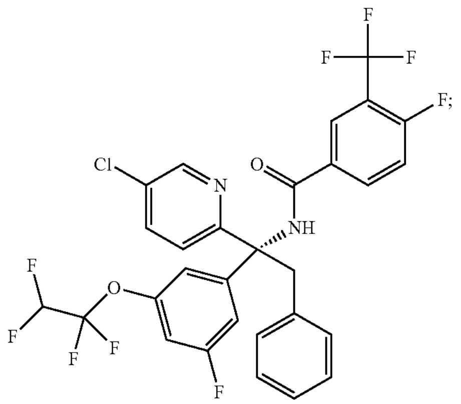

-continued
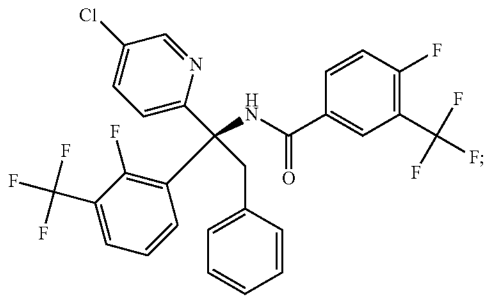
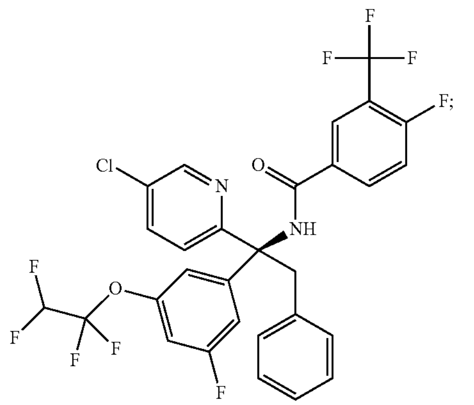
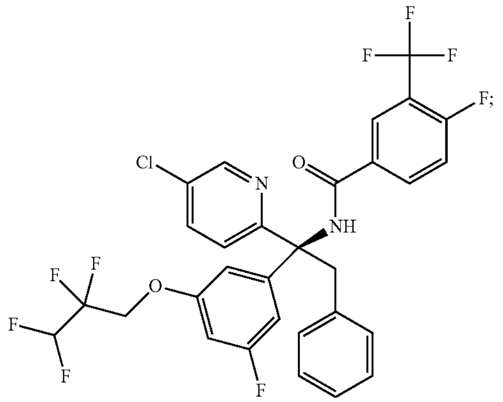
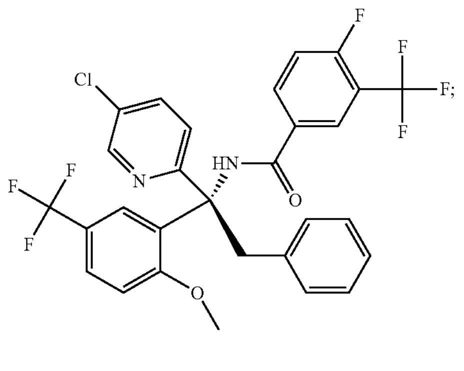
-continued
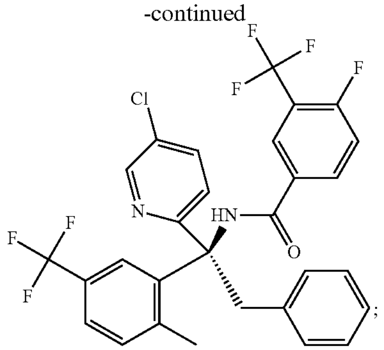
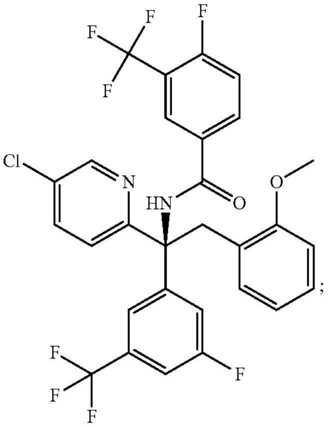
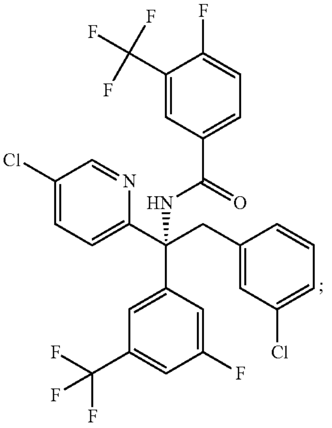
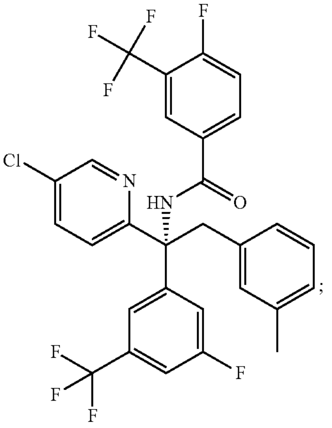

-continued
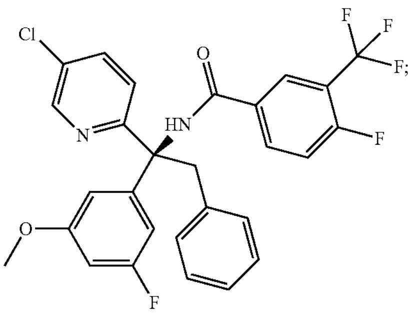
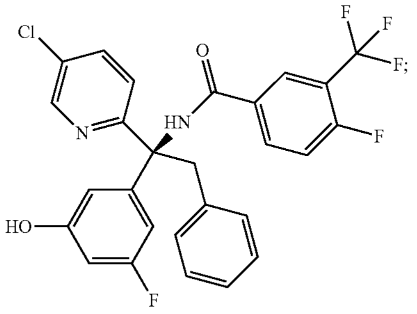
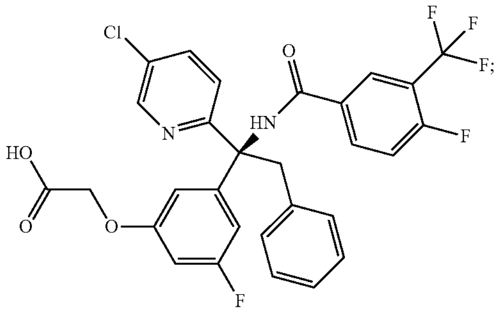
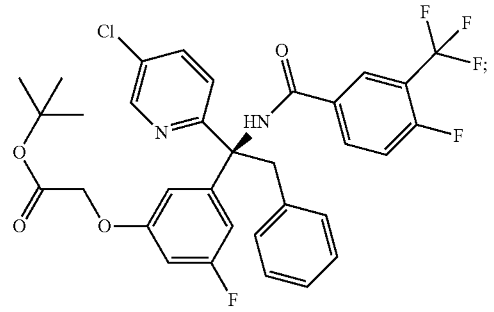
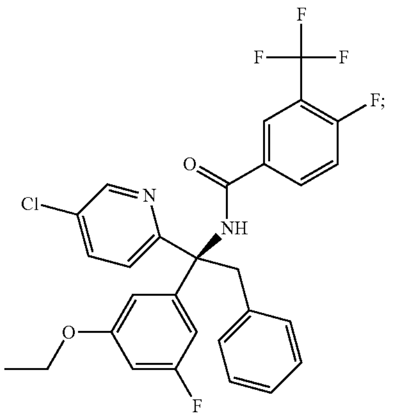
-continued
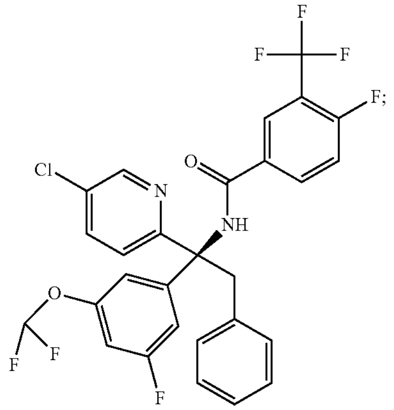
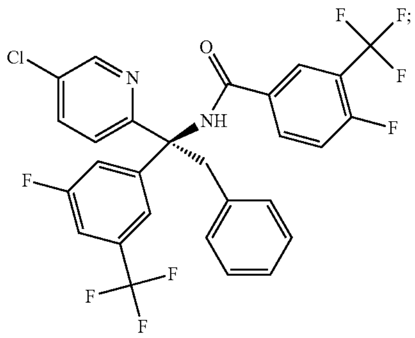
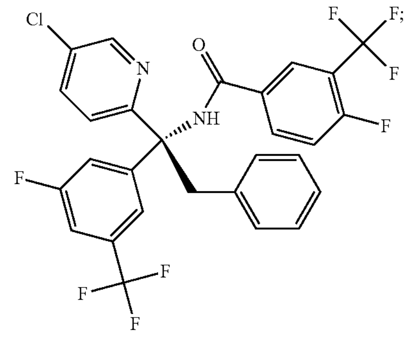
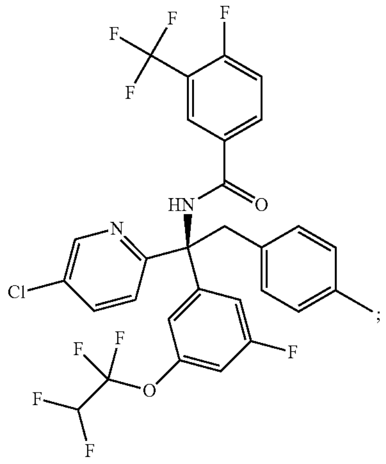

-continued
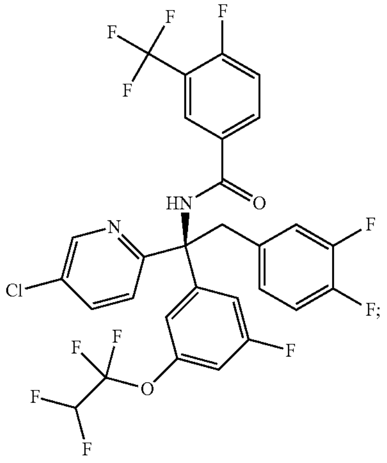
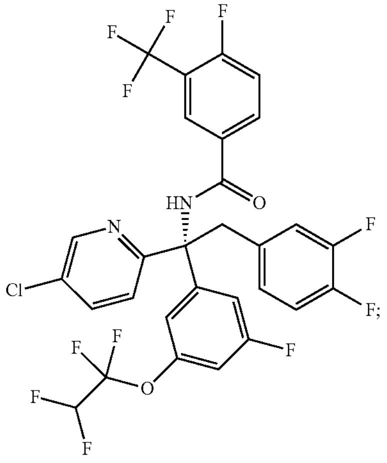
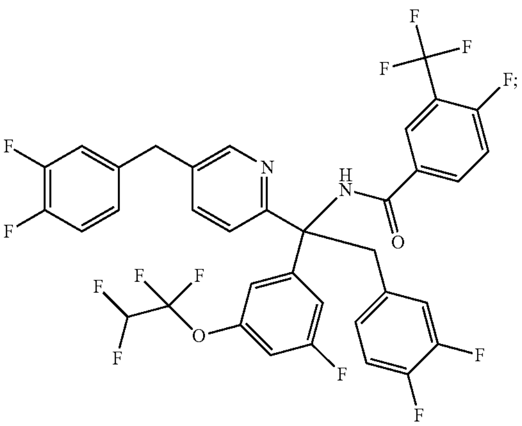
-continued
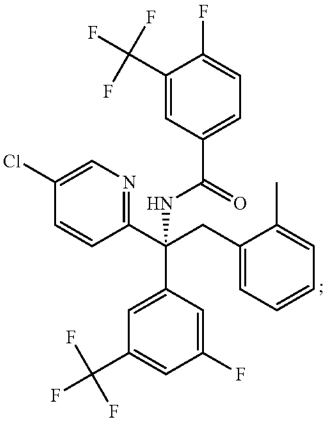
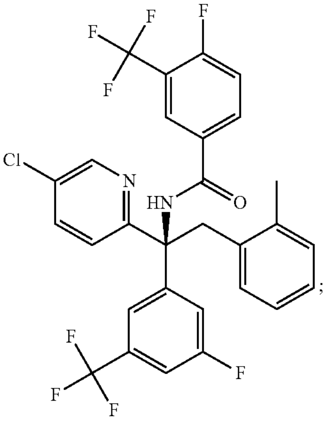
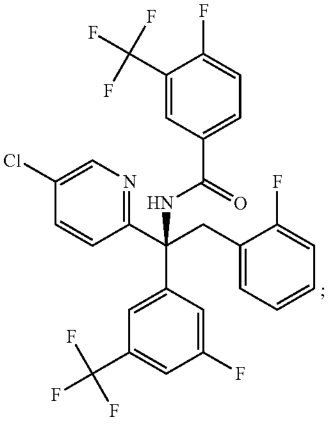
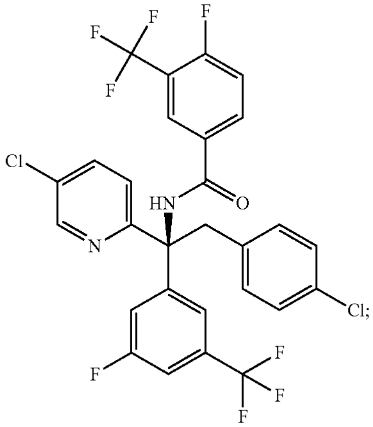

-continued
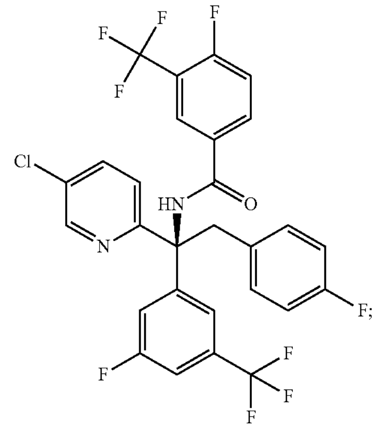
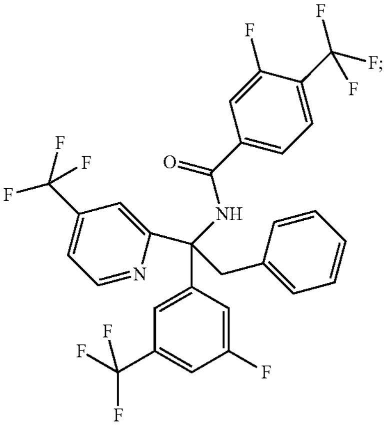
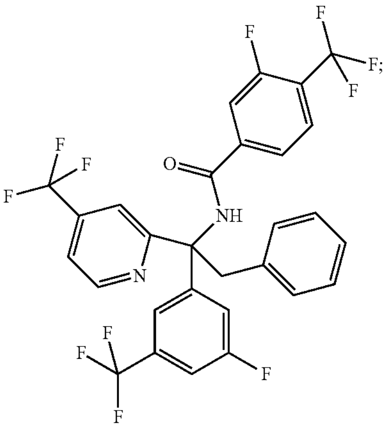
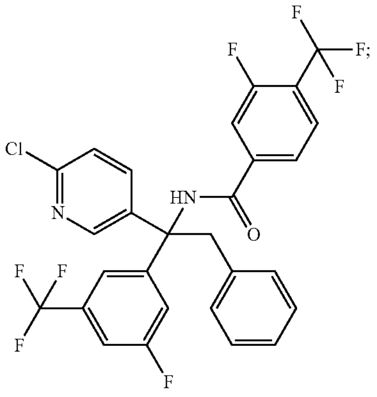
-continued
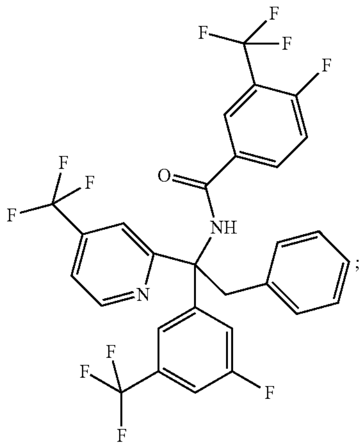
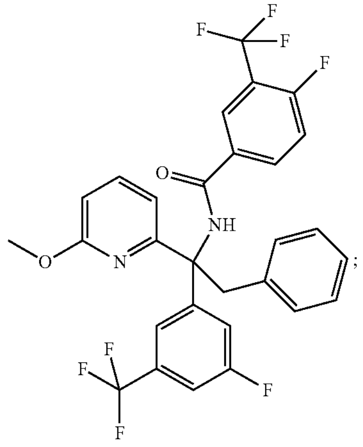
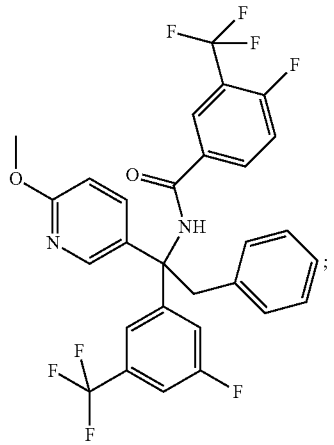
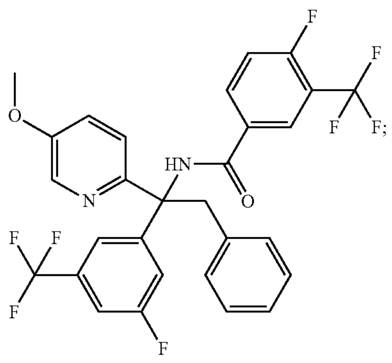

-continued
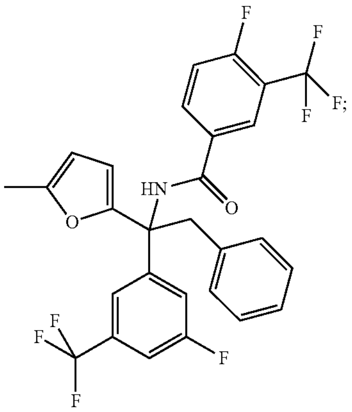
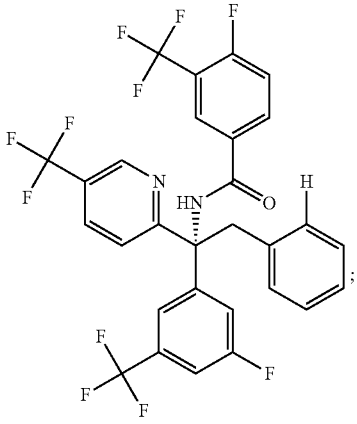
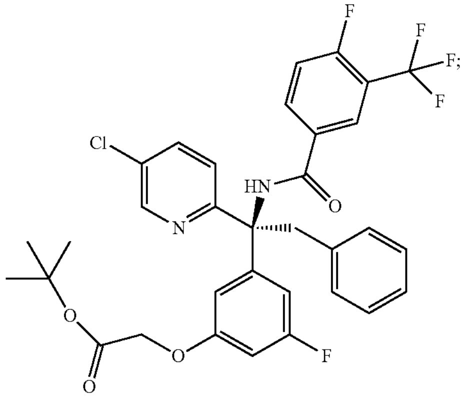
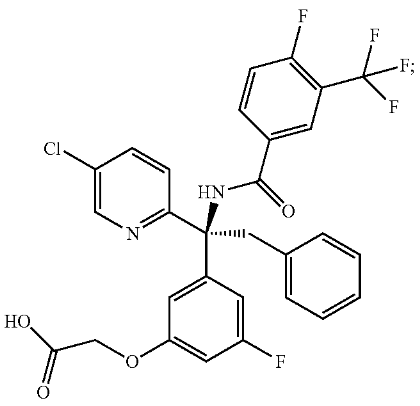
-continued
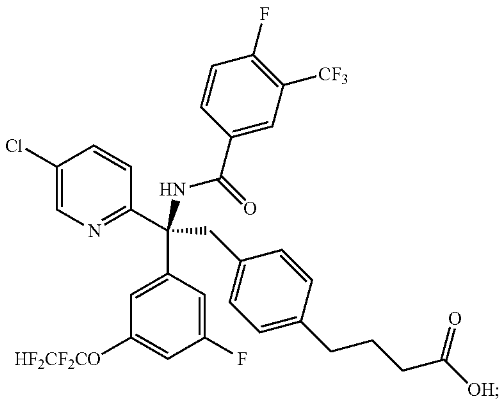
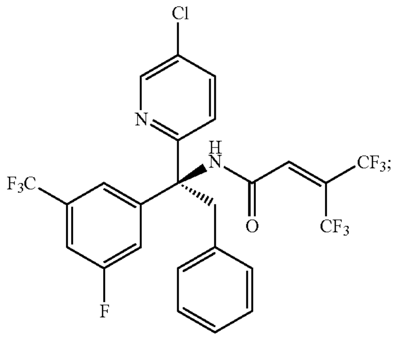
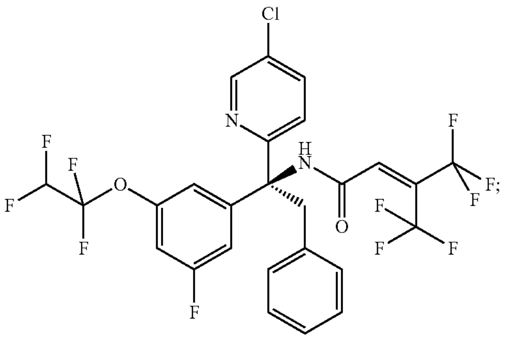
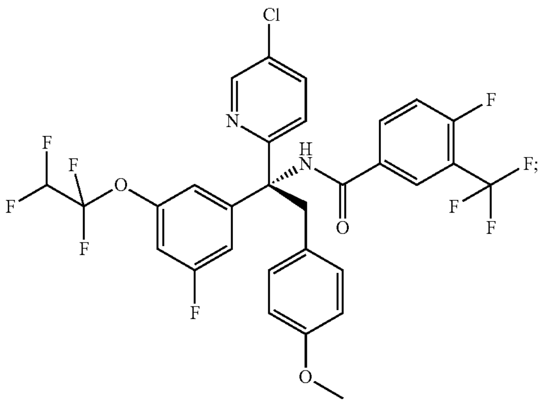

-continued
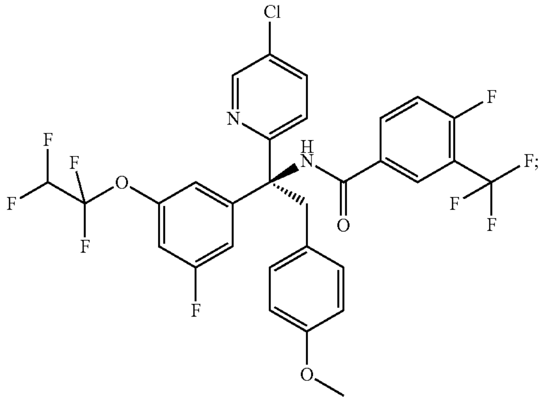
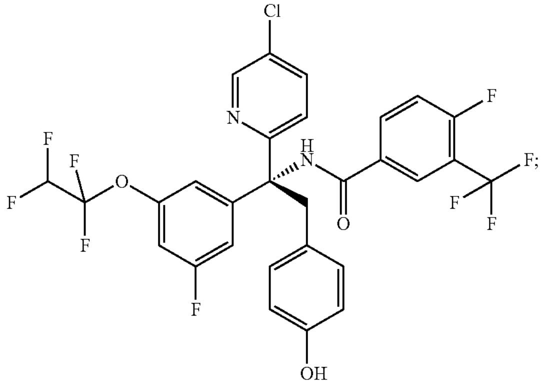
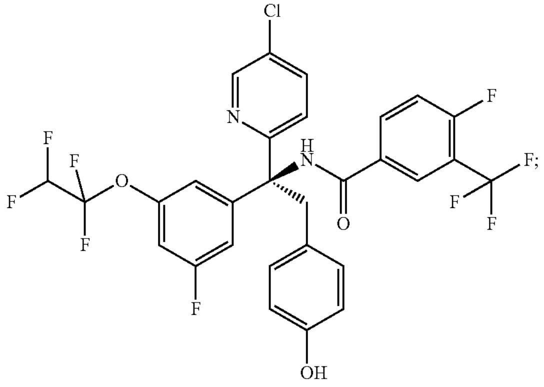
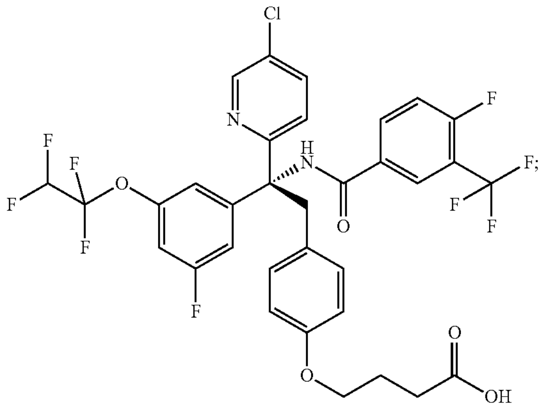
-continued
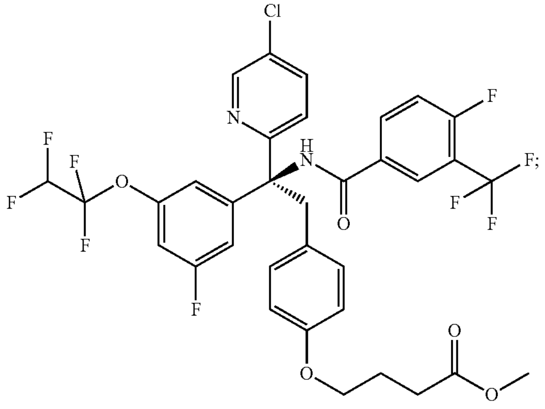
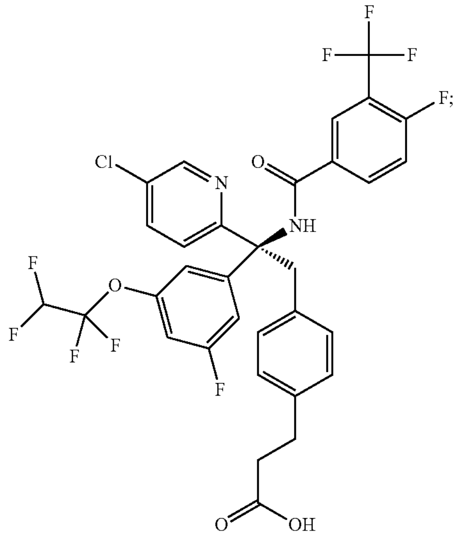
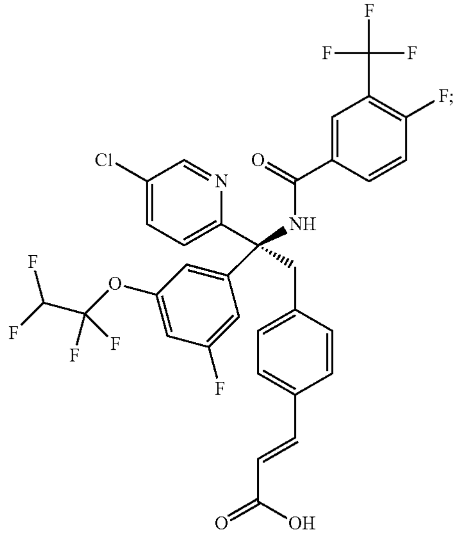

-continued
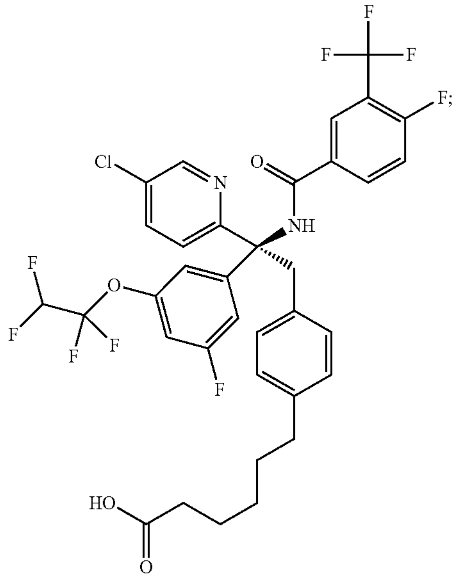
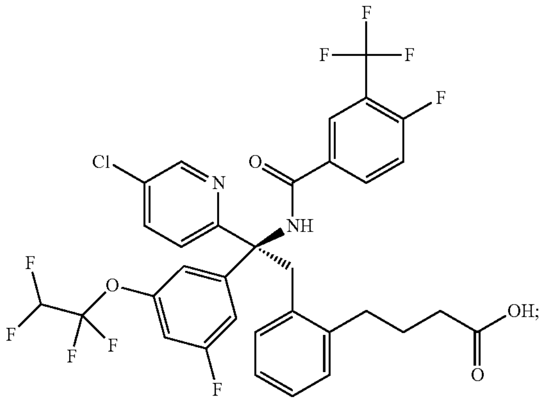
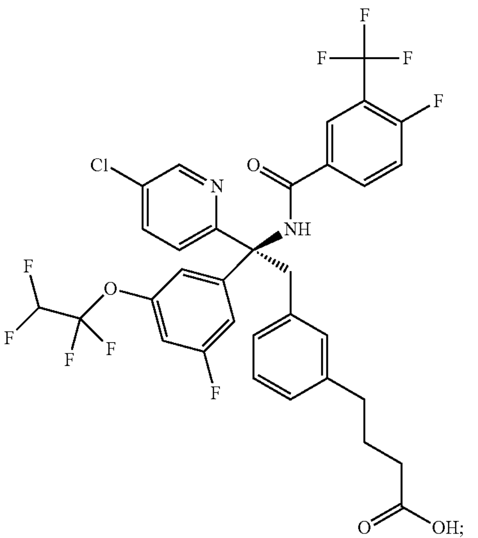
-continued
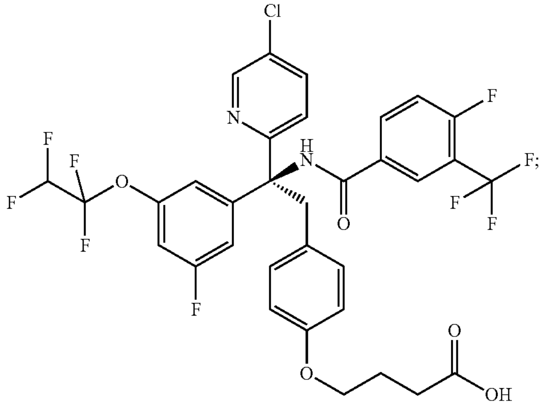
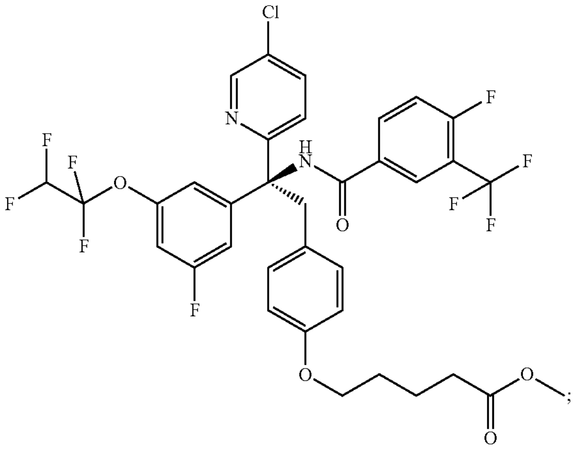
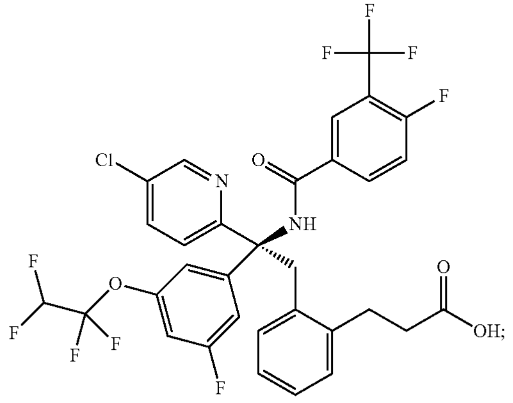
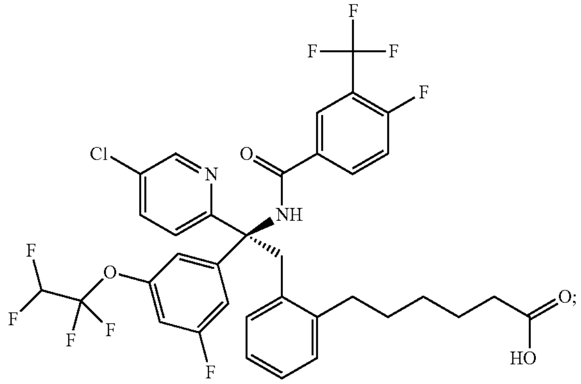

-continued
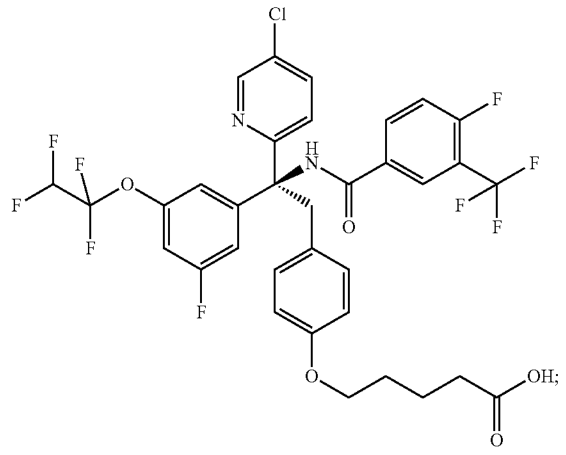
and
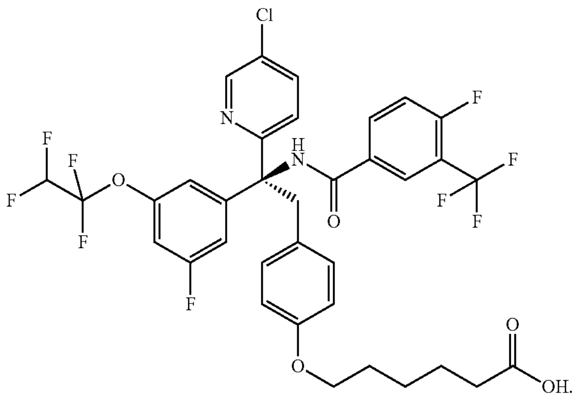
13. A compound of claim 1, wherein A is
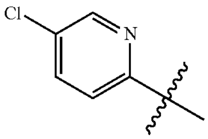
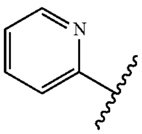
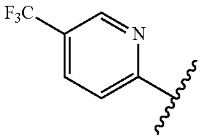
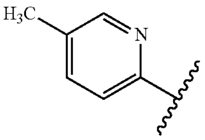
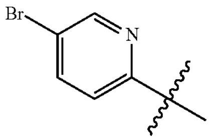
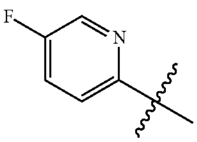
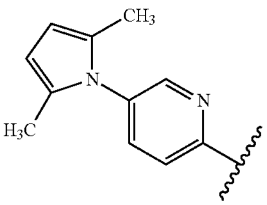
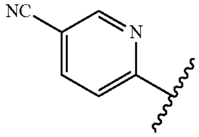
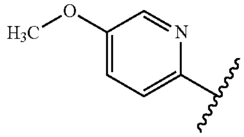
-continued
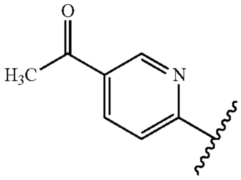
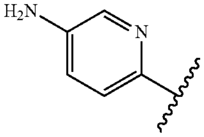
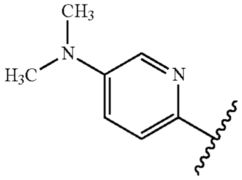
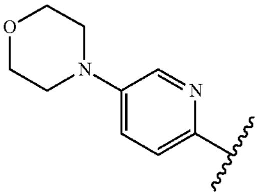
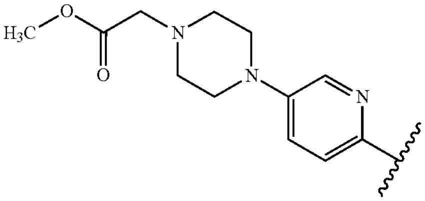
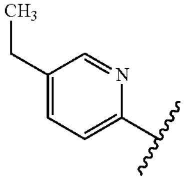
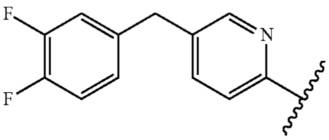
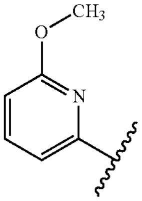
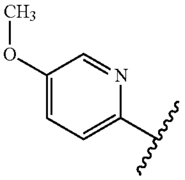
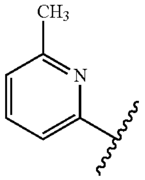
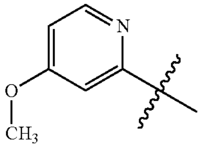
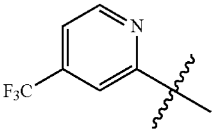
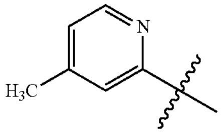
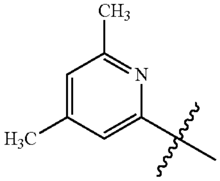
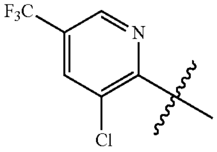
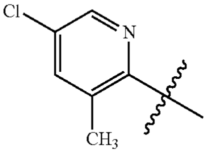
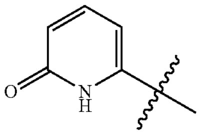
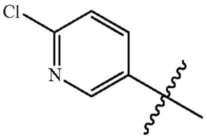

-continued
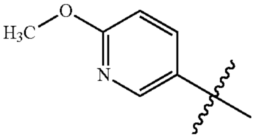
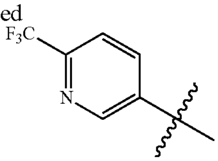
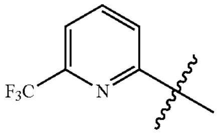
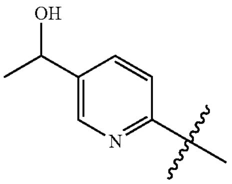
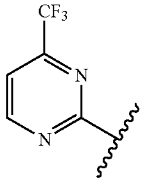
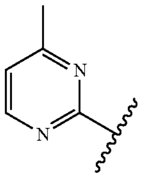
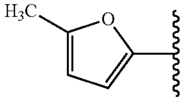
or
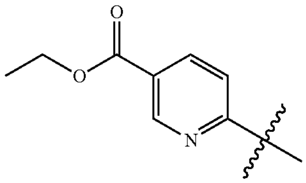
;
B is
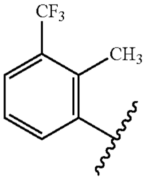
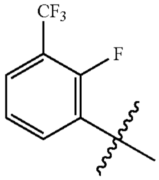
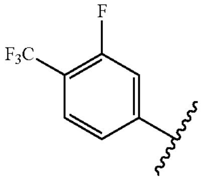
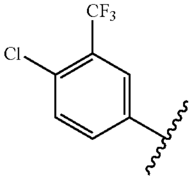
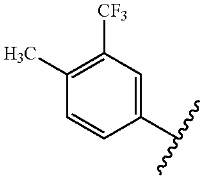
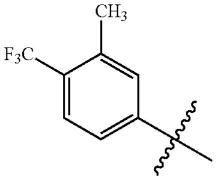
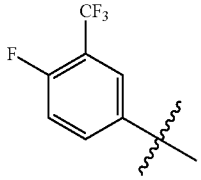
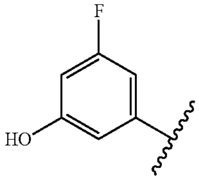
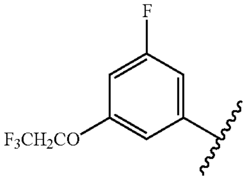
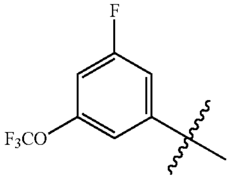
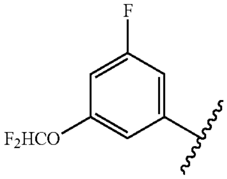
-continued
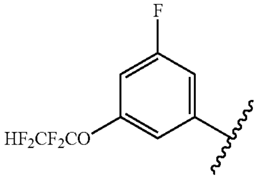
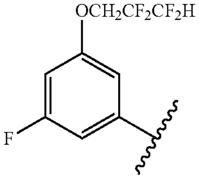
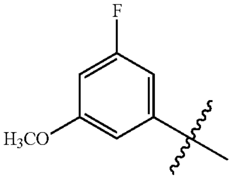
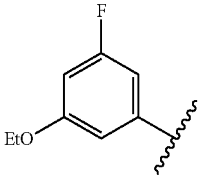
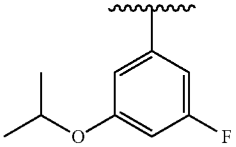
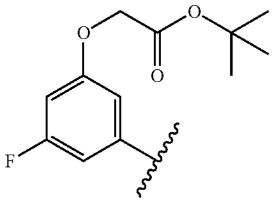
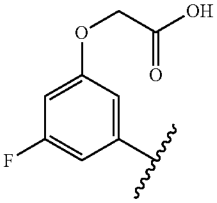
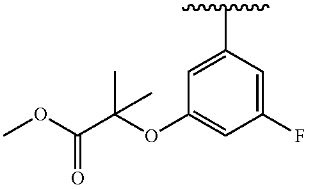
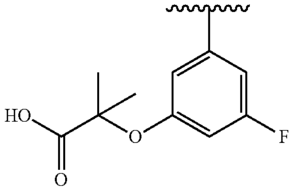
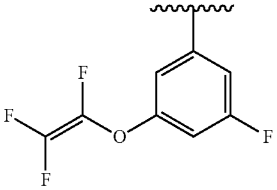
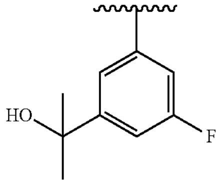
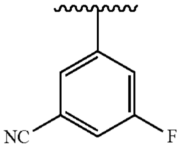
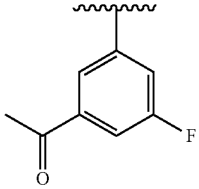
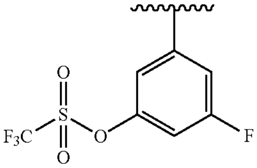
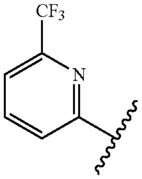
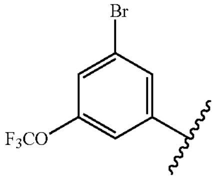
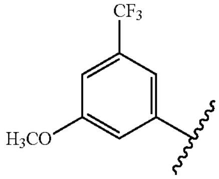
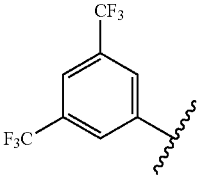

-continued
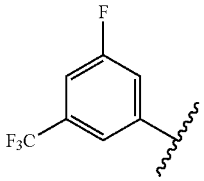
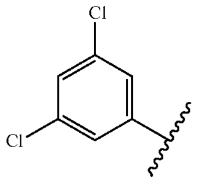
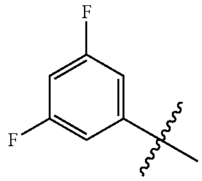
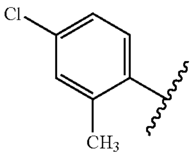
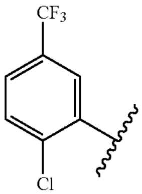
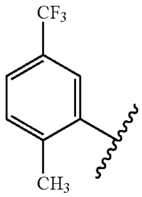
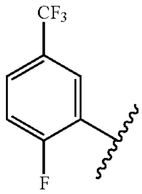
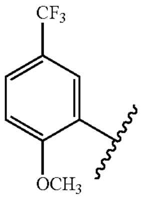
or
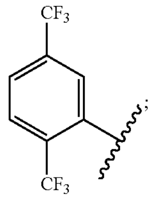
C is
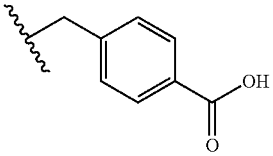
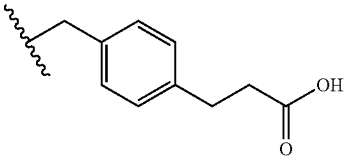
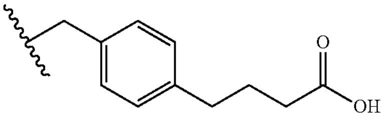
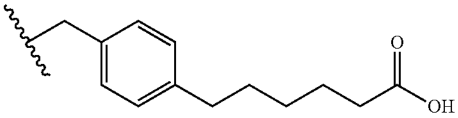
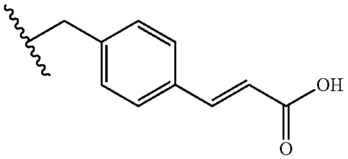
-continued
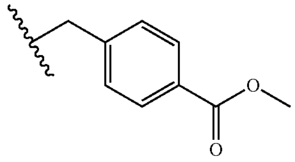
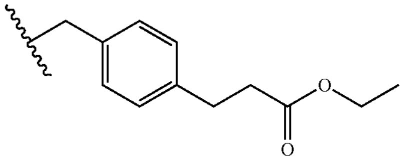
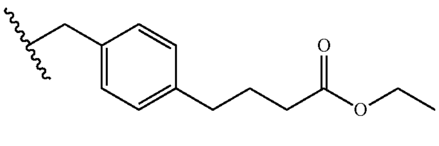
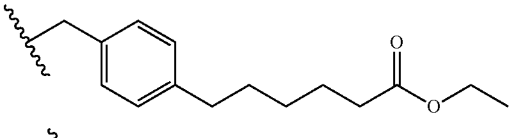
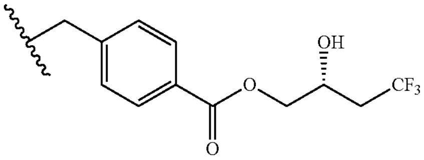
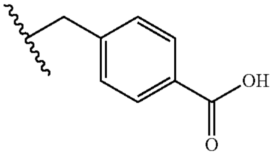
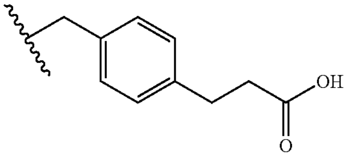
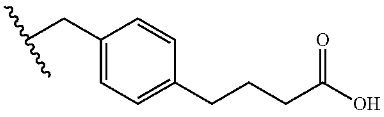
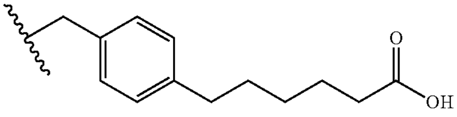
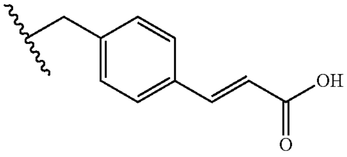
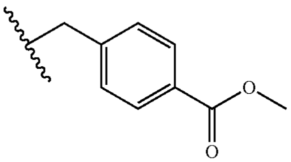

-continued
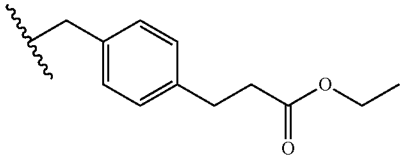
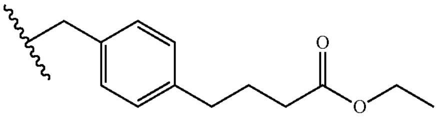
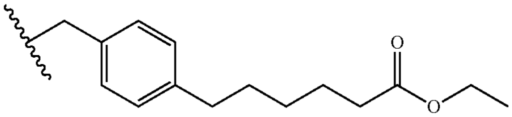
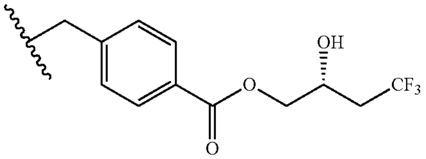
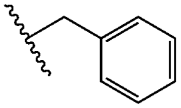
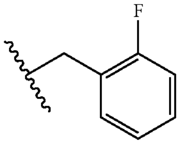
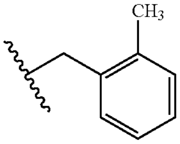
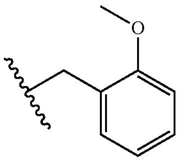
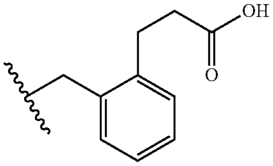
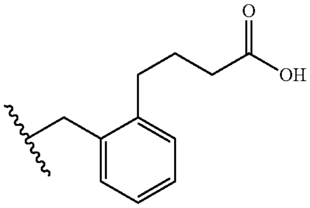
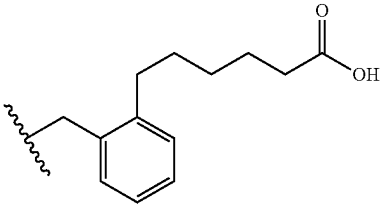
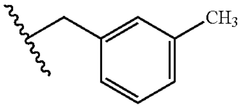
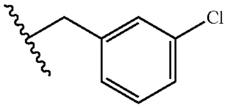
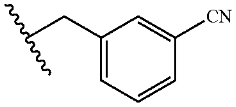
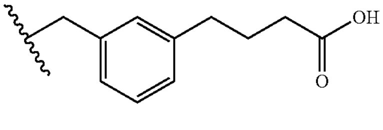
-continued
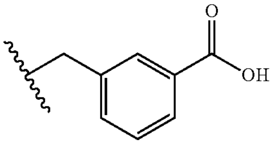
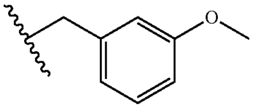
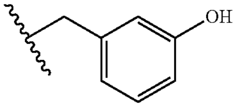
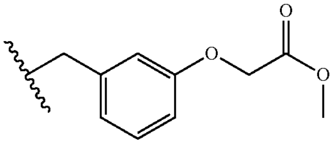
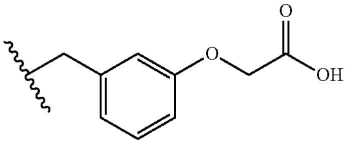
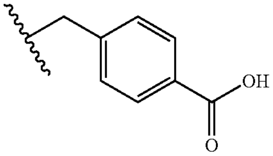
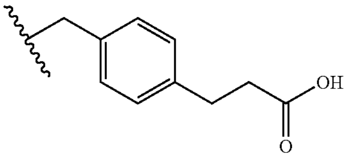
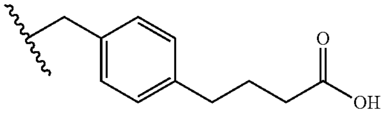
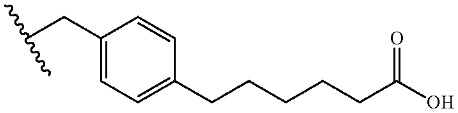
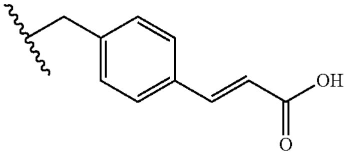
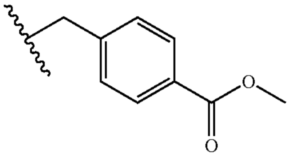
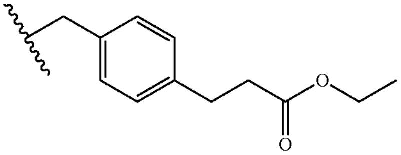
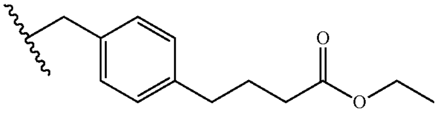
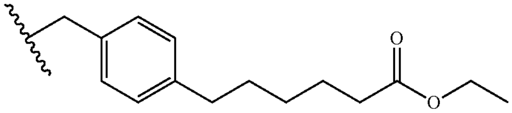

-continued
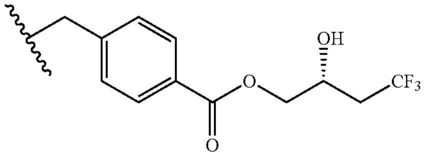
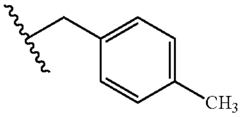
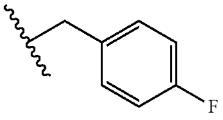
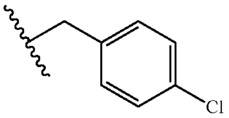
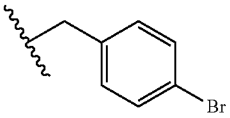
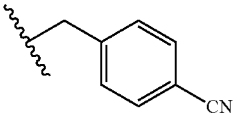
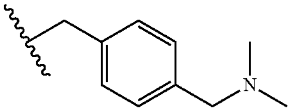
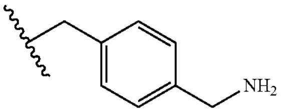
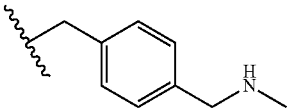
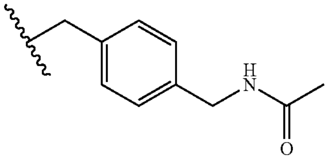
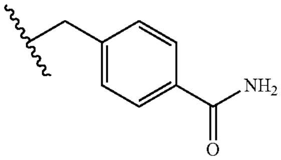
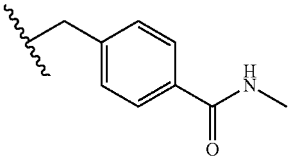
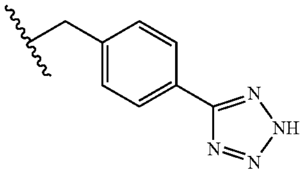
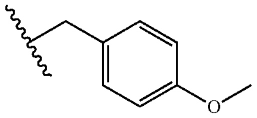
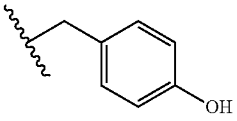
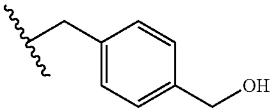
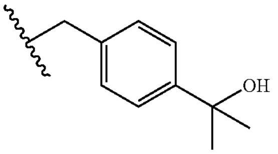
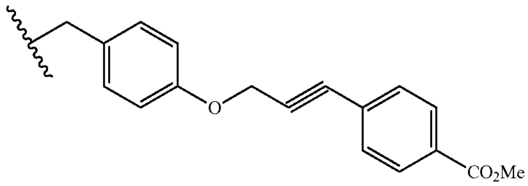
-continued
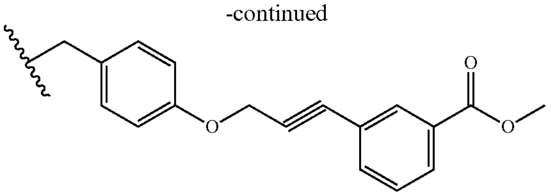
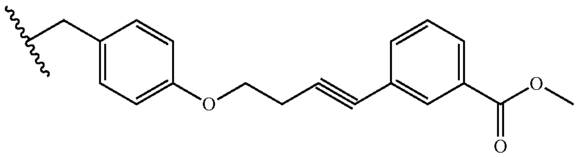
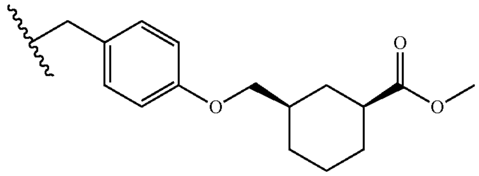
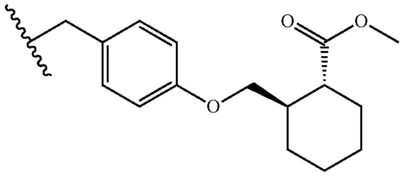
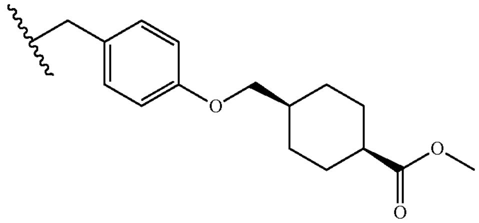
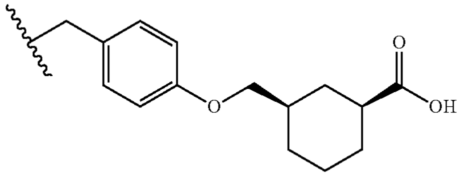
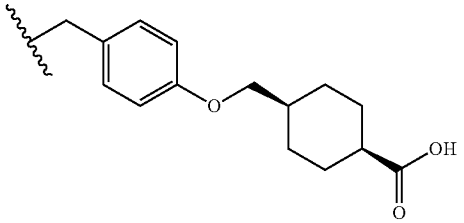
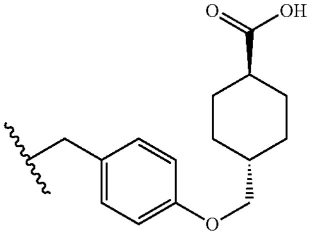
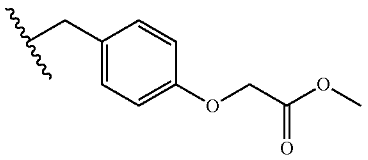

-continued
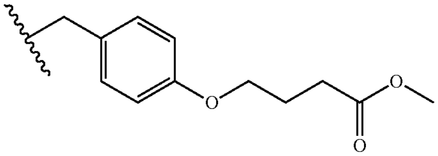
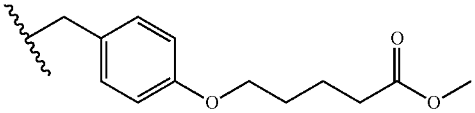
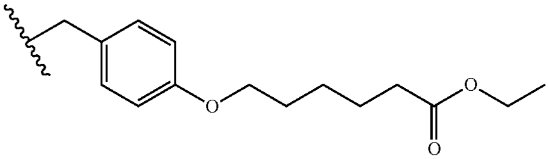
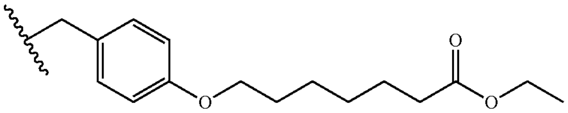
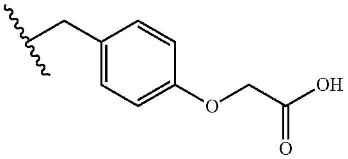
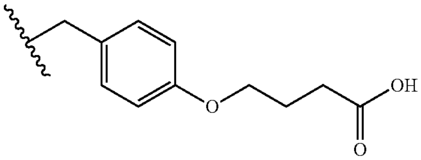
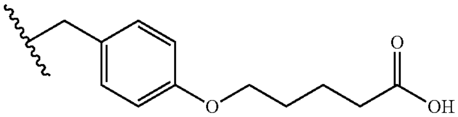
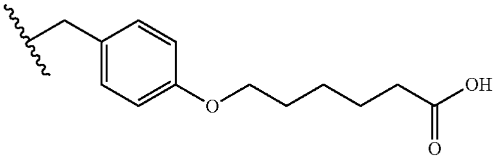
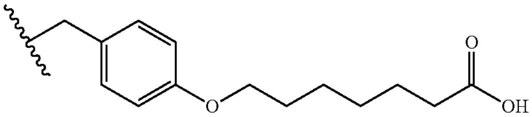
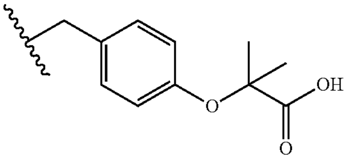
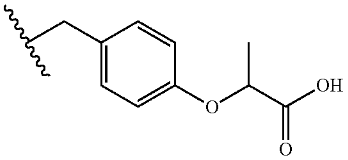
-continued
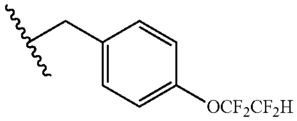
and
$R_1$ is —C(O)$R_3$, wherein $R_3$;
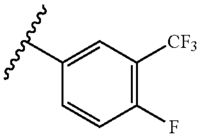 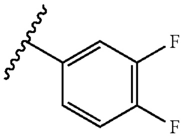
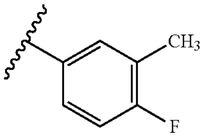 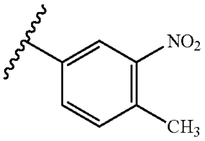
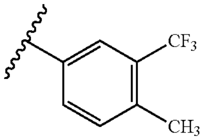 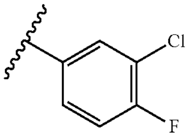
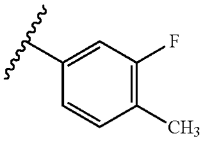 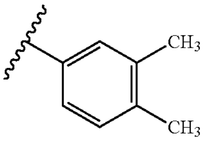
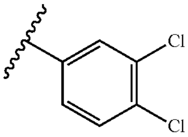 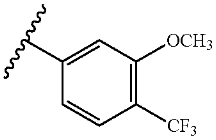
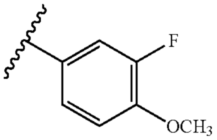 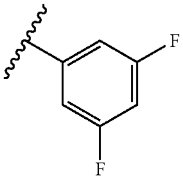
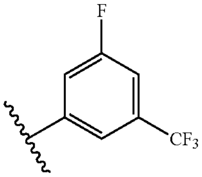 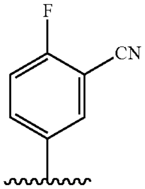
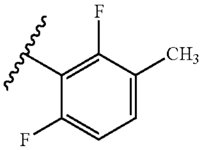 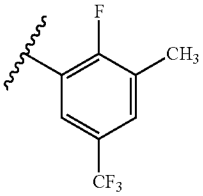

-continued
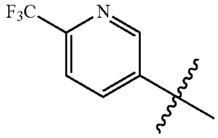
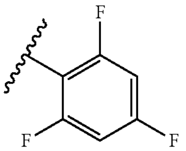
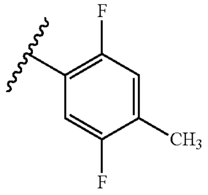
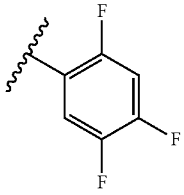
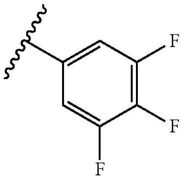
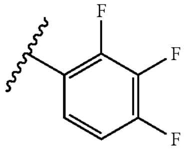
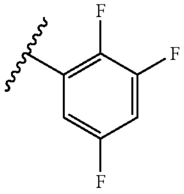
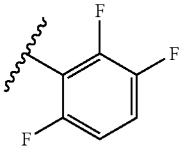
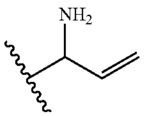
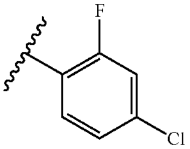
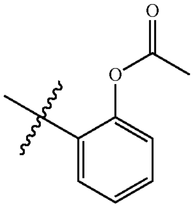
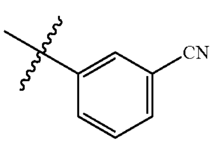
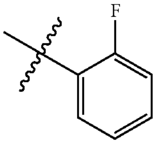
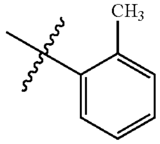
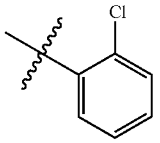
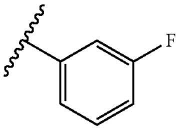
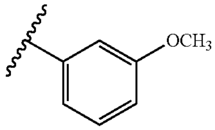
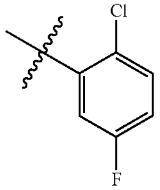
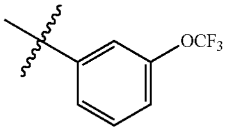
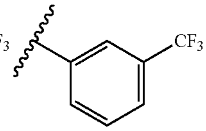
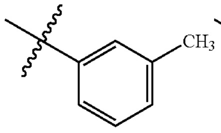
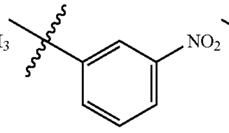
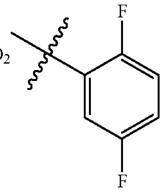
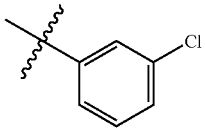
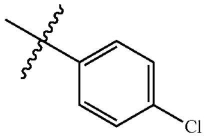
-continued
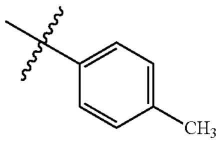
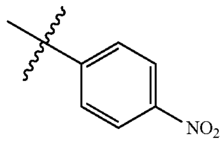
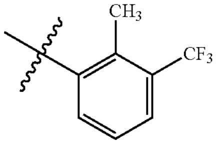
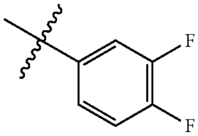
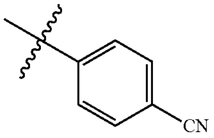
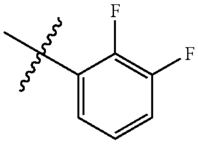
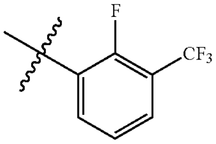
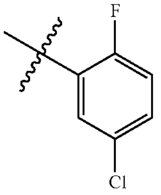
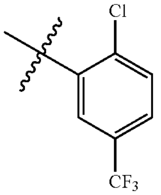
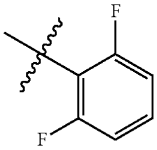
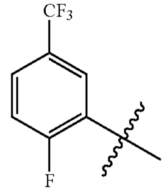
or
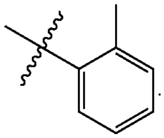
14. A compound of formula Ia
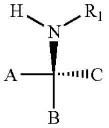
Ia
or stereoisomers or pharmaceutically acceptable salt forms thereof, wherein
A is:
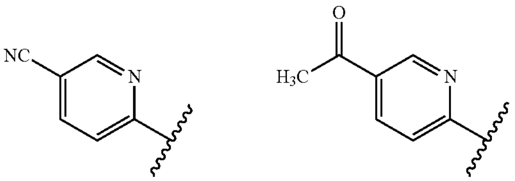
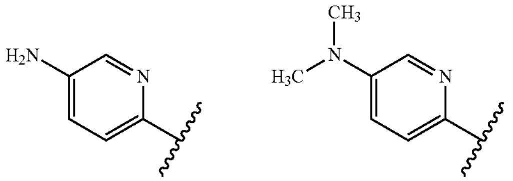

-continued
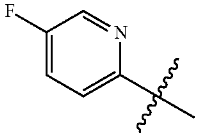
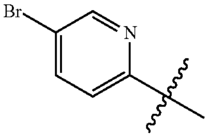
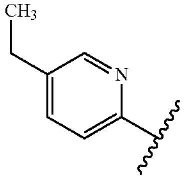
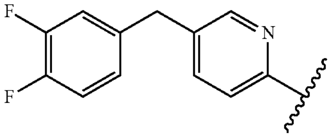
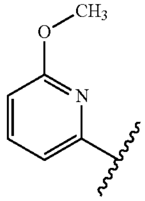
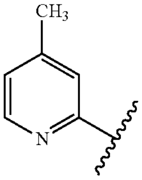
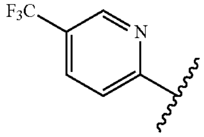
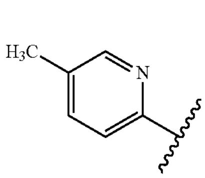
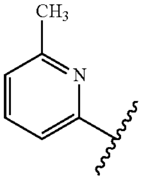
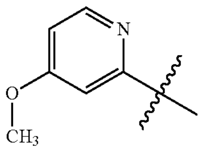
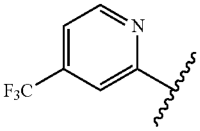
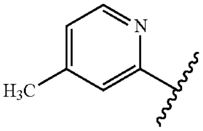
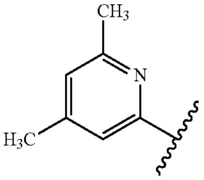
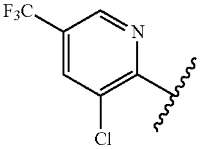
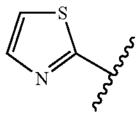
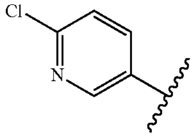
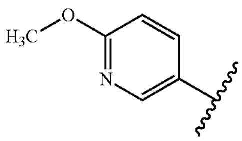
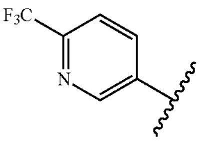
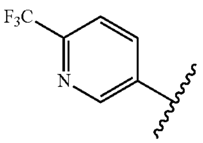
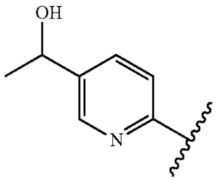
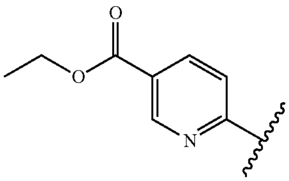
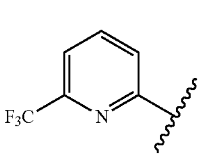
-continued
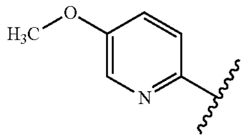
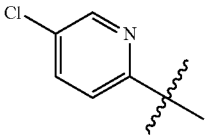
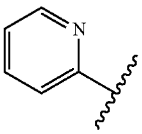
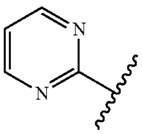
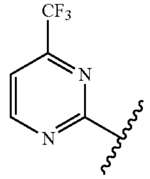
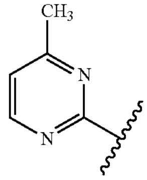
or
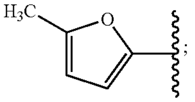
B is:
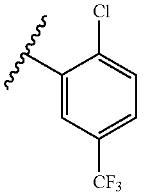
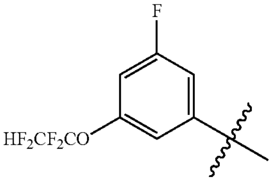
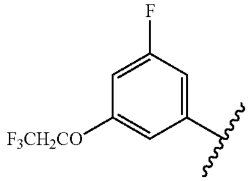
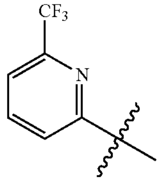
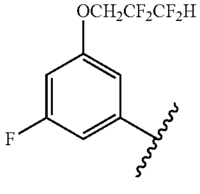
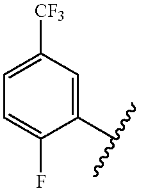
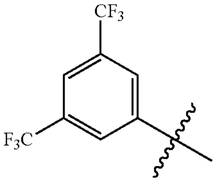
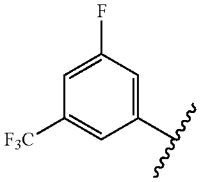
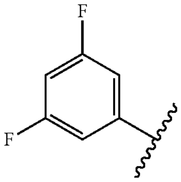
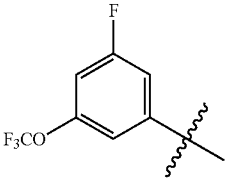
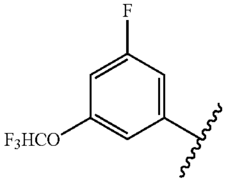

-continued
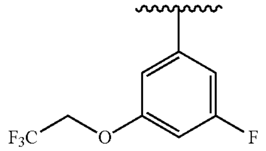
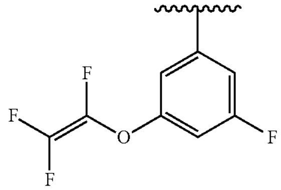
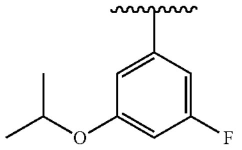
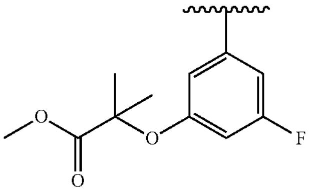
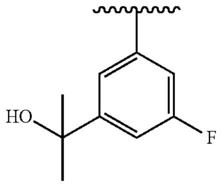
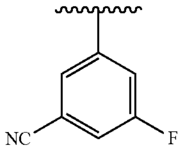
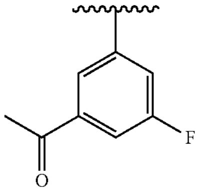
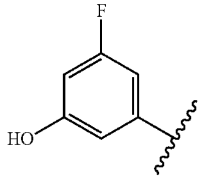
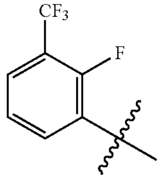
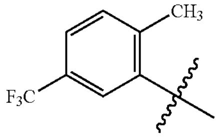
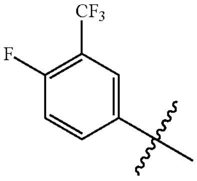
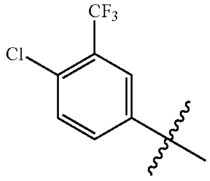
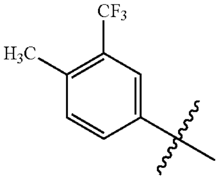
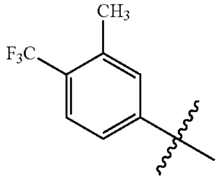
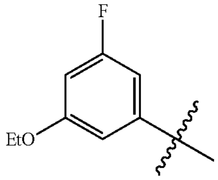
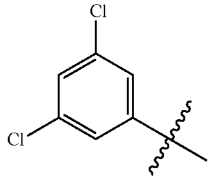
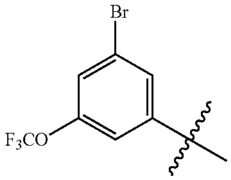
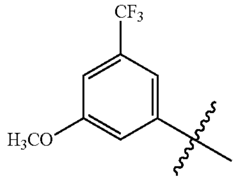
-continued
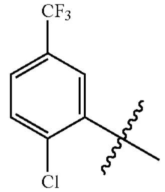
or
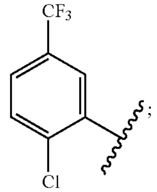
C is:
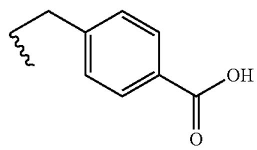
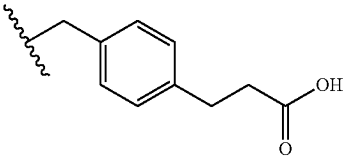
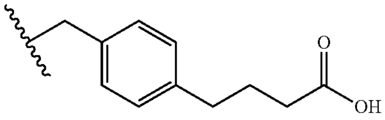
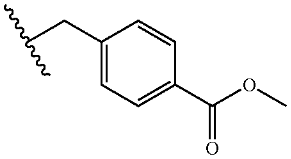
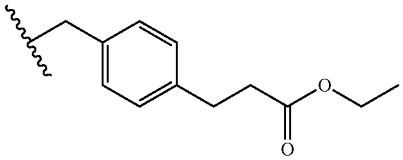
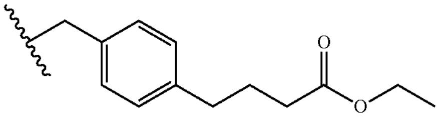
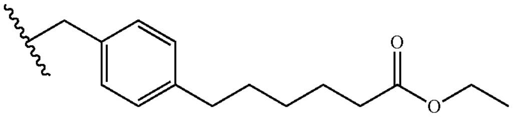
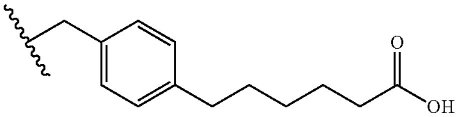
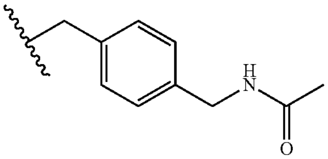
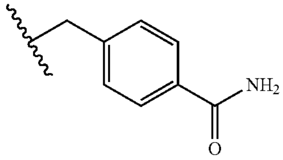
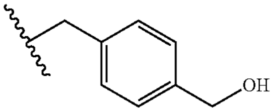

-continued
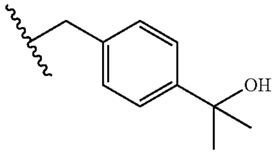
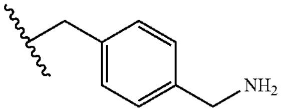
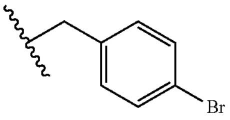
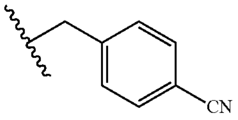
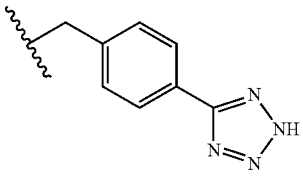
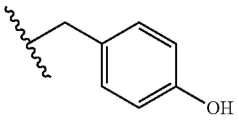
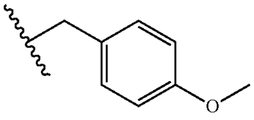
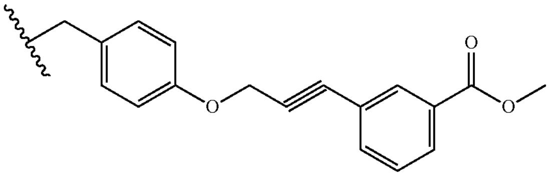
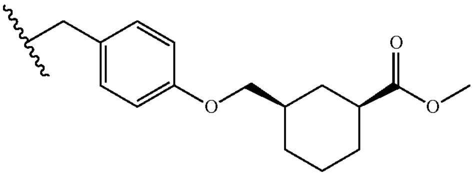
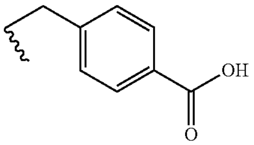
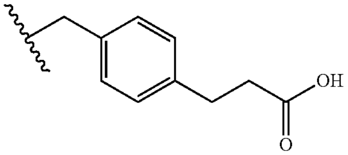
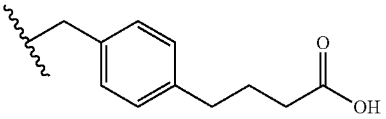
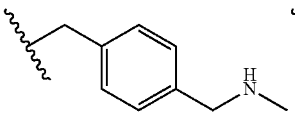
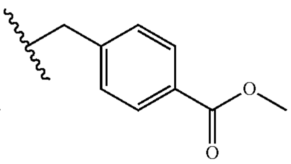
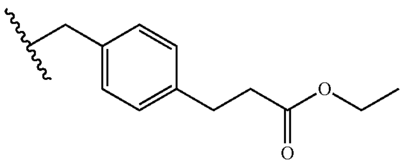
-continued
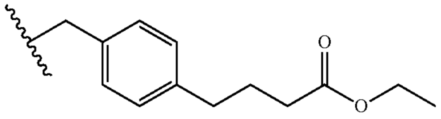
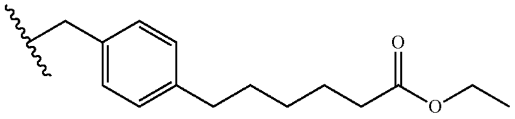
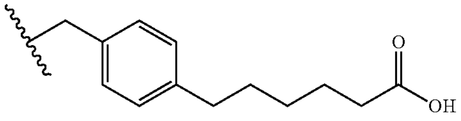
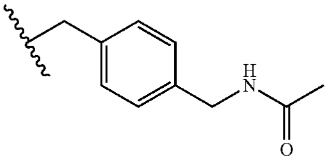
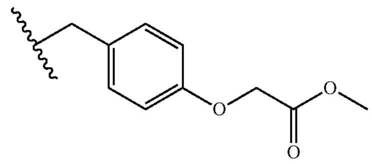
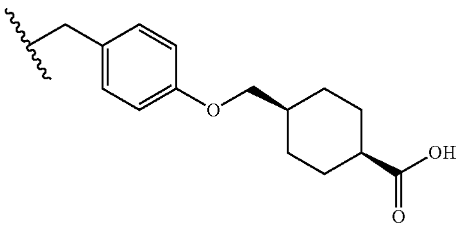
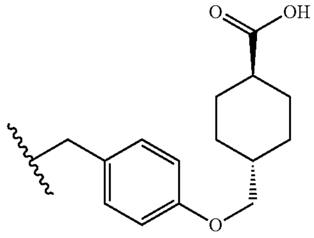
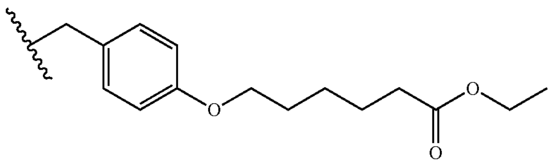
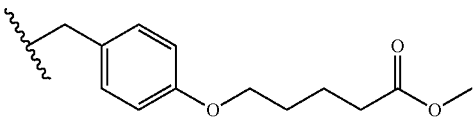
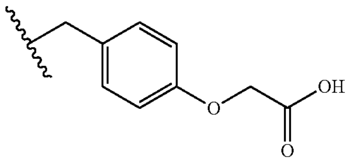

-continued
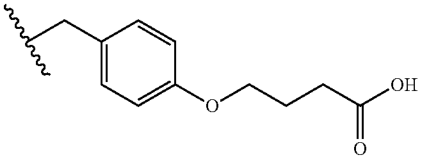
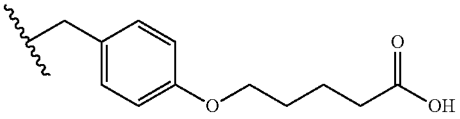
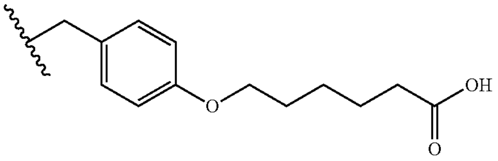
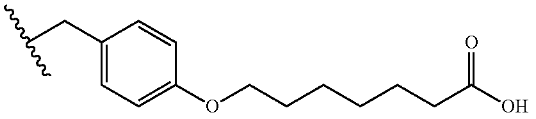
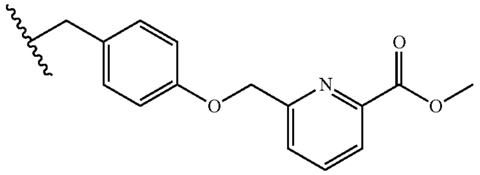
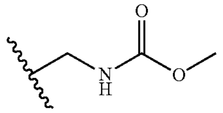
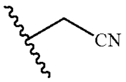
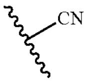
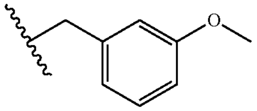
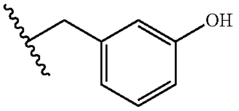
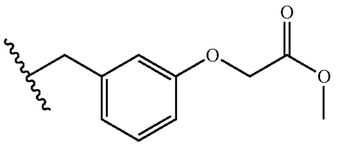
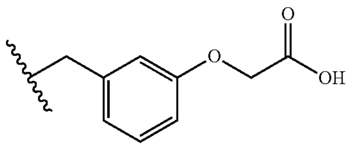
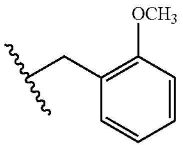
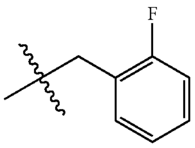
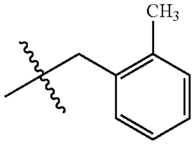
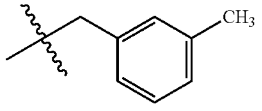
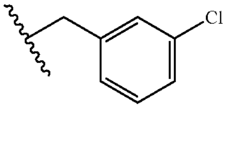
-continued
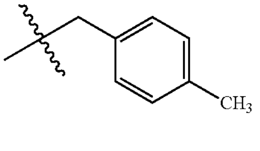
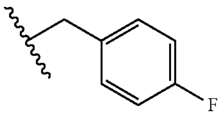
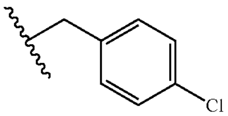
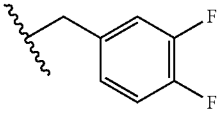
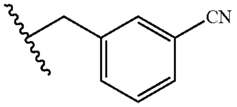
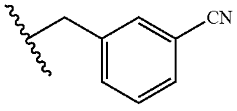
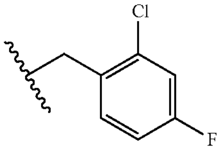
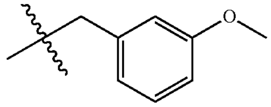
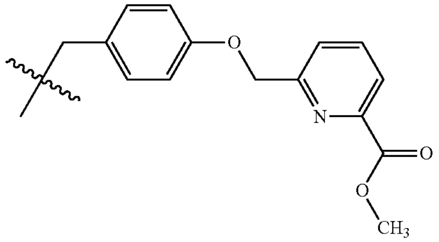
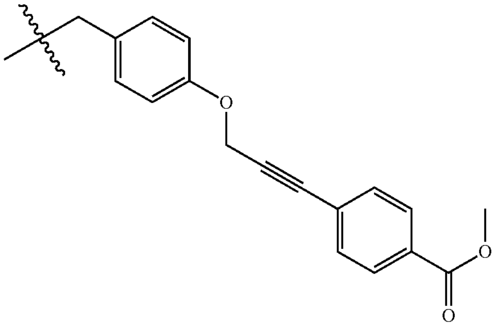
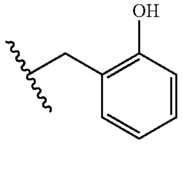
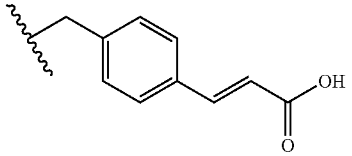
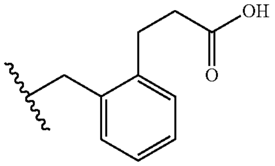
or
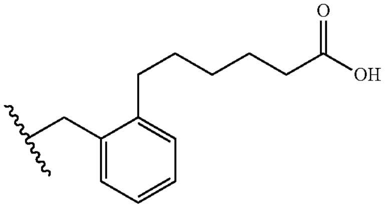

-continued
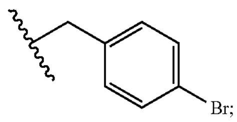
and
$R_1$ is —C(O)$R_3$, wherein $R_3$:
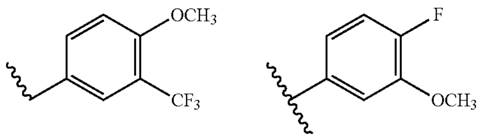
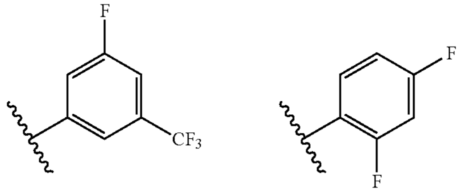
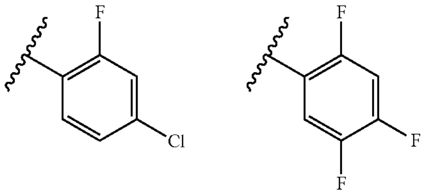
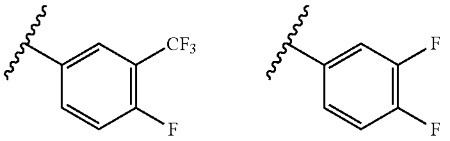
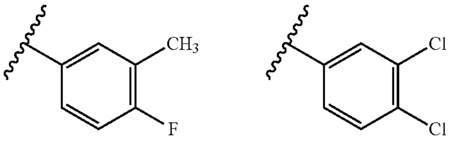
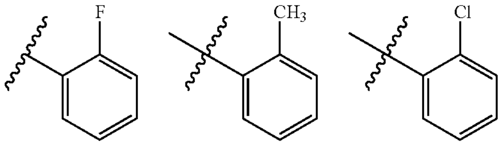
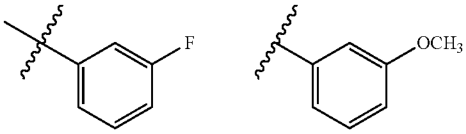
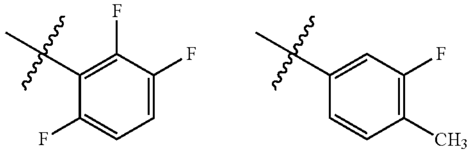
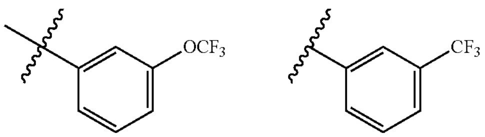
-continued
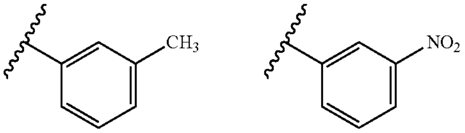
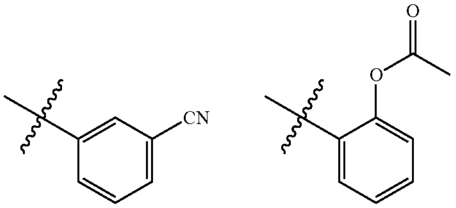
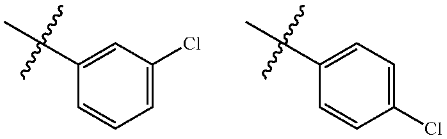
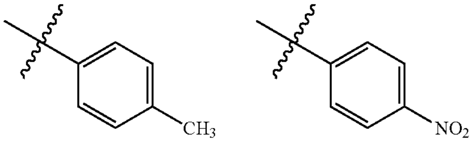
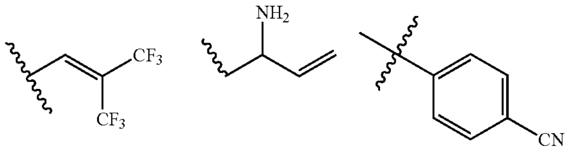
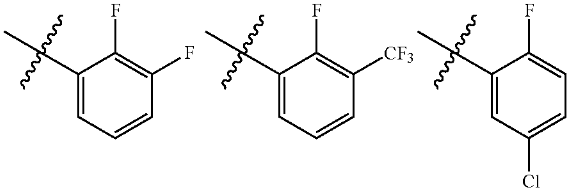
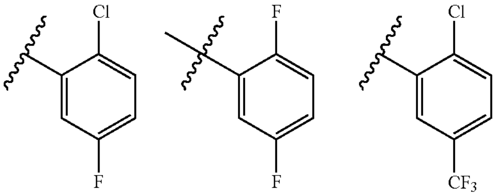
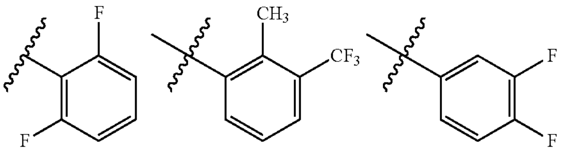
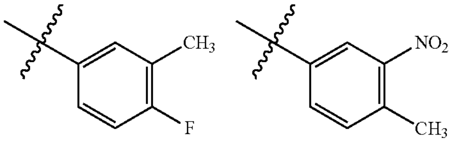
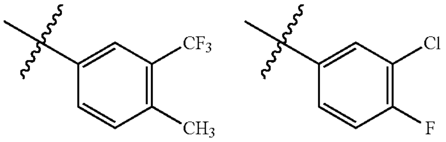

-continued
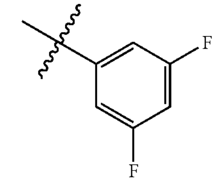
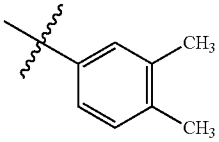
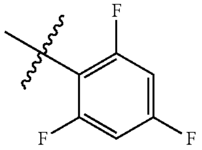
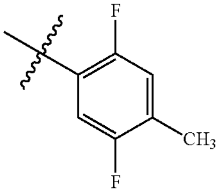
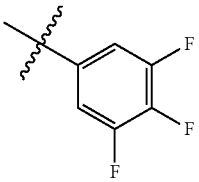
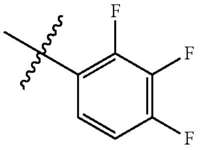
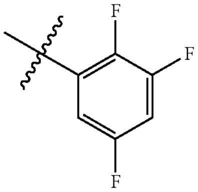
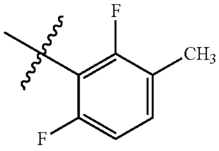
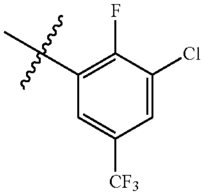
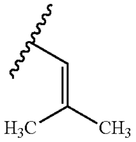
-continued
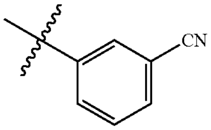
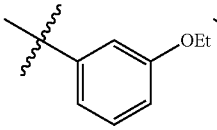
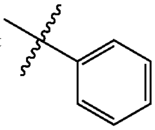
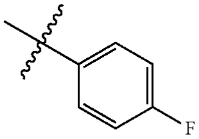
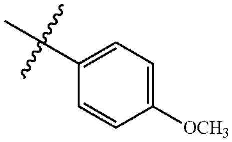
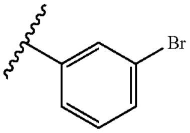
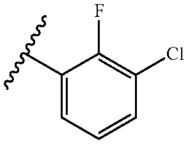
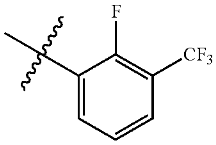
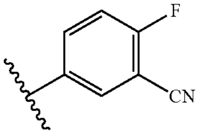
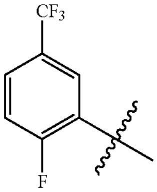
or
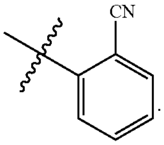
15. A pharmaceutical composition comprising a compound of claim 1.
16. The pharmaceutical composition of claim 15 further comprising a pharmaceutically acceptable carrier.
17. The pharmaceutical composition of claim 15 further comprising at least one additional therapeutic agent.
* * * * *

UNITED STATES PATENT AND TRADEMARK OFFICE

CERTIFICATE OF CORRECTION

PATENT NO. : 7,888,376 B2
APPLICATION NO. : 11/559930
DATED : February 15, 2011
INVENTOR(S) : Mark Salvati et al.

It is certified that error appears in the above-identified patent and that said Letters Patent is hereby corrected as shown below:

In the Claims:

Col. 999, Claim 1, line 60, delete "$R_{20}$'S;" and insert -- $R_{20}$'s; --, therefor.

Col. 1000, Claim 1, line 36, delete "is" and insert -- is: --, therefor.

Col. 1001, Claim 1, line 8, delete "$R_{20}$'S;" and insert -- $R_{20}$'s; --, therefor.

Col. 1001, Claim 1, line 19, delete "$C_6$) alkyl," and insert -- $C_6$)alkyl, --, therefor.

Col. 1003, Claim 1, line 30, delete "$C_6$) alkyl," and insert -- $C_6$)alkyl, --, therefor.

Col. 1004, Claim 1, line 57, delete "O)$O_{r]s}$alkyl," and insert -- O)$O_r]_s$alkyl, --, therefor.

Col. 1010, Claim 3, line 44, delete "$C_6$) alkyl," and insert -- $C_6$)alkyl, --, therefor.

Col. 1011, Claim 3, line 49, delete "$C_6$) alkyl," and insert -- $C_6$)alkyl, --, therefor.

Col. 1012, Claim 3, line 47, delete "($C_{1-C6}$)-alkyl," and insert -- ($C_1$-$C_6$)-alkyl, --, therefor.

Col. 1013, Claim 3, line 25, delete "$R_{21}$ 's;" and insert -- $R_{21}$'s; --, therefor.

Col. 1013, Claim 3, line 34, delete "$R_{21}$ 's;" and insert -- $R_{21}$'s; --, therefor.

Col. 1013, Claim 3, line 53, delete "$C_6$) alkyl," and insert -- $C_6$)alkyl, --, therefor.

Col. 1016, Claim 4, line 54, delete "$C_6$) alkyl," and insert -- $C_6$)alkyl, --, therefor.

Col. 1018, Claim 4, line 26, delete "$R_{20}$'s;" and insert -- $R_{21}$'s; --, therefor.

Col. 1018, Claim 4, line 38, delete "$R_{21}$ 's;" and insert -- $R_{21}$'s; --, therefor.

Col. 1020, Claim 4, line 7, delete "$R_{40}$ 's;" and insert -- $R_{40}$'s; --, therefor.

Col. 1023, Claim 5, line 20, delete "$R_{21}$ 's;" and insert -- $R_{21}$'s; --, therefor.

Col. 1024, Claim 5, line 7, delete "—$OR_{36}$5)" and insert -- —$OR_{36}$, 5) --, therefor.

Col. 1025, Claim 6, line 48, after "7)" delete "7)".

Col. 1025, Claim 6, line 59, delete "$R_{20}$'s:" and insert -- $R_{20}$'s; --, therefor.

Col. 1025, Claim 6, line 67, delete "—$NR_9R_{10b\,,\,8}$)" and insert -- —$NR_9R_{10}$, 8) --, therefor.

Col. 1028, Claim 6, line 7, delete "$R_{21}$ s;" and insert -- $R_{21}$'s; --, therefor.

Signed and Sealed this
Fourth Day of September, 2012

David J. Kappos
*Director of the United States Patent and Trademark Office*

In the Claims:

Col. 1030, Claim 7, delete "—$CONR_6$ $R_6$ $R_6$," and insert -- —$CONR_6$ $R_6$, --, therefor.

Col. 1032, Claim 7, line 40, delete "$R_{21}$'s; (n) halo($C_1$-$C_6$)" and insert -- $R_{21}$'s; (n) halo($C_1$-$C_6$) --, therefor.

Col. 1034, Claim 8, line 56, delete "7)aryl," and insert -- 7) aryl, --, therefor.

Col. 1037, Claim 8, line 13, delete "1 1)" and insert -- 11) --, therefor.

Col. 1041, Claim 9, line 18, delete "R 40" and insert -- $R_{40}$ --, therefor.

Col. 1043, Claim 11, line 30 approx., delete " 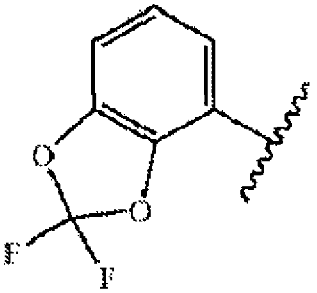 " and insert -- 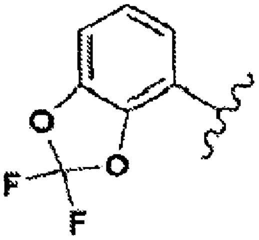 --, therefor.

Col. 1043, Claim 11, line 40 approx., delete " 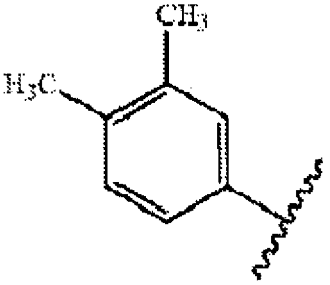 " and insert -- 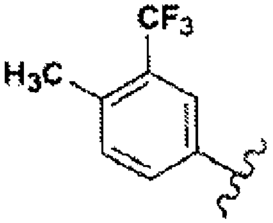 --, therefor.

In the Claims:
Col. 1044, Claim 11, line 64 approx., after " 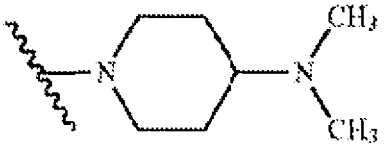 " delete ".".
Col. 1045, Claim 11, line 42 approx., after " 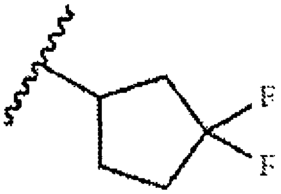 " insert -- . --.
Col. 1047, Claim 12, line 60 approx., delete " 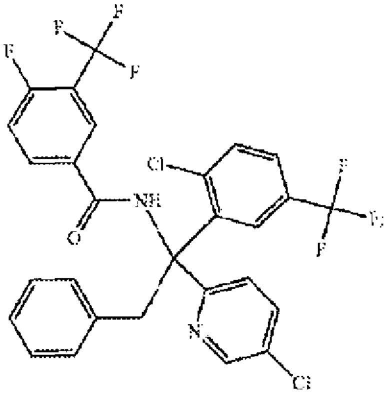 " and
insert -- 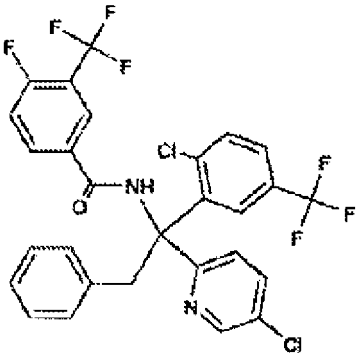 --, therefor.

In the Claims:
Col. 1051, Claim 12, line 60 approx., delete " 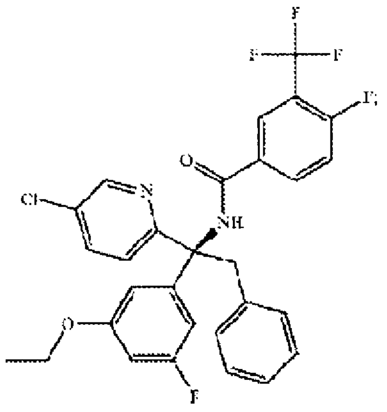 " and
insert -- 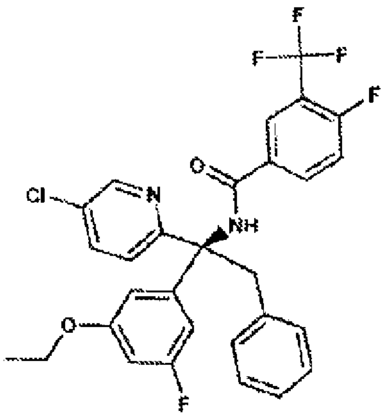 --, therefor.
Col. 1063, Claim 13, line 39, delete "wherein" and insert -- wherein: --, therefor.
Col. 1063, Claim 13, line 40, delete "is" and insert -- is: --, therefor.
Col. 1065, Claim 13, line 30, delete "is" and insert -- is: --, therefor.
Col. 1067, Claim 13, line 35, delete "is" and insert -- is: --, therefor.
Col. 1074, Claim 13, line 11, delete "$R_3$;" and insert -- $R_3$: --, therefor.

In the Claims:
Col. 1074, Claim 13, line 61 approx., delete " 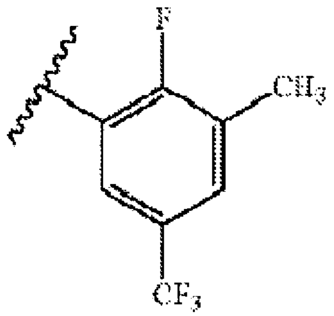 " and
insert -- 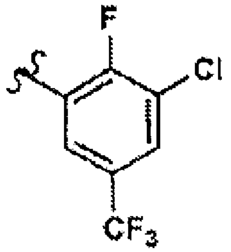 --, therefor.
Col. 1076, Claim 14, line 49, delete "wherein" and insert -- wherein: --, therefor.
Col. 1080, Claim 14, line 6 approx., delete " 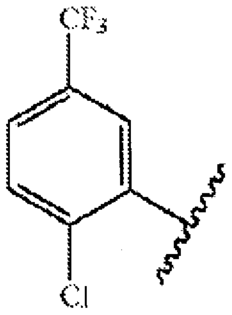 " and
insert -- 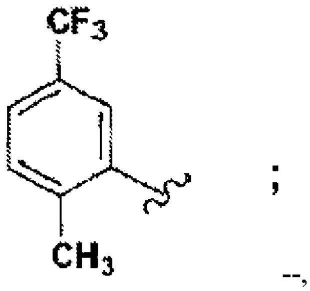 --, therefor.